(12) United States Patent
Ruddy et al.

(10) Patent No.: US 7,052,845 B2
(45) Date of Patent: May 30, 2006

(54) POLYMORPHISMS IN THE REGION OF THE HUMAN HEMOCHROMATOSIS GENE

(75) Inventors: David A. Ruddy, San Francisco, CA (US); Roger K. Wolff, Mill Valley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 212 days.

(21) Appl. No.: 10/301,844

(22) Filed: Nov. 20, 2002

(65) Prior Publication Data

US 2003/0100747 A1 May 29, 2003

Related U.S. Application Data

(60) Division of application No. 08/852,495, filed on May 7, 1997, which is a continuation-in-part of application No. 08/724,394, filed on Oct. 1, 1996, now Pat. No. 5,872,237, which is a continuation-in-part of application No. 08/630,912, filed on Apr. 4, 1996, now abandoned, which is a continuation-in-part of application No. 08/652,265, filed on May 23, 1996, now Pat. No. 6,025,130.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search .............. 435/6, 435/91.1, 91.2; 536/23.1, 24.3
See application file for complete search history.

(56) References Cited

U.S. PATENT DOCUMENTS

| | | | |
|---|---|---|---|
| 4,399,216 A | 8/1983 | Axel et al. | |
| 4,434,156 A | 2/1984 | Trowbridge | |
| 4,511,503 A | 4/1985 | Olson et al. | |
| 4,666,927 A | 5/1987 | Hider et al. | |
| 4,683,202 A | 7/1987 | Mullis | |
| 4,711,845 A | 12/1987 | Gelfand et al. | |
| 4,912,118 A | 3/1990 | Hider et al. | |
| 5,075,469 A | 12/1991 | Chevion | |
| 5,104,865 A | 4/1992 | Hider et al. | |
| 5,116,964 A | 5/1992 | Capon et al. | |
| 5,185,368 A | 2/1993 | Peter et al. | |
| 5,256,676 A | 10/1993 | Hider et al. | |
| 5,328,992 A | 7/1994 | Peter et al. | |
| 5,385,918 A | 1/1995 | Connell et al. | |
| 5,399,346 A | 3/1995 | Anderson et al. | |
| 5,420,008 A | 5/1995 | Nishida et al. | |
| 5,424,057 A | 6/1995 | Peter et al. | |
| 5,582,979 A | 12/1996 | Weber ................ | 435/6 |
| 5,705,343 A | 1/1998 | Drayna et al. | |
| 5,712,098 A | 1/1998 | Tsuchihashi et al. | |
| 5,719,125 A | 2/1998 | Suzuki et al. ........... | 514/12 |
| 5,753,438 A | 5/1998 | Drayna et al. | |
| 5,872,237 A | 2/1999 | Feder et al. ............ | 536/23.5 |
| 6,025,130 A | 2/2000 | Thomas et al. | |
| 6,140,305 A | 10/2000 | Thomas et al. | |
| 6,228,594 B1 | 5/2001 | Thomas et al. | |
| 6,284,732 B1 | 9/2001 | Feder et al. | |
| 6,391,852 B1 | 5/2002 | Feder et al. | |
| 2003/0092019 A1 * | 5/2003 | Meyer et al. ............ | 435/6 |

FOREIGN PATENT DOCUMENTS

| | | |
|---|---|---|
| CA | 2115221 | 8/1994 |
| CA | 2115222 | 8/1994 |
| CA | 2115224 | 8/1994 |
| DE | 208 609 | 4/1984 |
| DE | 4 327 226 | 2/1995 |
| EP | 0 315 434 | 5/1989 |
| EP | 0 346 281 | 12/1989 |
| EP | 97910741 | 6/2003 |
| GB | 2 293 269 | 3/1996 |
| WO | WO 92/06180 | 4/1992 |
| WO | WO 93/14188 | 7/1993 |
| WO | WO 93/15609 | 8/1993 |
| WO | WO 93/19768 | 10/1993 |
| WO | WO 93/20221 | 10/1993 |
| WO | WO 94/01463 | 1/1994 |
| WO | WO 94/04186 | 3/1994 |
| WO | WO 94/06922 | 3/1994 |
| WO | WO 94/06923 | 3/1994 |
| WO | WO 94/11367 | 5/1994 |
| WO | WO 94/21243 | 9/1994 |
| WO | WO 95/16663 | 6/1995 |
| WO | WO 96/06583 | 3/1996 |
| WO | WO 96/17870 | 6/1996 |
| WO | WO 96/35802 | 11/1996 |
| WO | WO 97/38137 | 10/1997 |

OTHER PUBLICATIONS

Hirschhorn et al. (Genetics in Medicine. vol. 4, No. 2, pp. 45–61, Mar. 2002).*

Ioannidis (Nature Genetics, vol. 29, pp. 306–309, Nov. 2001).*

Barton, J.C., et al., "*Blood Lead Concentrations in Hereditary Hemochromatosis,*" J. Lab. Clin. Med. (1994) 124(2):193–198 (0022–2143/94).

Beutler, E., et al., "*A Strategy for Cloning the Hereditary Hemochromatosis Gene,*" Blood Cells, Molecules, and Diseases (1995) 21(21):207–216 (1079–9796/95).

Bjorkman, P.J., et al., "*Structure, Function, and Diversity of Class I Major Histocompatibility Complex Molecules,*" Annu. Rev. Biochem. (1990) 59:253–288 (0066–4154/90).

Calandro, L.M., et al., "*Characterization of Recombinant That Locates the Hereditary Hemochromatosis Gene Telomeric to HLA–F,*" Hum. Genet. (1995) 96:339–342 (Kaiser Foundation Research Institute).

Camaschella, C., et al., "*Hereditary Hemochromatosis: Recent Advances in Molecular Genetics and Clinical Management,*" Haematologica (1997) 82:77–84 (BioMed).

(Continued)

*Primary Examiner*—Jeanine A. Goldberg
(74) *Attorney, Agent, or Firm*—Jones Day

(57) ABSTRACT

Polymorphic sites in the region surrounding the HH gene are provided. These polymorphisms are useful as surrogate markers in diagnostic assays for hemochromatosis.

48 Claims, 147 Drawing Sheets

OTHER PUBLICATIONS

Capecchi, M.R., "*Altering the Genome by Homologous Recombination,*" Science (1989) 244:1288–1292 (Univ. of Utah Medical Center).

Cartwright, G.E., et al., "*Inheritance of Hemochromatosis: Linkage to HLA,*" Trans. Assoc. Am. Phys. (1978) 91:273–281 (National Institutes of Health).

Chen, X., et al., "*Template–Directed Dye–Terminator Incorporation (TDI) Assay: A Homogeneous DNA Diagnostic Method Based on Fluorescence Resonance Energy Transfer,*" Nucl. Acids Res. (1997) 25(2):347–353 (U.S. Dept. of Energy).

Crawford, D.H.G., et al., "*Evidence That the Ancestral Haplotype in Australian Hemochromatosis Patients May be Associated With a Common Mutation in the Gene,*" Am. J. Hum. Genet. (1995) 57:362–367 (0002–9297/95).

Crystal, R.G., "*Gene Therapy Strategies for Pulmonary Disease,*" Am. J. Med. (1992) 92(6A):6A–44S–6A–52S (National Institutes of Health).

Dugast, I.J., et al., "*Identification of Two Human Ferritin H Genes on the Short Arm of Chromosome 6,*" Genomics (1990) 6:204–211 (0888–7543/90).

Edwards, C.Q., et al., "*The Locus for Hereditary Hemochromatosis Maps Between HLA–A and HLA–B,*" Cytogenet. Cell Genet. (1985) 40:620 (Univ. of Utah Medical Center).

El Kahloun, A., et al., "*Localization of Seven New Genes Around the HLA–A Locus,*" Hum. Molec. Genet. (1992) 2(1):55–60 (Institut National de la Sante et de la Recherche Medicale).

Friedmann, T., "*Progress Toward Human Gene Therapy,*" Science (1989) 244:1275–1281 (San Diego Univ. of Calif.).

Fullan, A., et al., "*A Polymorphic Dinucleotide Repeat at the Human HLA–F Locus,*" Hum. Mol. Genet. (1994) 3(12):2266 (Mercator Genetics).

Gasparini, P., et al., "*Linkage Analysis of 6p21 Polymorphic Markers and the Hereditary Hemochromatosis: Localization of the Gene Centromeric to HLA–F,*" Hum. Molec. Genet. (1993) 2(5):571–576 (National Research Council).

Gnirke, A., et al., "*Physical Calibration of Yeast Artificial Chromosome Contig Maps by RecA–Assisted Restriction Endonuclease (RARE) Cleavage,*" Genomics (1994) 24:199–210 (0888–7543/94).

Goei, V.L., et al., "*Isolation of Novel Non–HLA Gene Fragments From the Hemochromatosis Region (6p21.3) by cDNA Hybridization Selection,*" Am. J. Hum. Genet. (1994) 54:244–251 (0002–9297/94).

Gorski, J., "*HLA–DR β–Chain Polymorphism: Second Domain Polymorphism Reflect Evolutionary Relatedness of Alleles and May Explain Public Serologic Epitopes,*" J. Immunol. (1989) 143(1):329–333 (0022–1767/89).

Gruen, J.R., et al., "*Physical and Genetic Mapping of the Telomeric Major Histocompatibility Complex Region in Man and Relevance to the Primary Hemochromatosis Gene (HFE),*" Genomics (1992) 14:232–240 (0378–7543/92).

Halliday, J.W., "*Hemochromatosis and Iron Needs,*" Nutr. Rev. (1998) 56(2)S30–S37 (Queensland Institute of Medical Research).

Harlow, E., et a., "*Antibodies: A Laboratory Manual,*" Cold Spring Harbor Laboratory (1988) Chapter 5 pp. 75–81 (ISBN 0–87969–314–2).

Hashimoto, K., et al., "*Identification of a Mouse Homolog for the Human Hereditary Haemochromatosis Candidate Gene,*" Biochem. Biophys. Res. Comm. (1997) 230:35–39 (0006–291X/97).

Jakobovits, A., et al., "*Production of Antigen–Specific Human Antibodies from Mice Engineered with Human Heavy and Light Chain YACs*", Ann. N.Y. Acad. Sci (1995) 764:525–535 (Cell Genesys, Inc.).

Jazwinska, E.C., et al., "*Where Does the Gene for Hemochromatosis Lie in Relation to HLA–A?,*" Hepatology (1994) 19:1050–1051 (Queensland Institute of Medical Research).

Jazwinska, E.C., et al., "*Hemochromatosis and "HLA–H": Definite!*", Hepatology (1997) 25(2):495–496 (Queensland Institute of Medical Research).

Jouet, M.M.H., et al., "*Isolation of YAC Clones Containing Class I HLA Genes Which Map in the Vicinity of the Hereditary Haemochromatosis Gene,*" J. Med. Genet. (1991) 28(8):572 (St. Mary's Hospital, Manchester).

Koller, B.H., et al., "*Normal Development of Mice Deficient in $β_2$,M, MHC Class I Proteins, and $CD8^+$ T Cells,*" Science (1990) 248:1227–1230 (National Institutes of Health).

Kramer, M.F., et al., "*The Polymerase Chain Reaction,*" Current Protocols in Molecular Biology (1993) Chapter 15 pp. 15.0.1–15.1.14 (ISBN 0–471–30661–4).

Lemarchand, P., et al., "*Adenovirus–Mediated Transfer of a Recombinant Human $α_1$–Antitrypsin cDNA to Human Endothelial Cells,*" Proc. Natl. Acad. Sci. USA (1992) 89:6482–6486 (National Institutes of Health).

Lin, A.Y., et al., "*Expression of T Cell Antigen Receptor Heterodimers in a Lipid–Linked Form,*" Science (1990) 249:677–679 (Stanford Univ. School of Medicine).

Lipinski, M., et al., "*Idiopathic Hemochromatosis: Linkage with HLA,*" Tissue Antigens (1978) 11:471–474 (Hopital Saint–Louis, Paris).

Miyazaki, J.I., et al., "*Intracellular Transport Blockade Caused by Distruption of the Disulfide Bridge in the Third External Domain of Major Histocompatibility Complex Class I Antigen,*" Proc. Natl. Acad. Sci. USA (1986) 83:757–761 (National Institutes of Health).

Morgan, J.G., et al., "*The Selective Isolation of Novel cDNAs Encoded by the Regions Surrounding the Human Interleukin 4 and 5 Genes,*" Nucl. Acids Res. (1992) 20(19):5173–5179 (National Center for Human Genome Research).

Mulford, C.A., et al., "*Endocytosis of the Transferrin Receptor is Altered During Differentiation of Murine Erythroleukemic Cells,*" J. Biol. Chem. (1988) 263(11):5455–5461 (National Institutes of Health).

Murray, J.C., et al., "*A Comprehensive Human Linkage Map with Centimorgan Density,*" Science (1994) 265:2049–2054 (Univ. of Iowa).

Nickerson, D.A., et al., "*Automated DNA Diagnostics Using an ELISA–Based Oligonucleotide Ligation Assay,*" Proc. Natl. Acad. Sci. USA (1990) 87:8923–8927 (Whittier Foundation).

Nickerson, D.A., et al., "*Genotyping by Ligation Assays,*" Current Protocols in Human Genetics (1994) Chapter 2.6 pp. 2.6.1–2.6.4 (ISBN 0–471–03420–7).

Olynyk, J.K., et al., "*Hepatic Iron Concentration as a Predictor of Response to Interferon Alfa Therapy in Chronic Hepatitis C,*" Gastroentoroloy (1995) 108:1104–1109 (0016–5085/95).

Orphanos, V., et al., "*Thirteen Dinucleotide Repeat Polymorphisms on Chromosome 6,*" Hum. Mol. Genet. (1993) 2(12):2196 (Cancer Genetics).

Patterson, M., et al., "*Molecular Characterization of Cell Cycle Gene CDC7 From Saccharomyces Cerevisiae,*" Mol. Cell Biol. (1986) 6(5):1590–1598 (0270–7306/86).

Raha–Chowdhury, R., et al., "*Allelic Associations and Homozygosity at Loci from HLA–B to D6S299 in Genetic Haemochromatosis,*" J. Med. Genet. (1995) 32:446–452 (Univ. of Wales College of Medicine).

Roth, M.P., et al., "*The Human Myelin Oligodendrocyte Glycoprotein (MOG) Gene: Complete Nucleotide Sequence and Structural Characterization,*" (1995) Genomics 28:241–250 (0888–7543/95).

Rothenberg, B.E., et al., "*The Molecular Mechanisms of Iron Overload: An Animal for Hemochromatosis,*" FASEB J. (1994) 8. Abstract No. 5217, p. A900 (Univ. of California).

Salter, R.D., "*Intracellular Transport of Class I HLA Molecules is Affected by Polymorphic Residues in the Binding Groove,*" Immunogenetics (1994) 39:266–271 (American Cancer Society).

Schild, H., et al., "*The Nature of Major Histocompatibility Complex Recognition by γδ T Cells,*" Cell (1994) 76:29–37 (German Cancer Research Center).

Sevier, E.D., "*Monoclonal Antibodies in Clinical Immunology,*" Clin. Chem. (1981) 27(11):1797–1806 (Hybritech, Inc.).

Sood, A. K., et al., "*Isolation and Partial Nucleotide Sequence of a cDNA Clone for Human Histocompatibility Antigen HLA–B by Use of an Oligodeoxynucleotide Primer,*" Proc. Natl. Acad. Sci. USA (1981) 78(1):616–620 (National Institutes of Health).

Summers, K.M., et al., "*Fine Mapping of a Human Chromosome 6 Ferritin Heavy Chain Pseudogene: Relevance to Haemochromatosis,*" Hum. Genet. (1991) 88:175–178 (Queensland Institute of Medical Research).

Totaro, A., et al., "*New Polymorphisms and Markers in the HLA Class I Region: Relevance to Hereditary Hemochromatosis (HFE),*" Hum. Genet. (1995) 95:429–434 (Italian Ministry of Health).

Totaro, A., et al., "*Hereditary Hemochromatosis: Generation of a Transcription Map Within a Refined and Extended Map of the HLA Class I Region,*" Genomics (1996) 31:319–326 (0888–7543/96).

Weber, J.L., et al., "*Dinucleotide Repeat Polymorphism at the D6S105 Locus,*" Nucl. Acids Res. (1991) 19(4):968 (National Institutes of Health).

Wettstein, D.A., et al., "*Expression of a Class II Major Histocompatibility Complex (MHC) Heterodimer in a Lipid–Linked Form With Enhanced Peptide/Soluble MHC Complex Formation at Low pH,*" J. Exp. Med. (1991) 174:219–228 (0022–1007/91).

Zijlstra, M., et al., "*β2–Microglobulin Deficient Mice Lack $CD4^-8^+$ Cytolytic T Cells,*" Nature (1990) 344:742–746 (Cancer Research Institute).

Zinkernagel, R.M., et al., "*MHC–Restricted Cytotoxic T Cells: Studies on the Biological Role of Polymorphic Major Transplantation Antigens Determining T–Cell Restriction–Specificity, Function, and Responsiveness,*" Adv. In Immunol. (1979) 27:51–177 (ISBN 0–12–022427–5).

Boretto, J et al., Human Genetics. 89(1):33–36. Jan. 1992.

Campbell, Alisa M. in: Monoclonal Antibody Technology. Ed. Capbell. Elsevier Science Publishers, Amsterdam, NL. pp. 1–32. 1985.

Cornall, RJ et al. Genomics 10(4):874–881, Aug. 1991.

Vogel, F. and Motulsky, AG. In: Human Genetics. Vogel and Motulsky, eds. Springer–Verlag, Berlin. pp. 18–81, 1982.

Beutler, E. et al., "Mutation Analysis in Hereditary Hemochromatosis" *Blood Cells, Molecules, and Diseases* (1996), 22(16):187–194.

Gasparini, et al., "Where does the gene for Hemochromatosis lie in relation to HLA–A", *Hepatology* (1994), 19: 1050–1056.

Gandon et al., "Linkage Disequilibrium and Extended Haplotypes in the HLA–A to D6S105 Region: Implications for Mapping the Hemochromatosis Gene (HFE)," *J. Hum. Genet.* (1996) 97 (1):103–13.

Seese, et al., "Localization of the Hemochromatosis Disease Gene: Linkage Disequilibrium Analysis using an American Patient Collection," *Blood Cells, Molecules & Diseases* (1996) 22:36–46.

Altman, J.D. et al., "Phenotypic Analysis of Antigen–Specific T Lymphocytes," *Science* 274:94–96 (1996).

Anderson, G.J. et al., "Transferrin Receptor Distribution and Regulation in the Rat Small Intestine," *Gastroenterology* 98:576–585 (1990).

Arteaga, C.L. et al., "Tissue–targeted Antisense c–fos Retroviral Vector Inhibits Established Breast Cancer Xenografts in Nude Mice," *Canc. Res.* 56:10981103 (1996).

Banerjee, D. et al., "Transferrin Receptors in the Human Gastrointestinal Tract," *Gastroenterology* 91:861–869 (1986).

Brent, R. et al., "A bacterial repressor protein or a yeast transcriptional terminator can block upstream activation of a yeast gene," *Nature* 312:612–615 (1984).

Brent, R. et al., "A Eukaryotic Transcriptional Activator Bearing the DNA Specificity of a Prokaryotic Repressor," *Cell* 43:729–736 (1985).

Carbognani, P. et al., "Transferrin Receptor Expression in Nonsmall Cell Lung Cancer," *Cancer* 78(1):178–179 (1996).

Chien, C–T. et al., "The two–hybrid system: A method to identify and clone genes for proteins that interact with a protein of interest," *Proc. Natl. Acad. Sci. U.S.A.* 88:9578–9582 (1991).

Cook, J.D. et al., "Serum Transferrin Receptor," *Annu. Rev. Med.* 44:63–74 (1993).

Cox, G.A. et al., "Overexpression of dystrophin in transgenic mdx mice eliminates dystrophic symptoms without toxicity," *Nature* 364:725–729 (1993).

Curiel, D.T. et al., "Adenovirus enhancement of transferrin–polylysine–mediated gene delivery," *FXoc. Natl. Acad. Sci. U.S.A.* 88:8850–8854 (1991).

Dadone, M.M. et al., "Hereditary Hemochromatosis. Analysis of Laboratory Expression of the Disease by Genotype in 18 Pedigrees," *Am. J. Clin. Pathol.* 78(2):196–207 (1982).

Dalesandro, J. et al., "Cardiac and Pulmonary Replacement," *J. Thoracic and Cardio. Surgery* 111(2):416–422 (1996).

Delahunty, C. et al., "Testing the Feasibility of DNA Typing for Human Identification by PCR and an Oligonucleotide Ligation Assay," *Am. J. Hum. Genet.* 58:1239–1246 (1996).

Edwards, C.Q. et al., "Prevalence of Hemochromatosis Among 11,065 Presumably Healthy Blood Donors," *N. Engl. J. Med.* 318(21):1355–1362 (1988).

Fahnestock, M.L. et al., "Thermal Stability Comparison of Purified Empty and Peptide–Filled Forms of a Class I MHC Molecule," *Science* 258:1658–1662 (1992).

Fahnestock, M.L. et al., "The MHC Class I Homolog Encoded by Human Cytomegalovirus Binds Endogenous Peptides," *Immunity* 3:583–590 (1995).

Feder, J.N. et al., "The Hemochromatosis Founder Mutation in HLA–H Disrupts $\beta_2$–Microglobulin Interaction and Cell Surface Expression," *J. Biol. Chem.* 272(22):14025–14028 (1997).

Friedman, J.M. et al., "Cellular Promoters Incorporated into the Adenovirus Genome: Cell Specificity of Albumin and Immunoglobulin Expression," *Mol. Cell. Biol.* 6(11):3791–3797 (1986).

Gastinel, L.N. et al., "Expression and crystallization of a soluble and functional form of an Fc receptor related to class I histocompatibility molecules," *Proc. Natl. Acad. Sci. U.S.A.* 89:638–642 (1992).

Hatzoglou, M. et al., "Hepatic Gene Transfer in Animals Using Retroviruses Containing the Promoter from the Gene for Phosphoenolpyruvate Carboxykinase," *J. Biol. Chem.* 265(28):17285–17293 (1990).

Huber, B.E. et al., "Retroviral–mediated gene therapy for the treatment of hepatocellular carcinoma: An innovative approach for cancer therapy," *Proc. Natl. Acad. Sci. U.S.A.* 88:8039–8043 (1991).

Jahroudi, N. et al., "Endothelial–Cell–Specific Regulation of von Willebrand Factor Gene Expression," *Mol. Cell. Biol.* 14(2):999–1008 (1994).

Karin, M. et al., "Receptor–mediated Endocytosis of Transferrin in Developmentally Totipotent Mouse Teratocarcinoma Stem Cells," *J. Biol. Chem.* 256(7):3245–3252 (1981).

Keer, H.N. et al., "Elevated Transferrin Receptor Content in Human Prostate Cancer Cell Lines Assessed In Vitro and In Vivo," J. Urol., 143:381–385 (1990).

Klausner, R.D. et al., "Receptor–mediated Endocytosis of Transferrin in K562 Cells," *J. Biol: Chem.* 258:4715–4724 (1983).

Koc, O.N. et al., "Transfer of Drug Resistance Genes into Hemotopoietic Progenitors to Improve Chemotherapy Tolerance," *Sem. Oncol.* 23(1):46–65 (1996).

Letourneur, F. et al., "A Novel Di–Leucine Motif and a Tyrosine–Based Motif Independently Mediated Lysosomal Targeting and Endocytosis of CD 3 Chains," *Cell* 69:1143–1157 (1992).

Makarov, S.S., "Suppression of experimental arthritis by gene transfer of interleukin I receptor antagonist cDNA," *Proc. Natl. Acad. Sci. U.S.A.* 93:402406 (1996).

Marks, M.S. et al., "A Lysosomal Targeting Signal in the Cytoplasmic Tail of the (3 Chain Directs HLA–DM to MHC Class II Compartments," *J. Cell Biol.* 131:351–369 (1995).

Maxwell, I.H. et al., "Expressionof the Diptheria Toxin A–Chain Coding Sequence under the Control of Promoters and Enhancers from Immunoglobulin Genes as a Means of Directing Toxicity of B–Lymphoid Cells," *Canc. Res.* 51:4299–4304 (1991).

McClelland, A. et al., The Human Transferrin Receptor Gene: Genomic Organization, and the Complete Primary Structure of the Receptor Deduced from a cDNA Sequence, *Cell* 39:267–274 (1984).

McLaren, C.E. et al., "Prevalence of Heterozygotes for Hemochromatosis in the White Population of the United States," *Blood* 86(5):2021–2027 (1995).

Miller, N. et al., "Targeted vectors for gene therapy," *FASEB J.* 9:190–199 (1995).

Miyazaki, J–I. et al., "Expression vector system based on the chicken $\beta$–actin promoter directs efficient production of interleukin–5," *Gene* 79:269–277 (1989).

Nolta, J.A. et al., "Transduction of: pluripotent human hematopoietic stem cells demonstrated by clonal analysis after engraftment in immune–deficient mice," *Proc. Natl. Acad. Sci.– U.S.A.* 93:2414–2419 (1996).

Octave, J–N et al., "Transferrin Uptake by Cultured Rat Embryo Fibroblasts," *Eur. J. Biochem.* 123:235–240 (1982).

Oliveira, H.C.F. et al., "Human Cholesteryl Ester Transfer Protein Gene Proximal Promoter Contains Dietary Cholesterol Positive Responsive Elements and Mediates Expression in Small Intestine and Periphery While Predominant Liver and Spleen Expression is Controlled by 5'-distal Sequences," *J. Biol. Chem.* 271(510):31831–31838 (1996).

Omary, M.B. et al., "Biosynthesis of the Human Transferin Receptor in Cultured Cells," *J. Biol. Chem.* 256(24):12888–12892 (1981).

Parham, P et al., "Arginine 45 is a Major Part of the Antigenic Determinant of Human $\beta_2$–Microglobulin Recognized by Mouse Monoclonal Antibody BBM.1," *J. Biol. Chem.* 258(10):6179–6186 (1983).

Parkkila, S. et al., "Immunohistochemistry of HLA–H, the protein defective in patients with hereditary hemochromatosis, reveals unique pattern of expression in gastrointestinal tract," *Proc. Natl. Acad. Sci. U.S.A.* 94:2534–2539 (1997).

Petrylak, D.P. et al., Transferrin Receptor Expression in Testis Cancer, *J. Natl. Canc. Inst.* 86(8):636–637 (1994).

Plank, C. et al., "The Influence of Endosome–disruptive Peptides on Gene Transfer Using Synthetic Virus–like Gene Transfer Systems," *J. Biol. Chem.* 269(17):12918–12924 (1994).

Raghavan, M. et al., "The Class I Major Histocompatibility Complex Related Fc Receptor Shows pH–Dependent Stability Differences Correlating with Immunoglobulin Binding and Release," *Biochemistry* 32:8654–8660 (1993).

Raper, S.E. et al., "Safety and Feasibility of Liver–Directed Ex Vivo Gene Therapy for Homozygous Familial Hyperchoesterolemia," *Annal. of Surgery 223* (2):116–126 (1996).

Rotzschke, O. et al., "Isolation and analysis of naturally processed viral peptides as recognized by cytotoxic T cells," *Nature* 348:252–254 (1990).

Ruddy, D.A. et al., "A 1.1–Mb Transcript Map of the Hereditary Hemochromatosis Locus," *Genome Res.* 7:441–456 (1997).

Schaeffer, E. et al., "Complete structure of the human transferrin gene. Comparison with analogous chicken gene and human pseudogene," *Gene* 56:109–116 (1987).

Schneider, C. et al., "Primary structure of human transferrin receptor deduced from the mRNA sequence," *Nature* 311:675–678 (1984).

Seligman, P.A. et al., "Isolation arid Characterization of the Transferrin Receptor from Human Placenta," *J. Biol. Chem.* 254(20):9943–9946 (1979).

Sugita, M. et al., "Cytoplasmic Tail–Dependent Localization of CD1b Antigen–Presenting molecules to MIICs," *Science* 273:349–352 (1996).

Uhlmann, E. et al., "Antisense Oligonucleotides: A New Therapeutic Principle," *Chem. Rev.* 90(4):543–584 (1990).

Vandewalle, B. et al., "Transferrin Receptors in Cultured Breast Cancer Cells," *J. Canc. Res. Clin. Oncol.* 110:71–76 (1985).

Voorhees, P. et al., "An acidic sequence within the cytoplasmic domain of furin functions as a determinant of trans–Golgi network localization and internalization from the cell surface," *FMBO J.* 14(20):4961–4975 (1995).

Wada, H.G. et al., "Transferrin Receptor in Human Placental Brush Border Membranes," *J. Biol. Chem.* 254(24):12629–12635 (1979).

Ward, J.H. et al., "Regulation of HeLa Cell Transferrin Receptors," *J. Biol. Chem.* 257(17):10317–10323 (1982).

Waugh, S.M. et al., "Isolation of a :Proteolytically Derived Domain of the Insulin Receptor Containing the Major Site of Cross–Linking/Binding," *Biochemistry* 28:3448–3455 (1989).

Weiser, P. et al., "Endosomal Targeting by the Cytoplasmic Tail of Membrane Immunoglobulin," *Science* 276:407–409 (1997).

Williams, M.A. et al., "Accumulation of Membrane Glycoproteins in Lysosomes Requires a Tyrosine Residue at a Particular Position in the Cytoplasmic Tail," *J. Cell Biol.* 111:955–966 (1990).

Wu, G.Y. et al., "Receptor–mediated Gene Delivery and Expression in Vivo," *Biol. Chem.* 263(29):14621–14624 (1988).

Zou, L. et al., "Isolation of a Liver–Specific Promoter for Human Growth Hormone Receptor Gene," *Endocrin.* 138(4):1771–1774 (1997).

Alvarez et al., "Inhibition of the Receptor–Mediated Endocytosis of Differric Transferrin Is Associated with the Covalent Modification of the Transferrin Receptor with Palmitic Acid" JBC (1990) 265(27):16644–16655.

Alvarez et al., "A Point Mutation In the Cytoplasmic Domain of the Transferrin Receptor Inhibits Endocytosis", *Biochem J.* (1990): 267: 31–35.

Abravaya, K. et al., "Detection of point mutations with a modified ligase chain reaction (Gap–LCR)," *Nucl. Acids Res.* 23 (4):675–682 (1995).

Adams, M.D. et al., "Complementary DNA Sequencing: Expressed Sequence Tags and Human Genome Project," *Science* 252:1651–1656 (1991).

Amadou, C. et al., "Localization of New Genes and Markers to the Distal Part of the Human Major Histocompatibility Complex (MHC) Region and Comparison with the Mouse: New Insights into the Evolution of Mammalian Genomes," *Genomics* 26:9–20 (1995).

Anderson, J.R. et al., "Precipitating Autoantibodies in Sjögren's Disease," *Lancet* 2:456–460 (1961).

Bacon, B.R., "Causes of Iron Overload," *N. Engl. J. Med.* 326(2):126–127 (1992).

Barany, F., "Genetic disease detection and DNA amplification using cloned thermostable ligase," *Proc. Natl. Acad. Sci. U.S.A.* 88:189–193 (1991).

Balan, V. et al., "Screening for Hemochromatosis: A Cost-Effectiveness Study Based on 12,258 Patients," *Gastroentorology* 107:453–459 (1994).

Barton, J.C. et al., "Hemochromatosis: The genetic disorder of the twenty–first century," *Nature Medicine* 2:394–395 (1996).

Beaucage, S.L. et al., "Deoxynucleoside Phosphoarmidites–A New Class of Key Intermediates for Deoxypolynucleotide Synthesis," *Tetrahedron Letters* 22(20):1859–1862 (1981).

Beggs, J.D., "Transformation of yeast by replicating hybrid plasmid," *Nature* 275:104–109 (1978).

Benton, W.D. et al., "Screening λgt Recombinant Clones by Hybridization to Single Plagues in situ," *Science* 196:180–182 (1977).

Botstein, D. et al., "Sterile Host Yeast (SHY): A Eukaryotic System of Biological COntainment for Recombinant DNA Experiments,"*Gene* 8:17–24 (1979).

Broach, J.R. et al., "Transformation in Yeast: Development of a Hybrid Cloning Vector and Isolation of the CAN1 Gene," *Gene* 8:121–133 (1979).

Chong, S.S. et al., "Molecular Cloning of the cDNA Encoding a Human Renal Sodium Phosphate Transport Protein and Its Assignment to Chromosome 6p21.3–p23," *Genomics* 18:355–359 (1993).

Cotton, R.G.H. et al., "Reactivity of cytosine and thymine in single–base–pair mismatches with hydroxylamine and osmium tetroxide and its application to the study of mutations," *Proc. Natl. Acad. Sci. U.S.A.* 85:4397–4401 (1988).

Church, D.M. et al., "Isolation of genes from complex sources of mammalian genomic DNA using exon amplification," *Nature Genetics* 6:98–105 (1994).

Clark, G. et al., "Characterization of a soluble cytoplasmic antigen reactive with sera from patients with systemic lupus erythmatosus," *J. Immunol.* 102(1):117–122 (1969).

Dausset, J. et al., "Centre d'Etude du Polymorphisme Humain (CEPH) : Collaborative Genetic Mapping of the Human Genome," *Genomics* 6:575–577 (1990).

Edwards, C.Q. et al., "Screening for Hemochromatosis," *N. Engl. J. Med.* 328(22):1616–1620 (1993).

Faham, M. et al., "A Novel In Vivo Method to Detect DNA Sequence Variation," *Genome Res.* 5:474–482 (1995).

Fahy, E. et al., "Self–sustained Sequence Replication (3SR) : An Isothermal Transcription–based Amplification System Alternative to PCR," *PCR Methods Appl.* 1:25–33 (1992).

Feder, J.N. et al., "A novel MHC class I–like gene is mutated in patients with hereditary haemochromatosis," *Nature Genetics* 13:399–406 (1996).

Finch, C.A., "Hemochromatosis–Treatment is Easy, Diagnosis Hard," *West. J. Med.* 153:323–325 (1990).

Fischer, S.G. et al., "DNA fragments differing by single base–pair substitutions are separated in denaturing gradient gels: Correspondence with melting theory," *Proc. Natl. Acad. Sci. U.S.A.* 80:1579–1583 (1983).

Freemont, P.S. et al., "A Novel Cysteine–Rich Sequence Motif," *Cell* 64:483–484 (1991).

Grunstein, M. et al., "Colony hybridization: A method for the isolation of cloned DNAs that contain a specific gene," *Proc. Natl. Acad. Sci. U.S.A.* 72(10):3961–3965 (1975).

Gubler, U. et al., "A simple and very efficient method for generating cDNA libraries," *Gene* 25:263–269 (1983).

Gyapay, G. et al., "The 1993–94 Généthon human genetic linkage map," *Nature Genetics* 7:246–339 (1994).

Herskowitz, I. et al., "The lysis–lysogeny decision of phage λ: explicit programming and responsiveness," Ann. Rev. Genet. 14:399–445 (1980).

Hinnen, A. et al., "Transformation of yeast," *Proc. Natl. Acad. Sci. U.S.A.* 75(4):1929–1933 (1978).

Ito, H. et al., "Transformation of intact Yeast Cells Treated with Alkali Cations," *J. Bacteriol.* 153(1):163–168 (1983).

Jazwinska, E.C. et al., "Localization of the Hemochromatosis gene Close to D6S105," *Am. J. Hum. Genet.* 53:347–352 (1993).

Jazwinska, E.C. et al., "Haplotype Analysis in Australian Hemochromatosis Patients: Evidence for a Predominant Ancestral Haplotype Exclusively Associated with Hemochromatosis," *Am. J. Hum. Genet.* 56:428–433 (1995).

Jack, L.J.W. et al., "Cloning and Analysis of cDNA Encoding Bovine Butyrophilin, an Apical Glycoprotein Expressed in Mammary Tissue and Secreted in Association with the Milk–fat Globule Membrane during Lactation," *J. Biol. Chem.* 265(24):14481–14486 (1990).

Kan, Y.W. et al., "Antenatal Diagnosis of Sickle–Cell Anaemia by D.N.A. Analysis of Amniotic–Fluid Cells," *Lancet* ii:910–912 (1978).

Landegren, U. et al., "A Ligase–Mediated Gene Detection Technique," *Science* 241:1077–1080 (1988).

Levy–Lahad, E. et al., "Candidate Gene for the Chromosome 1 Familian Alzheimer's Disease," *Science* 269:973–977 (1995).

Lovett, M. et al., "Direct selection: A method for the isolation of cDNAs encoded by large genomic regions," *Proc. Natl. Acad. Sci. U.S.A.* 88:9628–9632 (1991).

Maskos, U. et al., "A novel method for the parallel analysis of multiple mutations in multiple samples," *Nucl. Acids Res.* 21(9):2269–2270 (1993).

Matteucci, M.D. et al., "Synthesis of Deoxyoligonucleotides on a Polymer Support," *J. Am. Chem. Soc.* 103:1385–3191 (1981).

Maxam, A.M. et al., "Sequencing End–Labeled DNA with Base–Specific Chemical Cleavages," *Meth. Enzymol.* 65:499–560 (1980).

Miller, M.M. et al., "Immunoglobulin variable–region–like domains of diverse sequence within the major hitocompatibility complex of the chicken," *Proc. Natl. Acad. Sci. U.S.A.* 88:4377–4381 (1991).

Myers, R.M. et al., "Detection of Single Base–Substitutions by Ribonuclease Cleavage at Mismatches in RNA:DNA Duplexes," *Science* 230:1242–1246 (1985).

Needham–VanDevanter, D.R. et al., "Characterization of an adduct between CC–1065 and a defined oligondeoxynucleotide duplex," *Nucl. Acids. Res.* 12:6159–6168 (1984).

Needleman, S.B. et al., "A General Method Applicable to the Search for Similarities in the Amino Acid Sequence of Two Proteins," *J. Mol. Biol.* 48:443–453 (1970).

Nierman, W.C., et al., "*ATCC/NIH Repository Catalogue of Human and Mouse DNA Probes and Libraries,*" Amer. Type Culture Coll. (1994) pp. 1–70 (ISBN 0–930009–56–8).

de Sousa, M., et al., "*Iron Overload in $\beta_2$–Microglobulin–Deficient Mice,*" Immun. Lett. (1994) 39:105–111 (0165–2478/94).

Rothenberg, B.E., et al., "$\beta_2$ *Knockout Mice Develop Parenchymal Iron Overload: A Putative Role for Class I Genes of the Major Histomcompatibility Complex in Iron Metabolism,*" Proc. Natl. Acad. Sci. USA (1996) 93:1529–1534 (National Institutes of Health).

Stone, C. et al., "Isolation of CA dinucleotide repeats close to D6S105; linkage disequilibrium with haemochromatosis," *Hum. Mol. Genet.* 3(11):2043–2046 (1994).

Strathmann, M. et al., "Transposon–faciliated DNA sequencing," *Proc. Natl. Acad. Sci. U.S.A.* 88:1247–1250 (1991).

Summers, K.M. et al., "HLA Determinants in an Australian Population of Hemochromatosis Patients and Their Families," *Am. J. Hum. Genet.* 45:41–48 (1989).

Syvänen, A.C. et al., "A Primer–Guided Nucleotide Incorporation Assay in the Genotyping of Apolipoprotein E," *Genomics* 8:684–692 (1990).

Taylor, M.R. et al., "Cloning and sequence analysis of human butyrophilin reveals a potential receptor function," *Biochimica Biophysica Acta* 1306:1–4 (1996).

Thiede, C. et al., "Simple and sensitive detection of mutations in the ras proto–oncogenes using PNA–mediated PCR clamping," *Nucl. Acids Res.* 24(5):983–984 (1996).

Vernet, C. et al., "Evolutionary Study of Multigenic Families Mapping Close to the Human MHC Class I Region," *J. Mol. Evol.* 37:600–612 (1993).

Wagner, R. et al., "Mutation detection using immobilized mismatch binding protein (MutS)," *Nucl. Acids Res.* 23(19):3944–3948 (1995).

Walker, G.T. et al., "Isothermal in vitro amplification of DNA by a restriction enzyme/DNA polymerase system," *Proc. Natl. Acad. Sci. U.S.A.* 89:392–396 (1992).

Wallace, R.B. et al., "Hybridization of synthetic oligonucleotides to $\phi\chi 174$ DNA: the effect of single based–pair mismatch," *Nucl. Acids Res.* 6:3543–3557 (1978).

Worwood, M. et al., "Alleles at D6S265 and D6S105 define a haemochromatosis–specific genotype," *Brit. J. Haemot.* 86:863–866 (1994).

Wu, D.Y. et al., "The Ligation Amplification Reaction (LAR) –Amplification of Specific DNA Sequences Using Sequential Rounds of Template–Dependent Ligation," *Genomics* 4:560–569 (1989).

Yanofsky, C. et al., "Repression is Relieved Before Attnuation in the trp Operon of *Escherichia coli* as Tryptophan Starvation Becomes Increasingly Severe," *J. Bacteriol.* 158(3):1018–1024 (1984).

Youil, R. et al., "Screening for mutations by enzyme mismatch cleavage with T4 endonuclease VII," *Proc. Natl. Acad. Sci. U.S.A.* 92:87–91 (1995).

Yu, C–E. et al., "Positional Cloning of the Werner's Syndrome Gene," *Science* 272:258–262 (1996).

Newton, C.R. et al., "Analysis of any point mutation in DNA. The amplification refractory mutation system (ARMS)," *Nucl. Acids Res.* 17(7):2503–2516 (1989).

Nikiforov, T.T., et al., "Genetic Bit Analysis: a solid phase method for typing single nucleotide polymorphisms," *Nucl. Acids Res.* 22(20):4167–4175 (1994).

Orita, M. et al., "Rapid and Sensitive Detection of Point Mutations and DNA Polymorphisms Using the Polymerase Chain Reaction," *Genomics* 5:874–879 (1989).

Ørum, H. et al., "Single base pair mutation analysis by PNA directed PCR clamping," *Nucl. Acid Res.* 21(23):5332–5336 (1993).

Pearson, J.D. et al., "High–Performance Anion–Exchange Cromatography of Oligonucleotides," *J. Chromatography* 255:137–149 (1983).

Pearson, W.R. et al., "Improved tools for biological sequence comparison," *Proc. Natl. Acad. Sci. U.S.A.* 85:2444–2448 (1988).

Phatak, P.D. et al., "Cost–effectiveness of Screening for Hereditary Hemochromatosis," *Arch. Intern. Med.* 154:769–776 (1994).

Queen, C. et al., "Cell–Type Specific Regulation of a κ Immunoglobulin Gene by Promoter and Enhancer Elements," *Immunol. Res.* 89:49–68 (1986).

Raha–Chowdhury, R. et al., "New polymorphic microsatellite markers place the haemochromatosis gene telomeric to D6S105," *Hum. Mol. Genet.* 4(10):1869–1874 (1995).

Roberts, A.G. et al., "Increased frequency of the haemochromatosis Cys282Tyr mutation in sporadic porphyria cutanea tarda," *Lancet* 349:321–323 (1997).

Saiki, R.K. et al., "Primer–Directed Enzymatic Amplification of DNA with a Thermostable DNA Polymerase," *Science* 239:487–491 (1988).

Saiki, R.K. et al., "Genetic analysis of amplified DNA with immobilized sequence–specific oligonucleotide probes," *Proc. Natl. Acad. Sci. U.S.A.* 86:6230–6234 (1989).

Schneider, I., "Cell lines derived from late embryonic stages of *Drosophila melanogaster*, " *J. Embryol. Exp. Morph.* 27(2):353–365 (1972).

Simon, M. et al., "Association of HLA–A3 and HLA–B14 antigens with idiopathic haemochromatosis," *Gut* 17:3332–334 (1976).

Simon, M. et al., "A Study of 609 HLA Haplotypes Marking for the Hemochromatosis Gene: (1) Mapping of the Gene near the HLA–A Locus and Characters Required to Define a Heterozygous Population and (2) Hypothesis Concerning the Underlying Cause of Hemochromatosis–HLA Association," *Am. J. Hum. Genet.* 41:89–105 (1987).

Smith, T.F. et al., "Comparison of Biosequences," *Adv. Appl. Math.* 2:481–489 (1981).

Sprague, J. et al., "Expression of a Recombinant DNA Gene Coding for the Vesicular Stomatitis Virus Nucleocapsid Protein," *J. Virol.* 45(2):773–781 (1983).

Summers, K.M., et al., "*HLA Determinants in an Australian Population of Hemochromatosis Patients and Their Families*," Am. J. Hum. Genet. (1989) 45:41–48 (0002–9297/89).

Syvänen, A.C., et al., "*A Primer–Guided Nucleotide Incorporation Assay in the Genotyping of Apolipoprotein E*," Genomics (1990) 8:684–692 (0888–7543/90).

Taylor, M.R., et al., "*Cloning and Sequence Analysis of Human Butyrophilin Reveal a Potential Receptor Function*," Biochimica et Biophysica Acta (1996) 1306:1–4 (0167–4781/96).

Thiede, C., et al., "*Simple and Sensitive Detection of Mutations in the Ras Proto–Oncogenes Using PNA–Mediated PCR Clamping*," Nucl. Acids Res. (1996) 24(5):983–984 (Wilhelm–Sander Stiftung).

Vernet, C., et al., "*Evolutionary Study of Multigenic Families Mapping Close to the Human MHC Class I Region*," J. Mol. Evol. (1993) 37:600–612 (National Science Foundation).

Wagner, R., et al., "*Mutation Detection Using Immobilized Mismatch Binding Protein (MutS)*," Nucl. Acids Res. (1995) 23(19):3944–3948 (Genecheck Inc.).

Walker, G.T., et al., "*Isothermal in vitro Amplification of DNA by a Restriction Enzyme/DNA Polymerase System*," Proc. Natl. Acad. Sci. USA (1992) 89:392–396 (Becton Dickinson Research Center).

Wallace, R.B., et al., "Hybridization of Synthetic Oligodeoxyribonucleotides to φ χ 74 DNA: The Effect of Single Base Pair Mismatch," *Nucl. Acids Res.* (1979) 6(11):3543–3557 (City of Hope National Medical Center).

Worwood, M., et al., "Alleles at D6S265 and D6S105 Define a Haemochromatosis–Specific Genotype," Brit. J. Hematol. (1994) 86:863–866 (Univ. of Wales College of Medicine).

Wu, D.Y., et al., "*The Ligation Amplification Reaction (LAR)–Amplification of Specific DNA Sequences Using Sequential Rounds of Template–Dependent Ligation*," Genomics (1989) 4:560–569 (0888–7543/89).

Yanofsky, C., et al., "*Repression is Relieved Before Attenuation in the trp Operon of Escherichia coli as Tryptophan Starvation Becomes Increasingly Severe*," J. Bacter. (1994) 158(3):1018–1024 (0021–9193/84).

Youil, R., et al., "*Screening for Mutations by Enzyme Mismatch Cleavage With T4 Endonuclease VII*," Proc. Natl. Acad. Sci. USA (1995) 92:87–91 (National Health and Medical Research Council of Australia).

Yu, C–E., et al., "*Positional Cloning of the Werner's Syndrome Gene*," Science (1996) 272:258–262 (National Institute on Aging).

Nikiforov, T.T., et al., "*Genetic Bit Analysis: A Solid Phase Method for Typing Single Nucleotide Polymorphisms*," Nucl. Acids Res. (1994) 22(20):4167–4175 (Molecular Tool, Inc.).

Orita, M., et al., "*Rapid and Sensitive Detection of Point Mutations and DNA Polymorphisms Using the Polymerase Chain Reaction*," Genomics (1989) 5:874–879 (0888–7543/89).

Orum, H., et al., "*Single Base Pair Mutation Analysis by PNA Directed PCR Clamping*," Nucl. Acids Res. (1993) 21(23):5332–5336 (Research Center for Medical Biotechnology).

Pearson, J.D., et al., "*High–Performance Anion–Exchange Chromatography of Oligonucleotides*," J. Chromatog. (1983) 255:137–149 (0021–9673/83).

Pearson, W.R., et al., "*Improved Tools for Biological Sequence Comparison*," Proc. Natl. Acad. Sci. USA (1988) 85:2444–2448 (National Institutes of Health).

Phatak, P.D., et al., "*Cost–Effectiveness of Screening for Hereditary Hemochromatosis*," Arch. Intern. Med. (1994) 154:769–776 (Rochester General Hospital, NY).

Queen, C., et al., "*Cell–Type Specific Regulation of α κ Immunoglobulin Gene by Promoter and Enhancer Elements*," Immunol. Rev. (1986) 89:49–68 (National Institutes of Health).

Raha–Chowdhury, R., et al., "*New Polymorphic Microsatellite Markers Place the Haemochromatosis Gene Telomeric to D6S105*," Hum. Mol. Genet. (1995) 4(10):1869–1874 (Univ. of Wales College of Medicine).

Roberts, A.G., et al., "*Increased Frequency of the Haemochromatosis Cys282Tyr Mutation in Sporadic Porphyria Cutanea Tarda*," Lancet (1997) 349:321–323 (Univ. of Wales College of Medicine).

Saiki, R.K., et al., "*Primer–Directed Enzymatic Amplification of DNA with a Thermostable DNA Polymerase*," Science (1988) 239:487–491 (Cetus Corp.).

Saiki, R.K., et al., "*Genetic Analysis of Amplified DNA With Immobilized Sequence–Specific Oligonucleotide Probes*," Proc. Natl. Acad. Sci. USA (1989) 86:6230–6234 (Cetus Corp.).

Schneider, I., "*Cell Lines Derived From Late Embryonic Stages of Drosophila Melanogaster*," J. Embryol. Exp. Morph. (1972) 27(2):353–365 (Walter Reed Army Institute of Research).

Simon M., et al., "*Association of HLA–A3 and HLA–B14 Antigens With Idiopathic Haemochromatosis*," Gut (1976) 17:332–334 (Hopital Pontchaillou, France).

Simon, M., et al., "*A Study of 609 HLA Haplotypes Marking for the Hemochromatosis Gene: (1) Mapping of the Gene Near the IILA–A Locus and Characters Required to Define a Heterozygous Population and (2) Hypothesis Concerning the Underlying Cause of Hemochromatosis–HLA Association*," Am. J. Hum. Genet. (1987) 41:89–105 (0002–9297/87).

Smith, T.F., et al., "*Comparison of Biosequences*," Adv. Appl. Math (1981) 2:482–489 (0196–8858/81).

Sprague, J., et al., "*Expression of a Recombinant DNA Gene Coding for the Vesicular Stomatitis Virus Nucleocapsid Protein*," J. Virol. (1983) 45(2):773–781 (0022–538X/83).

Stone, C., et al., "*Isolation of CA Dinucleotide Repeats Close to D6S105; Linkage Disequilibrium With Haemochromatosis,*" Hum. Molec. Genet. (1994) 3(11):2043–2046 (Queensland Institute of Medical Research).

Strathmann, M., et al., "*Transposon–Facilitated DNA Sequencing,*" Proc. Natl. Acad. Sci. USA (1991) 88:1247–1250 (U.S. Public Health Service Program).

Darnell, J., "*Molecular Cell Biology,*" Scientific American Books (1986) pp. 227–229 (Rockefeller Univ.).

Boretto, J., et al., "*Anonymous Markers Located on Chromosome 6 in the HLA–A Class I Region: Allelic Distribution in Genetic Haemochromatosis,*" Hum. Genet. (1992) 89:33–36 (Institut National de la Sante et de la Recherche Medicale).

Campbell, A.M., "*Monoclonal Antibody Technology,*" Elsevier Science Publishers (1985) Chapter 1 pp. 1–32 (ISBN 0–444–80592–3).

Cornall, R.J., et al., "*The Generation of a Library of PCR–Analyzed Microsatellite Variants for Genetic Mapping of the Mouse Genome,*" Genomics (1991) 10:874–881 (0888–7543/91).

Vogel, F. et al., "*Human Chromosomes,*" Springer–Verlag (1992) pp. 18–81 (ISBN 3–540–09459–8).

\* cited by examiner

```
   1 CACACACACA CACACACACA CACACACACA CACACAAATG AGGTATATAA AGGGTCTCCT
  61 AAAATGTCAT CTGATATTTG TTATTTCATA TTCTCAGATT TTTAATCCAT TTAGGTAGGT
 121 CTATTTTAGA TAGCCTTGTC TGAAACAGAG CTGGGACCTG ATGAGTGAAA ATGAGCTCAC
 181 CAGAAGAAAA ATCAAACAGG CATTTCAGAG ATTGAGGCCA AGAAGTTAAA TGTCTTAAAT
 241 GGGCAGAGCT TAGCTGCTTG ATGTGAAAAG AGACCAGCGT GGCTGGAACA GCAAAGGAGA
 301 ACAGCAGAAG AGGTGAACAG AGGCCAGAGA TGGTCACTGA GTGGGCCCTT AAGTCATGGT
 361 AAGGAGTATG GAGAATGAAT TATTGCATGT ATTGAATATG TAGGTGACGT GACTCACAGA
 421 TACTTTGGAT TTGTAGAGAT GAAGGAAATG TAGCAAGTGA CACTCTTAGA ATGTTGATTT
 481 GAGTAAATGG TAGTGTCAGT TATTGAACTG GGGAGAACTG GAAGGGATAA CAGGCTTAAG
 541 GAGCACGTTT ATTCCTGTGT CTTGGAAGTG TTTAGGGTGA AAGACCTATT AGAGTTCTAA
 601 ATGGAGATGT CAAGTGAAAA TGTGGCTACA CACATTTGCA TTTCAGAAAA AAGGTCAGGC
 661 TGGAGATGTA AAATTGGAAG TTTACTGCAT ATAGATAGTC TTTGGAACCG TAGTATTGAT
 721 GAAGCCATTA ATGAGACAGA ACAAAGACTA GGGACCAGAG CCAAGCTCCA AGTTTCTAAA
 781 ATTTAGAGGA TAGTATAGTC TGGTCATTTT GAGGTGAATA CTTAATAACA GAACAATTTG
 841 TTGAAGTGTA AATTTAGAGC CCTACACTTT TAGCTCTGAC TATTAACGAA TACAGGAAAG
 901 AATGGATATG GTTATCTGCC TGGTGTCTGT GAAATAATTT AAGCCAGGAA GAGATCCTCA
 961 CCAGAAACTG ACTATGCTGG CAACTTGGAT CTTAGATTTC CAGCCTGCAG AATTGTTAGA
1021 AAATAAATGT CTATCGTTTA AGCCACCAGT CTGTAGTATT TTGTTATGGC AGTCCAAGCT
1081 GACTAAGTTT TGGTACCCAG GCGTGGGATG CTGCAACAAC AAATACCTAA ACATGGGAA
1141 GTGGCTTTGG AAATTGGTGA TGGGTAAAGG CTGGAAGAGT TTGAGGTTCA TACTAGAAAA
1201 AGCCAATTGT GAAGGGACTA TTGAAAGAAA TATGGACATT AAAGGCAATT CTGGCAAAGG
1261 CTCAGAAAGG AAGAGAGCTG GACAGAAAGC TTCCATTTTC ATAGAAACTT AGATTTATAA
1321 CGATCATGGA TAGAATATTA AATATGCTGG TTAAAATATG GACTTTAGGC CAGGCGTGGT
1381 GGCTCACGCC TGTAATCTCA GCACTTTGGG AGGCTGAGGG CACAGATCAC GAGGTCGGGA
1441 GTTTGAGACC AGCCTGGCCA ATATGGCGAA ACCCTGTCTC TACTAAAAAT ACAAAAATTA
1501 GCTGGGCATG GTGATGTGCT TCTGTGGTCC CAGCTACTCG GGAGGCTGAG GCTGAAGAAT
1561 CGCTTAAACC CGGGGGGTGG AGGTTGCAGT GACCCAAGAT CACACCACTG CACTCCAGCC
1621 TGGGATACAG AGCAGGACTC CACTCCCCCC GCCACACACA CACAAAAAAT ATATATATAT
1681 GGACATTAAA GTCAACTCTT GTGAGGTCTC AGATGAAAAT GAGGGACAGG TTATTGGAAA
1741 CTGTAGAAAT CACTGTTCTT GTTACAATGT GTCAAGAACT TGGCTGAATT ACGCTGTAGT
1801 GTTTACTGGA AAGAACTTAT AAGCAGTAAA ACTGGATATT TACCAGAAGA GATGTCTAAG
1861 CAAAGTATTG AAGGTGTGAT TTAGGTCCTC CTTACTGCTT AAAGTGAAAT GTGAGAGGAA
1921 AGAGCCGAAA TAAAGAAGGA ATTTTTAAGC AAAACACAAT CAGAACTTGG AGATTTGGGA
1981 TAGATTTCTC AATCTATATT GTAAAAATTG AGAAAGTTTT TCTTGAAGAG GTATGGTTGA
2041 ACAATGTTTT CTTTTTCTTT TTTTTCTTG GTTTTATTTT TATTTTTATG TTTTTTGAGA
2101 CAGGGTCTGG CTATGTCATC CAGGCTGGAG TGCAGTGGCA CAATCTCAGT TCAGTGCAAC
2161 CTTTGCCTTC AGGCTCAAGC AATCCTCCCA CCTCAGCCTC CTAAGTAGCT GGGACTACAT
2221 GTATGCACCA CCACACCCTG GCTAATTTTT TGTTGTTGTT TATAGAGATG GGGTTTTGAC
2281 ATGTTGCCTA GGCTGGTCTC TAACTCCTGA GCTCAAGTGA TCTGCCCTCC TCAGTCTCCC
2341 AAAGTGTTGG GATTACAGGC GTGAAACACT GAGCCTAGCC TGAACAACCA TTTGATAAAG
2401 AGATAATGGG TGTGACCCAA GGATTAATC AGCCATCTCA GCAGAAGCCA GGAAGAGAGA
2461 TGGGATTATT CCAGCAGAGA CACTGCCAAT TTAAACTAAC GTAGGCAGAG AAAACAGAAA
2521 GGAACAAAGG AAGGTTGTCG ACTTTTTGAA TTCTATAGAA CAGGATCATA GAGCTACCTG
2581 GCTGTCAATG TGTACTATTC TTTAAGAAAA GGAAAGACTG ACCCACCAAA GGCAACTTAC
2641 AAGATCACTA GGGCTGACTC TTTTGTTTTT TCTTGAGGCA GTCTCACTGT CACCCAGGCT
2701 GTAGGGCAAT GGTGTGATCT CAGCTCACTG CAATCTCCAC CTCCCAGGTT CAAGGGATTC
2761 TCTTGCCTTA GACTCCCAAG TAGCTGGGAT TACAGGCTCT AAATCTGTAC CCTCCCGAGT
2821 AGCGCTCCTG CCACCACTTG CCCAGCTAAT TTTTGTATTT TTAGTAGAGA TGGGGTTTCA
2881 CTATGTTGGC CAGGCTAGTT TGGAACTCCT GACCTCAGT GATCCATTCT CATTGGCCTC
2941 CCAAAGTGCT GGGATTACAG GCAGGAGCCG CCAGGGCTGC CACTTTGATG TCAGACTCAG
3001 AGAGTACAGA TGGGATAGGG TGGGGGTGGG AACATGTAGT CAAGGCTGAC TCTACCTGTT
3061 TCAAAGATGC CCTGCAGAAC TGTGTGGGAG TCTCTCACAG ATGGCTGCCT GGGTGGGACC
```

Figure 1 (Page 1 of 73)

```
3121 CCACCAAACT GAAAGACCGA GACTTCAGGC AGGGCAGATG GAGTAGGCCA ACTACAGAGC
3181 CAGAGGTGAC ACTGAGACAC CACTGGGCCT GGAAATCAGG GCATCAAGCC AAAGAGGGTT
3241 TTTCTTAAGA CCTAACAGAA TTTGCCTTGC CAGGTTTTGG ACTTGATTAG GACACATTAC
3301 ACCTTCCTTC TTTCCTATTT CTCCATTTTC TAATGGGAAT GTCTATTATG CCTGTTTCAC
3361 CATTGTACCT TAGAAGCATG TAACATTTCT GGTTTCACAC GTTCAAAGCT GGAAAGGAAT
3421 TTTGTCTCTG GATGAATCAC ACATTGAGCC TCACCCGTAA CCTGATTTAG ATGATTTTTT
3481 AGATGACACT TTGAACTTTA GAATTGATGC TAGAATGAGT TAAGACTTTC AGGGGGCTGT
3541 TGGGATGGAA TAATTTTTTT TTTTTTTTTG AGACGGAGTC TAGCTCTGTC GCCCAGGCTG
3601 GAGTGCAGTG GCACCATCTT GGCTCACTGC AAGCTCTGCC TCCCGGGTTT ATGCCATTCT
3661 CATGTCTCAG CCTCCAGAGT AGCTGGGACT ACAGGCGCCC GCCACCACGC CTGGCTAATT
3721 TTTTTTTTAT TTTAGTAGAG ATGGGGTTTC ACCGTGTTAG CCAGAATGGT CTCGATCTCT
3781 TGACCTTCTG ATCCGCCTGC CTTGGCTTCC CAAAGTGCTG GGATTACACG TGTGAGCCAC
3841 CATGCCCGGC TGGGATGGAA TAAATTTATC TTGTATGGGA GAAGGACATA CATTTTGGCA
3901 GGTCAAGGAC AGAATGTTAT GGACTAAACT GTGTCCCCCA AAATTCATTT ATTAAAACCC
3961 TAAACCCCAG TGTGACTGCA TTTGGACATA GAGCCTTTAG GGGGTACATA AAACTAAAGA
4021 TCACAGGATA GGGCCCTAAT CCCATTGGGG CTGGTGTCCT TACAGAAGAT GAGACACTTA
4081 GAGCTCTCTC TCCACGCAGG CACCAAGGAA ACACCATACA AACACACAGT GAGATGGCAG
4141 CCATCTGTTA GCCAGGAACA GATTCTCACC ATAAACTATG TTGGCACCTT GATCTTAAAC
4201 TTCCAGGCTC CAAAACTGTG AGAAAATGAA TTTCTGTTCC AAGCCTCTTA GATATGGAAA
4261 AAAAGATTCT GTTGTTTAAG CCATCCAGTC TCTGGTATTT TGTTATGGCA GCCTGAGTAG
4321 GCTAAGACAA TGAAGGATGT GGTAAAACTT TACGTCCCAA CCACATACCA AAGAGGCTGG
4381 AATTTAGCAT GCTTTCTTCT TTCAACTGTA GGCAATGTGC ACAAGTTCTA AATCCTAAGA
4441 CATGTTGGCT CCTTTACTCT GCCCAAACTA CAACTCAAAC AAACAACTGT AATATAATAA
4501 CATCCAATGA AGTTCTGACA TTTCTTCAAC ATGAGTACAG TAATTCAATG CCAGAGAATT
4561 CATTTTATTT TGAAATCTAC ATGCCATATT CCAATTTCTG TTGAAGATGC AATGGTTATA
4621 TTTATTCTTT TTAATATAGA TTTATCAGAC TGGGCGCGGT GGCTCATACC TGTAATCCTA
4681 GCATTTGAGA GGCTGAGGTG GGCATATCAC CTGAGGTCAG GAGTTTGAGA CCAGGCTGGC
4741 CAACATGGTG AAACCCTGTC TCTACTATAA ATATAAAAAT TAGCTGGGTG TGGTGGTGCA
4801 TGCCTGTAGT CCCAGTTACT AGGGAGGCTG AGGTAGAATT GCTTGAACCT GGGAGCAGGA
4861 GGTTGCAATG AGTGGAAATC GCACCAGTAC ACTCCAGCCT GGATGACAGA GCAAAATAAT
4921 AAATAAATAC ATAAAATAGA TTTATCAGTT TATCAATAAT ATAGTTTTCT TTTCTAGGTG
4981 TAAATATAGG TAATGACTGT CCTTTAGTAC ATTTTCTCAT GATGCTCCTC TTACTTGGTT
5041 TGGTACAATA TTAAGTATTG AAATAAAATA GAGAATCCTG TCGCTACACA TGAGCACTTA
5101 TTCCATTTGC TCATCTCCAA TATGCACGGG AAATTCTCAA ATTGCTAATA ATCTTGTAAC
5161 ACACATGCAT TATATTCAAC AGGAATATAT AAATTTATAA TTATAATTTA GGATCAACAG
5221 ATGACAAACC TTTAGAAGGT TTGTATTTAA CCTTAAAATA TAATTTTTTA AAAATTGGTT
5281 ATAAAATTTC TAATACTTTC TTTTTTGTGA CCTCAAGGGG AAAATATAAT TCTTATAAAA
5341 GTTCAAATGA TTTACAGAAT ACAAAAGTG AATAGAGATG ATGAATGAAT TAAAGGAAAG
5401 GATATTGCTA CATAGATTTG GAAATTTAAA AAGGGAAATT ACGATTGTTG ATTTTGTGTT
5461 AAACTGATCT GCTTTGTTCA AGATACCTTA TGTACCAAAA AATGATTTTA TCTCAGCCTC
5521 ATATCTCAGT AAATTCCTGA GACAAACTTT AGTCCCTGGT GCCCAGGTGC CTTTGGTAAT
5581 TGGGAGACCT CTAGGTTTAG CATCCTCATC CACTCGCCCC AATTTAAATA GTCCTCCCCA
5641 GGGCCATTCA GGCAAGGGAG ATGAAAACTT GCTCAAGAGT TGGAATCCAA CTGAAGCTAC
5701 CGAAATTCAT TGCTCAATAG ATAATTTTCC CTGGAAGTAA CTAGGGCTTT TGAATATAAT
5761 AGTGGGCATT TCAAAGTAGA AGGTAAAGTA TTTTGGAGAT GAGGAGACAG GACAGAGCTA
5821 CGAGGAATGT CCTTTGCTTA GGGACTAGGC TCTTAGCAGT ACCTCTTAGG TAAGAACTGG
5881 TTAACTGGCA CCTTCTGTGT TTCTCTGAAG CTCCCTTTGC TTAGGGACTA GGCTCTTAGC
5941 AGTACCTCTT AGGTAAGAAC TGGTTAACTG ACACCTTCTA TGTGTCTGAA GCTCCCAGAA
6001 CAAACTGCCA GTGAAATTTG GATTTTGGA ATATAGTTTC TTTTTTCTTG TTACTTTTTG
6061 TTTTGTTGTT TTTTTTGAG AGTCTCACTC TCACTGCAAC CTCCCCCTCC TATATTCAAG
6121 TGATTCTCTT GCCTCAGCCT CCCGAGTAGC TGGGACTACA GGCGTGCACT AGCATGCCCA
6181 GCTAATTTTT GTATTTTTA GTAGAGATGG GGTTGGTTTT TTTTGAGAC GGAGTTTCAC
6241 TTTGTCGCCC AGGCTGGAGT GCAGTGGCAC GATCTTGGCT CACTACAACC TCCACCTCCC
6301 GGGGTTCAAG TGATTCTTCT GCCTCAGTCT CCTGAGTAGC TGGGACTACA GGCGCCTACA
```

Figure 1 (Page 2 of 73)

```
6361 GGTGAACACC GCCACACCTG ACTAATTTGT GTAGTTTTAT TAGAGATGGG GTTTCGCCAT
6421 GTTGGCCAGG CTGGTCTCAA ACTCCTGACC TCAGGTGATC TACCCACCTC AGCCTCCCCA
6481 AGTGCTGGGA TTACAGATGT GAGACACCAG ATCAGCCTCA GAAGACATTT TCTATTGGAA
6541 AGAGAAAACA CTATTAGCAA CCTATTAGTC TAATATTTAA TACTTAATGT CTTCCTTAGT
6601 AATAAACCAA CTCTCTACAA CAAAGTGCTT CCTGGCTGCC TAAGTCATTG ATTCATTCAG
6661 TTCAACATTT TCTCAATGCC CAACAGCCAA GTGTCTCTTG TATGCCAAGT TCTATGCTGA
6721 TTATCAGTAT TTGAATAAGA GGGGGTCTAC ATCTTAAGTA CTGCTTAAGA TGAAAGCCTC
6781 TAGGTTAACA AACTTAACAC AATGTATCAT TCACTACTAA ATAGACCGAA TACAAAATCT
6841 TGTTATTGGA GCCCAGAGAG AAGAATTGAA ATTCAAGTTT TCTCTCTCTC CTTTTCTCAC
6901 TCACCACAAT AAGTCAGTTG CACCAAGTCT TGTAGCTCTT TACTGAGCCA TGTTTTCACG
6961 TGTCCCTTTG TTTTATTTGC CACACCCTAA ATAAAAATTG TACTGGCTTT TTTTCCCTGG
7021 GTTTACAGTA TTAATACATT GTCAAGATTT ACCTCTTCGT GTAGATTCCC TGGGGAAAAT
7081 TACCTTTCCT CCTTCCCTTA AATTCTTCAG AGGTTAGAAA GCCATTAGTA ACATTCTGGT
7141 ATGTGGACAA AGTTTACCCA TTATGTATGG ATGTTTTACT CTTTCTATTT TTCTGACAAT
7201 AATCTCTTAA GGAGGTGTGG TTATAGAATA GTCAGCTGTT ATAAGTACTG TTTTCCTGGC
7261 CTTACAACTT AAGTTCTTTA AGCTGTTTCT TAGTTTGCTC ATCTCAAAAT TCGGAATAAG
7321 GATAAAACCT ATCTCTTAGA TTGTTGGATT AAATGAATTA ACATACTGGA AGCTCATGAA
7381 ATGTGCCTGG CACACAGTAG TGCCTAATAA ACCATCTCTC TTATTCAGCC TGTTTTCTGA
7441 TTTCAGAATC TACACTTGCT GAGCCAGGTT CTTTTCATTT CAAGGTGAGC AAAAGCATAC
7501 AAGGAAGAGA TGGAGGTAGG AAGAGATTAA GCCCTAGGCC AAGGTCACAC ACCGATTGGG
7561 AGCTGGAATC AAAGGCAATT TGGTCAGTGA ATAAAAAGGA TTCCAAGGCC CATAAGGCAA
7621 TTCTAACCTT AGGATCGAAA TTCTCGGACA TACAGGAAAT GCTGGGGGGG GAAAATCCGG
7681 TCTTCTCAGC CCAAGAGCCA TGTGAAACCA GACCTTCAAA TCTGATGATT CTCAGCCCAG
7741 CTGCCCATTA GAATCGTTGT AATTTAAAAA TACCCTCGGA AAATTCTAAT ATGTGGCTAT
7801 CAAAGGTGAT CATTTGCTTT TATGCCACTT TGTTTTCACC CAAATGGGAC ATCCAACCCT
7861 TTTCCTTTGA GAGTAGTTGT AGGGAAAGGA GGGGGTGGAG GGAGGGAAGA GCGGAAAAGG
7921 CTGGATCCGC CCTGAGCCGG TGTCAGTATC TGGGAAGTGG GAGGCGCGTC AGCAGTAAAC
7981 AGCTTCTGCT AGGATTATTA TCTCCTGCCA CACACTCGGA TTTGAAGGCT CCAAACGAAA
8041 CAATGCAAAA CGCTTCAGTG GAGTTCCAGA AGCGTTAGAC TAAACGACTG GGTCTGTTTG
8101 GCCAGTCTGA GCAGCTGGGC GCAGATGCAT AGGCAAGACT TAGCCCGCCT AGACTTTTCT
8161 GCCCACTTAA TTCCGATCAA AGCAGAAACC GGCCGGGCGC GGTGGCTCAC GCCTGTAATC
8221 CCAGCACTTT GGTAGGCAGA GGCTGGCGGA TCACCTGAGG TCAGGAGTTC GAGACCAGCC
8281 CGGCTAACCT GGTGAAACTC CGTTTCTACT GGTGGCGGGC GCTTGTAATC CCATCTACTA
8341 GGGAGGCTGA GGCCGGAGAG TCGTCTGAAC CCGGGAGGCG GAGTTTGTAT GCAGTGAGCC
8401 GAGATCGCGC CACTGCATTC CAGCTTGGGC AACAGGAGCA AAACTCCGTT TCAAAAAAGC
8461 AAGCAAACAA ACAAAAAAAT GCAGAAACCG AGATCCGGAA GAAAACCTCG GCGAGATTCA
8521 CAGAATCCAG GAAAATAGGT CTCTAGAAAT TTGTCCATGG TCCCAGATCT CCATTTCTTG
8581 TGGGTGGGGC AGCTGTTACC AGATCCCTAG AAGCAAAGGT TTTTTTGGGG GACCGTGTCT
8641 CACTGTTGCC CAGGCTGGAG GGCAGTGGCA CGATCTCGGC TTACTACAAC CTCCGCCTCC
8701 CAGGCTCAAG CGACTCTCCT GCGTCAGCTT CAAGAGTAGC TGGGATTACA AGGTATGTGC
8761 CACCACGCCC AACTTATTTT TTTATTTATT ATTTTTATTT AGTAGAGAGG TGTTTCACCA
8821 TGTTGGCCAG GTTAGTGTCG AAGTCGTGAC CTCAGGTGAT CAGCCCCCTC GGCCTCCCAA
8881 AGTGGTAGGA TTAGAGGGGT GAGCAGAAAG CAAAGGTTTT TGAGTGGCCA CAGGCCCCAC
8941 TCTATTTCCT TTTCTGCCTG TAATGGCAAC CTAGACGCTT GAGCTTCTTA AAATACAAGA
9001 GTAAGTTGCA TGTCAGGCAC CGTTCTACAT TAGGGACATT AGTCTGTTTT ACAGACACCT
9061 TTCAACTCCC TGGTTAACTT TTAGGTAATA TACTCTGCAC TTTAGCAGGA ATGGGACCTA
9121 TAACTCTCAC AGAATTAGGA AAGTGAGGCT GCCTACAGCC TAAATTGAGA AAAAAATAGA
9181 CGGGGGACTA GTCGGAGGAC CAAACAAGGT TACCAACACG TTAGAGTTTT GCCTTCAATT
9241 TACATTTTTA AAGTAATCAC AACGAAGTGT TTAGATCACG AGGCATCCCT GCATGTAAAC
9301 TGTTAGGCAC TAACTATGGT CGATCTTACA AAGCATTAAC TAGAATATTT CTTTAGAGTA
9361 TGATAGTACG TAACTGACCT ACTATTACAT ACAAACAGAC CAACCTTTAG TAACAGCGCT
9421 CCCCAAAAAC CGAAAAGCAG TAATACGCTT TGCTCAAGGT TGGCATAAAA TTAACTTACC
9481 TTAGTGCCTT TTTTCCTTCT ACCTACAAGC AGTGAGGTTA GCTCTTCCTT TGAAACGGTA
9541 GGGGGGCTCT GAAAAGAGCC TTTGGGTTTG ATAGCGTTTC CGGGAGCTCA GATACCTGTC
```

Figure 1 (Page 3 of 73)

```
 9601 AAATCACTTG CCCTTGGCCT TGTGGTGACT CTCGGTCTTC TTAGGCAGAA GCACGGCCTG
 9661 GATGTTAGGA AGGACGCCGC CCTGAGCAAT GGTCACCCGG CCTAGCAGTT TGTTGAGCTC
 9721 CTCGTCGTTG CGGATGGCCA GCTGCAAGTG GCGCGGGATG ATGCGAGTCT TCTTGTTGTC
 9781 GCGAGCCGCG TTGCCGGCCA GCTCCAGGAT CTCGGCGGTC AGGTACTCTA ACACCGCCGC
 9841 CAGGTACACC GGCGCGCCTG CCCCAACCCG CTCTGCGTAG TTGCCTTTAC GGAGCAGGCG
 9901 GTGCACTCGG CCCACCGGGA ACTGGAGACC AGCGCGAGAA GAGCGGGATT TCGCTTTGGC
 9961 GCGAGCTTTG CCTCCTTGCT TACCACGTCC AGACATTGCA ATCAGACAAA AATCACCAAA
10021 ACCAGCGGCC TAAGCTCACG AGAAAACAAA CAAAATCAAG AAATATGTAA AACATGGCCG
10081 CTTTTATAGG TAGTTCCTGG GGAGTAAATC CGACTTTTTG ATTGGTCGGT AGCAAATGCT
10141 AGTCAGATAG CCAATAGAAA AGCTGTACTT TCATACCTCA TTTGCATAGC TCTGCCCACG
10201 GATGACAACT GTGCAGTTTG TCTTCCAATT AACTAAGAGG TACTCTCCAT CCCTCATTAG
10261 CATAAAAGCC CTATAAGTAG CAGAAATCCG CTCTTTACTT TCGACACATT TCTGGTGTTT
10321 TAAGATGCCT GAGCCAGCCA AGTCTGCTCC CGCCCCGAAG AAGGGCTCCA AGAAGGCAGT
10381 GACCAAAGCG CAGAAGAAAG ATGGCAAGAA GCGCAAGCGC AGCCGCAAGG AGAGTTACTC
10441 TGTGTACGTG TACAAGGTGC TGAAACAGGT CCATCCCGAC ACTGGCATCT CTTCCAAGGC
10501 CATGGGCATC ATGAATTCTT TCGTTAACGA CATATTTGAG CGCATCGCGG GCGAGGCTTC
10561 CCGCCTGGCG CATTACAACA AGCGCTCGAC CATCACCTCC AGGGAGATCC AGACGGCCGT
10621 GCGCCTGCTG CTTCCCGGAG AGCTGGCCAA GCACGCCGTG TCGGAGGGCA CCAAGGCCGT
10681 CACCAAGTAC ACCAGCTCCA AGTAAACATT CCAAGTAAGC GTCTTAACAC CTAACCCCAA
10741 AGGCTCTTTT AAGAGCCACC CAGATACCCA CTAAAAGAGC TGTGGCCAGA CGCCAAATTT
10801 TATTTGGCGG CGGAGGGGTA TTAGAATATA GGAACTGGAG AGGGGTGGGG ACAAGTGTTG
10861 CAGCTTAGAG AGGGACAAAG GGTCCTGAAC CCGAAGAAG CCAGCCATTA AAAATGGCTT
10921 TGGGGTCAAT TCGTTGTGCT TAAATTTAAA ATGGAGACAA GCGGCCATTT TGCTAACTCG
10981 GCGTTCCCGG AAGAAACCGC AGGCTCGCTT AGGTTTCAGA CCCAGCTGTC TGTCCCTGTC
11041 TACGTCGCCA GGATCAACGG TTGCCGTAAT GTCATAATTT CGCCACCAGC TTCTAGCCAA
11101 TAGGCTGTCC TGTCATTTTA AATATTAACC AATCGAGGGA AAGCTGTTTT GAGACTCTGA
11161 TTTACATAGC GGACCGGAGT GGGAACCTGG GCAGTAACTG CCTAAGGAAG GACTCCCCCT
11221 CTGTTTTCGT GGCGCACACC TTCGTAGTAT ACTGAAGGGT GTGTCTCCTG GGTTTCCAAC
11281 TGCCCCGGTA ATAGTCTTTT AACCTAATAT GCGTCAGTTT TGATAACAAC ACTAAGGCAG
11341 TACAGAACTA AAGATGTAAG CACTGCGCCA GATGTTGCTT CATACATCTT ATTCTATTCA
11401 ACTGGTTTAT TCAAGATTCA AATCAAATCA AATTTTGCTT GAATCCCAGT GCTCAGTCAG
11461 CCATAAATGG TGTGTTGCCT GATTGAAACT TAAAATCTCC GTAGGGGCT TGTAACATGC
11521 AGACAAGTTT GAAAGTTGCT TTAGGAGAAG CCAACTCTTA ACTGCTGGGT AAATTGACAA
11581 GCCTTCGAAC ACTGAACTGA AGGCCAGTAA GGACTAGGCG CTGGGTGGGG GAGAATGAAG
11641 AGGAGACGTC ATTAAACTTA GCACATACAC TGTATCTCCT AGAGGACTCT CCCTTCCTAG
11701 ACAACTGCAG GCCGCTTTGT GGCCTGGGAA ATTCCACATT CCCTTAAGTA TTTTACTCAT
11761 GGTCTTTTCC AGGTAAAGAT TTAAGATGA AGGGTTAGAC GTAGTCTACC TATCTTTTTA
11821 TTCAAGTCTA GAACACGTTT TTAGCACCTA GAAGTTTGCT TTCTCCATTA AAAACCGGGA
11881 ATATACAATA AATAAAATTA GTGTTAAAGC AGATTTTTAC AAACTTAAAT ACCATGTAAT
11941 TTAGGTTACA GTTATTTAAC ATAAGGACTG TGTGATCTTA AATCTGCAAT TTCTTTCACA
12001 CCTGGGAAAT AAACTAAGGC CTGTCTTTGG TGCCAGACAA GGCCTTATAC TTGAACACTG
12061 CTGTGCAATC ACAGGCTGCC TTGCCTAGAT AACTTATCTG AGAAATTCTG ATGAGAAATG
12121 AAATTTCCAG AGTCCCTCAC AAGTAAATTT TTTTTTCTTT TTTTTTTTT TTTTTGAGAC
12181 GAAGTTTCTC TCTTGTTTCC CAGGCTGGAG TGCAATGGCG CGATCTTGGC TCACAGCAAC
12241 CTCCGCCTCC CGGGTTCAAG CCATTCTCCT GCCTCAGCCT CCGGAGTAGC TGGGATTACA
12301 GGCATGCGCC ACGACACCCT GGCTAATTTT GTATTTTTAG TAGAGACGAG GTTTCTCCAT
12361 GTCGGTCAGG CTGGTCTCGA ACTCCGGACA TCAGGTGATC TGCCCGCCTT GGCCTCCCAA
12421 AGTCCTGGAT TACAGGCTTG AGCCACCGCG CCGGGCCTAA ATGGTTTTTT TTTTTTCTAT
12481 GCCTCTAATG GACCTGGTCA CTTATTCCCA TTCAGACTGA CCGCTCTCCT ACCTGCCAAC
12541 TAACTAATCA GTGTAACCAA AATCTGCAAA CAAAATTCAG TATTCTTTCC CCGCCTTTTC
12601 CCCTTTCTCT TACATAGATT ATGTTTTTGC CTGTGTTAGA TGAAATAATT CTATTGCTTG
12661 TTCTCTCTTC TGTACAAGTA CCCAGTAAGC AAATTATTAA CTTCTTGGTC ATTTATTTCT
12721 GAATTTTCCA CCAAGACAGT GTTTATGTGA GTCATACAAT AAGAACCAAC AGAAATGTGT
12781 GTCTTGGAAA CAGGTTGTCT ATCCCTGGAC CCTTTGAGTT TTCTGTTCAC TTTCCTTTGG
```

```
12841 CTTTTGCATG CTAAAAGTTT ATCGTCCGCG TTTGTTTGTT TTGGTTATTC TAATTGGACT
12901 TGGCTGATTG GTTGCATATT GGTGGCAGTA GTAGAATTTG AATTCTGGTT TTCTGGTCAC
12961 ATCATTAAGT GATTAGTCAG TGGAGAGGAC AGGAAATCTG GTTTATTTAT TAACCTTTTT
13021 TTGGGGTGTT TTTGTTTGAA GATGTTGATA TTCTCTGTGA GGACACAGGG TTAGAGTTGG
13081 TGTTTTTCTT TCTGACTTTA CATGGGATTT GATGTTTTGT GCTTGTATGC CTCTTTCCAC
13141 CTTCCAAAAC TTGTCTTTTT TGAGTCCAAA TAGTTGTCGA TATCTGCAAA ACCAGTATTC
13201 CTGTGTTAAG ATGATATGAA TATAAAATGG CTGCCCTGTT ATAACTTTTG ACTTTAAGAA
13261 AGTGTTAGGA CTAACAGGAG ACAAAAAGGA AATCAAGGAA ACCGAATGTC TGGTCTCAAT
13321 AACTGCTATG GCAGAGGCTC TACAGCTTAT TATTAATTTT AGTAATTTCA CATTATTGCC
13381 CCTTCACGTT CTTTAAGTAA GGTTAGAGGA CAGAAGAAAC ATAATGTTGT TACAAATTGG
13441 ACTATTGAGT CAGGGAAAAA AAAGAGTGCT TTCAATATCT GAATAAAACA AAGATTTAAT
13501 ATTTTCTAAA CCTTAACGAG TTTATTGTAA GGGATGTGAT GCTGGAAACT AGGAAACTAG
13561 AATTTTCTTC TAAACTGAGA ATCAGAATTA TTCATATTCT CAGCAGTGGT GCCACCTGAG
13621 GGACTTCTGA TCTTAATTAC ATACTTTTAT TTCTTTAACT GATCAACATG CTAAATAGAT
13681 AACCTATGGC TCTGTTTTTA CCCACTTTAA ATTCTGTTCT ATTAGCACGG TTAGCTTTCC
13741 TAATTGGCAA TAAGATTGAG ACTATCTTTT TTTTTTTTTT GAGACAGAAT TTTGCTCTGT
13801 GGCCCAGGCT GGGGTGCAGT GGCACAATCT CGGCTCACTG CAACCTCTGC CTCCAGGGTT
13861 CTAGCAATTT TCCTGCCTCA GCCTCCCAG TAGCTGGGAT TACAGGTGCA CCACCACGCC
13921 TGGCTAATTT GTGCATTTTT AGTAGAGATG GGGTTTCGCC ATGTTGGCCA AACTGGTCTC
13981 GAACTCAGGT GATCCACCTC GGCCTCCCAA AGTGATGAGA TTACAGGCGT GAGCCACCGT
14041 GCCCAGAAAA GACTATCTTA TTTTATGAAT TTAAATAATT GTGAAATTAT CCACTTAAGG
14101 GAATTAATAA ATTATAATGT AATCTTAAAT TTTAGTTGGC TTACATAAAG ACTTAAAATA
14161 CATCAATTTA AATAAAAACT CATTTGTCTA AAAAAAAATC AAAATTTTC CTTGTGCTTT
14221 AAATGTGCTA CCTCTTTAAG TTCTAATTAA GAGAAAAAAA GTTAACTGT GAGTTTCATT
14281 AGTGGTCTTA GTTAACAGCT TAAAGTATTT TGTAAAAAAA ATACTTCACA ATTTTTAAAT
14341 AACTTAAAAA TATTAATACC TCTTTTATTA GGTTTTTTA ATAAGGAAAA TATATAATAC
14401 ATCTAATCAA GATTTTTTT GGACAAATTG GCTTAATAAT TTCATTTTAA AAATGGCTTC
14461 TTTATTCTTA TACTGTAAAA ATAATATTAG CAGAATATTA TAGTATACAC AAGTTTAGGG
14521 TTCATATTCT AAAAAACAAA AACAAAAGCT AATTTAACTT GCATTTACTA AATTTCTTCC
14581 ACTAGTTGTA CTGGTTACAT GAGTTAACAT CACTTTATTT ATTATTCTAA AATTGTAAAT
14641 TATTCATTGA ACCAAATTAA ATGATAATAG ATAATGTCAT TTTAAAAAT GGAATTAAAT
14701 TTTATGTTAC TAATTATAAG GATTCAATGT GTGAGCTTAA GTACTGAGTT CACAGTGTAT
14761 GATAACTTTA AGAATTTAGG TGAATATTAT TAAATTGAGT AAATTAATTC TCAATCTTTG
14821 GATACCTGGA CAATTTCTAA ATTGGAGGGT ACAAAATACA AATCACAAGA AACAGTGTAG
14881 TTTTATGCAA ATAACATTTT TACACAGTTT AGAATAACCA TTGATAAACA GATAAGAGAA
14941 CATATGATTG CCTTAGAATA GATACTGTTG CTTTCGCCAC TTTAGATTTG TAAATCACGT
15001 ACTGTATACG TGTGGGCGTA GAGGACCATG CAGGTTTTGG ATGACTGCCT CTGTTTTCGT
15061 CATGCCTATG CGGGAACACA ATTGCCTGCT TTGTTTAAGG CTATGGTTA ATCCAAACAG
15121 CTCTGACTCT ATCAAGTACT ATAGCTACAG AGAAACACAA GTAAGCATTC GAGATAATGA
15181 CTACCTTGAG CCTTTACTTA TTTAAAAGT TGTTACTGTT TGTTAATGTG GTACATTCAA
15241 TTTACTATGG ATTGTCACTC TAAAATAAGA CTTCAATCTT TTTCTTATTT TTATATAGCC
15301 ATGATTTATA TTCATATCTT AATGTAATAA CCAATCTTCT CTGACAACAT TATAACAATG
15361 CTGGAACCTC CATTTTCAGT ACTTCAAACA ACAAATACTG CTTTTATACT TCAGAGCAGA
15421 TGGATATGTG CTTCCCAGTG TAAACACATT TGGAATCTCA CTGAGAAATA CACTATCACT
15481 AAAAATACAG TTCTGAGATT CATTAAAAGA CCTCCAGAAT TCTGGAAGTA GGAAGTTTCC
15541 TCTTCAAAGT CTACAGAGGA AGATGAGGTC TGAAATAGAC AGCTTCTTCC TTCTTTTACC
15601 TGTGGTATTA TTCTGTTTTG TCCTTTTCTC CATTATCTGT CTTTCCAGTG ATGAAATTTT
15661 GATCTGGCCC TCCCAAGTAT TAAAAAACAA GCAAATAAAC AAATCTCAGT TATATTTTAC
15721 TAAGATATTG GCATGCTAAC TTTTTGCAGG TTTGTAACAA GGACCTTTAT AACTTGACTA
15781 AAAGTTCCTA AATAAGAATA TTTACTAGAA AATTTATTTC TGCCTGTGGC CCACATTTGA
15841 GTCAAAATAA TCAATTAGGA AAAATGAACT TGTTTAACTA AAGTTGACCA AACTGATCTT
15901 TGACCAAACT GATCTTTGAG ACCTATTCAT CTAAGACAAG CCAATTAAAT TCTTGGAGAC
15961 AATTTGTACT TTAAGGAATT CTTATAATAT TTGTAATTAC CCTCATAACT TTTTTTTTG
16021 CCCTACTTCT GTGCTTCTCT AATATGCAGA TTATTAAATG TTGTTACAAA GCCATTGTCA
```

Figure 1 (Page 5 of 73)

```
16081 AAAAAACAAA AAACAAAAAA CTAAACAAAC TCACATGGTT AGACTTGCTC CTTTATGAGA
16141 TATTTTTACC AAAAATGGAG GAGTTGAAAA ACTCTGGTGC CAGAAATCGT GAAGACATGG
16201 CCTACCTAAC ATGGAAATGT TGGTTGTCAG TGGAAAATAC TACACAGAGA TAGCCATAGT
16261 GCTGCACAGC CAATCTTAAG TGTTTCTAGA GAATCACTAA TTGTTTCTAG AGAATCACTA
16321 ATTGTTTTCT TTTAACATTC TTGGTTTATA CAAGAAGAGA GTATCCATAC TAAACTCTTT
16381 TCTACTGAAA ATAATGTGCA AACATAACAT CCTATTCCTA GACAGTTTGT AGTTTTTTTC
16441 TCCCATTTCT ATTTTATAAA TCATCTTTTT AAAATACTTT GTTGAGTGAA ATCAGTCCAT
16501 TGCTTGATAT ACCTTGAGCA CAAGTAAATA GTATGCCAAA AATTAAATGT CTTTCAGTCA
16561 CAGTTTGACA AACTCAACTA CCCTGAGCCT ATAGAGTGGT AATAATTGCC CTACTCATAA
16621 AGATGGGGTG AAGATTAAAT GAAATAGCAC CTATAGAACA CTAGTTCCAG ACGTGGTATC
16681 ATGCTAGTAA AATGGCTGCA CAGCACTGCT CAATGATGAC AAAAAGTGAA GCTTCTGGAG
16741 ACAGACTCCA AGTTTGACTC CCAGATCACC ACATATAAGA TGTGGGACTC TGAGGCAGGT
16801 CATTTAATCT CTCTGTGCAT TAGTATCCTT CTCTATACCT TTACAGTGAT GGTAATAGCA
16861 CCTACCTTCT AGAAGTATGT GAAGATTAAA GATCCTTAAT GCATATAAAC CACTGTGTTT
16921 ACTGCTGTTT GACAAATTTT ATTTATAACC ATCTTTACGC TCCTAAAAGG ACTTGAAGCA
16981 GCTTATGACT GAAGACTTTG GTAGGAGTTG GCCTTCTATA AATTATAAGA ATTTCATAAA
17041 TTATTTGATA TGAAAATGCC AGTTGATCAT AGTATGTTTA CCGGGGTCCA ACAGGTTGAG
17101 AAAAAATACA CTTTTTTTCC CTGAACATAT GAAATTAGCT CTCTAGGCAT ATTCCTAAGG
17161 ACTTAAAGAA TGATAACTAT CATTTCTCTT AAATCTTCCA GATTGGAAG GATATATATA
17221 TTCAGCACAT TGACAGACAA TCCCAGTAGT CCTAAATTAA AAGACATTAA AAATTAGTGA
17281 AACTTTTCCT ACCTTTAGCC TGTGTAATCC TGGATGACCA AGCATAAAAT TAAATTGAGT
17341 AGAGTATACC ACTGTAACAT TTCCTGAAAG GTATTCTAGG CTCTGAGTAA TTTCTTTGGG
17401 GTCTGAAGAT CAGTTTGACA TATCCTCAAG TATCATGAGT TCATTATAAT TAAGAAAAAG
17461 AGAGTAAATC TGGAGAATGA GCCACTTTCT TACTACTCCT TGACCTCAGT TCTTTTTTTC
17521 AGAGACAGGG TCTCACTTTG TTGCCCAGGC TGCCAGGCTG GAGTGTAGTG GCGCAATCGC
17581 ATCTCATTGT AACCTCCACC TTCTGGGCTG AAGCCATCCT CCTGCCTCAG CATCCTGAGT
17641 ATCTGGAACC ACAGCAGGTG CACACCACCA TGCCAAGCTA ATTTTTTAAA AAGTTTTTTG
17701 TAGAGATGGG GTCTTACTAT GTTGCCCAGG CTGGTCTCAA ACTCCTGGGC TTAAGTGATC
17761 CTCCTGCCTC AGCCTCCCAA ATTGTTGGGA TTACTAGTGT GAGTCACTGT ACCCCGCCCC
17821 ACTTCAGTTC TGAGGAGGAA AAAATATGTA ATAATAATGG GACTTTGGTT TGCTGATTTA
17881 AAGATTCATG TAACCTTATC ATCCAATGCG CAATTTGTAG AATAATTAAT AGAGACATCT
17941 GGTCTCATGT TTCTACAGTT GCTCATGCCT TGATAGTAGA TCTCCTTGCT GCTGGCTCAG
18001 AAGGGTAAAA GAGCAGAAAT GATGGGGCTT CTCTCATTCT ATGAGGAAAT AGACCTATGT
18061 AGAGGAGGCT ACCTGTGGTA AAACCTTATC CTCATCACTT AAAATTCTAG GCTTATTCTC
18121 TGACCATATC AAGTTTTCAA ATGGTAAAAG AATTGGATTC AAGAGAAATA TGAATAAACT
18181 TTTGTTTTCA CTTTTCTCCC TCCTCTCCCC CCATTCTCCC TTCCTTTATT TTCTTGTCCT
18241 TAGTTTTCTT TTCACTTTTT TGTCTACTAT TATTTGCCCA AACTCAACTG TAGGCTAGAA
18301 CAAAAAAAAA TTGAAAATTA AAATGTGCCC CTTTTGTTGT TAGACTTGCT TAAACAATTG
18361 GGGTAATGAA CCTTGGACAC TAGATTTTAA AACACACACA TTTGAGCTTC AGTGCACTGA
18421 AATAAATATA TTTTTAACAA TTAAAAATA AAATTGCATG TTTAAAAAAT CTGCAGAGAA
18481 CAATACACGT TGTGAGATCT TGAATGGAAG GAAAACTGCT AGCCTCAAGA GTGGATCAAA
18541 GATGCTCAGC AGGCAACAGA GTAAGAGCAT GTTGGAGGGT TTAGAGAGTG TGCTCAGGGT
18601 TCTAGGCTCT AAAAATCAGA CAGTCCCCAC GGCCTGGCCT TCGTCGCTGT ATCTTCTTTA
18661 TGAAAACAC TAAGTCTTTT TCCTCACTGG ATAAATTTTT ATCCTTCAAG TTTAGATCAA
18721 ATGGAACTTT AGGACACTGA CTAGGTTACA TTCATCTTTT AAGAGCGTAC AGACATTCAA
18781 GGGCTAGAGG ATGTGGGTTT ACTGCACAGG CTCATTATCC AACAGCTGTG CTACCTGGGA
18841 AACTTAACCT CTCTGTGCCT TAATTTCCTC ATCTATAACG CAGGGAGAAT GACAGTAGGT
18901 ATCTCATAAG GTTGTTGGAA CAACTAAATG CATTGGTATC TATTGTGTAA AGTGCTTAAA
18961 ACACTGCCTG GCACAGAGCA AACATCCAGT GAACTTTAGC CATCATCATT ATCATTGTTC
19021 TCAGAGTCAA ATACAATATC TCATATCTGA TAAATTACAG AAGTGAATCA ATCACTCTCT
19081 CTCTTTTCTC CAGGGGAGA CAACAGCTTT TAGACATATC TTTTCCAACA GTCGTCACTG
19141 CTGGACACTG TTTCATCTTG CAAATAAACC AATGAAAATG AGTGATCCTA AAGAAGATA
19201 AATGGAGGTA TTTTGAACAA TCAAAGAAGG ACAAATGAAC ACCTGGCTGA GAAAAATTAG
19261 CTCTTTTTTC TATGCATAAA ACTATTAAAA TATTCTTCAT AGAAATTTAT GACACAGGAA
```

Figure 1 (Page 6 of 73)

```
19321  ACATAAAGAC  AAAATTAAAA  TAACTCCTAG  TATCTCCTAT  TCTTTTTATA  TGTATATTAT
19381  ATATACTCAT  ATTCATATAT  ACATATATCT  CACATCATGT  ATCATATATA  AAATAAATTT
19441  AGGTGTCATG  ATATATATTT  AGATAAATAT  ACTTAGAAAC  TTTTTTATGG  ATGTATAATT
19501  TATGGATATA  TTGATAATTA  TGTATTTGTT  ATTGACTACT  TCAATTGATT  CCCATTTTTA
19561  TGCATTATAT  TATAGATTAT  ATAGCTCACA  CATCTTTGTA  CATAAATCTT  TGTTCAAATA
19621  TTATTTCCTA  AGGATAGACT  TCATGAAGTG  GAAATACTAA  ATCAAAAGTG  AAAAACATTT
19681  TCTAAGGTTC  TTAACATATA  CATTGCCAAA  TTGCTATTCA  GGATCATACC  AATTTATAAT
19741  CCCAAAATAA  TATGGAAATT  CCTGTTTTAT  AGCACTCATA  TTTACAATAA  ATTTTAAAAA
19801  TCACTGTTAA  CCTAATAGTC  CTTCAAAAGA  AAAAAAAATT  GAAATTACAT  TATTTTAATG
19861  ACTCTATTAG  TGAGGGTCAT  TCTTCCCATG  TTTCTTGTTA  GCCATGACCC  TATAAGAAAT
19921  AAACTGCACT  GCAAAATGAT  AAACATGACA  TCAATCATTA  CATGGGAAGG  CACTATATAA
19981  AGAATAATAC  CTTAGGTTAA  GGCCACATAA  ATATTTATCA  GGTGCCTTTT  CTGCGGAGGA
20041  CTCTGAAGGG  ATACTAAACT  GCATTAGCT  GCATGCAACT  GAAACTACTT  TTACCTACAT
20101  TGTCTCTTAT  AAACATTATA  ACTACTCTTT  GAGAAAGTGT  TTACTATGGA  CTGAATTGTC
20161  TCCCCATCCC  CCCAAATTCA  TATATTGAAG  CCATAAACCC  AATATGACT  CTATTCCTAG
20221  ACAGGACTTA  TAAGAGGTAA  TTAAGGTTAA  ATGAGGTCAT  TAGGATGGGT  TCCTAACTGG
20281  ATAGGATTGG  TGGCCTTATA  AGAAGAGGAA  GATTCTGCAC  TTGGTCTTCC  AAATTAAATA
20341  ATTTATTTAA  AAGAAAAAAA  AAAAAGAGGA  AGAGAGGGAG  CTCTGCACAT  ATACTGAGGA
20401  AAGGCTATGT  GAGCTCTCAC  AGTGAGAAGG  TAGCACTCTA  CAAGCCAGCA  AGAGAGCCCT
20461  CAACAGAATC  CAGCCATGCT  ATACCCTGCT  CTGAGACTTC  CAGCCTCCAG  AACTGTGATA
20521  AAATTTTGTT  GTTTAAACCA  CACAATCTAT  GGTATTTTTT  TATGGCAGCC  CAAGCCAACA
20581  AAGACAGCAT  CATTGCTGTC  ACTTACAGAC  AAGAAAACTA  AGACTAGGAG  AGAGAAAAGT
20641  TAAACTTGTC  CAAGGTCACA  AAAGCCAGAA  ACAAGTGAGG  TGAGAAGTTG  ACCTTGTTCT
20701  CCTCAATCCA  AGGCCAGGAC  TCCTCCACTC  CACATGTAGA  TAGCCACCTC  ACAGTCAACA
20761  GCCAAATGTC  CACACCCCAG  AGTCAGCATT  AGACCAAGAT  GTCTTACCAG  GAGACAAATG
20821  CCTCATCTTG  AATAAATATG  ATCTAACAAC  TTACCCATGT  AAAACATTGA  ATCTCATGAG
20881  AAACAAAAAT  GCAAAGTATG  TAGAAAACTA  TGTTTACCAC  TTAACTGACA  GTGATAAAAA
20941  GCTTAATGAT  ATCCTTATAG  TCTTGGAGGG  GTTTGTATAT  GTGGTGAAAC  AGGTGCTCAC
21001  GCACTGCTGA  TAGACTGTAA  ATTGGTCCTA  GAGAGAAAAA  TAAATAAACT  GGAAGGAGAT
21061  ATGCTGTATG  TTTACTTTTT  TTATGGAAAC  ATATGATATA  CCTGGAAATT  CGATTGACCA
21121  TGCATCTATT  TCTTCAATGG  GTATGCACAG  TTGAGCTGTT  CCCATGCACC  AGGCACTGTA
21181  ATGGGACAAC  TGCACATGAC  AGTCAAAAAT  CTCAGTCTCA  TGAAGTCGAC  ATGCTCATGG
21241  AGAGGTGCTA  CCCCACTAAAC  TAATATTTGT  ATATCAATTA  TGGATACATT  GGGCCACATT
21301  TACAGAAATT  CACTTACAGT  GGGTTACCAG  AAGGGATTTT  TTTTCTTGAT  TGGCAAGAAG
21361  GCTAGGCTGT  TTTGTTGGGG  GCTGGCAGGA  GCTGTCTAGG  CTGCCCAAGT  ATGCAGGTCT
21421  CTTCTATCAT  CCTGTGTTAA  CCATCTTCCA  TGTATCTTTC  AACCTCATGG  TCATCTGCAG
21481  CATGTCTAGG  GGTCATATCT  ATGTTCCATG  CAGGAAAAAA  GGGTAAAGGG  AAAGGGAAGT
21541  AGGCATGTAC  CATTTTAATG  CACACCTTGG  TTTTCAGAAA  ATTTAAGAAG  AAAGACTTTC
21601  TGCTTTTCTC  TGACTATTCT  GTATTCTGGA  TTACAACGCA  ACAGAAACGT  CACCTTAAAT
21661  TCTAATGTTT  TTCTCTCCTT  GCTTTCAAAA  ACTGACTCAT  TAACCTCCAC  GTGGCTTGGA
21721  AAAATTATTT  CAGTCATCCA  GTAATGAGCT  GTTCATAGAA  ATGTTTTGGA  CATCAAGTCT
21781  GTGTTGTTAG  CATTATACAT  GTTAAGCATT  GAATAAAAAA  CAACATGATG  TGGGTAAATT
21841  TCTTTACTTA  CATATAAGTA  CTTATATACT  TATAGCTGAA  AAGAGAGGTT  GAAATGTCAG
21901  GTGGAACAGA  AATAAGATTA  CCTAGATGTT  TCTCCTATGG  GTGATTTTCA  GCTATGCTGA
21961  TCTTTCTTCT  GGGTCAGGTA  CTCCCAGAAC  TTCCTAATTA  AATGGTGGCC  CTGATCTTAG
22021  TTCCTCTCTC  CTCTTAGACA  TTTTCCAGGA  CTACAGAAGA  TGTGCAGTTT  ATAAATGAGT
22081  AGCAGAAACC  TACTGAACAA  ATTATTCAGG  CTCATCTGAA  CAGAGAGGAC  ACCTTCTCTG
22141  CTATACTCTC  TCAGTGATTT  CCCTGCCTTG  GGGTCAATTA  TTGTCTTGGA  CATTGATTTA
22201  AGCACATAAT  AATTGTTGTC  ATTGCTTATG  TTTGGATTTC  ATCTCCCAAA  ATAGATGGTA
22261  AATTCTTTAG  TTTAGAGACC  AAGTAATACT  TAAAAAAAAA  TTTTGTGTGT  GTGTGTGTGT
22321  TTTTTCTGTG  TCTCTCAGCC  CTGTAATAGC  ATCGTACTTA  CACTTGTTAG  ATTTTTAGAG
22381  ACAACTTTTA  CAAAACATGG  AATTATCTAC  ATACCCTTTC  TACAAAACAG  ACAAATTAAA
22441  TACTCAGTAG  TTGAACCAAA  AAAAGCAGTT  CAAATAAAAT  ACTTGAAAAT  GAAGAAATCA
22501  TTTGAACAGA  GTTAAAGTTA  ATCGTAAAAT  AATGTCTGTA  AAAATTATTG  CCAATCAAAT
```

```
22561 ATAAAGTTCA AAAATAGTGC TTGAAAAAGG AAGAATCATA TGAAAAGGGA CTACTCATTT
22621 TAAAAATGTT AGATATCAGG AAAAGCCAAG AAGTGAGTAT GGTAAGAGTG CTGTCAAGTG
22681 AAACCCTGCT AATCTCACTG AACATGTAAA AATCTGTAGA TGCCTTTATT TTATTCACTC
22741 ACACACATAT GTAGAAAGAG AAATATATGG TAAACATTAA AAAAACCAAA TTAGAATGTA
22801 AAATTAATAC TTTAAAAAAT GGGCTGTATA CTTTTCTTAT CACCGGAGAT AAGAATTTAT
22861 TATTTTTAAA ATAAAGTTAT TTTCTCTGTG ACTGTTTCCA TGACTTTGCT ACTTAGAAGT
22921 TAGAGATGCC AAAGTTTATC TAAGAAAATG TTTATGAAA TATTATTTCA ATAATGAATG
22981 TTTAGAAGAC TGAATTTCCT GACTGGGCGC AGTGGCTCAT GCCTGTAATC CCAGCACTTT
23041 GAGAGGCTGA AGAAGGAGGA TCGCTTGAGT CCGGGAGTTC AAGAGCATCC TGGGCAACAC
23101 AGCGAGACCC TGCAGCAAAG TAAAAGAAA AAGAATTGA AAAAGGAAGA CTGAATTTCC
23161 TTTGGGCAAG TCATGTGACA TTCCTGTGCC TCAGTTTCTT CATCTATAAA GTTAATTCCT
23221 ACATTTTTGG GGAAGGGAGA GAAAACTTA GGATAGTGAC TGGCACAGAA GAAGCACTAT
23281 ATACTATATA TATGTGGATA TCATTTGTTT TTATGGTACC ATTTTAGCTA TCTAATGCAA
23341 AATATGAATC TTTTTTTTCT GGGTCTTAAA TTATGGAATG TAAGAATTTT CTAAATTCTC
23401 TAATTCTGTG TTAGTTTTAA AGCAATGGAG TAACGTATCT GTCAACTTGT AAATATAAGG
23461 ATCAACCTGA TCCACAATTT GACCCCTAGC CACTAATATT TAATAGTACA ACACTCAGAA
23521 ATTATCAAAG GTCAGAGAAG CCAAACAAAT GTAAAAACAT ACAGGTGCTC AGAAAGATGC
23581 ACCTGTAATC TCTCTAAGGA GAAATATTTT CCAAACTGAG TGACACGGTG CTTTAGTGAG
23641 TTGTGGAATC AATCTCATGA TTTCCAACCT AGTGTTCTTT TAAAAATGAA CTAGTCCACA
23701 GTAGAATATA CTAAAGTGCT GGTGCTTAAG ATAGTATTGT TTTCTGGAAA AAAAAAAAAA
23761 ATTTTTTTTT TTTGAGACAG GGTCTCGCTC TTGCCCAGGC TGAAGTGCAG TGGCACAATC
23821 ATGCTCACTG CAGCCTTGAC CTCCTGGGCC CAAGTGATTC TCCCACCTCA GCCTTTTGAG
23881 TAACTGGGAC CACAGGTACG TGCCACCACA CCCGGGTAAT TTTTTAATTG TAGAGACAGG
23941 GTCTTGCTAT GTGCTTAGGC TGGCCTTGTG AACTCCTGGG CTCTAGTGAT CCACTAGCCT
24001 CAGCCTCCCA AATTTATGGG ATTATAGGCA TGAGCCACCC TACCTGGCCT GTTCCCTGAA
24061 TTTTTTTTTC TTTCAGGTGT TTGTGCATAT GTGTGTGTGT ATGGGTATAA CAGAGAGACA
24121 GAGAGAAAGA AACTTTTCTA TCTCACTTTG CAATCAGAAG TTTGAAGTCT TATCTTTTGG
24181 CTTTTGTTTC AGAAATATTT CAAATGTAGA CTCTCTCCTT TACCACACTG TCCCCTTAGG
24241 CAAGGTCTTT GCCATTCTTC TGAGACTATT GCAACAGACT CCCAACTTCT GACTGTGGGC
24301 CCTTCTCAAA AATGATTGTT TATGCAATAA ATCTAAACCC AAGACAACTA CAACAATACA
24361 ACAAATTCTC TGCTTAAAAA CTTCCAATGT CTGCCGGGCG CGGCGGCTCA CGCATGTATT
24421 CCCAGCACTT TGGAGGCAGA GGCGGGCAGA TCACTTGAGG TGGGGAGTTC GAGACTAGCC
24481 TGGCCAACAT GATGAAACCC CATCTCTACT AAAAATACAA AAAATTAGCC AGGCATGGTG
24541 GTGGGCGCCT ATAATCCCAG CTAATTGGGA GGCTGAGGCA GGAGAATTGC CTGAACCTGG
24601 GAGGTGGAGG TTGCACTGAG CCAAGATCAC ACCATTGCAC TCCAGCCTGG CAACAAGAG
24661 CAAAACTCTG TCTCAAACCA AACCAAAACA AAACTTCTAA TATCTACCAA ATGTTTCACA
24721 CAAGTATTTG GGGATCTTCA CAAATGGCCC TTATGGAGTT TTCCTTTGCT GAGACCCTAT
24781 GCTCTGGCCA CACTAAACTC ATTCAGCATC CCAGAAAGGC CTCAGCCTTT GTGAGCAAGC
24841 TCTTATCTCC AGGCCTCTCA CAAAGACCTG TTCCAGTAGA AGCTCAGGGG AGCACACTGG
24901 ACATTATTCC AACAACCCTT TCCCCACAGC TATGCAGCCA AATCTGCCAG CTCAGTTAAT
24961 TAATTAAGCA ATTCAGAGAT GAGGGTCTGC CCAGGCTGGA GTGCAGTAGC TGCGACCTCA
25021 AGCTCCTGGG CTCTAAGTGA TCCTCTTCAG TCTACCCAGA AGCTGGGACT GCAGGCATGT
25081 GCCACCACAC CCAGCTAATT TTTTTTTTTT TCAGTAGGGA CCAGGCCAAC CTAGTCTTGA
25141 ACTCCTGGCC TCCAGCCTTC CGAAGTGCTG TAATTACAGG CATGAATCAC TGCGCCCAGC
25201 CAACCCGCCC AGTCTTGTTA GACATGGGGT CTGTAGTTTC TAGTAGGTTC TTGAGTCTAG
25261 GGTTCCTACC TCATGTTTTA TAGTTAATTT AGGGGAGGGA CTGTGTCTGT TTATCTGGGG
25321 ATGTAGGGGT GGGCAGGGGG ATAGAGGGA CTTCAATTAA TGAAACCAGA AGCAAACTC
25381 AGTTGAGGAC ACCGGTCATG AGAGTGGCCT GATTATGGCC AATCTTACAT AATGTGTGAG
25441 ATCTTGATAT TACCCCATCC TTGAGAGTCC TCTATAAAGC TACAGGGACT GGGAGCACC
25501 TTTAATTACA GACAACCCAT GTTCCTGTGG ATTATGATTT ATTAGATTGC ACATGCCTAA
25561 ATAAAGACAT CCTCTGCAGT CTTTTGACAA TTCTATAAGC ATCTTCTGAC TCCGCAATTA
25621 GACAGCTAAG AGATCTGTGT TACTTCCCTC ACATATATAA ATAATTTTAA ATAAAAATCA
25681 TGGCGTGAAT AATTTCTTTC CTCTACCGAT TTGAAGCTAT CCATTTGGAA GACCACTCTG
25741 AAGAGATGAA ATAAGTCTTC TGCCAAAGAT TACTTATTAA TTTACAAGGA AAAGGGGAAG
```

```
25801 TTTTGTTCCT CTCCGTGAAT TTGATTGAAA ATCGAGGGCT TTCTCGAATA GTTTTGGCAT
25861 CCAGGGTCAT TTTTCATTAA AAAGAGAAAA GTCATGTCAA ATATGAATTT CCGCAGATTA
25921 TTCAGCACTA GACCCTGGGA GATTCTGTAA AGAGGGGTTT TGTTATACTC AACTTTTCCG
25981 GGTAAAACAA ACACAAATAC TCCTCCTCCA AGGGGCGGGG GCGGTGCCTA GGTGATGCAC
26041 CAATCACAGC GCGCCCTACC CTATATAAGG CCCCGAGGCC GCCCGGGTGT TTCATGCTTT
26101 TCGCTGGTTA TTACATCTTG CGTTTCTCTG TTGTTATGTC TGAAACCGTG CCTGCAGCTT
26161 CTGCCAGTGC TGGTGTAGCC GCTATGGAGA AACTTCCAAC CAAGAAGCGA GGGAGGAAGC
26221 CGGCTGGCTT GATAAGTGCA AGTCGCAAAG TGCCGAACCT CTCTGTGTCC AAGTTGATCA
26281 CCGAGGCCCT TTCAGTGTCA CAGGAACGAG TAGGTATGTC TTTGGTTGCG CTCAAGAAGG
26341 CATTGGCCGC TGCTGGCTAC GACGTAGAGA AGAATAACAG CCGCATCAAA CTGTCCCTCA
26401 AGAGCTTAGT GAACAAGGGA ATCCTGGTGC AAACCAGGGG TACTGGTGCT TCCGGTTCCT
26461 TTAAGCTTAG TAAGAAGGTG ATTCCTAAAT CTACCAGAAG CAAGGCTAAA AAGTCAGTTT
26521 CTGCCAAGAC CAAGAAGCTG GTTTATCCA GGGACTCCAA GTCACCAAAG ACTGCTAAAA
26581 CCAATAAGAG AGCCAAGAAG CCGAGAGCGA CAACTCCTAA AACTGTTAGG AGCGGGAGAA
26641 AGGCTAAAGG AGCCAAGGGT AAGCAACAGC AGAAGAGCCC AGTGAAGGCA AGGGCTTCGA
26701 AGTCAAAATT GACCCAACAT CATGAAGTTA ATGTTAGAAA GGCCACATCT AAGAAGTAAA
26761 GAGCTTTCCG GGAGGCCAAT TTGGAAAGAA CCCAAAGGCT CTTTTAAGAG CCACCCACAT
26821 TATTTTAAGA TGGCGTAACA CTGGAAACAA GTTTCTGTGA CAGTTATCTA TAGGTTTAAG
26881 TTGTGATGCA GCTGAGTTGA AAAGGCTTGA GATTGGAGAA TTAATTCAGG CCAGGCTTCA
26941 AGACCATCCT GGGCAACATA GCCAGACTAC CATCTATACC AGGGGTCCTC ATTTCCCCGG
27001 CCACCGACCG GTAACCGGTC CCTGTCCATG GCACGTTATG AATTGAGCCG CACAGCTGAG
27061 GGGTGAGCGA ACATTAACCA ACTGAGCTCC ACCGCCTGTC AGGTTAGCTG CAGCATTAGA
27121 TAGATTCTCA TAAGCTCAAA CTGTATTGTG AATGGCACAT GCAAGGGATC TAGGTTTCAG
27181 GCTCCTTGTG ACAATCTAAT GCCTGATGAT CTGAGGTTGG AGCAGTTTTA GTCCGGAAAT
27241 CATTGCTCCC AGCCCTGCA CCCCTGGTC CGTGGTATAA TTGTCTTACA CAAAACGGTC
27301 TCTTGTGTCA AAAGGTTGG AGACTACTGG TTTTACAAAA AAGTAAATTA GTCAAGCATG
27361 GTTGGCACGC TCCCTTAGTC CCTGCACCCA GGCGTTTAAG GATACAGTGA GCTATGATGG
27421 TGCTACCTCA CTCCAGCCTG GGTGACAGCG AGTCAGACGT TGTCTCAAAA CTTAAAAAAA
27481 AAAAAAGTTA AAACAGAAAA AGGGCTTCTT GTCAGAGACT GCCGTATATC TAGAGGTCCA
27541 GGAACTAAAA AGTCTGATGT CCAATCCTGA AAAGCTCGAT GGTGCACTAG AGGAGGCTTT
27601 TACATGTAAG AGCATCTAAG TTCTGGAAAT GCCAGTGTCA GGGAAGGGAA GTGGAGAGCA
27661 ATTTGGCATC CAAACATAAC TTGCTGATAC TTTTTTTTTT TTTAACACAA GTACTACATT
27721 CTAGTCTTTC TGTGGTGTCA TTGTAACTAT TGTTTCTTAA TATGCTATCC ACTGACTTCA
27781 AGGGATCAAT AAATAGGAAT CAAGGTGTCC CAGAATATGG ATTAGGGGAG TTTTTTTGTT
27841 GTTGTTGTTG TTGTTGTTTT TCATCTATTC ATTATCCTGT AGCTGAAATT TAGAATTTTC
27901 TTCCATTGTG TGTGACTGAT AGAAATAACA AATTTGTAGG TTATAGTTGT TGCAAGAATC
27961 TGGAAATCGT GCTTGCTTAT TTCCGAAGTA CTATTAGGTA TATCAACAAA AACACACATA
28021 TTACGGTCAA GTGGTTTGAT AATTATTTTA ATATTATTGG TCTAATACAA TTGTAACCCT
28081 ATGAATTACT TTAAGTATCT TATTTATGAA AAGAATCTGT AAGTTTCATC AGACTACCAG
28141 AGCATACCGA AGACTGAAAA ATTTTAAGAA TCCAAACCTT AATGGAAATG TTGGAGGCTG
28201 CCCAATTAGG TTCTGAATTC CACCTTCCTG AATCACAAAC TTGTTTTAAC TCTCAGTCTG
28261 AGGTAAACTA CGTTTCTCTT TAAACAGACA TAGTTTAATT TTCCTTTGAT TTTTGATTTA
28321 GTATTCTTAC TGATCATCAT AAATAACCAA TGCTAATGTT AGTCTACTTT GGACCATGGT
28381 ATTTCGAGAA ACTTTGAACA AAGTCCCCTG CAAAACTATG CATTGCATTA TTTCACATAC
28441 ATTTATGTTT TCCAGACGGT TCAATAGTAC CTCACTTTTC TGAACTTATT TGTATAGTTT
28501 GGCATCTTTT TAAAAATTGT GTCCTATAAT GAAAGGTTGT AAACATTATG TTTTAAATTT
28561 GTATAGATAA AATCAACCAC AGACCTTTCC TTGCTTGGAT GTAATTGCCA TTGTTTCCCA
28621 ATGAGTTCGG AATTACTAGG ATTGTGCAAA AATATGCCTC ACTTGCCTGA CATAGCAGAG
28681 AGCCATTTTG CCTAAATGCT GTGCCCAGCA ATGGACTGTC ACCAGATTCT CATCACATAC
28741 AGTGAGGATG AACAACTAGC CTCTCCCAGC AGCTGGCCGG TCTCTCAATA ATATGGGACT
28801 CCCTCAAGAT GGCTTCCTGC ACCTTTGCTC CTCTAGCCTT GTATGTATAC AAGGCTAGCA
28861 TGCCTGGCAT ACATAAGGTT AAAAACAAAA TCAATAAGTT ATGGTTCTTC CTCCAGTTCT
28921 GGGGATTATT AGACCACTTT TTTGTTTTGT TTTGTTTTGG ATGGAGCCTC GCTCTGTCAC
28981 CCAGGCTAGA GTGCAGTGGC ACAATCTCGG TTCACTGCAA CCTCTGCCTC CTGGGTTCAA
```

Figure 1 (Page 9 of 73)

```
29041 GCAGTTCTCT GGCTCAGCCT CCCACGTAGC TGGGATTACA GGTGCCCGCC ACCACGCCCG
29101 GCTAATTTTT GTATTTTTAG TAGACGGGGT TTCACCATCT TGGCCAGGCT GGTCTTGAAC
29161 GCCAGACCTC GTGATCCACC CACCTTGGCC TACCAAACTG CTGGGAATAC AGGCGTGAGC
29221 CACCGCGCCC GGACTAGAC CACTTTGTTT TGGCCAATAG GACAACAGCC ATAGAACCCT
29281 CCGCAAATGA GAGCTTGTCC CTAAAGATGC TTTATTTACA TAGCTGTGTG CCGCATGAGC
29341 CAAAAGGTGA TAACCTTTGT TCAACACGCG CCTCCAGCCC TTCGGTTAAG TCCAAAGTAC
29401 CATTCTTAGA ATGCTCTAAA ATACATAATT TTTTTTTTTT TTTTTTTTTT TTTTTTTGAG
29461 GAGTCTCTCT CTGTCTCCCA GGCTGGAGGG GAGTGGCGCG ATCTCGGCTC ACTGCAATCT
29521 CTGCTTCCGG GCTAGCTGGG CCTACAGGTG CAGACCACCA CGCCCGGCTA AGTTTTGTAT
29581 TTTTTTTGGT AGAGGGGGTT TCACCATTTT GGCCAGGCTG GTCTCGGATT CTTGATCTCA
29641 AGTGATACAC TAGCTTTGGC CTCCCAAAGT GCTGGGATTA CAGTCGTGAG CCACTGCGCC
29701 CAGCAAAATG CTTTTTGTGG AGCCAATCAC TTTATTAGCG CTTACCTCTC TATGCCTACT
29761 TTATGCTTTG AAATTTTGTC ACAGTGTGGC CGGTCATGGC AAACACAATT CATTCTTATG
29821 CAGGATGTCA CGGTTATTTC TGTCATCCAA ACTCATTCTC GCAACGCATT TCAGCTCTTT
29881 AAACGACTTT GTGAGCGGCC CTGAAAAGGG CCTTTGGGTT TTTTTGTTTT TGTTTTTTGA
29941 AGTTCTCAGG AGACCGCGTA TTCTTAGATT CAGCCGCCGA AGCCATACAG AGTGCGCCCC
30001 TGACGTTTTA GGGCATATAC TACATCCATG GCTGTGACAG TTTTGCGCTT GGCGTGCTCC
30061 GTATAGGTGA CGGCGTCTCG AATAACGTTC TCTAAGAAAA CCTTAAGCAC ACCTCGAGTC
30121 TCCTCATAGA TAAGACCGGA AATGCGCTTG ACGCCACCGC GCCGAGCCAA ACGGCGAATA
30181 GCCGGTTTTG TAATGCCCTG GATGTTATCC CGGAGCACCT TACGATGGCG CTTAGCACCA
30241 CCCTTCCCCA AGCCTTTTCC GCCTTTGCCG CGACCAGACA TGATTCCTAT CGCAGTGGAA
30301 GGTATGAACT GAAACAGTTC CTTAAATACA AACTTGGCGG ACCTGATTGA AAACAACATG
30361 AGTTGGCGCG GTTTTTTTTT TTTTTCAAAT TTGGTCACCA AGTGGGTGGA GCAAGAAAAA
30421 CTGTTTCATT ATGGTTCATT GTTTTGATTG CCAGTGACA GCTTGCTCTT TGTGGGAGTG
30481 GAAGGGTGTT TGCAAGTTGA ATGCGCTGTA TTCCTGTCAG CTTAATGACG CTAAGCATAG
30541 CCCCATTCCA CATTTCTTTT TATTTCCACT TGCTAACTAA TAAATTACGG AATAGTTTAT
30601 TGGGGAACAT ACAAATAATG TTTAAAGGAG GTCAGATTTA TAGGTCAAGG GATTTACCCT
30661 CCCAATCATT TTAATATTTT TATTTAAACC AGGCATTTTG ATGGCCTTCT CTGTGCTGGA
30721 CAAGGTATAA GTTTGGCTAT GAAGTTTCAC TCCTAAAGAC CCTATGTTTT GGGAAGGCAA
30781 AAAGGTAGCC AAATAATTGC AAATTAAAAC CTCATAAGTG CAAACTTCTT CCTCGTCACT
30841 TTCCCTATCT CGATTCAAAT ATTTGTTGAA TGACTCATTT TTCTGCAAAA GTCTGAGAGA
30901 GACAGGGAAT ATAAACTTAA GTCTGGATAA TATGTTTTCC CGGGACGCTC TTCCTGGTCT
30961 GCTGTGCCTG TTTGCTGTGC CTGAAATTCC AAACACTCTT CCCTTCCCTC CGTTTTTAAT
31021 CCCCTTTCAA CTTGCTACAG CTTTAGAGAA AAGAACATTC GTTTTGTACA GTTGGGGATT
31081 AATTGAAGTG TAGGGCTAAT ACTTGATTAA GGTCATTACA AAATCTACAG GGTCTTCCTC
31141 TGGGAGGTTT TTGTGATAAG ATTATTGGTG TTAAAATAAG GCTAATCCCC TTGAAAAATA
31201 AATAGAATAG CAGAATTGGG TCTGAATGTG GTTGAAGAA AGGGACTTCT CAATTCAAAA
31261 TTTTATTCTT AGCTTCCTGC GGGAGCTTTC CAGAATGCCC ATAAGATCCA CTTTTGTTTA
31321 AAAAACAAAA ACAACCCCAC CCACCACTCT CTGGTTAATA AATGAATTTC TATTGGGAAT
31381 ATTTAGAATG GGGCTGTGGC CTGTGAGAGA CATTATATAG TAACCTCAGA CTTGCTCACA
31441 TGAAGAGAAG AAATCCAGGA ATGGAGAAAA AAGACCCAGG AAAGGCCAGA ATGCTCTACA
31501 TGTCATATTG TTTGTATCAC TTCTGAAATA ATTGATTACA TTCTTCTGCC CCAAATTGAG
31561 TTCTTAGGTT CTTCCACTCA CTGTCCACAT GCCACAACAC AGACCTTATA ACTAGAGACT
31621 TAGCTAGGAA GAAATGTCAA ACATTACAGA GAAAAAATGC AGAGTCTGAG ATCATAAGTA
31681 AAACTCTGAA ATCTCAACAT GCCTTTTAAT TCATGAAAAT AAAAAATATA GCAGCATATG
31741 CAATATGACA ATTCTCTGAA AACATACATC ATGTGAACTA CCCTGGAACA CATCTCGCCA
31801 AGTGCCATCT TCATTTTAAC CAGAGGTCTA GGATGCCTTT CCTTTATTTT GCCTATTATA
31861 TCATTTATAA AACCCCATTT TTATTTTGAT ATTTTATTTA CTTTCTATTT CCTGCTCCTA
31921 ATATCTCCTT TCTAAACTTT TCTCAATGAC AGTGACTCAA AAACAATGAA TGTCAGAACA
31981 AATATTTAAA GGATCTGTAC ATGTAGATAT ATATATTTAA AATGGATTCT TCCACTCTGC
32041 GAAGAATTCA GGCATACTCA ATCTTATGGT TAGGGAGAGA TTAGGCTCAC TCGCCTAATC
32101 TGTATGGCTT CTCGTTCGCT TTCCATTTCA CCTTCCTCTC ACCCATCAGA TCAAACTCAT
32161 TCATTGAACA AGAGACCTAA GCCCTTCAGA TTAAAACTCT GCAAACAAGT TGTGGTTGAG
32221 AGGATACATG AAGCATTCAA ACAAATAAAT CTATGATATT AATCAGAGGT TAATCTATGA
```

```
32281 TATTAATCAG AGGTTAATGC AGTGGCTCAC GGCTGTAATC CCAGCACTTC AGGAGGCTGA
32341 GTTGGGAGAA TCGCTTGAGC TCAGGAGTTC AAGACCATTT TGGGCAACAT AGCAAGTCTT
32401 CATCTCTACT TAAAAAAAAA TAACCAGAGG TGTTATGAAA ATATAAATTG TCCAGAACTA
32461 CCCTCCACAA ACTAACTCTC TCAGAATATT CGATATGAGG AATGAAATAT GGTGTGTGTG
32521 TGTGTGTGT GTGTGTATG TGTGTGTGT TGTGTGTGTA TGCACCTATA TATGGCACCT
32581 ATATATTCAA CAAACAATTC TGATAATTGG CCAGGGTTGA GAATGACTAG CAGCCCAGCA
32641 TACACTATCA GTTTTAAGTA TATAATTGCG CTTTAGTAAA ATGTAAAGAA ATCCCAGAGT
32701 AGAAATACTT TTAAGCTATA TTACAGGTGA GAAAATGCAT AAGTATAGTC TCACCCAACT
32761 TAGACTATGG GGGCTTTATA ATGTCACAAC AGTTGTTTCC AGGCATTTGG GGACATCACC
32821 ACTGGTCTTG GGCAAGAAAC TCCTCTAGCC AATGGCTGAT TTATCTCACT CCCATCTAAG
32881 GCTTCACTGC ATTTCTCTTT TTCAGCAACC TAACTTATTT AAAAATATCC ATTTTCTGAT
32941 TCATTTTTTT CTGAATTAAA CTGTCAGTAC CATTGGCACA CCTTTGGTTC CGTAGCATAC
33001 CTGTGTCTCT GCTGTGTTTT TTTTTACCT CCACTCCTTA CTTTTCTAGA AAAAAATCTC
33061 TGCTTTTTCT TTTCAGTTTA AATTATTTCA CAAAAAGTTT TCTTGACTTG CACTTCCTAG
33121 GCTTGCTGTC CTTGTGTGGG CACGCTCCCA TAAACACTAT TAATACACTT CGATTTGTTA
33181 AAAATAAAGA TATCTGGACA GAAAATTTCT TTTCTTTTTT TAAGATTTTA AAATTTTTAA
33241 TGTTTATTTT TTTCCTAGAC TGGAGTACAG TGGCACCATG ATGGCTCATG GTAGCCTACA
33301 CTTCCCCGGG CTCAAGTGAT CCTCCCACCT CAGCCTCCCA AGTAGCTGGG ACTACAGGTG
33361 TGCACAACCA CACCTGACTA ATTTTGTTTA TTTGTTTGTT TTGTTTTTTG AGATGGAGTT
33421 TCGCTCTTGT TGCCCAGGCT GGAGTGCAAT GGCGGGATCT CGGCTCACCG CAACCTCTAC
33481 CTCCCAGGTT CAAGCAATTC TCCTGCCTCA GCCTCCCGAG TAGCTGGGAT TACAGGCATG
33541 CATCACCACG CCCAGCTAAT TTTGTATTTT TAGTAGAGAC GGGGTTTCTC CATGTTGAGG
33601 CTGGTCTGGA ACTCCTGACC TCAGGTGATC TGCCCGCCTC GGCCTCCCAA AGTGCTGGGA
33661 TTACAGGCGT GAGCCACCAC GCTCGGCCAC TAATTTTGTA TATTTGTAG AGATGGGCTT
33721 TCCCTGTGTT GTCCAGGCTG GTCTTGAATT CCTGGGCTTA AGTGATCTGC CCACCTTGTC
33781 CTCCCAAAAT GCTAGGATTA CTGGCGTGAG CCACCAGGTC TGGCTGGAAA GATAATTTCT
33841 AACATTATCC TCTCTTAAAC ATTTGTTTCA AAAATTTTAC AAACATGAGA GTAATTAAAT
33901 TTGATTTTCA AAATTCCCTT GAATACTTTC TTAATAGCAC ACAGAAAGCA CAAAGTATTT
33961 TACATTTGTT TTAATGATGA AATTGTGAAC CCAAACTTAC ACAAAGAAAA ACCCGTAACA
34021 TTATACCCAT ACTTAAAACA GATGCCCTCA TATACATAGT AAAACTCTTG GGGGCAGTAG
34081 TGAAGTTGGT TATTTACTGT TTTATGAAAG TGCCATTCAG CCGGGTGCAG TGGCTCATGA
34141 CTGTAATCCC AGCACTTTGG GAGGTCGAGG CAGGCTGATC ACGAGGTCAG GAGTTCAAGA
34201 CCAGCCTGAC CAAAATGATG AAACCCTGTC TCTACTAAAA ATACAAACAT TAGCTGGGCG
34261 TGGTGGTGTG TGCCTGTAGT CCCAGCTACT CAGGAGGCTG GGGCAGGAGA ATCGCTTGAA
34321 CCTGGGAGGC GGAGATTGCA GTGAGCCGAG ATCGCACCAC CGCACTCCAG CCTGGGAGAC
34381 AGGGCGAGCT CCGTCTCGAA AAAAAAAAAC AAAAAAGTGC CGTCATAGTG ACTCAGTTTT
34441 AAGGAATAAA TCAAGGATAT TTAACTCAAT AGACTACAGT TAGCTAACGT GACTTGCACT
34501 GAAAGTTATA CGAATATTGG TACTTATTCC CCTGCCCCTG AAGTATGAAT TAAAGACTCC
34561 AAAATTCTTT TTAGAATCTT CAGAGTAAAA GCTAGAATTT GATTTTTTTA AATAATAAAA
34621 AAATACTTTG TATCTAAATC TGGTGTATAA ATAACTTGG TGGATGATGC TTCAAGGCTA
34681 TCCATCCCCA AATTTCTCCC TGAATGATAA AGAGAATAAA TGAATATGTC AATTCAAAAG
34741 TTAGAAATTT GGCCGGGCAC GGTGGCTCAC TCCTGATAAT CCTTTCGGAC GCTGAGGTGG
34801 GTGGATCGCA TGAGCTCCGG AGTTCAAGAC CAACCTGGGC AACATAGCCA GAACCCGTTT
34861 CAATAAATAA TAGAAAAAAA TGAGCCAGGC GTGGTGGTCC CAGCTACTCA GTAGGCTGAG
34921 GTGGGAGGAT CACTTGAGCT CAGGAGGTCG AGACTGCAGT GAGCCGTGAT CGCAGTACTG
34981 CACACCAGCC TTGGTGTCAG ACTGAGACCC TGTCTCAACA ACAACAAAAC AAGTTAGAAA
35041 TTTGGCTGGG CGCGGTAGCT CACGCCTGTA ATCCCAGCAC TTTGGGAGGC CAAAAGGGC
35101 GGATCATTTG AGGTCAGGAG TTCGAGACCA GCCTGGCCAA CATGGTGAAA CTCCATCTCT
35161 ACTAAAAATA CAAAAAAAAT TAGCCGTGCA TGGTGGCATG CGCCTGTAGT CTCAGCCACT
35221 TGGGAGGCTG AGGCAGGAAA ATTGCTTGAA CCCAGGAGGC AGAGGTTGCA GTGAGCCGAG
35281 ATCATGCCAC TGCATTCCAG CCTGGGTGAT AGAGTGAGAC TCCATCTCGA GAAAAAAAAA
35341 AAAATTCTGT ATGAACTGAA CAAAATATCC TTAAATTTTA AAATACATCT GAAAGATATT
35401 TCAAATATT TAGGAAAAAA ATTATAGGGA TCAGGCAAAT TCTGAGATTC CTTTTTCCCT
35461 GCAGCAAACA TTAGGAGTGC TGCTGTTCCT AAAAACATGG TAACTGTTGC CACACCGTAT
```

```
35521 GTTTCCTTGG CTCAGACATA AGGTTGTGTA GTTGTTATTC CAGAATAGCT AGAATAAAAA
35581 TCCAGCACAT CATTTTCTTC AGCAAGTTAA CTAACCTCTC TGTGCCTTGG TTTCATAACA
35641 GCAACATAAG CATAACAGAA TAGCAGCAAT AGCTCCTACC TACCTCATAA GATTCTTTGG
35701 AGGAATTAAA TTAAGATTCA GAACACAGCC TAATATCTAG TAAGTAATAA TAATTGGCTA
35761 AAAAAATTTT CTTAAGATTA TATATATTCA TGGGGTACAA GTACAATTTT GCTACATTAA
35821 TATATTGCAT TGTGGTGAAA TCAGGGCCTT CAATCCATCC CGGAAAAAAA AAGTTTTTGA
35881 AAAGATTTCT GCCATGGAAA ACTTTTAATG TACAAATTCA TCCATCCAAG AAATAGAAAA
35941 TATATAAGTA TCAACTCCAA ATCCACCATA TCTATCTCTT CTACACCTTA AACAATTACT
36001 CAGAAATAGA ATGCTTGAGA TACCAGAATG CATGCATATC AAGTAATAAA TGCATGCAGG
36061 ATGTCAACGC ATCCTAGGCT TTCAAATAAA ATTGTCATAC AAAATACTTT AATATTGTAG
36121 TAACATTCTA CATGTTAGAG TGTAGAAGTT AATCGCTGAT GCAAAAAAGG AAAAGAACAC
36181 ATTATACCCA AAGCCTACAG AGAGAATCAC AATTACAAAT ATCAGCCTGC ATGTGAAAAT
36241 CTTTAATTTG AAAGTCAGAA ATATTTAAAT GATAGTCATT GTTAAATCAG ATTGTGGTTT
36301 GAAAAAAAGT TAGTTTAAAA CTGAGTTTAT GAAAAATTTG GGGATTTTAG AGACAGTGTT
36361 TTGTTTTTAA ATGTGTGTGA GTTTGTGAAG AATGTTTTAT AAAATACTGA CAGTATTATA
36421 AGATGACATT ATTATAATAC AACATAAGAA TTTTGGCCTG TACCTCTCAG CAGTCCTCAA
36481 TCACCTGCTG TACTTGACTC AATGATTATC AGAGTGGTTT GTTTTCCTTC TGTTGTGTTC
36541 CCAGTTCAGG CAGCTCAGCA ATGGCCTGTG ATTCCAGCAA TTCAAATAGC TGGTAAGTAG
36601 TTTCTTGTTT GTTTTCTCAA ATTTTCAGGG GCTTTTCTCT ACAAGTGATT TCCAGTGCAC
36661 GCCCCTCCAC CCATTCTTTA TTCCTTTACC TTCAGGAAAA CCCTCAGCGC TGCATCTCTG
36721 GTCACCGGAC CACCGTGGTA CATTTACCTA TGGCCACCAG GTGTCACCCT TCTCTTTACT
36781 ACCATGGTTT GTGAATGGTT TTGCCAGAGG TGAATAAGAA TTTAAAATGC AGGTCTTTGA
36841 TTTTTCAAAT GTAGTTGACC TTAAGAATTT ATGAATAAAG CCAGAAAAAT TAAGCTTAAA
36901 AAACACCGAA AGAAAATGAG GACTTAAAAT TTCTATTAAA AAAATTAACA GGCCACAGTT
36961 GCTGATGTTT AGTAAATGTG TTAGTGAAAT GTGTTACTGT GAAGACTGGG GTGTTTCTTG
37021 AAATCTCAGC CCAGGTGAAA TAAAACCAAT ATAAAACAAA TGCTTACCTA ATAAATTAAT
37081 TGTAACATAT TCCTTATGAG GTAGAAGAGT AAGTGAAGCC TTATAGCAGT CTGCTTTCAG
37141 TATAGTAAGA TATTAAGAGA GAAATAATTT GTCATATGCT TTCAGAATGG TTTGCTGGTA
37201 AAATAACCAA TGTCTTACAA CTTAGACGAC AATGTCCCTA GAGTGAAGAA ACACGATTAA
37261 TTCGGCTACC ACAGTTGAAT GAAAATATTC CGTAAGACAA AATGTAAAGA AATTAGAAGC
37321 AAAATAAATG TCTCCAAAAT GACAAAGCGA TTAAGTATAT ACACAAGATG AACAAGAACT
37381 TCAATAAAAT CATGCAGTAT ACAATACAAT ATACATTTAT TAAAGTATAT GCATTTTTAA
37441 TGCAACAATA ATACTAACAG GTAATAGACA AGTTGTTAAT AGTTTTTCAC TGGCTAATTA
37501 AATAACAGCT TTAATTGTAT TCATTTTATA GCTTTTCTAC AATGAGCGTA AATCACATTT
37561 ACTTTTTTCT ACATAACTTT TCTAACCACA AAAAAAGAAA ATGGTTTAAA AGAAGAGATG
37621 AGATATCTTT GCTAAAATTT AATGCCTAAA GAAGAAACTT CTGAGCTGTA TATGGTATCC
37681 TGAAGCACCT GCCCTTCAAG ACAGAATGCT TGTACCACAT TTATGCAGCC AAGTGCATGT
37741 AGTAACATAA AGTAAACACA TGCCATCTGG ATATATATAT TAAGACTCTT TTGACGGCTG
37801 GGCAGGGTGG CTCACACCTG TAATCTCAGC ACTTTGGGAG GCCGAGGCAG GCGGATCACG
37861 AGGTCAGGAG AGTTCGAGAC CAGCCTGGCC AACATGGTGA AACCCTGTCT CTACTAAAAA
37921 TACAAAAATT AGCCGGGCAT GGTGGTGCAC GCCTGTAATC CCAGCTACTT GGGAGGCTGA
37981 GACAGGAGAA TCGCTTGAAC CTGGGAGGCA GAGGTTACAG TGAGCCGAGA TCATGCCATT
38041 GCACTCCAGC CTGGGCAATA GAGTCTCAAA AAAAAAAAAA AGACTCTTTT GAACATGGTG
38101 AACTGATTTC CCAGAATCTA GCAATTCCTG AATGTCCTGG TTAGATTTTT TTTTTAATGT
38161 GCACCGGAAC CCCAGTGGCT CCATGGAAGG ACCTGGGCAT CCTCTAAGCC ACTTGGTGGC
38221 TTCCATTATA CCATCTCAAA ATGAGAGAGC TTACTCCACT TCATTGAGGG AAATACCACC
38281 AGAGTTCTGA CTCCAGAGGC ACTGGCCTAG GGAGGACACC GTGTGTGAAG CCCAGCAGGG
38341 CCACTAGCTG TCCCCACCAA TTACAGTCCT TGCGTAGGGT CCAAAGAAAT GAATGCCAAA
38401 GAGAGCAACA GAGGAGCAAG GGAGTCACAT TCCAGGACCT TCCTTCAGGG ACTTTTAAAG
38461 GAAACATGAC AGCTGAGGAT CAGTTGGTTG TTTTCTGCTG TTCCCCTTCA TGTGATTCAA
38521 GCTCACTCAG AAGAAACACA ATGAGACAAG AGAAGAGCCA TCTCCTTCCT TCTCTATTTA
38581 TTCTAGGCAT CTAAACTACT GAATGTAGTG GTGTCTGAGA TGTATCAAAC GGTCAGATTG
38641 ACTGAGTTTG AAACCTGTTT CTATCACTGA CAAACTATGA GATACTCTAT ACTTCACTTT
38701 CTTTTTTTTT TCATTTTTTT ATTTTATTT TTATTTTTTT GAGATGGAGT CTCACTCTGT
```

Figure 1 (Page 12 of 73)

```
38761 CACCTAGGCT GGAGTGCAGT GGCGCAAACT CGGCTCACTG CAAGCTCTGC CTCCTGGGTT
38821 CATGCCATTC TCCTGCCTCA GCCTTCCGAG TAGCTGGGAC TACAGGCGTC TGCCACCACG
38881 CCCAGCTAAT TTTTTGTATT TTTATTAGAG ATGGGGTTTC ACCATGTTAG CCAGGATGGT
38941 CTCGATCTCC TGACCTCGTG ATCCACCCGC TTTGGCCTCC CAAAGTGCTG GGATTACAGG
39001 CGTGAGCCAC CGTGCCCGGC CTACTTCACT TTCTTCATTT AAAAAAGAAA TGGGGATAAT
39061 AGTACCTATC TCATAGAATT ATTGTAAGAA GTGCATGCAG TAATGCATGT AAGTAGGTGC
39121 TCAGAAGAGT CGGACACGAA GTAAGTGCTT TTATCATCCT TATCATAATT TTCATTATCA
39181 GAACAAGGAG AGACCAGGTA GAAAATTATT GTGATTCTTC AGGTCTGGAA TACTAGAGTA
39241 GCATCCCAAA TGAAGGCACC ATTAAACTTT GCAAATCTGT ATGACACCTT CATGCCAATT
39301 AGAAAAAACA CCTCTTCACA ACCCCTTTCA AGATATTTGC CTCCTACCTG CTAAAAACAC
39361 CCATCATACT ACCCACAGAT AGCCATGATG CTTTTTCTGG GACAGGTGCC TCTTCCATTC
39421 CTGCAGTGTA CAGCCTTCAT AGCTGTGCAA CTCACATCAC AATCAGATGG AAGAATCCCC
39481 AAGGCTTGGT GACAGATGAG TTACTGGGTA ACACAGAGAG AGGATTCAAA GGAAAAGTTG
39541 AACGGGTCCA GAAAATGCAT AGATACATGT GTAAAAATCT GGTAAGGTTA TGACTAGCCA
39601 CGTCCCAGGG TTCAAAGCTT TTCTCAGATG TTAAAATGAA TCATGTAAGT CCCCCAAATT
39661 TAAGGAGTCC TCTTCCAAAA ATAGGAAATG AAATGACATA GGTGTATGTC TCTGAGGTGA
39721 CGGAGGAAAT GAAGGAAGCC TCTAGATGCA GCTTGAGGTT CATGAGAGAC AGTTCCAGGG
39781 GAGAGGTCAC AGCTAGGGAT CACCGGCATG CAGGAACTCA GAAACCTAAA TGGGGAAATC
39841 TTTTTGAGGA AATGAACAGA GAAGGCTAAA ATCAAGGAGT TCGTCAGGCA ATTTCTATGT
39901 TTAGGTTCAA CTCTCTCCTG AAACATGAAG AGCTCATAAA TGCACTCCCT CTTTGAGTCT
39961 CTAGTTTTGT CTCCTTCCCA CAGTGAGTCT GCAGGCTGCG TGTCACTCAC GTTCAGCTAA
40021 GACGTAGTGC CCCATGGCTC CTCCTGTGGA GACAAGAGAC CCAGGAAAGA GGCATCACAA
40081 ACCTAGGCAC CATCTTGCCT CTTCTCTCTT CCTTATTTTC CTCATTCACC CATCTCAATT
40141 TAGACCTGGG CACTATTGGA TTTCAAGAAC CATTATCTCT CATCTGGAAA TGCTTATTGG
40201 CTTTCTAACT GGTCTCCTCA CCTCTCATCT AACTTCTTAA CAACACATTC ACCATATAAG
40261 GGAGATCGTG GTCCTCCTTT CTTAGGATCC TTCAATGACA CCCCAGTGAT CATAACCCAA
40321 TATCCCAAAA GACCCTTGGA CTCTGTATGA GCTGGCTTCT TTCTGATTCT CTTTTCCCTA
40381 CACCACAGAT GTTCAGGGGG TAGAAATGCA TAATTGGTGA GTGATAGCTA CGCAAACTCA
40441 GGGTTAAGGT ACAGTAATTA TTTCTAATCT CCCAGTATGC CTTATACTCT CCTACTTGGC
40501 ATGGTTGCTC CGTCTGTGTA GACCTCCCAT CATCTTCAAC CTCACCTAAT GGAATCCAGC
40561 TTCTCCTTCA AGATCCAGAA GGCTATCTTG ATCCCCAGCT GAATGTGATC ATTCTTTCCT
40621 TTGACACCCT AAGCATTTGC TTCCTGCCTG CTTTAGGACC TCATGGGGTC TTCTTTAACT
40681 ACATTTACTT GCTATCAATT TCATTCCCTA CCAGATTTGG GTTCTGAGAA TAGCCACAGT
40741 GACTTCTCAA CCTCAAAGCC CCTGTACTAC CTTAAACAGC TCTTGCAAAA TAGTAGGTGC
40801 TCTGAAGATG TTTGTTGAAT TAGAGACTTT CATTCTGGGG AGAACCATTA TTTTCTGTCT
40861 CCCAGGGAGC TGCTGGTGTC CCCAAAGAAT ATAAATGAGA AAAATGCTTC CCATGGATGC
40921 CAGATCCCCT CTGCCCCTCT TCCCACTGTG CCCTGGGGCA GAGGTACTAA GAGACTTCCC
40981 CCTTGTTCCT ACTCACTTGA ACCCTGCCTC TTCCTTAATA TTATGAACAA AATTCCAATG
41041 AACAAGATGA CGACAAAAAC AGCAATTCCA CTGATGACTC CAATGACTAG GGTGCCAGAC
41101 GGTGAGGGCT CTAAAACAGA AAAAGCAAGT TAAAGCCTTT GATTGCCACC CTCAGCCCAC
41161 CCCCTAACAA AGAGCAGATC CTCATCTCAC TGCCATAATT ACCTCCTCAG GCACTCCTCT
41221 CAACCCCCAA TAGATTTTCT CAGCTCCTGG CTCTCATCAG TCACATACCC CAGATCACAA
41281 TGAGGGGCTG ATCCAGGCCT GGGTGCTCCA CCTGGCACGT ATATCTCTGC TCTTCCCCAG
41341 GGGGTACAGC CAAGGTTATC CAGCCCTGGT AGGTCCCATC CCCATTGGGC AATACGTCTT
41401 TAGGTTCGAA CTCCTTGGCA TCCATTGGCT GCTTATCCTT CAGCCACTTC ATGGTGATGT
41461 TCTGGGGGTA GTAGTTCAAG GCCCGACACC GTAGAGTGGT CACTGAAGAG GTCACATGAT
41521 GTGTCACCTT CACCAAAGGA GGCACTTGAC AGGAAAGAGG AAGGATGAGG AGAGGGGATC
41581 TGTTTACCCT TGCCAGGAAG ACTGGAACTT TCACTTCCTT CTATAGGTTG GAGGAAGGAA
41641 ATACCCTTTT CAGAAAAAAA CAAGCTACAG GAGAGACACC ATTTTGTGTC CTAAGATTGG
41701 ACTCTAACAC AGTGTCACTT GGAGAGCAGT CAGATCAGCT TGTTCTCCTC ACATGTAAAT
41761 ATACATATCT GTTACCCATG TTCTTTGTTC TGATAGATAA AATTGCCCTT TATGTGCATT
41821 GAAAATGATT GAATACAGAT GGTCAGTTTC ACCTGGGTCA ACCTAGGAGG CATTGTTATA
41881 AGAAGCGGAC TTGTAAGATA GGTAGCTTCA GTGATTATTG CTATGTTCTA TGAAAGAAAC
41941 TTTTAACCTA AAGGATTCTT CTACTCTGAT AAGTGGCCTC ACTTGATATT TTGTCCTGGT
```

Figure 1 (Page 13 of 73)

```
42001 ATTCATATGA TAGCTGAGAT CTCTGAATTC TCTTTTTTTT TTTTTTTTTT TTTTTAAGAT
42061 GGAGTCTCAC TCTGCTGCCT AGGCTGGAGT GCAGTGGCGC GATCTTGGCT CAGTGCAACT
42121 TCCGCTTCCC AGGTTCAAGC GATGCTCCTG CCTCAGCCTT CCAATTAGCT GGGACTACAG
42181 GTGCGCATGA CTGTGACCAG CTAATTTTTG TATTTTTTTA GAGACGGGTT TCACCATGTT
42241 GGTCAGGCTG GTCTCAAACT CCTGACCTTG TGACCACCCG CCTCGGCCTC CCAAAGTGCT
42301 GGGATTACAG GGGTGAGCCA CCGTGCCCGG CCTTGACATT TCTGAATTTT TAACAGGTAT
42361 AAATATACAA AAGATTATTG GTTAAATAAA AAGCAAGGGC CATAGACACT TCCCTTTGAG
42421 CCATATGCAT GGAGAAAAGA AATTAAACCC ATGACTTGTG GCTGTCTCAT ACATCTCAAT
42481 TATAAGGTAG AGACTCTAGG ATTGAGAAAG TCCCTTCCCA GAATTTGGAG AGGCACACAG
42541 CCTCAGCCAC CTCTGAAACT CCAACCAGGG ATTCCGTGCC CTGCAACCTC CTCCACTCTG
42601 CCACTAGAGT ATAGGGGCAG AAGTGTGTTT CCACCATACC TTGTTGGTCC AAAACACCTC
42661 TCCCCAGCTC CAGCAACTGC TGCAGCTGTG CAGGGCAGTC CCTCTCCAGG TAGGCCCTGT
42721 TCTGCCTGGC CCGAATCTTG TGCCTTTCCC ACTCCAGCTT GGTGGGCCAG GCCCTGGGTT
42781 CTGCTGCTCT CCAATCCAGT GTGTCAGGGC AGAATTCAAG GTGGTCCTGC CCATCATACC
42841 CGTACTTCCA GTAGCCCTCG GTACTGTTGT CTTCTTGCAT TTCACAGCCC AGGATGACCT
42901 GCAGGGTGTG GGACTCTGGA AAAATCCCCA GCCTTGTTAA CTGCAACCAA AGGAATAGGT
42961 CCCTATTTCC ACCATCCCCA AGGACCAAAT GATCTCAGGA AGCAAATTCC TTCCCTCTTC
43021 CCTGCTCCCA CAAGACCTCA GACTTCCAGC TGTTTCCTTC AAGATGCATG AAAAGATGAA
43081 AAGCTCTGAC AACCTCAGGA AGGTGAGGCC CCCTCTCCAC ATACCCTTGC TGTGGTTGTG
43141 ATTTTCCATA ATAGTCCAGA AGTCAACAGT GAACATGTGA TCCCACCCTT TCAGACTCTG
43201 ACTCAGCTGC AGCCACATCT GGCTTGAAAT TCTACTGGAA ACCCATGGAG TTCGGGGCTC
43261 CACACGGCGA CTCTCATGAT CATAGAACAC GAACAGCTGG TCATCCACGT AGCCCAAAGC
43321 TTCAAACAAG GAAAGACCAA GGTCCTGCTC TGAGGCACCC ATGAAGAGGT AGTGCAGAGA
43381 GTGTGAACCT GGAGACAGAG CAACAGGCCT TAACCATGTG TAGTAGGAGG GGAGCAGGAT
43441 GTTGAGGCTC CACACACCTG CATCAACTCA TACCATCAGC TGTGTCTGGT CCTCATTTTG
43501 TGAAGGGTGA GTTGCAGTCC TGTCTTTCTT CCATATGACA GTCCTGGGTG CTCTTTCCTT
43561 GTGTGCTTTT CTCTGCCACA CGTGGCTGCC ACCCCCTCAC TGCCCCCAGA TCCTATTCCA
43621 ATACTCATGA TTAGACAGAC TCCACTAAAG CTGGTGGATT CTAGAAAATG TTAAGGTGTG
43681 TCTAGCCATG GTAGTTGAAC TCAGGAGTTG GTGCTCAGGG CAAATTAGAC CCAAATCCTG
43741 AGGAATAATT CCTTCAGTTT TTTTTTTTTT TTTTTTTTTT TTTTTTGAGA CAGAGTCTCA
43801 CTCTATACC CAGGCTGGAG TGCAGTGGCA CAATCTCAGC TCACTGCAAC CTGCACCTCC
43861 TGGGTTCAAG GGATTCTCCT ACCTAAGCCT CCTGAAAACC TGGGACTATA GGCGTGCGCC
43921 ACCACACCAG GCTAATTTTT GTATTTTTAG TAGACATGGG GTTTCACCAT GTTGGCCAAG
43981 CTTGTCTCAA ACTCCTGACC TCAAATGATC TACCTGCCTC AGCCACCAAA GTGCTGGGAT
44041 TACAGAAGTG AGCCACCGTG CCCAGCCTTG GTCCTGAATT CTTACACTGA ACTGCCTATG
44101 TGGCCTCACC ACTTGGAAGC CTGACTGGAA TCTCAAACTT AACATGTCCA AATGCAGATC
44161 CTTGATTTAC CCCAAACTGC TCTTTCCTCT GCCTTCACCA TCTCAGAAAT GGCATTGCCA
44221 ATTACCCCAC TGCTCAGGCC AATAAAATTA AAATAAAGAA CAAAGTCAAC TTTAACTCTT
44281 CTCTTTTTCA GGGGGTCAGG GGAGACAGGG TCTTGCTCTG TCACCTAGGC TGAAGTACAG
44341 TGGCACAGTC ATGGCTCACT GCAGCCTCAA CTTCCTGGGC TCAAGCAATA CCCTCCACCT
44401 CAGCCTCCCG AGTAGCTAGG ATCACAGGTC ATGCCACCA CACCCAGCTA ATTTTTGTAT
44461 TTTTTGTAGA GAAGGGGTTT GCTGTGTTG CCCAGGCTGG TCTTGAACTC CTGAGCTCAG
44521 GAATCTGCTC TCCTTGGCCT CCTCCTTGGC ATGAGCTACT ACACCCAGCC AATTCTTCTC
44581 TTTCTCTCAC ACAACATAGA ATCCTTCAGC AACTTCCTTC AGAATATATT CAGGAGACAA
44641 TGGTTTGTCA CTCCCTTTTC TGTTCCCACC CAGCCCACTC CACTACCTCT TGCCTGGACT
44701 GTGTAACAGC TTCCTGGCTG GGCTCCCTGC TTTTACTGTT GCTCCCTTCA TTCTGCTTTC
44761 CACATAGCAG CCAGAGCAAT CTTTTAAAAG CCTGTGACAG ATCACTGTTA CTCCTTGGCT
44821 AGAATTCACA CCACAGCCTA CAGGCGCCTG CACAACCTTG TTTGTGGCTC CTCTTCTGAG
44881 CCCATTACCT ACTTCTTGGC CTCTACTCCC CAGCACTACT TGTTTATTTT TTTCAACCCG
44941 AGCTTCTTAA CCAGGAGTTT GTCTACTAGG TGACATGTGG CAAAGTTTAG AGACATTTTT
45001 GGTTGTCAAG ACTGGGGGAG TGCTCCTAGC ACCTAGTGAG TAGGGAGGAC AGGATACTGC
45061 TAGACATCCT ACATGCAGAT GGTAGTCCCC CTTCCCACCC CCACGCCGCC CCCCCCCCC
45121 ACACACACAC ACATGAGTAG TGCTGAGAAA ACCCGCTTTT TAATCCAACT TGCCAGGCCC
45181 ACTCAGTTTG CCTGGGAAAT ACTGCTCCCA GTCAATATCA TTCTTATTTC CTTCATGTCT
```

Figure 1 (Page 14 of 73)

```
45241 CTGCTCAAGT GTCAGCCCCA GAGTGACTTG CCCTGACTTC TCTGCTTCTC ACAACACCCA
45301 TGATTTCCTG ATGTTGTATA TCTTTCTGCT CATTTGCTTA TTGTCATCTC TCCCACTAGA
45361 ATGCAAAATA TCAAAGGGTA AAGACTTGTT TCCCTGCTCT CTCCCTTGGG GCTTGAACAG
45421 TGCAACACAT GGCTGGGACT CATTTACACT TGTAAACAAT GAATATTTCT GCTCAACATG
45481 AAATTTTATT ATTCAACCTC TAATGCAGTG TGATGTTTAA GAATCATAGC TATGAAGTGG
45541 AGACATGAGC TCTGCCACCA AAGCCCAGTG TACCATTGAA TAAATTTGCC AGGAAGCAGG
45601 CCGTGCCATG CCTCATTCTT GTCATGTGTA AAATGTGGAT ACACGTAGTA CCAAAACTCA
45661 AAGTGCTGTG CTGAGGCCGG CGTGTGACCC ACAGAACACT GTGCTACACT ACAGGGCAAA
45721 ATCACTGTCA ACTAAGATTA GAAGCAGCTG TAGTACTTGA AATAACATCA GAAAACCAGA
45781 TTATTTATGT TCTTTGTAAC CTGAAAAGAG TTATATAATC TGAATTCCAG TTAACTTCTA
45841 GTAAAATAAA CGTATTATTA GCTCCTACCT CCCTATGCCT AGTGAAAATC AAATAAGATC
45901 AGATATGAAT GTAACTTAGA AGTGAGTGCA TTGCTTACAT GTTCATTATC AGTACTTTGT
45961 AGAGAGGCCT CTTAATTACA CAGCACATTG CAAATCAATA AAGCCTAGCC GAAAAGAGAA
46021 TTGTTCAGTT CAAACGTTCA AAACTAACAT ATACTTAATT TTCCAGGCAA AAGAACAATT
46081 GCCAAGAGTG GGGAAAGGCC CGAGGTAGGC CTCTCTCAGG AGCCTCCCAC CCTAGAGACC
46141 TCCACCCCAG GTCTCACCAA AAGTGGGTGG AATGGTGAAG AATTCAGATC CCCAACGCCA
46201 CTCTTTCGCG CCCCCACCGC CCAACGCATT CGTTCTGAGG TGGAAACCCC GTGCGGATCC
46261 TGCTGTGGGT TTGCTCAGCC TTCTCGGCAA GCACTCAGGG AAGAACTTCC TGTTTGGAGA
46321 TGACTGGGGA AAAAACTGCA CAGCTGACAT TGGAAATAAA CCCGAGTTCC AGGTTCAAGG
46381 AGCCCAGGC TTAGCTCAGC TCAAGTGAGG AACTACGAGA TTTATTTAAA AGCATTCTAG
46441 TTGGGGGAAG GGAGTGGGCG GTTCCAAAAG TCACTCCGCA GAGCCGGGAC AGCCGGGGGA
46501 GGGGGCAGGT CCTGGGGCGA GGGACCCCTA TCTGCAGTTC AGTGGTAGGC ACTCCCTCAC
46561 GGGGTCTGGA CGCAGAAAGT AGGGAGAGGG GCTTGCGGAT AGGGTTGAGC AGGTCCTCCA
46621 AAGTTAGCAA ACTCCCAAGC GCAAAGAAAA AGCTAGTTTC GATTTTTCCA CCCCCGCCGC
46681 GCCCCTAGTT CGCCCGCAGC CCTCGGACTC ACGCAGCAAG CGCCCCTGCA GGACCGCGGT
46741 CTGCAAAAGC ATCAGGAGGA GAAGCGCCGG CCTGGCTCGC GGGCCCATTT CCCCAGCTCT
46801 GGCCGCACGT CCCCGTTAAA TCTCCGCTTC TTTTGGGGGG CGGGGAAACG GGGATGGCTC
46861 CAGAAGTCAC CCTACAGCTA TTGCCTAGGC TCAGGAGATG CCCAGTAAAA CTTCCTGGTG
46921 AAAAGCAACA GGTCTTTCAG AACTTTAGTT CTCTCTCTCC TACAGCAGAA GGTACCTGCT
46981 TGTGAAACAC TAGGTGATCC AGTGTCCCCC TTGGTTTTTA AATCCTGAAG GGGTGTTGTT
47041 GATTGGGGAA AGTAGCTTCG CAATGTTCTG ATCTGAACTT TAGATATTTA AATATTTATG
47101 ATTTTCAAAA TTCAATCATA CATTTAAAAA TTTTATCTCA ACCTTAGACC AACTTATGTC
47161 TTATTTGACT TAGAAATATA AAGCTTTTTC ATTTTGTTTT TTGATTCAAA TTAATTAAGT
47221 CATAACATTA ACCAATTAGA TCCTACTGAA ACACCTTCCA CAGCCTTCAT AATTGAATTA
47281 TCTGACAAGT GTTTCACAAA CTTTACAGTA TTGGGATTAT CTGGAGAATG ATTAAACATA
47341 TTGAGGCCTG CTCCTAACCC CAGACACACT GATTTAATGG GTAATTGTTA GGTAGTTAGA
47401 CATTAGCAGT TGGGAGGGGA TGACAGAAGA GAGCGGAAAG GCTGTCACTA AGACAGCCAC
47461 TGGCCCACCT AAATTCAGGC CAAGACTAC CCTAATGCCA CCCTAAGGGA TGGAGTTTAT
47521 GATAAAGTCT GTGGCCAAAA TATCCTGGAG AAAGAGAAAG GAGGGTACAG GTGGAAATTC
47581 CCTAAGGTGG CACATGCCCA ACAACACAAA AGCCTGTCTT CAAGTTCACC CCAAGTTCAT
47641 CATGCCATCA TTATAATAGA ATTTACATAC AGTTTTGCCC CCCCATCCCT GGGAGGCTTT
47701 TCTTAACAAA TTATAGGTAA GACCATGCAC AGTTTAATTT TAGATTGTAT AGCTATACAC
47761 TTCAATCAAA TAACATCATC CTGTCACTCA GATACAGCCC AAACCTCAAC TCCTCCCCAC
47821 AAACCCCATA AAAGCACCTT GAGCTCTGTA AAGAAGTGCT GAGTTCACTT CGCAGAAATA
47881 AGCCCGCTGT CCCTCAGAGT GTATTATTGT GCTTCAATAA ACTTTGCTTT AAGCTTGCAT
47941 TTTGGTGTTA GTTTGTAGTT CTTTGCTCAC TATCACAAGA ACTGAGATTG CTGGTTCAGA
48001 GCTCCGGCTA TAATAATCTC CTCGGTTAAA GGATCCATCC CAATGCATAA TTCCCAGTAA
48061 CAGTATGGGA TGCCACCTGG GCAATGGGAT TTTAAAAGCT TTCCTTCTCC CTCAACGAAG
48121 TTTGGGAATT ATTGCCTTAG ACATTTCAAA CAATATTAAT AAATTTAATA CACCTGATTT
48181 GCTCCAAACC TTTACATATC TAGCAAATTC AACAGGCATT ATTTTTGTAA GCATGTATGC
48241 AAATTTTGGC AATTCAAGAA AATCAAACAG GATATCAGGG CCTCGACTGT AGGCAAACAG
48301 ATACAATAAC ATTGGAAACA TGTAGAATAT TGATGATGGG CACATTGGGG CTGATAGTAC
48361 TATTCCTTTT TTTCAATTTT TGGTAAGATA TAATTAGCAT ACCATATAAT TCATCTATGT
48421 AAAATGCAAA AATTGGCCCG GCTCAGTGGC TCACGCTTGT AATCCCAGCA CTTTGGGCGG
```

Figure 1 (Page 15 of 73)

```
48481 CCGAGGAAGG CAGATCACCT GAGATCAGGG GTTCGAGACC AGCCTGGCCA ACATGGTGAA
48541 ACCCCGTCTT TACTAAAAAT ACAAAAATTA GCCGGGCGTG ATAGCAGGCA ACTGTAATCC
48601 CAGCTACATT AGAGGCTGAG GCAGGAGAAT CGCTTGAACC CGGGAGGCGT AGGTTGCAGT
48661 GAGCTAAGAT CGTGCCATCA CACTCCAGCA TGGGAGACAA GAGCAAGACT TCATCTCAAA
48721 AAAAAAAAAT TAGCTGGGTG TGGTGGCATG CACCTGTAAT TCCAGCTACT CGGGAAGCTG
48781 AGACAGGAGA ATCGCTTGAA CCTGGGAGGC GGAGGTTGTG GTGAGCCGAG ATCATGCCAT
48841 TGCACTCCAG CCTGGGCAAC AAGAGCGAAA CTCCGTCTCA AAAATAAAAT AAATAAAATA
48901 AAATGCAAAA ATTAATGGAT TTTAGTATAT TTACAGAGAT GTGCAACCAT TACCAAAATT
48961 TTACATTTCT ATCTCCCCAA AAAGAAACCA TGTTCCCCTA ATTCAGTACC CTTAATTCAT
49021 CGCCTCCCAG ATTCCTCCAT TCTCCTCCTC CTCCCCTCCC AGCCCTAGAC AATCTTTAAT
49081 CTACTTTCTT TCTATTTGGA ACATTTAGTA TACATAGAGG CATATAATAT ATTGCTTTGC
49141 CGTGACTGGC TTCTTTCATT TAGCATAATG TTTTTATGTA TGTTTTTCAT GGACCAATAA
49201 TATCTATTAT AAGGACATAC CACAACATAT TTTATTTATT CATTCATCAG CCGATGGACA
49261 TTGGTTTGTT TCTACTTTAT GGCTATTGGG AATAGTGCTG TTATAAACAT TTATGTACAA
49321 GTTTTTTTGT AGACTTATGT TTTGATTTCT TTTGGTTATA TATCTAGAAG TGGGTTTGCT
49381 GGGTCATATG GTAACACTGT TTAACCTTTT GAGGAATTGC CACATTCTTT TCCAAAGTAA
49441 GCATTTTATC CTCCTATCAG CAGTGTATGA GAGTTCTGAT TTCTCTCCAT CTTTGCCTGG
49501 GTTTTTGAAT CAGGGCCCCA GATAGAACAA AAATGTGGTT ATTCAGTTGT TCCACCATCA
49561 CTTGTTGAGA AGACTCTTTT TTCATTGAAG TGTTTTGGCA CCCTTATCAA AAATCAATCT
49621 ACCATAAATG TGAGAGTTTA TTTCTGGAGT CTCAATTTTA TCCCATTATG CTATAATCTA
49681 TAATCCTATC TTTTTTTTTT TTTGACAGAG CCTCACTCTA TTGCCCAGGT TGGAGTGCAG
49741 TGGCCCAATC CCGGCCACTG GCTCCTCCTC CCAGGTTCAA GCAATTCTCC TGCCTCAGCC
49801 TCCCAAGCAG CTGGGATTAC AGGTACCTGC CACCATGCCT GGTTAATTTT TGTATTTTTA
49861 GTAGAGACGG GGTTTCACCA TGTTGGTCAG GCTGGTCTGG AACTCCTGAC CTCAGGTGAT
49921 CTGCCCACCT CAGCCTCCCA AAGTGCTGGG ATTACAGGCA TGAGCCACCA CACCCAGACT
49981 ATAATCCTAT CTTTATGTCA GGACTACACT GTCTTGATTA CTATAGCTTT TTAGTAAATT
50041 GAATTCAAGA AGTTTCTCAA CTTCAAATTT GATCTTTTTT TGGAAGACTA TATTAGCTAT
50101 TCTCAGTCTG CTGAATTTCC CTAGGAATTT TAGGATCTAT TATCAATGTC TATTCTATTT
50161 TTGTATATGT TTTAATATTT TCATAAGAAA CTTTTTTCAT TTAAACTTTT TTTTTTAAGA
50221 AAAATAGTGA AAATCAGAAC ACTGGGGGTC AGGCGCATTT AACAGGCAGA AGAAGAATAA
50281 AAACTTGTCA TATAAACAAA AAAGAAATGA CCAATCACAT TGTGGAAGCC ATGGAGTGGT
50341 TATAGGTGCC AAAGGCTGCA GAGAAATGGT GTCAGATATA CCTGAAAATT GTCCATTGTA
50401 TTTGGCCATT AAGAGACTTA GAAGACTTAA GCCATAGATT GCTCAGTGAG ACCCCGAGGG
50461 CAAATGGTCT GAAGGTGAAT AGATCATTTC ACCTTTAAGA GAGCAGGTAG GAAGCTATAA
50521 ATCCAAGATT AAAAAGTTGA CTGAACTGTT AAGGAAGAAA CTCTAATCTT GAGCCACCCT
50581 ATCCTGGCTC CACCTTCTGC TGCAAGCAAA CAGAAATGCT GAAATTCAAC ACTCACAAAG
50641 GCTGGTAAGC TGGAAATGAC AAAAATTACT CCTGGGAAAG TCAGATTTAG AATTAGGCCA
50701 TATTTGTTGG GGTTCAGATT TTCATGTACA CTTGGGAAAG GGTTTAGCTT ATAGGCACAT
50761 GCATGAAGGG AACTGGTATA GGGCTGTGTT CATAAGGTCA AGAGTTGAAG GCCAGGCATG
50821 GAGGCTCTTG CCTGTAATCC CAGCACTTTG GGAGGCCGAG GCAGGAGGAT GGCTTGAGCC
50881 CAGGAATTCA AGACCAGCCT GGGAAACATA GGGAGATGCT GTCTTCACAA AACAATTAAA
50941 AAATAAAATT AGTCAGGTGT GGTGGCACAC ACTTGTGGTC CCAGCCACTC AGGAGGTTGG
51001 GAAGATCACT TAAGCCTGGG ACATTGAGGC TGTAGTCAGC CATGATAGTG CTACTGCACA
51061 CCAGTCTAGG TGACAGAATG AGACCCTGTC TCCAAAAAAA GAGCTGTATC CACATCCCAG
51121 GAAAGTGGTT GAAGATCTAC TTTTCTCTGT AAACCTAATA AAGAATAGAG TGACAAATGT
51181 GTGTTGTGGA AAGAAATGGG GTGAGAGCTA CGTAGATGCA AAACAATACA TCCCCACATA
51241 CCACTTGTTA ATCATCCTTT TCCACCCACT TATGGGATGA ATTGCATCTC CCAAAAGAT
51301 ACTCTGTCCT AACCCTCAGT AGCTGTGAAC CTGACCTTAT CTGGAATACG GTGAGTTCAC
51361 TGGTTAAGAA GAGATTATAG TGGAATAGGG TGAGTCCTCC AACCAATGAC TGGGGTCCTC
51421 ACAGACACAG AGGGATGATG GCCAGGTAGA GATGGAGGCA GAGATTGGAG TTATGCTGCC
51481 ACAAACCAAA CACAGGAAGC TGCTAGAAGT GGAAACAGGC AAGAAAGAAT CCTTCCCCAG
51541 AGGCTACAGA GGGATCTTGG CCCTGATAAT ACCTTGATCT CAACTGGCCT ACGTAACTGT
51601 GAGAGAATAA ATTTCTTTTG TTCTAAGCCA CCCAGTTGAT AGTACTTTGT TACGGCAGCC
51661 CTAAGGAACT TGATATACAT TTCTTTTACT GTCATAGAAG TTTTGAATCT TTTAAGTAGG
```

Figure 1 (Page 16 of 73)

```
51721 TCTGTACCCT TCCTCCCAGT GTCAACACAT GGAATTCCTC TCCTTGTGCC TTGAAAAGTG
51781 AAAGGTGTTT GAACTGGTAA TGAAAGAAAT CTCAGCATGA GGCCAGATGC TGTACCTCAC
51841 ACCTGTAATC TCAGCACTTC GGGAGGATGA GGCGGGCAGA TCACTTGAGG TCAGGAGTTC
51901 TAGACTACTC TGGCCAACAT GGTGAAACCC CATCTCTACT AAAAACAAAA AATGTTATCC
51961 TAGCCGGGCA TGGTGCCTGT AGTCCCAGCT ACTCAGGAGG CTGAGGCAGG AGAATTGCTT
52021 GAACCCGGGA GGTGGAGGTT GCAGTGAACT GAGATCACGC CACTGCACTC TAGCCTTGGT
52081 GAGAGAGCAA GACTTGGTCT TAAAAAAGAG AAAAGAAAAA TGAAATTTCA GCATTATAGA
52141 ATAAAAATGT TTCCCCTTCC CCCCAAACTT TAAAAAAGCA GAAGTCTGCA TCATAAAATG
52201 GTCTTTGCCA ATGTTATTTT TATTATAACA AAGGAATCTT GCAAGGCTAC CAGATCTCAG
52261 CAATTGTCAC TATGTTCTGT AAAAATCACT TCCTAAAATG TCTGAATTGA CTGCTTGTCT
52321 CATTTATTTG TTTCTCGTGT CATACTGCAA TGGATATCTG TCTTGTTAGT ATAAATATTT
52381 GTGCATTTTG TTGTTGTTAA AACAGCTTTT TTGGCCTGTC TTCTTCCACC TATGAGGTAA
52441 TATAAAACTC ATGTTTAACA CTTATTTTTG TAGCAGGACA AGCTACAGAC AAAACCCCTC
52501 AGACACTGAG TTAAAGAAGG AAGGGCTTTA TTCAGCTGGG AGCTTGGCA AGACTCACAT
52561 CTCCAAAAAC CGAGCTCCCT GAGTGAGCAA TTCCTGTCCC TTTTAAGGGC TTGCAACTCT
52621 AAGGGGGTCT GTGTGAGAGG GTCATGATCG ACTGAGCAAG TGGGGGTATG TGACTGGCAG
52681 CTGCATGCAC CAGTAATCAG AACAGAACAG GGATTTTCAC AGTGTTTTTC CACACAATGT
52741 CTGGAATCTA TAGATAACAT AACCGGTTAG GTCGGGGTC AATCTTTAAC CAGACCCAGG
52801 GTGCAACACC AGGCTGTCTG CCTGTGGATT TCATTTCTGC CTTTTAGCTT TTACTTTTTC
52861 TTTCTTTGGA GGCAGAAATT GGGCATAAGA CAATATGAGG GGTGGTCGCC TCACTTATTC
52921 ACCCCCTTTG AGAATCTCAC TCATTAGTGG GAGTTCTCAC TTTTATTCTC ACTACCTATG
52981 TCTTCTTGAA AGACAGATTG ATAATGATTC ATATAGTACA CTTGTGCTGA AGCATTTTGG
53041 TGAGCTAAGG TAGTGATGAA GCTTTTATC ATTTGGAGAA GTACAGGTAG CAAACAAGGA
53101 AGCAGTAAGC AGGTTTCTAT TAATATTATA ACTCCTATTA TAAGAGTTTT AAATCTTCTT
53161 AGCACTCGGA ACCATTTTC AAACATGGCC CCAGAAACAA ATCCATACCA CACCTACATG
53221 GGCACATGTG CCACTTTTGT CATATTTCTA ACTATGTCTT CAACTACTTG CCCTTAATCA
53281 TCTATGTGTA GACAGCAATT AGTAAGGTTA AATTTCCTAC AGACCCCTCC TTCAGTTGCT
53341 AGCAAGTAGT CGAGAGCCAA TCCATTTTGA TAGATAGCAT TTTGCATCTG AGTTTCTTGC
53401 CAGGCCACAG TAGTCAGGGC TCTGCTGGTC TTATTAGTAA TTATTTCTAA GACAGCTTGT
53461 AACCGTATGA TTCAGTTGAG CATGTAAATG GGGGTCCCAT ATCCCCACAA GCCGTCTTGT
53521 GCCCAAGTAG CAGGCCCATA ATATTGTATG ATTCTCTCAG GGGGCCATTC ATTATTTTTC
53581 CAATTTTCTA TAGCTATGCT TTTTTTTTTT TTTTTTTTT TTTTTTTTT TTTTTGCGG
53641 GAAGCATATA CAGGGAAGCC CAGGAGTTTG CCTGTCTTTA TGGGCAGTAG AAGAAAGAT
53701 GGTTTAGTAG TGTCAATAAC ACAACTACCT GCCCACTGGT CAGGTAATTT GGCATAAGCT
53761 GTATGCCCAC ATATCCAGTA TAATCCAGTG GGGGCTGTCC AGTCCCGGTG GGACTCTGGG
53821 TGGGTCCACA CAGTTTGCAA CTTTGGGAAT TTACTAAATA GATTTTTCTT AGTGTGGTTT
53881 GAACTCCACT AGGTGGCTGT TTTTATAGTA CTATTATACA GTTTTGCCC AAGGCAGCTG
53941 AGTCTTCCCA CAGGAAGGGT GAAGTCCTTC CCCACTTTTG CTATACAGTA TTGTCTAATG
54001 ATTGAGGCTT TTAGGACCCA GAAGTTATCA GGGTGAGTCT TTTGAGCTGG GAATTTATCA
54061 GGAACTGGGT CTGTAGGTAC TAATTCTCGT GCTTCCCATG GCCATTGATC TCCCATTACA
54121 GTTCCTCCAC ATACATACAT AACATGAAGT GACATTGAGA GACTGGGCTA CATGCTCAGC
54181 TAATTGCAAA AACAAATTTC TTGTTTTTCC TGGAATTTCT AGTACTGGCA CATTCAGTTC
54241 ATCATAAGAA GGTTTGAAAT ACTGGCTCAG GGGAGCATTT ATAAACTTCT CCTCAAACCA
54301 CCATATTTAC TCAAGGATCC AGTCCAGCCC CAACTATTTC TAAGGTTACA CGATCCCCTT
54361 TTTTCCAGTG AGAATCAAGG GGGTTGGTTA TTACTAGTTC TAAGGGGTTA CACTGACCAC
54421 TGGTACAGGA AGGGCCACTT TTCCCTTTCT GAAGGTGGAC AGGATTCTTT TTATTTTTA
54481 ACCAAGTTGC CTAAATGACA CAAGACCAGT ATCTACATTT ATTTCCACGC AGTCTTAATT
54541 CATGACAAGC GTACTTATTT TCTGCCATAT AGCCTCTTTC CTAATGAACA GAACCACATC
54601 CTATTTCTAA CTTATTACTA TTAATGACAG CACAGGCATC AAATTTCAAG GTGACTTGTT
54661 TGGGCATTCC TTTTCTTCT GTTTTGGCTA ACACTTTACT CGTATCGTTT ATGAACCCCC
54721 ACCAGTCCTC AGTCCTCAAT CTTATTTCAA AAACTGTGGT CGTGGGAGGC TCAGATGGGT
54781 CATAACACAC ATCAGGTTGG TCATTTCTTG GGCTACCTAC CTTGTATAGA ATAGCATTAT
54841 ACAAACAAGT TATTTTTAGA GTCTTTGTAC ACTTATAATA ACCATAAAAT AATAAGACTG
54901 TAGCAACTTT TTGTCCTACC TCAGTGACTT GATGTATACA CTGGGAACAG CCCTCAGTCT
```

```
54961  GAGGAAGGTT  AGTTGAAGTC  TTTACTGTGC  AAGTCCAAAT  TTTAAGGAAA  ATGAGTCCCT
55021  TGATGAGTTT  TCTCATGTTT  CGGCCATGCA  TGGACCAGTC  AGCTTCCGGG  TGTGACTGGA
55081  GCAGGGCTTG  TTGTCTTCTT  CAGTCACTTT  GCAGGCGTTG  GCGAAGCTGC  CACGTACAGC
55141  TCACAGTCTA  CTGATGTTCA  AGGATGGTCT  TGGAAGTTGG  GCCCACTAGA  ATTAACTGAG
55201  TCCAATACCT  CTACTCAGTC  ACTTTCAACT  GGGCTTTCTG  ATACCAGGAG  CAAGGTGGCA
55261  GGTTTTAGGG  TGTTGCAAAT  TTCAATGGTT  ATGCAGGGAT  TTTCACATAG  CAAACTTTGG
55321  TACTTGGTTA  ATCTAGCATT  TGTTAGCCAA  TGATGTATTT  ATTAAAGTCA  CCACAGCATG
55381  GAGGGCCTTT  AAGTTTAGGT  TTTGTCCAAG  AGTTAGCTTA  TCTGCCTCTT  GTGCTAGCAG
55441  GGCTGTTGCT  GCCAAGGCTC  TTAAGCATGG  AGGCCAACCC  TTAGAAACTC  CATCTAGTTG
55501  TTTGGAGGCC  CAGCCTCGGC  CAGGGCCCCA  CAGTCTGGGT  CAAAACTCCA  ACCGCCATTT
55561  TTTCTCTTTC  TGACACATAG  AGTGTAAAGG  GTTTTGTCAG  GTCAGGTAGC  CCCAGGGCTG
55621  GGGCCGACAT  GAGTTTTTCT  TTTAACTCAT  GAAAACTCA  TTGCTGTTGG  TTGTAATAGA
55681  TGTAGTTTAT  CCAATCTACA  TTTTTATTAA  CTGTCACCCA  CCAAAATATT  GACTCAAATC
55741  CTGCAGCTAT  TTGATTTTGG  GATTTAAATT  GATCTGCTAT  TCCCTGTGGG  ACTCCAATTG
55801  CATCTAAATA  GATGTGAGAG  TTGAAAGACA  CATAAGGGTC  TTCTCTTGCT  TTACGATGTC
55861  TTATTTTTCC  TCCCTCTGGT  TGATGAAATG  CTAGGGTGAA  AGGGATAGCC  AATTGGACTA
55921  AAGTACAAGT  GCCGCTCCAG  TTATTTGGCA  GAGTGCCCAG  TAAAGGTCCA  CCACAATACC
55981  ACCACACATC  CGCTTGGGGA  TGAACAAAGG  CTGACTGATT  GAGAAGCTCC  TGAAAATTCT
56041  TAAGCTCACT  GCATCCCTTC  AGGTCTCCAA  GGAATGCTAA  GTTCCTCCC  TGTCATGAGA
56101  GACAAGAAGT  GAACTTAGTT  TTGGGAGATG  GAAGCTGGAT  GGCCCTCAGG  GGTTGACCTG
56161  CAGGGTGCTG  GACTTTGGGA  TATAGCAGAG  AGAGCTTGGC  ACGACTTATT  ACTCCAGGCT
56221  GTAGAATCCT  GGAAAACAGT  TACCATGCAG  CCCATGCCTG  GTCAACAGGA  GGACCACCTT
56281  AGTGGAAAGG  GGATAATCTG  GCCCTCTGGC  CTGCCATGTG  CACAAGCATA  ACAATTGGTT
56341  TTGTTTAATG  TGTGGACAGA  ATATTTGATC  CATTCCAACT  GGGCATTTGC  ATCTTGGTAT
56401  CCTGCTTAAT  TATCAAAGTT  TGTTTTAAGT  CTTTAACTTC  TATGACCCTC  TAGTAAAATG
56461  AATGTATGAT  TTTAGGAAAT  TACAAAAACC  GGTTGGGGCA  GTCCATCCTT  GCTCTTTAGT
56521  GGTCCACACA  ACATTCGACC  AACTATGGCA  TAAAAGCTCT  ACATCGGGGG  GCAAGACTCC
56581  TCGTTGACAC  TGGGGTCTTT  ATTGAAATCT  CTCTGGAATA  AATGGTCTCA  GTTTACTAAG
56641  GCTCAGTCTG  AGGAGAGTCA  GGAGGGACAG  AGGTACTTTT  CTGAAGTACA  GAGATGTCTT
56701  CGACTTGGCA  AGTCCCCACA  GGGTATAACA  AGGCAAGCAT  TAAATTCAAT  AGTTTGAGGC
56761  AAAATTGACT  TGGTTATGTT  AATAACTAGA  TGGTCAGAAA  TAGAGTGAGG  GAAGAAGAAA
56821  GAGTAATAGA  ATAGATGAAG  GAGTTAAATT  TTTCTTAGCT  TTAGTTTGGT  AGGGTTTTCC
56881  CCTGGGACTA  TGGCCCATGA  CTCTGGAGGG  GGTGGCACTT  TCTTGACTCG  GGTGTGATGA
56941  GTCCATCCCT  TTTTCACCGT  ATGAACAACA  GTCTCGGTGG  TTAGCAGCAC  AAGGTAGGGT
57001  CCTTCCTAGG  CTGGCTCAAG  TTTTCCTTCT  TTCCACCCTT  TGATGAGAAC  ATGATCTTCA
57061  GGCTGGTGCT  GGTTTACAGA  AAATTCTAGG  GGTGGTACAT  GTGCTAAAAG  ACTTTTAGTT
57121  TTGAGGGAAA  GGAAAGTGGA  AGATAAACCA  AGTATATAAC  TTTTAAGAAG  TTGACCTTTT
57181  GTTTTAAATG  TGGGGACATC  AGCAGTGGAC  TTTATAGTCC  TTGGTGCCTT  CTTACTGAGA
57241  AATTTCCTTT  AGCACCTATT  TTTATTAGTT  TTTAGACCAA  AGAAAGTCAA  ATGCCATTTT
57301  ATATTTGACA  ACGCTTCTTG  TATGTTTATA  CCAGATAAGC  TAGATTTCAC  CTTTATATTG
57361  GTGTGTTATT  AATGTTAAAC  TTAGTTTTAA  TAAAACTCTG  TAGACATATT  TATTTGATTT
57421  TTAATGTCTG  ACCATAAGGT  AAGATTTTTA  TAGACTTTTC  TTTAACCTTT  TATAATTTTT
57481  GTTAAAGAAC  AGGTTAGTGC  TTTAAGAAAA  ACCCGTTGTG  TTTTTATTTT  AATGTTCAGT
57541  TCACAGAAAA  ACTGTATGAT  ACCCCTTAAC  TTTAGCCAAT  ATGTTAGAC  ACAGAATTTT
57601  CTTTACAATT  AAGGTTTCAA  AACTTGCTTA  AACCTTCAAA  ACAATTTTTG  TAACCTTTTA
57661  ATGTAGGTAA  AAATCCACAT  TCTTATGCAT  CCTCATAATC  CTTTTACCAA  AGGTATATTT
57721  TACTTTCCTT  ACATACCTTG  CACATAAACT  GTTTATTCAA  TAGTTTTACA  TTTAGAAGGA
57781  GGCCTAATTA  CTTTTAAATT  ATACAACATT  TCTTACATAA  ATTTATTTTT  CTAACACACA
57841  TTTTTTTCAT  GACTTTCACA  GACAATTCTT  CGACATGCCT  CAACTTTCTG  ACTTATTGCA
57901  AACATCCCTT  TCTTTAAACA  ACTAGTTAAT  TTATCTCAGG  ACAAGGATTT  TCCATACAAC
57961  ATTCTTTTTT  ATATAAATTC  TGCCTCCTCT  TTATTTCCTT  TTTTTTTTTT  CCGAGGATGA
58021  TAACCATTCT  TTTCCAAAGC  GAACTTCTTT  TATGTCTGTG  GACTAGACTG  TCTAAGGCCA
58081  CAAGATTAGA  AGTTACTATA  ATACATGTTA  CACTGTTAAC  TTTTAGCAAA  CTTTACTTTT
58141  GTTGAAAACC  TTGTAAGTTT  GGGATTTCAA  TTATCCTTTG  CTATTAATAA  GACCTTATTT
```

Figure 1 (Page 18 of 73)

```
58201 AGTCCAAATT AACTTAGAAT TGGTATAGAT GGCTTTTTTT TTTTTTTAAT TACCTGGGAG
58261 GAACCATCTA TCCTCCTGTC CTGAAGGGAG TTCCTCCTAG GTCTGGTCAG AGCTTTGTAT
58321 GGTAATTAAG ATTTAGATCC CCTGTTAGGA AACCTGCCGG GTTAAGAGAA TTTTCAGTGG
58381 TTAATGTTAA ATCATCTTCT TTTTTCTTTT TTCCTTAGGA TACTTCTGAA CCGGTGAGGT
58441 GTGCTCACAA TGAGGTTTCC TGTAAAAGTT ATTTTTTTAC TTTCTTCTGT TAGCAAAGCA
58501 GTTGCCGCTA CAGATTGAAT GCATTTGGGC CATCCGCGGG TTACTGGGTT AAGGATTTTT
58561 GATAGGAAGG CCTTAATGCT TTTGGAATAT GCCCTGACAA CAAAGTGCCA GTTCCTTCCC
58621 GGTGTTCAGC CACTGCGTTG ATCCTCCACG AGGGCCTGCC ACGTGCTGCT CTGGTGAGGC
58681 GTTCCACCGG GGCAATTGCC TACCTGGGAG CGCTCTCCAG ATCTGTGTCG CTCAAACTGG
58741 CTGGAGTTCC CCGTAGGGAT GCTCCACAGG GCAGGCCTAA GTCGCCTAAG GGGCTGCCTT
58801 GACCGTCCGT TAATCACCTC TGTCTCCAAA AACCAGCTCC CTGAGTGAGC AATTCCTGTC
58861 CCTTTTAAGG GCTTACAACT CTAAGGGGGT CTGCATGAGA GGGTCGTGAT TGATTGAGCA
58921 AGCAGCGGGT ACGTGACTGG GGCTGCATGC ATCAGTAATC AGAACAGAAC AGAACAGCAC
58981 AGGGATTTTC ACAATGCTTT TCCATACAAT GTCTGGAATC TATAGATAAC ATAACCTGTT
59041 AGGTCAAAGG TCGATCTTTA ACCAGACCCA GGGTGCGGTG CCGGGCTGTT TGCCTGTGGA
59101 TTTCATTTCT CCCTTTTAAT TTTTACTTTT TCTTTCTTTG GAGGCAGAAA TTGGGCATAA
59161 GACAATATGA GGGGTGGTCT CCTCCCTTAA TTTAAACAAA ATTTTCAAAG TCCTACCCCA
59221 AGTAAATTGG CAAATATTAA TAAAGTTATG GCATAGAAAA TAAAAATGAT TGTAAAAGGC
59281 GTAAAGATAT TTCTGTGGGG AAAACATTTG TTCATTAGTT ATCAGTTAAA ATTCTGTGAA
59341 AAATAACCAC TAGAGACCCT AAAGTACCCA GGGGCTAATA ATAAGAAGGG AGGAACACCC
59401 TCTCACTCCC CACCGTTACC TGCCCAGAAG GGAAGAGGAA GAGGGTGACT CCAGGAGAGC
59461 TGTGGTCTCC CCTCCCCATA TGTCCACATA TACCTGACCT CCCCTCCCCA AAATATATAC
59521 CCAATATCTC TCCCATATAT ACATATTTAT CTGACCTCTC ACATATGTA TACCTAAACT
59581 TTCTCTATAT ATCCACATAT ACCTAACCCT CTCACACACA TATAGCTGAC CTCCAGTGGA
59641 GGAAAATGGG GAAGAGAGAA GAAGTTATCA AAGGATAAAT CTAGGTCATA CTCAGAAATG
59701 TGAAAAACAA AAACCACACA CAGAAAAAAA AAACACACAC AAAAAAGAAA TTGATAAATT
59761 TGTTTGTGTC AAAATTAAGA ATTCCGGTTC AATGAAGGAT CCCATGGATA AAGTTAAGAC
59821 ACTGCTGTAA GGATGGTAGA GAATTAAATG TCTGAATCAG ACGAAAGGAT GAGTAATTAG
59881 AATGCACAAG GCCAAGAAGA ACAAAACAGA AACTCCACAT AAAAAATGTA TGAGGCCGGG
59941 CGCGGTGGCT CATGCCAGTA ATCCCAGCGC TTTGGGAGGC CAGGGCGGGC CGATCAGGAG
60001 TTTGAGACCA GGCTGGCCAA CATTGTGAAA CCCCATCTCT ACAAAAAATA CAAAAAATTA
60061 GCCGGGCGTG GTGGTGGGTG CCTATAATCC CAGCTACTTG GGAGGCTGAG GCAGGAGAAT
60121 CACTTAAACT CAGGAGGCAG AGGTTGCAGT GAGCTGAGAT CACACCATTG CACTCCAGCC
60181 TGGGTGACAG TGTGAGACTC TGTCTCAAAA AAAAAAAAAA TTATATATAT ATATATATAT
60241 ATATATATAT ATATATATAT ATATGAAATA AATGAACAAG AAATTTAGAT ACAGGAAAAT
60301 CCAAAGCACT TGGTAATGAA AGAAAGGTAA AGTGATGTGT CCTTTTGCAT TTAAAAGAGA
60361 GCATTAACAA ATTAGAGAGC TGAATAATGC TCAGTATTGG TGTGGATATG GAGACTCAGG
60421 AATCCTCATA CACTGCTGAT GGGAGTGCCC ACTCCCTGGG AATATTTTCC AAATATCATC
60481 TCAAACATAT CCCATAAAGG TGACAGGAAA GTGTGGGCTG ACTGATATCC TTCACTGAGA
60541 GAGGTGGAGG TAAAATGAAG TCACTGCACA ATATAGAGTT GGAAGCAATG GATTAGATGT
60601 CCACATAGTT ACGTGGAAGA ATCCGTAAGA TACACACACA CACACACACA CACACACACC
60661 TTTGTGTATA TTGTTCCTGG CAGGTAGGCA TGGAGGTTTA GAGGCTTTCT ACATCACACC
60721 TACTGCACAC AGTAAATGGC CAGGCTGAGC ACTGACTTCC ATGAAGGGAG ATTGAAGGTA
60781 AGAGATTGAA GATTGTTCCC TGGTCTGGGA CCCTGCAACT GAATATGCAG AAAAAAGTAC
60841 ACCCCGCCAC CCCGCTTCCC ATCTTTCCTA CCTGATTAGA ATAGCTTTTT CAGAAAACGT
60901 TGGCCAGGGG TTGTGGCTCA CACCTGTAAT CCCAGCACTT TGGGAGGCTG AGGCGGGCAG
60961 ATCATCTGAG GTCAGAAGTT CCAGACCAGC CTGGCCAACA TGGCGAAACC CCATCTCTAC
61021 TAAAAATATA AAAAATTAGC AGGGCATGGT GGCACACACC TGTCATCCCA GCTACTCGGG
61081 AGCCTGAGGC AGGAGACTCA CTTGAAGCAC AGTGATGGAG GTTGAAGTTA GCTGAGATCT
61141 TGCCACTGCA CTCCAGCCTG GCAACAGAG TGACACTTTG TCTCAACAAC AACAACAAAA
61201 CCCACCAAAA CTTTAAATCT ACCTATGGCC AAATGCCTGC TAAAATGAGC ACCCAAGAAG
61261 CAGTGTTCAG GAAAGTCAGA TGAATACCCT AAAATTAGAT GCAATGTTGG CTGGTCACAG
61321 TGGCTCAGGC CCTGTAATCC CAATCCTTCT TGGGAGGCCG AGGCGACAGA TCGCTTAAGC
61381 TCAGGAGATC GAGACCAGTC TGGACAACAT GGTGAGACCG TGTCTCTACA AAACGTACA
```

```
61441 AAAATGAGCT GGGAGTGGTG GCGCGCACCT GTAGTCCCAG CTACTCAGGA AGCTGAGGTG
61501 GGAGGATCTC TTGAACCCAG AAGGCGGAGA CTGCAGTGAG CAGAGATCAT GCCACTACAC
61561 CCCAGCCTGG ATGATAGAGC CAGACCCCCA TCTCCAGAAA AAAAAAATAA AGAGAGAGAG
61621 AGATGCAATA TTTAGGGTTC AACAAGACTG AATTTCTGAC TCCTTTCCCT ACCTCTCCAG
61681 CATGTTAGAT TCTGGGTCCT TCATCCTAAC CCCCTGTTCA TGCCATAGCC ACCCTGTGGT
61741 ACCAACTTTG GAAGCCTGGA TCTTCATCCC CTCATGATAA TGAGTGTCCC ATCAGGTCTC
61801 CATGCTCAGC TTGGCAAGAG TATCTGTCTT CTCCTCATGG GACGGTCACA TTCACCCAGC
61861 ACTGACAGGT TCCATTCCCA CTAGGGTGGC ACCCTATATG GTCTGAGTCC AGGCCTTCCT
61921 GGTCCCTCAG TAATCTCAGC ATGGTAGCAC AATCGAAAAG GGCTAGGCAC GGCAGCACCA
61981 TTTCCCACCA AGAGGTCTGA TGGCTCATCA CATAGACTGA AGGAGATTCT GAAGAGCAGA
62041 GGTGGAATGA AGAATGAATC GTGGGCTCTG CTCTTCCTAG GCCTGTCTTC CTCTCTCCCG
62101 AGATGTTAGC TAACTCATGA GAGCCAGAAA CCAACTGCAG GCTGGCCTCA GGCACTTAGG
62161 TAGTGCTTCA GCCTCAGCAG TCCACATTCT AGGAACCCTC ATAATATGGG TTGAAGTATG
62221 CATTCCCACA AAAATAAAGT TGTTGAAGTC CTAACCACCA GTACTGAAAT GGGAAAAGTT
62281 CCCTTGTCCC GCTCGCATGG CATGTGATAG GAGTGTGGCT AATTTCTTCA GTGCCTGGCT
62341 GCTCAAACCT CTAGGGGAAC ATTAAGACGG GCAGGTTGTG GGTCTCCAAC CCCATGACCC
62401 CACCACAGTG TCTAGGGTTG AATGTTACA GCTCCTGAAG CCACAGTGGG TGTGTGTTAC
62461 AGGGTGCTCT TTTAGTTTTG CCATTTATAG GCAGCTGGTG TTAACCAACT CAATTAGACC
62521 GTCTACCTTG TCCCAAGGAC AGAAGAAGGC TTTCTGTATC CCAGGTTCTT GCCTTGGTGT
62581 ACCGGAATAA ATCAGACCAC ACCTGGGCTT AGAGAAAGAG TGCAAGGTTT TATTAAGTGG
62641 AGGTAGCTCT CAGCAGTTGG GCAAAGCCAA AAGTGGATGG AGTGGGAAAG TTTTCCCTTG
62701 GAGTCAGCCA CTCAGTGGCC CAGGCTCTCC TCCAACCACC CCAGTCAAAT TCCGCCTCAT
62761 TTTGCCAGGC AAACGTTTGT TGTGTGCTCT TCTGCCAGTG TGCTCCCCTG GACGTCCAGC
62821 TATTCGTGTC TTGTGGCAGG CCAGGGAGG TCTTGGGAAA TGCAACATTT GGGCAGGAAA
62881 ACAAAAATGC CTGTCCTCAC CGTGGTCCCT GGGCACAGGC CTGGGGTGG AGCCCTAGCC
62941 GGGGACCACG CCCTTCCCTT CCCCACTTCC ATATCATTTA AAGGGACCAT GCCCTTCCCT
63001 TCCCAGCACT TTCCCCCTCC TGTATCAGGA CCTGTGAATG TGGCCTTATT TGGAAATAGG
63061 GTCTTTGCAC TTCATCAGTT AAGATAAGAG TGGGCTCTAA CCCAACATAA AGGGTGTCCT
63121 TATAAAAAGG AGAAATGTCA TACACAGAGA CTGACACCTA TAGAGAGAAA ATGTGGTGAG
63181 TAGACACAGG GAGAATCACC ATTCAAGTCA AGCAATGAGT CTGGGGATAC CAGAAGCTGG
63241 GAGAGAAACC TGGAACAGAT TATCCCTCAT TGCCTTCAGA AGGAATCAAA CCTGATGATA
63301 CTTTGATTTC AGACTTCCAG CTTCCAGGAC TGTGTGACGA TAAATATCTG TTGTTAAGCC
63361 AACGAGTTTG AGGTACTTTG TTACTGCAGC CCCAGAAAAC TAATACAGTA GGTACTATGG
63421 ACTGAATTGA CTCCCCGTCG CAAAATTCAT ATGTTGAAAC CCTAACCCCC AGTGTGATGG
63481 TACTTGGAGC TGGGGCGTTT GGGAAGTCAT TATATTTAGA CAAACTCATC AGGATGTGTC
63541 TCTCATGATG AAATTCATGC CCTTATTAAA AGAGACAACA GGCCAGGTGC AGTGGCTCAT
63601 GCCTGTAATC CCAGCACTTT GGGAGGCTGA GGTGGATGGA TCACCTGAGG TTGGGAGTTT
63661 GAGACCAGCC TGGCCAACAT GGTAAACCC CATGTCTACT AAAAATACAA AAATTGGCCA
63721 GGTGTGGTGG TGCACGCTTG TACTCCCAGC TACCTGGGAG GCTGAGGCAG GAGAATCCCT
63781 TGAAACCAGG AGGTGGAAGT TGCAGTGAGA TCACACCACT GTACTCTAGC CTGGGTGATA
63841 GAGACTCCAT CTCAAAAAAA AAAAAAAAAA AGACAATAGA GCCAGGTGCT GCAGCTGATG
63901 CCTGTAATTC CAACACTATG AGAGGCTGAA GCAGGAGGCT CGCTTTAGCC CAGGAGTTCA
63961 AGACCAGCTT GGACAAAATA GTGAGACCCC CAACTTCTAA AAATTTAAAA AATGAACTGG
64021 GTGTGGTGGT ACACATCTGA GGCTCCAGCT ACTCTGGAGG CTGAGGTGGG AGGATTGCTT
64081 GAGCCCAGGA GGAGGCTGCA GTGAGCCATT GCTGTCCAGC CTGGGCTACA CGAGAACCTG
64141 TCTCGGGAAA AGGAGAAAAC AGTGAGACCT CTTTTTCTCT CCTCCTTCTC TCCACTGCCT
64201 AAGCCCTACA AGCACAAAAA GGACACCACA TGAGCACATA GTGAGAATGC TGCTGCCACC
64261 AACAAGTCAG GAAGAGAGCG TTCACCTAGA AACTGAATTG GCCAGCACCT GGATCTTCGA
64321 CTTCTGAGCT TCCAGAACTG TGAGAAAGTT ATTTTTTTTT TAGCGACTAA GTCTATAGTA
64381 TTTTATTACA GCAGCTCAAG GTAACTAACA TAGTAGAAGG GATGAATTAT GGAGATCACA
64441 AGTCCACGCC TCCAGAAAAA GACTTCCCTA AAAATTAGTC TGAGCAAAAT TCGAATGATG
64501 AATTATTTTT AAGAACTTTT AAGGGATCTG ACAAGTTTGC AAGAGCTAGA GAATGCTTTA
64561 CAACGTGATA ATAGAATGCT CTGTGATGAC AGAAATCTTT CCACACTGTT CAAAACTAGC
64621 TACTGGCCAC TTGTGACTAT TGTGCACTTG AAATGTGACT GGTGTCTGAG GAGCAGAATG
```

Figure 1 (Page 20 of 73)

```
64681 TTTAATTTTA CTTAATTTTA ATTCATTACA ATAGCTACAT GTAGCTAGGG GCTACTGGAT
64741 TGAACAGCAC AGCTCGAGTC TTTTAGAGGG AGACAGGACT CACCAAGATG GATGCTGGTG
64801 GCCAAGCAGC AATGGCAGGT AGTACACACA CAAGAGGCAG ATGATACAAC ACATCCTTCC
64861 CAAACCTGGA GATAAGCTCA CCCCACAATC CCGCCGCTGA AATAGAGTTG ATGTTACCAA
64921 TGTGCATTTT TATGTCCTTT TCCATACAGA AAGATCATTC AGCAAGTACT ATGGTACTTA
64981 AAAAACAACA TTCAATTCAT TATTATGACA AAATTAAATT AATAGCTCTT CCTTAAACTT
65041 TTAAATTCAA TTTACAATGC TTACTATTGG CATTTATTAA TCTACCAATT TTTTCCCATA
65101 GAACCCATAG AACAAATAAT CTACCAAATT TTTAACATTC ATTTTTGGCA AGGCTTTTGC
65161 AATTTGACGA ACTTTAAGAA GAAAACTTAT AAATTGCAAT TTTTAAATCT GACATACTGG
65221 ACTTTTAAAG TATCCAATTG ACTAATGAAC AAAACTGCTC CAAATTTTTC AATTCTTAAA
65281 AATCTTAAGA CAATACTTAA TATGGCAAAT CTTAACTTCT TAAACTTTGT AAGAATGCTA
65341 ATCAACTTAG ATTGGTATAA AGTTGAGTTA AAAATCACAG GATACATCAT CTCAGCTATA
65401 AGTTTTCATG AGTTGAGTTT TTACAATCAC TTGAAATGCT TAGAATAGGA AATACGTATA
65461 AATTATTTAA CATAAAATAT TGTTACAAAA CCTCTGGAGT GTCAGTTTCT CTGGCCAGAC
65521 TTTATGCTGC AGCACCTTTG CCTGAGTTCT TGTCCTGCAT CCAGGAAGAA TTAGGTACAG
65581 AGGCAAGAGT CAAGAAGATT AGTTTTCCAA TAGTTCAGCT CACCTAGTTA ACTCCTGTTC
65641 ACAATCTTCA AAGTTATCAG AAACCTGCAA TTGAGGGTTA TAATCCATTC TTTGCAGAGT
65701 TTCAAAACAA GACAACATTT GTCTATGAAT GTTAAAATGT CCTAGGGTAG TCACAGTCAA
65761 AAACACAATT GACAAAGAAA TTTAGTCACC TCTGTGATTT ACAATAGCCT AACACAATAA
65821 CTCTAATTAT AACTGATGAC ACAAACTCAG ATATCAGAAC TCTAGAAATC CCCTATAATT
65881 TTGGAACACA CATTCACAGT TTTCACTGAA ATATGACCTG AAGATCAAAT ATCACCTTAT
65941 TTCAACAATC CTATATAACT AAACGTGTCA AATGATCCTG TTTACCTCTC CTTTGGATAC
66001 TCCAGGGGCC CTCTGTAGCA TCCAAAAGTT AGGGGTTAGC AAAGACAATT TTGAAGCTGT
66061 AAAGGCTCAA AACACTTAAT GAACCTCTAG TCATATCTGT TCTCTACTCA CTAAATGCTA
66121 GTAGCACCTC TCAGTTGTGG CTAAGCTGGG AGGATCTCTT GAGCCTAGAA GTTTGGGGAC
66181 GCAGTGAGCT ATGATTATGC CACTGCACTC CAGCCTGGGC AACAATGCAA AATCCTGTCT
66241 CAAAACAAA AACAAAAAC AAATTGCCTA TGCTGTGGTT ATCTCACAAT TAATAAAAAG
66301 GAAAAAAAAA GTATGCAGTC TTTGTAGGTC CTTGGGGTTT GTTGGAACTC AGAAAACAAT
66361 ACCCAAAAAT AAAGACCGCA GAAGCCAAAG TTTTTCTCTG ATCTTCTCCT GCCCTCCTGT
66421 CTCTGAGTCC CATTCTCCCC GGAGTCTAGC CATAGAAATG AGAATTCCTC TTCCTCAAGT
66481 TAGGTCATAG AAATCAAAAC ACCTTTTCCC CAGAGCCCAG CCATAAAACC TAAAAATATT
66541 ACTCTAACTT TCCCTCTGTT TTTCTGTGTA AAAACTGGCC ATAAAGAAAT TATCTGAACT
66601 ACCTTATTTG ATCATAGATC ACCAGACCGC ATTCCAGAGA GGATCCAGAA GGAAGGAATG
66661 CTGCACAGAG AGGCGAAGAA GAATCTAGAC AGACAGGCCT TGCTGGGTTT CCCTACTCTG
66721 TTATTAGCA ATCCTATTTC TACACGGCGG CCCATACTTT GTTGAATCTA AAAAATAAAA
66781 ATGGACAATT TCCCCTGTAC ATGTTAATAC ACATTAATAA ATTGGATATA AATTGGATAA
66841 TTTATTAATA TACACATTAA TAAATTGGAT GCAGCCGGGT GCAATGGCTC ACGCCTGTAA
66901 TCCCAGCACT TTGGGAGCTG AGGCGGGCAG ACCACGAGGT CAAGACCACC CTAGCCGAAA
66961 TGGTGAAACC CCGTCTCTAT TAAAAATACA AAAGTTAGCT GGGCGTGGTG GCACATGCCT
67021 GTAGTCCCAG CTACTGGGGA GGCTGAGGCA GGAGAATTGC TTGAACTCGG GAGGCGGAGG
67081 TTGCAGTGAG CCGAGATTGC GCCACTGCAC TCCAGCCTGG TGACAGAGTG AGACTCCGTC
67141 TAAAAATAAT AATAATAATA ATAATAATAA TAATAATAAT AATAAATTGG ATGCATTTTA
67201 TCCTATTAAT CTTCCTCTTG TCGGTGGTTT TCAGCGACTC TTCAGAGGCC AAAGAGTAAG
67261 TTTTCCCTTA GCCCTACAG GTTCTTATGT TTAATTTGTT ACTCTCATTT AAGACATAAT
67321 TAAAGTGGCT TCTCCATGAA GATTATTTCT GCATCCATTA TTTGGTAAGA TTGGCCGTTT
67381 TCTCCTTTGA TCTCTACTTC ACACTGACCC ACATAAAACA TCACTGCCTG TTTTTTTGTT
67441 GTTGTTGTTT GGAGACGGAG TCTTGCTCTG TTGCCCAGGC TGGAGTGCAG TGGTGTGATC
67501 TCCGCTCACT GCAAGCTCCG CCTCCCGGAT TCACGCCATT CTCCTGCCTC AGCCTCCTGA
67561 GCAGCTGGGA CTACAGGCAC CACCACCAA GCCCGGCTAA TTTTTGTATT TTTAGTAGAT
67621 ACGGGGTTTC ACTTTGTTAA CCAGGATGGT CTCGATCTCC TGACCTCGTG ATCGGCCCGC
67681 CTCAGCCTCC CAAAGTGCTG GGATTACAGG AGTGAGCCAC TGCGCCCGGC CCGTTTTTT
67741 TTTTTGGTTT TTGCATGTCT TCTCCCTTTT ACTGTAAACT ATTTCCACTA CCAGCGTAGT
67801 TATCATTTCT ACTGCTTAAT AATTGTTTTG GGGAAGTGAA TGCATCAACC CACATGAATT
67861 TCTTGTCTAT TTGACAATTT ATTCTCTTTA GGAATAGTAT TAACTCCTAA GGTCCTGGGA
```

```
67921 GCCAGTCTCT GTACTTGGCT GCTCCAGGGT CCTACTTCAG TTTCCCAGCT TCTCAGTACT
67981 GTCACTGTCA ATTGTGGGTA ATAATTATTT TTGTCCACCA AAAGACTCTG TATGTGAATG
68041 AGTTTTGAAA TCTGCTGAGT AATACAGTGT CAACCCAGTT AATGATTTGC CGGGCGGCTT
68101 GATCAGGGGC TGTCCAACTA CCGGCATTTT GATTTGGAGC GTCATCTAGT GTCTGAAAGC
68161 ACAAACAACA TCCTACATTG TAAATGCCTT TGGCTACAGA GATTGAAACC AAAGCAAACC
68221 TATGTTTTGA ATTGTTATTC TTCAGCAGTT CTGCTAGCTT TGAAAAATCT AAAAGTTAAA
68281 AAAAAGCTTT ATATTTCATT TTCTGCCTAA ACTCTTTAAA ATTGCTAGTT GACAATTAGA
68341 TATTTCAAT TTAATGAAAT TTTTTTTTAG TTCACAGATT AATACACAAT GGGGGAGGGT
68401 TCTTATTCTG TTGGACTTTT ACATAACCTC CACTTTAGTG CAGTCTGCTT TATGGGTCT
68461 TGTTTGAGGT GTGTGTGTGT TTAAGGGAAT GTGGTTACA ATCAAAATAT TGGGTTGCTC
68521 TTAGGCACAT TGTAAAGTCA CACACCTGTA TTCTTATTGA TACATAATGA TTAATAACAT
68581 TATTATTACA GCCTGATCAC CATCATTATT GATATATCTA AATAATGAAT TTTATAATTT
68641 TGCTTCCTGT CAGGCAAGAG CCAATTTCAG TGCTACCATG TTTGTATAGC AGTATTTATG
68701 TCTGTCATCC TCAGTCATTT TACTTCACTT GTTCTTAGCC AAACGGCCGA GAAGCGATGG
68761 TCATTTTACT TCAAAAATGA AAGAATTAA TATTTTTACG TTTCCCTTAA AGACCCTATG
68821 TTTAACCTCC ACTCCTGGGT AAAATGGTCT AGTCCCTCCT TTTCATATCA TCTCTGATAT
68881 CTTTTGCACA GCCACTATTA CCTACCGTTT TCTAGATCCC TATTCTTCAA ACACCACCAT
68941 GAAGGTAGAG CCTGTCTGAA TTATTTTCTT GTCCCTGAA CTCAGTACAT TGTTAGGCTT
69001 CTTGAAGATG TTGATCAGTT GTTTGTGGAG TGAATGAATC AGCTAGCATG ATTTTTCTAG
69061 ACCACTGAGA CAAGTGTCTA AGACACTTGT TCCTTCCCAT GTTCTTGCCT GCCTGTGCAA
69121 TCCATGCAGT CTCATGGCTT CCCAGTGCCT CAGAATTATC CCCTGTCAAA CAGGCATTAT
69181 AATTTCTGTC CACTGAAAAG GACAAAAAAC TAAGTGTATA GCTAGAAGTT AAAAATTACC
69241 GGCCAGGTAC TGTGGCTCAC TCCTGTTATT CCAACATTTT GGGAGGCTGA GGCGGGCAGA
69301 TCACCTGAGG TCAGGAATTC GATACCAGGC TGGCTAACAT GGCGACCCCG TCTCTATCAA
69361 AAATGTAAAA GTTAGCCAGG TGTGGTGGCT CGCACCTGTG GCCCAGCTA CTCAGGAGGC
69421 TGAGGCAGGA GGATCGTTTG AGCCCTGGAG GTTGAGGCTG CAGAAAAATA GGAATATACT
69481 CTCTTTCAAG AGTTCGTGGT TTTGACTGCC ACCTAGCGTA CATCAGAAAA ACCGCATGAC
69541 ATAGGAAATG CCTGTGACAG AGGGGTAAGG TGAGAGAGGT TGATGAAGAA TGTATTGAAG
69601 GAGTGAAAAC GCTTCCATCC CTCTACTTAC TAAATATATT AGTTAAGTAG TTGGGGCATA
69661 TTTTAATTCA TGCATTTTGT AGATAGAAAA ACAAAAGTTT TATTCTGTTT GATTTAGTTG
69721 ATACTTTAAT ATGTGTGTGT TTAGGATGCA TGATTATAA TCAGTCTGCA GCACTTCTTG
69781 GAGAAGTCTG AATTCTCATT CTCCATTTCC TTATTGGCAA CGTGAGAATG ATTACAATGG
69841 TGGTTGTCTC ATAGAATGCA GGGAGTCAGA ATGAAAATAG TCCATATAAT GCCTGGTGCA
69901 GAGGAAGGGT TCAGTTAACT GTCTGTATTA ATATTACTGA TAACAGTCAT GACAAACAAA
69961 AGCTTAACAA CAACACCACC AACAACAGTT GCAGAATTGA GCCACCAATT TGCACACAAG
70021 ATTGTAGGTA GGATGTTTTA GAAAAGTTAT TATTTAATAT ATGTATATAT TTTTGTACTT
70081 AAAATATGTC AGAGGTTGTT CTAAGAACTA TTTAAATGTT AACTCCTTAA TCCTCATAAT
70141 GACCCATGAA ACAGGTAGGC TTATTATTGT CTCTTTACAT GTGAGAACAC TGAGACACGA
70201 AAAGGTTTAT TAACTCACCC AAAGTCACAC AGCTGGTAAA ACGGCAAAAT TGAATTTGAA
70261 CTCAGACATT CCAGGTTCCA AGACAGTCTA ATTATTCTTT TGACTAATAT ACTAAGCTGC
70321 CTCTGTATTT TTCCTTGATT ACTTTGTAAA AGTATGAGGA AAATATAAGT GCTTCAAGTA
70381 ACCATGAAAA ATATAAACAA TCTATGTATC AACTGAAGCA TAATTACAAA TCCTTTGATA
70441 AGCAAACATA ATAAAATTT GATATCAATC AAAACTTTCA TGTAATGTAA GCAGGTTGAG
70501 ATGAATTCTA TAGTAAAAAA GTGCAGAGTG CTGGAATACC ATGCTCCTAA TATATTGGCT
70561 AGGCACACCT GCCTGCTATC AAAGGTATGC ACACACCTTG GATACAGAAA GTTGGGACTG
70621 GGTAGTTATG TGAGTGTCAT CAGAATTCTT TCCCACTTGG GAAAGAATTG TCCATCATAA
70681 GCTTGGATGA TGGACAAGGA GTGAGCTCCC AGAACAGTGA TGTGGGGATA CATCCTCACA
70741 TCACAGTGAG AATGAGTGTT CTAGACTGTT TACACACCTA CCACTCCTAA ATGCACACAT
70801 ATAATTGCTT GCACACACAC ACATACACAC TCATCTCTTC TCTGGTGGTC CAGCTCTATC
70861 TCTTATCATT AGGCTTCTTG GGGCTAGTAC CTAGGGCCTG TATCCTTTCA GAGGCAGCTA
70921 AGGGAAGCAC ACATAATTAG AAAGAATGAA CCAGCTTGTT GGATTTGGTC TCTTCGCATC
70981 CAGCCCTCCA AGTTAAGGAG AGTACCATCT TTCTTAGGGT CACCAAAGGA AAAAAAAAA
71041 AAAGAAAGAA ACAGAAGGAT ATCATACAGC AAGGATCTAA TGCAAATATG CCTCAAATGA
71101 GAGGCTACTG TGTGCTGATC CCAATCCCAG GAACTGTATG CACATTATCT AATTTAATCC
```

Figure 1 (Page 22 of 73)

```
71161 TCACTGTATT TCTGGGAGTA TTATTCCCAT TTTACAGAGA AGGAACTTGG CAGGGTAACC
71221 AAGCTCATGA ATGGAGAAAC TGGGATTAAA TATAAAGCTT CCTTGCTCCA GAACTGCTGT
71281 CTTTCTGCTC TTCCACACTA CCAGCTCAGC TGTGCTCTCT ACATGCAGGC AGTTTTACAA
71341 GTTTCAGATT AGCCTGGGAC TTCCAGGGTT TTGAATGGGT TAGGGAATGG GGAACTTTTG
71401 GGTTTACTTT CCATTTTTTC TTCATACATA TGTAATATAT AACATAAATC TATGGTATAT
71461 ATGATAAATA TATGGCTACA TATGAACTAT ATAATCACAT ATATGCATTA TAAATAAATA
71521 TTAATTTTAT AATATTTTAA AGGTTATCAA ATAAATATTA ATATAAATAA TTAAATAATT
71581 AATACTCAGC TTTGTTTTCC AAAGTGATAA ATGCCTATAT TTAGCAAAAT ATTTTTTGGA
71641 GGCCTGATAG TTTTTAGGAG TGTAAAGAAG TCCTGATATC TAAATGTTTA AGAACCACTA
71701 TTTTAGGCTG TTGTCTTCTG TCTTATTTTC CCAGCTAGAC TGGTAAATAC TTGAAGGCAA
71761 ACGTTTAGCC AGCACATTAA CATTTATGT TTTTATTCTT TTGTGCTCTC AGTGGCTGTG
71821 TCTTTTCTAT CGATTCTCA CACTGTATGA TGGTTATATT TGTCTGTATC TGTCCCACCA
71881 GGTATAAGTT CTTGAGAGGA CACACTGCTA GGCTGATCTT AGTTTTTATT ATTTCTCCTG
71941 GTGTCCTGTG CTTAACAAGT GCTCATTAAG TGTGTAAAAA CACAGCACAG TAAAAAACTA
72001 GACATTAAAA AATAATGTCA ACCAATCTAT TGAAATTTGC ATTTCCATGT TTCTTCCAAT
72061 ATAGTCATTG TGTCAGGTTA TGTACTTATT CTGATGAAGA CTATTGCCTA ATATACGTTT
72121 GCATCTTGTG CTTTATAACT GCCTTCATAT AGACACAGAT TGAGAAGGTG TAAAAATGTG
72181 CATATCCTCA CAATTGACAA ATTCTTATCC TTTGAGGGTA GGTTTGACTT TCTGAAATGC
72241 TTTGACATCA TTTGAAAGAA GCTTGAAGAA TAAGATAGCT GTTAATGACC CAGTTTCCTA
72301 TGTCACTTAT ACAATTATAA TGGCAATTTC AAAATGTTAG GTAAATATAT TTTGCAATAT
72361 ATTGTTCCTT TTGTAATACT CTCTATGTAT TTATTTATAT TTTTAAATTT TATATTTATG
72421 TATTTATTTT TCTGGACAGA GTCTTGCTCT GTTGCCCAGG TTAGAGTGAA GTGTTGTGAT
72481 CATAGCTCTC TGCAACTTCA AACTGCTTGG CAAAAGTGAT CCTCCTGCCT CAGCCTCATG
72541 AGTAGAGTAG CGGGAACTAC AGGCGCATGC CACTGCACCC AGCTAATCAC TATTTATTAT
72601 GCTCCTACTG TGTGCTTTAG TATATTTTCT GTTGTTTTCT GCAACCCATT TTGAGGGCGT
72661 GTTAGGGAAT ACAGATGCAG TAACTTTCGT CTCAGCCCTT GAGGTGAGGA AATATTTAGC
72721 CTCAGGTTTA ATCTAATTGT TGGCCATTTG CCTTCAAAGA TTGAAATATG AGCAAAACTG
72781 TGGCTCTGGG TTATATGTTA AAAAAAAGTT TATGGGGCTG AAGCCAGGCA ACAGACAAGA
72841 GCCCCTACAA TCTTATTTAG GCTGAAAATA TCCTGGAGTC CCTGTATTGT TGGTCTCAAG
72901 CAGATAGCAA CACTAACACT TACTCTTTGA GGCAGGCACT GCCAGTGGGG TGGCTGTTAT
72961 TATTAGCTTC ATTAATTGGT GAGTCAGGAA AAAACAGCTT TAAATCATTC AAAGTTCTGG
73021 CCTATACAGG ATTTAGTAAT ATTAGGTTAG CTACATCCAA AAGATGACAG AACCCTACTC
73081 TAAGGCTGGG CTTGGTGGTT CACACCTATA ATCTCAAAAC TTTGGGAGGC TGAGGCAGGA
73141 GGATCACTTG GTGCCAAGAG TTTGAGACCA GCCTGAGCAA CATAGTGAGA CCCCTGTCTC
73201 TATCAAAAAC AAAGAACTCT AATTGGCATA GTAGAAGGAA AAAGTGAAAG AAAAACCAGC
73261 TGTCACCCTC ATTCCTTACA CCTGTCCTAA CAACTCCTCT CACTATCCTT TGAATATATC
73321 TTGGCTGTTT GAGTCTCTCT CTAGCCCCAT TACTGCTGTT TGGACTTGAC ATTTTGCTCT
73381 GCATTTTTAA CTTTTCTACC AGGGTTTCCA GACCCTGAAG AGTGTGGCAT GAAACAAAAC
73441 TAGTCAACCT ATAATATTTA TGATGTGTGT GTAAATAAAA GAATACACAA TATATTGCAT
73501 TACAATATTT TAACTGTGTC CTCAATTTGT TTGTGGCTTT CTTGAGGACA TCAGTTTTGG
73561 GTGGGACGAC CACATCCTTA ATCTGAACTT TCCCTTGGAG GTCATTCTTT TTTTTTTGAA
73621 ATAGAGTCTC GCTCTGTCAC CCAGGCTGGA GTGCAGTGGC GCAATCTCAG CTCACTGCAA
73681 CGTCCGCCTC CTGGGTTCAA GTGATTCTCC TGCCTCAGCC TTCCAAGTAG CTGGGATTAC
73741 AGATGCACGC CACCATGCCG AGCTAATTTT TGTATTTTTA GAAGAGACGG AATTTCACCA
73801 TGTTGGTCAG GCTGGTCTTA AACTCCTGAC CTCATGATCT GCCCACCTCA GCCTCCTAAA
73861 GTGCTGGGAT TACAGGCGTG AGCCACCCCG CCCGGCCAGA GGTCATTCTA ATAGACTTTT
73921 TTTTTGTTGT TGCTCACAGG CTTGTTCAAT CTTATTTCAA AATTTGAGAA ATACAGTTTC
73981 CATGGAACAC CAACCAGATA TCAGGTTGCT ATGGAGTTGA TAGTCAAAAG CTTTGTATCT
74041 TCCAGTTTTT CAGAATGGCT TCTAAAGGTT CTGATTCAGA GCTCTTAGGC GAAATTGAAC
74101 AACCAAGTGT CAAAGTACAA CATTCAGGAA GTTAAAAACA TGACTGACAT ATATGTACTA
74161 TATATAGTGA GCTTGTGTAT GTGTCAATGA ATGATTTAAT TCATTAATGA AGGAGGAAGC
74221 AGAATCACAA TTAGGTCAAA GGAAGATACG GGAGAATAAA ATATGTATTT GGTCAGGGAA
74281 AGGATGTATA CTGGAAGAGG AAGGGAAAAT CAGATATAAA GTTGTTTAAT GACTTATTAG
74341 GCAATACAAT AATAACTTTT AGGGTCATTT TTTCTATATT AAGAATTCAT TTCCATCTCT
```

Figure 1 (Page 23 of 73)

```
74401 ATGACAAAAT CCTTATTAAT TTATTAAACT TCTACAAGTG AATGTTTACT TTTAGATAGT
74461 CTGGACCCAA TAAAATGTAA ACATTAAGTC AGAGTTACTT TCACGTAGGA CAGTGTTGTC
74521 CAATAAGGTA CCACTAGCTA CACGTGATCA TTGACCATTT GGACTATAGC TAGACTGATT
74581 TAAAATGTTC TAAAAGTGTA AAATACACAC CAGGTTCTGA AGATTATCA TTTAAAAAAG
74641 AATGTCAACT GTCTTTTTTT TTAGCTTATT TATTATATGT TGAAGTGATA ATAGTTTAGA
74701 TATATTAAGT TAAATAAAAT ATCTTAAAAT TAATTTTACT TGTTTCTTTT CATTCTTTCA
74761 ATGTGACCAC TAGAAATCTG GAAAGTATTT ATGTGATTCA CATTCTATTT TACTGTCTAG
74821 TATTGCCTTA CATCATCAGG TACCCCATAA GTAGGCTTTT TAGATAATTC TCTAATATAG
74881 CTTGGAAGGA TATGGAGAAA TATTTTTGCG TTGCTTTTAA GTTTTGCATA ACTTTTTCAA
74941 CACACTTTAT AAAGGATCTA GAAAAGGGTT GGTTACATGT TTCTCTGTCT TCTGGCCTCC
75001 ACCATGTTGC CAGGAGGTTG GGGACAAGAT TCTGGGTGGC TGGATGTCCT AATGGCTTGA
75061 GGTCTGGACT TGAGATTTGC ATATAAAGAG ATGTGATTAG ATTGAGTCGA CTAGAAAAAT
75121 CATATTAGAG AACTGAATCA CAGCGATTAA ATTTACATGT CGATTTATAA ACCAGGACAC
75181 CAATTTATAG TGAAAGAAGG TCCAGTTACC TGGTAATCAA GACGTTTCAT AGCTATTTTC
75241 ATGATGGATA TACTTAGCTG AGTTTTAAAT GAGAAGGGGG TTCATTGCAC ATAGAATAAG
75301 ATCTAAGTGA AATGTTTATT TTATTTTTT TTTTTGACA TGGAGTCTTG CTCTGTTGCC
75361 CAGGCTGGAG TGCAATGAGG CAATCTCGGC TTCTGGAGTG CAATGAGGCA ATCTCGGCTT
75421 CTGGAGTGCA ACGAGGCAAT CTCGGCTCAC TGCAACCTCC ACCTCCCGGG TTCAAATGAT
75481 TCTCCTGCCT CAGTTTCCTG AGTAGCTGGG ATTAGAGTTG CCTGCCACCA CGCCAGGCTA
75541 ATTTTGTAT TTTTTTTAGT AGAGATGGGG TTTCACCATG CTGGCCAGGC TGGTCTCGAA
75601 CTCCTGACCT CAGGCGATCT GCCCGCCTCA GCCTCCCAAA GTGCTAGGAT TACAGGCGTG
75661 AGCCACCAAG CCTGGCCTAA GTGACATGTT CTTATATTGT TCCTTTCTTT CTTTTTTTT
75721 CGACTGAGTC TCACCCTGTT GCACAGGCTG GAGTGCAGTG GCGTCATTTC GGCTCATTGC
75781 AACCTCTGCT TCCCGGGTTC AAGCGATTCC CTTGCCTCAG CCTCCTGAGT GCCACCACCC
75841 CCAGCTAATT TTTGTACTTT TAGTAGAGAT GGTGTTTCAC CATGTCGGCT AGGCTGATCT
75901 CAAACTCCTG GCCTCAGGTG ATCCGCCCCC GAGTCTCCCA AAGTGCTAGG ATTACAGGCG
75961 TGGGCCACGG GGCCCAGCCT TATATTATTT CTTTTACTAC AATATATTAG TATGATGCAG
76021 GTGCTTCAAT TGTTTATACA CTTTCCATAA TTTTGTATAA TTCTTATACC CTGTCACTCT
76081 GAGGAATAGC CGGTCTAAGT GTTTTTCCAC CACTGCTAAT TCATCCATCA CTAATCTCAT
76141 TAGACTGTTA ATTCCCAGAG GACATAAGCA CACAAGCAGA CAATGTTTAC AAATGTTGGA
76201 CAAATGTTAT TTAATAAAAC AATGGGGTCA CCCTTAGTCT AAAAGATGTT TCACTTTTCA
76261 TTTGTCATTG AACTCTTATT TGTAGGTTCC CTTTTGACTT TCCCACAATC TAAGGCTGTT
76321 CTCTTTAACA CATATTTTCA TGAAACATA TATTTGAGCA GAAATTGTTG GGGAGTTGTA
76381 ATATTACCTT TGTCCCTAAA TATGAATCTA TAATTATATC AAATATATGG GCAGACAATT
76441 TACTTTGCCT TTAATCTCAA GAAAAAAATA GCAATTACTT GGGGTCGGAG AGTAAAATAA
76501 GAAGTAGTGA ACCTTAAAGT AGCAAACTTT AGAACAGAAT AGTTTCAGAG GGGATGAGAA
76561 GAGGTGATTT TTCAGCTCAT CAACAACAGA TCTTATAATA AATTACATGT TCTGGTACTT
76621 TTCTTGTCTT TCTGTGTTAA ATTTTGCTAT TTAAAAAAAT AAATTTCAAA TACATTGTTC
76681 ATCTTAAAAG TCAAGAGTGT GTTTTATTAA AGTCAGTTGC TTTATTTGCA ACTCAAAAGA
76741 TATATTTGAG TTCCCAACTG GAGATTGTCC TATATGGTAA CTTGCGTAAG GTATGGTTAC
76801 TGAAAGTAAC CTACAATTTT CATGGGCTGA AATTCATTTC TATATTGCAG CGTACAAAAA
76861 TAAATAAATA AAAAATGCTT GTTTTCTTTG AAAACATATT ATCTCAGTGC CTCTAACTGC
76921 CAAATCTATT GGCTTTTTTG CAGGCTTAAG GGCTCTCCCT TGTTCCTTTA TGATCTCTAT
76981 CTTGAGGGCC AGACCTCCTG CCTTACACAA CTCAGAGGGG GACCTCAGAG CTCTTTAAAA
77041 AGAGCCCAAT TTCTCGCCTG TAGAGAAGTG AAAAGGATGC CCCACCCCCA TCTATGAAAA
77101 GAGGGATTTG ATAGTTTCAA TGTCTTCAAA TCAAAGATTT AAGTCTGTAG CCCCCCACCA
77161 CCCCGGACCC TAGCAAGGCT CATGAACCCC CTCCCATCCC GCCCTAATTG CTTTGGACTG
77221 GCCGTGGAAT CCTTGTCCCA GTCCACAGTT CCTGTGCGAC TGCACGAAGA ATTCACAGAG
77281 GACCTGTGTT ACTTCCCTTG TGAAGAACA GAATTATCAT GAAAATTTAG GTGGAAACCA
77341 TTTCGCTTTT TTCTTCAAAA ATAAGGGAAG CATGTGCCCA ACCACCCCTG GGAAAAAGAA
77401 CCTTCAGGGG CAAAGGAGCG AACAGGTAAT TTATAAGAAA AACAGAAAGT GGTCTCTGAC
77461 TGCCCCAGAC TTCCTTCGGA GTTGGGGGAA TTGGGGACGC CTGGACGCGT TGTTTTTGTG
77521 TTTGTGGAAA AAATAAATGA AGAGCATGAA GCCCGAGGCT TCTGAGATCC TTTCCTGACC
77581 AAACCCAAGT GATTTGGTGC GGGGAATTTT AATATTTTTC CCCTTTTGTG AGGTGGAACA
```

Figure 1 (Page 24 of 73)

```
77641 AACACAACTT GGGAGCAGCG CAGCGGCTCA GAGCCTGCCA GCCAGGCGGG CGACCAGAGC
77701 ACCAATCAGA GCGCGCCTGC GCTCTATATA TACAGCGGCC CTGCCCAGGC GCTGCTTCAT
77761 CGGCGCTTTG CCACTTGTAC CCGAGTTTTT GATTCTCAAC ATGTCCGAGA CTGCTCCTGC
77821 CGCTCCCGCT GCCGCGCCTC CTGCGGAGAA GGCCCCTGTA AGAAGAAGG CGGCCAAAAA
77881 GGCTGGGGGT ACGCCTCGTA AGGCGTCTGG TCCCCCGGTG TCAGAGCTCA TCACCAAGGC
77941 TGTGGCCGCC TCTAAAGAGC GTAGCGGAGT TTCTCTGGCT GCTCTGAAAA AAGCGTTGGC
78001 TGCCGCCGGC TATGATGTGG AGAAAAACAA CAGCCGTATC AAACTTGGTC TCAAGAGCCT
78061 GGTGAGCAAG GCACTCTGG TGCAAACGAA AGGCACCGGT GCTTCTGGCT CCTTTAAACT
78121 CAACAAGAAG GCAGCCTCCG GGGAAGCCAA GCCCAAGGTT AAAAAGGCGG GCGGAACCAA
78181 ACCTAAGAAG CCAGTTGGGG CAGCCAAGAA GCCCAAGAAG GCGGCTGGCG GCGCAACTCC
78241 GAAGAAGAGC GCTAAGAAAA CACCGAAGAA AGCGAAGAAG CCGGCCGCGG CCACTGTAAC
78301 CAAGAAAGTG GCTAAGAGCC CAAAGAAGGC CAAGGTTGCG AAGCCCAAGA AAGCTGCCAA
78361 AAGTGCTGCT AAGGCTGTGA AGCCCAAGGC CGCTAAGCCC AAGGTTGTCA AGCCTAAGAA
78421 GGCGGCGCCC AAGAAGAAAT AGGCGAACGC CTACTTCTAA AACCCAAAAG GCTCTTTTCA
78481 GAGCCACCAC TGATCTCAAT AAAAGAGCTG GATAATTTCT TTACTATCTG CCTTTTCTTG
78541 TTCTGCCCTG TTACTTAAGG TTAGTCGTAT GGGAGTTACT GAGGTATCAG ACGAATTGGG
78601 TGACGGGGTT GGAGAGTGGC CGTGGTGAGG TTACAGCATT TAAACCTTTA TTGCGGCTTC
78661 TAGGTCCCTG ACCGGAGGCT TTTCTCGCTG GCGGATGGTT TTGGGATGGC AGTCCCGCCC
78721 CAGGCCTGTG AACGGCAGAA AAGACCGCAA AACAAGAGCC AGTTCTTAG TCTAAAGGGA
78781 TGTCCGGATT GGACTAAAAA ATTTTCAAAA GTCCCGCCCT GCTCCCGGGT TGGTCCGTTC
78841 TTCTAGTACA TGACTTTCAT TCTGTATTTA ATTGGATGGT GGAAGACGTT GCTTATTCTG
78901 TGTTTTTTGC TTTACTGTGA CTTAAAAGTT TTGCCTCTTT TCTCTTTATA TTAATGTCTG
78961 GGATTCGGA CGCTTTCCAT GTTGTTGGTA GTCAAGTTGA TGTCTCCTGG AGGTAGTGGC
79021 AACATCCAGC CCTGGGAGGA GAGTGCGTGC AGGTACCTTT GTCCTACATT CCTCTGCTGT
79081 TAATTTCTCA TTCCTGTGGC AACGAAGGAA TGCATTTAAA AAACAGCCAC AACAGCGGCA
79141 ATAGCCCTTC CTCCACCCAA GGCAATCGTG GACCTAGGGA GTTTTTGTG CCACATAACA
79201 TGTAGCCTTC CGCTAAACTG ACAGGTTTGA GCGTATCGAT TTTGAGCGTA TCGAAAGCAC
79261 AACTTTTAGC CAGCCATTTT GTCCTGCAT GACTACGGTT GCTTATCCTG TTTAGACAGA
79321 CAGCAACATT TAAAAATCGA AGTTCCTTTA AACGTATTTT GTTTGGCAGT CCAAATGTTT
79381 CTATGCAGAA AACAGTATTT GTACTATTAA CTATGAAGAG TGTATGGATA AATGGGAGAC
79441 ATTTCTAATA AAGGCCTTCG TTAATGGTTC CCTCTGTTTG ACATCCATGG TGCTTCTGAA
79501 TACAGAAAGC CTAGCGTCTT ATATTCGCTT CTTTTAAAAT CTGGTGGGCA CATTTTGGTG
79561 AGACCTAAAT TATGGGGACT GGGGCTTCTG GAGATAAGCT GCTCAATTAT TCTACCATCT
79621 CCACAATGAT TAATATAGTG AGTTGATTTG TTAGTGATAG TGACCACGGA TTCATCCCAA
79681 GAAAGAGAAA GGGGAGGGAG GCAAGCAGAG AGACAGGAAG ACAGAGGCAG GAAGAAGGA
79741 GAAAACATTC TCCCATGGTT TAAGTAATTT TGTGTTGTTA ATTTTACATT ACAACACGGT
79801 TTAACATGGT GAACCCTCTA TTTTGGTGTA AGGTTTAACA TATGGACATA TTTTTCCCAA
79861 GACCATTTAT GAACTTTCAT TTCTGCTTCC CCCTTCTTCC TCCCGTGCCA CCCTCCACGC
79921 TCCTATCAAT TTTGGCTGTT TTGTCATAGG CTAATACGCT ATAATTTCAT GGACAGTTGG
79981 ACTGTCTTAG GTTTCTCAGG TTTCTATTTT GTTCCTTTAG TCATTCCCAC AATTCTTAAG
80041 GTAGAATTGT ATTGTTTTAA ACATTGTGTT GTGTGCTATC CTCAATGCTG AGATGATTAT
80101 GTGACAAATG GCAAGTGTTC AACTAATACC TAAATCTGTA GTATCTTATC AAGCCTAATG
80161 CTACTTCACA ATGCCTACTC CATTCACCTC ACTTTATCTC ATTACTGGCA TTCTGTCATC
80221 TCACATCATC ACAAGTAAAA CGGTAAGCTA TTTTGAGAGA GATCACAGTC ATATAATTTA
80281 TATTTATATT TATTTATTTA TTTATGAGAC GGAGTTTCCC TCTGTCACCC AGGCTGGAGT
80341 GCTGTGGCAC GTTCTCGGCT CACTGCAACC TCCGCCTCAC GGGTTCAAGC GATTCTCCTG
80401 CCTCCGCCTC CCGAGTAGCT GAGATTACAG GGCCTGCCA CCATGCCCGG CTAATTTTTG
80461 TATTTTTAGT AGAGACGGGG TTTCACTAAG TTGGCCAGGC TGGTCTCGAA CTCCTGACCT
80521 CAGGTTATCC GCCCACCTCA TCCTGCCAAA GTGCTTAGAT TACAGGCGTG AACCACCGTT
80581 CACAGACTCA AATCATTTT ATTACAGTAT ATTGTTATAA TTGTTGTTTT ATTATCAGTT
80641 ATTGCTAATC TCTTACAGTG CCTGATTTAT AAATTAAATT CATCATTGCC ATGTGTATAT
80701 AGAAAAAAAC AGTGTATATA CGGTTCAGTA CTATCTGTGG TTTCAGGCAT CCACTGGGGG
80761 TGCAGTTTAT TAAACATGCA TTTACATTAG TCTCCCCTTT GGGAGACTAA TTAACTGAGA
80821 TGTTGTAACG TGACTTTAAT AGCAGATAGA GCTAATTTTC TCTCATTACT CTTCTTTTTC
```

Figure 1 (Page 25 of 73)

```
80881  AGAATTTTCC TGGTTATTCC ATTTTTTATT TTTCCATATG TATATTAAGA TCTCTTCCAC
80941  CTCCTCCTGT TTCTCCATCT CAACATCAAA CAATTAAAAA AAAAAAAAAG GCTGGGCGCG
81001  GTGGCTCACG CCTATAATCC CAGCTCTTTG GGAGGCCTAG GCGGGTGGAT CACGAGGTCA
81061  GGAGTTCAAG ACCAGCCTCG CCAAGATGGT GAAATCCCGT CTCTACTAAA AGTATAAAAA
81121  TTAGCCAACC ATGGTGGCAG GCGCCTGTAA TCCCGGCTAC TCGGGAGGCT GAGGCAGAGA
81181  ATTGCTTGAA CCTGGGAGGC GGAGGTTGCA GTGAGGCGAG ACCTTGCACT CCAGCCTGGG
81241  TGACACAGCG AGACTCCGTC ATAAAAAAAA AAAGCCGGAA GCAGTGGCTC ACGCCTGTAA
81301  TTCCAGCACT TTGGGAGGCT GAGTCAGGCA GATTACCTGA GGTCAGGAGT TCAGGACCAG
81361  CCTGGCCATG AAAATACAGC CTGGCCATGA AAACACACAA TAAATTAGCT GGGCGTGGTG
81421  TCACACACCT GTAATCCTAG CTACTCGGGA GGCTGAGACA GGAGAATCAC TTGAACCCAG
81481  GAGGCAGAGG TTGCAGTGAG TTAAGATGAC GCCACTGCAC TCCATCTGGG CGACAGAGCC
81541  AGACTCTCTC TCAAAAAACT AAATAAATAA AAATAAAGTT ATGGTACATT GAACTTCTGT
81601  GTTCCTTTCT CCCTTAGATA CTTTCATGGC TACCCATTTA ATTGATGTTC TTATCATCTC
81661  CAAGAGTTAG TCAGGAGAGG AATCAACCCA AGCAAAAATA GCTGATTTTC TAATTTTCCT
81721  TCAATGCCCT TTGGGGTCTT AATCCATTTG ATTTATGTAC TTTCAATTAA TCCTAACCTC
81781  GAATGTCTTC TGCAAACATG TTTCCACAGA TGAAACTCGT CAAATGAAAC ACATTCCTTT
81841  AATTTATAGA GTTAAAAATT AGAAAATTT TCAATTCTAT TTGGCCTTTA GATTCAGTCT
81901  TGCATATGTT TTCTCAATTT TGTTCATGCT CTTTAGTTTT GTTTTATTCC ATCACAATTG
81961  TTCACATAGC TTACTGGCTT AGGTCTAATG AACCATTCAT TTGGAAATTA AAATTGGCCA
82021  TTTTAAGATG AAAAAGATTC TTGCCTCAAT TTTACTTAGT TTTTGAAACT GTCAATGAGG
82081  ACACATGTTT TTCTGTACTC TTAGATTCAC TAAGTAGTGT CTTGCAAATT TAACTGACAA
82141  AGGACAGATT AACATGCGAA AAAAAGAGCA TGCAATTTTA TTAGTATATT ACATGCACAG
82201  AGTTCCCAAA GAAAAAAAAA TTGAAACCTT AAAAACGCGG TTAGACTCAC AGACTTATAC
82261  ACCATTCCAA CAAAGGAAAG GGAGTTTGCA CTTCATGGGA TGACGAATTT GGGAATGTGA
82321  CAAGGAAATA AATACATGGG CAATAAAAAC CATGGAAGAT AAAATGAAAG ATAGAAATAA
82381  TTGTAGTAAG GTTTGTTTTT GCAGAGTCAT CTCAGTGCCA ACCTTCCATA TCTAGTGATA
82441  AGAATTGCTC TCTTTTTCCT GGTATAGCAG TTGGGGACAC TTTTACAAGG GAAATTTCTG
82501  TCACCTTCAC AAAGGGAAAT TTGGGTAAAG AGAAGACAGA GACCTCTTCC TACACCTGTT
82561  GATTTTCAAT TGCCTTCAGC TGAAAATAAC TTTTATGCCA AGTAGAATA ATTTGGGGGT
82621  GACATCCTGA TATTCTTCAA AACTTATATT TAATTTCACA TTAGTAATTA TATCATTTTT
82681  GATTTTTAAA TTAGTTTTAT AAAATAATTT TGAAAACGG TAATAATATT CAAATAATTC
82741  CAGAAACACT GCTGATAAGC CAAAACATC AATGAATATT GCATAAACAA CTGATAATTC
82801  AACCATGAAA ATTTATGACA TTGTTCTTGT GTGATAAAAC TATGAGTAAC ATAAAAACTA
82861  GAGGCTACTT GTAATGCATT ATTCCAAACT TTCTGTTTTT TATTTATTTA TTTATTTATT
82921  TTGAGACATA GTCTCTCTCT GTCACCCAGG TTGGAGTGCA ATGGCGTGAT CTTGGTTCAC
82981  TGCAGCCTCC ACTTCCCCGG TTCAAGCAAT TCCTGCCT CAGCCTCCTG AGTAACTGGG
83041  ATTACAGGCA CCTGACACCA AACCCGGCTA ATTTTTTGT ATTTTAGTA GAGACGGGGT
83101  TTCGCCATGT TTGCCAGGCT AGTCTCGAAC TCCTGACCTC AGTGATCCAC CTACCTCGGC
83161  CTCCCAAAGT GCTAGGATTA CAGGCGTGAG CCACCATGCC CGGCGCATTA TTCCAAACTT
83221  TCATACACAG TGCTATCATG GCTACAAATT GAAGTATCAT ATTATACACT CCTAGGCAAA
83281  GCTCTGGATA TTTTGGCTAT ATAAGCCTGA GGGAAATGTA GTAAGGACAT TGTGGTTGAA
83341  ATTCATACCA GAGATGAACA GGCCCAGTGC AAGACAGAAT TACATCACTA AAGGATATCA
83401  GAAGAGAATA GGGATTTAGG GTACAGTGGC AACAACAGTT TTGGGAACTA GCATTTTTTG
83461  AGCACTTATT TACAATATGC CAAGCACTGT TGCTGATTAC TCTATATTTA TTTTCAAACA
83521  CATTCTTGTC ACAGCACTTT GAAGTAAGTG CCATTGTCAT TCCCACTTCA GGGTGAAGGA
83581  CTAAAGCTTG GTGTCATTAA GGATGTAGCT AGTTAGCTGT GTGTGTGTGT GTGTGTGT
83641  GTGCATTTTT TTTTAAATTT AAAGTCAATA AATTTTATT TGAAGAATTT CACATCAAGG
83701  TAAACTTTGT TCCTCTAAAG AGCTGGAGTC AAAATGTATC TTCAAAAGAT TCATCTTCAA
83761  GTTAGCCCTT CTTAATAGAA CTGATGCTTA ATCCACAGTT GTCAGCCCAC AGTTCTTTTA
83821  TTTTGACTTT TTTTTTTTTT TTTTTTGAG ACGGAGTCTC TCACTGTCAC CCAGGCTGCT
83881  GGGCAGTGGC GTGATCTCGG CTCGCTGCAA CCTCTGCCTC CCGGGTTCAA GTGATTCTCC
83941  TGCCTCAGCC TCCTTAGTAG CTGGGACCAC AGGCGCATGC CATCGTGCTC GGCTAATTTT
84001  TGTATTTTTA TTAGAGACAG GGTTTCACTA TGTTGGCCAG GCTGATCTCA AACTCCTGAC
84061  CTCATGATCC GCCTGCCTTG GCCTCTCAAA GTGCTGGGAT TACAGGTGTG AGCCACTGCA
```

```
84121  CCCGGCCTTA  TTTTGCCTTC  TTTAATCTCC  ATTTGAACAT  ACACATACTG  ATGAAAACTA
84181  CAACATTCTT  CACCAAAAAT  CTTTGGGATT  TAATTTCTTC  AACCACTTTA  CTTTGGGGTC
84241  ATTTTAAGAT  TAGGTGTATC  TGCCTGGTTC  TCAATTTGAC  ACCCTTTCTC  TCTAAACATG
84301  AATGAGTTCC  AATCATATTT  ATTCCTAAGC  TATCACACTC  AAATATACTA  CAGATCTGTG
84361  GAATATGCCA  AAAGTTAAGG  TGAAAAATTA  AATTATTAGG  TATTTCATAG  TTTTGCTAGT
84421  TTTTGATCTG  TGAGTGAATA  TAACTATCCT  CTATGTCCTG  GCACTGTTCC  TCAGAAACAT
84481  AGGGTCCACA  TATGTAATTT  TAAATTTTTT  AATAGGCACA  TTTTAAAAAG  TGAAAAAGA
84541  AATCTATTTT  AATGATTTGA  ATCCAGTGTA  ACCAAAAATT  GTTTCAACAA  GTATCTAAT
84601  ATTAAAATAT  TGAGTTTTTA  CTTTGTTATT  TTACTAGTTC  TTTGAAATCT  GGTGTGTATT
84661  TTACACTTAA  AGCACATCAC  AGTTTGGAGT  AGCCACATTT  CCAATGCTTA  ATACTCACAT
84721  ATGGTTAGTG  GCAACTATCT  TGGACAGGAC  AGCTTTTATA  CTCTGGGAAG  ACACAAGCAA
84781  ATACTTGCTC  TGCAGCAGAA  TCCAGATGTT  TTCCAAGAAA  ACACTTTTTC  TGACCTGTTC
84841  CTGAAACCCA  GGTAGTGTCT  CTAATACTTT  ATATTTTATT  GGTTTGTCCT  ATTGTAACCA
84901  CCCAACGGGC  TCTCCTTGTC  CACTTCCTAG  ACAGAGCTGA  TTTATCAAGA  CAGGGGAATT
84961  GCAATAAGGA  GCCAGCGCTA  CAGGAGACTA  GAGTTTTATT  ATTACTCAAA  TCAGTCTCCT
85021  TGAGAATTTG  GGGACCAAAG  TTTTTAAGGA  TAATTTGATT  GTAGGGGACC  AGTGAGTCGG
85081  GAGTGCTGCT  TGGTTGGGTC  AGAGATGAAA  TTATAGGGAG  CCTAAGCTGT  CCTCTTGTGC
85141  TAAATCAGTT  CCTGGGAGTG  GTGGGGTGGG  GGACTCAAGA  CCAGATAATC  CAGTTTATCT
85201  ATATGGGTGG  TGCCAGCTAA  TCCATTGTGT  TCAGGGTCTG  CAAAATAGCT  CAAGCATTGA
85261  TCTTAGGTTT  TAAAATAGTG  ATTTTATCCC  CAGGAGCAAT  TTGAGGTTTA  GAATCTTGTA
85321  GCTTCCAGCT  GCATGACTCC  TAAACCATAA  TTTATAATCT  TGTGGCTAAT  TTGTTAGTCC
85381  TGCAAAAGCA  GTCTGGTCCC  CAGGCAGGAA  AGGGGTTTGT  TTCTGAAAGG  GCTGTTATTG
85441  TTTTTGTTTA  AAAGCAAAAG  TATAAACTAA  GCTCCTCCCA  AAGTTAGTTA  ATCCCAAACT
85501  CAGGAATGAA  AAGGACAGCT  TGGAGTTTAG  ACGTTAGATG  GAGTCGGTTA  GGTAAGATCT
85561  CTTTCACTGT  AATAATTTTC  TCAGTTATGA  TTTTTGCAAA  GGCAGTTTCA  CTGTCCACTT
85621  CACCTCACAT  CAGGCCTCTG  ACTAGAGGAT  TCCAACAATA  CTTAGGCCAG  GACACCACCA
85681  TGTCTCCTTA  TCCACCCTGA  GGGAGTCCAA  TTTCTGAAAC  AAAGGAAACT  ATATATGATA
85741  GTATGAAACT  ATATATGAGA  AGGAAATTAT  ATATGATAAT  CAATTTTAGG  GTTATCTTAT
85801  TGATTAGAAG  ATATTAAAGT  GTGACACTGC  CTGGCAATGA  TATCTGCTGG  TAGTAAGAAT
85861  TTGGCGAATT  TAGTGAAATT  CCTGAGGCTG  AACCTCCACT  TCTGTAAAAT  GGAGACAGTG
85921  AGATAATTTG  CCTTACAATG  CTGAAGTAAG  AATTTTACAC  AATAATTCAG  ACCAACCACT
85981  TCATGTGGTA  CTTGGCCCGT  GGAAGACTAT  CAATGACAGT  TAGTTTATAG  TTTATACTAT
86041  TAATGAATCC  TTTGTTTCAT  TGTTATTTCC  TTCTACACGT  TGGCCTCTCT  AAAAGAAGGT
86101  AATATTCAAT  ACAAATAAAG  TTAAAACAGC  TTGCAGAGTT  GTCCCAGGGA  ACTCACTTAA
86161  CCACTGAAGT  GTTCAAATTG  CTTAAGGTTG  ACTTTATATT  CTCCTGACTA  ACCTTTCTCC
86221  TTCTGGTATT  TCTTCTGAGA  ACAGCACCAC  CATCCAAAGC  ATCATGCAAA  CAGTGGTCAT
86281  CCCAGACCAG  TAATTCTCAA  CTCACAGGGT  GCTCCTGCAG  AGATGTATTT  GAATAGAGTG
86341  GTAGGATGCT  GAAGAAGGCC  ACGTAAAATT  TGGCCAGTGA  TCTGGGGCAG  ATTTATCCTG
86401  AAGCTAATGA  AACACAAGTG  TAAGGGCCTG  TACTTCCAAG  GTGCAGAGAG  GGGCCCTACA
86461  AATGTGTTAG  TTTGTCTCTC  TCTCTCTCTC  TGATTTTAAA  ATTTGCAGTA  TTAAGGTACT
86521  TTAATCACGG  ATGGTTCAGG  CTGCTATTTT  CACTCAATCC  TCCTTTTTAT  TAAAATCACC
86581  ATTGTCTGAT  TATGTTAGAA  TCCTGATGAA  AATATTTGGA  ATTTGAGTAA  GAGAAAGTTT
86641  AGTTGAAGAT  GTATCTAGTA  TGGGGATAAT  AAGTTACGTG  ATTTGCATAT  GTGATCATGT
86701  GTACTTCATT  CGTTGCCAGC  CAATCTGACG  TAAGAATGGC  TTCAAGGAGG  CCGGGCGCGG
86761  TGGCTCACGC  CTGTAATCCT  AGCACTTTGG  GAGGCCGAGA  CGGGCGGATC  ACGAGGTCAG
86821  GAGATCGAGA  CCATCTTGGC  TAACACGGTG  AAACCCCGTT  TCTACTAAAA  ATACAAAAAA
86881  TTAGCCGGGC  GTGTTGGCGG  GCGCCTGTAG  TCCCAGCTAC  TTGGGAGGCT  GAGGCAGGAG
86941  AATGGCATGA  ACCTGGGAGG  CGGAGCTTGC  AGTGAGCCGA  GATTGCGCCA  CTGCACTCCA
87001  ACCTGGGAGA  CACAGCGAGA  CTCCGTCTCA  AAAAAAAAAA  AAAAAGAATG  GCTTCAAGGA
87061  ATGTTCCTAC  TGCTCACTGG  AATAACTCAC  CTAAATTCCT  GGCAAGATGC  AGGTCTAGAT
87121  AAAATGTTAT  GACATCTAAG  TATTCAAAAC  ACATTCCCAG  CACTGAGAGT  GAGTGTCTAG
87181  TGGAGAGTAG  AAACGTATAG  AGCCAGAAGC  TAGTCTGGAA  AGAATTCTTA  CAAAGTTTAC
87241  AACTTACATG  TGAAAGGAGC  TTAACAGAGG  ATTTTCCAAA  TTTGAAAACA  ATCCTAAAAA
87301  CTTACTTGAC  ATTACCAATA  ATGTGTTTTG  AAACTGAAAT  ACTTCTAAGT  TATGAAGAAA
```

Figure 1 (Page 27 of 73)

```
87361 ACATATTATC ATCAGCCACC CTGGAGGAAA GATTGAATTC TATTTCCATT ACCTATAGAC
87421 AACATTACAA AATAATTTCG ATCTGAAGAT GGAATCAGAG TATTCAGTCA AAACTACAGG
87481 AAAATATACT TGGTAGTGTC ATATTCAGAA GTTAATAAAA TATGCTATTT TCTGAATTTT
87541 GTGATGGCTG TTGTTTTGTC AGCTTTTATA AAATTGGAAT TTGATTTTAT TTTCCCATTA
87601 TAAATTTATA TTTACAGTCT GCAGTACTTT TGCATTTTTA ATTTTACATT ATAGTTTTTA
87661 ATAGTTAACA AGTTGTAAAA GGTTTGATCC CCAGAAAACC TTGATCTACC CCATCAGTTA
87721 AGTATACTAA TATATTTAGA AAATGGATGA AATCAGCATT TGAATATTTT TAAATATTTA
87781 TTAAAGAGG ACATGGGTAA AAGAGCTTTG CAGTTGCCAC CCTTCATTCT CAAATTCCCT
87841 GGATAAGGAT GACCGCATAA TCTTTGGATG GTCATACGCA AGTCTTGTGT ACTTGTTACA
87901 TAAATCTATT TAGTGGACTT TTGGCAGTGT GTACTGAGGC CAGTTCTTC CACCTGAGCT
87961 CTGACTCCAC CTCCAGCAGC CCAAAACCAA TACTGAATTT TGGGGTCAGC TATTGTTTTT
88021 GTGGACTTAG GTAACTACAC ACACATTGTC TTTATGATAG CTTTAATAAT ACTGCCATCA
88081 GAACTAAAAT TGTCACGTGG ATTAAAAGGA GTGACGGTGG TGTCCCCAGG AGCCTTTCAA
88141 TATGTAAGTA TTTACACATA TACATGCTAA AAAGACCCCT AGGAATTTTT TAACAAGGGC
88201 AAAACAGTAA CTCAGCTTGT TTTCTCGCAG TAAAACCGGT TGAAAAGGCC TGATAGACTT
88261 GTCTGCAGTT ACAAAACTTG TGTGTAGTTA TCACCTTTAT ATCTCCTGGA AACTAACATA
88321 GACAACCGAA TGGGTTACAA CTGTTTTTAA GTGAAATTGT GAGTGGCTCT GAAAAGAGCC
88381 TTTTCAATGA GGAAGAAACG GGCAGACTTA TGCCCTTTCC CCACGGATGC GACGTGCCAG
88441 CTGGATATCT TTGGGCATGA TGGTGACGCG TTTAGCGTGA ATAGCGCACA GATTGGTGTC
88501 TTCGAAGAGT CCCACCAGGT AGGCCTCACA AGCCTCCTGC AGCGCCATCA CCGCAGAGCT
88561 CTGGAAACGC AGGTCGGTTT TGAAGTCCTG GGCGATTTCT CGCACCAGGC GCTGGAACGG
88621 CAGCTTCCGG ATCAGCAGCT CGGTGGACTT CTGGTAGCGA CGGATTTCGC GCAAGGCCAC
88681 GGTGCCCGGG CGGTAGCGAT GAGGTTTCTT CACGCCACCG GTGGCCGGAG CGCTCTTACG
88741 GGCTGCTTTA GTAGCAAGCT GCTTGCGCGG AGCTTTGCCG CCGGTAGACT TGCGAGCTGT
88801 TTGCTTCGTA CGAGCCATTT GCAATGAGAG CACACACAAA AGTGTAGTGA ACTGAGAGCA
88861 AGTGGCCTTT AAATATAGTG AGAAACATTC TGATTGGTCC TGTAATATTT CAAAAGTCCC
88921 GCGCGATAAA ATCATTGGCT GAAGAGTGAC CAGACTGATT GGTTCATTAC TAGACAATCT
88981 TATTGGATGA GTTGCCCCAC CGCCCATCCT GTCCTTTTCG TTTCAGTTAT CTGCAGCGAC
89041 AAATTGTCTA AAATTCTAGT TCATCCAGTC CCAAAGAACA GAGTGTATAA CAAGGTATCT
89101 AAGGATTTTT AAAATGTAAA TTCCGATTCA GTAAGTTTGA GTGGGACTTG AAATTCTGCA
89161 TTCCTGACAG TCTCGCAAGT TATCAATGCT GGTGAACACT CACTAAACCA CCAGAAACGT
89221 TCAGACTCAT GTCGGGAAAT AACGCTTATA TTCAGAGAAT GAGATTCCAT GCTATTTGT
89281 TACTGGCGAA CAGCAAGTTT CCTTGCCCTT TGTTTTCTAA GTCCAAGTCA CATTCCCACC
89341 CTGCCTGTTC TCAAAATGTC TTATTTTGGT TGGCCTTAAG TTTCACTTTG TATACTCTAA
89401 AATGTACTTT CTAAAGGAAG GTGTTATTTT CTCGAAACTT AACTTTTTAA CACCATTAGG
89461 CTAGGGGGGC GGTGGCTCAC GCCTGTAATC CCAGCATTTT GGGAGGGCGA GATGGGACGA
89521 TCACTAGAGG CCAGGAGTTC AAGACAACCC TGGCTAAAAT GGTGAAACCC CGTCTCGCAT
89581 AAAAATACAA AAACTAGCTG GGCGCGGTAG CAGACGCCTG TAATCCCAAG TACACAGGAG
89641 GCTGAGGCAT GAGAACCGCG TGAAGCGGCG GGGTGGAGGT TGCAGTAAGC CGATATCGCG
89701 CCGCTGCACT CCAGCCTGGG TGACAGAACT AGACTGTCTC AAAACAAACC AATCCAAACG
89761 AAAAGCAAAA AATACCCTAA CAGAAGCAAG TTATCATCCT TTCTTGTGTA ACTATGGACG
89821 GCTCTGAAAA ATGCCGTTTC AAGTGTAAGC TACGTTTTCT GATTTGAGTG TTTACTTGAC
89881 CTTGGCCTTA TCGTGGCTCT GTTATTTTGG CAACAGGACG GCCTGAATAT TGGACAGGAC
89941 GCCTCCCTGA GCAATAGTGA CGTTGCCCAG CTGCTTGTTG ACCTCCTCGT CGTTTCGGAT
90001 GGCCAGCTGC AGGTGGCGGG GATGATGCT GCGGGTCTTG TCACGTATGG CGCTGCCCAC
90061 CAGTTCTAAG ATCTCGGCGG CCAGGTATTG TAAGTACACT GGCGCACCGG CTCCGACCGG
90121 CTCAAAATAA TTGCCCTTTC GAAAAGATG ACGGACTCTG CCCTATTGGG AACTGCAAGC
90181 CCGGTAGCGA CGAACAAGTT TTTGCTTTAG CTCCATTTTC CACGTCCGCA AATAGCGACC
90241 TATGAAAGCA GCGGAAAACT GTGAAAGACA AGCAAGCTGG AATGGCGCCT GAACAAATCC
90301 TTTTATACAA ACTGCAAGGC TGCAATAGGA AGCTATCCTA TTGGTCAATT ATGTTTGGTG
90361 CTTTATCCAA TAGAAAAAGA TAACATAAAT TCCATATTTG CATAAACCCC ACCCCTCAGT
90421 GAAACCGTGT TTCTTTTGTC CAATCAGAAG TGAGGAATCT TAAACCGTCA TTTGAATCTC
90481 AGGACTATAA ATACATGGGC TCTGAACTGT TCTCTGTACT ACTCTGTAGT GGAGAGTGTT
90541 AGTAGCTTTT CTATTCTGTT TAGGAATAGC AATGCCTGAA CCCTCTAAGT CTGCTCCAGC
```

Figure 1 (Page 28 of 73)

```
90601 CCCTAAAAAG GGTTCTAAGA AGGCTATCAC TAAGGCGCAG AAGAAGGATG GTAAGAAGCG
90661 TAAGCGCAGC CGCAAGGAGA GCTATTCTAT CTATGTGTAC AAGGTTCTGA AGCAGGTCCA
90721 CCCCGACACC GGCATCTCAT CCAAGGCCAT GGGGATCATG AATTCCTTCG TCAACGACAT
90781 CTTCGAGCGC ATCGCGGGCG AGGCTTCTCG CCTGGCTCAC TACAATAAGC GCTCGACCAT
90841 CACCTCCAGG GAGATTCAGA CGGCTGTGCG CCTGCTGCTG CCTGGGGAGC TGGCTAAGCA
90901 TGCTGTGTCC GAGGGCACTA AGGCAGTTAC CAAGTACACT AGCTCTAAAT AAGTGCTTAT
90961 GTAAGCACTT CCAAACCCAA AGGCTCTTTT CAGAGCCACC TACTTTGTCA CAAGGAGAGC
91021 TATAACCACA ATTTCTTAAG GTGGTGCTGC TGCTATTCTG TTTCAGTTCT AGAGGATCAA
91081 CTGGAATGTT AGCGAAGACA AGTTTTAGAG CCAAGGTTAA CTTGGACGGG GCCGTGCGCG
91141 GTGCCTCTTG CCTTTAATCC CGGCAATTTG GGAGGCCGAG GCGGGCGGAT CACGAGGTCA
91201 GGAGATGGAG ACCATCCTGC TTAACACGAT GAAACCCGT CTCTACTAAA AATACAAAAT
91261 AATTAGCTGG GCGTGATGGT GGGCGCCTGT AGTCCCAGCT ACTCGGGAGG CTGAGGCAGG
91321 AGAATGGCGT GAACGCGGGA GGCGGAGCTT GCAGTGAGCC GAGATCGCGC CATGGCACTC
91381 CAGCCTGGGT GACAGAGCGA GACTCCGTCT CAAAAAAAAA AAAAAAAAAA AATTAAAAAA
91441 ATATGAAGTT TTGAAGCAGA AATTATTTTG TCGTATGTTC TTTCATAAAT TTTTTGCCTG
91501 CCTGCCTTCT TCCTTTGTTA CAGAACTCCA ACACTTACCC AAAGGTAGCT GTTGGGTCAG
91561 GGTTTCTGTA CTATAGTCCC TTCTGTGGTG GCCAGAAATA TGTTACAGGA AAGAGGTCCC
91621 CATCCAGACC CCAAGAGAGG GTTCTTGGAT CCCGCGCAAG AAAGAGTTCA GGGTGAGTCC
91681 GCAGTGCAAA GTAAATGCAA GTTACTAAG AAAGTAAAGT GGTGAAACGA CAACTACTCC
91741 ATAGACGGAG CAGGACATTC CCGAAAGTAA GAGGAGGAAG GCATCCACCC TAGGTACAAT
91801 ACTTGTATAT ATGGGGAGAT GTGCTCTGCT ACAAGTTTGT GATAAAGGAT TAATTTTCTT
91861 AGTTACTATA TTTTGCAAGA ATCAACATTA TTATCTTTAA ACAAAATTAA GAATGCCTTT
91921 GTTCTCCAGA TATAGGGATA TCTGGACACT CCTAAGTCTG AGTCTGTTTA GTAAACATTA
91981 TTTATTTGTT CCCTTAACCG TAAACATCTA GAAGCTAGGA ATGACTGACT TTCTGGGAAT
92041 GCAGCCCAGA AAGTCTCAGC CTCATTTTCC TAGCCCTCAC TCAAAATGGA GTTACTCTGG
92101 TTCAAGTAAC TCTGACACTT TTCTTCTCTT TTTTTCTTCT TTTTTCCTTC CTTTATTTTT
92161 TATTTTTTAT TTTTGAAATA AGAAATCAAG AATACTTGAT GTTTCATCTA AAACAATACC
92221 CATAATTGAT AAGCCAAAAC AAAAACCTAG GTCTTCTAAC TCAAAACTAG GATGTTTTGC
92281 TGTCTCTGCT GATACTCGGC TGATCGTTAA TAGGTAATTA ACAAACAAGC CTTGCTATGT
92341 CCCCCTCAGT TTATTACCAT TAGATCATAT GCCTACTGTC AATCATATTA ATCCACAACT
92401 ATGCATTTCA CAAAACTTGC CATAAAAATT CACAGGTTTC CCGCTTCCCT CGAGTTTTCA
92461 TTTCCGAAGG GTCCCATGTA ATATAAAACT TATATTAAAT ACATTTGTAT GCTTTTCTCT
92521 TGCTAATCTT TTTTTTTGTT TTTGAGACT GAGCCTTGCT CTGTCACCCA GGCTGGAGTG
92581 CAATGGCGCG ATCTCGGCTC ACTGCAACCT CCGCTTCCCA GGTTCAAGCG ATTCTACTGC
92641 CTCGCCCTCC CGAGTAGCTG GGACCACAGA TACGTGCCAC CATGCCCCGC TAATTTTTGT
92701 ATTTTTAGTA GAGACAGGGT TTCACCGTGT TGGCCAGGAT GTTCTCAATC TCCTTACCTC
92761 GTGATCCGCC CGCCTCGTCC TGCCAAAGTG CTCGGATTAC AGACGTGAGC CACTGCACCC
92821 GACCAATCTG TCTTTTTGTA GAGGGGCCTC AAGCATGAAC TTACTGATGG GTGAGAAAAA
92881 CAGAATTTTC TTTTCCCCTA CAATATAAAC ATTAATTGTA ATGTTATCAT TCAGGACATT
92941 TTGGTGACCA ATCTTACAGA AATTTTATCT TGTGCAAGTC TATGCAAACC AATATGTAAA
93001 TCTTCTATAA GTGAGATTGT ATTTCACTTT TCTAGTATCC TTTTAAATTA ATAAAGAGA
93061 TTCTAATGAT TATTTTCATT ACTGCATTTC ATTGTAGGGA AGTAGATAAT TGCCCTTTAT
93121 TCACTGACCT TCGCTTTTTA AAAATTTAAA CCATGTTACC ATGAAAATGC TTTTCAGTAT
93181 TTCTCTACAC ACAAGATTGC TGTAAGGGCA AAAATAGAGA TAGGAATCAT GCATCCATTG
93241 ATATACATAT TTTGATTTTT AATACATGTT ACCAAGTTGC CTCCTGAAGG TCTGTTTACA
93301 CTCTCACCAA CAGGGTGTTT TTTCCTGACT TCCACAAATG CTCTTGAACA GTGGGTGTGT
93361 TAGTCTGTTC AAATTGCCGA CATGAACAAT TAAATCTCAT TGTTGTTTTT ATTTTAAGA
93421 CAATTATTGT TTGAGACTGC ACATTTGAT AATAACATTT CTTCTATTAT GGTTTGATTA
93481 CTCATGATTC TTGCCCATTT TCTTTTGGGA TGTTGCCTTA TGTACATTAT TTTAAATAGA
93541 TAGCTCCATG TATTAAAAGA TTATTAAGTT TGAGGGCTTA TGATATGTCA GTTACATTTC
93601 TAAGATTTTT TTTTTTTTTT TTTTGAGAC GGAGTTTCAC ACTTGTTGCC CAGGCTGGAG
93661 TGCAATGGTG CGATCTCGGC TCACCGCAAC CTCCGCCTCC AGGGTTCAAG CAATTCTCCT
93721 GCCTCAGCCT CCCCAGTAAT TGGGACTACT GGCAAGCGCC ACCACGCCTG GCTAATTTTG
93781 TATTTTTATT AGAGATGAGG TTTCTCCATG TTGGTCAGAC TGGTCTCGAA CTGCCGACCT
```

```
93841 CAGGTGATCC ACCCGCCTCG GCCTCCCAAA GTGCTGGGAT TACAGGTATG AGCCACTGGG
93901 CCCGGCCACA TTTCTAAATT CTTTATAAGT ATAAATTCAT TCAATCTTCA CCAAAACTCA
93961 ATGAAGTGTG AGTACTATTA TTATCATTGT TTTACAGATC AAAACAAGTA ATACAGTCAC
94021 TTACTGAGTT CTATACACCT GGTAATTTTT TTGTTTCGTT GTTCTATCAA TTATTGGGGA
94081 AGGGGTGTTG AAATCTCTAC CTTTAAATCA TGTATGTGTC TATTTCTCCT TTCGGTTCTA
94141 TCAGGTTTTG CTACACATAT TTTGCAGTTC TGTTATTTGG TGCATATACA TTTAGAATTG
94201 CTTGTTTTTC GTATTGGATT GACCCTGTTA TCATTATGTA ATATCCCTGT CTGTTCCTAG
94261 TAATTTTCTT TGCTCTGAAA TATACTTATC TGATATATCA TCCAAAAGAC CACCAGGATG
94321 GCTAAAGAGT AGAAAGGAGA GATTTACTGG CAATACTAAT TTGCAAGCCA GGAAGAGATG
94381 GTCCCAGAAC CTGCCAAAAT TACTCTCTCT TTGGGGAGAA GGAGCAGGTT GGTTATTTTT
94441 ATGCCTCATA GGCTATATAT TACACAATAG AGTCATACAT ATTTAGCACG TTTGGGGGGA
94501 CAGCTATATA TATTATGAGG GGTGCCAAGT GCATTCACAA TGGATAAACA CGTGTAATAT
94561 ACCTCCCATG TTCACTTCGA GGTTAAATTT TGGTTAAAAT GAGGTAGAAT TTAGGTCTTT
94621 ACATCACAAG GTGAACTATA GGAACAAAGT TTACGTGCTG CCTCTAGCAG CTGGCTGAAA
94681 ATGGCTTAAG GTCTACAATT ACGTGTAAGA ATAGAATGTG TGTCAAGGCG GTCCTCTGTC
94741 CAATCAGAGT TGTAGTGGAC TGGACTGTAA ATCAGAGTTA GGAGGGCTTC TGATAGCTCC
94801 TATAGTTAAG GAATTTAGCA AGTGTGAGTT TTTTGGTAGT CTTTGGAATT TAGGAATTTG
94861 CCATGCCAGC CAAGCCATGA ATGCTCTACC AGTAGGTAAC TTTGTTTGCT TAATCTTAGA
94921 GTCTGTCTTA GTTGGTATAG GGCATCTAT TTTGGTCTTT CAGATCCAG ATATTATTAA
94981 TACAGATACT CTTGCAGTTT TGGGCTGATG TTTATATGGC TTATCTTTTT TGCAGCCTTT
95041 AATTTCAACC TGCGTTATGT TTATATTTGA AGTGAGATTC TTGCAGACAG TGTACAGTTG
95101 TTGTTTTTTT TTTTTTGAGA TGGAATTTCA CTCTTGTTGT CCAGGCTGGG GTGCAGTGGC
95161 ACAGTCTCAG CTCACTGCAA CCTCCGCCTC CTGGGTTCAA GGGATTCTCC TGCCTCAGCC
95221 TCTTGAGCAG CTGGGATTGC AGCCATGCGC CACCACACCC GGCTAATTTT TGTATTTTTA
95281 GTAGAGACAG GATTCACCAT GTTGCCCAGG CTGGTCTCGA ACTCCTGACC TCAAGTGATC
95341 CGCCAGCCTC GGCCTACCAA AGTGCTGGGA TTACAGGTGT GAGACCTCGC GCCCAGCCAA
95401 ACTGTTTTTT TATGGGTGTA TTTATACCAC ACACATTTAA TGCAATTATT GATATCTTAG
95461 GGCTTAAGTT CATGAAGGGT AGTGTGGGAA CCATAGTCTC TTGGCCCACT AAATGTTTGC
95521 CAGAAATCAC TGACAAGGCA GATTGATTAA TAGGTGAAAA GGCATTTTAC CTATTGTTTA
95581 ACGTGTCTAT GTGGGAGCAT TCAGAATTAA TTACCTAACT TCCCAATGAG TTATAGATGC
95641 TTATATACCA TTTTTAGATC ACAGAAAGAA TTGGGGCTTA GATTCTGGTA AAACAGGTTA
95701 TGGGAGGCAA AAGAGGTTTG GCTTGCAAAG GTGGCCTTGT TAGGTAGGTG AAGCCTCCCT
95761 CAGAAAGAAC AGATGGTAAA TGTTTCTTTT ATGATTTTA AGTGTCAGAC TCTCAGTCTC
95821 TCCTGGATCT GGGGAAAGGT ATAGAAAGGT GAGGAGGCAT GGCTGCATTA ATGGAGATTC
95881 TCTACAGATG TAAAATTTTT CCCATTTAAG GCAGCTTTGC AAGCCCATTT CTGCCTGCTG
95941 GCCAAGCAGC AGCCATTTCA AAATATGTCA AGAAATATA TTTTGGGGTA AAATATTTTG
96001 ATTTCCTTTA GACTGGTGGC CTTATAAGAA AAGGAAGAGA CACCTGAGCT GACACACATA
96061 CCCTTGCTCT CTCAACATGT TATGATGCAG TAAGAAGGCC CTCACCAGAT ACTAATTCCA
96121 TGCCCTTAGC TTCCCAGGTT CTAGAACAGT AGGAAATAAA TTTCTTTTCT TTAAAAGTTA
96181 GCCAGTCTGT GGTATTCTGT TATAGTATCA CAAAATGGAC TAAGTAACTA TATTATGATC
96241 ATCTTACATG ACTGATCCCT CCTACATCAT ACACATACAC AGGCCACATT TGGAACATTG
96301 TTAGAGGTTC CTCTGCCCAG TACAAATGTA CTACAAATTA TATATGTATT TTTAAATTTT
96361 TGAGTATCTT CAATAGTATA TTTTCGTTAA CTTTTGTAGT CAAAATGTCA TTATAACATG
96421 TATTCAATAT GCATAATTAT TAGTCAGATG TTTTACATTC TTTCTTCATA CTAAGTGATA
96481 TGGTTTGGAT ATTTGTCCCC TCTAAATCTC ATGTTGAAAT GTAATCTCCA ATGTTGGAAG
96541 TGAAGCCTGG TGAAAGGTTT TTGGATCGTG AGGGTGAACC CCTCATGAAG CGCACTCTTC
96601 AGGGTAATCA ATGGGTTCTC ACTTTGAGTT CACAAGAGAT CTGGTTCTTT AAAAGAGTGT
96661 GACACCTCCC CCATCTCTCT CGCTCAGCTC TCACCATATG ATATGCCTAC TCCCTCTTCA
96721 CCTTCCACCA TGATTGGAAG TTTCCTGAGG ACTTGCCAGT AGCAGATGCC TGCACCACAC
96781 CTCCTGTACA GCCTGCACAA CCGTGAGCCA AAAAAAATTA CTTTTCTTTA TAAATTAGTC
96841 AGTTTCAGGG ATTCCCTTAT AGTAATGCAA GAACGAACTA ACACACTAAG TCTATTTCAT
96901 ATTTACAGAA TAGCTCAATC TGAAGTACCC TTTTCAACT TCACAGTAGC TACTTGTAGC
96961 TAGTGGGCAC TGATTTGGAG CGTGTTCAAG GGTGAATTGT ATTATGCAAT TAACAGATTT
97021 TTTTATTGT TTTCGCAAAC CACGAGGCAT AGATTGTCTT ACTTTCTCTG CTCCTGGTGT
```

```
97081  TGGAGTTGTT  ATTGGGAAAC  AACTTATTTT  CCTCTTATAT  TTATATGGAA  TAAATAACCC
97141  CCAATATTTC  CCTCCCCAAT  ATCTGCCTTT  TGTATGTTTT  TTGAAGGCAA  GTGCCTAGAA
97201  TTTACTGTTT  TTGAAGCACT  TACTGAAAGG  ATTGCCATCA  AGTTGTTTTG  CTAATAGTAC
97261  ATGCCAGGCG  CTTGTTGGTT  TGCTTAATTC  AAGGTAACTT  GGATGAGAAG  AAGAGTTTTT
97321  CTCATCCATG  GCTCAGTGGA  GTATAGATTA  CTGATATTGT  GACTGGATGT  ACTCCTGCTT
97381  TCTAGTCTGA  GTTTTTGAAG  CTACCCTTAA  TCTTGGTTTC  AATTTTATCT  AGCCCTGTAC
97441  ATATCCAAGG  CTCTTTCCAA  AATGGTCTAC  GATTTGTTTA  GGAAGTTAGA  ATAGCTGTAC
97501  TTTCTGAACC  ACGGTTCCTG  ACATTTTCTG  GACTTCAAAC  ACATCCAGCA  TTTTATCGAA
97561  GTATTTATCC  TTCCTACTTG  GCTGGCTTCT  TCCTTGCCTT  CAGGTCTGAA  TTCAAATGAC
97621  ATTCTCCTGA  TGAAACTTTC  CATCCTTATT  TCTATTCTTT  TTTCTTATCC  CCTTTCTTTA
97681  TTTTTCTCCA  CAGCACTCAT  CACTTATCTC  TACATTTTCA  TTATGTATTT  ACCTTATTGT
97741  GCACCTCCCA  CTACAAGACA  AGTAGCACCG  TAAGGAAACA  GGTTGTCTGC  TTTTTCACTG
97801  CTATGCTCCC  TGCACCTAGA  ACACTCTCTG  GCACTTAGCA  GGTTTTCAGT  AAATATATGC
97861  TGAACTAATA  ATGCTGGATA  TACATCTCCC  TCATGAACTC  TCTAAATCCT  TCTAATTTAC
97921  ATTGATCAAT  CTTCTTTTCC  ATGTGCTTTT  GTATGATTTA  TTGCTCAAAA  TCTTTATTTT
97981  ATATGCAGAA  CGTGCACTGC  TATTTAATCT  TCATGTACGT  AAGTCCTCCC  TTCTCTGAGT
98041  ATAATCTCTT  CAGGGCACTA  TCTGAGATAA  CTTTTTAACA  TCTCCATCAT  GAATCTTGTA
98101  CCTTTTCAAA  GAAAATGAGC  CAGTGATTAC  TGATGTTTAC  GGCTATTGTT  GAGGGTGAAG
98161  ATCATTATAA  TTTTGAAAAG  GGAAGTTGAA  TATTGTGAAG  GGAAAGATAA  CACTAGAGTC
98221  AGAAGACTTG  GGAGAAGGCA  AAAAACAAAC  TAAAAATGAG  CACTTTTAGT  CTCCTGACAG
98281  TTTCTCTGAA  TCAAATCCAT  AGTTCTGTGA  CAGCGTTGGC  TTAGAAGCAG  ATTTTTTTTT
98341  TTTTTTTTTT  TGAAATGGAG  TTTCGCTCTT  GCCCAGGCTG  GAGTGCAGTG  GCACGATCTC
98401  GGCTCACTGC  AACCTCTGTC  TCCAGGGTTC  AAGCGATTCT  CCTGCTTCAG  CCTATGGAGT
98461  AGCTGGGATT  ACAGGCTCCC  ACAACCACGC  CAGCTAATT   TTTTGTATTT  TTAGTGAAGA
98521  CTGGGGTTTC  ACCATGTTGG  CCAGGCTGGT  TACGAACTCC  TGTTCTCAAG  TGATCTGCCC
98581  GCCTTGGCCT  CCCAAAGTGT  TGGGATTACA  GGCATCAGCC  ACCGTGCCCA  GCCAGGAGCA
98641  GATTTTTTTA  CACTCATGTT  TCTTTTTCCT  TCTGTCATCC  TGTTTCAGTA  TAAGCAGACC
98701  ACAGATAGAA  GTAGTAGATA  CCTCAGAAAT  TCCTGGAATA  ATTAATCCAC  GTTCATCTGT
98761  ACTCCATCTG  CTCCTATCTC  ATGGAATATA  AAAGGAAAAA  CACCAAGATT  TCCCTAGGCA
98821  ATCTGTCTTG  ATTTTAGGTT  CCTCAACAGG  AGAGCCAGAC  AATGGCTGTA  ATAATATTGT
98881  CCCGGCCAAG  GAAAACTTC   CCCTTTGCCC  TCCCAAGGTT  TATGGAAAAT  TACTGGCAAA
98941  ACACAGATTA  ACTGGAGAAA  AGGCATATAT  ATTTATTTCA  TCACAATTTT  ACAGGAGATT
99001  TTAGAATTAA  GACTGAAAGA  TACAGGGGAA  ATTGCCCATT  TTTATGCTTA  GGTTCAACAA
99061  GATAAACAGC  TGTATAGGGT  ACGATCTAAT  GCTAACAGAC  TGAGTGGGA   AGCCCCGCAA
99121  GGCTTGTCTG  TCAAGATTCT  TCTTGACCTC  TCAGTGCAGC  ATTTCTTCCT  TCTGGTTATA
99181  GGACAAGACT  CTCTTTTAGA  ATGGGGGTC   TTATGACCTA  CAGGCAAACA  AGGTAGGTTA
99241  GAGTAATACT  TTTAGGTTTT  ATGGCTGGTT  CTAGGGAAAA  GGAGTTCTGG  TTTGTATGGC
99301  CTACCTTGAG  GAGGAATTCT  GGTTTCTATG  GCTAGACTTT  GGGGAGAATG  GGACTTACAG
99361  ACAGGAAGGC  AGAAGGTGGT  CAGTGAAACA  CTTTTATAAT  CATAATCCCA  TTTTGAGTAT
99421  TTCTGTGTTA  TGGAATGTTT  GTTCTCTCAT  TTCCTGAAAG  ATTCCAGAGA  CTCCTCATTC
99481  AGTGTTGTGA  AAAAGTTCAG  GAAATGCAAC  TCAAAAATGT  GCCACTTTGT  TACGCTGATT
99541  TCTTTGAACT  GAGGGCACCT  AGGAAACAGT  AAATTCAAGG  AAGGGCTTTC  GCTGAACTCT
99601  AATCAAAAAT  TTGAAAATTA  AAAAAAAATT  CAAAAAGGAA  TTTAGTTGTT  AAGATTCACT
99661  TCCCTGGGGA  ATCTCATCAA  CCAGAGAAGA  TTAACTGTAT  CACAGGAGAG  GAGACTGGTG
99721  GTTAACACCA  TCTAAACAGA  CTTTGTCACA  GCTGTCACCT  ATTCTTTGAA  ACACCCATTT
99781  ATTTTTCTCC  AAAATCATAT  ACTCTCCCCT  AAGTTGCCTA  CATCCCCCTT  CTTTCTCCCT
99841  TATGAATCAA  GAGAGCTTAT  AAGCTTCTAC  AGTTCACTGG  GATTTGGGT   ATTCGCTTTT
99901  CTTCCCTCCC  ACTCCCCCTC  CCCTTTTTTT  GTCTTTGAGA  CACAGTCTTC  TGGCTCTGTC
99961  GCCCACGCTG  GAGTGTGGTG  GCTCTATGTG  AACTCACTGC  AACCTCCTCC  TCTCGGGTTC
100021 AAGCGATCCT  CCCACCTCAG  CTTCTCGAGT  AACTGGAACT  ACAGGCGTGC  ACTACCAAGC
100081 CCGGCTTTTT  TTTTTCTTTT  TCTCCCCCGT  TTCTTTTTTG  GTTATTTTAC  TGGAGACAGG
100141 GTTTCTCCAT  GTTGTCCACG  CTGGTCTCGA  ACGCCTGACC  CGCCGTCCTC  GGCCTCCCAA
100201 AGTGCTGGTA  TTACGGGCAT  GAGCCACTGC  GCCCGATTTG  AAGGACCTCT  TAAATATCTA
100261 TTTAGAAATT  GGTCGGAGTC  CACTCCTTTC  CAAAAACATG  AGTCACAATC  CGGGAAAAGC
```

```
100321  ACGAGCGGCT  GAAAGTCAAA  ATAACCAGAA  CAAAACCTCC  ACTCATGCTT  AAAAAAGGTA
100381  TTTTGACAAA  ATCCTAATTC  GGCCAATTAT  TATTAGTATT  CAAGTCGAAG  GCTCGTCAAG
100441  CCAGACTGGG  GATTGGGTCA  AACATAAACC  TTACACCAGA  CGGAAGGATT  ACATGCAAAT
100501  GAAGGATGCA  GATTCTGATT  TCCCATTGGG  TATTTGACAT  TAGCCAATGG  GAGAATTCCT
100561  CACAGCCTAC  CTCCAGTCAG  TATAAATACT  TCTCTGCCTT  GCGTTCTAAT  GTAGTTTCAT
100621  TACATTTTCT  TGTGGCGATT  TTCCCTTATC  AGAAGTAGTT  ATGTCTGGTC  GCGGCAAACA
100681  AGGCGGTAAA  GCTCGCGCCA  AGGCTAAGAC  TCGGTCTTCT  CGTGCAGGTT  TGCAGTTTCC
100741  TGTGGGCCGA  GTGCACCGCC  TGCTCCGCAA  AGGCAACTAC  TCCAGCGCG   TCGGGCTGG
100801  CGCGCCGGTG  TATCTCGCGG  CGGTGCTTGA  GTACCTGACC  GCCGAGATCC  TGGAGCTGGC
100861  GGGCAATGCG  GCCCGCGACA  ACAAGAAGAC  CCGCATCATC  CCGCGCCACC  TGCAATTGGC
100921  CATCCGCAAT  GACGAGGAGC  TTAATAAACT  CTTGGGGCGT  GTGACCATCG  CGCAGGGTGG
100981  CGTTTTGCCT  AATATTCAGG  CGGTGCTGCT  GCCTAAGAAA  ACTGAGAGCC  ATCATAAGGC
101041  CAAGGGAAAG  TGAAGAGTTA  ACGCTTCATG  CACTGCTGTT  TTTCTGTCAG  CAGACAAAAT
101101  CAGCCTAACA  GCAAAGGCTC  TTTTCAGAGC  CACCTACGAC  TTCCATTAAA  TGAGCTGTTG
101161  TGCTTTGGAT  TATGCCGCCC  ATAAAGATGT  TTTTGAGGTG  TTTTTAATGG  CTTTGAGTGT
101221  GGCACTTTTA  GTAATTTGTC  CTGCAGAAAT  TAGATCCATA  GAAACCTCAG  GAATTCTAGG
101281  TATGTGGGAG  AAGTGCCATG  CAGCACAAAA  CATGTTTACA  GGGGTGATTC  GCGTTAAGTT
101341  TCACACACAG  CAGTTACTAC  ATTTTAGAGG  AAGGAAATTA  TACCCATGAG  TGCATTCCTA
101401  ACTATCTTGA  ATGGAAGTGT  TAAAACCCGC  ATGCCCCACA  CAAGTTTGAA  TATGTCATAC
101461  CATTTGCTGT  AGCAATTAAT  GGCATACACA  ATTGAGAGCA  CACACATTAC  CACTGAACAT
101521  TTGAGTATGT  ATTTCCCAAA  ATGAGCTTTT  TTCCAGTTTG  GGGATGTTTT  GCTTTGTTTT
101581  GGGGTGGAGT  CTCCCTCTCG  CCCAAGCTGC  AGTGCAGCGG  CGTGATAACA  GCTCACTGTA
101641  ACCTCGAACT  CGGGCTCAAG  CGATCCTCTT  GACAGCCTTC  TGAGTAGCTG  GGATTACAGG
101701  CGAGAGCCGC  CACGCCCGGC  TAAGAGCATT  TTTCTAATTG  CCCACACTTC  TTATGCGACA
101761  CCCAGAAAAA  TACAATTTTA  AATAAAGCGC  ATATGCAAAT  TTCCCTAATC  GTCTCCAATA
101821  TTCTCTGATT  TCTTTTTTAT  ATTTTAACTA  GAAACAATTG  GAGGTTTCCG  CGTTGCTTTG
101881  TGTGGTTGTA  AATTTTAAGA  CTTCAGGAAA  CTTTTCCAGT  ACAAGACTTG  TCCACAGTGG
101941  ATATAGCAGC  TAAGGGGTTA  ACAAAATGAC  GTCAGAGTAG  CTACGGTAAT  GGGCAGGAGC
102001  CTCTCTTAAT  CTGCAACCAG  GCACAGAGAT  GGACCAATCC  AAGAAGGGCG  CGGGGATTTT
102061  TGAATTTTCT  TGGGTCCAAT  AGTTGGTGGT  CTGACTCTAT  AAAAGAAGAG  TAGCTCTTTC
102121  CTTTCCTCCA  CAGACGTCTC  TGCAGGCAAG  CTTTTCTGTG  GTTTTGCCAT  GGCTCGTACT
102181  AAACAGACAG  CTCGGAAATC  CACCGGCGGT  AAAGCGCCAC  GCAAGCAGCT  GGCTACCAAG
102241  GCTGCTCGCA  AGAGCGCGCC  GGCTACCGGC  GGCGTGAAAA  AGCCTCACCG  TTACCGCCCG
102301  GGCACTGTGG  CTCTGCGCGA  GATCCGCCGC  TACCAAAAGT  CGACCGAGTT  GCTGATTCGG
102361  AAGCTGCCGT  TCCAGCGCCT  GGTGCGAGAA  ATCGCCCAAG  ACTTCAAGAC  CGATCTTCGC
102421  TTCCAGAGCT  CTGCGGTGAT  GGCGCTGCAG  GAGGCTTGTG  AGGCCTACTT  GGTAGGGCTC
102481  TTTGAGGACA  CAAACCTTTG  CGCCATCCAT  GCTAAGCGAG  TGACTATTAT  GCCCAAAGAC
102541  ATCCAGCTCG  CTCGCCGCAT  TCGCGGAGAA  AGAGCGTAAA  TGTAAAGTCA  CTTTTTCATC
102601  AGTCTTAAAA  CCCAAAGGCT  CTTTTCAGAG  CCACCCACTT  ATTCCAACGA  AAGTAGCTGT
102661  GATAATTTTT  TGTTGTCTTA  ACAGAACAAA  TTTCTAAGGA  CCCCCCCGGA  AAGCATTAGA
102721  CTATGGTCTT  AAAGTTGATT  AACAGAAATA  ACGGTTTGGT  CAGTCTTGCA  GTGTAGGTTA
102781  TTTCTGACCT  TATTAAGGTG  CTATTTGGAG  AGAAGCTGTG  TAAGTCCACT  ATCATTCAGG
102841  CCTCTAGCTT  GCTATGATTA  GCATTTGTTT  AAACAACTTT  GTAAGAGTAA  GGGAAAAATC
102901  TGGTAAGTAG  TTAACTGGCG  CTTACTAGGC  ATTTTTGCAA  AGCTTTGAAA  AGATTAGAAA
102961  ATTGTGTCTT  GCGAGTTCCA  GTGTCTTCCT  CAAAATGCTT  AGGAAGATTT  TCTCAGCTCA
103021  ATACATAGTC  CCCTAGGTTT  TCTCATATAT  TATATATATA  TATATATATA  TATATACTGT
103081  TAAATTCATT  TGGCTGTTAA  CATTAACCTG  AAATTTATTC  TGGTGCAAAA  TGTGAGGCAG
103141  GGATCTAACT  GGCTCTCATT  TTATCCATAG  CTAGCTACCC  ACTTTAAATC  TGTCAGTCTG
103201  TCGACCAAGC  ATAATTTAAT  CCCTTATATA  TGAATTTTA   TATGTGTGGC  TTTGCTTGTA
103261  AATAGTCTAT  CTGGTTGCAT  TGCTTTGTCT  CCTCTAGGAC  TATGCACCAT  GACATGCCAC
103321  ATTCTTTTTT  TCAGTACTTC  TTGCCTGTAG  TTATTAAAAT  CTAGAATTTA  CAAGTTTTAA
103381  CCATTTTCTT  TCTGTTGATC  TTGCTTTTCG  GTTTGGAGG   TTGGGGATTG  AGTACTGGAA
103441  GAAATTTAG   AGGGATGGGA  ATACTGTACG  CAAACAAAAG  TAATATTTAC  TTTAAAATTT
103501  TTATATTTTG  TATTTTTTA   TCATATAGCT  TTTACATCAC  ATTTTACAGA  CTAACTTTAG
```

Figure 1 (Page 32 of 73)

```
103561 AACAACCACA GAATGTCCAA CATTAAAACT ACTAATTCCA AAGACCTTGC CTCACATTCT
103621 TTTTTACAAT AAATATTTTT TACACCTAAC ATTCTTTCTT GGCCTACATC TAGAATGTAA
103681 ACTGATGTAC CATACTAAAA TCGCCTGACC AACTGTCAAC AACAACAAAT CACACACACA
103741 AAAGATTAAA TTTGAATTGC ATCGTTTACT TAAATTCATT TGTGTTCCAG CTTTTAATAA
103801 GGCAGTTTTT GGTTTATAAA GTAATATTTG CATTTTAAAA ATTATGAAAA TGAATATGTC
103861 AGTTTGTTTT ATGATTCGTT TTTCTTGACT CTTATACAAG CGACTCTAAC TGGCATAGAC
103921 ATTTGTTATC CACAGACAGT ATAGATATGT TAGAGATGCC AATGGACTTG GTCTATGCCA
103981 AGGTGACTAC TCACAAGCTC TGGGCCCAGC TGAAGGTCAA GTATTTTTTT TCCAGTTATA
104041 GATGTGCTGG ATCTGATGTA TAGCGCTTGA CTTTTTATAT TTTCTTTATC TGTAGGAAAC
104101 AAATGTGTTG GAGGTACTGG GTCTGACGAA TAGCATAAAA GAATAAAGTT ACATTACTGT
104161 CTGAGGATCA GATGGACAGG GGGTGGTAGC TCAGTCCAGC TATTTTCCAC TCCCTCACTT
104221 ACATTCTTTG CCCCCTCCTC AACAGAACAA GGATTCTGCT GTAACTCTTC ATTGACAGTT
104281 GATATTTAAA AATTAACGAA TGGATGAAAT TCTCATTTGT GAAAGAAAAT TTATTGAGCA
104341 TTTTGTATTT GTGAGTAGTG CAAACATTTT AATATTATAT TAAGAATCTA TTGTTTTGTA
104401 TTAGAGGAGT AATTAAGGAG AGATTGGAGA CAAAAAGGGG GTGTTGTTTG CAGAATATAC
104461 CATCCAAAAA TAGACCACTG TGGGATCAGG ATTCTTTTGA GCTAAAGGCA CTTCAAAAAC
104521 AGCATTCAAG AAGGGAATTC TTCTAAACTT TTCTTTCTGA AAACAGGAGA TAAAAGTTCC
104581 AATGTGAAAA ATGCTCTGCT TGTACCAGGT GAAAAGACAT ATTCTTCAGC CCAGAGGCAT
104641 AGATGAGATA ATTCTGCACA AACACAGCAG GGAGTCATAG CCGAGAGACT TCTATACACA
104701 AACAAACCTT GTTAAAATAA TCATATATTC CTTTAATCTC CTCATATGGT TTACTTTCCC
104761 ACAATTGCCT CTCTTTAACT TAATGTGAAA GCATTTAGCT TTTGCCATTT CTTTGGGGCT
104821 TCACTTTTTT ATGAGGGTTC TCCTGTCCCA TAAAATTTAC ATTAAATACA TTTGTATGCT
104881 TTCATTCTGC TAATCTGTTT TATGGCAAAT GAATTATCAG GTCCAGCTGG AGACCCTAAC
104941 AGAGTAGAGG TAAAATTTTG CCTCCCTACA AGATAGAGAT TGTGTGCATT AAATGTTGTT
105001 TGTTCCCAGT TGTTCAGTTT GTCAGGCCTC TGAGCCGAAG CTAAGCCATC ATATCCCCTG
105061 TGAACTGCAC GTATGCCTCT AGATGGCCTG AAGTAACTGA AGAAACACAA AAGAAGTGAA
105121 AATGCCCTGT TCCTGCCTTA ACTGATGACA TTACCTTGTG AAATTCCTTC TCCTGGCTCA
105181 TCCTGACTCA AAAGCTCCCC CACTGAGCAC CTTGTGACCC CCACCCCTGC CAGCCAGAGA
105241 ACAACCCCCT TTGACTGTAA TTTTCCACTA TCTACCCAAA TCTTATAAAA CGGACCCACC
105301 CCATCTCCCT TCGCTGACTC TTTTCGGACT CAGCCCGCCT GCACCCAGGT AGAATAAACA
105361 GCCTTGTTGC TCACACAAAC CCTGTTTGAT GGTCTCTTCA CACGGACGCG CCTGAAACAG
105421 TTTAACAGGG TTTTTCCTGC CCAGTCACAA CAAAGTGATG TTATGCTGCA GGCTGAAGTT
105481 TACAGCTAAT GCTGTTGAAG TCTAAAATCA GTTTTGGTTT GTTAGATTTG GGTGAGATGG
105541 CTAAGATTCT CAGAGAAAGA AGTCAAGTTT GGGGTGCATT TTTCAGACTT AAAAATTTAG
105601 CAGTAGCCCT TGCAGTTTTT CCAATAGAAG TGATTTAAGA ATGTTTTCAG GAAATTTAAA
105661 ACAACAGTGA GAAGCGTGTA TGGAGAGTTG AACTACACTC CAGACTTGGC TATAGGAAAG
105721 CACGAATGCT GCTATTGTAT TGCACCTTGG AAAAGAGAAC AAAGGAATAT TTTCGGACAA
105781 TTTTAACATG TCACATATGA AAAGCTAAAC GGAATCTGTC AACACCTTGT ACGTTATTAC
105841 AGGCTGTGAT TTTAAAAAAA CAATCCTTAC TAATACATAC ATAGTTGCTG CTAGCAATAT
105901 AGTGTTGGGA GTAAAAACAC GAAAATGAGA GTTCAGGACA ATATCCCAAC TCTGAGCAGA
105961 TTTTTTTAAG TAGTAACATC TAAAATTAAA CCATATTATG TAATATTTAT TTCTTTTCCA
106021 CAGTCTCTTC TCATGCCTCG TTCACATTAG CTAATTAAAA GTCCCCTGAG TATCATCATA
106081 ACCGATTTA CAGATGAAGG CACGGTTGCA ATGAGCTATC ACCCTCTTCT GAATGAGACA
106141 GTACAGTGTG AAGGATAGCA AAACTCCACT CCCATCCTCT TAGGGCTCTG GCTGGACCAG
106201 CAAATTAAAT TAATGTAAAA TGGATTAACA GGAGAAAGGT ATATGCATTT ATTTAACACA
106261 GGTTTTACGT GACACAGGTG CTCTCATAAG GTAATGAAAG CCCAAAAAAA GCAGTTAGCT
106321 ACTTATATAA TGAATTGGAC AATTAGTAAA ATGTAAAAAT GCGCTAAAGC AAAGGGATTT
106381 AGGCTAGAAT ATATAACTGT GTAGAGAAGC GCCCAGCAAG GGCTAGTGCA AGGTTTGTAC
106441 AGAATTCTCT TGGCCTCAGC CTCCTATCCT TGAGAAGAAT GTTGCTTTTT TTAAACTACA
106501 GTGAGAACAT CTTTCATATG AGAATTTCAC CTACTGCTTC TAAGAAACAG GTCAGCTTTC
106561 AAGAAAACAT AAGGCCAGAG TGATCTTTTC ACGCCTGCTC TTTTAAGTAC CTTTGAATAG
106621 TCAATATGTC TTCAAGCACT TGAAAGACTT AAAAAGTTTA CCACTCCGGC ATATTAGTGA
106681 AAGCCCTTAA TATAAGCCCT TATTAAAATT CTCAGTCGAG GTATAAAATT CAGATTCAAA
106741 TAGTAGTGTC GTAAACGGGA GGGAAAAACT AAAGGGATTA AAAAGTGAAA CTATTGTGTT
```

Figure 1 (Page 33 of 73)

```
106801 CTCCCTCGCA GTCCTTAGGT CACTGCCCCT CGAGGGGCGG AGCAAAAAGT GAGGCAGCAA
106861 CGCCTCCTTA TCCTCGCTCC CGCTTTCAGT TCTCAATAAG GTCCGATGTT CGTGTATAAA
106921 TGCTCGTGGC TTGCTTTCTT TTCGCGTACC TGGTTTTTGT TGTCAGCTGG TTAGACATGT
106981 CTGGTCGCGG CAAAGGCGGT AAAGGTTTGG GTAAGGGAGG TGCCAAGCGT CACCGAAAAG
107041 TGCTGCGGGA TAACATCCAA GGCATCACCA AACCGGCCAT TCGGCGCCTT GCTAGGCGTG
107101 GTGGGGTTAA GCGAATTTCC GGTTTGATTT ATGAGGAGAC TCGTGGCGTT CTCAAGGTGT
107161 TTCTGGAGAA CGTGATCCGG GACGCCGTGA CCTACACGGA GCACGCCAAG CGCAAGACTG
107221 TCACTGCCAT GGATGTGGTT TACGCGCTCA AGCGTCAAGG ACGCACTCTG TACGGCTTCG
107281 GCGGTTAATC TTTTCGTCAG TTTTCTTCCA ATGGCCCTTT TCAGGGCCGC CCACTCCCTC
107341 TCAGAAAGAG CTGTGATTGT ATTCTTTCGG ATGGTAACAT CTCAATGGCT TTACTCGGCT
107401 ATTCTGCCTA GTATGTAGAA CTATTATAAA CCAGTTGGGA GAGACCAGGT TGTTTGGTCT
107461 GAGTGGCTGC TAAAGCAGAA ATCAGCTAAG TAAACGAGGT CTCCAGATA AGTGAGCTAT
107521 AAACTTCAAT GCTATAGTTT TGACATGTCA AGCAACTTAA CGTGCAGCGC GAGTCCGATA
107581 AATGAGTAGC TCAGCTTTTT AGTTTTAAAA ACGAGTTGTG CGTTATTTGT ACGAGAGCCT
107641 AAGATGCTAG CTGCCTGGAA CTGAGTAGGT GGATTAAAAT GGGTGTCAGG TCTGTTTTCC
107701 CAGGCGTATC TGACTTAACG TCAGCAAAAG CTGTACTTTT AGCTTCCCTG GTAACACCTG
107761 CCGTCCTTAA CCGCCCCCTG CCGGTAGCGC CAGAAGCCTT TACTTCCATT TCTAGTTGAG
107821 CTTGGCGTCC TGCTGAGTGA CGTCACCTCC CCCTTCTCTG GAGTAGGACT GGCGGTTAAA
107881 GCTGCTTTGC TATTTTCAGT CCTCAGGCTG GAGGCTCCCC TAAGCAGGCT GCCTACGCAG
107941 TTCGTAAATT CCCACTTAGT AGACTAAGGG AGTCTGTTTT ATAAATAAGG ACTCAAATTT
108001 CTTCTGACTC CGAGGTCCGT GGCAGCAGCT ATAAGATGGA AGCCCCCTCT GATGTAAGAT
108061 TCTCAGATGA CTTGCATCTT CACTGTACCT GTCAACCCAA TAGTCTTCTA TTCCTGCCTT
108121 AAATTGTAAA TTCCAAAACT GATTTAATTG TGAAAGTTTC AAACTGTACG ACCTAGGAAG
108181 TGTCAAAGTT AGGTGACCAG ATTTTTAGAA GTCAGCCAAA TATTCAGCAT CTTTGATTTA
108241 GTAACAAATA TATTGATGGC TACTTCAGCA AAAAAAATCA ACTTTGTTTT CTGGTTACTT
108301 TGCTAACAAG CTTCTCCTGA CAGGAGGATA TAGTGAATAG GCAGTTGAAT AAGTGAGTTC
108361 GGGTGAGAGG TCTGAGCTGG AGATAAAAAT GTGTGAGTCA TCAGCAGATA AATAAATGCT
108421 GAGACCAGAT GAGATGGCTA AAAACTGAAA CATAATGTAG TGCAGCATTG TTTGTAATAG
108481 TAAATGAGTG GCAACTGTAA AGTTTTCATC AGAAAGGACT AGAGTGATCT ATACATCCAT
108541 AAAATAGAGT ATTTCTCTAC ACAGCCCTAC TAAAGAATGA GAAAGCTGTA CTCCACTACA
108601 TACTCTGGTG TACTCTGGCT CAGTTCTTGG ACTCCTCTTT TCTTGGCTAA CTCAACTGGC
108661 CTCACCACTT ACATGCTCTG TGCTCTGTCA AATAGTTTGT TCAACAGAAC ACCACGGCCT
108721 AGCTGTAAGT GCCACGTTAA CTTCTAGCAA TGCCAAAGCC TGTGATAGTG GCAGCTTCGG
108781 GCTGTTTCTC ATTCCCGGGA TGCCTAACCA CCTCTCCAAA TTCTATCAGT TTGCTTCCAC
108841 CCACTTCAAG CTTCAGAACG AAACATAGAG CTTAAGAAAT ATAGGCCCGG CAAGGTGGCT
108901 CACGCCTGTA ATCCCGGCAC TTTGGAAAGC TGAGCCTGGT GGATCACCTG GGTCAGGGG
108961 TTCGAGACCA GCCTGGCCAA TATTGTGAAA CCCCGTCTCT ACTAAAAAAA AAAAAAAAT
109021 TAGCTGGGCA TGGTTGCGGG CGACTGTAAT CCAAGCTACT CGGGAGGGTG AGACAGGAGA
109081 ATAGCTTGAA CTCGGGAGGC AGAAGTTGCA GTGAGTTGAG ATCGCGCTAT TACACTTAGG
109141 CCTGGGAGAC AAGAGTGAAA CTGTGTCTCT AAATAAGTGT TTGCAATTAT AAACCATCTC
109201 CCTGACCTTA AATCTCTAGA CTCATATACA ACTGCATATT TGATGTATCT AATTGAATAA
109261 TGGGCATCTC GAACTTGTCC AAAATATGTT TATACGTAAA CACCAAGTCT GTTCTTCCTC
109321 TGATATTTGT CATGTCAATC AATAGAACTC CATTCTTCAA GCAGCTTGGG CCAGGAATTG
109381 TGCAATATTG TTTGTCCTGA GCTTCTTACA ACTTTCACCC AATGCAGTCA GCTCTGTTGA
109441 AAATCAATCA GAATACCTTT CATTGTTTTC TTTGCTGCTT CTCTAGGAGC AAGCTGCCAT
109501 GGCGGTTTGT CTGAATGACC ACAGTGACCC CAAACTGGTC TTTGTTTTCA CTTTTAATCC
109561 CCCTGTCATA CAGTTTTTTC TCTATCCAGC ATCAACAGTG ATCCTTTTTG AAGGTATTAT
109621 GTCCACTGTC TGCTGAAAAG ATTCCACTGG CTTTCCATCA CCTTCATAAT AAAAACCAGC
109681 ATCCTTATCA TAGCCTACAA GTAAGATGAC CAACCATTAC AGTTTGCCTG ACTCTCAGGG
109741 GTTTCTCAGG GTGTAAGACT TACAGTGCTG AAACTTAGAA AGTTCCAAGC AAACTAGGAT
109801 GAGCTGCTCA ACCTACTAGA TCTGTACTCT GGCTACCCTC TGACCTCATT CTCTTCGCAG
109861 TTCTTTCTCT TCACTGACCT TGCTGTTTCT GGAATGGACC AAGCATTTCC AGCATCAGCA
109921 CCTTTATATC TATTCTTTCT CCCTAGAAGG GTCTTGTCCT GGATATCTGA ATGGCTCTAG
109981 ATCTCATTTC ATTCAAGCCT CTCCTCAAAT ACCAACCTTA CGAAAGAGAC CTCCCATAAT
```

Figure 1 (Page 34 of 73)

```
110041 CATCCCTTGT AAAATAAGCT TTTCTGCTCA TTTAGCATAT ATATATATAG TTGACTATCC
110101 TCAATAGCAT ATATATATAA CATTTCCCCA CCTAGAATTA TATATGTAAT AATATATTTA
110161 ACAAAAAATA CATATAACTA GATATATTTT ATTTTGTGTT TGTTCTCTCT CCCCCAACTG
110221 GAATATATTT TTTGAAGGTA GGGACTTTGT TTTGTCCCAG AAGTATCCCT AGCACCTTGA
110281 ACAGGGCTGA CGTTAACAG GTAGTTTATG GAGGTTTGTT GAATGAAAGG ATGTGTGAAT
110341 TTTCTATGTA AGTCTCCAGG CTCTCCACTA AGCCCACCAG AATGCTAACA CAATCAATTC
110401 CCCATCTCAT TCCTTGACCT GCCACTGCCT GAAGCAATCA GCGTGCAGTT TCTCTTTAGA
110461 AAATCTGGGG GATAGTCTAG GGGTTGCAAA TTAAGCAACA TTATCTTTGT TCTGAACAAG
110521 GACTGCATGA GTGTTAGGAC TGAAGAAGGC CCAAGGTGGT GGTGGGTATG CCTAAGATGA
110581 GTATGACATA TCAGCAATGC TATGAACATA GCAATGCTAT GAAAGGCCAG GCAAAACGTA
110641 ACAGGAGCTA GTCGTGGCTT ATTGTTACAA CGACTATACC TCCCATATGG GTAATCGATA
110701 TCCACACACC CCTCTACATT GACTCTGGAA TTCAGGAAAG GGAATTAAAA TTTTCTAACT
110761 TATGTACCCC AATGATTTCA ACAATATCTG GCATATGAGA TCAATAAATA TCTTTAAAAT
110821 ACCAACTAAG AAAGACATAA AATGACCCAC CCTCCATACC AGGCTCATTT TTGCTCCTCT
110881 GATTCCTGAA ACTATCCAGA ATGCAGCTAT GAATTCTCTC CATTGTCAGT TTTAAATTAA
110941 GCCAAGCTGG GTACTTGTGT AATTCCTCAA GAAATCCTGG ATGAAAACTG TCAGGTGGAA
111001 AACAGGACCT CAAAATAAAG AGACATCCAT CACTGAAGCT AACATCGTGA GGCTGAAATC
111061 AGTCCTATAA CAATGGTACC AAAAAGAGCA CAATGAGAGG CATTTGTGAA TATTTACTCA
111121 GATGAGAGTA AGATATTTCC CTATCAGCTA ACCTGAAGTT CACATCCCTT TTCCAGCTGA
111181 GTTCTGAAGC TAGATGTACT TAACTGGAAC ACATAACTGC ATCAGGAACA TCCTTTAAAA
111241 CTATGGCTAC CATGGCTTGA CTGGACAAAC CCCAGGCTTC CAGGTTTAGC ACAGGTGGCC
111301 CTTCACAGAC CAACATTGCC TATGCTACCA ACCTCATGTC CTACCACCCT GCTTGCATCA
111361 TTTCTCTCTC TGCATATATA AAAATATATG TGTATGTATA TAATCAGCTT TATTGATATT
111421 TAATGTACCA CAAAATTTGC CCACTTTAGG TACAGTTCAA TGAATTTTAC CGTGTTTTCT
111481 TAGTTGTACA ACCATCATCA CAATTTAATT TCGAATATT TCTATCACCC AAATTTCCAT
111541 TTCTGCGTAA AGGGGAAAA AAAAAGGTTA ACTGCTGAAG GCCGCGGTAA CACTGAAAAA
111601 GGTGCCTTTT CTCTCTAAAA CAGATTTTAA TCTCCCCTGA ATTTAGTGTC CTGGGTATTC
111661 CAGGAGTCTG AATAGGGTTT CAATTTTCAG GGTCTTTTTA ATAGAGTAAA ACTGTATTGG
111721 TGGCGATAAA TTTAGTATTG CTCTCAGTAC ATGATTGAGG GATACTTAAA TGTCTCTGTG
111781 ATTTTATTTC ATAATCGCTA AAAGATGGTT TTTTTTTTTC CTAAAACAGG GTTTTTGTTT
111841 TTTCTCAATA AGCTTCTTAG CTTCCCCTCC GGCTCCCTGG CTTGCCTCAG GAAATATTAG
111901 CTCATCAGTT CTGATTGGTT GACAGCTACG AATGGCCCTC ATTGATTGGG CAGCGCTTCT
111961 TTGTCCCTTG GAAACTAATA CAAATTTTTA ACACTACTTT TTTTCCACTC TTTCTTCAGA
112021 GTTGGAATAT CGTTGCTCCC CTACCATATT GTAGTGAGTG GAGGGCAAAC TTGGAGTTCC
112081 CCTAATCTTT CCTTTTAGG ATGTCAGCTC AGTATCATTC ATCTTAATTA CACATTGAGC
112141 TTCTTGACTT AATGGATACA GCTCTTCTTT TGTTTAGTTG GGCGGCCCTG AAAAGGGCCT
112201 TTGGTTCAGA AATGCAAGCT GTGGAGAAAT CAGCAACCTT AACCGCCAAA GCCATAAAGG
112261 GTGCGTCCCT GGCGCTTAAG CGCGTAGACC ACGTCCATGG CAGTGACTGT CTTGCGCTTG
112321 GCGTGCTCCG TATAGGTGAC AGCGTCACGG ATCACGTTCT CCAAAAACAC CTTGAGCACC
112381 CCGCGAGTCT CCTCGTAGAT CAGACCAGAG ATCCGCTTCA CACCGCCACG CCGGGCCAGA
112441 CGCCGGATGG CCGGCTTGGT GATGCCCTGG ATGTTGTCAC GCAACACCTT GCGGTGGCGC
112501 TTGGCACCCC CCTTACCCAA ACCCTTCCCG CCCTTACCAC GTCCAGACAT GACTTCCCAA
112561 GAAGTGAACC AAGAGCAAGT GAGAGAATAG GAAACCGATC TTTATATATC TACGTTACCC
112621 CTGCCCCAC CTCCAGCGGA CACTGAGACT GAAAAGCGCG CAGGCGGGAA ATGTGACGCC
112681 TACAGTCCGC TCCTTTAACC CCTCCTCCAA GCCCCAGGAA ATGGCGGGAG CAGCGATTGG
112741 GGGAGGGTGG GGAGATGAGG GTGGGACCAA GCAGGCTTGA CCAATGGCCT TTATTTTCTT
112801 AACAGAGCTA CAGGCTTTGA GGAACTGGGT TAAGAATTAA ATGTAAACCC ATTCTGACTC
112861 CAGAATTATT TTAAGTCGAA CTTTTTTTTT AACCGAATCT CTCTGTCGCC CAGACTGGAG
112921 TACATTAGAG CCATCTCGAT TCACTGAAAC CTCTGCCTCT CAGGTTCAAG TGTTTCTCCT
112981 GCCTCAGCCT TCAGAGTGTA GCTGGGATTA CAAGCGCTCG CCGTCGCGCC CGGCGTGTTT
113041 TTGTATTTTT CGTAGAGACG GGATTCGGCC ATGTTGGCCA GGCTGATCCC GAACTCCTGA
113101 TTTCTGGTAA TCCGCCCGCC TCAGCCTCTC AAAGTGCTTG AATTACAGGC GTGAGTCACC
113161 GCGACCGGCC GAAATCGATT GGTTTTGAAG CCTTCAGTAG CATTAAAACG AAAAGTGCTC
113221 CCAATGCATT CCCTTTTGTC TTAAATTGGT TTCTTACAGC TACTTTACTT GAAAAGGTGG
```

Figure 1 (Page 35 of 73)

```
113281 TGGCTCTGAA AAGAGCCTTT GCTTGGACCG TCAGAGAGAC CACAGTAATC ACGCCCTCTC
113341 TCCGCGGATG CGGCGGGCGA GCTGGATGTC CTTGGGCATG ATAGTGACGC GCTTGGCGTG
113401 GATGGCGCAC AGGTTAGTGT CCTCAAATAG CCCTACCAAG TAGGCCTCGC ACGCCTCCTG
113461 CAGAGCCATC ACAGCGGAGC TCTGGAAACG CAGGTCTGTT TTAAAGTCCT GCGAATCTC
113521 GCGCACCAGG CGCTGGAAAG GTAGTTTACG AATAAGCAGT TCAGTGGACT TCTGATAACG
113581 GCGGATCTCG CGCAGAGCCA CGGTGCCCGG CCGGTAGCGG TGGGGCTTTT TCACGCCGCC
113641 GGTGGCCGGA GCGCTTTTGC GGGCTGCCTT AGTGGCCAAC TGTTTGCGTG GCGCCTTGCC
113701 ACCAGTAGAC TTCCGAGCAG TTTGCTTAGT GCGAGCCATG ACGGAAAAAC AGCACAGCGG
113761 AACACCCAAC ACTAGCGCAA ATACGCCCAT GAGCTGCTCT ATTTATAGTG TGTAAAGTGC
113821 AGTGATTGGA TGATAGAAGA CGCTAAATAT GACGTTACAC ACTCTGATTG GTCTATCTTT
113881 AAGCCAGCAA CAATCGTGCA GTTTCACCGG CTACTATATT CTATTCCAAC TCTACAGATG
113941 ATTATTTAAG TGGTATTTTA TTACTACTAT TATTTTATTT TACTTTTGCT TTGTTCCCCA
114001 AGCTGGTCTT AAACTTGGGC TCAAAGGATC TTCCCGCCTC AGCATCCAGA GTAGCTGGGA
114061 TTACAGGGGA GCCCCACTGC GCCGGCTTGG ACTTTAATTT TTTAAACTTG TCCTCTTCTA
114121 CATCTGGTTT TCATAACCTG AAGGCTGTGT TTATTTTCCA TAAAACAAGG CATTGATTCC
114181 AAAGGTATTA TAATTCCCCA ATTCCGTATA ACCTTCAGCT CTTTAGGAAA AAAAAAAAA
114241 AAAAAAAAAA GAGGGAATAC TGCTCACCTC CTCTCCGGAA ATGTACCCTT TACGGGAATT
114301 TCTGAAACCT TTCACAAGAA TTGGATTCCT TTGTAATGCT TTAATTGACT TAGGAGTGTT
114361 ATTGAAATCT ACAAAGCATC TCAAACATAG TAGGATTACA CTATTACTCA GAAACATTTT
114421 CTATGAGACG TCTTTCTCTT GATTATGCTC TTTGAATCCT AAACTTGCAG CGTTCTGCAG
114481 CTTTTGTTTT CTAAAGCCTA GGTGTACTCT GCCAGTCACA AAATGGCGTT TCTCCAGCAC
114541 TGCCGCCAGG TACCACCAGC TGGGAGTTGT TCCTCTTGCG GAGCAGGAGG TGGACTTGGC
114601 CCAAGAGAAA CTGGATAGTG GTTCGCAAGG AACATAATTT AGCATTGCCA AGAGCTAATG
114661 CAATCATTTT GAAAATCTCA AAACACTGAA AAGTGGATTG TGACCTTTTT AAATTCACAA
114721 GAGACAGGCC ACATTCTATC TTTTGATTGG TTTAGGCTAT TTTCTTGAAC AGCCATTTAG
114781 AAAGCAGATC TATCATCCTT CATTTGCATG GAGCGTTCCC ATTTTATTTG AAACCAGTTT
114841 AACCCAATAG AAAAAAGGGA GGCAGAACCC ATTATTTAAA GTGGAAACTC CTGAATCAGA
114901 TAATTAGGAG TATTTCCTTT TCAAAAGTTG CGTTTTTTCA GATACCTCGC TTATTACACT
114961 AAGAAAGGTT TATATCTTTC ACAAAGGGTT TACTTACAAA AATCTTCCAA TTTTGTATAC
115021 CTGTGTTTCA TAACTGACTA GCCGTCAAAC CAAGATGTAG AGTTTCCAAC CGTTATTTTC
115081 CAAATTTTTA GAAATTACGT GAAATATTTG AATGCATGCC TTCTCAATAA AATGGGACGT
115141 AGGAAGCACT GGTGCAGAAG ATGGGTACAA TACTTATCTG GACCACTCC ATTATTTGGT
115201 TGGCACGTTG TTTGAACAAA AAGGGGAAAA GCTCAGGTTA CTTAGCATGG TTCGGACTTA
115261 TTTGAAAACT ACCACAGCAG GAGCGGAAAT AAGACCGCAT TACCTCACTC TCTGCTGTGC
115321 TGTGCTAGGG GGTTATCCAG AATAGGATTG TAGAAGTGGA TGTCGATTTA ATAGTTTTTT
115381 ATTCTCCCAT TAGCTGAGTC TCTGATTGGC AATGTGAGAT CGTTTTAGCT TATTGATACT
115441 TTGAAATGCA CTTAACAGCC ACAAACAAGT TAAAGGGTTG TTACCATAAA ATCTTATCCC
115501 CAGGGTGTGC TTGCATTTAT CACCCGTGTT TGCTTTCACA CTAAGTGGAC TTAACTCCCC
115561 AGCAGAATGC CTGTCAGGGA ACCGGTTTCG TGGACCCAGC ATTTAACGCC TTTCGCAGGC
115621 TTGTGAGGCC CATAAATATT TGTTAATAA AAGAATGAGT TGACCATGTC ATGGTGCGCT
115681 GATTGCGTGT GCTGACATGG AACACAGGTT GTAAACCTTA ATACCAATTT GGGGCATGTT
115741 GTATGGATGA AAAGGGCATT GGAAATTCCT GAAGTGCATC CCACATTGGA CTGTGGAAAT
115801 AAGTTGCAAG TGCAGAAACG TTTCCACACT TGCAGTTTGA GTATTAATTG CAGCGTTTGT
115861 GAATTCTGGT GTTGTCTACG ATTCATTCTT GTTTGACGTG AAAGGTATTC GCGAGACACA
115921 TCGCTCTAAA ACATTGCCAG AAAATGTAAT AGAGTTGATG ACAACTGGCC TAACACGGC
115981 CTAAAACTCG CACTTTTCTC TCCCTCCGCA ACTATTCAAA ACACTGTATT TTACATTTCT
116041 TGCAAATTAA AAACTAACAT CTCTGGCAAC GGACCTCTAA AAATTTCTAA TAAAACTCCT
116101 CGGATGCTTG TGGCACTGCA TTTGTAAACC GCCCCCTCTC AACCTACTCC CTAAAAAGA
116161 GCTGCTTTTT GAGAGAGAAG CGGTACCCTC TGATGTTACT GGGCGGCAGT CTGCCTACAA
116221 TTTCCTTCAC AATGAGGCAA CCAGAGCGGC TTTTTCTGTG TGTTTGCTTG CGTTGAGGGG
116281 AGCAGGACCA TAGGCCCTAG AGGCCCCCAG CTGCCTTCTG AGACTGGGCG AAACCCTCGG
116341 CAGCGCGCAG GGGGCGCTAG GGCGCGAGGG GCGGGCACTG ACGGGCACCA ATCACGGCGC
116401 AGTCCCACCC TATAAATAGG CTGCGTTGGG GCCTTTTTTT CGCATCCTGC TTCGTCAGGT
116461 TTATACCACT TTATTTGGTG TGCTGTGTTA GTCACCATGT CTGAAACAGT GCCTCCGCC
```

```
116521 CCCGCCGCTT CTGCTGCTCC TGAGAAACCT TTAGCTGGCA AGAAGGCAAA GAAACCTGCT
116581 AAGGCTGCAG CAGCCTCCAA GAAAAAACCC GCTGGCCCTT CCGTGTCAGA GCTGATCGTG
116641 CAGGCTGCTT CCTCCTCTAA GGAGCGTGGT GGTGTGTCGT TGGCAGCTCT TAAAAAGGCG
116701 CTGGCGGCCG CAGGCTACGA CGTGGAGAAG AACAACAGCC GCATTAAGCT GGGCATTAAG
116761 AGCCTGGTAA GCAAGGGAAC GTTGGTGCAG ACAAAGGGTA CCGGAGCCTC GGGTTCCTTC
116821 AAGCTCAACA AGAAGGCGTC CTCCGTGGAA ACCAAGCCCG GCGCCTCAAA GGTGGCTACA
116881 AAAACTAAGG CAACGGGTGC ATCTAAAAAG CTCAAAAAGG CCACGGGGGC TAGCAAAAAG
116941 AGCGTCAAGA CTCCGAAAAA GGCTAAAAAG CCTGCGGCAA CAAGGAAATC CTCCAAGAAT
117001 CCAAAAAAAC CCAAAACTGT AAAGCCCAAG AAAGTAGCTA AAAGCCCTGC TAAAGCTAAG
117061 GCTGTAAAAC CCAAGGCGGC CAAGGCTAGG GTGACGAAGC AAAGACTGC CAAACCCAAG
117121 AAAGCGGCAC CCAAGAAAAA GTAAATTCAG TTAGAAGTTT CTTCTAGTAA CCCAACGGCT
117181 CTTTTAAGAG CCACCTACGC ATTTCAGGAA AAGAGCTGTA GTACACAGAT GAAATCCCCC
117241 AAGCAAATGC AACACGCCCT CAATTATATT AGAATCACTT GGAGAGTCGA TAGAACTTTA
117301 ACATAGCCTC ATCTAGTAAG AATTTACTAC TCAATCTATC AAAGATAGCA AGGTGAATTC
117361 AAATGCACCG AGTTAAAATC GAGTTTTAAA GTCACCTGGG TTTCGGTAGC CGGAAGTCCC
117421 GCGTCTCACG ACTCCAAGCT AATTAGTCAT AACCGTATTG AACCAAGGTT GAAGCCCAGT
117481 CCCAGGCTTG AGGCTTTTTA TTATACAAGG TTAAAGTGGG GATATTGCGT TTTGGGGTCA
117541 ATATTGCTAA AGTAGCATTT TCCGAAATTG GGTGGTCCTA AGAAATGCTT CTGGGATAGT
117601 TGGCAAAATA TATGGCTTAA CCACGCCCTC TCCACAGGAG TGGCTAGCGA GCTGTCTGTC
117661 CTTGGGAAGG ACGGTGACCC TGCTGGCGTG GCTGGCGCCC ACGTTGGCGT CCTCTGAAAG
117721 CCCCGCCAGG TAGGCCTAGC TCGCTTGCTT TCTGCAGCGC CATCATGACA AAGCTTTGAA
117781 ACGCAAATG CTTTCTTTGT GCAGCGCCTT ACCATGGGTG CACTTACGGG CTGTCGACTT
117841 GGTTTAGGCC CTTGTCAGGA CAAAGGAGCT TAGTTTGTTG GAGTTTTAGA GCTGCAACCC
117901 AAAATCCCTT GCTCGGTTTC TCTGTTTTTA GAAACGGAAG CGCCCTGATT GGATATTTGA
117961 AAATTACTGT GCTTAACTGG ATCGTGTTTC ATCAGTCGTG CAGGATTTTC AACCCTGGTG
118021 GAGCCCACAC ATTCAAAACT GAAGATCCTT TTCTCAGAAC TGCCCCTTTA AGCTTTTGCA
118081 ATTTTAATTC TGGGGGTCAG ATTTTAATAA TTGGACTTTT TTGTTTACAT CTGACAAGAG
118141 TATATGATGA GCCAAGTTTA CTCACTTTTA CTTAGTGCAG TTCAATTCTA AAAGTTTATT
118201 TTTGCGTGTG TGCATATGAG TTAATAATCA GTTGTATTTT TCAAACGGTC TTTTTTCAAT
118261 TGTTTTGCTT AGCTCCTTCC ATCGTCTAAA GTCAGGGATA CAGGCACATC ACATCCCTGT
118321 TCCCCCTTCC TCAAACTAAT ATGTAGCTAC CTAGGTTTAT CCTTTAAAAC AAAAATTCTC
118381 ACCTATTTTT GTGAGAAATA TACATGTTTT TCTTTGAACT AAGTATTTTA CATACACCTA
118441 TCTATATACA TGCATACTTG TGGTTTTGTT TTTTTAAAAA AAAAAAAAAA AAAACACGTT
118501 ATCTTTTGAG ACTGGGTCTC AGTCTGTTGC CCAGACTGGA CTGCAGTGGC ATAATCACAG
118561 CACACTGTAA CCTCCAACTC CTGGGCTCAG GCTATCCTGC AGCCTCAGCA TCCGGAGTAG
118621 CTGGGATTGC ATGCACGCAC CACCAAGCCG GGCTTTTTGT TTTTATTTTT TGTGGAGACA
118681 GTCACACCAT GTTGTCCAAG CTGGTCTAGA AATGGCCTCA AGTGATCATC GACCTCCCAA
118741 AGTGTTGGGA TTACGGTCAC TGTGCCTGGC CTTGTATGCA TAATTGTTTT GTCTTTTGAT
118801 TAGGGTTATT AATTTAAAAA ACAAAGCCTG GACGCAGTGG CTCACATCTG TAATCCCAGC
118861 ACTTTAGGAA GCCAGATGGG CAGATTACTT GAGCTCAGGA GTTCAAGACC AGCCTGGGCA
118921 ACATGGTGAA ATCCCATCTT GACAAAAAAT ACAAAAAATT AGCAAGGCCC AGTGGCACGC
118981 ACTTATAGTC CCAGCTACTT GGGAGGCTGG GGTGGGAAGA TGACTGGAAC CTGGGAGGTA
119041 GAGGCTGCAG TGAGCAGAGA TCGTGCCACT GCACTCAAGC CTAGGTGACA GAATGAGACC
119101 CAGTCTCAAA ACAAAAATAA TAAAAATTTT TTACAACGAT GTTATATACA CTTCTGCATG
119161 TTGCTTTTCT CTTAACCAAA CTTTTCTAAA ACCCTGTCAT GAAAAAGAA ATCCTTCACA
119221 TGGAATAGCA TAAGTTATTC ATCCATTTCT TATTGATAAG CATTGATGTT TCCAGTTACC
119281 ACTGCTGAAC ATGGTGCAAT TGAATAGAAT TCCAGGGCTG AGATTGCTAG GTTTTAGGTT
119341 GTATTTATT ATTTATTTA TTTATTTATT TATTTAGACA GAGTCTTACT CTGTCACCCA
119401 TGGTGGAGTA CAGTGCCATG ACCTCAGTTG CAACCTTTGC CTCCTGAGTT CAAGCGATTC
119461 TCATGCCTCT GGTCTCCCGA GTAGCTGGGA TTACAGGCAC CTGCCACCAG GCCTGGCTAA
119521 TTTTTGTATT TTTAGGAGAG ATGGGGTTTC ACCATGTTGG CCAGACTGGT CTCAAACTCC
119581 TGGCCTCAAG TGATCTGGCC ACCTCGGCCT CCCGAAGTGC TGGGATTACA GGTGTGAGCC
119641 ATGGCGCCAG ACCTGGACTT TGTCTTCTGT TTCATCAGTC CTTCTGTTGG TTCAAGCACA
119701 GTATCACACT GAAGACTGAT GATTCTATAT AAATATGGTA AAGACTGTAC ACCCTAACTG
```

Figure 1 (Page 37 of 73)

```
119761 TTCTTATTTT TTAATTTTAA GGCAATTTTA GATTCCAGCT TTCCAAAGAA TTGTGGAATG
119821 CTTAGAGCTA GAGAAGCCTT GGAAGTCATT TAGTTTTTGT TTTGTCAGAG AAAATTCTGT
119881 AGAGACTCTG TCCTGCTCTC ACTGAATACC ATCCCATAGT ACCCCCCAAC AGCTTTAAAG
119941 GGCAATAATA CCTTATGGAC AGTATGCTTT TCCTCAAATA TATTCTAAGC CATGGTCAAT
120001 GCAAAAGAGT GAGAAGGAAA GTAGAATAAG TTATCTAAGA ATCAGTGGGT GCTCTCTTTA
120061 AACTGATTTA TCACTCCCCC TTCCAAACTC TCTTGAAGGT CACTCTGCCT CCCTTTCTAC
120121 ATAAGAACTC CTAACTCCAA GGGAGGAAGG TAAGTTATTC TTATTCCTTG CTTAGAAAAA
120181 GAGAAAATAG GTTTGGTAAG CATCCGCTTT CTGCTACCAT TCTCTGTGTT TCTGTGTTTT
120241 TTATAGGATC ATTCAATTAT TGGTTGGCTC TTGAGAGGGA ATGCAAGGTT CAAGGACACA
120301 AGCCTAGATC TTGCCTGTAT AGAACCTCAT GATGTTATGC TTCTCTAAAA TGAGGCCTGG
120361 AGGAGACATG TTGAAAGTGA CCCATAAATC TGCAGTATCT CATGTCTCTC AATGGGGACA
120421 AGGAGTACCA TGGGAAATAG CATTAGGTCA ATGACAGTAA CAACTCCCAG GTGAGTTGAT
120481 TTATTCTTTT ATTTATAAAG TTGTTAATAT GCTACATAGT CCCTAATTTT GCCACAAATA
120541 GTCATTATTT TAATTTCATA TTTCACTATT GATAAATGAA GGAAAAAATG AGTAGCAGTT
120601 AAGCAGTCCA TAAACCTACA TATAAAGCAA ATTGGAGATT TTAAAATTGA TTCTGGATGC
120661 TTAAAATCCT TCTCATTGAA AAAAAATTTC GTATTAGAAG ATTTCAACAT TCTTTAAACT
120721 GAGAAGCATA ACATATAAAC AGAAAACCAC AGCAAAACAA AAATGCAAAG CTCAATAAAT
120781 GAACACAAAG TGAACACCAT AATAATTGCC ACACAAGTAA AAAAACAGAA AATCAGCCAA
120841 CCCTCCCAGA GCCGCCTGAT GCTTGCTTCC AGTCACATTA TCACTCCATC TGCCCTAAAC
120901 ATAACCCCTA TTTTGATTTC CAATGCTGTA ATTTAGTATG CCTGTTTTTG AAACATATAA
120961 AATGGAAATA AAACAAATGT AATCCTATGT ACCTGACATA TTTCACTCCA GAACATTAGG
121021 TTTGAATAGA TTCATCTGTG TTGCTGTGTA TAACTTTAAT TCATTTTTAT TGTTATGTAA
121081 TATTCCATGT TATGAGTGCA ACAATTTAGG TGTCTACTGT TGATGCATAT TTGCTTCCCT
121141 TTTTCAGCTA ATATAAACAA TACCGTGAAT ATTCCTGTGT ATGTGTCTTG GTATATATAG
121201 GAATACATAT TTTGTTTGTA TACCTAGGAG AGGAATTGTT GGGTCAAATG CTAAACTCTT
121261 TTTGAAAGTG GTGATATTAG GTTACATGC GATGAAATGA AAATTAAAAC CACAGTTATA
121321 AACAGCATGG ATGAACCTCA CAAACCTAAT GTTGATGGAA TCTAGCTGGG AATTCCTGTT
121381 CTTCCATATA CTTCCCAATA TTTTTTTCCA ATTAAAATTG TTAATCTTTT GAAGATGTTA
121441 TCCATTGTGG CAGATGTGCA GTATTATCTC ATTATGGTTT TATTTTACAT CTTTTGCCCA
121501 TTTTTTCTTA ATTGGATTGT ATATCAGTCG ACTTGGGCTG CCATAACAAA AATACTAGAC
121561 TAGGTAGCTT GAACAAAAGG AGTTTATTAC CTCACAGTTC TAAAGGCCAG GCCAGAAATC
121621 CTAAATTGAG GTGCCAAGAG ATTCAGTTTC TAGTGAGGGC TCTCTTATTG ACCTGAAGAT
121681 AGTTGCTGTC TTAGATTGTT TGGTGCTGAA CAGAATACCA GAGACCAAAT AATTTATAAA
121741 GAATACAGAT TTATTTCTTA CAATTCTGGT GGCTATAAAG CCTATGGTCG AGGGGCCCAC
121801 CTCTGGCAAG GGCCTTCTTA CTGTTATGGC AGATGTGAGA TGTCATCTCA TATTCAAACC
121861 ACAGCAGTCG CCTTTTGTGT CCTCATGTGG CCTCTTCATA TGCCCATAAA ATGACCTCAT
121921 GTCTCTTCCT TTTCTTATAA GGACACCAGA TCTATCAGAC TACTGGCCTA CTCTTATGAC
121981 CTCATTTAAC CTTAAATATC TCCATAAAGT CCCAAAATCC CTATCTCCAA ATATAGGCAC
122041 ATTGGGTGTT AGAGTTTCAA CATCAATTTT GGGGGAACAC AATTTAGGCC AAAAAGATTG
122101 TGTTTTTTCT TGTTGGTTTA AGATAGCTGT CTTTTTGTCC TTTTTGTCCT TTCTTTTTTT
122161 TTGAGGTGGA CTCTTGCTGT GTCACCCGGG TTGGAGTGCA GTGGCGCTGT CTCAGCTCAC
122221 TGCAACCTCC ACCTCCTGGG TTCAAGAAAT TCTCCTCCTC CAAGTAGCT GGGACTACAG
122281 GTGCATACCA CCGCGCCCTG CTAATTTTTG TATTTTTGAT AGAGACGGGG TTTCACCATG
122341 TTGGCCAGGC TGGTCTCAAA CTCCTGACCT CAGGTGATCC ACCTGCCTCG GCCTCCCAAA
122401 ATGCTGAGAT TACAGGTGTG AGCCACCAAA CCTGGCCTGT CTTTTCTGTT TTAAGTTTTT
122461 AAATTTTGCT CACGAACCCT TTATCCATTT TATGTGTTGC AGGTATTTCC TCTGTAACTT
122521 GTCTTCACTC TGTCAGAGGC TGGAGTGCAG TGGCACAATC ACAGCTCACT GCAGCCTCCA
122581 CCTCCCAGGA TCAAGCGATC CTCCCATCTT ATCCTCCTTA GTAGGTGGGA CTACATGTGC
122641 AGGCCACCAT GCCCAGCTAA TCTTTGTATT TTTTGTAGA GATGGTGCTG TTGCCCAAGT
122701 TGGTCTCAAA CTCCTGAGCT CAAGCAATCC ATCAACCTTG GCCTCCCAAA GTGTTGGGAC
122761 TAGAGGTGTG AGCCACCACT GCACCCAGCC AATGATATCT CATGATGCAT TAAAGTCATT
122821 AATTTAGTGT ACTCAAATTA AGCACACTGC CCTTTTATGC ACAACCTTTT TTGTATCTTA
122881 TTTAAAAAAT CATTTTCTAT TTCAAGGTCA TGAAGATCTT ATTTTATAAT ACCTTCTTGT
122941 GAAATTAGTT CTCAAGACTA CCCTCACTTC TAACACCAAT TATAAGTTGG GAGGTCTGTG
```

Figure 1 (Page 38 of 73)

```
123001 GTTCCCAATC AACCTTAGGT TAGTAATTTG CTAAAAGGAC TCACAGAACT TGCTGAAGCT
123061 GTTAGCCTCA TGGTTACAAT TTATTATAGG ATATATAGCT TATTATGTCA TTCCAATGCA
123121 ATGTAAAATT ATACAACTAC TTTTAAAAAG ATTTTAGCAT TTGACCCAAC AATTTCACTC
123181 TGAGGTATAC AAACAGCAGA TATGTGTGCA CATATATACC AAGACACATA CACAGCAAAA
123241 TTCATTGTTT GTAATAGTTG AAAAGGGGAA ACAACTCAAG GAATAAAGAT TAAAATCAGC
123301 TGAGAAAAGA AACACACAAG GCAGTATTAT GGATCGAATT GTATGCAGAT CTCCCTTGCC
123361 CCCAGAAGAT ATGTTTAAAG TCCCAACTCC CAGTACCTCA GAATTGTGGC CTTATTTGGA
123421 AATAGGATAG TTGCAGATAT AATTAGTTAA GATGAGGTTA TAGTACAGTA TGATGGGCTG
123481 GTGACTTAGA AGAAGTAGTA TATATATATT TTTTAATAGA ACTAGTATTC TTCTAAGGTG
123541 GTCACGTGAA GACAGACACA CACAGGCAGA GACTGAGGTT ATGCAGCTGC AGGTCAAGGA
123601 ATGTCAAAGG TTGCCAGCAA GTACGAGAAG CTAGGAAGAG TCAAGGAAGG ATTTTCCTAC
123661 AGGCTTCAGT GGAAGCATAG ATCTAATGAT ACCTTCATGT CAGATTTCTA GCTTCCAGAA
123721 CTACAAGAGA ATATATTTGT TGTTTTAAGC CACCCTAGCT TCTAGCTCTT TGTTACAGCA
123781 GCCCTAGGAA ACTAATATAG GCACAATCCA GGCAAGTTCC AAATATGAGC TTCCAGTTGT
123841 CCTCTCCCAG TAATATGAAC AGTATTACTT TCCCAGCATT AATGTGTGAC AATACACATG
123901 ACGTACAGAG CAGTCCCCAC TTATGCACAA AACATATGTT CCAGGACCTC CAGTGGATGT
123961 CTGAAACCAT GGATAGTACT GAACTCTATA TAGCTGTTTT TTCCTATACA GACACAGCTA
124021 TGATAAGGCT TAATTTATAA ATTAGGCACA GTAAGAGATT AATAACAATA AATTAGAATA
124081 ATTGTTAAGA ATATACTGTA TAAAAGTTAG GTGAATGTTT ATTTCTGAAA TTTACCGTTT
124141 ATTATTTTTG GACTGCAGTA GACCACAGGA ACTAAAACCA TGTAGAAACC GTATACAAGA
124201 GAACTGTATT TCACCCGAGC CTCAGTGTGC AGTTTTAATG GCCTGCCATG GTTGACTGCT
124261 CACATGGCCG ATCTTTTAGT CTACCTCCAC AGGTAGAGCT GATACTGTGT GGCTCAAAGT
124321 TCCTATTATA AATCACATTG TTGACTGTGT GGTGGTCAAA ACCTCCAGGT AAACAAAGAC
124381 ACACTTATCA GTGAGAACAT TTCAAGGGTC TAAAATTCAT CTCCCAGTAG CTGAGGGCAA
124441 AGGCTAGACC TCTTTTTGGG TAAGATAAAT TTTTTACCAT ATACTTTATT TTGCTTTTCA
124501 TGTTTAACTT TATTTTGCTT TTCATGTTAG TTCCCTGGA ATTGTTTTTT GTGTATAGTG
124561 TGAAGTAGGG GGTCAAGTTT CTTTTTTTTT CCTTTTTGTT CTTTTTCTGT TTAAAAGGCT
124621 ATACAATTGT CCCATGCCAT TTATTTACAA GAGTCCTTTC ACCATTGTTG TATGGTGCCA
124681 CTTTAGATGT AAATCAATGT CCATATTTGT TTGAGCCTGT TCCATTCGTT TGTCTATTTT
124741 TGGACAACAC TGCCCTGATT ATTGTCATTT TATCAGTTTT GATATTTAAT AAAGCAACAG
124801 ATTTGTTTAT TTTGGGCCCT TGGATTTGTG TATTAAATTT GAACCCTGTT TGTCAATTTC
124861 TATAATAAAG CTTATTGGGA ATCTGATTAG GATTACAATG GTTTTGTAGA TCAGTTTGGG
124921 GACAATTAAT ACCTTTAAAA TATTGACCGC TTCAACTGTA AATATACTCC TCCATTATTT
124981 AGTTTTCCTG TTTAATTTAT CTGAGTAATA CATTATAGTT TTCTTCGTAG AAGTCAGATA
125041 CGTAGAAAAT TCAAAGCCCA AGTGCAATAG CTCATGTCTG TAATACCAGC ACTTTGGGAG
125101 GCCGATGTGG GTGGATCACC TGAGGTCAGG AGTTTGAGAC CAGACTGGCC AACATGGTGA
125161 AACCTCATCT CTAGTAAAAA TACAAAAATT AGCTGGGTGT GGTGGCGGGC ACCTGTAATC
125221 CCAGCTAATC AGGAGACTGA GGCAGGAGAA TCGCTTGAAC CCAGGAGGCA GAGGTTGCAG
125281 TGAGCCAAGT TCCTGTCACT GCACCCCACC CTGGGCGACA GAGCGAGACT TCGTCTCAAA
125341 AAAACAAAAA AAAGAACATT CAAATAATCA ATGTAGATAA TTCAAATAAC TAAAAAATGA
125401 ACAGTTATTA AAATATCAGG ATATAAAAGC AAAAAAATCA ATAACCTCCA TATATACAAA
125461 ATGGCCAGTT AGAGAAAAAA AAAAGAATAG GCGAGACTTA AAAAGGCTGG AATCTCCCT
125521 GAAAATCTTT GAGAGCCTTG GCCCTGCCCT CAGGGATTTC TCTGGCTTCA TGCCCAGATA
125581 CGGGTACAGT TCCTTGTTTA AAAAAATTTT GCTCCATCAA TCAACAAGGG GCTCCTTCCT
125641 CAGAGCACAA GGACCTCCAT AACACCGGAC ACTAGATGTC TAAGGGACAC CTCTTAAGGA
125701 AGTTAGACTT CCAAAGAATG GTGTTTCCTC TGTCCCCAAA CTCTGGAACT CACAGCACAA
125761 CTGCTCCTTG GAGTTCGGTT TCAAATCTAC AAGGCTGTCA TGGAGGTTGC AGACCAAGTC
125821 CGTGGCCTCA GTGTCCGGAT GTACGGTGGC CTTGGCACCT GAATGTGAGA ACATGACCTC
125881 CCTGAAACCA CCACAAGTAT TGTTTCATGT TATGTATGTT TTTCTTATC TGAAATTCCT
125941 TTTCTTTAAA AATTCAAATT ACATATTTTG CAAGCCCCTG AACAAGCTTC ATGAGCATTT
126001 ATTGAACCCA CAGCTTTTAA AACCTACTGA ACACTTTGCT CTATGTTGTC ATTCACTATC
126061 CACCAATTAT TTAATTATTG ATCAATATTG TTTCCTTAGT GTTGGGATCA TTTATGCATG
126121 TATTTCTTTT ATATTGCATA TTTTATATTT CTGCATTACA GTTATTACAT ATTACTTTTG
126181 CTACAGTAAT AGTTCAAAAG TGTACATCCA AAATTTAGCT GTGAAGTGGA TGGACTGAGG
```

```
126241 CAGAACTGGA GGCAAGAAAA TGTCACAGTA ATTCTAAAAA AGATGATGTA CAATTAGAGC
126301 AAGAGAGTAG CACTGAAATT GAAGAAAAAT AGATGCGTTT GAGAGAAAAT TAGGAGGTAG
126361 AATCAACAGA TTAGATGTAG GGATGAGAAG GGTCAAAGAT GACACTAGGG TTTTTAACTG
126421 GAGCAAGTAG GTAGACAGAA CATTTCTTCC TGAAAGGGCA GGTCAGATCA TGTGTTGTCT
126481 CAAAGGGCAT GAAGAGTAGA AAGCCTGGGA CAGATCCTGA GATGACCAAT ACCCATGGTG
126541 CAGGGAGAGG GAGGGAGATC TGCTAAAAAG ACTGCAAATG TCAGGATAGT AGAAAATCAT
126601 GAGTGTGTGA TGTCCTGGAA GTTGAGACAG TATCACATTT GAGAACATTT AAATTGGTAA
126661 CTCTGACAAA AAGCTGGAGG CCAACTGTGA ATGCCCATGA GAGTGAGAAG CTCCCACACT
126721 TTTGTGGGCA TCAGAAAGCC CACCAGGTTC CTGCAGTGAA GATCTGAGAA GGATCCTCTT
126781 GTGGCTTTGG CAGGGAGAGA AGAATTATTA TGAAATACAC CCCAGAACCT TCTTCAAAAC
126841 AAAGGCCTAC TCTCAAGGGG AAAACATTTT GCCAGAGTCT TATCCCAGCT GGGAGAAGGT
126901 AATTCTTCCC ACTGCAGCCT CATCTAGGCT TTCTGTCTCA CTTAAGGGAA GAAAATTAGT
126961 CAACAGGGAT CAGAGCTTCA TGAAAATAAA TTGGAAATGG TGCAGCCAGG AAAGGAGCAA
127021 AGGTCTGAGG AGGAGGAGAA GGAGGAAGAG GAGTTGTATC ATTATAAATA CTTGAGGAAG
127081 AGGAGGAGAA GGAGGAGGAG GAGGAGTTGT ATCATTATAA ACACTTGAGG AAGAGGAGGA
127141 GGAGAAGGAG GAGGAGGAGT TGTATCATTA TAAACACTTG AGGAAGAGGA GGAGGAGAAG
127201 GAGGAGGAGG AGGAGTTGTA TCATTATAAA CACTTGTGAC GGTCCCAGCC CAAGATATA
127261 GGCATGCTAA TAAACTGAGG CTTAACACTT TGACTACAGA ATGCTGCTTC TCCCTAACAC
127321 CATCAAGGCT CCAACTGAAT AACAATGAAT TATGAATGAA AGAGCTGTAA GGAGAGACAA
127381 AAGTTAGAAT GAGACAAGTA TTGTTATCTA GAGATGCCAA GAAGGCAAGG AAGATAACTA
127441 AAAAGGCACT CTGGATTTAG AAATAGGAAG TCATTAGTGA CCTTGTAAAT AATGGAGCCA
127501 GAGGAATACC AAGGGCAGAA GCCTCACTAT AGTGTGTTGC ACCTGTCAGA GGTCAGGAGG
127561 TGTAACTGAC TCTCCCACAG TGTGGCTTTG GAAGAGAGAA GTCAGCAGCT GCATGGAGAT
127621 TTGGGAGAGG GAAAGCTTTT TTTTTTTTTT TTTAATTGGA AAAGACTGAG CTATGTGTAA
127681 ATAGAATAAG ACAGGAAGAG TGTAGACACA GGAAAGAGGG CAGACAAAAA CAAGTGCACA
127741 GTTATCTAAG GGAAACAATG GGATCAAGCT GCAAGTATAT AAACTTGTCT TGATAGAAGA
127801 ATCCTTGATC TGGTTTATTC AGTGTTTGGT CCAAACCCAC ATCCCTGTTC TGCCTGTCTC
127861 TGACTTGCTC TGTGCCCCAG AAGCCCAGCT TCTACAGATA GCATTAGCTG GGCAGCCCTG
127921 CCCTCTTGCA ACAGCTGGAT TTGGCCAGTG ATCAGCCCAG CAGGAATGTA GATGGCAAAG
127981 GAGAGAGAGG TTAGTGTACT TATTCCCTGC ATCACCCCCC TGCTTGGTGG GCAGCTCTTC
128041 CTCCACAGTC CCAGCTCTGG CCTAGCTCTG GTTACAGGTT CCCTCCCATT GCCTCTTCAG
128101 ATTTAAAGGT GTGTCTGTCA GGGTATAACT GGGAGCTAGA AATTGCACTG AAATTGAACA
128161 AAGAATTTTA TGGGAATGGT TGTTAACTAG TTATAAGAGG ACTGAAAATG GAAAAGTGGA
128221 CAAACGTATC AGAGATAGTA ATGACAGAAA GCAACTACCA CCTCCAGGTT TAGGAGAACA
128281 AGGAAAAGAT TCTTTGAAGA GATCCCCAGA ACTGGGACCT CTGAGGAGTG TATGCTGGAC
128341 CACTGATGAT GATATGTCTG TAGATAGAGG CATGATGAGG CTGATTTTAG GAGCATGGAA
128401 GATCTCCAAA CTGAAGCCAA CTGCTGTTAC TGGATTCAAC TGCCACTGCC AGGTTGAAGA
128461 ACCCATTCTG TGAGGATGTC AACAAACAAA GTGGGAAATC TTTTCACATC CTTCCAGCCC
128521 TCTAGTCTTC CTCCAGTGCT TTCTATTGGT AGGGTTTGGG GAGGTGGCTA GCAAAGCGGT
128581 ATTGGAAAAG ATAGAAGAGA CTAAATCTTC ATAACCAGCA CAGGGTGACA CTGGATCACT
128641 ACTGTTGCTG ATCTTGGGCT GCCTCATATC CCCTGTTCTT CCCATTAGCC CTGTCACAAC
128701 TTTGTAGATA TCCCTTCATT ATATGCCCTT CATATATTCT TTTGGTTTAA CTTTTTCTGT
128761 TGGAATCCTA ATATGGCACT CCTCCATTTT TCAGGACCAA AAGAGTATAA AAGATTATCT
128821 TTTACCAAAA AAAAGACAAA AAACTGATCT AATTCCTGAT TTGATCATTA CACAATCTAT
128881 ACATGTATCA AAATATCACA TAGTACCCCA TAAATATATA CAACTGTGTC CATTAAAAAT
128941 AAAAATTAAA GAAAAGATGG TAAATATAGC TCTGTCAGGC AGTGGAGGTT TTACCACGAT
129001 GGCTGTTATT TCCCCCATGA AGGGGGAGT GAGGGAGCAG CTGAAAGTAG GTGCTTATAG
129061 GGGTATAGAG GGGCTCAAAG CTTTGAGAGA GGAGAATGTC TGAAAGAGCT GCCAAATAGC
129121 ATGCAGGTCC CATGGGGGCA GAGCCTCTGC TCATTCACCA GTGCCTCTTC AATATCTACA
129181 CTTAAGCCTA ACACAAAGTG TGTGCTTAAT AAGTATTTGC TGAGTATGTA AAGTGGAAAC
129241 AGAACCAATC TGGCAAACTT TGTAGGACTG GTGGGCAATG AAGATCAGTC AGGTAAAATC
129301 TGTGGATATA AATTTATATT GATCAAAAAA TTCAAGGTTA GGTGTTTTTC TTCAGTCATG
129361 CTCAACGATG CTTCAGCCAT GCTCAACTCT TCTGTAGCCA CAGAAAAAAG TTTACCCATA
129421 ATCGAGCTGT GTCTGTGTCT GAATAATGAA AAGACCATGA TGCAAGGGAG TTGGAGACAC
```

Figure 1 (Page 40 of 73)

```
129481  AGAAACAGTG  TTTGAAGTAA  TGGGTAATGG  AAGCATGCTA  CCAGGGAAAG  GAAAGAAGTG
129541  GCAATAGGAA  GGAACAGAGA  TCTGTGGTCC  TATGTCCCCT  GAGCATATTC  ACATGTTAAA
129601  GCTAATTCAG  TTTTCAATCA  TCATTAAAAT  TTTGTTCCTA  AATATATGGC  CATTATTTTC
129661  CACAACCACA  CTAAAACTTT  ATTACCTCTG  GCAAGTGACT  ATGCAAGTAA  CTAAGAGCAA
129721  AAATATCCAC  AACTACCATT  TGAGCTATCA  ATTTAGGGAA  AGTCATCTGG  CTATAATCTA
129781  AGTGACCCTC  CACTGAATGT  CAGTATCTTT  GCATATGTGA  TTTAAATCTG  GGCCTTCGCA
129841  ACACCATGAA  CTGTTCTTGT  CTTGAATATC  CAGATTGAAG  GAAATAATCT  GAGTAGTTAC
129901  GAGTCCTGAA  GCTAGAAAGA  TGGAAACCCC  ATTTGCTCAT  CAGAAAGCCT  TAGAGCTTGG
129961  GCGCTGGCGG  GTCCTGTCTC  ACCGGGACAG  AGGGGCTCTT  TCCTCCCCAT  CTGATAGTCT
130021  GATAACTAGA  GAAGCCGGCC  AACTTATTCT  CCAAGAAGGA  GCCATCTTAG  TTCCTCCTGA
130081  AATGTTCATA  TTTAGAAATT  ATTGTTTGTC  AGTAATTTAA  CCCCTTAATG  GGCTTGCCTT
130141  GTGGTCCATA  CCACTGAGTG  CAGAGCTTGC  CTGGAAGAAT  TGTGAGGGCC  ATTCCATCTT
130201  CCAGGCAGTA  GAGTTCAGTA  CTTCTTTAAA  ATTGCTGCTG  AACTCTGTAT  TTGAAAAGAA
130261  AGAATCATTT  GGGTGTGGTA  GCTCACACCT  GTAATCCTAG  CGCTTTGGGA  GGCTGAGGTG
130321  GGAGGATCAT  TTGATGCCAG  GAGGACCACT  TGAGACCACC  CTGGGTAACA  TAGCAAGACC
130381  CTGTCTTTAG  AAAAAAAAAA  TACAATAAAA  TAAATACAAT  AAAAATAAAA  GCAAAAAGAA
130441  AGAGTCCATC  TTAGGGACAG  ACTGTAACTA  CTCACTGGAG  CTTACCTTTA  CATAGTTCAG
130501  GATCAATTAT  AATAAAACAC  TTTTGTGCAG  ATTCAATAGG  ATTATTTTAA  TCCCCATCAT
130561  CTCTCTGAGT  TTCCAGTCAG  TTTCTCTGCA  TGTAGACACC  CTTCTCCAGC  CCACCATTGT
130621  CTCTCCTCCT  ATAGCTCCAC  CAACAAATCA  GAACTTTTTC  TAACTGCACC  TAGTGCACCT
130681  AGAGTCTACT  CCAGAATGCT  CATGGAGAAA  GTTTCTGAAA  GGTAAAACTC  TGAATGATAT
130741  TTGTAGCTAA  AGGGAGACTT  GCTAGAGACA  ATAAGCTAAT  AGTTGTAGAC  TTCAGTAGAA
130801  GAGGAATGAC  ACTGCAATGT  CAGGGTGCAG  GACTTCAAGA  GGGCAGAGTA  TGGAAACCCA
130861  ATGGGAAAAA  TGCTCACCAG  GAACATGAAG  AGAAGGAATT  ACGTGTAAGG  ATTTCTCAAT
130921  GTGTTCCCAA  ATTGCCCAG   CAGAGGGAGG  CCTCGGGTTG  ATGGCAGGCT  GACCACACAA
130981  TTAAAGAAGG  CTGAACCTGG  GGGCTTTTAA  CAACCATCGT  GGGCTCTACT  GTAAGCATTT
131041  AGAAAAAGAA  AGTTATCCAT  TCAAAAATAT  ATATATTTTT  AAACTTCAGA  ACAAAATTAT
131101  GAAGAGCTAT  ATTTACTTTT  CTACATTCTA  ATTTTTATAA  ATCTGAGTAT  ATTTTGCATA
131161  TATTGTTATA  GTACATATTC  AATTTGTAT   TTGCTGTTT   TCACTTAACC  ATTTTTACTA
131221  GATTACTCTG  TGTTCATAAT  AATCACTTTT  TTAAAACTTT  TATTTTTATT  TATTTATTTT
131281  TTTTTTGAGT  CAGAGTCACA  CTCTGTCGCC  CAGGCTGGAG  TGCAGTGGCG  TGATCTTGGC
131341  TTACTGCAAC  TTCCACCTCC  TGGATTCAAG  CAGTTCTCCT  GCCTTAGCCT  CCTGAGCAGC
131401  TGGGATTACA  GGTGTGCACC  ACCAAGCCCG  GCTAATTTTT  GTATTTTTAG  TAAAGACGGG
131461  GTTTCACCAT  GTTGGTCAGG  CTGGTCTCCA  ACTCCTGACC  TCATGATCTG  CCCACCTTGG
131521  CCTCCCAAAG  TGCTGGGATA  ATCACTTTTT  ATGCTGCATA  ATTCTTCAGA  TTTGTCAGTA
131581  CGACTGTATT  TACACTCATT  TGTTTTATTA  GAAAGAATTC  CAGAATATTT  TGGCTGCCCT
131641  AATTAATTTT  ACAATTAATA  TGATTTTGAA  ATTGGGTATT  GGCTCCTTCT  GAATTGGTTT
131701  ATTAAAATAT  ATTCTAATGT  AATTTATGAC  ATTTTCATCA  TATTAGCATA  TTTATTCTGT
131761  TAGAATTTCA  TAATTTATAA  AGCTACAAAC  TGTATGTGAT  ATAGCTTGTA  ACTTATCTC
131821  ATAACTTTAT  GCAGTTACAA  GTAGAAATAA  AATGTTCCCC  TCAAGATTGC  TTAAAATTTT
131881  ATTATAAACA  AGTGTAAAAA  ACAAAATCAC  TAAAACACTC  CCTCTTTTTT  CCCCAAAAT
131941  GCATGTTTCC  ATTTTAACAG  AACCCGTATT  TAATCAGCAG  ATTTCTATGG  TGGCTAGATT
132001  TGTAGACTAA  ATATTAAAAG  TCCCAAAGCA  AATGCATTTT  TCTCTTAAAT  TTTACTGACT
132061  TTTTTTTTTT  TTCTTTTTCT  GAGACGGAGT  CTTGCTCTGT  CGCCCAGGCT  GGAATGCAGT
132121  GGCACAATCT  CGGCTCACTG  CAACCTCCGC  CTCCCGGATT  CACGCCATTC  TCCTGCCTCA
132181  ACCTCCCGAG  TAGCTGGGAC  CACAGGCGCC  CGCCACCACG  CCCAGCTAAT  TTTTTGTATT
132241  TTTAGTAGAG  ACAGGGTTTC  ACCGTGTTAG  CCGGGATGGT  CTCGATCTCC  TGACCTCATG
132301  ATCTGCCCAC  CTCAGCCTCC  CAAAGTGCTA  GGATCACAGG  CATGAGCCAC  CGCGCCCGC
132361  CTACTGACTT  TTATCCAAAG  AAAATATAAG  AGCTCTTCAT  CATAACGTAT  GTTTCTTGCT
132421  CTTGTTATTA  AATATGACAC  ATTTAGACTT  AAACTGATTT  GAAGGTTTAT  GACATTGTTT
132481  AAGTTATTAC  ATAATTAATT  CATAAAGATA  ATGACTAGTT  TGAACTACTG  ACAGCTCACA
132541  CATCATCAGT  TGAACAGCAG  AAAGCTTACT  AAGCTACTTT  CTTATGTTTC  TGTCTCCCAG
132601  CTACTAAAAG  AAACGAAACC  CTTCCAGGTG  TTAAGGCAAA  ACTTTCCTCC  CCCTTTCTTC
132661  TATAAATCTG  ATTCCATGTT  AGTGAAATTT  CTACTGATGG  CTTTGGTTTC  CTCTATAGTA
```

Figure 1 (Page 41 of 73)

```
132721 GAATAGAGAT CCTATGGCAA AAGTCATGTC TGACATGGTA GCAAATAGAA ATGGGGAAAA
132781 GGAAGGTCTG CAAGAGCCAA TGTGGGAAAT GGGGAGAGGA CTGACTACAA AAACCCAGCA
132841 GGAATTCCAG AAGAAAACTC CTCAGGACGG GCACATTGGC TCATGCCTGT AATCCCAGTA
132901 CTTTGGGAGG CCGAGGTGGG CAGATCACTT GAGTCCAGGA GTTTGAGACC AGCCTGGTCA
132961 ACATGGCGAA ACCTCATCTC TACAAAAAAT AAAAAAATTT GTCAGGCGTG GTGGCATGCA
133021 CCTGTAGTCC CAGCTACTCA AGAGACTTAA GTGGGAGAAT CACTCGAGCC TTGGAGGTGG
133081 AGGTTGGTGA GCCGAGATCA CGCCACTGCA TTCCAGCCTG GGCGACAAAG TGAGACGCCA
133141 TCTCAATCAA TCAGTCTCCT CGAAAAGCAA CATTATGGAG AGACAGGATT CCGTCAAGGC
133201 CTGGGGCACA CAGGAAAATA TTAAGGCAGA AGAGAGTTTC CTCCCCACAC CACACCGTAT
133261 CCCACAGGCA CTGCGGATGT GCATATGCAA GAGGGGTTGA TCCTAAGAAT TTAGAGTCAC
133321 AGAGGAGGAG GCACCAAGCA GACTGTGGAG AAAGTCATGA CCAGAAAGGG ACAGAATGTA
133381 AAGCTTCAGC TGATTATCTG GCCTCAGGGA TTCCAGAGGA ACTGGTCCCA ATGGTCTCCT
133441 GGTGATGTAG GTTCTTAGGT TTCTTTTACA GGGGTTTTCT GGGAGATCGT TGACCCAGTT
133501 AGCATTCAAG CAACTTCCAC CCTGCACTTT TATTCTTTCC CCTTCACCTG CTTAGGTTTT
133561 ATCTGTCCAG GAAATAATAA TAAAATTATT GAGCCCTGGA CATGTACCTG TAAAGCTCCT
133621 TAAAGATGAT GCCTTCTAAC TCCTCATTCA ACAGATACAA AAACATTACA ATAAAATGAC
133681 TCATGCAAGA CACCCAGGTA GTTTATAGCA GCTAATAAAA ACAGAATAAC TATAAAATAT
133741 GGTAAGTTTA TAAAGTTAC ATTGAGTATA CTTTATAAGA ACTGCTTATT GAGTTTGCCT
133801 AATAACCACA CAGCACAATA ATAATATGTA TATATTTTA AATATGTGTA AATATGTGTA
133861 ACACAAACTT GTAGAAGGTA TATCTGAGTA CAACCCTATT CTGTTTGGTT ACCTTTTCTA
133921 GTTCATTATG TAAGTGGCAT AGCTACCTAA GGACTTATGC TTATAAATGT TACTCAAAAA
133981 AATACAGAGG ACATATGTGG ATAGATAATG GAAGAGATAA GATAGGTAGG TTGAAGGGTT
134041 GGGCTGCCCC TCCACACCTG TGGTTGTTTC TCGTTAGGTG GAATGAGAGA CTTGGAAAAG
134101 AAAGAGACAC AGAGACAAAG TATAGAGAAA GAAAAAAGG GGTCCAGGGG ACCGGTGTTC
134161 AGCATACGGA GGATCCCACC GGCCTCTGAG TTCCCTTAGT ATTTATTGAT CATTATTGGG
134221 TGTTTCTCGG AGAGGGGGAT GTGGCAGGGT CAAAGGATAA TAGTGGAGAG AAGGTCAGCA
134281 GGTAAACACG TGAACAAAGG TCTCTGCATC ATAAACAAGG TAAAGAATTA AGTGCTGTGC
134341 TTTAGATATG CATACACATA AACATCTCAA TGACTTGAAG AGCAGTATTG CTGCCAGCAT
134401 GTCCCACCTC CAGCCCTAAG GCAGTTTTCC CCTATCTCAG TAGATGGAAT ATACAATCGG
134461 GTTTTACACT GAGACATTCC ATTGCCCAGG GACGAGCAGG AGACAGATGC CTTCCTCTTG
134521 TCTCAACTGC AAAGAGGCGT TCCTTCCTCT TTTACTAATC CTCCTCAGCA CAGACCCTTT
134581 ACGGGTGTCG GGCTGGGGGA CGGTCAGGTC TTTCCCTTCC CACGAGGCCA CATTTCAGAC
134641 TATCACATGG GGAGAAACCT TGGACAATAC CTGGCTTTCC TAGGCAGAGG TCCCTGTGGC
134701 CTTCCTCAGT GTTTTGTGTC CCTGAGTACT TGAGATTAGG GAGTGGAGAT GACTCTTAAC
134761 GAGCATGCTG CCTTCAAGCA TTTCTTTAAC AAAGCACATC TTGCACAGCC CTTAATCCAT
134821 TTAACCCTGA GTTGACACAG CATATGTCTC AGGGAGCACA GGGTTGGGGC TAGGGTTAGA
134881 TTAACAGCAT CTCAAGGCAG AAGAATTTTT CTTAGTACAG AACAAAATGG AGTCTCCTAT
134941 GTCTACTTCT TTCTACACAG ACACAGTAAC AATGTGATCT CTCTCTCTTT TCCCCACAGG
135001 AGGTGATGGC CGGAAGAACA TGGCAGAGGG CAAAACAAAA CAGCATTGGG AACAAGCTCT
135061 GTTTAAAAGG AGACTTGTGA ACAGCAAAGA GTAGAAAGGG TTCTCTTACA ACTGAAGCCC
135121 ATGGAAGACA AATGTGTACT GCGTGAGTTT TAAGGCAATA GGAGTAGTGG GACCTAGGGC
135181 ACACCAGAGA GCATATTAAC TCTCAAACTT TTAAAAACAT TATATCTGCT GGACACAGTG
135241 GCTCACACCT TAATCCTACA ACTTTGGGAG GCCGAGGCGG GCGGGTGTAG CTTGAGCCCA
135301 GGAGTTCGAG ACCAACCTGG GCAACATGGC AAAATCCCGT CCCTACAAAA CAAACAAACA
135361 AAAACAAAA TTAGCCAGGC ACGGTGATGC GTACCTGTGG TCCCAGCTAC TCAGAGGCTG
135421 AGGTGGGAGG ATCGCTTGAG CCCCGGAGG TTAAGGCTGC AGTGAGCCAT GATAATGCCA
135481 CTGCATCTCA GCCTGGGCAA CAGAGGGAGA ACCTGTCTCA AACAAAAAC AAAAACACAC
135541 CATACCCAAC CACAATGCAT CTGTCTTAAG TACCAGTACC ACACCCTCT ACTCACTACT
135601 AAATAGGTGA GTTCCCAATC CCTGGTAGCA GGTTTAAGCA TGTTATATTA AAGGTCTTAG
135661 GCTAGTGACT CATTCACTCA TTAAACAAAT ACTTATTGTG CATCTACTAT AAACTAAGTA
135721 CTGTGCTAGG TACAAAAGCA AATAATCTAA GCTCTATAAA CTTTACTTTC TTCATCAACA
135781 AAATGGAGAT GTTTTAGGCA TCTACTCATC ATTCTGAGCT CCATCTTTTG TGACTGTAGT
135841 TGGCAGAGCT TTTTATCAGT TTCTCTAAAT AGCTCTACCA GTCCCTGGTG GATGCTGGCA
135901 TGCCCAAAGG ATCCATCCTG ATGGCCCTGT CTGCTTACCT TACCTGCCTG CCTTTGCAGC
```

Figure 1 (Page 42 of 73)

```
135961 ACCGCTCTGC TCTTCTGCAG GACTTCCCTT ATCCTTTGGG GTCTTGCTGC TCTTAGGCTG
136021 CTCTGCTTGT TTTGATCTGC TTTGCATCAC ATGTATGTAA AGGTCCTTTC CTTATTTACC
136081 CATGACCAAG GTATTATGAG ATTCTGGAAT TTCCCCAAAC CACATTGATT GCTGGGAGAA
136141 TAGAAGAAGT GGATTACAAG TGGAACTTAG AAGGGGAGTA TTCGAGAAGA CGTCTCTGCA
136201 AATCCATTTA GAGAGACCTT TCTCCAGTGG TGACTCAAAG ATGCAGCTCC TTTCATCCTG
136261 TGGCTTGGCC ATCTTCAGCA CATGGCTCCC AAGGATGTCC TCAGGATGGT CTCTAATCCA
136321 AGGAGCCTGA AGAGAAAAAA AGGCATGGAG TATTGTGAGT GGTAGGTGGT TATGGACCAG
136381 TTATGGAAGA ATACACATCA CTTTTGCCCA CCTTCTACTA ACCAGAACTC ACACAGCCAT
136441 AGACACTGAC AAGTAGGACT TAACAAGAAT CTAATTTTGA GTCTAGGAAT ACGACTGTAG
136501 CAAATATTTA ACAGCTTCAA ACACAGGTGC ATTGCTATCA CTATGCTTGG CCCAGGCCTG
136561 TCTCCCTTTC CTGCCATGTC ACAGGGGCCA GCATTTATGT CTAGATTGGG TTGGTTGGGA
136621 TATTAAGACA ATAATGAACC AATACAACAT CTTGAGCATA AAACCAACTG ATACAATGAT
136681 GTACAAGTCA GATGATTCTG ATGATTATGA ATTATGTCAA TAAAAGAAAT GTGATAACTA
136741 AGGTAATTTT TGTTTTGGCA AATTTTTGTT TGTTCATGAC AGGATGAAAT CCTGTCATTT
136801 GTAGCAACAT GGATGGAATT GCAGGATACT ACATTAAGTG AAATAAGCCA GAAACAGAAA
136861 GTTAAACACC ACATGTTCTC ACTTATATGC AGAAGCTAGC TAACTAAGTA AATAAGTTTA
136921 TCTCATTGAA GTAAAAAGTA CAACAGAGAT TACTAGAGGC TGGGAATGGT AGGGGAAAGA
136981 GATGATAAAG AGAGATTCGT TAAAATAAGT TACAGCTAGA TAAGAGCAAT CAGTTCTAGT
137041 GTTCTATTTG TACTACAGAA TGGCAATAGT TAACAGTAAT AAATAATTTC AAAGAGCTAG
137101 AAAAGAGGAC ATTGAATGTT TCCAACACAA AGAAATGAGA AATGCTTGAA ATAATGGATA
137161 TTCTAATTAA TTACCCTGAT CTGATCACTA TACACAGTAT GTATAAAAAT AACACTATGG
137221 GCTGGGCGCA GTGGCTCACA CCTGTAATCC CAGCACTTTG GGAGGCCAAG GTAAGCAGAT
137281 CACTTGAGGT CAGGAGTTAG AGACCAGTCT GGCCAACATA GTGAAACTCC ATCCCTACTA
137341 AAAATACAAA AATCAGCCAG GCGTGGTGGC ATGTGCCTGT AATCCCAGCT ACTCAGGAGG
137401 CTGAGGCAAG AGAATTGCTT GAACCCAGGA GGCGGAGGTT GCAGTGAGCC GAAATCGCGC
137461 CACTGCACTC CAGCCTGGGT AACAGAGCAA GGCTCTGTTT CAAAAATAAA TAAATACATA
137521 AATAAATATT TTTTAAAAAA AGAACATCAC TATGCACCCC ATATATACAT ATAATTATTA
137581 TGTCAATTTG AAACATAATT TTGAAAAATG AAAAAATGAA ACACAAATAT GAATCAATCC
137641 TCTCCAAGTT GATATACTTA AAAGGAAAAA AGTCCGAGGG CTTAAACTAT TCAATCAAAA
137701 TTTTATTAAA ATGCTATAGT AATCTGGAAA GTATTTCAGA ATGAATTGGT ATAAGGTTAG
137761 ACACAAAGAT CAGTGAAACA AAACAGAGAA CCCAGAAATA GATTCACACA TCTATGGACA
137821 ACTGGTTTTG ACAAAGGTGT CAAGGCTATT TAATAAGTAA AAAAATCGTC TTTTCAGTAA
137881 ATGTTTCTTG AACAAGTAGA CATCCGGTGT GGGGGAGAGG AGCAGGAGCC TTACCTCAAA
137941 CTTTATGCAA AAATTAACTC AAAATAGACC ATAGACTTAA ATGTAAAGC TAAAATTATA
138001 AAACTTCTTT AAAAAATAGG AGAAAATCAT CAACACCCTA GGATTAGCAA AGATTTCTTT
138061 AAAACAAAAC AACAGGTTTA TAGTTTATAA AACATAAATA ACAAAATGAT AAATTTCATC
138121 AAAAGTGAAA ATTTGCTTTT CAAAAAACAT TATAAAATGA AAAGCAGGAG GCTGAGGCAT
138181 GAGAATCACT GGAACCCGGG AGCTACAGGT TGCAGTGAGC CAAGATGGTG CCACTGCACT
138241 CCAGCCTGGG TGACAAAGTG AGACTCTTCC TAAAAAATAA ATAAATAAAT AAATAAATAG
138301 AAAAGAAAAA GAAAAATCAC AGGCTGAGAG AAAATATTTA TAATACATGT ATCTGACAAA
138361 GGACTCGCAC CTGGAAAATA TAAGGAACCT TATAACTTAG TAAGATGACA AGCCAAAACA
138421 AAGAGTAAAA GTTTTCAACA GACATTTCAC AAAAGAAAAC ATACAAATGG CCAGTATGCA
138481 CATGAAAAGA TTTTAAACAT CATTAGTTAC TAGGGAAATG CAAGTCAAAA CCACAATGAG
138541 ATACTTCACA TTCAACAGAA TAGCTAATGT TAAAGGACT GACAATCCCC AGGGTGAGCA
138601 AGGGTGTGGA GGAAACTACT CTCATATATT GTGAATGTAA GAGGACAATG TTACAACTAC
138661 TTTGAAAAAA GTTTGGCTGT TTCTAACATA AAATTAAACA CTTATACAGC CAGCAATAT
138721 TTCTGGGTCA TTTCTCCCAG ATAAATGAAC ACATGTCCAT ACTATGACAT GTACAAATGT
138781 TCATACTGGC TTTGTTTCAC AATGCTATAA ACTGGAAACA ACCCACGTGT CCATCAACAG
138841 GTGAATGGGT AAATAAATTG TAATATATCG GCCAGACGCA GTGGTTCATG CCTGTAATCC
138901 CAGAACTTTG GGAGGCCAAG ATGTACGGAT CACCTGAGAT CAGGAGTTTG AGACCAGCCC
138961 ATCCAACATG GTGAAACCCC ATCTCTACTA AAAATTAGC TGGGCATGGT CACGGGCGCC
139021 TGTAATCCCA GCTACTCGGA AGGCTGAGGC AAGAGAATCA CTTGAACCGA AGAGGCGGAG
139081 GTTGCAGTGA GCCAAGACCA TGCCATTGCA CTTCAGCCTG GCAACAAGA TGGAAACTCC
139141 ATCTCAAAAA AAAAAAAAT TGCAATATAT CTATATCTTG GAATATTATA AAGCAATAAA
```

Figure 1 (Page 43 of 73)

```
139201 AGGGAATAAA CTACTGATAT ATACACAAAA TGGATGAATC TCAAAAATGT GAAGGAAAAT
139261 AAAAAATACA TATGATATAA ATTCCATTCA TATGAAATTT TAGGAATGGG AAAACTAAGC
139321 TGTAATTATG GAAAGTACAT CAGTGGCTGC CTGGGGCCAA GAGGATGGAA GAGGCGGCAC
139381 AGGTGATACT ACAAATGGAA ACTATCTAGG TTGACGAAG TGTTCTGTAA CTTGATTACA
139441 GTAGTAACTG TTTGGGTATA TAAAACGCAT CAAATTGTAT AATTAATACA GGTGTATTTT
139501 ACTGTGTATA AATTATTCCT CAATAAAGTT GATTTTTCAT TAAATATATT ATTTGCTAAA
139561 ATGAGGAGAG ACAACTATTA TCTTAAAATA GTTAAGCACA ATAAAAATAC TACAATCAAC
139621 TCATTATATA TGGAAATTAA AGGAGAAAAA TAGTGGTATG ATTAATTAAA ATAAAAAGAA
139681 AACCTTCTAA ATTTTATCTT AGCTCATAGT TGTAAAAGCT GCCATCCCTA ACCAAGGCCA
139741 CCCTTGACCC TTTCTCATGT TCCATCTTTC TGTTTGTTTC ATAGTTTATG TCTCACCAAA
139801 ATCTATCAGA TAAACGTATT CATATGAAGA TTTAAATATA TTACATGTTA AGCCTTAGCG
139861 AATACTTCAA TATCTAAAGA AGGTACAAAC AAAACAAAAA TCAACACTTA GTTATAAGAG
139921 ATTACATACT CTCCAGGGAA GACCTGAAGA CTAGCCCCTT TCTGGATCCC ACTAGCCCCT
139981 CATCCCACTC CAAGCCCTCC CCTCCAATCC CATATGCACT GGGCATTCAT ACAAATAAGA
140041 CCATCAGCTC TGGATATCTG TACTGATTGA TGCTCCTGCT AACTACCTGA ATGATTGCGA
140101 TGTAAGGACA GCACTGCCTG AATCCTATTT ATCTCTCGCT ATGCCATAGC GGCCTTCCAT
140161 GCTGATGGCG TGTTTGAGGA TCCAGAGGGG TCTTTGGTTG GCAGGATTGT TTTATTTCCC
140221 CAAGAGGAGA GCCTTGATGC AAAAATAGGT GAAGAAATCA GTACAACAAA ACAGAAAGCC
140281 TAGAAACTAC TATGAACACA ATAGAGCAGA AGTAGCCTTA AGAGTTGGTG GAGAAAGGAT
140341 GGTCTATTCA ATTACCTGGG CTGAGAAACT GGCTTTCATA TGGAATAAAA ATAAAATTAT
140401 AGCTATACCC CATATCATAC ACAAAAGTTT CTACATCTAA CAAAGACACA GATAGAAAAT
140461 GTTTTAAAAT TTTAGAAGAA AATAGTGCAG AATTTTAGTG CAGAATTTCT TAGACTAGAT
140521 GCAAAAACAA AAATGATTAA AGTGGCCAGG CACGGTGGCT TATGCCTGTA ATCTCAGCAC
140581 TCTGGGAGGC CGAGGTAGGT GGATTAGTGG AGGTCATGAT TTCGAGACCA GCCTGGACAA
140641 CATAGTGAAA CCCCATCTCT ACTAAAATAC AAAAATTGGT AGGGTGTGGT GGCTCACGCT
140701 TTTAATCCCA GCTACTTGGG AGTCTGAGGC AGGAGAATCA CTTGAACCTG GGAGGCAGAG
140761 GTTGCAGTGA GGGGAGATGG CGCCACTGCA CTCCAGCCTG AGCAACACAG CGAGACTCTG
140821 TCTCAAAAAA ATCTAAAAAT AAAAAGATTA TTTTTAAAAG ACTATTTAA ACAAAAAAAA
140881 TCGTTTAAAT GATATGACAC ACTACATCTA ATATTTGGAA AAGTACTTCT TAATACTTTT
140941 AATAAAAAGA GGCGCTGAGA GCATACAACC TATCCTCAGA AGAGTGTTTG ACCTCTAGGA
141001 GGGACGCAAG CGCGTTCTTC CTTCATTTTA ACTGGTCATT TTCATTTATT TCAGGAACAT
141061 CTGAAGTAAA CACAGTCACA CGTTAACCTT TAAAAATCTA GGAGGTGCGT ACGCATAGTT
141121 CCATTACTTC AATTTTTGTA CTTTTGCATT TTAAAATATC ACAGGGAAGC TCGGTACAGC
141181 TTCAAGGCTA GGAGGGGTGG CTCTCTCTTA AGCCCTGTCC CCGCCAGCCC CAGACCTCTC
141241 GTCCCGCCCC CATTGCCCAG TCCCCACCCT CACTTCCCCA TTTCCCCACT CCCGCGGTCT
141301 CTTAACGCAC CTCGTTTTTC GTCCAGTGGA CTCAGACCTG TAGTCTTCCA CCAGGATCGG
141361 CTCCTTTCCC GGAGCTCTCG CTCTTAGAGG AAATTGAGAG AAGCATCAGC GGAGACCCAT
141421 CTGTGGCTCT CCAGAGGGCG CGGCATTCAG ACCCCAGATC CAGCTGTGAG AACGGACCCC
141481 AGGCTCACAC CAGGCCTGCG GGAGGCGGCC CACCAGAGGC GCTAGAAAAC AAGCCTCGCG
141541 GGGAGGCGCG CAGGGCGACT GCAAGCTGTA GGGGGCGCTG GCGCCCTCAC AGGCCAGGGG
141601 CAGGGCCGGC GCTGCGGGCG GGGCTCCTGC GGCGTGAGGG GCGGCCCCAG GCCAGCAGCT
141661 GCGCCCTGGC TGGGAGCCGG GGAGCCATTTG CTGCTCTGCT GGACCCTGAG TCTGGCGGCG
141721 GCGGCCTCC TCTCCGCTCC CCGCCCGCCA TCCCCAACT CCCGATCTCT CTGCTGCGTC
141781 TGGCCTCAGG CTGAGACCCC AACGAATCAT TCCCCGCATG GAACATTTT ATGATATAAC
141841 TGAATTCAGT TTTATGTATA ACTGAATTAC GGATATGAGA ATCTCAAATG AGGACGAATG
141901 GTTTTACGC ACAAAACATG AGACACAAAT CTGTAAGAAA TATAAAGTCG TGACCACGTC
141961 CTTTCAGAAC TTTAACCTGT TTGCTGAAGT ACGTCAGTAA CAATGGCAGG GAAAGGGTAT
142021 CTTAAATTTC ACCACAGCCT CAAAGAGGCC ATTTCGTGGA TCCGCTGAGG CTTGGAGTCG
142081 GCCTTCTGAC CACGAGTCCT GCGGCTATGA AAGAGGAAGC CGCGGTTCAG GGCGTCCTCG
142141 CGAGTCGTGC AGCCCGCCCT GCTCCAGCTG GGACACCGG TGGTCACGGC GCTTTCCAGC
142201 TGCAGATCCA GGCGGCAGCC CAAGATTTGG TCCAGCCGCC AAGGGGTGGC TCGAGTGACT
142261 GACGGGCCTT GAACGCTCCC AGGACCCACA TCTGGAGAGG GAGGTGGGGG TGGGGTGCTG
142321 AAGTCATTCT TGGGGCCCCT GGGGCGGGC ATGGACCTGG GTAAGGCCAG AGAAATTGAC
142381 ACCTCGTGAC ATCCCTGGAA GAGAAGTACG TTCAGTGTCA CTCCAGAGCT GAAACCGCCT
```

```
142441 TCTGGCTGGT CCCTCCTCAC CTACATACTT TTCTAATTTG TCTGGAGCAG GCCGGGCATC
142501 TGTATTATCT GGTTATTTAA ATATCTGGTT ATTTAAAAGC TCTCCATTAA ATTCACATAC
142561 ACGAAAATAA AAATTAAAAA AAATTTTAAA AAAAAGAAAC AAAAGCTCTC TAATGACCAA
142621 GTCCTACACG ATAGTGAATA AATTTTTTG TGTGGTCCCT AAAATTGAGT TCATGCCTTT
142681 TCTGAAGTAA TAGACGCCCA GAGAAGGGAT CGACTTACCC ATCATGCCAC AGAGATTAAT
142741 TGGCCCCAGA ATTCTTTAGC AGACCGTGTA TATGAACGTC CTTTGCAATC ATATAAATTA
142801 ACTGGGAAAA CCTCATTTAG TATGTTACAT GCCTAGCGTT TTGTGCCTGA ACACCTTACA
142861 AGAACCAGGG ACTATTGCCC CAATATTATA TTTCAGGAAA GGAAGGCCCA GACAAATGGT
142921 GTCACTGGTC CACTTTCACC CAGTTGGTAA ATGAAACCAG AAATTATAGC TGTACCACAG
142981 AAAGGTGAAA ACGTTTCTTT TATAATTTCA CATACAATCT TTAATGGACC CAGTGTCCAA
143041 CACATTAAAG CAAGTGCTCA GGAGTGACAT CAAGATGTAA AAAATAGTCC TGTCCTCAGG
143101 GAGTTTAGGT CTTGAGAAA AGAGACCCAA GGAGACACAA GACAAGGGG AAAGAGAAGG
143161 AGCGCTGAAG ACTGAGGACC CTGCCTGTGG ACTGAAGTGA GGATGGGGAC ACCCGATGCC
143221 CGGAATATGA CAGTTTGGAG GGGCCTGAAG GACTCTTCTA TTCTCTATCA GAAAAACAGA
143281 ATTACTCTCC TAACCAGAAA AGGTATTTCA ATTTATATTT TCCATCACAG CACTTTTCTG
143341 GTGATAATTT AATGTGTTTT AAAAAATGTA TCACAGTGAT GGCCTGGTGT GAAATAAATA
143401 ATAAAATTTT AAGAATTAAA AAATATAAAA ATCTTTTATA TAGACATTAG GAGTTACAAG
143461 GATAACTGTG AATTATAATT AGTAATTAAA TTGAAATACT GATTATTTTC ATTTTTATTT
143521 AATTATTTAA TAAAACCTAT TTAACATTTA ATATTTATCA GTAATTAAAT CTAATTGTTA
143581 ATATTTATTA TTATAAATTA TTTTAGAATT AAAAATAAGT GTAGAAGCGA GGCATGGTGG
143641 CTCAAGCCTG TAATCCCAAC ACTTTGGGAG GCTAAGGTGG GAGGATTGCT TGAGCCCAGT
143701 AGTTCAAGAC CAGCCTGGGC AACATGGAGA AACCCTGTCT CAATACAAAA AAATGAGCCA
143761 TGTGTGGTGG TGCGTGCCTG TAGTCCCAGC CATTCTGGAG GCTGAGGTGG GAGGATGACT
143821 TGAGCCTAGG CAGTCAAGGC TGCAGTGAGC CCTGATCTTG CCACTGCACT CCAGTCTGGG
143881 CAACAGAGCA AGACCCTGTG TCAATATACA TATGGACAAA CTTAAAATTT AAAATGAAAG
143941 CATACTACTG ATACAGAATT GAGTAGAGAT GCAAAGCTAG TCCTATAACC AGAACAATAA
144001 AGATAAAAAG GAGAGTGGAA GAAGGTATGT CATGAATTTC ATGATAAATG GCAATTGCAA
144061 ATATCCTGTA GCAGAACAAA ACAACAAAAC TGTAGATAAA ACATATCCAA CCCTTTGGAA
144121 GGCCAAGGAG GGAGGATTGT TTGAGCCCAG AAGTTGGAGA CCAGCCTGGG CAACATAGTG
144181 AGACCCTGTA TCTAAAAAGG AAGAAAGAAA AAAAAAAAA GGATGATAAA GTAGACAATA
144241 TTGAAAGCCA TTTTCTGCAA ATACATAGTG AATTTGATCA GTAATTTTCT TCCAACAGTG
144301 CAAAAATGAA TAGATATTAG TTGCCTGAAA TAAAAATCAA ATATCCAACA AAAAATATTG
144361 ACTATCTAAT AGTATCTAAG CTAGTAAATT TGGCCAGTTA TAAAATGTCT TAAATTTTTA
144421 TTTAAAAAAA GAAAACCATA TTTATAAGAA GAGGTGATAA AGAGAAATTA TTTCAGTTAT
144481 GAAGATTTTG TTAGAAAACT ATGAGAAAAA AACTATTTTT TGTTTTCAAA AAGTGAAAGA
144541 TTAAGTTACC AAACAGTTGC TAAAGAATAC CAGATGGCTG AGCGTGGTGA CTTATGCCTG
144601 TAATCCCAGT ACTTTGGAAG GCCAAGGCAG GAGGATCATT TTAGGCCTGG AGTTCGAGAC
144661 CAGCCTGGGC ACTGTAGCAA GACCCGTCTC TATTAAAAAA AAAAAAAAA AAAAAAAGA
144721 ATACAAGACC TTGCTAACAA TAGCAAAGAT CAATTAATTC AAAATTTGAA AAACTGTAAT
144781 TTATTTAGCT TTAGAGTACT CTCGTGATAT GAGATTGCCA AATTAATACT TTGGGTGCAT
144841 TTCTTTTCTC AAAGGACTTG CAAATTTACA AAGAAGTGTT GAAGAAAAGC CACACATTGG
144901 CAGGTAATGT TTGCAAAAGA CAGATCTGAT GAAGAACAAT ATTTTTAGAA TATACAAAGA
144961 ATACTTAAAA CTCAACAGTA AGAAAATAAC CTGATTTAAA GCAGGCCAAT GACCTGAACA
145021 TCTGTTCACC AAAGAAGATA CACAGATGCA AGTATGCATA TGAAAAGATG CTTGACATCA
145081 TGTCATTAGG GAACTGCAAA TTAAACAAG TAGATACCAC TGCATACCTA GTAGAATGAC
145141 CAAATTTAG AACACTGTCA GCACCAAAGG TTGCAAAGAT ATGTAGCAAT AGTAACTTGT
145201 TCATTACTGG TGAGAATGCA AAATGTGCAA TCACTTTGGA AGACAGTTTG GTGGTTTCTT
145261 ACAAAAGTAA CCATACTTTT ACCATAAGAT TCACCAATCA CACTCCTTAG TATTTATCCA
145321 AAGGAATTGA AAACTTATCT CCACACAAAA ACCTGCACAT AGATGTTTAT AGCAGCTTTA
145381 TTCATAATTT ATCCAAAACT TGGAAACAAG ATGTCTTTCA GTAGGTAAGT GGATAACTGT
145441 GGTACTTCTG AATAATGGAA TGTTATTTAG AGTTAAAAAG AAATGCATTC ACTTTGGGAG
145501 GCCGAAGTGG GTGGATTGCT TGAGGCCAGG AGTTTGAGAC CAGCCTGGTC AACATGGGAA
145561 AACCCCAATT AGCCGGGCAT AGTGGCGTGA GCCTGTAATC CCAGCTACTC GGGAGGCTGA
145621 GATATGAGAA TCGTTTGAAC CTGGGAGATG GAGGTTGCAG TGAGCCAGTG CCACTGCACT
```

Figure 1 (Page 45 of 73)

```
145681 TCAGCCTGGG CAACAGAGCA AGACTCCTCT GTCTCAAAAA AAAAAAAAAA AAGAAAGAAA
145741 AGAAAAAAGA AAAAGAAAAA GAAAAGAAAC GATCAAGCCA TGAAAACACA TGAAGGAAAC
145801 TTAAATGTAT GTTACTAAAA AGCCAACCTG AAAAGACTGC ATACTATATG ACTCCAACTG
145861 ATGCAGGGCA AGCAAGCCAA AAATTAGGGC TTAGCCCGGG AAGAATTCAA GGGTGAAGTG
145921 GTGGTGTTAG CAACTTTTAC TGAAGCAGCA GTGTACAACA GCAGAACAGG TACTGCTCCT
145981 TGCTGAGCAG GGCTAACCCA TAAGTAATGT GCCCAGAGTA GCAGCTCAGG GGCAGTTCTG
146041 CAGTAATATA CCTGCTTTTA GTTAAGTGCA TGTTAAGGGG GATTATGCAG AAATTTCTAG
146101 AAAAAGAGTG GTAACTTCGG AGTAGGTACA GAGGAAAGAA GTCGATAATG TCCTGTTGTT
146161 GCCATGGCAA CGAAAACTG ACATGGCGCT GGTGGGCGTG TCTTATGGAG AGGTGCTTTA
146221 ACCTCGTCCC TGTTTCGGCT AGTCTTCAAT CTGGTCCGGA GTAAAGTCCC TGCCTCCGGA
146281 GTTCACTCCT GCTTCCTGCT TCACAACTGT ATGACACTCT AGAAAAGACA GTAACTATGG
146341 ACACAGTCAA AAGATTAGTT GATAGAAATT GGGTGACAGG AAGTGTTGAA AAGGCAGAAC
146401 ACAGGATTTT TAGGGCAGTG AAACTTCTGT GATACTATAA TGGTGAATAC ATGACATTAT
146461 ACATTTGTCA AAACCCATAG AAAGCACAAC ACCAAGAATA AACCCTAATG TAAATTACAG
146521 ACTTTCGTTG ATAATGACGT GTCAATGTAA GTTCAATTGT AATAAATGTA CTACTGTGGT
146581 GCTGGATGTC TATGGTGGGG GGACATTTTT GCTTCAATAG TTACAGTTGA AGTAAATGTT
146641 TGTGTTTCCC ACAATGCATA TGTAGAAACT CTCACATTCA ATGTGATGGT CTTTGGAGGT
146701 GGGCTCTTTG GGTGATAGTT AGGTTTAGTT GAGATCCTAG CAGATCGAGT CTTCATGATG
146761 GGCATGATGG GACTGGTCCC TTATAAGAAA AGACCAGAAA GCTAGCTCTC TCTTTGCCAT
146821 GTGAAGACAT AGCAGGAAGG TAGCCATCTG CAAGCTAGGA AAGGGCCTTC ACAAAGAATC
146881 AACTCAGACC TCAGAACAGT GAGAGATAAA TTGTCGTTGT TTAAGTCACT CAGGCTGTGG
146941 TATTTTGTTT CAGCAGCCCA ACCTAAGACT GTTAATTGGA TTAGAAATTT CCTTTTGGGG
147001 ATGGTGTGTG GCGGGCGGGG GGCGGGGAGT ACCTTTGTTA AGCTTTTATA TCAATGAGTT
147061 TGTAGGCTTT TCTTTTTTGG TCATTGACTA GGACAGTTTA AATAGTATGA GTGTGAAGGA
147121 GATTGTTGGT CATCTATTCG ATGTCCCTTC TCTGTTTTTT AATATGAGAA CTCCTGATTT
147181 TCAGCCAACT ACCCTGGAAA AAAAGCTAAT CTTTCTGACT TCTTAAGTGT GGCCATGTAC
147241 TAAATTCTGG CTAATGCAAG GCAAGCCAAA GGTTTTATGA TAGGTTTTAG GACACTAGAG
147301 TAAAAGAGAG CTGTTGCACA CATGCTCTTC ACCCTACTTT TGTGTCCTTT TTTCCATCCT
147361 ACAACTTGGG TTGTGAGTAT GATGGCTGGA ACTTTAGTGG CTCTCTTGGA TCCCAGGGGT
147421 AATTGAGGGG TGGCTGGAAG GAATCTGTGA TTTTCTGGAG TTTCCATACA CAAACAAGAC
147481 CTGGATTTTC TGGGCTTCCC AGACTTCCAC ATCTAGACTT GCTTAAATG GGAGATAAAT
147541 AAACTTGTTT CAGCCACTGT CATTTGGGC TATTTTATAG AACTTAATCT AATCTTCAAG
147601 GGTACATGAA TTGCTTTTCC TTAAAAAAAA AATCAGCCAT AAAATCATCT TCTTTTTTCT
147661 TTTGTTCCCC ACATTATTTA GTTGGAGCTC TGTAACTTTT TTTTTTTTTT TTTTTGAGAC
147721 AAGGTCTTGC TCTGTCACTT AGGCTGGAAT TCAGTGGCAT GACCATGGCT CACTGCAGCC
147781 TTGCCCTCCT AGGCTCAAGC AATCCTCGTC TCAGCCTCCT GAGTAGCTGA AACTAAGGCA
147841 CATGCCACCA TGCCCAGCTA ATTTCTTTTC TTTTAGAGAT GGGAGCCTTG CCCAGGCTAG
147901 TCTCAAACTC CTAGCCTCAA GTGATCCTCC CATCTCAGCC TCCCAAAGTG ACAGGATTAC
147961 AGGTGTGAGC CACCATGCCT GGCTGCTCTG TAAGTGTCTG AATTTCATTT TGTATTTATC
148021 AGTCTGTTTA GATTTTCTTT CCCTTCTTGG GTCAGTTAGG CCATTGGTTT CTTTTTAAAG
148081 GTTTTCAAAT TTATTTGCAT CTAATTCTTC AAATTACTCT CAAAATTATT CCAGTATATA
148141 TTCTTTTGTT CCTATTTTCT TCTGTATTCT TTATTAAAAT AGCTAATGAT TTATCTAGCA
148201 GGACTTATAT TCTTTCCATA ACTTTCCTGC ACCCCAATTA ATCTCCAATT TTATATTTCT
148261 TCTGGCCTTC CTTATAGTTT CCACAGGTTT ATTTTATTCA TTTTTAAAA CTTTTATTTA
148321 ATTGTTTATT TTATTATCAT TCTTTCTTAT TCAGCAATCT AAGTGCTTAG GGATATAGAA
148381 TTTCCTCTAA GCAGCATATG CTAGGCTTTA ACAATGTTAG GGAGGCCTCC CCTTTCTGGG
148441 GAAGACCACA CTTACATTAA CACAGGACTG TGGGATGCCA AGAGGTAGAG AAGAGCTTAT
148501 GAATATCCAG ATTACATCTT CACTGATCCT GCACAAAGGT GGGGTTCCTC GGTTACCCAC
148561 TGGGTCCTAT TACCCAAGTC TGGGTCAGCA TACCGAGACT ACGGGTATAT AGAACAAGTG
148621 CAACTGGCGA TAATCCTTCT GTTGGGGAGA AAAATCTTTT TTTTCTATTC ATCTTAGGTT
148681 CTCCATCTGT GGCCCTATCA AGTAGACTAA CAAAAGACAG ATTGACAAGA CAGAAACAAA
148741 GCATGTGCAT TGTACAAACA CAGGGGAGTA CTGAGATGAA TACTCAAAAG AGGATTTAGA
148801 ACTTGGGCTT ATATAGCATT TTAAGAAAAG AATACATTTT TTAAGTGACA AGGAAGACGA
148861 AAAGGACTTT GAGTTTCTAG TGCAGTAAAT TGTGGGAAGG CAACTTTTTC TTTCCCTTTT
```

```
148921 TTTTTTTTTT TTTTTAAAAA AAAAGACTTC TCTGGTGCTA TGTCCAGGCT GATAAGAGTC
148981 TAAAGTCTCT GGTGACTAAC TTTTGTTCTT CCCCGAGTAA GAAGACACCT TCACAATTTC
149041 ATATCCTGCT TTTAGGCAAA TAGGGAGAGG GCAGAGGTGT TTGTTTGTTT TTAATCTATT
149101 TTTTTTCTCA ATTGTCTTCA ACTCAAAATA CTTCTTATGC CAAAGATGGC ATATTCTGCT
149161 ACCCTTCACT TACTACTTAC AACCCAGCCT CTATCATCAT AATTAGAACT TCTGACCCTG
149221 GGGAACATGG GCAATAGTTT GAACTCTTTT ATATCTCCCT TAGGCAGAGA TGGAGGCCCA
149281 GCCATGCCTC TGACATCTAG ACACAACTGT TGCTTCATTT CTCCTATTCT CAGAGGTGAT
149341 GTTGTAGGAC TTCAACAAAT ATCAGTAAAC ATTAATTTTT TTTTTCCTTG AGGCACAGCA
149401 TGATCTTGGC TTACTGCAGC TGCTGCAGGC TCAAGCAATT CTCCTGCCTT GGCCTCACGA
149461 GTAGCTGGGT TACAGGCCCC TACCACCATG CCCGGCTAAT TTTTGTATTT TTAGTAGAGA
149521 CAGGGTTTCA CCATGTTGGC CAGGCTGGTG TTGAACTCCT GACCTCAAGT GATCCACCTG
149581 CCTCAGCCTC ACATAGTTCT GGGATTACAG GCGTGAGCCA CCATGCCTGG CCATCAATTT
149641 TTATGTCAAC TCTAAATTAT AACATTAGC AATTTTGTGA CTTTTTATGG TCATCATTAA
149701 TGTTGTTTAT GTTTAGTTG TAGTCCTGTC ATTACTCACT CGGGTATGGT AATTTGGTCT
149761 TTTTCAAAAT GAAGTTAAGG TCTATTTGCT CTTCTCTGAA TCATAATAAG AACTGCCAAC
149821 AGCCATTTCA GCAATAACTA TTTACTGAGA TTTTAAAATA TTTCAAGGTA ATTGGTCCTA
149881 GCAGACTGGA AAATACCAAA TTCTTTTCCA GAACTGAATC CCCCATCAAA GTTCAATTTT
149941 ACTCATAATT CCCTTTTCAT TTGAAGCATC TCATTGTAAG CCAGTCTTAA CCCTTCTCTC
150001 ACACTTTGCT TGGCTGTTTC TCAGGTAGAA CTCAGTAAGT CTGGTAGCCT CCAGGACTGC
150061 CGCTTAGATT ATTAAACAAC ATGTCAGTGG TTGGAAGAGT CAATGTTATT TTGATTTTTC
150121 TGTTTGTTT TGTTTTAAAT GCAGTTGGCG GATAATTGCA GCTTTCTTTC ATTCCCTACA
150181 TGAGTTCAAA TGGCAGCAAA CAAACTAGGA GAACGCAGAC CTTCTGACTT GTGGGTACCC
150241 CTACTCATCA CCTGAAGACC CTTGGAAATC AAAGCCCTGA CCCATTAAAG ACGGATGGAG
150301 ACAGCAACAT ACGATCATCA CTATTATCTT GCTTTGCCCC AGTCCAGGTT AACCATCTGT
150361 GGTATTTTTA GTTGCTAAGT CCATATATTC AACATAAATC AATTATATAT CCACTAAAAT
150421 CTCAGCACTA GTCTAACTAC TAAGGAAATG ACAGCGAAGA AAACAGACCA AACGTCTGCC
150481 CTTATGGGAT TTATATTATT TTCTCTGTGC TGGTTAAACC AAGGAGCTTC TGCTCTTTTC
150541 CTTAGTCACC TGGGGGAGGC AGAAACAAAG GAGAATATTG ATAAACCTGG AAATAGGGCC
150601 GGAGAGTATC AGAGAAGGAA GCCTTCGGGA AAGTAAAGAT GTGGCAGCCA GTATTCCCGT
150661 TATAAAAGGA TACAACTCCG GCCTCATAGT CCAGAAAAAT TCCCACAAGC AGGGGCTGCT
150721 CATGCAGATG AAGGGAAGTT GGGGGAGAAG TAAGTGCTAC ATAGCCTTTC TTTTTGCACA
150781 GCCTGAGGGT CCAGAATCCA GACTGAGGCT CTTGCTTCAT GCCAGTGCCC CTCTGCACAT
150841 TTTCCATACA AACTCCTAAA TCCCATCCGG TTCCTTCGCC AACATCCACT TCAAAGTAAC
150901 GTCTTCCTGA GGTGAAGCCT TCACAACCCA AGACACAGGG GAAGGCAGTA AATCTCCTGG
150961 AAGATGTGTC CTGATTCTCC TGGGTGTATC CACGAGTCAC TTGTCTCCGA TCCTCAGAGA
151021 GAATTAGTTC GTGATGAGCT GTATCTGGAT CCAGAGTCAC ACTAACTGCA AAACAAAACA
151081 AAACAAACAA AATAATTTT GTTGCTGTGA AGAACACAGG TTATTTTATT TTATTTTATT
151141 TTGAGATGGA GTGTTGCTGT CACCCAGGCT GGAGTGCACT GGCACTATCT CAACTCACTG
151201 CAACCTCCAC CTCCTGGATT CAGGCAATTC TCCTGCCTCA GCCTCCGGAG TAACTGCGAC
151261 TACAGGTGCG CACCACCACA AGTGGCTAAT TTTTTTAAAT TTTCTGTAGA GATGGGGTTT
151321 CGCCATGTTG GCCAGGCTGG TCTCAAACTC CTGACCTGAA GTGTTCCACC CACCTCGGCC
151381 TCCCAAAGTG CTGGATTACA CAGGTGTGAG CCACCATGCC CAGCCACAAG TTATTTTCAA
151441 TAAAACCAGC CTGTGTTCAA ACCCAACTAT TGTTTCTTAT AAACTGGGTG AGCTTAGGCA
151501 AATCATTTAA CTTTCTGAGC CTCAGTTTGT TAACTATAAA GTGGAAATTA CCGTATTTGT
151561 TGCAGAGAAT GGTGGGTAGG ATTGAATAAG CTTATGTTTG CTTAATGCTT GGTAAAATTC
151621 CTGGTACATG GTAACCACCT AATAAGTGGT AGTTGTTGGG GTGATCAGGC CCAACACCAG
151681 GCCGTGGGGG CTACAAAGTC CGGCGGGGTC AAAGGAATGA GAAAAGACAA GTTAAGAGTG
151741 CATAAAGTGG GTCCAGGGTG CCAGCACTAG ATTGGAGGCT GCAAAGGCCC TAAGCTCTGG
151801 GAGCCCACAC TATTTATTGG TGATCAAACA AAGAAGCAGG TGGTGAGGAC GTGAGGGTAA
151861 ACAGGTGAGG GCATGAGGAC ATGGGGTAG AAAGGTAGTG GTGCATTAAG CGTAGCTGTG
151921 ACAGTTTAGC ATTTTCTTTG ACACATGTAG AATATACTCT GCTGCTTGAG ATAGTAGAGG
151981 ACACGTTTAT GAGTGAAAAG CAAGGAACCA ACAAGTCTGT GCACTTTCCA GAGGCTATGA
152041 GGGGTTTTAT GCCCTGAGCC CTGGGTTCCA TCCAAGCCAC AAGGGGTTTT ATGCCCTAGG
152101 CTTAGATTTG TGGTGCGGCA GGGCAGCCTT CCACCATTTG GCACAGAGCT TGGTGTTCCA
```

```
152161 AAGGCCACGA GGGGTTTTGG ACCCTGGACC CCGGACATCT TCCAAGACTC TTTTACATTA
152221 TGACAGACAA GCCAGTCCTG CTTCAGCTCT TCTAACAACA TGTAGTAATA ATGATATCAT
152281 CAACATCATC TTCGTCTTAA TTATTCAAGG ATGCCAAGGT ACAGAACTAA CCTGTTAATA
152341 TGGTTACCAT CCTGTCCAAA GTTCTTCTCC CATGCAGGAC TTCCAGGAAT CATGAGACAG
152401 TTGAGCAGAA AGATACCTTT TCCCTTCTCT ACTGAATAAC CACCAACATT GAGAATCAGA
152461 GAGGGAAAAT GACTCAGCTA ATGTCTTAGC TTGTTATTGG AAGACCCAGG TCTCATGACA
152521 CATGCCTAGT CCCATGACTT TTAATTGTAA GCTCTTCTCT TTCCCCTCAG ATAATGTTCC
152581 ATAAGCATTA GTATGAGATA ATAATACACT GAGGACCAAT ATACATGAAA AATATCAGAC
152641 TAGAATCAAA CAAGACAGAA AAAAGATCTG ATAACCTAAA GTGAGATACT GAACAGTATG
152701 CAGTTTTAAA AATAAAAAAT GGTAATAGGA TGTTCTAACA AGAGAGTTAA GAAACCACTG
152761 TGCTACTGAG TTAAATGTTG ATCAGTTGGT CTGTGACAAT TAAGGAATTC AAGTATTCAG
152821 AAACACTTCC TGTGCTGGAT GCTCTCTGTT TGTTCTTCCA ATAATCCCT CACTTTTCCC
152881 TGTCTTGCTC TGTGCCCAGG AAGGCTGACA TGGACAGATT AACCAGGCTT TCCGCCCTCT
152941 GGCTTGGTTC AGCCAATGGG AAGCACCAGA GGAGACCATA GGCACAAAG AAGCAGCCTT
153001 GGGAGTATTC AGTACCCCAG TCCCACGCTA TGATTTGGAG GGTCTGCATT CCTCTGCCTC
153061 TGGGCACACT CTAGTATAGT TACAGCTCCC TACACCTGCC ACTTGAGGCC CAGAGGAGGT
153121 GATGGCTCTC TAACTGTTCC TAGTTCTGGG TGCTTCCTGT TCCTTGTGGA TTTCCCAACT
153181 CCTCACCTTT GTAAATACCC TCCTTTTTCA AACTCTATTC AGTTAGCTTT TATCAGCCTG
153241 ACTCACAGAA GTTTGGGGTT TCAATTCATA TTACCTGAAT GACCCAGGAA AACCCATGTT
153301 GAGAAATTAA AATGTTTACG GGGTGGTAAT ACCACTTAAG AGAAAAATA TCAATTGGAT
153361 TTTTAAAATT CCACCTATCT ATTGGTGTGA CACATCAACA AAAACATATA GAAAGATTGG
153421 AAGCTAAAAG ATAGATAATA TAGTCATATA CTGTTATAGT ATTATATCAA AAGATATTAA
153481 GTCAGAGCAT TATTAAGAAT GGAAGAAGGG CCAGGTGTGG TGGCTCATGC CTGTAATCCC
153541 AGCACTTTGG GAGGCCAAGG CAGGCGGATC ACTTGAAGCC AGGAGTTCAA GACCAGCCTG
153601 CCCAACATGG CAAAACCCTG GCTCTACCAA AAATACAACA ATTAGCTGGG CATTGTGGCA
153661 CATGCCTGTA ATCCCAGCTA CTTGGGAGGC TGAAGCACAA GAATCACTTG AACCGGGGAG
153721 GCAGAGGTTG CAGTGAGCTG AGATTTCGCC ACTACACTAC AGCCTGGGTG ACAGAGAGAG
153781 ATTCTGTCTC AAAAAAAAAA AAAAGAAAG AATGAAGGA GTCACCTAAA AAAGATAACA
153841 CAATTTTAAA CATAAATGTA CTACATTATT AGTGAATTCA TGTTTAGAAT TGTGTTAATA
153901 TACAAAGCAA AAATTGTAGA ATTATAGGAG AAATGGACAA ATCTACAATC ATCATGGGAT
153961 GTTTTAACAT TCTTCTTTCC ATAATTGATA GATCAGGCAG ACCAAAAGAA AGAAATAAGG
154021 GAAGATACGG AAGGTCTGAA CAATCTAAGA AGCGCAATCT CATAGTCAAT ACATAAAGCT
154081 CAGCAATTGT TTAATAATAG TAAGCAGAGA ATATGCAGTT TTCTCAGGTA TAGATGGAAC
154141 ATGCACTAAC TGAGTAAATA CTAGGCAGAA AACAGTCTGA ACAAGTTTCA ATAAATCTGT
154201 ATTACACAGA TCATTTCTC TAGCCTCAAT ATAAGATTAT AAACCAATAA TAAAAGATG
154261 ACTAAAAAGA TTCTAAATAT TAGGAAATGT AAACTACTAA TAAGTCATTA GAAGATGTAT
154321 AGAATGGAAC AATAATAAAA AGTTATTTAT AAAAATATAC AATGAAGCTA AAGCAGAATT
154381 TTAAGGAAAA TTTGTAGGCT TTAAATGCTT ATCTTAGAAA AATTAAAAAG CTGAACATTA
154441 ATGAGCCAAG CATCTAATTT AAATTTTAAA AAGAACATAG AAAGCCAAAT ATAATTTTTT
154501 AAAAAGAAAA AATAGATATT AAACAATATA ACAGTGAAGT TAAAGAAAAC AAGAATGCAA
154561 TAAAGAGGAA AAACAAACAA AAAAAAGGT AGCTTCTTTT AAAAGAAATT TAATAAAATA
154621 GACATACCTC CAATGAGATT TATCAAAGTA AGACAGAAGG CACAAATGGA ATGAATACAG
154681 AAACTTTTTA AATATTACAG AACTTTATAA TAAATCTTAT GCTACTAATA AAATTGAAAG
154741 TACTGATAAA ATTATTACTT CCTAGAAAAA ATATTTCTGA GTAAAACTCA CTCAAAAAAC
154801 AAATAAAGCA TGGGCAGACC TAACATTAAA GAAATGAAAT CACTACTTTA AATTTTACCG
154861 ACAGATAATA AAACGTGCAT CTTTATCAAG CAAAAATGGA ACTTGTCAGT TTTATAGGAA
154921 ATTTAGAAGT CAAGGCATGA GTAATGCCAA TCTCATACCA AATCCTACAA AGAATAGAAA
154981 ATTATGGCTC CCGCTTATAG ACATAGATAT AGAACTCCTG CACAAAATAA TATAAATAAC
155041 AAACCAAATT TTATATTTGC AACTATACAT ATTATATGTG TATGTATTAT ATATGTTAAC
155101 ATATACATAT ATAATATGTA TAGCATATGT TCTACATATT ATATATGTAT AGTGTATGTA
155161 TTTTACAATA TATAAATGAA AACCCAATCT TTAATATATT CATCTAGATT GTCATATATG
155221 ACATATATAA TACATTACAT CAAAAATGTG TACAATAATC AGGCCAGGCA CAGTGACTCA
155281 TGCCTGTAAT CCCAGCACGT TGGGAGGCTG AGGCGGGTCA ATCACTTGAG TCCAAGAGTT
155341 TGAGACCAGC CTGGTCAATA TGGCCAAATT CCATCTCTAC AAAAAATATG AAAAATTATC
```

```
155401 CAGGCATTGT GGTGCACACC AATAGTCCCA GCTACTCGGG AAGCTGAGGT GAGAGGATCA
155461 CTTGAGCCTG GGAGGTGGAG ATTGCAGTGA GTCGAGATTG CGCCAGTGCA CTCCAGCCTG
155521 GGTGGCAAAG GGAGACCCTG TCTCAAAAAA AAATTAAAAA ATTAGCCAGG TATGGTGGCC
155581 TGTTCCTGTA GTCCCAGCAA CTGGGGAGGC TGAGGTGAGA AGATCACTTT AGCTCAGGTG
155641 GTGGAGCCAT GATCGCACCA CTGTACCACT CGGCTTGGGC AACAGAGTGA GAGCCTGTCT
155701 CGAAAAAACA AATATATACA CACAGTAATC AATATATATA TTATATGTAC CAATCAATGC
155761 TTCACTTTTA TATATAATAT AGATTACATC TTATTAGATA TATAGTATTC CTTCTCCATA
155821 GATAGATAGA TACAGATATA GACATAGTAT CCTCTATCCA TATTAGAGAG AGGATACTAT
155881 ATATATCTAT AGCATATAGA GATGCTGTCT CAAAAAAATT TAAACATCAG CCAGATGTGG
155941 TGGCCCATGC CTGTAGTCCC AGCTACTGGG GAGGCTGAAA TGAGAGGATT GCCATTGATC
156001 CTCTCATTGG TTGAGCCATA ATCGCACTAC TGCACCACTC AGCCTGGGAG ACAGAGGGAG
156061 ACCTGAGGTG GAAGGATATA GATATAGATA TATAAATAAA TATGTATAGA GAGAATATAA
156121 TATATGTGTG TATGTGTATA TATATATATT ATGAAGACAC TGGGAGAGAA TACTATATAT
156181 ATATGTGTGT GTGTATATAT ATATTATGAA GACACTGGTG GGATGGTTTC ATTACCAATT
156241 GGACCAAGAG TCCAGGTATG GAGCCAACAT GCAATGTTGT TGTTGACTGA GCTGGCAGAG
156301 CACTGGTCAT AGTTACGGGA AAAGAAGGTC TCCAATGAGA CATACTTAAC AAAATATATG
156361 AACTTGCCAT ATACGTGGAG AGTTCTGGTG TGTATATAGC CTTCTCTCAC CAACCTAGCA
156421 ATTGTCTTCA TCATCATTAT AATGCTATCA GAGCAAAGAT GACAGCTAAA TTTTTTTGTC
156481 CCTTTCTTCT TCTTTCTCTT CCTTCCCCTC CCCCACCTCT TTCTCTTCCT CCTCCTCCTT
156541 CATCTCTCTT CTTTTTTTTT TTGAGATGGA GTCTTACTCT GTCGCTCAAG CTGGAGTGCA
156601 GTGGCACAAT CTCAGCTCAC TGCAACCTCT GCCTTCTGGG TTCAAGCAAT CTGCCTAAG
156661 CCTCCAGAGT AGCTAGGACT GCAAGTGCAC ACCACCACAC CTGGCTAATT TTTGTATTTT
156721 TAGTAGAGAT AGGGTTTCAC AATGCTGGCC AGGCTGGTCT CAAACTCCTG CCCTCAAGTG
156781 ATCCTCCTGC CTCGGCCTCC CAATGTGCTG GGATTACAGG CGTAAGCCAC TGTACCCGGC
156841 CTCCTCCTTT AATAGACAGG GTCTAGCTCT GTTGCCCAGG CTGGGTACAG TGGCGTGATC
156901 ATAGCTTACT GCAGCCTCGA ACTCCTGGGC TCAGGAGATC CTCCTGCCCT AGTCTCCCCA
156961 GTAGCTGGAA CTACAGGCAT AGCACACGGG GCTAATAAAA TTAATTAGGT GATAAAATTC
157021 ACTGCCCACT GATGACTAAG CTCTTTGGAC ATAAAGACA CAGACCTTGA AGGAAAATGT
157081 GTCTACTTAA TTTTGAAACC CTATTTATCA AAAAACAGGA TGAAAATGCA AAATGCCATC
157141 CACATGCCAG AAGATATCAG CTATAATAAG TTCCCATAAA TCAATAAGGA AAAGAACCCA
157201 ATAAAAATTA TTAAACCACA GTAAATCATG GGTAAATCAC AGAGGCCTGA AGGGCTAATG
157261 GACATACAAA AAGAATCTCA ATCTCACTAG TGAAATCAGA AAAGCACAAA TTAAGTACAC
157321 AATTAGGTAC CATTTTAAAT CTGTAAGACT GTCAAAATCA TAAATTATAT AAGTAAAGAC
157381 TCAGGGAGTT TTGGAGGAGT GAGAGCTCTT ATATTGCTTG TGGGGTAGAA TTGGAACAAT
157441 TTCAAGATCT GTAGTATCTG GTAAAATTAT GATATGCATC CCTCACACCA GCATGTCACT
157501 CCAAGGTATC TCCCTGGAGG GAACATTTAC GGGACACAAG GAAGCATGGA TAAGAATGTT
157561 CACAGTAGTA TTGTCTGCAA CAGCAACAAC AACAAAAAAA CCCAACTACA CACAACTTCA
157621 ATGCCCAGTC CACAAGGCAA TGGATTAAAT AAACTTCAGG CCGGAGATGG TGGTTCATGC
157681 CTGTAATCCC AACACTTTAG AAGGCCGAGG CGAGAGGACT GCTTGAGCCC AGGAGTTCAA
157741 GACCAGCCTG AACAAAATAA AGAGATAGTG TTTCTACAAA AAATTTTTAA AAAATTAGCC
157801 AGACGTGGCA GTGCTTGCCT GTGGTCCCAG CTACTGGGGA AGCTGACGTG GGAGGATTGC
157861 TTAAGCCCAG GAATTTAAGG CTGCAGGGAG CCATGATGGG GCCATTGCAC TCCAGCCTGG
157921 GTGACAGAGT GAGACCCTGT CTAAAGAGA TAAGTAAATA ACAACTTTGC ATTTTCTGCC
157981 ACATTGCAAA ATGGTGAGAG AGTGGTTTCT AGACTCTAGA CTCTTTCTAT GACTACCTTC
158041 TAGTTATGAG ATCCTACAAC ACTCACCTAA CCTCTCTGTG TCATATTTCC TCCTCTATAA
158101 AGCAAAAATG CCCCATATAG AGAGGACTGT GATATAAAAC AAGAACCAAG AAAAGTAAAG
158161 CTTTTCTAAT CTGTCACAGA CTAAAGAGTG CTCAGTATAT GTGAGTCATT ATTCCTGGTG
158221 CTGGTAGGAG TGTATGTTAC AACTTTGAGT CAAGTAATAT GGTACCATAT ATTAAGATTA
158281 ACAACAACCT CGGCAATCCC AGTTTGGGGT ATGTTCCCAA AAGAAATGAA AGCACCAGGA
158341 TATAAGGATG CATGGACTAG AAAGTTATTG TAGCAACATT GTAATAACTA AGTTCTAAAA
158401 ACAGCCTGAA GCTCCATCAG TAGGGATATG GTTACATATA TTTATTATAT TCTTATGGAA
158461 TATTAGACAT AAAAAGTAAC GAGTAACATA GAAGAGACAG TGTATATATG TTACGTTTGT
158521 ACAAACTTAG GGAAAGATAT AGATCACCCT ACCTAGAGAA GTCAGATTGG AGACGGGTGG
158581 GAAAAACCTT GAACTTTCTC CTTATATCCT TTATATTGTT TGACTGATTA AAATGTATTT
```

Figure 1 (Page 49 of 73)

```
158641 GTTGCATCTG CTTGAAGGCA ATGTAAAATA AAATAAACAT ACATTTAAAA ATAAAAATAA
158701 AATTTATTCC TATCACTTTT GTAATAAAGC TGGGCACAGT GACTAACACT TGTAATCCTA
158761 GCACTTTGGG AGGCAGAGAC AGGCAGATCA CCTGAGGTCA GGGGTTTGAG ACCAGCCTGG
158821 CCAACATTGT GAAACCCCAT CTCTACTAAA AATACAAAAA TCAGCCAGGC ATAGTGGTGC
158881 GTACCTGTAA TCCCACGCTA CCCGGGAGGC TGAGGCGCTG GAACCCAGGA GGCAGAGGCT
158941 GCAGTGAGCT GAGATTGCGG CACTGCAAGC CAGCCTGGGT AACAGCGAGA CTCCATCTCA
159001 AAAAAAAATT TGAAAAAAGA AAAATTTTAA TAAACAGTGT TTAAGAGGGG AGAAATATTT
159061 AGTTAAAAGA TAAGCCCATT TAAGAAATAG TTTCACTTGA CCCGGAAGGC GGAGCTTGCA
159121 GTGAGCCGAG ATCGCACCAC TGCACTCCAG CCTGGGCGAC AGAGCGAGAC TCTGTCTCAA
159181 AAAAAAAAAA AAAGAAAGAA AGAAAGAAAG AAATAGTTTC ACTTGAACCA TATTATGATT
159241 CCTTCTGTAA AAGATGAGAG TAGGCAAATT GACTCAGTGA ATCCCAGCA AAACTTACAC
159301 AAAGTCTTGT TCTTCCTTCC TGTCATCTGT ATAGGATGAA ATACAGAGTG CTTTTGGGTT
159361 TTGTTGTTGT TTGTTGTTGT GTATTTGAGG GGAACACAGG TCTATAATTC CTTTTCTGAA
159421 ATCCCTGGAA CAAAATGGGC TTTGCCATTC AAATTAGTTT AGAAGTTATA AAGGCAAAAA
159481 AATGCATATA CTCTAAAGTT CAACCCCATC ATGGCCTAAG GCAGAGCCCT GTAATCAAAT
159541 TCATCAATAT ATCTGCAGCA AAACATTTAT TCAAATTAAG TGGGATAAAT AAAGACTTTT
159601 AAATAGTCTC ATCTCAGTGC CGTTCAGGGT TGGCCACTGT GGAAGACAGA CTCAAGGGTG
159661 GCCTTCTATG ATTCCTGCCT CTTGGTGTTC ACACCCTCGT AAAATTCCTT GTCTTTGAGT
159721 GTGAGCAGGG CTTATGAATT GCTTCTGACC AATAGGATAT GGCAAAGATG ATGGGATATA
159781 ATTTCTATGA TTACGTTTCA TTATGTAAGA CTCCATCTTG CTGGCAGATT TTCTCTAAAG
159841 AGTCTGTCTC CTGAGCTCTC TCTGAAGAAA TAACTGGCCA TGTTAGAAGC CCATGTGCAA
159901 AGAGCTGAGG GGTGGCCTGT AGAAGCTGTG GGCAACCTCC AGCCAACAGC CAGAAATAAC
159961 CAGGGCCAAA GTCCTGCAAC CATCAGGAAA GAAATTCTGC CTGCTACCTC AGTGAGCTTG
160021 GAAGTGGATT CTTCCTTAGC CTAGCCTCCA GATAAGAACA CAGCCTGACC AACACCTTAA
160081 CTGCAGCCTT ATCAGACCCT AAGCAGCAGG CCCAACTAAG CTGTGCCCAG ATTCCTGAAC
160141 CACAAAAATT GAGATAACAT ATCAGTGTTG TATTAAGGTT CTAAATTATG GTAATTTGTT
160201 TGTACTAATA GATAACTAAT ATAACCACCA AATCATTTCA GGTTAGGCCA GATTTTTGTA
160261 GCCAAATGAA TCATGATAAA ACTTTCCATT TTCAGGGGTT TTTTTGATTT TGTACTTACG
160321 GATACAAATT TGTGAAAGTA TAGTCAGCAC TGATTTAAAA AATCAAGGGA GCAGGAAACT
160381 CAGTAAATGG TTCTAACATT TTGGAATCTG TAAATTGGTT GTAACATTTG TCATCTGTGT
160441 TATCTAAGTC AAGTTCCTAA AATATGTGAA TGATAGGTTA TCATACTCAC CTACTTTTCT
160501 TGCATTGCTC TAAGAGTTGG CTGAGCTATT GATAATAAAC ACTATGATCA GATCTAATAC
160561 CATGATGTGC TATTATGATC ATGTGTCAGT CACAGGGCTA AGCACTTTGT ACATGTTGAT
160621 GCATTTAATT TTGATGATAA CTCAATGAAG TAGGAGCTGT TAATATTTTC ATTTTCAGA
160681 GGGGGAAACC AAGTCACTTG GAGTAACATG GCTAATAAGT GAAAGAATAA GAATTTGAAA
160741 GGTTTGCACA GATAACCAGA ATGCAATGCT CATCACATTC ACTGAGCAGT GAATCATACT
160801 AACTAGAGAA AGTATGAAAG CTCTACTGAA ATTAACTAAA CAACCTCTCT GGCTGTGAGC
160861 CTGCCAAGGG ACAGGTGGTA AACTTGGTTA CTGCATAAGG CCCCTTCTAT CCACAGTATT
160921 CAGGAATTCT TTAGTGAACA TACCTTGATG ACTCCTTAAC ATTTTCTTCA CATCGAAGTA
160981 AAGCTTGGAA ACATTGCACA TAGTATGAAG TTCCAAGGAG ACAGCCTCTG ATGTTCCAG
161041 CTTCACAGCC CAACTCCTAG AATAAGCAGA GGCGAGAGAT TTCTTCAGAG GTGCATTCCA
161101 TTCATTTCTA TATACGCACA CCCCTCCCCT CCTGCATTCA AACAGGACTT ACCTGCTCAA
161161 AGTGTCATTC ACATTCTATA AAGAAACAAA AAGAAAAGGT GAGCATGGGA ACATCGGTAT
161221 TTCATGGGGC TTGTCATGCA GGGCTATTCT TCTTTGCTTT ACCCGAAGAA GTAAAGAGAG
161281 TTACCCTAGT CTTAGTCTTA GATATTGATG GATACTCAAA CAAAGTAATT CCCACCAGTC
161341 TTAGGTATTG ATGGATACCC AGATGGAATA ATTCCTACCA GCTTCTGGGA GATTCAGCAT
161401 GGCAGGATGT TTATCAACAT TTGCATCTAT TCTCATCCTT GCTGAAGTCT GAGGGCCAGG
161461 AGCTTTGTCC ATGCTCCCTC TGTAAGGACT AGCTTTTGGT GATCGGATTT CCTTCACAGT
161521 GAGCCCAGAT TAGAGAACAC TTATCATAAA GGTCCTTAGT GGTGAATCTG TGCACAGCCC
161581 TGAGACTGGG CCACTGCCAC TAAGATGGTG GTAGCAGGTA TCACACAGTG GTAAAGCAAT
161641 CATGCTATAC ACTCAGCCTT ACAGTATAGT CACCAATCCT GTTAGTTAGA ACCAGAATTA
161701 ATGGCTCCAG ATGTTTATCT TCCTACAGAT AAAGCTGTAG ATTGTACCAT AACAGCTCTG
161761 GAGCAAGGGT TCTACAAGCA AATCAGGGAA AAGGTTATCA CTCATTTTGG CTGCCCCACT
161821 TCATCACCCA TCAGTCACCT AGTGGAGTAT TTCAGGAGAG AGTCAACAAC CAGGGTTCTC
```

Figure 1 (Page 50 of 73)

```
161881 TGCACATGGG CCAAGGAGGC AAACAGTGGT AAATGTTATC CCGTGGTTTC ATTTGGCCAA
161941 GCTGTGTTCC CTCAGAAGTT TATTTTTCTA ATTGACATAA AGGTACCCTA TAAATTAGTG
162001 AAGGCCAGCC TGATGGCACT GATGTACATC TAAAAGAAAC ATTACTTTAT CTTCCCATGC
162061 TTCCTTACCA TTCTCCTTTA ATAGCACTAT AACATACCTT TTTTCCCTAC TCCAAGTACA
162121 CAGCCTCACC TGCAGCAATT TCTGGGCTGA GCCCTGACAT TTTTCCTCCA GTTCCAGGAT
162181 GTGGCTCTTG AGTTCATTGC TCTTCAGCCC CAGACCAGCC TCATAGTCCC TCAGTCTACT
162241 CAGAGTCTGT TGTTCTTCTT TCTCCAGCCT CCAGAGATAA GACTTCTCTT CCTCATGTAG
162301 GAAACACTGG AGATTCTTAA AGTCAGACCG GATTTTTTGT CTCTGAATCT GTACCTTCTC
162361 CTGGAGTCAA GAAAGTATGG TCAAAGGTG GAAGTAAACC AAATGTCCAT CTATGGATGA
162421 ATGGATAAAC AAGAATGAAA GTCTGACACA CGCTACTACA TGACAAGCCT TGAAGACATT
162481 CAAGCAAAAT AAGCCAGAAA CAAAAGGGCA AATATTGTAA GACTTTGCTT ATACAAGGCA
162541 TCTGGAGTAG TTAAGTTCAT AGAGACAGAA AGTAAAATAG TGGTTACAAG GTGTTGGCAA
162601 GACCAGAAAA TGGACAGTTA TTGTTTAATG GGTAGTGAGT TTCAGTTTAG AAGATGAAAG
162661 ATGAAACTGA GTTGCAGTTT GGAGATGGGA ATGGTGATGG TTGCACAACA ATGTAACAAT
162721 GTAAAAGCAC TTAATTCTAC TGAACTATAT ACTTAAAAGT GGTTAAATGC TTAAGTGTTA
162781 TATATATTTT CACACAAACA CACACACACA CACAATCAGC CACTGGGACA TTATTTTCTC
162841 ATGAGTCACT GAAGCTGGAA GAATGTCCCC AGTTTCCTGC TGCAGAGTCA TGTGTGGGAG
162901 GCAGGCACTC AGATGTGGAA GAGGTTGCCT CAGATTCCTT ATAGTCACCC AATTAATTTT
162961 CTTGTTCTTC AGCCAAGACA CAGGAGAAAG CTGGGTTAGG AGTGCTAGAT AATTTAATTG
163021 TGAAACTAGG GCCAAGTTCA AACACTTTAT CAGTTACAAG GATAAAAAGA GGTTTTTACT
163081 TATGATTTAA GAAGTTAGAT TTCTGAGTTG GAGCGATTTT CTTGAAGTAA AAGCTTATAA
163141 TGAACATCAC CCAGACTGGA TTTTAAGACA ACCAGGCTGG TAAGAGGGTC CATAATTCTT
163201 GGCAGGGGGA GCTTTGAGTG TGACAGGCAT TTATTATGGT TAACTGAGAA ATACTGTTCT
163261 ACTACCCTAG GGTCATCTTA AGCATTCCTA TGTGTAAGAC TGACAGAAAT CAAGTGAAAC
163321 TCTCATCTGA GGAGATGTAA AGTTGCAATT TCCATTAGTG CTGTCTAAAT TAATGCAGTG
163381 GGAGTGTGTA TTCAGGGCAA TTTGAATCTA TGTTCTTGGA TTGCAGTCTT CAAACTTGGC
163441 CCAAATAAAC TCTCTACTTA TCTTAAAAAA ATAAAAATTA AAAAATAAAA ATAAATTCAT
163501 ACAGTGTTTT GATGACTATG ATATAGAAGA AGGGTCTTTG ACTTAGGATG AGGTGGAATT
163561 TTTGTGTAGG AGACAGGTGC AGCTTTAACT CTTGTATAGA CGGGTTTTCA TATATGTTAG
163621 TTACAATCAA GGTCTTCCCC ATTGCCCAAG ATCCTAGAAA TGGGGGAAGT AAGAGTGTAC
163681 TCAGGAGCTC AAGAGCAACA TCCACAAACA AAGATCAGGG TAGAGGTTAG AGAGGACTCC
163741 TGAAAGAGAG AAAATTGGTA ATCAGCTTGT GGGATTTTAC TGCAAGCTAG TGAATTATAT
163801 AAATATAAAG ATTGGTGCAA AAGTAATTGT GGTTTTTGCC TTTACTTTAA TGGCAAAGAC
163861 CGCAATTACT TTTGCACAAA CCTAAATATT TCCATAAAAG AATGTGGCTC TGATAATGTG
163921 GAGGTTAGTC AGCCACGGAA ATAATCTGAA AGTTTGTAGT TGCAAGTGTG TAGGTTGTTG
163981 CATTACTTGT GATGTACTTA TAAATCAAGT ATAGGCCGGG TGCAGTGGCT CACGCCTGTA
164041 ATCCCAGCAC TTTGGGAGGC TGAGGTGGGT GAATCACGAG GTCAGGAGAT CAAGACCATC
164101 CTGGCCAACA TGGTGAAACC CCGTCTCTAC TAAAATACAA AAAATTAGCC AGGCATGGTA
164161 GCACATGCCT GTAATCCCAG CTACTCAAGA GGCTGAGGCA GGGGAATTGC TTGAACCCGG
164221 GAGGTGGACA TTGCAGTGAG CTGAGATCGC ACCACTACAC TCCAGCAAGA CTCCATCTCA
164281 AAAAATAGTA ATAATTTAAA AATAAATAAA TAAATAAAGT ATATTTCTTT CATCAGCTTC
164341 ATGAGCTAGA GTAGTATGAA TTTCAATCTG GAGTGATCCT GTTTTCTAAG TGTTCACAAA
164401 GCTTGGTTTC TGTACCTGTA AAGTTGAGAG CCAGATGCTC CACTGTGGTA AAAGTGCCAG
164461 GGTAATGAGT TGAGGCCTGC AAACCAGGTT TATTTGACG TATTTAAAGT TTGAGACCCA
164521 CTCGATGCTT TTTCTAGGTA AATAGTCATA CTAATTCTGC TTCTTCTGAC TGAAGTATCA
164581 GGAATCCCAG CCAACTACAG TTTAAAGATG GAAAGATTGG TGCTAAATAC TCATGGATGT
164641 AAACCTGGAA CCAGGGGCAT AAGTACAAAT AATGGTTTCT TCCTTGGGTT TCATTTTTTC
164701 AATCTGGTTT AGTGAGAATA AATCCTCATT GTGCTTTTCC TCAATCATCC CCTATGCCTA
164761 AGCTCTAGAA TGGAAAATAG CTTGAGATCA ATGAAGTCAG ATTCTTACTT TCCATTTAGT
164821 TATTCGCATT GCTGTGGACA GCTTCTGCTC CGTACATCTG TCTTCAAGTT GCTTCAGTTT
164881 TGTCACAGCT TTCTGGAGCT TTTCCTGAAG GAAAAATTTG ATAAGTGAAG CCTATTCAAT
164941 TTGACTCTTC ATTAGGGACC TAGGGGGAAT CCCAATCTTC TAAGATATAT TTGAATAATA
165001 GTGAATATTT ATAGAGTCCT CATTGTTTTT TGCTAGAGAG CATGCTAAAG GCTATATGTG
165061 CAGGAACATA CTGATCCCCT TGGCAACCCT GAATAGTTGG TAGGATTTTA AACTTCATTT
```

```
165121 CTGTGCTGTA GAAAATGAGA CTAAGAAAGG GGTAAAATAA CTTGCCCAAA GGGCTATGAC
165181 TGCCAGGTGG TGGAGCAACA ATTGCAATCT CATCTGCTGA CCCAGAGCCT GAGCTATGTC
165241 CACCACTAGA GTCCTGCCAG GAAAAGTTG GATATAGAAC AAGGTAATCA TCATCTAAAA
165301 GATTTTGTAA AACAACATGC TGAACCAAGC AAAACCAATA CCAGTGTTTG GCACACATGA
165361 AATTTTGTGT CTTATGAGTC AGGAAAAATC AGGATGCCAG CTGGTTATTA GAAACAGTTC
165421 ATGGAAGAGG GGAATTCTGG TATCTTTTGA ACAATGGTAT CATGAATCCA ATTTAAAATG
165481 ATTTAGTATT CATGTCAAGC TTTTAGCTTA TTCTTCAAAA CAGTTTCTCA TATTTCTATT
165541 GAAAGTGATT TGAAGCTGAC CCAAATTGCT AATTGTAGTC AATGCTGAAA GAATTGTCTC
165601 CTGTCCTCTG TAAACCCAAC AAGTATACTC ATTCATTCTC GAGTGTTCTC AGGAAAAGGT
165661 TCTATGTAAC TGTTTTAGCA AAAGATGACA TTGTCCTTAC TATATGCCAA GTGCTATTCT
165721 ATGCATTCTA TATTTTAATG TCCTCAAAGC TTATAACCAC CTCCTGTGTA TGTGTTTTAG
165781 GGAGGGAGGA CACTGCTATT ATCCCCATTT ACAGATGGAG AAACCAAGGT GTGAAGACAT
165841 TAAGTAACGT GCCCAAAATT GCCCATCTAG TAAGTGACAA AACTCAATTT CAACATAAGC
165901 TGGTTCCTTT TCTTACTACT TGGTGGAAAA GTAATTCAAA TGGGAATATG ATCATCGCAG
165961 TTATTAGCTG CTCCATGGAG TTTAAGGAAG AGCTGCCATG AGCTGAGTGG TGGTCATGAT
166021 TGACATGTCC TTAGAAGGAC TTAGAGCCTT CATACAAGAC CACCTCTGCC TCATGGAGGA
166081 CAGAATAAGG AGCCTGACAC TGGAGACAAC ATTTTCCTCA AATTTAGGCA GGACAGAGAA
166141 GGAAAAAGGA CATCAGGACT ATGCCCATTC CTCCATGCTG CCAACAGCAA AGTCCCACCT
166201 TCCTTAATAT GCTTTCTGGC AAGAAATCTG GATGGTACAC AAAACCTCTC CCTCTGCTTC
166261 ACCTTCCACA ACCAAGCATT TCCAAATCTT TGACTCTTCT TCCTGAATCG TGCTTAAAAT
166321 CTGCCCTCTC CTCCCTTTCT TATACGGATA GTTTGAATTT TACTCCTTGA TATTCCTTTT
166381 ATCATAGACA TGCCACAGTA GCTGGGCACA GTGGTTCATG CCTCTAATCC CAGCATTTTG
166441 GGAGGCTGAG ATGGGAGGGA GACCAGGGGT TTGAGGCCAG TATAAGCAAG AAAGGCAGAC
166501 CATGTCTCTA CAAAAAATAA AAAATTATC CAGGTATGGT GGGGCATCCC TGTAGTCCTA
166561 GCTACTTGGG AGGCTGAGGT GGGAGGATTG CTTGAGCCCC AGAAGGTTGA GGCTGCAGTG
166621 AGCCGAGATT GCACCATTGT ACTCCAACCT GGGATACAGA GCAAGACCCT ACCTCAGGAA
166681 AAAAAAAAAA AAAAAAAAAA AAAAGTAGAG GTACCAGAGT GATATTTTCA ATGTCACTGA
166741 CCCTTCATTC CCCAAATGAA AATCCCCCAA TAGGTGTTCA ATTTTTACGT GTCCTTCAGG
166801 AGTTACTTCT AAGATGAACC ACTCTCTACC CTAAATGTCC CTCCCCACCA CCAAAACCAG
166861 GGACCTCCAG GCAGACATTT TTGATGGTTT GTTTTCTTTA CTAGACTGTA GATACCTAAA
166921 AGGTGATGGG TCTTTCTTCC CTGTTTTCAG GCCCTACTGC ATGGCTTTAC ATATTGTGGT
166981 TTTTCAAATG ATATTCATGG TGTGAAACAA GAAAAAATGC GGGTGTTTGG TTTGAGAACA
167041 ACCTGTTCTA AAGCAAAAAG AAATTCATCA TAACACAAAT GGATAGAGAT AAGAGTCCAA
167101 CCATCCCATT GAAGGTCAGG ATGGACAGTC TAGATAATTG AGCAAGAAAT CATCATAAAC
167161 TATTTTTCAG AAGAATGACA TGATGAAAGC TGTATTTCCA AGTCATAATG TTAGGTTTCA
167221 AGTTAAATCA TCTCAGCTCC TGGGGAGCAG GATAAGACTT GGTACTTACC AAAGCTCCCG
167281 GGCCCACACA CTCACCTTGT AGCCCTGGCA TACGTCTTCA ACAAGAGCTG TGGTGTGCCC
167341 TTTGTGCTGT GGTGCCCGCT CACAGCGCCA GCAGATGAGC TGCCCCTCGT CTTCGCAGAA
167401 CAGGTGGAAC TGCTCTCCGT GTTCCTCACA TGACATTTCT TGATCCGTCT CTTTGAGGGC
167461 TTCAATGAGG CTTCCCAGCT GCTTGTTGGG TCGGAGGCTA TCCATATGAA ATGGAGCCCG
167521 ACACTGGGGA CAGCAGAATG TCTCCTGCCT CAGTTGCTTT TGGCTTGGGT TTTTAAAGAA
167581 GTCTGTTATA CACAAGTGGC AGTAGCTGTG TCCACAGTTG ATGCTTACTG GGTTCGTCAT
167641 CAGGCTCAGG CAGATGGAGC AGGTGGCTTC CTCCATCATC TTCTTGGTGC TGGTGGTTGA
167701 GGCCATAGCT TTTATTGAAA AGCTCCAATA TTGGCTCTAG AGATGGAGAT GAAGCAGCCA
167761 GAATTTTCCA CCGTGATGAA AATACACCTC ACCTGCACCT CTATGTGATG AGCTGGCTGC
167821 AACTGACTTC CATAGGTCTT GAAGGTTTTC CTTCCAACCC CTATTATCTC ATTTTGTATT
167881 GAAGAAAGA GGACCTAAAA GGAAGAAGTT GAGGCTGAGG TTGTTTGGGC CACGTTTGAG
167941 AACTGCAACC CAAGTGCAGA GTTTCAAGTT GCCCTCATTA GCAAGCAGTT ACAAGTGGTT
168001 GTTTAGAGGA AAAAAGCAG TTTTAAAGCA GTTTTAAAGT TGTTTGCCAA GAATTTACAT
168061 TAAAATAGCA TAAGCTTTTG ACTGGCTATA CATTGTTCTT TGTATTACAA ATCTCGGGAA
168121 TATGTAGGTA ATAGATGAGG CAGCCAGTCA GGAACAAAAT GCTTTTAAAC ATGGGGTCTT
168181 AACTGAAGAC CTATACTCCT GCCTCACTTG TCCTGATAAA TTTTGCATAC CTCACATAGC
168241 TCAGACTGCT CTAAATTATT TCATTATTTT TCTTTTCTCA GTCTTCTAAC TTTTTTTTTT
168301 TTTTTAATG AGACGGAGTC TCACTCTGTC ACCCAGGCTG GAGTGCAGTG ACGCTATCTC
```

Figure 1 (Page 52 of 73)

```
168361 GGCTCACTGC ACCTCCGCCT CCCGGGTTCA AGCGATTCTC CTGCCTCAGC CTCCCGAGTA
168421 GTAGCTGGGT CTACAGGTGT GCACCACTAC GCCCAGCTAA TTTTTGTATT TTTAGTAGAG
168481 ATGGGGTTTC ACCATGTTGG TTGGCTCGAT CTCTTGACCT TGTGATCCAC CCGCCTCAGC
168541 CTCCCAAAGT GCCAGGATTA CAGGCATGAG CCACCGTGCC CAGCCTCTTT TTCTTTTCTT
168601 ATAAGACAAG TTCTCGCTCT CTTGCCCAGG CTGTAGTGGA GGGCAGTGGC ATGACCACAG
168661 CTCACTGCAG CCTCGACCTC CTGGGTTTAA GCAATCCTCC TGCCTCACCC TGGCAGAGTG
168721 GCTGGGACTA CAGGTATGTG CCACCATGTC CAGCTAAAGT CTTCTCTCCA GAAAGAAGAA
168781 ATGCATTGGA ATTTAGAGGA TACACAAACA TCTAGCTGTA TAGCTAATAC AGTAGCCACT
168841 ATCATGAGTA GGAATTTAAA TTTAACTTAA TAAAAATTAA AATGAAAAAA TTCAGTTTTT
168901 CTGTTCCAGT TGCCACATTT TGATTGCTTA ATAGTTGCAT GTGACTAGTG GCTACATAAC
168961 AGCCTCAATA TACAACATTC TGTTATCACA GAAAGTTACC TTGGACCAAG TGCTGGGAGA
169021 AGCAATGCAG GCTTCCTCAC AAAAGCTGTA AAAGAGAGAA CTCAGGAGT GTGAAACTCT
169081 TTCCTATTCT AGTTAACTTC AAGAATAATT GTTACCAGGC CAGCACGGTG GCTCACGCCT
169141 GTAATCCTAG CACTTTGGGA AGCCGAGGCG GGCAGATCAC CTGAGGTCAG GAGTTTGAGA
169201 CCAGCCTGAC CAACATGGCA AAACCTCATC TCTACTAAAA ATACAAAAAG TTAGCTAGAT
169261 GTGGTGGTGC ACACCTGTAA TCCCAGCTGC TCAGGAGGCT GAGGAAGGAG AATGACTTGA
169321 GCTCCGGAGG GGGAGGTTGC AGTGAGCCCA GATTACACCA CTGCACTCCA GCCTGGGTGA
169381 AAGAGCGAGA ATCTGTCTTA AAAAAAAAA AAAGAATAAT TGGTACCAGA ATTACTCTTT
169441 GTAATTAGTA GTAACACTTA TGCAATTGGG TGATCTGTGA CAGATTCCAT TGAAGGAGTA
169501 TGGGGAGCTT CACCCCAATA TATGACTCCC TGGTATAATG AGTATTTGA ATTAAAGGCC
169561 CTTAGAGATC AGCAGATGCT GGAAGAGACT TTTCCCCTAT CTACATAAAG ACCAGTCACA
169621 CTAGACAAGA AGAACAATTG TTTTTCCTTC CAACCCCTAT TATCTCATTT TGTACTGAAG
169681 AAAAGAGGAC TAAGAATGTA ACCAGACCTA ATCAGACACT TTCACAAAAT AATGTCTGTC
169741 TCTCAGGCTC ATTCATTTC CAAAGAGAAC CATTTACAAG TTAAACTCTG TTCCTCCATT
169801 CATTCATCCT CCCAAATATT CATTTATTCT CCCTAGTAAT CATTTACTGC CCCTCAAAGA
169861 ATTACCTATA TTCTCCTGAT ATCACCCTTC CCCTCTGAAA TAAATATGTA TACATGTATA
169921 AACGTTATAC ATACATATTT ATACAGTATA CATACATATT TATACATACA TACATATGCA
169981 TACATATTTA TATTTATGTA TTTATACATA AGTATTTATA AATAAGGCTA TATAAGTATC
170041 TACCCCCATT GGCAGAGGGG GTAATCACTC TGTGATTCTA GCCCATGTAC TTGTTAATAA
170101 ATTTGTATGC CTTTTCTCCA ATTAGCCTGC CTTTTGTGAG TCGATTTTTC AGTGAACTTC
170161 AGAAGGCAAA GGGGAAGTGT TCCCTTGGCT CCTACACCAT CATGACAATA AAATTTGACT
170221 CCACCTCGAC CCCCCCCATC CCCCACAAAG AACAACAACC AACACTGGTT AATAAGGTCG
170281 GTTGTTTTTT GTTTGTGTTT TTGTTGTTGT TGTTTTTGCT TTCAGGAGCA GAGGTATAAT
170341 AGGCAAAAGA AAGAGAAAGG AGAATAGTGA ATACCTCTTC TGCAGAGAGG GGTGCCTAAG
170401 TGGGACTTCC CTGGCTAATA ACGTCTTGCT AGAGACCCAA CCAGGAGGAT AATGGAAGCA
170461 ATCAAGGCAA CCAGAACAAC CAGAAGAACC GGTTTATCCT TTTTGTGCCC TCTCCCTAAA
170521 CTGAGGGAAT AAGAATTGGA AAGAAGGCTG CAGAGCAGAG GGTTTGCTCC TGAGGAGCAG
170581 TTATTTCTAT GGGATCAGAG CTCCTGCAGA ACTGGGGAGT TTACTTTTAC TATCTCTTCT
170641 CCAGGACAGG ACCTATCTCA AGAGACATGT TCAGAGTGAT TGCAACATAA AGAGTTTGCA
170701 GACCCAAGGA GGTAGGGAAG GCAGAAAGAA GATGGGGGAG GCCAGGGATA GGCAACAGAG
170761 GAGTGACCAG GAGCGAAAAA GCCTGCCTCT TCTGAGAACC TAGCTGGGCT CTCCCTGTAC
170821 CCCCGATCCC TCCCCCCCGC CCGCCCCCAC ACCCCTACTC CTGGGAGCTC CTCTAGGACA
170881 GGGGCAGAGT CAGGAGGAAG TTTGAAGAGT GCCTAGAATA AAAAACAGTA ATTTAACTAC
170941 AATTACCGGG TAGGCTGTTT TCCTCTCACA ATTTGATCAG TCTCTTGAAG CCACACAGAA
171001 TTTCTTCTGA AGACGTGTAT TCCTTGGCAG GCTATTTCCT CCAGTGATAC ACCAGGCCCC
171061 TCTCTGCTGG GGTCACTGCT CTTCTGGGA GATGGGCTC CCCTCCTTCC AAGGCTCCAG
171121 GGTTCCTGTC CTGGGCCCCA CTCATCTAAG TTCTGAATCT CTGAGATTT GGTGTAAAGT
171181 CTGGTGAAAG AAAGAGCAGG AAAGAGGTGA GAGCTGTAAA ACAAAGAAAG TCCTGACCAT
171241 TTTCAGAGTT GGAGGGGCCC TGCTGTCACG AAATATATTC CCCACCCCAC TTGCCATCAG
171301 TACACACTCA CATATCCACT GAGAAAACCT TAGCCTGGAC CTTTTCCGTA ACCTTCACTG
171361 CTCAGACACT TACATATTCG CTGCTAGTCC CCTCTGTTGC TGCCACTTCC TGGGTCAGGA
171421 AGTTAACTCA GACCGGATTA AACTGAGAAG TGAAACTACT GTGGGAGGCG GGGCTCATAA
171481 GATTTAGGAG AAAACTAGTG ACGTTGTTCA TATCATTTGC ACTCCGCCTC TCCGGTAAAG
171541 GAGGGGGAAA CGTAGGAAGA AAATATCCTT CTTTTACAGC AATAAAAAGA AGGAACCAAT
```

```
171601 TAATAACCCT GTAAACTATC ATGTGACCCC AACACAGAGT ATCTAAAAAC AGGAAGCCTG
171661 CAGAGGTTCA GTTCACAGAC TCTGATTTGA GATCTTTCTA CTTTTGCCAC CAACTCCCTT
171721 GGGAGTCCTT AAGCCTTCCT AGCTGATGTT ACTTCTTTTG CTATTTATGG GTTGCTTGTG
171781 GTTCTATAAC TGCTCTGAAG GGTGTGGTGG AAAAAGGGGT GGTAACAGCA GTAGGACTCA
171841 TTGGCATCAC AAAATTCATC TGAGTCAGCT TTCTATTCTT CTCTGTCCCG TTCTGTGTCT
171901 TGTTTTTCTC CTTGCTGTCC TTCTGCAGGA CTCAGATCTT CTTCAATAGC GAGGGTCAGC
171961 CAGGATAGAA AATGGGAGTC ACTAGTGGCC CAGCAGTGAG TGCCCCAGC TTAGAGCTGT
172021 GTGGGATCCC TGGGACCATC ACTCTGCTTT GTGCTTTGTG GAGAAAAGGC TGTGGGGTCC
172081 AGGGTCAAGT CCTTAATGAC TTAGCTCCAG CTTCTCCACT TCAAAATGAA AGGAAAAGTA
172141 CTATCACCAC CCGTTAGAAT TATTATTTCA TGGGGAAAAA AGATGGATTA CTATCTCACA
172201 ATAAGAGCTT GTCACATTTA TAAGTCTCAG GTGTAAGAGG CATTTATGAT AACAACATAA
172261 TAAATGCTGG CTTAAGTAGA TGCAGTGGTC CAAGGGAACC AGTAAGGGGA GCTCAGGACA
172321 CAGGTGGGAG GAGAAATTAA ACTTGAATTC TGGGAGCCAC TGGCCTGTCT GGGCCCCTGG
172381 CCTGCCTGCT GACCCTGATA GCCAATGGAA CATGGAGTTT GGCCCAGCTG CAATCCCTCT
172441 GGTCCAACTA CTCAAAATAA AGGCAAGATT GGGAAACACG TTCCTTTCTT CCTATACCAA
172501 GCAGAAGACT CTTCAGCACT GCACCCTCCT GGGTGCTCAC AGAGCCTTCT GTTGTTTTGC
172561 CACCTACGAT TCATCATGCC CTGGCATGAT GGTTGCAGAC CCCATGCATA GCATGGGACA
172621 TTCTACTCCT GAGGCAACCA GCACACAGAG AGAGGAGAAA GAATGAGCCC CTGAATCCTT
172681 GGTCCCACGA TGAGTCCTTG CAGATATCTA CAACTTTCAT TGTTGTGGAT GTGACTCTGT
172741 ACCCAGGCAT GGCTCATTCC AGATCTGTCC TATTGTCAGA GGTGTTCAAA CCAGAATGAC
172801 TCCATTTTGA ATGGGGCTA GGTAAAATAA GGCTGAGACC TACTGGGCTG CATTCCCAGG
172861 AAGTTAGGCA TTGTAAGTCA CAGGATGAAA TAGGCAGTTG GCACAAGACA CAGGTCATAA
172921 AGATCTTGCT GATAAAACAG GTTGCAGTAA AGAAGCTGAC CAAAACCCAC CAAAATCAAG
172981 ATGGCAACAA GAGTGGCCTC TAGTCATTCT CATTGCTCAT TATACACGAA TTATAATGTG
173041 TTAGCAAGTT AGAAGGCATT CCCACCAGCT CCATAGTGGT TTATAAATAC CATGGCGATG
173101 TCAGGAAGCT ACCCTATATA GTCTAAAAAG GGGAGGAACG CTTGGTTCTG GGAATTGCCC
173161 ACATCTTTCC CAGAAAACAT ATGAATAATC CACTCCTTGT TTAGTACATA ATCAAGAAAT
173221 AACTGTAAGT ATCTGTATTA GTCCATTTTC ACACTGCTGA TCCAGACATA CCTGAGACTG
173281 AGTAATTTAT ACCAGGAAAA AATGTTTCAT GCTCTTACAG TCCCACGTGT CTGGGGAGAC
173341 CTCACAACCA CAGCAGAAGG CAAGGAGGAG CAAGTCAGGT CTTACATGGA TGGCAGCAGG
173401 CAAAGAGCTT GTGCAGGGAA ATTCCTTTCT ATAAAACCAT CAGGTCTCAT GAAACTTATT
173461 GACTATCATG AGAACAGCAG TATAAATTAC TCAGGGAAAG ACCTGCCCCC ATGATTCAAT
173521 TACCTCCCAC CAGGTCCCTC CCACAATATG TGGGAATTTA AGATGAGAGT TAGGTGGGGA
173581 CACAGCCAAA CCATATCAGT ATCCTTAGTC CAGAAGCTGA TGCTCTGCCT GTAGAGTAGC
173641 CGTTCTTTTA TTCCTTTACT TTCTTGCTTT CACTTTACTG TGTAGACTTG CCCCAAATTC
173701 TTTCTCACAC GAGATCTAAG AACCTTCTCT TAGGGTCTGG GTTGGGACCC CCTTTCTGGT
173761 AACACTATCA AAGGATCAGG AAAAGGAAGC TAGTGAATGC TAAAAAGGAA ACAAACTACC
173821 ATTACCAATA ATAACAGCAA GACAAAAGCA AAACGGATTG TGACAGCTGT CCCATCTCAC
173881 ACCTGTTTCC CATTGCAGGA AGGAGGGGCT GGTTCATGCA CAGAGTGGCC AATATTAGAA
173941 GCAGAGATGG GGTGCAGATG AGACTTCAGG AATATGTTGA CAAAGGCAGG CCTAGGGAGA
174001 AATCAACCTG AACTATCCCC AAGGAGGAAT GCATTATCTC TAATATGTAA AGTTAGGCTT
174061 GATCCTGTGA TTATGGGATA TAGGAGTCCA AAGACTCACA ATGGGAAGTA GGTCACTAGA
174121 GTCTCCTTCA GAAGCTCTGT ACTGTGTGTT CCCACTGTGG GCAAGAGTCA GCACTCAGCT
174181 ATTCCTAGAA TGCCTTTCCT CAACTCCTTC AGATTTTGCC TCTCAACTAA CCCTATCCTG
174241 ACCACTTGTT AGCAAGTGTA CCCCTCTCTC CCTCCCAAAC ATTTTCAAAT CTATTTTGTT
174301 CCCATGGCAC TTATCACTGA ATATTTTACT AATTTATTTT GTTTAGTGTT TGCTTCCCTC
174361 ATGAGAATGC AAAGGGATGG ATTTTTTTCA ATATTGTTCA CTGATGAATC CCAGTAACTA
174421 GAATATTTCT AAGCATAGTG ATGTGCATTA AATCAAAGAG TAACTTTCTG AATTGCACTA
174481 AACACACATC ACAAGAGGTG TGTGCACATA TGTGCATGAT GCACGTAGTG TGGTGTGGGT
174541 GTTGTGTGGG GTATGTGGTA CTGTGTGTGC TGTGTGTGGT ATGTGATACA TAGTTTGTGT
174601 TAGTGTGATG CATGTGATGT GGTATGTGTG TGCGTGTCCA TACATATTAG GGGTGGCGGG
174661 GATGTTAATA TGTCAAATGG TACTAGAAAG TATCAGAACT CATGGTCCTT ACTGGTTTCC
174721 CAGAGAGCTG CTTCTCTCCC ACCTGTAGGA TATACTGATG GTTTGGACAG AGAAGAAATA
174781 AAAAGAAGGC TGTGACCTAC TGGGCTGAGG AAATAAAAAC GAAAGTAAAA GAAGAGCTGG
```

```
174841 GAAAAGAGAG TGGAGGGGCC AAGGGAAATT TCCCCTTTGG CTTCTGGGGA AACTTTGCTG
174901 AAAAATCAAC TCACAAATTT ATTAACATGT ACACAGGGAG AACCATAGAA TGATTATCCA
174961 CTTCCCAAGA GGGCTTAAAA GCTTATATAT TATCCTGGCA AAACAGATTA TGGGAGGGGA
175021 AGAAGAGAAA CTCTGTTGAT GGGATTACTG TTGCGGATTT TTGCTCCTTC GCTCAGCTAG
175081 GTCCGGGTTT TTGTCTCACA GCCAGGAAGA ATTAGGCATG CAGCCATCAA AGAATGAGTG
175141 GAGTAGAATT TATTAAGTGA AAGGAAAGCT CTCAGCAAAG ACAAGGGTCC TGAAAGCAGA
175201 TTTCTGGTTT GCTCTTCACA GTTGAATACT AGGGCTTAAG ACTCAAATTC CTGACAACTC
175261 CACCCTGTCC TACCAGTGCA TGCAGGCCTT TAGACTGAGC TACTCCATAT TGATTAATTT
175321 CCTGAACTGT GCATGTGTTA AGGAAAGGAA TCATCCACTG CAGGCATGTT TAGGCAAGCC
175381 CCCTGTGCAA GTTCCCTTAT CTGCACAAAA CATCCGGTGT AAGCACTTGT GGGGCAGGTC
175441 AGAGGTTCTC TGGGTACCAT TCCCTTACTG TCTGCCTAAA GCAAGCTGGC CAACTCCTTT
175501 CATTACTAGG GAGAGTAAGT AGATCAGGGA ACAGAGATTA ACTTGAACAT TATCTTGTGA
175561 AAGTCCGTTC GGGCATGGTT ACATTCTTGG TCTTACAGGA AGGGTAAATA AAAATAATTG
175621 CTCTTTTTGG TGGGTCTGGA TCTTAGGTAG ATAAAGAAAC TTTAATTCCA CGATGTGTTT
175681 TGGTAGGGAT AGTTGGTGGC AGGGATGTCA GAGAGACTTT GAGGCTTCTT CAGTTCAATA
175741 TGACCAAGGG CCATATATTA GGGTATCAAT TTCTGAGCCC CAACAAGAGC TTAGGAGAGA
175801 TGTGATAGCA TCACAGTGTG AAAGCAATTT TTTGTTTGTT TTTAGAGACA GGCTCTTGCA
175861 CTGTCACCCT GGCTGAAGTA CAATGGTACG ATCACAGCTC ACTGTAATCT TGAACTGGGT
175921 TCAAATGATC CTCCCATCTA AGCATTTCAA AGTGTTGGGA TTACAGGCAT GAGCCACGGT
175981 ACCCAGCCTG AAACTGCACC CACTTTCTGA TAAACTTTTC AAATGACTAA AGGGGAGAGA
176041 GTAAGCACTA CTCAGAGGTA GGAAGAAAGG ACACAGGATT ATAGGATTAA AACAACAACC
176101 ACCAAAAAAA ACCAGACCGG TGTGGTGGCT CACACCTGTA ATCACAGCAC TTGGGGAGGC
176161 TGAGGTGGGG GGAGTCACTG GAGGCCAGGA GTTCGAGACG AGCCTGGCCA ACATAGCAAG
176221 ATGCTGTCTC TATTAAAAAA AAAAAATACC TGCCTTGAGC TAATCAGAAT CATGGACCCT
176281 GACAAAGGAT GTCCCAAAGT AAGTCTTAGC ATTTTTTTTT TTTTTTGAG ACAGTCTCGC
176341 TGTGTTGCCC AGGCTGAAGT TCAGTGGCGT GATCTCGGCT CACTGCAACA GCTGCCTCCC
176401 AGGCTCAAGC AATTCTCCCT GCCTTCAGCC TCCCAAGTAG CTGGGATTAC AGATGCCCAC
176461 CACCACGCCT GGCTAATTTT TGTTTTTTTT AATAGAGATG GGGTTTTGCC ATGTTAACCA
176521 GGCAGGTCTT GAACTCCTGA CCTCAAGTGA TCTGCCCACC TTGGCCCCTC CATAGTGCTG
176581 GGATTACAGG CGTGAGTCAC TGCACCCGGC AAAGTCTTAG CATTCTTTAC AAACAGTTTG
176641 TACCCGTATC TCTAAAAGGG AGTAGTGAAT TTCACCCCAA AATGTGGCTT CCTGATATAA
176701 TGAGTATTTT GAATGAAAAA CTCTTAGAGA TCAACAGACA CTAAAGAGAC TTTTCCCTAG
176761 GTACATAAAA ATAGGATGGC CCCACCAGCG AGAACAATTG TTCTTTTCTC CCTCTCTGTT
176821 ATCTCATTGT GCATTATAGG AAAGACCAAG AATGTAACCA CACCTGAACA GACCCTTTTA
176881 TAAGATAATC AGTCTCTAAG CATCATTTAA ATTCCAAGGA GAACTATTTA CAAATTTATC
176941 TGTTCTTTGA TCCAATTAGT CTCTCCTGGT AGTTACATAT TGCCCCTCAA CAGAATTCCT
177001 CTTCTTCTGT TTCCCATAAC CTATTTTGCA AGGATCAAGC CCCTGTTATT TCTTCAACTT
177061 CAAGGTGGCA TATAAGCTTC TAAATTCCAC TGGGATATTG GTACTATGTG CATGAGGAGA
177121 ACCACAGAGT AATTAAATTG TAAAGCCTTT TATCTTATGA ATCTGCCTTT TTTTGTGTTC
177181 ATTTTTCAGC AAAACTTCCA AGGGCAAAGG TATAAAACAA AAATAAAATT CTAAAGCCCC
177241 CCAACCATCT GAATAGACTT TCTCTTCAGT CAGGCTTCTT AAAATGTAAC CTGAAAGACT
177301 GGCTCAGGCC ATTAAGGGAA GTGGGGGTTG AACATGCCTC ATTATTCCTC TCTGGCATTA
177361 ACATCAACAC AGCTTTTAAG TCTGATAAGA AACATTTTAC AACCTATTCT CTCTGAAGCC
177421 TGCTAGCTAA AAACTTCATC CCATAGTACA ACTTTGGTCT TCACAACCTG TTATCACAAC
177481 CTAGTGCTCC TTTCTATTAA TCCCAAATCT TTATACAAAC TCAACCAATT GTCATCACCT
177541 CCACCCCACT CCTCCGCTGC TTCCAGTTGT CCCGCCTCTC TGGACCAAAC CAGTGTACAT
177601 TTCTTAAACG TATTTGATTG ATGTCCCATG CCTCCCTAAA ATGTATAAAG CCAAGGTGCA
177661 TCCCAACCAC CTTGAGCGCT TGTTCTCAGG ACCTCCTGAG GGCTGTGTCA TGGGCCATGG
177721 TCACTCAAAT TTGGCTCAGA ATAAATCTCT TCAAATGTTT TACAGAGTTT GGCTCTTGTC
177781 ATGACACAGA TGACTGCTTC ACTGAAGCCT GCTCTGGAAG TGAGTGGGGG TTTTGCAAGG
177841 ATAATTTTCC CCGGATAGCC CCAGAAGCAG CTAGTAATAA TACACTTAAA GGTAGCTAAA
177901 ATGCATTGAA CACTTGTTTT GTGCCAGACC TATGTCAACA TTTGCTTTGT GCCAGGCTTA
177961 TGCCAGTACT CCTGATTTGT TAATACATTC TAAATAAAAA TTCTGGAGTT TCAAATATAA
178021 TAACTGAAAA ACAGAAAATA AATAAAAATA TATAATAACT GAAATAAAAA TTTACTAAGG
```

Figure 1 (Page 55 of 73)

```
178081 CTGGGGATGG TGGCTCACTC ACACCTGTAA TCCTGTTACC GGAAAGGGGT CCGTCCAGAT
178141 CCAGACCCCA AGAGAGGGTT CTTGGATCTC ACACAAGAAA GAATTCGGGC GAGTCTGTAA
178201 AGTGAAAGCA AGTTTATTAA GAAAGTAGAG GAATAAAAGA ACGGCTACTC CATAGGCAGA
178261 GCAGCTCTGA GGGCTGCTGG TCGCTCATTT TTATGGTTAT TTCTTGATTA TGTGCTAAAC
178321 AAGGGGTGGA TAATTCATGC CTCCATTTTT TAGACCATAT AAAGTAACTT CCTGACGTTG
178381 CCATGGCATT CGTAAACTGT CGTGGCGCTG GTATGAGCAT AGCAGTGAGG ACGACCAGAG
178441 GTCACTCTCA TCGCCATCTT GGATTTGGTG GGGAGCAGTG AGGATGACCA GAGGTCACTC
178501 TCATCGCCAT CTTGGATTTG GTGGGGTTTA GCCAGCTTCT TTACTTTTTT CTTTTTTTTT
178561 TTTGCCCAGG CTGGAGTGCA GTGGCACGAT CTCAGCTCAC TGAAACCTCC AATTTCTGAG
178621 TTCAAGCGAT TCTCGTGCCT CAGCCTCCCA AGTAGCTGGG ATTACAGGCA TGTGCCACCA
178681 CACCCAGCTA ATTTTTTATA TTTTTAATAG AGACCGGGTT TCGCCATGTT GCCTACGCTG
178741 ATCTCCAACT CCTGCGCTCA AGCCATCCAG CCACCTTAGC CTCCCAAAGT GCTGGGCTTA
178801 TAGGTGTGAG CCACCCCACC TGGCCTAGCC GGCTTCTTTA CTGCAACCTG TTTTATCAGC
178861 AAGGTCTTTA TGACCTGTAT TTTGTGCCCA CTGCCTGCCT CATCCTGTGG CTTACAATGC
178921 CTAACTTACA GGGAATGCAG CCCAGCAGGA CTCAGCCTTA TTTCACCCAG CTCCTATTCA
178981 AGATGGAGTC TTTCTTGTTC AAATACCTCT GACAAGCCCA ACACTTTGGG AGGATGACAC
179041 AGGAGGATTG CTTTAGCCTA GGAGCTCAAG ACCAGCCTGG GCAACACAGT GAGACCCCAT
179101 CTCTAAAAAA AAAAATACAA AAAATTAGC CAGGCATGAT GGTGTGTGCC TGTAGTCCCT
179161 GCTACTCAGG AGGCTGAAGT GGGAAGATGG CTTCAGCCCA GGAATTCAAG GCTGCATTGT
179221 CAGAGGCATT TGAACCAGAA TGACTCTATC TTGAATAGGC GCTGGATAAA ATAAGGCTGA
179281 CACCTGCTAG GCTGCATTTC CAGTATGTTA GGCATTCTTA GTCACAGGAT GAGATAGGAA
179341 GTCAGCACAA GGTACACATC ACAAAGACCT TGCTGATAAA ATAGGTTGTG GTAAAGAAGT
179401 TGGCCAAAAC CCATCAAAAC CAACATGGCC ACCAAAGGGA CCTCTGGTTG TCTTCACTGC
179461 TCATTATATG TTAATTATAA TGTATTAACA TGCTAAAAGA CACTCCTACC AGCATCATGA
179521 CAGCTTACAA ATACTGCGGC AATATCTGGA CTTTACCTTA TATGGTCTAA AAGGTGGAGG
179581 AACCCTCAAT TTTGGGAATT GTCCACCCCT TTTTTGGAAT GCTCATGAAT AATCCACCCC
179641 TTGTTTAGCA CATAATCCAG AAATAACTAT AAGTATGCTT ATTTGAGCAG ACCACGCTGC
179701 TGTTCTGCCT ACAGAGTAGC CATTCTTTTA TTTCCTTACT TTCTTAATAA ACCTGCTTTC
179761 ACTTTACTGT ATGGACTTGC CCTAAATTCT TTCTTGTGTG AGATCCAAGA ACCCTCTCTT
179821 GGGGTCTGGA TCAAGACCCC TTTCTGGTAA CATCTTTCTG GTGACCACGA AGGGACAATA
179881 CTGAGGAGAC TCTGAAGCCA AGGAAACAG ACTACAGCAC CAACTGGCTG ACTTTGGGTA
179941 AGTGGTGGAG TCCCCGGGTA AAGGATAGGA TTGGGTTAGA GGTGCAACTT AGGGGAGATA
180001 GGGTCTCTCC TAAGACAGAG AGGGTTTCAG TCCGCTCTTA ATAAAGGGCA AGAATGCTTG
180061 ACCGAACTTG GGTTTGAGAC CCAACTTAGG AAGGCTACAG TCCTTAAGAT TTAAGGGGTT
180121 AGAGGCCCCT CTCAGTAAAG TCTCTCTTGG TTAAAAACGG ATTTAGCATT AGGGGATGTT
180181 AACTGCTATT CTGTTTGTAT TAATCTTCCC TGTGCTCTTT GCTGACAGCT ATGGGTGACA
180241 GGATTAGGCA TGTACAGGAT CACGGGACAT TGGGAACTTT TCTTCTCTCC AAAAGGGGAA
180301 GCTTGACAGC TGATAGGACT GTTGGAAAAG ATCCCTTTGC TATGACAAGC AGCCGCCTGA
180361 ACTTTTGATT CAGTGTTGCT GCAATGGGTG GGTCTTTCTC TGGCCTCTGT GAACTCCTCA
180421 CCTTCCCCAT CTCACCACAG GCAATGCTTT TCTCCCTTTC TCTCTTTTCT CTTTTCTGTC
180481 TTTTCTGTTA CTTGAGACAA CCATCTTGCC CAGAGACCAT ATGTTGAAAC TCCTGGTCAG
180541 AAGTTTGATT AAAGATGAAA GGGCCTATCT GGGGGCAAGT TTGAGCCTTC CCAGTTAGAT
180601 ATTGGGTGCT AAGTGGAGTG GCCAATGTCT ATGTTTTGTC ACATGTATAT TGCTCTGGCT
180661 GAAATGGAAA ACGTTAATTT GGTTACTTTA TGTGGCCATT GGGCAGCATC TTACAAAAGT
180721 GAGAGACATT TATTTGCCTG TGGTTCCATG AAACAGAAAA AAGTTGGTTT TCTTTTGTGT
180781 CGTAGCTTGG ACCCAAGGGC TTTGCAGTGA GCAAGGTTGC TAGTGCTGCT CAGTGAAAGA
180841 GAACCCAGAA ACCTGGCATG CCAGCAAAAG GGTAAAGATT TCTTACCAGT CAGGCTTCTG
180901 GCCTCTCTCT CTTAGTGAAA ACTGAATGAA TGGTAAAAAT CACTGTTTAT CACCTCTGTA
180961 AAGTTTTGAT TAATGGGAAC AAGGATTTGT GGGGCTAGTC TTAAGCTGTA ATGAATCTGG
181021 TATACTTTGT GATATCAATT TGTCTTTCTG TATTACTCTG TCATAAAGAG GAATATGGTA
181081 GGATAGAACA TGGGCTCAGG ACTCCATAAG CCTGCTGTTC AAGCCAGCCC AGTAAACTGG
181141 TCCGTTGCAA AGTTTATTAC AGGTCCCTGG AAAAAAAAAA AAATAAAAAC TGGATGAAGT
181201 TTCCTTCTCA TCTTGTTTTA TGTCCTTTGG AGCTTCACCT TGTAACCACG TGGCGGTACT
181261 TTCTCTTGGT CTCTGCCATC CAGGGAACAG GAATTTGGG GTTTATGTAA TAGTTAACTC
```

Figure 1 (Page 56 of 73)

```
181321 TAAAAATTAT CTCAAGCCAT TGCAAGCTCA AAATTGGCTG CTCTGGACCC CTTCTGGGAA
181381 GGGCAATGGA AACTAACCAG TGTTGTAGCT CAGCAGCTAA GGATTTGTCA TTTTATAATG
181441 GCGGCCAAGG TTCAATCCTG GCTTAGGGAA TGAGTACTTT CTGATTGATA TCTGTGTGAC
181501 CTTTACCATT TGTTGATTCT GTTCTCTTCC CCTCCACACA CTGTCTTGAG TTTTCCTCTC
181561 TCTGAGAACC TGGGAGATTA TCTTTGGTAA AGTTCAAAAG CCAGAAATAA TGGCCGTGTG
181621 GGATGGCTAA AGTTGAGTAA TAAGAAACTT AAAAGGACTC CTTTTTTTTT TGCTTTAGAG
181681 TGCTATGGTT TATGGTTAAA AGCTTAATTA AAAGTGGATA TTCAATCTCT AAAAGCCTGG
181741 GACTCCTTGG GAAAAGCAGA GGAGGCACCA CAGACCCCAT TTTGGGAAAA CCTCTGTTTT
181801 CCTCATGAAA CCCCAGGAAC TGGAAGTGGA TAGATCCTTC GCAAAATCTA AGGCTCTGTT
181861 TGGCTTTGCA TTATGTTATC TGATGTTTTT GACTTTTGGG GGTATCAGAA ATTACTTTGC
181921 ATTATGAGGG AGATCTGGTG TGTAATAACC AGGTAGGAAA TATACTTCTG GGGATAGCTA
181981 AAGGCAAATA TAGGTGAATA CTTGGCTATT TGCACTTTTG GATCACAAGA AGCATTCTCT
182041 TGACTACCTA GAAGGTATGG AAATGTCTCC ATCCCCACCG AGAGATAAGA TTCCCAGGGG
182101 AGATGGCTGA TCCCCCAAAA GAGGGCTGAT TCCTCTTTT GGGATCCAGG ATCTGGTATA
182161 AAAATGGGAC CCTGGCCAGG CACAGTGGCT CACGCCTGTA ATCTCAACAC TTTGGGAAGC
182221 CTCAGAGTTA TGAATGTCTC ACCATACTGA CACTTTGTGA CTGAGCTCCT CTCTACCCTG
182281 GACACAAGAG ACCCTAATAA TTAGACAGGA ATATCATTGC CCCTATTTAG TCTGAAGAAG
182341 TTATAGAAGA CGGATCTTTA TCCCACTGCA ATCCTTAGGA TTAAGGGTTC CCTGGTAAAA
182401 GGGAGTGGGA AAATATGTCA GAGGCATTTG AATCAGAGTG ACTCCATCTT GAATAGGGGC
182461 TGGGTAAAAT AAGGCTGAGG CCTGCTGGGT TAGGTTAGGC ATTCTAACCA GGAGTTTAGT
182521 CACAGGATGA GATAGAAGGT TGCACAAGGT ACCCGTCACA AAGACCTTGC TGATAAAATA
182581 GGTAACGGTA AAGAAGCCAG CTAAAGCCCA CCAAAACCAA CATGGCCACA AAAGTGACCT
182641 CTTGTCATCC TCACTGCTCA TATACACTAA TTATACTGCA TTAGCATGCT ACAAGACACT
182701 CCCACCAGTG CCACGACAGT TTACAAATAC CATGACAACA TCTGGACGTT ACCTTATATG
182761 GTCTAAAACG GGGAAGAACC CTTAGTTCTG GAATTGTCC ACCTCTTTCC TGAAAAATTC
182821 TTGAATAATC CATTAGTTTA GCACATAATC CAGAAATAAC TATACGTCTG CTTATTTGAG
182881 CAGTCCATAC TGCTGCTCTG CCTATGGAGT AGCCATTCTT TTCTTTTATT TTTATTTTTT
182941 AGATAAAGAC TCGCTCTGTC ACTCAGGCTG GAGTCTGGAG TGCAGTGACG TGTTTTGGCT
183001 CACTGCAACC TTCACCTCCC GGGTTCAAGC AATTCTCCTG CCTCAGCCTC CCAACTAGCT
183061 GGGACCACAG GTGGGTGCCA CCATGCCTGG CTAATTTTTG TATTATTAGT AGAGATGGGG
183121 TTTCGCCATG TTGGCCAGGC TGGTCTCGAA CTCCTGGCCT CAAGCGATCC ACTTGCCTTG
183181 GCCTCCCAAA GTGCTAGGAT TACAGGCATT ACCCACTATG CATGACCCAT TCTTTTATTT
183241 CTTAACTTTT TTTTGTTTTT TTGAGACAGA GTCTCACTCT GTCACCCAGG CTAGAGGCTG
183301 GAGTGCAGTG GTGCGATCTT GGTTCACTGC AACCTCTGCC TCCTGGGTTC AAGCGATTCT
183361 TCTGCCTCAG TCTCCTGAGG AGCTGGGACT ACAGACATGT GCCACTACAC CCAGCTAATT
183421 TTGTATTTTT AGTAGAGACA GTGTCTTGCC ATGTTTGTCA GGCTTGTCTC GAACTCCTAA
183481 CCTCAAGTGG TCTGCCTGCC TCAGCCTCCC AAAGTGCTGT GATTACAGGC ATAAATCACT
183541 GCGCTCGGCC CTTCTTTACT TTCTTAATAA ACTTGTTTTC ACTTTACTGT ATGGACTAGC
183601 CCCAAATTCC TTCTTGTGTG AGATCCAATA ACCCTTTTGT GTGTGAAAGA ATGTATTGCT
183661 GCTGTTCAGG CTGGAGCAAG CTGGAGCTCA TGCTGCTGCT CAGACTGGAG CATGCGTGAT
183721 CTGTGATCCC AGTAAGAGGA TCATGGTCAC TCCAGCCTGA ACGACAGCAT GATATCTCAT
183781 CTGTAAGAAA AAAAAATTAC TAGAGGGCTT TAACAGCAAA TTTGAGCAGC AAAAAGAAGT
183841 AATCAGTGAA CTCAAAGATA GGTCAATTGA AATGATCTAC TCTGAAAAAC AGAAAGAAGA
183901 CAGAATGAAG AAAAAGAAAT AGAGCCTTAG AGACAGGGGA TACCATCAAG CATACTAATA
183961 TATGCATAAT GGGACTCCTA GAAGGAGAAA AGTGAGAGGA CAGGGAGAGA GAATGTTTGG
184021 AGAAATAATT TCTCAAAGCT TCCCATGTTT GGCAAAAAAG CATTAACTTG CATACATATT
184081 TTAGGAGCTC AATGAATTCC AAGTAGGATA CACTCAAAGA GATCCATACC TAGACACATC
184141 ATAATCAGAT TATCAAAAGA TGAAGAAGAT GAATCTTGAG AGCAGAAAGA AAGGAACAAT
184201 TCATCACATA CAAATAGTAC TCAAAGATG TCTGGAGTAG GTATACTAAT ATCAGACAAA
184261 ATAAACTTTA AGATAAGCAT TGTTATAATA AATAAAGAAA GGTATTTTGT AATGATAAAA
184321 GTGTCAATTC ATCAAGAAAA CATAACATTA TAAACATACA TGCACCTAAC AACAGAGCCC
184381 TAATATTCAT GAAACAAAAC TGACAGAATT GAAGGGAGAA ATAGAAAATT CGACAATAAT
184441 AGTTGGAGAC ATCAATACCT CACTAGTTAG ACAAGATCAA CAAAAAAATA GAAGACTTAA
184501 CACTTGAAAA CACCTAACCT GACCCTAACA TAAATCTATA GGTCACTACA CCCCAAAACA
```

```
184561 GCAGAATAAA CATCCTTCTG AAGCTCACAT GAAACATTTT TCAGGATAGA CTGTATATTA
184621 CTTCATGAAA TAAGTCTCAA TAAATGTAAA AGGACTATAA TAATAGAGTA TATATTCTCT
184681 GACCAAAGTG GAATGAAGAT AGAAATCAAT AACTAGGCTG GGCGTGATGG CTCACGCCTG
184741 TAATCCCAGC ACTTTGGGAG GCCAAGGCGG ACAGATCACG AGGTCAGGAG TTTGAGACCA
184801 GCCTGACCAA CATGGTGAAA CCCTGTCTCT ACTAACAAAA TACAAAAATT AGCCAGGCCT
184861 GGTGGCATCT GCCTGTAGTC CCAGCTACTC GGGACACTGA GGCAGGAGAA TCACTTGAAC
184921 CCAGGAGGCA GAGATTGCAG TGAGCTGAGA TCGCGCCACT GCATTCCAGC CTGGGAGACA
184981 GAGCGAGACT CCGTCTCAAA ATTAAAAAAA AAAAAGAAAC TAGAAAAATA AGAACAAATC
185041 AAACCCAAAG CAAGCAAGAG GAAAATGAAA AATTTCAAAG CAGCCAAGAA CAAAAGGCAC
185101 ATTATGTACA GAAGAACAAG TGTATAGATC ACATATTTCT CATAGACACA ATATAAGCAA
185161 AAAGACAGTG GAGCAAAATT TTTTAGATTA ATGAAAGACC TACAATTCTG TACCAAGCAA
185221 AAAAACTCCC CCCAAATGAG GGTGAAATAA GACAATTTAA TACAGAGAAA AGAGGAAGGA
185281 ATTTATCTAG TCATATGTGA GAGTTTTATG ATACATTTTG TACTGTATAT GTGGATGTTT
185341 TCTATTTCAT TTAAAAAATC AACCGTGCAA TTAAATGGTA GATTGTCTTG CTTCTTTTTG
185401 ATTGACACAG TCATTAACTA AAATATTGTA GTATTTTTTT ATCTCCCTGC CTAAAGGCAA
185461 TAAACATCTA ATCAGCAGAC TAGAACAATA AAAAATATTT TTTAAAAGTC CTTTAGGCAG
185521 AATGATAAAA GTCCCTTAGG CATATTGAAA TTCCTATTTA TACAAAGGAA TAAACAGTAC
185581 TAGAAATTGT AACTATGTGA GTAAACAGAT AATATTTTTT CTCCATAAAA TGTGGTTGAC
185641 TATTTTCACA AAAATAGTTA ACAATGTAAT GTGTGATTTA TAGCATTTAA AAGTAAAACA
185701 GGCCGGGCAC AAAGGTTCGT GCCTGTAATC CCAGCACTTT TGGAGGCCGA GGCGTGCAGA
185761 TCACTTGAGG ACAGGAGTTC AAGACCAGCC TGGCTAACAT GGCAAAACCC CATCTCTACT
185821 AAAAATACAA AAATTAACCA GGCGTGGTGG TGCACGCCTG TAATCCCAGC TACTCTGGAG
185881 GCTGAGGCAC AAGAATCACT TGAATCCAGG AGGTGGAAGT TGCAGTGAGG CAAAATTATA
185941 CCACTGTGCT CCAGCCTAGG CAACAGAGCT AGACTCTGTC ACACACACAC ACACACACAA
186001 AAGAAAGTG TATGACAACA ACAGTGCAAA AGAAGTGGAA ATGAAAATAA TGTTATTTTA
186061 TATAAGTGGT ATACTTTTAG ATGAACTACG ATAAATTAAT GATGTATACT ATAAACTCTA
186121 AGGCAACCAC TGAAATAATG AAACGAAGAA TTATGGCTAA CAAGCCACAA AAAGAAATAA
186181 AATAGAATGA GAAAAAATAT TTAAGTTGTT CAACAGATGG GAAAAAAAAG AGGAAAAAGA
186241 GAACAAAGAA CAGATGGGAC AAATGGGAAA GTAATAGCAA GATGATAGAC TTAACTCTAC
186301 CCATATAGAT TATCACACTT AAGGTAAATG ATCTAAATAC TCTAATACAA AAGCAGAGGT
186361 TGTCAGATTG AATTAAAAAA ACAGACAACA ACAAAAAAAA GCAAAAAAAG AGCCACAACA
186421 TGCTGCCTAC AAAAAATTCA CTTTAATATA AAGACACAAA TAGTCTAGAA CACCATCACT
186481 TTTAACCTTA TTTACTCAAA CCTCCTGATC CCTATTTATT TATTTATTTA TTTATTTATT
186541 TATTTATTTA TTTATTTATT TTTGAGACAG AGTCTGACTC TGTTGCCCAG GCTGGAGTGC
186601 AGTGGCACCA TCTAGGCTCA CTGCAGCCTC TACCTCTCGG GTTCAAGCGA TTCTCCTGCC
186661 TCAGGCCTCC CAAGTAGCTG GGACTATAGG CACATGCCAC CATGCCCAGC TAATTATTAT
186721 ATTTTTAGTA GAGACGGGGT TTTGCCATGT TGGCCAGGTT GGTCTCAAAC GCCTGACCTC
186781 AGCCTCCCAA AGTGCTGGGA TTACAGGCGT GAGCCACAGC ACCCAGCTCC TCTTCATTTA
186841 TTCTTGCTAC GCTTCCTCCA ATCCATTTTG TGCATTTGAT GATTTTGCCA GTAACTTCTT
186901 TATTTTTCTG GTAAAATTAC TTATGGGTCA CTGAGGACTG GGATGTTCTT TCTTCTAGAG
186961 GGGGTTTGTG TCTGCTTTTG CCAGGAAGCT GGGGTACCAC CAGTCAAGTA TTACTTTAAA
187021 CTCAATTCAT GAATTGAGAC TTTTTTTTTT TTTTTTTTTT TTACGCAGAG TCCTACTCTG
187081 TCACCCAGGC TGGAGTGCAG CGGTGTGAAC ATGGCTCACT GCAGCCTCAA CCTACTGAGC
187141 TCAAGCAATC CTTCTGCCTC ACCATTCTGT ATAGCTAGGA CTACAGGTGT GTGCCACCAT
187201 GCCTGACTAA TTTTTTAAAT ATTTTTTTA GAGATGGGGC TCACTTGTT GCCCAGGCCA
187261 GTCTCGAGCT CCTGGGCTCA AGTGATCCTC CCACCTTGGT CTCCCAAAGT GCTGGGGTTA
187321 CAGGCATGAG CCTCTGTGGC TAGCCAAGAC TTTTTATTTT TTAGCCTAAA TGTGTATAAA
187381 AGTTGGCTTG TGGTTACAAC TTATCAGGAT TGATGATCTC TCTCTCTCTC TCTCTCTCTC
187441 TCTGTCTCTC CCCACCTCTC TCACATCCCT TGCTCTGCTG AGAAGCAGAG CAAACATTCT
187501 AGCAGTTTCC AGAGAGTAGG ATGGGATTAC TTCTAGTTTA CTTTTATCAT CCTTTGGGAT
187561 CGCAGTATTA CTGGGAGAAC ACAAGTATCT CTTATTAGAC ATACCACCTT TGTAGAATCT
187621 GGACTTTCAT TTTAGACTTT ATTTGTTTTC TACTATAAGC AATTTAAGTT ACAGATCTCT
187681 CTACACACTG TTTAAGTTGC ATCCCATGAA TTTTGATGTG CTTTATTGTC ATTATTATAT
187741 AGTACAATGT ATTTTGTAAT TTTTTGTGAT TTGTTTGGAG AGATTGATTA ATTAGAATGA
```

Figure 1 (Page 58 of 73)

```
187801 TGTTTAATTT CCAAATATGT GTGTTTTTTT CTACATTTCT TATTTTTATT GATTTCAAAT
187861 TTATTTCTAC TGTAGTCAGA TTTAATAATT CATTTATTTT TATTATTTTC ATTTTTTTAG
187921 AGACAGGGCC TTTCTGTGTT GCCCAGGTTT GTCCCAAACT CCTAGTCCCA AGCAGTTCTC
187981 CTGCCTCAGC CACCCAAAGT GCTGGGATTA TAGGCACGAG CCACCCGTGC ACAACCAACA
188041 ATTCATTTAA AAAGTGGGCA AGTGAACTGA ACAGACATTT CTCAAAAGAA GGCATACAAT
188101 TGGCCAACAA ATATATGAAA GAATGCTCAA CATCACTGTA TTAGTCTGTT TTCATGCTGC
188161 TAATAAAGAC TTAACCTGAG ACTGGGGAAT TTACAAGAGA AAGAGGTTTA ATGGACTTAC
188221 AGTTCCACAT GGCTGGAGAG ATCTCACAAT CATGGTGGAA GGCAAGGAGG AGCAAGTCAC
188281 ATCTTACATG GATGGCAGCA GGCAAAGAGA GAGCTTGTGC AGGGAAACTC CCGTTTTTAA
188341 AACCATCAGA TCTCGTGAGA CTCATTCACT ATCATAAGAA CAGCATAGGA AAGACCCGGC
188401 CCATAATTCA GTCACCTCCC ACTGGGTTCC TCCCAGGACA CATGGGAATT GTGGGAGTTA
188461 CAATTCAAGA TGAGATTTGG GTAGGGACAC AGCCAAACCA TATAAATAAC TAATCATCAG
188521 GGAAATGCAA ATCAAAACCA CAATAAGGTA TCATCTCACC CCAGTTAGAA TGGCTATTGT
188581 CAAAAAAACA AAAAATAACA AATGCTGGTG AGGATGTACA GAAGAGGGGA CTCTTATGTC
188641 CCACTGGTGG AAATGTCAAT TAGCATAGCC ATTATGCAAA ATAGTATGGA AGTGAGGTAG
188701 GTTACATAGG GTGGTCACAG CCTCCCTTGA AAGGAAACAA GAAACTTGTC AAATTGATGG
188761 AGAGAACAAA TCTCTTGACA TTACACAAAC TGCATCTGGG GCTAGTGGTT AGAATATCCT
188821 CAGTCAAGGA GGTAGAAGAG CAGGAGGGAA AATCCCTAAG TTCGTGCAAG TGCAGAAACC
188881 CACAAGCTGT GTTCTCAGGT TGACATATAC TCATTTTAAT AGTAAGAAAC ACACCCTTGG
188941 GTAGAGAATT AAAATGCTAA TAATACATGT GATGTATGTA CTAGCGTGTA TGGCAATATT
189001 GCATGCACAT TCAAGAGACC ACCCAAAACA TATTTAACAA CAATGCCCAT TCCCACCCCC
189061 TCATGGATAA TCACGTAGGA CTCCCATAAC GGGAGTTTCT TCAGTGTCAA TTGGTGCTGA
189121 AGTAGCCGAC CCTGACTCTG CTATCAGCGT GTACTTTCAC CTTGCAATAA ACTCCTTTGC
189181 CTACTTTTAC TTTGGACTGG CTTTCAAATT CTTTTGTGCA GGGAATTCAA GAATCTGAAC
189241 CAGCCTACTG ACAACAGAGG TTTCTCAGAA ACCTAAAAAT AGATCTACCA GATGAGGCTG
189301 AAAATCTGCT ACTGGCTATT TATCCAAAGG GAAGGAAATC AGTATACAAA GAGACACCTA
189361 CATCCCCATG TTTATTGCGT CACTCTTCAC AAGAGCTGAT ATATAGAGTC AACCCTAAAT
189421 GTTCATTAAC AGACAAATGG ATAGAAAATG TGGCATATAT ACACAATGAA ATACTATTTG
189481 GCCATGAGAA GAATGCAATC TTGTCATTTG TGGCAACGTA GATGAAACTG GAGAACATTA
189541 TGTTAAGTAA GATAAGCTAG GATTGGAAAG ATAAATACTA CATGTTATCA CTCATATGTG
189601 AAAGTAGAGA AAAATTTTTA GCTCATGGAT TTAGAGAACA GAACTGTGGG TACCGGAAGC
189661 TGGGAAGGGT AGCAAGGAGG GGAGGATAGG GAGAGGTTGG TTAATGGTGA CAAAATTACA
189721 GCTAGATTGT AGAAATGAGT TCCGGTGTTC TGCACCATTG TAGGGTGCAT ATGGTTAACT
189781 CTCATTTATT GTATATTTTC AAAAAGCTAG AAAAGAATTT TGAATACTCA CAACAAAATA
189841 AATGATAAAT GTTTAAGGTG ATGGATATAC TAATTACTCT GATTTGATTA TTACACATTG
189901 TGTACACATA TAAAAATATC ACTCTTTATC CCGTATATAT GTACAGTTAT TATATGTCAA
189961 CTAAAAATAA AAGAAAAAAA GAATATGATC TATCATGATG TATATATCAT GTGTACTTGA
190021 GCAAAATGTG CATGCAGATA TTGTGTATAA TGTTCTATAA ATCAATTAGC TCAAGATAAT
190081 AGATAGGATT GTTCAGATCT TCTGTGTCTT TACTGATATT TTGTCTAGTT ATTGCATCAT
190141 TACCAAAAAA AGGGTGTTAA ACTCTCCAAA TGTGATTGTA GAATTGTCTA TTTTGTCTTT
190201 TCTTTTCCAT TTTTACTTTA TGTATTTTGA AACTCTGTTA TGACATTTTG CTATGTATTT
190261 TAAAACTTCG TTATGTATTT TGAAACTCTG TTGTTAGAAT CATACATTTA TGATTATTAT
190321 GTTTCTTGA TGAAATGACA CTTTTCTATT GTCATTGTTT TTGTTTTTTC TGAAATGGAG
190381 TCTCACTCTG TTGCCCAGGC TGGAGTACAG TGGCACAATC TTGGTTCACT GCAACCTCCA
190441 CCTCCTGGGT TCAAGCGAGT CTCCTGACTC AGCCTCCAAG TAGCTGGGAT TACAGGCATG
190501 TGCCAGCATG CCAAACTAAT TTTGTATTTT TATTAGAGAC AGAGTTTCAC CACGTTGGCC
190561 AGGCTGGTCT CGAACCTCTG ACCTCAGGTG ATCCGCCCAC CTCGGCATTT TTATTTTATT
190621 TTATTTTTTT GAGACAGAGT CTCACTCTGT CACCCAGGGT AGAATGCGGT GGTGTGATCT
190681 TGGCTCACTG CAACCTCCGC CTCCTGGGTT CAAGCAATTC CCATGCCTCA GCCTCCCGAG
190741 TAGCTGGGAT TACAGGCACA TACCACCATG ACTGGCTAAT TTTTGTATTT TTAGTAGAGA
190801 TGGGGTTTTT CTATGTTGGC CAGGCTGGCA ACTGACTCCT TAACAATAC AAAAATATCAC
190861 TCTGTCTCTG GTAACACTCT CTGTCTTAAA CTCTATTTTA GCTGTTATTA TTATAGCCAT
190921 TTAGTCTTTT TTATGCTTTC TGTTTGCATA GTGTATATAT TTTAATATGT TTATTCTCAA
190981 GTTATCTGTG TTTTTATATT TAAGATGTTT CTCTTCTAGC CAACGTGTTT GGTTCTTGCA
```

Figure 1 (Page 59 of 73)

```
191041 TTTTTAAGTC GATTCTAACA ATCTTTGCCT TTCAATTGAA ATATTTACAC CATTAACATC
191101 TAACATTAAC ATTTATTTTT CTTTCCACAG TACACTGGCT AGCATCTCCC ATATAATATT
191161 GAACATAAAG TGTGATAACT GACATCCTTA TTTCATTCCT ACTCTGAGTG GAAAGGGCAG
191221 GGGTGGAGAA AGCATTCAAC AATTTGCCAT AATTATAATG CTTTTTGTTA CACTGTTTTC
191281 TTCTGCATTA AAAAATATCA TTACATTTTG CATGAATTAT TAGGAGAAAA TATTTTCCAA
191341 TTTTCCTGGA AAATGCCATA ACCACGTCTC TCAATTTTGT TTCCATCTTT CTTCCACATT
191401 TTACATAACC TACATAAGAG ACACATTATC AAGTATATTT TACATGGCTT CTCAGTGTCT
191461 TCTCTGTCTG CTAACAGGTT TACCAAGAGA TGGCACTCTT GTATTTCTGG TGGCTATGTC
191521 CATATCGTTT TGCCTTTAAG ACAGCGTAAC TACTTCTTTC ACCAGTATTA AAGACATGTA
191581 CATTTGATCT GGTTCTTGTG GATGATTTTA AATGACTCAA GCTAATAATC CTAATTTTAC
191641 CTAAACACTC CATTATTTTA AAATGTATTC CTTTATGCCC ACAATAAACA TTTATTGACA
191701 TTAGGCTGGA CATTAGGCTT CTCTATGGCA GACATTAGGC TGGACCCTAG CCATATATCT
191761 ATTGAGGGAA AAAAATTAT TTTCTATATA AGTTTCCAGA AAGCCAAGAT GTGTTTTAAA
191821 AACAAAACAA AACATTACAT TCTAAATGCT GTAACAAGAT AAGAAAAAGT GTTGAGGCTG
191881 AGAGAAGAAC AAAGCAGCAA GCAACTCCTG GAAGGACCAC TGCTGCAGAG GTAATAACTG
191941 GTGAACCATG TTTTGGAGAA GGAAAAGGTC ACCAAGAGAA GGAGGGGGTC CAGGGTGTTC
192001 AGAAAGATTG CATGCATAAA GATCAAGGGT AATAAAAAAA ATTCCGTATT ATGTAAATGT
192061 GAAGTTCCAG GACCATGAGC TTGGAGAGCA TGAAGTACAG GAGGAGGGTT GGTTTCAAAT
192121 AAATCTGGGA ATGAAACAGT GAAGCCTCTG GCAGAACTCA CATCTCTTTC CTCCCCTCTT
192181 CCTTGCACAT TCCCTTTATG GAGTAATTGC AGGGATGGGA AAAGTTCAAA ACCACCACTG
192241 AGCCTAGGAA GTGCTAGGGT AAAGTGGAGA ATGAACCTGC GTGATTTGCT CATCCTAAAC
192301 TAGGTTCTTC TAGGAGAGCC CTTCCCCATA AAATCTGCCC TCCTCGAAGG GGCCCAGACA
192361 GCCTAAGCTC ACCTCCCAAA GACCCCTTAC TTGCTGACTG AATCTGATTC CACCCAGACA
192421 TGGCCTAAAA CCCTTCCATA ACTCTATAGC CAAATTCAAT TTTAGACAGG CCTCATACCA
192481 ACCTTTCTTC CTCTAAGTCT GCCACCCTAG GCAATTCTCA ACATTCTCTA CACACTTTGG
192541 GGCCATAGAC GTGCTACCAA GTCCAGAC CTAGACCTGA TGGAGCAGTG CTGTAATGAG
192601 ACGACCACTG GCCTTTGAAC CAGACCCTTC TCTGTGGCTC CTATGCATCT CCAACCTGTT
192661 TTGAGCACTG CTGCCAAGAC ATCTTTGGCA CTTTGTTGTG AAGTTTTAAA ACTGAACTAA
192721 TCTACAAAAC ACCTAACCTT TAAAAATTCA TTGTCATTTC ATATCATGAA AGATAAAGAA
192781 AGGCCAGGAA ACTGTTCCAG GTTAATAGAG ACTAAAGAGA TAGCAACCAA ATGCAATTTG
192841 TGATCCTGGA TTGAGGGGAA AAAGTGTTGT CAGAGACATG ATTGGGACAG CTGGTAAAAT
192901 TTGAATTTGA ATTTAAAGAT AAAGTATTGA GTAATATAGG AAGATGATTA TCTGCAACTT
192961 TCAAATGTTT CAGTAAGTAT ATATATATAT AAAGAGATAT AAAGACATAT AAATAAATGG
193021 ATAGGTAGAG AAAAAGCAAA TGTATAATAT TAACAATCTA GGTAAAAAGT ATATGAGTGT
193081 TCTTTGTACT GTTTTTCTGA TTTTTCTATA TGTTTGAAAT CATTTTAAAA TAAGAAGGTT
193141 TTTGGGTTTT TTTTGTTTGT TTTTTGTTTT TAGAGACAGC ATCTTATTCT GTCACCAGGC
193201 TGTAGCTCAG TGGCCCAATC ATTGCTCACT GCAGCCTCAA CTTCCTGGGC TCCAGTAATT
193261 CCCCCTACCT CAGGCTCATG AGTAGCTGGT ACTTCAGGTG TGCACCACTG CACTCAGCTA
193321 ATTTTTATTT TTTAAATTTT TGTAGAGATG GCATGTTGCT ATGTCACCCA GGCTAGTCTC
193381 AAACTCCTGC CCCCAAGTGA TCCTCCCACT TTGGCCTCCC AAAGTGCTAG AATTATAGGC
193441 ATGAGCCACT GCACCCAGCC CCAAATAAAA AAGTATTTTA TTTTAATTAA CTAATTAACT
193501 TTGAGTCAGA GTTTCACCCT TGTCACCCAG GCTGGAGTGC AATGGCATGA TGTTGGCTCA
193561 CTGCAAACTC TGCCTCCTGT GTTTAAGCGA TTCTCTTGCC TCAGACTCCT GAGTAGCTGA
193621 GATTACAGGT GCCTGCCACC ATGCCCAGCT AATTTTTATA TTTTTAGTAG AGACGGGGTT
193681 TCAGCATGTT GGTCAAGCTT GTCTCAAACT CCTGACCTCA GGTGATCCAC CCACCTCCGC
193741 CTCCGAAAGT GTTGATGAGC CACCACACCC GGTCTAAAAA GTATTTAAA ACCACAGTCC
193801 CACTCTACCT TGTCCTACAC TACCAGGGGC TAGGATCACC CCATGTCTTC TAGGCTATGA
193861 GATAGAGGAA TCCAAGGAAG AAGATAAGCT ACTTGGTTCC TCTATAGGGT CTTGTGTGTG
193921 CTCTCATGTG CTCTCTCTCT CTCTCTCTCT CTCACACACA CACACACACA CACACACACA
193981 CACATGAATA CCAGAGCTAT CACTTTCCCA GTCTAGTACT CATCTCATCC CAAGGGTTTT
194041 GTGTTGTAGT GGTTTGCTCA TTTCTTTGTT TTGTTTGTTT GCTTGGATTA TTCTTTTTCT
194101 CTTTTTGCAG CTGAAGGGAG AATTTCCAGG CCAGCCCTTT GGCCATTAGA GTTACAGTGC
194161 CTCTATTCAG GCTTCATAGA GAGACCTGGG ATTCAGTAGT GGGGGGCTTT TATCCAGTTC
194221 AAAATAATGC ATTCTCACCA AGATGTACTT TGAAATAAAA CAATACTAAA ACACAAAATT
```

```
194281 TTATTTATGC TGAACATTGA ATCACTTTTT TCTGTATTTT GTGTAGAAAG TTATACACAC
194341 ACAAACACAT TTGCTCCTGC TTTGTTTATT GGCCCAGGGG TATGTTTGGT AATACTTCAT
194401 CAGGCATGAG TAGTACGTCT TGGAAGGTGT GGTCTAAAGC CTAGACTCCT ATCTGCTTCC
194461 TTCAGCATTC TCCAGTGTAT CTGTCATCTG TCTACCTTAG GATAGGGGTC TCCAGAACTT
194521 CCATTCACAT TTAGAAGAGG GCAGCGGCTT TCTATGGAAA ATATGAACTC TCATTCATCT
194581 CTATTCCTTC TTCTAGCTAT GGTCCAGCTC AGCTGTTTGG AATAAAGTAT CTATATGAAG
194641 TCTGCGAATG GTTCTCAGAC TGGTTGAACA TTAGAATCAC CTGAGTACCT TCTAAAATTC
194701 TTATTACCCA GGGCATATCT CAGAATGAGT ACCGCAGGGT AGGGATAGGA TTAGGGATCA
194761 TGATCTCTGG AGTCTGGTTT AGGCACTAGT GCTGTTTAAA ACTACGTTCA TGAGGTGGAG
194821 GTTGCAGTGA GCCGAGATGG CGCCACTGCA CTCCAACCTG GGCGACAGAG TGAGAGTCTG
194881 TCTCAACAAA ACAAAACAAA AAAAACCAAC TACCCTTGTG ATTTGAATGT CCATCCAAAA
194941 TTGAGAACCA TTAGGTAAGG CCAAGCTGTA TAATTAAAGA GCAGTTTTCA TTTGTCTGGT
195001 GTGGTGGCAG CTTTTTGATA AGGGAAGTAT TGTTGCCATC CACATACCTG AGCCTCACTC
195061 CTGAGAACAC TGGTGTGTAT GTTGCTAAAA TTCCCCAGGT GATTCTGAGG TTCCTTCCTG
195121 GATAAAAACC ACTGACCCTG GAATGTACC CACTGCCAAT CTCCTGCGTA AACCTTGGAT
195181 ACTGGGAAGC CTACAGTTGA AAATATTGGG CTTGAGATCC TGAAACAAAT CTTGTATTTC
195241 ATTAAGACTA ATATTTGGTA CAGTGCAGCA AATCAAGGGA ATTTTGGTGG CTGAGTTCTT
195301 TTAGAACTTT TGCATTGAAA TAGGTTCAAG CAGCAATAAG TTAAAACTAC AACCTCAGCT
195361 AAAGGATTAA AAGACACGTG AGCTGGGTAG GATGAGGTCT AAGGTTGGGT GTGGCGGCTC
195421 ATACCTGTAA TCCCAGCACT TTGGGAGACT GAGGTGGGTG GATCACTTGA GGTCAGGAGT
195481 TCAAACCAG CCTGGCCAAC ATGGTGAAAA CCCATCTCTA CTAAGAATAC AAAAAAATTA
195541 GCTGGGCGAG GTGCCAGGCA CCTGTAATCC CAGCTACTGG GGAGGCTGAG GGAGGACAAT
195601 CACTTGAACT CAGGAGGCAG AGGTTGTAGT GAGCTGAGAT CGCACCACTG CACTCCAGCC
195661 TGGGTGACAG AGCAAGACTC CATTTAAAAA AAAAATAATA ATAATAACAA TAATAATAAT
195721 TCAGACATAT CCAGGCATCA AACAGATACC TGGGGCAGAT GAATAGTCTT GAGATTCAAG
195781 TCACACATGA AATTTAGGTG GAAAATGACA TTGGAGAAAT TTGAGATTAT GATGAATGGA
195841 AATTTTTCAA AGAGGAATTT CAGGCTCTGT TCTTGAGGGG ATAGATGGAC TTCCAACAGC
195901 AATAACACAG GATTAATGAG GACTTGGGAT GTTACATAAA TTAGAGATGT TAGATGGATA
195961 AAGAGATAAA AGTACTCTCT CTAAGAACAT GGGACCAGAG ATAGGCTCAC TTCTAACCAT
196021 CAGATATAAC TAGCAGACTA AACGGTCTAA AAATAAAAAT CATGCCCCAC TCCTGCTTAA
196081 GACATTTTAA TTACTCTCAG TAACTCTTCA GTTTTTCTAC TGTGTTATCT TTAACTACAG
196141 GGTTGGTCTG GGTGTGCAAC ACAAGAAAGC CTGGCATATA CATGGATTCA AGTGTATGCC
196201 ATGTGCAGGT ATTCTTTCAT GTACTATTTC ATGTATTCTT TTTCACATCT GTTTTTTCCT
196261 TCATTGAAGT CAATGGCTGA TATTAGATTC TACTATTCAT GTGTACTAGT TATATATAAT
196321 TGTTACAAAA CAAATTAGCA AAAACTTAGT GGCTTAAAGC AACACACATT TATTATTACC
196381 TAAGGTCTGT GGATAGAAGT TCTGACATGG CTTAACTGGG TTCCCTGCTT CAAGCCTCAT
196441 GTGGCTGCAA TCCAGGTGTT GGCTGAGTCT GAATTCTCAT CAGAGGCTTG ATTGTGGAAA
196501 TTTCCACTTC CAAGCTCCCT CAGGTTTGTT GAAAAATTCA GTTCTTTGCA CCGGTAGAAG
196561 CTTCTTGGTA GAGGCTGATT CAACTTCTAG AGGCTGTCTG CAGTTCCTGT CACCCAGGGT
196621 GGAGTGCAGT GGAGCAATCA TAGCTCACTG CAGCCTTGAC CTCCCAGAAT CAATCTGTTC
196681 TCCACCTCA GCATCCTGAG TAGCTGGGAC CACAAGTGTG TGCCATCACA CCTGCCTAAA
196741 AAACAAACAA ACGAAAAAAA ACCCCAGAG AACTTGTAG AGACAAGCTG GTCTGGAACT
196801 CCTGCGCTCA AGCAATTCTC CTGCCTTAGC CTAAAAGTTC TGGGATTATA GGTATAAGCC
196861 ACCATACCTG GCATATGGCA AGTCTTGAGC AGGACAAATA CAGATGATTT ATGTCTGTCT
196921 TCCATGGTAT TCTAGGTTAT TGTTGAGATG GTCCTCTATT GTCTTGTTCC ATCTATTGAT
196981 TAGATAAAAC GTTGTTCCTT CTGTTATTTT TCAACAGTAG CTTTTATGTG TCTCTCTTTA
197041 TCTTAAAATT CTAACCAAAG AGCTGCTCTT TTCTTGGTGT ACTTTACCTT TGGTTGATCC
197101 TTCTTAACCT CTTCTTGCCC TCTGGGGCCT AAGATGAGGG CTGTTATCAG ATGTGAGTCT
197161 ATGGGAAAGC AAGCAAGAGG TTCTTCAGCC TCCGTTCAGC CTTAAATGTC TAGGTAGAAA
197221 TCAGTCATGG CCCTTCCAAT GTGGTACAGA CCAGATCACA GAGACAGGGG TCTCAGCCAA
197281 GGTCTTGTGG CCTAAGCCTT ATAGAAATAA TGAGTGTTTA CTTACTTGGA GAACTCCCTT
197341 GGAATATCTT TTTTTGTGAA CCTGAGGCAA CTTTTGGTGA TTTCTTGATG TCTTGGGAAT
197401 CTTGGTCTAG AGCCATTTCA ACCCGATTTC TTTTCATGTC AGTGGCATTT TGTGACCAGA
197461 TAGTAAATAA GTTCTATGAT GTTCACTCAG AGAAATACAA TGACTTATGA TGCGAAGCTT
```

Figure 1 (Page 61 of 73)

```
197521 CTGTGGTTCA GCCCTTACTT CATCTTCATT CCCTCTTATC TGCATCTGTC TCCTGCTTGG
197581 GAACAAAAGT CTGGCTTCAT TCTATGACCC CCACGTTGAG TTTCTTAGTA GCACTTACTT
197641 TTCAATTAGG AGTGTCCTCA CTTCTATCCG TCAGACATAA CTAGCCGACT AAACAGTCTA
197701 AATATAAAAA TCATGTCCTA CTCCTGCTGA AAACATTTTA ATTACTCCCC ATCATTTAAT
197761 TTTTTCTACT GGGTTATCTT TAACTTCAGA GTTGGTCTTG TGTGCAACAC AAGAAAACCT
197821 GGCATATACA TGGATTCAAG TGTATGCCAC GTGCATGTAT TCCTTCATGT ACTATTTCAT
197881 GTATTCTTTT TCACATCTGT TTTTTCCTCT AAAATTTATT TCCTTTTAAA AATGAAAATT
197941 TTGCATTTGA CTAAATTTGT CAAATTTAGT CAAATTTGTT TAAAACCATT TTTAAAATGT
198001 TTCCCGAAGT TTTGAGTGAA GTTAGTACTT CAGAAAAACT GTTTTGTATT TTTCCTGTGA
198061 CCTCAGTGCA CTGCTGTGCA TTTCCATTTC TGCGTCCACA CACATTTGTT TTGAGGAAAT
198121 ATAGGAACGA CAAGATAAAG TTCAAGCTCC TGGACATTGC ATAAAAGACC GTCATGACCT
198181 GGTCCTGTTG ACTTCCCTAG ATTTCCCGCT ATTTCCTAAG TTGAGATTTT TGGTTTGGAT
198241 GCTTTGTGTT TTCCTAAAAT CAAAATAGGT TTTTGCCTTT TATGATTATA CAGTAAATAA
198301 ATGCTATTTG TGTGAAACTT TAAACAATAC AAAAAAAACC TAAGGAAGAA AGTCAGATTC
198361 ATCTAAAAAT CCTTGTGGCC AGAATTAACT ACCTTAGTTA CTATTTTCTC TATCTCTCTC
198421 TCTCAATGTA TATTTGGTGT AGGTATAGGG GTGTGTGTAG TGTGTGTGTA TGTATATATC
198481 TGTTTCTATT CCTGTATGTG GATGTGCACA ACGCATCCTG CTTTGTACAC TACAGTACTA
198541 GCATTTTTCT AATGTAATTC AATATTGTTG AAAACATTTT AAAAAAGCTT GTATATATAC
198601 ACACACATAC ACATACATGC ATGTATGTAC ATATACACAT ACAGACAAAA ATGTATCCTA
198661 TGTATATTCA CACATGTATA CACACTCACA CATACATAGA GTTTTACATC CATAGTTTAT
198721 AAATGTTGCT TTTTTTTGGT CACCTTTTTG CTAAGTCTTA CACTTTTTTT TTTTTTTTT
198781 GAGACGGAGT TTTGTTGTCA TTGCCCAGGC TTAGTGCAGT AGCGCGATCT CACCTCACTG
198841 CAACCTCGAC CTCCCGGGTT CAAGCGGTTC TCCTGCCTTA GCCTCCTGAG TAGCTGGTAC
198901 TACAGGTGTG CGCCACCATG CCTGGCTAAT TTTTGTAGTT TTTTATAGA GACGAGGTTT
198961 CACCATGTTG GCCAAGCTGG TCTGGAACTC CTGACCTCAA GTGATCTGCC TGCCTCAGAT
199021 TCCCAAAGTT CTGGGATTAC AGATGTGAGC CACTGCACCC GGCCAAGTCT TACACATCTT
199081 TTTTTTACCA CTAAACTGTT TACCCAAACC TGATAACCCA AGTCAACAGC TATTATGGCT
199141 CACACAATCT TATGTAAACA AAGATACAGA TATATAGAAT TTTCTTGATT AATATTCAGA
199201 AAAAAATGGA GTCCCTTTAT ACGTCCTTAG TATCTGCTTT ACTCATTTAA AAATGTATTA
199261 CATTATATGA AAGTATTCAG GTCAAATGTT ATAGATGTGA TTCATTCTTT TTAACTGTGT
199321 TATTTTTCTG CAATGACTAT GTATCACAAA GTACTCAGTC TTCCACTGAT GAAAATTTGG
199381 GCTATTTCCA GTTTGTCTTC CATTTTTCTT TCTTCCTCTT GGATTTTCAC TCAATGTGTT
199441 TACTAATTTA GGAAGAATCA ATAGTTTTTA TGGTATTACT CTCCCATTC AAGAATATAG
199501 CATATGGTAT AGTATAGTAG AGTACTTAGT TTAATTTAGC CAGATCCTGT TTTCTGCCCT
199561 TTAATAAAAT TCTATCATTT TCTGCCTTTG AGTCACATTT TCCTTGTTCA TATAATTCTT
199621 AAAAAATGTA TAGTTTTCAT TCTAAGGGAA CATAAAAACT TCTTTCCATT TCTATTCCTG
199681 TCTAGTTAAT TCTACTATTG GGAAAAGTAA CTGTTAAAAA AAATTCTTAT CTTTCCAGTC
199741 AGTTCACCAC ATTTCCTTTA TACCTTTGTA CTTTAATCCC CAGTCATGTT GAACACTTCT
199801 TATTCCTCAC ACCAAGCCTC AACGGGTTTG CTCTTTCTGG AAGGTGCTTC CCCTGTATTA
199861 CTGACTTATT CATACCACAC ATGGAGACTG GCGCAGCCCT GTTCTGCCTG GGAAGCTTC
199921 CCCTGATACC CCCAGTTGGC AGGAGTCTTC ATTTGTTCTT TTCTAGTCAC CTGTGCAAGT
199981 TTGTATTGTT CATGTTTATC ATCCTTCATT CTAGTTGTCT GTCTCTGTGT GTGGTCTCAT
200041 TCAGTGGACT CTGAACTCTT ATGAAGTCAT GTCATGGGTC AGATCTTAAT AAATTAATAT
200101 TGTCGGAAGC TAATGTCATG TCTAGAATAC AGAAAATTTA TCAAAAAAAA ATATAGTATG
200161 TTGGCTGGGC GCAGTGGATC AAGCCCGTAA TCCCAGCACT TGGGAGGCC GAGGCAGGAG
200221 GATCACATGA GGTCAGAAAT TCAAGACCAG CCTGGCCAAA ATGGTGAAAC CTCATCTCTA
200281 CTAAAAATAC AAAAGTAGC CAGGCGTGGT GGTGCCCACC TGTAATCCCA GCTACTCAGG
200341 AGGCTGAAGC GGGAGGATCA CTTGAACCTG GGAGGCAGAG ATTGCAATGA GCTGAGATCA
200401 TGCCACTGCA CTCCAGCCTG GGCGACAGTG AGACTCCATC TCAAAATAAT AATAATAATA
200461 ATAATAATAA TAATAATAAT AATTGTATGG AATTGAACTG CTCTGATTGG AAATAGCTGT
200521 TTTTTAAAAA ATTATTATTT TTAAGTTCC TGGGTACAAG TACAGGATGT GCAGGTTTGT
200581 TACATAGGTA AACGTGTGCC ATGGTGATTT GCTGCACCTA TCAACCCATC ACCTAGGTAT
200641 TAAGTACAGC ATGCATTAGC TCTTTTACCT AATGTTCTCC CACACCCCA CCCCATCCTC
200701 CCCCAACAGG CCCCAGTGAG TGTTGTTCCC CTCCCTGTGT CCACATGTTC TCATTGTTCA
```

Figure 1 (Page 62 of 73)

```
200761 GCTCCCACTC ATAAGTGAGA ACATGAGGTG TTTGGTTTTC TGTTCCTGCC TTAGCTGTTA
200821 ATGTCAGGCC AGAGAGGCTT AAATTTTTAA GGATCTCTGG ACTTTTCTTC TACATTACTC
200881 TTGATGTTTA TAAATGTTAC AACTTCTTTA ATTTCATTTA ATGTATACCT TATTGAGTTG
200941 ATTTAACTGA GTTAACTTTG TTATATGAAA ATCATGATTG GGAGTGAGGG GGTTAAACCA
201001 GCTACAGAGA TCTTGATTGT TGGTGGTGAA GCAATGCAAG AATTCATTCA TTCAGTAAAC
201061 TAATGTTTAT TAAGCGTGTA CTGTCTTAGT CTGTTCAGAC TGCTGTAACA AAATATCATA
201121 AACTGGGTGA CTTATAAACA ACAAAAAATT TATTTCTTAC AGTTCTGGAG GTGGGAAGTC
201181 TAAGATTAAG GCCCTGGCAA ATTTAGTGTC TGGTGAGGAC AGGTAGCCAT CTTTTTGCTG
201241 AGTCCTAACA TGGCAGAAGG GTTGAATAAA CTTCCTTGGG TTTCTTTTAT AAGGACACTA
201301 ATCCTAGTGA TGAGGTTTCT GCCCTCATGG TATAACTACT GCCCAAAGAC CCCTCCTTCT
201361 AATATTATCA CTTTGTGGGT TAGGATTTCA ACATGAGTTT TGAGAGGATA CAGACATTTG
201421 GATCATAGCA CACACCATAG ACAGACACT GTGCCAAGAA TTGTGGATAT AGTGATTCTC
201481 AAAATGAACA AGATCCCCTC AGAGAGCTTG CAAAATCCAG CTATAAAATT ATGCTTTTTA
201541 AACAAATTAT GCAGTTTGAA AAATCTACTC TGAATCTTAC TTGTGGCATT GAATACTTTC
201601 GGCCACTCTT TCCTTATTAT ATTAAATATT TACTCTTGTT TGGGGATCC AGTCTCACCT
201661 ACTTTTTCTA CCAGAACTGG TATCAGCTCA TGCTCTGCCT TATGCAAATT AAGAAAATAT
201721 CATACCTTTT GGGTAAATTA AGCCAAGAAA GTTCTCCTTT CTTCTCTTTC TCTCTTTCTT
201781 TCTTTCTCTC TTTCTCTTTC TTTCTTTCTC TCTCTCTCTT TCTTTCTTTC TTTCTTTCTT
201841 TCTTTCTTTC TTTCTTTCTT TTTCTTTCTG ACAGGGTCTT GCTCTATTGC CTAGGCTGGA
201901 GTGCAGTGGT GCAATCTCAG CTCACTGCAG CCTTGAACTC CAGGGCTCAA GCAATCCTCC
201961 TGAGTAGCTG GGACTATAGG CATGTGCCAC AACATCAAGC TAATTTTTGC ATTTTTTTGT
202021 GGAGACGGGA TCTCCCTATG TTGCTAAGGC TGGTCTTGGA TTCCTGGGCT TATGCGATTC
202081 TCCTGCCTCA GCCTCCCAAA GTCCTGGGAT TACAGGCATG AGCCACTGCC CCTGGCCATT
202141 ATAACTATTT TCATTGGCTT ATCAGGCACA TGATAACTAT AATAAATCAA TAACCAGAAT
202201 TTTTAAATAA AGAAAGGAAG GAATTGTTTC AACTCTTCCT GCTACCCCTC TATCCCTCAA
202261 AAGGGTAGGC TGAATGTTGT CCTCCAAAGA TATCCATGTC CTAATCCCCA GAACCTGTAA
202321 ATATATTACC TTATATGACA AAAGGGACTT TACATGTTTA ATAAGTTAAG AATTTTGAGA
202381 TGGGCAGATT TTCCTGAATT TTGCAGATGG GCCCTAGTGT AATCACAAGG GTCCTTATAA
202441 GAGACAGGCA GAAGAGTCAG AATAAGAGAA AAATACTTCA AGATGTTACA CTGCTGGCTT
202501 TAAGGTGGAG GAAAGGCCAA GAGCCAAAAA ATGCAGTGGT CACTACAAGC TGAAAAGAAA
202561 AAGAAATGGA TTTTCCCCTA AAGCCTCTGG AGGGGGCACA ACCTTGCCAA TACCTTGATT
202621 TTGGCTCAGT GAAACCCATT TTGGACTTCT GACCTTTAGA ATTGTAAATA AATAAATAAT
202681 TTTGTGTTGT TTCAAGCCAT CACAGTTGTG GTAATTTACT ACAACAGCAA TAAAATAGAA
202741 TTAAATACAG AGATCTGAGG AGTTGAGTAG GATAAGCCTA CTCCAGCAGG TTATTTCGGG
202801 AGTATGGTGA GACTCACTAG GATGGCGGAA CTCAATTAAG GAAGTCTGAA GCTGATAAGC
202861 CAGAGAGGGA AGGCTCTCAT TTCATTTTAT AAGGGTTGCG TCACACTAGG AAGATCCAAT
202921 AGCAACCACA GTCTCAAAAT TAATGATTAC AAATAGGACA CAATTCCAAG AGTCGGGAGC
202981 CAAGCAGAAA ATGGATTAGG GAAGACATGG ATGATATGAA ACAGGAAGGA GGGGTACAAG
203041 GCAGCTTCCT GGGAAGTTGC CAGGGCAGTC ACAGTTCACA TTCATTAGGC TGTGGGCACC
203101 AAATGCATAT GGAAAATCTA GCTGACTTAA CTGAACTCCT GAAGAGGAAT GAACACCTCA
203161 TTTATTGAGG AGCTACTACC AATTAGAATA TGTATTTCAT TTGTTCAATA ACCCCATGAG
203221 TACAGTAACA CAATCCTTGC TTTACTAAAG CGGAAGCCAA TTCAAAGAGG TTCAGTGACT
203281 TGTCCAAGCT CAGGGAAAAC ACTAGGAAGT GAATATGGGT CTGACTCCAT CACTGATTTC
203341 AGGAGCCCTG CCCTTTCCTC CACACCATGC CCCCTTGCTT TCAGAAAAAA AGGCTTGTTG
203401 ACTGAATGGT TGTATGCACA GTTCAAAGCA GAAACACACG ATGACATCTT TTGAGATACT
203461 CTAACAGTGA GAACTTGAAA ATGAAGTTAA AAATTAAGCG GCAAAACCAA GCCGAGGCTT
203521 TCTGAGAAAG TGGGGCCAAA CCTGTTGCCG TCTGACTGCC ACGTGGCTCA CTATTTATCC
203581 CTGTAAAAAT CTGCAAAAGT ATTTGAAAGG GAAGAAGGGA CAGAAAACTC CCTCCTTTTC
203641 CAAGTTAGCC TTATAGTCTA GGGCTTAAAA TACTGGTTTA ATGGTGAAGG TAAGTGCTTT
203701 TCTTCTTTTT GGGTAGAAGG ATTATTACTA ACTTACCAAA GGTCCATTAA GGGGAGGGAA
203761 CAGTTTTAGG AGAAGTCAGA GAAAAGACAT TAACAGCAAC ATAAGGATCT CCATCTGGTA
203821 ATATTGCCTA ATTCCAAAAT GAAGAGACTC TCTGAAAAAG ATAACTGATT CAATGAAGAC
203881 CCTAGGGCAA GGCTTGAGAA GCCACTGGTA CCAATGGACA CTGTGGACAA TGGTCATTTC
203941 TCCAAGGACG CTGTGAGTAT TAACTGTGAT GCTGTGATTA GTCAGACTGG GATTGGCTGT
```

Figure 1 (Page 63 of 73)

```
204001 GGAATGAAAT ACTGATCAGA ACTGACAAGA TTTGTGTTTG GGACTGTGGC TAACGAGTCT
204061 TTTCAGACTT CTATATGAAT TTGAAATGGT CTCTCAGGAA AAGGAGAACA TGGCCGGGCC
204121 TGGTGGCTCA CGCCTGTAAT CCCAGCACTT TGGCAGGCTG AGGCGGGCAG ATCACTTGAG
204181 GTCAGGAGTT TGAGACCAGC CTGGCCAACA TGGTGAAACC CTGTCTCCAC TAAAAATACA
204241 AAAATTAGCA GGGCGTAGCG GCGCGTGCAC CTATGCGCAT GCATAGTGCG CGTGCCAGCT
204301 ATTCAGAAGG CTGAGGCAGG AGAATTGCTT GAACCCAGGA CGTAGAGGTT GCAGTAGTTG
204361 AGATCATACC ACTGCACTCC AGCCTAGGTG ACAGAGTAAG ACTCTGTCTC AAAAAAATAA
204421 TAATAATAAA AGAAAAGGAG AACATGACCA AAGTTATGAA TAAGACTGAA GGCAAGAAAA
204481 TTGTACGCTT GTAGAGATCA CCTAGCTTGT TGCCCTCATT GTACAGCTAA GAAAAGGCAC
204541 CCAGGGACAT TGTGGTCAGC ACCAATTTCT CAGAAAGATA GGCAGATGAT GAGAGGGCCC
204601 TCAGTTTTTC TAACACTGAA GGAATTGCTT CTATGTTTTC TGGTGAACTC CTCCCCACTC
204661 ATCTTGAGGA TTCCAGGCCA GAAGAATCCA CTTTAAAAAA GAAACATTTA AAACCAATTT
204721 AACAACCAAT CAAAGGCACT TTTATAGAAA TACATTTCAT TTGCTGTAGG CCTGTATTTA
204781 TGGATCTGAG AGGGCTAGAC TGCCAATATT GTGACTGTTT ATTATTATTG CTGTTGCTAG
204841 TATCTAGAAT ATTATACAAC ATATAACACT TTGCAATTTA CGAGGCATGT CTCATACTTT
204901 TGTTTTCACT CCAAACTGCC CAGTGAAGTA ACATTATCCC AATTCTTCCT ATGAAACAGT
204961 GAAAGCCCTA AGAGTTTTTG AAACTTTACC TGGTTTACTC AATTTGGAA TGGCAGAGCA
205021 GAATTCAGTC CTTGAATATC CTCCCACTGC AGGTTCATGC TCTTTGATCT AGGTGTAACA
205081 TTTACTCTGA GTAAACTAGG ACTCTGGGCT AACAGAGATG AAGCAAGACA GGCTGGATAT
205141 TAGGAGAATC TAAGAGCAAT CTAACGACCA TTATAATAAA ATCATGAGTT CTAGACTTAA
205201 AAAAAGGGAA AAACCTGTTT TTTTGCTTAT GCGTATACCA TAATATTTAC ATTATTTATT
205261 TTTTTCTCAA ATTCAACCTA TACTGTGTCA AGTAATTTTT TTAATATAA CATTTTCCTT
205321 TAACTTAATT TCAATTCATT TTTCTGTGTC TACTTACAAC TTTGGCACTA GAATTCACAA
205381 TTTTTTTTTA GAGGTATATC TCCTTAAAGG GAAGGGTTCT GACACTGTTA CATGTTCTCA
205441 ATTGTTTGCA AATAGGTTAA TAATTATTCC AGTGTCTCTA AGTACATATC AACCATGCCA
205501 GTGTTCAGCC TCCATAATTT TATTAGCTTC TGTGCTTATT TTGGAAAAAC ATTTCCCATT
205561 ACCATGAAAG ACCTCAGTTT AGGATGGTTT GGTATGTTAG CCTGATTTCT GCATTCGTCT
205621 CATGCAAAGG AAAATAGGAA ACGAAGAACT GAAATTACCT ATTGATACAA AATCAAAGTA
205681 GCATTTGAAA CCATAAAACT TAAGTAGGGC TTTTCATCCT TTCTCGTTAG ACAGCAACAG
205741 AGAATGGGAA GAAAAACTAA AGTGATGGGT TTGTGATACA ATTCCAGTAA CATAAAGAGC
205801 AAGGAGAAGT AGTTTTGTTG TGTTTATGTT TAATATTCAA AGCTCAACCT AAAAGTATTT
205861 TTCATTATCA AACTTCCTTC TAGAATAAAT GATTAAAACT TGATTTAAAA TATACAAATT
205921 CTCCTTTATA ATACCTCAAA ATGGAGCTAC CCCATTGAGT TTTAAGCTTG TGATTAAAAT
205981 ATTACGAAAA CAAAGGGGAA GTTGTAATAG GTAGAACAAG CAGTAGTCTA GGCATTAGGG
206041 GATCTGGTGC TGGCTCTGTG CATCATGTGG TTTCAGGCAA CTTTTCAAAT TTTCTACGCA
206101 AATTTTCTTA TCAATAAAAT AAACAGTTGG GCCAGAGGAT CTCTGAGTCT CTTTCAGCTT
206161 TCAGTGTTTA TAAGATTGGA GAAGTTGGTG GGAAAGCTTT AAGTGGAGTG TAAGTAATTG
206221 CAGCTGCATG TACAGTTAAA GAGTTGCCTT CAGCCAAGCC ACGGGATCTT GCATAAAAAG
206281 TGAAATCAAA TAGAAAATGG TCCAAACTCT GGGTTTGACC ACAGATGACT TCAGCTAGGA
206341 TCTGAGTGTA GAGCAATGAG CTGAACTCCT GATATCCAGA TGTTAGCAAG ACTTGGAGGC
206401 CTTCTAAGGC AGAGCAACAA CCAGTATCTG TCCTGGTGCT GACCTGATCT TACTAGCAAT
206461 TGGGCCTCCA TTTGGGTCCA TTGTACAAAA CAACAACAAC AACAACAATA AAATCTCCAA
206521 ACACCCAAAA TTCAAAATTT AGATGGAGAG ATACTATTCC CAGAATTCTA GAGATATTTG
206581 GAAAGCAGAA AACTATACTT GCCATGCTGA TGAAGTCCAA TTATTGCTCT TTTAAATACA
206641 TTTAGCTACT TCTGAATATA AAATGAGTAT CTACTAATTA TTTACAAAAT CACTTGGTAA
206701 ATATAGAAAG TCACAAAGAA TGAAGTGATC ATCCTGTTTT GTAACCCAGA AATAGTCATT
206761 ACTGGCACTT GTGTGAATCA GTTTCTATTC CTGTATGTGG ATGTGCACAG CGTATCCTGC
206821 TTTGTACACT AGAGTACTAG CATTTTTCTA ATGTAATTCA ATATTGTCGA AAACATTTTA
206881 AAATAGCTTC CATCACAATA ATCTATCAAA TTGACTTGCC AGACTCTCAT TATTAGGTTA
206941 ATTTATCTCT AACATTATGC AGTCATGAGT AATACTACAA AGGATATTTT TGGACACAAT
207001 TTTTCATCTA TGCCTTTCTT TATAATCCTT CATCCTAAGG TCACAGATTA TGAATATCTT
207061 TAAAGTACGG ACAAGTCTTT TAAATTTTGT GTGCAAAAAC AGTGCAAAGC CTTGAATGAT
207121 AAAATAGAGG TTTGATATAT GTGTTTTTTT GTTTGTTTGT TTTGAGACGG ATTCCTGCTC
207181 TGTCCCCCAA GCTGTAGTGC AGTGGCACGA TCTTGGCTCA CTGCAACCTT TGCCTCTTGG
```

Figure 1 (Page 64 of 73)

```
207241 GTTCAAGCAA TTATCCTGCC TCAGCCTCCT TAGTAGCAGG GTCTACAGGC ATGTGCCACC
207301 ACACCCGGCT GTTTTGTAT TTTTAGTAGA GATGGGGTTT CACCATGTTG GCCAGGATGA
207361 TCTCGAACAC CTGACCTCAA GTGATCCACC CACCTCAGTC TCCCAAAGTG CTGGGATTAC
207421 AGGTGTGAGC CACTGCACCC GGCCGATACA TGTGTTTTA AAGTCACAGA AATTTCAGAT
207481 GTCTTGAAGG ATTTTAAGCA ATTTAAAAAA TAAAGTCATA GAAGCTTCAA TTTAGGAATG
207541 AATGGAAAAT TGATGATATT CTTAGGATAT GGATTTTTCC TAAAAGAAAC AAATGTATGC
207601 ATCCCCAAAG ATAATTTGAT TAGTATACAA ATATTAAATT AAACATGTCC ATATTTAGAG
207661 CCATGAATTC TCTTTGCCTG TCACAATAGC TGGATTTATT CACAATTGTA GTAATTAGTC
207721 CCTGTTCATT ATAATTTTCT AGGTGATATG AAGACTTTGT CAGTCCAAGC AAGTGTCCAC
207781 ATTGTGTGTA GCAAACATGA GAATAAACAT TTTAAACTTT TAAATGTAAT ACATATTAGT
207841 GTTATGTAAT GTCATCCTTC ATGTTCGAAG GCACATGGAA CATTGTTCTG GTGGTACAGA
207901 GGGGAGAGAA ACACCATCAG AATGAAAGGA AAGACCGCTC TGGAACCTTC CTCCTTAGCT
207961 CTTGAGCTTA GTTAATTGT CCTGTCTTAT GGTCTGCTAC AAGCAATACC ACTCTTCACC
208021 TTCGCATGCT TCTCTGTGGT TTGATAAAGT ACATGCAATT TTTCATTTAA TTCTTCCAGC
208081 TGCACTAAGA AAGGAGCCTT ATCTTTATTG AACAGATGAG GAAATGAATG ATTAGAGAAT
208141 TTAAATGACT AGCTCTAGGT CACACAGCTG GAACTTACAG CCAGATTTCC TTTTAACAAT
208201 CCTGTAACCA AAAGCATACC AGTAGTGCCC CATAAAATGT AAGTTATAGA GCTGTGTTGG
208261 GTCAAAACTT TTACTGATGC TAAGAGGAGG CAACATTAAC AAGGGGAAAT TATTTGTGTA
208321 TTATGTTTTG GATTATGTTC TCTCCATAGA TAAAAGACTG TCGTAGTAAA AGAGATTCAG
208381 GGCACAGGGA AACTCCACCA CAAAGCGTGG TACCATTTCC CACAGAAGCT AAATGGACGG
208441 GAAGCCTGCC ACCAGGAAAG GTAAAGCCAC TGCTCTTGTT TGCAGGCTAT GTTAATAAGC
208501 TGAAGCTTAT TCCGACACAT TTACACATCT CTGCATCACA CTGACCCTTC GTAAAGATAC
208561 TCCCAGTGTA ACATTGGAGC CAGCTCCAGC CCTGATCCT GTTGCTTTTT CCTTAGCCCC
208621 ATGAAATCAT CTGTGAGAAA TTAAGCCAAA TAAGCAATAA ATCCTGGGAT CTAGGGAGTG
208681 GAATAAGTTT TGGGAAAGTC TTTTTTTTTT TTTTTTTGA CTGAGTCTTG CTCTGTCTCA
208741 CAGGCTGGAG TGCAGTGGTG CGATCTCGGC TCACTGCAAC CTCTGCCTCC GGGTTCAAG
208801 TGATTCTCCT GCCTCAGCCT CCCGAGTAGC TTGGACTACA GGCACACACC ACCATGCCCA
208861 GATGAATTTT TGTATTTTA GTAGAGATGG AGTTTCGCCG TGTTAGCCAG GATGGTCTCG
208921 ATCTCCTGAC CTCGTGATCC ACCGGCCTCG GCCTCCCAAA GTGCTGGGAT TACAGGCATG
208981 GGCCACCACG CCTGGCCCGG GAAAGTCATT TTAAACCAAC CTATGTATGA ATCCCTACTA
209041 TAATATTCTC ACCAAGCGGC TGGCTCTTTC TCCTGAGCTT GGAAACCTCC AGTAAAATGG
209101 AAATAATTAT TTCCCAGACC ACCACTCTTA TCTGTGAGCT TTTTTGGCCA TTAAAAATTA
209161 TTTCTTCCAT TATATTTTA TCTGTGTCTT CACAGGTTTT CTCTTTCTTT CACTTTAGTG
209221 CTTTTCTTCA AATAAGCAGG AAAAATCCAA TCTATCATGC ACATGGGAAC CCTTTCAATA
209281 TTGGTCTGTG GTTGTTCCAT TTTATGGGGA TGCTTTTAAA GAAAAAATTT GTCCTTTCAA
209341 TATATTGAAT ATCTTCCAGC ACCACATCAC CTGCAAGCTT TGTAAAAATA GTTCTACATA
209401 TTAATTTTTT TTTTTTTTTT GAGATTGAGT CTCATTCTGT CACCCAGGCT GGAGTACAGT
209461 GACATGATCT TGGCTCATTG CAACCTCTGC CTCCTGGGTT CAAGTGATTC TCCTGACTCA
209521 GCCTCCCGAG TAGCTGGGAT TACAGGCATG CATCACCATG CCTGGGTAAT TTTTGTATTT
209581 TTAGTAGAGA TGGGGTTTCA CCATGTTGAC CAGGCTGGTC TCAAACTCCT GACCTCAAGT
209641 GATCCACCTG CCTTAGCCTC CCAAAATGCT GGGACTACAG GCGTGAGCCA CTGCACCCCA
209701 CGTAGTTTTT TTTTTTTTT AAGTTGAACA TATGTGAAGG CAGGACCTAG TGACACATAG
209761 CAATAACATT TCCAAGTAGA CATTACACTA GGGAATTAGT CGAAGTGCTC ATTTAAAGTA
209821 CCATCTCTCA AATGTATTAA AAGAGAATCC TTGGATGTGC AATACCTTAA TTCAAAGGCA
209881 GCTCGTTATG TATAAACTCT CAAGCTTTGT GATAAACAAA TGTGCATAAC AGATGGGACT
209941 ATTCACTTAC AGCCCAGGGA ATTTTATTGA CGCTGAGAAG GTTATGTGAC TGGCTCTGCC
210001 ACTGTCATCC CCATTCACTT CATTTTGGAG CAATAGACA TAAATGCCTT ACATGTGGGT
210061 TTTCTCTATT TATCATGTGT TTCCTATCCC CTTGAAAGAT GGCCATATTT GCTTTACTTG
210121 GTTATAAGAT CCCATATTCG CTGTCTTGAA GCCAACCAAA TAATTGACA AAGTGGGTTT
210181 GTAGTGCTGG CTATTTTGGT GAAAAAAGA CAATGAGACT TCATGTGTCA TCCAAAGTTC
210241 TATCAGATCG AGCTGTGAGA GAAAGGAAAA GAAAGGGGTC TCAGTCAGGA TGCTCACTAC
210301 ATACATCTGT GTTGTTGTCT AGGTCCAGAT TTCTGTTCAT TACGCTATGG GCTGGCTCTT
210361 ATCATGCACT TCTCAAACTT CACCATGATA ACGCAGCGTG TGAGTCTGAG CATTGCGATC
210421 ATCGCCATGG TGAACACCAC TCAGCAGCAA GGTCTATCTA ATGCCTCCAC TGAGGGGCCT
```

Figure 1 (Page 65 of 73)

```
210481 GTTGCAGATG CCTTCAATAA CTCCAGCATA TCCATCAAGG AATTTGATAC AAAGGTAAGT
210541 ATGATGGAAA ATAGGGCTCT TTGTTGAGAG AAAAAACTTT GAAAGGAAGG CATAGATCTT
210601 GATTCTGTGG AGTATGGAAG TATACATTTC CAATGACAAA TTAAAACTGA CTGGAACTAT
210661 TTTTCTTTGA GACATTGCTT ACTTCAATAA TAAAAATAAG ATTTCATTGA GGTTATTATG
210721 ATTATAAGGT GGGGGAACTG TAGAGTTAAA TGTGAAAAAT TTAAAAATGG AACAGTTTAT
210781 GTGATGTCTT CAATGAAAAA CTAGGTATTA CCTGGGCACA TTCTTATAGG TTACTCAATC
210841 CTATTCAGTT CTCTGCCTGT TTTATTGTTT CTGAGCAATT TTATATCCCT GTAAATTCTA
210901 TATAACCAAT AGAAATGCAA ACGATTCTTG TCCATAGCTT TGCAAATAAA TTTTGCCAAG
210961 AGAAAAATCA GTTAAAACTT TTCTCCACTC ACCTCCCAGT TGAATTAGCC AATTTTGCTG
211021 TTTGTTTGTT TGTTTGTTTT TTGAGATAGA GTCTTCCTCT GTCATTCAGG CTGGAGTGCA
211081 GTGGCATGAT CTCAGCTCAC TGCAGCCTCC GCCTCCCGGG TTCAAGAGAT TTTCCTGTCT
211141 CGGCCTCCCA AGTAGCTGGG AGTAAGGGGG CATGCCACCG CGGCTGGCTA ATTTTTGTAT
211201 TTTTAGTAGA GACAGGGTTT CACTAGGCTG GTCTCGAACT CCTGACCTCA GGTGATCCAC
211261 CCGCCTCGGC CTCCCAAAGT GTTGGGATTA CAGGTGTGAG CCACTGTGCC AGGCTCTGCT
211321 GTATATTTAA AGTCTATTTC AGCATTGCTT CCTGCTTGTG TTATGCGTGA TTCTTTGAGT
211381 TTTCCTTTGA ACCAGTTATA ACATCTTACT TACTTCCTCC ATTAATCAAT GAGTTAAATA
211441 AAATCTTTGT TGTATGTTTA TTTTACATTT ATATGAAAAC CATGAATTTA CCCAATTAAA
211501 AAAATTATCC TTTAAATTAT CTTGTACTGT ACATTTCCCA TGTCATCCCT ATAATTCATG
211561 ATTAATGATT TTATTACATT GGACCTAGCT TATTTACAAT GAGTACATAA ATTTATTGTC
211621 TCCAGTCTTT CCTCCATTAT CCCGTCTACA TATCCACACT GAGTAGATTC ACTACTCAGG
211681 AATCTTGGAC ACCTTCAAGT TGCCAAACAT GCAGTGTTCA CTGGACATGC TGTGTTCCTT
211741 CAGAATTTGG GCCTGCTTCT CAGCACACTC ACATCTGCTA TCAATGACCC ATGGAAAGTT
211801 TTTGCCCTGA GCAAGCCAGA GTCCCTGTTA GTTTCTTCCA AATGCTACAA GTTCACTTTT
211861 GCTATTTTTT CCGATGAGAT AAAATTTTCC TTTTTGACTT TCTACAAATC ATAGTCATTT
211921 TTCAAGGGAT AGTTCAAGTA TTGCTTCCTT TCTGGGACCT TCCCAAATTA TTATTTTCTC
211981 CTCTCAAAGT CTCTGTTTTA TTTATGTTCA TCCTCAAATC TTGATTCTCA CATGAATCAT
212041 ATACCTTGTA TTATTTATAG TTTTTTTGAG TGGGTAAAAT ATTTCATATT TTATATTCTT
212101 TGGCTCTCTA CTTTATAGCA TGATGCCAGA TATTTAGGGG CCTTATTGCA TTTATTTTTT
212161 ATTTTATTTT AAAATCTATT TTATTTTTTA TTTATTTATT TTAAAATCTA TTTATTTTTA
212221 GGTAAATATT CAGGTAATAT AATTTATGTA ATTATTTAGG AATTTTAGGT AGTTATTTTA
212281 AAATAATTCA AATTATTTAT TGAGTTATAT CAGAAGAATG TGATCTTATT CATTTGTAAT
212341 ATGTGTTTTA GGAACTCAGT TCAGCCAGGG CAGACCATGA TTCCCAAACT TGACTTTTCT
212401 TTTTAATTAG GCACTGATTT TGGTTAAGAG TTCAGTAAAG TTTTGTGTGT GTGTTTTAAA
212461 AAATTCTTTG ATATAAGAGT CAAGATGTTA CTCAACTTTT ACTAGAAGCA AAATAGAGGA
212521 AGTGCTTTCA CAGATGAAAT ATCTCTCAAT GTTTTCTTCC ATTTACTTCT TCCTATTATT
212581 CATCTATATA ATCATTTTCT TTACCTCTTT TCTTCATTTC TTCTGTTTTT CTCTCCTTCT
212641 ACTAAGACAA GCAAATTAGG GGTATAATTG GTTATTTGGG AAGGTAGGAA GAATATAGAG
212701 AGAAACAAAA ATCAATATTT TATACTAGGG TCTCACTAAC CTCAAGCAAC TCTGACTGTA
212761 AAGTAGATTT TCATAATAGG ACTTCTTGAC AAAGAGTTTT CCTATTTTTC CCCCAGGCCT
212821 CTGTGTATCA ATGGAGCCCA GAAACTCAGG GTATCATCTT TAGCTCCATC AACTATGGGA
212881 TAATACTGAC TCTGATCCCA AGTGGATATT TAGCAGGGAT ATTTGGAGCA AAAAAAATGC
212941 TTGGTGCTGG TTTGCTGATC TCTTCCCTTC TCACCCTCTT TACACCACTG GCTGCTGACT
213001 TCGGAGTGAT TTTGGTCATC ATGGTTCGGA CAGTCCAGGG CTTGGCCCAG GTATCCAGAT
213061 ACTTTCTCAT TCTTGGTGGG ATCCAGATTT CTGAATTCTA CAAAATATCA AAGGTCTTAA
213121 TGATTTTCAT TTCAGGGAAT GGCATGGACA GGTCAGTTTA CTATTTGGGC AAAGTGGGCT
213181 CCTCCACTTG AACGAAGCAA GCTCACCACC ATTGCAGGAT CAGGTAAGTG TGCACAGATG
213241 GGTCATAGCT TTGTCATCTG TTCCATCCCA CTGTGTCTTA TCTTCTATGA ATCAAATGGT
213301 TTGGGGAAGA GAGAGAAAAA GTACTGCTGA AAAATTCAAC AATATAAGAC ACTTGCATCA
213361 CAAATAGGAA AGATGCATCT GTGCAGTAAA GACATTGAAG CTTAGAAGTA GAAAAACCA
213421 TTGTGAGCTA GGTTTCAGCT CAGAAAAGCC TTAGTAGTCA GAAAAGCCTT AGTAGTCAGA
213481 AAAGCCTTGT CGGAAAAAGT TTAAACCTTT AAGAATTGCA CACATGGAAA AGATCAAGT
213541 AAGCTATATA TACACCATCT TAGCAATGAT TTTGAAGTGA GAATTAAGGC TACCACAGCT
213601 CCAGGTGGTA AGGAGAGAAA TCAGGCTGGA AGAGTTTGAA GTTTCTGTAT TATTCTAAGC
213661 TCTTTACTAT TCTATTATGA GCTCATTAAT TCTCACAACA ACCCTCTCAT ATAAGTACCA
```

Figure 1 (Page 66 of 73)

```
213721 TTTTAAATTC TTATTTTACA GAGAAGGGAG TTAAGGAAGG TGGAGATTAA GAAAATTGCC
213781 CAAATACAAA TAGCCAGCAG GTGGTAGGTC TGAGATTTAA GCCCATGCAG ATTTTAGCCC
213841 CAGAGCAGAC ATTCTCAATC ACTATGCTAG ACTGCCTTTC CATGGTATGT GATCCTACTC
213901 AGGCCTCTAC AGCTTTATCA TTGCTGTTCT CCCCAGCCTG TCGTGCTGAG AGTATATACT
213961 CGAAGAGCAG AACTAAAATT CCATCCAGCT TCTCACTCCT AGGTCCACTA CACAGCTGCA
214021 TCCTGCAGAC TTTTACCTCA AGCAACCCTC CTGCGTTCTT GCTTCCTTCC ATCATAGTTG
214081 TAACCATCTC CTCTATTTGC AAATACTATC TGCTGATCTC TCTCTTCTAG ACTGGTTTCT
214141 TTCAACCTTC TTCCCACCAA AACCAAGTTA GCTTGCTAAA ATAAAGATGG CACATTTTTA
214201 CTCACCCGCT TGAGAATTTT CAATGTGTTC CTTCATGCTT ACAGAGTAAA GCCTGACCTC
214261 TTTATTGCAT GAATACAAAA GTTCTTAGCC ATCTGGCCCC AACCTTGTTC CACTCAACTC
214321 CCCTGTGCAA GCATGGCTCC AGTGGCACTG GACATTGGCT GCTCTCCACA TAGATCTGCA
214381 CTGCACTTCC CTCTGGCTCT GCTCCCGTTA GTTTATATGC CTGGAAAGTT CTTTGCCCCT
214441 GTTCCTTGTG CCAAAATTCC ATCTATCCTA TTGCATAGCT TATGTAAAAA CTTCCTAAAC
214501 CTTTTTTTTT TTTTTTTTTT TTTTTTTTG AGACGGTGTC TCACTCTTTC GCCCAGGCCG
214561 GACTGCAGTA GCGCTATCTC GGCTCACTGC AAGCTCCGCC TCCCGGGTTC ACGCCATTTT
214621 CCTGCCTCAG CCTCCCGAGT AGCTGGGACT ACAGGCGCCT GCCACCATGA CCGGCTAATT
214681 TTTTGTATTT TTAGTAGAGA CGGGGTTTCA AGCCAGGATG GTCTCAATCT CCTGACCTCG
214741 TGATCCGCCC GCCTCGGCCT CCCAAAGTGC TGGGATTACA GGCGTGAGCC ACCGCGCCCG
214801 GCCAAAACTT CCTAAATCTT ATAATTATTA TCAATTTATC CTCAGATATA CTTCCACGTA
214861 CATTGTAGTT TTATTATATT TATATTTTAC ATCTTTTTTT TCAAATTTCA GTTGGGACC
214921 CATTAGTGAG TCATAAAATC CATTGAGCGG GTTAAAATCA TTATTTTAAA AAATGAATAG
214981 AATAGAATAG AAATTGTTGG AGTGCATTGG ACATGGTAAA GTTAAATATC GATTCATGAA
215041 ACCATCGTTT GAGGCATATG TGTGTGGTTG TATGTACAAG TGTTTATGCA TATTGGTGTG
215101 TGTGTTATGT TACCCTGTAA AATGCATTTC TTACTATAGG TCTCTGTGAA ATATGTGTCT
215161 TGTTGTTTTT TAATGTAGAC TTCCAAAGCC TACATGGCAT TTCACTAGTG ACAATCAATT
215221 TTATTCACAT TTTTCTCTCC AATTGGACCA GAAGCTCTTT GAGGGCAGGG GCTGTATCTT
215281 ACCGATTTTT GTAAGTCTTT CATTTCCTGC CCCTAGCCTC ATATTAGATC ATGCAAGAAT
215341 GCAACTGTAA TCACAAGAAA ATGCTAATGG GCTGTGATAG CAGAGAGTTA CTGTGACAAA
215401 CTAAGGGATT TAGATTTGGT CACATTGGTG TTGAGGAGCC ATTGAAGAAT CAGAGAGTGT
215461 GTTACTATTA TTTGTTAATT TTAATTATAT CATATTACTT TACTGGGGAA AATCTGTGAG
215521 CTATTTTAGA AATAAATACT CTCATTGCCC AATAATTCTA AGTCTGCCAC CTCACTGTTG
215581 GGACATTGTT TAGGGAGGCC ACGAAGTCTC AGCCTTTGAT ATTTTCATAA GTGTTTTTCT
215641 CCCTTTTTCC TTTAGGGTCA GCATTTGGAT CCTTCATCAT CCTCTGTGTG GGGGACTAA
215701 TCTCACAGGC CTTGAGCTGG CCTTTTATCT TCTACATCTT TGGTGAGTCA CTTTCTCTTA
215761 AATCCTAACG CCTCCATTTC CTGAGCATCC ATTTGGCAC CTACACCACC CACATTCTTC
215821 CTATATGAAA GAAAATGTCC TTTATCAAAT GGAAGATGAT AAAAAATGTC AACGGTTGGT
215881 ATCATTTTTA ATCTAGTCAC ACAACCTGAT TAACACCTTC CTGGTGGTTC TGGGAAGCCA
215941 CACGCACAAG GTAGAGGAGT TGACTATTCA CATGGCACCC ACCGACTTGT GATGCAGTCT
216001 TGTCCTTCCA TATCAAGCAC CTTCTGCAGA ATCTCTACCA CCACATCTGA AGTGCCTGCT
216061 ATATGCAGTT AAGATGTCAA AGATAGTGAA GTACATTTTC AATGTGTCTT CATATTTCAT
216121 TATAATTATT ATTTCTGTCC AAGATGCCTT TCACCTGTTC TCTACCAAGT TAATCTTGCA
216181 AAGTTCAATT CAAATGTTCC CTTCCCCATG GGCCCTTCCA GGGCTTACCC TATCAGATTC
216241 TGGCATTCTC TCCTTTATGA TATTTCCTCT CTAGGTTATG TTGGTGTGTA ATTATTTATT
216301 TCTCCTTTTC TTTCCACTAG ACTGTGAAAT GCTTGAGGCA AGGAATCCAT TCTATGTTTT
216361 CATCACTTGG GTGTCATCAT GGTGCCTGAT TTTTAGCTTT AAAATAAAAG AATCAGTGAA
216421 TCCAGTAATT AGAGGGGATT TAAAGAAAAC TAGTCCTCAG AATCTTTTAA CATAGAATGT
216481 TCTTCAAATA AGGAATTCCA ATAATAAGAC AATTTTCTAC ACTTGATTTT GTTTTATAG
216541 CCAAATGGTG TCATTAAATA TAGTCCTGGC CTGAATGGCT TTCTCATTAA TGATGCTAAT
216601 TATTTTGGTT TGTACATGTT AACCAGGTAT TGTACAAAAA TATTTCTTTT GGGAATCCAT
216661 AATGGATGTA TGGCTTGAAT ACAAATAATA CTGTCTCTTG TAAGTGCATT GGAAATTTTT
216721 CCCTGCCACA TGATTTCATG GAAGGTTGTT TCGTGTATGT ATGACTGCAA ACCTGACTAT
216781 TCAGATCTTC CGCAACAAGA CAACTTATGT GTGCATTAAG AAGTTGCTGC CTAAAATACA
216841 TAACACTGTA ATCATTGGAG ACTTTAAAGT AATTAATCAG CTATGCAATG CCACGCTCCT
216901 GTTATCTCCA GAGGGCTCTG ACATTGACAA ATGGTGGCTT TCTATTTGAG ACGTAATATC
```

```
216961 TAAAAAGCTT TAACAGGTTT GTAGAAGGAT TGAAAGAAAG AATGGGAACA TTTAGGTCCT
217021 TATGGTAGAA TAAGCATTAA TTGATTAGTG TGTAGAAGGG AGAGGCATGC CACTTCAGAG
217081 GAAACTTCCT TCCCCCAGTA AACAAATCTA CCTAAAAACT AATTTTATCC CTTCTTCCCA
217141 GGTAGCACTG GCTGTGTCTG CTGTCTCCTA TGGTTCACAG TGATTTATGA TGACCCCATG
217201 CATCACCCGT GCATAAGTGT TAGGGAAAAG GAGCACATCC TGTCCTCACT GGCTCAACAG
217261 GTACAGTGCA CACCTTGTAC CTGTGGCCCA TGCAGAGGTC TCTAGGGCAG GGTGTGGATC
217321 TCCTCTGAGA GGCACCATCT TGGCTGCTCT AATACTCATG CTGATTAGAT CTTTCTTTTC
217381 AGCCCAGTTC TCCTGGACGA GCTGTCCCCA TAAAGGCGAT GGTCACATGC CTACCACTTT
217441 GGGCCATTTT CCTGGGTTTT TTCAGCCATT TCTGGTTGTG CACCATCATC CTAACATACC
217501 TACCAACGTA TATCAGTACT CTGCTCCATG TTAACATCAG AGATGTGAGT TTACTTCCTA
217561 TACTTCTACG AAAATGATAA TGGTAATAAG GAGAAACAGT TCTGTGTTAC CTATTACATT
217621 CTGGCTTTAC ATATAACCAT TAATTTAACC TTCACAATGA CCTTGAGAGA GGCATTGTTA
217681 TAATTCCCTT TTCACAGATG TGGAAACAGG ACACTTAGAG GTGAGATAAC TTGCCCCAGG
217741 TTGCACAATA CTAAGTGATA GAGCTGCTGC AGCATCCATA TTCTTAACCA CTATGCTATA
217801 CTACCACACC AGCTGATTCC AAAGCTTCTT TTAGAAATAA TATTGCTGGG CCAGGCATGG
217861 TGGCTCATGC CTGTAATTCC AGCACTTTGG GAGGCCGAGG CAGGCAGATC ATGAGGTCAG
217921 GAATGCAAGA CCAGCCTGAC CAATATGGTT TACTAAATAT CATCTACTAA AAATACAAAA
217981 ATTAGCCAGG TGTGGTGGCA GGCACCTGTA ATCCCAGCTA TTCAGGAGGC TGAGACAGGA
218041 GAATCGCTTG AACCCAGGAG GTGGAGGTTG CATTGAGCCA AGATCATGCC ACTGCACTCC
218101 AGCCTGGGCG ACAGAGTAAG ACTCCGTTTC AAAAACAAAA AACCCAAGAA ATTAATATTG
218161 CTTTTATCTG GAGCCCAGAG TGATGCAGCT TCTGGCCCTC TTATCTGAGA CAGTGTTCTT
218221 TTAGTGTGAA AAAGGATGCT AATTTTCCCC CAAACAACCC ACAGTATCAT GGGGGTAAGT
218281 TAATGGCTGG TCTGTGTAAC TGACAAATTT TGGTGCTAAC GTATCTCTAT AACTACTCTG
218341 TATAAACTTC CTTCCTTCAG AGTGGAGTTC TGTCCTCCCT GCCTTTATT GCTGCTGCAA
218401 GCTGTACAAT TTTAGGAGGT CAGCTGGCAG ATTTCCTTTT GTCCAGGAAT CTTCTCAGAT
218461 TGATCACTGT GCGAAAGCTC TTTTCATCTC TTGGTAAGGA TAAGCGTGTG GGCCCATTTA
218521 ACCAATCCCT TTTCTGCACA TGGTCTCAGA GGGTTCCCTG ACAGCATGTC CTCATTGCCC
218581 AGGGCTCCTC CTTCCATCAA TATGTGCTGT GGCCCTGCCC TTTGTGGCCT CCAGTTACGT
218641 GATAACCATT ATTTTGCTGA TACTTATTCC TGGGACCAGT AACCTATGTG ACTCAGGGTT
218701 TATCATCAAC ACCTTAGATA TCGCCCCCAG GTAAGAGCTC TACCTGTTTT TTCCCCTCCT
218761 CCAGACCCCT CCAGAGGTGT TAGACCTCAG TGGTCGCCGT GAAACTCTTT AATGTTACTG
218821 ACATTGCACT AATGGCAGAA TGACAAATAA CTACAAATAT CTGTCTGTGG CCATTTTTAG
218881 AACAACAAAT GTGGCATTTT TAGAACAACA ATTTCCAATC TTGGCCAGTA ATCATTTTGA
218941 CAAAAACCTT CCCAAGCTTC CCTAACAGAG ATTGAACTGT GTATGCTGGG AAAAGGCCCA
219001 CACACAGGTG ATTTGGAAAA GTTTCCATGG TGTTGTTCAT ATTAGCTACC ATATATATAT
219061 ATATATATAT ATATATATAT ATACAGTCAC AATAAGCCAG CTCCTGTGCC AAGACTTGCC
219121 ATATATCAAC ACATCTAATC CTCACAGTTA TATTAGGTAG GCCCTATTGT TATCCCCATT
219181 TTATAAGGGA GAAGGCTGAG GCACAAGGAG GTTAAATGGT GTGACTATGG TCACATAAAG
219241 GCAGAGCCAG GATTTGGACT GGGGGAGTCT GGCTTTGGAG TCTGTGTCCT GCCCGTTGCA
219301 CAAACTGGCT TCTCCACTGA GCAGCCGGGG TAAAGAAACG TGGTTCCCAG AGAGACTGCA
219361 TTGCTCCCTG GTTATTGACT TGGTAGATTG GTAATTTCAG GTTTGGCAAA TAGACATTGC
219421 CCTGAATGTC TTTAGGTGAA TGAAAACTG CATTAAGCAA AATGACTTTG CCATTAGAGC
219481 TGAATTGCAT TAAAGTTGAG TTGCTGCAGA AGCTGTAGGT GGCTTTCTAT ATAAAATCAT
219541 TTATAAAATC ATCTTCCCAC AGATATGCAA GTTTCCTCAT GGGAATCTCA AGGGGATTTG
219601 GGCTCATCGC AGGAATCATC TCTTCCACTG CCACTGGATT CCTCATCAGT CAGGTTGGGC
219661 CAGTTTATTG AACATCTTCA AGTGGCAGGT ATTGTTTTAG GTGTTGGAGA TACACACGGT
219721 GCTCTAAAGA TCTGGATGGC AACACAATTA CTCTATTTAC ATGAGCCTCT AAATCAGACT
219781 CTGGTAGGTC AGATTTCCCA GAGGAAGAAA AATATAAGCT TATTTTCTCA AGATGAATAG
219841 ATGTTAGATT GATTAAAATG AGCTGTTCCG GTGCAGAAGA CAGCACGTGT GACTTCCTAG
219901 AGGTACATGA GCATGAAACA GTTCTTAGTT ATGACCAGAA TGAAAGACAC ATGTCAAGGA
219961 ATAGCAAGAG ACGAAGACAG AGGGGCAAAA GAAGATCATG AAGAATATGT TCAGACTAAT
220021 CCAATTTTTA AAAAATCACA AAAGGGAAAC AAAGTGTCCT AGGCCAGTTT AAAGATAATT
220081 TAATGTCTGG AAACAGATCG GCTGTGAGAC ATTGCAAGGA GGCTTGCTCG GTGTTTGGAA
220141 ATGCAGGCTC ATGAGGAAGA TGAAAAGACA GACCCAGGCA GGGATGGAAG GACTGACGAG
```

```
220201 AACCAACTTA CAAAGAGAAG TTTTGTTTTT ACTACATTTC TATGTGATCA AGTTCCCAGG
220261 TTAATATTTG ACTAAACTGC TAGGAATCCA CTGTGACTAT AATGCTGGAA ATGACTTAGT
220321 AGGGCTTTCT GAGGAGGGTC ACACAGAAGA CCAAAGAGAA CTCATGTTGA ATTGAGATGG
220381 GTTGTAGTGA TAGTTGTCAA CAGCCAATAC AGAAACAAAA AAAAACAAAA CAAACAGCAA
220441 CAACAACAAC AAAAAAAAAC AGAGAAGACA CAAACACAAT GCCACAATGC CATTTTAGGC
220501 ATAATTTTAA ATGAGTAATA TTATATGTTG AAATCCAAAT TTTCAGAAAA ACATTAGTGT
220561 ATTTTATTTT TGTTTAAAGA AATAACCATC TCAACTCAGA ACCCCATGTG CATTTTGGCC
220621 ATTTTGTTTC CAATAGTTTC ATAAACTTTC TTAAGTAACT ACTGCACATT GTTCCTTATA
220681 TTCCTTGTGA TCAACATTGC AATACACAAC TGGGAGGGCT ACTAGAACTG GTGTAGAAGG
220741 AACTTGTGAG ATTGATCATT TTCTCTGTTT TTTACATCTA GGATTTTGAG TCTGGTTGGA
220801 GGAATGTCTT TTTCCTGTCT GCTGCAGTCA ACATGTTTGG CCTGGTCTTT TACCTCACGT
220861 TTGGACAAGC AGAACTTCAA GACTGGGCCA AAGAGAGGAC CCTTACCCGC CTCTGAGGAC
220921 ATAAAGTTAC AAACTTAAAT GTGGTACTGA GCATGAACTT TTTAAACATT TTTTACTTCT
220981 CTCCATATTC CTGACCATAG ACTCAGCAGT TCTTAACTCT GGCTGTGTGT TAGTCTTCCC
221041 TGGGGAGCCT TTATAAGACA CTGATACTTG GGACCCACTC CAGAGATTCT GAATGAATTG
221101 GTCTGGGGTG GAACCCAGAT ACTACTAATT TTTAGATACT CCTTAGAGGT TTCTAGCATG
221161 CGCCCGGGGT TGACAACAGC TGGACAAACT TGAAAAGTCA ATTCATGTGG CCTTTGAATT
221221 TTCCTCATTG GAAAGTACTA AATAAATAAA AATTCATGTG AAAATGATCA CTGATAAATA
221281 TCTTCATGGT GGGGCAGGTT ATTGATGCA GAGAAGATCT GCTCGGAATT GTAGCCATAT
221341 GTTACAGATC TCAGCACCGA TCGGAACTGT AAAGCTATAA TCCCCAGAAT TAAAGTTTTT
221401 ATTATTTTTT ATACATTGTA AAACATAGAC GTTTATTTAT GTGATTAAAT TCTATTAAAA
221461 TTTACATGCT AAAATAAAAT AGACCATTTT CAAATTATTT AGATCCAGAT ATTTCCATCA
221521 GATTAAACAG ATATTTATTT ATCCTAGCCC AATTGCAAGA GATTAATGAT GAGAAAATGA
221581 CCAATACAAG ATTAAATAAA TGAGGTTAAC TTAGAAATCA AGGACAGAGA AGATAGAACT
221641 GGAAGGCTTG TATTGTGAGA AGAATGAATG TGAAGGAAGG CAATGTAGAC ACTTCCAGAA
221701 GGGATAGCAA TATAGTTTAG ACCATATAAT GAAAATTGGA GAGAGATGAC AGAGACACTT
221761 TCAAGTGAAA TGACAATTTA TATGGGGGAG AAAAATATTG AAGACATAAC AAGATGAGAA
221821 AAGGCATAGA AATGTATCAC ATACAAGGCA TAGAAGTGTA TCACATACAA GAGAAGTTCC
221881 TTTTGAGCGT AGAAAAAGAT AATTTAACCT TCTTCATATT TTTCTTACTT TCCCAAGATA
221941 CTCAGATAGG CAGCGTCAAC TCTAACAGGA ATTAATTTGG CTCCTAACAC TTAAGACATA
222001 TCCTTTAGTT TGTCTCCTCA CACAGAACTG ATTCTGGTTT TGCCACAACA TGTCTAGAGA
222061 AGAAGTTCCC ACCATATTTT AAATCCTATT AAAAAACTGC TTGGACAAGA ACCTTGGGTT
222121 AATTCAGCAG ATGAAGAGAA TCTCCTAATG CAAATCAATG GGTATTTTTG AGCAAGTTTT
222181 TCAGAAAAAC AGAGTGTCAG GCCCTGAGGG TGGTACTAAG ATGAGAACAT TGATTTTGCC
222241 TTCATGATAT TGACAACACA AAGAGGAAAG GGGGTTTGCA GAAAACTAAA AGAAGAAGTA
222301 GAAGAAAAAA GAAAGACATA GTATAATAGG TAGTCAAATT ATGTACAGAA AAAAGAGAAA
222361 AAAAAAACAA AAAAGGGTGG GGGACAGACA ACCCAACTAA AAAATGGGCC AATGACTTGA
222421 ACAGGGACTT CATAAAAGAG AAAATGTAAG TGGCTCCTTA ACATATAAAA AGATGTTCAA
222481 CTTCATTAGT CATTACAGAA ATGAAAATCA AAACTACAAT GAAATACCAC TATAAAATTA
222541 ACTAATGGAT AAAATGAAAG GAGATGGAAA ACAAAATGTT GCCAGACATG TGGAGCAACT
222601 GGAACTTTCA TACGTTACGA ATGTGAACTT TGGAAAGCTG CTCGGCAATA TCTCCTAAAG
222661 CTAAATGTAC AATTCCAGTG ACTCAAACAT TTTACTTAGA AATGCACATA TACATCCATA
222721 AAACATGTAC AACAATGTTC ATAGGAGCAC TATCTGTAAT AGCCTGAACA GGAAGTTGTC
222781 TGTTAAAAAA AGAATGAGTA AATAAACCAC GGTCTATTTG TATAGCAATG AGAATTAACA
222841 GACCCAATA TATAATAGAT GAATGGGTCT CATAAGCACA ATATTGATTA AAGGAAGACA
222901 AAACGCACAT TCTTTTAAAG GTTTATAAAA TACTTTTTAA AAACAGCTAC AACCAATCTG
222961 TCCTGTTAAA AATCAGTGAG CGATTTCCCT TGTGCAGGGA TGGGGGTTGT GGCTGGATGG
223021 ATGGTACTTA AGAAGTGCTC CTGGGGTACT AGAAATATTT TATTTCTTGA CTTGGATGTG
223081 TGTTTACTTT GTGAATATTG TACATTTATG ATTTGTGCAC GTTTATGAAT GTAGAAAATA
223141 AAACAGAAAG CAAATTCAAA GTATCATCCT TTTGAGAGCT TCTGCTCTGA CTTCGTTTTG
223201 ACCAATGGAG CAGTTGGGAA GGGGTCTTGG TCCTTCGGTC CTTTGCTTTT TTTTTTTTTT
223261 TTTTTTTTTT TAGACAGAGT CTTACTCTGT CGCCCGGGCT GGAGTGCAGT GGCTCGATCT
223321 TAGCTCACTG AAAGCTTTGC CTCCCGGGTT CATGCCATTC TCCTGCCTCA GCCTCCCCAG
223381 TAGCTGGGAC TACAGGCACC TGCCACCATG CCCGGCTAAT TTTTTGTATT TTTTAGTAGA
```

```
223441 GACGGGGTTT CACCATGTTA GCCAGGATGG TCTCGATCTC CTGACCTCGT GATCCGCCCA
223501 CCTGAGCCTC CCAAAGTGCT GGGATTACAG GTGTGAGCCA CCGCGCCCGG CCCCTGGTCC
223561 TCTGCTTTCA TGTTCTTCTT GGTCCTGTTC CTCCTCCTCT TTTGTTGGAA CTTCCAGTAT
223621 CAGAGCAGGA AGGAAGGCAA TGGGTCAATC GATGCTGTCA GCTTTTGGAT CAAACTGCAA
223681 GTTCTCAAAC AGCAAAATTA ATGAGCTCAG GCTTTGAAGA AACCATGACC CTGAAAGCAT
223741 CAGTTGCTTC CAATTGCATC AGTTGCCACG GGTGATAAGA ACAATGATGA CTCAGAATGC
223801 CTAGGTTTTC CCAGCAGCTT CTCTGAGGTT TTCCCAGCAG CTTCTCTGAT TGATTCCTGA
223861 CAGATGACTT CGGTGTGTCA GACTTTCAGG GTATCTTTCC TTATGTGATG GTTGAGGAA
223921 GAGTTACCAT TCACATTCCT AATGGCTTCA GAATAGATGC AATTGTGAAC TGATAGGAAA
223981 CATTTCTAAT TCATCTCCCC TCCCCATCCC TAAAGGATTG TTTCTAACAA TAGTCATGAA
224041 AATTAATTCA CTTTTCTCAA ATAGTTTATT GTCATCTACC TAATGATGAG ATGACTTACT
224101 TTTTCTCCTT GACTGTTAAA TATTATGAAT TATATTAATG TATTTCTTAA TGTTGAGCTT
224161 TCCCTTGAAT ATTCTTTTGA TGTACGACAG AATTTGATTC ACTAATAGTT TATTTAGGAC
224221 TTTGGCTGAT GTACTGATAT ATGAGATTGG CTCTGTATGC ATACATGTGT TTTGTGTATC
224281 TTTTTTGTGT CTGGATATGG AGCTTATGCT GATTTCAAAA ACAAGAAAGG AGAACTTTCC
224341 TTTTTCCCCA TTACTCTGAA AAAGATTGAC TAGAATGGAA TTTTTATAAT TGCTGTTGTT
224401 ATTTGAAAGC TTGAAAGCAT TGGTTTGTAA AAATCATGCA GGCTGAAAGC CATTTTGAGG
224461 AGACTTTGAT AACTTTCTCA ATTTCCTTCA GTTACTGGTC TTTTAAGGGG TTTTATATTT
224521 TTCTTTGATC AATTTTGACC ATTTATGTTA TCTTGGAGGA TCATCTATTT TACACACTAT
224581 TTAAAGTATA TTTGCAAAAA TTCAACTGTT TTATCAGGCT ATCTTTTTAA TAATATATTC
224641 ATTTTATCTA TATCTGAGGT TTTAGCTTCT TTGTACTTCT GACCCAATTG CATGTGTGCT
224701 TTCTTTCTCC TTCATTAGAC TACTTAGTCA TTTACTAATT TTAAGAATAG CTTGTCTTTT
224761 ATTTATTTAC TTATTTATTT TGAGACGGA GTCTCACTCT GTCACCCAGG CTGGAGTGCA
224821 GTGGCGCGAT CTCGGCTCAC TGCAACCTCC GCCTCCGGG TTCAAGTGAT TCTCCTGCCT
224881 CAGACTCCCG AGTAGCTGGG ATTACAGTCA TGCACCACCA TGTCTGGCTA ATTTCTGTAT
224941 TTTTAATAGA GATGGGGTTT TGCTATGTTG GCCAAGCTGG TCTCAAACTC CTGACCTTAG
225001 ATGATCTACC CACCTTGGCC TCCCAAAGTG CTGGGATTAC AGGCATGAGC CACTGCGCCC
225061 AGCCCTGCTT GTCTTTTTAT TTTATATTTG ATTAGCTTTA TCTTTTATCA AGCTTATGTC
225121 CTATTTCCCT TTGCTTTACT TCATATAAAT TTTGTTTTGG ATAGTTTATT TATTTTTCAT
225181 TTAATTATGA AACAGGTTAA AGCTTAGAGG AAAATTGCTC CTCTAAGTCC AATTTGTGG
225241 GCAGATTACA TTTTGCTGTG TTGTGCTCCC AAATTCATTG TTCTTTTAAT GCTTATTTC
225301 TCAAGTTAAT AACCTATATA GTAAAAAGT GGCTGTTGAC TCTCAGCTTT TTTTTTTTT
225361 TTTTTTTTTT GTAGATACAG GATCTTGCT GTGTTGCTCA GGCTGGTCTG AAACTGCTGG
225421 CTTCAAGGGA TCCTCCTGCC TTGGTCTCAC AAAATGCTGG GATGACAGAC ATGAGACACC
225481 ATGCCTAGCC ATGTCTCTCT CCTTATATAT AATAAGAAAA CAGACACACT GAGGCATCCT
225541 ATCATCTCAC TCTTGGTTTC ACTACTGTTC TCTGGAAGTT TTGCTCTGAC CTTTTGCAGT
225601 TAATGTATTA ATTTTGCATT GAGTAGTTTC CATAGAAGAA TTATAGCATT TGCATTCTGT
225661 TGGGTATTAT ACTTTTCACT GTTATTGAA CATAATTTGA GGGCTGAAAC CAAGATGAGG
225721 CAAGTGAGGT GCCCAGGAAG CAATATTTAA GGAGGCATCC TTTCTTAGGC TCATGCAAGA
225781 ACAGAATTGG CACATGAGAG TGAGTGCCTC CTTAATTTTG AGTGCTGGAC ACTTCTTGCT
225841 CACTTAGCAT ACCCCTGGAC AATGAAGTGT TTTTGTTTT GTTTTTCAT GTCCATCCTT
225901 TATCCTTCTT CATCTCAAAA CATTTCAATG GAGTATTTTT TTGGAGCAGT ACTTGGATGA
225961 GCCTCTGAGT CCCACAGTAG CTGAGAATTT ATTTCATAGT ACTCTTATG ATCACTGTGG
226021 AGCCTTAAAA CATTGTAATA TTAACTTAGC TGGGAACAGA AATTTTGTTC CACAATTTGT
226081 CTTATTCAGA ACAGTATTGA CTTCCTGCTA GTCTCTTCTG ATGTCCAATA TGAGGAAGTC
226141 TAGTTAGCCA GCTACTTTTT GTAGGAGAGC TATGTTTAGG CTAGGTGCTA TAGGATTCTC
226201 TTTATCCTGG AATTCCTTCA CCAAGATGTG CCAAGGTGTT AATCATTTTC TCTTGCTTTT
226261 TGGCTGGTGG TCTTAGAGTT TCCTTCGATT TTGTTTTATT TAGTGATTGT CCTCAATTTG
226321 TTTTCTTTAC TAAGAATCTC TCTTCTATTT ATCTGTATGG TAAAACCTTG TTGCCCATCT
226381 TTCTGGTTTC TGCTGACTTT CATTTTGGA CCTTTTACTT TGCTTTCTCC ATGGACTTTT
226441 TGGTAGTGGA GGCAGGCAAA CACTTTCCAA AGTCTTTCTC AATTTCCATC AATTTCAACT
226501 TATTTCCTAA AATTGCCTCA GAATGTGCCT ATGTCCACAA TATCCCTCCT TCCACTTTAG
226561 AAAGGAAAGG CATCCACACT TTATTTAGGT GCAATGCCTG AAGTGTAAAC ACTTTCTGGT
226621 TGTCAACAAA GGAGTACTTC CAAATATTGG TTTGGGGATA ACCTGCTAAT GATTAACACA
```

Figure 1 (Page 70 of 73)

```
226681 TTCACCTTGG CTCTTGGTTT GCCTGCTCCC TCTTCTTTTA TCTGCTGTGT GTATTTTTTT
226741 TAATCACTGA GAATATGCAC AGTATTGTAT GTTTTATTAT AAGAGAGGAC TGGCCAGAGT
226801 GGGAATGTTC TGAATTCAGA ATAACTGAAG CAGTACAGGA TAGGAACTCA TTCTTTCAAA
226861 TGAAGCTGGC ATATTTTCCC AGAGCACCAA ATTTCAATAT ATATTTAAAA AACTTGATAT
226921 GAATGATACA ATAAAGTGGT TAGAACTTTT ATTAAAATAA ACTTATGTCA TGAAATACTT
226981 ATTCTAATTA TAGTCACTCT TCATCTTATT TCATCTTATA ACATGTTTAA TGTTTTCTTT
227041 TATTTACAAA ACAATTTATT TTTTGATGAA AAGTTTTAGA AATCAAGTTA AAAATATTCA
227101 AAGGAATGCC TAAAGTTTTC AAAATTCTTT TACATGTTGT ACAATCAAAA GAGTCTGAAG
227161 ACCATTTAGC TATCCAAATT GTTTATTTTT AAGCAGTATC CCTTCTAATA TTTACTATTT
227221 ATAATCCTTA AAAATTTGCC TTAGCACAGG AGAATTGCTT GAACCCAGGA GACGGAGGTT
227281 GCAGTGAGCC AACACAGTGC CACTGCCCTC CAGCCTCGGC GACAGAGTGA GACTCTGTCT
227341 CAAAAAAAAA AAAAAAAAAA AAAAAAAAAG GCCAAAAACA AATAAACAAA CAAAAAAATC
227401 CGCCTTAACA TTATTTGTTC ATTAAAAACT TTCTTTAATA CTACTAGTTT CCCTTTCCTC
227461 TCAGCCCATT GTCATATTTT GATTTTTATC ACTTGCTTTG TAGGACATAT GAGGTTTTTG
227521 TTTTTTTTTT TTTTGGAGA TGCAGTCTCC CTCTGTTGCC CGTGCTGGAG TGCAATGGCG
227581 CAATCTTGGC TCACTGCAAC CTCTGCCTCC TGGGTTCAAG CAATTCTCCT GCCTCAGCCT
227641 TCCAAGTAGC TGGGATTACA GGCACCCACT ACCACGCCTG GCTAATTTTT GTATTTCTGG
227701 TAGAGACGGG GTTTCACCAT GTTGGCCAGG CTGGTCTCGA ACTCCTGACC TCAAGTGATC
227761 CACAATCCTT GGCCTCCCAA AGTGCTATGA TTACAAGCAT GAGCCACCTG CCCAGCCAGA
227821 ATATATGTTC ATTTTGAGTC CTTTAACAAA GTCATAAGAA TTTTAGGAAT TCAGTTACTT
227881 TCTTGAGAAA ATCTCTGAAA AGATGCCAAT AATTTGTAGC CAATTATATT GATTTCTCTT
227941 TTTCATATTG AGAATTGTTT TTTAAAAAGT TTGTATGTGT GAAGATTTTT GCACTGTAGT
228001 TAAAGAAACC ACCTGTGTGT TGGTTAAGCC ATAAGTACAT GTATTCAAAT AAATTGAGGT
228061 GGGGTTACTC TGAGAATCAA AGGAAAACCT GAAGAAACAG GCAGCCTCAA AAGGTCTTAG
228121 CTGTAGCAAC TTGCTCCATT GTTGAAATAA ATAGGCTTGA ACTTGTATTT TCCCTCTACT
228181 CAACATTTAA GGTCTCAGAA GATAATATAA TTGGTGAAAT TTAAGTAAAG TGCTCACTCT
228241 TTTGCTTTAA CAAACCCTAG AGAGCTGGTA GGCAGAGCCT CAACAGACCG TTTTAGCTTC
228301 CAAAGGGAGT TCAGGACACC ATGATTCACG ACCACAATAC ATCACACATA ATTGAGAAAA
228361 GATAGTTCCA CCAAATAAAG TTGAAATGCT GACAAGAAGG GGTAAGAAAT CTTGGAAATA
228421 AGTTTATATA AAATTTATTT TTTCCTTTTT TATTGTTATG GAATAGGACC AGTTCTACTT
228481 AAGCCACCCA TTTGCCAAAA TAAAGTGAGA ATCGTTTCTT TTGGGGACTC CTCTTTGTAG
228541 CTCCAAGTGC CACTAACAAT TCTTAGGACC TGAGCTATAA GCCAGGTGAT TTCAGTTAAT
228601 ATGATCAATT ATTTCATTTA AATGGCTCTA ATGTGCAGAG GGAACGGAGC CCATCAGCAT
228661 TCCCTGCAGG GAACTGCAGT GGCTTTTATC AACTTGAACA GCTAGCTTTC AACTGTTTTG
228721 AAATCACTTT CAGGGTGGTC ATGTAGTTGC TTTTTTGAAA TCAGAAGATG ATTCTGCCTC
228781 TTTTAATATG TGACTCCTCA GATTCAGAAA GTGCTCGCTA GTCTTAAGAG TGAATTACCC
228841 TCAGTGGTCC AGCGCTTATG AACCCACATC TAACCCTATC CCCTGGGGGA ACTATCAGAG
228901 AAATTGGTGC CATGGACATA AGAGGAAGGC ACAGTGAAGC AGAGAGCCCC GCATGATGAA
228961 AATCAGTGGA CAGCATCATT ATTTACAACT TTGTAATCAC CCAGGAGCAT GAAAATCCAG
229021 GCCAATCTGG CACCATGAGC TCTAATTTTT GTTGGAGTTC TTGGAACCGA TTCTGATGAA
229081 TGACTGTTTA GCCATTTTAG AGTGTGGCAT ACGTGGCTGC TGGCATACAG AGGTTGGATG
229141 TAAACGGGCC TTTGCCCTCT CTTATGAACA TAGACAGGAA CTAAACTGTG TCACATAGGT
229201 TCCAAATGGT GGCCTGAATA CTATTTACAA CTAAGGTACA ATGAAATTGA GTAAGTCTTT
229261 TCCTCTTTTG CAGATACCAT CATTATTCAT ATATTTCTTC AAAGTTAACT ATTTGTATTT
229321 GGTAATTTTT AATAGAAATG TAATAATTGC TTCTCAAGTT TAGTCTTTAG TCTTAAGGTT
229381 GATGCTCTCC ATGTCCTTCC AAAAAAAGGT ATGTTGCTTT TATTATATCC TCGCCTTCAG
229441 ATGGGATTAT TCCATTTTGT TCTTTGTTAA TATATACTTT GAGCCACTTT TTTTGTGGCT
229501 CTGGGTGAGA TGCTATAGGT ACAATGACAA GTGATACGTG TGTTGTCCCT GTCACAAAAG
229561 TGGATAGCCT AAGTGGTGAC TTTTACCTCC ACTCCAAATA TATGTATCAC ACACCAGCCG
229621 TATGCCAGGC ACCACTCTAG GTGCTAGGGA TACAGCAGTA AACAGACAAA TGCAACCCCT
229681 GCCCATGTGA AAGAGAATAA GACAATAAAT AAGTAAAGTG CATGTTATAT GGAGGTGGCA
229741 AATGCTAAAA AGAAAAATTA AGCAGGCAAG AGGACTCATT GAAAAGATGA CATTTGGGTA
229801 AAAGCCCATG TATATATGTT CTATTGGTTT TATTTCTCTG GAGAGCCCTG ACTAATACAC
229861 AATGACTTTG AGAAGTTACT GGCTTTTGAT TTATCACACT ATTCGGAGTG CTGAGAGCCT
```

Figure 1 (Page 71 of 73)

```
229921 TCTTAGTGTG TATTCAGTGT TTTAAGAGAG CTTGTGGATG AATAATAAAT AGGACAAAAT
229981 TTATCCAAAC TTAAGCCTTG CTTTAGGTAA AAGGGCTCCT CTTACAAGGT AGAAGGTTAT
230041 TATTTGGCAT TTAAATCCAA CTGAAGACTA ATAAGACTAA TTAATTAAAA GTTTTTAAAT
230101 CACAACTGGG TGCAAAATAA ATGGAACTGC CATGCTCGCC AAGTGTGCAT GAGTGGTGTG
230161 CATGGGAGAC AGCACGAAGC TAATCCCACT CATCTTGCAG GTTGCTCCAT TTTTCTCCTA
230221 AAATCAGTAA GACAGAAGCT GGTCAGATTA TCAAGAGCCC TAGTTAAACA CAGCAGTAGC
230281 ATTTGGAAGG GGTTGCTCTC ATTAGGCAGT GCCTGACCAC AACAAGAGAT GAACAAGCCC
230341 TGTATCTGAA GCCATCATGC CTAGTTATGG TCCCCCACTG TTCATGATGC CTGAAAGGGA
230401 GGCCCCCTGC ACCCTAGAAA GCTGGGTGGG TTCTACTGTC TGCTTTACTG CTAAAAACCC
230461 TCTTCTTTGG ATCTGGACTT TACCTCTATC TGATTTTTTT TTCTAATATA TGATTTGGCA
230521 CTGAGTCTGT CACTGCTGCT AACTCAGCAG TTCTAGGGTC ATTGCCCCAT TGCCTCACAG
230581 AAAGAATTTC ATAGCTTCCA GCATCCTCTC TCCTTCATTA TACTTTGATT TCAGCATTGC
230641 TATTTTTTCT CTTGGGTGTT GCAGCTCTCT CTCTCCTTCC CATGTCTTGT TGGTTTTCTG
230701 CTAACTCCTG CTTTTTTTCT TTTTTTTTTT TTGAGACGGA GTCTCGTTCT GTCACCCAGG
230761 CTGGAGTGCA GTGGCACAAT CTCGGCTCAC TGCAACCTCC GCCTCCCGGG TTCAAGCTAT
230821 TCTCCTGCCT CAGCCTCCCA AGTAGCTGGG ACTACAGGCG CTCACCACTA TGCCCCACTA
230881 ATTTTTGTAT TTTTAGTATT GCTGTCATCA ATCCACATGT CCAGAAGCAC CTAGAAACTC
230941 TAATTCTTTG TAGGTATCAA ACCCTAGGAC TCTTTCCTCT AATCACAATA TATAATCCCT
231001 GATTCCCAAA CACGGTCTTT TCATATACAT TTTCCACTGT ACATACTTTC TGACCTGGAA
231061 AGCTCTTACA CAAACACGCC CTCCCCTAGG AAGCCTTTAT AAATGTTCCC AGGAAGAATC
231121 AGTCACCCAA CAGTGTCCTT GTCACATCTT AGGTTCTACA CCTTTATTTG TTCTATCTGA
231181 ATGTAATCTC CCAGAGGGTG TTATCATCTT TTTTTTTGAG ATGGAATCTT GCTTTGCTGC
231241 CCAGGCTGGA GTGCAGTGGC ATGATCTCGG CTCACAGCAA CCTCCACCTC CTGGGTTCAA
231301 GTGATTCTCC TGCCTCAGCC TCCTGAGTAG CTGGGATTAC AGACGTGTGT CACCACACCT
231361 GGCTAATTTT TGTATTTTTA GTAGAGACAG GGTTTCACCG TGTTGGCAAG GCTTTCCTCG
231421 AACTCCCAAA CTCAGGTGAT CCACCCGCCT CAGCCTCCCA AAGTGCTGGG ATTACAGGTG
231481 TGAGCCACCA TGTCCAGCCC CATCTTTTTC TTTTAGTTTA GTTCTTAACA AATAGTCTGA
231541 CACAAAGTGG ATATAACAAT ATTTTGAATT ATGAATAACT AAATGAATAT TTCCAGATTT
231601 CCTGGTGCTC TCAAAGTTTT ATGTTACAAA AGAAAAACAA GTCTAAAATA CCTGCCTCAA
231661 GTTTTTATCT GTACTATGAT TTCAAACCAA ATAAAAAACA GGTGGGGTAA AAACTGAAAC
231721 AGGAAATACA TATAACTGAA AAATTTTGGT ATGTTAGTAT GATAATACTA GGTCATTTTT
231781 CCTGTTTCCC CAACTTCATT TTCTATAGCA ATAAAAAGAA ACAAGTAAAT GTATATTAAT
231841 TTAATTTAAA AGAAGTAGTC TACCATCTCT TCTGTTAAAA AGAAAAAAGT ATTTTAAAAA
231901 ATTATCTCTG GAAGGATACA CAGGGAACAT TGCTCTGGTT TCTTCCAAGA GAGAAATGAG
231961 GAACTAGAGA GCATGGCCAA GTGGGGTTTT GCTTTTGTTT TTGTTTGTCT ATCTGTTAGC
232021 TTTTTATTAT TTTCTTTTGT AGGTTTGAAT TCAAACCAC ATAAATCTGT TACATGCTCA
232081 TAATAATAAG TTTAAAATAA AACTTTTGGC TGGGTGCAAT GACTTACACC TGTAATCCCA
232141 GCGCTTTGGG AAGCAGAGGT GGGAGGATAC TTGAGGCCAG GAATTTGAGA TCAGCCTGGG
232201 CAACATAGTG AGACCCTGCC TCTGTAGAAA TAAACAAAAA TTAGCTGGAT ATGGTGGTGC
232261 ATGCTTGTAC TCCTAGCTAC TTGGGAGGTT GAGGCAGGAG GATCCTTTGA GTCCAGGAGT
232321 TTGAGGCTGC AGTGAGCTAT AATCACCCAC TGCACTATAG CATGGGCAAT AAGGTGAGAA
232381 CTTGTCTCAA AAAAAAAAAA AGGGGGGGGG AAACAAATAA ATAAATATAA ACAAAACTTT
232441 TGTTTCAAAA TATGTAATAT TTAGCACTAA AGAATTCTGA ATTGTAGAGC TAAAAAGTAC
232501 TTAAAAGTTA ATAATTATTG TCTCCTTTAA AAGAATTGTT ATCAAAGTAT AATTTTTATC
232561 CAGAAAATCA TCCATATCAG CAAGCTAAAC TTTCTCAAAA TGACATATCC ATGTAATTAG
232621 CTCCCAGGTA ATTAGCAGGC AGCCTCTACT CAGGTTGAGT ATTCCTAATC TAAAAATTGG
232681 AAATTCAAAA TGCTCCAAAA TCGGCAACTT TTTGAATGCT AACATGATTC TCAAGGAGT
232741 GCTCATGGAA TATTTCAGAT TTTGGATTTT TGGATTTGAG ATACTCAGTA TAATGCAAAC
232801 ATTCCAAATC TGAAAAAATC TGAAATACTT CTGGTTCTAA GCATAAGGGA TACTCAACGT
232861 GTGTTAGCTA ATTAGACCCT TCATGGTCTC TTCTAGACCT CAGCTTCTTC AAGGTAACCT
232921 CTATCCTCAC TTCTAATAGC ATGAACTTTT CTGTTTTAGA ATAATTTGGA TTTTCAGGAA
232981 AGTTGCAAAG ATAGTACAAA GACAGTACAG GAGAGTTCCC ATATATCTTT CACCCTAGCTT
233041 TCCCCCATTG TTAGGATTTT ACATTATTAT GATACATTTG TCAAATATAA GCAACTCACA
233101 TTGATACATG AAACTCTATT AACCAAACCC TAGCTTTAT GTGGATTTCA CCACTGTTTC
```

Figure 1 (Page 72 of 73)

```
233161 CACTAATGTT TTCTTTCTGT TCCAAGGTCC AATCTGGAAT ACCACACTGC ATTTTCTTGT
233221 CATATCTCCC TAGTCTTTTT TTGTCTGTGA CAATGTCTCA GTCTTTTCTT GCTTTTCATG
233281 ACCTTAACAG TCCTGAAGAT CATTTGCTTT TTTTTCATAA TTACACCGGA GTTATAGATT
233341 TTTTGAAATA ATACCACAAG GGCAAAGGGC CCTTCTTGTC ACATCATTTT AGGGAGAACA
233401 TGATATCCAC ATGACATCAC TGATATTAAC CTTCATCATG TGGTTTAGGT AATGTTTCAG
233461 GTTTCTCTAC TGCAAAGTGA TTTTTTTCCC TTAATTTAGC CCACCTGAAC TTATCAATTT
233521 TGTTTTCTTC CATGACTAAT ACTTTTGTTA TTATAGCTAA AACTTCATTG GGGCCAAATC
233581 TTAGATCATG TAAATTTTCT TCTATATTTT ATTCTAAAAG CTTGTAATGT TTGATACATT
233641 CTAAAAGATG TAATGTTTGA TACATTACAT CTAGTCCTTT GATTTATTTT TAGTTACTTT
233701 TGTATAAGGT GTGAGAGATG TCTCCAGTTT CACTTTATTA ACACATTGTG GTGTTCCAGT
233761 ACTATTTGTT GCTAAGACTA TCTTTTTTCC ATTGATTACC TTTGCCTTAG TTGGCAATAT
233821 TTTTGTTGGT TTATTTCTAG ACTGTTTATC TCATTCCACT GATTTGTGTC TATCTTTTTG
233881 ACAAAACTGT TGATTACAGT AAGCTTTGAA ATAGTTCATT TTTTGTGTCA ACTTGACTGA
233941 GTCAGGGGAT AACCAGCTAT CTGGTTAAAC ATTATTTCTG GCTGTGTTTG TGAGCGTGTT
234001 TCTGGATGAG ATTAGCCTTT GAATAGGTGA TCCTAGTAAA GTAAACTGTC TTTCCCAGTG
234061 TGGATGGCAT TATGCCACCT GATATTCAGG GTCTGAATAG AAGAAAAGGC AGAGGAAGGG
234121 GGAATTTGGG CCTTTTTTTC TGCCTCACTG CTTGAGCTGG GACATCTCAT CTGGTCTCCT
234181 GCTCTTGAAC TGGGATTTAC ATCATCAGTT CCTCTGGTTC TCAGGCCTTC AGATTCAGAC
234241 TGAATCATAC CACCAGCTTT CCTGGGTCTC CAGCTTGCAG ATTACAGATC ATGGGACTCC
234301 TCATCTTCCA TAAATGCATG AGCCAATTCA GTCTATGTCC TTGAAAACTG CCCCACTGCA
234361 GATTAAGGCT TTTTTCCACT AGGTGAAATA AAGAAGCTTG TTAGACAGAT TTCCCTTCAT
234421 CCAGTGCCCT CTCCTCTTTA AGTTACAACA CATTGGCTAC ACCTAAGTGC AGGGGTGGGG
234481 ATGAGGGTAT AGTCCTCTTG TTTGCTGAGA AGAGAACTGT ATTGGGAAAG CTCTAGAAGT
234541 GTTGATACA TACATAAACA AGGCATGGTT TTTGCACTTA ATTTCACATT ACATTTTTCC
234601 CAGAAAAAAA GGAATGTATA GGCATCACGT AACTGTACTA GCTGGAGTCA TTCTTCCTGA
234661 TTATCAAAGG TAAACAGTTA TTAATCCTAT ACCAAGATGT CAAGGAGAAG TACTTTTGGA
234721 ACACAAGGAA TTCTCTGGGA GTCCTTACTA CTCTCAAGCC CAGTGAAAAA GTTAATGAAA
234781 AACTATAGTA CCTTCCTATA AGCTGGATGA CTAATTACCA GGCTCATTTA GGAATTTGCC
234841 TTACCAAGTA AAACATAAGG GCAGCTGAGG TGCTGACTGA AGACAAATGG AGCATAGAAT
234901 AAGAGTAGTA AAGAATGCCA AAAATGCTGT CATGTATCCA TTGACAAAAG GAGCTATAAA
234961 GCCTTTAGGT ATTTTCACAC TTGCTCTGTT ACGTAAATGT ATGTGTGTGT GTGTGTGTGT
235021 GTGTGTGTGT GTG
//
```

```
   1 CACACACACA CACACACACA CACACACACA CACAAATGAG GTATATAAAG GGTCTCCTAA
  61 AATGTCATCT GATATTTGTT ATTTCATATT CTCAGATTTT TAATCCATTT AGGTAGGTCT
 121 ATTTTAGATA GCCTTGTCTG AAACAGAGCT GGGACCTGAT GAGTGAAAAT GAGCTCACCA
 181 GAAGAAAAAT CAAACAGGCA TTTCAGAGAT TGAGGCCAAG AAGTTAAATG TCTTAAATGG
 241 GCAGAGCTTA GCTGCTTGAT GTGAAAAGAG ACCAGCGTGG CTGGAACAGC AAAGGAGAAC
 301 AGCAGAAGAG GTGAACAGAG GCCAGAGATG GTCACTGAGT GGGCCCTTAA GTCATGGTAA
 361 GGAGTATGGA GAATGAATTA TTGCATGTAT TGAATATGTA GGTGACGTGA CTCACAGATA
 421 CTTTGGATTT GTAGAGATGA AGGAAATGTA GCAAGTGACA CTCTTAGAAT GTTGATTTGA
 481 GTAAATGGTA GTGTCAGTTA TTGAACTGGG GAGAACTGGA AGGGATAACA GGCTTAAGGA
 541 GCACGTTTAT TCCTGTGTCT TGGAAGTGTT TAGGGTGAAA GACCTATTAG AGTTCTAAAT
 601 GGAGATGTCA AGTGAAAATG TGGCTACACA CATTTGCATT TCAGAAAAAA GGTCAGGCTG
 661 GAGATGTAAA ATTGGAAGTT TACTGCATAT AGATAGTCTT TGGAACCGTA GTATTGATGA
 721 AGCCATTAAT GAGACAGAAC AAAGACTAGG GACCAGAGCC AAGCTCCAAG TTTCTAAAAT
 781 TTAGAGGATA GTATAGTCTG GTCATTTTGA GGTGAATACT TAATAACAGA ACAATTTGCT
 841 GAAGTGTAAA TTTAGAGCCC TACACTTTTA GCTCTGACTA TTAACGAATA CAGGAAAGAA
 901 TGGATATGGT TATCTGCCTG GTGTCTGTGA AATAATTTAA GCCAGGAAGA GATCCTCACC
 961 AGAAACTGAC TATGCTGGCA ACTTGGATCT TAGATTTCCA GCCTGCAGAA TTGTTAGAAA
1021 ATAAATGTCT ATCGTTTAAG CCACCAGTCT GTAGTATTTT GTTATGGCAG TCCAAGCTGA
1081 CTAAGTTTTG GTACCCAGGC GTGGGATGCT GCAACAACAA ATACCTAAAC ATGGGGAAGT
1141 GGCTTTGGAA ATTGGTGATG GGTAAAGGCT GGAAGAGTTT GAGGTTCATA CTAGAAAAAG
1201 CCAATTGTGA AGGGACTATT GAAAGAAATA TGGACATTAA AGGCAATTCT GGCAAAGGCT
1261 CAGAAAGGAA GAGAGCTGGA CAGAAAGCTT CCATTTTCAT AGAAACTTAG ATTTATAACG
1321 ATCATGGATA GAATATTAAA TATGCTGGTT AAAATATGGA CTTTAGGCCA GGCGTGGTGG
1381 CTCACGCCTG TAATCTCAGC ACTTTGGGAG GCTGAGGGCA CAGATCACGA GGTCGGGAGT
1441 TTGAGACCAG CCTGGCCAAT ATGGCGAAAC CCTGTCTCTA CTAAAAATAC AAAAATTAGC
1501 TGGGCATGGT GATGTGCTTC TGTGGTCCCA GCTACTCGGG AGGCTGAGGC TGAAGAATCG
1561 CTTAAACCCG GGGGGTGGAG GTTGCAGTGA CCCAAGATCA CACCACTGCA CTCCAGCCTG
1621 GGATACAGAG CAGGACTCCA CTCCCCCCGC CACACACACA CAAAAAATAT ATATATATGG
1681 ACATTAAAGT CAACTCTTGT GAGGTCTCAG ATGAAAATGA GGGACAGGTT ATTGGAAACT
1741 GTAGAAATCA CTGTTCTTGT TACAATGTGT CAAGAACTTG GCTGAATTAC GCTGTAGTGT
1801 TTACTGGAAA GAACTTATAA GCAGTAAAAC TGGATATTTA CCAGAAGAGA TGTCTAAGCA
1861 AAGTATTGAA GGTGTGATTT AGGTCCTCCT TACTGCTTAA AGTGAAATGT GAGAGGAAAG
1921 AGCCGAAATA AAGAAGGAAT TTTAAGCAA AACACAATCA GAACTTGGAG ATTTGGGATA
1981 GATTTCTCAA TCTATATTGT AAAAATTGAG AAAGTTTTTC TTGAAGAGGT ATGGTTGAAC
2041 AATGTTTTCT TTTTCTTTTT TTTCTTGGT TTTATTTTTA TTTTTATGTT TTTTGAGACA
2101 GGGTCTGGCT ATGTCATCCA GGCTGGAGTG CAGTGGCACA ATCTCAGTTC AGTGCAACCT
2161 TTGCCTTCAG GCTCAAGCAA TCCTCCCACC TCAGCCTCCT AAGTAGCTGG GACTACATGT
2221 ATGCACCACC ACACCCTGGC TAATTTTTTG TTGTTGTTTA TAGAGATGGG GTTTTGACAT
2281 GTTGCCTAGG CTGGTCTCTA ACTCCTGAGC TCAAGTGATC TGCCCTCCTC AGTCTCCCAA
2341 AGTGTTGGGA TTACAGGCGT GAAACACTGA GCCTAGCCTG AACAACCATT TGATAAAGAG
2401 ATAATGGGTG TGACCCAAGG ATTTAATCAG CCATCTCAGC AGAAGCCAGG AAGAGAGATG
2461 GGATTATTCC AGCAGAGACA CTGCCAATTT AAACTAACGT AGGCAGAGAA AACAGAAAGG
2521 AACAAAGGAA GGTTGTCGAC TTTTTGAATT CTATAGAACA GGATCATAGA GCTACCTGGC
2581 TGTCAATGTG TACTATTCTT TAAGAAAAGG AAAGACTGAC CCACCAAAGG CAACTTACAA
2641 GATCACTAGG GCTGACTCTT TTTTGTTTTT TCTTGAGGCA GTCTCACTGT CACCCAGGCT
2701 GTAGGCAATG GTGTGATCT CAGCTCACTG CAATCTCCAC CTCCCAGGTT CAAGGGATTC
2761 TCTTGCCTTA GACTCCCAAG TAGCTGGGAT TACAGGCTCT AAATCTGTAC CCTCCCGAGT
2821 AGCGCTCCTG CCACCACTTG CCCAGCTAAT TTTTGTATTT TTAGTAGAGA TGGGGTTTCA
2881 CTATGTTGGC CAGGCTAGTT TGGAACTCCT GACCTCCAGT GATCCATTCT CATTGGCCTC
2941 CCAAAGTGCT GGGATTACAG GCAGGAGCCG CCAGGGCTGC CACTTTGATG TCAGACTCAG
3001 AGAGTACAGA TGGGATAGGG TGGGGGTGGG AACATGTAGT CAAGGCTGAC TCTACCTGTT
3061 TCAAAGATGC CCTGCAGAAC TGTGTGGGAG TCTCTCACAG ATGGCTGCCT GGGTGGGACC
```

Figure 2 (Page 1 of 74)

```
3121 CCACCAAACT GAAAGACCGA GACTTCAGGC AGGGCAGATG GAGTAGGCCA ACTACAGAGC
3181 CAGAGGTGAC ACTGAGACAC CACTGGGCCT GGAAATCAGG GCATCAAGCC AAAGAGGGTT
3241 TTTCTTAAGA CCTAACAGAA TTTGCCTTGC CAGGTTTTGG ACTTGATTAG GACACATTAC
3301 ACCTTCCTTC TTTCCTATTT CTCCATTTTC TAATGGGAAT GTCTATTATG CCTGTTTCAC
3361 CATTGTACCT TAGAAGCATG TAACATTTCT GGTTTCACAC GTTCAAAGCT GGAAAGGAAT
3421 TTTGTCTCTG GATGAATCAC ACATTGAGCC TCACCCGTAA CCTGATTTAG ATGATTTTTT
3481 AGATGACACT TTGAACTTTA GAATTGATGC TAGAATGAGT TAAGACTTTC AGGGGGCTGT
3541 TGGGATGGAA TAATTTTTTT TTTTTTTTTG AGACGGAGTC TAGCTCTGTC GCCCAGGCTG
3601 GAGTGCAGTG GCACCATCTT GGCTCACTGC AAGCTCTGCC TCCCGGGTTT ATGCCATTCT
3661 CATGTCTCAG CCTCCAGAGT AGCTGGGACT ACAGGCGCCC GCCACCACGC CTGGCTAATT
3721 TTTTTTTTAT TTTAGTAGAG ATGGGGTTTC ACCGTGTTAG CCAGAACGGT CTCGATCTCT
3781 TGACCTTCTG ATCCGCCTGC CTTGGCTTCC CAAAGTGCTG GGATTACAGG TGTGAGCCAC
3841 CATGCCCGGC TGGGATGGAA TAAATTTATC TTGTATGGGA GAAGGACATA CATTTTGGCA
3901 GGTCAAGGAC AGAATGTTAT GGACTAAACT GTGTCCCCCA AAATTCATTT ATTAAAACCC
3961 TAAACCCCAG TGTGACTGCA TTTGGACATA GAGCCTTTAG GGGGTACATA AAACTAAAGA
4021 TCACAGGATA GGGCCCTAAT CCCATTGGGG CTGGTGTCCT TACAGAAGAT GAGACACTTA
4081 GAGCTCTCTC TCCACGCAGG CACCAAGGAA ACACCATACA AACACACAGT GAGATGGCAG
4141 CCATCTGTTA GCCAGGAACA GATTCTCACC ATAAACTATG TTGGCACCTT GATCTTAAAC
4201 TTCCAGGCTC CAAAACTGTG AGAAAATGAA TTTCTGTTCC AAGCCTCTTA GATATGGAAA
4261 AAAAGATTCT GTTGTTTAAG CCATCCAGTC TCTGGTATTT TGTTATGGCA GCCTGAGTAG
4321 GCTAAGACAA TGAAGGATGT GGTAAAACTT TACGTCCCAA CCACATACCA AAGAGGCTGG
4381 AATTTAGCAT GCTTTCTTCT TTCAACTGTA GGCAATGTGC ACAAGTTCTA AATCCTAAGA
4441 CATGTTGGCT CCTTTACTCT GCCCAAACTA CAACTCAAAC AAACAACTGT AATATAATAA
4501 CATCCAATGA AGTTCTGACA TTTCTTCAAC ATGAGTACAG TAATTCAATG CCAGAGAATT
4561 CATTTTATTT TGAAATCTAC ATGCCATATT CCAATTTCTG TTGAAGATGC AATGGTTATA
4621 TTTATTCTTT TTAATATAGA TTTATCAGAC TGGGCGCGGT GGCTCATACC TGTAATCCTA
4681 GCATTTGAGA GGCTGAGGTG GGCATATCAC CTGAGGTCAG GAGTTTGAGA CCAGGCTGGC
4741 CAACATGGTG AAACCCTGTC TCTACTATAA ATATAAAAAT TAGCTGGGTG TGGTGGTGCA
4801 TGCCTGTAGT CCCAGTTACT AGGGAGGCTG AGGTAGAATT GCTTGAACCT GGGAGCAGGA
4861 GGTTGCAATG AGTGGAAATC GCACCAGTAC ACTCCAGCCT GGATGACAGA GCAAAATAAT
4921 AAATACATAA AATAGATTTA TCAGTTTATC AATAATATAG TTTTCTTTTC TAGGTGTAAA
4981 TATAGGTAAT GACTGTCCTT TAGTACATTT TCTCATGATG CTCCTCTTAC TTGGTTTGGT
5041 ACAATATTAA GTATTGAAAT AAAATAGAGA ATCCTGTCGC TACACATGAG CACTTATTCC
5101 ATTTGCTCAT CTCCAATATG CACGGGAAAT TCTCAAATTG CTAATAATCT TGTAACACAC
5161 ATGCATTATA TTCAACAGGA ATATATAAAT TTATAATTAT AATTTAGGAT CAACAGATGA
5221 CAAACCTTTA GAAGGTTTGT ATTTAACCTT AAAATATAAT TTTTTAAAAA TTGGTTATAA
5281 AATTTCTAAT ACTTTCTTTT TTGTGACCTC AAGGGGAAAA TATAATTCTT ATAAAAGTTC
5341 AAATGATTTA CAGAATACAA AAAGTGAATA GAGATGATGA ATGAATTAAA GGAAAGGATA
5401 TTGCTACATA GATTTGGAAA TTTAAAAAGG GAAATTACGA TTGTTGATTT TGTGTTAAAC
5461 TGATCTGCTT TGTTCAAGAT ACCTTATGTA CCAAAAAATG ATTTTATCTC AGCCTCATAT
5521 CTCAGTAAAT TCCTGAGACA AACTTTAGTC CCTGGTGCCC AGGTGCCTTT GGTAATTGGG
5581 AGACCTCTAG GTTTAGCATC CTCATCCACT CGCCCCAATT TAAATAGTCC TCCCCAGGGC
5641 CATTCAGGCA AGGGAGATGA AAACTTGCTC AAGAGTTGGA ATCCAATTGA AGCTACCGAA
5701 ATTCATTGCT CAATAGATAA TTTTCCCTGG AAGTAACTAG GGCTTTTGAA TATAATAGTG
5761 GGCATTTCAA AGTAGAAGGT AAAGTATTTT GGAGATGAGG AGACAGGACA GAGCTACGAG
5821 GAATGTCCTT TGCTCAGGGA CTAGGCTCTT AGCAGTACCT CTTAGGTAAG AACTGGTTAA
5881 CTGGCACCTT CTGTGTTTCT CTGAAGCTCC CTTTGCTTAG GGACTAGGCT CTTAGCAGTA
5941 CCTCTTAGGT AAGAACTGGT TAACTGACAC CTTCTATGTG TCTGAAGCTC CCAGAACAAA
6001 CTGCCAATGA AATTTGGATT TTTGGAATAT AGTTTCTTTT TGTTGTTAC TTTTTGTTTT
6061 GTTGTTTTTT TTTGAGAGTC TCACTCTCAC TGCAACCTCC CCTCCTATA TTCAAGTGAT
6121 TCTCTTGCCT CAGCCTCCCG AGTAGCTGGG ACTACAGGCG TGCACTAGCA TGCCCAGCTA
6181 ATTTTTGTAT TTTTTAGTAG AGATGGGGTT GGTTTTTTTT TGAGACAGAG TTTCACTTTG
6241 TCGCCCAGGC TGGAGTGCAG TGGCACGATC TTGGCTCACT ACAACCTCCA CCTCCCGGGG
6301 TTCAAGTGAT TCTTCTGCCT CAGTCTCCTG AGTAGCTGGG ACTACAGGCG CCTACAGGTG
```

Figure 2 (Page 2 of 74)

```
6361 AACACCGCCA CACCTGACTA ATTTGTGTAG TTTTATTAGA GATGGGGTTT CGCCATGTTG
6421 GCCAGGCTGG TCTCAAACTC CTGACCTCAG GTGATCTACC CACCTCAGCC TCCCCAAGTG
6481 CTGGGATTAC AGATGTGAGA CACCAGATCA GCCTCAGAAG ACATTTTCTA TTGGAAAGAG
6541 AAAACACTAT TAGCAACCTA TTAGTCTAAT ATTTAATACT TAATGTCTTC CTTAGTAATA
6601 AACCAACTCT CTACAACAAA GTGCTTCCTG GCTGCCTAGT CATTGATTCA TTCAGTTCAA
6661 CATTTTCTCA ATGCCCAACA GCCAAGTGTC TCCTGTATGC CAAGTTCTAT GCTGATTATC
6721 AGTATTTGAA TAAGAGGGGG TCTACATCTT AAGTACTGCT TAAGATGAAA GCCTCTAGGT
6781 TAACAAACTT AACACAATGT ATCATTCACT ACTAAATAGA CCGAATACAA AATCTTGTTA
6841 TTGGAGCCCA GAGAGAAGAA TTGAAATTCA AGTTTTCTCT CTCTCCTTTT CTCACTCACC
6901 ACAATAAGTC AGTTGCACCA AGTCTTGTAG CTCTTTACTG AGCCATGTTT TCACGTGTCC
6961 CTTTGTTTTA TTTGCCACAC CCTAAATAAA AATTGTACTG GCTTTTTTTC CCTGGGTTTA
7021 CAGTATTAAT ACATTGTCAA GATTTACCTC TTCGTGTAGA TTCCCTGGGG AAAATTACCT
7081 TTCCTCCTTC CCTTAAATTC TTCAGAGGTT AGAAAGCCAT TAGTAACATT CTGGTATGTG
7141 GACAAAGTTT ACCCATTATG TATGGATGTT TTACTCTTTC CATTTTTCTG ACAATAATCT
7201 CTTAAGGAGG TGTGGTTATA GAATAGTCAG CTGTTATAAG TACTGTTTTC CTGGCCTTAC
7261 AACTTAAATT CTTTAAGCTG TTTCTTAGTT TGCTCATCTC AAAATTCGGA ATAAGGATAA
7321 AACCTATCTC TTAGATTGTT GGATTAAATG AATTAACATA CTGGAAGCTC ATGAAATGTG
7381 CCTGGCACAC AGTAGTGCCT AATAAACCAT CTCTCTTATT CAGCCTGTTT TCTGATTTCA
7441 GAATCTACAC TTGCTGAGCC AGGTTCTTTT CATTTCAAGG TGAGCAAAAG CATACAAGGA
7501 AGAGATGGAG GTAGGAAGAG ATTAAGCCCT AGGCCAAGGG AGCTGGAATC AAAGGCAATT
7561 TGGTCAGTGA ATAAAAGGA TTCCAAGGCC CATAAGGCAA TTCTAACCTT AGGATCGAAA
7621 TTCTCGGACA TACAGGAAAT GCTGGGGGGG GGAAAATCCG GTCTTCTCAG CCCAAGAGCC
7681 ATGTGAAACC AGACCTTCAA ATCTGATGAT TCTCAGCCCA GCTGCCCATT AGAATCGTTG
7741 TAATTTAAAA ATACCCTCGG AAAATTCTAA TATGTGGCTA TCAAAGGTGA TCATTTGCTT
7801 TTATGCCACT TTGTTTTCAC CCAAATGGGA CATCCAACCC TTTTCCTTTG AGAGTAGTTG
7861 TAGGGAAAGG AGGGGGTGGA GGGAGGGAAG AGCGGAAAAG GCTGGATCCG CCCCGAGCCG
7921 GTGTCAGTAT CTGGGAAGTG GGAGGCGCGT CAGCAGTAAA CAGCTTCTGC TAGGATTATT
7981 ATCTCCTGCC ACACACTCGG ATTTGAAGGC TCCAAACGAA ACAATGCAAA ACGCTTCAGT
8041 GGAGTTCCAG AAGCGTTAGA CTAAACGACT GGGTCTGTTT GGCCAGTCTG AGCAGCTGGG
8101 CGCAGATGCA TAGGCAAGAC TTAGCCCGCC TAGACTTTTC TGCCCACTTA ATTCCGATCA
8161 AAGCAGAAAC CGGCCGGGCG CGGTGGCTCA CGCCTGTAAT CCCAGCACTT TGGTAGGCAG
8221 AGGCTGGCGG ATCACCTGAG GTCAGGAGTT CGAGACCAGC CCGGCTAACC TGGTGAAACT
8281 CCGTTTCTAC TGGTGGCGGG CGCTTGTAAT CCCATCTACT AGGGAGGCTG AGGCCGGAGA
8341 GTCGTCTGAA CCCGGGAGGC GGAGTTTGTA TGCAGTGAGC CGAGATCGCG CCACTGCATT
8401 CCAGCTTGGG CAACAGGAGC AAAACTCCGT TCAAAAAAG CAAGCAAACA AACAAAAAAA
8461 TGCAGAAACC GAGATCCGGA AGAAACCTC GGCGAGATTC ACAGAATCCA GGAAAATAGG
8521 TCTCTAGAAA TTTGTCCATG GTCCAGATC TCCATTTCTT GTGGGTGGGG CAGCTGTTAC
8581 CAGATCCCTA GAAGCAAAGG TTTTTTTGGG GGACCGTGTC TCACTGTTGC CCAGGCTGGA
8641 GGGCAGTGGC ACGATCTCGG CTTACTACAA CCTCCGCCTC CCAGGCTCAA GCGACTCTCC
8701 TGCGTCAGCT TCAAGAGTAG CTGGGAGTAC AAGGTATGTG CCACCACGCC CAACTTATTT
8761 TTTTATTTAT TATTTTTATT TAGTAGAGAG GTGTTTCACC ATGTTGGCCA GGTTAGTGTC
8821 GAAGTCGTGA CCTCAGGTGA TCAGCCCCCT CGGCCTCCCA AAGTGGTAGG ATTAGAGGGG
8881 TGAGCAGAAA GCAAAGGTTT TTGAGTGGCC ACAGGCCCCA CTCTATTTCC TTTTCTGCCT
8941 GTAATGCAA CCTAGACGCT TGAGCTTCTT AAAATACAAG AGTAAGTTGC ATGTCAGGCA
9001 CCGTTCTACA TTAGGGACAT TAGTCTGTTT TACAGACACC TTTCAACTCC CTGGTTAACT
9061 TTTAGGTAAT ATACTCTGCA CTTTAGCAGG AATGGAACCT ATAACTCTCA CAGAATTAGG
9121 AAAGTGAGGC TGCCTACAGC CTAAATTGAG AAAAAAATAG ACGGGGACT AGTCGGAGGA
9181 CCAAACAAGG TTACCAACAC GTTAGAGTTT TGCCTTCAAT TTACATTTTT AAAGTAATCA
9241 CAACGAAGTG TTTAGATCAC GAGGCATCCC TGCATGTAAA CTGTTAGGCA CTAACTATGG
9301 TCGATCTTAC AAAGCATTAA CTAGAATATT TCTTTAGAGT ATGATAGTAC GTAACTGACC
9361 TACTATTACA TACAAACAGA CCAACCTTTA GTAACAGCGC TCCCCAAAAA CCGAAAAGCA
9421 GTAATACGCT TTGCTCAAGG TTGGCATAAA ATTAACTTAC CTTAGTGCCT TTTTTCCTTC
9481 TACCTACAAG CAGTGAGGTT AGCTCTTCCT TTGAAACGGT AGGGGGCTC TGAAAAGAGC
9541 CTTTGGGTTT GATAGCGTTT CCGGGAGCTC AGATACCTGT CAAATCACTT GCCCTTGGCC
```

Figure 2 (Page 3 of 74)

```
 9601 TTGTGGTGAC TCTCGGTCTT CTTAGGCAGA AGCACGGCCT GGATGTTAGG AAGGACGCCG
 9661 CCCTGAGCAA TGGTCACCCG GCCTAGCAGT TTGTTGAGCT CCTCGTCGTT GCGGATGGCC
 9721 AGCTGCAAGT GGCGCGGGAT GATGCGAGTC TTCTTGTTGT CGCGAGCCGC GTTGCCGGCC
 9781 AGCTCCAGGA TCTCGGCGGT CAGATACTCT AACACCGCCG CCAGGTACAC CGGCGCGCCT
 9841 GCCCCAACCC GCTCTGCGTA GTTGCCTTTA CGGAGCAGGC GGTGCACTCG GCCCACCGGG
 9901 AACTGGAGAC CAGCGCGAGA AGAGCGGGAT TTCGCTTTGG CGCGAGCTTT GCCTCCTTGC
 9961 TTACCACGTC CAGACATTGC AATCAGACAA AAATCACCAA AACCAGCAGC TAAGCTCAC
10021 GAGAAAACAA ACAAAATCAA GAAATATGTA AAACATGGCC GCTTTTATAG GTAGTTCCTG
10081 GGGAGTAAAT CCGACTTTTT GATTGGTCGG TAGCAAATGC TAGTCAGATA GCCAATAGAA
10141 AAGCTGTACT TTCATACCTC ATTTGCATAG CTCTGCCCAC GGATGACAAC TGTGTAGTTT
10201 GTCTTCCAAT TAACTAAGAG GTACTCTCCA TCCCTCATTA GCATAAAAGC CCTATAAGTA
10261 GCAGAAATCC GCTCTTTACT TTCGACACAT TTCTGGTGTT TTAAGATGCC TGAGCCAGCC
10321 AAGTCTGCTC CCGCCCCGAA GAAGGGCTCC AAGAAGGCAG TGACCAAAGC GCAGAAGAAA
10381 GATGGCAAGA AGCGCAAGCG CAGCCGCAAG GAGAGTTACT CTGTGTACGT GTACAAGGTG
10441 CTGAAACAGG TCCATCCCGA CACTGGCATC TCTTCCAAGG CCATGGGCAT CATGAATTCT
10501 TTCGTTAACG ACATATTTGA GCGCATCGCG GGCGAGGCTT CCCGCCTGGC GCATTACAAC
10561 AAGCGCTCGA CCATCACCTC CAGGGAGATC CAGACGGCCG TGCGCCTGCT GCTTCCGGGA
10621 GAGCTGGCCA AGCACGCCGT GTCGGAGGGC ACCAAGGCCG TCACCAAGTA CACCAGCTCC
10681 AAGTAAACAT TCCAAGTAAG CGTCTTAACA CCTAACCCCA AAGGCTCTTT TAAGAGCCAC
10741 CCAGATACCC ACTAAAAGAG CTGTGGCCAG ACGCCAAATT TTATTTGGCG GCGGAGGGGT
10801 ATTAGAATGT AGGAACTGGA GAGGGTGGG GACAAGTGTT GCAGCTTAGA GAGGGACAAA
10861 GGGTCCTGAA CCCGAAAGAA GCCAGCCATT AAAAATGGGT TTGGGGTCAA TTCGTTGTGC
10921 TTAAATTTAA AATGGGGACA AGCGGCCATT TTGCTAACTC GGCGTTCCCG GAAGAAACCG
10981 CAGGCTCGCT TAGGTTTCAG ACCCAGCTGT CTGTCCCTGT CTACGTCGCC AGGATCAACG
11041 GTTGCCGTAA TGTCATAATT TCGCCACCAG CTTCTAGCCA ATAGGCTGTC CTGTCATTTT
11101 AAATATTAAC CAATCGAGGG AAAGCTGTTT TGAGACTCTG ATTTACATAG CGGACCGGAG
11161 TGGGAACCTG GGCAGTAACT GCCTAAGGAA GGACTCCCCC TCTGTTTTCG TGGCGCACAC
11221 CTTCGTAGTA TACTGAAGGG TGTGTCTCCT GGGTTTCCAA CTGCCCCGGT AATAGTCTTT
11281 TAACCTAATA TGCGTCAGTT TTGATAACAA CACTAAGGCA GTACAGAACT AAAGATGTAA
11341 GCACTGCGCC AGATGTTGCT TCATACATCT TATTCTATTC AACTGGTTTA TTCAAGATTC
11401 AAATCAAATC AAATTTTGCT TGAATCCCAG TGCTCAGTCA GCCATAAATG GTGTGTTGCC
11461 TGATTGAAAC TTAAAATCTC CGTAGGGGGC TTGTAACATG CAGAAAAGTT TGAAAGTTGC
11521 TTTAGGAGAA GCCAACTCTT AACTGCTGGG TAAATTGACA AGCCTTCGAA CACTGAACTG
11581 AAGGCCAGTA AGGACTAGGC GCTGGGTGGG GGAGAATGAA GAGGAGACGT CATTAAACTT
11641 AGCACATACA CTGTGTCTCC TAGAGGACTC TCCCTTCCTA GACAACTGCA GGCCGCTTTG
11701 TGGCCTGGGA AATTCCACAT TCCCTTAAGT ATTTTACTCA TGGTCTTTTC CAGGTAAAGA
11761 TTTTAAGATG AAGGGTTAGA CGTAGTCTAC CTATCTTTTT ATTCAAGTCT AGAACACGTT
11821 TTTAGCACCT AGAAGTTTGC TTTCTCCATT AAAAACCGGG AATATACAAT AAATAAAATT
11881 AGTGTTAAAG CAGATTTTTA CAAACTTAAA TACCATGTAA TTTAGGTTAC AGTTACTTAA
11941 CATAAGGACT GTGTGATCTT AAATCTGCAA TTTCTTTCAC ACCTGGGAAA TAAACTAAGG
12001 CCTGTCTTTG GTGCCAGACA AGGCCTTATA CTTGAACACT GCTGTGCAAT CACAGGCTGC
12061 CTTGCCTAGA TAACTTATCT GAGAAATTCT GATGAGAAAT GAAATTTCCA GAGTCCCTCA
12121 CAAGTAAATT TTTTTTTCTT TTTTTTTTT TTTGAGACGA AGTTTCTCTC TTGTTTCCCA
12181 GGCTGGAGTG CAATGGCGCG ATCTTGGCTC ACAGCAACCT CCGCCTCCCG GGTTCAAGCC
12241 ATTCTCCTGC CTCAGCCTCC GGAGTAGCTG GGATTACAGG CATGCGCCAC GACACCCTGG
12301 CTAATTTTGT ATTTTTAGTA GAGACGAGGT TTCTCCATGT CGGTCAGGCT GGTCTCGAAC
12361 TCCGGACATC AGGTGATCTG CCCGCCTTGG CCTCCCAAAG TCCTGGATTA CAGGCTTGAG
12421 CCACCGCGCC GGGCCTAAAT GGTTTTTTTT TTTTCTATGC CTCTAATGGA CCTGGTCACT
12481 TATTCCCATT CAGACTGACC GCTCTCCTAC CTGCCAACTA ACTAATCAGT GTAACCAAAA
12541 TCTGCAAACA AAATTCAGTA TTCTTTCCCC GCCTTTTCCC CTTTCTCTTA CATAGATTAT
12601 GTTTTTGCCT GTGTTAGATG AAATAATTCT ATTGCTTGTT CTCTCTTCTG TACAAGTACC
12661 CAGTAAGCAA ATTATTAACT TCTTGGTCAT TTATTTCTGA ATTTTCCACC AAGCACAGTG
12721 TTATGTGAGT CATACAATAA GAACCAACAG AAATGTGTGT CTTGGAAACA GGTTGTCTAT
12781 CCCTGGACCC TTTGAGTTTT CTGTTCACTT TCCTTTGGCT TTGCATGCT AAAAGTTTAT
```

Figure 2 (Page 4 of 74)

```
12841 CGTCCGCGTT TGTTTGTTTT GGTTATTCTA ATTGGACTTG GCTGATTGGT TGCATATTGG
12901 TGGCAGTAGT AGAATTTGAA TTCTGGTTTT CTGGTCACAT CATTAAGTGA TTAGTCAGTG
12961 GAGAGGACAG GAAATCTGGT TTATTTATTA ACCTTTTTTT GGGGTGTTTT TGTTTGAAGA
13021 TGTTGATATT CTCTGTGAGG ACACAGGGTT AGAGTTGGTG TTTTTCTTTC TGACTTTACA
13081 TGGGATTTGA TGTTTTGTGC TTGTATGCCT CTTTCCACCT TCCAAAACTT GTCTTTTTTG
13141 AGTCCAAATA GTTGTCGATA TCTGCAAAAC CAGTATTCCT GTGTTAAGAT GATATGAATA
13201 TAAAATGGCT GCCCTGTTAT AACTTTTGAC TTTAAGAAAG TGTTAGGACT AACAGGAGAC
13261 AAAAAGGAAA TCAAGGAAAC CAAATGTCTG GTCTCAATAA CTGCTATGGC AGAGGCTCTA
13321 CAGCTTATTA TTAATTTTAG TAATTTCACA TTATTGCCCC TTCACGTTCT TTAAGTAAGG
13381 TTAGAGGACA GAAGAAACAT AATGTTGTTA CAAATTGGAC TATTGAGTCA GGAAAAAAAA
13441 AGAGTGCTTT CAATATCTGA ATAAAACAAA GATTTAATAT TTTCTAAACC TTAACGAGTT
13501 TATTGTAAGG GATGTGATGC TGGAAACTAG GAAACTAGAA TTTTCTTCTA AACTGAGAAT
13561 CAGAATTATT CATATTCTCA GCAGTGGTGC CACCTGAGGG ACTTCTGATC TTAATTACAT
13621 ACTTTTATTT CTTTAACTGA TCAACATGCT AAATAGATAA CCTATGGCTC TGTTTTACC
13681 CACTTTAAAT TCTGTTCTAT TAGCACGGTT AGCTTTCCTA ATTGGCAATA AGATTGAGAC
13741 TATCTTTTTT TTTTTTTTGA GACAGAATTT TGCTCTGTGG CCCAGGCTGG GGTGCAGTGG
13801 CACAATCTCG GCTCACTGCA ACCTCTGCCT CCAGGGTTCT AGCAATTTTC TGCCTCAGC
13861 CTCCCCAGTA GCTGGGATTA CAGGTGCACC ACCACGCCTG GCTAATTTGT GCATTTTTAG
13921 TAGAGATGGG GTTTCGCCAT GTTGGCCAAA CTGGTCTCGA ACTCAGGTGA TCCACCTCGG
13981 CCTCCCAAAG TGATGAGATT ACAGGCGTGA GCCACCGTGC CCAGAAAAGA CTATCTTATT
14041 TTATGAATTT AAATAATTGT GAAATTATCC ACTTAAGGGA ATTAATAAAT TATAATGTAA
14101 TCTTAAATTT TAGTTGGCTT ACATAAAGAC TTAAAATACA TCAATTTAAA TAAAAACTCA
14161 TTTGTCTAAA AAAAAATCAA AAATTTTCCT TGTGCTTTAA ATGTGCTACC TCTTTAAGTT
14221 CTAATTAAGA GAAAAAAAGT TTAACTGTGA GTTTCATTAG TGGTCTTAGT TAACAGCTTA
14281 AAGTATTTTG TAAAAAAAAT ACTTCACAAT TTTTAAATAA CTTAAAAATA TTAATACCTC
14341 TTTTATTAGG TTTTTTTAAT AAGGAAAATA TATAATACAT CTAATCAAGA TTATTTTTTG
14401 GACAAATTGG CTTAATAATT TCATTTTAAA AATGGCTTCT TTATTCTTAT ACTGTAAAAA
14461 TAATATTAGC AGAATATTAT AGTATACACA AGTTTAGGGT TCATATTCTA AAAAACAAAA
14521 ACAAAAGCTA ATTTAACTTG CATTTACTAA ATTTCTTCCA CTAGTTGTAC TGGTTACATG
14581 AGTTAACATC ACTTTATTTA TTATTCTAAA ATTGTAAATT ATTCATTGAA CCAAATTAAA
14641 TGATAATAGA TAATGTCATT TTTAAAAATG GAATTAAATT TTATGTTACT AATTATAAGG
14701 ATTCAATGTG TGAGCTTAAG TACTGAGTTC ACAGTGTATG ATAACTTTAA GAATTTAGGT
14761 GAATATTATT AAATTGAGTA AATTAATTCT CAATCTTTGG ATACCTGGAC AATTTCTAAA
14821 TTGGAGGGTA CAAAATACAA ATCACAAGAA ACAGTGTAGT TTTATGCAAA TAACATTTTT
14881 ACACAGTTTA GAATAACCAT TGATAAACAG ATAAGAGAAC ATATGATTGC CTTAGAATAG
14941 ATACTGTTGC TTTCGCCACT TTAGATTTGT AAATCATGTA CTGTATACGT GTGGGCGTAG
15001 AGGACCATGC AGGTTTTGGA TGACTGCCTC TGTTTTCGTC ATGCCTATGC GGGAACACAA
15061 TTGCCTGCTT TGTTTAAGGG CTATGGTTAA TCCAAACAGC TCTGACTCTA TCAAGTACTA
15121 TAGCTACAGA GAAACACAAG TAAGCATTCG AGATAATGAC TACCTTGAGC CTTTACTTAT
15181 TTAAAAAGTT GTTACTGTTT GTTAATGTGG TACATTCAAT TTACTATGGA TTGTCACTCT
15241 AAAATAAGAC TTCAATCTTT TTCTTATTTT TATATAGCCA TGATTTATAT TCATATCTTA
15301 ATGTAATAAC CAATCTTCTC TGACAACATT ATAACAATGC TGGAACCTCC ATTTTCAGTA
15361 CTTCAAACAA CAAATACTGC TTTTATACTT CAGAGCAGAT GGATATGTGC TTCCCAGTGT
15421 AAACACATTT GGAATCTCAC TGAGAAATAC ACTATCACTA AAAATACAGT TCTGAGATTC
15481 ATTAAAAGAC CTCCAGAATT CTGGAAGTAG GAAGTTTCCT CTTCAAAGTC TACAGAGGAA
15541 GACGAGGTCT GAAATAGACA GCTTCTTCCT TCTTTTACCT GTGGTATTAT TCTGTTTTGT
15601 CCTTTTCTCC ATTATCTGTC TTTCCAGTGA TGAAATTTTG ATCTGGCCCT CCCAAGTATT
15661 AAAAAACAAG CAAATAAACA AATCTCAGTT ATATTTTACT AAGATATTGG CATGCTAACT
15721 TTTTGCAGGT TTGTAACAAG GACCTTTATA ACTTGACTAA AAGTTCCTAA ATAAGAATAT
15781 TTACTAGAAA ATTTATTTCT GCCTGTGGCC CACATTTGAG TCAAAATAAT CAATTAGGAA
15841 AAATGAACTT GTTTAACTAA AGTTGGCCAA ACTGATCTTT GAGACCTATT CATCTAAGAC
15901 AAGCCAATTA AATTCTTGGA GACAATTTGT ACTTTAAGGA ATTCTTATAA TATTTGTAAT
15961 TACCCTCATA ACTTTTTTTT TGCCCTACTT CTGTGCTTCT CTAATATGCA GATTATTAAA
16021 TGTTGTTACA AAGCCATTGT CAAAAAAACA AAAACAAAA AACTAAACAA ACTCACATGG
```

Figure 2 (Page 5 of 74)

```
16081 TTAGACTTGC TCCTTTATGA GATATTTTTA CCAAAAATGG AGGAGTTGAA AAACTCTGGT
16141 GCCAGAAATC GTGAAGACAT GGCCTACCTA ACTTGGAAAT GTTGGTTGTC AGTGGAAAAT
16201 ACTACACAGA GATAGCCATA GTGCTGCACA GCCAATCTTA AGTGTTTCTA GAGAATCACT
16261 AATTGTTTCT AGAGAATCAC TAATTGTTTT CTTTTAACAT TCTTGGTTTA TACAAGAAGA
16321 GAGTATCCAT ACTAAACTCT TTTCTACTGA AAATAATGTG CAAACATAAC ATCCTATTCC
16381 TAGACAGTTT GTAGTTTTTT TCTCCCATTT CTATTTTATA AATCATCTTT TTAAAATACT
16441 TTGTTGAGTG AAATCAGTCC ATTGCTTGAT ATACCTTGAG CACAAGTAAA TAGTATGCCA
16501 AAAATTAAAT GTCTTTCAGT CACAGTTTGA CAAACTCAAC TACCCTGAGC CTATAGAGTG
16561 GTAATAATTG CCCTACTCAT AAAGATGGGG TGAAGATTAA ATGAAATAGC ACCTATAGAA
16621 CACTAGTTCC AGACGTGGTA TCATGCTAGT AAAATGGCTG CACAGCACTG CTCAATGATG
16681 ACAAAAAGTG AAGCTTCTGG AGACAGACTC CAAGTTTGAC TCCAGATCA CCACATATAA
16741 GATGTGGGAC TCTGAGGCAG GTCATTTAAT CTCTCTGTGC ATTAGTATCC TTCTCTATAC
16801 CTTTACAGTG ATGGTAATAG CACCTACCTT CTAGAAGTAT GTGAAGATTA AAGATCCTTA
16861 ATGCATATAA ACCACTGTGT TTACTGCTGT TTGACAAATT TTATTTATAA CCATCTTTAC
16921 GCTCCTAAAA GGACTTGAAG CAGCTTATGA CTGAAGACTT TGGTAGGAGT TGGCCTTCTA
16981 TAAATTATAA GAATTTCATA AATTATTTGA TATGAAAATG CCAGTTGATC ATAGTATGTT
17041 TACCGGGGTC CAACAGGTTG AGAAAAAATA CACTTTTTTT CCCTGAACAT ATGAAATTAG
17101 CTCTCTAGGC ATATTCCTAA GGACTTAAAG AATGATAACT ATCATTTCTC TTAAATCTTC
17161 CAGATTTGGA AGGATATATA TATTCAGCAC ATTGACAGAC AATCCCAGTA GTCCTAAATT
17221 AAAAGACATT AAAAATTAGT GAAACTTTTC CTACCTTTAG CCTGTGTAAT CCTGGATGAC
17281 CAAGCATAAA ATTAAATTGA GTAGAGTATA CCACTGTAAC ATTTCCTGAA AGGTATTCTA
17341 GGCTCTGAGT AATTTCTTTG GGGTCTGAAG ATCAGTTTGA CATATCCTCA AGTATCATGA
17401 GTTCATTATA ATTAAGAAAA AGGGAGTAAA TCTGGAGAAT GAGCCACTTT CTTACTACTC
17461 CTTGACCTCA GTTCTTTTTT TCAGAGACAG GGTCTCACTT TGTTGCCCAG GCTGCCAGGC
17521 TGGAGTGTAG TGGCGCAATC GCATCTCATT GTAACCTCCA CCTTCTGGGC TGAAGCCATC
17581 CTCCTGCCTC AGCATCCTGA GTATCTGGAA CCACAGCAGG TGCACACCAC CATGCCAAGC
17641 TAATTTTTTA AAAGTTTTT TGTAGAGATG GGGTCTTACT ATGTTGCCCA GGCTGGTCTC
17701 AAACTCCTGG GCTTAAGTGA TCCTCCTGCC TCAGCCTCCC AAATTGTTGG GATTACTAGT
17761 GTGAGTCACT GTACCCCGCC CCACTTCAGT TCTGAGGAGG AAAAAATATG TAATAATAAT
17821 GGGACTTTGG TTTGCTGATT TAAAGATTCA TGTAACCTTA TCATCCAATG CGCAATTTGT
17881 AGAATAATTA ATAGAGACAT CTGGTCTCAT GTTTCTACAG TTGCTCATGC CTTGATAGTA
17941 GATCTCCTTG CTGCTGGCTC AGAAGGGTAA AAGAGCAGAA ATGATGGGGC TTCTCTCATT
18001 CTATGAGGAA ATAGACCTAT GTAGAGGAGG CTACCTGTGG TAAAACCTTA TCCTCATCAC
18061 TTAAAATTCT AGGCTTATTC TCTGACCATA TCAAGTTTTC AAATGGTAAA AGAATTGGAT
18121 TCAAGAGAAA TATGAATAAA CTTTTGTTTT CACTTTTCTC CCTCCTCTCC CCCCATTCTC
18181 CCTTCCTTTA TTTTCTTGTC CTTAGTTTTC TTTTCACTTT TTTGTCTACT ATTATTTGCC
18241 CAAACTCAAC TGTAGGCTAG AACAAAAAAA AATTGAAAAT TAAAATGTGC CCCTTTTGTT
18301 GTTAGACTTG CTTAAACAAT TGGGGTAATG AACCTTGGAC ACTAGATTTT AAAACACACA
18361 CATTTGAGCT TCAGTGCACT GAAATAAATA TATTTTTAAC AATTAAAAAA TAAAATTGCA
18421 TGTTTAAAAA ATCTGCAGAG AACAATACAC GTTGTGAGAT CTTGAATGGA AGGAAAACTG
18481 CTAGCCTCAA GAGTGGATCA AAGATGCTCA GCAGGCAACA GAGTAAGAGC ATGTTGGAGG
18541 GTTAGAGAG TGTGCTCAGG GTTCTAGGCT CTAAAAATCA GACAGTCCCC ACGGCCTGGC
18601 CTTCGTCGCT GTATCTTCTT TATGAAAAAC ACTAAGTCTT TTTCCTCACT GGATAAATTT
18661 TTATCCTTCA AGTTTAGATC AAATGAAACT TTAGGACACT GACTAGGTTA CATTCATCTT
18721 TTAAGAGCGT ACAGACATTC AAGGGCTAGA GGATGTGGGT TTACTGCACA GGCTCATTAT
18781 CCAACAGCTG TGCTACCTGG GAAACTTAAC CTCTCTGTGC CTTAATTTCC TCATCTATAA
18841 CGCAGGGAGA ATGACAGTAG GTATCTCATA AGGTTGTTGG AACAACTAAA TGCATTGGTA
18901 TCTATTGTGT AAAGTGCTTA AAACACTGCC TGGCACAGAG CAAACATCCA GTGAACTTTA
18961 GCCATCATCA TTATCATTGT TCTCAGAGTC AAATACAATA TCTCATATCT GATAAATTAC
19021 AGAAGTGAAT CAATCACTCT CTCTCTTTTC TCCAGGGGGA GACAACAGCT TTTAGACATA
19081 TCTTTTCCAA CAGTCGTCAC TGCTGGACAC TGTTTCATCT TGCAAATAAA CCAATGAAAA
19141 TGAGTGATCC TAGAAGAAGA TAAATGGAGG TATTTTGAAC AATCAAAGAA GGACAAATGA
19201 ACACCTGGCT GAGAAAAATT AGCTCTTTTT TCTATGCATA AAACTATTAA AATATTCTTC
19261 ATAGAAATTT ATGACACAGG AAACATAAAG ACAAAATTAA AATAACTCCT AGTATCTCCT
```

Figure 2 (Page 6 of 74)

```
19321 ATTCTTTTTA TATGTATATT ATATATACTC ATATTCATAT ATACATATAT CTCACATCAT
19381 GTATCATATA TAAAATAAAT TTAGGTGTCA TGATATATAT TTAGATAAAT ATACTTAGAA
19441 ACTTTTTTAT GGATGTATAA TTTATGGATA TATTGATAAT TATGTATTTG TTATTGACTA
19501 CTTCAATTGA TTCCCATTTT TATGCATTAT ATTATAGATT ATATAGCTCA CACATCTTTG
19561 TACATAAATC TTTGTTCAAA TATTATTTCC TAAGGATAGA CTTCATGAAG TGGAAATACT
19621 AAATCAAAAG TGAAAACAT TTTCTAAGGT TCTTAACATA TACATTGCCA AATTGCTATT
19681 CAGGATCATA CCAATTTATA ATCCCAAAAT AATATGAAAA TTCCTGTTTT ATAGCACTCA
19741 TATTTACAAT AAATTTTAAA AATCACTGTT AACCTAATAG TCCTTCAAAA GAAAAAAAAA
19801 TTGAAATTAC ATTATTTTAA TGACTCTATT AGTGAGGGTC ATTCTTCCCA TGTTTCTTGT
19861 TAGCCATGAC CCTATAAGAA ATAAACTGCA CTGCAAAATG ATAAACATGA TATCAATCAT
19921 TACATGGGAA GGCACTATAT AAAGAATAAT ACCTTAGGTT AAGGCCACAT AAATATTTAT
19981 CAGGTGCCTT TTCTGCGGAG GACTCTGAAG GGATACTAAA CTGCATTTAG CTGCATGCAA
20041 CTGAAATTAC TTTTACCTAC ATTGTCTCTT ATAAACATTA TAACTACTCT TTGAGAAAGT
20101 GTTTACTATG GACTGAATTG TCTCCCCATC CCCCCAAATT CATATATTGA AGCCATAAAC
20161 CCCAATATGA CTCTATTCCT AGACAGGACT TATAAGAGGT AATTAAGGTT AAATGAGGTC
20221 ATTAGGATGG GTTCCTAACT GGATAGGATT GGTGGCCTTA TAAGAAGAGG AAGATTCTGC
20281 ACTTGGTCTT CCAAATTAAA TAATTTATTT AAAAGAAAAA AAAAAAAAGA GGAAGAGAGG
20341 GAGCTCTGCA CATATACTGA GGAAAGGCTA TGTGAGCTCT CACAGTGAGA AGGTAGCACT
20401 CTACAAGCCA GCAAGAGAGC CCTCACCAGA ATCCAGCCAT GCTATACCCT GCTCTGAGAC
20461 TTCCAGCCTC CAGAACTGTG ATAAAATTTT GTTGTTTAAA CCACACAATC TATGGTATTT
20521 TTTTATGGCA GCCCAAGCCA ACAAAGACAG CATCATTGCT GTCACTTACA GACAAGAAAA
20581 CTAAGACTAG GAGAGAGAAA AGTTAAACTT GTCCAAGGTC ACAAAAGCCA GAAACAAGTG
20641 AGGTGAGAAG TTGACCTTGT TCTCCTCAAT CCAAGGCCAG GACTCCTCCA CTCCACATGT
20701 AGATAGCCAC CTCACAGTCA ACAGCCAAAT GTCCACACCC CAGAGTCAGC ATTAGACCAA
20761 GATGTCTTAC CAGGAGACAA ATGCCTCATC TTGAATAAAT ATGTTCTAAC AACTTACCCA
20821 TGTAAAACAT TGAATCTCAT GAGAAACAAA AATGCAAAGT ATGTAGAAAA CTATGTTTAC
20881 CACTTAACTG ACAGTGATAA AAAGCTTAAT GATATCCTTA TAGTCTTGGA GGGGTTTGTA
20941 TATGTGGTGA ACAGGTGCT CACGCACTGC TGATAGACTG TAAATTGGTC CTAGAGAGAA
21001 AAATAAATAA ACTGGAAGGA GTTATGCTGT ATGTTTACTT TTTTATGGA AACATATGAT
21061 ATACCTGGAA ATTCGATTGG CCATGCATCT ATTTCTTCAA TGGGTATGCA CAGTTGAGCT
21121 GTTCCCATGC ACCAGGCACT GTAATGGGAC AACTGCACAT GACAGTCAAA AATCTCAGTC
21181 TCATGAAGTC GACATGCTCA TGGAGAGGTG CTACCCACTA AACTAATATT TGTATATCAA
21241 TTATGGATAC ATTGGGCCAC ATTTACAGAA ATTCACTTAC AGTGGGTTAC CAGAAGGGAT
21301 TTTTTTTCTT GATTGGCAAG AAGGCTAGGC TGTTTTGTTG GGGGCTGGCA GGAGCTGTCT
21361 AGGCTGCCCA AGTATGCAGG TCTCTTCTAT CATCCTGTGT TAACCATCTT CCATGTATCT
21421 TTCAACCTCA TGGTCATCTG CAGCATGTCT AGGGGTCATA TCTATGTTCC ATGCAGGAAA
21481 AAAGGGTAAA GGGAAAGGGA AGTAGGCATG TACCATTTTA ATGCACACCT TGGTTTTCAG
21541 AAAATTTAAG AAGAAAGACT TTCTGCTTTT CTCTGACTAT TCTGTATTCT GGATTACAAC
21601 GCAACAGAAA CGTCACCTTA AATTCTAATG TTTTTCTCTC CTTGCTTTCA AAACTGACT
21661 CATTAACCTC CACGTGGCTT GGAAAAATTA TTTCAGTCAT CCAGTAATGA GCTGTTCATA
21721 GAAATGTTTT GGACATCAAG TCTGTGTTGT TAGCATTATA CATGTTAAGC ATTGAATAAA
21781 AAACAACATG ATGTGGGTAC ATTTCTTTAC TTACATATAA GTACTTATAT ACTTATAGCT
21841 GAAAAGAGAG GTTGAAATGT CAGGTGGAAC AGAAATAAGA TTACCTAGAT GTTTCTCCTA
21901 TGGGTGATTT TCAGCTATGC TGATCTTTCT TCTGGGTCAG GTACTCCCAG AACTTCCTAA
21961 TTAAATGGTG GCCCTGATCT TAGTTCCTCT CTCCTCTTAG ACATTTTCCA GGACTACAGA
22021 AGATGTGCAG TTTATAAATG AGTAGCAGAA ACCTACTGAA CAAATTATTC AGGCTCATCT
22081 GAACAGAGAG GACACCTTCT CTGCTATACT CTCTCAGTGA TTTCCCTGCC TTGGGGTCAA
22141 TTATTGTCTT GGACATTGAT TTAAGCACAT AATAATTGTT GTCATTGCTT ATGTTTGGAT
22201 TTCATCTCCC AAAATAGATG GTAAATTCTT TAGTTTAGAG ACCAAGTAAT ACTTACAAAA
22261 AAATTTTGTG TGTGTGTGTG TGTTTTTTCT GTGTCTCTCA GCCCTGTAAT AGCATCGTAC
22321 TTACACTTGT TAGATTTTTA GAGACAACTT TTACAAAACA TGGAATTATC TACATACCCT
22381 TTCTACAAAA CAGACAAATT AAATACTCAG TAGTTGAACC AAAAAAAGCA GTTCAAATAA
22441 AATACTTGAA AATGAAGAAA TCATTTGAAC AGAGTTAAAG TTAATCGTAA AATAATGTCT
22501 GTAAAAATTA TTGCCAATCA AATATAAAGT TCAAAAATAG TGCTTGAAAA AGGAAGAATC
```

Figure 2 (Page 7 of 74)

```
22561 ATATGAAAAG GGACTACTCA TTTTAAAAAT GTTAGATATC AGGAAAAGCC AAGAAGTGAG
22621 TATGGTAAGA GTGCTGTCAA GTGAAACCCT GCTAATCTCA CTGAACATGT AAAAATCTGT
22681 AGATGCCTTT ATTTTATTCA CTCACACACA TATGTAGAAA GAGAAATATA TGGTAAACAT
22741 TAAAAAAAAC AAATTAGAAT GTAAAATTAA TACTTTAAAA AATGGGCTGT ATACTTTTCT
22801 TATCACCGGA GATAAGAATT TATTATTTTT AAAATAAAGT TATTTTCTCT GTGACTGTTT
22861 CCATGACTTT GCTACTTAGA AGTTAGAGAT GCCAAAGTTT ATCTAAGAAA ATGTTTATGG
22921 AAATATTATT TCAATAATGA ATGTTTAGAA GACTGAATTT CCTGACTGGG CACAGTGGCT
22981 CATGCCTGTA ATCCCAGCAC TTTGAGAGGC TGAAGAAGGA GGATCGCTTG AGTCCGGGAG
23041 TTCAAGAGCA TCCTGGGCAA CACAGCGAGA CCCTGCAGCA AGTAAAAAG AAAAAAGAAT
23101 TGAAAAAGGA AGACTGAATT TCCTTTGGGC AAGTCATGTG ACATTCCTGT GCCTCAGTTT
23161 CTTCATCTAT AAAGTTAATT CCTACATTTT TGGGGAAGGG AGAGAAAAAC TTAGGATAGT
23221 GACTGGCACA GAAGAAGCAC TATATACTAT ATATATGTGG ATATCATTTG TTTTTATGGT
23281 ACCATTTTAG CTATCTAATG CAAAATATGA ATCTTTTTTT TCTGGGTCTT AAATTATGGA
23341 ATGTAAGAAT TTTCTAAATT CTCTAATTCT GTGTTAGTTT TAAAGCAATG GAGTAACGTA
23401 TCTGTCAACT TGTAAATATA AGGATCAACC TGATCCACAA TTTGACCCCT AGCCACTAAT
23461 ATTTAATAGT ACAACACTCA GAAATTATCA AAGGTCAGAG AAGCCAAACA AATGTAAAAA
23521 CATACAGGTG CTCAGAAAGA TGCACCTGTA ATCTCTCTAA GGAGAAATAT TTTCCAAACT
23581 GAGTGACACG GTGCTTTAGT GAGTTGTGGA ATCAATCTCA TGATTTCCAA CCTAGTGTTC
23641 TTTTAAAAAT GAACTAGTCC ACAGTAGAAT ATACTAAAGT GCTGGTGCTT AAGATAGTAT
23701 TGTTTTCTGG AAAAAAAAAA AAAATTTTTT TTTTTGAGA CAGGGTCTCG CTCTTGCCCA
23761 GGCTGAAGTG CAGTGGCACA ATCATGCTCA CTGCAGCCTT GACCTCCTGG GCCCAAGTGA
23821 TTCTCCCACC TCAGCCTTTT GAGTAACTGG GACCACAGGT ACGTGCCACC ACACCCGGGT
23881 AATTTTTTAA TTGTAGAGAC AGGGTCTTGC TATGTGCTTA GGCTGGCCTT GTGAACTCCT
23941 GGGCTCTAGT GATCCACTAG CCTCAGCCTC CCAAATTTAT GGGATTATAG CATGAGCCA
24001 CCCTACCTGG CCTGTTCCCT GAATTTTTTT TTCTTTCAGG TGTTTGTGCA TATGTGTGTG
24061 TGTATGGGTA TAACAGAGAG ACAGAGAGAA AGAAACTTTT CTATCACACT TTGCAATCAG
24121 AAGTTTGAAG TCTTATCTTT TGGCTTTTGT TTCAGAAATA TTTCAAATGT AGACTCTCTC
24181 CTTTACCACA CTGTCCCCTT AGGCAAGGTC TTTGCCATTC TTCTGAGACT ATTGCAACAG
24241 ACTCCCAACT TCTGACTGTG GGCCCTTCTC AAAAATGATT GTTTATGCAA TAAATCTAAA
24301 CCCAAGACAA CTACAACAAT ACAACAAATT CTCTGCTTAA AAACTTCCAA TGTCTGCCGG
24361 GCGCGGCGGC TCACGCATGT ATTCCCAGCA CTTTGGAGGC AGAGGCGGGC AGATCACTTG
24421 AGGTGGGGAG TTCGAGACTA GCCTGGCCAA CATGATGAAA CCCCATCTCT ACTAAAAATA
24481 CAAAAATTA GCCAGGCATG GTGGTGGGCG CCTATAATCC CAGCTAATTG GGAGGCTGAG
24541 GCAGGAGAAT TGCCTGAACC TGGGAGGTGG AGGTTGCACT GAGCCAAGAT CACACCATTG
24601 CACTCCAGCC TGGGCAACAA GAGCAAAACT CTGTCTCAAA CCAAACCAAA ACAAAACTTC
24661 TAATATCTAC CAAATGTTTC ACACAAGTAT TTGGGGATCT TCACAAATGG CCCTTATGGA
24721 GTTTTCCTTT GCTGAGACCC TATGCTCTGG CCACACTAAA CTCATTCAGC ATCCCAGAAA
24781 GGCCTCAGCC TTTGTGAGCA AGCTCTTATC TCCAGGCCTC TCACAAAGAC CTGTTCCAGT
24841 AGAAGCTCAG GGGAGCACAC TGGACATTAT TCCAACAACC CTTTCCCCAC AGCTATGCAG
24901 CCAAATCTGC CAGCTCAGTT AATTAATTAA GCAATTCAGA GATGAGGGTC TGCCCAGGCT
24961 GGAGTGCAGT AGCTGCGACC TCAAGCTCCT GGGCTCTAAG TGATCCTCTT CAGTCTACCC
25021 AGAAGCTGGG ACTGCAGGCA TGTGCCACCA CACCCAGCTA ATTTTTTTTT TTTTCAGTAG
25081 GGACCAGGCC AACCTAGTCT TGAACTCCTG GCCTCCAGCC TTCCGAAGTG CTGTAATTAC
25141 AGGCATGAAT CACTGCGCCC AGCCAACCCG CCCAGTCTTG TTAGACATGG GGTCTGTAGT
25201 TTCTAGTAGG TTCTTGAGTC TAGGGTTCCT ACCTCATGTT TTATAGTTAA TTTAGGGGAG
25261 GGACTGTGTC TGTTTATCTG GGGATGTAGG GGTGGGCAGG GGGATAGAGG GGACTTCAAT
25321 TAATGAAACC AGAAGCAAAA CTCAGTTGAG GACACCGGTC ATGAGAGTGG CCTGATTATG
25381 GCCAATCTTA CATAATGTGT GAGATCTTGA TATTACCCCA TCCTTGAGAG TCCTCTATAA
25441 AGCTACAGGG ACTTGGGAGC ACCTTTAATT ACAGACAACC CATGTTCCTG TGGATTATGA
25501 TTTATTAGAT TGCACATGCC TAAATAAAGA CATCCTCTGC AGTCTTTTGA CAATTCTATA
25561 AGCATCTTCT GACTCCGCAA TTAGACAGCT AAGAGATCTG TGTTACTTCC CTCACATATA
25621 TAAATAATTT TAAATAAAAA TCATGGCGTG AATAATTTCT TTCCTCTACC GATTTGAAGC
25681 TATCCATTTG GAAGACCACT CTGAAGAGAT GAAATAAGTC TTCTGCCAAA GATTACTTAT
25741 TAATTTACAA GGAAAAGGGG AAGTTTTGTT CCTCTCCGTG AATTTGATTG AAAATCGAGG
```

Figure 2 (Page 8 of 74)

```
25801 GCTTTCTCGA ATAGTTTTGG CATCCAGGGT CATTTTTCAT TAAAAAGAGA AAAGTCATGT
25861 CAAATATGAA TTTCCGCAGA TTATTCAGCA CTAGACCCTG GGAGATTCTG TAAAGAGGGG
25921 TTTTGTTATA CTCAACTTTT CCGGGTAAAA CAAACACAAA TACTCCTCCT CCAAGGGGCG
25981 GGGGCGGTGC CTAGGTGATG CACCAATCAC AGCGCGCCCT ACCCTATATA AGGCCCCGAG
26041 GCCGCCCGGG TGTTTCATGC TTTTCGCTGG TTATTACATC TTGCGTTTCT CTGTTGTTAT
26101 GTCTGAAACC GTGCCTGCAG CTTCTGCCAG TGCTGGTCTA GCCGCTATGG AGAAACTTCC
26161 AACCAAGAAG CGAGGGAGGA AGCCGGCTGG CTTGATAAGT GCAAGTCGCA AAGTGCCGAA
26221 CCTCTCTGTG TCCAAGTTGA TCACCGAGGC CCTTTCAGTG TCACAGGAAC GAGTAGGTAT
26281 GTCTTTGGTT GCGCTCAAGA AGGCATTGGC CGCTGCTGGC TACGACGTAG AGAAGAATAA
26341 CAGCCGCATC AAACTGTCCC TCAAGAGCTT AGTGAACAAG GAATCCTGG TGCAAACCAG
26401 GGGTACTGGT GCTTCCGGTT CCTTTAAGCT TAGTAAGAAG GTGATTCCTA AATCTACCAG
26461 AAGCAAGGCT AAAAGTCAG TTTCTGCCAA GACCAAGAAG CTGGTTTTAT CCAGGGACTC
26521 CAAGTCACCA AAGACTGCTA AACCAATAA GAGAGCCAAG AAGCCGAGAG CGACAACTCC
26581 TAAAACTGTT AGGAGCGGGA GAAAGGCTAA AGGAGCCAAG GGTAAGCAAA AGCAGAAGAG
26641 CCCAGTGAAG GCAAGGGCTT CGAAGTCAAA ATTGACCCAA CATCATGAAG TTAATGTTAG
26701 AAAGGCCACA TCTAAGAAGT AAAGAGCTTT CCGGGAGGCC AATTTGGAAA GAACCCAAAG
26761 GCTCTTTTAA GAGCCACCCA CATTATTTTA AGATGGCGTA ACACTGGAAA CAAGTTTCTG
26821 TGACAGTTAT CTATAGGTTT AAGTTGTGAT GCAGCTGAGT TGAAAAGGCT TGAGATTGGA
26881 GAATTAATTC AGGCCAGGCT TCAAGACCAT CCTGGGCAAC ATAGCCAGAC TACCATCTAT
26941 ACCAGGGGTC CTCATTCCCC CGGCCACCGA CCGGTAACCG GTCCCTGTCC ATGGCACGTT
27001 ATGAATTGAG CCGCACAGCT GAGGGGTGAG CGAACATTAA CCAACTGAGC TCCACCGCCT
27061 GTCAGGTTAG CTGCAGCATT AGATAGATTC TCATAAGCTC AAACTGTATT GTGAATGGCA
27121 CATGCAAGGG ATCTAGGTTT CAGGCTCCTT GTGACAATCT AATGCCTGAT GATCTGAGGT
27181 TGGAGCAGTT TTAGTCCGGA AATCATTGCT CCCAGCCCCT GCACCCCTG GTCCGTGGTA
27241 TAATTGTCTT ACACAAAACG GTCTCTTGTG TCAAAAAGGT TGGAGACTAC TGGTTTTACA
27301 AAAAGTAAA TTAGTCAAGC ATGGTTGGCA CGCTCCCTTA GTCCCTGCAC CCAGGCGTTT
27361 AAGGATACAG TGAGCTATGA TGGTGCTACC TCACTCCAGC CTGGGTGACA GCGAGTCAGA
27421 CGTTGTCTCA AAACTTAAAA AAAAAAAAG TTAAAACAGA AAAAGGGCTT CTTGTCAGAG
27481 ACTGCCGTAT ATCTAGAGGT CCAGGAACTA AAAAGTCTGA TGTCCAATCC TGAAAAGCTC
27541 GATGGTGCAC TAGAGGAGGC TTTTACATGT AAGAGCATCT AAGTTCTGGA AATGCCAGTG
27601 TCAGGGAAGG GAAGTGGAGA GCAATTTGGC ATCCAAACAT AACTTGCTGA TACTTTTTTT
27661 TTTTTAACA CAAGTACTAC ATTCTAGTCT TTCTGTGGTG TCATTGTAAC TATTGTTTCT
27721 TAATATGCTA TCCACTGACT TCAAGGGATC AATAAATAGG AATCAAGGTG TCCCAGAATA
27781 TGGATTAGGG GAGTTTTTTT TTTGTTGTTG TTGTTGTTGT TTTCATCTAT TCATTATCCT
27841 GTAGCTGAAA TTTAGAATTT TCTTCCATTG TGTGTGACTG ATAGAAATAA CAAATTTGTA
27901 GGTTATAGTT GTTGCAAGAA TCTGGAAATC GTGCTTGCTT ATTTCCGAAG TACTATTAGG
27961 TATATCAACA AAAACACACA TATTACGGTC AAGTGGTTTG ATAATTATTT TAATATTATT
28021 GGTCTAATAC AATTGTAACC CTATGAATTA CTTTAAGTAT CTTATTTATG AAAAGAATCT
28081 GTAAGTTTCA TCAAACTACC AGAGCATACC GAAGACTGAA AAATTTTAAG AATCCAAACC
28141 TTAATGGAAA TGTTGGAGGC TGCCCAATTA GGTTCTGAAT TCCACCTTCC TGAATCACAA
28201 ACTTGTTTTA ACTCTCAGTC TGAGGTAAAC TACGTTTCTC TTTAAACAGA CATAGTTTAA
28261 TTTTCCTTTG ATTTTTGATT TAGTATTCTT ACTGATCATC ATAAATAACC AATGCTAATG
28321 TTAGTCTACT TTGGACCATG GTATTTCGAG AAACTTTGAA CAAAGTCCCC TGCAAAACTA
28381 TGCATTGCAT TATTTCACAT ACATTTATGT TTTCCAGACG GTTCAATAGT ACCTCACTTT
28441 TCTGAACTTA TTTGTATAGT TTGGCATCTT TTTAAAAATT GTGTCCTATA ATGAAAGGTT
28501 GTAAACATTA TGTTTTAAAT TTGTATAGAT AAAATCAACC ACAGACCTTT CCTTGCTTGG
28561 ATGTAATTGC CATTGTTTCC CAATGAGTTC GGAATTACTA GGATTGTGCA AAAATATGCC
28621 TCACTTGCCT GACATAGCAG AGAGCCATTT TGCCTAAATG CTGTGCCCAG CAATGGACTG
28681 TCACCAGATT CTCATCACAT ACAGTGAGGA TGAACAACTA GCCTCTCCCA GCAGCTGGCC
28741 GGTCTCTCAA TAATATGGGA CTCCCTCAAG ATGGCTTCCT GCACCTTTGC TCCTCTAGCC
28801 TTGTATGTAT ACAAGGCTAG CATGCCTGGC ATACATAAGG TTAAAAACAA AATCAATAAG
28861 TTATGGTTCT TCCTCCAGTT CTGGGGATTA TTAGACCACT TTTTGTTTT GTTTTGTTTT
28921 GGATGGAGCC TCGCTCTGTC ACCCAGGCTA GAGTGCAGTG GCACAATCTC GGTTCACTGC
28981 AACCTCTGCC TCCTGGGTTC AAGCAGTTCT CTGGCTCAGC CTCCCACGTA GCTGGGATTA
```

Figure 2 (Page 9 of 74)

```
29041 CAGGTGCCCG CCACCACGCC CAGCTAATTT TTGTATTTTT AGTAGACGGG GTTTCACCAT
29101 CTTGGCCAGG CTGGTCTTGA ACGCCAGACC TCGTGATCCA CCCACCTTGG CCTACCAAAC
29161 TGCTGGGAAT ACAGGCGTGA GCCACCGCGC CCGGACTTAG ACCACTTTGT TTTGGCCAAT
29221 AGGACAACAG CCATAGAACC CTCCGCAAAT GAGAGCTTGT CCCTAAAGAT GCTTTATTTA
29281 CATAGCTGTG TGCCGCATGA GCCAAAAGGT GATAACCTTT GTTCAACACG CGCCTCCAGC
29341 CCTTCGGTTA AGTCCAAAGT ACCATTCTTA GAATGCTCTA AAATACATAA TTTTTTTTTT
29401 TTTTTTTTTT TTTTGAGGA GTCTCTCTCT GTCTCCCAGG CTGGAGGGGA GTGGCGCGAT
29461 CTCGGCTCAC TGCAATCTCT GCTTCCGGGC TAGCTGGGCC TACAGGTGCA GACCACCACG
29521 CCCGGCTAAG TTTTGTATTT TTTTTGGTAG AGGGGGTTTC ACCATTTTGG CCAGGCTGGT
29581 CTCGGATTCT TGATCTCAAG TGATACACTA GCTTTGGCCT CCCAAAGTGC TGGGATTACA
29641 GTCGTGAGCC ACTGCGCCCA GCAAAATGCT TTTTGTGGAG CCAATCACTT TATTAGCGCT
29701 TACCTCTCTA TGCCTACTTT ATGCTTTGAA ATTTGTCAC AGTGGGGCCG GTCATGGCAA
29761 ACACAATTCA TTCTTATGCA GGCTGTCACG GTTATTTCTG TCATCCAAAC TCATTCTCGC
29821 AACGCATTTC AGCTCTTTAA ACGACTTTGT GAGCGGCCCT GAAAAGGGCC TTTGGGTTTT
29881 TTTGTTTTTG TTTTTTGAAG TTCTCAGGAG ACCGCGTATT CTTAGATTCA GCCGCCGAAG
29941 CCATACAGAG TGCGCCCCTG ACGTTTCAGG GCATATACTA CATCCATGGC TGTGACAGTT
30001 TTGCGCTTGG CGTGCTCCGT ATAGGTGACG GCGTCTCGAA TAACGTTCTC TAAGAAAACC
30061 TTAAGCACAC CTCGAGTCTC CTCATAGATA AGACCGGAAA TGCGCTTGAC GCCACCGCGC
30121 CGAGCCAAAC GGCGGATAGC CGGTTTTGTA ATGCCCTGGA TGTTATCCCG GAGCACCTTA
30181 CGATGGCGCT TAGCACCACC CTTCCCCAAG CCTTTTCCGC CTTTGCCGCG ACCAGACATG
30241 ATTCCTATCG CAGTGGAAGG TATGAACTGA ACAGTTCCT TAAATACAAA CTTGGCGGAC
30301 CTGATTGAAA ACAACATGAG TTGGCGCGGT TTTTTTTTTT TTTCAAATTT GGTCACCGAG
30361 TGGGTGGAGC AAGAAAAACT GTTTCATTAT GGTTCATTGT TTTGATTGGC CAGTGACAGC
30421 TTGCTCTTTG TGGGAGTGGA AGGGTGTTTG CAAGTTGAAT GCGCTGTATT CCTGTCAGCT
30481 TAATGACGCT AAGCATAGCC CCATTCCACA TTTCTTTTTA TTTCCACTTG CTAACTAATA
30541 AATTACGGAA TAGTTTATTG GGGAACATAC AAATAATGTT TAAAGGAGGT CAGATTTATA
30601 GGTCAAGGGA TTTACCCTCC CAATCATTTT AATATTTTA TTTAAACCAG GCATTTTGAT
30661 GGCCTTCTCT GTGCTGGACA AGGTATAAGT TTGGCTATGA AGTTTCACTC CTAAAGACCC
30721 TATGTTTTGG GAAGGCAAAA AGGTAGCCAA ATAATTGCAA ATTAAAACCT CATAAGTGCA
30781 AACTTCTTCC TCGTCACTTT CCCTATCTCG ATTCAAATAT TTGTTGAATG ACTCATTTTT
30841 CTGCAAAAGT CTGAGAGAGA CAGGGAATAT AAACTTAAGT CTGGATAATA TGTTTCCCG
30901 GGACGCTCTT CCTGGTCTGC TGTGCCTGTT TGCTGTGCCT GAAATTCCAA ACACTCTTCC
30961 CTTCCCTCCG TTTTTAATCC CCTTTCAACT TGCTACAGCT TTAGAGAAAA GAACATACGT
31021 TTTGTACAGT TGGGGATTAA TTGAAGTGTA GGGCTAATAC TTGATTAAGG TCATTACAAA
31081 ATCTACAGGG TCTTCCTCTG GGAGGTTTTT GTGATAAGAT TATTGGTGTT AAAATAAGGC
31141 TAATCCCCTT GAAAATAAA TAGAATAGCA GAATTGGGTC TGAATGTGGT TTGAAGAAAG
31201 GGACTTCTCA ATTCAAATT TTATTCTTAG CTTCCTGTGG GAGCTTTCCA GAATGCCCAT
31261 AAGATCCACT TTTGTTTAAA AAACAAAAAC AACCCCACCC ACCACTCTCT GGTTAATAAA
31321 TGAATTTCTA TTGGGAATAT TTAGAATGGG GCTGTGGCCT GTGAGAGACA TTATATAGTA
31381 ACCTCAGACT TGCTCACATG AAGAGAAGAA ATCCAGGAAT GGAGAAAAAA GACCCAGGAA
31441 AGGCCAGAAT GCTCTACATG TCATATTGTT TGTATCACTT CTGAAATAAT TGATTACATT
31501 CTTCTGCCCC AAATTGAGTT CTTAGGTTCT TCCACTCACT GTCCACATGC CACAACACAG
31561 ACCTTATAAC TAGAGACTTA GCTAGGAAGA AATGTCAAAC ATTACAGAGA AAAAATGCAG
31621 AGTCTGAGAT CATAAGTAAA ACTCTGAAAT CTCAACATGC CTTTTAATTC ATGAAAATAA
31681 AAAATATAGC AGCATATGCA ATATGATAAT TCTCTGAAAA CATACATCAT GTGAACTACC
31741 CTGGAACACA TCTCGCCAAG TGCCATCTTC ATTTTAACCA GAGGTCTAGG ATGCCTTTCC
31801 TTTATTTTGC CTATTATATC ATTTATAAAA CCCCATTTTT ATTTTGATAT TTTATTTACT
31861 TTCTATTTCC TGCTCCTAAT ATCTCCTTTC TAAACTTTTC TCAATGACAG TGACTCAAAA
31921 ACAATGAATG TCAGAACAAA TATTTAAAGG ATCTGTACAT GTAGATATAT ATATTTAAAA
31981 TGGATTCTTC CACTCTGGGA AGAATTCAGG CATACTCAAT CTTATGGTTA GGGAGAGATT
32041 AGGCTCACTC GCCTAATCTG TATGGCTTCT CGTTCGCTTT CCATTTCACC TTCCTCTCAC
32101 CCATCAGATC AAACTCATTC ATTGAACAAG AGACCTAAGC CCTTCAGATT AAAACTCTGC
32161 AAACAAGTTG TGGTTGAGAG GATACATGAA GCATTCAAAC AAATAAATCT ATGATATTAA
32221 TCAGAGGTTA ATCTATGATA TTAATCAGAG GTTAATGCAG TGGCTCACGG CTGTAATCCC
```

Figure 2 (Page 10 of 74)

```
32281 AGCACTTCAG GAGGCTGAGT TGGGAGAATC GCTTGAGCTC AGGAGTTCAA GACCATTTTG
32341 GGCAACATAG CAAGTCTTCA TCTCTACTTA AAAAAAAATA ACCAGAGGTG TTATGAAAAT
32401 ATAAATTGTC CAGAACTACC CTCCACAAAC TAACTCTCTC AGAATATTCG ATATGAGGAA
32461 TGAAATATGG TGTGTGTGT GTGTGTGTGT TATGTGTGT TGTGTGTGT TGTATGCACC
32521 TATATATGGC ACCTATATAT TCAACAAACA ATTCTGATAA TTGGCCAGGG TTGAGAATGA
32581 CTAGCAGCCC AGCATACACT ATCAGTTTTA AGTATATAAT TGCGCTTTAG TAAAATGTAA
32641 AGAAATCCCA GAGTAGAAAT ACTTTTAAGC TATATTACAG GTGAGAAAAT GCATAAGTAT
32701 AGTCTCACCC AACTTAGACT ATGGGGCTT TATAATGTCA CAACAGTTGT TTCCAGGCAT
32761 TTGGGGACAT CACCACTGGT CTTGGGCAAG AAACTCCTCT AGCCAATGGC TGATTTATCT
32821 CACTCCCATC TAAGGCTTCA CTGCATTTCT CTTTTTCAGC AACCTAACTT ATTTAAAAAT
32881 ATCCATTTTC TGATTCATTT TTTTCTGAAT TAAACTGTCA GTACCATTGG CACACCTTTG
32941 GTTCCGTAGC ATACCTGTGT CTCTGCTGTG GTTTTTTTA CCTCCACTCC TTACTTTTCT
33001 AGAAAAAAAT CTCTGCTTTT TCTTTTCAGT TTAAATTATT TCACAAAAG TTTTCTTGAC
33061 TTGCACTTCC TAGGCTTGCT GTCCTTGTGT GGGCACGCTC CCATAAACAC TATTAATACA
33121 CTTCGATTTG TTAAAATAA AGATATCTGG ACAGAAAATT TCTTTTCTTT TTTTAAGATT
33181 TTAAAATTTT TAATGTTTAT TTTTTTCCTA GACTGGAGTA CAGTGGCACC ATGATGGCTC
33241 ATGGTAGCCT ACACTTCCCC GGGCTCAAGT GATCCTCCCA CCTCAGCCTC CAAGTAGCT
33301 GGGACTACAG GTGTGCACAA CCACACCTGA CTAATTTGT TTATTTGTTT GTTTTGTTTT
33361 TTGAGATGGA GTTTCGCTCT TGTTGCCCAG GCTGGAGTGC AATGGCGGGA TCTCGGCTCA
33421 CCGCAACCTC TACCTCCCAG GTTCAAGCAA TTCTCCTGCC TCAGCCTCCC GAGTAGCTGG
33481 GATTACAGGC ATGCATCACC ACGCCAGCT AATTTTGTAT TTTTAGTAGA GACGGGGTTT
33541 CTCCATGTTG AGGCTGGTCT GGAACTCCTG ACCTCAGGTG ATCTGCCCGC CTCGGCCTCC
33601 CAAAGTGCTG GGATTACAGG CGTGAGCCAC CACGCTCGGC CACTAATTTT GTATATTTTG
33661 TAGAGATGGG CTTTCCCTGT GTTGTCCAGG CTGGTCTTGA ATTCCTGGGC TTAAGTGATC
33721 TGCCCACCTT GTCCTCCAA AATGCTAGGA TTACTGGCGT GAGCCACCAG GTCTGGCTGG
33781 AAAGATAATT TCTAACATTA TCCTCTCTTA AACATTTGTT TCAAAAATTT TACAAACATG
33841 AGAGTAATTA AATTTGATTT TCAAAATTCC CTTGAATACT TTCTTAATAG CACACAGAAA
33901 GCACAAAGTA TTTTACATTT GTTTTAATGA TGAAATTGTG AACCCAAACT TACACAAAGA
33961 AAAACCGTAA CATTATACCC ATACTTAAAA CAGATGCCCT CATATACATA GTAAAACTCT
34021 TGGGGGCAGT AGTGAAGTTG GTTATTTACT GTTTTATGAA AGTGCCATTC AGCCGGGTGC
34081 AGTGGCTCAT GACTGTAATC CCAGCACTTT GGGAGGTCGA GGCAGGCTGA TCACGAGGTC
34141 AGGAGTTCAA GACCAGCCTG ACCAAAATGA TGAAACCCTG TCTCTACTAA AAATACAAAC
34201 ATTAGCTGGG CGTGGTGGTG TGTGCCTGTA GTCCCAGCTA CTCAGGAGGC TGGGGCAGGA
34261 GAATCGCTTG AACCTGGGAG GCGGAGATTG CAGTGAGCCG AGATCGCACC ACCGCACTCC
34321 AGCCTGGGAG ACAGGGCGAG CTCCGTCTCG AAAAAAAAAA ACAAAAAAGT GCCGTCATAG
34381 TGACTTAGTT TTAAGGAATA AATCAAGGAT ATTTAACTCA ATAGACTACA GTTAGCTAAC
34441 GTGACTTGCA CTGAAAGTTA TACGAATATT GGTACTTATT CCCCTGCCCC TGAAGTATGA
34501 ATTAAAGACT CCAAAATTCT TTTTAGAATC TTCAGAGTAA AAGCTAGAAT TTGATTTTTT
34561 TAAATAATAA AAAAATACTT TGTATCTAAA TCTGGTGTAT AAAATAACTT GGTGGATGAT
34621 GCTTCAAGGC TATCCATCCC CAAATTTCTC CCTGAATGAT AAAGAGAATA AATGAATATG
34681 TCAATTCAAA AGTTAGAAAT TTGGCCGGGC ACGGTGGCTC ACTCCTGATA ATCCTTTCGG
34741 ACGCTGAGGT GGGTGGATCG CATGAGCTCC GGAGTTCAAG ACCAACCTGG GCAACATAGC
34801 CAGAACCCGT TTCAATAAAT AATAGAAAAA AATGAGCCAG GCGTGGTGGT CCCAGCTACT
34861 CAGTAGGCTG AGGTGGGAGG ATCACTTGAG CTCAGGAGGT CGAGACTGCA GTGAGCCGTG
34921 ATCGCAGTAC TGCACACCAG CCTGGTGTC AGACTGAGAC CCTGTCTCAA CAACAACAAA
34981 ACAAGTTAGA AATTTGGCTG GGCGCGGTAG CTCACGCCTG TAATCCCAGC ACTTTGGGAG
35041 GCCAAAAAGG GCGGATCATT TGAGGTCAGG AGTTCGAGAC CAGCCTGGCC AACATGGTGA
35101 AACTCCATCT CTACTAAAAA TACAAAAAAA CTTAGCCGTG CATGGTGGCA TGCGCCTGTA
35161 GTCTCAGCCA CTTGGGAGGC TGAGGCAGGA AAATTGCTTG AACCCAGGAG GCAGAGGTTG
35221 CAGTGAGCCG AGATCATGCC ACTGCATTCC AGCCTGGGTG ATAGAGTGAG ACTCCATCTC
35281 GAGAAAAAAA AAAAAATTCT GTATGAACTG AACAAAATAT CCTTAAATTT TAAAATACAT
35341 CTGAAAGATA TTTCAAAATA TTTAGGAAAA AAATTATAGG GATCAGGCAA ATTCTGAGAT
35401 TCCTTTTTCC CTGCAGCAAA CATTAGGAGT GCTGCTGTTC CTAAAAACAT GGTAACTGTT
35461 GCCACACCGT ATGTTTCCTT GGCTCAGACA TAAGGTTGTG TAGTTGTTAT TCCAGAATAG
```

Figure 2 (Page 11 of 74)

```
35521 CTAGAATAAA AATCCAGCAC ATCATTTTCT TCAGCAAGTT AACTAACCTC TCTGTGCCTT
35581 GGTTTCATAA CAGCAACATA AGCATAACAG AATAGCAGCA ATAGCTCCTA CCTACCTCAT
35641 AAGATTCTTT GGAAGAATTA AATTAAGATT CAGAACACAG CCTAATATCT AGTAAGTAAT
35701 AATAATTGGC TAAAAAAATT TTCTTAAGAT TATATATATT CATGGGGTAC AAGTACAATT
35761 TTGCTACATT AATATATTGC ATTGTGGTGA AATCAGGGCC TTCAATCCAT CCCGGAAAAA
35821 AAAAGTTTTT GAAAAGATTT CTGCCATGGA AAACTTTTAA TGTACAAATT CATCCATCCA
35881 AGAAATAGAA AATATATAAG TATCAACTCC AAATCCACCA TATCTATCTC TTCTGCACCT
35941 TAAACAATTA CTCAGAAATA GAATGCTTGA GATACCAGAA TGCATGCATA TCAAGTAATA
36001 AATGCATGCA GGATGTCAAC GCATCCTAGG CTTTCAAATA AAATTGTCAT ACAAAATACT
36061 TTAATATTGT AGTAACATTC TACATGTTAG AGTGTAGAAG TTAATCGCTG ATGCAAAAAA
36121 GGAAAAGAAC ACATTATACC CAAAGCCTAC AGAGAGAATC ACAATTACAA ATATCAGCCT
36181 GCATGTGAAA ATCTTTAATT TGAAAGTCAG AAATATTTAA ATGATAGTCA TTGTTAAATC
36241 AGATTGTGGT TTGAAAAAAA GTTAGTTTAA AACTGAGTTT ATGAAAAATT TGGGGATTTT
36301 AGAGACAGTG TTTTGTTTTT AAATGTGTGT GAGTTTGTGA AGAATGTTTT ATAAAATACT
36361 GACAGTATTA TAAGATGACA TTATTATAAT ACAACATAAG AATTTTGGCC TGTACCTCTC
36421 AGCAGTCCTC AATCACCTGC TGTACTTGAC TCAATGATTA TCAGAGTGGT TTGTTTTCCT
36481 TCTGTTGTGT TCCCAGTTCA GGCAGCTCAG CAATGGCCTG TGATTCCAGC AATTCAAATA
36541 GCTGGTAAGT AGTTTCTTGT TTGTTTTCTC AAATTTTCAG GGGCTTTTCT CTACAAGTGA
36601 TTTCCAGTGC ACGCCCCTCC ACCCATTCTT TATTCCTTTA CCTTCAGGAA AACCCTCAGC
36661 GCTGCATCTC TGGTCACCGG ACCACCGTGG TACATTTACC TATGGCCACC AGGTGTCACC
36721 CTTCTCTTTA CTACCATGGT TTGTGAATGG TTTTGCCAGA GGTGAATAAG AATTTAAAAT
36781 GCAGGTCTTT GATTTTTCAA ATGTAGTTGA CCTTAAGAAT TTATGAATAA AGCCAGAAAA
36841 ATTAAGCTTA AAAACACCG AAAGAAAATG AGGACTTAAA ATTTCTATTA AAAAAATTAA
36901 CAGGCCACAG TTGCTGATGT TTAGTAAATG TGTTAGTGAA ATGTGTTACT GTGAAGACTG
36961 GGGTGTTTCT TGAAATCTCA GCCCAGGTGA AATAAAACCA ATATAAAACA AATGCTTACC
37021 TAATAAATTA ATTGTAACAT ATTCCTTATG AGGTAGAAGA GTAAGTGAAG CCTTATAGCA
37081 GTCTGCTTTC AGTATAGTAA GATATTAAGA GAGAAATAAT TTGTCATATG CTTTCAGAAT
37141 GGTTTGCTGG TAAAATAACC AATGTCTTAC AACTTAGACG ACAATGTCCC TAGAGTGAAG
37201 AAACACGATT AATTCGGCTA CCACAGTTGA ATGAAAATAT TCCGTAAGAC AAAATGTAAA
37261 GAAATTAGAA GCAAATAAA TGTCTCCAAA ATGACAAAGC GATTAAGTAT ATACACAAGA
37321 TGAACAAGAA CTTCAATAAA ATCATGCAGT ATACAATACA ATGTACATTT ATTAAAGTAT
37381 ATGCATTTTT AATGCAACAA TAATACTAAC AGGTAATAGA CAAGTTGTTA ATAGTTTTTC
37441 ACTGGCTAAT TAAATAACAG CTTTAATTGT ATTCATTTTA TAGCTTTTCT ACAATGAGCG
37501 TAAATCACAT TTACTTTTTT CTACATAACT TTTCTAACCA CAAAAAAAGA AAATGGTTTA
37561 AAAGAAGAGA TGAGATATCT TTGCTAAAAT TTAATGCCTA AAGAAGAAAC TTCTGAGCTG
37621 TATATGGTAT CCTGAAGCAC CTGCCCTTCA AGACAGAATG CTTGTACCAC ATTTATGCAG
37681 CCAAGTGCAT GTAGTAACAT AAAGTAAACA CATGCCATCT GGATATATAT ATTAAGACTC
37741 TTTTGACGGC TGGGCAGGGT GGCTCACACC TGTAATCTCA GCACTTTGGG AGGCCGAGGC
37801 AGGCGGATCA CGAGGTCAGG AGAGTTCGAG ACCAGCCTGG CCAACATGGT GAAACCCTGT
37861 CTCTACTAAA AATACAAAAA TTAGCCGGGC ATGGTGGTGC ACGCCTGTAA TCCCAGCTAC
37921 TTGGGAGGCT GAGACAGGAG AATCGCTTGA ACCTGGGAGG CAGAGGTTAC AGTGAGCCGA
37981 GATCATGCCA TTGCACTCCA GCCTGGGCAA TAGAGTCTCA AAAAAAAAAA AAAGACTCTT
38041 TTGAACATGG TGAACTGATT TCCCAGAATC TAGCAATTCC TGAATGTCCT GGTTAGATTT
38101 TTTTTTTAAT GTGCACCGGA ACCCCAGTGG CTCCATGAAA GGACCTGGGC ATCCTCTAAG
38161 CCACTTGGTG GCTTCCATTA TACCATCTCA AAATGAGAGA GCTTACTCCA CTTCATTGAG
38221 GGAAATACCA CCAGAGTTCT GACTCCAGAG GCACTGGCCT AGGGAGGACA CCGTGTGTGA
38281 AGCCCAGCAG GGCCACTAGC TGTCCCCACC AATTACAGTC CTTGCGTAGG GTCCAAAGAA
38341 ATGAATGCCA AAGAGAGCAA CAGAGGAGCA AGGGAGTCAC ATTCCAGGAC CTTCCTTCAG
38401 GGACTTTTAA AGGAAACATG ACAGCTGAGG ATCAGTTGGT TGTTTCTGC TGTTCCCCTT
38461 CATGTGATTC AAGCTCATTC AGAAGAAACA CAATGAGACA AGAAGAGAGC CATCTCCTTC
38521 CTTCTCTATT TATTCTAGGC ATCTAAACTA CTGAATGTAG TGGTGTCTGA GATGTATCAA
38581 ACGGTCAGAT TGACTGAGTT TGAAACCTGT TTCTATCACT GACAAACTAT GAGATACTCT
38641 ATACTTCACT TTCTTTTTTT TTTCATTTTT TTATTTTTAT TTTTATTTTT TTGAGATGGA
38701 GTCTCACTCT GTCACCTAGG CTGGAGTGCA GTGGCGCAAA CTCGGCTCAC TGCAAGCTCT
```

Figure 2 (Page 12 of 74)

```
38761 GCCTCCTGGG TTCATGCCAT TCTCCTGCCT CAGCCTTCCG AGTAGCTGGG ACTACAGGCG
38821 TCTGCCACCA CGCCCAGCTA ATTTTTTGTA TTTTTATTAG AGATGGGGTT TCACCATGTT
38881 AGCCAGGATG GTCTCGATCT CCTGACCTCG TGATCCACCC GCTTTGGCCT CCCAAAGTGC
38941 TGGGATTACA GGCGTGAGCC ACCGTGCCCG GCCTACTTCA CTTTCTTCAT TTAAAAAAGA
39001 AATGGGGATA ATAGTACCTA TCTCATAGAA TTATTGTAAG AAGTGCATGC AGTAATGCAT
39061 GTAAGTAGGT GCTCAGAAGA GTCGGACACG AAGTAAGTGC TTTTATCATC CTTATCATAA
39121 TTTTCATTAT CAGAACAAGG AGAGACCAGG TAGAAAATTA TTGTGATTCT TCAGGTCTGG
39181 AATACTAGAG TAGCATCCCA AATGAAGGCA CCATTAAACT TTGCAAATCT GTATGACACC
39241 TTCATGCCAA TTAGAAAAAA CACCTCTTCA CAACCCCTTT CAAGATATTT GCCTCCTACC
39301 TGCTAAAAAC ACCCATCATA CTACCCACAG ATAGCCATGA TGCTTTTTCT GGGACAGGTG
39361 CCTCTTCCAT TCGTGCAGTG TACAGCCTTC ATAGCTGTGC AACTCACATC ACAATCAGAT
39421 GGAAGAATCC CCAAGGCTTG GTGACAGATG AGTTACTGGG TAACACAGAG AGAGGATTCA
39481 AAGGAAAAGT TGAACGGGTC CAGAAATGC ATAGATACAT GTGTAAAAAT CTGGTAAGGT
39541 TATGACTAGC CACGTCCCAG GGTTCAAAGC TTTTCTCAGA TGTTAAAATG AATCATGTAA
39601 GTCCCCCAAA TTTAAGGAGT CCTCTTCCAA AAATAGGAAA TGAAATGACA TAGGTGTATG
39661 TCTCTGAGGT GACGGAGGAA ATGAAGGAAG CCTCTAGATG CAGCTTGAGG TTCATGAGAG
39721 ACAGTTCCAG GGGAGAGGTC ACAGCTAGGG ATCACCGGCA TGCAGGAACT CAGAAACCTA
39781 AATGGGGAAA TCTTTTTGAG GAAATGAACA GAGAAGGCTA AAATCAAGGA GTTCGTCAGG
39841 CAATTTCTAT GTTTAGGTTC AACTCTCTCC TGAAACATGA AGAGCTCATA AATGCACTCC
39901 CTCTTTGAGT CTCTAGTTTT GTCTCCTTCC CACAGTGAGT CTGCAGGCTG CGTGTCACTC
39961 ACGTTCAGCT AAGACGTAGT GCCCCATGGC TCCTCCTGTG GAGACAAGAG ACCCAGGAAA
40021 GAGGCATCAC AAACCTAGGC ACCATCTTGC CTCTTCTCTC TTCCTTATTT TCCTCATTCA
40081 CCCATCTCAA TTTAGACCTG GGCACTATTG GATTTCAAGA ACCATTATCT CTCATCTGGA
40141 AATGCTTATT GGCTTTCTAA CTGGTCTCCT CACCTCTCAT CTAACTTCTT AACAACACAT
40201 TCACCATATA AGGGAGATCG TGGTCCTCCT TTCTTAGGAT CCTTCAATGA CACCCCAGTG
40261 ATCATAACCC AATATCCAA AAGACCCTTG GACTCTGTAT GAGCTGGCTT CTTTCTGATT
40321 CTCTTTTCCC TACACCACAG ATGTTCAGGG GGTAGAAATG CATAATTGGT GAGTGATAGC
40381 TAAGCAAACT CAGGGTTAAG GTACAGTAAT TATTTCTAAT CTCCCAGTAT GCCTTATACT
40441 CTCCTACTTG GCATGGTTGC TCCGTCTGTG TAGACCTCCC ATCATCTTCA ACCTCACCTA
40501 ATGGAATCCA GCTTCTCCTT CAAGATCCAG AAGGCTATCT TGATCCCCAG CTGAATGTGA
40561 TCATTCTTTC CTTTGACACC CTAAGCATTT GCTTCCTGCC TGCTTTAGGA CCTCATGGGG
40621 TCTTCTTTAA CTACATTTAC TTGCTATCAA TTTCATTCCC TACCAGATTT GGGTTCTGAG
40681 AATAGCCACA GTGACTTCTC AACCTCAAAG CCCCTGTACT ACCTTAAACA GCTCTTGCAA
40741 AATAGTAGGT GCTCTGAAGA TGTTTGTTGA ATTAGAGACT TCATTCTGG GGAGAACCAT
40801 TATTTCTGT CTCCCAGGGA GCTGCTGGTG TCCCAAAGA ATATAAATGA GAAAAATGCT
40861 TCCATGGAT GCCAGATCCC CTCTGCCCCT CTTCCCACTG TGCCCTGGGG CAGAGGTACT
40921 AAGAGACTTC CCCCTTGTTC CTACTCACTT GAACCCTGCC TCTTCCTTAA TATTATGAAC
40981 AAAATTCCAA TGAACAAGAT GACGACAAAA ACAGCAATTC CACTGATGAC TCCAATGACT
41041 AGGGTGCCAG ACGGTGAGGG CTCTAAAACA GAAAAAGCAA GTTAAAGCCT TTGATTGCCA
41101 CCCTCAGCCC ACCCCCTAAC AAAGAGCAGA TCCTCATCTC ACTGCCATAA TTACCTCCTC
41161 AGGCACTCCT CTCAACCCCC AATAGATTTT CTCAGCTCCT GGCTCTCATC AGTCACATAC
41221 CCCAGATCAC AATGAGGGC TGATCCAGGC CTGGGTGCTC CACCTGGTAC GTATATCTCT
41281 GCTCTTCCCC AGGGGGTACA GCCAAGGTTA TCCAGCCCTG GTAGGTCCCA TCCCCATTGG
41341 GCAATACGTC TTTAGGTTCG AACTCCTTGG CATCCATTGG CTGCTTATCC TTCAGCCACT
41401 TCATGGTGAT GTTCTGGGGG TAGTAGTTCA AGGCCCGACA CCGTAGAGTG GTCACTGAAG
41461 AGGTCACATG ATGTGTCACC TTCACCAAAG GAGGCACTTG ACAGGAAAGA GGAAGGATGA
41521 GGAGAGGGA TCTGTTTACC CTTGCCAGGA AGACTGGAAC TTTCACTTCC TTCTATAGGT
41581 TGGAGGAAGG AAATACCCTT TTCAGAAAAA AACAAGCTAC AGGAGAGACA CCATTTTGTG
41641 TCCTAAGATT GGACTCTAAC ACAGTGTCAC TTGGAGAGCA GTCAGATCAG CTTGTTCTCC
41701 TCACATGTAA ATATACATAT CTGTTACCCA TGTTCTTTGT TCTGATAGAT AAAATTGCCC
41761 TTTATGTGCA TTGAAAATGA TTGAATACAG ATGGTCAGTT TCACCTGGGT CAACCTAGGA
41821 GGCATTGTTA TAAGAAGCGG ACTTGTAAGA TAGGTAGCTT CAGTGATTAT TGCTATGTTC
41881 TATGAAAGAA ACTTTTAACC TAAAGGATTC TTCTACTCTG ATAAGTGGCC TCACTTGATA
41941 TTTTGTCCTG GTATTCATAT GATAGCTGAG ATCTCTGAAT TCTCTTTTTT TTTTTTTTT
```

Figure 2 (Page 13 of 74)

```
42001 TTTTTAAGAT GGAGTCTCAC TCTGCTGCCT AGGCTGGAGT GCAGTGGCGC GATCTTGGCT
42061 CAGTGCAACT TCCGCTTCCC AGGTTCAAGC GATGCTCCTG CCTCAGCCTT CCAATTAGCT
42121 GGGACTACAG GTGCGCATGA CTGTGACCAG CTAATTTTTG TATTTTTTTA GAGACGGGTT
42181 TCACCATGTT GGTCAGGCTG GTCTCAAACT CCTGACCTTG TGACCACCCG CCTCGGCCTC
42241 CCAAAGTGCT GGGATTACAG GGGTGAGCCA CCGTGCCCGG CCTTGACATT TCTGAATTTT
42301 TAACAGGTAT AAATATACAA AAGATTATTG GTTAAATAAA AAGCAAGGGC CATAGACACT
42361 TCCCTTTGAG CCATATGCAT GGAGAAAAGA AATTAAACCC ATGACTTGTG GCTGTCTCAT
42421 ACATCTCAAT TATAAGGTAG AGACTCTAGG ATTGAGAAAG TCCCTTCCCA GAATTTGGAG
42481 AGGCACACAG CCTCAGCCAC CTCTGAAACT CCAACCAGGG ATTCCGTGCC CTGCAACCTC
42541 CTCCACTCTG CCACTAGAGT ATAGGGGCAG AAGTGTGTTT CCACCATACC TTGTTGGTCC
42601 AAAACACCTC TCCCCAGCTC CAGCAACTGC TGCAGCTGTG CAGGGCAGTC CCTCTCCAGG
42661 TAGGCCCTGT TCTGCCTGGC CCGAATCTTG TGCCTTTCCC ACTCCAGCTT GGTGGGCCAG
42721 GCCCTGGGTT CTGCTGCTCT CCAATCCAGT GTGTCAGGGC AGAATTCAAG GTGGTCCTGC
42781 CCATCATACC CGTACTTCCA GTAGCCCTCG GTACTGTTGT CTTCTTGCAT TTCACAGCCC
42841 AGGATGACCT GCAGGGTGTG GGACTCTGGA AAAATCCCCA GCCTTGTTAA CTGCAACCAA
42901 AGGAATAGGT CCCTATTTCC ACCATCCCCA AGGACCAAAT GATCTCAGGA AGCAAATTCC
42961 TTCCCTCTTC CCTGCTCCCA CAAGACCTCA GACTTCCAGC TGTTTCCTTC AAGATGCATG
43021 AAAAGATGAA AAGCTCTGAC AACCTCAGGA AGGTGAGGCC CCCTCTCCAC ATACCCTTGC
43081 TGTGGTTGTG ATTTTCCATA ATAGTCCAGA AGTCAACAGT GAACATGTGA TCCCACCCTT
43141 TCAGACTCTG ACTCAGCTGC AGCCACATCT GGCTTGAAAT TCTACTGGAA ACCCATGGAG
43201 TTCGGGGCTC CACACGGCGA CTCTCATGAT CATAGAACAC GAACAGCTGG TCATCCACGT
43261 AGCCCAAAGC TTCAAACAAG GAAAGACCAA GGTCCTGCTC TGAGGCACCC ATGAAGAGGT
43321 AGTGCAGAGA GTGTGAACCT GGAGACAGAG CAACAGGCCT TAACCATGTG TAGTAGGAGG
43381 GGAGCAGGAT GTTGAGGCTC CACACACCTG CATCAACTCA TACCATCAGC TGTGTCTGGT
43441 CCTCATTTTG TGAAGGGTGA GTTGCAGTCC TGTCTTTCTT CCATATGACA GTCCTGGGTG
43501 CTCTTTCCTT GTGTGCTTTT CTCTGCCACA CGTGGCTGCC ACCCCCTCAC TGCCCCCAGA
43561 TCCTATTCCA ATACTCATGA TTAGACAGAC TCCACTAAAG CTGGTGGATT CTAGAAAATG
43621 TTAAGGTGTG TCTAGCCATG GTAGTTGAAC TCAGGAGTTG GTGCTCAGGG CAAATTAGAC
43681 CCAAATCCTG AGGAATAATT CCTTCAGTTT TTTTTTTTTT TTTTTTTTTT TTTTTTTTTT
43741 GAGACAGAGT CTCACTCTAT CACCCAGGCT GGAGTGCAGT GGCACAATCT CAGCTCACTG
43801 CAACCTGCAC CTCCTGGGTT CAAGGGATTC TCCTACCTAA GCCTCCTGAA AACCTGGGAC
43861 TATAGGCGTG CGCCACCACA CCAGGCTAAT TTTTGTATTT TTAGTAGACA TGGGGTTTCA
43921 CCATGTTGGC CAAGCTTGTC TCAAACTCCT GACCTCAAAT GATCTACCTG CCTCAGCCAC
43981 CAAAGTGCTG GGATTACAGA AGTGAGCCAC CGTGCCCAGC CTTGGTCCTG AATTCTTACA
44041 CTGAACTGCC TATGTGGCCT CACCACTTGG AAGCCTGACT GGAATCTCAA ACTTAACATG
44101 TCCAAATGCA GATCCTTGAT TTACCCCAAA CTGCTCTTTC CTCTGCCTTC ACCATCTCAG
44161 AAATGGCATT GCCAATTACC CCACTGCTCA GGCCAATAAA ATTAAAATAA AGAACAAAGT
44221 CAACTTTAAC TCTTCTCTTT TTCAGGGGGT CAGGGGAGAC AGGGTCTTGC TCTGTCACCT
44281 AGGCTGAAGT ACAGTGGCAC AGTCATGGCT CACTGCAGCC TCAACTTCCT GGGCTCAAGC
44341 AATACCCTCC ACCTCAGCCT CCCGAGTAGC TAGGATCACA GGTGCATGCC ACCACACCCA
44401 GCTAATTTTT GTATTTTTTG TAGAGAAGGG GTTTTGCTGT GTTGCCCAGG CTGGTCTTGA
44461 ACTCCTGAGC TCAGGAATCT GCTCTCCTTG GCCTCCTCCT TGGCATGAGC TACTACACCC
44521 AGCCAATTCT TCTCTTTCTC TCACACAACA TAGAATCCTT CAGCAACTTC CTTCAGAATA
44581 TATTCAGGAG ACAATGGTTT GTCACTCCCT TTTCTGTTCC CACCCAGCCC ACTCCACTAC
44641 CTCTTGCCTG GACTGTGTAA CAGCTTCCTG GCTGGGCTCC CTGCTTTTAC TGTTGCTCCC
44701 TTCATTCTGC TTTCCACATA GCAGCCAGAG CAATCTTTTA AAAGCCTGTG ACAGATCACT
44761 GTTACTCCTT GGCTAGAATT CACACCACAG CCTACAGGCG CCTGCACAAC CTTGTTTGTG
44821 GCTCCTCTTC TGAGCCCATT ACCTACTTCT TGGCCTCTAC TCCCCAGCAC TACTTGTTTA
44881 TTTTTTTCAA CCCGAGCTTC TTAACCAGGA GTTTGTCTAC TAGGTGACAT GTGGCAAAGT
44941 TTAGAGACAT TTTTGGTTGT CAAGACTGGG GGAGTGCTCC TAGCACCTAG TGAGTAGGGA
45001 GGACAGGATA CTGCTAGACA TCCTACATGC AGATGGTAGT CCCCCTTCCC ACCCCCACGC
45061 CGCCCCCCCC CCCACACACA CACACATGAG TAGTGCTGAG AAAACCCGCT TTTTAATCCA
45121 ACTTGCCAGG CCCACTCAGT TTGCCTGGGA AATACTGCTC CCAGTCAATA TCATTCTTAT
45181 TTCCTTCATG TCTCTGCTCA AGTGTCAGCC CCAGAGTGAC TTGCCCTGAC TTCTCTGCTT
```

Figure 2 (Page 14 of 74)

```
45241 CTCACAACAC CCATGATTTC CTGATGTTGT ATATCTTTCT GCTCATTTGC TTATTGTCAT
45301 CTCTCCCACT AGAATGCAAA ATATCAAAGG GTAAAGACTT GTTTCCCTGC TCTCTCCCTT
45361 GGGGCTTGAA CAGTGCAACA CATGGCTGGG ACTCATTTAC ACTTGTAAAC AATGAATATT
45421 TCTGCTCAAC ATGAAATTTT ATTATTCAAC CTCTAATGCA GTGTGATGTT TAAGAATCAT
45481 AGCTATGAAG TGGAGACATG AGCTCTGCCA CCAAAGCCCC GTGTACCATT GAATAAATTT
45541 GCCAGGAAGC AGGCCGTGCC ATGCCTCATT CTTGTCATGT GTAAAATGTG GATACACGTA
45601 GTACCAAAAC TCAAAGTGCT GTGCTGAGGC CGGCGTGTGA CCCACAGAAC ACTGTGCTAC
45661 ACTACAGGGC AAAATCACTG TCAACTAAGA TTAGAAGCAG CTGTAGTACT TGAAATAACA
45721 TCAGAAAACC AGATTATTTA TGTTCTTTGT AACCTGAAAA GAGTTATATA ATCTGAATTC
45781 CAGTTAACTT CTAGTAAAAT AAACGTATTA TTAGCTCCTA CCTCCCTATG CCTAGTGAAA
45841 ATCAAATAAG ATCAGATATG AATGTAACTT AGAAGTGAGT GCATTGCTTA CATGTTCATT
45901 ATCAGTACTT TGTAGAGAGG CCTCTTAATT ACACAGCACA TTGCAAATCA ATAAAGCCTA
45961 GCCGAAAAGA GAATTGTTCA GTTCAAACGT TCAAAACTAA CATATACTTA ATTTTCCAGG
46021 CAAAAGAACA ATTGCCAAGA GTGGGGAAAG GCCCGAGGTA GGCCTCTCTC AGGAGCCTCC
46081 CACCCTAGAG ACCTCCACCC CAGGTCTCAC CAAAAGTGGG TGGAATGGTG AAGAATTCAG
46141 ATCCCCAACG CCACTCTTTC GCGCCCCCAC CGCCCAACGC ATTCGTTCTG AGGTGGAAAC
46201 CCCGTGCGGA TCCTGCTGTG GGTTTGCTCA GCCTTCTCGG CAAGCACTCA GGGAAGAACT
46261 TCCTGTTTGG AGATGACTGG GGAAAAAACT GCACAGCTGA CATTGGAAAT AAACCCGAGT
46321 TCCAGGTTCA AGGAGCCCCA GGCTTAGCTC AGCTCAAGTG AGGAACTACG AGATTTATTT
46381 AAAAGCATTC TAGTTGGGGG AAGGGAGTGG GCGGTTCCAA AAGTCACTCC GCAGAGCCGG
46441 GACAGCCGGG GGAGGGGGCA GGTCCTGGGG CGAGGGACCC CTATCTGCAG TTCAGTGGTA
46501 GGCACTCCCT CACGGGGTCT GGACGCAGAA AGTAGGGAGA GGGGCTTGCG GATTGGGTTG
46561 AGCAGGTCCT CCAAAGTTAG CAAACTCCCA AGCGCAAAGA AAAAGCTAGT TTCGATTTTT
46621 CCACCCCCGC CGCGCCCCTA GTTCGCCCGC AGCCCTCGGA CTCACGCAGC AAGCGCCCCT
46681 GCAGGACCGC GGTCTGCAAA AGCATCAGGA GGAGAAGCGC CGGCCTGGCT CGCGGGCCCA
46741 TTTCCCCAGC TCTGGCCGCA CGTCCCCGTT AAATCTCCGC TTCTTTTGGG GGGCGGGGAA
46801 ACGGGGATGG CTCCAGAAGT CACCCTACAG CTATTGCCTA GGCTCAGGAG ATGCCCAGTA
46861 AAACTTCCTG GTGAAAAGCA ACAGGTCTTT CAGAACTTTA GTTCTCTCTC TCCTACAGCA
46921 GAAGGTACCT GCTTGTGAAA CACTAGGTGA TCCAGTGTCC CCCTTGGTTT TTAAATCCTG
46981 AAGGGGTGTT GTTGATTGGG GAAAGTAGCT TCGCAATGTT CTGATCTGAA CTTTAGATAT
47041 TTAAATATTT ATGATTTTCA AAATTCAATC ATACATTTAA AAATTTTATC TCAACCTTAG
47101 ACCAACTTAT GTCTTATTTG ACTTAGAAAT ATAAAGCTTT TTCATTTTGT TTTTTGATTC
47161 AAATTAATTA AGTCATAACA TTAACCAATT AGATCCTACT GAAACACGTT CCACAGCCTT
47221 CATAATTGAA TTATCTGACA AGTGTTTCAC AAACTTTACA GTATTGGGAT TATCTGGAGA
47281 ATGATTAAAC ATATTGAGGC CTGCTCCTAA CCCCAGACAC ACTGATTTAA TGGGTAATTG
47341 TTAGGTAGTT AGACATTAGC AGTTGGGAGG GGATGACAGA AGAGAGCGGA AAGGCTGTCA
47401 CTAAGACAGC CACTGGCCCA CCTAAATTCA GGCCCAAGAC TACCCTAATG CCACCCTAAG
47461 GGATGGAGTT TATGATAAAG TCTGTGGCCA AAATATCCTG GAGAAAGAGA AAGGAGGGTA
47521 CAGGTGGAAA TTCCCTAAGG TGGCACATGC CCAACAACAC AAAAGCCTGT CTTCAAGTTC
47581 ACCCAAGTT CATCATGCCA TCATTATAAT AGAATTTACA TACAGTTTTG CCCCCCCATC
47641 CCTGGGAGGC TTTTCTTAAC AAATTATAGG TAAGACCATG CACAGTTTAA TTTTAGATTG
47701 TATAGCTATA AACTTCAATC AAATAACATC ATCCTGTCAC TCAGATACAG CCCAAACCTC
47761 AACTCCTCCC CACAAACCCC ATAAAGCAC CTTGAGCTCT GTAAAGAAGT GCTGAGTTCA
47821 CTTCGCAGAA ATAAGCCCGC TGTCCCTCAG AGTGTATTAT TGTGCTTCAA TAAACTTTGC
47881 TTTAAGCTTG CATTTTGGTG TTAGTTTGTA GTTCTTTGCT CACTATCACA AGAACTGAGA
47941 TTGCTGCTTC AGAGCTCCGG CTATAATAAT CTCCTCGGTT AAAGGATCCA TCCCAATGCA
48001 TAATTCCAG TAACAGTATG GGATGCCACC TGGGCAATGG GATTTTAAAA GCTTTCCTTC
48061 TCCCTCAACG AAGTTTGGGA ATTATTGCCT TAGACATTTC AAACAATATT AATAAATTTA
48121 ATACACCTGA TTTGCTCCAA ACCTTTACAT ATCTAGCAAA TTCAACAGGC ATTATTTTTG
48181 TAAGCATGTA TGCAAATTTT GGCAATTCAA GAAAATCAAA CAGGATATCA GGGCCTCGAC
48241 TGTAGGCAAA CAGATACAAT AACATTGGAA ACATGTAGAA TATTGATGAT GGGCACATTG
48301 GGGCTGATAG TACTATTCCT TTTTTTCAAT TTTTGGTAAG ATATAATTAG CATACCATAT
48361 AATTCATCTA TGTAAAATGC AAAAATTGGC CCAGCTCAGT GGCTCACGCT TGTAATCCCA
48421 GCACTTTGGG CGGCCGAGGA AGGCAGATCA CCTGAGATCA GGGGTTCGAG ACCAGCCTGG
```

```
48481 CCAACATGGT GAAACCCCGT CTTTACTAAA AATACAAAAA TTAGCCGGGC GTGATAGCAG
48541 GCAACTGTAA TCCCAGCTAC ATTAGAGGCT GAGGCAGGAG AATCGCTTGA ACCCGGGAGG
48601 CGGAGGTTGC AGTGAGCTAA GATCGTGCCA TCGCACTCCA GCATGGGAGA CAAGAGCAAG
48661 ACTTCATCTC AAAAAAAAAA AATTAGCTGG GTGTGGTGGC ATGCACCTGT AATTCCAGCT
48721 ACTCGGGAAG CTGAGACAGG AGAATCGCTT GAACCTGGGA GGCGGAGGTT GTGGTGAGCC
48781 GAGATCATGC CATTGCACTC CAGCCTGGGC AACAAGAGCG AAACTCCGTC TCAAAAATAA
48841 AATAAATAAA ATAAAATGCA AAAATTAATG GATTTTAGTA TATTTACAGA GATGTGCAAC
48901 CATTACCAAA ATTTTACATT TCTATCTCCC CAAAAAGAAA CCATGTTCCC CTAATTCAGT
48961 ACCCTTAATT CATCGCCTCC CAGATTCCTC CATTCTCCTC CTCCTCCCCT CCCAGCCCTA
49021 GACAATCTTT AATCTACTTT CTTTCTATTT GGAACATTTA GTATACATAG AGGCATATAA
49081 TATATTGCTT TGCCGTGACT GGCTTCTTTC ATTTAGCATA ATGTTTTTAT GTATGTTTTT
49141 CATGGACCAA TAATATCTAT TATAAGGACA TACCACAACA TATTTTATTT ATTCATTCAT
49201 CAGCCGATGG ACATTGGTTT GTTTCTACTT TATGGCTATT GGGAATAGTG CTGTTATAAA
49261 CATTTATGTA CAAGTTTTTT TGTAGACTTA TGTTTTGATT TCTTTTGGTT ATATATCTAG
49321 AAGTGGGTTT GCTGGGTCAT ATGGTAACAC TGTTTAACCT TTTGAGGAAT TGCCACATTC
49381 TTTTCCAAAG TAAGCATTTT ATCCTCCTAT CAGCAGTGTA TGAGAGTTCT GATTCTCTC
49441 CATCTTTGCC TGGGTTTTTG AATCAGGGCC CCAGATAGAA CAAAAATGTG GTTATTCAGT
49501 TGTTCCACCA TCACTTGTTG AGAAGACTCT TTTTTCATTG AAGTGTTTTG GCACCCTTAT
49561 CAAAAATCAA TCTACCATAA ATGTGAGAGT TTATTTCTGG AGTCTCAATT TTATCCCATT
49621 ATGCTATAAT CTATAATCCT ATCTTTTTTT TTTTTTGACA GAGCCTCACT CTATTGCCCA
49681 GGTTGGAGTG CAGTGGCCCA ATCCCGGCCA CTGGCTCCTC CTCCCAGGTT CAAGCAATTC
49741 TCCTGCCTCA GCCTCCCAAG CAGCTGGGAT TACAGGTACC TGCCACCATG CCTGGTTAAT
49801 TTTTGTATTT TTAGTAGAGA CGGGGTTTCA CCATGTTGGT CAGGCTGGTC TGGAACTCCT
49861 GACCTCAGGT GATCTGCCCA CCTCAGCCTC CCAAAGTGCT GGGATTACAG GCATGAGCCA
49921 CCACACCCAG ACTATAATCC TATCTTTATG TCAGGACTAC ACTGTCTTGA TTACTATAGC
49981 TTTTTAGTAA ATTGAATTCA AGAAGTTTCT CAACTTCAAA TTTGATCTTT TTTTGGAAGA
50041 CTATATTAGC TATTCTCAGT CTGCTGAATT TCCCTAGGAA TTTTAGGATC TATTATCAAT
50101 GTCTATTCTA TTTTTGTATA TGTTTTAATA TTTTCATAAG AAACTTTTTT CATTTAAACT
50161 TTTTTTTTTA AGAAAAATAG TGAAAATCAG AATACTGGGG GTCAGGCGCA TTTAACAGGC
50221 AGAAGAAGAA TAAAAACTTG TCATATAAAC AAAAAAGAAA TGACCAATCA CATTGTGGAA
50281 GCCATGGAGT GGTTATAGGT GCCAAAGGCT GCAGAGAAAT GGTGTCAGAT ATACCTGAAA
50341 ATTGTCCATT GTATTTGGCC ATTAAGAGAC TTAGAAGACT TAAGCCATAG ATTGCTCAGT
50401 GAGACCCCGA GGGCAAATGG TCTGAAGGTG AATAGATCAT TTCACCTTTA AGAGAGCAGG
50461 TAGGAAGCTA TAAATCCAAG ATTAAAAAGT TGACTGAACT GTTAAAGAAG AAACTCTAAT
50521 CTTGAGCCAC CCTATCCTTG CTCCACCTTC TGCTGCAAGC AAACAGAAAT GCTGAAATTC
50581 AACACTCACA AAGGCTGGTA AGCTGGAAAT GACAAAAATT ACTCCTGGGA AAGTCAGATT
50641 TAGAATTAGG CCATATTTGT TGGGGTTCAG ATTTTCATGT ACACTTGGGA AAGGGTTTAG
50701 CTTATAGGCA CATGCATGAA GGGAACTGGT ATAGGGCTGT GTTCATAAGG TCAAGAGTTG
50761 AAGGCCAGGC ATGGAGGCTC TTGCCTGTAA TCCCAGCACT TTGGGAGGCC GAGGCAGGAG
50821 GATGGCTTGA GCCCAGGAAT TCAAGACCAG CCTGGGAAAC ATAGGGAGAT GCTGTCTTCA
50881 CAAAACAATT AAAAAATAAA ATTAGTCAGG TGTGGTGGCA CACACTTGTG GTCCCAGCCA
50941 CTCAGGAGGT TGGGAAGATC ACTTAAGCCT GGGACATTGA GGCTGTAGTC AGCCATGATA
51001 GTGCTACTGC ACACCAGTCT AGGTGACAGA ATGAGACCCT GTCTCCAAAA AAAGAGCTGT
51061 ATCCACATCC CAGGAAAGTG GTTGAAGATC TACTTTTCTC TGTAAACCTA ATAAAGAATA
51121 GAGTGACAAA TGTGTGTTGT GGAAAGAAAT GGGGTGAGAG CTACGTAGAT GCAAAACAAT
51181 ACATCCCCAC ATACCACTTG TTAATCATCC TTTTCCACCC ACTTATGGGA TGAATTGCAT
51241 CTCCCCAAAA GATACTCTGT CCTAACCCTC AGTACCTGTG AACCTGACCT TATCTGGAAT
51301 ACGGTGAGTT CACTGGTTAA GAAGAGATTA TAGTGGAATA GGGTGAGTCC TCCAACCAAT
51361 GACTGGGGTC CTCACAGACA CAGAGGGATG ATGGCCAGGT AGAGATGGAG GCAGAGATTG
51421 GAGTTATGCT GCCACAAACC AAACACAGGA AGCTGCTAGA AGTGGAAACA GGCAAGAAAG
51481 AATCCTTCCC CAGAGGCTAC AGAGGGATCT TGGCCCTGAT AATACCTTGA TCTCAACTGG
51541 CCTACGTAAC TGTGAGAGAA TAAATTTCTT TTGTTCTAAG CCACCCAGTT GATAGTACTT
51601 TGTTACGGCA GCCCTAAGGA ACTTGATATA CATTTCTTTT ACTGTCATAG AAGTTTTGAA
51661 TCTTTTAAGT AGGTCTGTAC CCTTCCTCCC AGTGTCAACG CATGGAATTC CTCTCCTTGT
```

Figure 2 (Page 16 of 74)

```
51721 GCCTTGAAAA GTGAAAGGTG TTTGAACTGG TAATGAAAGA AATCTCAGCA TGAGGCCAGA
51781 TGCTGTACCT CACACCTGTA ATCTCAGCAC TTCGGGAGGA TGAGGCGGGC AGATCACTTG
51841 AGGTCAGGAG TTCTAGACTA CTCTGGCCAA CATGGTGAAA CCCCATCTCT ACTAAAAACA
51901 AAAATGTTA TCCTAGCCGG GCATGGTGCC TGTAGTCCCA GCTACTCAGG AGGCTGAGGC
51961 AGGAGAATTG CTTGAACCCG GGAGGTGGAG GTTGCAGTGA ACTGAGATCA CGCCACTGCA
52021 CTCTAGCCTT GGTGAGAGAG CAAGACTTGG TCTTAAAAAA GAGAAAAGAA AAATGAAATT
52081 TCAGCATTAT AGAATAAAAA TGTTTCCCCT TCCCCCCAAA CTTTAAAAAA GCAGAAGTCT
52141 GCATCATAAA ATGGTCTTTG CCAATGTTAT TTTATTATA ACAAAGGAAT CTTGCAAGGC
52201 TACCAGATCT CAGCAATTGT CACTATGTTC TGTAAAAATC ACTTCCTAAA ATGTCTGAAT
52261 TGACTGCTTG TCTCATTTAT TTGTTTCTCG TGTCATACTG CAATGGATAT CTGTCTTGTT
52321 AGTATAAATA TTTGTGCATT TTGTTGTTGT TAAAACAGCT TTTTTGGCCT GTCTTCTTCC
52381 ACCTATGAGG TAATATAAAA CTCATGTTTA ACACTTATTT TTGTAGGAGG ACAAGCTACA
52441 GACAAAACCC CTCAGACACT GAGTTAAAGA AGGAAGGGCT TTATTCAGCT GGGAGCTTTG
52501 GCAAGACTCA CATCTCCAAA AACCGAGCTC CCTGAGTGAG CAATTCCTGT CCCTTTTAAG
52561 GGCTTGCAAC TCTAAGGGGG TCTGTGTGAG AGGGTCATGA TCGACTGAGC AAGTGGGGGT
52621 ATGTGACTGG CAGCTGCATG CACCAGTAAT CAGAACAGAA CAGGGATTTT CACAGTGTTT
52681 TTCCATACAA TGTCTGGAAT CTATAGATAA CATAACCGGT TAGGTCGGGG GTCAATCTTT
52741 AACCAGACCC AGGGTGCAAC ACCAGGCTGT CTGCCTGTGG ATTTCATTTC TGCCTTTTAG
52801 CTTTTACTTT TTCTTTCTTT GGAGGCAAAA ATTGGGCATA AGACAATATG AGGGGTGGTC
52861 GCCTCACTTA TTCACCCCCT TTGAGAATCT CACTCATTAG TGGGAGTTCT CACTTTTATT
52921 CTCACTACCT ATGTCTTCTT GAAAGACAGA TTGATAATGA TTCATATAGT ACACTTGTGC
52981 TGAAGCATTT TGGTGAGCTA AGGTAGTGAT GAAGCTTTTT ATCATTTGGA GAAGTACAGG
53041 TAGCAAACAA GGAAGCAGTA AGCAGGTTTC TATTAATATT ATAACTCCTA TTATAAGAGT
53101 TTTAAATCTT CTTAGCACTC GGAACCATTT TTCAAACATG GCCCAGAAA CAAATCCATA
53161 CCACACCTAC ATGGGCACAT GTGCCACTTT TGTCATATTT CTAACTATGT CTTCAACTAC
53221 TTGCCCTTAA TCATCTATGT GTAGACAGCA ATTAGTAAGG TTAAATTTCC TACAGACCCC
53281 TCCTTCAGTT GCTAGCAAGT AGTCGAGAGC CAATCCATTT TGATAGATAG CATTTTGCAT
53341 CTGAGTTTCT TGCCAGGCCA CAGTAGTCAG GGCTCTGCTG GTCTTATTAG TAATTATTTC
53401 TAAGACAGCT TGTAACCGTA TGATTCAGTT GAGCATGTAA ATGGGGGTCC CATATCCCCA
53461 CAAGCCGTCT TGTGCCCAAG TAGCAGGCCC ATAATATTGT ATGATTCTCT CAGGGGGCCA
53521 TTCATTATTT TTCCAATTTT CTATAGCTAT GCTTTTTTTT TTTTTTTTT TTTTTTTTT
53581 TTGCGGGAAG CATATACAGG GAAGCCCAGG AGTTTGCCTG TCTTTATGGG CAGTAGGAAG
53641 AAAGATGGTT TAATAGTGTC AATAACACAA CTACCTGCCC ACTGGTCAGG TAATTTGGCA
53701 TAAGCTGTAT GCCCACATAT CCAGTATAAT CCAGTGGGGG CTGTCCAGTC CCGGTGGGAC
53761 TCTGGGTGGG TCCACACAGT TTGCAACTTT GGGAATTTAC TAAATAGATT TTTCTTAGTG
53821 TGGTTTGAAC TCCACTAGGT GGCTGTTTTT ATAGTACTAT TATACAGTTT TTGCCCAAGG
53881 CAGCTGAGTC TTCCCACAGG AAGGGTGAAG TCCTTCCCCA CTTTTGCTAT ACAGTATTGT
53941 CTAATGATTG AGGCTTTTAG GACCCAGAAG TTATCAGGGT GAGTCTTTTG AGCTGGGAAT
54001 TTATCAGGAA CTGGGTCTGT AGGTACTAAT TCTCGTGCTT CCCATGGCCA TTGATCTCCC
54061 ATTACAGTTC CTCCACATAC ATACATAACA TGAAGTGACA TTGAGAGACT GGGCTACATG
54121 CTCAGCTAAT TGCAAAAACA AATTTCTTGT TTTTCCTGGA ATTTCTAGTA CTGGCACATT
54181 CAGTTCATCA TAAGAAGGTT TGAAATACTG GCTCAGGGGA GCATTTATAA ACTTCTCCTC
54241 AAACCACCAT ATTTACTCAA GGATCCAGTC CAGCCCCAAC TATTTCTAAG GTTACACGAT
54301 CCCCTTTTTT CCAGTGAGAA TCAAGGGGGT TGGTTATTAC TAGTTCTAAG GGGTTACACT
54361 GACCACTGGT ACAGGAAGGG CCACTTTTCC CTTTCTGAAG GTGGACAGGA TTCTTTTTAT
54421 TTTTTAACCA AGTTGCCTAA ATGACACAAG ACCAGTATCT ACATTTATTT CCACGCAGTC
54481 TTAATTCATG ACAAGCGTAC TTATTTTCTG CCATATAGCC TCTTTCCTAA TGAACAGAAC
54541 CACATCCTAT TTCTAACTTA TTACTATTAA TGACAGCACA GGCATCAAAT TTCAAGGTGA
54601 CTTGTTTGGG CATTCCTTTT TCTTCTGTTT TGGCTAACAC TTTACTCGTA TCGTTTATGA
54661 ACCCCCACCA GTCCTCAGTC CTCAATCTTA TTTCAAAAAC TGTGGTCGTG GGAGGCTCAG
54721 ATGGGTCATA ACACACATCA GGTTGGTCAT TTCTTGGGCT ACCTGCCTTG TATAGAATAG
54781 CATTATACAA ACAAGTTATT TTTAGAGTCT TTGTACACTT ATAATAACCA TAAAATAATA
54841 AGACTGTAGC AACTTTTTGT CCTACCTCAG TGACTTGATG TATACACTGG GAACAGCCCT
54901 CAGTCTGAGG AAGGTTAGTT GAAGTCTTTA CTGTGCAAGT CCAAATTTTA AGGAAAATGA
```

Figure 2 (Page 17 of 74)

```
54961 GTCCCTTGAT GAGTTTTCTC ATGTTTCGGC CATGCATGGA CCAGTCAGCT TCCGGGTGTG
55021 ACTGGAGCAG GGCTTGTTGT CTTCTTCAGT CACTTTGCAG GCGTTGGCGA AGCTGCCACG
55081 TACAGCTCAC AGTCTACTGA TGTTCAAGGA TGGTCTTGGA AGTTGGGCCC ACTAGAATTA
55141 ACTGAGTCCA ATACCTCTAC TCAGTCACTT TCAACTGGGC TTTCTGATAC CAGGAGCAAG
55201 GTGGCAGGTT TTAGGGTGTT GCAAATTTCA ATGGTTATGC AGGGATTTTC ACATAGCAAA
55261 CTTTGGTACT TGGTTAATCT AGCATTTGTT AGCCAATGAT GTATTATTA AAGTCACCAC
55321 AGCATGGAGG GCCTTTAAGT TTAGGTTTTG TCCAAGAGTT AGCTTATCTG CCTCTTGTGC
55381 TAGCAGGGCT GTTGCTGCCA AGGCTCTTAA GCATGGAGGC CAACCCTTAG AAACTCCATC
55441 TAGTTGTTTG GAGGCCCAGC CTCGGCCAGG GCCCCACAGT CTGGGTCAAA ACTCCAACCG
55501 CCATTTTTTC TCTTTCTGAC ACATAGAGTG TAAAGGGTTT TGTCAGGTCA GGTAGCCCCA
55561 GGGCTGGGGC CGACATGAGT TTTTCTTTTA ACTCATGAAA AACTCATTGC TGTTGGTTGT
55621 AATAGATGTA GTTTATCCAA TCTACATTTT TATTAACTGT CACCCACCAA AATATTGACT
55681 CAAATCCTGC AGCTATTTGA TTTTGGGATT TAAATTGATC TGCTATTCCC TGTGGGACTC
55741 CAATTGCATC TAAATAGATG TGAGAGTTGA AAGACACATA AGGGTCTTCT CTTGCTTTAC
55801 GATGTCTTAT TTTTCCTCCC TCTGGTTGAT GAAATGCTAG GGTGAAAGGG ATAGCCAACT
55861 GGACTAAAGT ACAAGTGCCG CTCCAGTTAT TTGGCAGAGT GCCCAGTAAA GGTCCACCAC
55921 AATACCACCA CACATCCGCT TGGGGATGAA CAAAGGCTGA CTGATTGAGA AGCTCCTGAA
55981 AATTCTTAAG CTCACTGCAT CCCTTCAGGT CTCCAAGGAA TGCTAAGTTT CCTCCCTGTC
56041 ATGAGAGACA AGAAGTGAAC TTAGTTTTGG GAGATGAAG CTGGATGGCC CTCAGGGGTT
56101 GACCTGCAGG GTGCTGGACT TTGGGATATA GCAGAGAGAG CTTGGCACGA CTTATTACTC
56161 CAGGCTGTAG CATCCTGGAA AACAGTTACC ATGCAGCCCA TGCCTGGTCA ACAGGAGGAC
56221 CACCTTAGTG GAAAGGGGAT AATCTGGCCC TCTGGCCTGC CATGTGCACA AGCATAACAA
56281 TTGGTTTTGT TTAATGTGTG GACAGAATAT TTGATCCATT CCAACTGGGC ATTTGCATCT
56341 TGGTATCCTG CTTAATTATC AAAGTTTGTT TTAAGTCTTT AACTTCTATG ACCCTCTAGT
56401 AAAATGAATG TATGATTTTA GGAAATTACA AAAACCGGTT GGGGCAGTCC ATCCTCGCTC
56461 TTTAGTGGTC CACACAACAT TCGACCAACT ATGGCATAAA AGCTCTACAT CAGGGGGCAA
56521 GACTCCTCGT TGACACTGGG GTCTTTATTG AAATCTCTCT GGATTAAATG GTCTCAGTTT
56581 ACTAAGGCTC AGTCTGAGGA GAGTCAGGAG GGACAGAGGT ACTTTTCTGA AGTACAGAGA
56641 TGTCTTCGAC TTGGCAAGTC CCACAGGGT ATAACAAGGC AAGCATTAAA TTCAATAGTT
56701 TGAGGCAAAA TTGACTTGGT TATGTTAATA ACTAGATGGT CAGAAATAGA GTGAGGGAAG
56761 AAGAAAGAGT AATAGAATAG ATGAAGGAGT TAAATTTTTC TTAGCTTTAG TTTGGTAGGG
56821 TTTTCCCCTG GGACTATGGC CCATGACTCT GGAGGGGGTG GCACTTTCTT GACTCGGGTG
56881 TGATGAGTCC ATCCCTTTTT CACCGTATGA ACAACAGTCT CGGTGGTTAG CAGCACAAGG
56941 TAGGGTCCTT CCTAGGCTGG CTCAAGTTTT CCTTCTTTCC ACCCTTTGAT GAGAACATGA
57001 TCTTCAGGCT GGTGCTGGTT TACAGAAAAT TCTAGGGGTG GTACATGTGC TAAAAGACTT
57061 TTAGTTTTGA GGGAAAGGAA AGTGGAAGAT AAACCAAGTA TATAACTTTT AAGAAGTTGA
57121 CCTTTTGTTT TAAATGTGGG GACATCAGCA GTGGACTTTA TAGTCCTTGG TGCCTTCTTA
57181 CTGAGAAATT TCCTTTAGCA CCTATTTTTA TTAGTTTTTA GACCAAAGAA AGTCAAATGC
57241 CATTTTATAT TTGACAACGC TTCTTGTATG TTTATACCAG ATAAGCTAGA TTTCACCTTT
57301 ATATTGGTGT GTTATTAATG TTAAACTTAG TTTTAATAAA ACTCTGTAGA CATATTTATT
57361 TGATTTTTAA TGTCTGACCA TAAGGTAAGA TTTTTATAGA CTTTTCTTTA ACCTTTTATA
57421 ATTTTTGTTA AAGAACAGGT TAGTGCTTTA AGAAAAACCC GTTGTGTTTT TATTTTAATG
57481 TTCAGTTCAC AGAAAACTG TATGATACCC CTTAACTTTA GCCAATATGT TTAGACACAG
57541 AATTTCTTT ACAATTAAGG TTTCAAAACT TGCTTAAACC TTCAAAACAA TTTTTGTAAC
57601 CTTTTAATGT AGGTAAAAAT CCACATTCTT ATGCATCCTC ATAATCCTTT TACCAAAGGT
57661 ATATTTACT TTCCTTACAT ACCTTGCACA TAAACTGTTT ATTCAATAGT TTTACATTTA
57721 GAAGGAGGCC TAATTACTTT TAAATTATAC AACATTTCTT GCATAAATTT ATTTTTCTAA
57781 CACACATTTT TTTCATGACT TTCACAGACA ATTCTTCGAC ATGCCTCAAC TTTCTGACTT
57841 ATTGCAAACA TCCCTTTCTT TAAACAACTA GTTAATTTAT CTCAGGACAA GGATTTTCCA
57901 TACAACATTC TTTTTTATAT AAATTCTGCC TCCTCTTTAT TTCCTTTTTT TTTTTCCGAG
57961 GATGATAACC ATTCTTTTCC AAAGCGAACT TCTTTTATGT CTGTGGACTA GACTGTCTAA
58021 GGCCACAAGA TTAGAAGTTA CTATAATACA TGTTACACTG TTAACTTTTA GCAAACTTTA
58081 CTTTTGTTGA AAACCTTGTA AGTTTGGGAT TTCAATTATC CTTTGCTATT AATAAGACCT
58141 TATTTAGTCC AAATTAACTT AGAATTGGTA TAGATGGCTT TTTTTTTTTT TTTAATTACC
```

Figure 2 (Page 18 of 74)

```
58201 TGGGAGGAAC CATCTATCCT CCTGTCCTGA AGGGAGTTCC TCCTAGGTCT GGTCAGAGCT
58261 TTGTATGGTA ATTAAGATTT AGATCCCCTG TTAGGAAACC TGCCGGGTTA AGAGAATTTT
58321 CAGTGGTTAA TGTTAAATCA TCTTCTTTTT TCTTTTTTCC TTAGGATACT TCTGAACCGG
58381 TGAGGTGTGC TCACAATGAG GTTCCTGTA AAAGTTATTT TTTTACTTTC TTCTGTTAGC
58441 AAAGCAGTTG CCGCTACAGA TTGAATGCAT TTGGGCCATC CGCGGGTTAC TGGGTTAAGG
58501 ATTTTTGATA GGAAGGCCTT AATGCTTTTG GAATATGCCC TGACAACAAA GTGCCAGTTC
58561 CTTCCCGGTG TTCAGCCACT GCGTTGATCC TCCACGAGGG CCTGCCACGT GCTGCTCTGG
58621 TGAGGCGTTC CACCGGGGCA ATTGCCTACC TGGGAGCGCT CTCCAGATCT GTGTCGCTCA
58681 AACTGGCTGG AGTTCCCCGT AGGGATGCTC CACAGGGCAG GCCTAAGTCG CCTAAGGGGC
58741 TGCCTTGACC GTCCGTTAAT CACCTCTGTC TCCAAAAACC AGCTCCCTGA GTGAGCAATT
58801 CCTGTCCCTT TTAAGGGCTT ACAACTCTAA GGGGTCTGC ATGAGAGGGT CGTGATTGAT
58861 TGAGCAAGCA GGGGGTACGT GACTGGGGCT GCATGCATCA GTAATCAGAA CAGAACAGAA
58921 CAGCACAGGG ATTTTCACAA TGCTTTTCCA TACAATGTCT GGAATCTATA GATAACATAA
58981 CCTGTTAGGT CAAAGGTCGA TCTTTAACCA GACCCAGGGT GCGGTGCCGG GCTGTTTGCC
59041 TGTGGATTTC ATTTCTCCCT TTTAATTTTT ACTTTTTCTT TCTTTGGAGG CAGAAATTGG
59101 GCATAAGACA ATATGAGGGG TGGTCTCCTC CCTTAATTTA AACAAAATTT TCAAAGTCCT
59161 ACCCCAAGTA AATTGGCAAA TATTAATAAA GTTATGGCAT AGAAAATAAA AATGATTGTA
59221 AAAGGCGTAA AGATATTTCT GTGGGGAAAA CATTTGTTCA TTAGTTATCA GTTAAAATTC
59281 TGTGAAAAAT AACCACTAGA GACCCTAAAG TACCCAGGGG CTAATAATAA GAAGGGAGGA
59341 ACACCCTCTC AGTCCCCACC GTTACCTCCC CAGAAGGGAA GAGGAAGAGG GTGACTCCAG
59401 GAGAGCTGTG GTCTCCCCTC CCCATATGTC CACATATACC TGACCTCCCC TCCCCAAAAT
59461 ATATACCCAA TATCTCTCCC ATATATACAT ATTTATCTGA CCTCTCCACA TATGTATACC
59521 TAAACTTTCT CTATATATCC ACATATACCT AACCCTCTCA CACACATATA GCTGACCTCC
59581 AGTGGAGGAA AATGGGGAAG AGAGAAGAAG TTATCAAAGG ATAAATCTAG GTCATACTCA
59641 GAAATGTGAA AAACAAAAAC CACACACAGA AAAAAAAAAC ACACACAAAA AAGAAATTGA
59701 TAAATTTGTT TGTGTCAAAA TTAAGAATTC CGGTTCAATG AAGGATCCCA TGGATAAAGT
59761 TAAGACACTG CTGTAAGGAT GGTAGAGAAT TAAATGTCTG AATCAGACGA AAGGATGAGT
59821 AATTAGAATG CACAAGGCCA AGAAGAACAA AACAGAAACT CCACATAAAA AATGTATGAG
59881 GCCGGGCGCG GTGGCTCATG CCAGTAATCC CAGCGCTTTG GGAGGCCAGG GCGGGCCGAT
59941 CAGGAGTTTG AGACCAGGCT GGCCAACATT GTGAAACCCC ATCTCTACAA AAAATACAAA
60001 AAATTAGCCG GGCGTGGTGG TGGGTGCCTA TAATCCCAGC TACTTGGGAG GCTGAGGCAG
60061 GAGAATCACT TAAACTCAGG AGGCAGAGGT TGCAGTGAGC TGAGATCACA CCATTGCACT
60121 CCAGCCTGGG TGACAGTGTG AGACTCTGTC TCAAAAAAAA AAAAAAATTA TATATATATA
60181 TATATATATA TATATATATA TATATATATA TGAAATAAAT GAACAAGAAA TTTAGATACA
60241 GGAAAATCCA AAGCACTTGG TAATGAAAGA AAGGTAAAGT GATGTGTCCT TTTGCATTTA
60301 AAAGAGAGCA TTAACAAATT AGAGAGCTGA ATAATGCTCA GTATTGGTGT GGATATGGAG
60361 ACTCAGGAAT CCTCATACAC TGCTGATGGG AGTGCCCACT CCCTGGGAAT ATTTTCCAAA
60421 TATCATCTCA AACATATCCC ATAAAGGTGA CAGGAAAGTG TGGGCTGACT GATATCCTTC
60481 ACTGAGAGAG GTGGAGGTAA AATGAAGTCA CTGCACAATA TAGAGTTGGA AGCAATGGAT
60541 TAGATGTCCA CATAGTTACG TGGAAGAATC CGTAAGATAC ACACACACAC ACACACACAC
60601 ACCTTTGTGT ATATTGTTCC TGGCAGGTAG GCATGGAGGT TTAGAGGCTT TCTACATCAC
60661 ACCTACTGCA CACAGTAAAT GGCCAGGCTG AGCACTGACT TCCATGAAGG GAGATTGAAG
60721 GTAAGAGATT GAAGATTGTT CCCTGGTCTG GACCCTGCA ACTGAATATG CAGAAAAAAG
60781 TACACCCCGC CACCCCGCTT CCCATCTTTC CTACCTGATT AGAATAGCTT TTTCAGAAAA
60841 CGTTGGCCAG GGGTTGTGGC TCACACCTGT AATCCCAGCA CTTTGGGAGG CTGAGGCGGG
60901 CAGATCATCT GAGGTCAGAA GTTCCAGACC AGCCTGGCCA ACATGGCGAA ACCCCATCTC
60961 TACTAAAAAT ATAAAAATT AGCAGGGCAT GGTGGCACAC ACCTGTCATC CCAGCTACTC
61021 GGGAGCCTGA GGCAGGAGAC TCACTTGAAG CACAGTGATG GAGGTTGAAG TTAGCTGAGA
61081 TCTTGCCACT GCACTCCAGC CTGGACAACA GAGTGACACT TTGTCTCAAC AACAACAACA
61141 AAACCCACCA AAACTTTAAA TCTACCTATG GCCAAATGCC TGCTAAAATG AGCACCCAAG
61201 AAGCAGTGTT CAGGAAAGTC AGATGAATAC CCTAAAATTA GATGCAATGT TGGCTGGTCA
61261 CAGTGGCTCA GGCCCTGTAA TCCCAATCCT TCTTGGGAGG CCGAGGCGAC AGATCGCTTA
61321 AGCTCAGGAG ATCGAGACCA GTCTGGACAA CATGGTGAGA CCGTGTCTCT ACAAAAACGT
61381 ACAAAAATGA GCTGGGAGTG GTGGCGCACA CCTGTAGTCC CAGCTACTCA GGAAGCTGAG
```

```
61441 GTGGGAGGAT CTCTTGAACC CAGAAGGCGG AGACTGCAGT GAGCAGAGAT CATGCCACTA
61501 CACCCCAGCC TGGATGATAG AGCCAGACCC CCATCTCCAG AAAAAAAAAT AAAGAGAGAG
61561 AGAGATGCAA TATTTAGGGT TCAACAAGAC TGAACTTCTG ACTCCTTTCC CTACCTCTCC
61621 AGCATGTTAG ATTCTGGGTC CTTCATCCTA ACCCCTGTT CATGCCATAG CCACCCTGTG
61681 GTACCAACTT TGGAAGCCTG GATCTTCATC CCCTCATGAT AATGAGTGTC CCATTCAGGT
61741 CTCCATGCTC AGCTTGGCAA GAGTATCTGT CTTCTCCTCA TGGGACGGTC ACATTCACCC
61801 AGCACTGACA GGTTCCATTC CCACTAGGGT GGCACCCTAT ATGGTCTGAG TCCAGGCCTT
61861 CCTGGTCCCT CAGTAATCTC AGCATGGTAG CACAATCGAA AAGGGCTAGG CACGGCAGCA
61921 CCATTTCCCA CCAAGAGGTC TGATGGCTCA TCACATAGAC TGAAGGAGAT TCTGAAGAGC
61981 AGAGGTGGAA TGAAGAATGA ATCCTGGGCT CTGCTCTTCC TAGGCCTGTC TTCCTCTCTC
62041 CCGAGATGTT AGCTAACTCA TGAGAGCCAG AAACCAACTG CAGGCTGGCC TCAGGCACTT
62101 AGGTAGTGCT TCAGCCTCAG CAGTCCACAT TCTAGGAACC CTCATAATAT GGGTTGAAGT
62161 ATGCATTCCC ACAAAAATAA AGTTGTTGAA GTCCTAACCA CCAGTACTGA AATGGGAAAA
62221 GTTCCCTTGT CCCGCTCGCA TGGCATGTGA TAGGAGTGTG GCTAATTTCT TCAGTGCCTG
62281 GCTGCTCAAA CCTCTAGGGG AACAGTAAGA CGGGCAGGTT GTGGGTCTCC AACCCCATGA
62341 CCCCACCACA GTGTCTAGGG TTGAATGTTT ACAGCTCCTG AAGCCACAGT GGGTGTGTGT
62401 TACAGGGTGC TCTTTTAGTT TTGCCATTTA TAGGCAGCTG GTGTTAACCA ACTCAATTAG
62461 ACCGTCTACC TTGTCCCAAG GACAGAAGAA GGCTTTCTGT ATCCCAGGTT CTTGCCTTGG
62521 TGTACCGGAA TAAATCAGAC CACACCTGGG CTTAGAGAAA GAGTGCAAGG TTTTATTAAG
62581 TGGAGGTAGC TCTCAGCAGT TGGGCAAAGC CAAAAGTGGA TGGAGTGGGA AAGTTTTCCC
62641 TTGGAGTCAG CCACTCAGTG GCCCAGGCTC TCCTGCAACC ACCCCAGTCA AATTCCGCCT
62701 CATTTGCCA GGCAAACGTT TGTTGTGTGC TCTTCTGCCA GTGTGCTCCC CTGGACGTCC
62761 AGCTATTCGT GTCTTGTGGC AGGCCAGGGG AGGTCTTGGG AAATGCAACA TTTGGGCAGG
62821 AAAACAAAAA TGCCTGTCCT CACCGTGGTC CCTGGGCACA GGCCTGGGGG TGGAGCCCTA
62881 GCCGGGGACC ACGCCCTTCC CTTCCCCACT TCCATATCAT TTAAAGGGAC CATGCCCTTC
62941 CCTTCCCAGC ACTTTCCCCC TCCTGTATCA GGACCTGTGA ATGTGGCCTT ATTTGGAAAT
63001 AGGGTCTTTG CACTTCATCA GTTAAGATAA GAGTGGGCTC TAACCCAACA TAAAGGGTGT
63061 CCTTATAAAA AGGAGAAATG TCATACACAG AGACTGACAC CTATAGAGAG AAAATGTGGT
63121 GAGTAGACAC AGGGAGAATC ACCATTCAAG TCAAGCAATG AGTCTGGGA TACCAGAAGC
63181 TGGGAGAGAA ACCTGGAACA GATTATCCCT CATTGCCTTC AGAAGGAATC AAACCTGATG
63241 ATACTTTGAT TTCAGACTTC CAGCTTCCAG GACTGTGTGA CGATAAATAT CTGTTGTTAA
63301 GCCAACAAGT TTGAGGTACT TTGTTACTGC AGCCCCAGAA AACTAATACA GTAGGTACTA
63361 TGGACTGAAT TGTGACTCCC CGTCGCAAAA TTCATATGTT GAAACCCTAA CCCCCAGTGT
63421 GATGGTACTT GGAGCTGGGG CGTTTGGGAA GTCATTATAT TTAGACAAAC TCATCAGGAT
63481 GTGTCTCTCA TGATGAAATT CATGCCCTTA TTAAAAGAGA CAACAGGCCA GGTGCAGTGG
63541 CTCATGCCTG TAATCCCAGC ACTTTGGGAG GCTGAGGTGG ATGGATCACC TGAGGTTGGG
63601 AGTTTGAGAC CAGCCTGGCC AACATGGTAA AACCCCATGT CTACTAAAAA TACAAAAATT
63661 GGCCAGGTGT GGTGGTGCAC GCTTGTACTC CCAGCTACTT GGGAGGCTGA GGCAGGAGAA
63721 TCCCTTGAAC CCAGGAGGTG GAAGTTGCAG TGAGATCACA CCACTGTACT CTAGCCTGGG
63781 TGATAGAGAC TCCATCTCAA AAAAAAAAA AAAAAAAGAC AATAGAGCCA GGTGCTGCAG
63841 CTGATGCCTG TAATTCCAAC ACTATGAGAG CTGAAGCAG GAGGCTCGCT TTAGCCCAGG
63901 AGTTCAAGAC CAGCTTGGAC AAAATAGTGA GACCCCAAC TTCTAAAAAT TTAAAAAATG
63961 AACTGGGTGT GGTGGTACAC ATCTGAGGCT CCAGCTACTC TGGAGGCTGA GGTGGGAGGA
64021 TTGCTTGAGC CCAGGAGGAG GCTGCAGTGA GCCATTGCTG TCCAGCCTGG GCTACACGAG
64081 AACCTGTCTC GGGAAAAGGA GAAACAGTG AGACCTCTTT TTCTCTCCTC CTTCTCTCCA
64141 CTGCCTAAGC CCTACAAGCA CAAAAAGGAC ACCACATGAG CACATAGTGA GAATGCTGCT
64201 GCCACCAACA AGTCAGGAAG AGAGCGTTCA CCTAGAAACT GAATTGGCCA GCACCTGGAT
64261 CTTGGACTTC TGAGCTTCCA GAACTGTGAG AAAGTTATTT TTTTTTTAGC GACTAAGTCT
64321 ATAGTATTTT ATTACAGCAG CTCAAGGTAA CTAACATAGT AGAAGGGATG AATTATGGAG
64381 ATCACAAGTC CACGCCTCCA GAAAAGACT TCCCTAAAAA TTAGTCTGAG CAAAATTCGA
64441 ATGATGAATT ATTTTTAAGA ACTTTTAAGG GATCTGACAA GTTTGCAAGA GCTAGAGAAT
64501 GCTTTACAAC GTGATAATAG AATGCTCTGT GATGACAGAA ATCTTTCCAC ACTGTTCAAA
64561 ACTAGCTACT GGCCACTTGT GACTATTGTG CACTTGAAAT GTGACTGGTG TCTGAGGAGC
64621 AGAATGTTTA ATTTTACTTA ATTTTAATTC ATTACAATAG CTACATGTAG CTAGGGGCTA
```

```
64681 CTGGATTGAA CAGCACAGCT CGAGTCTTTT AGAGGGAGAC AGGACTCACC AAGGTGGATG
64741 CTGGTGGCCA AGCAGCAATG GCAGGTAGTA CACACACAAG AGGCAGATGA TACAACACAT
64801 CCTTCCCAAA CCTGGAGATA AGCTCACCCC ACAATCCCGC CGCTGAAATA GAGTTGATGT
64861 TACCAATGTG CATTTTTATG TCCTTTTCCA TACAGAAAGA TCATTCAACA AGTACTATGG
64921 TACTTAAAAA ACAACATTCA ATTCATTATT ATGACAAAAT TAAATTAATA GCTCTTCCTT
64981 AAACTTTTAA ATTCAATTTA CAATGCTTAC TATTGGCATT TATTAATCTA CCAATTTTTT
65041 CCCATAGAAC CCATAGAACA AATAATCTAC CAAATTTTTA ACATTCATTT TTGGCAAGGC
65101 TTTTGCAATT TGACGAACTT TAAGAAGAAA ACTTATAAAT TGCAATTTTT AAATCTGACA
65161 TACTGGACTT TTAAAGTATC CAATTGACTA ATGAACAAAA CTGCTCCAAA TTTTTCAATT
65221 CTTAAAAATC TTAAGACAAT ACTTAATATG GCAAATCTTA ACTTCTTAAA CTTTGTAAGA
65281 ATGCTAATCA ACTTAGATTG GTATAAAGTT GAGTTAAAAA TCACAGGATA CATCATCTCA
65341 GCTATAAGTT TTCATGAGTT GAGTTTTTAC AATCACTTGA AATGCTTAGA ATAGGAAATA
65401 CGTATAAATT ATTTAACATA AAATATTGTT ACAAAACCTC TGGAGTGTCA GTTTCTCTGG
65461 CCAGACTTTA TGCTGCAGCA CCTTTGCCTG AGTTCTTGTC CTGCATCCAG GAAGAATTAG
65521 GTACAGAGGC AAGAGTCAAG AAGATTAGTT TTCCAATAGT TCAGCTCACC TAGTTAACTC
65581 CTGTTCACAA TCTTCAAAGT TATCAGAAAC CTGCAATTGA GGGTTATAAT CCATTCTTTG
65641 CAGAGTTTCA AAACAAGACA ACATTTGTCT ATGAATGTTA AAATGTCCTA GGGTAGTCAC
65701 AGTCAAAAAC ACAATTGACA AAGAAATTTA GTCACCTCTG TGATTTACAA TAGCCTAACA
65761 CAATAACTCT AATTATAACT GATGACACAA ACTCAGATAT CAGAACTCTA GAAATCCCCT
65821 ATAATTTTGG AACACATATT CACAGTTTTC ACTGAAATAT GACCTGAAGA TCAAATATCA
65881 CCTTATTTCA ACAATCCTAT ATAACTAAAC GTGTCAAATG ATCCTGTTTA CCTCTCCTTT
65941 GGATACTCCA GGGGCCCTCT GTAGCATCCA AAAGTTAGGG GTTAGCAAAG ACAATTTGA
66001 AGCTGTAAAG GCTCAAAACA CTTAATGAAC CTCTAGTCAT ATCTGTTCTC TACTCACTAA
66061 ATGCTAGTAG CACCTCTCAG TTGTGGCTAA GCTGGGAGGA TCTCTTGAGC CTAGAAGTTT
66121 GGGGACGCAG TGAGCTATGA TTATGCCACT GCACTCCAGC CTGGGCAACA ATGCAAAATC
66181 CTGTCTCAAA AACAAAAACA AAAACAAAT TGCCTATGCT GTGGTTATCT CACAATTAAT
66241 AAAAAGGAAA AAAAAGTAT GCAGTCTTTG TAGGTCCTTG GGGTTTGTTG GAACTCAGAA
66301 AACAATACCC CAAAATAAAG ACCGCAGAAG CCAAAGTTTT TCTCTGATCT TCTCCTGCCC
66361 TCCTGTCTCT GAGTCCCATT CTCCCCGGAG TCTAGCCATA GAAATGAGAA TTCCTCTTCC
66421 TCAAGTTAGG TCATAGAAAT CAAAACACCT TTTCCCCAGA GCCCAGCCAT AAAACCTAAA
66481 AATATTACTC TAACTTTCCC TCTGTTTTTC TGTGTAAAAA CTGGCCATAA AGAAATTATC
66541 TGAACTACCT TATTTGATCA TAGATCACCA GACCGCATTC CAGAGAGGAT CCAGAAGGAA
66601 GGAATGCTGC ACAGAGAGGC CAAGAAGAAT CTAGACAGAC AGGCCTTGCT GGGTTTCCCT
66661 ACTCTGTTTA TTAGCAATCC TATTTCTACA CGGCGGCCCA TACTTTGTTG AATCTAAAAA
66721 ATAAAATGG ACAATTTCCC CTGTACATGT TAATACACAT TAATAAATTG GATATAAATT
66781 GGATAATTTA TTAATATACA CATTAATAAA TTGGATGCAG CCGGGTGCAA TGGCTCACGC
66841 CTGTAATCCC AGCACTTTGG GAGCTGAGGC GGGCAGACCA CGAGGTCAAG ACCACCCTAG
66901 CCGAAATGGT GAAACCCCGT CTCTATTAAA AATACAAAAG TTAGCTGGGC GTGGTGGCAC
66961 ATGCCTGTAG TCCCAGCTAC TGGGGAGGCT GAGGCAGGAG AATTGCTTGA ACTCGGGAGG
67021 CGGAGGTTGC AGTGAGCCGA GATTGCGCCA CTGCACTCCA GCCTGGTGAC AGAGTGAGAC
67081 TCCGTCTAAA AATAATAATA ATAATAATAA TAATAATAAT AATAATAATA ATAAATTGGA
67141 TGCATTTTAT CCTATTAATC TTCCTCTTGT CGGTGGTTTT CAGCGACTCT TCAGAGGCCA
67201 AAGAGTAAGT TTTCCCTTAG CCCCTACAGG TTCTTATGTT TAATTTGTTA CTCTCATTTA
67261 AGACATAATT AAAGTGGCTT CTCCATGAAG ATTATTTCTG CATCCATTAT TTGGTAAGAT
67321 TGGCCGTTTT CTCCTTTGAT CTCTACTTCA CACTGACCCA CATAAAACAT CACTGCCTGT
67381 TTTTTTGTTG TTGTTGTTTG GAGACGGAGT CTTGCTCTGT TGCCCAGGCT GGAGTGCAGT
67441 GGTGTGATCT CCGCTCACTG CAAGCTCCGC CTCCCGGATT CACGCCATTC TCCTGCCTCA
67501 GCCTCCTGAG CAGCTGGGAC TACAGGCACC CACCACCAAG CCCGGCTAAT TTTTGTATTT
67561 TTAGTAGATA CGGGGTTTCA CTTTGTTAAC CAGGATGGTC TCGATCTCCT GACCTCGTGA
67621 TCGGCCCGCC TCAGCCTCCC AAAGTGCTGG GATTACAGGA GTGAGCCACT GCGCCCGGCC
67681 CCGTTTTTTT TTTTTGGTT TTTGCATGTC TTCTCCCTTT TACTGTAAAC TATTTCCACT
67741 ACCAGCGTAG TTATCATTTC TACTGCTTAA TAATTGTTTT GGGGAAGTGA ATGCATCAAC
67801 CCACATGAAT TTCTTGTCTA TTTGACAATT TATTCTCTTT AGGAATAGTA TTAACTCCTA
67861 AGGTCCTGGG AGCCAGTCTC TGTACTTGGC TGCTCCAGGG TCCTACTTCA GTTTCCCAGC
```

Figure 2 (Page 21 of 74)

```
67921 TTCTCAGTAC TGTCACTGTC AATTGTGGGT AATAATTATT TTTGTCCACC AAAAGACTCT
67981 GTATGTGAAT GAGTTTTGAA ATCTGCTGAG TAATACAGTG TCAACCCAGT TAATGATTTG
68041 CCGGGCGGCT TGATCAGGGG CTGTCCAACT ACCGGCATTT TGATTTGGAG CGTCATCTAG
68101 TGTCTGAAAG CACAAACAAC ATCCTACATT GTAAATGCCT TTGGCTACAG AGATTGAAAC
68161 CAAAGCAAAC CTATGTTTTG AATTGTTATT CTTCAGCAGT TCTGCTAGCC TTGAAAAATC
68221 TAAAAGTTAA AAAAAAGCTT TATATTTCAT TTTCTGCCTA AACTCTTTAA AATTGCTAGT
68281 TGACAATTAG ATATTTTCAA TTTAATGAAA TTTTTTTTTA GTTCACAGAT TAATACACAA
68341 TGGGGGAGGG TTCTTATTCT GTTGGACTTT TACATAACCT CCACTTTAGT GCAGTCTGCT
68401 TTATGGGGTC TTGTTTGAGG TGTGTGTGTG TTTAAGGGAA TGTGGTTTAC AATCAAAATA
68461 TTGGGTTGCT CTTAGGCACA TTGTAAAGTC ACACACCTGT ATTCTTATTG ATACATAATG
68521 ATTAATAACA TTATTATTAC AGCCTGATCA CCATCATTAT TGATATATCT AAATAATGAA
68581 TTTTATAATT TTGCTTCCTG TCAGGCAAGA GCCAATTTCA GTGCTACCAT GTTTGTATAG
68641 CAGTATTTAT GTCTGTCATC CTCAGTCATT TTACTTCACT TGTTCTTAGC CAAACGGCCG
68701 AGAAGCGATG GTCATTTTAC TTCAAAAATG AAAAGAATTA ATATTTTTAC GTTTCCCTTA
68761 AAGACCCTAT GTTAACCTC CACTCCCGGG TAAAATGGTC TAGTCCCTCC TTTTCATATC
68821 ATCTCTGATA TCTTTTGCAC AGCCACTATT ACCTACCGTT TTCTAGATCC CTATTCTTCA
68881 AACACCACCA TGAAGGTAGA GCCTGTCTGA ATTATTTTCT TGTCCCGTGA ACTCAGTACA
68941 TTGTTAGGCT TCTTGAAGAT GTTGATCAGT TGTTTGTGGA GTGAATGAAT CAGCTAGCAT
69001 GATTTTTCTA GACCACTGAG ACAAGTGTCT AAGACACTTG TTCCTTCCCA TGTTCTTGCC
69061 TGCCTGTGCA ATCCATGCAG TCTCATGGCT TCCCAGTGCC TCAGAATTAT CCCCTGTCAA
69121 ACAGGCATTA TAATTTCTGT CCACTGAAAA GGACAAAAAA CTAAGTGTAT AGCTAGAAGT
69181 TAAAAATTAC CGGCCAGGTA CTGTGGCTCA CTCCTGTTAT TCCAACATTT TGGGAGGCTG
69241 AGGCGGGCAG ATCACCTGAG GTCAGGAATT CGATACCAGG CTGGCTAACA TGGCGACCCC
69301 GTCTCTATCA AAAATGTAAA AGTTAGCCAG GTGTGGTGGC TCGCACCTGT GGCCCCAGCT
69361 ACTCAGGAGG CTGAGGCAGG AGGATCGTTT GAGCCCTGGA GGTTGAGGCT GCAGAAAAAT
69421 AGGAATATAC TCTCTTTCAA GAGTTCGTGG TTTTGACTGC CACCTAGCGT ACATCAGAAA
69481 AACCGCATGA CATAGGAAAT GCCTGTGACA GAGGGGTAAG GTGAGAGAGG TTGATGAAGA
69541 ATGTATTGAA GGAGTGAAAA CGCTTCCATC CCTCTACTTA CTAAATATAT TAGTTAAGTA
69601 GTTGGGGCAT ATTTTAATTC ATGCATTTTG TAGATAGAAA AACAAAAGTT TTATTCTGTT
69661 TGATTTAGTT GATACTTTAA TATGTGTGTG TTTAGGATGC ATGATTTATA ATCAGTCTGC
69721 AGCACTTCTT GGAGAAGTCT GAATTCTCAT TCTCCATTTC CTTATTGGCA ACGTGAGAAT
69781 GATTACAATG GTGGTTGTCT CATAGAATGC AGGGAGTCAG AATGAAAATA GTCCATATAA
69841 TGCCTGGTGC AGAGGAAGGG TTCAGTTAAC TGTCTGTATT AATATTACTG ATAACAGTCA
69901 TGACAAACAA AAGCTTAACA ACAACACCAC CAACAACAGT TGCAGAATTG AGCCACCAAT
69961 TTGCACACAA GATTGTAGGT AGGATGTTTT AGAAAAGTTA TTATTTAATA TATGTATATA
70021 TTTTTGTACT TAAAATATGT CAGAGGTTGT TCTAAGAACT ATTTAAATGT TAACTCCTTA
70081 ATCCTCATAA TGACCCATGA AACAGGTAGG CTTATTATTG TCTCTTTACA TGTGAGAACA
70141 CTGAGACACG AAAAGGTTTA TTAACTCACC CAAAGTCACA CAGCTGGTAA AACGGCAAAA
70201 TTGAATTTGA ACTCAGACAT TCCAGGTTCC AAGACAGTCT AATTATTCTT TTGACTAATA
70261 TACTAAGCTG CCTCTGTATT TTTCCTTGAT TACTTTGTAA AGTATGAGG AAAATATAAG
70321 TGCTTCAAGT AACCATGAAA AATATAAACA ATCTATGTAT CAACTGAAGC ATAATTACAA
70381 ATCCTTTGAT AAGCAAACAT AATAAAAATT TGATATCAAT CAAAACTTTC ATGTAATGTA
70441 AGCAGGTTGA GATGAATTCT ATAGTAAAAA AGTGCAGAGT GCTGGAATAC CATGCTCCTA
70501 ATATATTGGC TAGGCACACC TGCCTGCTAT CAAAGGTATG CACACACCTT GGATACAGAA
70561 AGTTGGGACT GGGTAGTTAT GTGAGTGTCA TCAGAATTCT TTCCCACTTG GGAAAGAATT
70621 GTCCATCATA AGCTTGGATG ATGGACAAGG AGTGAGCTCC CAGAACAGTG ATGTGGGGAT
70681 ACATCCTCAC ATCACAGTGA GAATGAGTGT TCTAGACTGT TTACACACCT ACCACTCCTA
70741 AATGCACACA TATAATTGCT TGCACACACA CACATACACA CTCATCTCTT CTCTGGTGGT
70801 CCAGCTCTAT CTCTTATCAT TAGGCTTCTT GGGGCTAGTA CCTAGGGCCT GTATCCTTTC
70861 AGAGGCAGCT AAGGGAAGCA CACATAATTA GAAAGAATGA ACCAGCTTGT TGGATTTGGT
70921 CTCTTCGCAT CCAGCCCTCC AAGTTAAGGA GAGTACCATC TTTCTTAGGG TCACCAAAGG
70981 AAAAAAAAAA AAAAGAAAGA AACAGAAGGA TATCATACAG CAAGGATCTA ATGCAAATAT
71041 GCCTCAAATG AGAGGCTACT GTGTGCTGAT CCCAATCCCA GGAACTGTAT GCACATTATC
71101 TAATTTAATC CTCACTGTAT TTCTGGGAGT ATTATTCCCA TTTTACAGAG AAGGAACTTG
```

Figure 2 (Page 22 of 74)

```
71161 GCAGGGTAAC CAAGCTCATG AATGGAGAAA CTGGGATTAA ATATAAAGCT TCCTTGCTCC
71221 AGAACTGCTG TCTTTCTGCT CTTCCACACT ACCAGCTCAG CTGTGCTCTC TACATGCAGG
71281 CAGTTTTACA AGTTTCAGAT TAGCCTGGGA CTTCCAGGGT TTTGAATGGG TTAGGGAATG
71341 GGGAACTTTT GGGTTACTT TCCATTTTTT CTTCATACAT ATGTAATATA TAACATAAAT
71401 CTATGGTATA TATGATAAAT ATATGGCTAC ATATGAACTA TATAATCACA TATATGCATT
71461 ATAAATAAAT ATTAATTTTA TAATATTTTA AAGGTTATCA AATAAATATT AATATAAATA
71521 ATTAAATAAT TAATACTCAG CTTTGTTTTC CAAAGTGATA AATGCCTATA TTTAGCAAAA
71581 TATTTTTTGG AGGCCTGATA GTTTTAGGA GTGTAAAGAA GTCCTGATAT CTAAATGTTT
71641 AAGAACCACT ATTTTAGGCT GTTGTCTTCT GTCTTATTTT CCCAGCTAGA CTGGTAAATA
71701 CTTGAAGGCA AACGTTTAGC CAGCACATTA ACATTTATG TTTTTATTCT TTTGTGCTCT
71761 CAGTGGCTGT GTCTTTTCTA TCGATTTCTC ACACTGTATG ATGGTTATAT TTGTCTGTAT
71821 CTGTCCCACC AGGTATAAGT TCTTGAGAGG ACACACTGCT AGGCTGATCT TAGTTTTTAT
71881 TATTTCTCCT GGTGTCCTGT GCTTAACAAG TGCTCATTAA GTGTGTAAAA ACACAGCACA
71941 GTAAAAAACT AGACATTAAA AATAATGTC AACCAATCTA TTGAAATTTG CATTTCCATG
72001 TTTCTTCCAA TATAGTCATT GTGTCAGGTT ATGTACTTAT TCTGATGAAG ACTATTGCCT
72061 AATATACGTT TGCATCTTGT GCTTTATAAC TGCCTTCATA TAGACACAGA TTGAGAAGGT
72121 GTAAAAATGT GCATATCCTC ACAATTGACA AATTCTTATC CTTTGAGGGT AGGTTTGACT
72181 TTCTGAAATG CTTTGACATC ATTTGAAAGA AGCTTGAAGA ATAAGATAGC TGTTAATGAC
72241 CCAGTTTCCT ATGTCACTTA TACAATTATA ATGGCAATTT CAAAATGTTA GGTAAATATA
72301 TTTTGCAATA TATTGTTCCT TTTGTAATAC TCTCTATGTA TTTATTTATA TTTTTAAATT
72361 TTATATTTAT GTATTTATTT TTCTGGACAG AGTCTTGCTC TGTTGCCCAG GTTAGAGTGA
72421 AGTGTTGTGA TCATAGCTCT CTGCAACTTC AAACTGCTGG GCAAAAGTGA TCCTCCTGCC
72481 TCAGCCTCAT GAGTAGAGTA GCGGGAACTA CAGGCGCATG CCACTGCACC AGCTAATCA
72541 CTATTTATTA TGCTCCTACT GTGTGCTTTA GTATATTTTC TGTTGTTTTC TGCAACCCAT
72601 TTTGAGGGCG TGTTAGGGAA TACAGATGCA GTAACTTTGG TCTCAGCCCT TGAGGTGAGG
72661 AAATATTTAG CCTCAGGTTT AATCTAATTG TTGGCCATTT GCCTTCAAAG ATTGAAATAT
72721 GAGCAAAACT GTGGCTCTGG GTTATATGTT AAAAAAAGT TTATGGGCT GAAGCCAGGC
72781 AACAGACAAG AGCCCCTACA ATCTTATTTA GGCTGAAAAT ATCCTGGAGT CCCTGTATTG
72841 TTGGTCTCAA GCAGATAGCA ACACTAACAC TTACTCTTTG AGGCAGGCAC TGCCAGTGGG
72901 GTGGCTGTTA TTATTAGCTT CATTAATTGG TGAGTCAGGA AAAACAGCT TTAAATCATT
72961 CAAAGTTCTG GCCTATACAG GATTTAGTAA TATTAGGTTA GCTACATCCA AAAGATGACA
73021 GAACCCTACT CTAAGGCTGG GCTTGGTGGT TCACACCTAT AATCTCAAAA CTTTGGGAGG
73081 CTGAGGCAGG AGGATCACTT GGTGCCAAGA GTTTGAGACC AGCCTGAGCA ACATAGTGAG
73141 ACCCCTGTCT CTATCAAAAA CAAAGAACTC TAATTGGCAT AGTAGAAGGA AAAAGTGAAA
73201 GAAAAACCAG CTGTCACCCT CATTCCTTAC ACCTGTCCTA ACAACTCCTC TCACTATCCT
73261 TTGAATATAT CTTGGCTGTT TGAGTCTCTC TCTAGCCCCA TTACTGCTGT TTGGACTTGA
73321 CATTTTGCTC TGCATTTTTA ACTTTTCTAC CAGGGTTTCC AGACCCTGAA GAGTGTGGCA
73381 TGAAACAAAA CTAGTCAACC TATAATATTT ATGATGTGTG TGTAAATAAA AGAATACACA
73441 ATATATTGCA TTACAATATT TTAACTGTGT CCTCAATTTG TTTGTGGCTT TCTTGAGGAC
73501 ATCAGTTTTG GGTGGGACGA CCACATCCTT AATCTGAACT TTCCCTTGGA GGTCATTCTT
73561 TTTTTTTTGA AATAGAGTCT CGCTCTGTCA CCCAGGCTGG AGTGCAGTGG CGCAATCTCA
73621 GCTCACTGCA ACGTCCGCCT CCTGGGTTCA AGTGATTCTC CTGCCTCAGC CTTCCAAGTA
73681 GCTGGGATTA CAGATGCACG CCACCATGCC GAGCTAATTT TTGTATTTTT AGAAGAGACG
73741 GAATTTCACC ATGTTGGTCA GGCTGGTCTT AAACTCCTGA CCTCATGATC TGCCCACCTC
73801 AGCCTCCTAA AGTGCTGGGA TTACAGGCGT GAGCCACCCC GCCCGGCCAG AGGTCATTCT
73861 AATAGACTTT TTTTTTGTTG TTGCTCACAG GCTTGTTCAA TCTTATTTCA AAATTTGAGA
73921 AATACAGTTT CCATGGAACA CCAACCAGAT ATCAGGTTGC TATGGAGTTG ATAGTCAAAA
73981 GCTTTGTATC TTCCAGTTTT TCAGAATGGC TTCTAAAGGT TCTGATTCAG AGCTCTTAGG
74041 CGAAATTGAA CAACCAAGTG TCAAAGTACA ACATTCAGGA AGTTAAAAAC ATGACTGACA
74101 TATATGTACT ATATATAGTG AGCTTGTGTA TGTGTCAATG AATGATTTAA TTCATTAATG
74161 AAGGAGGAAG CAGAATCACA ATTAGGTCAA AGGAAGATAC GGGAGAATAA AATATGTATT
74221 TGGTCAGGGA AGGATGTAT ACTGGAAGAG GAAGGGAAAA TCAGATATAA AGTTGTTTAA
74281 TGACTTATTA GGCAATACAA TAATAACTTT TAGGGTCATT TTTTCTATAT TAAGAATTCA
74341 TTTCCATCTC TATGACAAAA TCCTTATTAA TTTATTAAAC TTCTACAAGT GAATGTTTAC
```

Figure 2 (Page 23 of 74)

```
74401 TTTTAGATAG TCTGGACCCA ATAAAATGTA AACATTAAGT CAGAGTTACT TTCACGTAGG
74461 ACAGTGTTGT CCAATAAGGT ACCACTAGCT ACACGTGATC ATTGACCATT TGGACTATAG
74521 CTAGACTGAT TTAAAATGTT CTAAAAGTGT AAAATACACA CCAGGTTCTG AAGATTTATC
74581 ATTTAAAAAA GAATGTCAAC TGTCTTTTTT TTTAGCTTAT TTATTATATG TTGAAGTGAT
74641 AATAGTTTAG ATATATTAAG TTAAATAAAA TATCTTAAAA TTAATTTTAC TTGTTTCTTT
74701 TCATTCTTTC AATGTGACCA CTAGAAATCT GGAAAGTATT TATGTGATTC ACATTCTATT
74761 TTACTGTCTA GTATTGCCTT ACATCATCAG GTACCCATA AGTAGGCTTT TTAGATAATT
74821 CTCTAATATA GCTTGGAAGG ATATGGAGAA ATATTTTGC GTTGCTTTTA AGTTTTGCAT
74881 AACTTTTTCA ACACACTTTA TAAAGGATCT AGAAAAGGGT TGGTTACATG TTTCTCTGTC
74941 TTCTGGCCTC CACCATGTTG CCAGGAGGTT GGGGACAAGA TTCTGGGTGG CTGGATGTCC
75001 TAATGGCTTG AGGTCTGGAC TTGAGATTTG CATATAAAGA GATGTGATTA GATTGAGTCG
75061 ACTAGAAAAA TCATATTAGA GAACTGAATC ACAGCGATTA AATTTACATG TCGATTTATA
75121 AACCAGGACA CCAATTTATA GTGAAGAAG GTCCAGTTAC CTGGTAATCA AGACGTTTCA
75181 TAGCTATTTT CATGATGGAT ATACTTAGCT GAGTTTTAAA TGAGAAGGGG GTTCATTGCA
75241 CATAGAATAA GATCTAAGTG AAATGTTTAT TTATTTTTT TTTTTTTGA CATGGAGTCT
75301 TGCTCTGTTG CCCAGGCTGG AGTGCAATGA GGCAATCTCG GCTTCTGGAG TGCAATGAGG
75361 CAATCTCGGC TTCTGGAGTG CAACGAGGCA ATCTCGGCTC ACTGCAACCT CCACCTCCCG
75421 GGTTCAAATG ATTCTCCTGC CTCAGTTTCC TGAGTAGCTG GGATTAGAGT TGCCTGCCAC
75481 CACGCCAGGC TAATTTTTGT ATTTTTTTA GTAGAGATGG GGTTTCACCA TGCTGGCCAG
75541 GCTGGTCTCG AACTCCTGAC CTCAGGCGAT CTGCCCGCCT CAGCCTCCCA AAGTGCTAGG
75601 ATTACAGGCG TGAGCCACCA AGCCTGGCCT AAGTGACATG TTCTTATATT GTTCCTTTCT
75661 TTCTTTTTTT TTCGACTGAG TCTCACCCTG TTGCACAGGC TGGAGTGCAG TGGCGTCATT
75721 TCGGCTCATT GCAACCTCTG CTTCCCGGGT TCAAGCGATT CCCTTGCCTC AGCCTCCTGA
75781 GTGCCACCAC CCCCAGCTAA TTTTTGTACT TTTAGTAGAG ATGGTGTTTC ACCATGTCCG
75841 CTAGGCTGAT CTCAAACTCC TGGCCTCAGG TGATCCGCCC CCGAGTCTCC CAAAGTGCTA
75901 GGATTACAGG CGTGGGCCAC GGGGCCCAGC CTTATATTAT TTCTTTTACT ACAATATATT
75961 AGTATGATGC AGGTGCTTCA ATTGTTTATA CACTTTCCAT AATTTTGTAT AATTCTTATA
76021 CCCTGTCACT CTGAGGAATA GCCGGTCTAA GTGTTTTTCC ACCACTGCTA ATTCATCCAT
76081 CACTAATCTC ATTAGACTGT TAATTCCCAG AGGACATAAG CACACAAGCA GACAATGTTT
76141 ACAAATGTTG GACAAATGTT ATTTAATAAA ACAATGGGGT CACCCTTAGT CTAAAAGATG
76201 TTTCACTTTT CATTTGTCAT TGAACTCTTA TTTGTAGGTT CCCTTTTGAC TTTCCCACAA
76261 TCTAAGGCTG TTCTCTTTAA CACATATTTT CATGAAAACA TATATTTGAG CAGAAATTGT
76321 TGGGGAGTTG TAATATTACC TTTGTCCCTA AATATGAATC TATAATTATA TCAAATATAT
76381 GGGCAGACAA TTTACTTTGC CTTTAATCTC AAGAAAAAAA TAGCAATTAC TTGGGGTCGG
76441 AGAGTAAAAT AAGAAGTAGT GAACCTTAAA GTAGCAAACT TTAGAACAGA ATAGTTTCAG
76501 AGGGGATGAG AAGAGGTGAT TTTTCAGCTC ATCAACAACA GATCTTATAA TAAATTACAT
76561 GTTCTGGTAC TTTTCTTGTC TTTCTGTGTT AAATTTGCT ATTTAAAAAA ATAAATTTCA
76621 AATACATTGT TCATCTTAAA AGTCAAGAGT GTGTTTTATT AAAGTCAGTT GCTTTATTTG
76681 CAACTCAAAA GATATATTTG AGTTCCCAAC TGGAGATTGT CCTATATGGT AACTTGCGTA
76741 AGGTATGGTT ACTGAAAGTA ACCTACAATT TTCATGGGCT GAAATTCATT TCTATATTGC
76801 AGCGTACAAA AATAAATAAA TAAAAAATGC TTGTTTTCTT TGAAAACATA TTATCTCAGT
76861 GCCTCTAACT GCCAAATCTA TTGGCTTTTT TGCAGGCTTA AGGGCTCTCC CTTGTTCCTT
76921 TATGATCTCT ATCTTGAGGG CCAGACCTCC TGCCTTACAC AACTCAGAGG GGGACCTCAG
76981 AGCTCTTTAA AAAGAGCCCA ATTTCTCGCC TGTAGAGAAG TGAAAAGGAT GCCCCACCCC
77041 CATCTATGAA AAGAGGGATT TGATAGTTTC AATGTCTTCA AATCAAAGAT TTAAGTCTGT
77101 AGCCCCCCAC CACCCCGGAC CCTAGCAAGG CTCATGAACC CCCTCCCATC CCGCCCTAAT
77161 TGCTTTGGAC TGGCCGTGGA ATCCTTGTCC CAGTCCACAG TTCCTGTGCG ACTGCACGAA
77221 GAATTCACAG AGGACCTGTG TTACTTCCCT TGTGAAGAAA CAGAATTATC ATGAAAATTT
77281 AGGTGGAAAC CATTTCGCTT TTTTCTTCAA AAATAAGGGA AGCATGTGCC CAACCACCCC
77341 TGGGAAAAAG AACCTTCAGG GGCAAAGGAG CGAACAGGTA ATTTATAAGA AAAACAGAAA
77401 GTGGTCTCTG ACTGCCCCAG ACTTCCTTCG GAGTTGGGGG AATTGGGGAC GCCTGGACGC
77461 GTTGTTTTTG CGTTTGTGGA AAAAATAAAT GAAGAGCATG AAGCCCGAGG CTTCTGAGAT
77521 CCTTTCCTGA CCAAACCCAA GTGATTTGGT GCGGGGAATT TTAATATTTT TCCCCTTTTG
77581 TGAGGTGGAA CAAACACAAC TTGGGAGCAG CGCAGCGGCT CAGAGCCTGC CAGCCAGGCG
```

Figure 2 (Page 24 of 74)

```
77641 GGCGACCAGA GCACCAATCA GAGCGCGCCT GCGCTCTATA TATACAGCGG CCCTGCCCAG
77701 ACGCTGCTTC ATCGGCGCTT TGCCACTTGT ACCCGAGTTT TTGATTCTCA ACATGTCCGA
77761 GACTGCTCCT GCCGCTCCCG CTGCCGCGCC TCCTGCGGAG AAGGCCCCTG TAAAGAAGAA
77821 GGCGGCCAAA AAGGCTGGGG GTACGCCTCG TAAGGCGTCC GGTCCCCCGG TGTCAGAGCT
77881 CATCACCAAG GCTGTGGCCG CCTCTAAAGA GCGTAGCGGA GTTTCTCTGG CTGCTCTGAA
77941 AAAAGCGTTG GCTGCCGCCG GCTATGATGT GGAGAAAAAC AACAGCCGTA TCAAACTTGG
78001 TCTCAAGAGC CTGGTGAGCA AGGGCACTCT GGTGCAAACG AAAGGCACCG GTGCTTCTGG
78061 CTCCTTTAAA CTCAACAAGA AGGCAGCCTC CGGGGAAGCC AAGCCCAAGG TTAAAAAGGC
78121 GGGCGGAACC AAACCTAAGA AGCCAGTTGG GGCAGCCAAG AAGCCCAAGA AGGCGGCTGG
78181 CGGCGCAACT CCGAAGAAGA GCGCTAAGAA AACACCGAAG AAAGCGAAGA AGCCGGCCGC
78241 GGCCACTGTA ACCAAGAAAG TGGCTAAGAG CCCAAAGAAG GCCAAGGTTG CGAAGCCCAA
78301 GAAAGCTGCC AAAAGTGCTG CTAAGGCTGT GAAGCCGAAG GCCGCTAAGC CCAAGGTTGT
78361 CAAGCCTAAG AAGGCGGCGC CCAAGAAGAA ATAGGCGAAC GCCTACTTCT AAAACCCAAA
78421 AGGCTCTTTT CAGAGCCACC ACTGATCTCA ATAAAAGAGC TGGATAATTT CTTTACTATC
78481 TGCCTTTTCT TGTTCTGCCC TGTTACTTAA GGTTAGTCGT ATGGGAGTTA CTGAGGTATC
78541 AGAGACGAAT TGGGTGACGG GGTTGGAGAG TGGCCGTGGT GAGGTTACAG CATTTAAACC
78601 TTTATTGCGG CTTCTAGGTC CCTGACCGGA GGCTTTTCTC GCTGGCGGAT GGTTTTGGGA
78661 TGGCAGTCCC GCCCCAGGCC TGTGAACGGC AGAAAAGACC GCAAAACAAG AGCCAGTTTC
78721 TTAGTCTAAA GGGATGTCCG GATTGGACTA AAAAATTTTC AAAAGTCCCG CCCTGCTCCC
78781 GGGTTGGTCC GTTCTTCTAG TACATGACTT TCATTCTGTA TTTAATTGGA TGGTGGAAGA
78841 CGTTGCTTAT TCTGTGTTTT TTGCTTTACT GTGACTTAAA AGTTTTGCCT CTTTTCTCTT
78901 TATATTAATG TCTGGGATTT CGGACGCTTT CCATGTTGTT GGTAGTCAAG TTGATGTCTC
78961 CTGGAGGTAG TGGCAACATC CAGCCCTGGG AGGAGAGTGC GTGCAGGTAC CTTTGTCCTA
79021 CATTCCTCTG CTGTTAATTT CTCATTCCTG TGGCAACGAA GGAATGCATT TAAAAAACAG
79081 CCACAACAGC GGCAATAGCC CTTCCTCCAC CCAAGGCAAT CGTGGACCTA GGGAGTTTTT
79141 TGTGCCACAT AACATGTAGC CTTCCGCTAA ACTGACAGGT TTGAGCGTAT CGATTTTGAG
79201 CGTATCGAAA GCACAACTTT TAGCCAGCCA TTTTGTCCTC GCATGACTAC GGTTGCTTAT
79261 CCTGTTTAGA CAGACAGCAA CATTTAAAAA TCGAAGTTCC TTTAAACGTA TTTTGTTTGG
79321 CAGTCCAAAT GTTTCTATGC AGAAAACAGT ATTTGTACTA TTAACTATGA AGAGTGTATG
79381 GATAAATGGG AGACATTTCT AATAAAGGCC TTCGTTAATG GTTCCCTCTG TTTGACATCC
79441 ATGGTGCTTC TGAATACAGA AAGCCTAGCG TCTTATATTC GCTTCTTTTA AAATCTGGTG
79501 GGCACATTTT GGTGAGACCT AAATTATGGG GACTGGGGCT TCTGGAGATA AGCTGCTCAA
79561 TTATTCTACC ATCTCCACAA TGATTAATAT AGTGAGTTGA TTTGTTAGTG ATAGTGACCA
79621 CGGATTCATC CCAAGAAAGA GAAAGGGGAG GGAGGCAAGC AGAGAGACAG GAAGACAGAG
79681 GCAGGGAAGA AGGAGAAAAC ATTCTCCCAT GGTTTAAGTA ATTTTGTGTT GTTAATTTTA
79741 CATTACAACA CGGTTTAACA TGGTGAACCC TCTATTTTGG TGTAAGGTTT AACATATGGA
79801 CATATTTTTC CCAAGACCAT TTATGAACTT TCATTTCTGC TTCCCCCTTC TTCCTCCCGT
79861 GCCACCCTCC ACGCTCCTAT CAATTTTGGC TGTTTTGTCA TAGGCTAATA CGCTATAATT
79921 TCATGGACAG TTGGACTGTC TTAGGTTTCT CAGGTTTCTA TTTTGTTCCT TTAGTCATTC
79981 CCACAATTCT TAAGGTAGAA TTGTATTGTT TTAAACATTG TGTTGTGTGC TATCCTCAAT
80041 GCTGAGATGA TTATGTGACA AATGGCAAGT GTTCAACTAA TACCTAAATC TGTAGTATCT
80101 TATCAAGCCT AATGCTACTT CACAATGCCT ACTCCATTCA CCGCACTTTA TCTCATTACT
80161 GGCATTCTGT CATCTCACAT CATCACAAGT AAAACGGTAA GCTATTTTGA GAGAGATCAC
80221 AGTCATATAA TTATATTTAT ATTTATTTAT TTATTTATGA GACGGAGTTT CCCTCTGTCA
80281 CCCAGGCTGG AGTGCTGTGG CACGTTCTCG GCTCACTGCA ACCTCCGCCT CACGGGTTCA
80341 AGCGATTCTC CTGCCTCCGC CTCCCGAGTA GCTGAGATTA CAGGGGCCTG CCACCATGCC
80401 CGGCTAATTT TTGTATTTTT AGTAGAGACG GGGTTTCACT AAGTTGGCCA GGCTGGTCTC
80461 GAACTCCTGA CCTCAGGTTA TCCGCCCACC TCATCCTGCC AAAGTGCTTA GATTACAGGC
80521 GTGAACCACC GTTCACAGAC TCAAATCATT TTTATTACAG TATATTGTTA TAATTGTTGT
80581 TTTATTATCA GTTATTGCTA ATCTCTTACA GTGCCTGATT TATAAATTAA ATTCATCATT
80641 GCCATGTGTA TATAGAAAAA AACAGTGTAT ATACGGTTCA GTACTATCTG TGGTTTCAGG
80701 CATCCACTGG GGGTGCAGTT TATTAAACAT GCATTTACAT TAGTCTCCCC TTTGGGAGAC
80761 TAATTAACTG AGATGTTGTA ACGTGACTTT AATAGCAGAT AGAGCTAATT TTCTCTCATT
80821 ACTCTTCTTT TTCAGAATTT TCCTGGTTAT TCCATTTTTT ATTTTTCCAT ATGTATATTA
```

Figure 2 (Page 25 of 74)

```
80881 AGATCTCTTC CACCTCCTCC TGTTTCTCCA TCTCAACATC AAACAATTAA AAAAAAAAAA
80941 AAAGGCTGGG CGCGGTGGCT CACGCCTATA ATCCCAGCTC TTTGGGAGGC CTAGGCGGGT
81001 GGATCACGAG GTCAGGAGTT CAAGACCAGC CTCGCCAAGA TGGTGAAATC CCGTCTCTAC
81061 TAAAAGTATA AAAATTAGCC AACCATGGTG GCAGGCGCCT GTAATCCCGG CTACTCGGGA
81121 GGCTGAGGCA GAGAATTGCT TGAACCCGGG AGGCGGAGGT TGCAGTGAGG CGAGACCTTG
81181 CACTCCAGCC TGGGTGACAC AGCGAGACTC CGTCATAAAA AAAAAGCCG GAAGCAGTGG
81241 CTCACGCCTG TAATTCCAGC ACTTTGGGAG GCTGAGTCAG GCAGATTACC TGAGGTCAGG
81301 AGTTCAGGAC CAGCCTGGCC ATGAAAATAC AGCCTGGCCA TGAAAACACA CAATAAATTA
81361 GCTGGGCGTG GTGTCACACA CCTGTAATCC TAGCTACTCG GGAGGCTGAG ACAGGAGAAT
81421 CACTTGAACC CAGGAGGCAG AGGTTGCAGT GAGTTAAGAT GACGCCACTG CACTCCATCT
81481 GGGCGACAGA GCCAGACTCT CTCTCAAAAA ACTAAATAAA TAAAAATAAA GTTATGGTAC
81541 ATTGAACTTC TGTGTTCCTT TCTCCCTTAG ATACTTTCAT GGCTACCCAT TTAATTGATG
81601 TTCTTATCAT CTCCAAGAGT TAGTCAGGAG AGGAATCAAC CCAAGCAAAA ATAGCTGATT
81661 TTCTAATTTT CCTTCAATGC CCTTTGGGGT CTTAATCCAT TTGATTTATG TACTTTCAAT
81721 TAATCCTAAC CTCGAATGTC TTCTGCAAAC ATGTTTCCAC AGATGAAACT CGTCAAATGA
81781 AACACATTCC TTTAATTTAT AGAGTTAAAA ATTAGAAAAA TTTTCAATTC TATTTGGCCT
81841 TTAGATTCAG TCTTGCATAT GTTTTCTCAA TTTTGTTCAT GCTCTTTAGT TTTGTTTTAT
81901 TCCATCACAA TTGTTCACAT AGCTTACTGG CTTAGGTCTA ATGAACCATT CATTTGGAAA
81961 TTAAAATTGG CCATTTTAAG ATGAAAAGA TTCTTGCCTC AATTTTACTT AGTTTTGAA
82021 ACTGTCAATG AGGACACATG TTTTTCTGTA CTCTTAGATT CACTAAGTAG TGTCTTGCAA
82081 ATTTAACTGA CAAAGGACAG ATTAACATGC GAAAAAAAAA GCATGCAATT TTATTAGTAT
82141 ATTACATGCA CAGAGTTCCC AAAGAAAAAA AAATTGAAAC CTTAAAAACG CGGTTAGACT
82201 CACAGACTTA TACACCATTC CAACAAAGGA AAGGGAGTTT GCACTTCATG GGATGACGAA
82261 TTTGGGAATG TGACAAGGAA ATAAATACAT GGGCAATAAA AACCATGGAA GATAAATGA
82321 AAGATAGAAA TAATTGTAGT AAGGTTTGTT TTTGCAGAGT CATCTCAGTG CCAACCTTCC
82381 ATATCTAGTG ATAAGAATTG CTCTCTTTTT CCTGGTATAG CAGTTGGGGA CACTTTTACA
82441 AGGGAAATTT CTGTCACCTT CACAAAGGGA AATTTGGGTA AAGAGAAGAC AGAGACCTCT
82501 TCCTACACCT GTTGATTTTC AATTGCCTTC AGCTGAAAAT AACTTTTATG CCAAAGTAGA
82561 ATAATTTGGG GGTGACATCC TGATATTCTT CAAAACTTAT ATTTAATTTC ACATTAGTAA
82621 TTATATCATT TTTGATTTTT AAATTAGTTT TATAAAATAA TTTTGAAAAA CGGTAATAAT
82681 ATTCAAATAA TTCCAGAAAC ACTGCTGATA AGCCAAAAAC ATCAATGAAT ATTGCATAAA
82741 CAACTGATAA TTCAACCATG AAAATTTATG ACATTGTTCT TGTGTGATAA AACTATGAGT
82801 AACATAAAAA CTAGAGGCTA CTTGTAATGC ATTATTCCAA ACTTTCTGTT TTTTATTTAT
82861 TTATTTATTT ATTTTGAGAC ATAGTCTCTC TCTGTCACCC AGGTTGGAGT GCAATGGCGT
82921 GATCTTGGTT CACTGCAGCC TCCACTTCCC CGGTTCAAGC AATTCTCCTG CCTCAGCCTC
82981 CTGAGTAACT GGGATTACAG GCACCTGACA CCAAACCCGG CTAATTTTTT TGTATTTTTA
83041 GTAGAGACGG GGTTTCGCCA TGTTTGCCAG GCTAGTCTCG AACTCCTGAC CTCAGTGATC
83101 CACCTACCTC GGCCTCCCAA AGTGCTAGGA TTACAGGCGT GAGCCACCAT GCCCGGCGCA
83161 TTATTCCAAA CTTTCATACA CAGTGCTATC ATGGCTACAA ATTGAAGTAT CATATTATAC
83221 ACTCCTAGGC AAAGCTCTGG ATATTTGGC TATATAAGCC TGAGGGAAAT GTAGTAAGGA
83281 CATTGTGGTT GAAATTCATA CCAGAGATGA ACAGGCCCAG TGCAAGACAG AATTACATCA
83341 CTAAAGGATA TCAGAAGAGA ATAGGGATTT AGGGTACAGT GGCAACAACA GTTTTGGGAA
83401 CTAGCATTTT TTGAGCACTT ATTTACAATA TGCCAAGCAC TGTTGCTGAT TACTCTATAT
83461 TTATTTTCAA ACACATTCTT GTCACAGCAC TTTGAAGTAA GTGCCATTGT CATTCCCACT
83521 TCAGGGTGAA GGACTAAAGC TTGGTGTCAT TAAGGATGTA GCTAGTTAGC TGTGTGTGTG
83581 TGTGTGTGTG TGTGTGCATT TTTTTTAAA TTTAAAGTCA ATAAATTTTT ATTTGAAGAA
83641 TTTCACATCA AGGTAAACTT TGTTCCTCTA AAGAGCTGGA GTCAAAATGT ATCTTCAAAA
83701 GATTCATCTT CAAGTTAGCC CTTCTTAATA GAACTGATGC TTAATCCACA GTTGTCAGCC
83761 CACAGTTCTT TTATTTTGAC TTTTTTTTTT TTTTTTTTTG AGACGGAGTC TCTCACTGTC
83821 ACCCAGGCTG CTGGGCAGTG GCGTGATCTC GGCTCGCTGC AACCTCTGCC TCCCGGGTTC
83881 AAGTGATTCT CCTGCCTCAG CCTCCTTAGT AGCTGGGACC ACAGGCGCAT GCCATCGTGC
83941 TCGGCTAATT TTTGTATTTT TATTAGAGAC AGGGTTTCAC TATGTTGGCC AGGCTGATCT
84001 CAAACTCCTG ACCTCATGAT CCGCCTGCCT TGGCCTCTCA AAGTGCTGGG ATTACAGGTG
84061 TGAGCCACTG CACCCGGCCT TATTTTGCCT TCTTTAATCT CCATTTGAAC ATGGACATAC
```

```
84121 TGATGAAAAC TACAACATTC TTCACCAAAA ATCTTTGGGA TTTAATTTCT TCAACCACTT
84181 TACTTTGGGG TCATTTTAAG ATTAGGTGTA TCTGCCTGGT TCTCAATTTG ACACCCTTTC
84241 TCTCTAAACA TGAATGAGTT CCAATCATAT TTATTCCTAA GCTATCACAC TCAAATATAC
84301 TACAGATCTG TGGAATATGC CAAAAGTTAA GGTGAAAAAT TAAATTATTA GGTATTTCAT
84361 AGTTTTGCTA GTTTTTGATC TGTGAGTGAA TATAACTATC CTCTATGTCC TGGCACTGTT
84421 CCTCAGAAAC ATAGGGTCCA CATATGTAAT TTTAAATTTT TTAATAGGCA CATTTTAAAA
84481 AGTGGAAAAA GAAATCTATT TTAATGATTT GAATCCAGTG TAACCAAAAA TTGTTTCAAC
84541 AAGGTATCTA ATATTAAAAT ATTGAGTTTT TACTTTGTTA TTTTACTAGG TCTTTGAAAT
84601 CTGGTGTGTA TTTTACACTT AAAGCACATC ACAGTTTGGA GTAGCCACAT TTCCAATGCT
84661 TAATACTCAC ATATGGTTAG TGGCAACTAT CTTGGACAGG ACAGCTTTTA TACTCTGGGA
84721 AGACACAAGC AAATACTTGC TCTGCAGCAG AATCCAGATG TTTTCCAAGA AAACACTTTT
84781 TCTGACCTGT TCGTGAAACC CAGGTAGTGT CTCTAATACT TTATATTTTA TTGGTTTGTC
84841 CTATTGTAAC CACCCAACGG GCTCTCCTTG TCCACTTCCT AGACAGAGCT GATTTATCAA
84901 GACAGGGGAA TTGCAATAAG GAGCCAGCGC TACAGGAGAC TAGAGTTTTA TTATTACTCA
84961 AATCAGTCTC CTTGAGAATT TGGGGACCAA AGTTTTTAAG GATAATTTGA TTGTAGGGGA
85021 CCAGTGAGTC GGGAGTGCTG CTTGGTTGGG TCAGAGATGA AATTATAGGG AGCCTAAGCT
85081 GTCCTCTTGT GCTAAATCAG TTCCTGGGAG TGGTGGGGTG GGGGACTCAA GACCAGATAA
85141 TCCAGTTTAT CTATATGGGT GGTGCCAGCT AATCCATTGT GTTCAGGGTC TGCAAAATAG
85201 CTCAAGCATT GATCTTAGGT TTTAAAATAG TGATTTTATC CCCAGGAGCA ATTTGAGGTT
85261 TAGAATCTTG TAGCTTCCAG CTGCATGACT CCTAAACCAT AATTTATAAT CTTGTGGCTA
85321 ATTTGTTAGT CCTGCAAAAG CAGTCTGGTC CCCAGGCAGG AAAGGGGTTT GTTTCTGAAA
85381 GGGCTGTTAT TGTTTTTGTT TAAAAGCAAA AGTATAAACT AAGCTCCTCC CAAAGTTAGT
85441 TAATCCCAAA CTCAGGAATG AAAAGGACAG CTTGGAGGTT AGACGTTAGA TGGAGTCGGT
85501 TAGGTAAGAT CTCTTTCACT GTAATAATTT TCTCAGTTAT GATTTTGCA AAGGCAGTTT
85561 CACTGTCCAC TTCACCTCAC ATCAGGCCTC TGACTAGAGG ATTCCAACAA TACTTAGGCC
85621 AGGACACCAC CATGTCTCCT TATCCACCCT GAGGGATTCC AATTTCTGAA ACAAAGGAAA
85681 CTATATATGA TAGTATGAAA CTATATATGA GAAGGAAATT ATATATGATA ATCAATTTTA
85741 GGGTTATCTT ATTGATTAGA AGATATTAAA GTGTGACACT GCCTGGCAAT GATATCTGCT
85801 GGTAGTAAGA ATTTGGCGAA TTTAGTGAAA TTCCTGAGGC TGAACCTCCA CTTCTGTAAA
85861 ATGGAGACAG TGAGATAATT TGCCTTACAA TGCTGAAGTA AGAATTTTAC ACAATAATTC
85921 AGACCAACCA CTTCATGTGG TACTTGGCCC GTGGAAGACT ATCAATGACA GTTAGTTTAT
85981 AGTTTATACT ATTAATGAAT CCTTTGTTTC ATTGTTATTT CCTTCTACAC GTTGGCCTCT
86041 CTAAAAGAAG GTAATATTCA ATACAAATAA AGTTAAAACA GCTTGCAGAG TTGTCCCAGG
86101 GAACTCACTT AACCACTGAA GTGTTCAAAT TGCTTAAGGT TGACTTTATA TTCTCCTGAC
86161 TAACCTTTCT CCTTCTGGTA TTTCTTCTGA GAACAGCACC ACCATCCAAA GCATCATGCA
86221 AACAGTGGTC ATCCCAGACC AGTAATTCTC AACTCACAGG GTGCTCCTGC AGAGATGTAT
86281 TTGAATAGAG TGGTAGGATG CTGAAGAAGG CCACGTAAAA TTTGGCCAGT GATCTGGGGC
86341 AGATTTATCC TGAAGCTAAT GAAACACAAG TGTAAGGGCC TGTACTTCCA AGGTGCAGAG
86401 AGGGGCCCTA CAAATGTGTT AGTTTGTCTC TCTCTCTCTC TCTGATTTTA AAATTTGCAG
86461 TATTAAGGTA CTTTAATCAC GGATGGTTCA GGCTGCTATT TTCACTCAAT CCTCCTTTTT
86521 ATTAAAATCA CCATTGTCTG ATTATGTTAG AATCCTGATG AAAATATTTG GAATTTGAGT
86581 AAGAGAAAGT TTAGTTGAAG ATGTATCTAG TATGGGGATA ATAAGTTACG TGATTTGCAT
86641 ATGTGATCAT GTGTACTTCA TTCGTTGCCA GCCAATCTGA CGTAAGAATG GCTTCAAGGA
86701 GGCCGGGCGC GGTGGCTCAC GCCTGTAATC CTAGCACTTT GGGAGGCCGA GACGGGCGGA
86761 TCACGAGGTC AGGAGATCGA GACCATCTTG GCTAACACGG TGAAACCCCG TTTCTACTAA
86821 AAATACAAAA AATTAGCCGG GCGTGTTGGC GGGCGCCTGT AGTCCCAGCT ACTTGGGAGG
86881 CTGAGGCAGG AGAATGGCAT GAACCTGGGA GGCGGAGCTT GCAGTGAGCC GAGATCGCGC
86941 CACTGCACTC CAACCTGGGA GACACAGCGA GACTCCGTCT CAAAAAAAAA AAAAAAGAA
87001 TGGCTTCAAG GAATGTTCCT ACTGCTCACT GGAATAACTC ACCTAAATTC CTGGCAAGAT
87061 GCAGGTCTAG ATAAAATGTT ATGACATCTA AGTATTCAAA ACACATTCCC AGCACTGAGA
87121 GTGAGTGTCT AGTGGAGAGT AGAAACGTAT AGAGCCAGAA GCTAGTCTGG AAAGAATTCT
87181 TACAAAGTTT ACAACTTACA TGTGAAAGGA GCTTAACAGA GGATTTTCCA AATTTGAAAA
87241 CAATCCTAAA AACTTACTTG ACATTACCAA TAATGTGTTT TGAAACTGAA ATACTTCTAA
87301 GTTATGAAGA AAACATATTA TCATCAGCCA CCCTGGAGGA AAGATTGAAT TCTATTTCCA
```

Figure 2 (Page 27 of 74)

```
87361  TTACCTATAG ACAACATTAC AAAATAATTT CGATCTGAAG ATGGAATCAG AGTATTCAGT
87421  CAAAACTACA GGAAAATATA CTTGGTAGTG TCATATTCAG AAGTTAATAA AATATGCTAT
87481  TTTCTGAATT TTGTGATGGC TGTTGTTTTG TCAGCTTTTA TAAAATTGGA ATTTGATTTT
87541  ATTTTCCCAT TATAAATTTA TATTTACAGT CTGCAGTACT TTTGCATTTT TAATTTTACA
87601  TTATAGCTTT TAATAGTTAA CAAGTTGTAA AAGGTTTGAT CCCCAGAAAA CCTTGATCTA
87661  CCCCCTCAGT TAAGTATACT AATATATTTA GAAAATGGAT GAAATCAGCA TTTGAATATT
87721  TTTAAATATT TATTAAAAGA GGACATGGGT AAAAGAGCTT TGCAGTTGCC ACCCTTCATT
87781  CTCAAATTCC CTGGATAAGG ATGACCGCAT AATCTTTGGA TGGTCATACG CAAGTCTTGT
87841  GTATTTGTTA CATAAATCTA TTTAGTGGAC TTTTGGCAGT GTGTACTGAG GCCAGTTTCT
87901  TCCACCTGAG CTCTGACTCC ACCTCCAGCA GCCCAAACC AATACTGAAT TTGGGGTCA
87961  GCTATTGTTT TTGTGGACTT AGGTAACTAC ACACACATTG TCTTTATGAT AGCTTTAATA
88021  ATACTGCCAT CAGAACTAAA ATTGTCACGT GGATTAAAAG GAGTGACGGT GGTGTCCCCA
88081  GGAGCCTTTC AATATGTAAG TATTTACACA TATACATGCT AAAAAGACCC CTAGGAATTT
88141  TTTTAACAAG GGCAAAACAG TAACTCAGCT TGTTTTCTCG CAGTAAAACC GGTTGAAAAG
88201  GCCTGATAGA CTTGTCTGCA GTTACAAAAC TTGTGTGTAG TTATCACCTT TATATCTCCT
88261  GGAAACTAAC ATAGACAACC GAATGGGTTA CAACTGTTTT TAAGTGAAAT TGTGAGTGGC
88321  TCTGAAAAGA GCCTTTTCAA TGAGGAAGAA ACGGGCAGAC TTATGCCCTT TCCCCACGGA
88381  TGCGACGTGC CAGCTGGATA TCTTTGGGCA TGATGGTGAC GCGTTTAGCG TGAATAGCGC
88441  ACAGATTGGT GTCTTCGAAG AGTCCCACCA GGTAGGCCTC GCAAGCCTCC TGCAGCGCCA
88501  TCACCGCAGA GCTCTGGAAA CGCAGGTCGG TTTTGAAGTC CTGGGCGATT TCTCGCACCA
88561  GGCGCTGGAA CGGCAGCTTC CGGATCAGCA GCTCGGTGGA CTTCTGGTAG CGACGGATTT
88621  CGCGCAAGGC CACGGTGCCC GGGCGGTAGC GATGAGGTTT CTTCACGCCA CCGGTGGCCG
88681  GAGCGCTCTT ACGGGCTGCT TTAGTAGCAA GCTGCTTGCG CGGAGCTTTG CCGCCGGTAG
88741  ACTTGCGAGC TGTTTGCTTC GTACGAGCCA TTTGCAATGA GAGCACACAC AAAAGTGTAG
88801  TGAACTGAGA GCAAGTGGCC TTTAAATATA GTGAGAAACA TTCTGATTGG TCCTGTAATA
88861  TTTCAAAAGT CCCGCGCGAT AAAATCATTG GCTGAAGAGT GACCAGACTG ATTGGTTCAT
88921  TACTAGACAA TCTTATTGGA TGAGTTGCCC CACCGCCCAT CCTGTCCTTT TCGTTTCAGT
88981  TATCTGCAGC GACAAATTGT CTAAAATTCT AGTTCATCCA GTCCCAAAGA ACAGAGTGTA
89041  TAACAAGGTA TCTAAGGATT TTTAAAATGT AAATTCCGAT TCAGTAAGTT TGAGTGGGAC
89101  TTGAAATTCT GCATTCCTGA CAGTCTCGCA AGTTATCAAT GCTGGTGAAC ACTCACTAAA
89161  CCACCAGAAA CGTTCAGACT CATGTCGGGA AATAACGCTT ATATTCAGAG AATGAGATTC
89221  CATGCTATTT TGTTACTGGC GAACAGCAAG TTTCCTTGCC CTTTGTTTTC TAAGTCCAAG
89281  TCACATTCCC ACCCTGCCTG TTCTCAAAAT GTCTTATTTT GGTTGGCCTT AAGTTTCACT
89341  TTGTATACTC TAAAATGTAC TTTCTAAAGG AAGGTGTTAT TTTCTCGAAA CTTAACTTTT
89401  TAACACCATT AGGCTAGGGG GGCGGTGGCT CACGCCTGTA ATCCCAGCAT TTGGGAGGG
89461  CGAGATGGGA CGATCACTAG AGGCCAGGAG TTCAAGACAA CCCTGGCTAA AATGGTGAAA
89521  CCCCGTCTCG CATAAAAATA CAAAAACTAG CTGGGCGCGG TAGCAGACGC CTGTAATCCC
89581  AAGTACACAG GAGGCTGTGG CATGAGAACC GCGTGAAGCG GCGGGGTGGA GGTTGCAGTA
89641  AGCCGATATC GCGCCGCTGC ACTCCAGCCT GGGTGACAGA GCTAGACTGT CTCAAAACAA
89701  ACCAATCCAA ACGAAAAGCA AAAATACCC TAACAGAAGC AAGTTATCAT CCTTTCTTGT
89761  GTAACTATGG ACGGCTCTGA AAAATGCCGT TTCAAGTGTA AGCTACGTTT TCTGATTTGA
89821  GTGTTTACTT GACCTTGGCC TTATCGTGGC TCTGTTATTT TGGCAACAGG ACGGCCTGAA
89881  TATTGGACAG GACGCCTCCC TGAGCAATAG TGACGTTGCC CAGCTGCTTG TTGACCTCCT
89941  CGTCGTTTCG GATGGCCAGC TGCAGGTGGC GGGGGATGAT GCTGCGGGTC TTGTCACGTA
90001  TGGCGCTGCC CACCAGTTCT AAGATCTCGG CGGCCAGGTA CTGTAAGTAC ACTGGCGCAC
90061  CGGCTCCGAC CGGCTCAAAA TAATTGCCCT TCGAAAAAG ATGACGGACT CTGCCCTATT
90121  GGGAACTGCA AGCCCGGTAG CGACGAACAA GTTTTTGCTT TAGCTCCATT TTCCACGTCC
90181  GCAAATAGCG ACCTATGAAA GCAGCGGAAA ACTGTGAAAG ACAAGCAAGC TGGAATGGCG
90241  CCTGAACAAA TCCTTTTATA CAAACTGCAA GGCTGCAATA GAAGCTATC CTATTGGTCA
90301  ATTATGTTTG GTGCTTTATC CAATAGAAAA AGATAACATA AATTCCATAT TTGCATAAAC
90361  CCCACCCCTC AGTGAAACCG TGTTTCTTTT GTCCAATCAG AAGTGAGGAA TCTTAAACCG
90421  TCATTTGAAT CTCAGGACTA TAAATACATG GGCTCTGAAC TGTTCTCTGT ACTACTCTGT
90481  AGTGGAGAGT GTTAGTAGCT TTTCTATTCT GTTTAGGAAT AGCAATGCCT GAACCCTCTA
90541  AGTCTGCTCC AGCCCCTAAA AAGGGTTCTA GAAGGCTAT CACTAAGGCG CAGAAGAAGG
```

```
90601 ATGGTAAGAA GCGTAAGCGC AGCCGCAAGG AGAGCTATTC TATCTATGTG TACAAGGTTC
90661 TGAAGCAGGT CCACCCCGAC ACCGGCATCT CATCCAAGGC CATGGGGATC ATGAATTCCT
90721 TCGTCAACGA CATCTTCGAG CGCATCGCGG GCGAGGCTTC TCGCCTGGCT CACTACAATA
90781 AGCGCTCGAC CATCACCTCC AGGGAGATTC AGACGGCTGT GCGCCTGCTG CTGCCTGGGG
90841 AGCTGGCTAA GCATGCTGTG TCCGAGGGCA CTAAGGCAGT TACCAAGTAC ACTAGCTCTA
90901 AATAAGTGCT TATGTAAGCA CTTCCAAACC CAAAGGCTCT TTTCAGAGCC ACCTACTTTG
90961 TCACAAGGAG AGCTATAACC ACAATTTCTT AAGGTGGTGC TGCTGCTATT CTGTTTCAGT
91021 TCTAGAGGAT CAACTGGAAT GTTAGCGAAG ACAAGTTTTA GAGCCAAGGT TAACTTGGAC
91081 GGGGCCGTGC GCGGTGCCTC TTGCCTTTAA TCCCGGCAAT TGGGAGGCC GAGGCGGGCG
91141 GATCACTTGA GGTCGGGAGT TCGAGACTAG CCCGGCCAAC ATGGCGAAAG CCCGTCTCTA
91201 CTAAAATACA AATGATAGAC GGTCGTGATG GCGCTCTTTC TCATCTGTCT TAGCAAACTT
91261 CTTTGTTCCC CCTGGGTAAG CCTTCGGGTA CTATGTATAA TTCCTTTGAT AAGGTCACTA
91321 CTCCCTCCCT GGTCTAGTAC AGGAAACTTC CCTTTCTGGA TAATGAAGCA GGTAATGGAA
91381 TTCAGGGTAT AGTGTTCCTG TGGGGTCAT TAGCCGTTAA CTTCTTGTGA GATGCGGGGG
91441 AGGGGAGCAG AAAAGTCTAA GCGACAAAAG GGCATGTAGG GATATTTGCT CCTGCAGCTT
91501 GCCTATGCTG TAAATTCTTA CTTCAAGTAT TGAGGAAACA ATAAGCGAAG TCTGATTTCC
91561 CGGGCGCCTT TATACGGAAT ATTTCCCGCT CCACAAAATG AAATCGCAGT AGTTTTGAGT
91621 TATAATTGTT TATCAATGAC AACAGCTATG TAGTTTACAT ATTTCATGCA TCCCAGAAAT
91681 CCAGATTCCC ATTTCCTAAG CCACTTAACG TTCTGATTTC CAGCTCTGCG AGATACAAAA
91741 GGGTTTGGAT TTTGTGCCCT TCCCCATCTG GCGCCACTGC AAAGCTTACT AGGAGGGCCC
91801 CACTTGGAGA GGGAAATCTT TTTCGAGAAG TCCAGGACGC CAAAAACAAT ATAGCTAAAA
91861 AAAAAAAAAA AAAAAAGGCA GGAAGAGCAC TAGTTGAGGA GGAGGACTCA ATGGGCCAAT
91921 TCTGGGGCTG GGGCTGGGGG AAGAAATGCA AGAAGAAAAG ACACTTGTTG ACTGCACAGT
91981 AAGCAGGAGG GGGTGGGGGA ATCGGAGGGG AGTATTTTCA GCGAATTTAT GGGCATTATA
92041 TGTAGGTGAC ATACAGCAGT GTCTTTGGAT GAAGAAATAA AGTTTCTCAA ACAGTTCTTG
92101 TTTTTGTTTT GAGAAAGGGC CTTTCTCTGT CGGCCAGGCG CCATCATAGC TCACTGCAAC
92161 CTCGACTTCC CCAGCTCAAG CGATCCTCTT ACTTCAGCCC CTTGAGTGGC TGGGACTAGA
92221 GAAATGCACC ACCATACCCA GTTAATTTTT TAATTTTTTG TGGAGGCAAA GGGTCTTACT
92281 TTGTTGCCCA GGCTGGTCAA GCGAACTCCT GGGCTCAAAT GATCCTCCCG CCTTGGCCTC
92341 CCAAAGTCCT GGGATTATAG GAATGAGTCA CCGCGCCCGG CCCAGATTTA ATTTTTAAGA
92401 ATCTTTTAAA AGAGGTTCTG GGCCGGGTGT GGTGCAGCTC ACGCCTGTAA TACCAGCATT
92461 TTGGGAGGCC AAGGTGGGAG GATCACTTGA GCCCAGGAGC TCAAGACCAG TCTGGGCAAC
92521 TTAGTGAGAC CTTTTGTCTC CACCAAAAAT TTAAAAAATT AACCAGGCCT GGTGGCACAT
92581 TTCTGTAGTC CCAAGTACTG GGGAGGCTGA AGTGGGAGGA TCATTTGAGC CTGGAAGGTG
92641 GAGGTTGCAG TAAGCTGTGA CGGCACAACT GCACTCCAGT CTGGGTGAGG ACAGACCCTG
92701 TCTCAAAAAT AAAAAATAAA AAAAAATCTG GATGCCACAC AAAATGTCAG TGAACAACTG
92761 TAAGTGAAGC ACTTCCCATC CTAGTACTGT ATATGCAAAC TGCCGTTGTG AAAGTGACGC
92821 TTGGCTTAAA AATCTACATT CTTTTTTTAA TTATAAAACT ACCACATCCC CAAAAACAT
92881 TACTAAGGAA TTGAGGCTGC AGTTTAAGAA GCTGATATTT AGGATCTATC TCCGGAGAAG
92941 TGAGACCTGG TAATATAAGC ATTTTCAAAA TGAACTTTTG GCCAGGTGA GGTGTGTCAT
93001 GCCTGTAATC CCAGCACTTT GGGAGACCTA GTCAGGCAGA TCACTTGAGC TCACAATTCG
93061 AGACCAGCCT GAGCAACATG GCGAAATCCA GTCTCTACAA AAAATTAGCA GGGCGTGGTG
93121 GCATATGCCT ATAGTTCCAG CTACTATAGA GGCTGAGGTG GGAGGATTAC TTGAGCCCGG
93181 GAGGCAGAGG TTGCAGCAAG CCAAGATCGC GCCGCCACAG CCTGAGCGAC AGAATGAGAT
93241 ATGCACCCAC GCCCTAAAAA AAAGCATGAC TCATTAAAAA AAAAAAATTT AGCCGGTCGC
93301 GGTGGCTCAC GCCTGTAATC CCAGCACTTT GGGAGGCCGA GGCGGGCGGA TCACGAGGTC
93361 AGGAGATGGA GACCATCCTG CTTAACACGA TGAAACCCCG TCTCTACTAA AAATACAAAA
93421 TAATTAGCTG GGCGTGATGG TGGGCGCCTG TAGTCCCAGC TACTCGGGAG GCTGAGGCAG
93481 GAGAATGGCG TGAACGCGGG AGGCGGAGCT TGCAGTGAGC CGAGATCGCG CCACGGCACT
93541 CCAGCCTGGG TGACAGAGCG AGACTCCGTC TCAAAAAAAA AAAAAAAAA AAAATTAAAA
93601 AAATATGAAG TTTTGAAGCA GAAATTATTT TGTCGTATGT TCTTTCATAA ATTTTTTGCC
93661 TGCCTGCCTT CTTCCTTTGT TACAGAACTC CAACACTTAC CCAAGGTAG CTGTTGGGTC
93721 AGGGTTTCTG TACTATAGTC CCTTCTGTGG TGGCCAGAAA TATGTTACAG GAAAGAGGTC
93781 CCCATCCAGA CCCCAAGAGA GGGTTCTTGG ATCCCGCGCA AGAAAGAGTT CAGGGTGAGT
```

```
93841  CCGCAGTGCA AAGTAAATGC AAGTTTACTA AGAAAGTAAA GTGGTGAAAC GACAACTACT
93901  CCATAGACAG AGCAGGACAT TCCCGAAAGT AAGAGGAGGA AGGCATCCAC CCTAGGTACA
93961  ATACTTGTAT ATATGGGGAG ATGTGCTCTG CTACAAGTTT GTGATAAAGG ATTAATTTTC
94021  TTAGTTACTA TATTTTGCAA GAATCAACAT TATTATCTTT AAACAAAATT AAGAATGCCT
94081  TTGTTCTCCA GATATAGGGA TATCTGGACA CTCCTAAGTC TGAGTCTGTT TAGTAAACAT
94141  TATTTATTTG TTCCCTTAAC CGTAAACATC TAGAAGCTAG GAATGACTGA CTTTCTGGGA
94201  ATGCAGCCCA GAAAGTCTCA GCCTCATTTT CCTAGCCCTC ACTCAAAATG GAGTTACTCT
94261  GGTTCAAGTA ACTCTGACAC TTTTCTTCTC TTTTTTTCTT CTTTTTTCCT TCCTTTATTT
94321  TTTATTTTTT ATTTTTGAAA TAAGAAATCA AGAATACTTG ATGTTTCATC TAAAACAATA
94381  CCCATAATTG ATAAGCCAAA ACAAAAACCT AGGTCTTCTA ACTCAAAACT AGGATGTTTT
94441  GCTGTCTCTG CTGATACTCG GCTGATCGTT AATAGGTAAT TAACAAACAA GCCTTGCTAT
94501  GTCCCCCTCA GTTTATTACC ATTAGATCAT ATGCCTACTG TCAATCATAT TAATCCACAA
94561  CTATGCATTT CACAAAACTT GCCATAAAAA TTCACAGGTT TCCCGCTTCC CTCGAGTTTT
94621  CATTTCCGAA GGGTCCCATG TAATATAAAA CTTATATTAA ATACATTTGT ATGCTTTTCT
94681  CTTGCTAATC TTTTTTTTTG TTTTTTGAGA CTGAGCCTTG CTCTGTCACC CAGGCTGGAG
94741  TGCAATGGCG CGATCTCGGC TCACTGCAAC CTCCGCTTCC CAGGTTCAAG CGATTCTACT
94801  GCCTCGCCCT CCCGAGTAGC TGGGACCACA GATACGTGCC ACCATGCCCC GCTAATTTTT
94861  GTATTTTTAG TAGAGACAGG GTTTCACCGT GTTGGCCAGG ATGTTCTCAA TCTCCTTACC
94921  TCGTGATCCG CCCGCCTCGT CCTGCCAAAG TGCTCGGATT ACAGACGTGA GCCACTGCAC
94981  CCGACCAATC TGTCTTTTTG TAGAGGGGCC TCAAGCATGA ACTTACTGAT GGGTGAGAAA
95041  AACAGAATTT TCTTTTCCCC TACAATATAA ACATTAATTG TAATGTTATC ATTCAGGACA
95101  TTTTGGTGAC CAATCTTACA GAAATTTTAT CTTGTGCAAG TCTATGCAAA CCAATATGTA
95161  AATCTTCTAT AAGTGAGATT GTATTTCACT TTTCTAGTAT CCTTTTAAAT TAATAAAAGA
95221  GATTCTAATG ATTATTTTCA TTACTGCATT TCATTGTAGG GAAGTAGATA ATTGCCCTTT
95281  ATTCACTGAC CTTCGCTTTT TAAAAATTTA AACCATGTTA CCATGAAAAT GCTTTTCAGT
95341  ATTTCTCTAC ACACAAGATT GCTGTAAGGG CAAAAATAGA GATAGGAATC ATGCATCCAT
95401  TGATATACAT ATTTTGATTT TTAATACATG TTACCAAGTT GCCTCCTGAA GGTCTGTTTA
95461  CACTCTCACC AACAGGGTGT TTTTTCCTGA CTTCCACAAA TGCTCTTGAA CAGTGGGTGT
95521  GTTAGTCTGT TCAAATTGCC GACATGAACA ATTAAATCTC ATTGTTGTTT TTATTTTTAA
95581  GACAATTATT GTTTGAGACT GCACATTTTG ATAATAACAT TTCTTCTATT ATGGTTTGAT
95641  TACTCATGAT TCTTGCCCAT TTTCTTTTGG GATGTTGCCT TATGTACATT ATTTTAAATA
95701  GATAGCTCCA TGTATTAAAA GATTATTAAG TTTGAGGGCT TATGATATGT CAGTTACATT
95761  TCTAAGATTT TTTTTTTTTT TTTTTTGAGA CGGAGTTTCA CACTTGTTGC CCAGGCTGGA
95821  GTGCAATGGT GCGATCTCGG CTCACCGCAA CCTCCGCCTC CAGGGTTCAA GCAATTCTCC
95881  TGCCTCAGCC TCCCCAGTAA TTGGGACTAC TGGCAAGCGC CACCACGCCT GGCTAATTTT
95941  GTATTTTTAT TAGAGATGAG GTTTCTCCAT GTTGGTCAGA CTGGTCTCGA ACTGCCGACC
96001  TCAGGTGATC CACCCGCCTC GGCCTCCCAA AGTGCTGGGA TTACAGGTAT GAGCCACTGG
96061  GCCCGGCCAC ATTTCTAAAT TCTTTATAAG TATAAATTCA TTCAATCTTC ACCAAAACTC
96121  AATGAAGTGT GAGTACTATT ATTATCATTG TTTTACAGAT CAAAACAAGT AATACAGTCA
96181  CTTACTGAGT TCTATACACC TGGTAATTTT TTTGTTTCGT TGTTCTATCA ATTATTGGGG
96241  AAGGGGTGTT GAAATCTCTA CCTTTAAATC ATGTATGTGT CTATTTCTCC TTTCGGTTCT
96301  ATCAGGTTTT GCTACACATA TTTTGCAGTT CTGTTATTTG GTGCATATAC ATTTAGAATT
96361  GCTTGTTTTT CGTATTGGAT TGACCCTGTT ATCATTATGT AATATCCCTG TCTGTTCCTA
96421  GTAATTTTCT TTGCTCTGAA ATATACTTAT CTGATATATC ATCCAAAAGA CCACCAGGAT
96481  GGCTAAAGAG TAGAAGGAG AGATTTACTG GCAATACTAA TTTGCAAGCC AGGAAGAGAT
96541  GGTCCCAGAA CCTGCCAAAA TTACTCTCTC TTTGGGGAGA AGGAGCAGGT TGGTTATTTT
96601  TATGCCTCAT AGGCTATATA TTACACAATA GAGTCATACA TATTTAGCAC GTTTGGGGGG
96661  ACAGCTATAT ATATTATGAG GGGTGCCAAG TGCATTCACA ATGGATAAAC ACGTGTAATA
96721  TACCTCCCAT GTTCACTTCG AGGTTAAATT TTGGTTAAAA TGAGGTAGAA TTTAGGTCTT
96781  TACATCACAA GGTGAACTAT AGGAACAAAG TTTACGTGCT GCCTCTAGCA GCTGGCTGAA
96841  AATGGCTTAA GGTCTACAAT TACGTGTAAG AATAGAATGT GTGTCAAGGC GGTCCTCTGT
96901  CCAATCAGAG TTGTAGTGGA CTGGACTGTA AATCAGAGTT AGGAGGGCTT CTGATAGCTC
96961  CTATAGTTAA GGAATTTAGC AAGTGTGAGT TTTTTGGTAG TCTTTGGAAT TTAGGAATTT
97021  GCCATGCCAG CCAAGCCATG AATGCTCTAC CAGTAGGTAA CTTTGTTTGC TTAATCTTAG
```

Figure 2 (Page 30 of 74)

```
 97081  AGTCTGTCTT AGTTGGTATA GGGGCATCTA TTTTGGTCTT TCAGATCCCA GATATTATTA
 97141  ATACAGATAC TCTTGCAGTT TTGGGCTGAT GTTTATATGG CTTATCTTTT TTGCAGCCTT
 97201  TAATTTCAAC CTGCGTTATG TTTATATTTG AAGTGAGATT CTTGCAGACA GTGTACAGTT
 97261  GTTGTTTTTT TTTTTTTTGA GATGGAATTT CACTCTTGTT GTCCAGGCTG GGGTGCAGTG
 97321  GCACAGTCTC AGCTCACTGC AACCTCCGCC TCCTGGGTTC AAGGGATTCT CCTGCCTCAG
 97381  CCTCTTGAGC AGCTGGGATT GCAGCCATGC GCCACCACAC CCGGCTAATT TTTGTATTTT
 97441  TAGTAGAGAC AGGATTCACC ATGTTGCCCA GGCTGGTCTC GAACTCCTGA CCTCAAGTGA
 97501  TCCGCCAGCC TCGGCCTACC AAAGTGCTGG GATTACAGGT GTGAGACCTC GCGCCCAGCC
 97561  AAACTGTTTT TTTATGGGTG TATTTATACC ACACACATTT AATGCAATTA TTGATATCTT
 97621  AGGGCTTAAG TTCATGAAGG GTAGTGTGGG AACCATAGTC TCTTGGCCCA CTAAATGTTT
 97681  GCCAGAAATC ACTGACAAGG CAGATTGATT AATAGGTGAA AAGGCATTTT ACCTATTGTT
 97741  TAACGTGTCT ATGTGGGAGC ATTCAGAATT AATTACCTAA CTTCCCAATG AGTTATAGAT
 97801  GCTTATATAC CATTTTTAGA TCACAGAAAG AATTGGGGCT TAGATTCTGG TAAAACAGGT
 97861  TATGGGAGGC AAAAGAGGTT TGGCTTGCAA AGGTGGCCTT GTTAGGTAGG TGAAGCCTCC
 97921  CTCAGAAAGA ACAGATGGTA AATGTTTCTT TTATGATTTT TAAGTGTCAG ACTCTCAGTC
 97981  TCTCCTGGAT CTGGGGAAAG GTATAGAAAG GTGAGGAGGC ATGGCTGCAT TAATGGAGAT
 98041  TCTCTACAGA TGTAAAATTT TTCCCATTTA AGGCAGCTTT GCAAGCCCAT TTCTGCCTGC
 98101  TGGCCAAGCA GCAGCCATTT CAAAATATGT CAAAGAAATA TATTTTGGGG TAAAATATTT
 98161  TGATTTCCTT TAGACTGGTG GCCTTATAAG AAAAGGAAGA GACACCTGAG CTGACACACA
 98221  TACCCTTGCT CTCTCAACAT GTTATGATGC AGTAAGAAGG CCCTCACCAG ATACTAATTC
 98281  CATGCCCTTA GCTTCCAGG TTCTAGAACA GTAGGAAATA AATTTCTTTT CTTTAAAAGT
 98341  TAGCCAGTCT GTGGTATTCT GTTATAGTAT CACAAAATGG ACTAAGTAAC TATATTATGA
 98401  TCATCTTACA TGACTGATCC CTCCTACATC ATACACATAC ACAGGCCACA TTTGGAACAT
 98461  TGTTAGAGGT TCCTCTACCC AGTACAAATG TACTACAAAT TATATATGTA TTTTTAAATT
 98521  TTTGAGTATC TTCAATAGTA TATTTTCGTT AACTTTTGTA GTCAAAATGT CATTATAACA
 98581  TGTATTCAAT ATGCATAATT ATTAGTCAGA TGTTTTACAT TCTTTCTTCA TACTAAGTGA
 98641  TATGGTTTGG ATATTTGTCC CCTCTAAATC TCATGTTGAA ATGTAATCTC CAATGTTGGA
 98701  AGTGAAGCCT GGTGAAAGGT TTTTGGATCG TGAGGGTGAA CCCCTCATGA AGCGCACTCT
 98761  TCAGGGTAAT CAATGGGTTC TCACTTTGAG TTCACAAGAG ATCTGGTTCT TTAAAAGAGT
 98821  GTGACACCTC CCCCATCTCT CTCGCTCAGC TCTCACCATA TGATATGCCT ACTCCCTCTT
 98881  CACCTTCCAC CATGATTGGA AGTTTCCTGA GGACTTGCCA GTAGCAGATG CCTGCACCAC
 98941  ACCTCCTGTA CAGCCTGCAC AACCGTGAGC CAAAAAAAT TACTTTTCTT TATAAATTAG
 99001  TCAGTTTCAG GGATTCCCTT ATAGTAATGC AAGAACGAAC TAACACACTA AGTCTATTTC
 99061  ATATTTACAG AATAGCTCAA TCTGAAGTAC CCTTTTTCAA CTTCACAGTA GCTACTTGTA
 99121  GCTAGTGGGC ACTGATTTGG AGCGTGTTCA AGGGTGAATT GTATTATGCA ATTAACAGAT
 99181  TTTTTTTATT GTTTTCGCAA ACCACGAGGC ATAGATTGTC TTACTTTCTC TGCTCCTGGT
 99241  GTTGGAGTTG TTATTGGGAA ACAACTTATT TTCCTCTTAT ATTTATATGG AATAAATAAC
 99301  CCCCAATATT TCCCTCCCCA ATATCTGCCT TTTGTATGTT TTTTGAAGGC AAGTGCCTAG
 99361  AATTTACTGT TTTTGAAGCA CTTACTGAAA GGATTGCCAT CAAGTTGTTT TGCTAATAGT
 99421  ACATGCCAGG CGCTTGTTGG TTTGCTTAAT TCAAGGTAAC TTGGATGAGA AGAAGAGTTT
 99481  TTCTCATCCA TGGCTCAGTG GAGTATAGAT TACTGATATT GTGACTGGAT GTACTCCTGC
 99541  TTTCTAGTCT GAGTTTTTGA AGCTACCCTT AATCTTGGTT TCAATTTTAT CTAGCCCTGT
 99601  ACATATCCAA GGCTCTTTCC AAAATGGTCT ACGATTTGTT TAGGAAGTTA GAATAGCTGT
 99661  ACTTTCTGAA CCACGGTTCC TGACATTTTC TGGACTTCAA ACACATCCAG CATTTTATCG
 99721  AAGTATTTAT CCTTCCTACT TGGCTGGCTT CTTCCTTGCC TTCAGGTCTG AATTCAAATG
 99781  ACATTCTCCT GATGAAACTT TCCATCCTTA TTTCTATTCT TTTTTCTTAT CCCCTTTCTT
 99841  TATTTTTCTC CACAGCACTC ATCACTTATC TCTACATTTT CATTATGTAT TTACCTTATT
 99901  GTGCACCTCC CACTACAAGA CAAGTAGCAC CGTAAGGAAA CAGGTTGTCT GCTTTTTCAC
 99961  TGCTATGCTC CCTGCACCTA GAACACTCTC TGGCACTTAG CAGGTTTTCA GTAAATATAT
100021  GCTGAACTAA TAATGCTGGA TATACATCTC CCTCATGAAC TCTCTAAATC CTTCTAATTT
100081  ACATTGATCA ATCTTCTTTT CCATGTGCTT TTGTATGATT TATTGCTCAA AATCTTTATT
100141  TTGTATGCAG AACGTGCACT GCTATTTAAT CTTCATGTAC GTAAGTCCTC CCTTCTCTGA
100201  GTATAATCTC TTCAGGGCAC TATCTGAGAT AACTTTTTAA CATCTCCATC ATGAATCTTG
100261  TACCTTTTCA AAGAAAATGA GCCAGTGATT ACTGATGTTT ACGGCTATTG TTGAGGGTGA
```

Figure 2 (Page 31 of 74)

```
100321 AGATCATTAT AATTTTGAAA AGGGAAGTTG AATATTGTGA AGGGAAAGAT AACACTAGAG
100381 TCAGAAGACT TGGGAGAAGG CAAAAAACAA ACTAAAAATG AGCACTTTTA GTCTCCTGAC
100441 AGTTTCTCTG AATCAAATCC ATAGTTCTGT GACAGCGTTG GCTTAGAAGC AGATTTTTTT
100501 TTTTTTTTTT TTGAAATGGA GTTTCGCTCT TGCCCAGGCT GGAGTGCAGT GGCACGATCT
100561 CGGCTCACTG CAACCTCTGT CTCCAGGGTT CAAGCGATTC TCCTGCTTCA GCCTATGGAG
100621 TAGCTGGGAT TACAGGCTCC CACAACCACG CCCAGCTAAT TTTTTGTATT TTTAGTGAAG
100681 ACTGGGGTTT CACCATGTTG GCCAGGCTGG TTACGAACTC CTGTTCTCAA GTGATCTGCC
100741 CGCCTTGGCC TCCCAAAGTG TTGGGATTAC AGGCATCAGC CACCGTGCCC AGCCAGGAGC
100801 AGATTTTTTT ACACTCATGT TTCTTTTTCC TTCTGTCATC CTGTTTCAGT ATAAGCAGAC
100861 CACAGATAGA AGTAGTAGAT ACCTCAGAAA TTCCTGGAAT AATTAATCCA CGTTCATCTG
100921 TACTCCATCT GCTCCTATCT CATGAATAT AAAAGGAAAA ACACCAAGAT TTCCCTAGGC
100981 AATCTGTCTT GATTTTAGGT TCCTCAACAG GAGAGCCAGA CAATGGCTGT AATAATATTG
101041 TCCCGGCCAA GGAAAAACTT CCCCTTTGCC CTCCCAAGGT TTATGGAAAA TTACTGGCAA
101101 AACACAGATT AACTGGAGAA AAGGCATATA TATTTATTTC ATCACAATTT TACAGGAGAT
101161 TTTAGAATTA AGACTGAAAG ATACAGGGGA AATTGCCCAT TTTTATGCTT AGGTTCAACA
101221 AGATAAACAG CTGTATAGGG TACGATCTAA TGCTAACAGA CTGAGTGGGG AAGCCCCGCA
101281 AGGCTTGTCT GTCAAGATTC TTCTTGACCT CTCAGTGCAG CATTTCTTCC TTCTGGTTAT
101341 AGGACAAGAC TCTCTTTTAG AATGGGGGT CTTATGACCT ACAGGCAAAC AAGGTAGGTT
101401 AGAGTAATAT TTTTAGGTTT TATGGCTGGT TCTAGGGAAA AGGAGTTCTG GTTTGTATGG
101461 CCTACCTTGA GGAGGAATTC TGGTTTCTAT GGCTAGACTT TGGGGAGAAT GGGACTTACA
101521 GACAGGAAGG CAGAAGGTGG TCAGTGAAAC ACTTTTATAA TCATAATCCC ATTTGAGTA
101581 TTTCTGTGTT ATGGAATGTT TGTTCTCTCA TTTCCTGAAA GATTCCAGAG ACTCCTCATT
101641 CAGTGTTGTG AAAAAGTTCA GGAAATGCAA CTCAAAAATG TGCCACTTTG TTACGCTGAT
101701 TTCTTTGAAC TGAGGGCACC TAGGAAACAG TAAATTCAAG GAAGGGCTTT CGCTGAACTC
101761 TAATCAAAAA TTTGAAAATT AAAAAAAAAT TCAAAAAGGA ATTTAGTTGT TAAGATTCAC
101821 TTCCCTGGGG AATCTCATCA ACCAGAGAAG ATTAACTGTA TCACAGGAGA GGAGACTGGT
101881 GGTTAACACC ATCTAAACAG ACTTTGTCAC AGCTGTCACC TATTCTTTGA AACACCCATT
101941 TATTTTTCTC CAAAATCATA TACTCTCCCC TAAGTTGCCT ACATCCCCCT TCTTTCTCCC
102001 TTATGAATCA AGAGAGCTTA TAAGCTTCTA CAGTTCACTG GGATTTGGGG TATTCGCTTT
102061 TCTTCCCTCC CACTCCCCCT CCCCTTTTTT TGTCTTTGAG ACACAGTCTT CTGGCTCTGT
102121 CGCCCACGCT GGAGTGTGGT GGCTCTATGT GAACTCACTG CAACCTCCTC CTCTCGGGTT
102181 CAAGCGATCC TCCCACCTCA GCTTCTCGAG TAACTGGAAC TACAGGCGTG CACTACCAAG
102241 CCCGGCTTTT TTTTTTTCTT TTTCTCCCCC GTTTCTTTTT TGGTTATTTT ACTGGAGACA
102301 GGGTTTCTCC ATGTTGTCCA CGCTGGTCTC GAACGCCTGA CCCGCCGTCC TCGGCCTCCC
102361 AAAGTGCTGG TATTACGGGC ATGAGCCACT GCGCCCGATT GAAGGACCT CTTAAATATC
102421 TATTTAGAAA TTGGTCGGAG TCCACTCCTT TCCAAAAACA TGAGTCACAA TCCGGGAAAA
102481 GCACGAGCGG CTGAAAGTCA AAATAACCAG AACAAAACCT CCACTCATGC TTAAAAAAGG
102541 TATTTTGACA AAATCCTAAT TCGGCCAATT ATTATTAGTA TTCAAGTCGA AGGCTCGTCA
102601 AGCCAGACTG GGGATTGGGT CAAACATAAA CCTTACACCA GACGGAAGGA TTACATGCAA
102661 ATGAAGGATG CAGATTCTGA TTTCCCATTG GGTATTTGAC ATTAGCCAAT GGGAGAATTC
102721 CTCACAGCCT ACCTCCAGTC AGTATAAATA CTTCTCTGCC TTGCGTTCTA ATGTAGTTTC
102781 ATTACATTTT CTTGTGGCGA TTTTCCCTTC TTATCAGAAG TAGTTATGTC TGGTCGCGGC
102841 AAACAAGGCG GTAAAGCTCG CGCCAAGGCT AAGACTCGGT CTTCTCGTGC AGGTTTGCAG
102901 TTTCCTGTGG GCCGAGTGCA CCGCCTGCTC CGCAAAGGCA ACTACTCCGA GCGCGTCGGG
102961 GCTGGCGCGC CGGTGTATCT CGCGGCGGTG CTTGAGTACC TGACCGCCGA GATCCTGGAG
103021 CTGGCGGGCA ATGCGGCCCG CGACAACAAG AAGACCCGCA TCATCCCGCG CCACCTGCAA
103081 TTGGCCATCC GCAATGACGA GGAGCTTAAT AAACTTTTGG GGCGTGTGAC CATCGCGCAG
103141 GGTGGCGTTT TGCCTAATAT TCAGGCGGTG CTGCTGCCTA AGAAACTGA GAGCCATCAT
103201 AAGGCCAAGG GAAAGTGAAG AGTTAACGCT TCATGCACTG CTGTTTTTCT GTCAGCAGAC
103261 AAAATCAGCC TAACAGCAAA GGCTCTTTTC AGAGCCACCT ACGACTTCCA TTAAATGAGC
103321 TGTTGTGCTT TGGATTATGC CGCCCATAAA GATGTTTTTG AGGTGTTTTT AATGGCTTTG
103381 AGTGTGGCAC TTTTAGTAAT TTGTCCTGCA GAAATTAGAT CCATAGAAAC CTCAGGAATT
103441 CTAGGTATGT GGGAGAAGTG CCATGCAGCA CAAAACATGT TTACAGGGGT GATTCGCGTT
103501 AAGTTTCACA CACAGCAGTT ACTACATTTT AGAGGAAGGA AATTATACCC ATGAGTGCAT
```

```
103561 TCCTAACTAT CTTGAATGGA AGTGTTAAAA CCCGCATGCC CCACACAAGT TTGAATATGT
103621 CATACCATTT GCTGTAGCAA TTAATGGCAT ACACAATTGA GAGCACACAC ATTACCACTG
103681 AACATTTGAG TATGTATTTC CCAAAATGAG CTTTTTTCCA GTTTGGGGAT GTTTTGCTTT
103741 GTTTTGGGGT GGAGTCTCCC TCTCGCCCAA GCTGGAGTGC AGCGGCGTGA TAACAGCTCA
103801 CTGTAACCTC GAACTCGGGC TCAAGCGATC CTCTTGACAG CCTTCTGAGT AGCTGGGATT
103861 ACAGGCGAGA GCCGCCACGC CCGGCTAAGA GCATTTTTCT AATTGCCCAC ACTTCTTATG
103921 CGACACCCAG AAAAATACAA TTTTAAATAA AGCGCATATG CAAATTTCCC TAATCGTCTC
103981 CAATATTCTC TGATTTCTTT TTTATATTTT AACTAGAAAC AATTGGAGGT TTCCGCGTTG
104041 CTTTGTGTGG TTGTAAATTT TAAGACTTCA GGAAACTTTT CCAGTACAAG ACTTGTCCAC
104101 AGTGGATATA GCAGCTAAGG GGTTAACAAA ATGACGTCAG AGTAGCTACG GTAATGGGCA
104161 GGAGCCTCTC TTAATCTGCA ACCAGGCACA GAGATGGACC AATCCAAGAA GGGCGCGGGG
104221 ATTTTTGAAT TTTCTTGGGT CCAATAGTTG GTGGTCTGAC TCTATAAAAG AAGAGTAGCT
104281 CTTTCCTTTC CTCCACAGAC GTCTCTGCAG GCAAGCTTTT CTGTGGTTTT GCCATGGCTC
104341 GTACTAAACA GACAGCTCGG AAATCCACCG GCGGTAAAGC GCCACGCAAG CAGCTGGCTA
104401 CCAAGGCTGC TCGCAAGAGC GCGCCGGCTA CCGGCGGCGT GAAAAAGCCT CACCGTTACC
104461 GCCCGGGCAC TGTGGCTCTG CGCGAGATCC GCCGCTACCA AAAGTCGACC GAGTTGCTGA
104521 TTCGGAAGCT GCCGTTCCAG CGCCTGGTGC GAGAAATCGC CCAAGACTTC AAGACCGATC
104581 TTCGCTTCCA GAGCTCTGCG GTGATGGCGC TGCAGGAGGC TTGTGAGGCC TACTTGGTAG
104641 GGCTCTTTGA GGACACAAAC CTTTGCGCCA TCCATGCTAA GCGAGTGACT ATTATGCCCA
104701 AAGACATCCA GCTCGCTCGC CGCATTCGCG GAGAAAGAGC GTAAATGTAA AGTTACTTTT
104761 TCATCAGTCT TAAAACCCAA AGGCTCTTTT CAGAGCCACC CACTTATTCC AACGAAAGTA
104821 GCTGTGATAA TTTTTTGTTG TCTTAACAGA ACAAATTTCT AAGGACCCCC CCGGAAAGCA
104881 TTAGACTATG GTCTTAAAGT TGATTAACAG AAATAACGGT TTGGTCAGTC TTGCAGTGTA
104941 GGTTATTTCT GACCTTATTA AGGTGCTATT TGGAGAGAAG CTGTGTAAGT CCACTATCAT
105001 TCAGGCCTCT AGCTTGCTAT GATTAGCATT TGTTTAAACA ACTTTGTAAG AGTAAGGGAA
105061 AAATCTGGTA AGTAGTTAAC TGGCGCTTAC TAGGCATTTT TGCAAAGCTT TGAAAAGATT
105121 AGAAAATTGT GTCTTGCGAG TTCCAGTGTC TTCCTCAAAA TGCTTAGGAA GATTTTCTCA
105181 GCTCAATACA TAGTCCCCTA GGTTTTCTCA TATATTATAT ATATATATAT ATATATATAT
105241 ATATATATAT ATATACTGTT AAATTCATTT GGCTGTTAAC ATTAACCTGA AATTTATTCT
105301 GGTGCAAAAT GTGAGGCAGG GATCTAACTG GCTCTCATTT TATCCATAGC TAGCTACCCA
105361 CTTTAAATCT GTCAGTCTGT CGACCAAGCA TAATTTAATC CCTTATATAT GAATTTTTAT
105421 ATGTGTGGCT TTGCTTGTAA ATAGTCTATC TGGTTGCATT GCTTTGTCTC CTCTAGGACT
105481 ATGCACCATG ACATGCCACA TTCTTTTTTT CAGTACTTCT TGCCTGTAGT TATTAAAATC
105541 TAGAATTTAC AAGTTTTAAC CATTTTCTTT CTGTTGATCT TGCTTTTCGG TTTTGGAGGT
105601 TGGGGATTGA GTACTGGAAG AAAATTTAGA GGGATGGGAA TACTGTACGC AAACAAAAGT
105661 AATATTTACT TTAAAATTTT TATATTTTGT ATTTTTTTAT CATATAGCTT TTACATCACA
105721 TTTTACAGAC TAACTTTAGA ACAACCACAG AATGTCCAAC ATTAAAACTA CTAATTCCAA
105781 AGACCTTGCC TCACATTCTT TTTTACAATA AATATTTTTT ACACCTAACA TTCTTTCTTG
105841 GCCTACATCT AGAATGTAAA CTGATGTACC ATACTAAAAT CGCCTGACCA ACTGTCAACA
105901 ACAACAAATC ACACACACAA AAGATCAAAT TGAATTGCA TCGTTTACTT AAATTCATTT
105961 GTGTTCCAGC TTTTAATAAG GCAGTTTTTG GTTTATAAAG TAATATTTGC ATTTTAAAAA
106021 TTATGAAAAT GAATATGTCA GTTTGTTTTA TGATTCGTTT TTCTTGACTC TTATACAAGC
106081 GACTCTAACT GGCATAGACA TTTGTTATCC ACAGACAGTA TAGATATGTT AGAGATGCCA
106141 ATGGACTTGG TCTATGCCAA GGTGACTACT CACAAGCTCT GGGCCCAGCT GAAGGTCAAG
106201 TATTTTTTTT CCAGTTATAG ATGTGCTGGA TCTGATGTAT AGCGCTTGAC TTTTTATATT
106261 TTCTTTATCT GTAGGAAACA AATGTGTTGG AGGTACTGGG TCTGACGAAT AGCATAAAAG
106321 AATAAAGTTA CATTACTGTC TGAGGATCAG ATGGACAGGG GGTGGTAGCT CAGTCCAGCT
106381 ATTTTCCACT CCCTCACTTA CATTCTTTGC CCCCTCCTCA ACAGAACAAG GATTCTGCTG
106441 TAACTCTTCA TTGACAGTTG ATATTAAAA ATTAACGAAT GGATGAAATT CTCATTTGTG
106501 AAAGAAAATT TATTGAGCAT TTGTATTTG TGAGTAGTGC AAACATTTTA ATATTATATT
106561 AAGAATCTAT TGTTTGTAT TAGAGGAGTA ATTAAGGAGA GATTGGAGAC AAAAAGGGGG
106621 TGTTGTTTGC AGAATATACC ATCCAAAAAT AGACCACTGT GGGATCAGGA TTCTTTTGAG
106681 CTAAAGGCAC TTCAAAAACA GCATTCAAGA AGGGAATTCT TCTAAACTTT TCTTTCTGAA
106741 AACAGGAGAT AAAAGTTCCA ATGTGAAAAA TGCTCTGCTT GTACCAGGTG AAAAGACATA
```

Figure 2 (Page 33 of 74)

```
106801 TTCTTCAGCC CAGAGGCATA GATGAGATAA TTCTGCACAA ACACAGCAGG GAGTCATAGC
106861 CGAGAGACTT CTATACACAA ACAAACCTTG TTAAAATAAT CATATATTCC TTTAATCTCC
106921 TCATATGGTT TACTTTCCCA CAATTGCCTC TCTTTAACTT AATGTGAAAG CATTTAGCTT
106981 TTGCCATTTC TTTGGGCTT CACTTTTTTA TGAGGGTTCT CCTGTCCCAT AAAATTTACA
107041 TTAAATACAT TTGTATGCTT TCATTCTGCT AATCTGTTTT ATGGCAAATG AATTATCAGG
107101 TCCAGCTGGA GACCCTAACA GAGTAGAGGT AAAATTTTGC CTCCCTACAA GATAGAGATT
107161 GTGTGCATTA AATGTTGTTT GTTCCCAGTT GTTCAGTTTG TCAGGCCTCT GAGCCGAAGC
107221 TAAGCCATCA TATCCCCTGT GAACTGCACG TATGCCTCTA GATGGCCTGA AGTAACTGAA
107281 GAAACACAAA AGAAGTGAAA ATGCCCTGTT CCTGCCTTAA CTGATGACAT TACCTTGTGA
107341 AATTCCTTCT CCTGGCTCAT CCTGACTCAA AAGCTCCCCC ACTGAGCACC TTGTGACCCC
107401 CACCCCTGCC AGCCAGAGAA CAACCCCCTT TGACTGTAAT TTTCCACTAT CTACCCAAAT
107461 CTTATAAAAC GGACCCACCC CATCTCCCTT CGCTGACTCT TTTCGGACTC AGCCGCCTG
107521 CACCCAGGTA GAATAAACAG CCTTGTTGCT CACACAAACC CTGTTTGATG GTCTCTTCAC
107581 ACGGACGCGC CTGAAACAGT TTAACAGGGT TTTTCCTGCC CAGTCACAAC AAAGTGATGT
107641 TATGCTGCAG GCTGAAGTTT ACAGCTAATG CTGTTGAAGT CTAAAATCAG TTTTGGTTTG
107701 TTAGATTTGG GTGAGATGGC TAAGATTCTC AGAGAAAGAA GTCAAGTTTG GGGTGCATTT
107761 TTCAGACTTA AAAATTTAGC AGTAGCCCTT GCAGTTTTTC CAATAGAAGT GATTTACGAA
107821 TGTTTTCAGG AAATTTAAAA CAACAGTGAG AAGCGTGTAT GGAGAGTTGA ACTACACTCC
107881 AGACTTGGCT ATAGGAAAGC ACGAATGCTG CTATTGTATT GCACCTTGGA AAAGAGAACA
107941 AAGGAATATT TTCGGACAAT TTTAACATGT CACATATGAA AAGCTAAACG GAATCTGTCA
108001 ACACCTTGTA CGTTATTACA GGCTGTGATT TTAAAAAAAC AATCCTTACT AATACATACA
108061 TAGTTGCTGC TAGCAATATA GTGTTGGGAG TAAAAACACG AAAATTAAAC TTCAGGACAA
108121 TATCCCAACT CTGAGCAGAT TTTTTTAAGT AGTAACATCT AAAATTAAAC CATATTATGT
108181 AATATTTATT TCTTTTCCAC AGTCTCTTCT CATGCCTCGT TCACATTAGC TAATTAAAAG
108241 TCCCCTGAGT ATCATCATAA CCCGATTTAC AGATGAAGGC ACGGTTGCAA TGAGCTATCA
108301 CCCTCTTCTG AATGAGACAG TACAGTGTGA AGGATAGCAA AACTCCACTC CCATCCTCTT
108361 AGGGCTCTGG CTGGACCAGC AAATTAAATT AATGTAAAAT GGATTAACAG GAGAAAGGTA
108421 TATGCATTTA TTTAACACAG GTTTTACGTG ACACAGGTGC TCTCATAAGG TAATGAAAGC
108481 CCAAAAAAAG CAGTTAGCTA CTTATATAAT GAATTGGACA ATTAGTAAAA TGTAAAAATG
108541 CGCTAAAGCA AAGGGATTTA GGCTAGAATA TATAACTGTG TAGAGAAGCG CCCAGCAAGG
108601 GCTAGTGCAA GGTTTGTACA GAATTCTCTT GGCCTCAGCC TCCTATCCTT GAGAAGAATG
108661 TTGCTTTTTT TAAACTACAG TGAGAACATC TTTCATATGA GAATTTCACC TACTGCTTCT
108721 AAGAAACAGG TCAGCTTTCA AGAAAACATA AGGCCAGAGT GATCTTTTCA CGCCTGCTCT
108781 TTTAAGTACC TTTGAATAGT CAATATGTCT TCAAGCACTT GAAAGACTTA AAAAGTTTAC
108841 CACTCCGGCA TATTAGTGAA AGCCCTTAAT ATAAGCCCTT ATTAAAATTC TCAGTCGAGG
108901 GTATAAATTC AGATTCAAAT AGTAGTGTCG TAAACGGGAG GGAAAAACTA AAGGGATTAA
108961 AAAGTGAAAC TATTGTGTTC TCCCTCGCAG TCCTTAGGTC ACTGCCCCTC GAGGGGCGGA
109021 GCAAAAGTG AGGCAGCAAC GCCTCCTTAT CCTCGCTCCC GCTTTCAGTT CTCAATAAGG
109081 TCCGATGTTC GTGTATAAAT GCTCGTGGCT TGCTTTCTTT TCGCGTACCT GGTTTTTGTT
109141 GTCAGCTGGT TAGACATGTC TGGTCGCGGC AAAGGCGGTA AAGGTTTGGG TAAGGGAGGT
109201 GCTAAGCGTC ACCGAAAAGT GCTGCGGGAT AACATCCAAG GCATCACCAA ACCGGCCATT
109261 CGGCGCCTTG CTAGGCGTGG TGGGGTTAAG CGAATTTCCG GTTTGATTTA TGAGGAGACT
109321 CGTGGCGTTC TCAAGGTGTT TCTGGAGAAC GTGATCCGGG ACGCCGTGAC CTACACGGAG
109381 CACGCCAAGC GCAAGACTGT CACTGCCATG GATGTGGTTT ACGCGCTCAA GCGTCAAGGA
109441 CGCACTCTGT ACGGCTTCGG CGGTTAATCT TTTCGTCAGT TTTCTTCCAA TGGCCCTTTT
109501 TAGGGCCGCC CACTCCCTCT CAGAAAGAGC TGTGATTGTA TTCTTTCGGA TGGTAACATC
109561 TCAATGGCTT TACTCGGCTA TTCTGCCTAG TATGTAGAAC TATTATAAAC CAGTTGGGAG
109621 AGACCAGGTT GTTTGGTCTG AGTGGCTGCT AAAGCAGAAA TCAGCTAAGT AAACGAGGTC
109681 TCCGAGATAA GTGAGCTATA AACTTCAATG CTATAGTTTT GACATGTCAA GCAACTTAAC
109741 GTGCAGCGCG AGTCCGATAA ATGAGTAGCT CAGCTTTTTA GTTTTAAAAA CGAGTTGTGC
109801 GTTATTTGTA CGAGAGCCTA AGATGCTAGC TGCCTGGAAC TGAGTAGGTG GATTAAAATG
109861 GGTGTCAGGT CTGTTTTCCC AGGCGTATCT GACTTAACGT CAGCAAAGC TGTACTTTTA
109921 GCTTCCCTGG TAACACCTGC CGTCCTTAAC CGCCCCTGC CGGTAGCGCC AGAAGCCTTT
109981 ACTTCCATTT CTAGTTGAGC TTGGCGTCCT GCTGAGTGAC GTCACCTCCC CCTTCTGTGG
```

Figure 2 (Page 34 of 74)

```
110041 AGTAGGACTG GCGGTTAAAG CTGCTTTGCT ATTTTCAGTC CTCAGGCTGG AGGCTCCCCT
110101 AAGCAGGCTG CCTACGCAGT TCGTAAATTC CCACTTAGTA GACTAAGGGA GTCTGTTTTA
110161 TAAATAAGGA CTCAAATTTC TTCTGACTCC GAGGTCCGTG GCAGCAGCTA TAAGATGGAA
110221 GCCCCCTCTG ATGTAAGATT CTCAGATGAC TTGCATCTTC ACTGTACCTG TCAACCCAAT
110281 AGTCTTCTAT TCCTGCCTTA AATTGTAAAT TCCAAAACTG ATTTAATTGT GAAAGTTTCA
110341 AACTGTACGA CCTAGGAAGT GTCAAAGTTA GGTGACCAGA TTTTTAGAAG TCAGCCAAAT
110401 ATTCAGCATC TTTGATTTAG TAACAAATAT ATTGATGGCT ACTTCAGCAA AAAAAATCAA
110461 CTTTGTTTTC TGGTTACTTT GCTAACAAGC TTCTCCTGAC AGGAGGATAT AGTGAATAGG
110521 CAGTTGAATA AGTGAGTTCG GGTGAGAGGT CTGAGCTGGA GATAAAAATG TGTGAGTCAT
110581 CAGCAGATAA ATAAATGCTG AGACCAGATG AGATGGCTAA AAACTGAAAC ATAATGTAGT
110641 GCAGCATTGT TTGTAATAGT AAATGAGTGG CAACTGTAAA GTTTTCATCA GAAAGGACTA
110701 GAGTGATCTA TACATCCATA AAATAGAGTA TTTCTCTACA CAGCCCTACT AAAGAATGAG
110761 AAAGCTGTAC TCCACTACAT ACTCTGGTGT ACTCTGGCTC AGTTCTTGGA CTCCTCTTTT
110821 CTTGGCTAAC TCAACTGGCC TCACCACTTA CATGCTCTGT GCTCTGTCAA ATAGTTTGTT
110881 CAACAGAACA CCACGGCCTA GCTGTAAGTG CCACGTTAAC TTCTAGCAAT GCCAAAGCCT
110941 GTGATAGTGG CAGCTTCGGG CTGTTTCTCA TTCCCGGGAT GCCTAACCAC CTCTCCAAAT
111001 TCTATCAGTT TGCTTCCACC CACTTCAAGC TTCAGAACGA AACATAGAGC TTAAGAAATA
111061 TAGGCCCGGC AAGGTGGCTC ACGCCTGTAA TCCCGGCACT TTGGAAAGCT GAGCCTGGTG
111121 GATCACCTGG GGTCAGGGGT TCGAGACCAG CCTGGCCAAT ATTGTGAAAC CCCGTCTCTA
111181 CTAAAAAAAA AAAAAAATTA GCTGGGCATG GTTGCGGGCG ACTGTAATCC AAGCTACTCG
111241 GGAGGGTGAG ACAGGAGAAT AGCTTGAACT CGGGAGGCAG AAGTTGCAGT GAGTTGAGAT
111301 CGCGCTATTA CACTTAGGCC TGGGAGACAA GAGTGAAACT GTGTCTCTAA ATAAGTGTTT
111361 GCAATTATAA ACCATCTCCC TGACCTTAAA TCTCTAGACT CATATACAAC TGCATATTTG
111421 ATGTATCTAA TTGAATAATG GGCATCTCGA ACTTGTCCAA AATATGTTTA TACGTAAACA
111481 CCAAGTCTGT TCTTCCTCTG ATATTTGTCA TGTCAATCAA TAGAACTCCA TTCTTCAAGC
111541 AGCTTGGGCC AGGAATTGTG CAATATTGTT TGTCCTGAGC TTCTTACAAC TTTCACCCAA
111601 TGCAGTCAGC TCTGTTGAAA ATCAATCAGA ATACCTTTCA TTGTTTTCTT TGCTGCTTCT
111661 CTAGGAGCAA GCTGCCATGG CGGTTTGTCT GAATGACCAC AGTGACCCCA AACTGGTCTT
111721 TGTTTTCACT TTTAATCCCC CTGTCATACA GTTTTTCTCT ATCCAGCATC AACAGTGATC
111781 CTTTTTGAAG GTATTATGTC CACTGTCTGC TGAAAAGATT CCACTGGCTT TCCATCACCT
111841 TCATAATAAA AACCAGCATC CTTATCATAG CCTACAAGTA AGATGACCAA CCATTACAGT
111901 TTGCCTGACT CTCAGGGGTT TCTCAGGGTG TAAGACTTAC AGTGCTGAAA CTTAGAAAGT
111961 TCCAAGCAAA CTAGGATGAG CTGCTCAACC TACTAGATCT GTACTCTGGC TACCCTCTGA
112021 CCTCATTCTC TTCGCAGTTC TTTCTCTTCA CTGACCTTGC TGTTTCTGGA ATGGACCAAG
112081 CATTTCCAGC ATCAGCACCT TTATATCTAT TCTTTCTCCC TAGAAGGGTC TTGTCCTGGA
112141 TATCTGAATG GCTCTAGATC TCATTTCATT CAAGCCTCTC CTCAAATACC AACCTTAAGA
112201 AAGAGACCTC CCATAATCAT CCCTTGTAAA ATAAGCTTTT CTGCTCATTT AGCATATATA
112261 TATATAGTTG ACTATCCTCA ATAGCATATA TATATAACAT TTCCCCACCT AGAATTATAT
112321 ATGTAATAAT ATATTTAACA AAAAATACAT ATAACTAGAT ATATTTATT TTGTGTTTGT
112381 TCTCTCTCCC CCAACTGGAA TATATTTTTT GAAGGTAGGG ACTTTGTTTT GTCCCAGAAG
112441 TATCCCTAGC ACCTTGAACA GGGCTGACGT TTAACAGGTA GTTTATGGAG GTTTGTTGAA
112501 TGAAAGGATG TGTGAATTTT CTATGTAAGT CTCCAGGCTC TCCACTAAGC CCACCAGAAT
112561 GCTAACACAA TCAATTCCCC ATCTCATTCC TTGACCTGCC ACTGCCTGAA GCAATCAGCG
112621 TGCAGTTTCT CTTTAGAAAA TCTGGGGGAT AGTCTAGGGG TTGCAAATTA AGCAACATTA
112681 TCTTTGTTCT GAACAAGGAC TGCATGAGTG TTAGGACTGA AGAAGGCCCA AGGTGGTGGT
112741 GGGTATGCCT AAGATGAGTA TGACATATCA GCAATGCTAT GAACATAGCA ATGCTATGAA
112801 AGGCCAGGCA AAACGTAACA GGAGCTAGTC GTGGCTTATT GTTACAACGA CTATACCTCC
112861 CATATGGGTA ATCGATATCC ACACACCCCT CTACATTGAC TCTGGAATTC AGGAAAGGGA
112921 ATTAAAATTT TCTAACTTAT GTACCCCAAT GATTTCAACA ATATCTGGCA TATGAGATCA
112981 ATAAATATCT TTAAAATACC AACTAAGAAA GACATAAAAT GACCCACCCT CCATACCAGG
113041 CTCATTTTTG CTCCTCTGAT TCCTGAAACT ATCCAGAATG CAGCTATGAA TTCTCTCCAT
113101 TGTCAGTTTT AAATTAAGCC AAGCTGGGTA CTTGTGTAAT TCCTCAAGAA ATCCTGGATG
113161 AAACTGTCA GGTGGAAAAC AGGACCTCAA AATAAAGAGA CATCCATCAC TGAAGCTAAC
113221 ATCGTGAGGC TGAAATCAGT CCTATAACAA TGGTACCAAA AAGAGCACAA TGAGAGGCAT
```

Figure 2 (Page 35 of 74)

```
113281 TTGTGAATAT TTACTCAGAT GAGAGTAAGA TATTTCCCTA TCAGCTAACC TGAAGTTCAC
113341 ATCCCTTTTC CAGCTGAGTT CTGAAGCTAG ATGTACTTAA CTGGAACACA TAACTGCATC
113401 AGGAACATCC TTTAAAACTA TGGCTACAAT GGCTTGACTG GACAAACCCC AGGCTTCCAG
113461 GTTTAGCACA GGTGGCCCTT CACAGACCAA CATTGCCTAT GCTACCAACC TCATGTCCTA
113521 CCACCCTGCT TGCATCATTT CTCTCTCTGC ATATATAAAA ATATATGTGT ATGTATATAA
113581 TCAGCTTTAT TGATATTTAA TATACCACAA AATTTGCCCA CTTTAGGTAC AGTTCAATGA
113641 ATTTTACCGT GTTTTCTTAG TTGTACAACC ATCATCACAA TTTAATTTCG GAATATTTCT
113701 ATCACCCAAA TTTCCATTTC TGCGTAAAGG GGGAAAAAAA AAGGTTAACT GCTGAAGGCC
113761 GCGGTAACAC TGAAAAAGGT GCCTTTTCTC TCTAAAACAG ATTTTAATCT CCCCTGAATT
113821 TAGTGTCCTG GGTATTCCAG GAGTCTGAAT AGGGTTTCAA TTTTCAGGGT CTTTTTAATA
113881 GAGTAAAACT GTATTGGTGG CGATAAATTT AGTATTGCTC TCAGTACATG ATTGAGGGAT
113941 ACTTAAATGT CTCTGTGATT TTATTTCATA ATCGCTAAAA GATGGTTTTT TTTTTTCCTA
114001 AAACAGGGTT TTTGTTTTTT CTCAATAAGC TTCTTAGCTT CCCCTCCGGC TCCCTGGCTT
114061 GCCTCAGGAA ATATTAGCTC ATCAGTTCTG ATTGGTTGAC AGCTACGAAT GGCCCTCATT
114121 GATTGGGCAG CGCTTCTTTG TCCCTTGGAA ACTAATACAA ATTTTTAACA CTACTTTTTT
114181 TCCACTCTTT CTTCAGAGTT GGAATATCGT TGCTCCCCTA CCCATATGTA GTGAGTGGAG
114241 GGCAAACTTG GAGTTCCCCT AATCTTTCCT TTTTAGGATG TCAGCTCAGT ATCATTCATC
114301 TTAATTACAC ATTGAGCTTC TTGACTTAAT GGATACAGCT CTTCTTTTGT TTAGTTGGGC
114361 GGCCCTGAAA AGGGCCTTTG GTTCAGAAAT GCAAGCTGTG GAGAAATCAG CAACCTTAAC
114421 CGCCAAAGCC ATAAAGGGTG CGTCCCTGGC GCTTAAGCGC GTAGACCACG TCCATGGCAG
114481 TGACTGTCTT GCGCTTGGCG TGCTCCGTAT AGGTGACAGC GTCACGGATC ACGTTCTCCA
114541 AAAACACCTT GAGCACCCCG CGAGTCTCCT CGTAGATCAG ACCAGAGATC CGCTTCACAC
114601 CGCCACGCCG GGCCAGACGC CGGATGGCCG GCTTGGTGAT GCCCTGGATG TTGTCACGCA
114661 ACACCTTGCG GTGGCGCTTG GCACCCCCCT TACCCAAACC CTTCCCGCCC TTACCACGTC
114721 CAGACATGAC TTCCCAAGAA GTGAACCAAG AGCAAGTGAG AGAATAGGAA ACCGATCTTT
114781 ATATATCTAC GTTACCCCTG CCCCCACCTC CAGCGGACAC AGAGACTGAA AAGCGCGCAG
114841 GCGGGAAATG TGACGCCTAC AGTCCGCTCC TTTAACCCCT CCTCCAAGCC CCAGGAAATG
114901 GCGGGAGCAG CGATTGGGGG AGGGTGGGGA GATGAGGGTG GGACCAAGCA GGCTTGACCA
114961 ATGGCCTTTA TTTTCTTAAC AGAGCTACAG GCTTTGAGGA ACTGGGTTAA GAATTAAATG
115021 TAAACCCATT CTGACTCCAG AATTATTTTA AGTCGAACTT TTTTTTTAAC CGAATCTCTC
115081 TGTCGCCCAG ACTGGAGTAC ATTAGAGCCA TCTCGATTCA CTGAAACCTC TGCCTCTCAG
115141 GTTCAAGTGT TTCTCCTGCC TCAGCCTTCA GAGTGTACCT GGGATTACAA GCGCTCGCCG
115201 TCGCGCCCGG CGTGTTTTTG TATTTTTCGT AGAGACGGGA TTCGGCCATG TTGGCCAGGC
115261 TGATCCCGAA CTCCTGATTT CTGGTAATCC GCCCGCCTCA GCCTCTTAAA GTGCTTGAAT
115321 TACAGGCGTG AGTCACCGCG ACCGGCCGAA ATCGATTGGT TTTGAAGCCT TCAGTAGCAT
115381 TAAAACGAAA AGTGCTCCCA ATGCATTCCC TTTTGTCTTA AATTGGTTTC TTACAGCTAC
115441 TTTACTTGAA AAGGTGGTGG CTCTGAAAAG AGCCTTTGCT TGGACCGTCA GAGAGACCAC
115501 AGTAATCACG CCCTCTCTCC GCGGATGCGG CGGGCGAGCT GGATGTCCTT GGGCATGATA
115561 GTGACGCGCT TGGCGTGGAT GGCGCACAGG TTAGTGTCCT CAAATAGCCC TACCAAGTAG
115621 GCCTCGCACG CCTCCTGCAG AGCCATCACA GCGGAGCTCT GGAAACGCAG GTCTGTTTTA
115681 AAGTCCTGCG CAATCTCGCG CACCAGGCGC TGGAAAGGTA GTTTACGAAT AAGCAGTTCA
115741 GTGGACTTCT GATAACGGCG GATCTCGCGC AGAGCCACGG TGCCCGGCCG GTAGCGGTGG
115801 GGCTTTTTCA CGCCGCCGGT GGCCGGAGCG CTTTTGCGGG CTGCCTTAGT GGCCAACTGT
115861 TTGCGTGGCG CCTTGCCACC AGTAGACTTC CGAGCAGTTT GCTTAGTGCG AGCCATGACG
115921 GAAAAACAGC ACAGCGGAAC ACCCAACACT AGCGCAAATA CGCCCATGAG CTGCTCTATT
115981 TATAGTGTGT AAAGTGCAGT GATTGGATGA TAGAAGACGC TAAATATGAC GTTACACACT
116041 CTGATTGGTC TATCTTTAAG CCAGCAACAA TCGTGCAGTT TCACCGGCTA CTATATTCTA
116101 TTCCAACTCT ACAGATGATT ATTTAAGTGG TATTTTATTA CTACTATTAT TTTATTTTAC
116161 TTTTGCTTTG TTCCCAAGC TGGTCTTAAA CTTGGGCTCA AAAGATCTTC CCGCCTCAGC
116221 ATCCAGAGTA GCTGGGATTA CAGGGGAGCC CCACTGCGCC GGCTTGGACT TTAATTTTTT
116281 AAACTTGTCC TCTTCTACAT CTGGTTTTCA TAACCTGAAG GCTGTGTTTA TTTTCCATAA
116341 AACAAGGCAT TGATTCCAAA GGTATTATAA TTCCCCAATT CCGTATAACC TTCAGCTCTT
116401 TAGGAAAAAA AAAAAAAAAA AAAAAGAGG GAATACTGCT CACCTCCTCT CCGGAAATGT
116461 ACCCTTTACG GGAATTTCTG AAACCTTTCA CAAGAATTGG ATTCCTTTGT AATGCTTTAA
```

Figure 2 (Page 36 of 74)

```
116521 TTGACTTAGG AGTGTTATTG AAATCTACAA AGCATCTCAA ACATAGTAGG ATTACACTAT
116581 TACTCAGAAA CATTTTCTAT GAGACGTCTT TCTCTTGATT ATGCTCTTTG AATCCTAAAC
116641 TTGCAGCGTT CTGCAGCTTT TGTTTTCTAA AGCCTAGGTG TACTCTGCCA GTCACAAAAT
116701 GGCGTTCTC CAGCACTGCC GCCAGGTACC ACCAGCTGGG AGTTGTTCCT CTTGCGGAGC
116761 AGGAGGTGGA CTTGGCCCAA GAGAAACTGG ATAGTGGTTC GCAAGGAACA TAATTTAGCA
116821 TTGCCAAGAG CTAATGCAAT CATTTTGAAA ATCTCAAAAC ACTGAAAAGT GGATTGTGAC
116881 CTTTTTAAAT TCACAAGAGA CAGGCCACAT TCTATCTTTT GATTGGTTTA GGCTATTTTC
116941 TTGAACAGCC ATTTAGAAAG CAGATCTATC ATCCTTCATT TGCATGGAGC GTTCCCATTT
117001 TATTTGAAAC CAGTTTAACC CAATAGAAAA AAGGGAGGCA GAACCCATTA TTTAAAGTGG
117061 AAACTCCTGA ATCAGATAAT TAGGAGTATT TCCTTTTCAA AAGTTGCGTT TTTTCAGATA
117121 CCTCGCTTAT TACACTAAGA AAGGTTTATA TCTTTCACAA AGGGTTTACT TACAAAAATC
117181 TTCCAATTTT GTATACCTGT GTTTCATAAC TGACTAGCCG TCAAACCAAG ATGTAGAGTT
117241 TCCAACCGTT ATTTTCCAAA TTTTTAGAAA TTACGTGAAA TATTTGAATG CATGCCTTCT
117301 CAATAAAATG GGACGTAGGA AGCACTGGTG CAGAAGATGG GTACAATACT TATCTGGGAC
117361 CACTCCATTA TTTGGTTGGC ACGTTGTTTG AAGAAAAAGG GGAAAAGCTC AGGTTACTTA
117421 GCATGGTTCG GACTTATTTG AAAACTACCA CAGCAGGAGC GGAAATAAGA CCGCATTACC
117481 TCACTCTCTG CTGTGCTGTG CTAGGGGGTT ATCCAGAATA GGATTGTAGA AGTGGATGTC
117541 GATTTAATAG TTTTTTATTC TCCCATTAGC TGAGTCTCTG ATTGGCAATG TGAGATCGTT
117601 TTAGCTTATT GATACTTTGA AATGCACTTA ACAGCCACAA ACAAGTTAAA GGGTTGTTAC
117661 CATAAAATCT TATCCCCAGG GTGTGCTTGC ATTTATCACC CGTGTTTGCT TTCACACTAA
117721 GTGGACTTAA CTCCCCAGCA GAATGCCTGT CAGGGAACCG GTTTCGTGGA CCCAGCATTT
117781 AACGCCTTTC GCAGGCTTGT GAGGCCCATA AATATTTGTT GAATAAAAGA ATGAGTTGAC
117841 CATGTCATGG TGCGCTGATT GCGTGTGCTG ACATGGAACA CAGGTTGTAA ACCTTAATAC
117901 CAATTTGGGG CATGTTGTAT GGATGAAAAG GGCATTGGAA ATTCCTGAAG TGCATCCCAC
117961 ATTGGACTGT GGAAATAAGT TGCAAGTGCA GAAACGTTTC CACACTTGCA GTTTGAGTAT
118021 TAATTGCAGC GTTTGTGAAT TCTGGTGTTG TCTACGATTC ATTCTTGTTT GACGTGAAAG
118081 GTATTCGCGA GACACATCGC TCTAAAACAT TGCCAGAAAA TGTAATAGAG TTGATGACAA
118141 CTGGCCCTAA CACGGCCTAA AACTCGCACT TTTCTCTCCC TCCGCAACTA TTCAAAACAC
118201 TGTATTTTAC ATTTCTTGCA AATTAAAAAC TAACATCTCT GGCAACGGAC CTCTAAAAAT
118261 TTCTAATAAA ACTCCTCGGA TGCTTGTGGC ACTGCATTTG TAAACCGCCC CCTCTCAACC
118321 TACTCCCTAA AAAAGAGCTG CTTTTTGAGA GAGAAGCGGT ACCCTCTGAT GTTACTGGGC
118381 GGCAGTCTGC CTACAATTTC CTTCACAATG AGGCAACCAG AGCGGCTTTT TCTGTGTGTT
118441 TGCTTGCGTT GAGGGGAGCA GGACCATAGG CCCTAGAGGC CCCCAGCTGC CTTCTGAGAC
118501 TGGGCGAAAC CCTCGGCAGC GCGCAGGGGG CGCTAGGGCG CGAGGGGCGG GCACTGACGG
118561 GCACCAATCA CGGCGCAGTC CCACCCTATA AATAGGCTGC GTTGGGGCCT TTTTTTCGCA
118621 TCCTGCTTCG TCAGGTTTAT ACCACTTTAT TTGGTGTGCT GTGTTAGTCA CCATGTCTGA
118681 AACAGTGCCT CCCGCCCCCG CCGCTTCTGC TGCTCCTGAG AAACCTTTAG CTGGCAAGAA
118741 GGCAAAGAAA CCTGCTAAGG CTGCAGCAGC CTCCAAGAAA AAACCCGCTG GCCCTTCCGT
118801 GTCAGAGCTG ATCGTGCAGG CTGCTTCCTC CTCTAAGGAG CGTGGTGGTG TGTCGTTGGC
118861 AGCTCTTAAA AAGGCGCTGG CGGCCGCAGG CTACGACGTG GAGAAGAACA ACAGCCGCAT
118921 TAAGCTGGGC ATTAAGAGCC TGGTAAGCAA GGGAACGTTG GTGCAGACAA AGGGTACCGG
118981 AGCCTCGGGT TCCTTCAAGC TCAACAAGAA GGCGTCCTCC GTGGAAACCA AGCCCGGCGC
119041 CTCAAAGGTG GCTACAAAAA CTAAGGCAAC GGGTGCATCT AAAAAGCTCA AAAAGGCCAC
119101 GGGGGCTAGC AAAAAGAGCG TCAAGACTCC GAAAAAGGCT AAAAAGCCTG CGGCAACAAG
119161 GAAATCCTCC AAGAATCCAA AAAAACCCAA AACTGTAAAG CCCAAGAAAG TAGCTAAAAG
119221 CCCTGCTAAA GCTAAGGCTG TAAAACCCAA GGCGGCCAAG GCTAGGGTGA CGAAGCCAAA
119281 GACTGCCAAA CCCAAGAAAG CGGCACCCAA GAAAAGTAA ATTCAGTTAG AAGTTTCTTC
119341 TAGTAACCCA ACGGCTCTTT TAAGAGCCAC CTACGCATTT CAGGAAAAGA GCTGTAGTAC
119401 ACAGATGAAA TCCCCCAAGC AAATGCAACA CGCCCTCAAT TATATTAGAA TCACTTGGAG
119461 AGTCGATAGA ACTTTAACAT AGCCTCATCT AGTAAGAATT TACTACTCAA TCTATCAAAG
119521 ATAGCAAGGT GAATTCAAAT GCACCGAGTT AAAATCGAGT TTTAAAGTCA CCTGGGTTTC
119581 GGTAGCCGGA AGTCCCGCGT CTCACGACTC CAAGCTAATT AGTCATAACC GTATTGAACC
119641 AAGGTTGAAG CCCAGTCCCA GGCTTGAGGC TTTTTATTAT ACAAGGTTAA AGTGGGGATA
119701 TTGCGTTTTG GGGTCAATAT TGCTAAAGTA GCATTTTCCG AAATTGGGTG GTCCTAAGAA
```

```
119761 ATGCTTCTGG GATAGTTGGC AAAATATATG GCTTAACCAC GCCCTCTCCA CAGGAGTGGC
119821 TAGCGAGCTG TCTGTCCTTG GGAAGGACGG TGACCCTGCT GGCGTGGCTG GCGCCCACGT
119881 TGGCGTCCTC TGAAAGCCCC GCCAGGTAGG CCTAGCTCGC TTGCTTTCTG CAGCGCCATC
119941 ATGACAAAGC TTTGAAACGC AAAATGCTTT CTTTGTGCAG CGCCTTACCA TGGGTGCACT
120001 TACGGGCTGT CGACTTGGTT TAGGCCCTTG TCAGGACAAA GGAGCTTAGT TTGTTGGAGT
120061 TTTAGAGCTG CAACCCAAAA TCCCTTGCTC GGTTTCTCTG TTTTTAGAAA CGGAAGCGCC
120121 CTGATTGGAT ATTTGAAAAT TACTGTGCTT AACTGGATCG TGTTTCATCA ATCGTGCAGG
120181 ATTTTCAACC CTGGTGGAGC CCACACATTC AAAACTGAAG ATCCTTTTCT CAGAACTGCC
120241 CCTTTAAGCT TTTGCAATTT TAATTCTGGG GGTCAGATTT TAATAATTGG ACTTTTTGT
120301 TTACATCTGA CAAGAGTATA TGATGAGCCA AGTTTACTCA CTTTTACTTA GTGCAGTTCA
120361 ATTCTAAAAG TTTATTTTTG CGTGTGTGCA TATGAGTTAA TAATCAGTTG TATTTTTCAA
120421 ACGGTCTTTT TTCAATTGTT TTGCTTAGCT CCTTCCATCG TCTAAAGTCA GGGATACAGG
120481 CACATCACAT CCCTGTTCCC CCTTCCTCAA ACTAATATGT AGCTACCTAG GTTATCCTT
120541 TAAAACAAAA ATTCTCACCT ATTTTGTGA GAAATATACA TGTTTTTCTT TGAACTAAGT
120601 ATTTTACATA CACCTATCTA TATACATGCA TACTTGTGGT TTTGTTTTTT TAAAAAAAAA
120661 AAAAAAAAAA CACGTTATCT TTTGAGACTG GTCTCAGTC TGTTGCCCAG ACTGGACTGC
120721 AGTGGCATAA TCACAGCACA CTGTAACCTC CAACTCCTGG GCTCAGGCTA TCCTGCAGCC
120781 TCAGCATCCG GAGTAGCTGG GATTGCATGC ACGCACCACC AAGCCGGGCT TTTTGTTTTT
120841 ATTTTTTGTG GAGACAGTCA CACCATGTTG TCCAAGCTGG TCTAGAAATG GCCTCAAGTG
120901 ATCATCGACC TCCCAAAGTG TTGGGATTAC GGTCACTGTG CCTGGCCTTG TATGCATAAT
120961 TGTTTTGTCT TTTGATTAGG GTTATTAATT TAAAAAACAA AGCCTGGACG CAGTGGCTCA
121021 CATCTGTAAT CCCAGCACTT TAGGAAGCCG GATGGGCAGA TTACTTGAGC TCAGGAGTTC
121081 AAGACCAGCC TGGGCAACAT GGTGAAATCC CATCTTGACA AAAATACAA AAAATTAGCA
121141 AGGCCCAGTG GCACGCACTT ATAGTCCCAG CTACTTGGGA GGCTGGGGTG GGAAGATGAC
121201 TGGAACCTGG GAGGTAGAGG CTGCAGTGAG CAGAGATCGT GCCACTGCAC TCAAGCCTAG
121261 GTGACAGAAT GAGACCCAGT CTCAAAACAA AAATAATAAA AATTTTTTAC AACGATGTTA
121321 TATACACTTC TGCATGTTGC TTTTCTCTTA ACCAAACTTT TCTAAAACCC TGTCATGAAA
121381 AAAGAAATCC TTCACATGGA ATAGCATAAG TTATTCATCC ATTTCTTATT GATAAGCATT
121441 GATGTTTCCA GTTACCACTG CTGAACATGG TGCAATTGAA TAGAATTCCA GGGCTGAGAT
121501 TGCTAGGTTT TAGGTTGTAT TTTATTATTT TATTTATTTA TTTATTTATT TAGACAGAGT
121561 CTTACTCTGT CACCCATGGT GGAGTACAGT GCCATGACCT CAGTTGCAAC CTTTGCCTCC
121621 TGAGTTCAAG CGATTCTCAT GCCTCCGGTC TCCCGAGTAG CTGGGATTAC AGGCACCTGC
121681 CACCAGGCCT GGCTAATTTT TGTATTTTTA GGAGAGATGG GGTTTCACCA TGTTGGCCAG
121741 ACTGGTCTCA AACTCCTGGC CTCAAGTGAT CTGGCCACCT CGGCCTCCCG AAGTGCTGGG
121801 ATTACAGGTG TGAGCCATGG CTCCAGACCT GGACTTTGTC TTCTGTTTCA TCAGTCCTTC
121861 TGTTGGTTCA AGCACAGTAT CACACTGAAG ACTGATGATT CTATATAAAT ATGGTAAAGA
121921 CTGTACACCC TAACTGTTCT TATTTTTTAA TTTTAAGGCA ATTTTAGATT CCAGCTTTCC
121981 AAAGAATTGT GGAATGCTTA GAGCTAGAGA AGCCTTGGAA GTCATTTAGT TTTTGTTTTG
122041 TCAGAGAAAA TTCTGTAGAG ACTCTGTCCT GCTCTCACTG AATACCATCC CATAGTACCC
122101 CCCAACAGCT TTAAAGGGCA ATAATACCTT ATGGACAGTA TGCTTTTCCT CAAATATATT
122161 CTAAGCCATG GTCAATGCAA AAGAGTGAGA AGGAAAGTAG AATAAGTTAT CTAAGAATCA
122221 GTGGGTGCTC TCTTTAAACT GATTTATCAC TCCCCCTTCC AAACTCTCTT GAAGGTCACT
122281 CTGCCTCCCT TTCTACATAA GAACTCCTAA CTCCAAGGGA GGAAGGTAAG TTATTCTTAT
122341 TCCTTGCTTA GAAAAAGAGA AAATAGGTTT GGTAAGCATC CGCTTTCTGC TACCATTCTC
122401 TGTGTTTCTG TGTTTTTTAT AGGATCATTC AATTATTGGT TGGCTCTTGA GAGGGAATGC
122461 AAGGTTCAAG GACACAAGCC TAGATCTTGC CTGTATAGAA CCTCATGATG TTATGCTTCT
122521 CTAAAATGAG GCCTGGAGGA GACATGTTGA AAGTGACCCA TAAATCTGCA GTATCTCATG
122581 TCTCTCAATG GGGACAAGGA GTACCATGGG AAATAGCATT AGGTCAATGA CAGTAACAAC
122641 TCCCAGGTGA GTTGATTTAT TCTTTATTTT ATAAAGTTGT AATATGCTA CATAGTCCCT
122701 AATTTTGCCA CAAATAGTCA TTATTTTAAT TTCATATTTC ACTATTGATA AATGAAGGAA
122761 AAAATGAGTA GCAGTTAAGC AGTCCATAAA CCTACATATA AAGCAAATTG GAGATTTTAA
122821 AATTGATTCT GGATGCTTAA AATCCTTCTC ATTGAAAAAA AATTTCGTAT TAGAAGATTT
122881 CAACATTCTT TAAACTGAGA AGCATAACAT ATAAACAGAA AACCACAGCA AAACAAAAAT
122941 GCAAAGCTCA ATAAATGAAC ACAAAGTGAA CACCATAATA ATTGCCACAC AAGTAAAAAA
```

Figure 2 (Page 38 of 74)

```
123001 ACAGAAAATC AGCCAACCCT CCCAGAGCTG CCTGATGCTT GCTTCCAGTC ACATTATCAC
123061 TCCATCTGCC CTAAACATAA CCCCTATTTT GATTTCCAAT GCTGTAATTT AGTATGCCTG
123121 TTTTTGAAAC ATATAAAATG GAAATAAAAC AAATGTAATC CTATGTACCT GACATATTTC
123181 ACTCCAGAAC ATTAGGTTTG AATAGATTCA TCTGTGTTGC TGTGTATAAC TTTAATTCAT
123241 TTTTATTGTT ATGTAATATT CCATGTTATG AGTGCAACAA TTTAGGTGTC TACTGTTGAT
123301 GCATATTTGC TTCCCTTTTT CAGCTAATAT AAACAATACC GTGAATATTC CTGTGTATGT
123361 GTCTTGGTAT ATATAGGAAT ACATATTTTG TTTGTATACC TAGGAGAGGA ATTGTTGGGT
123421 CAAATGCTAA ACTCTTTTTG AAAGTGGTGA TATTAGGTTT ACATGCGATG AAATGAAAAT
123481 TAAAACCACA GTTATAAACA GCATGGATGA ACCTCACAAA CCTAATGTTG ATGGAATCTA
123541 GCTGGGAATT CCTGTTCTTC CATATACTTC CCAATATTTT TTTCCAATTA AAATTGTTAA
123601 TCTTTTGAAG ATGTTATCCA TTGTGGCAGA TGTGCAGTAT TATCTCATTA TGGTTTTATT
123661 TTACATCTTT TGCCCATTTT TTCTTAATTG GATTGTATAT CAGTCGACTT GGGCTGCCAT
123721 AACAAAAATA CTAGACTAGG TAGCTTGAAC AAAAGGAATT TATTACCTCA CAGTTCTAAA
123781 GGCCAGGCCA GAAATCCTAA ATTGAGGTGC CAAGAGATTC AGTTTCTAGT GAGGGCTCTC
123841 TTATTGACCT GAAGATAGTT GCTGTCTTAG ATTGTTGGT GCTGAACAGA ATACCAGAGA
123901 CCAAATAATT TATAAAGAAT ACAGATTTAT TTCTTACAAT TCTGGTGGCT ATAAAGCCTA
123961 TGGTCGAGGG GCCCACCTCT GGCAAGGGCC TTCTTACTGT TATGGCAGAT GTGAGATGTC
124021 ATCTCATATT CAAACCACAG CAGTCGCCTT TTGTGTCCTC ATGTGGCCTC TTCATATGCC
124081 CATAAAATGA CCTCATGTCT CTTCCTTTTC TTATAAGGAC ACCAGATCTA TCAGACTACT
124141 GGCCTACTCT TATGACCTCA TTTAACCTTA AATATCTCCA TAAAGTCCCA AAATCCCTAT
124201 CTCCAAATAT AGGCACATTG GGTGTTAGAG TTTCAACATC AATTTTGGGG GAACACAATT
124261 TAGGCCAAAA AGATTGTGTT TTTTCTTGTT GGTTTAAGAT AGCTGTCTTT TTGTCCTTTT
124321 TGTCCTTTCT TTTTTTTTGA GGTGGACTCT TGCTGTGTCA CCCGGGTTGG AGTGCAGTGG
124381 CGCTGTCTCA GCTCACTGCA ACCTCCACCT CCTGGGTTCA AGAAATTCTC CTCCTCCCAA
124441 GTAGCTGGGA CTACAGGTGC ATACCACCGC GCCCTGCTAA TTTTTGTATT TTTGATAGAG
124501 ACGGGGTTTC ACCATGTTGG CCAGGCTGGT CTCAAACTCC TGACCTCAGG TGATCCACCT
124561 GCCTCGGCCT CCCAAAATGC TGAGATTACA GGTGTGAGCC ACCAAACCTG GCCTGTCTTT
124621 TCTGTTTTAA GTTTTTAAAT TTTGCTCACG AACCCTTTAT CCATTTTATG TGTTGCAGGT
124681 ATTTCCTCTG TAACTTGTCT TCACTCTGTC AGAGGCTGGA GTGCAGTGGC ACAATCACAG
124741 CTCACTGCAG CCTCCACCTC CCAGGATCAA GCGATCCTCC CATCTTATCC TCCTTAGTAG
124801 GTGGGACTAC ATGTGCAGGC CACCATGCCC AGCTAATCTT TGTATTTTTT TGTAGAGATG
124861 GTGCTGTTGC CCAAGTTGGT CTCAAACTCC TGAGCTCAAG CAATCCATCA ACCTTGGCCT
124921 CCCAAAGTGT TGGGACTAGA GGTGTGAGCC ACCACTGCAC CAGCCAATG ATATCTCATG
124981 ATGCATTAAA GTCATTAATT TAGTGTACTC AAATTAAGCA CACTGCCCTT TTATGCACAA
125041 CCTTTTTTGT ATCTTATTTA AAAAATCATT TTCTATTTCA AGGTCATGAA GATCTTATTT
125101 TATAATACCT TCTTGTGAAA TTAGTTCTCA AGACTACCCT CACTTCTAAC ACCAATTATA
125161 AGTTGGGAGG TCTGTGGTTC CCAATCAACC TTAGGTTAGT AATTTGCTAA AAGGACTCAC
125221 AGAACTTGCT GAAGCTGTTA GCCTCATGGT TACAATTTAT TATAGGATAT ATAGCTTATT
125281 ATGTCATTCC AATGCAATGT AAAATTATAC AACTACTTTT AAAAAGATTT TAGCATTTGA
125341 CCCAACAATT TCACTCTGAG GTATACAAAC AGCAGATATG TGTGCACATA TATACCAAGA
125401 CACATACACA GCAAAATTCA TTGTTTGTAA TAGTTGAAAA GGGGAAACAA CTCAAGGAAT
125461 AAAGATTAAA ATCAGCTGAG AAAAGAAACA CACAAGGCAG TATTATGGAT CGAATTGTAT
125521 GCAGATCTCC CTTGCCCCCA GAAGATATGT TTAAAGTCCC AACTCCCAGT ACCTCAGAAT
125581 TGTGGCCTTA TTTGGAAATA GGATAGTTGC AGATATAATT AGTTAAGATG AGGTTATAGT
125641 ACAGTATGAT GGGCTGGTGA CTTAGAAGAA GTAGTATATA TATATTTTTT AATAGAACTA
125701 GTATTCTTCT AAGGTGGTCA CGTGAAGACA GACACACACA GGCAGAGACT GCGGTTATGC
125761 AGCTGCAGGT CAAGGAATGT CAAAGGTTGC CAGCAAGTAC GAGAAGCTAG GAAGAGTCAA
125821 GGAAGGATTT TCCTACAGGC TTCAGTGGAA GCATAGATCT AATGATACCT TCATGTCAGA
125881 TTTCTAGCTT CCAGAACTAC AAGAGAATAT ATTTGTTGTT TTAAGCCACC CTAGCTTCTA
125941 GCTCTTTGTT ACAGCAGCCC TAGGAAACTA ATATAGGCAC AATCCAGGCA AGTTCCAAAT
126001 ATGAGCTTCC AGTTGTCCTC TCCCAGTAAT ATGAACAGTA TTACTTTCCC AGCATTAATG
126061 TGTGACAATA CACATGACGT ACAGAGCAGT CCCCACTTAT GCACAAAACA TATGTTCCAG
126121 GACCTCCAGT GGATGTCTGA AACCATGGAT AGTACTGAAC TCTATATAGC TGTTTTTTCC
126181 TATACAGACA CAGCTATGAT AAGGCTTAAT TTATAAATTA GGCACAGTAA GAGATTAATA
```

Figure 2 (Page 39 of 74)

```
126241 ACAATAAATT AGAATAATTG TTAAGAATAT ACTGTATAAA AGTTAGGTGA ATGTTTATTT
126301 CTGAAATTTA CCGTTTATTA TTTTTGGACT GCAGTAGACC ACAGGAACTA AAACCATGTA
126361 GAAACCGTAT ACAAGAGAAC TGTATTTCAC CCGAGCCTCA GTGTGCAGTT TTAATGGCCT
126421 GCCATGGTTG ACTGCTCACA TGGCCGATCT TTTAGTCTAC CTCCACAGGT AGAGCTGATA
126481 CTGTGTGGCT CAAAGTTCCT ATTATAAATC ACATTGTTCA CTGTGTGGTG GTCAAAACCT
126541 CCAGGTAAAC AAAGACACAC TTATCAGTGA GAACATTTCA AGGGTCTAAA ATTCATCTCC
126601 CAGTAGCTGA GGGCAAAGGC TAGACCTCTT TTTGGGTAAG ATAAATTTTT TACCATATAC
126661 TTTATTTTGC TTTTCATGTT TAACTTTATT TTGCTTTTCA TGTTAGTTCC CCTGGAATTG
126721 TTTTTTGTGT ATAGTGTGAA GTAGGGGGTC AAGTTTCTTT TTTTTTCCTT TTTGTTCTTT
126781 TTCTGTTTAA AAGGCTATAC AATTGTCCCA TGCCATTTAT TTACAAGAGT CCTTTCACCA
126841 TTGTTGTATG GTGCCACTTT AGATGTAAAT CAATGTCCAT ATTTGTTTGA GCCTGTTCCA
126901 TTCGTTTGTC TATTTTTGGA CAACACTGCC CTGATTATTG TCATTTTATC AGTTTTGATA
126961 TTTAATAAAG CAACAGATTT GTTTATTTTG GGCCCTTGGA TTTGTGTATT AAATTTGAAC
127021 CCTGTTTGTC AATTTCTATA ATAAAGCTTA TTGGGAATCT GATTAGGATT ACAATGGTTT
127081 TGTAGATCAG TTTGGGGACA ATTAATACCT TTAAATATT GACCGCTTCA ACTGTAAATA
127141 TACTCCTCCA TTATTTAGTT TTCCTGTTTA ATTTATCTGA GTAATACATT ATAGTTTTCT
127201 TCGTAGAAGT CAGATACGTA GAAAATTCAA AGCCCAAGTG CAATAGCTCA TGTCTGTAAT
127261 ACCAGCACTT TGGGAGGCCG ATGTGGGTGG ATCACCTGAG GTCAGGAGTT TGAGACCAGA
127321 CTGGCCAACA TGGTGAAACC TCATCTCTAG TAAAAATACA AAAATTAGCT GGGTGTGGTG
127381 GCGGGCACCT GTAATCCCAG CTAATCAGGA GACTGAGGCA GGAGAATCGC TTGAACCCAG
127441 GAGGCAGAGG TTGCAGTGAG CCAAGTTCCT GTCACTGCAC CCCACCCTGG GCGACAGAGC
127501 GAGACTTCGT CTCAAAAAAA CAAAAAAAAG AACATTCAAA TAATCAATGT AGATAATTCA
127561 AATAACTAAA AAATGAACAG TTATTAAAAT ATCAGGATAT AAAAGCAAAA AAATCAATAA
127621 CCTCCATATA TACAAAATGG CCAGTTAGAG AAAAAAAAA GAATAGGCGA GACTTAAAAA
127681 GGCTGGGAAT CTCCCTGAAA ATCTTTGAGA GCCTTGGCCC TGCCCTCAGG GATTTCTCTG
127741 GCTTCATGCC CAGATATGGG TACAGTTCCT TGTTTAAAAA AATTTTGCTC CATCAATCAA
127801 CAAGGGGCTC CTTCCTCAGA GCACAAGGAC CTCCATAACA CCGGACACTA GATGTCTAAG
127861 GGACACCTCT TAAGGAAGTT AGACTTCCAA AGAATGGTGT TTCCTCTGTC CCCAAACTCT
127921 GGAACTCACA GCACAACTGC TCCTTGGAGT TCGGTTTCAA ATCTACAAGG CTGTCATGGA
127981 GGTTGCAGAC CAAGTCCGTG GCCTCAGTGT CCGGATGTAC GGTGGCCTTG GCACCTGAAT
128041 GTGAGAACAT GACCTCCCTG AAACCACCAC AAGTATTGTT TCATGTTATG TATGTTTTTT
128101 CTTATCTGAA ATTCCTTTTC TTTAAAAATT CAAATTACAT ATTTTTCAAG CCCCTGAACA
128161 AGCTTCATGA GCATTTATTG AACCCACAGC TTTTAAAACC TACTGAACAC TTTGCTCTAT
128221 GTTGTCATTC ACTATCCACC AATTATTTAT TTATTGATCA ATATTGTTTC CTTAGTGTTG
128281 GGATCATTTA TGCATGTATT TCTTTTATGT TGCATATTTT ATATTTCTGC ATTACAGTTA
128341 TTACATATTA CTTTTGCTAC AGTAATAGTT CAGAAGTGTA CATCCAAAAT TTAGCTGTGA
128401 AGTGGATGGA CTGAGGCAGA ACTGGAGGCA AGAAAATGTC ACAGTAATTC TAAAAAAGAT
128461 GATGTACAAT TAGAGCAAGA GAGTAGCACT GAAATTGAAG AAAAATAGAT GCGTTTGAGA
128521 GAAAATTAGG AGGTAGAATC AACAGATTAG ATGTAGGGAT GAGAAGGGTC AAAGATGACA
128581 CTAGGGTTTT TAACTGGAGC AAGTAGGTAG ACAGAACATT TCTTCCTGAA AGGGCAGGTC
128641 AGATCATGTG TTGTCTCAAA GGGCATGAAG AGTAGAAAGC CTGGGACAGA TCCTGAGATG
128701 ACCAATACCC ATGGTGCAGG GAGAGGGAGG GAGATCTGCT AAAAAGACTG CAAATGTCAG
128761 GATAGTAGAA AATCATGAGT GTGTGATGTC CTGGAAGTTG AGACAGTATC ACATTTGAGA
128821 ACATTTAAAT TGGTAACTCT GACAAAACCT GGAGGCCAAC TGTGAATGCC CATGAGAGTG
128881 AGAAGCTCCC ACACTTTTGT GGGCATCAGA AGCCCACCA GGTTCCTGCA GTGAAGATCT
128941 GAGAAGGATC CTCTTGTGGC TTTGGCAGGG AGAGAAGAAT TATTATGAAA TACACCCCAG
129001 AACCTTCTTC AAAACAAAGG CCTACTCTCA AGGGGAAAAC ATTTTGCCAG AGTCTTATCC
129061 CAGCTGGGAG AAGGTAATTC TTCCCACTGC AGCCTCATCT AGGCTTTCTG TCTCACTTAA
129121 GGGAAGAAAA TTAGTCAACA GGGATCAGAG CTTCATGAAA ATAAATTGGA AATGGTGCAG
129181 CCAGGAAAGG AGCAAAGGTC TGAGGAGGAG GAGAAGGAGG AAGAGGAGTT GTATCATTAT
129241 AAATACTTGA GGAAGAGGAG GAGAAGGAGG AGGAGGAGGA GTTGTATCAT TATAAACACT
129301 TGAGGAAGAG GAGGAGGAGA AGGAGGAGGA GGAGTTGTAT CATTATAAAC ACTTGAGGAA
129361 GAGGAGGAGG AGAAGGAGGA GGAGGAGGAG TTGTATCATT ATAAACACTT GTGACGGTCC
129421 CAGCCCCAAG ATATAGGCAT GCTAATAAAC TGAGGCTTAA CACTTTGACT ACAGAATGCT
```

Figure 2 (Page 40 of 74)

```
129481 GCTTCTCCCT AACACCATCA AGGCTCCAAC TGAATAACAA TGAATTATGA ATGAAAGAGC
129541 TGTAAGGAGA GACAAAAGTT AGAATGAGAC AAGTATTGTT ATCTAGAGAT GCCAAGAAGG
129601 CAAGGAAGAT AACTAAAAAG GCACTCTGGA TTTAGAAATA GGAAGTCATT AGTGACCTTG
129661 TAAATAATGG AGCCAGAGGA ATACCAAGGG CAGAAGCCTC ACTATAGTGT GTTGCACCTG
129721 TCAGAGGTCA GGAGGTGTAA CTGACTCTCC CACAGTGTGG CTTTGGAAGA GAGAAGTCAG
129781 CAGCTGCATG GAGATTTGGG AGAGGGAAAG CTTTTTTTTT TTTTTTTTAA TTGGAAAAGA
129841 CTGAGCTATG TGTAAATAGA ATAAGACAGG AAGAGTGTAG ACACAGGAAA GAGGGCAGAC
129901 AAAAACAAGT GCACAGTTAT CTAAGGGAAA CAATGGGATC AAGCTGCAAG TATATAAACT
129961 TGTCTTGATA GAAGAATCCT TGATCTGGTT TATTCAGTGT TTGGTCCAAA CCCACATCCC
130021 TGTTCTGCCT GTCTCTGACT TGCTCTGTGC CCCAGAAGCC CAGCTTCTAC AGATAGCATT
130081 AGCTGGGCAG CCCTGCCCTC TTGCAACAGC TGGATTTGGC CAGTGATCAG CCCAGCAGGA
130141 ATGTAGATGG CAAAGGAGAG AGAGGTTAGT GTACTTATTC CCTGCATCAC CCCCCTGCTT
130201 GGTGGGCAGC TCTTCCTCCA CAGTCCCAGC TCTGGCCTAG CTCTGGTTAC AGGTTCCCTC
130261 CCATTGCCTC TTCAGATTTA AAGGTGTGTC TGTCAGGGTA TAACTGGGAG CTAGAAATTG
130321 CACTGAAATT GAACAAAGAA TTTTATGGGA ATGGTTGTTA ACTAGTTATA AGAGGACTGA
130381 AAATGGAAAA GTGGAACAAA CGTATCAGAG ATAGTAATGA CAGAAAGCAA CTACCACCTC
130441 CAGGTTTAGG AGAACAAGGA AAAGATTCTT TGAAGAGATC CCCAGAACTG GGACCTCTGA
130501 GGAGTGTATG CTGGACCACT GATGATGATA TGTCTGTAGA TAGAGGCATG ATGAGGCTGA
130561 TTTTAGGAGC ATGGAAGATC TCCAAACTGA AGCCAACTGC TGTTACTGGA TTCAACTGCC
130621 ACTGCCAGGT TGAAGAACCC ATTCTGTGAG GATGTCAACA AACAAAGTGG GAAATCTTTT
130681 CACATCCTTC CAGCCCTCTA GTCTTCCTCC AGTGCTTTCT ATTGGTAGGG TTTGGGGAGG
130741 TGGCTAGCAA AGCGGTATTG GAAAAGATAG AAGAGACTAA ATCTTCATAA CCAGCACAGG
130801 GTGACACTGG ATCACTACTG TTGCTGATCT TGGGCTGCCT CATATCCCCT GTTCTTCCCA
130861 TTAGCCCTGT CACAACTTTG TAGATATCCC TTCATTATAT GCCCTTCATA TATTCTTTTG
130921 GTTTAACTTT TTCTGTTGGA ATCCTAATAT GGCACTCCTC CATTTTTCAG GACCAAAAGA
130981 GTATAAAAGA TTATCTTTTA CCAAAAAAAA GACAAAAAAC TGATCTAATT CCTGATTTGA
131041 TCATTACACA ATCTATACAT GTATCAAAAT ATCACATAGT ACCCCATAAA TATATACAAC
131101 TGTGTCCATT AAAAATAAAA ATTAAAGAAA AGATGGTAAA TATAGCTCTG TCAGGCAGTG
131161 GAGGTTTTAC CACGATGGCT GTTATTTCCC CCATGAAGGG GGGAGTGAGG GAGCAGCTGA
131221 AAGTAGGTGC TTATAGGGGT ATAGAGGGGC TCAAAGCTTT GAGAGAGGAG AATGTCTGAA
131281 AGAGCTGCCA AATAGCATGC AGGTCCCATG GGGGCAGAGC CTCTGCTCAT TCACCAGTGC
131341 CTCTTCAATA TCTACACTTA AGCCTAACAC AAAGTGTGTG CTTAATAAGT ATTTGCTGAG
131401 TATGTAAAGT GGAAACAGAA CCAATCTGGC AAACTTTGTA GGACTGGTGG GCAATGAAGA
131461 TCAGTCAGGT AAAATCTGTG GATATAAATT TATATTGATC AAAAAATTCA AGGTTAGGTG
131521 TTTTTCTTCA GTCATGCTCA ACGATGCTTC AGCCATGCTC AACTCTTCTG TAGCCACAGA
131581 AAAAAGTTTA CCCATAATCG AGCTGTGTCT GTGTCTGAAT AATGAAAAGA CCATGATGCA
131641 AGGGAGTTGG AGACACAGAA ACAGTGTTTG AAGTAATGGG TAATGGAAGC ATGCTACCAG
131701 GGAAAGGAAA GAAGTGGCAA TAGGAAGGAA CAGAGATCTG TGGTCCTATG TCCCCTGAGC
131761 ATATTCACAT GTTAAAGCTA ATTCAGTTTT CAATCATCAT TAAAATTTTG TTCCTAAATA
131821 TATGGCCATT ATTTTCCACA ACCACACTAA AACTTTATTA CCTCTGGCAA GTGACTATGC
131881 AAGTAACTAA GAGCAAAAAT ATCCACAACT ACCATTTGAG CTATCAATTT AGGGAAAGTC
131941 ATCTGGCTAT AATCTAAGTG ACCCTCCACT GAATGTCAGT ATCTTTGCAT ATGTGATTTA
132001 AATCTGGGCC TTCGCAACAC CATGAACTGT TCTTGTCTTG AATATCCAGA TTGAAGGAAA
132061 TAATCTGAGT AGTTACGAGT CCTGAAGCTA GAAAGATGGA AACCCCATTT GCTCATCAGA
132121 AAGCCTTAGA GCTTGGGCGC TGGCGGGTCC TGTCTCACCG GGACAGAGGG GCTCTTTCCT
132181 CCCCATCTGA TAGTCTGATA ACTAGAGAAG CCGGCCAACT TATTCTCCAA GAAGGAGCCA
132241 TCTTAGTTCC TCCTGAAATG TTCATATTTA GAAATTATTG TTTGTCAGTA ATTTAACCCC
132301 TTAATGGGCT TGCCTTGTGG TCCATACCAC TGAGTGCAGA GCTTGCCTGG AAGAATTGTG
132361 AGGGCCATTC CATCTTCCAG GCAGTAGAGT TCAGTACTTC TTTAAAATTG CTGCTGAACT
132421 CTGTATTTGA AAAGAAAGAA TCATTTGGGT GTGGTAGCTC ACACCTGTAA TCCTAGCGCT
132481 TTGGGAGGCT GAGGTGGGAG GATCATTTGA TGCCAGGAGG ACCACTTGAG ACCACCCTGG
132541 GTAACATAGC AAGACCCTGT CTTTAGAAAA AAAAAATACA ATAAAATAAA TACAATAAAA
132601 ATAAAAGCAA AAAGAAAGAG TCCATCTTAG GGACAGACTG TAACTACTCA CTGGAGCTTA
132661 CCTTTACATA GTTCAGGATC AATTATAATA AAACACTTTT GTGCAGATTC AATAGGATTA
```

Figure 2 (Page 41 of 74)

```
132721 TTTTAATCCC CATCATCTCT CTGAGTTTCC AGTCAGTTTC TCTGCATGTA GACACCCTTC
132781 TCCAGCCCAC CATTGTCTCT CCTCCTATAG CTCCACCAAC AAATCAGAAC TTTTTCTAAC
132841 TGCACCTAGT GCACCTAGAG TCTACTCCAG AATGCTCATG GAGAAAGTTT CTGAAAGGTA
132901 AAACTCTGAA TGATATTTGT AGCTAAAGGG AGACTTGCTA GAGACAATAA GCTAATAGTT
132961 GTAGACTTCA GTAGAAGAGG AATGACACTG CAATGTCAGG GTGCAGGACT TCAAGAGGGC
133021 AGAGTATGGA AACCCAATGG GAAAAATGCT CACCAGGAAC ATGAAGAGAA GGAATTACGT
133081 GTAAGGATTT CTCAATGTGT TCCCAAATTT GCCCAGCAGA GGGAGGCCTC GGGTTGATGG
133141 CAGGCTGACC ACACAATTAA AGAAGGCTGA ACCTGGGGGC TTTTAACAAC CATCGTGGGC
133201 TCTACTGTAA GCATTTAGAA AAAGAAAGTT ATCCATTCAA AAATATATAT ATTTTTAAAC
133261 TTCAGAACAA AATTATGAAG AGCTATATTT ACTTTTCTAC ATTCTAATTT TTATAAATCT
133321 GAGTATATTT TGCATATATT GTTATAGTAC ATATTCAATT TTGTATTTTG CTGTTTTCAC
133381 TTAACCATTT TTACTAGATT ACTCTGTGTT CATAATAATC ACTTTTTTAA AACTTTTATT
133441 TTTATTTATT TATTTTTTTT TTGAGTCAGA GTCACACTCT GTCGCCCAGG CTGGAGTGCA
133501 GTGGCGTGAT CTTGGCTTAC TGCAACTTCC ACCTCCTGGA TTCAAGCAGT TCTCCTGCCT
133561 TAGCCTCCTG AGCAGCTGGG ATTACAGGTG TGCACCACCA AGCCCGGCTA ATTTTTGTAT
133621 TTTTAGTAAA GACGGGGTTT CACCATGTTG GTCAGGCTGG TCTCCAACTC CTGACCTCAT
133681 GATCTGCCCA CCTTGGCCTC CCAAAGTGCT GGGATAATCA CTTTTTATGC TGCATAATTC
133741 TTCAGATTTG TCAGTACGAC TGTATTTACA CTCATTTGTT TTATTAGAAA GAATTCCAGA
133801 ATATTTTGGC TGCCCTAATT AATTTTACAA TTAATATGAT TTGAAATTG GGTATTGGCT
133861 CCTTCTGAAT TGGTTTATTA AAATATATTC TAATGTAATT TATGACATTT TCATCATATT
133921 AGCATATTTA TTCTGTTAGA ATTTCATAAT TTATAAAGCT ACAAACTGTA TGTGATATAG
133981 CTTGTAACTT TATCTCATAA CTTTATGCAG TTACAAGTAG AAATAAAATG TTCCCCTCAA
134041 GATTGCTTAA AATTTTATTA TAAACAAGTG TAAAAAACAA AATCACTAAA ACACTCCCTC
134101 TTTTTTCCCC CAAAATGCAT GTTTCCATTT TAACAGAACC CGTATTTAAT CAGCAGATTT
134161 CTATGGTGGC TAGATTTGTA GACTAAATAT TAAAAGTCCC AAAGCAAATG CATTTTTCTC
134221 TTAAATTTTA CTGACTTTTT TTTTTTTTCT TTTTCTGAGA CGGAGTCTTG CTCTGTCGCC
134281 CAGGCTGGAA TGCAGTGGCA CAATCTCGGC TCACTGCAAC CTCCGCCTCC CGGATTCACG
134341 CCATTCTCCT GCCTCAACCT CCCGAGTAGC TGGGACCACA GGCGCCCGCC ACCACGCCCA
134401 GCTAATTTTT TGTATTTTTA GTAGAGACAG GGTTTCACCG TGTTAGCCGG GATGGTCTCG
134461 ATCTCCTGAC CTCATGATCT GCCCACCTCA GCCTCCCAAA GTGCTAGGAT CACAGGCATG
134521 AGCCACCGCG CCCCGCCTAC TGACTTTTAT CCAAAGAAAA TATAAGAGCT CTTCATCATA
134581 ACGTATGTTT CTTGCTCTTG TTATTAAATA TGACACATTT AGACTTAAAC TGATTTGAAG
134641 GTTTATGACA TTGTTTAAGT TATTACATAA TTAATTCATA AAGATAATGA CTAGTTTGAA
134701 CTACTGACAG CTCACACATC ATCAGTTGAA CAGCAGAAAG CTTATTAAGC TACTTTCTTA
134761 TGTTTCTGTC TCCCAGCTAC TAAAAGAAAC GAAACCCTTC CAGGTGTTAA GGCAAAACTT
134821 TCCTCCCCCT TTCTTCTATA AATCTGATTC CATGTTAGTG AAATTTCTAC TGATGGCTTT
134881 GGTTTCCTCT ATAGTAGAAT AGAGATCCTA TGGCAAAAGT CATGTCTGAC ATGGTAGCAA
134941 ATAGAAATGG GGAAAAGGAA GGTCTGCAAG AGCCAATGTG GGAAATGGGG AGAGGACTGA
135001 CTACAAAAAC CCAGCAGGAA TTCCAGAAGA AAACTCCTCA GGACGGGCAC ATTGGCTCAT
135061 GCCTGTAATC CCAGTACTTT GGGAGGCCGA GGTGGGCAGA TCACTTGAGT CCAGGAGTTT
135121 GAGACCAGCC TGGTCAACAT GGCGAAACCT CATCTCTACA AAAAATAAAA AAATTTGTCA
135181 GGCGTGGTGG CATGCACCTG TAGTCCCAGC TACTCAAGAG ACTTAAGTGG GAGAATCACT
135241 CGAGCCTTGG AGGTGGAGGT TGGTGAGCCG AGATCACGCC ACTGCATTCC AGCCTGGGCG
135301 ACAAAGTGAG ACGCCATCTC AATCAATCAG TCTCCTCGAA AAGCAACATT ATGGAGAGAC
135361 AGGATTCCGT CAAGGCCTGG GGCACACAGG AAAATATTAA GGCAGAAGAG AGTTTCCTCC
135421 CCACACCACA CCGTATCCCA CAGGCACTGC GGATGTGCAT ATGCAAGAGG GGTTGATCCT
135481 AAGAATTTAG AGTCACAGAG GAGGAGGCAC CAAGCAGACT GTGGAGAAAG TCATGACCAG
135541 AAAGGGACAG AATGTAAAGC TTCAGCTGAT TATCTGGCCT CAGGGATTCC AGAGGAACTG
135601 GTCCCAATGG TCTCCTGGTG ATGTAGGTTC TTAGGTTTCT TTTACAGGGG TTTTCTGGGA
135661 GATCGTTGAC CCAGTTAGCA TTCAAGCAAC TTCCACCCTG CACTTTTATT CTTTCCCCTT
135721 CACCTGCTTA GGTTTATCT GTCCAGGCAA TAATAATAAA ATTATTGAGC CCTGGACATG
135781 TACCTGTAAA GCTCCTTAAA GATGATGCCT TCTAACTCCT CATTCAACAG ATACAAAAAC
135841 ATTACAATAA AATGACTCAT GCAAGACACC CAGGTAGTTT ATAGCAGCTA ATAAAAACAG
135901 AATAACTATA AAATATGGTA AGTTTATAAA AGTTACATTG AGTATACTTT ATAAGAACTG
```

Figure 2 (Page 42 of 74)

```
135961 CTTATTGAGT TTGCCTAATA ACCACACAGC ACAATAATAA TATGTATATA TTTTTAAATA
136021 TGTGTAAATA TGTGTAACAC AAACTTGTAG AAGGTATATC TGAGTACAAC CCTATTCTGT
136081 TTGGTTACCT TTTCTAGTTC ATTATGTAAG TGGCATAGCT ACCTAAGGAC TTATGCTTAT
136141 AAATGTTACT CAAAAAAATA CAGAGGACAT ATGTGGATAG ATAATGGAAG AGATAAGATA
136201 GGTAGGTTGA AGGGTTGGGC TGCCCCTCCA CACCTGTGGG TGTTTCTCGT TAGGTGGAAT
136261 GAGAGACTTG GAAAAGAAAG AGACACAGAG ACAAAGTATA GAGAAAGAAA AAAAGGGGTC
136321 CAGGGGACCG TGTTCAGCA TACGGAGGAT CCCACCGGCC TCTGAGTTCC CTTAGTATTT
136381 ATTGATCATT ATTGGGTGTT TCTCGGAGAG GGGGATGTGG CAGGGTCAAA GGATAATAGT
136441 GGAGAGAAGG TCAGCAGGTA AACACGTGAA CAAAGGTCTC TGCATCATAA ACAAGGTAAA
136501 GAATTAAGTG CTGTGCTTTA GATATGCATA CACATAAACA TCTCAATGAC TTGAAGAGCA
136561 GTATTGCTGC CAGCATGTCC CACCTCCAGC CCTAAGGCAG TTTTCCCCTA TCTCAGTAGA
136621 TGGAATATAC AATCGGGTTT TACACTGAGA CATTCCATTG CCCAGGGACG AGCAGGAGAC
136681 AGATGCCTTC CTCTTGTCTC AACTGCAAAG AGGCGTTCCT TCCTCTTTTA CTAATCCTCC
136741 TCAGCACAGA CCCTTTACGG GTGTCGGGCT GGGGGACGGT CAGGTCTTTC CCTTCCCACG
136801 AGGCCACATT TCAGACTATC ACATGGGGAG AAACCTTGGA CAATACCTGG CTTTCCTAGG
136861 CAGAGGTCCC TGTGGCCTTC CTCAGTGTTT TGTGTCCCTG AGTACTTGAG ATTAGGGAGT
136921 GGAGATGACT CTTAACGAGC ATGCTGCCTT CAAGCATTTC TTTAACAAAG CACATCTTGC
136981 ACAGCCCTTA ATCCATTTAA CCCTGAGTTG ACACAGCATA TGTCTCAGGG AGCACAGGGT
137041 TGGGGCTAGG GTTAGATTAA CAGCATCTCA AGGCAGAAGA ATTTTTCTTA GTACAGAACA
137101 AAATGGAGTC TCCTATGTCT ACTTCTTTCT ACACAGACAC AGTAACAATG TGATCTCTCT
137161 CTCTTTTCCC CACAGGAGGT GATGGCCGGA AGAACATGGC AGAGGGCAAA ACAAAACAGC
137221 ATTGGGAACA AGCTCTGTTT AAAAGGAGAC TTGTGAACAG CAAAGAGTAG AAAGGGTTCT
137281 CTTACAACTG AAGCCCATGG AAGACAAATG TGTACTGCGT GAGTTTTAAG GCAATAGGAG
137341 TAGTGGGACC TAGGGCACAC CAGAGAGCAT ATTAACTCTC AAACTTTTAA AAACATTATA
137401 TCTGCTGGAC ACAGTGGCTC ACACCTTAAT CCTACAACTT TGGGAGGCCG AGGCGGGCGG
137461 GTGTAGCTTG AGCCCAGGAG TTCGAGACCA ACCTGGGCAA CATGGCAAAA TCCCGTCCCT
137521 ACAAAACAAA CAAACAAAAA ACAAAATTAG CCAGGCACGG TGATGCGTAC CTGTGGTCCC
137581 AGCTACTCAG AGGCTGAGGT GGGAGGATCG CTTGAGCCCC GGGAGGTTAA GGCTGCAGTG
137641 AGCCATGATA ATGCCACTGC ATCTCAGCCT GGGCAACAGA GGGAGAACCT GTCTCAAAAC
137701 AAAAACAAAA ACACACCATA CCCAACCACA ATGCATCTGT CTTAAGTACC AGTACCACAC
137761 CCCTCTACTC ACTACTAAAT AGGTGAGTTC CCAATCCCTG GTAGCAGGTT TAAGCATGTT
137821 ATATTAAAGG TCTTAGGCTA GTGACTCATT CACTCATTAA ACAAATACTT ATTGTGCATC
137881 TACTATAAAC TAAGTACTGT GCTAGGTACA AAAGCAAATA ATCTAAGCTC TATAAACTTT
137941 ACTTCTTCA TCAACAAAAT GGAGATGTTT TAGGCATCTA CTCATCATTC TGAGCTCCAT
138001 CTTTTGTGAC TGTAGTTGGC AGAGCTTTTT ATCAGTTTCT CTAAATAGCT CTACCAGTCC
138061 CTGGTGGATG CTGGCATGCC CAAAGGATCC ATCCTGATGG CCCTGTCTGC TTACCTTACC
138121 TGCCTGCCTT TGCAGCACCG CTCTGCTCTT CTGCAGGACT TCCCTTATCC TTTGGGGTCT
138181 TGCTGCTCTT AGGCTGCTCT GCTTGTTTTG ATCTGCTTTG CATCACATGT ATGTAAAGGT
138241 CCTTTCCTTA TTTACCCATG ACCAAGGTAT TATGAGATTC TGGAATTTCC CCAAACCACA
138301 TTGATTGCTG GGAGAATAGA AGAAGTGGAT TACAAGTGGA ACTTAGAAGG GGAGTATTCG
138361 AGAAGACGTC TCTGCAAATC CATTTAGAGA GACCTTTCTC CAGTGGTGAC TCAAAGATGC
138421 AGCTCCTTTC ATCCTGTGGC TTGGCCATCT TCAGCACATG GCTCCAAGG ATGTCCTCAG
138481 GATGGTCTCT AATCCAAGGA GCCTGAAGAG AAAAAAAGGC ATGGAGTATT GTGAGTGGTA
138541 GGTGGTTATG GACCAGTTAT GGAAGAATAC ACATCACTTT TGCCCACCTT CTACTAACCA
138601 GAACTCACAC AGCCATAGAC ACTGACAAGT AGGACTTAAC AAGAATCTAA TTTTGAGTCT
138661 AGGAATACGA CTGTAGCAAA TATTTAACAG CTTCAAACAC AGGTGCATTG CTATCACTAT
138721 GCTTGGCCCA GGCCTGTCTC CCTTTCCTGC CATGTCACAG GGGCCAGCAT TTATGTCTAG
138781 ATTGGGTTGG TTGGGATATT AAGACAATAA TGAACCAATA CAACATCTTG AGCATAAAAC
138841 CAACTGATAC AATGATGTAC AAGTCAGATG ATTCTGATGA TTATGAATTA TGTCAATAAA
138901 AGAAATGTGA TAACTAAGGT AATTTTTGTT TTGGCAAATT TTTGTTTGTT CATGACAGGA
138961 TGAAATCCTG TCATTTGTAG CAACATGGAT GGAATTGCAG GATACTACAT TAAGTGAAAT
139021 AAGCCAGAAA CAGAAAGTTA AACACCACAT GTTCTCACTT ATATGCAGAA GCTAGCTAAC
139081 TAAGTAAATA AGTTTATCTC ATTGAAGTAA AAAGTACAAC AGAGATTACT AGAGGCTGGG
139141 AATGGTAGGG GAAAGAGATG ATAAAGAGAG ATTCATTAAA ATAAGTTACA GCTAGATAAG
```

```
139201 AGCAATCAGT TCTAGTGTTC TATTTGTACT ACAGAATGGC AATAGTTAAC AGTAATAAAT
139261 AATTTCAAAG AGCTAGAAAA GAGGACATTG AATGTTTCCA ACACAAAGAA ATGAGAAATG
139321 CTTGAAATAA TGGATATTCT AATTAATTAC CCTGATCTGA TCACTATACA CAGTATGTAT
139381 AAAAATAACA CTATGGGCTG GGCGCAGTGG CTCACACCTG TAATCCCAGC ACTTTGGGAG
139441 GCCAAGGTAA GCAGATCACT TGAGGTCAGG AGTTAGAGAC CAGTCTGGCC AACATAGTGA
139501 AACTCCATCC CTACTAAAAA TACAAAAATC AGCCAGGCGT GGTGGCATGT GCCTGTAATC
139561 CCAGCTACTC AGGAGGCTGA GGCAAGAGAA TTGCTTGAAC CCAGGAGGCG GAGGTTGCAG
139621 TGAGCCGAAA TCGCGCCACT GCACTCCAGC CTGGGTAACA GAGCAAGGCT CTGTTTCAAA
139681 AATAAATAAA TACATAAATA AATATTTTTT AAAAAAAGAA CATCACTATG CACCCCATAT
139741 ATACATATAA TTATTATGTC AATTTGAAAC ATAATTTTGA AAAATGAAAA AATGAAACAC
139801 AAATATGAAT CAATCCTCTC CAAGTTGATA TACTTAAAAG GAAAAAGTC CGAGGGCTTA
139861 AACTATTCAA TCAAAATTTT ATTAAAATGC TATAGTAATC TGGAAAGTAT TTCAGAATGA
139921 ATTGGTATAA GGTTAGACAC AAAGATCAGT GAAACAAAAT AGAGAACCCA GAAATAGATT
139981 CACACATCTA TGGACAACTG GTTTTGACAA AGGTGTCAAG GCTATTTAAT AAGTAAAAAA
140041 ATCGTCTTTT CAGTAAATGT TTCTTGAACA AGTAGACATC CGGTGTGGGG GAGAGGAGCA
140101 GGAGCCTTAC CTCAAACTTT ATGCAAAAAT TAACTCAAAA TAGACCATAG ACTTAAATGT
140161 AAAAGCTAAA ATTATAAAAC TTCTTTAAAA AATAGGAGAA AATCATCAAC ACCCTAGGAT
140221 TAGCAAAGAT TTCTTTAAAA CAAAACAACA GGTTTATAGT TTATAAAACA TAAATAACAA
140281 AATGATAAAT TTCATCAAAA GTGAAAATTT GCTTTTCAAA AACATTATA AAATGAAAAG
140341 CAGGAGGCTG AGGCATGAGA ATCACTGGAA CCCGGGAGCT ACAGGTTGCA GTGAGCCAAG
140401 ATGGTGCCAC TGCACTCCAG CCTGGGTGAC AAAGTGAGAC TCTTCCTAAA AATAAATAA
140461 ATAAATAAAT AAATAGAAAA GAAAAGAAA AATCACAGGC TGAGAGAAAA TATTTATAAT
140521 ACATGTATCT GACAAAGGAC TCGCACCTGG AAAATATAAG GAACCTTATA ACTTAGTAAG
140581 ATGACAAGCC AAAACAAAGA GTAAAAGTTT CAACAGACA TTTCACAAAA GAAAACATAC
140641 AAATGGCCAG TATGCACATG AAAAGATTTT AAACATCATT AGTTACTAGG GAAATGCAAG
140701 TCAAACCAC AATGAGATAC TTCACATTCA ACAGAATAGC TAATGTTAAA AGGACTGACA
140761 ATCCCCAGGG TGAGCAAGGG TGTGGAGGAA ACTACTCTCA TATATTGTGA ATGTAAGAGG
140821 ACAATGTTAC AACTACTTTG AAAAAAGTTT GGCTGTTTCT AACATAAAAT TAAACACTTA
140881 TACAGCCCAG CAATATTTCT GGGTCATTTC TCCCAGATAA ATGAACACAT GTCCATACTA
140941 TGACATGTAC AAATGTTCAT ACTGGCTTTG TTTCACAATG CTATAAACTG GAAACAACCC
141001 ACGTGTCCAT CAACAGGTGA ATGGGTAAAT AAATTGTAAT ATATCGGCCA GACGCAGTGG
141061 TTCATGCCTG TAATCCCAAA ACTTTGGGAG GCCAAGATGT ACGGATCACC TGAGATCAGG
141121 AGTTTGAGAC CAGCCCATCC AACATGGTGA AACCCCATCT CTACTAAAAA ATTAGCTGGG
141181 CATGGTCACG GGCGCCTGTA ATCCCAGCTA CTCGGAAGGC TGAGGCAAGA GAATCACTTG
141241 AACCGAAGAG GCGGAGGTTG CAGTGAGCCA AGACCATGCC ATTGCACTTC AGCCTGGGCA
141301 ACAAGATGGA AACTCCATCT CAAAAAAAAA AAAAAATTGC AATATATCTA TATCTTGGAA
141361 TATTATAAAG CAATAAAAGG GAATAAACTA CTGATATATA CACAAAATGG ATGAATCTCA
141421 AAAATGTGAA GGAAAATAAA AAATACATAT GATATAAATT CCATTCATAT GAAATTTTAG
141481 GAATGGGAAA ACTAAGCTGT AATTATGGAA AGTACATCAG TGGCTGCCTG GGGCCAAGAG
141541 GATGGAAGAG GCGGCACAGG TGATACTACA AATGGAAACT ATCTAGGTTG ACGGAAGTGT
141601 TCTGTAACTT GATTACAGTA GTAACTGTTT GGGTATATAA AACGCATCAA ATTGTATAAT
141661 TAATACAGGT GTATTTTACT GTGTATAAAT TATTCCTCAA TAAAGTTGAT TTTTCATTAA
141721 ATATATTATT TGCTAAAATG AGGAGAGACA ACTATTATCT TAAAATAGTT AAGCACAATA
141781 AAAATACTAC AATCAACTCA TTATATATGG AAATTAAAGG AGAAAAATAG TGGTATGATT
141841 AATTAAAATA AAAAGAAAAC CTTCTAAATT TTATCTTAGC TCATAGTTGT AAAAGCTGCC
141901 ATCCCTAACC AAGGCCACCC TTGACCCTTT CTCATGTTCC ATCTTTCTGT TTGTTTCATA
141961 GTTTATGTCT CACCAAAATC TATCAGATAA ACGTATTCAT ATGAAGATTT AAATATATTA
142021 CATGTTAAGC CTTAGCGAAT ACTTCAATAT CTAAAGAAGG TACAAACAAA ACAAAAATCA
142081 ACACTTAGTT ATAAGAGATT ACATACTCTC CAGGGAAGAC CTGAAGACTA GCCCCTTTCT
142141 GGATCCCACT AGCCCCTCAT CCCACTCCAA GCCCTCCCCT CCAATCCCAT ATGCACTGGG
142201 CATTCATACA AATAAGACCA TCAGCTCTGG ATATCTGTAC TGATTGATGC TCCTGCTAAC
142261 TACCTGAATG ATTGCGATGT AAGGACAGCA CTGCCTGAAT CCTATTTATC TCTCGCTATG
142321 CCATAGCGGC CTTCCATGCT GATGGCGTGT TTGAGGATCC AGAGGGGTCT TTGGTTGGCA
142381 GGATTGTTTT ATTTCCCCAA GAGGAGAGCC TTGATGCAAA AATAGGTGAA GAAATCAGTA
```

Figure 2 (Page 44 of 74)

```
142441 CAACAAAACA GAAAGCCTAG AAACTACTAT GAACACAATA GAGCAGAAGT AGCCTTAAGA
142501 GTTGGTGGAG AAAGGATGGT CTATTCAATT ACCTGAGCTG AGAAACTGGC TTTCATATGG
142561 AATAAAAATA AAATTATAGC TATACCCCAT ATCATACACA AAAGTTTCTA CATCTAACAA
142621 AGACACAGAT AGAAAATGTT TTAAAATTTT AGAAGAAAAT AGTGCAGAAT TTTAGTGCAG
142681 AATTTCTTAG ACTAGATGCA AAAACAAAAA TGATTAAAGT GGCCAGGCAC GGTGGCTTAT
142741 GCCTGTAATC TCAGCACTCT GGGAGGCCGA GGTAGGTGGA TTAGTGGAGG TCATGATTTC
142801 GAGACCAGCC TGGACAACAT AGTGAAACCC CATCTCTACT AAAATACAAA AATTGGTAGG
142861 GTGTGGTGGC TCACGCTTTT AATCCCAGCT ACTTGGGAGT CTGAGGCAGG AGAATCACTT
142921 GAACCTGGGA GGCAGAGGTT GCAGTGAGGG GAGATGGCGC CACTGCACTC CAGCCTGAGC
142981 AACACAGCGA GACTCTGTCT CAAAAAAATC TAAAAATAAA AAGATTATTT TTAAAAGACT
143041 ATTTTAAACA AAAAAAATCG TTTAATGAT ATGATACACT ACATCTAATA TTTGAAAAG
143101 TACTTCTTAA TACTTTTAAT AAAAAGAGGC GCTGAGAGCA TACAACCTAT CCTCAGAAGA
143161 GTGTTTGACC TCTAGGAGGG ACGCAAGCGC GTTCTTCCTT CATTTTAACT GGTCATTTTC
143221 ATTTATTTCA GGAACATCTG AAGTAAACAC AGTCACACGT TAACCTTTAA AAATCTAGGA
143281 GGTGCGTACG CATAGTTCCA TTACTTCAAT TTTTGTACTT TTGCATTTTA AAATATCACA
143341 GGGAAGCTCG GTACAGCTTC AAGGCTAGGA GGGGTGGCTC TCTCTTAAGC CCTGTCCCCG
143401 CCAGCCCAG ACCTCTCGTC CCGCCCCCAT TGCCCAGTCC CCACCCTCAC TTCCCCATTT
143461 CCCCACTCCC GCGGTCTCTT AACGCACCTG TTTTTCGTCC AGTGGACTCA GACCTGTACT
143521 CTTCCACCAG GATCGGCTCC TTTCCGGAG CTCTCGCTCT TAGAGGAAAT TGAGAGAAGC
143581 ATCAGCGGAG ACCCATCTGT GGCTCTCCAG AGGGCGCGGC ATTCAGACCC CAGATCCAGC
143641 TGTGAGAACG GACCCCAGGC TCACACCAGG CCTGCGGGAG GCGGCCCACC AGAGGCGCTA
143701 GAAAACAAGC CTCGCGGGGA GGCGCGCAGG GCGACTGCAA GCTGTAGGGG GCGCTGGCGC
143761 CCTCACAGGC CAGGGGCAGG GCCGGCGCTG CGGGCGGGCC TCCTGCGGCG TGAGGGCGG
143821 CCCCAGGCCA GCAGCTGCGC CCTGGCTGGG AGCCGGGGAG CATTTGCTGC TCTGCTGGAC
143881 CCTGAGTCTG GCGGCGGGCG GCCTCCTCTC CGCTCCCCGC CGCCATCCC CCAACTCCCG
143941 ATCTCTCTGC TGCGTCTGGC CTCAGGCTGA GACCCCAACG AATCATTCCC CGCATGGGAA
144001 CATTTTATGA TATAACTGAA TTCAGTTTTA TGTATAACTG AATTACGGAT ATGAGAATCT
144061 CAAATGAGGA CGAATGGTTT TTACGCACAA AACATGAGAC ACAAATCTGT AAGAAATATA
144121 AAGTCGTGAC CACGTCCTTT CAGAACTTTA ACCTGTTTGC TGAAGTACGT CAGTAACAAT
144181 GGCAGGGAAA GGGTATCTTA AATTTCACCA CAGCCTCAAA GAGGCCATTT CGTGGATCCG
144241 CTGAGGCTTG GAGTCGGCCT TCTGACCACG AGTCCTGCGG CTATGAAAGA GGAAGCCGCG
144301 GTTCAGGGCG TCCTCGCGAG TCGCGCAGCC CGCCCTGCTC CAGCTGGGGA CACAGGTGGT
144361 CACGGCGCTT TCCAGCTGCA GATCCAGGCG GCAGCCCAAG ATTTGGTCCA GCCGCCAAGG
144421 GGTGGCTCGA GTGACTGACG GGCCTTGAAC GCTCCCAGGA CCCACATCTG GAGAGGGAGG
144481 TGGGGGTGGG GTGCTGAAGT CATTCTTGGG GCCCCTGGGG GCGGGCATGG ACCTGGGTAA
144541 GGCCAGAGAA ATTGACACCT CGTGACATCC CTGGAAGAGA AGTACGTTCA GTGTCACTCC
144601 AGAGCTGAAA GATACCGCCT TCTGGCTGGT CCCTCCTCAC CTACATACTT TTCTAATTTG
144661 TCTGGAGCAG GCCGGCATC TGTATTATCT GGTTATTTAA ATATCTGGTT ATTTAAAAGC
144721 TCTCCATTAA ATTCACATAC ACGAAAATAA AAATTAAAAA AATTTTAAA AAAAAGAAAC
144781 AAAAGCTCTC TAATGACCAA GTCCTACACG ATAGTGAATA AATTTTTTTG TGTGGTCCCT
144841 AAAATTGAGT TCATGCCTTT TCTGAAGTAA TAGACGCCCA GAGAAGGGAT CGACTTACCC
144901 ATCATGCCAC AGAGATTAAT TGGCCCCAGA ATTCTTTAGC AGACCGTGTA TATGAACGTC
144961 CTTTGCAATC ATATAAATTA ACTGGGAAAA CCTCATTTAG TATGTTACAT GCCTAGCGTT
145021 TTGTGCCTGA ACACCTTACA AGAACCAGGG ACTATTGCCC CAATATTATA TTTCAGGAAA
145081 GGAAGGCCCA GACAAATGGT GTCACTGGTC CACTTTCACC CAGTTGGTAA ATGAAACCAG
145141 AAATTATAGC TGTACCACAG AAAGGTGAAA ACGTTTCTTT TATAATTTCA CATACAATCT
145201 TTAATGGACC CAGTGTCCAA CACATTAAAG CAAGTGCTCA GGAGTGACAT CAAGATGTAA
145261 AAAATAGTCC TGTCCTCAGG GAGTTTAGGT CTTGGAGAAA AGAGACCCAA GGAGACACAA
145321 GACAAGGGG AAAGAGAAGG AGCGCTGAAG ACTGAGGACC CTGCCTGTGG ACTGAAGTGA
145381 GGATGGGGAC ACCCGATGCC CGGAATATGA CAGTTTGGAG GGGCCTGAAG GACTCTTCTA
145441 TTCTCTATCA GAAAACAGA ATTACTCTCC TAACCAGAAA AGGTATTTCA ATTTATATTT
145501 TCCATCACAG CACTTTTCTG GTGATAATTT AATGTGTTTT AAAAAATGTA TCACAGTGAT
145561 GGCCTGGTGT GAAATAAATA ATAAAATTTT AAGAATTAAA AATATAAAA ATCTTTTATA
145621 TAGACATTAG GAGTTACAAG GATAACTGTG AATTATAATT AGTAATTAAA TTGAAATACT
```

Figure 2 (Page 45 of 74)

```
145681  GATTATTTTC  ATTTTTATTT  AATTATTTAA  TAAAACCTAT  TTAACATTTA  ATATTTATCA
145741  GTAATTAAAT  CTAATTGTTA  ATATTTATTA  TTATAAATTA  TTTTAGAATT  AAAAATAAGT
145801  GTAGAAGCGA  GGCATGGTGG  CTCAAGCCTG  TAATCCCAAC  ACTTTGGGAG  GCTAAGGTGG
145861  GAGGATTGCT  TGAGCCCAGT  AGTTCAAGAC  CAGCCTGGGC  AACATGGAGA  AACCCTGTCT
145921  CAATACAAAA  AAATGAGCCA  TGTGTGGTGG  TGCGTGCCTG  TATTCCCAGC  CATTCTGGAG
145981  GCTGAGGTGG  GAGGATGACT  TGAGCCTAGG  CAGTCAAGGC  TGCAGTGAGC  CCTGATCTTG
146041  CCACTGCACT  CCAGTCTGGG  CAACAGAGCA  AGACCCTGTG  TCAATATACA  TATGGACAAA
146101  CTTAAAATTT  AAAATGAAAG  CATACTACTG  ATACAGAATT  GAGTAGAGAT  GCAAAGCTAG
146161  TCCTATAACC  AGAACAATAA  AGATAAAAAG  GAGAGTGGAA  GAAGGTATGT  CATGAATTTC
146221  ATGATAAATG  GCAATTGCAA  ATATCCTGTA  GCAGAACAAA  ACAACAAAAT  TGTAGATAAA
146281  ACATATCCAA  CCCTTTGGAA  GGCCAAGGAG  GGAGGATTGT  TTGAGCCCAG  AAGTTGGAGA
146341  CCAGCCTGGG  CAACATAGTG  AGACCCTGTA  TCTAAAAGG  AAGAAAGAAA  AAAAAAAAAA
146401  AGGATGATAA  AGTAGACAAT  ATTGAAAGCC  ATTTCTGCA  AATACATAGT  GAATTTGATC
146461  AGTAATTTTC  TTCCAACAGT  GCAAAAATGA  ATAGATATTA  GTTGCCTGAA  ATAAAAATCA
146521  AATATCCAAC  AAAAAATATT  GACTATCTAA  TAGTATCTAA  GCTAGTAAAT  TTGGCCAGTT
146581  ATAAAATGTC  TTAAATTTTT  ATTTAAAAAA  AGAAAACCAT  ATTTATAAGA  AGAGGTGATA
146641  AAGAGAAATT  ATTTCAGTTA  TGAAGATTTT  GTTAGAAAAC  TATGAGAAAA  AAACTATTTT
146701  TTGTTTTCAA  AAAGTGAAAG  ATTAAGTTAC  CAAACAGTTG  CTAAAGAATA  CCAGATGGCT
146761  GAGCGTGGTG  ACTTATGCCT  GTAATCCCAG  TACTTTGGAA  GGCCAAGGCA  GGAGGATCAT
146821  TTAGGCCTG  GAGTTCGAGA  CCAGCCTGGG  CACTGTAGCA  AGACCCGTCT  CTATTAAAAA
146881  AAAAAAAAAA  AAAAAAAAAG  AATACCAGAC  CTTGCTAACA  ATAGCAAAGA  TCAATTAATT
146941  CAAAATTTGA  AAAACTGTAA  TTTATTTAGC  TTTAGAGTAC  TCTCGTGATA  TGAGATTGCC
147001  AAATTAATAC  TTTGGGTGCA  TTTCTTTTCT  CAAAGGACTT  GCAAATTTAC  AAAGAAGTGT
147061  TGAAGAAAAG  CCACACATTG  GCAGGTAATG  TTTGCAAAAG  ACAGATCTGA  TGAAGAACAA
147121  TATTTTTAGA  ATATACAAAG  AATACTTAAA  ACTCAACAGT  AAGAAAATAA  CCTGATTTAA
147181  AGCAGGCCAA  TGACCTGAAC  ATCTGTTCAC  CAAAGAAGAT  ACACAGATGC  AAGTATGCAT
147241  ATGAAAAGAT  GCTTGACATC  ATGTCATTAG  GGAACTGCAA  ATTAAAACAA  GTAGATACCA
147301  CTGCATACCT  AGTAGAATGA  CCAAAATTTA  GAACACTGTC  AGCACCAAAG  GTTGCAAAGA
147361  TATGTAGCAA  TAGTAACTTG  TTCATTACTG  GTGAGAATGC  AAAATGTGCA  ATCACTTTGG
147421  AAGACAGTTT  GGTGGTTTCT  TACAAAAGTA  ACCATACTTT  TACCATAAGA  TTCACCAATC
147481  ACACTCCTTA  GTATTTATCC  AAAGGAATTG  AAAACTTATC  TCCACACAAA  AACCTGCACA
147541  TAGATGTTTA  TAGCAGCTTT  ATTCATAATT  TATCCAAAAC  TTGGAAACAA  GATGTCTTTC
147601  AGTAGGTAAG  TGGATAACTG  TGGTACTTCT  GAATAATGGA  ATGTTATTTA  GAGTTAAAAA
147661  GAAATGCATT  CACTTTGGGA  GGCCGAAGTG  GGTGGATTGC  TTGAGGCCAG  GAGTTTGAGA
147721  CCAGCCTGGT  CAACATGGGA  AAACCCCAAT  TAGCCGGGCA  TAGTGGCGTG  AGCCTGTAAT
147781  CCCAGCTACT  CGGGAGGCTG  AGATATGAGA  ATCGTTTGAA  CCTGGGAGAT  GGAGGTTGCA
147841  GTGAGCCAGT  GCCACTGCAC  TTCAGCCTGG  GCAACAGAGC  AAGACTCCTC  TGTCTCAAAA
147901  AAAAAAAAAA  AAAAAAAAAA  AAAAAAAGAA  AGAAAAGAAA  AAAGAAAAAG  AAAAAGAAAA
147961  GAAACGATCA  AGCCATGAAA  ACACATGAAG  GAAACTTAAA  TGTATGTTAC  TAAAAAGCCA
148021  ACCTGAAAAG  ACTGCATACT  ATATGACTCC  AACTGATGCA  GGGCAAGCAA  GCCAAAAATT
148081  AGGGCTTAGC  CCGGGAAGAA  TTCAAGGGTG  AAGTGGTGGT  GTTAGCAACT  TTTACTGAAG
148141  CAGCAGTGTA  CAACAGCAGA  ACAGGTACTG  CTCCTTGCTG  AGCAGGGCTA  ACCCATAAGT
148201  AATGTGCCCA  GAGTAGCAGC  TCAGGGGCAG  TTCTGCAGTA  ATATACCTGC  TTTTAGTTAA
148261  GTGCATGTTA  AGGGGGATTA  TGCAGAAATT  TCTAGAAAAA  GAGTGGTAAC  TTCGGAGTAG
148321  GTACAGAGGA  AAGAAGTCGA  TAATGTCCTG  TTGTTGCCAT  GGCAACGAAA  AACTGACATG
148381  GCGCTGGTGG  GCGTGTCTTA  TGGAGAGGTG  CTTTAACCTC  GTCCCTGTTT  CGGCTAGTCT
148441  TCAATCTGGT  CCGGAGTAAA  GTCCCTGCCT  CCGGAGTTCA  CTCCTGCTTC  CTGCTTCACA
148501  ACTGTATGAC  ACTCTAGAAA  AGACAGTAAC  TATGGACACA  GTCAAAGAT   TAGTTGATAG
148561  AAATTGGGTG  ACAGGAAGTG  TTGAAAAGGC  AGAACACAGG  ATTTTTAGGG  CAGTGAAACT
148621  TCTGTGATAC  TATAATGGTG  AATACATGAC  ATTATACATT  TGTCAAAACC  CATAGAAAGC
148681  ACAACACCAA  GAATAAACCC  TAATGTAAAT  TACAGACTTT  CGTTGATAAT  GACGTGTCAA
148741  TGTAAGTTCA  ATTGTAATAA  ATGTACTACT  GTGGTGCTGG  ATGTCTATGG  TGGGGGGACA
148801  TTTTTGCTTC  AATAGTTACA  GTTGAAGTAA  ATGTTTGTGT  TTCCCACAAT  GCATATGTAG
148861  AAACTCTCAC  ATTCAATGTG  ATGGTCTTTG  GAGGTGGGCT  CTTTGGGTGA  TAGTTAGGTT
```

Figure 2 (Page 46 of 74)

```
148921 TAGTTGAGAT CCTAGCAGAT CGAGTCTTCA TGATGGGCAT GATGGGACTG GTCCCTTATA
148981 AGAAAAGACC AGAAAGCTAG CTCTCTCTTT GCCATGTGAA GACATAGCAG GAAGGTAGCC
149041 ATCTGCAAGC TAGGAAAGGG CCTTCACAAA GAATCAACTC AGACCTCAGA ACAGTGAGAG
149101 ATAAATTGTC GTTGTTTAAG TCACTCAGGC TGTGGTATTT TGTTTCAGCA GCCCAACCTA
149161 AGACTGTTAA TTGGATTAGA AATTTCCTTT TGGGGATGGT GTGTGGCGGG GGGTGCGGGG
149221 AGTACCTTTG TTAAGCTTTT ATATCAATGA GTTTGTAGGC TTTTCTTTTT TGGTCATTGA
149281 CTAGGACAGT TTAAATAGTA TGAGTGTGAA GGAGATTGTT GGTCATCTAT TCGATGTCCC
149341 TTCTCTGTTT TTTAATATGA GAACTCCTGA TTTTCAGCCA ACTACCCTGG AAAAAAAGCT
149401 AATCTTTCTG ACTTCTTAAG TGTGGCCATG TACTAAATTC TGGCTAATGC AAGGCAAGCC
149461 AAAGGTTTTA TGATAGGTTT TAGGACACTA GAGTAAAAGA GAGCTGTTGC ACACATGCTC
149521 TTCACCCTAC TTTTGTGTCC TTTTTTCCAT CCTACAACTT GGGTTGTGAG TATGATGGCT
149581 GGAACTTTAG TGGCTCTCTT GGATCCCAGG GGTAATTGAG GGGTGGCTGG AAGGAATCTG
149641 TGATTTTCTG GAGTTTCCAT ACACAAACAA GACCTGGATT TTCTGGGCTT CCCAGACTTC
149701 CACATCTAGA CTTGCTTTAA ATGGGAGAGA AATAAACTTG TTTCAGCCAC TGTCATTTTG
149761 GGCTATTTTA TAGAACTTAA TCTAATCTTC AAGGGTACAT GAATTGCTTT TCCTTAAAAA
149821 AAAAATCAGC CATAAAATCA TCTTCTTTTT TCTTTTGTTC CCCACATTAT TTAGTTGGAG
149881 CTCTGTAACT TTTTTTTTTT TTTTTTTGA GACAAGGTCT TGCTCTGTCA CTTAGGCTGG
149941 AATTCAGTGG CATGACCATG GCTCACTGCA GCCTTGCCCT CCTAGGCTCA AGCAATCCTC
150001 GTCTCAGCCT CCTGAGTAGC TGAAACTAAG GCACATGCCA CCATGCCCAG CTAATTTCTT
150061 TTCTTTTAGA GATGGGAGCC TTGCCCAGGC TAGTCTCAAA CTCCTAGCCT CAAGTGATCC
150121 TCCCATCTCA GCCTCCCAAA GTGACAGGAT TACAGGTGTG AGCCACCATG CCTGGCTGCT
150181 CTGTAAGTGT CTGAATTTCA TTTTGTATTT ATCAGTCTCT TTAGATTTTC TTTCCCTTCT
150241 TGGGTCAGTT AGGCCATTGG TTTCTTTTTA AAGGTTTTCA AATTTATTTG CATCTAATTC
150301 TTCAAATTAC TCTCAAAATT ATTCCAGTAT ATATTCTTTT GTTCCTATTT TCTTCTGTAT
150361 TCTTTATTAA AATAGCTAAT GATTTATCTA GCAGGACTTA TATTCTTTCC ATAACTTTCC
150421 TGCACCCCAA TTAATCTCCA ATTTTATATT TCTTCTGGCC TTCCTTATAG TTTCCACAGG
150481 TTTATTTTAT TCATTTTTTA AAACTTTTAT TTAATTGTTT ATTTTATTAT CATTCTTTCT
150541 TATTCAGCAA TCTAAGTGCT TAGGGATATA GAATTTCCTC TAAGCAGCAT ATGCTAGGCT
150601 TTAACAATGT TAGGGAGGCC TCCCCTTTCT GGGGAAGACC ACACTTACAT TAACACAGGA
150661 CTGTGGGATG CCAAGAGGTA GAGAAGAGCT TATGAATATC CAGATTACAT CTTCACTGAT
150721 CCTGCACAAA GGTGGGGTTC CTCGGTTACC CACTGGGTCC TATTACCCAA GTCTGGGTCA
150781 GCATACCGAG ACTACGGGTA TATAGAACAA GTGCAACTGG CGATAATCCT TCTGTTGGGG
150841 AGAAAAATCT TTTTTTTCTA TTCATCTTAG GTTCTCCATC TGTGGCCCTA TCAAGTAGAC
150901 TAACAAAAGA CAGATTGACA AGACAGAAAC AAAGCATGTG CATTGTACAA ACACAGGGGA
150961 GTACTGAGAT GAATACTCAA AAGAGGATTT AGAACTTGGG CTTATATAGC ATTTTAAGAA
151021 AAGAATACAT TTTTTAAGTG ACAAGGAAGA CGAAAAGGAC TTTGAGTTTC TAGTGCAGTA
151081 AATTGTGGGA AGGCAACTTT TTCTTTCCCT TTTTTTTTTT TTTTTTTTA AAAAAAAGAC
151141 TTCTCTGGTG CTATGTCCAG GCTGATAAGA GTCTAAAGTC TCTGGTGACT AACTTTGTT
151201 CTTCCCCGAG TAAGAAGACA CCTTCACAAT TTCATATCCT GCTTTAGGC AAACAGGGAG
151261 AGGGCAGAGG TGTTTGTTTG TTTTTAATCT ATTTTTTTTC TCAATTGTCT TCAACTCAAA
151321 ATACTTCTTA TGCCAAAGAT GGCATATTCT GCTACCCTTC ACTTACTACT TACAACCCAG
151381 CCTCTATCAT CATAATTAGA ACTTCTGACC CTGGGGAACA TGGGCAATAG TTTGAACTCT
151441 TTTATATCTC CCTTAGGCAG AGATGGAGGC CCAGCCATGC CTCTGACATC TAGACACAAC
151501 TGTTGCTTCA TTTCTCCTAT TCTCAGAGGT GATGTTGTAG GACTTCAACA AATATCAGTA
151561 AACATTAATT TTTTTTTTCC TTGAGGCACA GCATGATCTT GGCTTACTGC AGCTGCTGCA
151621 GGCTCAAGCA ATTCTCCTGC CTTGGCCTCA CGAGTAGCTG GGTTACAGGC CCCTACCACC
151681 ATGCCCGGCT AATTTTTGTA TTTTTAGTAG AGACAGGGTT TCACCATGTT GGCCAGGCTG
151741 GTGTTGAACT CCTGACCTCA AGTGATCCAC CTGCCTCAGC CTCACATAGT TCTGGGATTA
151801 CAGGCGTGAG CCACCATGCC TGGCCATCAA TTTTTATGTC AACTCTAAAT TATAACATTT
151861 AGCAATTTTG TGACTTTTTA TGGTCATCAT TAATGTTGTT TATGTTTTAG TTGTAGTCCT
151921 GTCATTACTC ACTCGGGTAT GGTAATTTGG TCTTTTTCAA AATGAAGTTA AGGTCTATTT
151981 GCTCTTCTCT GAATCATAAT AAGAACTGCC AACAGCCATT TCAGCAATAA CTATTTACTG
152041 AGATTTTAAA ATATTTCAAG GTAATTGGTC CTAGCAGACT GGAAAATACC AAATTCTTTT
152101 CCAGAACTGA ATCCCCCATC AAAGTTCAAT TTTACTCATA ATTCCCTTTT CATTTGAAGC
```

Figure 2 (Page 47 of 74)

```
152161 ATCTCATTGT AAGCCAGTCT TAACCCTTCT CTCACACTTT GCTTGGCTGT TTCTCAGGTA
152221 GAACTCAGTA AGTCTGGTAG CCTCCAGGAC TGCCGCTTAG ATTATTAAAC AACATGTCAG
152281 TGGTTGGAAG AGTCAATGTT ATTTTGATTT TTCTGTTTTG TTTTGTTTTA AATGCAGTTG
152341 GCGGATAATT GCAGCTTTCT TTCATTCCCT ACATGAGTTC AAATGGCAGC AAACAAACTA
152401 GGAGAACGCA GACCTTCTGA CTTGTGGGTA CCCCTACTCA TCACCTGAAG ACCCTTGGAA
152461 ATCAAAGCCC TGACCCATTA AAGACGGATG GAGACAGCAA CATACGATCA TCACTATTAT
152521 CTTGCTTTGC CCCAGTCCAG GTTAACCATC TGTGGTATTT TTAGTTGCTA AGTCCATATA
152581 TTCAACATAA ATCAATTATA TATCCACTAA AATCTCAGCA CTAGTCTAAC TACTAAGGAA
152641 ATGACAGCGA AGAAAACAGA CCAAACGTCT GCCCTTATGG GATTTATATT ATTTTCTCTG
152701 TGCTGGTTAA ACCAAGGAGC TTCTGCTCTT TTCCTTAGTC ACCTGGGGGA GGCAGAAACA
152761 AAGGAGAATA TTGATAAACC TGGAAATAGG GCCGGAGAGT ATCAGAGAAG GAAGCCTTCG
152821 GGAAAGTAAA GATGTGGCAG CCAGTATTCC CGTTATAAAA GGATACAACT CCGGCCTCAT
152881 AGTCCAGAAA AATTCCCACA AGCAGGGGCT GCTCATGCAG ATGAAGGGAA GTTGGGGGAG
152941 AAGTAAGTGC TACATAGCCT TTCTTTTTGC ACAGCCTGAG GGTCCAGAAT CCAGACTGAG
153001 GCTCTTGCTT CATGCCAGTG CCCCTCTGCA CATTTTCCAT ACAAACTCCT AAATCCCATC
153061 CGGTTCCTTC GCCAACATCC ACTTCAAAGT AACGTCTTCC TGAGGTGAAG CCTTCACAAC
153121 CCAAGACACA GGGGAAGGCA GTAAATCTCC TGGAAGATGT GTCCTGATTC TCCTGGGTGT
153181 ATCCACGAGT CACTTGTCTC CGATCCTCAG AGAGAATTAG TTCGTGATGA GCTGTATCTG
153241 GATCCAGAGT CACACTAACT GCAAAACAAA ACAAAACAAA CAAAATAAT TTTGTTGCTG
153301 TGAAGAACAC AGGTTATTTT ATTTTATTTT ATTTGAGAT GGAGTGTTGC TGTCACCCAG
153361 GCTGGAGTGC ACTGGCACTA TCTCAACTCA CTGCAACCTC CACCTCCTGG ATTCAGGCAA
153421 TTCTCCTGCC TCAGCCTCCG GAGTAACTGC GACTACAGGT GCGCACCACC ACAAGTGGCT
153481 AATTTTTTTA AATTTTCTGT AGAGATGGGG TTTCGCCATG TTGGCCAGGC TGGTCTCAAA
153541 CTCCTGACCT GAAGTGTTCC ACCCACCTCG GCCTCCCAAA GTGCTGGATT ACACAGGTGT
153601 GAGCCACCAT GCCCAGCCAC AAGTTATTTT CAATAAAACC AGCCTGTGTT CAAACCCAAC
153661 TATTGTTTCT TATAAACTGG GTGAGCTTAG GCAAATCATT TAACTTTCTG AGCCTCAGTT
153721 TGTTAACTAT AAAGTGAAA TTACCGTATT TGTTGCAGAG AATGGTGGGT AGGATTGAAT
153781 AAGCTTATGT TTGCTTAATG CTTGGTAAAA TTCCTGGTAC ATGGTAACCA CCTAATAAGT
153841 GGTAGTTGTT GGGGTGATCA GGCCCAACAC CAGGCCGTGG GGGCTACAAA GTCCGGCGGG
153901 GTCAAAGGAA TGAGAAAAGA CAAGTTAAGA GTGCATAAAG TGGGTCCAGG GTGCCAGCAC
153961 TAGATTGGAG GCTGCAAAGG CCCTAAGCTC TGGGAGCCCA CACTATTTAT TGGTGATCAA
154021 ACAAAGAAGC AGGTGGTGAG GACGTGAGGG TAAACAGGTG AGGGCATGAG GACATGGGGG
154081 TAGAAAGGTA GTGGTGCATT AAGCGTAGCT GTGACAGTTT AGCATTTTCT TTGACACATG
154141 TAGAATATAC TCTGCTGCTT GAGATAGTAG AGGACACGTT TATGAGTGAA AAGCAAGGAA
154201 CCAACAAGTC TGTGCACTTT CCAGAGGCTA TGAGGGGTTT TATGCCCTGA GCCCTGGGTT
154261 CCATCCAAGC CACAAGGGGT TTTATGCCCT AGGCTTAGAT TTGTGGTGCG GCAGGGCAGC
154321 CTTCCACCAT TTGGCACAGA GCTTGGTGTT CCAAAGGCCA CGAGGGGTTT TGGACCCTGG
154381 ACCCCGGACA TCTTCCAAGA CTCTTTTACA TTATGACAGA CAAGCCAGTC CTGCTTCAGC
154441 TCTTCTAACA ACATGTAGTA ATAATGATAT CATCAACATC ATCTTCGTCT TAATTATTCA
154501 AGGATGCCAA GGTACAGAAC TAACCTGTTA ATATGGTTAC CATCCTGTCC AAAGTTCTTC
154561 TCCCATGCAG GACTTCCAGG AATCATGAGA CAGTTGAGCA GAAAGATACC TTTTCCCTTC
154621 TCTACTGAAT AACCACCAAC ATTGAGAATC AGAGAGGGAA AATGACTCAG CTAATGTCTT
154681 AGCTTGTTAT TGGAAGACCC AGGTCTCATG ACACATGCCT AGTCCCATGA CTTTTAATTG
154741 TAAGCTCTTC TCTTTCCCCT CAGATAATGT TCCATAAGCA TTAGTATGAG ATAATAATAC
154801 ACTGAGGACC AATATACATG AAAAATATCA GACTAGAATC AAACAAGACA GAAAAAGAT
154861 CTGATAACCT AAAGTGAGAT ACTGAACAGT ATGCAGTTTT AAAAATAAAA AATGGTAATA
154921 GGATGTTCTA ACAAGAGAGT TAAGAAACCA CTGTGCTACT GAGTTAAATG TTGATCAGTT
154981 GGTCTGTGAC AATTAAGGAA TTCAAGTATT CAGAAACACT TCCTGTGCTG GATGCTCTCT
155041 GTTTGTTCTT CCAAATAATC CCTCACTTTT CCCTGTCTTG CTCTGTGCCC AGGAAGGCTG
155101 ACATGGACAG ATTAACCAGG CTTTCCGCCC TCTGGCTTGG TTCAGCCAAT GGGAAGCACC
155161 AGAGGAGACC ATAGGGCACA AAGAAGCAGC CTTGGGAGTA TTCAGTACCC CAGTCCCACG
155221 CTATGATTTG GAGGGTCTGC ATTCCTCTGC CTCTGGGCAC ACTCTAGTAT AGTTACAGCT
155281 CCCTACACCT GCCACTTGAG GCCCAGAGGA GGTGATGGCT CTCTAACTGT TCCTAGTTCT
155341 GGGTGCTTCC TGTTCCTTGT GGATTTCCCA ACTCCTCACC TTTGTAAATA CCCTCCTTTT
```

```
155401 TCAAACTCTA TTCAGTTAGC TTTTATCAGC CTGACTCACA GAAGTTTGGG GTTTCAATTC
155461 ATATTACCTG AATGACCCAG GAAACCCAT GTTGAGAAAT TAAAATGTTT ACGGGGTGGT
155521 AATACCACTT AAGAGAAAAA ATATCAATTG GATTTTAAA ATTCCACCTA TCTATTGGTG
155581 TGACACATCA ACAAAAACAT ATAGAAAGAT TGGAAGCTAA AAGATAGATA ATATAGTCAT
155641 ATACTGTTAT AGTATTATAT CAAAGATAT TAAGTCAGAG CATTATTAAG AATGGAAGAA
155701 GGGCCAGGTG TGGTGGCTCA TGCCTGTAAT CCCAGCACTT TGGGAGGCCA AGGCAGGCGG
155761 ATCACTTGAA GCCAGGAGTT CAAGACCAGC CTGCCCAACA TGGCAAAACC CTGGCTCTAC
155821 CAAAAATACA ACAATTAGCT GGGCATTGTG GCACATGCCT GTAATCCCAG CTACTTGGGA
155881 GGCTGAAGCA CAAGAATCAC TTGAACCGGG GAGGCAGAGG TTGCAGTGAG CTGAGATTTC
155941 GCCACTACAC TACAGCCTGG GTGACAGAGA GAGATTCTGT CTCAAAAAAA AAAAAAAGA
156001 AAGAATGAAA GGAGTCACCT AAAAAGATA ACACAATTTT AAACATAAAT GTACTACATT
156061 ATTAGTGAAT TCATGTTTAG AATTGTGTTA ATATACAAAG CAAAAATTGT AGAATTATAG
156121 GAGAAATGGA CAAATCTACA ATCATCATGG GATGTTTTAA CATTCTTCTT TCCATAATTG
156181 ATAGATCAGG CAGACCAAAA GAAAGAAATA AGGGAAGATA CGGAAGGTCT GAACAATCTA
156241 AGAAGCGCAA TCTCATAGTC AATACATAAA GCTCAGCAAT TGTTTAATAA TAGTAAGCAG
156301 AGAATATGCA GTTTTCTCAG GTATAGATGG AACATGCACT AACTGAGTAA ATACTAGGCA
156361 GAAAACAGTC TGAACAAGTT TCAATAAATC TGTATTACAC AGATCATTTT CTCTAGCCTC
156421 AATATAAGAT TATAAACCAA TAATAAAAAG ATGACTAAAA AGATTCTAAA TATTAGGAAA
156481 TGTAAACTAC TAATAAGTCA TTAGAAGATG TATAGAATGG AACAATAATA AAATGTTATT
156541 TATAAAAATA TACAATGAAG CTAAAGCAGA ATTTTAAGGA AAATTTGTAG GCTTTAAATG
156601 CTTATCTTAG AAAAATTAAA AAGCTGAACA TTAATGAGCC AAGCATCTAA TTTAAATTTT
156661 AAAAGAACA TAGAAAGCCA AATATAATTT TTTAAAAAGA AAAAATAGAT ATTAAACAAT
156721 ATAACAGTGA AGTTAAAGAA AACAAGAATG CAATAAAGAG GAAAAACAAA CAAAAAAAAA
156781 AGTAGCTTCT TTTAAAAGAA ATTTAATAAA ATAGACATAC CTCCAATGAG ATTTATCAAA
156841 GTAAGACAGA AGGCACAAAT GGAATGAATA CAGAAACTTT TTAAATATTA CAGAACTTTA
156901 TAATAAATCT TATGCTACTA ATAAAATTGA AAGTACTGAT AAAATTATTA CTTCCTAGAA
156961 AAAATATTTC TGAGTAAAAC TCACTCAAAA AACAAATAAA GCATGGGCAG ACCTAACATT
157021 AAAGAAATGA AATCACTACT TTAAATTTTA CCGACAGATA ATAAAACGTG CATCTTTATC
157081 AAGCAAAAAT GGAACTTGTC AGTTTTATAG GAAATTTAGA AGTCAAGGCA TGAGTAATGC
157141 CAATCTCATA CCAAATCCTA CAAAGAATAG AAAATTATGG CTCCGCTTA TAGACATAGA
157201 TATAGAACTC CTGCACAAAA TAATATAAAT AACAAACCAA ATTTTATATT TGCAACTATA
157261 CATATTATAT GTGTATGTAT TATATATGTT AACATATACA TATATAATAT GTATAGCATA
157321 TGTTCTACAT ATTATATATG TATAGTGTAT GTATTTTACA ATATATAAAT GAAAACCCAA
157381 TCTTTAATAT ATTCATCTAG ATTGTCATAT ATGACATATA TAATACATTA CATCAAAAAT
157441 GTGTACAATA ATCAGGCCAG GCACAGTGAC TCATGCCTGT AATCCCAGCA CGTTGGGAGG
157501 CTGAGGCGGG TCAATCACTT GAGTCCAAGA GTTTGAGACC AGCCTGGTCA ATATGGCCAA
157561 ATTCCATCTC TACAAAAAAT ATGAAAAATT ATCCAGGCAT TGTGGTGCAC ACCAATAGTC
157621 CCAGCTACTC GGGAAGCTGA GGTGAGAGGA TCACTTAAGC CTGGGAGGTG GAGATTGCAG
157681 TGAGTCGAGA TTGCGCCAGT GCACTCCAGC CTGGGTGGCA AAGGGAGACC CTGTCTCAAA
157741 AAAAAATTAA AAAATTAGCC AGGTATGGTG GCCTGTTCCT GTAGTCCCAG CAACTGGGGA
157801 GGCTGAGGTG AGAAGATCAC TTTAGCTCAG GTGGTGGAGC CATGATCGCA CCACTGTACC
157861 ACTCGGCTTG GCAACAGAG TGAGAGCCTG TCTCGAAAAA ACAAATATAT ACACACAGTA
157921 ATCAATATAT ATATTATATG TACCAATCAA TGCTTCACTT TTATATATAA TATAGATTAC
157981 ATCTTATTAG ATATATAGTA TTCCTTCTCC ATAGATAGAT AGATACAGAT ATAGACATAG
158041 TATCCTCTAT CCATATTAGA GAGAGGATAC TATATATATC TATAGCATAT AGAGATGCTG
158101 TCTCAAAAAA ATTTAAACAT CAGCCAGATG TGGTGGCCCA TGCCTGTAGT CCCAGCTACT
158161 GGGGAGGCTG AAATGAGAGG ATTGCCATTG ATCCTCTCAT TGGTTGAGCC ATAATCGCAC
158221 TACTGCACCA CTCAGCCTGG GAGACAGAGG GAGACCTGAG GTGAAGGAT ATAGATATAG
158281 ATATATAAAT AAATATGTAT AGAGAGAATA TAATATATGT GTGTATGTGT ATATATATAT
158341 ATTATGAAGA CACTGGGAGA GAATACTATA TATATATGTG TGTGTGTATA TATATATTAT
158401 GAAGACACTG GTGGGATGGT TTCATTACCA ATTGGACCAA GAGTCCAGGT ATGGAGCCAA
158461 CATGCAATGT TGTTGTTGAC TGAGCTGGCA GAGCACTGGT CATAGTTACG GGAAAAGAAG
158521 GTCTCCAATG AGACATACTT AACAAATAT ATGAACTTGC CATATACGTG GAGAGTTCTG
158581 GTGTGTATAT AGCCTTCTCT CACCAACCTA GCAATTGTCT TCATCATCAT TATAATGCTA
```

Figure 2 (Page 49 of 74)

```
158641 TCAGAGCAAA GATGACAGCT AAATTTTTTT GTCCCTTTCT TCTTCTTTCT CTTCCTTCCC
158701 CTCCCCCACC TCTTTCTCTT CCTCCTCCTC CTTCATCTCT CTTCTTTTTT TTTTTGAGAT
158761 GGAGTCTTAC TCTGTCGCTC AAGCTGGAGT GCAGTGGCAC AATCTCAGCT CACTGCAACC
158821 TCTGCCTTCT GGGTTCAAGC AATTCTGCCT AAGCCTCCAG AGTAGCTAGG ACTGCAAGTG
158881 CACACCACCA CACCTGGCTA ATTTTTGTAT TTTTAGTAGA GATAGGGTTT CACAATGCTG
158941 GCCAGGCTGG TCTCAAACTC CTGCCCTCAA GTGATCCTCC TGCCTCGGCC TCCCAATGTG
159001 CTGGGATTAC AGGCGTAAGC CACTGTACCC GGCCTCCTCC TTTAATAGAC AGGGTCTAGC
159061 TCTGTTGCCC AGGCTGGGTA CAGTGGCGTG ATCATAGCTT ACTGCAGCCT CGAACTCCTG
159121 GGCTCAGGAG ATCCTCCTGC CCTAGTCTCC CCAGTAGCTG AACTACAGG CATAGCACAC
159181 GGGGCTAATA AAATTAATTA GGTGATAAAA TTCACTGCCC ACTGATGACT AAGCTCTTTG
159241 GACATAAAAG ACACAGACCT TGAAGGAAAA TGTGTCTACT TAATTTTGAA ACCCTATTTA
159301 TCAAAAAACA GGATGAAAAT GCAAAATGCC ATCCACATGC CAGAAGATAT CAGCTATAAT
159361 AAGTTCCCAT AAATCAATAA GGAAAAGAAC CCAATAAAAA TTATTAAACC ACAGTAAATC
159421 ATGGGTAAAT CACAGAGGCC TGAAGGGCTA ATGGACATAC AAAAAGAATC TCAATCTCAC
159481 TAGTGAAATC AGAAAAGCAC AAATTAAGTA CACAATTAGG TACCATTTTA AATCTGTAAG
159541 ACTGTCAAAA TCATAAATTA TATAAGTAAA GACTCAGGGA GTTTTGGAGG AGTGAGAGCT
159601 CTTATATTGC TTGTGGGTA GAATTGGAAC AATTTCAAGA TCTGTAGTAT CTGGTAAAAT
159661 TATGATATGC ATCCCTCACA CCAGCATGTC ACTCCAAGGT ATCTCCCTGG AGGGAACATT
159721 TACGGGACAC AAGGAAGCAT GGATAAGAAT GTTCACAGTA GTATTGTCTG CAACAGCAAC
159781 AACAACAAAA AAACCCAACT ACACACAACT TCAATGCCCA GTCCACAAGG CAATGGATTA
159841 AATAAACTTC AGGCCGGAGA TGGTGGTTCA TGCCTGTAAT CCCAACACTT TAGAAGGCCG
159901 AGGCGAGAGG ACTGCTTGAG CCCAGGAGTT CAAGACCAGC CTGAACAAAA TAAAGAGATA
159961 GTGTTTCTAC AAAAAATTTT TAAAAAATTA GCCAGACGTG GCAGTGCTTG CCTGTGGTCC
160021 CAGCTACTGG GGAAGCTGAC GTGGGAGGAT TGCTTAAGCC CAGGAATTTA AGGCTGCAGG
160081 GAGCCATGAT GGGGCCATTG CACTCCAGCC TGGGTGACAG AGTGAGACCC TGTCTAAAAG
160141 AGATAAGTAA ATAACAACTT GCATTTTCT GCCACATTGC AAAATGGTGA GAGAGTGGTT
160201 TCTAGACTCT AGACTCTTTC TATGACTACC TTCTAGTTAT GAGATCCTAC AACACTCACC
160261 TAACCTCTCT GTGTCATATT TCCTCCTCTA TAAAGCAAAA ATGCCCATA TAGAGAGGAC
160321 TGTGATATAA AACAAGAACC AAGAAAAGTA AAGCTTTTCT AATCTGTCAC AGACTAAAGA
160381 GTGCTCAGTA TATGTGAGTC ATTATTCCTG GTGCTGGTAG GAGTGTATGT TACAACTTTG
160441 AGTCAAGTAA TATGGTACCA TATATTAAGA TTAACAACAA CCTCGGCAAT CCCAGTTTGG
160501 GGTATGTTCC CAAAAGAAAT GAAAGCACCA GGATATAAGG ATGCATGGAC TAGAAAGTTA
160561 TTGTAGCAAC ATTGTAATAA CTAAGTTCTA AAAACAGCCT GAAGCTCCAT CAGTAGGGAT
160621 ATGGTTACAT ATATTTATTA TATTCTTATG GAATATTAGA CATAAAAGT AACGAGTAAC
160681 ATAGAAGAGA CAGTGTATAT ATGTTACGTT TGTACAAACT TAGGGAAAGA TATAGATCAC
160741 CCTACCTAGA GAAGTCAGAT TGGAGAGGGG TGGGAAAAAC CTTGAACTTT CTCCTTATAT
160801 CCTTTATATT GTTTGACTGA TTAAAATGTA TTTGTTGCAT CTGCTTGAAG GCAATGTAAA
160861 ATAAAATAAA CATACATTTA AAAATAAAAA TAAAATTTAT TCCTATCACT TTTGTAATAA
160921 AGCTGGGCAC AGTGACTAAC ACTTGTAATC CTAGCACTTT GGGAGGCAGA GACAGGCAGA
160981 TCACCTGAGG TCAGGGGTTT GAGACCAGCC TGGCCAACAT TGTGAAACCC CATCTCTACT
161041 AAAAATACAA AAATCAGCCA GGCATAGTGG TGCGTACCTG TAATCCCACG CTACCCGGGA
161101 GGCTGAGGCG CTGGAACCCA GGAGGCAGAG CTGCAGTGA GCTGAGATTG CGGCACTGCA
161161 AGCCAGCCTG GGTAACAGCG AGACTCCATC TCAAAAAAAA ATTTGAAAAA AGAAAAATTT
161221 TAATAAACAG TGTTTAAGAG GGGAGAAATA TTTAGTTAAA AGATAAGCCC ATTTAAGAAA
161281 TAGTTTCACT TGACCCGGAA GGCGGAGCTT GCAGTGAGCC GAGATCGCAC CACTGCACTC
161341 CAGCCTGGGC GACAGAGCGA GACTCTGTCT CAAAAAAAAA AAAAAAGAAA GAAAGAAAGA
161401 AAGAAATAGT TTCACTTGAA CCATATTATG ATTCCTTCTG TAAAAGATGA GAGTAGGCAA
161461 ATTGACTCAG TGAAATCCCA GCAAAACTTA CACAAAGTCT TGTTCTTCCT TCCTGTCATC
161521 TGTATAGGAT GAAATACAGA GTGCTTTTGG GTTTTGTTGT TGTTTGTTGT TGTGTATTTG
161581 AGGGGAACAC AGGTCTATAA TTCCTTTTCT GAAATCCCTG AACAAAATG GCTTTGCCA
161641 TTCAAATTAG TTTAGAAGTT ATAAAGGCAA AAAAATGCAT ATACTCTAAA GTTCAACCCC
161701 ATCATGGCCT AAGGCAGAGC CCTGTAATCA AATTCATCAA TATATCTGCA GCAAAACATT
161761 TATTCAAATT AAGTGGGATA AATAAAGACT TTTAAATAGT CTCATCTCAG TGCCGTTCAG
161821 GGTTGGCCAC TGTGGAAGAC AGACTCAAGG GTGGCCTTCT ATGATTCCTG CCTCTTGGTG
```

Figure 2 (Page 50 of 74)

```
161881  TTCACACCCT  CGTAAAATTC  CTTGTCTTTG  AGTGTGAGCA  GGGCTTATGA  ATTGCTTCTG
161941  ACCAATAGGA  TATGGCAAAG  ATGATGGGAT  ATAATTTCTA  TGATTACGTT  TCATTATGTA
162001  AGACTCCATC  TTGCTGGCAG  ATTTTCTCTA  AAGAGTCTGT  CTCCTGAGCT  CTCTCTGAAG
162061  AAATAACTGG  CCATGTTAGA  AGCCCATGTG  CAAAGAGCTG  AGGGGTGGCC  TGTAGAAGCT
162121  GTGGGCAACC  TCCAGCCAAC  AGCCAGAAAT  AACCAGGGCC  AAAGTCCTGC  AACCATCAGG
162181  AAAGAAATTC  TGCCTGCTAT  CTCAGTGAGC  TTGGAAGTGG  ATTCTTCCTT  AGCCTAGCCT
162241  CCAGATAAGA  ACACAGCCTG  ACCAACACCT  TAACTGCAGC  CTTATCAGAC  CCTAAGCAGC
162301  AGGCCCAACT  AAGCTGTGCC  CAGATTCCTG  AACCACAAAA  ATTGAGATAA  CATATCAGTG
162361  TTGTATTAAG  GTTCTAAATT  ATGGTAATTT  GTTTGTACTA  ATAGATAACT  AATATAACCA
162421  CCAAATCATT  TCAGGTTAGG  CCAGATTTTT  GTAGCCAAAT  GAATCATGAT  AAAACTTTCC
162481  ATTTTCAGGG  GTTTTTTTGA  TTTTGTACTT  ACGGATACAA  ATTTGTGAAA  GTATAGTCAG
162541  CACTGATTTA  AAAAATCAAG  GGAGCAGGAA  ACTCAGTAAA  TGGTTCTAAC  ATTTTGGAAT
162601  CTGTAAATTG  GTTGTAACAT  TTGTCATCTG  TGTTATCTAA  GTCAAGTTCC  TAAAATATGT
162661  GAATGATAGG  TTATCATACT  CACCTACTTT  TCTTGCATTG  CTCTAAGAGT  TGGCTGAGCT
162721  ATTGATAATA  AACACTATGA  TCAGATCTAA  TACCATGATG  TGCTATTATG  ATCATGTGTC
162781  AGTCACAGGG  CTAAGCACTT  TGTACATGTT  GATGCATTTA  ATTTTGATGA  TAACTCAATG
162841  AAGTAGGAGC  TGTTAATATT  TTCATTTTTC  AGAGGGGGAA  ACCAAGTCAC  TTGGAGTAAC
162901  ATGGCTAATA  AGTGAAAGAA  TAAGAATTTG  AAAGGTTTGC  ACAGATAACC  AGAATGCAAT
162961  GCTCATCACA  TTCACTGAGC  AGTGAATCAT  ACTAACTAGA  GAAAGTATGA  AAGCTCTACT
163021  GAAATTAACT  AAACAACCTC  TCTGGCTGTG  AGCCTGCCAA  GGGACAGGTG  GTAAACTTGG
163081  TTACTGCATA  AGGCCCCTTC  TATCCACAGT  ATTCAGGAAT  TCTTTAGTGA  ACATACCTTG
163141  ATGACTCCTT  AACATTTTCT  TCACATCGAA  GTAAAGCTTG  GAAACATTGC  ACATAGTATG
163201  AAGTTCCAAG  GAGACAGCCT  CTGATGTTTC  CAGCTTCACA  GCCCAACTCC  TAGAATAAGC
163261  AGAGGCGAGA  GATTTCTTCA  GAGGTGCATT  CCATTCATTT  CTATATACGC  ACACCCCTCC
163321  CCTCCTGCAT  TCAAACAGGA  CTTACCTGCT  CAAAGTGTCA  TTCACATTCT  ATAAAGAAAC
163381  AAAAAGAAAA  GGTGAGCATG  GGAACATCGG  TATTTCATGG  GGCTTGTCAT  GCAGGGCTAT
163441  TCTTCTTTGC  TTTACCCGAA  GAAGTAAAGA  GAGTTACCCT  AGTCTTAGTC  TTAGATATTG
163501  ATGGATACTC  AAACAAAGTA  ATTCCCACCA  GTCTTAGGTA  TTGATGGATA  CCCAGATGGA
163561  ATAATTCCTA  CCAGCTTCTG  GGAGATTCAG  CATGGCAGGA  TGTTTATCAA  CATTTGCATC
163621  TATTCTCATC  CTTGCTGAAG  TCTGAGGGCC  AGGAGCTTTG  TCCATGCTCC  CTCTGTAAGG
163681  ACTAGCTTTT  GGTGATCGGA  TTTCCTTCAC  AGTGAGCCCA  GATTAGAGAA  CACTTATCAT
163741  AAAGGTCCTT  AGTGGTGAAT  CTGTGCACAG  CCCTGAGACT  GGGCCACTGC  CACTAAGATG
163801  GTGGTAGCAG  GTATCACACA  GTGGTAAAGC  AATCATGCTA  TACACTCAGC  CTTACAGTAT
163861  AGTCACCAAT  CCTGTTAGTT  AGAACCAGAA  TTAATGGCTC  CAGATGTTTA  TCTTCCTACA
163921  GATAAAGCTG  TAGATTGTAC  CATAACAGCT  CTGGAGCAAG  GGTTCTACAA  GCAAATCAGG
163981  GAAAAGGTTA  TCACTCATTT  TGGCTGCCCC  ACTTCATCAC  CCATCAGTCA  CCTAGTGGAG
164041  TATTTCAGGA  GAGAGTCAAC  AACCAGGGTT  CTCTGCACAT  GGGCCAAGGA  GGCAAACAGT
164101  GGTAAATGTT  ATCCCGTGGT  TTCATTTGGC  CAAGCTGTGT  TCCCTCAGAA  GTTTATTTTT
164161  CTAATTGACA  TAAAGGTACC  CTATAAATTA  GTGAAGGCCA  GCCTGATGGC  ACTGATGTAC
164221  ATCTAAAAGA  AACATTACTT  TATCTTCCCA  TGCTTCCTTA  CCATTCTCCT  TTAATAGCAC
164281  TATAACATAC  CTTTTTTCCC  TACTCCAAGT  ACACAGCCTC  ACCTGCAGCA  ATTTCTGGGC
164341  TGAGCCCTGA  CATTTTTCCT  CCAGTTCCAG  GATGTGGCTC  TTGAGTTCAT  TGCTCTTCAG
164401  CCCCAGACCA  GCCTCATAGT  CCCTCAGTCT  ACTCAGAGTC  TGTTGTTCTT  CTTTCTCCAG
164461  CCTCCAGAGA  TAAGACTTCT  CTTCCTCATG  TAGGAAACAC  TGGAGATTCT  TAAAGTCAGA
164521  CCGGATTTTT  TGTCTCTGAA  TCTGTACCTT  CTCCTGGAGT  CAAGAAAGTA  TGGTCAAAAG
164581  GTGGAAGTAA  ACCAAATGTC  CATCTATGGA  TGAATGGATA  AACAAGAATG  AAAGTCTGAC
164641  ACACGCTACT  ACATGACAAG  CCTTGAAGAC  ATTCAAGCAA  AATAAGCCAG  AAACAAAAGG
164701  GCAAATATTG  TAAGACTTTG  CTTATACAAG  GCATCTGGAG  TAGTTAAGTT  CATAGAGACA
164761  GAAAGTAAAA  TAGTGGTTAC  AAGGTGTTGG  CAAGACCAGA  AAATGGACAG  TTATTGTTTA
164821  ATGGGTAGTG  AGTTCAGTT  TAGAAGATGA  AAGATGAAAC  TGAGTTGCAG  TTTGGAGATG
164881  GGAATGGTGA  TGGTTGCACA  ACAATGTAAC  AATGTAAAAG  CACTTAATTC  TACTGAACTA
164941  TATACTTAAA  AGTGGTTAAA  TGCTTAAGTG  TTATATATAT  TTTCACACAA  ACACACACAC
165001  ACACACAATC  AGCCACTGGG  ACATTATTTT  CTCATGAGTC  ACTGAAGCTG  GAAGAATGTC
165061  CCCAGTTTCC  TGCTGCAGAG  TCATGTGTGG  GAGGCAGGCA  CTCAGATGTG  GAAGAGGTTG
```

Figure 2

```
165121 CCTCAGATTC CTTATAGTCA CCCAATTAAT TTTCTTGTTC TTCAGCCAAG ACACAGGAGA
165181 AAGCTGGGTT AGGAGTGCTA GATAATTTAA TTGTGAAACT AGGGCCAAGT TCAAACACTT
165241 TATCAGTTAC AAGGATAAAA AGAGGTTTTT ACTTATGATT TAAGAAGTTA GATTTCTGAG
165301 TTGGAGCGAT TTTCTTGAAG TAAAAGCTTA TAATGAACAT CACCCAGACT GGATTTTAAG
165361 ACAACCAGGC TGGTAAGAGG GTCCATAATT CTTGGCAGGG GGAGCTTTGA GTGTGACAGG
165421 CATTTATTAT GGTTAACTGA GAAATACTGT TCTACTACCC TAGGGTCATC TTAAGCATTC
165481 CTATGTGTAA GACTGACAGA AATCAAGTGA AACTCTCATC TGAGGAGATG TAAAGTTGCA
165541 ATTTCCATTA GTGCTGTCTA AATTAATGCA GTGGGAGTGT GTATTCAGGG CAATTTGAAT
165601 CTATGTTCTT GGATTGCAGT CTTCAAACTT GGCCCAAATA AACTCTCTAC TTATCTTAAA
165661 AAAATAAAAA TTAAAAAATA AAAATAAATT CATACAGTGT TTTGATGACT ATGATATAGA
165721 AGAAGGGTCT TTGACTTAGG ATGAGGTGGA ATTTTTGTGT AGGAGACAGG TGCAGCTTTA
165781 ACTCTTGTAT AGACGGGTTT TCATATATGT TAGTTACAAT CAAGGTCTTC CCCATTGCCC
165841 AAGATCCTAG AAATGGGGGA AGTAAGAGTG TACTCAGGAG CTCAAGAGCA ACATCCACAA
165901 ACAAAGATCA GGGTAGAGGT TAGAGAGGAC TCCTGAAAGA GAGAAAATTG GTAATCAGCT
165961 TGTGGGATTT TACTGCAAGC TAGTGAATTA TATAAATATA AAGATTGGTG CAAAAGTAAT
166021 TGTGGTTTTT GCCTTTACTT TAATGGCAAA GACCGCAATT ACTTTTGCAC AAACCTAAAT
166081 ATTTCCATAA AAGAATGTGG CTCTGATAAT GTGGAGGTTA GTCAGCCACG GAAATAATCT
166141 GAAAGTTTGT AGTTGCAAGT GTGTAGGTTG TTGCATTACT TGTGATGTAC TTATAAATCA
166201 AGTATAGGCC GGGTGCAGTG GCTCACGCCT GTAATCCCAG CACTTTGGGA GGCTGAGGTG
166261 GGTGAATCAC GAGGTCAGGA GATCAAGACC ATCCTGGCCA ACATGGTGAA ACCCCGTCTC
166321 TACTAAAATA CAAAAAATTA GCCAGGCATG GTAGCACATG CCTGTAATCC CAGCTACTCA
166381 AGAGGCTGAG GCAGGGGAAT TGCTTGAACC CGGGAGGTGG ACATTGCAGT GAGCTGAGAT
166441 CGCACCACTA CACTCCAGCA AGACTCCATC TCAAAAAATA GTAATAATTT AAAAATAAAT
166501 AAATAAATAA AGTATATTTC TTTCATCAGC TTCATGAGCT TGAGTAGTAT GAATTTCAAT
166561 CTGGAGTGAT CCTGTTTTCT AAGTGTTCAC AAAGCTTGGT TTCTGTACCT GTAAAGTTGA
166621 GAGCCAGATG CTCCACTGTG GTAAAGTGC CAGGGTAATG AGTTGAGGCC TGCAAACCAG
166681 GTTTATTTTG AGGTATTTAA AGTTTGAGAC CCACTCGATG CTTTTCTAG GTAAATAGTC
166741 ATACTAATTC TGCTTCTTCT GACTGAAGTA TCAGGAATCC CAGCCAACTA CAGTTTAAAG
166801 ATGGAAAGAT TGGTGCTAAA TACTCATGGA TGTAAACCTG GAACCAGGGG CATAAGTACA
166861 AATAATGGTT TCTTCCTTGG GTTTCATTTT TTCAATCTGG TTTAGTGAGA ATAAATCCTC
166921 ATTGTGCTTT TCCTCAATCA TCCCTATGC CTAAGCTCTA GAATGGAAAA TAGCTTGAGA
166981 TCAATGAAGT CAGATTCTTA CTTTCCATTT AGTTATTCGC ATTGCTGTGG ACAGCTTCTG
167041 CTCCGTACAT CTGTCTTCAA GTTGCTTCAG TTTTGTCACA GCTTTCTGGA GCTTTTCCTG
167101 AAGGAAAAAT TTGATAAGTG AAGCCTATTC AATTTGACTC TTCATTAGGG ACCTAGGGGG
167161 AATCCCAATC TTCTAAGATA TATTTGAATA ATAGTGAATA TTTATAGAGT CCTCATTGTT
167221 TTTTGCTAGA GAGCATGCTA AAGGCTATAT GTGCAGGAAC ATACTGATCC CCTTGGCAAC
167281 CCTGAATAGT TGGTAGGATT TTAAACTTCA TTTCTGTGCT GTAGAAAATG AGACTAAGAA
167341 AGGGGTAAAA TAACTTGCCC AAAGGGCTAT GACTGCCAGG TGGTGGAGCA ACAATTGCAA
167401 TCTCATCTGC TGACCCAGAG CCTGAGCTAT GTCCACCACT AGAGTCCTGC CAGGAAAAG
167461 TTGGATATAG AACAAGGTAA TCATCATCTA AAAGATTTTG TAAAACAACA TGCTGAACCA
167521 AGCAAAACCA ATACCAGTGT TTGGCACACA TGAAATTTTG TGTCTTATGA GTCAGGAAAA
167581 ATCAGGATGC CAGCTGGTTA TTAGAAACAG TTCATGGAAG AGGGGAATTC TGGTATCTTT
167641 TGAACAATGG TATCATGAAT CCAATTTAAA ATGATTTAGT ATTCATGTCA AGCTTTTAGC
167701 TTATTCTTCA AAACAGTTTC TCATATTTCT ATTGAAAGTG ATTTGAAGCT GACCCAAATT
167761 GCTAATTGTA GTCAATGCTG AAAGAATTGT CTCCTGTCCT CTGTAAACCC AACAAGTATA
167821 CTCATTCATT CTCGAGTGTT CTCAGGAAAA GGTTCTATGT AACTGTTTTA GCAAAGATG
167881 ACATTGTCCT TACTATATGC CAAGTGCTAT TCTATGCATT CTATATTTTA ATGTCCTCAA
167941 AGCTTATAAC CACCTCCTGT GTATGTGTTT TAGGGAGGGA GGACACTGCT ATTATCCCCA
168001 TTTACAGATG GAGAAACCAA GGTGTGAAGA CATTAAGTAA CGTGCCCAAA ATTGCCCATC
168061 TAGTAAGTGA CAAAACTCAA TTTCAACATA AGCTGGTTCC TTTTCTTACT ACTTGGTGGA
168121 AAAGTAATTC AAATGGGAAT ATGATCATCG CAGTTATTAG CTGCTCCATG GAGTTTAAGG
168181 AAGAGCTGCC ATGAGCTGAG TGGTGGTCAT GATTGACATG TCCTTAGAAG GACTTAGAGC
168241 CTTCATACAA GACCACCTCT GCCTCATGGA GGACAGAATA AGGAGCCTGA CACTGGAGAC
168301 AACATTTTCC TCAAATTTAG GCAGGACAGA GAAGGAAAAA GGACATCAGG ACTATGCCCA
```

Figure 2 (Page 52 of 74)

```
168361  TTCCTCCATG CTGCCAACAG CAAAGTCCCA CCTTCCTTAA TATGCTTTCT GGCAAGAAAT
168421  CTGGATGGTA CACAAAACCT CTCCCTCTGC TTCACCTTCC ACAACCAAGC ATTTCCAAAT
168481  CTTTGACTCT TCTTCCTGAA TCGTGCTTAA AATCTGCCCT CTCCTCCCTT TCTTATACGG
168541  ATAGTTTGAA TTTTACTCCT TGATATTCCT TTTATCATAG ACATGCCACA GTAGCTGGGC
168601  ACAGTGGTTC ATGCCTCTAA TCCCAGCATT TTGGGAGGCT GAGATGGGAG GGAGACCAGG
168661  GGTTTGAGGC CAGTATAAGC AAGAAAGGCA GACCATGTCT CTACAAAAAA TAAAAAAATT
168721  ATCCAGGTAT GGTGGGGCAT CCCTGTAGTC CTAGCTACTT GGGAGGCTGA GGTGGGAGGA
168781  TTGCTTGAGC CCCAGAAGGT TGAGGCTGCA GTGAGCCGAG ATTGCACCAT TGTACTCCAA
168841  CCTGGGATAC AGAGCAAGAC CCTACCTCAG AAAAAAAAAA AAAAAAAAAA AAAGTAGAGG
168901  TACCAGAGTG ATATTTTCAA TGTCACTGAC CCTTCATTCC CCAAATGAAA ATCCCCCAAT
168961  AGGTGTTCAA TTTTTACGTG TCCTTCAGGA GTTACTTCTA AGATGAACCA CTCTCTACCC
169021  TAAATGTCCC TCCCCACCAC CAAAACCAGG GACCTCCAGG CAGACATTTT TGATGGTTTG
169081  TTTTCTTTAC TAGACTGTAG ATACCTAAAA GGTGATGGGT CTTTCTTCCC TGTTTTCAGG
169141  CCCTACTGCA TGGCTTTACA TATTGTGGTT TTTCAAATGA TATTCATGGT GTGAAACAAG
169201  AAAAAATGCG GGTGTTTGGT TTGAGAACAA CCTGTTCTAA AGCAAAAGA AATTCATCAT
169261  AACACAAATG GATAGAGATA AGAGTCCAAC CATCCCATTG AAGGTCAGGA TGGACAGTCT
169321  AGATAATTGA GCAAGAAATC ATCATAAACT ATTTTTCAGA AGAATGACAT GATGAAAGCT
169381  GTATTTCCAA GTCATAATGT TAGGTTTCAA GTTAAATCAT CTCAGCTCCT GGGGAGCAGG
169441  ATAAGACTTG GTACTTACCA AAGCTCCCGG GCCCACACAC TCACCTTGTA GCCCTGGCAT
169501  ACGTCTTCAA CAAGAGCTGT GGTGTGCCCT TTGTGCTGTG GTGCCCGCTC ACAGCGCCAG
169561  CAGATGAGCT GCCCCTCATC TTCGCAGAAC AGGTGGAACT GCTCTCCGTG TTCCTCACAT
169621  GACATTTCTT GATCCGTCTC TTTGAGGGCT TCAATGAGGC TTCCCAGCTG CTTGTTGGGT
169681  CGGAGGCTAT CCATATGAAA TGGAGCCCGA CACTGGGGAC AGCAGAATGT CTCCTGCCTC
169741  AGTTGCTTTT GGCTTGGGTT TTTAAAGAAG TCTGTTATAC ACAAGTGGCA GTAGCTGTGT
169801  CCACAGTTGA TGCTTACTGG GTTCGTCATC AGGCTCAGGC AGATGGAGCA GGTGGCTTCC
169861  TCCATCATCT TCTTGGTGCT GGTGGTTGAG GCCATAGCTT TTATTGAAAA GCTCCAATAT
169921  TGGCTCTAGA GATGGAGATG AAGCAGCCAG AATTTTCCAC CGTGATGAAA ATACACCTCA
169981  CCTGCACCTC TATGTGATGA GCTGGCTGCA ACTGACTTCC ATAGGTCTTG AAGGTTTTCC
170041  TTCCAACCCC TATTATCTCA TTTTGTATTG AAGAAAGAG GACCTAAAAG GAAGAAGTTG
170101  AGGCTGAGGT TGTTTGGGCC ACGTTTGAGA ACTGCAACCC AAGTGCAGAG TTTCAAGTTG
170161  CCCTCATTAG CAAGCAGTTA CAAGTGGTTG TTTAGAGGAA AAAAAGCAGT TTTAAAGCAG
170221  TTTTAAAGTT GTTTGCCAAG AATTTACATT AAAATAGCAT AAGCTTTTGA CTGGCTATAC
170281  ATTGTTCTTT GTATTACAAA TCTCGGGAAT ATGTAGGTAA TAGATGAGGC AGCCAGTCAG
170341  GAACAAAATG CTTTTAAACA TGGGGTCTTA ACTGAAGACC TATACTCCTG CCTCACTTGT
170401  CCTGATAAAT TTTGCATACC TCACATAGCT CAGACTGCTC TAAATTATTT CATTATTTTT
170461  CTTTTCTCAG TCTTCTAACT TTTTTTTTTT TTTTTAATGA GACGGAGTCT CACTCTGTCA
170521  CCCAGGCTGG AGTGCAGTGA CGCTATCTCG GCTCACTGCA CCTCCGCCTC CCGGGTTCAA
170581  GCGATTCTCC TGCCTCAGCC TCCCGAGTAG TAGCTGGGTC TACAGGTGTG CACCACTACG
170641  CCCAGCTAAT TTTTGTATTT TTAGTAGAGA TGGGGTTTCA CCATGTTGGT TGGCTAGGAT
170701  GGTCTCGATC TCTCGACCTT GTGATCCACC CGCCTCAGCC TCCCAAAGTG CCAGGATTAC
170761  AGGCATGAGC CACCGTGCCC AGCCTCTTTT TCTTTTCTTA TAAGACAAGT TCTGCTCTC
170821  TTGCCCAGGC TGTAGTGGAG GGCAGTGGCA TGACCACAGC TCACTGCAGC CTCGACCTCC
170881  TGGGTTTAAG CAATCCTCCT GCCTCACCCT GGCAGAGTGG CTGGGACTAC AGGTATGTGC
170941  CACCATGTCC AGCTAAAGTC TTCTCTCCAG AAAGAAGAAA TGCATTGGAA TTTAGAGGAT
171001  ACACAAACAT CTAGCTGTAT AGCTAATACA GTAGCCACTA TCATGAGTAG GAATTTAAAT
171061  TTAACTTAAT AAAAATTAAA ATGAAAAAAT TCAGTTTTTC TGTTCCAGTT GCCACATTTT
171121  GATTGCTTAA TAGTTGCATG TGACTAGTGG CTACATAACA GCCTCAATAT ACAACATTCT
171181  GTTATCACAG AAAGTTACCT TGGACCAAGT GCTGGGAGAA GCAATGCAGG CTTCCTCACA
171241  AAAGCTGTAA AAGAGAGAAC TCAGGGAGTG TGAAACTCTT TCCTATTCTA GTTAACTTCA
171301  AGAATAATTG TTACCAGGCC AGCACGGTGG CTCACGCCTG TAATCCTAGC ACTTTGGGAA
171361  GCCGAGGCGG GCAGATCACC TGAGGTCAGG AGTTTGAGAC CAGCCTGACC AACATGGCAA
171421  AACCTCATCT CTACTAAAAA TACAAAAAGT TAGCTAGATG TGGTGGTGCA CACCTGTAAT
171481  CCCAGCTGCT CAGGAGGCTG AGGAAGGAGA ATGACTTGAG CTCCGGAGGG GGAGGTTGCA
171541  GTGAGCCCAG ATTACACCAC TGCACTCCAG CCTGGGTGAA AGAGCGAGAA TCTGTCTTAA
```

```
171601  AAAAAAAAAA AAAAGAATAA TTGGTACCAG AATTACTCTT TGTAATTAGT AGTAACACTT
171661  ATGCAATTGG GTGATCTGTG ACAGATTCCA TTGAAGGAGT ATGGGGAGCT TCACCCCAAT
171721  ATATGACTCC CTGGTATAAT GAGTATTTTG AATTAAAGGC CCTTAGAGAT CAGCAGATGC
171781  TGGAAGAGAC TTTTCCCCTA TCTACATAAA GACCAGTCAC ACTAGACAAG AAGAACAATT
171841  GTTTTTCCTT CCAACCCCTA TTATCTCATT TTGTACTGAA GAAAAGAGGA CTAAGAATGT
171901  AACCAGACCT AATCAGACAC TTTCACAAAA TAATGTCTGT CTCTCAGGCT CATTCATTTT
171961  CCAAAGAGAA CCATTTACAA GTTAAACTCT GTTCCTCCAT TCATTCATCC TCCCAAATAT
172021  TCATTTATTC TCCCTAGTAA TCATTTACTG CCCCTCAAAG AATTACCTAT ATTCTCCTGA
172081  TATCACCCTT CCCCTCTGAA ATAAATATGT ATACATGTAT AAACGTTATA CATACATATT
172141  TATACAGTAT ACATACATAT TTATACATAC ATACATATGC ATACATATTT ATATTTATGT
172201  ATTTATACAT AAGTATTTAT AAATAAGGCT ATATAAGTAT CTACCCCCAT TGGCAGAGGG
172261  GGTAATCACT CTGTGATTCT AGCCCATGTA CTTGTTAATA AATTTGTATG CCTTTTCTCC
172321  AATTAGCCTG CCTTTTGTGA GTCGATTTTT CAGTGAACTT CAGAAGGCAA AGGGGAAGTG
172381  TTCCCTTGGC TCCTACACCA TCATGACAAT AAAATTTGAC TCCACCTCGA CCCCCCCCAT
172441  CCCCCACAAA GAACAACAAC CAACACTGGT TAATAAGGTC GGTTGTTTTT TGTTTGTGTT
172501  TTTGTTGTTG TTGTTGTTGT TGTTGTTTTT GCTTTCAGGA GCAGAGGTAT AATAGGCAAA
172561  AGAAAGAGAA AGGAGAATAG TGAATACCTC TTCTGCAGAG AGGGGTGCCT AAGTGGGACT
172621  TCCCTGGCTA ATAACGTCTT GCTAGAGACC CAACCAGGAG GATAATGGAA GCAATCAAGG
172681  CAACCAGAAC AACCAGAAGA ACCAGTTTAT CCTTTTTGTG CCCTCTCCCT AAACTGAGGG
172741  AATAAGAATT GGAAAGAAGG CTGCAGAGCA GAGGGTTTGC TCCTGAGGAG CAGTTATTTC
172801  TATGGGATCA GAGCTCCTGC AGAACTGGGG AGTTTACTTT TACTATCTCT TCTCCAGGAC
172861  AGGACCTATC TCAAGAGACA TGTTCAGAGT GATTGCAACA TAAAGAGTTT GCAGACCCAA
172921  GGAGGTAGGG AAGGCAGAAA GAAGATGGGG GAGGCCAGGG ATAGGCAACA GAGGAGTGAC
172981  CAGGAGCGAA AAAGCCTGCC TCTTCTGAGA ACCTAGCTGG GCTCTCCCTG TACCCCCGAT
173041  CCCTCCCCCC CGCCCGCCCC CACACCCCTA CTCCTGGGAG CTCCTCTAGG ACAGGGGCAG
173101  AGTCAGGAGG AAGTTTGAAG AGTGCCTAGA ATAAAAAACA GTAATTTAAC TACAATTACC
173161  GGGTAGGCTG TTTTCCTCTC ACAATTTGAT CAGTCTCTTG AAGCCACACA GAATTTCTTC
173221  TGAAGACGTG TATTCCTTGG CAGGCTATTT CCTCCAGTGA TACACCAGGC CCCTCTCTGC
173281  TGGGGTCACT GCTCTTCTGG GGAGATGGGG CTCCCCTCCT TCCAAGGCTC CAGGGTTCCT
173341  GTCCTGGGCC CCACTCATCT AAGTTCTGAA TCTTCTGAGA TTTGGTGTAA AGTCTGGTGA
173401  AAGAAAGAGC AGGAAAGAGG TGAGAGCTGT AAAACAAAGA AAGTCCTGAC CATTTTCAGA
173461  GTTGGAGGGG CCCTGCTGTC ACGAAATATA TTCCCCACCC CACTTGCCAT CAGTACACAC
173521  TCACATATCC ACTGAGAAAA CCTTAGCCTG GACCTTTTCC GTAACCTTCA CTGCTCAGAC
173581  ACTTACATAT TCGCTGCTAG TCCCCTCTGT TGCTGCCACT TCCTGGGTCA GGAAGTTAAC
173641  TCAGACCGGA TTAAACTGAG AAGTGAAACT ACTGTGGGAG GCGGGCTCA  TAAGGATTTAG
173701  GAGAAAACTA GTGACGTTGT TCATATCATT TGCACTCCGC CTCTCCGGTA AGGAGGGGG
173761  AAACGTAGGA AGAAAATATC CTTCTTTTAC AGCAATAAAA AGAAGGAACC AATTAATAAC
173821  CCTGTAAACT ATCATGTGAC CCCAACACAG AGTATCTAAA AACAGGAAGC CTGCAGAGGT
173881  TCAGTTCACA GACTCTGATT TGAGATCTTT CTACTTTTGC CACCAACTCC CTTGGGAGTC
173941  CTTAAGCCTT CCTAGCTGAT GTTACTTCTT TTGCTATTTA TGGGTTGCTT GTGGTTCTAT
174001  AACTGCTCTG AAGGGTGTGG TGGAAAAAGG GGTGGTAACA GCAGTAGGAC TCATTGGCAT
174061  CACAAAATTC ATCTGAGTCA GCTTTCTATT CTTCTCTGTC CCGTTCGTGT TCTTGTTTTT
174121  CTCCTTGCTG TCCTTCTGCA GGACTCAGAT CTTCTTCAAT AGCGAGGGTC AGCCAGGATA
174181  GAAAATGGGA GTCACTAGTG GCCCAGCAGT GAGTGGGAAA GCTTAGAGC  TGTGTGGGAT
174241  CCCTGGGACC ATCACTCTGC TTTGTGCTTT GTGGAGAAAA GGCTGTGGGG TCCAGGGTCA
174301  AGTCCTTAAT GACTTAGCTC CAGCTTCTCC ACTTCAAAAT GAAAGGAAAA GTACTATCAC
174361  CACCCGTTAG AATTATTATT TCATGGGGAA AAAAGATGGA TTACTATCTC ACAATAAGAG
174421  CTTGTCACAT TTATAAGTCT CAGGTGTAAG AGGCATTTAT GATAACAACA TAATAAATGC
174481  TGGCTTAAGT AGATGCAGTG GTCCAAGGGA ACCAGTAAGG GGAGCTCAGG ACACAGGTGG
174541  GAGGAGAAAT TAAACTTGAA TTCTGGGAGC CACTGGCCTG TCTGGGCCCC TGGCCTGCCT
174601  GCTGACCCTG ATAGCCAATG GAACATGGAG TTTGCCCAG  CTGCAATCCC TCTGGTCCAA
174661  CTACTCAAAA TAAAGGCAAG ATTGGGAAAC ACGTTCCTTT CTTCCTATAC CAAGCAGAAG
174721  ACTCTTCAGC ACTGCACCCT CCTGGGTGCT CACAGAGCCT TCTGTTGTTT TGCCACCTAC
174781  GATTCATCAT GCCCTGGCAT GATGGTTGCA GACCCCATGC ATAGCATGGG ACATTCTACT
```

```
174841 CCTGAGGCAA CCAGCACACA GAGAGAGGAG AAAGAATGAG CCCCTGAATC CTTGGTCCCA
174901 CGATGAGTCC TTGCAGATAT CTACAACTTT CATTGTTGTG GATGTGACTC TGTACCCAGG
174961 CATGGCTCAT TCCAGATCTG TCCTATTGTC AGAGGTGTTC AAACCAGAAT GACTCCATTT
175021 TGAATGGGGG CTAGGTAAAA TAAGGCTGAG ACCTACTGGG CTGCATTCCC AGGAAGTTAG
175081 GCATTGTAAG TCACAGGATG AAATAGGCAG TTGGCACAAG ACACAGGTCA TAAAGATCTT
175141 GCTGATAAAA CAGGTTGCAG TAAAGAAGCT GACCAAAACC CACCAAAATC AAGATGGCAA
175201 CAAGAGTGGC CTCTAGTCAT TCTCATTGCT CATTATACAC GAATTATAAT GTGTTAGCAA
175261 GTTAGAAGGC ATTCCCACCA GCTCCATAGT GGTTTATAAA TACCATGGCG ATGTCAGGAA
175321 GCTACCCTAT ATAGTCTAAA AAGGGGAGGA ACGCTTGGTT CTGGGAATTG CCCACATCTT
175381 TCCCAGAAAA CATATGAATA ATCCACTCCT TGTTTAGTAC ATAATCAAGA AATAACTGTA
175441 AGTATCTGTA TTAGTCCATT TCACACTGC TGATCCAGAC ATACCTGAGA CTGAGTAATT
175501 TATACCAGGA AAAAATGTTT CATGCTCTTA CAGTCCCACG TGTCTGGGGA GACCTCACAA
175561 CCACAGCAGA AGGCAAGGAG GAGCAAGTCA GGTCTTACAT GGATGGCAGC AGGCAAAGAG
175621 CTTGTGCAGG GAAATTCCTT CCTATAAAAC CATCAGGTCT CATGAAACTT ATTGACTATC
175681 ATGAGAACAG CAGTATAAAT TACTCAGGGA AAGACCTGCC CCATGATTC AATTACCTCC
175741 CACCAGGTCC CTCCCACAAT ATGTGGGAAT TTAAGATGAG AGTTAGGTGG GGACACAGCC
175801 AAACCATATC AGTATCCTTA GTCCAGAAGC TGATGCTCTG CCTGTAGAGT AGCCATTCTT
175861 TTATTCCTTT ACTTTCTTGC TTTCACTTTA CTGTGTAGAC TTGCCCCAAA TTCTTTCTCA
175921 CACGAGATCT AAGAACCTTC TCTTAGGGTC TGGGTTGGGA CCCCCTTTCT GGTAACACTA
175981 TCAAAGGATC AGGAAAAGGA AGCTAGTGAA TGCTAAAAAG GAAACAAACT ACCATTACCA
176041 ATAATAACAG CAAGACAAAA GCAAACGGA TTGTGACAGC TGTCCCATCT CACACCTGTT
176101 TCCCATTGCA GGAAGGAGGG GCTGGTTCAT GCACAGAGTG GCCAATATTA GAAGCAGAGA
176161 GGGGGTGCAG ATGAGACTTC AGGAATATGT TGACAAAGGC AGGCCTAGGG AGAAATCAAC
176221 CTGAACTATC CCCAAGGAGG AATGCATTAT CTCTAATATG TAAAGTTAGG CTTGATCCTG
176281 TGATTATGGG ATATAGGAGT CCAAAGACTC ACAATGGGAA GTAGGTCACT AGAGTCTCCT
176341 TCAGAAGCTC TGTACTGTGT GTTCCCACTG TGGGCAAGAG TCAGCACTCA GCTATTCCTA
176401 GAATGCCTTT CCTCAACTCC TTCAGATTTT GCCTCTCAAC TAACCCTATC CTGACCACTT
176461 GTTAGCAAGT GTACCCTCT CTCCCTCCCA AACATTTTCA AATCTATTTT GTTCCCATGG
176521 CACTTATCAC TGAATATTTT ACTAATTTAT TTTGTTTAGT GTTTGCTTCC CTCATGAGAA
176581 TGCAAAGGGA TGGATTTTT TCAATATTGT TCACTGATGA ATCCCAGTAA CTAGAATATT
176641 TCTAAGCATA GTGATGTGCA TTAAATCAAA GAGTAACTTT CTGAATTGCA CTAAACACAC
176701 ATCACAAGAG GTGTGTGCAC ATATGTGCAT GATGCACGTA GTGTGGTGTG GGTGTTGTGT
176761 GGGGTATGTG GTACTGTGTG TGCTGTGTGT GGTATGTGAT ACATAGTTTG TGTTAGTGTG
176821 ATGCATGTGA TGTGGTATGT GTGTGCGTGT CCATACATAT TAGGGGTGGC GGGGATGTTA
176881 ATATGTCAAA TGGTACTAGA AAGTATCAGA ACTCATGGTG CTTACTGGTT TCCCAGAGAG
176941 CTGCTTCTCT CCCACCTGTA GGATATACTG ATGGTTTGGA CAGAGAAGAA ATAAAAGAA
177001 GGCTGTGACC TACTGGGCTG AGGAAATAAA AACGAAAGTA AAGAAGAGC TGGGAAAAGA
177061 GAGTGGAGGG GCCAAGGGAA ATTTCCCCTT TGGCTTCTGG GGAAACTTTG CTGAAAAATC
177121 AACTCACAAA TTTATTAACA TGTACACAGG GAGAACCATA GAATGATTAT CCACTTCCCA
177181 AGAGGGCTTA AAAGCTTATA TATTATCCTG GCAAAACAGA TTATGGGAGG GGAAGAAGAG
177241 AAACTCTGTT GATGGGATTA CTGTTGCGGA TTTTTGCTCC TTCGCTCAGC TAGGTCCGGG
177301 TTTTTGTCTC ACAGCCAGGA AGAATTAGGC ATGCAGCCAT CAAAGAATGA GTGGAGTAGA
177361 ATTTATTAAG TGAAAGGAAA GCTCTCAGCA AAGACAAGGG TCCTGAAAGC AGATTTCTGG
177421 TTTGCTCTTC ACAGTTGAAT ACTAGGGCTT AAGACTCAAA TTCCTGACAA CTCCACCCTG
177481 TCCTACCAGT GCATGCAGGC CTTTAGACTG AGCTACTCCA TATTGATTAA TTTCCTGAAC
177541 TGCGCATGTG TTAAGGAAAG GAATCATCCA CTGCAGGCAT GTTAGGCAA GCCCCCTGTG
177601 CAAGTTCCCT TATCTGCACA AAACATCCGG TGTAAGCACT TGTGGGGCAG GTCAGAGGTT
177661 CTCTGGGTAC CATTCCCTTA CTGTCTGCCT AAAGCAAGCT GGCCAACTCC TTTCATTACT
177721 AGGGAGAGTA AGTAGATCAG GAACAGAGA TTAACTTGAA CATTATCTTG TGAAAGTCCG
177781 TTCGGGCATG GTTACATTCT TGGTCTTACA GGAAGGGTAA ATAAAAATAA TTGCTCTTTT
177841 TGGTGGGTCT GGATCTTAGG TAGATAAAGA AACTTTAATT CCACGATGTG TTTTGGTAGG
177901 GATAGTTGGT GGCAGGGATG TCAGAGAGAC TTTGAGGCTT CTTCAGTTCA ATATGACCAA
177961 GGGCCATATA TTAGGGTATC AATTTCTGAG CCCCAACAAG AGCTTAGGAG AGATGTGATA
178021 GCATCACAGT GTGAAAGCAA TTTTTTGTCT GTTTTTAGAG ACAGGCTCTT GCACTGTCAC
```

Figure 2 (Page 55 of 74)

```
178081 CCTGGCTGAA GTACAATGGT ACGATCACAG CTCACTGTAA TCTTGAACTG GGTTCAAATG
178141 ATCCTCCCAT CTAAGCATTT CAAAGTGTTG GGATTACAGG CATGAGCCAC GGTACCCAGC
178201 CTGAAACTGC ACCCACTTTC TGATAAACTT TTCAAATGAC TAAAGGGGAG AGAGTAAGCA
178261 CTACTCAGAG GTAGGAAGAA AGGACACAGG ATTATAGGAT TAAAACAACA ACCACCAAAA
178321 AAAACCAGAC CGGTGTGGTG GCTCACACCT GTAATCACAG CACTTGGGGA GGCTGAGGTG
178381 GGGGGAGTCA CTGGAGGCCA GGAGTTCGAG ACCAGCCTGG CCAACATAGC AAGACGCTGT
178441 CTCTATTAAA AAAAAAAAAT ACCTGCCTTG AGCTAATCAG AATCATGGAC CCTGACAAAG
178501 GATGTCCCAA AGTAAGTCTT AGCATTTTTT TTTTTTTTTT GAGACAGTCT CGCTGTGTTG
178561 CCCAGGCTGA AGTTCAGTGG CGTGATCTCG GCTCACTGCA ACAGCTGCCT CCCAGGCTCA
178621 AGCAATTCTC CTGCCTTCA GCCTCCCAAG TAGCTGGGAT TACAGATGCC CACCACCACG
178681 CCTGGCTAAT TTTTGTTTTT TTTAATAGAG ATGGGGTTTT GCCATGTTAA CCAGGCTGGT
178741 CTTGAACTCC TGACCTCAAG TGATCTGCCC ACCTTGGCCC CTCCATAGTG CTGGGATTAC
178801 AGGCGTGAGT CACTGCACCC GGCAAAGTCT TAGCATTCTT TACAAACAGT TTGTACCCGT
178861 ATCTCTAAAA GGGAGTAGTG AATTTCACCC CAAAATATGG CTTCCTGATA TAATGAGTAT
178921 TTGAATGAA AAACTCTTAG AGATCAACAG ACACTAAAGA GACTTTTCCC TAGGTACATA
178981 AAAATAGGAT GGCCCCACCA GCGAGAACAA TTGTTCTTTT CTCCCTCCCT GTTATCTCAT
179041 TGTGCATTAT AGGAAAGACC AAGAATGTAA CCACACCTGA ACAGACCCTT TTATAAGATA
179101 ATCAGTCTCT AAGCATCATT TAAATTCCAA GGAGAACTAT TTACAAATTT ATCTGTTCTT
179161 TGATCCAATT AGTCTCTCCT GGTAGTTACA TATTGCCCCT CAACAGAATT CCTCTTCTTC
179221 TGTTTCCCAT AACCTATTTT GCAAGGATCA AGCCCCTGTT ACTTCTTCAA CTTCAAGTTG
179281 GCATATAAGC TTCTAAATTC CACTGGGATA TTGGTACTAT GTGCATGAGG AGAACCACAG
179341 AGTAATTAAA TTGTAAAGCC TTTTATCTTA TGAATCTGCC TTTTTTTGTG TTCATTTTTC
179401 AGCAAAACTT CCAAGGGCAA AGGTATAAAA CAAAAATAAA ATTCTAAAGC CCCCCAACCA
179461 TCTGAATAGA CTTTCTCTTC AGTCAGGCTT CTTAAAATGT AACCTGAAAG ACTGGCTCAG
179521 GCCATTAAGG GAAGTGGGGG TTGAACATGC CTCATTATTC CTCTCTGGCA TTAACATCAA
179581 CACAGCTTTT AAGTCTGATA AGAAACATTT TACAACCTAT TCTCTCTGAA GCCTGCTAGC
179641 TAAAAACTTC ATCCCATAGT ACAACTTTGG TCTTCACAAC CTGTTATCAC AACCTAGTGC
179701 TCCTTTCTAT TAATCCCAAA TCTTTATACA AACTCAACCA ATTGTCATCA CCTCCACCCC
179761 ACTCCTCCGC TGCTTCCAGT TGTCCCGCCT CTCTGGACCA AACCAGTGTA CATTTCTTAA
179821 ACGTATTTGA TTGATGTCCC ATGCCTCCCT AAAATGTATA AAGCCAAGGT GCATCCCAAC
179881 CACCTTGAGC GCTTGTTCTC AGGACCTCCT GAGGGCTGTG TCATGGGCCA TGGTCACTCA
179941 AATTTGGCTC AGAATAAATC TCTTCAAATG TTTTACAGAG TTTGGCTCTT GTCATGACAC
180001 AGATGACTGC TTCACTGAAG CCTGCTCTGG AAGTGAGTGG GGGTTTTGCA AGGATAATTT
180061 TCCCCGGATA GCCCCAGAAG CAGCTAGTAA TAATACACTT AAAGGTAGCT AAAATGCATT
180121 GAACACTTGT TTTGTGCCAG ACCTATGTCA ACATTTGCTT TGTGCCAGGC TTATGCCAGT
180181 ACTCCTGATT TGTTAATACA TTCTAAATAA AAATTCTGGA GTTTCAAATA TAATAACTGA
180241 AAAACAGAAA ATAAATAAAA ATATATAATA ACTGAAATAA AAATTTACTA AGGCTGGGGA
180301 TGGTGGCTCA CTCACACCTG TAATCCTGTT ACCGGAAAGG GGTCCGTCCA GATCCAGACC
180361 CCAAGAGAGG GTTCTTGGAT CTCACACAAG AAAGAATTCG GCGAGTCTG TAAAGTGAAA
180421 GCAAGTTTAT TAAGAAAGTA GAGGAATAAA AGAACGGCTA CTCCATAGGC AGAGCAGCTC
180481 TGAGGGCTGC TGGTCGCCCA TTTTTATGGT TATTTCTTGA TTATGTGCTA AACAAGGGGT
180541 GGATAATTCA TGCCTCCATT TTTTAGACCA TATAAAGTAA CTTCCTGACG TTGCCATGGC
180601 ATTCGTAAAC TGTCGTGGCG CTGGTATGAG CATAGCAGTG AGGACGACCA GAGGTCACTC
180661 TCATCGCCAT CTTGGATTTG GTGGGGAGCA GTGAGGATGA CCAGAGGTCA CTCTCATCGC
180721 CATCTTGGAT TTGGTGGGGT TTAGCCAGCT TCTTTACTTT TTTCCTTTTT TTTTTTTTT
180781 TTTTTTTTTT GCCCAGGCTG GAGTGCAGTG GCACGATCTC AGCTCACTGA AACCTCCAAT
180841 TTCTGAGTTC AAGCGATTCT CGTGCCTCAG CCTCCCAAGT AGCTGGGATT ACAGGCATGT
180901 GCCACCACAC CCAGCTAATT TTTTATATTT TTAATAGAGA CCGGGTTTCG CCATGTTGCC
180961 TACGCTGATC TCCAACTCCT GCGCTCAAGC CATCCAGCCA CCTTAGCCTC CCAAAGTGCT
181021 GGGCTTATAG GTGTGAGCCA CCCCACCTGG CCTAGCCGGC TTCTTTACTG CAACCTGTTT
181081 TATCAGCAAG GTCTTTATGA CCTGTATTTT GTGCCCACTG CCTGCCTCAT CCTGTGGCTT
181141 ACAATGCCTA ACTTACAGGG AATGCAGCCC AGCAGGACTC AGCCTTATTT CACCCAGCTC
181201 CTATTCAAGA TGGAGTCTTT CTTGTTCAAA TACCTCTGAC AAGCCCAACA CTTTGGGAGG
181261 ATGACACAGG AGGATTGCTT TAGCCTAGGA GCTCAAGACC AGCCTGGGCA ACACAGTGAG
```

Figure 2 (Page 56 of 74)

```
181321 ACCCCATCTC TAAAAAAAAA AAATACAAAA AAATTAGCCA GGCATGATGG TGTGTGCCTG
181381 TAGTCCCTGC TACTCAGGAG GCTGAAGTGG AAGATGGCT TCAGCCCAGG AATTCAAGGC
181441 TGCATTGTCA GAGGCATTTG AACCAGAATG ACTCTATCTT GAATAGGGGC TGGATAAAAT
181501 AAGGCTGAGA CCTGCTAGGC TGCATTTCCA GTATGTTAGG CATTCTTAGT CACAGGATGA
181561 GATAGGAAGT CAGCACAAGG TACACATCAC AAAGACCTTG CTGATAAAAT AGGTTGTGGT
181621 AAAGAAGTTG GCCAAAACCC ATCAAAACCA ACATGGCCAC CAAAGGGACC TCTGGTTGTC
181681 TTCACTGCTC ATTATATGTT AATTATAATG TATTAACATG CTAAAAGACA CTCCTACCAG
181741 CATCATGACA GCTTACAAAT ACTGCGGCAA TATCTGGACT TTACCTTATA TGGTCTAAAA
181801 GGTGGAGGAA CCCTCAATTT TGGGAATTGT CCACCCCTTT TTTGGAATGC TCATGAATAA
181861 TCCACCCCTT GTTTAGCACA TAATCCAGAA ATAACTATAA GTATGCTTAT TTGAGCAGAC
181921 CACGCTGCTG TTCTGCCTAC AGAGTAGCCA TTCTTTTATT TCCTTACTTT CTTAATAAAC
181981 CTGCTTTCAC TTTACTGTAT GGACTTGCCC TAAATTCTTT CTTGTGTGAG ATCCAAGAAC
182041 CCTCTCTTGG GGTCTGGATC AAGACCCCTT TCTGGTAACA TCTTTCTGGT GACCACGAAG
182101 GGACAATACT GAGGAGACTC TGAAGCCAAA GGAAACAGAC TACAGCACCA ACTGGCTGAC
182161 TTTGGGTAAG TGGTGGAGTC CCCGGGTAAA GGATAGGATT GGGTTAGAGG TGCAACTTAG
182221 GGGAGATAGG GTCTCTCCTA AGACAGAGAG CGTTTCAGTC CGCTCTTAAT AAAGGGCAAG
182281 AATGCTTGAC CGAACTTGGG TTTGAGACCC AACTTAGGAA GGCTACAGTC CTTAAGATTT
182341 AAGGGGTTAG AGGCCCCTCT CAGTAAAGTC TCTCTTGGTT AAAAACGGAT TTAGCATTAG
182401 GGGATGTTAA CTGCTATTCT GTTTGTATTA ATCTTCCCTG TGCTCTTTGC TGACAGCTAT
182461 GGGTGACAGG ATTAGGCATG TACAGGATCA CGGGACATTG GAACTTTTC TTCTCTCCAA
182521 AAGGGGAAGC TTGACAGCTG ATAGGACTGT TGGAAAAGAT CCCTTTGCTA TGACAAGCAG
182581 CCGCCTGAAC TTTTGATTCA GTGTTGCTGC AATGGGTGGG TCTTTCTCTG GCCTCTGTGA
182641 ACTCCTCACC TTCCCCACCT CACCACAGGC AATGCTTTC TCCCTTTCTC TCTTTTCTCT
182701 TTTCTGTCTT TTCTGTTACT TGAGACAACC ATCTTGCCCA GAGACCATAT GTTGAAACTC
182761 CTGGTCAGAA GTTTGATTAA AGATGAAAGG GCCTATCTGG GGGCAAGTTT GAGCCTTCCC
182821 AGTTAGATAT TGGGTGCTAA GTGGAGTGGC CAATGTCTAT GTTTTGTCAC ATGTATATTG
182881 CTCTGGCTGA AATGGAAAAC GTTAATTTGG TTACTTTATG TGGCCATTGG GCAGCATCTT
182941 ACAAAAGTGA GAGACATTTA TTTGCCTGTG GTTCCATGAA ACAGAAAAAA GTTGGTTTTC
183001 CTTTGTGTCG TAGCTTGGAC CCAAGGGCTT TGCAGTGAGC AAGGTTGCTA GCGCTGCTCA
183061 GTGAAAGAGA ACCCAGAAAC CTGGCATGCC AGCAAAAGGG TAAAGATTTC TTACCAGTCA
183121 GGCTTCTGGC CTCTCTCT TAGTGAAAAC TGAATGAATG GTAAAAATCA CTGTTTATCA
183181 CCTCTGTAAA GTTTTGATTA ATGGGAACAA GGATTTGTGG GGCTAGTCTT AAGCTGTAAT
183241 GAATCTGGTA TACTTTGTGA TATCAATTTG TCTTTCTGTA TTACTCTGTC ATAAAGAGGA
183301 ATATGGTAGG ATAGAACATG GGCTTAGGAC TCCATAAGCC TGCTGTTCAA GCCAGCCCAG
183361 TAAACTGGTC CGTTGCAAAG TTTATTACAG GTCCCTGGAA AAAAAAAAA TTAAAAACTG
183421 GATGAAGTTT CCTTCTCATC TTGTTTTATG TCCTTTGGAG CTTCACCTTG TAACCACGTG
183481 GCGGTACTTT CTCTTGGTCT CTGCCATCCA GGAACAGGA ATTTTGGGGT TTATGTAATA
183541 GTTAACTCTA AAAATTATCT CAAGCCATTG CAAGCTCAAA ATTGGCTGCT CTGGACCCCT
183601 TCTGGGAAGG GCAATGGAAA CTAACCAGTG TTGTAGCTCA GCAGCTAAGG ATTTGTCATT
183661 TTATAATGGC GGCCAAGGTT CAATCCTGGC TTAGGGAATG AGTACTTTCT GATTGATATC
183721 TGTGTGACCT TTACCATTTG TTGATTCTGT TCTCTTCCCC TCCACACACT GTCTTGAGTT
183781 TTCCTCTCTC TGAGAACCTG GGAGATTATC TTTGGTAAAG TTCAAAAGCC AGAAATAATG
183841 GCCGTGTGGG ATGGCTAAAG TTGAGTAATA AGAAACTTAA AAGGACTCCT TTTTTTTTTG
183901 CTTTAGAGTG CTATGGTTTA TGGTTAAAAG CTTAATTAAA AGTGGATATT CAATCTCTAA
183961 AAGCCTGGGA CTCCTTGGGA AAAGCAGAGG AGGCACCACA GACCCCATTT TGGGAAAACC
184021 TCTGTTTTCC TCATGAAACC CCAGGAACTG GAAGTGGATA GATCCTTCGC AAAATCTAAG
184081 GCTCTGTTTG GCTTTGCATT ATGTTATCTG ATGTTTTTGA CTTTTGGGGG TATCAGAAAT
184141 TACTTTGCAT TATGAGGGAG ATCTGGTGTG TAATAACCAG GTAGGAAATA TACTTCTGGG
184201 GATAGCTAAA GGCAAATATA GGTGAATACT TGGCTATTTG CACTTTTGGA TCACAAGAAG
184261 CATTCTCTTG ACTACCTAGA AGGTATGGAA ATGTCTCCAT CCCCACCGAG AGATAAGATT
184321 CCCAGGGGAG ATGGCTGATC CCCCAAAAGA GGGCTGATTC CCTCTTTTGG GATCCAGGAT
184381 CTGGTATAAA AATGGGACCC TGGCCAGGCA CAGTGGCTCA CGCCTGTAAT CTCAACACTT
184441 TGGAAGCCT CAGAGTTATG AATGTCTCAC CATACTGACA CTTTGTGACT GAGCTCCTCT
184501 CTACCCTGGA CACAAGAGAC CCTAATAATT AGACAGGAAT ATCATTGCCC CTATTTAGTC
```

Figure 2 (Page 57 of 74)

```
184561 TGAAGAAGTT ATAGAAGATG GATCTTTATC CCACTGCAAT CCTTAGGATT AAGGGTTCCC
184621 TGGTAAAAGG GAGTGGGAAA ATATGTCAGA GGCATTTGAA TCAGAGTGAC TCCATCTTGA
184681 ATAGGGGCTG GGTAAAATAA GGCTGAGGCC TGCTGGGTTA GGTTAGGCAT TCTAACCAGG
184741 AGTTTAGTCA CAGGATGAGA TAGAAGGTTG CACAAGGTAC CCGTCACAAA GACCTTGCTG
184801 ATAAAATAGG TAACGGTAAA GAAGCCAGCT AAAGCCCACC AAAACCAACA TGGCCACAAA
184861 AGTGACCTCT TGTCATCCTC ACTGCTCATA TACACTAATT ATACTGCATT AGCATGCTAC
184921 AAGACACTCC CACCAGTGCC ACGACAGTTT ACAAATACCA TGACAACATC TGGACGTTAC
184981 CTTATATGGT CTAAAACGGG GAAGAACCCT TAGTTCTGGG AATTGTCCAC CTCTTTCCTG
185041 AAAAATTCTT GAATAATCCA TTAGTTTAGC ACATAATCCA GAAATAACTA TACGTCTGCT
185101 TATTTGAGCA GTCCATACTG CTGCTCTGCC TATGGAGTAG CCATTCTTTT CTTTTATTTT
185161 TATTTTTTAG ATAAAGACTC GCTCTGTCAC TCAGGCTGGA GTCTGGAGTG CAGTGACGTG
185221 TTTTGGCTCA CTGCAACCTT CACCTCCCGG GTTCAAGCAA TTCTCCTGCC TCAGCCTCCC
185281 AACTAGCTGG GACCACAGGT GGGTGCCACC ATGCCTGGCT AATTTTTGTA TTATTAGTAG
185341 AGATGGGGTT TCGCCATGTT GGCCAGGCTG GTCTCGAACT CCTGGCCTCA AGCGATCCAC
185401 TTGCCTTGGC CTCCCAAAGT GCTAAGATTA CAGGCATTAC CCACTATGCA TGACCCATTC
185461 TTTTATTTCT TAACTTTTTT TTGTTTTTTT GAGACAGAGT CTCACTCTGT CACCCAGGCT
185521 AGAGGCTGGA GTGCAGTGGT GCGATCTTGG TTCACTGCAA CCTCTGCCTC CTGGGTTCAA
185581 GCGATTCTTC TGCCTCAGTC TCCTGAGGAG CTGGGACTAC AGACATGTGC CACTACACCC
185641 AGCTAATTTT GTATTTTTAG TAGAGACAGT GTCTTGCCAT GTTTGTCAGG CTTGTCTCGA
185701 ACTCCTAACC TCAAGTGGTC TGCCTGCCTC AGCCTCCCAA AGTGCTGTGA TTACAGGCAT
185761 AAATCACTGC GCTCGGCCCT TCTTTACTTT CTTAATAAAC TTGTTTTCAC TTTACTGTAT
185821 GGACTAGCCC CAAATTCCTT CTTGTGTGAG TTCCAATAAC CCTTTTGTGT GTGAAAGAAT
185881 TTATGGCTGC TGTTCAGGCT GGAGCAAGCT GGAGCTCATG CTGCTGCTCA GACTGGAGCA
185941 TGCGTGATCT GTGATCCCAG TAAGAGGATC ATGGTCACTC CAGCCTGAAC GACAGCATGA
186001 TATCTCATCT GTAAGAAAAA AAAAATTACT AGAGGGCTTT AACAGCAAAT TTGAGCAGCA
186061 AAAAGAAGTA ATCAGTGAAC TCAAAGATAG GTCAATTGAA ATGATCTACT CTGAAAAACA
186121 GAAAGAAGAC AGAATGAAGA AAAAGAAATA GAGCCTTAGA GACAGGGGAT ACCATCAAGC
186181 ATACTAATAT ATGCATAATG GGACTCCTAG AAGGAGAAAA GTGAGAGGAC AGGGAGAGAG
186241 AATGTTTGGA GAAATAATTT CTCAAAGCTT CCCATGTTTG GCAAAAAAAC ATTAACTTGC
186301 ATACATATTT TAGGAGCTCA ATGAATTCCA AGTAGGATAC ACTCAAAGAG ATCCATACCT
186361 AGACACATCA TAATCAGATT ATCAAAAGAT GAAGAAGATG AATCTTGAGA GCAGAAAGAA
186421 AGGAACAATT CATCACATAC AAATAGTACT CAAAAGATGT CTGGAGTAGG TATACTAATA
186481 TCAGACAAAA TAAACTTTAA GATAAGCATT GTTATAATAA ATAAAGAAAG GTATTTTGTA
186541 ATGATAAAAG TGTCAATTCA TCAAGAAAAC ATAACATTAT AAACATACAT GCACCTAACA
186601 ACAGAGCCCT AATATTCATG AAACAAAACT GACAGAATTG AAGGGAGAAA TAGAAAATTC
186661 GACAATAATA GTTGGAGACA TCAATACCTC ACTAGTTAGA CAAGATCAAC AAAAAAATAG
186721 AAGACTTAAC ACTTGAAAAC ACCTAACCTG ACCTAACAT AAATCTATAG GTCACTACAC
186781 CCCAAAACAG CAGAATAAAC ATCCTTCTGA AGCTCACATG AAACATTTTT CAGGATAGAC
186841 TGTATATTAC TTCATGAAAT AAGTCTCAAT AAATGTAAAA GGACTATAAT AATAGAGTAT
186901 ATATTCTCTG ACCAAAGTGG AATGAAGATA GAAATCAATA ACTAGGCTGG GCGTGATGGC
186961 TCACGCCTGT AATCCCAGCA CTTTGGGAGG CCAAGGCGGA CAGATCACGA GGTCAGGAGT
187021 TTGAGACCAG CCTGACCAAC ATGGTGAAAC CCTGTCTCTA CTAACAAAAT ACAAAAATTA
187081 GCCAGGCCTG GTGGCATCTG CCTGTAGTCC CAGCTACTCG GGACACTGAG GCAGGAGAAT
187141 CACTTGAACC CAGGAGGCAG AGATTGCAGT GAGCTGAGAT CGCGCCACTG CATTCCAGCC
187201 TGGGAGACAG AGCGAGACTC CATCTCAAAA TTAAAAAAAA AAAAGAAACT AGAAAAATAA
187261 GAACAAATCA AACCCAAAGC AAGCAAGAGG AAAATGAAAA ATTTCAAAGC AGCCAAGAAC
187321 AAAAGGCACA TTATGTACAG AAGAACAAGT GTATAGATCA CATATTTCTC ATAGACACAA
187381 TATAAGCAAA AAGACAGTGG AGCAAAATTT TTTAGATTAA TGAAAGACCT ACAATTCTGT
187441 ACCAAGCAAA AAAACTCCCC CCAAATGAGG GTGAAATAAG ACAATTTAAT ACAGAGAAAA
187501 GAGGAAGGAA TTTATCTAGT CATATGTGAG AGTTTTATGA TACATTTTGT ACTGTATATG
187561 TGGATGTTTT CTATTTCATT TAAAAAATCA ACCGTGCAAT TAAATGGTAG ATTGTCTTGC
187621 TTCTTTTTGA TTGACACAGT CATTAACTAA AATATTGTAG TATTTTTTTA TCTCCCTGCC
187681 TAAAGGCAAT AAACATCTAA TCAGCAGACT AGAACAATAA AAAATATTTT TTAAAAGTCC
187741 TTTAGGCAGA ATGATAAAAG TCCCTTAGGC ATATTGAAAT TCCTATTTAT ACAAAGGAAT
```

```
187801 AAACAGTACT AGAAATTGTA ACTATGTGAG TAAACAGATA ATATTTTTTC TCCATAAAAT
187861 GTGGTTGACT ATTTTCACAA AAATAGTTAA CAATGTAATG TGTGATTTAT AGCATTTAAA
187921 AGTAAAACAG GCCGGGCACA AAGGTTCGTG CCTGTAATCC CAGCACTTTT GGAGGCCGAG
187981 GCGTGCAGAT CACTTGAGGA CAGGAGTTCA AGACCAGCCT GGCTAACATG GCAAAACCCC
188041 ATCTCTACTA AAAATACAAA AATTAACCAG GCGTGGTGGT GCACGCCTGT AATCCCAGCT
188101 ACTCTGGAGG CTGAGGCACA AGAATCACTT GAATCCAGGA GGTGGAGGTT GCAGTGAGGC
188161 AAAATTATAC CACTGTGCTC CAGCCTAGGC AACAGAGCTA GACTCTGTCA CACACACACA
188221 CACACACAAA AGAAAGTGT ATGACAACAA CAGTGCAAAA GAAGCGGAAA TGAAAATAAT
188281 GTTATTTTAT ATAAGTGGTA TACTTTTAGA TGAACTACGA TAAATTAATG ATGTATACTA
188341 TAAACTCTAA GGCAACCACT GAAATAATGA AACGAAGAAT TATGGCTAAC AAGCCACAAA
188401 AAGAAATAAA ATAGAATGAG AAAAAATATT TAAGTTGTTC AACAGATGGG AAAAAAAAGA
188461 GGAAAAAGAG AACAAAGAAC AGATGGGACA AATGGGAAAG TAATAGCAAG ATGATAGACT
188521 TAACTCTACC CATATAGATT ATCACACTTA AGGTAAATGA TCTAAATACT CTAATACAAA
188581 AGCAGAGGTT GTCAGATTGA ATTAAAAAAA CAGACAACAA CAAAAAAAAG CAAAAAAAGA
188641 GCCACAACAT GCTGCCTACA AAAAATTCAC TTTAATATAA AGACACAAAT AGTCTAGAAC
188701 ACCATCACTT TTAACCTTAT TTACTCAAAC CTCCTAACTG ATCCCTATTT ATTTATTTAT
188761 TTATTTATTT ATTTATTTAT TTATTTTTGA GACAGAGTCT GACTCTGTTG CCCAGGCTGG
188821 AGTGCAGTGG CACCATCTAG GCTCACTGCA GCCTCTACCT CTCGGGTTCA AGCGATTCTC
188881 CTGCCTCAGG CCTCCCAAGT AGCTGGGACT ATAGCACATG CCACCATGCC CAGCTAATTA
188941 TTATATTTTT AGTAGAGACG GGGTTTTGCC ATGTAGGCCA GGTTGGTCTC AAACGCCTGA
189001 CCTCAGCCTC CCAAAGTGCT GGGATTACAG GCGTGAGCCA CAGCACCCAG CTCCTCTTCA
189061 TTTATTCTTG CTACGCTTCC TCCAATCCAT TTTGTGCATT TGATGATTTT GCCAGTAACT
189121 TCTTTATTTT TCTGGTAAAA TTACTTATGG GTCACTGAGG ACTGGGATGT TCTTTCTTCT
189181 AGAGGGGGTT TGTGTCTGCT TTTGCCAGGA AGCTGGGGTA CCACCAGTCA AGTATTACTT
189241 TAAACTCAAT TCATGAATTG AGACTTTTTT TTTTTTTTTT TTTTTTACGC AGAGTCCTAC
189301 TCTGTCACCC AGGCTGGAGT GCAGCGGTGT GAACATGGCT CACTGCAGCC TCAACCTACT
189361 GAGCTCAAGC AATCCTTCTG CCTCACCATT CTGTATAGCT AGGACTACAG GTGTGTGCCA
189421 CCATGCCTGA CTAATTTTTT AAATGTTTTT TTTAGAGATG GGGCTCACTT TGTTGCCCAG
189481 GCCGGTCTCG AGCTCCTGGG CTCAAGTGAT CCTCCCACCT TGGTCTCCCA AAGTGCTGGG
189541 GTTACAGGCA TGAGCCTCTG TGGCTAGCCA AGACTTTTTA TTTTTTAGCC TAAATGTGTA
189601 TAAAAGTTGG CTTGTGGTTA CAACTTATCA GGATTGATGA TCTCTCTCTC TCTCTCTCTC
189661 TCTGTCTCTC CCCACCTCTC TCACATCCCT TGCTCTGCTG AGAAGCAGAG CAAACATTCT
189721 AGCAGTTTCC AGAGAGTAGG ATGGGATTAC TTCTAGTTTA CTTTTATCAT CCTTTGGGAT
189781 CGCAGTATTA CTGGGAGAAC ACAAGTATCT CTTATTAGAC ATACCACCTT TGTAGAATCT
189841 GGACTTTCAT TTTAGACTTT ATTTGTTTTC TACTATAAGC AATTTAAGTT ACAGATCTCT
189901 CTACACACTG TTTAAGTTGC ATCCCATGAA TTTTGATGTG CTTTATTGTC ATTATTATAT
189961 AGTACAATGT ATTTTGTAAT TTTTTGTGAT TTGTTTGGAG AGATTGATTA ATTAGAATGA
190021 TGTTTAATTT CCAAATATGT GTGTTTTTTT CCTACATTTC TTATTTTTAT TGATTTCAAA
190081 TTTATTTCTA CTGTAGTCAG ATTTAATAAT TCATTTATTT TTATTATTTT CATTTTTTTA
190141 GAGACAGGGC CTTTCTGTGT TGCCCAGGTT TGTCCCAAAC TCCTAGTCCC AAGCAGTTCT
190201 CCTGCCTCAG CCACCCAAAG TGCTGGGATT ATAGGCACGA GCCACCCGTG CACAACCAAC
190261 AATTCATTTA AAAAGTGGGC AAGTGAACTG AACAGACATT TCTCAAAAGA AGGCATACAA
190321 TTGGCCAACA AATATATGAA AGAATGCTCA ACATCACTGT ATTAGTCTGT TTTCATGCTG
190381 CTAATAAAGA CTTAACCTGA GACTGGGGAA TTTACAAGAG AAAGAGGTTT AATGGACTTA
190441 CAGTTCCACA TGGCTGGAGA GATCTCACAA TCATGGTGGA AGGCAAGGAG GAGCAAGTCA
190501 CATCTTACAT GGATGGCAGC AGGCAAAGAG AGAGCTTGTG CAGGGAAACT CCCGTTTTTA
190561 AAACCATCAG ATCTCGTGAG ACTCATTCAC TATCATAAGA ACAGCATAGG AAAGACCCGG
190621 CCCATAATTC AGTCACCTCC CACTGGGTTC CTCCCAGGAC ACATGGGAAT TGTGGGAGTT
190681 ACAATTCAAG ATGAGATTTG GGTAGGGACA CAGCCAAACC ATATAAATAA CTAATCATCA
190741 GGGAAATGCA AATCAAAACC ACAATAAGGT ATCATCTCAC CCCAGTTAGA ATGGCTATTG
190801 TCAAAAAAAC AAAAAATAAC AAATGCTGGT GAGGATGTAC AGAAGAGGGG ACTCTTATAT
190861 CCTACTGGTG GAAATGTCAA TTAGCATAGC CATTATGCAA AATAGTATGG AAGTGAGGTA
190921 GGTTACATAG GGTGGTCACA GCCTCCCTTG AAAGGAAACA AGAAACTTGT CAAATTGATG
190981 GAGAGAACAA ATCTCTTGAC ATTACACAAA CTGCATCTGG GGCTAGTGGT TAGAATATCC
```

Figure 2 (Page 59 of 74)

```
191041 TCAGTCAAGG AGGTAGAAGA GCAGGAGGGA AAATCCCTAA GTTCGTGCAA GTGCAGAAAC
191101 CCACAAGCTG TGTTCTCAGG TTGACATATA CTCATTTTAA TAGTAAGAAA CACACCCTTG
191161 GGTAGAGAAT TAAAATGCTA ATAATACATG TGATGTATGT ACTAGCGTGT ATGGCAATAT
191221 TGCATGCACA TTCAAGAGAC CACCCAAAAC ATATTTAACA ACAATGCCCA TTCCCACCCC
191281 CTCATGGATA ATCACGTAGG ACTCCCATAA CGGGAGTTTC TTCAGTGTCA ATTGGTGCTG
191341 AAGTAGCCGA CCCTGACTCT GCTATCAGCG TGTACTTTCA CCTTGCAATA AACTCCTTTG
191401 CCTACTTTTA CTTTGGACTG GCTTTCAAAT TCTTTTGTGC AGGGAATTCA AGAATCTGAA
191461 CCAGCCCACT GACAACAGAG GTTTCTCAGA AACCTAAAAA TAGATCTACC AGATGAGGCT
191521 GAAAATCTGC TACTGGCTAT TTATCCAAAG GGAAGGAAAT CAGTATACAA AGAGACACCT
191581 ACATCCCCAT GTTTATTGCG TCACTCTTCA AAGAGCTGA TATATAGAGT CAACCCTAAA
191641 TGTTCATTAA CAGACAAATG GATAGAAAAT GTGGCATATA TACACAATGA AATACTATTT
191701 GGCCATGAGA AGAATGCAAT CTTGTCATTT GTGGCAACGT AGATGAAACT GGAGAACATT
191761 ATGTTAAGTA AGATAAGCTA GGATTGGAAA GATAAATACT ACATGTTATC ACTCATATGT
191821 GAAAGTAGAG AAAAATTTTT AGCTCATGGA TTTAGAGAAC AGAACTGTGG GTACCGGAAG
191881 CTGGGAAGGG TAGCAAGGAG GGAGGATAG GGAGAGGTTG GTTAATGGTG ACAAAATTAC
191941 AGCTAGATTG TAGAAATGAG TTCCGGTGTT CTGCACCATT GTAGGGTGCA TATGGTTAAC
192001 TCTCATTTAT TGTATATTTT CAAAAGCTA GAAAAGAATT TTGAATACTC ACAACAAAAT
192061 AAATGATAAA TGTTTAAGGT GATGGATATA CTAATTACTC TGATTTGATT ATTACACATT
192121 GTGTACACAT ATAAAAATAT CACTCTTTAT CCCGTATATA TGTACAGTTA TTATATGTCA
192181 ACTAAAAATA AAAGAAAAAA AGAATATGAT CTATCATGAT GTATATAATCA TGTGTACTTG
192241 AGCAAAATGT GCATGCAGAT ATTGTGTATA ATGTTCTATA AATCATTAG CTCAAGATAA
192301 TAGATAGGAT TGTTCAGATC TTCTGTGTCT TTACTGATAT TTTGTCTAGT TATTGCATCA
192361 TTACCAAAAA AAGGGTGTTA AACTCTCCAA ATGTGATTGT AGAATTGTCT ATTTTGTCTT
192421 TTCTTTTCCA TTTTTACTTT ATGTATTTTG AAACTCTGTT ATGACATTTT GCTATGTATT
192481 TTAAAACTTC GTTATGTATT TTGAAACTCT GTTGTTAGAA TCATACATTT ATGATTATTA
192541 TGTTTTCTTG ATGAAATGAC CCTTTTCTAT TGTCGTTGTT TTTGTTTTTT CTGAAATGGA
192601 GTCTCACTCT GTTGCCCAGG CTGGAGTACA GTGGCACAAT CTTGGTTCAC TGCAACCTCC
192661 ACCTCCTGGG TTCAAGCGAG TCTCCTGACT CAGCCTCCAA GTAGCTGGGA TTACAGGCAT
192721 GTGCCAGCAT GCCAAACCTCT TTTTGTATTT TTATTAGAGA CAGAGTTTCA CCACGTTGGC
192781 CAGGCTGGTC TCGAACCTCT GACCTCAGGT GATCCGCCCA CCTCGGCATT TTTATTTTAT
192841 TTTATTTTTT TGAGACAGAG TCTCACTCTG TCACCCAGGG TAGAATGCGG TGGTGTGATC
192901 TTGGCTCACT GCAACCTCCG CCTCCTGGGT TCAAGCAATT CCCATGCCTC AGCCTCCCGA
192961 GTAGCTGGGA TTACAGGCAC ATGCCACCAT GACTGGCTAA TTTTTGTATT TTTAGTAGAG
193021 ATGGGGTTTT TCTATGTTGG CCAGGCTGGC AACTGACTCC TTTAACAATA CAAAATATCA
193081 CTCTGTCTCT GGTAACACTC TCTGTCTTAA ACTCTATTTT AGCTGTTATT ATTATAGCCA
193141 TTTTAGTCTT TTTATGCTTT CTGTTTGCAT AGTGTATATA TTTTAATATG TTTATTCTCA
193201 AGTTATCTGT GTTTTTATAT TTAAGATGTT TCTCTTCTAG CCAACGTGTT TGGTTCTTGC
193261 ATTTTTAAGT CGATTCTAAC AATCTTTGCC TTTCAATTGA AATATTTACA CCATTAACAT
193321 CTAACATTAA CATTTATTTT TCTTTCCACA GTACACTGGC TAGCATCTCC CATATAATAT
193381 TGAACATAAA GTGTGATAAC TGACATCCTT ATTTCATTCC TACTCTGAGT GGAAAGGGCA
193441 GGGGTGGAGA AAGCATTCAA CAATTTGCCA TAATTATAAT TCTTTTTGTT ACACTGTTTT
193501 CTTCTGCATT AAAAAATATC ATTACATTTT GCATGAATTA TTAGGAGAAA ATATTTTCCA
193561 ATTTTCCTGG AAAATGCCAT AACCACGTCT CTCAATTTTG TTTCCATCTT TCTTCCACAT
193621 TTTACATAAC CTACATAAGA GACACATTAT CAAGTATATT TTACATGGCT TCTCAGTGTC
193681 TTCTCTGTCT GCTAACAGGT TTACCAAGAG ATGGCACTCT TGTATTTCTG GTGGCTATGT
193741 CCATATCGTT TTGCCTTTAA GACAGCGTAA CTACTTCTTT CACCAGTATT AAAGACATGT
193801 ACATTTGATC TGGTTCTTGT GGATGATTTT AAATGACTCA AGCTAATAAT CCTAATTTTA
193861 CCTAAACACT CCATTATTTT AAAATGTATT CCTTTATGCC CACAATAAAC ATTTATTGAC
193921 ATTAGGCTGG ACATTAGGCT TCTCTATGGC AGACATTAGG CTGGACCCTA GCCATATATC
193981 TATTGAGGGA AAAAAAATTA TTTTCTATAT AAGTTCCAG AAAGCCAAGA TGTGTTTTAA
194041 AAACAAAACA AAACATTACA TTCTAAATGC TGTAACAAGA TAAGAAAAAG TGTTGAGGCT
194101 GAGAGAAGAA CAAAGCAGCA AGCAACTCCT GGAAGGACCA CTGCTGCAGA GGTAATAACT
194161 GGTGAACCAT GTTTTGGAGA AGGAAAAGGT CACCAAGAGA AGGAGGGGGT CCAGGGTGTT
194221 CAGAAAGATT GCATGCATAA AGATCAAGGG TAATAAAAAA AATTCCGTAT TATGTAAATG
```

```
194281 TGAAGTTCCA GGACCATGAG CTTGGAGAGC ATGAAGTACA GGAGGAGGGT TGGTTTCAAA
194341 TAAATCTGGG AATGAAACAG TGAAGCCTCT GGCAGAACTC ACATCTCTTT CCTCCCCTCT
194401 TCCTTGCACA TTCCCTTTAT GGAGTAATTG CAGGGATGGG AAAAGTTCAA AACCACCACT
194461 GAGCCTAGGA AGTGCTAGGG TAAAGTGGAG AATGAACCTG CGTGATTTGC TCATCCTAAA
194521 CTAGGTTCTT CTAGGAGAGC CCTTCCCCAT AAAATCTGCC CTCCTCGAAG GGGCCCAGAC
194581 AGCCTAAGCT CACCTCCCAA AGACCCCTTA CTTGCTGACT GAATCTGATT CCACCCAGAC
194641 ATGGCCTAAA ACCCTTCCAT AACTCTATAG CCAAATTCAA TTTTAGACAG GCCTCATACC
194701 AACCTTTCTT CCTCTAAGTC TGCCACCCTA GGCAATTCTC AACATTCTCT ACACACTTTG
194761 GGGCCATAGA CGTGCTACCA AGTCTCCAGA CCTAGACCTG ATGGAGCAGT GCTGTAATGA
194821 GACGACCACT GGCCTTTGAA CCAGACCCTT CTCTGTGGCT CCTATGCATC TCCAACCTGT
194881 TTTGAGCACT GCTGCCAAGA CATCTTTGGC ACTTTGTTGT GAAGTTTTAA AACTGAACTA
194941 ATCTACAAAA CACCTAACCT TTAAAAATTC ATTGTCATTT CATATCATGA AAGATAAAGA
195001 AAGGCCAGGA AACTGTTCCA GGTTAATAGA GACTAAAGAG ATAGCAACCA AATGCAATTT
195061 GTGATCCTGG ATTGAGGGGA AAAAGTGTTG TCAGAGACAT GATTGGGACA GCTGGTAAAA
195121 TTTGAATTTG AATTTAAAGA TAAAGTATTG AGTAATATAG AAGATGATT ATCTGCAACT
195181 TTCAAATGTT TCAGTAAGTA TATATATATA TAAAGAGATA TAAAGACATA TAAATAAATA
195241 GATGGATAGG TAGAGAAAAA GCAAATGTAT AATATTAACA ATCTAGGTAA AAAGTATATG
195301 AGTGTTCTTT GTACTGTTTT TCTGATTTTT CTATATGTTT GAAATCATTT TAAAATAAGA
195361 AGGTTTTTGG GGTTTTTTTG TTTGTTTTTT GTTTTAGAG ACAGCATCTT ATTCTGTCAC
195421 CCAGGCTGTA GCTCAGTGGC CCAATCATTG CTCACTGCAG CCTCAACTTC CTGGGCTCCA
195481 GTAATTCCCC CTACCTCAGG CTCATGAGTA GCTGGTACTT CAGGTGTGCA CCACTGCACT
195541 CAGCTAATTT TTATTTTTTA AATTTTTGTA GAGATGGCAT GTTGCTATGT CACCCAGGCT
195601 AGTCTCAAAC TCCTGCCCCC AAGTGATCCT CCCACTTTGG CCTCCCAAAG TGCTAGAATT
195661 ATAGGCATGA GCCACTGCAC CCAGCCCCAA ATAAAAAGT ATTTATTTT AATTAACTAA
195721 TTAATTTTGA GTCAGAGTTT CACCCTTGTC ACCCAGGCTG GAGTGCAATG CATGATGTT
195781 GGCTCACTGC AAACTCTGCC TCCTGTGTTT AAGCGATTCT CTTGCCTCAG ACTCCTGAGT
195841 AGCTGAGATT ACAGGTGCCT GCCACCATGC CCAGCTAATT TTTATATTTT TAGTAGAGAC
195901 GGGGTTTCAG CATGTTGGTC AAGCTTGTCT CAAACTCCTG ACCTCAGGTG ATCCACCCAC
195961 CTCGGCCTCC GAAAGTGTTG ATGAGCCACC ACACCCGGTC TAAAAAGTAT TTTAAAACCA
196021 CAGTCCCACT CTACCTTGTC CTACACTACC AGGGGCTAGG ATCACCCCAT GTCTTCTAGG
196081 CTATGAGATA GAGGAATCCA AGGAAGAAGA TAAGCTACTT GGTTCCTCTA TAGGGTCTTG
196141 TGTGTGCTCT CATGTGCTCT CTCTCTCTCT CTCTCTCTCA CACACACACA CACACACACA
196201 CACACACACA CACACACATG AATACCAGAG CTATCACTTT CCCAGTCTAG TACTCATCTC
196261 ATCCCAAGGG TTTTGTGTTG TAGTGGTTTG CTCATTTGTT TGTTTTGTTT GTTTGCTTGG
196321 ATTATTCTTT TTCTCTTTTT GCAGCTGAAG GGAGAATTTC CAGGCCAGCC CTTTGGCCAT
196381 TAGAGTTACA GTGCCTCTAT TCAGGCTTCA TAGAGAGACC TGGGATTCAG TAGTGGGGGG
196441 CTTTTATCCA GTTCAAAATA ATGCATTCTC ACCAAGATGT ACTTTGAAAT AAAACAATAC
196501 TAAAACACAA AATTTTATTT ATGCTGAACA TTGAATCACT TTTTTCTGTA TTTTGTGTAG
196561 AAAGTTATAC ACACACAAAC ACATTTGCTC CTGCTTTGTT TATTGGCCCA GGGGTATGTT
196621 TGGTAATACT TCATCAGGCA TGAGTAGTAC GTCTTGGAAG GTGTGGTCTA AAGCCTAGAC
196681 TCCTATCTGC TTCCTTCAGC ATTCTCCAGT GTATCTGTCA TCTGTCTACC TTAGGATGGG
196741 GTCTCCAGAA CTTCCATTCA CATTTAGAAG AGGGCAGCGG CTTTCTATGG AAAATATGAA
196801 CTCTCATTCA TCTCTATTCC TTCTTCTAGC TATGGTCCAG CTCAGCTGTT TGGAATAAAG
196861 TATCTATATG AAGTCTGCGA ATGGTTCTCA GACTGGTTGA ACATTAGAAT CACCTGAGTA
196921 CCTTCTAAAA TTCTTATTAC CCAGGGCATA TCTCAGAATG AGTACCACAG GGTAGGGATA
196981 GGATTAGGGA TCATGATCTC TGGAGTCTGG TTTAGGCACT AGTGCTGTTT AAAACTACGT
197041 TCATGAGGTG GAGGTTGCAG TGAGCCGAGA TGGCGCCACT GCACTCCAAC CTGGGCGACA
197101 GAGTGAGAGT CTGTCTCAAC AACACAAAAC AAAAAAAACC AACTACCCTT GTGATTTGAA
197161 TGTCCATCCA AAATTGAGAA CCATTAGGTA AGGCCAAGCT GTATAATTAA AGAGCAGTTT
197221 TCATTTGTCT GGTGTGGTGG CAGCTTTTTG ATAAGGGAAG TATTGTTGCC ATCCACATAC
197281 CTGAGCCTCA CTCCTGAGAA CACTGGTGTG TATGTTGCTA AAATTCCCCA GGTGATTCTG
197341 AGGTTCCTTC CTGGATAAAA ACCACTGACC CTGGGAATGT ACCCACTGCC AATCTCCTGC
197401 GTAAACCTTG GATACTGGGA AGCCTACAGT TGAAAATATT GGGCTTGAGA TCCTGAAACA
197461 AATCTTGTAT TTCATTAAGA CTAATATTTG GTACAGTGCA GCAAATCAAG GGAATTTTGG
```

Figure 2 (Page 61 of 74)

```
197521 TGGCTGAGTT CTTTTAGAAC TTTTGCATTG AAATAGGTTC AAGCAGCAAT AAGTTAAAAC
197581 TACAACCTCA GCTAAAGGAT TAAAAGACAC GTGAGCTGGG TAGGATGAGG TCTAAGATTG
197641 GGTGTGGCGG CTCATACCTG TAATCCCAGC ACTTTGGGAG ACTGAGGTGG GTGGATCACT
197701 TGAGGTCAGG AGTTCAAAAC CAGCCTGGCC AACATGGTGA AAACCCATCT CTACTAAGAA
197761 TACAAAAAAA TTAGCTGGGC GAGGTGCCAG GCACCTGTAA TCCCAGCTAC TGGGGAGGCT
197821 GAGGGAGGAC AATCACTTGA ACTCAGGAGG CAGAGGTTGT AGTGAGCTGA GATCGCACCA
197881 CTGCACTCCA GCCTGGGTGA CAGAGCAAGA CTCCATTTAA AAAAATAATA ATAATAATAA
197941 CAATAATAAT AATTCAGACA TATCCAGGCA TCAAACAGAT ACCTGGGCA GATGAATAGT
198001 CTTGAGATTC AAGTCACACA TGAAATTTAG GTGGAAAATG ACATTGGAGA AATTTGAGAT
198061 TATGATGAAT GGAAATTTTT CAAAGAGGAA TTTCAGGCTC TGTTCTTGAG GGATAGATG
198121 GACTTCCAAC AGCAATAACA CAGGATTAAT GAGGACTTGG GATGTTACAT AAATTAGAGA
198181 TGTTAGATGG ATAAAGAGAT AAAAGTACTC TCTCTAAGAA CATGGGACCA GAGATAGGCT
198241 CACTTCTAAC CATCAGATAT AACTAGCAGA CTAAACGGTC TAAAAATAAA AATCATGCCC
198301 CACTCCTGCT TAAGACATTT TAATTACTCT CAGTAACTCT TCAGTTTTTC TACTGTGTTA
198361 TCTTTAACTA CAGGGTTGGT CTGGGTGTGC AACACAAGAA AGCCTGGCAT ATACATGGAT
198421 TCAAGTGTAT GCCATGTACA GGTATTCTTT CATGTACTAT TTCATGTATT CTTTTTCACA
198481 TCTGTTTTTT CCTTCATTGA AGTCAATGGC TGATATTAGA TTCTACTATT CATGTGTACT
198541 AGTTATATAT AATTGTTACA AAACAAATTA GCAAAAACTT AGTGGCTTAA AGCAACACAC
198601 ATTTATTATT ACCTAAGGTC TGTGGATAGA AGTTCTGACA TGGCTTAACT GGGTTCCCTG
198661 CTTCAAGCCT CATGTGGCTG CAATCCAGGT GTTGGCTGAG TCTGAATTCT CATCAGAGGC
198721 TTGATTGTGG AAATTTCCAC TTCCAAGCTC CCTCAGGTTT GTTGAAAAAT TCAGTTCTTT
198781 GCACCGGTAG AAGCTTCTTG GTAGAGGCTG ATTCAACTTC TAGAGGCTGT CTGCAGTTCC
198841 TGTCACCCAG GGTGGAGTGC AGTGGAGCAA TCATAGCTCA CTGCAGCCTT GACCTCCCAG
198901 AATCAATCTG TTCTCCCACC TCAGCATCCT GAGTAGCTGG GACCACAAGT GTGTGCCATC
198961 ACACCTGCCT AAAAAACAAA CAAACGAAAA AAAACCCCCA GAGAACTTTG TAGAGACAAG
199021 CTGGTCTGGA ACTCCTGCGC TCAAGCAATT CTCCTGCCTT AGCCTAAAAG TTCTGGGATT
199081 ATAGGTATAA GCCACCATAC CTGGCATATG GCAAGTCTTG AGCAGGACAA ATACAGATGA
199141 TTTATGTCTG TCTTCCATGG TATTCTAGGT TATTGTTGAG ATGGTCCTCT ATTGTCTTGT
199201 TCCATCTATT GATTAGATAA AACGTTGTTC CTTCTGTTAT TTTTCAACAG TAGCTTTTAT
199261 GTGTCTCTCT TTATCTTAAA ATTCTAACCA AAGAGCTGCT CTTTTCTTGG TGTACTTTAC
199321 CTTTGGTTGA TCCTTCTTAA CCTCTTCTTG CCCTCTGGGG CCTAAGATGA GGGCTGTTAT
199381 CAGATGTGAG TCTATGGGAA AGCAAGCAAG AGGTTCTTCA GCCTCCGTTC AGCCTTAAAT
199441 GTCTAGGTAG AAATCAGTCA TGGCCCTTCC AATGTGGTAC AGACCAGATC ACAGAGACAG
199501 GGGTCTCAGC CAAGGTCTTG TGGCCTAAGC CTTATAGAAA TAATGAGTGT TTACTTACTT
199561 GGAGAACTCC CTTGGAATAT CTTTTTTTGT GAACCTGAGG CAACTTTTGG TGATTTCTTG
199621 ATGTCTTGGG AATCTTGGTC TAGAGCCATT TCAACCTGAT TTCTTTTCAT GTCAGTGGCA
199681 TTTTGTGACC AGATAGTAAA TAAGTTCTAT GATGTTCACT CAGAGAAATA CAATGACTTA
199741 TGATGTGAAG CTTCTGTGGT TCAGCCCTTA CTTCATCTTC ATTCCCTCTT ATCTGCATCT
199801 GTCTCCTGCT TGGAACAAA AGTCTGGCTT CATTCTATGA CCCCCACGTT GAGTTTCTTA
199861 GTAGCACTTA CTTTTCAATT AGGAGTGTCC TCACTTCTAT CCATCAGACA TAACTAGCCG
199921 ACTAAACAGT CTAAATATAA AAATCATGTC CTACTCCTGC TGAAAACATT TTAATTACTC
199981 CCCATCATTT AATTTTTTCT ACTGGGTTAT CTTTAACTTC AGAGTTGGTC TTGTGTGCAA
200041 CACAAGAAAA CCTGGCATAT ACATGGATTC AAGTGTATGC CACGTGCATG TATTCCTTCA
200101 TGTACTATTT CATGTATTCT TTTTCACATC TGTTTTTCC TCTAAAATTT ATTTCCTTTT
200161 AAAAATGAAA ATTTTGCATT TGACTAAATT TGTCAAATTT AGTCAAATTT GTTTAAAACC
200221 ATTTTTAAAA TGTTTCCCGA AGTTTTGAGT GAAGTTAGTA CTTCAGAAAA ACTGTTTTGT
200281 ATTTTTCATG TGACCTCAGT GCACTGCTGT GCATTTCCAT TTCTGCGTCC ACACACATTT
200341 GTTTTGAGGA AATATAGGAA CGACAAGATA AAGTTCAAGC TCCTGGACAT TGCATAAAAG
200401 ACCGTCATGA CCTGGTCCTG TTGACTTCCC TAGATTTCCC GCTATTTCCT AAGTTGAGAT
200461 TTTTGGTTTG GATGCTTTGT GTTTTCCTAA AATCAAAATA GGTTTTTGCC TTTTATGATT
200521 ATACAGTAAA TAAATGCTAT TTGTGTGAAA CTTTAAACAA TACAAAAAAA ACCTAAGGAA
200581 GAAAGTCAGA TTCATCTAAA AATCCTTGTG GCCAGAATTA ACTACCTTAG TTATTATTTT
200641 CTCTATCTCT CTCTCTCAAT GTATATTTGG TGTAGGTATA GGGGTGTGTG TAGTGTGTGT
200701 GTATGTATAT ATCTGTTTCT ATTCCTGTAT GTGGATGTGC ACAACGCATC CTGCTTTGTA
```

Figure 2

```
200761 CACTACAGTA CTAGCATTTT TCTAATGTAA TTCAATATTG TTGAAAACAT TTTAAAAAAG
200821 CTTGTATATA TACACACACA TACACATACA TGCATGTATG TACATATACA CATACAGACA
200881 AAAATGTATC CTATGTATAT TCACACATGT ATACACACTC ACACGTACAT AGAGTTTTAC
200941 ATCCATAGTT TATAAATGTT GCTTTTTTTT GGTCACCTTT TTGCTAAGTC TTACACTTTT
201001 TTTTTTTTTT TTGAGACGGA GTTTTGTTGT CATTGCCCAG GCTTAGTGCA GTAGCGCGAT
201061 CTCACCTCAC TGCAACCTCG ACCTCCCGGG TTCAAGCGGT TCTCCTGCCT TAGCCTCCTG
201121 AGTAGCTGGT ACTACAGGTG TGCGCCACCA TGCCTGGCTA ATTTTTGTAG TTTTTTTATA
201181 GAGACGAGGT TTCACCATGT TGGCCAAGCT GGTCTGGAAC TCCTGACCTC AAGTGATCTG
201241 CCTGCCTCAG ATTCCCAAAG TGCTGGGATT ACAGATGTGA GCCACTGCAC CCGGCCAAGT
201301 CTTACACATC TTTTTTTTAC CACTAAACTG TTTACCCAAA CCTGATAACC CAAGTCAACA
201361 GCTATTATGG CTCACACAAT CTTATGTAAA CAAAGATACA GATATATAGA ATTTTCTTGA
201421 TTAATATTCA GAAAAAAATG GAGTCCCTTT ATACGTCCTT AGTATCTGCT TTACTCATTT
201481 AAAAATGTAT TACATTATAT GAAAGTATTC AGGTCAAATG TTATAGATGT GATTCATTCT
201541 TTTTAACTGT GTTATTTTTC TGCAATGACT ATGTATCACA AAGTACTCAG TCTTCCACTG
201601 ATGAAAATTT GGGCTATTTC CAGTTTGTCT TCCATTTTTC TTTCTTCCTC TTGGATTTTC
201661 ACTCAATGTG TTTACTAATT TAGGAAGAAT CAATAGTTTT TATGGTATTA CTTCTCCCAT
201721 TCAAGAATAT AGCATATGGT ATAGTATAGT AGAGTACTTA GTTAATTTA GCCAGATCCT
201781 GTTTTCTGCC CTTTAATAAA ATTCTATCAT TTTCTGCCTT TGAGTCACAT TTTCCTTGTT
201841 CATATAATTC TTAAAAAATG TATAGTTTTC ATTCTAAGGG AACATAAAAA CTTCTTTCCA
201901 TTTCTATTCC TGTCTAGTTA ATTCTACTAT TGGGAAAAGT AACTGTTAAA AAAAATTCTT
201961 ATCTTTCCAG TCAGTTCACC ACATTTCCTT TATACCTTTG TACTTTAATC CCCAGTCATG
202021 TTGAACACTT CTTATTCCTC ACACCAAGCC TCAACGGGTT TGCTCTTTCT GGAAGGTGCT
202081 TCCCCTGTAT TACTGACTTA TTCATACCAC ACATGGAGAC TGGCGCAGCC CTGTTCTGCC
202141 TGGGAAGCCT TCCCCTGATA CCCCTAGTTG GCAGGAGTCT TCATTTGTTC TTTTCTAGTC
202201 ACCTGTGCAA GTTTGTATTG TTCATGTTTA TCATCCTTCA TTCTAGTTGT CTGTCTCTAT
202261 GTGTGGTCTC ATTCAGTGGA CTCTGAACTC TTATGAAGTC ATGTCATGGG TCAGATCTTA
202321 ATAAATTAAT ATTGTCGGAA GCTAATGTCA TGTCTAGAAT ACAGAAAATT TATCAAAAAA
202381 AAATATAGTA TGTTGGCTGG GCGCAGTGGA TCAAGCCCGT AATCCCAGCA CTTTGGGAGG
202441 CCGAGGCAGG AGGATCACAT GAGGTCAGAA ATTCAAGACC AGCCTGGCCA AAATGGTGAA
202501 ACCTCATCTC TACTAAAAAT ACAAAAAGTA GCCAGGCGTG GTGGTGCCCA CCTGTAATCC
202561 CAGCTACTCA GGAGGCTGAA GCGGGAGGAT CACTTGAACC TGGGAGGCAG AGATTGCAAT
202621 GAGCTGAGAT CATGCCACTG CACTCCAGCC TGGGCGACAG TGAGACTCCA ACTCAAAATA
202681 ATAGTAATAA TAATAATAAT AATTGTATGG AATTGAACTG CTCTGATTGG AAATAGCTGT
202741 TTTTTAAAAA ATTATTATTT TTTAAGTTCC TGGGTACATG TACAGGATGT GCAGGTTTGT
202801 TACATAGGTA AACGTGTGCC ATGGTGATTT GCTGCACCTA TCAACCCATC ACCTAGGTAT
202861 TAAGTACAGC ATGCATTAGC TCTTTTACCT AATGTTCTCC CACACCCCCA CCCCATCCTC
202921 CCCCAACAGG CCCCAGTGAG TGTTGTTCCC CTCCCTGTGT CCACGTGTTC TCATTGTTCA
202981 GCTCCCACTC ATAAGTGAGA ACATGAGGTG TTTGGTTTTC TGTTCCTGCC TTAGCTGTTA
203041 ATGTCAGGCC AGAGAGGCTT AAATTTTTAA GGATCTCTGG ACTTTTCTTC TACATTACTC
203101 TTGATGTTTA TAAATGTTAC AACTTCTTTA ATTTCATTAA ATGTATACCT TATTGAGTTG
203161 ATTTAACTGA GTTAACTTTG TTATATGAAA ATCATGATTG GGAGTGAGGG GGTTAAACCA
203221 GCTACAGAGA TCTTGATTGT TGGTGGTGAA GCAATGCAAG AATTCATTCA TTCAGTAAAC
203281 TAATGTTTAT TAAGCGTGTA CTGTCTTAGT CTGTTCAGAC TGCTGTAACA AAATATCATA
203341 AACTGGGTGA CTTATAAACA ACAAAAAATT TATTTCTTAC AGTTCTGGAG GTGGGAAGTC
203401 TAAGATTAAG GCCCTGGCAA ATTTAGTGTC TGGTGAGGAC AGGTAGCCAT CTTTTTGCTG
203461 AGTCCTAACA TGGCAGAAGG GTTGAATAAA CTTCCTTGGG TTTCTTTTAT AAGGACACTA
203521 ATCCTAGTGA TGAGGTTTCT GCCCTCATGG TATAACTACT GCCCAAAGAC CCCTCCTTCT
203581 AATATTATCA CTTTGTGGGT TAGGATTTCA ACATGAGTTT TGAGAGGATA CAGACATTTG
203641 GATCATAGCA CACACCATAG GACAGACACT GTGCCAAGAA TTGTGGATAT AGTGATTCTC
203701 AAAATGAACA AGATCCCCTC AGAGAGCTTG CAAAATCCAG CTATAAAATT ATGCTTTTTA
203761 AACAAATTAT GCAGTTTGAA AAATCTACTC TGAATCTTAC TTGTGGCATT GAATACTTTC
203821 GGCCACTCTT TCCTTATTAT ATTAAATATT TACTCTTGTT TGGGGATCC AGTCTCACCT
203881 ACTTTTTCTA CCAGAACTGG TATCAGCTCA TGCTCTGCCT TATGCAAATT AAGAAAATAT
203941 CATACCTTTT GGGTAAATTA AGCCAAGAAA GTTCTCCTTT CTTCTCTTTC TCTCTTTCTT
```

Figure 2 (Page 63 of 74)

```
204001 TCTTTCTCTC TTTCTCTTTC TTTCTTTCTC TCTCTTTCTT TCTTTCTTTC TTTCTTTCTT
204061 TCTTTCTTTC TTTCTTTCTT TCTTTCTTTC TTTTTCTTTC TTTCTTTCTT TCTTTCTTTC
204121 TTTTTCTTTC TGACAGGGTC TTGCTCTATT GCCTAGGCTG GAGTGCAGTG GTGCAATCTC
204181 AGCTCACTGC AGCCTTGAAC TCCAGGGCTC AAGCAATCCT CCTGAGTAGC TGGGACTATA
204241 GGCATGTGCC ACAACATCAA GCTAATTTTT GCATTTTTTT GTGGAGACGG GATCTCCCTA
204301 TGTTGCTAAG GCTGGTCTTG GATTCCTGGG CTTATGCGAT TCTCCTGCCT CAGCCTCCCA
204361 AAGTCCTGGG ATTACAGGCA TGAGCCACTG CCCCTGGCCA TTATAACTAT TTTCATTGGC
204421 TTATCAGGCA CATGATAACT ATAATAAATC AATAACCAGA ATTTTTAAAT AAAGAAAGGA
204481 AGGAATTGTT TCAACTCTTC CTGCTACCCC TCTATCCCTC AAAAGGGTAG GCTGAATGTT
204541 GTCCTCCAAA GATATCCATG TCCTAATCCC CAGAACCTGT AAATATATTA CCTTATATGA
204601 CAAAAGGGAC TTTACATGTT TAATAAGTTA AGAATTTTGA GATGGGCAGA TTTTCCTGAA
204661 TTTTGCAGAT GGGCCCTAGT GTAATCACAA GGGTCCTTAT AAGAGACAGG CAGAAGAGTC
204721 AGAATAAGAG AAAAATACTT CAAGATGTTA CACTGCTGGC TTTAAGGTGG AGGAAAGGCC
204781 AAGAGCCAAA AAATGCAGTG GTCACTACAA GCTGAAAAGA AAAGAAATG GATTTTCCCC
204841 TAAAGCCTCT GGAGGGGGCA CAACCTTGCC AATACCTTGA TTTTGGCTCA GTGAAACCCA
204901 TTTTGGACTT CTGACCTTTA GAACTGTAAA TAAATAAATA ATTTTGTGTT GTTTCAAGCC
204961 ATCACAGTTG TGGTAATTTA CTACAACAGC AATAAAATAG AATTAAATAC AGAGATCTGA
205021 GGAGTTGAGT AGGATAAGCC TACTCCAGCA GGTTATTTCG GGAGTATGGT GAGACTCACT
205081 AGGATGGCGG AACTCAATTA AGGAAGTCTG AAGCTGATAA GCCAGAGAGG GAAGGCTCTC
205141 ACTTCATTTT ATAAGGGTTG CGTCACACTA GGAAGATCCA ATAGCAACCA CAGTCTCAAA
205201 ATTAATGATT ACAAATAGGA CACAATTCCA AGAGTCGGGA GCCAAGCAGA AAATGGATTA
205261 GGGAAGACAT GGATGATATG AAACAGGAAG GAGGGGTACA AGGCAGCTTC CTGGGAAGTT
205321 GCCAGGGCAG TCACAGTTCA CATTCATTAG GCTGTGGGCA CCAAATGCAT ATGGAAAATC
205381 TAGCTGACTT AACTGAACTC CTGAAGAGGA ATGAACACCT CATTTATTGA GGAGCTACTA
205441 CCAATTAGAA TATGTATTTC ATTTGTTCAA TAACCCCATG AGTACAGTAA CACAATCCTT
205501 GCTTTACTAA AGCGGAAGCC AATTCAAAGA GGTTCAGTGA CTTGTCCAAG CTCAGGGAAA
205561 ACACTAGGAA GTGAATATGG GTCTGACTCC ATCACTGATT TCAGGAGCCC TGCCCTTTCC
205621 TCCACACCAT GCCCCCTTGC TTTCAGAAAA AAAGGCTTGT TGACTGAATG GTTGTATGCA
205681 CAGTTCAAAG CAGAAACACA CGATGACATC TTTTGAGATA CTCTAACAGT GAGAACTTGA
205741 AAATGAAGTT AAAAATTAAG CGGCAAAACC AAGCCGAGGC TTTCTGAGAA AGTGGGGCCA
205801 AACCTGTTGC CGTCTGACTG CCACGTGGCT CACTATTTAT CCCTGTAAAA ATCTGCAAAA
205861 GTATTTGAAA GGGAAGAAGG GACAGAAAAC TCCCTCCTTT TCCAAGTTAG CCTTATAGTC
205921 TAGGGCTTAA AATACTGGTT TAATGGTGAA GGTAAGTGCT TTTCTTCTTT TTGGGTAGAA
205981 GGATTATTAC TAACTTACCA AAGGTCCATT AAGGGGAGGG AACAGTTTTA GGAGAAGTCA
206041 GAGAAAAGAC ATTAACAGCA ACATAAGGAT CTCCATCTGG TAATATTGCC TAATTCCAAA
206101 ATGAAGAGAC TCTCTGAAAA AGATAACTGA TTCAATGAAG ACCCTAGGGC AAGGCTTGAG
206161 AAGCCACTGG TACCAATGGA CACTGTGGAC AATGGTCATT TCTCCAAGGA CGCTGTGAGT
206221 ATTAACTGTG ATGCTGTGAT TAGTCAGACT GGGATTGGCT GTGGAATGAA ATACTGATCA
206281 GAACTGACAA GATTTGTGTT TGGGACTGTG GCTAACGAGT CTTTTCAGAC TTCTATATGA
206341 ATTTGAAATG GTCTCTCAGG AAAAGGAGAA CATGGCCGGG CCTGGTGGCT CACGCCTGTA
206401 ATCCCAGCAC TTTGGCAGGC TGAGGCGGGC AGATCACTTG AGGTCAGGAG TTTGAGACCA
206461 GCCTGGCCAA CATGGTGAAA CCCTGTCTCC ACTAAAAATA CAAAAATTAG CAGGGCGTAG
206521 CGGCGCGTGC ACCTATGCGC ATGCATAGTT CGCGTGCCAG CTATTCAGAA GGCTGAGGCA
206581 GGAGAATTGC TTGAACCCAG GATGTAGAGG TTGCAGTAGT TGAGATCATA CCACTGCACT
206641 CCAGCCTAGG TGACAGAGTA AGACTCTGTC TCAAAAAAAT AATAATAATA AAAGAAAAGG
206701 AGAACATGAC CAAAGTTATG AATAAGACTG AAGGCAAGAA AATTGTACGC TTGTAGAGAT
206761 CACCTAGCTT GTTGCCCTCA TTGTACAGCT AAGAAAAGGC ACCCAGGGAC ATTGTGGTCA
206821 GCACCAATTT CTCAGAAAGA TAGGCAGATG ATGAGAGGGC CCTCAGTTTT TCTAACACTG
206881 AAGGAATTGC TTCTATGTTT TCTGGTGAAC TCCTCCCCAC TCATCTTGAG GATTCCAGGC
206941 CAGAAGAATC CACTTTAAAA AAGAAACATT TAAAACCAAT TTAACAACCA ATCAAAGGCA
207001 CTTTTATAGA AATACATTTC ATTTGCTGTT GGCCTGTATT TATGGATCTG AGAGGGCTAG
207061 ACTGCCAATA TTGTGACTGT TTATTATTAT TGCTGTTGCT AGTATCTAGA ATATTATACA
207121 ACATATAACA CTTTGCAATT TACGAGGCAT GTCTCATACT TTTGTTTTCA CTCCAAACTG
207181 CCCAGTGAAG TAACATTATC CCAATTCTTC CTATGAAACA GTGAAAGCCC TAAGAGTTTT
```

```
207241 TGAAACTTTA CCTGGTTTAC TCAATTTGGG AATGGCAGAG CAGAATTCAG TCCTTGAATA
207301 TCCTCCCACT GCAGGTTCAT GCTCTTTGAT CTAGGTGTAA CATTTACTCT GAGTAAACTA
207361 GGACTCTGGG CTAACAGAGA TGAAGCAAGA CAGGCTGGAT ATTAGGAGAA TCTAAGAGCA
207421 ATCTAACGAC CATTATAATA AAATCATGAG TTCTAGACTT AAAAAAAGGG AAAAACCTGT
207481 TTTTTTGCTT ATGCGTATAC CATAATATTT ACATTATTTA TTTTTTTCTC AAATTCAACC
207541 TATACGGTGT CAAGTAATTT TTTTTAATAT AACATTTTCC TTTAACTTAA TTTCAATTCA
207601 TTTTTCTGTG TCTACTTACA ACTTTGGCAC TAGAATTCAC AATTTTTTTT TAGAGGTATA
207661 TCTCCTTAAA GGGAAGGGTT CTGACACTGT TACATGTTCT CAATTGTTTG CAAATAGGTT
207721 AATAATTATT CCAGTGTCTC TAAGTACATA TCAACCATGC CAGTGTTCAG CCTCCATAAT
207781 TTTATTAGCT TCTGTGCTTA TTTTGGAAAA ACATTTCCCA TTACCATGAA AGACCTCAGT
207841 TTAGGATGGT TTGGTATGTT AGCCTGATTT CTGCATTCGT CTCATGCAAA GGAAAATAGG
207901 AAACGAAGAA CTGAAATTAC CTATTGATAC AAAATCAAAG TAGCATTTGA AACCATAAAA
207961 CTTAAGTAGG GCTTTTCATC CTTTCTCGTT AGACAGCAAC AGAGAATGGG AAGAAAAACT
208021 AAAGTGATGG GTTTGTGATA CAATTCCAGT AACATAAAGA GCAAGGAGAA GTAGTTTTGT
208081 TGTGTTTATG TTTAATATTC AAAGCTCAAC CTAAAAGTAT TTTTCATTAT CAAACTTCCT
208141 TCTAGAATAA ATGATTAAAA CTTGATTTAA AATATACAAA TTCTCCTTTA TAATACCTCA
208201 AAATGGAGCT ACCCCATTGA GTTTAAGCT TGTGATTAAA ATATTACGAA AACAAAGGGG
208261 AAGTTGTAAT AGGTAGAACA AGCAGTAGTC TAGGCATTAG GGGATCTGGT GCTGGCTCTG
208321 TGCATCATGT GGTTTCAGGC AACTTTCAA ATTTTCTACG CAAATTTTCT TATCAATAAA
208381 ATAAACAGTT GGGCCAGAGG ATCTCTGAGT CTCTTTCAGC TTTCAGTGTT TATAAGATTG
208441 GAGAAGTTGG TGGGAAAGCT TTAAGTGGAG TGTAAGTAAT TGCAGCTGCA TGTACAGTTA
208501 AAGAGTTGCC TTCAGCCAAG CCACGGGATC TTGCATAAAA AGTGAAATCA AATAGAAAAT
208561 GGTCCAAACT CTGGGTTTGA CCACAGATGA CTTCAGCTAG GATCTGAGTG TAGAGCAATG
208621 AGCTGAACTC CTGATATCCA GATGTTAGCA AGACTTGGAG GCCTTCTAAG GCAGAGCAAC
208681 AACCAGTATC TGTCCTGGTG CTGACCTGAT CTTACTAGCA ATTGGGCCTC CATTTGGGTC
208741 CATTGTACAA AACAACAACA ACAACAACAA TAAAATCTCC AAACACCCAA AATTCAAAAT
208801 TTAGATGGAG AGATACTATT CCCAGAATTC TAGAGATATT TGGAAAGCAG AAAACTATAC
208861 TTGCCATGCT GATGAAGTCC AATTATTGCT CTTTTAAATA CATTTAGCTA CTTCTGAATA
208921 TAAAATGAGT ATCTACTAAT TATTTACAAA ATCACTTGGT AAATATAGAA AGTCACAAAG
208981 AATGAAGTGA TCATCCTGTT TTGTAACCCA GAAATAGTCA TTACTGGCAC TTGTGTGAAT
209041 CAGTTTCTAT TCCTGTATGT GGATGTGCAC AGCGTATCCT GCTTTGTACA CTAGAGTACT
209101 AGCATTTTTC TAATGTAATT CAATATTGTC GAAAACATTT TAAAATAGCT TCCATCACAA
209161 TAATCTATCA AATTGACTTG CCAGACTCTC ATTATTAGGT TAATTTATCT CTAACATTAT
209221 GCAGTCATGA GTAATACTAC AAAGGATATT TTTGGACACA ATTTTTCATC TATGCCTTTC
209281 TTTATAATCC TTCATCCTAA GGTCACAGAT TATGAATATC TTTAAAGTAC GGACAAGTCT
209341 TTTAAATTTT GTGTGCAAAA ACAGTGCAAA GCCTTGAATG ATAAAATAGA GGTTTGATAT
209401 ATGTGTTTTT TTGTTTGTTT GTTTTGAGAC GGATTCCTGC TCTGTCCCCC AAGCTGTAGT
209461 GCAGTGGCAC GATCTTGGCT CACTGCAACC TTTGCCTCTT GGGTTCAAGC AATTATCCTG
209521 CCTCAGCCTC CTTAGTAGCA GGGTCTACAG GCATGTGCCA CCACACCCGG CTGTTTTTGT
209581 ATTTTTAGTA GAGATGGGGT TTCACCATGT TGGCCAGGAT GATCTCGAAC ACCTGACCTC
209641 AAGTGATCCA CCCACCTCAG TATCCCAAAG TGCTGGGATT ACAGGTGTGA GCCACTGCAC
209701 CCGGCCGATA CATGTGTTTT TAAAGTCACA GAAATTTCAG ATGTCTTGAA GGATTTTAAG
209761 CAATTTAAAA AATAAAGTCA TAGAAGCTTC AATTTAGGAA TGAATGGAAA ATTGATGATA
209821 TTCTTAGGAT ATGGATTTTT CCTAAAAGAA ACAAATGTAT GCATCCCCAA AGATAATTTG
209881 ATTAGTATAC AAATATTAAA TTAAACATGT CCATATTTAG AGCCATGAAT TCTCTTTGCC
209941 TGTCACAATA GCTGGATTTA TTCACAATTG TAGTAATTAG TCCCTGTTCA TTATAATTTT
210001 CTAGGTGATA TGAAGACTTT GTCAGTCCAA GCAAGTGTCC ACATTGTGTG TAGCAAACAT
210061 GAGAATAAAC ATTTTAAACT TTTAAATGTA ATACATATTA GTGTTATGTA ATGTCATCCT
210121 TCATGTTCGA AGGCACATGG AACATTGTTC TGGTGGTACA GAGGGGAGAG AAACACCATC
210181 AGAATGAAAG GAAAGACCGC TCTGGAACCT TCCTCCTTAG CTCTTGAGCT TAGTTTAATT
210241 GTCCTGTCTT ATGGTCTGCT ACAAGCAATA CCACTCTTCA CCTTCGCATG CTTCTCTGTG
210301 GTTTGATAAA GTACATGCAA TTTTTCATTT AATTCTTCCA GCTGCACTAA GAAAGGAGCC
210361 TTATCTTTAT TGAACAGATG AGGAAATGAA TGATTAGAGA ATTTAAATGA CTAGCTCTAG
210421 GTCACACAGC TGGAACTTAC AGCCAGATTT CCTTTTAACA ATCCTGTAAC CAAAAGCATA
```

Figure 2 (Page 65 of 74)

```
210481 CCAGTAGTGC CCCATAAAAT GTAAGTTATA GAGCTGTGTT GGGTCAAAAC TTTTACTGAT
210541 GCTAAGAGGA GGCAACATTA ACAAGGGGAA ATTATTTGTG TATTATGTTT TGGATTATGT
210601 TCTCTCCATA GATAAAAGAC TGTCGTAGTA AAAGAGATTC AGGGCACAGG GAAACTCCAC
210661 CACAAAGCGT GGTACCATTT CCCACAGAAG CTAAATGGAC GGGAAGCCTG CCACCAGGAA
210721 AGGTAAAGCC ACTGCTCTTG TTTGCAGGCT ATGTTAATAA GCTGAAGCTT ATTCCGACAC
210781 ATTTACACAT CTCTGCATCA CACTGACCCT TCGTAAAGAT ACTCCCAGTG TAACATTGGA
210841 GCCAGCTCCA GCCCCTGATC CTGTTGCTTT TTCCTTAGCC CCATGAAATC ATCTGCGAGA
210901 AATTAAGCCA AATAAGCAAT AAATCCTGGG ATCTAGGGAG TGGAATAAGT TTTGGGAAAG
210961 TCTTTTTTTT TTTTTTTTTG ACTGAGTCTT GCTCTGTCTC ACAGGCTGGA GTGCAGTGGT
211021 GCGATCTCGG CTCACTGCAA CCTCTGCCTC CCGGGTTCAA GTGATTCTCC TGCCTCAGCC
211081 TCCCGAGTAG CTTGGACTAC AGGCACACAC CACCATGCCC AGCTGAATTT TTGTATTTTT
211141 AGTAGAGATG GAGTTTCGCC GTGTTAGCCA GGATGGTCTC GATCTCCTGA CCTCGTGATC
211201 CACCGGCCTC GGCCTCCCAA AGTGCTGGGA TTACAGGCAT GGGCCACCAC GCCTGGCCCG
211261 GGAAAGTCAT TTTAAACCAA CCTATGTATG AATCCCTACT ATAATATTCT CACCAAGCGG
211321 CTGGCTCTTT CTCCTGAGCT TGGAAACCTC CAGTAAAATG GAAATAATTA TTTCCCAGAC
211381 CACCACTCTT ATCTGTGAGC TTTTTTGGCC ATTAAAAATT ATTTCTTCCA TTATATTTTT
211441 ATCTGTGTCT TCACAGGTTT TCTCTTTCTT TCACTTTAGT GCTTTTCTTC AAATAAGCAG
211501 GAAAAATCCA ATCTATCATG CACATGGAA CCCTTTCAAT ATTGGTCTGT GGTTGTTCCA
211561 TTTTATGGGG ATGCTTTTAA AGAAAAAATT TGTCCTTTCA ATATATTGAA TATCTTCCAG
211621 CACCACATCA CCTGCAAGCT TTGTAAAAAT AGTTCTACAT ATTAATTTTT TTTTTTTTG
211681 AGATTGAGTC TCATTCTGTC ACCCAGGCTG GAGTACAGTG ACATGATCTT GGCTCATTGC
211741 AACCTCTGCC TCCTGGGTTC AAGTGATTCT CCTGACTCAG CCTCCCGAGT AGCTGGGATT
211801 ACAGGCATGC ATCACCATGC CTGGGTAATT TTTGTATTTT TAGTAGAGAT GGGGTTTCAC
211861 CATGTTGACC AGGCTGGTCT CAAACTCCTG ACCTCAAGTG ATCCACCTGC CTTAGCCTCC
211921 CAAAATGCTG GGACTACAGG CGTGAGCCAC TGCACCCCAC GTAGTTTTTT TTTTTTTTA
211981 AGTTGAACAT ATGTGAAGGC AGGACCTAGT GACACATAGC AATAACATTT CCAAGTAGAC
212041 ATTACACTAG GGAATTAGTC AAAGTGCTCA TTTAAAGTAC CATCTCTCAA ATGTATTAAA
212101 AGAGAATCCT TGGATGTGCA ATACCTTAAT TCAAAGGCAG CTCGTTATGT ATAAACTCTC
212161 AAGCTTTGTG ATAAACAAAT GTGCATAACA GATGGGACTA TTGACTTACA GCCCAGGGAA
212221 TTTTATTGAC GCTGAGAAGG TTATGTGACT GGCTCTGCCA CTGTCATCCC CATTCACTTC
212281 ATTTTGGAGC AATATGACAT AAATGCCTTA CATGTGGGTT TTCTCTATTT ATCATGTGTT
212341 TCCTATCCCC TTGAAAGATG GCCATATTTG CTTTACTTGG TTATAAGATC CCATATTCGC
212401 TGTCTTGAAG CCAACCAAAT AATTTGACAA AGTGGGTTTG TAGTGCTGGC TATTTTGGTG
212461 AAAAAAAGAC AATGAGACTT CATGTGTCAT CCAAAGTTCT ATCAGATCGA GCTGTGAGAG
212521 AAAGGAAAAG AAAGGGGTCT CAGTCAGGAT GCTCACTGCA TACATCTGTG TTGTTGTCTA
212581 GGTCCAGATT TCTGTTCATT ACGCTATGGG CTGGCTCTTA TCATGCACTT CTCAAACTTC
212641 ACCATGATAA CGCAGCGTGT GAGTCTGAGC ATTGCGATCA TCGCCATGGT GAACACCACT
212701 CAGCAGCAAG GTCTATCTAA TGCCTCCACT GAGGGGCCTG TTGCAGATGC CTTCAATAAC
212761 TCCAGCATAT CCATCAAGGA ATTTGATACA AAGGTAAGTA TGATGGAAAA TAGGGCTCTT
212821 TGTTGAGAGA AAAACTTTG AAAGGAAGGC ATAGATCTTG ATTCTGTGGA GTATGGAAGT
212881 ATACATTTCC AATGACAAAT TAAAACTGAC TGGAACTATT TTTCTTTGAG ACATTGCTTA
212941 CTTCAATAAT AAAAATAAGA TTTCATTGAG GTTATTATGA TTATAAGGTG GGGGAACTGT
213001 AGAGTTAAAT GTGAAAAATT TAAAATGGA ACAGTTTATG TGATGTCTTC AATGAAAAAC
213061 TAGGTATTAC CTGGGCACAT TCTTATAGGT TACTCAATCC TATTCAGTTC TCTGCCTGTT
213121 TTATTGTTTC TGAGCAATTT TATATCCCTG TAAATTCTAT ATAACCAATA GAAATGCAAA
213181 CGATTCTTGT CCATAGCTTT GCAAATAAAT TTTGCCAAGA GAAAAATCAG TTAAAACTTT
213241 TCTCCACTCA CCTCCCAGTT GAATTAGCCA ATTTTGCTGT TTGTTTGTTT GTTTGTTTTT
213301 TGAGATAGAG TCTTCCTCTG TCATTCAGGC TGGAGTGCAG TGGCATGATC TCAGCTCACT
213361 GCAGCCTCCG CCTCCCGGGT TCAAGAGATT TTCCTGTCTC AGCCTCCCAA GTAGCTGGGA
213421 GTAAGGGGC ATGCCACCGC GGCTGGCTAA TTTTTGTATT TTAGTAGAG ACAGGGTTTC
213481 ACTAGGCTGG TCTCGAACTC CTGACCTCAG GTGATCCACC CGCCTCGGCC TCCCAAAGTG
213541 TTGGGATTAC AGGTGTGAGC CACTGTGCCA GGCTCTGCTG TATATTTAAA GTCTATTTCA
213601 GCATTGCTTC CTGCTTGTGT TATGCGTGAT TCTTTGAGTT TTCCTTTGAA CCAGTTATAA
213661 CATCTTACTT ACTTCCTCCA TTAATCAATG AGTTAAATAA AATCTTTGTT GTATGTTTAT
```

Figure 2 (Page 66 of 74)

```
213721  TTTACATTTA  TATGAAAACC  ATGAATTTAC  CCAATTAAAA  AAATTATCCT  TTAAATTATC
213781  TTGTACTGTA  CATTTCCCAT  GTCATCCCTA  TAATTCATGA  TTAATGATTT  TATTACATTG
213841  GACCTAGCTT  ATTTACAATG  AGTACATAAA  TTTATTGTCT  CCAGTCTTTC  CTCCATTATC
213901  CCGTCTACAT  ATCCACACTG  AGTAGATTCA  CTACTCAGGA  ATCTTGGACA  CCTTCAAGTT
213961  GCCAAACATG  CAGTGTTCAC  TGGACATGCT  GTGTTCCTTC  AGAATTTGGG  CCTGCTTCTC
214021  AGCACACTCA  CATCTGCTAT  CAATGACCCA  TGGAAAGTTT  TTGCCCTGAG  CAAGCCAGAG
214081  TCCCTGTTAG  TTTCTTCCAA  ATGCTACAAG  TTCACTTTTG  CTATTTTTTC  CGATGAGATA
214141  AAATTTTCCT  TTTTGACTTT  CTACAAATCA  TAGTCATTTT  TCAAGGGATA  GTTCAAGTAT
214201  TGCTTCCTTT  CTGGGACCTT  CCCAAATTAT  TATTTTCTCC  TCTCAAAGTC  TCTGTTTTAT
214261  TTATGTTCAT  CCTCAAATCT  TGATTCTCAC  ATGAATCATA  TACCTTGTAT  TATTTATAGT
214321  TTTTTTGAGT  AGGTAAAATA  TTTCATATTT  TATATTCTTT  GGCTCTCTAC  TTTATAGCAT
214381  GATGCCAGAT  ATTTAGGGGC  CTTACTGCAT  TTATTTTTTA  TTTTATTTTA  AAATCTATTT
214441  TATTTTTTAT  TTATTTATTT  TAAAATCTAT  TTATTTTTAG  GTAAATATTC  AGGTAATATA
214501  ATTTATGTAA  TTATTTAGGA  ATTTTAGGTA  GTTATTTTAA  AATAATTCAA  ATTATTTATT
214561  GAGTTATATC  AGAAGAATGT  GATCTTATTC  ATTTGTAATA  TGTGTTTTAG  GAACTCAGTT
214621  CAGCCAGGGC  AGACCATAAT  TCCCAAACTT  GACTTTTCTT  TTTAATTAGG  CACTGATTTT
214681  GGTTAAGAGT  TCAGTAAAGT  TTTGTGTGTG  TGTTTTAAAA  AATTCTTTGA  TATAAGAGTC
214741  AAGATGTTAC  TCAACTTTTA  CTAGAAGCAA  AATAGAGGAA  GTGCTTTCAC  AGATGAAATA
214801  TCTCTCAATG  TTTTCTTCCA  TTTACTTCTT  CCTATTATTC  ATCTATATAA  TCATTTTCTT
214861  TACCTCTTTT  CTTCATTTCT  TCTGTTTTTC  TCTCCTACTA  AGACAAGCAA  ATTAGGGGTA
214921  TAATTGGTTA  TTTGGGAAGG  TAGGAAGAAT  ACAGAGAGAA  ACAAAAATCA  ATATTTTATA
214981  CTAGGGTCTC  ACTAACCTCA  AGCAACTCTG  ACTGTAAAGT  AGATTTTCAT  AATAGGACTT
215041  CTTGACAAAG  AGTTTTCCTA  TTTTTCCCCC  AGGCCTCTGT  GTATCAATGG  AGCCCAGAAA
215101  CTCAGGGTAT  CATCTTTAGC  TCCATCAACT  ATGGGATAAT  ACTGACTCTG  ATCCCAAGTG
215161  GATATTTAGC  AGGGATATTT  GGAGCAAAAA  AAATGCTTGG  TGCTGGTTTG  CTGATCTCTT
215221  CCCTTCTCAC  CCTCTTTACA  CCACTGGCTG  CTGACTTCGG  AGTGATTTTG  GTCATCATGG
215281  TTCGGACAGT  CCAGGGCATG  GCCCAGGTAT  CCAGATACTT  TCTCATTCTT  GGTGGGATCC
215341  AGATTTCTGA  ATTCTACAAA  ATATCAAAGG  TCTTAATGAT  TTTCATTTCA  GGGAATGGCA
215401  TGGACAGGTC  AGTTTACTAT  TTGGGCAAAG  TGGGCTCCTC  CACTTGAACG  AAGCAAGCTC
215461  ACCACCATTG  CAGGATCAGG  TAAGTGTGCA  CAGATGGGTC  ATAGCTTTGT  CATCTGTTCC
215521  ATCCCACTGT  GTCTTATCTT  CTATGAATCA  AATGGTTTGG  GGAAGAGAGA  GAAAAGTAC
215581  TGCTGAAAAA  TTCAACAATA  TAAGACACTT  GCATCACAAA  TAGGAAAGAT  GCATCTGTGC
215641  AGTAAAGACA  TTGAAGCTTA  GAAGTAGAAA  AAACCATTGT  GAGCTAGGTT  TCAGCTCAGA
215701  AAAGCCTTAG  TAGTCAGAAA  AGCCTTAGTA  GTCAGAAAAG  CCTTGTCGGA  AAAAGTTTAA
215761  ACCTTTAAGA  ATTGCACACA  TGGAAAAAGA  TCAAGTAAGC  TATATATACA  CCATCTTAGC
215821  AATGATTTTG  AAGTGAGAAT  TAAGGCTACC  ACAGCTCCAG  GTGGTAAGGA  GAGAAATCAG
215881  GCTGAAGAG  TTTGAAGTTT  CTGTATTATT  CTAAGCTCTT  TACTATTCTA  TTATGAGCTC
215941  ATTAATTCTC  ACAACAACCC  TCTCATATAA  GTACCATTTT  AAATTCTTAT  TTTACAGAGA
216001  AGGGAGTTAA  GGAAGGTGGA  GATTAAGAAA  ATTGCCCAAA  TACAAATAGC  CAGCAGGTGG
216061  TAGGTCTGAG  ATTTAAGCCC  ATGCAGATTT  TAGCCCCAGA  GCAGACATTC  TCAATCACTA
216121  TGCTAGACTG  CCTTTCCATG  GTATGTGATC  CTACTCAGGC  CTCTACAGCT  TTATCATTGC
216181  TGTTCTCCCC  AGCCTGTCGT  GCTGAGAGTA  TATACTCGAA  GAGCAGAACT  AAAATTCCAT
216241  CCAGCTTCTC  ACTCCTAGGT  CCACTACACA  GCTGCATCCT  GCAGACTTTT  ACCTCAAGCA
216301  ACCCTCCTGC  GTTCTTGCTT  CCTTCCATCA  TAGTTGTAAC  CATCTCCTCT  ATTTGCAAAT
216361  ACTATCTGCT  GATCTCTCTC  TTCTAGACTG  GTTTCTTTCA  ACCTTCTTCC  CACCAAAACC
216421  AAGTTAGCTT  GCTAAAATAA  AGATGGCGCA  TTTTTACTCA  CCCGCTTGAG  AATTTTCAAT
216481  GTGTTCCTTC  ATGCTTACAG  AGTAAAGCCT  GACCTCTTTA  TTGCATGAAT  ACAAAGTTC
216541  TTAGCCATCT  GGCCCAACC  TTGTTCCACT  CAACTCCCCT  GTGCAAGCAT  GGCTCCAGTG
216601  GCACTGGACA  TTGGCTGCTC  TCCACATAGA  TCTGCACTGC  ACTTCCCTCT  GGCTCTGCTC
216661  CCGTTAGTTT  ATATGCCTGG  AAAGTTCTTT  GCCCTGTTC  CTTGTGCCAA  AATTCCATCT
216721  ATCCTATTGC  ATAGCTTATG  TAAAAACTTC  CTAAACCTTT  TTTTTTTTTT  TTTTTTTTT
216781  TTTTTTTTT  TTTTTGAGA  CGGTGTCTCA  CTCTTCCGCC  CAGGCCGGAC  TGCAGTAGCG
216841  CTATCTCGGC  TCACTGCAAG  CTCCGCCTCC  CGGGTTCACG  CCATTTTCCT  GCCTCAGCCT
216901  CCCGAGTAGC  TGGGACTACA  GGCGCCTGCC  ACCATGACCG  CTAATTTTT  TGTATTTTTA
```

```
216961 GTAGAGACGG GGTTTCAAGC CAGGATGGTC TCAATCTCCT GACCTCGTGA TCCGCCCGCC
217021 TCGGCCTCCC AAAGTGCTGG GATTACAGGC GTGAGCCACC GTGCCCGGCC AAAACTTCCT
217081 AAATCTTATA ATTATTATCA ATTTATCCTC AGATATACTT CCACGTACAT TGTAGTTTTA
217141 TTATATTTAT ATTTTACATC TTTTTTTTCA AATTGCAGTT TGGGACCCAT TAGTGAGTCA
217201 TAAAATCCAT TGAGCGGGTT AAAATCATTA TTTTAAAAAA TGAGTAGAAT AGAATAGAAA
217261 TTGTTGGAGT GCATTGGACA TGGTAAAGTT AAATATCGAT TCATGAAACC ATCGTTTGAG
217321 GCATATGTGT GTGGTTGTAT GTACAAGTGT TTATGCATAT TGGTGTGTGT GTTATGTTAC
217381 CCTGTAAAAT GCATTTCTTA CTATAGGTCT CTGTGAAATA TGTGTCTTGT TGTTTTTTAA
217441 TGTAGACTTC AAAGCCTAC ATGGCATTTC ACTAGTGACA ATCAATTTTA TTCACATTTT
217501 TCTCTCCAAT TGGACCAGAA GCTCTTTGAG GGCAGGGGCT GTATCTTACC GATTTTTGTA
217561 AGTCTTTCAT TTCCTGCCCC TAGCCTCATA TTAGATCATG CAAGAATGCA ACTGTAATCA
217621 CAAGAAAATG CTAATGGGCT GTGATAGCAG AGAGTTACTG TGACAAACTA AGGGATTTAG
217681 ATTTGGTCAC ATTGGTGTTG AGGAGCCATT GAAGAATCAG AGAGTGTGTT ACTATTATTT
217741 GTTAATTTTA ATTATATCAT ATTACTTTAC TGGGGAAAAT CTGTGAGCTA TTTTAGAAAT
217801 AAATACTCTC ATTGCCCAAT AATTCTAAGT CTGCCACCTC ACTGTTGGGA CATTGTTTAG
217861 GGAGGCCACG AAGTCTCAGC CTTTGATATT TTCATAAGTG TTTTTCTCCC TTTTTCCTTT
217921 AGGGTCAGCA TTTGGATCCT TCATCATCCT CTGTGTGGGG GGACTAATCT CACAGGCCTT
217981 GAGCTGGCCT TTTATCTTCT ACATCTTTGG TGAGTCACTT TCTCTTAAAT CCTAATGCCT
218041 CCATTTCCTG AGCATCCATT TTGGCACCTA CACCACCCAC ATTCTTCCTA TATGAAAGAA
218101 AATGTCCTTT ATCAAATGGA AGATGATAAA AAATGTCAAC GGTTGGTATC ATTTTTAATC
218161 TAGTCACACA ACCTGATTAA CACCTTCCTG GTGGTTCTGG AAGCCACAC GCAAAAGGTA
218221 GAGGAGTTGA CTATTCACAT GGCACCCACC GACTTGTGAT GCAGTCTTGT CCTTCCATAT
218281 CAAGCACCTT CTGCAGAATC TCTACCACCA CATCTGAAGT GCCTGCTATA TGCAGTTAAG
218341 ATGTCAAAGA TAGTGAAGTA CATTTTCAAT GTGTCTTCAT ATTTCATTAT AATTATTATT
218401 TCTGTCCAAG ATGCCTTTCA CCTGTTCTCT ACCAAGTTAA TCTTGCAAAG TTCAATTCAA
218461 ATGTTCCCTT CCCCATGGGC CCTTCCAGGG CTTACCCTGT CAGATTCTGG CATTCTCTCC
218521 TTTATGATAT TTCCTCTCTA GGTTATGTTG GTGTGTAATT ATTTATTTCT CCTTTTCTTT
218581 CCACTAGACT GTGAAATGCT TGAGGCAAGG AATCCATTCT ATGTTTTCAT CACTTGGGTG
218641 TCATCATGGT GCCTGATTTT TAGCTTTAAA ATAAAAGAAT CAGTGAATCC AGTAATTAGA
218701 GGGGATTTAA AGAAAACTAG TCCTCAGAAT CTTTTAACAT AGAATGTTCT TCAAATAAGG
218761 AATTCCAATA ATAAGACAAT TTTCTACACT TGATTTGTT TTTATAGCCA AATGGTGTCA
218821 TTAAATATAG TCCTGGCCTG AATGGCTTTC TCATTAATGA TGCTAATTAT TTTGGTTTGT
218881 ACATGTTAAC CAGGTATTGT ACAAAAATAT TTCTTTTGGG AATCCATAAT GGATGTATGG
218941 CTTGAATACA AATAATACTG TCTCTTGTAA GTGCATTGGA AATTTTTCCC TGCCACATGA
219001 TTTCATGGAA GGTTGTTTCG TGTATGTATG ACTGCAAACC TGACTATTCA GATCTTCCGC
219061 AACAAGACAA CTTATGTGTG CATTAAGAAG TTGCTGCCTA AAATACATAA CACTGTAATC
219121 ATTGGAGACT TTAAAGTAAT TAATCAGCTA TGCAATGCCA CGCTCCTGTT ATCTCCAGAG
219181 GGCTCTGACA TTGACAAATG GTGGCTTTCT ATTTGAGACG TAATATCTAA AAAGCTTTAA
219241 CAGGTTTGTA GAAGGATTGA AAGAAAGAAT GGGAACATTT AGGTCCTTAT GGTAGAATAA
219301 GCATTAATTG ATTAGTGTGT AGAAGGGAGA GGCATGCCAC TTCAGAGGAA ACTTCCTTCC
219361 CCCAGTAAAC AAATCTACCT AAAAACTAAT TTTATCCCTT CTTCCCAGGT AGCACTGGCT
219421 GTGTCTGCTG TCTCCTATGG TTCACAGTGA TTTATGATGA CCCCATGCAT CACCCGTGCA
219481 TAAGTGTTAG GGAAAAGGAG CACATCCTGT CCTCACTGGC TCAACAGGTA CAGTGCACAC
219541 CTTGTACCTG TGGCCCATGC AGAGGTCTCT AGGGCAGGGT GTGGATCTCC TCTGAGAGGC
219601 ACCATCTTGG CTGCTCTAAT ACTCATGCTG ATTAGATCTT TCTTTTCAGC CCAGTTCTCC
219661 TGGACGAGCT GTCCCCATAA AGGCGATGGT CACATGCCTA CCACTTTGGG CCATTTTCCT
219721 GGGTTTTTTC AGCCATTTCT GGTTATGCAC CATCATCCTA ACATACCTAC CAACGTATAT
219781 CAGTACTCTG CTCCATGTTA ACATCAGAGA TGTGAGTTTA CTTCCTATAC TTCTACGAAA
219841 ATGATAATGG TAATAAGGAG AAACAGTTCT GTGTTACCTA TTACATTCTG GCTTTACATA
219901 TAACCATTAA TTTAACCTTC ACAATGACCT TGAGAGAGGC ATTGTTATAA TTCCCTTTTC
219961 ACAGATGTGG AAACAGGACA CTTAGAGGTG AGATAACTTG CCCCAGGTTG CACAATACTA
220021 AGTGATAGAG CTGCTGCAGC ATCCATATTC TTAACCACTA TGCTATACTA CCACACCAGC
220081 TGATTCCAAA GCTTCTTTTA GAAATAATAT TGCTGGGCCA GGCATGGTGG CTCATGCCTG
220141 TAATTCCAGC ACTTTGGGAG GCCGAGGCAG GCAGATCATG AGGTCAGGAA TGCAAGACCA
```

Figure 2 (Page 68 of 74)

```
220201 GCCTGACCAA TATGGTTTAC TAAATATCAT CTACTAAAAA TACAAAAATT AGCCAGGTGT
220261 GGTGGCAGGC ACCTGTAATC CCAGCTATTC AGGAGGCTGA GACAGGAGAA TCGCTTGAAC
220321 CCAGGAGGTG GAGGTTGCAT TGAGCCAAGA TCATGCCACT GCACTCCAGC CTGGGCGACA
220381 GAGTAAGACT CCGTTTCAAA AACAAAAAAC CAAGAAATT AATATTGCTT TTATCTGGAG
220441 CCCAGAGTGA TGCAGCTTCT GGCCCTCTTA TCTGAGACAG TGTTCTTTTA GTGTGAAAAA
220501 GGATGCTAAT TTTCCCCCAA ACAACCCACA GTATCATGGG GGTAAGTTAA TGGCTGGTCT
220561 GTGTAACTGA CAAATTTTGG TGCTAACGTA TCTCTATAAC TACTCTGTAT AAACTTCCTT
220621 CCTTCAGAGT GGAGTTCTGT CCTCCCTGCC TTTTATTGCT GCTGCAAGCT GTACAATTTT
220681 AGGAGGTCAG CTGGCAGATT TCCTTTTGTC CAGGAATCTT CTCAGATTGA TCACTGTGCG
220741 AAAGCTCTTT TCATCTCTTG GTAAGGATAA GCGTGTGGGC CCATTTAACC AATCCCTTTT
220801 CTGCACATGG TCTCAGAGGG TTCCTGACA GCATGTCCTC ATTGCCCAGG GCTCCTCCTT
220861 CCATCAATAT GTGCTGTGGC CCTGCCCTTT GTGGCCTCCA GTTACGTGAT AACCATTATT
220921 TTGCTGATAC TTATTCCTGG GACCAGTAAC CTATGTGACT CAGGGTTTAT CATCAACACC
220981 TTAGATATCG CCCCCAGGTA AGAGCTCTAC CTGTTTTTTC CCCTCCTCCA GACCCCTCCA
221041 GAGGTGTTAG ACCTCAGTGG TCGCCGTGAA ACTCTTTAAT GTTACTGACA TTGCACTAAT
221101 GGCAGAATGA CAAATAACTA CAAATATCTG TCTGTGGCCA TTTTTAGAAC AACAAATGTG
221161 GCATTTTTAG AACAACAATT TCCAATCTTG GCCAGTAATC ATTTTGACAA AAACCTTCCC
221221 AAGCTTCCCT AACAGAGATT GAACTGTGTA TGCTGGGAAA AGGCCCACAC ACAGGTGATT
221281 TGGAAAAGTT TCCATGGTGT TGTTCATATT AGCTACCACA TATATATATA TATATATATA
221341 TATATATATA TATATATATA TATATATATA TACAGTCACA ATAAGCCAGC TCCTGTGCCA
221401 AGACTTGCCA TATATCAACA CATCTAATCC TCACAGTTAT ATTAGGTAGG CCCTATTGTT
221461 ATCCCCATTT TATAAGGGAG AAGGCTGAGG CACAAGGAGG TTAAATGGTG TGACTATGGT
221521 CACATAAAGG CAGAGCCAGG ATTTGGACTG GGGGAGTCTG GCTTTGGAGT CTGTGTCCTG
221581 CCCGTTGCAC AAACTGGCTT CTACACTGAG CAGCCAGGGT AAAGAAACGT GGTTCCCAGA
221641 GAGACTGCAT TGCTCCCTGG TTATTGACTT GGTAGATTGG TAATTTCAGG TTTGGCAAAT
221701 AGACATTGCC CTGAATGTCT TTAGGTGAAT GAAAACTGC ATTAAGCAAA ATGACTTTGC
221761 CATTAGAGCT GAATTGCATT AAAGTTGAGT TGCTGCAGAA GCTGTAGGTG GCTTTCTATA
221821 TAAAATCATT TATAAAATCA TCTTCCCATA GATATGCAAG TTTCCTCATG GAATCTCAA
221881 GGGGATTTGG GCTCATCGCA GGAATCATCT CTTCCACTGC CACTGGATTC CTCATCAGTC
221941 AGGTTGGGTC AGTTTATTGA ACATCTTCAA GTGGCAGGTA TTGTTTTAGG TGTTGGAGAT
222001 ACACACGGTG CTCTAAAGAT CTGGATGGCA ACACAATTAC TCTATTTACA TGAGCCTCTA
222061 AATCAGACTC TGGTAGGTCA GATTTCCCAG AGGAAGAAAA ATATAAGCTT ATTTTCTCAA
222121 GATGAATAGA TGTTAGATTG ATTAAAATGA GCTGTTCCGG TGCAGAAGAC AGCACGTATG
222181 ACTTCCTAGA GGTACATGAG CATGAAACAG TTCTTAGTTA TGACCAGAAT GAAAGACACA
222241 TGTCAAGGAA TAGCAAGAGA CGAAGACAGA GGGGCAAAAG AAGATCATGA AGAATATGTT
222301 CAGACTAATC CAATTTTTAA AAAATCACAA AAGGGAAACA AAGTGTCCTA GGCCAGTTTA
222361 AAGATAATTT AATGTCTGGA AACAGATCGG CTGTGAGACA TTGCAAGGAG GCTTGCTCGG
222421 TGTTTGGAAA TGCAGGCTCA TGAGGAAGAT GAAAAGACAG ACCCAGGCAG GGATGGAAGG
222481 ACTGACTAGA ACCAACTTAC AAAGAGAAGT TTTGTTTTTA CTACATTTCT ATGTGATCAA
222541 GTTCCCAGGT TAATATTTGA CTAAACTGCT AGGAATCCAC TGTGACTATA ATGCTGGAAA
222601 TGACTTAGTA GGGCTTTCTG AGGAGGGTCA CACAGAAGAC CAAAGAGAAC TCATGTTGAA
222661 TTGAGATGGG TTATAGTGAT AGTTGTCAAC AGCCAATACA GAAACAAAAA AAAACAAAAC
222721 AAACAGCAAC AACAACAACA ACAAAAAAAA AAAACAGAGA AGACACAAAC ACAATGCCAC
222781 AATGCCATTT TAGGCATAAT TTTAAATGAG TAATATTATA TGTTGAAATC CAAATTTTCA
222841 GAAAAACATT AGTGTATTTT ATTTTGTTT AAAGAAATAA CCATCTCAAC TCAGAACCCC
222901 ATGTGCATTT TGGCCATTTT GTTTCCAATA GTTTCATAAA CTTTCTTAAG TAACTACTGC
222961 ACATTGTTCC TTATATTCCT TGTGATCAAC ATTGCAATAC ACAACTGGGA GGGCTACTAG
223021 AACTGGTGTA GAAGGAACTT GTGAGATTGA TCATTTCTC TGTTTTTTAC ATCTAGGATT
223081 TTGAGTCTGG TTGGAGGAAT GTCTTTTTCC TGTCTGCTGC AGTCAACATG TTTGGCCTGG
223141 TCTTTTACCT CACGTTTGGA CAAGCAGAAC TTCAAGACTG GCCAAAGAG AGGACCCTTA
223201 CCCGCCTCTG AGGACATAAA GTTACAAACT TAAATGTGGT ACTGAGCATG AACTTTTTAA
223261 ACATTTTTTA CTTCTCTCCA TATTCCTGAC CATAGACTCA GCAGTTCTTA ACTCTGGCTG
223321 TGTGTTAGTC TTCCCTGGGG AGCCTTTATA AGACACTGAT ACTTGGGACC CACTCCAGAG
223381 ATTCTGAATG AATTGGTCTG GGGTGGAACC CAGATACTAC TAATTTTTAG ATACTCCTTA
```

Figure 2 (Page 69 of 74)

```
223441 GAGGTTTCTA GCATGCGCCC GGGGTTGACA ACAGCTGGAC AAACTTGAAA AGTCAATTCA
223501 TGTGGCCTTT GAATTTTCCT CATTGGAAAG TACTAAATAA ATAAAAATTC ATGTGAAAAT
223561 GATCACTGAT AAATATCTTC ATGGTGGGGC AGGTTATTGG ATGCAGAGAA GATCTGCTCG
223621 GAATTGTAGC CATATGTTAC AGATCTCAGC ACCGATCAGA ACTGTAAAGC TATAATCCCC
223681 AGAATTAAAG TTTTTATTAT TTTTTATACA TTGTAAAACA TAGACGTTTA TTTATGTGAT
223741 TAAATTCTAT TAAAATTTAC ATGCTAAAAT AAAATAGACC ATTTTCAAAT TATTTAGATC
223801 CAGATATTTC CATCAGATTA AACAGATATT TATTTATCCT AGCCCAATTG CAAGAGATTA
223861 ATGATGAGAA AATGACCAAT ACAAGATTAA ATAAATGAGG TTAACTTAGA AATCAAGGAC
223921 AGAAGATA GAACTGGAAA GCTTGTATTG TGAGAAGAAT GAATGTGAAG GAAGGCAATG
223981 TAGACACTTC CAGAAGGGAT AGCAATATAG TTTAGACCAT ATAATGAAAA TTGGAGAGAG
224041 ATGACAGAGA CACTTTCAAG TGAAATGACA ATTTATATGG GGGAGAAAAA TATTGAAGAC
224101 ATAACAAGAT GAGAAAAGGC ATAGAAATGT ATCACATACA AGGCATAGAA GTGTATCACA
224161 TACAAGAGAA GTTCCTTTTG AGCGTAGAAA AAGATAATTT AACCTTCTTC ATATTTTTCT
224221 TACTTTCCCA AGATACTCAG ATAGGCAGCG TCAACTCTAA CAGGAATTAA TTTGGCTCCT
224281 AACACTTAAG ACATATCCTT TAGTTTGTCT CCTCACACAG AACTGATTCT GGTTTTGCCA
224341 CAACATGTCT AGAGAAGAAG TTCCCACCAT ATTTAAATC CTATTAAAAA ACTGCTTGGA
224401 CAAGAACCTT GGGCTAATTC AGCAGATGAA GAGAATCTCC TAATGCAAAT CAATGGGTAT
224461 TTTTGAGCAA GTTTTTCAGA AAAACAGAGT GTCAGGCCCT GAGGGTGGTA CTAAGATGAG
224521 AACATTGATT TTGCCTTCAT GATATTGACA ACACAAAGAG GAAAGGGGGT TTGCAGAAAA
224581 CTAAAAGAAG AAGTAGAAGA AAAAAGAAAG ACATAGTATA ATAGGTAGTC AAATTATGTA
224641 CAGAAAAAAG AGGAAAAAAA ACCAAAAAAG GGTGGGGGAC AGACAACCCA ACTAAAAAAT
224701 GGGCCAATGA CTTGAACAGG GACTTCATAA AAGAGAAAAT GTAAGTGGCT CCTTAACATA
224761 TAAAAAGATG TTCAACTTCA TTAGTCATTA CAGAAATGAA AATCAAAACT ACAATGAAAT
224821 ACCACTATAA AATTAACTAA TGGATAAAAT GAAAGGAGAT GGAAAACAAA ATGTTGCCAG
224881 ACATGTGGAG CAACTGGAAC TTTCATACGT TACGAATGTG AACTTTGGAA AGCTGCTCGG
224941 CAATATCTCC TAAAGCTAAA TGTACAATTC CAGTGACTCA GACATTTTAC TTAGAAATGC
225001 ACATATACAT CCATAAAACA TGTACAACAA TGTTCATAGG AGCACTATCT GTAATAGCCT
225061 GAACAGGAAG TTGTCTGTTA AAAAAAGAAT GAGTAAATAA ACCACGGTCT ATTTGTATAG
225121 CAATGAGAAT TAACAGACCC CAATATATAA TAGATGAATG GGTCTCATAA GCACAATATT
225181 GATTAAAGGA AGACAAAACG CACATTCTTT TAAAGGTTTA TAAAATACTT TTTAAAAACA
225241 GCTACAACCA ATCCGTCCTG TTAAAAATCA GTGAGCGATT TCCCTTGTGC AGGGATGGGG
225301 GTTGTGGCTG GATGGATGGT ACTTAAGAAG TGCTCCTGGG GTACTAGAAA TATTTTATTT
225361 CTTGACTTGG ATGTGTGTTT ACTTTGTGAA TATTGTACAT TTATGATTTG TGCACGTTTA
225421 TGAATGTAGA AAATAAAACA GAAAGCAAAT TCAAAGTATC ATCCTTTTGA GAGCTTCTGC
225481 TCTGACTTCG TTTTGACCAA TGGAGCAGTT GGGAAGGGGT CTTGGTCCTT CGGTCCTTTG
225541 CTTTTTTTTT TTTTTTTTTT TTTTAGACAG AGTCTCACTC TGTCGCCCGG GCTGGAGTGC
225601 AGTGGCTCGA TCTTAGCTCA CTGAAAGCTT TGCCTCCCGG GTTCATGCCA TTCTCCTGCC
225661 TCAGCCTCCC CAGTAGCTGG GACTACAGGC ACCTGCCACC ATGCCCGGCT AATTTTTTGT
225721 ATTTTTTAGT AGAGACGGGG TTTCACCATG TTAGCCAGGA TGGTCTCGAT CTCCTGACCT
225781 CGTGATCCGC CCACCTGAGC CTCCCAAAGT GCTGGGATTA CAGGTGTGAG CCACCGCGCC
225841 CGGCCCCTGG TCCTCTGCTT TCATGTTCTT CTTGGTCCTG TTCCTCCTCC TCTTTTGTTG
225901 GAACTTCCAG TATCAGAGCA GGAAGGAAGG CAATGGGTCA ATCGATGCTG TCAGCTTTTG
225961 GATCAAACTG CAAGTTCTCA AACAGCAAAA TTAATGAGCT CAGGCTTTGA AGAAACCATG
226021 ACCCTGAAAG CATCAGTTGC TTCCAATTGC ATCAGTTGCC ACGGGTGATA AGAACAATGA
226081 TGACTCAGAA TGCCTAGGTT TTCCCAGCAG CTTCTCTGAG GTTTTCCCAG CAGCTTCTCT
226141 GATTGATTCC TGACAGATGA CTTCGGTGTG TCAGACTTTC AGGGTATCTT TCCTTATGTG
226201 ATGGTTTGAG GAAGAGTTAC CATTCACATT CCTAATGGCT TCAGAATAGA TGCAATTGTG
226261 AACTGATAGG AAACATTTCT AATTCATCTC CCCTCCCCAT CCCTAAAGGA TTGTTTCTAA
226321 CAATAGTCAT GAAAATTAAT TCACTTTTCT CAAATAGTTT ATTGTCATCT ACCTAATGAT
226381 GAGATGACTT ACTTTTCTC CTTGACTGTT AAATATTATG AATTATATTA ATGTATTTCT
226441 TAATGTTGAG CTTTCCCTTG AATATTCTTT TGATGTACGA CAGAATTTGA TTCACTAATA
226501 GTTTATTTAG GACTTTGGCT GATGTACTGA TATATGAGAT TGGCTCTGTA TGCATACATG
226561 TGTTTTGTGT ATCTTTTTTG TGTCTGGATA TGGAGCTTAT GCTGATTTCA AAAACAAGAA
226621 AGGAGAACTT TCCTTTTTCC CCATTACTCT GAAAAGATT GACTAGAATG GAATTTTTAT
```

```
226681 AATTGCTGTT GTTATTTGAA AGCTTGAAAG CATTGGTTTG TAAAAATCAT GCAGGCTGAA
226741 AGCCATTTTG AGGAGACTTT GATAACTTTC TCAATTTCCT TCAGTTACTG GTCTTTTAAG
226801 GGGTTTTATA TTTTTCTTTG ATCAATTTTG ACCATTTATG TTATCTTGGA GGATCATCTA
226861 TTTTACACAC TATTTAAAGT ATATTTGCAA AAATTCAACT GTTTTATCAG GCTATCTTTT
226921 TAATAATATA TTCATTTTAT CTATATCTGA GGTTTTAGCT TCTTTGTACT TCTGACCCAA
226981 TTGCATGTGT GCTTTCTTTC TCCTTCATTA GACTACTTAG TCATTTACTA ATTTTAAGAA
227041 TAGCTTGTCT TTTATTTATT TACTTATTTA TTTTTGAGAC GGAGTCTCAC TCTGTCACCC
227101 AGGCTGGAGT GCAGTGGCGC GATCTCGGCT CACTGCAACC TCCGCCTCCC GGGTTCAAGT
227161 GATTCTCCTG CCTCAGACTC CCGAGTAGCT GGGATTACAG TCATGCACCA CCATGTCTGG
227221 CTAATTTCTG TATTTTAAT AGAGATGGGG TTTTGCCATG TTGGCCAAGC TGGTCTCAAA
227281 CTCCTGACCT TAGATGATCT ACCCACCTTG GCCTCCCAAA GTGCTGGGAT TACAGGCATG
227341 AGCCACTGCG CCCAGCCCTG CTTGTCTTTT TATTTTATAT TTGATTAGCT TTATCTTTTA
227401 TCAAGCTTAT GTCCTATTTC CCTTTGCTTT ACTTCATATA AATTTGTTT TGGATAGTTT
227461 ATTTATTTTT CATTTAATTA TGAAACAGGT TAAAGCTTAG AGGAAAATTG CTCCTCTAAG
227521 TCCACTTTTG TGGGCAGATT ACATTTGCT GTGTTGTGCT CCCAAATTCA TTGTTCTTTT
227581 AATGCTTTAT TTCTCAAGTT AATAACCTAT ATAGTAAAAA AGTGGCTGTT GACTCTCAGC
227641 TTTTTTTTTT TTTTTTTTT TTTTTTGTA GATACAGGGA TCTTGCTGTG TTGCTCAGGC
227701 TGGTCTGAAA CTCCTGGCTT CAAGGGATCC TCCTGCCTTG GTCTCACAAA ATGCTGGGAT
227761 GACAGACATG AGACACCATG CCCAGCCATG TCTCTCTCCT TATATATAAT AAGAAAACAG
227821 ACACACTGAG GCATCCTATC ATCTCACTCT TGGTTTCACT ACTGTTCTCT GGAAGTTTTG
227881 CTCTGACCTT TTGCAGTTAA TGTATTAATT TTGCATTGAG TAGTTTCCAT AGAAGAATTA
227941 TAGCATTTGC ATTCTGTTGG GTATTATACT TTTCACTGTT ATTTGAACAT AATTTGAGGG
228001 CTGAAACCAA GATGAGGCAA GTGAGGTGCC CAGGAAGCAA TATTTAAGGA GGCATCCTTT
228061 CTTAGGCTCA TGCAAGAACA GAATTGGCAC ATGAGAGTGA GTGCCTCCTT AATTTTGAGT
228121 GCTGGACACT TCTTGCTCAC TTAGCATACC CCTGGACAAT GAAGTGTTTT TTGTTTTGTT
228181 TTTTCATGTC CATCCTTTAT CCTTCTTCAT CTCAAAACAT TTCAATGGAG TATTTTTTTG
228241 GAGCAGTACT TGGATGAGCC TCTGAGTCCC ACAGTAGCTG AGAATTTATT TCATAGTACT
228301 CTTTATGATC ACTGTGGAGC CTTAAAACAT TGTAATATTA ACTTAGCTGG GAACAGAAAT
228361 TTTGTTCCAC AATTTGTCTT ATTCAGAACA GTATTGACTT CCTGCTAGTC TCTTCTGATG
228421 TCCAATATGA GGAAGTCTAG TTAGCCAGCT ACTTTTTGTA GGAGAGCTAT GTTTAGGCTA
228481 GGTGCTATAG GATTCTCTTT ATCCTGGAAT TCCTTCACCA AGATGTGCCA AGGTGTTAAT
228541 CATTTTCTCT TGCTTTTTGG CTGGTGGTCT TAGAGTTTCC TTCGATTTTG TTTTATTTAG
228601 TGATTGTCCT CAATTTGTTT TCTTTACTAA GAATCTCTCT TCTATTTATC TGTATGGTAA
228661 AACCTTGTTG CCCATCTTTC TGGTTTCTGC TGACTTTCAT TTTTGGACCT TTTACTTTGC
228721 TTTCTCCATG GACTTTTTGG TAGTGGAGGC AGGCAAACAC TTTCCAAAGT CTTTCTCAAT
228781 TTCCATCAAT TTCAACTTAT TTCCTAAAAT TGCCTCAGAA TGTGCCTATG TCCACAATAT
228841 CCCTCCTTCC ACTTTAGAAA GGAAAGGCAT CCACACTTTA TTTAGGTGCA ATGCCTGAAG
228901 TGTAAACACT TTCTGGTTGT CAACAAAGGA GTACTTCCAA ATATTGGTTT GGGGATAACC
228961 TGCTAATGAT TAACACATTC ACCTTGGCTC TTGGTTTGCC TGCTCCCTCT TCTTTTATCT
229021 GCTGTGTGTA TTTTTTTTAA TCACTGAGAA TATGCACAGT ATTGTATGTT TTATTATAAG
229081 AGAGGACTGG CCAGAGTGGG AATGTTCTGA ATTCAGAATA ACTGAAGCAG TACAGGATAG
229141 GAACTCATTC TTTCAAATGA AGCTGGCATA TTTTCCCAGA GCACCAAATT TCAATATATA
229201 TTTAAAAAAC TTGATATGAA TGATACAATA AAGTGGTTAG AACTTTTATT AAAATAAACT
229261 TATGTCATGA AATACTTATT CTAATTATAG TCACTCTTCA TCTTATTTCA TCTTATAACA
229321 TGTTTAATGT TTTCTTTTAT TTACAAAACA ATTTATTTTT TGATGAAAAG TTTTAGAAAT
229381 CAAGTTAAAA ATATTCAAAG GAATGCCTAA AGTTTTCAAA ATTCTTTTAC ATGTTGTACA
229441 ATCAAAAGAG TCTGAAGACC ATTTAGCTAT CCAAATTGTT TATTTTAAG CAGTATCCCT
229501 TCTAATATTT ACTATTTATA ATCCTTAAAA ATTTGCCTTA GCACAGGAGA ATTGCTTGAA
229561 CCCAGGAGAC GGAGGTTGCA GTGAGCCAAC ACAGTGCCAC TGCCCTCCAG CCTCGGCGAC
229621 AGAGTGAGAC TCTGTCTCAA AAAAAAAAA AAAAAAAAA AAAAAGGCC AAAAACAAAT
229681 AAACAAACAA AAAATCCGC CTTAACATTA TTTGTTCATT AAAAACTTTC TTTAATACTA
229741 CTAGTTTCCC TTTCCTCTCA GCCCATTGTC ATATTTTGAT TTTTATCACT TGCTTTGTAG
229801 GACATATGAG GTTTTTGTTT TTTTTTTTTT TTGGAGATGC AGTCTCCCTC TGTTGCCCGT
229861 GCTGGAGTGC AATGGCGCAA TCTTGGCTCA CTGCAACCTC TGCCTCCTGG GTTCAAGCAA
```

Figure 2 (Page 71 of 74)

```
229921  TTCTCCTGCC  TCAGCCTTCC  AAGTAGCTGG  GATTACAGGC  ACCCACTACC  ACGCCTGGCT
229981  AATTTTTGTA  TTTCTGGTAG  AGACGGGGTT  TCACCATGTT  GGCCAGGCTG  GTCTCGAACT
230041  CCTGACCTCA  AGTGATCCAC  AATCCTTGGC  CTCCCAAAGT  GCTATGATTA  CAAGCATGAG
230101  CCACCTGCCC  AGCCAGAATA  TATGTTCATT  TTGAGTCCTT  TAACAAAGTC  ATAAGAATTT
230161  TAGGAATTCA  GTTACTTTCT  TGAGAAAATC  TCTGAAAAGA  TGCCAATAAT  TTGTAGCCAA
230221  TTATATTGAT  TTCTCTTTTT  CATATTGAGA  ATTGTTTTTT  AAAAAGTTTG  TATGTGTGAA
230281  GATTTTTGCA  CTGTAGTTAA  AGAAACCACC  TGTGTGTTGG  TTAAGCCATA  AGTACATGTA
230341  TTCAAATAAA  TTGAGGTGGG  GTTACTCTGA  GAATCAAAGG  AAAACCTGAA  GAAACAGGCA
230401  GCCTCAAAAG  GTCTTAGCTG  TAGCAACTTG  CTCCATTGTT  GAAATAAATA  GGCTTGAACT
230461  TGTATTTTCC  CTCTACTCAA  CATTTAAGGT  CTCAGAAGAT  AATATAATTG  GTGAAATTTA
230521  AGTAAAGTGC  TCACTCTTTT  GCTTTAACAA  ACCCTAGAGA  GCTGGTAGGC  AGAGCCTCAA
230581  CAGACCGTTT  TAGCTTCCAA  AGGGAGTTCA  GGACACCATG  ATTCACGACC  ACAATACATC
230641  ACACATAATT  GAGAAAGAT   AGTTCCACCA  AATAAAGTTG  AAATGCTGAC  AAGAAGGGGT
230701  AAGAAATCTT  GGAAATAGGT  TTATATAAAA  TTTATTTTTT  CCTTTTTTAT  TGTTATGGAA
230761  TAGGACCAGT  TCTACTTAAG  CCACCCATTT  GCCAAAATAA  AGTGAGAATC  GTTTCTTTTG
230821  GGGACTCCTC  TTTGTAGCTC  CAAGTGCCAC  TAACAATTCT  TAGGACCTGA  GCTATAAGCC
230881  AGGTGATTTC  AGTTAATATG  ATCAATTATT  TCATTTAAAT  GGCTCTAATG  TGCAGAGGGA
230941  ACGGAGCCCA  TCAGCATTCC  CTGCAGGGAA  CTGCAGTGGC  TTTTATCAAC  TTGAACAGCT
231001  AGCTTTCAAC  TGTTTTGAAA  TCACTTTCAG  GGTGGTCATG  TAGTTGCTTT  TTTGAAATCA
231061  GAAGATGATT  CTGCCTCTTT  TAATATGTGA  CTCCTCAGAT  TCAGAAAGTG  CTCGCTAGTC
231121  TTAAGAGTGA  ATTACCCTCA  GTGGTCCAGC  GCTTATGAAC  CCACATCTAA  CCCTATCCCC
231181  TGGGGAACT   ATCAGAGAAA  TTGGTGCCAT  GGACATAAGA  GGAAGGCACA  GTGAAGCAGA
231241  GAGCCCCGCA  TGATGAAAAT  CAGTGGACAG  CATCATTATT  TACAACTTTG  TAATCACCCA
231301  GGAGCATGAA  AATCCAGGCC  AATCTGGCAC  CATGAGCTCT  AATTTTTGTT  GGAGTTCTTG
231361  GAACCGATTC  TGATGAATGA  CTGTTTAGCC  ATTTTAGAGT  GTGGCATACG  TGGCTGCTGG
231421  CATACAGAGG  TTGGATGTAA  ACGGGCCTTT  GCCCTCTCTT  ATGAACATAG  ACAGGAACTA
231481  AACTGTGTCA  CATAGGTTCC  AAATGGTGGC  CTGAATACTA  TTTACAACTA  AGGTACAATG
231541  AAATTGAGTA  AGTCTTTTCC  TCTTTTGCAG  ATACCATCAT  TATTCATATA  TTTCTTCAAA
231601  GTTAACTATT  TGTATTTGGT  AATTTTTAAT  AGAAATGTAA  TAATTGCTTC  TCAAGTTTAG
231661  TCTTTAGTCT  TAAGGTTGAT  GCTCTCCATG  TCCTTCCAAA  AAAAGGTATG  TTGCTTTTAT
231721  TATATCCTCG  CCTTCAGATG  GGATTATTCC  ATTTTGTTCT  TTGTTAATAT  ATACTTTGAG
231781  CCACTTTTTT  TGTGGCTCTG  GGTGAGATGC  TATAGGTACA  ATGACAAGTG  ATACGTGTGT
231841  TGTCCCTGTC  ACAAAAGTGG  ATAGCCTAAG  TGGTGACTTT  TACCTCCACT  CCAAATATAT
231901  GTATCACACA  CCAGCCGTAT  GCCAGGCACC  ACTCTAGGTG  CTAGGGATAC  AGCAGTAAAC
231961  AGACAAATGC  AACCCCTGCC  CATGTGAAAG  AGAATAAGAC  AATAAATAAG  TAAAGTGCAT
232021  GTTATATGGA  GGTGGCAAAT  GCTAAAAAGA  AAAATTAAGC  AGGCAAGAGG  ACTCATTGAA
232081  AAGATGACAT  TTGGGTAAAA  GCCCATGTAT  ATATGTTCTA  TTGGTTTTAT  TTCTCTGGAG
232141  AGCCCTGACT  AATACACAAT  GACTTTGAGA  AGTTACTGGC  TTTTGATTTA  TCACACTATT
232201  CGGAGTGCTG  AGAGCCTTCT  TAGTGTGTAT  TCAGTGTTTT  AAGAGAGCTT  GTGGATGAAT
232261  AATAAATAGG  ACAAAATTTA  TCCAAACTTA  AGCCTTGCTT  TAGGTAAAAG  GGCTCCTCTT
232321  ACAAGGTAGA  AGGTTATTAT  TTGACATTTA  AATCCAACTG  AAGACTAATA  AGACTAATTA
232381  ATTAAAAGTT  TTTAAATCAC  AACTGCGTGC  AAAATAAATG  GAACTGCCAT  GCTCGCCAAG
232441  TGTGCATGAG  TGGTGTGCAT  GGGAGACAGC  ACGAAGCTAA  TCCCACTCAT  CTTGCAGGTT
232501  GCTCCATTTT  TCTCCTAAAA  TCAGTAAGAC  AGAAGCTGGT  CAGATTATCA  AGAGCCCTAG
232561  TTAAACACAG  CAGTAGCATT  TGGAAGGGGT  TGCTCTCATT  AGGCAGTGCC  TGACCACAAC
232621  AAGAGATGAA  CAAGCCCTGT  ATCTGAAGCC  ATCATGCCTA  GTTATGGTCC  CCGACTGTTC
232681  ATGATGCCTG  GAAGGGAGGC  CCCCTGCACC  CTAGAAAGCT  GGGTGGGTTC  TACTGTCTGC
232741  TTTACTGCTA  AAAACCCTCT  TCTTTGGATC  TGGACTTTAC  CTCTATCTGA  TTTTTTTTTC
232801  TAATATATGA  TTTGGCACTG  AGTCTGTCAC  TGCTGCTAAC  TCAGCAGTTC  TAGGGTCATT
232861  GCCCCATTGC  CTCACAGAAA  GAATTTCATA  GCTTCCAGCA  TCCTCTCTCC  TTCATTATAC
232921  TTTGATTTCA  GCATTGCTAT  TTTTTCTCTT  GGGTGTTGCA  GCTCTCTCTC  TCCTTCCCAT
232981  GTCTTGTTGG  TTTTCTGCTA  ACTCCTGCTT  TTTTTCTTTT  TTTTTTTTTG  AGACGGAGTC
233041  TCGTTCTGTC  ACCCAGGCTG  GAGTGCAGTG  GCACAATCTC  GGCTCACTGC  AACCTCCGCC
233101  TCCCGGGTTC  AAGCTATTCT  CCTGCCTCAG  CCTCCCAAGT  AGCTGGGACT  ACAGGCGCTC
```

Figure 2 (Page 72 of 74)

```
233161 ACCACTATGC CCCACTAATT TTTGTATTTT TAGTATTGCT GTCATCAATC CACATGTCCA
233221 GAAGCACCTA GAAACTCTAA TTCTTTGTAG GTATCAAACC CTAGGACTCT TTCCTCTAAT
233281 CACAATATAT AATCCCTGAT TCCCAAACAC GGTCTTTTCA TATACATTTT CCACTGTACA
233341 TACTTTCTGA CCTGGAAAGC TCTTACACAA ACACGCCCTC CCCTAGGAAG CCTTTATAAA
233401 TGTTCCCAGG AAGAATCAGT CACCCAACAG TGTCCTTGTC ACATCTTAGG TTCTACACCT
233461 TTATTTGTTC TATCTGAATG TAATCTCCCA GAGGGTGTTA TCATCTTTTT TTTTGAGATG
233521 GAGTCTTGCT TTGCTGCCCA GGCTGGAGTG CAGTGGCATG ATCTCGGCTC ACAGCAACCT
233581 CCACCTCCTG GGTTCAAGTG ATTCTCCTGC CTCAGCCTCC TGAGTAGCTG GGATTACAGA
233641 CGTGTGTCAC CACACCTGGC TAATTTTTGT ATTTTTAGTA GAGACAGGGT TTCACCGTGT
233701 TGGCAAGGCT TTCCTCGAAC TCCCAAACTC AGGTGATCCA CCCACCTCAG CCTCCCAAAG
233761 TGCTGGGATT ACAGGTGTGA GCCACCATGT CCAGCCCCAT CTTTTTCTTT TAGTTTAGTT
233821 CTTAACAAAT AGTCTGACAC AAAGTGGATA TAACAATATT TTGAATTATG AATAACTAAA
233881 TGAATATTTC CAGATTTCCT GGTGCTCTCA AGTTTTATG TTACAAAAGA AAAACAAGTC
233941 TAAAATACCT GCCTCAAGTT TTTATCTGTA CTATGATTTC AAACCAAATA AAAAACAGGT
234001 GGGGTAAAAA CTGAAACAGG AAATACATAT AACTGAAAAA TTTTGGTATG TTAGTATGAT
234061 AATACTAGGT CATTTTTCCT GTTTCCCCAA CTTCATTTTC TATAGCAATA AAAAGAAACA
234121 AGTAAATGTA TGTTAATTTA ATTTAAAAGA AGTAGTCTAC CATCTCTTCT GTTAAAAAGA
234181 AAAAAGTATT TTAAAAAATT ATCTCTGGAA GGATACACAG GGAACATTGC TCTGGTTTCT
234241 TCCAAGAGAG AAATGAGGAA CTAGAGATGCA TGGCCAAGTG GGGTTTTGCT TTTGTTTTTG
234301 TTTGTCTATC TGTTAGCTTT TTATTATTTT CTTTTGTAGG TTTGAATTTC AAACCACATA
234361 AATCTGTTAC ATGCTCATAA TAATAAGTTT AAAATAAAAC TTTTGGCTGG GTGCAATGAC
234421 TTACACCTGT AATCCCAGCG CTTTGGGAAG CAGAGGTGGG AGGATACTTG AGGCCAGGAA
234481 TTTGAGATCA GCCTGGGCAA CATAGTGAGA CCCTGCCTCT GTAGAAATAA ACAAAAATTA
234541 GCTGGATATG GTGGTGCATG CTTGTACTCC TAGCTACTTG GGAGGTTGAG GCAGGAGGAT
234601 CCTTTGAGTC CAGGAGTTTG AGGCTGCAGT GAGCTATAAT CACCCACTGC ACTATAGCAT
234661 GGGCAATAAG GTGAGAACTT GTCTCAAAAA AAAAAGGGGG GGGGGAAACA AATAAATAAA
234721 TATAAACAAA ACTTTTGTTT CAAAATATGT AATATTTAGC ACTAAAGAAT TCTGAATTGT
234781 AGAGCTAAAA AGTACTTAAA AGTTAATAAC TATTGTCTCC TTTAAAAGAA TTGTTATCAA
234841 AGTATAATTT TTATCCAGAA AATCATCCAT ATCAGCAAGC TAAACTTTCT CAAAATGACA
234901 TATCCATGTA ATTAGCTCCC AGGTAATTAG CAGGCAGCCT CTACTCAGGT TGAGTATTCC
234961 TAATCTAAAA ATTGGAAATT CAAAATGCTC CAAAATCTGC AACTTTTGA ATGCTAACAT
235021 GATTCTCAAA GGAGTGCTCA TGGAGTATTT CAGATTTTGG ATTTTTGGAT TTGAGATACT
235081 CAGTATAATG CAAACATTCC AAATCTGAAA AAATCTGAAA TACTTCTGGT TCTAAGCATA
235141 AGGGATACTC AACGTGTGTT AGCTAATTAG ACCCTTCATG GTCTCTTCTA GACCTCAGCT
235201 TCTTCAAGGT AACCTCTATC CTCACTTCTA ATAGCATGAA CTTTTCTGTT TTAGAATAAT
235261 TTGGATTTTC AGGAAAGTTG CAAAGATAGT ACAAAGACAG TACAGGAGAG TTCCCATATA
235321 TCTTTCACCT AGCTTTCCCC CATTGTTAGG ATTTTACATT ATTATGATAC ATTTGTCAAA
235381 TATAAGCAAC TCACATTGAT ACATGAAACT CTATTAACCA AACCCTAGAC TTTATGTGGA
235441 TTTCACCACT GTTTCCACTA ATGTTTTCTT TCTGTTCCAA GGTCCAATCT GGAATACCAC
235501 ACTGCATTTT CTTGTCATAT CTCCCTAGTC TTTTTTTGTC TGTGACAATG TCTCAGTCTT
235561 TTCTTGCTTT TCATGACCTT AACAGTCCTG AAGATCATTT GCTTTTTTTT CATAATTACA
235621 CCGGAGTTAT AGATTTTTG AAATAATACC ACAAGGGCAA AGGGCCCTTC TTGTCACATC
235681 ATTTTAGGGA GAACATGATA TCCACATGAC ATCACTGATA TTAACCTTCA TCATGTGGTT
235741 TAGGTAATGT TTCAGGTTTC TCTACTGCAA AGTGATTTTT TTCCCTTAAT TTAGCCCACC
235801 TGAACTTATC AATTTTGTTT TCTTCCATGA CTAATACTTT TGTTATTATA GCTAAAACTT
235861 CATTGGGGCC AAATCTTAGA TCATGTAAAT TTCTTCTAT ATTTTATTCT AAAAGCTTGT
235921 AATGTTTGAT ACATTCTAAA AGATGTAATG TTTGATACAT TACATCTAGT CCTTTGATTT
235981 ATTTTAGTT ACTTTGTAT AAGGTGTGAG AGATGTCTCC AGTTTCACTT TATTAACACA
236041 TTGTGGTGTT CCAGTACTAT TTGTTGCTAA GACTATCTTT TTTCCATTGA TTACCTTTGC
236101 CTTAGTTGGC AATATTTTTG TTGGTTTATT TCTAGACTGT TTATCTCATT CCACTGATTT
236161 GTGTCTATCT TTTTGACAAA ACTGTTGATT ACAGTAAGCT TTGAAATAGT TCATTTTTG
236221 TGTCAACTTG ACTGAGTCAG GGGATAACCA GCTATCTGGT TAAACATTAT TTCTGGCTGT
236281 GTTTGTGAGC GTGTTTCTGG ATGAGATTAG CCTTTGAATA GGTGATCCTA GTAAAGTAAA
236341 CTGTCTTTCC CAGTGTGGAT GGCATTATGC CACCTGATAT TCAGGGTCTG AATAGAAGAA
```

Figure 2 (Page 73 of 74)

```
236401 AAGGCAGAGG AAGGGGGAAT TTGGGCCTTT TTTTCTGCCT CACTGCTTGA GCTGGGACAT
236461 CTCATCTGGT CTCCTGCTCT TGAACTGGGA TTTACATCAT CAGTTCCTCT GGTTCTCAGG
236521 CCTTCAGATT CAGACTGAAT CATACCACCA GCTTTCCTGG GTCTCCAGCT TGCAGATTAC
236581 AGATCATGGG ACTCCTCATC TTCCATAAAT GCATGAGCCA ATTCAGTCTA TGTCCTTGAA
236641 AACTGCCCCA CTGCAGATTA AGGCTTTTTT CCACTAGGTG AAATAAAGAA GCTTGTTAGA
236701 CAGATTTCCC TTCATCCAGT GCCCTCTCCT CTTTAAGTTA CAACACATTG GCTACACCTA
236761 AGTGCAGGGG TGGGGATGAG GGTATAGTCC TCTTGTTTGC TGAGAAGAGA ACTGTATTGG
236821 GAAAGCTCTA GAAGTGTTTG ATACATACAT AAACAAGGCA TGGTTTTTGC ACTTAATTTC
236881 ACATTACATT TTTCCCAGAA AAAAGGAAT GTATAGGCAT CACGTAACTG TACTAGCTGG
236941 AGTCATTCTT CCTGATTATC AAAGGTAAAC AGTTATTAAT CCTATACCAA GATGTCAAGG
237001 AGAAGTACTT TTGGAACACA AGGAATTCTC TGGGAGTCCT TACTACTCTC AAGCCCAGTG
237061 AAAAAGTTAA TGAAAAACTA TAGTACCTTC CTATAAGCTG GATGACTAAT TACCAGGCTC
237121 ATTTAGGAAT TTGCCTTACC AAGTAAAACA TAAGGGCAGC TGAGGTGCTG ACTGAAGACA
237181 AATGGAGCAT AGAATAAGAG TAGTAAAGAA TGCCAAAAAT GCTGTCATGT ATCCATTGAC
237241 AAAAGGAGCT ATAAAGCCTT TAGGTATTTT CACACTTGCT CTGTTACGTA AATGTATGTG
237301 TGTGTGTGTG TGTGTGTGTG TGTGTG
//
```

Figure 2 (Page 74 of 74)

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 235033 base pairs
      (B) TYPE: nucleic acid
      (C) STRANDEDNESS: single
      (D) TOPOLOGY: linear (xi) SEQUENCE DESCRIPTION: SEQ ID NO: 1:

```
CACACACACA CACACACACA CACACACACA CACACAAATG AGGTATATAA AGGGTCTCCT      60

AAAATGTCAT CTGATATTTG TTATTTCATA TTCTCAGATT TTTAATCCAT TTAGGTAGGT     120

CTATTTTAGA TAGCCTTGTC TGAAACAGAG CTGGGACCTG ATGAGTGAAA ATGAGCTCAC     180

CAGAAGAAAA ATCAAACAGG CATTTCGAG ATTGAGGCCA AGAAGTTAAA TGTCTTAAAT      240

GGGCAGAGCT TAGCTGCTTG ATGTGAAAAG AGACCAGCGT GGCTGGAACA GCAAAGGAGA    300

ACAGCAGAAG AGGTGAACAG AGGCCAGAGA TGGTCACTGA GTGGGCCCTT AAGTCATGGT    360
```

```
AAGGAGTATG GAGAATGAAT TATTGCATGT ATTGAATATG TAGGTGACGT GACTCACAGA    420

TACTTTGGAT TTGTAGAGAT GAAGGAAATG TAGCAAGTGA CACTCTTAGA ATGTTGATTT    480

GAGTAAATGG TAGTGTCAGT TATTGAACTG GGGAGAACTG GAAGGGATAA CAGGCTTAAG    540

GAGCACGTTT ATTCCTGTGT CTTGGAAGTG TTTAGGGTGA AAGACCTATT AGAGTTCTAA    600

ATGGAGATGT CAAGTGAAAA TGTGGCTACA CACATTTGCA TTTCAGAAAA AAGGTCAGGC    660

TGGAGATGTA AAATTGGAAG TTTACTGCAT ATAGATAGTC TTTGAACCG TAGTATTGAT     720

GAAGCCATTA ATGAGACAGA ACAAAGACTA GGGACCAGAG CCAAGCTCCA AGTTTCTAAA    780

ATTTAGAGGA TAGTATAGTC TGGTCATTTT GAGGTGAATA CTTAATAACA GAACAATTTG    840

TTGAAGTGTA AATTTAGAGC CCTACACTTT TAGCTCTGAC TATTAACGAA TACAGGAAAG    900

AATGGATATG GTTATCTGCC TGGTGTCTGT GAAATAATTT AAGCCAGGAA GAGATCCTCA    960

CCAGAAACTG ACTATGCTGG CAACTTGGAT CTTAGATTTC CAGCCTGCAG AATTGTTAGA   1020

AAATAAATGT CTATCGTTTA AGCCACCAGT CTGTAGTATT TTGTTATGGC AGTCCAAGCT   1080

GACTAAGTTT TGGTACCCAG GCGTGGGATG CTGCAACAAC AAATACCTAA ACATGGGGAA   1140

GTGGCTTTGG AAATTGGTGA TGGGTAAAGG CTGGAAGAGT TTGAGGTTCA TACTAGAAAA   1200

AGCCAATTGT GAAGGGACTA TTGAAAGAAA TATGGACATT AAAGGCAATT CTGGCAAAGG   1260

CTCAGAAAGG AAGAGAGCTG GACAGAAAGC TTCCATTTTC ATAGAAACTT AGATTTATAA   1320

CGATCATGGA TAGAATATTA AATATGCTGG TTAAAATATG GACTTTAGGC CAGGCGTGGT   1380

GGCTCACGCC TGTAATCTCA GCACTTTGGG AGGCTGAGGG CACAGATCAC GAGGTCGGGA   1440

GTTTGAGACC AGCCTGGCCA ATATGGCGAA ACCCTGTCTC TACTAAAAAT ACAAAAATTA   1500

GCTGGGCATG GTGATGTGCT TCTGTGGTCC CAGCTACTCG GGAGGCTGAG GCTGAAGAAT   1560

CGCTTAAACC CGGGGGGTGG AGGTTGCAGT GACCCAAGAT CACACCACTG CACTCCAGCC   1620

TGGGATACAG AGCAGGACTC CACTCCCCCC GCCACACACA CACAAAAAAT ATATATATAT   1680

GGACATTAAA GTCAACTCTT GTGAGGTCTC AGATGAAAAT GAGGGACAGG TTATTGGAAA   1740

CTGTAGAAAT CACTGTTCTT GTTACAATGT GTCAAGAACT TGGCTGAATT ACGCTGTAGT   1800

GTTTACTGGA AAGAACTTAT AAGCAGTAAA ACTGGATATT TACCAGAAGA GATGTCTAAG   1860

CAAAGTATTG AAGGTGTGAT TTAGGTCCTC CTTACTGCTT AAAGTGAAAT GTGAGAGGAA   1920

AGAGCCGAAA TAAAGAAGGA ATTTTTAAGC AAAACACAAT CAGAACTTGG AGATTTGGGA   1980

TAGATTTCTC AATCTATATT GTAAAAATTG AGAAAGTTTT CTTGAAGAG GTATGGTTGA    2040

ACAATGTTTT CTTTTTCTTT TTTTTTCTTG GTTTTATTTT TATTTTTATG TTTTTTGAGA   2100

CAGGGTCTGG CTATGTCATC CAGGCTGGAG TGCAGTGGCA CAATCTCAGT TCAGTGCAAC   2160

CTTTGCCTTC AGGCTCAAGC AATCCTCCCA CCTCAGCCTC CTAAGTAGCT GGGACTACAT   2220

GTATGCACCA CCACACCCTG GCTAATTTTT TGTTGTTGTT TATAGAGATG GGGTTTTGAC   2280

ATGTTGCCTA GGCTGGTCTC TAACTCCTGA GCTCAAGTGA TCTGCCCTCC TCAGTCTCCC   2340

AAAGTGTTGG GATTACAGGC GTGAAACACT GAGCCTAGCC TGAACAACCA TTTGATAAAG   2400

AGATAATGGG TGTGACCCAA GGATTTAATC AGCCATCTCA GCAGAAGCCA GGAAGAGAGA   2460

TGGGATTATT CCAGCAGAGA CACTGCCAAT TTAAACTAAC GTAGGCAGAG AAAACAGAAA   2520

GGAACAAAGG AAGGTTGTCG ACTTTTTGAA TTCTATAGAA CAGGATCATA GAGCTACCTG   2580

GCTGTCAATG TGTACTATTC TTTAAGAAAA GGAAAGACTG ACCCACCAAA GGCAACTTAC   2640

AAGATCACTA GGGCTGACTC TTTTGTTTTT TCTTGAGGCA GTCTCACTGT CACCCAGGCT   2700
```

```
GTAGGGCAAT GGTGTGATCT CAGCTCACTG CAATCTCCAC CTCCCAGGTT CAAGGGATTC    2760

TCTTGCCTTA GACTCCCAAG TAGCTGGGAT TACAGGCTCT AAATCTGTAC CCTCCCGAGT    2820

AGCGCTCCTG CCACCACTTG CCCAGCTAAT TTTTGTATTT TTAGTAGAGA TGGGGTTTCA    2880

CTATGTTGGC CAGGCTAGTT TGGAACTCCT GACCTCCAGT GATCCATTCT CATTGGCCTC    2940

CCAAAGTGCT GGGATTACAG GCAGGAGCCG CCAGGGCTGC CACTTTGATG TCAGACTCAG    3000

AGAGTACAGA TGGGATAGGG TGGGGGTGGG AACATGTAGT CAAGGCTGAC TCTACCTGTT    3060

TCAAAGATGC CCTGCAGAAC TGTGTGGGAG TCTCTCACAG ATGGCTGCCT GGGTGGGACC    3120

CCACCAAACT GAAAGACCGA GACTTCAGGC AGGGCAGATG GAGTAGGCCA ACTACAGAGC    3180

CAGAGGTGAC ACTGAGACAC CACTGGGCCT GGAAATCAGG GCATCAAGCC AAAGAGGGTT    3240

TTTCTTAAGA CCTAACAGAA TTTGCCTTGC CAGGTTTTGG ACTTGATTAG ACACATTAC    3300

ACCTTCCTTC TTTCCTATTT CTCCATTTTC TAATGGGAAT GTCTATTATG CCTGTTTCAC    3360

CATTGTACCT TAGAAGCATG TAACATTTCT GGTTTCACAC GTTCAAAGCT GGAAAGGAAT    3420

TTTGTCTCTG GATGAATCAC ACATTGAGCC TCACCCGTAA CCTGATTTAG ATGATTTTTT    3480

AGATGACACT TTGAACTTTA GAATTGATGC TAGAATGAGT TAAGACTTTC AGGGGGCTGT    3540

TGGGATGGAA TAATTTTTTT TTTTTTTTTG AGACGGAGTC TAGCTCTGTC GCCCAGGCTG    3600

GAGTGCAGTG GCACCATCTT GGCTCACTGC AAGCTCTGCC TCCCGGGTTT ATGCCATTCT    3660

CATGTCTCAG CCTCCAGAGT AGCTGGGACT ACAGGCGCCC GCCACCACGC CTGGCTAATT    3720

TTTTTTTTAT TTTAGTAGAG ATGGGGTTTC ACCGTGTTAG CCAGAATGGT CTCGATCTCT    3780

TGACCTTCTG ATCCGCCTGC CTTGGCTTCC CAAAGTGCTG GGATTACACG TGTGAGCCAC    3840

CATGCCCGGC TGGGATGGAA TAAATTTATC TTGTATGGGA GAAGGACATA CATTTTGGCA    3900

GGTCAAGGAC AGAATGTTAT GGACTAAACT GTGTCCCCCA AAATTCATTT ATTAAAACCC    3960

TAAACCCCAG TGTGACTGCA TTTGGACATA GAGCCTTTAG GGGGTACATA AAACTAAAGA    4020

TCACAGGATA GGGCCCTAAT CCCATTGGGG CTGGTGTCCT TACAGAAGAT GAGACACTTA    4080

GAGCTCTCTC TCCACGCAGG CACCAAGGAA ACACCATACA AACACACAGT GAGATGGCAG    4140

CCATCTGTTA GCCAGGAACA GATTCTCACC ATAAACTATG TTGGCACCTT GATCTTAAAC    4200

TTCCAGGCTC CAAAACTGTG AGAAAATGAA TTTCTGTTCC AAGCCTCTTA GATATGGAAA    4260

AAAAGATTCT GTTGTTTAAG CCATCCAGTC TCTGGTATTT TGTTATGGCA GCCTGAGTAG    4320

GCTAAGACAA TGAAGGATGT GGTAAAACTT TACGTCCCAA CCACATACCA AAGAGGCTGG    4380

AATTTAGCAT GCTTTCTTCT TTCAACTGTA GGCAATGTGC ACAAGTTCTA AATCCTAAGA    4440

CATGTTGGCT CCTTTACTCT GCCCAAACTA CAACTCAAAC AAACAACTGT AATATAATAA    4500

CATCCAATGA AGTTCTGACA TTTCTTCAAC ATGAGTACAG TAATTCAATG CCAGAGAATT    4560

CATTTTATTT TGAAATCTAC ATGCCATATT CCAATTTCTG TTGAAGATGC AATGGTTATA    4620

TTTATTCTTT TTAATATAGA TTTATCAGAC TGGGCGCGGT GGCTCATACC TGTAATCCTA    4680

GCATTTGAGA GGCTGAGGTG GGCATATCAC CTGAGGTCAG GAGTTTGAGA CCAGGCTGGC    4740

CAACATGGTG AAACCCTGTC TCTACTATAA ATATAAAAAT TAGCTGGGTG TGGTGGTGCA    4800

TGCCTGTAGT CCCAGTTACT AGGGAGGCTG AGGTAGAATT GCTTGAACCT GGGAGCAGGA    4860

GGTTGCAATG AGTGGAAATC GCACCAGTAC ACTCCAGCCT GGATGACAGA GCAAAATAAT    4920

AAATAAATAC ATAAAATAGA TTTATCAGTT TATCAATAAT ATAGTTTTCT TTTCTAGGTG    4980

TAAATATAGG TAATGACTGT CCTTTAGTAC ATTTTCTCAT GATGCTCCTC TTACTTGGTT    5040

TGGTACAATA TTAAGTATTG AAATAAAATA GAGAATCCTG TCGCTACACA TGAGCACTTA    5100
```

```
TTCCATTTGC TCATCTCCAA TATGCACGGG AAATTCTCAA ATTGCTAATA ATCTTGTAAC    5160

ACACATGCAT TATATTCAAC AGGAATATAT AAATTTATAA TTATAATTTA GGATCAACAG    5220

ATGACAAACC TTTAGAAGGT TTGTATTTAA CCTTAAAATA TAATTTTTTA AAAATTGGTT    5280

ATAAAATTTC TAATACTTTC TTTTTTGTGA CCTCAAGGGG AAAATATAAT TCTTATAAAA    5340

GTTCAAATGA TTTACAGAAT ACAAAAAGTG AATAGAGATG ATGAATGAAT TAAAGGAAAG    5400

GATATTGCTA CATAGATTTG GAAATTTAAA AAGGGAAATT ACGATTGTTG ATTTTGTGTT    5460

AAACTGATCT GCTTTGTTCA AGATACCTTA TGTACCAAAA AATGATTTTA TCTCAGCCTC    5520

ATATCTCAGT AAATTCCTGA GACAAACTTT AGTCCCTGGT GCCCAGGTGC CTTTGGTAAT    5580

TGGGAGACCT CTAGGTTTAG CATCCTCATC CACTCGCCCC AATTTAAATA GTCCTCCCCA    5640

GGGCCATTCA GGCAAGGGAG ATGAAAACTT GCTCAAGAGT TGGAATCCAA CTGAAGCTAC    5700

CGAAATTCAT TGCTCAATAG ATAATTTTCC CTGGAAGTAA CTAGGGCTTT TGAATATAAT    5760

AGTGGGCATT TCAAAGTAGA AGGTAAAGTA TTTTGGAGAT GAGGAGACAG GACAGAGCTA    5820

CGAGGAATGT CCTTTGCTTA GGGACTAGGC TCTTAGCAGT ACCTCTTAGG TAAGAACTGG    5880

TTAACTGGCA CCTTCTGTGT TTCTCTGAAG CTCCCTTTGC TTAGGGACTA GGCTCTTAGC    5940

AGTACCTCTT AGGTAAGAAC TGGTTAACTG ACACCTTCTA TGTGTCTGAA GCTCCCAGAA    6000

CAAACTGCCA GTGAAATTTG GATTTTTGGA ATATAGTTTC TTTTTTCTTG TTACTTTTTG    6060

TTTTGTTGTT TTTTTTGAG AGTCTCACTC TCACTGCAAC CTCCCCCTCC TATATTCAAG    6120

TGATTCTCTT GCCTCAGCCT CCCGAGTAGC TGGGACTACA GGCGTGCACT AGCATGCCCA    6180

GCTAATTTTT GTATTTTTTA GTAGAGATGG GGTTGGTTTT TTTTTGAGAC GGAGTTTCAC    6240

TTTGTCGCCC AGGCTGGAGT GCAGTGGCAC GATCTTGGCT CACTACAACC TCCACCTCCC    6300

GGGGTTCAAG TGATTCTTCT GCCTCAGTCT CCTGAGTAGC TGGGACTACA GGCGCCTACA    6360

GGTGAACACC GCCACACCTG ACTAATTTGT GTAGTTTTAT TAGAGATGGG GTTTCGCCAT    6420

GTTGGCCAGG CTGGTCTCAA ACTCCTGACC TCAGGTGATC TACCCACCTC AGCCTCCCCA    6480

AGTGCTGGGA TTACAGATGT GAGACACCAG ATCAGCCTCA GAAGACATTT TCTATTGGAA    6540

AGAGAAAACA CTATTAGCAA CCTATTAGTC TAATATTTAA TACTTAATGT CTTCCTTAGT    6600

AATAAACCAA CTCTCTACAA CAAAGTGCTT CCTGGCTGCC TAAGTCATTG ATTCATTCAG    6660

TTCAACATTT TCTCAATGCC CAACAGCCAA GTGTCTCTTG TATGCCAAGT TCTATGCTGA    6720

TTATCAGTAT TTGAATAAGA GGGGTCTAC ATCTTAAGTA CTGCTTAAGA TGAAAGCCTC    6780

TAGGTTAACA AACTTAACAC AATGTATCAT TCACTACTAA ATAGACCGAA TACAAAATCT    6840

TGTTATTGGA GCCCAGAGAG AAGAATTGAA ATTCAAGTTT TCTCTCTCTC CTTTTCTCAC    6900

TCACCACAAT AAGTCAGTTG CACCAAGTCT TGTAGCTCTT TACTGAGCCA TGTTTTCACG    6960

TGTCCCTTTG TTTTATTTGC CACACCCTAA ATAAAAATTG TACTGGCTTT TTTTCCCTGG    7020

GTTTACAGTA TTAATACATT GTCAAGATTT ACCTCTTCGT GTAGATTCCC TGGGGAAAAT    7080

TACCTTTCCT CCTTCCCTTA AATTCTTCAG AGGTTAGAAA GCCATTAGTA ACATTCTGGT    7140

ATGTGGACAA AGTTTACCCA TTATGTATGG ATGTTTTACT CTTTCTATTT TTCTGACAAT    7200

AATCTCTTAA GGAGGTGTGG TTATAGAATA GTCAGCTGTT ATAAGTACTG TTTTCCTGGC    7260

CTTACAACTT AAGTTCTTTA AGCTGTTTCT TAGTTTGCTC ATCTCAAAAT TCGGAATAAG    7320

GATAAAACCT ATCTCTTAGA TTGTTGGATT AAATGAATTA ACATACTGGA AGCTCATGAA    7380

ATGTGCCTGG CACACAGTAG TGCCTAATAA ACCATCTCTC TTATTCAGCC TGTTTTCTGA    7440
```

```
TTTCAGAATC TACACTTGCT GAGCCAGGTT CTTTTCATTT CAAGGTGAGC AAAAGCATAC    7500

AAGGAAGAGA TGGAGGTAGG AAGAGATTAA GCCCTAGGCC AAGGTCACAC ACCGATTGGG    7560

AGCTGGAATC AAAGGCAATT TGGTCAGTGA ATAAAAAGGA TTCCAAGGCC CATAAGGCAA    7620

TTCTAACCTT AGGATCGAAA TTCTCGGACA TACAGGAAAT GCTGGGGGGG GAAAATCCGG    7680

TCTTCTCAGC CCAAGAGCCA TGTGAAACCA GACCTTCAAA TCTGATGATT CTCAGCCCAG    7740

CTGCCCATTA GAATCGTTGT AATTTAAAAA TACCCTCGGA AAATTCTAAT ATGTGGCTAT    7800

CAAAGGTGAT CATTTGCTTT TATGCCACTT TGTTTTCACC CAAATGGGAC ATCCAACCCT    7860

TTTCCTTTGA GAGTAGTTGT AGGGAAAGGA GGGGGTGGAG GGAGGGAAGA GCGGAAAAGG    7920

CTGGATCCGC CCTGAGCCGG TGTCAGTATC TGGGAAGTGG GAGGCGCGTC AGCAGTAAAC    7980

AGCTTCTGCT AGGATTATTA TCTCCTGCCA CACACTCGGA TTTGAAGGCT CCAAACGAAA    8040

CAATGCAAAA CGCTTCAGTG GAGTTCCAGA AGCGTTAGAC TAAACGACTG GGTCTGTTTG    8100

GCCAGTCTGA GCAGCTGGGC GCAGATGCAT AGGCAAGACT TAGCCCGCCT AGACTTTTCT    8160

GCCCACTTAA TTCCGATCAA AGCAGAAACC GGCCGGGCGC GGTGGCTCAC GCCTGTAATC    8220

CCAGCACTTT GGTAGGCAGA GGCTGGCGGA TCACCTGAGG TCAGGAGTTC GAGACCAGCC    8280

CGGCTAACCT GGTGAAACTC CGTTTCTACT GGTGGCGGGC GCTTGTAATC CCATCTACTA    8340

GGGAGGCTGA GGCCGAGAG TCGTCTGAAC CCGGGAGGCG GAGTTTGTAT GCAGTGAGCC    8400

GAGATCGCGC CACTGCATTC CAGCTTGGGC AACAGGAGCA AAACTCCGTT TCAAAAAGC    8460

AAGCAAACAA ACAAAAAAAT GCAGAAACCG AGATCCGGAA GAAAACCTCG GCGAGATTCA    8520

CAGAATCCAG GAAAATAGGT CTCTAGAAAT TTGTCCATGG TCCCAGATCT CCATTTCTTG    8580

TGGGTGGGGC AGCTGTTACC AGATCCCTAG AAGCAAAGGT TTTTTTGGGG GACCGTGTCT    8640

CACTGTTGCC CAGGCTGGAG GGCAGTGGCA CGATCTCGGC TTACTACAAC CTCCGCCTCC    8700

CAGGCTCAAG CGACTCTCCT GCGTCAGCTT CAAGAGTAGC TGGGATTACA AGGTATGTGC    8760

CACCACGCCC AACTTATTTT TTTATTTATT ATTTTTATTT AGTAGAGAGG TGTTTCACCA    8820

TGTTGGCCAG GTTAGTGTCG AAGTCGTGAC CTCAGGTGAT CAGCCCCCTC GGCCTCCCAA    8880

AGTGGTAGGA TTAGAGGGGT GAGCAGAAAG CAAAGGTTTT TGAGTGGCCA CAGGCCCCAC    8940

TCTATTTCCT TTTCTGCCTG TAATGGCAAC CTAGACGCTT GAGCTTCTTA AAATACAAGA    9000

GTAAGTTGCA TGTCAGGCAC CGTTCTACAT TAGGGACATT AGTCTGTTTT ACAGACACCT    9060

TTCAACTCCC TGGTTAACTT TTAGGTAATA TACTCTGCAC TTTAGCAGGA ATGGGACCTA    9120

TAACTCTCAC AGAATTAGGA AAGTGAGGCT GCCTACAGCC TAAATTGAGA AAAAAATAGA    9180

CGGGGGACTA GTCGGAGGAC CAAACAAGGT TACCAACACG TTAGAGTTTT GCCTTCAATT    9240

TACATTTTTA AAGTAATCAC AACGAAGTGT TTAGATCACG AGGCATCCCT GCATGTAAAC    9300

TGTTAGGCAC TAACTATGGT CGATCTTACA AAGCATTAAC TAGAATATTT CTTTAGAGTA    9360

TGATAGTACG TAACTGACCT ACTATTACAT ACAAACAGAC CAACCTTTAG TAACAGCGCT    9420

CCCCAAAAAC CGAAAAGCAG TAATACGCTT TGCTCAAGGT TGGCATAAAA TTAACTTACC    9480

TTAGTGCCTT TTTTCCTTCT ACCTACAAGC AGTGAGGTTA GCTCTTCCTT TGAAACGGTA    9540

GGGGGGCTCT GAAAAGAGCC TTTGGGTTTG ATAGCGTTTC CGGGAGCTCA GATACCTGTC    9600

AAATCACTTG CCCTTGGCCT TGTGGTGACT CTCGGTCTTC TTAGGCAGAA GCACGGCCTG    9660

GATGTTAGGA AGGACGCCGC CCTGAGCAAT GGTCACCCGG CCTAGCAGTT TGTTGAGCTC    9720

CTCGTCGTTG CGGATGGCCA GCTGCAAGTG GCGCGGGATG ATGCGAGTCT TCTTGTTGTC    9780

GCGAGCCGCG TTGCCGGCCA GCTCCAGGAT CTCGGCGGTC AGGTACTCTA ACACCGCCGC    9840
```

```
CAGGTACACC GGCGCGCCTG CCCCAACCCG CTCTGCGTAG TTGCCTTTAC GGAGCAGGCG   9900
GTGCACTCGG CCCACCGGGA ACTGGAGACC AGCGCGAGAA GAGCGGGATT TCGCTTTGGC   9960
GCGAGCTTTG CCTCCTTGCT TACCACGTCC AGACATTGCA ATCAGACAAA AATCACCAAA  10020
ACCAGCGGCC TAAGCTCACG AGAAAACAAA CAAAATCAAG AAATATGTAA AACATGGCCG  10080
CTTTTATAGG TAGTTCCTGG GGAGTAAATC CGACTTTTTG ATTGGTCGGT AGCAAATGCT  10140
AGTCAGATAG CCAATAGAAA AGCTGTACTT TCATACCTCA TTTGCATAGC TCTGCCCACG  10200
GATGACAACT GTGCAGTTTG TCTTCCAATT AACTAAGAGG TACTCTCCAT CCCTCATTAG  10260
CATAAAAGCC CTATAAGTAG CAGAAATCCG CTCTTTACTT TCGACACATT TCTGGTGTTT  10320
TAAGATGCCT GAGCCAGCCA AGTCTGCTCC CGCCCCGAAG AAGGGCTCCA AGAAGGCAGT  10380
GACCAAAGCG CAGAAGAAAG ATGGCAAGAA GCGCAAGCGC AGCCGCAAGG AGAGTTACTC  10440
TGTGTACGTG TACAAGGTGC TGAAACAGGT CCATCCCGAC ACTGGCATCT CTTCCAAGGC  10500
CATGGGCATC ATGAATTCTT TCGTTAACGA CATATTTGAG CGCATCGCGG GCGAGGCTTC  10560
CCGCCTGGCG CATTACAACA AGCGCTCGAC CATCACCTCC AGGGAGATCC AGACGGCCGT  10620
GCGCCTGCTG CTTCCCGGAG AGCTGGCCAA GCACGCCGTG TCGGAGGGCA CCAAGGCCGT  10680
CACCAAGTAC ACCAGCTCCA AGTAAACATT CCAAGTAAGC GTCTTAACAC CTAACCCCAA  10740
AGGCTCTTTT AAGAGCCACC CAGATACCCA CTAAAGAGC TGTGGCCAGA CGCCAAATTT  10800
TATTTGGCGG CGGAGGGGTA TTAGAATATA GGAACTGGAG AGGGGTGGGG ACAAGTGTTG  10860
CAGCTTAGAG AGGGACAAAG GGTCCTGAAC CCGAAAGAAG CCAGCCATTA AAAATGGCTT  10920
TGGGGTCAAT TCGTTGTGCT TAAATTTAAA ATGGAGACAA GCGGCCATTT TGCTAACTCG  10980
GCGTTCCCGG AAGAAACCGC AGGCTCGCTT AGGTTTCAGA CCCAGCTGTC TGTCCCTGTC  11040
TACGTCGCCA GGATCAACGG TTGCCGTAAT GTCATAATTT CGCCACCAGC TTCTAGCCAA  11100
TAGGCTGTCC TGTCATTTTA AATATTAACC AATCGAGGGA AAGCTGTTTT GAGACTCTGA  11160
TTTACATAGC GGACCGGAGT GGGAACCTGG GCAGTAACTG CCTAAGGAAG GACTCCCCCT  11220
CTGTTTTCGT GGCGCACACC TTCGTAGTAT ACTGAAGGGT GTGTCTCCTG GGTTTCCAAC  11280
TGCCCCGGTA ATAGTCTTTT AACCTAATAT GCGTCAGTTT TGATAACAAC ACTAAGGCAG  11340
TACAGAACTA AAGATGTAAG CACTGCGCCA GATGTTGCTT CATACATCTT ATTCTATTCA  11400
ACTGGTTTAT TCAAGATTCA AATCAAATCA AATTTTGCTT GAATCCCAGT GCTCAGTCAG  11460
CCATAAATGG TGTGTTGCCT GATTGAAACT TAAAATCTCC GTAGGGGCT TGTAACATGC  11520
AGACAAGTTT GAAAGTTGCT TTAGGAGAAG CCAACTCTTA ACTGCTGGGT AAATTGACAA  11580
GCCTTCGAAC ACTGAACTGA AGGCCAGTAA GGACTAGGCG CTGGGTGGGG GAGAATGAAG  11640
AGGAGACGTC ATTAAACTTA GCACATACAC TGTATCTCCT AGAGGACTCT CCCTTCCTAG  11700
ACAACTGCAG GCCGCTTTGT GGCCTGGGAA ATTCCACATT CCCTTAAGTA TTTTACTCAT  11760
GGTCTTTTCC AGGTAAAGAT TTTAAGATGA AGGGTTAGAC GTAGTCTACC TATCTTTTTA  11820
TTCAAGTCTA GAACACGTTT TTAGCACCTA GAAGTTTGCT TTCTCCATTA AAACCGGGA   11880
ATATACAATA AATAAAATTA GTGTTAAAGC AGATTTTTAC AAACTTAAAT ACCATGTAAT  11940
TTAGGTTACA GTTATTTAAC ATAAGGACTG TGTGATCTTA AATCTGCAAT TTCTTTCACA  12000
CCTGGGAAAT AAACTAAGGC CTGTCTTTGG TGCCAGACAA GGCCTTATAC TTGAACACTG  12060
CTGTGCAATC ACAGGCTGCC TTGCCTAGAT AACTTATCTG AGAAATTCTG ATGAGAAATG  12120
AAATTTCCAG AGTCCCTCAC AAGTAAATTT TTTTTTCTTT TTTTTTTTT  TTTTTGAGAC  12180
```

```
GAAGTTTCTC TCTTGTTTCC CAGGCTGGAG TGCAATGGCG CGATCTTGGC TCACAGCAAC    12240

CTCCGCCTCC CGGGTTCAAG CCATTCTCCT GCCTCAGCCT CCGGAGTAGC TGGGATTACA    12300

GGCATGCGCC ACGACACCCT GGCTAATTTT GTATTTTTAG TAGAGACGAG GTTTCTCCAT    12360

GTCGGTCAGG CTGGTCTCGA ACTCCGGACA TCAGGTGATC TGCCCGCCTT GGCCTCCCAA    12420

AGTCCTGGAT TACAGGCTTG AGCCACCGCG CCGGGCCTAA ATGGTTTTTT TTTTTTCTAT    12480

GCCTCTAATG GACCTGGTCA CTTATTCCCA TTCAGACTGA CCGCTCTCCT ACCTGCCAAC    12540

TAACTAATCA GTGTAACCAA AATCTGCAAA CAAAATTCAG TATTCTTTCC CCGCCTTTTC    12600

CCCTTTCTCT TACATAGATT ATGTTTTTGC CTGTGTTAGA TGAAATAATT CTATTGCTTG    12660

TTCTCTCTTC TGTACAAGTA CCCAGTAAGC AAATTATTAA CTTCTTGGTC ATTTATTTCT    12720

GAATTTTCCA CCAAGACAGT GTTTATGTGA GTCATACAAT AAGAACCAAC AGAAATGTGT    12780

GTCTTGGAAA CAGGTTGTCT ATCCCTGGAC CCTTTGAGTT TTCTGTTCAC TTTCCTTTGG    12840

CTTTTGCATG CTAAAAGTTT ATCGTCCGCG TTTGTTTGTT TTGGTTATTC TAATTGGACT    12900

TGGCTGATTG GTTGCATATT GGTGGCAGTA GTAGAATTTG AATTCTGGTT TTCTGGTCAC    12960

ATCATTAAGT GATTAGTCAG TGGAGAGGAC AGGAAATCTG GTTTATTTAT TAACCTTTTT    13020

TTGGGGTGTT TTTGTTTGAA GATGTTGATA TTCTCTGTGA GGACACAGGG TTAGAGTTGG    13080

TGTTTTTCTT TCTGACTTTA CATGGGATTT GATGTTTTGT GCTTGTATGC CTCTTTCCAC    13140

CTTCCAAAAC TTGTCTTTTT TGAGTCCAAA TAGTTGTCGA TATCTGCAAA ACCAGTATTC    13200

CTGTGTTAAG ATGATATGAA TATAAAATGG CTGCCCTGTT ATAACTTTTG ACTTTAAGAA    13260

AGTGTTAGGA CTAACAGGAG ACAAAAAGGA AATCAAGGAA ACCGAATGTC TGGTCTCAAT    13320

AACTGCTATG GCAGAGGCTC TACAGCTTAT TATTAATTTT AGTAATTTCA CATTATTGCC    13380

CCTTCACGTT CTTTAAGTAA GGTTAGAGGA CAGAAGAAAC ATAATGTTGT TACAAATTGG    13440

ACTATTGAGT CAGGGAAAAA AAAGAGTGCT TTCAATATCT GAATAAAACA AAGATTTAAT    13500

ATTTTCTAAA CCTTAACGAG TTTATTGTAA GGGATGTGAT GCTGGAAACT AGGAAACTAG    13560

AATTTTCTTC TAAACTGAGA ATCAGAATTA TTCATATTCT CAGCAGTGGT GCCACCTGAG    13620

GGACTTCTGA TCTTAATTAC ATACTTTTAT TTCTTTAACT GATCAACATG CTAAATAGAT    13680

AACCTATGGC TCTGTTTTTA CCCACTTTAA ATTCTGTTCT ATTAGCACGG TTAGCTTTCC    13740

TAATTGGCAA TAAGATTGAG ACTATCTTTT TTTTTTTTTT GAGACAGAAT TTTGCTCTGT    13800

GGCCCAGGCT GGGGTGCAGT GGCACAATCT CGGCTCACTG CAACCTCTGC CTCCAGGGTT    13860

CTAGCAATTT TCCTGCCTCA GCCTCCCCAG TAGCTGGGAT TACAGGTGCA CCACCACGCC    13920

TGGCTAATTT GTGCATTTTT AGTAGAGATG GGGTTTCGCC ATGTTGGCCA AACTGGTCTC    13980

GAACTCAGGT GATCCACCTC GGCCTCCCAA AGTGATGAGA TTACAGGCGT GAGCCACCGT    14040

GCCCAGAAAA GACTATCTTA TTTTATGAAT TTAAATAATT GTGAAATTAT CCACTTAAGG    14100

GAATTAATAA ATTATAATGT AATCTTAAAT TTTAGTTGGC TTACATAAAG ACTTAAAATA    14160

CATCAATTTA AATAAAAACT CATTTGTCTA AAAAAAAATC AAAAATTTTC CTTGTGCTTT    14220

AAATGTGCTA CCTCTTTAAG TTCTAATTAA GAGAAAAAAA GTTAACTGT GAGTTTCATT    14280

AGTGGTCTTA GTTAACAGCT TAAAGTATTT TGTAAAAAAA ATACTTCACA ATTTTTAAAT    14340

AACTTAAAAA TATTAATACC TCTTTTATTA GGTTTTTTTA ATAAGGAAAA TATATAATAC    14400

ATCTAATCAA GATTTTTTTT GGACAAATTG GCTTAATAAT TTCATTTTAA AAATGGCTTC    14460

TTTATTCTTA TACTGTAAAA ATAATATTAG CAGAATATTA TAGTATACAC AAGTTTAGGG    14520

TTCATATTCT AAAAAACAAA AACAAAAGCT AATTTAACTT GCATTTACTA AATTTCTTCC    14580
```

```
ACTAGTTGTA CTGGTTACAT GAGTTAACAT CACTTTATTT ATTATTCTAA AATTGTAAAT    14640

TATTCATTGA ACCAAATTAA ATGATAATAG ATAATGTCAT TTTTAAAAAT GGAATTAAAT    14700

TTTATGTTAC TAATTATAAG GATTCAATGT GTGAGCTTAA GTACTGAGTT CACAGTGTAT    14760

GATAACTTTA AGAATTTAGG TGAATATTAT TAAATTGAGT AAATTAATTC TCAATCTTTG    14820

GATACCTGGA CAATTTCTAA ATTGGAGGGT ACAAAATACA AATCACAAGA AACAGTGTAG    14880

TTTTATGCAA ATAACATTTT TACACAGTTT AGAATAACCA TTGATAAACA GATAAGAGAA    14940

CATATGATTG CCTTAGAATA GATACTGTTG CTTTCGCCAC TTTAGATTTG TAAATCACGT    15000

ACTGTATACG TGTGGGCGTA GAGGACCATG CAGGTTTTGG ATGACTGCCT CTGTTTTCGT    15060

CATGCCTATG CGGGAACACA ATTGCCTGCT TTGTTTAAGG GCTATGGTTA ATCCAAACAG    15120

CTCTGACTCT ATCAAGTACT ATAGCTACAG AGAAACACAA GTAAGCATTC GAGATAATGA    15180

CTACCTTGAG CCTTTACTTA TTTAAAAAGT TGTTACTGTT TGTTAATGTG GTACATTCAA    15240

TTTACTATGG ATTGTCACTC TAAAATAAGA CTTCAATCTT TTTCTTATTT TTATATAGCC    15300

ATGATTTATA TTCATATCTT AATGTAATAA CCAATCTTCT CTGACAACAT TATAACAATG    15360

CTGGAACCTC CATTTTCAGT ACTTCAAACA ACAAATACTG CTTTTATACT TCAGAGCAGA    15420

TGGATATGTG CTTCCCAGTG TAAACACATT TGGAATCTCA CTGAGAAATA CACTATCACT    15480

AAAAATACAG TTCTGAGATT CATTAAAAGA CCTCCAGAAT TCTGGAAGTA GGAAGTTTCC    15540

TCTTCAAAGT CTACAGAGGA AGATGAGGTC TGAAATAGAC AGCTTCTTCC TTCTTTTACC    15600

TGTGGTATTA TTCTGTTTTG TCCTTTTCTC CATTATCTGT CTTTCCAGTG ATGAAATTTT    15660

GATCTGGCCC TCCCAAGTAT TAAAAAACAA GCAAATAAAC AAATCTCAGT TATATTTTAC    15720

TAAGATATTG GCATGCTAAC TTTTTGCAGG TTTGTAACAA GGACCTTTAT AACTTGACTA    15780

AAAGTTCCTA AATAAGAATA TTTACTAGAA AATTTATTTC TGCCTGTGGC CCACATTTGA    15840

GTCAAAATAA TCAATTAGGA AAAATGAACT TGTTTAACTA AAGTTGACCA AACTGATCTT    15900

TGACCAAACT GATCTTTGAG ACCTATTCAT CTAAGACAAG CCAATTAAAT TCTTGGAGAC    15960

AATTTGTACT TTAAGGAATT CTTATAATAT TTGTAATTAC CCTCATAACT TTTTTTTTTG    16020

CCCTACTTCT GTGCTTCTCT AATATGCAGA TTATTAAATG TTGTTACAAA GCCATTGTCA    16080

AAAAAACAAA AAACAAAAAA CTAAACAAAC TCACATGGTT AGACTTGCTC CTTTATGAGA    16140

TATTTTTACC AAAAATGGAG GAGTTGAAAA ACTCTGGTGC CAGAAATCGT GAAGACATGG    16200

CCTACCTAAC ATGGAAATGT TGGTTGTCAG TGGAAAATAC TACACAGAGA TAGCCATAGT    16260

GCTGCACAGC CAATCTTAAG TGTTTCTAGA GAATCACTAA TTGTTTCTAG AGAATCACTA    16320

ATTGTTTTCT TTTAACATTC TTGGTTTATA CAAGAAGAGA GTATCCATAC TAAACTCTTT    16380

TCTACTGAAA ATAATGTGCA AACATAACAT CCTATTCCTA GACAGTTTGT AGTTTTTTTC    16440

TCCCATTTCT ATTTTATAAA TCATCTTTTT AAAATACTTT GTTGAGTGAA ATCAGTCCAT    16500

TGCTTGATAT ACCTTGAGCA CAAGTAAATA GTATGCCAAA AATTAAATGT CTTTCAGTCA    16560

CAGTTTGACA AACTCAACTA CCCTGAGCCT ATAGAGTGGT AATAATTGCC CTACTCATAA    16620

AGATGGGGTG AAGATTAAAT GAAATAGCAC CTATAGAACA CTAGTTCCAG ACGTGGTATC    16680

ATGCTAGTAA AATGGCTGCA CAGCACTGCT CAATGATGAC AAAAAGTGAA GCTTCTGGAG    16740

ACAGACTCCA AGTTTGACTC CCAGATCACC ACATATAAGA TGTGGGACTC TGAGGCAGGT    16800

CATTTAATCT CTCTGTGCAT TAGTATCCTT CTCTATACCT TTACAGTGAT GGTAATAGCA    16860

CCTACCTTCT AGAAGTATGT GAAGATTAAA GATCCTTAAT GCATATAAAC CACTGTGTTT    16920
```

```
ACTGCTGTTT GACAAATTTT ATTTATAACC ATCTTTACGC TCCTAAAAGG ACTTGAAGCA    16980
GCTTATGACT GAAGACTTTG GTAGGAGTTG GCCTTCTATA AATTATAAGA ATTTCATAAA    17040
TTATTTGATA TGAAAATGCC AGTTGATCAT AGTATGTTTA CCGGGGTCCA ACAGGTTGAG    17100
AAAAAATACA CTTTTTTTCC CTGAACATAT GAAATTAGCT CTCTAGGCAT ATTCCTAAGG    17160
ACTTAAAGAA TGATAACTAT CATTTCTCTT AAATCTTCCA GATTTGGAAG GATATATATA    17220
TTCAGCACAT TGACAGACAA TCCCAGTAGT CCTAAATTAA AAGACATTAA AAATTAGTGA    17280
AACTTTTCCT ACCTTTAGCC TGTGTAATCC TGGATGACCA AGCATAAAAT TAAATTGAGT    17340
AGAGTATACC ACTGTAACAT TTCCTGAAAG GTATTCTAGG CTCTGAGTAA TTTCTTTGGG    17400
GTCTGAAGAT CAGTTTGACA TATCCTCAAG TATCATGAGT TCATTATAAT TAAGAAAAAG    17460
AGAGTAAATC TGGAGAATGA GCCACTTTCT TACTACTCCT TGACCTCAGT TCTTTTTTTC    17520
AGAGACAGGG TCTCACTTTG TTGCCCAGGC TGCCAGGCTG GAGTGTAGTG GCGCAATCGC    17580
ATCTCATTGT AACCTCCACC TTCTGGGCTG AAGCCATCCT CCTGCCTCAG CATCCTGAGT    17640
ATCTGGAACC ACAGCAGGTG CACACCACCA TGCCAAGCTA ATTTTTTAAA AAGTTTTTTG    17700
TAGAGATGGG GTCTTACTAT GTTGCCCAGG CTGGTCTCAA ACTCCTGGGC TTAAGTGATC    17760
CTCCTGCCTC AGCCTCCCAA ATTGTTGGGA TTACTAGTGT GAGTCACTGT ACCCCGCCCC    17820
ACTTCAGTTC TGAGGAGGAA AAAATATGTA ATAATAATGG GACTTTGGTT TGCTGATTTA    17880
AAGATTCATG TAACCTTATC ATCCAATGCG CAATTTGTAG AATAATTAAT AGAGACATCT    17940
GGTCTCATGT TTCTACAGTT GCTCATGCCT TGATAGTAGA TCTCCTTGCT GCTGGCTCAG    18000
AAGGGTAAAA GAGCAGAAAT GATGGGGCTT CTCTCATTCT ATGAGGAAAT AGACCTATGT    18060
AGAGGAGGCT ACCTGTGGTA AAACCTTATC CTCATCACTT AAAATTCTAG GCTTATTCTC    18120
TGACCATATC AAGTTTTCAA ATGGTAAAAG AATTGGATTC AAGAGAAATA TGAATAAACT    18180
TTTGTTTTCA CTTTTCTCCC TCCTCTCCCC CCATTCTCCC TTCCTTTATT TTCTTGTCCT    18240
TAGTTTTCTT TTCACTTTTT TGTCTACTAT TATTTGCCCA AACTCAACTG TAGGCTAGAA    18300
CAAAAAAAAA TTGAAAATTA AAATGTGCCC CTTTTGTTGT TAGACTTGCT TAAACAATTG    18360
GGGTAATGAA CCTTGGACAC TAGATTTTAA AACACACACA TTTGAGCTTC AGTGCACTGA    18420
AATAAATATA TTTTTAACAA TTAAAAAATA AAATTGCATG TTTAAAAAAT CTGCAGAGAA    18480
CAATACACGT TGTGAGATCT TGAATGGAAG GAAAACTGCT AGCCTCAAGA GTGGATCAAA    18540
GATGCTCAGC AGGCAACAGA GTAAGAGCAT GTTGGAGGGT TTAGAGAGTG TGCTCAGGGT    18600
TCTAGGCTCT AAAAATCAGA CAGTCCCCAC GGCCTGGCCT TCGTCGCTGT ATCTTCTTTA    18660
TGAAAAACAC TAAGTCTTTT TCCTCACTGG ATAAATTTTT ATCCTTCAAG TTTAGATCAA    18720
ATGGAACTTT AGGACACTGA CTAGGTTACA TTCATCTTTT AAGAGCGTAC AGACATTCAA    18780
GGGCTAGAGG ATGTGGGTTT ACTGCACAGG CTCATTATCC AACAGCTGTG CTACCTGGGA    18840
AACTTAACCT CTCTGTGCCT TAATTTCCTC ATCTATAACG CAGGGAGAAT GACAGTAGGT    18900
ATCTCATAAG GTTGTTGGAA CAACTAAATG CATTGGTATC TATTGTGTAA AGTGCTTAAA    18960
ACACTGCCTG GCACAGAGCA ACATCCAGT GAACTTTAGC CATCATCATT ATCATTGTTC    19020
TCAGAGTCAA ATACAATATC TCATATCTGA TAAATTACAG AAGTGAATCA ATCACTCTCT    19080
CTCTTTTCTC CAGGGGGAGA CAACAGCTTT TAGACATATC TTTTCCAACA GTCGTCACTG    19140
CTGGACACTG TTTCATCTTG CAAATAAACC AATGAAAATG AGTGATCCTA GAAGAAGATA    19200
AATGGAGGTA TTTTGAACAA TCAAAGAAGG ACAAATGAAC ACCTGGCTGA GAAAAATTAG    19260
CTCTTTTTTC TATGCATAAA ACTATTAAAA TATTCTTCAT AGAAATTTAT GACACAGGAA    19320
```

-continued

```
ACATAAAGAC AAAATTAAAA TAACTCCTAG TATCTCCTAT TCTTTTTATA TGTATATTAT    19380

ATATACTCAT ATTCATATAT ACATATATCT CACATCATGT ATCATATATA AAATAAATTT    19440

AGGTGTCATG ATATATATTT AGATAAATAT ACTTAGAAAC TTTTTTATGG ATGTATAATT    19500

TATGGATATA TTGATAATTA TGTATTTGTT ATTGACTACT TCAATTGATT CCCATTTTTA    19560

TGCATTATAT TATAGATTAT ATAGCTCACA CATCTTTGTA CATAAATCTT TGTTCAAATA    19620

TTATTTCCTA AGGATAGACT TCATGAAGTG GAAATACTAA ATCAAAGTG AAAACATTT      19680

TCTAAGGTTC TTAACATATA CATTGCCAAA TTGCTATTCA GGATCATACC AATTTATAAT    19740

CCCAAAATAA TATGGAAATT CCTGTTTTAT AGCACTCATA TTTACAATAA ATTTTAAAAA    19800

TCACTGTTAA CCTAATAGTC CTTCAAAAGA AAAAAAATT GAAATTACAT TATTTTAATG     19860

ACTCTATTAG TGAGGGTCAT TCTTCCCATG TTTCTTGTTA GCCATGACCC TATAAGAAAT    19920

AAACTGCACT GCAAAATGAT AAACATGACA TCAATCATTA CATGGGAAGG CACTATATAA    19980

AGAATAATAC CTTAGGTTAA GGCCACATAA ATATTTATCA GGTGCCTTTT CTGCGGAGGA    20040

CTCTGAAGGG ATACTAAACT GCATTTAGCT GCATGCAACT GAAACTACTT TTACCTACAT    20100

TGTCTCTTAT AAACATTATA ACTACTCTTT GAGAAAGTGT TTACTATGGA CTGAATTGTC    20160

TCCCCATCCC CCCAAATTCA TATATTGAAG CCATAAACCC CAATATGACT CTATTCCTAG    20220

ACAGGACTTA TAAGAGGTAA TTAAGGTTAA ATGAGGTCAT TAGGATGGGT TCCTAACTGG    20280

ATAGGATTGG TGGCCTTATA AGAAGAGGAA GATTCTGCAC TTGGTCTTCC AAATTAAATA    20340

ATTTATTTAA AAGAAAAAAA AAAAAGAGGA AGAGAGGGAG CTCTGCACAT ATACTGAGGA    20400

AAGGCTATGT GAGCTCTCAC AGTGAGAAGG TAGCACTCTA CAAGCCAGCA AGAGAGCCCT    20460

CAACAGAATC CAGCCATGCT ATACCCTGCT CTGAGACTTC CAGCCTCCAG AACTGTGATA    20520

AAATTTGTT GTTTAAACCA CACAATCTAT GGTATTTTTT TATGGCAGCC CAAGCCAACA     20580

AAGACAGCAT CATTGCTGTC ACTTACAGAC AAGAAAACTA AGACTAGGAG AGAGAAAAGT    20640

TAAACTTGTC CAAGGTCACA AAAGCCAGAA ACAAGTGAGG TGAGAAGTTG ACCTTGTTCT    20700

CCTCAATCCA AGGCCAGGAC TCCTCCACTC CACATGTAGA TAGCCACCTC ACAGTCAACA    20760

GCCAAATGTC CACACCCCAG AGTCAGCATT AGACCAAGAT GTCTTACCAG GAGACAAATG    20820

CCTCATCTTG AATAAATATG ATCTAACAAC TTACCCATGT AAAACATTGA ATCTCATGAG    20880

AAACAAAAAT GCAAAGTATG TAGAAAACTA TGTTTACCAC TTAACTGACA GTGATAAAAA    20940

GCTTAATGAT ATCCTTATAG TCTTGGAGGG GTTTGTATAT GTGGTGAAAC AGGTGCTCAC    21000

GCACTGCTGA TAGACTGTAA ATTGGTCCTA GAGAGAAAAA TAAATAAACT GGAAGGAGAT    21060

ATGCTGTATG TTTACTTTTT TTATGGAAAC ATATGATATA CCTGGAAATT CGATTGACCA    21120

TGCATCTATT TCTTCAATGG GTATGCACAG TTGAGCTGTT CCCATGCACC AGGCACTGTA    21180

ATGGACAAC TGCACATGAC AGTCAAAAAT CTCAGTCTCA TGAAGTCGAC ATGCTCATGG     21240

AGAGGTGCTA CCCACTAAAC TAATATTTGT ATATCAATTA TGGATACATT GGGCCACATT    21300

TACAGAAATT CACTTACAGT GGGTTACCAG AAGGGATTTT TTTTCTTGAT TGGCAAGAAG    21360

GCTAGGCTGT TTTGTTGGGG GCTGGCAGGA GCTGTCTAGG CTGCCCAAGT ATGCAGGTCT    21420

CTTCTATCAT CCTGTGTTAA CCATCTTCCA TGTATCTTTC AACCTCATGG TCATCTGCAG    21480

CATGTCTAGG GGTCATATCT ATGTTCCATG CAGGAAAAAA GGGTAAAGGG AAAGGGAAGT    21540

AGGCATGTAC CATTTAATG CACACCTTGG TTTTCAGAAA ATTTAAGAAG AAAGACTTTC     21600

TGCTTTTCTC TGACTATTCT GTATTCTGGA TTACAACGCA ACAGAAACGT CACCTTAAAT    21660
```

-continued

```
TCTAATGTTT TTCTCTCCTT GCTTTCAAAA ACTGACTCAT TAACCTCCAC GTGGCTTGGA      21720
AAAATTATTT CAGTCATCCA GTAATGAGCT GTTCATAGAA ATGTTTTGGA CATCAAGTCT      21780
GTGTTGTTAG CATTATACAT GTTAAGCATT GAATAAAAAA CAACATGATG TGGGTAAATT      21840
TCTTTACTTA CATATAAGTA CTTATATACT TATAGCTGAA AAGAGAGGTT GAAATGTCAG      21900
GTGGAACAGA AATAAGATTA CCTAGATGTT TCTCCTATGG GTGATTTTCA GCTATGCTGA      21960
TCTTTCTTCT GGGTCAGGTA CTCCCAGAAC TTCCTAATTA AATGGTGGCC CTGATCTTAG      22020
TTCCTCTCTC CTCTTAGACA TTTTCCAGGA CTACAGAAGA TGTGCAGTTT ATAAATGAGT      22080
AGCAGAAACC TACTGAACAA ATTATTCAGG CTCATCTGAA CAGAGAGGAC ACCTTCTCTG      22140
CTATACTCTC TCAGTGATTT CCCTGCCTTG GGGTCAATTA TTGTCTTGGA CATTGATTTA      22200
AGCACATAAT AATTGTTGTC ATTGCTTATG TTTGGATTTC ATCTCCCAAA ATAGATGGTA      22260
AATTCTTTAG TTTAGAGACC AAGTAATACT TAAAAAAAAA TTTTGTGTGT GTGTGTGTGT      22320
TTTTTCTGTG TCTCTCAGCC CTGTAATAGC ATCGTACTTA CACTTGTTAG ATTTTTAGAG      22380
ACAACTTTTA CAAAACATGG AATTATCTAC ATACCCTTTC TACAAAACAG ACAAATTAAA      22440
TACTCAGTAG TTGAACCAAA AAAAGCAGTT CAAATAAAAT ACTTGAAAAT GAAGAAATCA      22500
TTTGAACAGA GTTAAAGTTA ATCGTAAAAT AATGTCTGTA AAAATTATTG CCAATCAAAT      22560
ATAAAGTTCA AAAATAGTGC TTGAAAAAGG AAGAATCATA TGAAAAGGGA CTACTCATTT      22620
TAAAAATGTT AGATATCAGG AAAAGCCAAG AAGTGAGTAT GGTAAGAGTG CTGTCAAGTG      22680
AAACCCTGCT AATCTCACTG AACATGTAAA AATCTGTAGA TGCCTTTATT TTATTCACTC      22740
ACACACATAT GTAGAAAGAG AAATATATGG TAAACATTAA AAAACCAAA TTAGAATGTA      22800
AAATTAATAC TTTAAAAAAT GGGCTGTATA CTTTTCTTAT CACCGGAGAT AAGAATTTAT      22860
TATTTTTAAA ATAAAGTTAT TTTCTCTGTG ACTGTTTCCA TGACTTTGCT ACTTAGAAGT      22920
TAGAGATGCC AAAGTTTATC TAAGAAAATG TTTATGGAAA TATTATTTCA ATAATGAATG      22980
TTTAGAAGAC TGAATTTCCT GACTGGGCGC AGTGGCTCAT GCCTGTAATC CCAGCACTTT      23040
GAGAGGCTGA AGAAGGAGGA TCGCTTGAGT CCGGGAGTTC AAGAGCATCC TGGGCAACAC      23100
AGCGAGACCC TGCAGCAAAG TAAAAAGAAA AAAGAATTGA AAAGGAAGA CTGAATTTCC      23160
TTTGGGCAAG TCATGTGACA TTCCTGTGCC TCAGTTTCTT CATCTATAAA GTTAATTCCT      23220
ACATTTTTGG GGAAGGGAGA GAAAAACTTA GGATAGTGAC TGGCACAGAA GAAGCACTAT      23280
ATACTATATA TATGTGGATA TCATTTGTTT TTATGGTACC ATTTTAGCTA TCTAATGCAA      23340
AATATGAATC TTTTTTTTCT GGGTCTTAAA TTATGGAATG TAAGAATTTT CTAAATTCTC      23400
TAATTCTGTG TTAGTTTTAA AGCAATGGAG TAACGTATCT GTCAACTTGT AAATATAAGG      23460
ATCAACCTGA TCCACAATTT GACCCCTAGC CACTAATATT TAATAGTACA ACACTCAGAA      23520
ATTATCAAAG GTCAGAGAAG CCAAACAAAT GTAAAAACAT ACAGGTGCTC AGAAAGATGC      23580
ACCTGTAATC TCTCTAAGGA GAAATATTTT CCAAACTGAG TGACACGGTG CTTTAGTGAG      23640
TTGTGGAATC AATCTCATGA TTTCCAACCT AGTGTTCTTT TAAAAATGAA CTAGTCCACA      23700
GTAGAATATA CTAAAGTGCT GGTGCTTAAG ATAGTATTGT TTTCTGGAAA AAAAAAAAA      23760
ATTTTTTTTT TTTGAGACAG GGTCTCGCTC TTGCCCAGGC TGAAGTGCAG TGGCACAATC      23820
ATGCTCACTG CAGCCTTGAC CTCCTGGGCC CAAGTGATTC TCCCACCTCA GCCTTTTGAG      23880
TAACTGGGAC CACAGGTACG TGCCACCACA CCCGGGTAAT TTTTTAATTG TAGAGACAGG      23940
GTCTTGCTAT GTGCTTAGGC TGGCCTTGTG AACTCCTGGG CTCTAGTGAT CCACTAGCCT      24000
CAGCCTCCCA AATTTATGGG ATTATAGGCA TGAGCCACCC TACCTGGCCT GTTCCCTGAA      24060
```

```
TTTTTTTTTC TTTCAGGTGT TTGTGCATAT GTGTGTGTGT ATGGGTATAA CAGAGAGACA    24120
GAGAGAAAGA AACTTTTCTA TCTCACTTTG CAATCAGAAG TTTGAAGTCT TATCTTTTGG    24180
CTTTTGTTTC AGAAATATTT CAAATGTAGA CTCTCTCCTT TACCACACTG TCCCCTTAGG    24240
CAAGGTCTTT GCCATTCTTC TGAGACTATT GCAACAGACT CCCAACTTCT GACTGTGGGC    24300
CCTTCTCAAA AATGATTGTT TATGCAATAA ATCTAAACCC AAGACAACTA CAACAATACA    24360
ACAAATTCTC TGCTTAAAAA CTTCCAATGT CTGCCGGGCG CGGCGGCTCA CGCATGTATT    24420
CCCAGCACTT TGGAGGCAGA GGCGGGCAGA TCACTTGAGG TGGGGAGTTC GAGACTAGCC    24480
TGGCCAACAT GATGAAACCC CATCTCTACT AAAAATACAA AAAATTAGCC AGGCATGGTG    24540
GTGGGCGCCT ATAATCCCAG CTAATTGGGA GGCTGAGGCA GGAGAATTGC CTGAACCTGG    24600
GAGGTGGAGG TTGCACTGAG CCAAGATCAC ACCATTGCAC TCCAGCCTGG GCAACAAGAG    24660
CAAAACTCTG TCTCAAACCA AACCAAAACA AAACTTCTAA TATCTACCAA ATGTTTCACA    24720
CAAGTATTTG GGGATCTTCA CAAATGGCCC TTATGGAGTT TTCCTTTGCT GAGACCCTAT    24780
GCTCTGGCCA CACTAAACTC ATTCAGCATC CCAGAAAGGC CTCAGCCTTT GTGAGCAAGC    24840
TCTTATCTCC AGGCCTCTCA CAAAGACCTG TTCCAGTAGA AGCTCAGGGG AGCACACTGG    24900
ACATTATTCC AACAACCCTT TCCCCACAGC TATGCAGCCA AATCTGCCAG CTCAGTTAAT    24960
TAATTAAGCA ATTCAGAGAT GAGGGTCTGC CCAGGCTGGA GTGCAGTAGC TGCGACCTCA    25020
AGCTCCTGGG CTCTAAGTGA TCCTCTTCAG TCTACCCAGA AGCTGGGACT GCAGGCATGT    25080
GCCACCACAC CCAGCTAATT TTTTTTTTTT TCAGTAGGGA CCAGGCCAAC CTAGTCTTGA    25140
ACTCCTGGCC TCCAGCCTTC CGAAGTGCTG TAATTACAGG CATGAATCAC TGCGCCCAGC    25200
CAACCCGCCC AGTCTTGTTA GACATGGGGT CTGTAGTTTC TAGTAGGTTC TTGAGTCTAG    25260
GGTTCCTACC TCATGTTTTA TAGTTAATTT AGGGAGGGA CTGTGTCTGT TTATCTGGGG    25320
ATGTAGGGGT GGGCAGGGGG ATAGAGGGGA CTTCAATTAA TGAAACCAGA AGCAAAACTC    25380
AGTTGAGGAC ACCGGTCATG AGAGTGGCCT GATTATGGCC AATCTTACAT AATGTGTGAG    25440
ATCTTGATAT TACCCCATCC TTGAGAGTCC TCTATAAAGC TACAGGGACT TGGGAGCACC    25500
TTTAATTACA GACAACCCAT GTTCCTGTGG ATTATGATTT ATTAGATTGC ACATGCCTAA    25560
ATAAAGACAT CCTCTGCAGT CTTTTGACAA TTCTATAAGC ATCTTCTGAC TCCGCAATTA    25620
GACAGCTAAG AGATCTGTGT TACTTCCCTC ACATATATAA ATAATTTTAA ATAAAAATCA    25680
TGGCGTGAAT AATTTCTTTC CTCTACCGAT TTGAAGCTAT CCATTTGGAA GACCACTCTG    25740
AAGAGATGAA ATAAGTCTTC TGCCAAAGAT TACTTATTAA TTTACAAGGA AAAGGGGAAG    25800
TTTTGTTCCT CTCCGTGAAT TTGATTGAAA ATCGAGGGCT TTCTCGAATA GTTTTGGCAT    25860
CCAGGGTCAT TTTTCATTAA AAAGAGAAAA GTCATGTCAA ATATGAATTT CCGCAGATTA    25920
TTCAGCACTA GACCCTGGGA GATTCTGTAA AGAGGGTTT TGTTATACTC AACTTTTCCG     25980
GGTAAAACAA ACACAAATAC TCCTCCTCCA AGGGGCGGGG GCGGTGCCTA GGTGATGCAC    26040
CAATCACAGC GCGCCCTACC CTATATAAGG CCCCGAGGCC GCCGGGTGT TTCATGCTTT     26100
TCGCTGGTTA TTACATCTTG CGTTTCTCTG TTGTTATGTC TGAAACCGTG CCTGCAGCTT    26160
CTGCCAGTGC TGGTGTAGCC GCTATGGAGA AACTTCCAAC CAAGAAGCGA GGGAGGAAGC    26220
CGGCTGGCTT GATAAGTGCA AGTCGCAAAG TGCCGAACCT CTCTGTGTCC AAGTTGATCA    26280
CCGAGGCCCT TTCAGTGTCA CAGGAACGAG TAGGTATGTC TTTGGTTGCG CTCAAGAAGG    26340
CATTGGCCGC TGCTGGCTAC GACGTAGAGA AGAATAACAG CCGCATCAAA CTGTCCCTCA    26400
```

```
AGAGCTTAGT GAACAAGGGA ATCCTGGTGC AAACCAGGGG TACTGGTGCT TCCGGTTCCT   26460

TTAAGCTTAG TAAGAAGGTG ATTCCTAAAT CTACCAGAAG CAAGGCTAAA AAGTCAGTTT   26520

CTGCCAAGAC CAAGAAGCTG GTTTTATCCA GGGACTCCAA GTCACCAAAG ACTGCTAAAA   26580

CCAATAAGAG AGCCAAGAAG CCGAGAGCGA CAACTCCTAA AACTGTTAGG AGCGGGAGAA   26640

AGGCTAAAGG AGCCAAGGGT AAGCAACAGC AGAAGAGCCC AGTGAAGGCA AGGGCTTCGA   26700

AGTCAAAATT GACCCAACAT CATGAAGTTA ATGTTAGAAA GGCCACATCT AAGAAGTAAA   26760

GAGCTTTCCG GGAGGCCAAT TTGGAAAGAA CCCAAAGGCT CTTTTAAGAG CCACCCACAT   26820

TATTTTAAGA TGGCGTAACA CTGGAAACAA GTTTCTGTGA CAGTTATCTA TAGGTTTAAG   26880

TTGTGATGCA GCTGAGTTGA AAAGGCTTGA GATTGGAGAA TTAATTCAGG CCAGGCTTCA   26940

AGACCATCCT GGGCAACATA GCCAGACTAC CATCTATACC AGGGGTCCTC ATTTCCCCGG   27000

CCACCGACCG GTAACCGGTC CCTGTCCATG GCACGTTATG AATTGAGCCG CACAGCTGAG   27060

GGGTGAGCGA ACATTAACCA ACTGAGCTCC ACCGCCTGTC AGGTTAGCTG CAGCATTAGA   27120

TAGATTCTCA TAAGCTCAAA CTGTATTGTG AATGGCACAT GCAAGGGATC TAGGTTTCAG   27180

GCTCCTTGTG ACAATCTAAT GCCTGATGAT CTGAGGTTGG AGCAGTTTTA GTCCGGAAAT   27240

CATTGCTCCC AGCCCCTGCA CCCCCTGGTC CGTGGTATAA TTGTCTTACA CAAACGGTC    27300

TCTTGTGTCA AAAAGGTTGG AGACTACTGG TTTTACAAAA AAGTAAATTA GTCAAGCATG   27360

GTTGGCACGC TCCCTTAGTC CCTGCACCCA GGCGTTTAAG GATACAGTGA GCTATGATGG   27420

TGCTACCTCA CTCCAGCCTG GGTGACAGCG AGTCAGACGT TGTCTCAAAA CTTAAAAAAA   27480

AAAAAAGTTA AAACAGAAAA AGGGCTTCTT GTCAGAGACT GCCGTATATC TAGAGGTCCA   27540

GGAACTAAAA AGTCTGATGT CCAATCCTGA AAAGCTCGAT GGTGCACTAG AGGAGGCTTT   27600

TACATGTAAG AGCATCTAAG TTCTGGAAAT GCCAGTGTCA GGGAAGGGAA GTGGAGAGCA   27660

ATTTGGCATC CAAACATAAC TTGCTGATAC TTTTTTTTTT TTAACACAA GTACTACATT    27720

CTAGTCTTTC TGTGGTGTCA TTGTAACTAT TGTTTCTTAA TATGCTATCC ACTGACTTCA   27780

AGGGATCAAT AAATAGGAAT CAAGGTGTCC CAGAATATGG ATTAGGGGAG TTTTTTTGTT   27840

GTTGTTGTTG TTGTTGTTTT TCATCTATTC ATTATCCTGT AGCTGAAATT TAGAATTTTC   27900

TTCCATTGTG TGTGACTGAT AGAAATAACA AATTTGTAGG TTATAGTTGT TGCAAGAATC   27960

TGGAAATCGT GCTTGCTTAT TTCCGAAGTA CTATTAGGTA TATCAACAAA AACACACATA   28020

TTACGGTCAA GTGGTTTGAT AATTATTTTA ATATTATTGG TCTAATACAA TTGTAACCCT   28080

ATGAATTACT TTAAGTATCT TATTTATGAA AAGAATCTGT AAGTTTCATC AGACTACCAG   28140

AGCATACCGA AGACTGAAAA ATTTTAAGAA TCCAAACCTT AATGGAAATG TTGGAGGCTG   28200

CCCAATTAGG TTCTGAATTC CACCTTCCTG AATCACAAAC TTGTTTTAAC TCTCAGTCTG   28260

AGGTAAACTA CGTTTCTCTT TAAACAGACA TAGTTTAATT TTCCTTTGAT TTTTGATTTA   28320

GTATTCTTAC TGATCATCAT AAATAACCAA TGCTAATGTT AGTCTACTTT GGACCATGGT   28380

ATTTCGAGAA ACTTTGAACA AAGTCCCCTG CAAAACTATG CATTGCATTA TTTCACATAC   28440

ATTTATGTTT TCCAGACGGT TCAATAGTAC CTCACTTTTC TGAACTTATT TGTATAGTTT   28500

GGCATCTTTT TAAAAATTGT GTCCTATAAT GAAAGGTTGT AAACATTATG TTTTAAATTT   28560

GTATAGATAA AATCAACCAC AGACCTTTCC TTGCTTGGAT GTAATTGCCA TTGTTTCCCA   28620

ATGAGTTCGG AATTACTAGG ATTGTGCAAA AATATGCCTC ACTTGCCTGA CATAGCAGAG   28680

AGCCATTTTG CCTAAATGCT GTGCCCAGCA ATGGACTGTC ACCAGATTCT CATCACATAC   28740

AGTGAGGATG AACAACTAGC CTCTCCCAGC AGCTGGCCGG TCTCTCAATA ATATGGGACT   28800
```

```
CCCTCAAGAT GGCTTCCTGC ACCTTTGCTC CTCTAGCCTT GTATGTATAC AAGGCTAGCA    28860

TGCCTGGCAT ACATAAGGTT AAAAACAAAA TCAATAAGTT ATGGTTCTTC CTCCAGTTCT    28920

GGGGATTATT AGACCACTTT TTTGTTTTGT TTTGTTTTGG ATGGAGCCTC GCTCTGTCAC    28980

CCAGGCTAGA GTGCAGTGGC ACAATCTCGG TTCACTGCAA CCTCTGCCTC CTGGGTTCAA    29040

GCAGTTCTCT GGCTCAGCCT CCCACGTAGC TGGGATTACA GGTGCCCGCC ACCACGCCCG    29100

GCTAATTTTT GTATTTTTAG TAGACGGGGT TTCACCATCT TGGCCAGGCT GGTCTTGAAC    29160

GCCAGACCTC GTGATCCACC CACCTTGGCC TACCAAACTG CTGGGAATAC AGGCGTGAGC    29220

CACCGCGCCC GGACTTAGAC CACTTTGTTT TGGCCAATAG GACAACAGCC ATAGAACCCT    29280

CCGCAAATGA GAGCTTGTCC CTAAAGATGC TTTATTTACA TAGCTGTGTG CCGCATGAGC    29340

CAAAAGGTGA TAACCTTTGT TCAACACGCG CCTCCAGCCC TTCGGTTAAG TCCAAAGTAC    29400

CATTCTTAGA ATGCTCTAAA ATACATAATT TTTTTTTTTT TTTTTTTTTT TTTTTTTGAG    29460

GAGTCTCTCT CTGTCTCCCA GGCTGGAGGG GAGTGGCGCG ATCTCGGCTC ACTGCAATCT    29520

CTGCTTCCGG GCTAGCTGGG CCTACAGGTG CAGACCACCA CGCCCGGCTA AGTTTTGTAT    29580

TTTTTTTGGT AGAGGGGGTT TCACCATTTT GGCCAGGCTG GTCTCGGATT CTTGATCTCA    29640

AGTGATACAC TAGCTTTGGC CTCCCAAAGT GCTGGGATTA CAGTCGTGAG CCACTGCGCC    29700

CAGCAAAATG CTTTTTGTGG AGCCAATCAC TTTATTAGCG CTTACCTCTC TATGCCTACT    29760

TTATGCTTTG AAATTTTGTC ACAGTGTGGC CGGTCATGGC AAACACAATT CATTCTTATG    29820

CAGGATGTCA CGGTTATTTC TGTCATCCAA ACTCATTCTC GCAACGCATT TCAGCTCTTT    29880

AAACGACTTT GTGAGCGGCC CTGAAAAGGG CCTTTGGGTT TTTTTGTTTT TGTTTTTTGA    29940

AGTTCTCAGG AGACCGCGTA TTCTTAGATT CAGCCGCCGA AGCCATACAG AGTGCGCCCC    30000

TGACGTTTTA GGGCATATAC TACATCCATG GCTGTGACAG TTTTGCGCTT GGCGTGCTCC    30060

GTATAGGTGA CGGCGTCTCG AATAACGTTC TCTAAGAAAA CCTTAAGCAC ACCTCGAGTC    30120

TCCTCATAGA TAAGACCGGA AATGCGCTTG ACGCCACCGC GCCGAGCCAA ACGGCGAATA    30180

GCCGGTTTTG TAATGCCCTG GATGTTATCC CGGAGCACCT TACGATGGCG CTTAGCACCA    30240

CCCTTCCCCA AGCCTTTTCC GCCTTTGCCG CGACCAGACA TGATTCCTAT CGCAGTGGAA    30300

GGTATGAACT GAAACAGTTC CTTAAATACA AACTTGGCGG ACCTGATTGA AAACAACATG    30360

AGTTGGCGCG GTTTTTTTTT TTTTTCAAAT TTGGTCACCA AGTGGGTGGA GCAAGAAAAA    30420

CTGTTTCATT ATGGTTCATT GTTTTGATTG GCCAGTGACA GCTTGCTCTT TGTGGGAGTG    30480

GAAGGGTGTT TGCAAGTTGA ATGCGCTGTA TTCCTGTCAG CTTAATGACG CTAAGCATAG    30540

CCCCATTCCA CATTTCTTTT TATTTCCACT TGCTAACTAA TAAATTACGG AATAGTTTAT    30600

TGGGAACAT ACAAATAATG TTTAAAGGAG GTCAGATTTA TAGGTCAAGG GATTTACCCT     30660

CCCAATCATT TTAATATTTT TATTTAAACC AGGCATTTTG ATGGCCTTCT CTGTGCTGGA    30720

CAAGGTATAA GTTTGGCTAT GAAGTTTCAC TCCTAAAGAC CCTATGTTTT GGGAAGGCAA    30780

AAAGGTAGCC AAATAATTGC AAATTAAAAC CTCATAAGTG CAAACTTCTT CCTCGTCACT    30840

TTCCCTATCT CGATTCAAAT ATTTGTTGAA TGACTCATTT TTCTGCAAAA GTCTGAGAGA    30900

GACAGGGAAT ATAAACTTAA GTCTGGATAA TATGTTTTCC CGGGACGCTC TTCCTGGTCT    30960

GCTGTGCCTG TTTGCTGTGC CTGAAATTCC AAACACTCTT CCCTTCCCTC CGTTTTTAAT    31020

CCCCTTTCAA CTTGCTACAG CTTTAGAGAA AAGAACATTC GTTTTGTACA GTTGGGGATT    31080

AATTGAAGTG TAGGGCTAAT ACTTGATTAA GGTCATTACA AAATCTACAG GGTCTTCCTC    31140
```

```
TGGGAGGTTT TTGTGATAAG ATTATTGGTG TTAAAATAAG GCTAATCCCC TTGAAAAATA  31200
AATAGAATAG CAGAATTGGG TCTGAATGTG GTTTGAAGAA AGGGACTTCT CAATTCAAAA  31260
TTTTATTCTT AGCTTCCTGC GGGAGCTTTC CAGAATGCCC ATAAGATCCA CTTTTGTTTA  31320
AAAAACAAAA ACAACCCCAC CCACCACTCT CTGGTTAATA AATGAATTTC TATTGGGAAT  31380
ATTTAGAATG GGGCTGTGGC CTGTGAGAGA CATTATATAG TAACCTCAGA CTTGCTCACA  31440
TGAAGAGAAG AAATCCAGGA ATGGAGAAAA AAGACCCAGG AAAGGCCAGA ATGCTCTACA  31500
TGTCATATTG TTTGTATCAC TTCTGAAATA ATTGATTACA TTCTTCTGCC CCAAATTGAG  31560
TTCTTAGGTT CTTCCACTCA CTGTCCACAT GCCACAACAC AGACCTTATA ACTAGAGACT  31620
TAGCTAGGAA GAAATGTCAA ACATTACAGA GAAAAAATGC AGAGTCTGAG ATCATAAGTA  31680
AAACTCTGAA ATCTCAACAT GCCTTTTAAT TCATGAAAAT AAAAAATATA GCAGCATATG  31740
CAATATGACA ATTCTCTGAA AACATACATC ATGTGAACTA CCCTGGAACA CATCTCGCCA  31800
AGTGCCATCT TCATTTTAAC CAGAGGTCTA GGATGCCTTT CCTTTATTTT GCCTATTATA  31860
TCATTTATAA AACCCCATTT TTATTTTGAT ATTTTATTTA CTTTCTATTT CCTGCTCCTA  31920
ATATCTCCTT TCTAAACTTT TCTCAATGAC AGTGACTCAA AAACAATGAA TGTCAGAACA  31980
AATATTTAAA GGATCTGTAC ATGTAGATAT ATATATTTAA AATGGATTCT TCCACTCTGC  32040
GAAGAATTCA GGCATACTCA ATCTTATGGT TAGGGAGAGA TTAGGCTCAC TCGCCTAATC  32100
TGTATGGCTT CTCGTTCGCT TTCCATTTCA CCTTCCTCTC ACCCATCAGA TCAAACTCAT  32160
TCATTGAACA AGAGACCTAA GCCCTTCAGA TTAAAACTCT GCAAACAAGT TGTGGTTGAG  32220
AGGATACATG AAGCATTCAA ACAAATAAAT CTATGATATT AATCAGAGGT TAATCTATGA  32280
TATTAATCAG AGGTTAATGC AGTGGCTCAC GGCTGTAATC CCAGCACTTC AGGAGGCTGA  32340
GTTGGGAGAA TCGCTTGAGC TCAGGAGTTC AAGACCATTT TGGGCAACAT AGCAAGTCTT  32400
CATCTCTACT TAAAAAAAAA TAACCAGAGG TGTTATGAAA ATATAAATTG TCCAGAACTA  32460
CCCTCCACAA ACTAACTCTC TCAGAATATT CGATATGAGG AATGAAATAT GGTGTGTGTG  32520
TGTGTGTGTG TGTGTGTATG TGTGTGTGTG TGTGTGTGTA TGCACCTATA TATGGCACCT  32580
ATATATTCAA CAAACAATTC TGATAATTGG CCAGGGTTGA GAATGACTAG CAGCCCAGCA  32640
TACACTATCA GTTTTAAGTA TATAATTGCG CTTTAGTAAA ATGTAAAGAA ATCCCAGAGT  32700
AGAAATACTT TTAAGCTATA TTACAGGTGA GAAAATGCAT AAGTATAGTC TCACCCAACT  32760
TAGACTATGG GGGCTTTATA ATGTCACAAC AGTTGTTTCC AGGCATTTGG GGACATCACC  32820
ACTGGTCTTG GGCAAGAAAC TCCTCTAGCC AATGGCTGAT TTATCTCACT CCCATCTAAG  32880
GCTTCACTGC ATTTCTCTTT TTCAGCAACC TAACTTATTT AAAAATATCC ATTTTCTGAT  32940
TCATTTTTTT CTGAATTAAA CTGTCAGTAC CATTGGCACA CCTTTGGTTC CGTAGCATAC  33000
CTGTGTCTCT GCTGTGTTTT TTTTTTACCT CCACTCCTTA CTTTTCTAGA AAAAAATCTC  33060
TGCTTTTTCT TTTCAGTTTA AATTATTTCA CAAAAAGTTT TCTTGACTTG CACTTCCTAG  33120
GCTTGCTGTC CTTGTGTGGG CACGCTCCCA TAAACACTAT TAATACACTT CGATTTGTTA  33180
AAAATAAAGA TATCTGGACA GAAAATTTCT TTTCTTTTTT TAAGATTTTA AAATTTTTAA  33240
TGTTTATTTT TTTCCTAGAC TGGAGTACAG TGGCACCATG ATGGCTCATG GTAGCCTACA  33300
CTTCCCCGGG CTCAAGTGAT CCTCCCACCT CAGCCTCCCA AGTAGCTGGG ACTACAGGTG  33360
TGCACAACCA CACCTGACTA ATTTTGTTTA TTTGTTTGTT TTGTTTTTTG AGATGGAGTT  33420
TCGCTCTTGT TGCCCAGGCT GGAGTGCAAT GGCGGGATCT CGGCTCACCG CAACCTCTAC  33480
CTCCCAGGTT CAAGCAATTC TCCTGCCTCA GCCTCCCGAG TAGCTGGGAT TACAGGCATG  33540
```

```
CATCACCACG CCCAGCTAAT TTTGTATTTT TAGTAGAGAC GGGGTTTCTC CATGTTGAGG    33600

CTGGTCTGGA ACTCCTGACC TCAGGTGATC TGCCCGCCTC GGCCTCCCAA AGTGCTGGGA    33660

TTACAGGCGT GAGCCACCAC GCTCGGCCAC TAATTTTGTA TATTTTGTAG AGATGGGCTT    33720

TCCCTGTGTT GTCCAGGCTG GTCTTGAATT CCTGGGCTTA AGTGATCTGC CCACCTTGTC    33780

CTCCCAAAAT GCTAGGATTA CTGGCGTGAG CCACCAGGTC TGGCTGGAAA GATAATTTCT    33840

AACATTATCC TCTCTTAAAC ATTTGTTTCA AAAATTTTAC AAACATGAGA GTAATTAAAT    33900

TTGATTTTCA AAATTCCCTT GAATACTTTC TTAATAGCAC ACAGAAAGCA CAAAGTATTT    33960

TACATTTGTT TTAATGATGA AATTGTGAAC CCAAACTTAC ACAAGAAAA ACCCGTAACA     34020

TTATACCCAT ACTTAAAACA GATGCCCTCA TATACATAGT AAAACTCTTG GGGCAGTAG     34080

TGAAGTTGGT TATTTACTGT TTTATGAAAG TGCCATTCAG CCGGGTGCAG TGGCTCATGA    34140

CTGTAATCCC AGCACTTTGG GAGGTCGAGG CAGGCTGATC ACGAGGTCAG GAGTTCAAGA    34200

CCAGCCTGAC CAAAATGATG AAACCCTGTC TCTACTAAAA ATACAAACAT TAGCTGGGCG    34260

TGGTGGTGTG TGCCTGTAGT CCCAGCTACT CAGGAGGCTG GGGCAGGAGA ATCGCTTGAA    34320

CCTGGGAGGC GGAGATTGCA GTGAGCCGAG ATCGCACCAC CGCACTCCAG CCTGGGAGAC    34380

AGGGCGAGCT CCGTCTCGAA AAAAAAAAAC AAAAAAGTGC CGTCATAGTG ACTCAGTTTT    34440

AAGGAATAAA TCAAGGATAT TTAACTCAAT AGACTACAGT TAGCTAACGT GACTTGCACT    34500

GAAAGTTATA CGAATATTGG TACTTATTCC CCTGCCCCTG AAGTATGAAT TAAAGACTCC    34560

AAAATTCTTT TTAGAATCTT CAGAGTAAAA GCTAGAATTT GATTTTTTA AATAATAAAA     34620

AAATACTTTG TATCTAAATC TGGTGTATAA AATAACTTGG TGGATGATGC TTCAAGGCTA    34680

TCCATCCCCA AATTTCTCCC TGAATGATAA AGAGAATAAA TGAATATGTC AATTCAAAAG    34740

TTAGAAATTT GGCCGGGCAC GGTGGCTCAC TCCTGATAAT CCTTTCGGAC GCTGAGGTGG    34800

GTGGATCGCA TGAGCTCCGG AGTTCAAGAC CAACCTGGGC AACATAGCCA GAACCCGTTT    34860

CAATAAATAA TAGAAAAAAA TGAGCCAGGC GTGGTGGTCC CAGCTACTCA GTAGGCTGAG    34920

GTGGGAGGAT CACTTGAGCT CAGGAGGTCG AGACTGCAGT GAGCCGTGAT CGCAGTACTG    34980

CACACCAGCC TTGGTGTCAG ACTGAGACCC TGTCTCAACA ACAACAAAAC AAGTTAGAAA    35040

TTTGGCTGGG CGCGGTAGCT CACGCCTGTA ATCCCAGCAC TTTGGGAGGC CAAAAAGGGC    35100

GGATCATTTG AGGTCAGGAG TTCGAGACCA GCCTGGCCAA CATGGTGAAA CTCCATCTCT    35160

ACTAAAAATA CAAAAAAAAT TAGCCGTGCA TGGTGGCATG CGCCTGTAGT CTCAGCCACT    35220

TGGGAGGCTG AGGCAGGAAA ATTGCTTGAA CCCAGGAGGC AGAGGTTGCA GTGAGCCGAG    35280

ATCATGCCAC TGCATTCCAG CCTGGGTGAT AGAGTGAGAC TCCATCTCGA GAAAAAAAA    35340

AAAATTCTGT ATGAACTGAA CAAAATATCC TTAAATTTTA AAATACATCT GAAAGATATT    35400

TCAAAATATT TAGGAAAAAA ATTATAGGGA TCAGCAAAT TCTGAGATTC CTTTTTCCCT     35460

GCAGCAAACA TTAGGAGTGC TGCTGTTCCT AAAAACATGG TAACTGTTGC CACACCGTAT    35520

GTTTCCTTGG CTCAGACATA AGGTTGTGTA GTTGTTATTC CAGAATAGCT AGAATAAAAA    35580

TCCAGCACAT CATTTTCTTC AGCAAGTTAA CTAACCTCTC TGTGCCTTGG TTTCATAACA    35640

GCAACATAAG CATAACAGAA TAGCAGCAAT AGCTCCTACC TACCTCATAA GATTCTTTGG    35700

AGGAATTAAA TTAAGATTCA GAACACAGCC TAATATCTAG TAAGTAATAA TAATTGGCTA    35760

AAAAAATTTT CTTAAGATTA TATATATTCA TGGGGTACAA GTACAATTTT GCTACATTAA    35820

TATATTGCAT TGTGGTGAAA TCAGGGCCTT CAATCCATCC CGGAAAAAAA AAGTTTTTGA    35880
```

```
AAAGATTTCT GCCATGGAAA ACTTTTAATG TACAAATTCA TCCATCCAAG AAATAGAAAA    35940

TATATAAGTA TCAACTCCAA ATCCACCATA TCTATCTCTT CTACACCTTA AACAATTACT    36000

CAGAAATAGA ATGCTTGAGA TACCAGAATG CATGCATATC AAGTAATAAA TGCATGCAGG    36060

ATGTCAACGC ATCCTAGGCT TTCAAATAAA ATTGTCATAC AAAATACTTT AATATTGTAG    36120

TAACATTCTA CATGTTAGAG TGTAGAAGTT AATCGCTGAT GCAAAAAAGG AAAAGAACAC    36180

ATTATACCCA AAGCCTACAG AGAGAATCAC AATTACAAAT ATCAGCCTGC ATGTGAAAAT    36240

CTTTAATTTG AAAGTCAGAA ATATTTAAAT GATAGTCATT GTTAAATCAG ATTGTGGTTT    36300

GAAAAAAAGT TAGTTTAAAA CTGAGTTTAT GAAAAATTTG GGGATTTTAG AGACAGTGTT    36360

TTGTTTTTAA ATGTGTGTGA GTTTGTGAAG AATGTTTTAT AAAATACTGA CAGTATTATA    36420

AGATGACATT ATTATAATAC AACATAAGAA TTTTGGCCTG TACCTCTCAG CAGTCCTCAA    36480

TCACCTGCTG TACTTGACTC AATGATTATC AGAGTGGTTT GTTTTCCTTC TGTTGTGTTC    36540

CCAGTTCAGG CAGCTCAGCA ATGGCCTGTG ATTCCAGCAA TTCAAATAGC TGGTAAGTAG    36600

TTTCTTGTTT GTTTTCTCAA ATTTTCAGGG GCTTTTCTCT ACAAGTGATT TCCAGTGCAC    36660

GCCCCTCCAC CCATTCTTTA TTCCTTTACC TTCAGGAAAA CCCTCAGCGC TGCATCTCTG    36720

GTCACCGGAC CACCGTGGTA CATTTACCTA TGGCCACCAG GTGTCACCCT TCTCTTTACT    36780

ACCATGGTTT GTGAATGGTT TTGCCAGAGG TGAATAAGAA TTTAAAATGC AGGTCTTTGA    36840

TTTTTCAAAT GTAGTTGACC TTAAGAATTT ATGAATAAAG CCAGAAAAAT TAAGCTTAAA    36900

AAACACCGAA AGAAAATGAG GACTTAAAAT TTCTATTAAA AAAATTAACA GGCCACAGTT    36960

GCTGATGTTT AGTAAATGTG TTAGTGAAAT GTGTTACTGT GAAGACTGGG GTGTTTCTTG    37020

AAATCTCAGC CCAGGTGAAA TAAAACCAAT ATAAAACAAA TGCTTACCTA ATAAATTAAT    37080

TGTAACATAT TCCTTATGAG GTAGAAGAGT AAGTGAAGCC TTATAGCAGT CTGCTTTCAG    37140

TATAGTAAGA TATTAAGAGA GAAATAATTT GTCATATGCT TTCAGAATGG TTTGCTGGTA    37200

AAATAACCAA TGTCTTACAA CTTAGACGAC AATGTCCCTA GAGTGAAGAA ACACGATTAA    37260

TTCGGCTACC ACAGTTGAAT GAAAATATTC CGTAAGACAA AATGTAAAGA AATTAGAAGC    37320

AAAATAAATG TCTCCAAAAT GACAAAGCGA TTAAGTATAT ACACAAGATG AACAAGAACT    37380

TCAATAAAAT CATGCAGTAT ACAATACAAT ATACATTTAT TAAAGTATAT GCATTTTTAA    37440

TGCAACAATA ATACTAACAG GTAATAGACA AGTTGTTAAT AGTTTTTCAC TGGCTAATTA    37500

AATAACAGCT TTAATTGTAT TCATTTTATA GCTTTTCTAC AATGAGCGTA AATCACATTT    37560

ACTTTTTTCT ACATAACTTT TCTAACCACA AAAAAGAAA ATGGTTTAAA AGAAGAGATG    37620

AGATATCTTT GCTAAAATTT AATGCCTAAA GAAGAAACTT CTGAGCTGTA TATGGTATCC    37680

TGAAGCACCT GCCCTTCAAG ACAGAATGCT TGTACCACAT TTATGCAGCC AAGTGCATGT    37740

AGTAACATAA AGTAAACACA TGCCATCTGG ATATATATAT TAAGACTCTT TTGACGGCTG    37800

GGCAGGGTGG CTCACACCTG TAATCTCAGC ACTTTGGGAG GCCGAGGCAG GCGGATCACG    37860

AGGTCAGGAG AGTTCGAGAC CAGCCTGGCC AACATGGTGA AACCCTGTCT CTACTAAAAA    37920

TACAAAAATT AGCCGGGCAT GGTGGTGCAC GCCTGTAATC CCAGCTACTT GGGAGGCTGA    37980

GACAGGAGAA TCGCTTGAAC CTGGGAGGCA GAGGTTACAG TGAGCCGAGA TCATGCCATT    38040

GCACTCCAGC CTGGGCAATA GAGTCTCAAA AAAAAAAAA AGACTCTTTT GAACATGGTG    38100

AACTGATTTC CCAGAATCTA GCAATTCCTG AATGTCCTGG TTAGATTTTT TTTTTAATGT    38160

GCACCGGAAC CCCAGTGGCT CCATGGAAGG ACCTGGGCAT CCTCTAAGCC ACTTGGTGGC    38220

TTCCATTATA CCATCTCAAA ATGAGAGAGC TTACTCCACT TCATTGAGGG AAATACCACC    38280
```

```
AGAGTTCTGA CTCCAGAGGC ACTGGCCTAG GGAGGACACC GTGTGTGAAG CCCAGCAGGG    38340

CCACTAGCTG TCCCCACCAA TTACAGTCCT TGCGTAGGGT CCAAAGAAAT GAATGCCAAA    38400

GAGAGCAACA GAGGAGCAAG GGAGTCACAT TCCAGGACCT TCCTTCAGGG ACTTTTAAAG    38460

GAAACATGAC AGCTGAGGAT CAGTTGGTTG TTTTCTGCTG TTCCCCTTCA TGTGATTCAA    38520

GCTCACTCAG AAGAAACACA ATGAGACAAG AGAAGAGCCA TCTCCTTCCT TCTCTATTTA    38580

TTCTAGGCAT CTAAACTACT GAATGTAGTG GTGTCTGAGA TGTATCAAAC GGTCAGATTG    38640

ACTGAGTTTG AAACCTGTTT CTATCACTGA CAAACTATGA GATACTCTAT ACTTCACTTT    38700

CTTTTTTTTT TCATTTTTTT ATTTTTATTT TTATTTTTTT GAGATGGAGT CTCACTCTGT    38760

CACCTAGGCT GGAGTGCAGT GGCGCAAACT CGGCTCACTG CAAGCTCTGC CTCCTGGGTT    38820

CATGCCATTC TCCTGCCTCA GCCTTCCGAG TAGCTGGGAC TACAGGCGTC TGCCACCACG    38880

CCCAGCTAAT TTTTTGTATT TTTATTAGAG ATGGGGTTTC ACCATGTTAG CCAGGATGGT    38940

CTCGATCTCC TGACCTCGTG ATCCACCCGC TTTGGCCTCC CAAAGTGCTG GGATTACAGG    39000

CGTGAGCCAC CGTGCCCGGC CTACTTCACT TTCTTCATTT AAAAAAGAAA TGGGGATAAT    39060

AGTACCTATC TCATAGAATT ATTGTAAGAA GTGCATGCAG TAATGCATGT AAGTAGGTGC    39120

TCAGAAGAGT CGGACACGAA GTAAGTGCTT TTATCATCCT TATCATAATT TTCATTATCA    39180

GAACAAGGAG AGACCAGGTA GAAAATTATT GTGATTCTTC AGGTCTGGAA TACTAGAGTA    39240

GCATCCCAAA TGAAGGCACC ATTAAACTTT GCAAATCTGT ATGACACCTT CATGCCAATT    39300

AGAAAAAACA CCTCTTCACA ACCCCTTTCA AGATATTTGC CTCCTACCTG CTAAAAACAC    39360

CCATCATACT ACCCACAGAT AGCCATGATG CTTTTTCTGG GACAGGTGCC TCTTCCATTC    39420

GTGCAGTGTA CAGCCTTCAT AGCTGTGCAA CTCACATCAC AATCAGATGG AAGAATCCCC    39480

AAGGCTTGGT GACAGATGAG TTACTGGGTA ACACAGAGAG AGGATTCAAA GGAAAAGTTG    39540

AACGGGTCCA GAAAATGCAT AGATACATGT GTAAAAATCT GGTAAGGTTA TGACTAGCCA    39600

CGTCCCAGGG TTCAAAGCTT TTCTCAGATG TTAAAATGAA TCATGTAAGT CCCCCAAATT    39660

TAAGGAGTCC TCTTCCAAAA ATAGGAAATG AAATGACATA GGTGTATGTC TCTGAGGTGA    39720

CGGAGGAAAT GAAGGAAGCC TCTAGATGCA GCTTGAGGTT CATGAGAGAC AGTTCCAGGG    39780

GAGAGGTCAC AGCTAGGGAT CACCGGCATG CAGGAACTCA GAAACCTAAA TGGGGAAATC    39840

TTTTTGAGGA AATGAACAGA GAAGGCTAAA ATCAAGGAGT TCGTCAGGCA ATTTCTATGT    39900

TTAGGTTCAA CTCTCTCCTG AAACATGAAG AGCTCATAAA TGCACTCCCT CTTTGAGTCT    39960

CTAGTTTTGT CTCCTTCCCA CAGTGAGTCT GCAGGCTGCG TGTCACTCAC GTTCAGCTAA    40020

GACGTAGTGC CCCATGGCTC CTCCTGTGGA GACAAGAGAC CCAGGAAAGA GGCATCACAA    40080

ACCTAGGCAC CATCTTGCCT CTTCTCTCTT CCTTATTTTC CTCATTCACC CATCTCAATT    40140

TAGACCTGGG CACTATTGGA TTTCAAGAAC CATTATCTCT CATCTGGAAA TGCTTATTGG    40200

CTTTCTAACT GGTCTCCTCA CCTCTCATCT AACTTCTTAA CAACACATTC ACCATATAAG    40260

GGAGATCGTG GTCCTCCTTT CTTAGGATCC TTCAATGACA CCCCAGTGAT CATAACCCAA    40320

TATCCCAAAA GACCCTTGGA CTCTGTATGA GCTGGCTTCT TTCTGATTCT CTTTTCCCTA    40380

CACCACAGAT GTTCAGGGGG TAGAAATGCA TAATTGGTGA GTGATAGCTA CGCAAACTCA    40440

GGGTTAAGGT ACAGTAATTA TTTCTAATCT CCCAGTATGC CTTATACTCT CCTACTTGGC    40500

ATGGTTGCTC CGTCTGTGTA GACCTCCCAT CATCTTCAAC CTCACCTAAT GGAATCCAGC    40560

TTCTCCTTCA AGATCCAGAA GGCTATCTTG ATCCCCAGCT GAATGTGATC ATTCTTTCCT    40620
```

```
TTGACACCCT AAGCATTTGC TTCCTGCCTG CTTTAGGACC TCATGGGTC  TTCTTTAACT   40680

ACATTTACTT GCTATCAATT TCATTCCCTA CCAGATTTGG GTTCTGAGAA TAGCCACAGT   40740

GACTTCTCAA CCTCAAAGCC CCTGTACTAC CTTAAACAGC TCTTGCAAAA TAGTAGGTGC   40800

TCTGAAGATG TTTGTTGAAT TAGAGACTTT CATTCTGGGG AGAACCATTA TTTTCTGTCT   40860

CCCAGGGAGC TGCTGGTGTC CCCAAAGAAT ATAAATGAGA AAAATGCTTC CCATGGATGC   40920

CAGATCCCCT CTGCCCCTCT TCCCACTGTG CCCTGGGGCA GAGGTACTAA GAGACTTCCC   40980

CCTTGTTCCT ACTCACTTGA ACCCTGCCTC TTCCTTAATA TTATGAACAA AATTCCAATG   41040

AACAAGATGA CGACAAAAAC AGCAATTCCA CTGATGACTC CAATGACTAG GGTGCCAGAC   41100

GGTGAGGGCT CTAAAACAGA AAAAGCAAGT TAAAGCCTTT GATTGCCACC CTCAGCCCAC   41160

CCCCTAACAA AGAGCAGATC CTCATCTCAC TGCCATAATT ACCTCCTCAG GCACTCCTCT   41220

CAACCCCCAA TAGATTTTCT CAGCTCCTGG CTCTCATCAG TCACATACCC CAGATCACAA   41280

TGAGGGGCTG ATCCAGGCCT GGGTGCTCCA CCTGGCACGT ATATCTCTGC TCTTCCCCAG   41340

GGGGTACAGC CAAGGTTATC CAGCCCTGGT AGGTCCCATC CCCATTGGGC AATACGTCTT   41400

TAGGTTCGAA CTCCTTGGCA TCCATTGGCT GCTTATCCTT CAGCCACTTC ATGGTGATGT   41460

TCTGGGGTA GTAGTTCAAG GCCCGACACC GTAGAGTGGT CACTGAAGAG GTCACATGAT    41520

GTGTCACCTT CACCAAAGGA GGCACTTGAC AGGAAAGAGG AAGGATGAGG AGAGGGGATC   41580

TGTTTACCCT TGCCAGGAAG ACTGGAACTT TCACTTCCTT CTATAGGTTG GAGGAAGGAA   41640

ATACCCTTTT CAGAAAAAAA CAAGCTACAG GAGAGACACC ATTTTGTGTC CTAAGATTGG   41700

ACTCTAACAC AGTGTCACTT GGAGAGCAGT CAGATCAGCT TGTTCTCCTC ACATGTAAAT   41760

ATACATATCT GTTACCCATG TTCTTTGTTC TGATAGATAA AATTGCCCTT TATGTGCATT   41820

GAAAATGATT GAATACAGAT GGTCAGTTTC ACCTGGGTCA ACCTAGGAGG CATTGTTATA   41880

AGAAGCGGAC TTGTAAGATA GGTAGCTTCA GTGATTATTG CTATGTTCTA TGAAAGAAAC   41940

TTTTAACCTA AAGGATTCTT CTACTCTGAT AAGTGGCCTC ACTTGATATT TTGTCCTGGT   42000

ATTCATATGA TAGCTGAGAT CTCTGAATTC TCTTTTTTTT TTTTTTTTT  TTTTTAAGAT   42060

GGAGTCTCAC TCTGCTGCCT AGGCTGGAGT GCAGTGGCGC GATCTTGGCT CAGTGCAACT   42120

TCCGCTTCCC AGGTTCAAGC GATGCTCCTG CCTCAGCCTT CCAATTAGCT GGGACTACAG   42180

GTGCGCATGA CTGTGACCAG CTAATTTTTG TATTTTTTA  GAGACGGGTT TCACCATGTT   42240

GGTCAGGCTG GTCTCAAACT CCTGACCTTG TGACCACCCG CCTCGGCCTC CCAAAGTGCT   42300

GGGATTACAG GGGTGAGCCA CCGTGCCCGG CCTTGACATT TCTGAATTTT TAACAGGTAT   42360

AAATATACAA AAGATTATTG GTTAAATAAA AAGCAAGGGC CATAGACACT TCCCTTTGAG   42420

CCATATGCAT GGAGAAAAGA AATTAAACCC ATGACTTGTG GCTGTCTCAT ACATCTCAAT   42480

TATAAGGTAG AGACTCTAGG ATTGAGAAAG TCCCTTCCCA GAATTTGGAG AGGCACACAG   42540

CCTCAGCCAC CTCTGAAACT CCAACCAGGG ATTCCGTGCC CTGCAACCTC CTCCACTCTG   42600

CCACTAGAGT ATAGGGGCAG AAGTGTGTTT CCACCATACC TTGTTGGTCC AAAACACCTC   42660

TCCCCAGCTC CAGCAACTGC TGCAGCTGTG CAGGGCAGTC CCTCTCCAGG TAGGCCCTGT   42720

TCTGCCTGGC CCGAATCTTG TGCCTTTCCC ACTCCAGCTT GGTGGGCCAG GCCCTGGGTT   42780

CTGCTGCTCT CCAATCCAGT GTGTCAGGGC AGAATTCAAG GTGGTCCTGC CCATCATACC   42840

CGTACTTCCA GTAGCCCTCG GTACTGTTGT CTTCTTGCAT TTCACAGCCC AGGATGACCT   42900

GCAGGGTGTG GGACTCTGGA AAAATCCCCA GCCTTGTTAA CTGCAACCAA AGGAATAGGT   42960

CCCTATTTCC ACCATCCCCA AGGACCAAAT GATCTCAGGA AGCAAATTCC TTCCCTCTTC   43020
```

```
CCTGCTCCCA CAAGACCTCA GACTTCCAGC TGTTTCCTTC AAGATGCATG AAAAGATGAA     43080
AAGCTCTGAC AACCTCAGGA AGGTGAGGCC CCCTCTCCAC ATACCCTTGC TGTGGTTGTG     43140
ATTTTCCATA ATAGTCCAGA AGTCAACAGT GAACATGTGA TCCCACCCTT TCAGACTCTG     43200
ACTCAGCTGC AGCCACATCT GGCTTGAAAT TCTACTGGAA ACCCATGGAG TTCGGGCTC      43260
CACACGGCGA CTCTCATGAT CATAGAACAC GAACAGCTGG TCATCCACGT AGCCCAAAGC     43320
TTCAAACAAG GAAAGACCAA GGTCCTGCTC TGAGGCACCC ATGAAGAGGT AGTGCAGAGA     43380
GTGTGAACCT GGAGACAGAG CAACAGGCCT TAACCATGTG TAGTAGGAGG GGAGCAGGAT     43440
GTTGAGGCTC CACACACCTG CATCAACTCA TACCATCAGC TGTGTCTGGT CCTCATTTTG     43500
TGAAGGGTGA GTTGCAGTCC TGTCTTTCTT CCATATGACA GTCCTGGGTG CTCTTTCCTT     43560
GTGTGCTTTT CTCTGCCACA CGTGGCTGCC ACCCCCTCAC TGCCCCAGA TCCTATTCCA      43620
ATACTCATGA TTAGACAGAC TCCACTAAAG CTGGTGGATT CTAGAAAATG TTAAGGTGTG     43680
TCTAGCCATG GTAGTTGAAC TCAGGAGTTG GTGCTCAGGG CAAATTAGAC CCAAATCCTG     43740
AGGAATAATT CCTTCAGTTT TTTTTTTTTT TTTTTTTTTT TTTTTTGAGA CAGAGTCTCA     43800
CTCTATCACC CAGGCTGGAG TGCAGTGGCA CAATCTCAGC TCACTGCAAC CTGCACCTCC     43860
TGGGTTCAAG GGATTCTCCT ACCTAAGCCT CCTGAAAACC TGGGACTATA GGCGTGCGCC     43920
ACCACACCAG GCTAATTTTT GTATTTTTAG TAGACATGGG GTTTCACCAT GTTGGCCAAG     43980
CTTGTCTCAA ACTCCTGACC TCAAATGATC TACCTGCCTC AGCCACCAAA GTGCTGGGAT     44040
TACAGAAGTG AGCCACCGTG CCCAGCCTTG GTCCTGAATT CTTACACTGA ACTGCCTATG     44100
TGGCCTCACC ACTTGGAAGC CTGACTGGAA TCTCAAACTT AACATGTCCA AATGCAGATC     44160
CTTGATTTAC CCCAAACTGC TCTTTCCTCT GCCTTCACCA TCTCAGAAAT GGCATTGCCA     44220
ATTACCCCAC TGCTCAGGCC AATAAAATTA AATAAAGAA CAAAGTCAAC TTTAACTCTT       44280
CTCTTTTTCA GGGGGTCAGG GGAGACAGGG TCTTGCTCTG TCACCTAGGC TGAAGTACAG     44340
TGGCACAGTC ATGGCTCACT GCAGCCTCAA CTTCCTGGGC TCAAGCAATA CCCTCCACCT     44400
CAGCCTCCCG AGTAGCTAGG ATCACAGGTG CATGCCACCA CACCCAGCTA ATTTTTGTAT     44460
TTTTTGTAGA GAAGGGGTTT TGCTGTGTTG CCCAGGCTGG TCTTGAACTC CTGAGCTCAG     44520
GAATCTGCTC TCCTTGGCCT CCTCCTTGGC ATGAGCTACT ACACCCAGCC AATTCTTCTC     44580
TTTCTCTCAC ACAACATAGA ATCCTTCAGC AACTTCCTTC AGAATATATT CAGGAGACAA     44640
TGGTTTGTCA CTCCCTTTTC TGTTCCCACC CAGCCCACTC CACTACCTCT TGCCTGGACT     44700
GTGTAACAGC TTCCTGGCTG GGCTCCCTGC TTTTACTGTT GCTCCCTTCA TTCTGCTTTC     44760
CACATAGCAG CCAGAGCAAT CTTTTAAAAG CCTGTGACAG ATCACTGTTA CTCCTTGGCT     44820
AGAATTCACA CCACAGCCTA CAGGCGCCTG CACAACCTTG TTTGTGGCTC CTCTTCTGAG     44880
CCCATTACCT ACTTCTTGGC CTCTACTCCC CAGCACTACT TGTTTATTTT TTCAACCCG      44940
AGCTTCTTAA CCAGGAGTTT GTCTACTAGG TGACATGTGG CAAAGTTTAG AGACATTTTT     45000
GGTTGTCAAG ACTGGGGGAG TGCTCCTAGC ACCTAGTGAG TAGGGAGGAC AGGATACTGC     45060
TAGACATCCT ACATGCAGAT GGTAGTCCCC CTTCCCACCC CCACGCCGCC CCCCCCCCC      45120
ACACACACAC ACATGAGTAG TGCTGAGAAA ACCCGCTTTT TAATCCAACT TGCCAGGCCC     45180
ACTCAGTTTG CCTGGGAAAT ACTGCTCCCA GTCAATATCA TTCTTATTTC CTTCATGTCT     45240
CTGCTCAAGT GTCAGCCCCA GAGTGACTTG CCCTGACTTC TCTGCTTCTC ACAACACCCA     45300
TGATTTCCTG ATGTTGTATA TCTTTCTGCT CATTTGCTTA TTGTCATCTC TCCCACTAGA     45360
```

```
ATGCAAAATA TCAAAGGGTA AAGACTTGTT TCCCTGCTCT CTCCCTTGGG GCTTGAACAG   45420

TGCAACACAT GGCTGGGACT CATTTACACT TGTAAACAAT GAATATTTCT GCTCAACATG   45480

AAATTTTATT ATTCAACCTC TAATGCAGTG TGATGTTTAA GAATCATAGC TATGAAGTGG   45540

AGACATGAGC TCTGCCACCA AAGCCCAGTG TACCATTGAA TAAATTTGCC AGGAAGCAGG   45600

CCGTGCCATG CCTCATTCTT GTCATGTGTA AAATGTGGAT ACACGTAGTA CCAAAACTCA   45660

AAGTGCTGTG CTGAGGCCGG CGTGTGACCC ACAGAACACT GTGCTACACT ACAGGGCAAA   45720

ATCACTGTCA ACTAAGATTA GAAGCAGCTG TAGTACTTGA AATAACATCA GAAAACCAGA   45780

TTATTTATGT TCTTTGTAAC CTGAAAAGAG TTATATAATC TGAATTCCAG TTAACTTCTA   45840

GTAAAATAAA CGTATTATTA GCTCCTACCT CCCTATGCCT AGTGAAAATC AAATAAGATC   45900

AGATATGAAT GTAACTTAGA AGTGAGTGCA TTGCTTACAT GTTCATTATC AGTACTTTGT   45960

AGAGAGGCCT CTTAATTACA CAGCACATTG CAAATCAATA AAGCCTAGCC GAAAAGAGAA   46020

TTGTTCAGTT CAAACGTTCA AAACTAACAT ATACTTAATT TTCCAGGCAA AGAACAATT    46080

GCCAAGAGTG GGAAAGGCC CGAGGTAGGC CTCTCTCAGG AGCCTCCCAC CCTAGAGACC    46140

TCCACCCCAG GTCTCACCAA AAGTGGGTGG AATGGTGAAG AATTCAGATC CCCAACGCCA   46200

CTCTTTCGCG CCCCCACCGC CCAACGCATT CGTTCTGAGG TGGAAACCCC GTGCGGATCC   46260

TGCTGTGGGT TTGCTCAGCC TTCTCGGCAA GCACTCAGGG AAGAACTTCC TGTTTGGAGA   46320

TGACTGGGGA AAAAACTGCA CAGCTGACAT TGGAAATAAA CCCGAGTTCC AGGTTCAAGG   46380

AGCCCCAGGC TTAGCTCAGC TCAAGTGAGG AACTACGAGA TTTATTTAAA AGCATTCTAG   46440

TTGGGGGAAG GGAGTGGGCG GTTCCAAAAG TCACTCCGCA GAGCCGGGAC AGCCGGGGA    46500

GGGGGCAGGT CCTGGGGCGA GGGACCCCTA TCTGCAGTTC AGTGGTAGGC ACTCCCTCAC   46560

GGGGTCTGGA CGCAGAAAGT AGGGAGAGGG GCTTGCGGAT AGGGTTGAGC AGGTCCTCCA   46620

AAGTTAGCAA ACTCCCAAGC GCAAAGAAAA AGCTAGTTTC GATTTTTCCA CCCCCGCCGC   46680

GCCCCTAGTT CGCCCGCAGC CCTCGGACTC ACGCAGCAAG CGCCCCTGCA GGACCGCGGT   46740

CTGCAAAAGC ATCAGGAGGA GAAGCGCCGG CCTGGCTCGC GGGCCCATTT CCCCAGCTCT   46800

GGCCGCACGT CCCCGTTAAA TCTCCGCTTC TTTTGGGGGG CGGGGAAACG GGGATGGCTC   46860

CAGAAGTCAC CCTACAGCTA TTGCCTAGGC TCAGGAGATG CCCAGTAAAA CTTCCTGGTG   46920

AAAAGCAACA GGTCTTTCAG AACTTTAGTT CTCTCTCTCC TACAGCAGAA GGTACCTGCT   46980

TGTGAAACAC TAGGTGATCC AGTGTCCCCC TTGGTTTTTA AATCCTGAAG GGGTGTTGTT   47040

GATTGGGGAA AGTAGCTTCG CAATGTTCTG ATCTGAACTT TAGATATTTA AATATTTATG   47100

ATTTTCAAAA TTCAATCATA CATTTAAAAA TTTTATCTCA ACCTTAGACC AACTTATGTC   47160

TTATTTGACT TAGAAATATA AAGCTTTTTC ATTTTGTTTT TTGATTCAAA TTAATTAAGT   47220

CATAACATTA ACCAATTAGA TCCTACTGAA ACACCTTCCA CAGCCTTCAT AATTGAATTA   47280

TCTGACAAGT GTTTCACAAA CTTTACAGTA TTGGGATTAT CTGGAGAATG ATTAAACATA   47340

TTGAGGCCTG CTCCTAACCC CAGACACACT GATTTAATGG GTAATTGTTA GGTAGTTAGA   47400

CATTAGCAGT TGGGAGGGGA TGACAGAAGA GAGCGGAAAG GCTGTCACTA AGACAGCCAC   47460

TGGCCCACCT AAATTCAGGC CCAAGACTAC CCTAATGCCA CCCTAAGGGA TGGAGTTTAT   47520

GATAAAGTCT GTGGCCAAAA TATCCTGGAG AAAGAGAAAG GAGGGTACAG GTGGAAATTC   47580

CCTAAGGTGG CACATGCCCA ACAACACAAA AGCCTGTCTT CAAGTTCACC CCAAGTTCAT   47640

CATGCCATCA TTATAATAGA ATTTACATAC AGTTTTGCCC CCCCATCCCT GGGAGGCTTT   47700

TCTTAACAAA TTATAGGTAA GACCATGCAC AGTTTAATTT TAGATTGTAT AGCTATACAC   47760
```

```
TTCAATCAAA TAACATCATC CTGTCACTCA GATACAGCCC AAACCTCAAC TCCTCCCCAC    47820

AAACCCCATA AAAGCACCTT GAGCTCTGTA AAGAAGTGCT GAGTTCACTT CGCAGAAATA    47880

AGCCCGCTGT CCCTCAGAGT GTATTATTGT GCTTCAATAA ACTTTGCTTT AAGCTTGCAT    47940

TTTGGTGTTA GTTTGTAGTT CTTTGCTCAC TATCACAAGA ACTGAGATTG CTGGTTCAGA    48000

GCTCCGGCTA TAATAATCTC CTCGGTTAAA GGATCCATCC CAATGCATAA TTCCCAGTAA    48060

CAGTATGGGA TGCCACCTGG GCAATGGGAT TTTAAAAGCT TTCCTTCTCC CTCAACGAAG    48120

TTTGGGAATT ATTGCCTTAG ACATTTCAAA CAATATTAAT AAATTTAATA CACCTGATTT    48180

GCTCCAAACC TTTACATATC TAGCAAATTC AACAGGCATT ATTTTTGTAA GCATGTATGC    48240

AAATTTTGGC AATTCAAGAA AATCAAACAG GATATCAGGG CCTCGACTGT AGGCAAACAG    48300

ATACAATAAC ATTGGAAACA TGTAGAATAT TGATGATGGG CACATTGGGG CTGATAGTAC    48360

TATTCCTTTT TTTCAATTTT TGGTAAGATA TAATTAGCAT ACCATATAAT TCATCTATGT    48420

AAAATGCAAA AATTGGCCCG GCTCAGTGGC TCACGCTTGT AATCCCAGCA CTTTGGGCGG    48480

CCGAGGAAGG CAGATCACCT GAGATCAGGG GTTCGAGACC AGCCTGGCCA ACATGGTGAA    48540

ACCCCGTCTT TACTAAAAAT ACAAAAATTA GCCGGGCGTG ATAGCAGGCA ACTGTAATCC    48600

CAGCTACATT AGAGGCTGAG GCAGGAGAAT CGCTTGAACC CGGGAGGCGT AGGTTGCAGT    48660

GAGCTAAGAT CGTGCCATCA CACTCCAGCA TGGGAGACAA GAGCAAGACT TCATCTCAAA    48720

AAAAAAAAAT TAGCTGGGTG TGGTGGCATG CACCTGTAAT TCCAGCTACT CGGGAAGCTG    48780

AGACAGGAGA ATCGCTTGAA CCTGGGAGGC GGAGGTTGTG GTGAGCCGAG ATCATGCCAT    48840

TGCACTCCAG CCTGGGCAAC AAGAGCGAAA CTCCGTCTCA AAAATAAAAT AAATAAAATA    48900

AAATGCAAAA ATTAATGGAT TTTAGTATAT TTACAGAGAT GTGCAACCAT TACCAAAATT    48960

TTACATTTCT ATCTCCCCAA AAAGAAACCA TGTTCCCCTA ATTCAGTACC CTTAATTCAT    49020

CGCCTCCCAG ATTCCTCCAT TCTCCTCCTC CTCCCCTCCC AGCCCTAGAC AATCTTTAAT    49080

CTACTTTCTT TCTATTTGGA ACATTTAGTA TACATAGAGG CATATAATAT ATTGCTTTGC    49140

CGTGACTGGC TTCTTTCATT TAGCATAATG TTTTTATGTA TGTTTTTCAT GGACCAATAA    49200

TATCTATTAT AAGGACATAC CACAACATAT TTTATTTATT CATTCATCAG CCGATGGACA    49260

TTGGTTTGTT TCTACTTTAT GGCTATTGGG AATAGTGCTG TTATAAACAT TTATGTACAA    49320

GTTTTTTTGT AGACTTATGT TTTGATTTCT TTTGGTTATA TATCTAGAAG TGGGTTTGCT    49380

GGGTCATATG GTAACACTGT TTAACCTTTT GAGGAATTGC CACATTCTTT TCCAAAGTAA    49440

GCATTTTATC CTCCTATCAG CAGTGTATGA GAGTTCTGAT TTCTCTCCAT CTTTGCCTGG    49500

GTTTTTGAAT CAGGGCCCCA GATAGAACAA AAATGTGGTT ATTCAGTTGT TCCACCATCA    49560

CTTGTTGAGA AGACTCTTTT TTCATTGAAG TGTTTTGGCA CCCTTATCAA AAATCAATCT    49620

ACCATAAATG TGAGAGTTTA TTTCTGGAGT CTCAATTTTA TCCCATTATG CTATAATCTA    49680

TAATCCTATC TTTTTTTTTT TTTGACAGAG CCTCACTCTA TTGCCCAGGT GGAGTGCAG    49740

TGGCCCAATC CCGGCCACTG GCTCCTCCTC CCAGGTTCAA GCAATTCTCC TGCCTCAGCC    49800

TCCCAAGCAG CTGGGATTAC AGGTACCTGC CACCATGCCT GGTTAATTTT TGTATTTTA    49860

GTAGAGACGG GGTTTCACCA TGTTGGTCAG GCTGGTCTGG AACTCCTGAC CTCAGGTGAT    49920

CTGCCCACCT CAGCCTCCCA AAGTGCTGGG ATTACAGGCA TGAGCCACCA CACCCAGACT    49980

ATAATCCTAT CTTTATGTCA GGACTACACT GTCTTGATTA CTATAGCTTT TTAGTAAATT    50040

GAATTCAAGA AGTTTCTCAA CTTCAAATTT GATCTTTTTT TGGAAGACTA TATTAGCTAT    50100
```

```
TCTCAGTCTG CTGAATTTCC CTAGGAATTT TAGGATCTAT TATCAATGTC TATTCTATTT     50160

TTGTATATGT TTTAATATTT TCATAAGAAA CTTTTTTCAT TTAAACTTTT TTTTTTAAGA     50220

AAAATAGTGA AAATCAGAAC ACTGGGGGTC AGGCGCATTT AACAGGCAGA AGAAGAATAA     50280

AAACTTGTCA TATAAACAAA AAAGAAATGA CCAATCACAT TGTGGAAGCC ATGGAGTGGT     50340

TATAGGTGCC AAAGGCTGCA GAGAAATGGT GTCAGATATA CCTGAAAATT GTCCATTGTA     50400

TTTGGCCATT AAGAGACTTA GAAGACTTAA GCCATAGATT GCTCAGTGAG ACCCCGAGGG     50460

CAAATGGTCT GAAGGTGAAT AGATCATTTC ACCTTTAAGA GAGCAGGTAG GAAGCTATAA     50520

ATCCAAGATT AAAAAGTTGA CTGAACTGTT AAGGAAGAAA CTCTAATCTT GAGCCACCCT     50580

ATCCTGGCTC CACCTTCTGC TGCAAGCAAA CAGAAATGCT GAAATTCAAC ACTCACAAAG     50640

GCTGGTAAGC TGGAAATGAC AAAAATTACT CCTGGGAAAG TCAGATTTAG AATTAGGCCA     50700

TATTTGTTGG GGTTCAGATT TTCATGTACA CTTGGGAAAG GGTTTAGCTT ATAGGCACAT     50760

GCATGAAGGG AACTGGTATA GGGCTGTGTT CATAAGGTCA AGAGTTGAAG GCCAGGCATG     50820

GAGGCTCTTG CCTGTAATCC CAGCACTTTG GGAGGCCGAG GCAGGAGGAT GGCTTGAGCC     50880

CAGGAATTCA AGACCAGCCT GGGAAACATA GGGAGATGGT GTCTTCACAA AACAATTAAA     50940

AAATAAAATT AGTCAGGTGT GGTGGCACAC ACTTGTGGTC CCAGCCACTC AGGAGGTTGG     51000

GAAGATCACT TAAGCCTGGG ACATTGAGGC TGTAGTCAGC CATGATAGTG CTACTGCACA     51060

CCAGTCTAGG TGACAGAATG AGACCCTGTC TCCAAAAAAA GAGCTGTATC CACATCCCAG     51120

GAAAGTGGTT GAAGATCTAC TTTTCTCTGT AAACCTAATA AAGAATAGAG TGACAAATGT     51180

GTGTTGTGGA AAGAAATGGG GTGAGAGCTA CGTAGATGCA AAACAATACA TCCCCACATA     51240

CCACTTGTTA ATCATCCTTT TCCACCCACT TATGGGATGA ATTGCATCTC CCCAAAAGAT     51300

ACTCTGTCCT AACCCTCAGT AGCTGTGAAC CTGACCTTAT CTGGAATACG GTGAGTTCAC     51360

TGGTTAAGAA GAGATTATAG TGGAATAGGG TGAGTCCTCC AACCAATGAC TGGGGTCCTC     51420

ACAGACACAG AGGGATGATG GCCAGGTAGA GATGGAGGCA GAGATTGGAG TTATGCTGCC     51480

ACAAACCAAA CACAGGAAGC TGCTAGAAGT GGAAACAGGC AAGAAAGAAT CCTTCCCCAG     51540

AGGCTACAGA GGGATCTTGG CCCTGATAAT ACCTTGATCT CAACTGGCCT ACGTAACTGT     51600

GAGAGAATAA ATTTCTTTTG TTCTAAGCCA CCCAGTTGAT AGTACTTTGT TACGGCAGCC     51660

CTAAGGAACT TGATATACAT TTCTTTTACT GTCATAGAAG TTTTGAATCT TTTAAGTAGG     51720

TCTGTACCCT TCCTCCCAGT GTCAACACAT GGAATTCCTC TCCTTGTGCC TTGAAAAGTG     51780

AAAGGTGTTT GAACTGGTAA TGAAAGAAAT CTCAGCATGA GGCCAGATGC TGTACCTCAC     51840

ACCTGTAATC TCAGCACTTC GGGAGGATGA GGCGGGCAGA TCACTTGAGG TCAGGAGTTC     51900

TAGACTACTC TGGCCAACAT GGTGAAACCC CATCTCTACT AAAAACAAAA AATGTTATCC     51960

TAGCCGGGCA TGGTGCCTGT AGTCCCAGCT ACTCAGGAGG CTGAGGCAGG AGAATTGCTT     52020

GAACCCGGGA GGTGGAGGTT GCAGTGAACT GAGATCACGC CACTGCACTC TAGCCTTGGT     52080

GAGAGAGCAA GACTTGGTCT TAAAAAGAG AAAAGAAAAA TGAAATTTCA GCATTATAGA      52140

ATAAAAATGT TTCCCCTTCC CCCCAAACTT TAAAAAAGCA GAAGTCTGCA TCATAAAATG     52200

GTCTTTGCCA ATGTTATTTT TATTATAACA AAGGAATCTT GCAAGGCTAC CAGATCTCAG     52260

CAATTGTCAC TATGTTCTGT AAAAATCACT TCCTAAAATG TCTGAATTGA CTGCTTGTCT     52320

CATTTATTTG TTTCTCGTGT CATACTGCAA TGGATATCTG TCTTGTTAGT ATAAATATTT     52380

GTGCATTTTG TTGTTGTTAA AACAGCTTTT TTGGCCTGTC TTCTTCCACC TATGAGGTAA     52440

TATAAAACTC ATGTTTAACA CTTATTTTTG TAGCAGGACA AGCTACAGAC AAAACCCCTC     52500
```

```
AGACACTGAG TTAAAGAAGG AAGGGCTTTA TTCAGCTGGG AGCTTTGGCA AGACTCACAT    52560

CTCCAAAAAC CGAGCTCCCT GAGTGAGCAA TTCCTGTCCC TTTTAAGGGC TTGCAACTCT    52620

AAGGGGGTCT GTGTGAGAGG GTCATGATCG ACTGAGCAAG TGGGGGTATG TGACTGGCAG    52680

CTGCATGCAC CAGTAATCAG AACAGAACAG GGATTTTCAC AGTGTTTTTC CACACAATGT    52740

CTGGAATCTA TAGATAACAT AACCGGTTAG GTCGGGGTC AATCTTTAAC CAGACCCAGG     52800

GTGCAACACC AGGCTGTCTG CCTGTGGATT TCATTTCTGC CTTTTAGCTT TTACTTTTTC    52860

TTTCTTTGGA GGCAGAAATT GGGCATAAGA CAATATGAGG GGTGGTCGCC TCACTTATTC    52920

ACCCCCTTTG AGAATCTCAC TCATTAGTGG GAGTTCTCAC TTTTATTCTC ACTACCTATG    52980

TCTTCTTGAA AGACAGATTG ATAATGATTC ATATAGTACA CTTGTGCTGA AGCATTTTGG    53040

TGAGCTAAGG TAGTGATGAA GCTTTTTATC ATTTGGAGAA GTACAGGTAG CAAACAAGGA    53100

AGCAGTAAGC AGGTTTCTAT TAATATTATA ACTCCTATTA TAAGAGTTTT AAATCTTCTT    53160

AGCACTCGGA ACCATTTTTC AAACATGGCC CCAGAAACAA ATCCATACCA CACCTACATG    53220

GGCACATGTG CCACTTTTGT CATATTTCTA ACTATGTCTT CAACTACTTG CCCTTAATCA    53280

TCTATGTGTA GACAGCAATT AGTAAGGTTA AATTTCCTAC AGACCCCTCC TTCAGTTGCT    53340

AGCAAGTAGT CGAGAGCCAA TCCATTTTGA TAGATAGCAT TTTGCATCTG AGTTTCTTGC    53400

CAGGCCACAG TAGTCAGGGC TCTGCTGGTC TTATTAGTAA TTATTTCTAA GACAGCTTGT    53460

AACCGTATGA TTCAGTTGAG CATGTAAATG GGGGTCCCAT ATCCCACAA GCCGTCTTGT     53520

GCCCAAGTAG CAGGCCCATA ATATTGTATG ATTCTCTCAG GGGGCCATTC ATTATTTTTC    53580

CAATTTCTA TAGCTATGCT TTTTTTTTTT TTTTTTTTT TTTTTTTTT TTTTTGCGG        53640

GAAGCATATA CAGGGAAGCC CAGGAGTTTG CCTGTCTTTA TGGGCAGTAG GAAGAAAGAT    53700

GGTTTAGTAG TGTCAATAAC ACAACTACCT GCCCACTGGT CAGGTAATTT GGCATAAGCT    53760

GTATGCCCAC ATATCCAGTA TAATCCAGTG GGGGCTGTCC AGTCCGGTG GGACTCTGGG     53820

TGGGTCCACA CAGTTTGCAA CTTTGGGAAT TTACTAAATA GATTTTTCTT AGTGTGGTTT    53880

GAACTCCACT AGGTGGCTGT TTTTATAGTA CTATTATACA GTTTTTGCCC AAGGCAGCTG    53940

AGTCTTCCCA CAGGAAGGGT GAAGTCCTTC CCCACTTTTG CTATACAGTA TTGTCTAATG    54000

ATTGAGGCTT TTAGGACCCA GAAGTTATCA GGGTGAGTCT TTTGAGCTGG GAATTTATCA    54060

GGAACTGGGT CTGTAGGTAC TAATTCTCGT GCTTCCCATG GCCATTGATC TCCCATTACA    54120

GTTCCTCCAC ATACATACAT AACATGAAGT GACATTGAGA GACTGGGCTA CATGCTCAGC    54180

TAATTGCAAA AACAAATTTC TTGTTTTTCC TGGAATTTCT AGTACTGGCA CATTCAGTTC    54240

ATCATAAGAA GGTTTGAAAT ACTGGCTCAG GGGAGCATTT ATAAACTTCT CCTCAAACCA    54300

CCATATTTAC TCAAGGATCC AGTCCAGCCC CAACTATTTC TAAGGTTACA CGATCCCCTT    54360

TTTTCCAGTG AGAATCAAGG GGGTTGGTTA TTACTAGTTC TAAGGGGTTA CACTGACCAC    54420

TGGTACAGGA AGGGCCACTT TTCCCTTTCT GAAGGTGGAC AGGATTCTTT TTATTTTTA    54480

ACCAAGTTGC CTAAATGACA CAAGACCAGT ATCTACATTT ATTTCCACGC AGTCTTAATT    54540

CATGACAAGC GTACTTATTT TCTGCCATAT AGCCTCTTTC CTAATGAACA GAACCACATC    54600

CTATTTCTAA CTTATTACTA TTAATGCAG CACAGGCATC AAATTTCAAG GTGACTTGTT     54660

TGGGCATTCC TTTTTCTTCT GTTTTGGCTA ACACTTTACT CGTATCGTTT ATGAACCCCC    54720

ACCAGTCCTC AGTCCTCAAT CTTATTTCAA AAACTGTGGT CGTGGGAGGC TCAGATGGGT    54780

CATAACACAC ATCAGGTTGG TCATTTCTTG GGCTACCTAC CTTGTATAGA ATAGCATTAT    54840
```

```
ACAAACAAGT TATTTTTAGA GTCTTTGTAC ACTTATAATA ACCATAAAAT AATAAGACTG    54900

TAGCAACTTT TTGTCCTACC TCAGTGACTT GATGTATACA CTGGGAACAG CCCTCAGTCT    54960

GAGGAAGGTT AGTTGAAGTC TTTACTGTGC AAGTCCAAAT TTTAAGGAAA ATGAGTCCCT    55020

TGATGAGTTT TCTCATGTTT CGGCCATGCA TGGACCAGTC AGCTTCCGGG TGTGACTGGA    55080

GCAGGGCTTG TTGTCTTCTT CAGTCACTTT GCAGGCGTTG GCGAAGCTGC CACGTACAGC    55140

TCACAGTCTA CTGATGTTCA AGGATGGTCT TGGAAGTTGG GCCCACTAGA ATTAACTGAG    55200

TCCAATACCT CTACTCAGTC ACTTTCAACT GGGCTTTCTG ATACCAGGAG CAAGGTGGCA    55260

GGTTTTAGGG TGTTGCAAAT TTCAATGGTT ATGCAGGGAT TTTCACATAG CAAACTTTGG    55320

TACTTGGTTA ATCTAGCATT TGTTAGCCAA TGATGTATTT ATTAAAGTCA CCACAGCATG    55380

GAGGGCCTTT AAGTTTAGGT TTTGTCCAAG AGTTAGCTTA TCTGCCTCTT GTGCTAGCAG    55440

GGCTGTTGCT GCCAAGGCTC TTAAGCATGG AGGCCAACCC TTAGAAACTC CATCTAGTTG    55500

TTTGGAGGCC CAGCCTCGGC CAGGGCCCCA CAGTCTGGGT CAAAACTCCA ACCGCCATTT    55560

TTTCTCTTTC TGACACATAG AGTGTAAAGG GTTTTGTCAG GTCAGGTAGC CCCAGGGCTG    55620

GGGCCGACAT GAGTTTTTCT TTTAACTCAT GAAAAACTCA TTGCTGTTGG TTGTAATAGA    55680

TGTAGTTTAT CCAATCTACA TTTTTATTAA CTGTCACCCA CCAAAATATT GACTCAAATC    55740

CTGCAGCTAT TTGATTTTGG GATTTAAATT GATCTGCTAT TCCCTGTGGG ACTCCAATTG    55800

CATCTAAATA GATGTGAGAG TTGAAAGACA CATAAGGGTC TTCTCTTGCT TTACGATGTC    55860

TTATTTTTCC TCCCTCTGGT TGATGAAATG CTAGGGTGAA AGGGATAGCC AATTGGACTA    55920

AAGTACAAGT GCCGCTCCAG TTATTTGGCA GAGTGCCCAG TAAAGGTCCA CCACAATACC    55980

ACCACACATC CGCTTGGGGA TGAACAAAGG CTGACTGATT GAGAAGCTCC TGAAAATTCT    56040

TAAGCTCACT GCATCCCTTC AGGTCTCCAA GGAATGCTAA GTTTCCTCCC TGTCATGAGA    56100

GACAAGAAGT GAACTTAGTT TTGGGAGATG GAAGCTGGAT GGCCCTCAGG GGTTGACCTG    56160

CAGGGTGCTG GACTTTGGGA TATAGCAGAG AGAGCTTGGC ACGACTTATT ACTCCAGGCT    56220

GTAGAATCCT GGAAAACAGT TACCATGCAG CCCATGCCTG GTCAACAGGA GGACCACCTT    56280

AGTGGAAAGG GGATAATCTG GCCCTCTGGC CTGCCATGTG CACAAGCATA ACAATTGGTT    56340

TTGTTTAATG TGTGGACAGA ATATTTGATC CATTCCAACT GGGCATTTGC ATCTTGGTAT    56400

CCTGCTTAAT TATCAAAGTT TGTTTTAAGT CTTTAACTTC TATGACCCTC TAGTAAAATG    56460

AATGTATGAT TTTAGGAAAT TACAAAAACC GGTTGGGGCA GTCCATCCTT GCTCTTTAGT    56520

GGTCCACACA ACATTCGACC AACTATGGCA TAAAAGCTCT ACATCGGGGG GCAAGACTCC    56580

TCGTTGACAC TGGGGTCTTT ATTGAAATCT CTCTGGAATA AATGGTCTCA GTTTACTAAG    56640

GCTCAGTCTG AGGAGAGTCA GGAGGGACAG AGGTACTTTT CTGAAGTACA GAGATGTCTT    56700

CGACTTGGCA AGTCCCCACA GGGTATAACA AGGCAAGCAT TAAATTCAAT AGTTTGAGGC    56760

AAAATTGACT TGGTTATGTT AATAACTAGA TGGTCAGAAA TAGAGTGAGG GAAGAAGAAA    56820

GAGTAATAGA ATAGATGAAG GAGTTAAATT TTTCTTAGCT TTAGTTTGGT AGGGTTTTCC    56880

CCTGGGACTA TGGCCCATGA CTCTGGAGGG GGTGGCACTT TCTTGACTCG GGTGTGATGA    56940

GTCCATCCCT TTTTCACCGT ATGAACAACA GTCTCGGTGG TTAGCAGCAC AAGGTAGGGT    57000

CCTTCCTAGG CTGGCTCAAG TTTTCCTTCT TTCCACCCTT TGATGAGAAC ATGATCTTCA    57060

GGCTGGTGCT GGTTTACAGA AAATTCTAGG GGTGGTACAT GTGCTAAAAG ACTTTTAGTT    57120

TTGAGGGAAA GGAAAGTGGA AGATAAACCA AGTATATAAC TTTTAAGAAG TTGACCTTTT    57180

GTTTTAAATG TGGGGACATC AGCAGTGGAC TTTATAGTCC TTGGTGCCTT CTTACTGAGA    57240
```

```
AATTTCCTTT AGCACCTATT TTTATTAGTT TTTAGACCAA AGAAAGTCAA ATGCCATTTT    57300

ATATTTGACA ACGCTTCTTG TATGTTTATA CCAGATAAGC TAGATTTCAC CTTTATATTG    57360

GTGTGTTATT AATGTTAAAC TTAGTTTTAA TAAAACTCTG TAGACATATT TATTTGATTT    57420

TTAATGTCTG ACCATAAGGT AAGATTTTTA TAGACTTTTC TTTAACCTTT TATAATTTTT    57480

GTTAAAGAAC AGGTTAGTGC TTTAAGAAAA ACCCGTTGTG TTTTTATTTT AATGTTCAGT    57540

TCACAGAAAA ACTGTATGAT ACCCCTTAAC TTTAGCCAAT ATGTTTAGAC ACAGAATTTT    57600

CTTTACAATT AAGGTTTCAA AACTTGCTTA AACCTTCAAA ACAATTTTTG TAACCTTTTA    57660

ATGTAGGTAA AAATCCACAT TCTTATGCAT CCTCATAATC CTTTTACCAA AGGTATATTT    57720

TACTTTCCTT ACATACCTTG CACATAAACT GTTTATTCAA TAGTTTTACA TTTAGAAGGA    57780

GGCCTAATTA CTTTTAAATT ATACAACATT TCTTACATAA ATTTATTTTT CTAACACACA    57840

TTTTTTTCAT GACTTTCACA GACAATTCTT CGACATGCCT CAACTTTCTG ACTTATTGCA    57900

AACATCCCTT TCTTTAAACA ACTAGTTAAT TTATCTCAGG ACAAGGATTT TCCATACAAC    57960

ATTCTTTTTT ATATAAATTC TGCCTCCTCT TTATTTCCTT TTTTTTTTTT CCGAGGATGA    58020

TAACCATTCT TTTCCAAAGC GAACTTCTTT TATGTCTGTG GACTAGACTG TCTAAGGCCA    58080

CAAGATTAGA AGTTACTATA ATACATGTTA CACTGTTAAC TTTTAGCAAA CTTTACTTTT    58140

GTTGAAAACC TTGTAAGTTT GGGATTTCAA TTATCCTTTG CTATTAATAA GACCTTATTT    58200

AGTCCAAATT AACTTAGAAT TGGTATAGAT GGCTTTTTTT TTTTTTTAAT TACCTGGGAG    58260

GAACCATCTA TCCTCCTGTC CTGAAGGGAG TTCCTCCTAG GTCTGGTCAG AGCTTTGTAT    58320

GGTAATTAAG ATTTAGATCC CCTGTTAGGA AACCTGCCGG GTTAAGAGAA TTTTCAGTGG    58380

TTAATGTTAA ATCATCTTCT TTTTTCTTTT TTCCTTAGGA TACTTCTGAA CCGGTGAGGT    58440

GTGCTCACAA TGAGGTTTCC TGTAAAAGTT ATTTTTTTAC TTTCTTCTGT TAGCAAAGCA    58500

GTTGCCGCTA CAGATTGAAT GCATTTGGGC CATCCGCGGG TTACTGGGTT AAGGATTTTT    58560

GATAGGAAGG CCTTAATGCT TTTGGAATAT GCCCTGACAA CAAAGTGCCA GTTCCTTCCC    58620

GGTGTTCAGC CACTGCGTTG ATCCTCCACG AGGGCCTGCC ACGTGCTGCT CTGGTGAGGC    58680

GTTCCACCGG GGCAATTGCC TACCTGGGAG CGCTCTCCAG ATCTGTGTCG CTCAAACTGG    58740

CTGGAGTTCC CCGTAGGGAT GCTCCACAGG GCAGGCCTAA GTCGCCTAAG GGCTGCCTT     58800

GACCGTCCGT TAATCACCTC TGTCTCCAAA AACCAGCTCC CTGAGTGAGC AATTCCTGTC    58860

CCTTTTAAGG GCTTACAACT CTAAGGGGGT CTGCATGAGA GGGTCGTGAT TGATTGAGCA    58920

AGCAGCGGGT ACGTGACTGG GGCTGCATGC ATCAGTAATC AGAACAGAAC AGAACAGCAC    58980

AGGGATTTTC ACAATGCTTT TCCATACAAT GTCTGGAATC TATAGATAAC ATAACCTGTT    59040

AGGTCAAAGG TCGATCTTTA ACCAGACCCA GGGTGCGGTG CCGGGCTGTT TGCCTGTGGA    59100

TTTCATTTCT CCCTTTTAAT TTTTACTTTT TCTTTCTTTG GAGGCAGAAA TTGGGCATAA    59160

GACAATATGA GGGGTGGTCT CCTCCCTTAA TTTAAACAAA ATTTTCAAAG TCCTACCCCA    59220

AGTAAATTGG CAAATATTAA TAAAGTTATG GCATAGAAAA TAAAAATGAT TGTAAAAGGC    59280

GTAAAGATAT TTCTGTGGGG AAAACATTTG TTCATTAGTT ATCAGTTAAA ATTCTGTGAA    59340

AAATAACCAC TAGAGACCCT AAAGTACCCA GGGGCTAATA ATAAGAAGGG AGGAACACCC    59400

TCTCACTCCC CACCGTTACC TGCCCAGAAG GGAAGAGGAA GAGGGTGACT CCAGGAGAGC    59460

TGTGGTCTCC CCTCCCCATA TGTCCACATA TACCTGACCT CCCCTCCCCA AAATATATAC    59520

CCAATATCTC TCCCATATAT ACATATTTAT CTGACCTCTC CACATATGTA TACCTAAACT    59580
```

```
TTCTCTATAT ATCCACATAT ACCTAACCCT CTCACACACA TATAGCTGAC CTCCAGTGGA    59640

GGAAAATGGG GAAGAGAGAA GAAGTTATCA AAGGATAAAT CTAGGTCATA CTCAGAAATG    59700

TGAAAAACAA AAACCACACA CAGAAAAAAA AAACACACAC AAAAAAGAAA TTGATAAATT    59760

TGTTTGTGTC AAAATTAAGA ATTCCGGTTC AATGAAGGAT CCCATGGATA AAGTTAAGAC    59820

ACTGCTGTAA GGATGGTAGA GAATTAAATG TCTGAATCAG ACGAAAGGAT GAGTAATTAG    59880

AATGCACAAG GCCAAGAAGA ACAAAACAGA AACTCCACAT AAAAAATGTA TGAGGCCGGG    59940

CGCGGTGGCT CATGCCAGTA ATCCCAGCGC TTTGGGAGGC CAGGGCGGGC CGATCAGGAG    60000

TTTGAGACCA GGCTGGCCAA CATTGTGAAA CCCCATCTCT ACAAAAAATA CAAAAAATTA    60060

GCCGGGCGTG GTGGTGGGTG CCTATAATCC CAGCTACTTG GGAGGCTGAG GCAGGAGAAT    60120

CACTTAAACT CAGGAGGCAG AGGTTGCAGT GAGCTGAGAT CACACCATTG CACTCCAGCC    60180

TGGGTGACAG TGTGAGACTC TGTCTCAAAA AAAAAAAAA TTATATATAT ATATATATAT    60240

ATATATATAT ATATATATAT ATATGAAATA AATGAACAAG AAATTTAGAT ACAGGAAAAT    60300

CCAAAGCACT TGGTAATGAA AGAAAGGTAA AGTGATGTGT CCTTTTGCAT TTAAAAGAGA    60360

GCATTAACAA ATTAGAGAGC TGAATAATGC TCAGTATTGG TGTGGATATG GAGACTCAGG    60420

AATCCTCATA CACTGCTGAT GGGAGTGCCC ACTCCCTGGG AATATTTTCC AAATATCATC    60480

TCAAACATAT CCCATAAAGG TGACAGGAAA GTGTGGGCTG ACTGTATACC TTCACTGAGA    60540

GAGGTGGAGG TAAAATGAAG TCACTGCACA ATATAGAGTT GGAAGCAATG GATTAGATGT    60600

CCACATAGTT ACGTGGAAGA ATCCGTAAGA TACACACACA CACACACACA CACACACACC    60660

TTTGTGTATA TTGTTCCTGG CAGGTAGGCA TGGAGGTTTA GAGGCTTTCT ACATCACACC    60720

TACTGCACAC AGTAAATGGC CAGGCTGAGC ACTGACTTCC ATGAAGGGAG ATTGAAGGTA    60780

AGAGATTGAA GATTGTTCCC TGGTCTGGGA CCCTGCAACT GAATATGCAG AAAAAAGTAC    60840

ACCCCGCCAC CCCGCTTCCC ATCTTTCCTA CCTGATTAGA ATAGCTTTTT CAGAAAACGT    60900

TGGCCAGGGG TTGTGGCTCA CACCTGTAAT CCCAGCACTT GGGAGGCTG AGGCGGGCAG    60960

ATCATCTGAG GTCAGAAGTT CCAGACCAGC CTGGCCAACA TGGCGAAACC CCATCTCTAC    61020

TAAAAATATA AAAAATTAGC AGGGCATGGT GGCACACACC TGTCATCCCA GCTACTCGGG    61080

AGCCTGAGGC AGGAGACTCA CTTGAAGCAC AGTGATGGAG GTTGAAGTTA GCTGAGATCT    61140

TGCCACTGCA CTCCAGCCTG GGCAACAGAG TGACACTTTG TCTCAACAAC AACAACAAAA    61200

CCCACCAAAA CTTTAAATCT ACCTATGGCC AAATGCCTGC TAAAATGAGC ACCCAAGAAG    61260

CAGTGTTCAG GAAAGTCAGA TGAATACCCT AAAATTAGAT GCAATGTTGG CTGGTCACAG    61320

TGGCTCAGGC CCTGTAATCC CAATCCTTCT TGGGAGGCCG AGGCGACAGA TCGCTTAAGC    61380

TCAGGAGATC GAGACCAGTC TGGACAACAT GGTGAGACCG TGTCTCTACA AAACGTACA    61440

AAAATGAGCT GGGAGTGGTG GCGCGCACCT GTAGTCCCAG CTACTCAGGA AGCTGAGGTG    61500

GGAGGATCTC TTGAACCCAG AAGGCGGAGA CTGCAGTGAG CAGAGATCAT GCCACTACAC    61560

CCCAGCCTGG ATGATAGAGC CAGACCCCCA TCTCCAGAAA AAAAAATAA AGAGAGAGAG    61620

AGATGCAATA TTTAGGGTTC AACAAGACTG AATTTCTGAC TCCTTTCCCT ACCTCTCCAG    61680

CATGTTAGAT TCTGGGTCCT TCATCCTAAC CCCCTGTTCA TGCCATAGCC ACCCTGTGGT    61740

ACCAACTTTG GAAGCCTGGA TCTTCATCCC CTCATGATAA TGAGTGTCCC ATCAGGTCTC    61800

CATGCTCAGC TTGGCAAGAG TATCTGTCTT CTCCTCATGG GACGGTCACA TTCACCCAGC    61860

ACTGACAGGT TCCATTCCCA CTAGGGTGGC ACCCTATATG GTCTGAGTCC AGGCCTTCCT    61920

GGTCCCTCAG TAATCTCAGC ATGGTAGCAC AATCGAAAAG GGCTAGGCAC GGCAGCACCA    61980
```

```
TTTCCCACCA AGAGGTCTGA TGGCTCATCA CATAGACTGA AGGAGATTCT GAAGAGCAGA   62040

GGTGGAATGA AGAATGAATC GTGGGCTCTG CTCTTCCTAG GCCTGTCTTC CTCTCTCCCG   62100

AGATGTTAGC TAACTCATGA GAGCCAGAAA CCAACTGCAG GCTGGCCTCA GGCACTTAGG   62160

TAGTGCTTCA GCCTCAGCAG TCCACATTCT AGGAACCCTC ATAATATGGG TTGAAGTATG   62220

CATTCCCACA AAAATAAAGT TGTTGAAGTC CTAACCACCA GTACTGAAAT GGGAAAAGTT   62280

CCCTTGTCCC GCTCGCATGG CATGTGATAG GAGTGTGGCT AATTTCTTCA GTGCCTGGCT   62340

GCTCAAACCT CTAGGGGAAC ATTAAGACGG GCAGGTTGTG GGTCTCCAAC CCCATGACCC   62400

CACCACAGTG TCTAGGGTTG AATGTTTACA GCTCCTGAAG CCACAGTGGG TGTGTGTTAC   62460

AGGGTGCTCT TTTAGTTTTG CCATTTATAG GCAGCTGGTG TTAACCAACT CAATTAGACC   62520

GTCTACCTTG TCCCAAGGAC AGAAGAAGGC TTTCTGTATC CCAGGTTCTT GCCTTGGTGT   62580

ACCGGAATAA ATCAGACCAC ACCTGGGCTT AGAGAAAGAG TGCAAGGTTT TATTAAGTGG   62640

AGGTAGCTCT CAGCAGTTGG GCAAAGCCAA AAGTGGATGG AGTGGGAAAG TTTTCCCTTG   62700

GAGTCAGCCA CTCAGTGGCC CAGGCTCTCC TCCAACCACC CCAGTCAAAT TCCGCCTCAT   62760

TTTGCCAGGC AAACGTTTGT TGTGTGCTCT TCTGCCAGTG TGCTCCCCTG GACGTCCAGC   62820

TATTCGTGTC TTGTGGCAGG CCAGGGGAGG TCTTGGGAAA TGCAACATTT GGGCAGGAAA   62880

ACAAAAATGC CTGTCCTCAC CGTGGTCCCT GGGCACAGGC CTGGGGTGG AGCCCTAGCC   62940

GGGGACCACG CCCTTCCCTT CCCCACTTCC ATATCATTTA AAGGGACCAT GCCCTTCCCT   63000

TCCCAGCACT TTCCCCCTCC TGTATCAGGA CCTGTGAATG TGGCCTTATT TGGAAATAGG   63060

GTCTTTGCAC TTCATCAGTT AAGATAAGAG TGGGCTCTAA CCCAACATAA AGGGTGTCCT   63120

TATAAAAAGG AGAAATGTCA TACACAGAGA CTGACACCTA TAGAGAGAAA ATGTGGTGAG   63180

TAGACACAGG GAGAATCACC ATTCAAGTCA AGCAATGAGT CTGGGGATAC CAGAAGCTGG   63240

GAGAGAAACC TGGAACAGAT TATCCCTCAT TGCCTTCAGA AGGAATCAAA CCTGATGATA   63300

CTTTGATTTC AGACTTCCAG CTTCCAGGAC TGTGTGACGA TAAATATCTG TTGTTAAGCC   63360

AACGAGTTTG AGGTACTTTG TTACTGCAGC CCCAGAAAAC TAATACAGTA GGTACTATGG   63420

ACTGAATTGA CTCCCCGTCG CAAAATTCAT ATGTTGAAAC CCTAACCCCC AGTGTGATGG   63480

TACTTGGAGC TGGGGCGTTT GGGAAGTCAT TATATTTAGA CAAACTCATC AGGATGTGTC   63540

TCTCATGATG AAATTCATGC CCTTATTAAA AGAGACAACA GGCCAGGTGC AGTGGCTCAT   63600

GCCTGTAATC CCAGCACTTT GGGAGGCTGA GGTGGATGGA TCACCTGAGG TTGGGAGTTT   63660

GAGACCAGCC TGGCCAACAT GGTAAAACCC CATGTCTACT AAAAATACAA AAATTGGCCA   63720

GGTGTGGTGG TGCACGCTTG TACTCCCAGC TACCTGGGAG GCTGAGGCAG GAGAATCCCT   63780

TGAAACCAGG AGGTGGAAGT TGCAGTGAGA TCACACCACT GTACTCTAGC CTGGGTGATA   63840

GAGACTCCAT CTCAAAAAAA AAAAAAAAA AGACAATAGA GCCAGGTGCT GCAGCTGATG   63900

CCTGTAATTC CAACACTATG AGAGGCTGAA GCAGGAGGCT CGCTTTAGCC CAGGAGTTCA   63960

AGACCAGCTT GGACAAAATA GTGAGACCCC CAACTTCTAA AAATTTAAAA AATGAACTGG   64020

GTGTGGTGGT ACACATCTGA GGCTCCAGCT ACTCTGGAGG CTGAGGTGGG AGGATTGCTT   64080

GAGCCCAGGA GGAGGCTGCA GTGAGCCATT GCTGTCCAGC CTGGGCTACA CGAGAACCTG   64140

TCTCGGGAAA AGGAGAAAAC AGTGAGACCT CTTTTTCTCT CCTCCTTCTC TCCACTGCCT   64200

AAGCCCTACA AGCACAAAAA GGACACCACA TGAGACACATA GTGAGAATGC TGCTGCCACC   64260

AACAAGTCAG GAAGAGAGCG TTCACCTAGA AACTGAATTG GCCAGCACCT GGATCTTGGA   64320
```

```
CTTCTGAGCT TCCAGAACTG TGAGAAAGTT ATTTTTTTTT TAGCGACTAA GTCTATAGTA    64380

TTTTATTACA GCAGCTCAAG GTAACTAACA TAGTAGAAGG GATGAATTAT GGAGATCACA    64440

AGTCCACGCC TCCAGAAAAA GACTTCCCTA AAAATTAGTC TGAGCAAAAT TCGAATGATG    64500

AATTATTTTT AAGAACTTTT AAGGGATCTG ACAAGTTTGC AAGAGCTAGA GAATGCTTTA    64560

CAACGTGATA ATAGAATGCT CTGTGATGAC AGAAATCTTT CCACACTGTT CAAAACTAGC    64620

TACTGGCCAC TTGTGACTAT TGTGCACTTG AAATGTGACT GGTGTCTGAG GAGCAGAATG    64680

TTTAATTTTA CTTAATTTTA ATTCATTACA ATAGCTACAT GTAGCTAGGG GCTACTGGAT    64740

TGAACAGCAC AGCTCGAGTC TTTTAGAGGG AGACAGGACT CACCAAGATG GATGCTGGTG    64800

GCCAAGCAGC AATGGCAGGT AGTACACACA CAAGAGGCAG ATGATACAAC ACATCCTTCC    64860

CAAACCTGGA GATAAGCTCA CCCCACAATC CCGCCGCTGA AATAGAGTTG ATGTTACCAA    64920

TGTGCATTTT TATGTCCTTT TCCATACAGA AAGATCATTC AGCAAGTACT ATGGTACTTA    64980

AAAAACAACA TTCAATTCAT TATTATGACA AAATTAAATT AATAGCTCTT CCTTAAACTT    65040

TTAAATTCAA TTTACAATGC TTACTATTGG CATTTATTAA TCTACCAATT TTTTCCCATA    65100

GAACCCATAG AACAAATAAT CTACCAAATT TTTAACATTC ATTTTGGCA AGGCTTTTGC    65160

AATTTGACGA ACTTTAAGAA GAAAACTTAT AAATTGCAAT TTTTAAATCT GACATACTGG    65220

ACTTTTAAAG TATCCAATTG ACTAATGAAC AAAACTGCTC CAAATTTTTC AATTCTTAAA    65280

AATCTTAAGA CAATACTTAA TATGGCAAAT CTTAACTTCT TAAACTTTGT AAGAATGCTA    65340

ATCAACTTAG ATTGGTATAA AGTTGAGTTA AAAATCACAG GATACATCAT CTCAGCTATA    65400

AGTTTTCATG AGTTGAGTTT TTACAATCAC TTGAAATGCT TAGAATAGGA AATACGTATA    65460

AATTATTTAA CATAAAATAT TGTTACAAAA CCTCTGGAGT GTCAGTTTCT CTGGCCAGAC    65520

TTTATGCTGC AGCACCTTTG CCTGAGTTCT TGTCCTGCAT CCAGGAAGAA TTAGGTACAG    65580

AGGCAAGAGT CAAGAAGATT AGTTTTCCAA TAGTTCAGCT CACCTAGTTA ACTCCTGTTC    65640

ACAATCTTCA AAGTTATCAG AAACCTGCAA TTGAGGGTTA TAATCCATTC TTTGCAGAGT    65700

TTCAAAACAA GACAACATTT GTCTATGAAT GTTAAAATGT CCTAGGGTAG TCACAGTCAA    65760

AAACACAATT GACAAAGAAA TTTAGTCACC TCTGTGATTT ACAATAGCCT AACACAATAA    65820

CTCTAATTAT AACTGATGAC ACAAACTCAG ATATCAGAAC TCTAGAAATC CCTATAATT    65880

TTGGAACACA CATTCACAGT TTTCACTGAA ATATGACCTG AAGATCAAAT ATCACCTTAT    65940

TTCAACAATC CTATATAACT AAACGTGTCA AATGATCCTG TTTACCTCTC CTTTGGATAC    66000

TCCAGGGGCC CTCTGTAGCA TCCAAAAGTT AGGGGTTAGC AAAGACAATT TTGAAGCTGT    66060

AAAGGCTCAA AACACTTAAT GAACCTCTAG TCATATCTGT TCTCTACTCA CTAAATGCTA    66120

GTAGCACCTC TCAGTTGTGG CTAAGCTGGG AGGATCTCTT GAGCCTAGAA GTTTGGGAC    66180

GCAGTGAGCT ATGATTATGC CACTGCACTC CAGCCTGGGC AACAATGCAA AATCCTGTCT    66240

CAAAAACAAA AACAAAAAAC AAATTGCCTA TGCTGTGGTT ATCTCACAAT TAATAAAAAG    66300

GAAAAAAAAA GTATGCAGTC TTTGTAGGTC CTTGGGGTTT GTTGGAACTC AGAAAACAAT    66360

ACCCCAAAAT AAAGACCGCA GAAGCCAAAG TTTTTCTCTG ATCTTCTCCT GCCCTCCTGT    66420

CTCTGAGTCC CATTCTCCCC GGAGTCTAGC CATAGAAATG AGAATTCCTC TTCCTCAAGT    66480

TAGGTCATAG AAATCAAAAC ACCTTTTCCC CAGAGCCCAG CCATAAAACC TAAAAATATT    66540

ACTCTAACTT TCCCTCTGTT TTTCTGTGTA AAAACTGGCC ATAAAGAAAT TATCTGAACT    66600

ACCTTATTTG ATCATAGATC ACCAGACCGC ATTCCAGAGA GGATCCAGAA GGAAGGAATG    66660

CTGCACAGAG AGGCGAAGAA GAATCTAGAC AGACAGGCCT TGCTGGGTTT CCCTACTCTG    66720
```

-continued

```
TTTATTAGCA ATCCTATTTC TACACGGCGG CCCATACTTT GTTGAATCTA AAAAATAAAA    66780
ATGGACAATT TCCCCTGTAC ATGTTAATAC ACATTAATAA ATTGGATATA AATTGGATAA    66840
TTTATTAATA TACACATTAA TAAATTGGAT GCAGCCGGGT GCAATGGCTC ACGCCTGTAA    66900
TCCCAGCACT TTGGGAGCTG AGGCGGGCAG ACCACGAGGT CAAGACCACC CTAGCCGAAA    66960
TGGTGAAACC CCGTCTCTAT TAAAAATACA AAAGTTAGCT GGGCGTGGTG GCACATGCCT    67020
GTAGTCCCAG CTACTGGGGA GGCTGAGGCA GGAGAATTGC TTGAACTCGG GAGGCGGAGG    67080
TTGCAGTGAG CCGAGATTGC GCCACTGCAC TCCAGCCTGG TGACAGAGTG AGACTCCGTC    67140
TAAAAATAAT AATAATAATA ATAATAATAA TAATAATAAT AATAAATTGG ATGCATTTTA    67200
TCCTATTAAT CTTCCTCTTG TCGGTGGTTT TCAGCGACTC TTCAGAGGCC AAAGAGTAAG    67260
TTTTCCCTTA GCCCCTACAG GTTCTTATGT TTAATTTGTT ACTCTCATTT AAGACATAAT    67320
TAAAGTGGCT TCTCCATGAA GATTATTTCT GCATCCATTA TTTGGTAAGA TTGGCCGTTT    67380
TCTCCTTTGA TCTCTACTTC ACACTGACCC ACATAAAACA TCACTGCCTG TTTTTTTGTT    67440
GTTGTTGTTT GGAGACGGAG TCTTGCTCTG TTGCCCAGGC TGGAGTGCAG TGGTGTGATC    67500
TCCGCTCACT GCAAGCTCCG CCTCCCGGAT TCACGCCATT CTCCTGCCTC AGCCTCCTGA    67560
GCAGCTGGGA CTACAGGCAC CCACCACCAA GCCCGGCTAA TTTTTGTATT TTTAGTAGAT    67620
ACGGGGTTTC ACTTTGTTAA CCAGGATGGT CTCGATCTCC TGACCTCGTG ATCGGCCCGC    67680
CTCAGCCTCC CAAAGTGCTG GGATTACAGG AGTGAGCCAC TGCGCCCGGC CCCGTTTTTT    67740
TTTTTGGTTT TTGCATGTCT TCTCCCTTTT ACTGTAAACT ATTTCCACTA CCAGCGTAGT    67800
TATCATTTCT ACTGCTTAAT AATTGTTTTG GGGAAGTGAA TGCATCAACC CACATGAATT    67860
TCTTGTCTAT TTGACAATTT ATTCTCTTTA GGAATAGTAT TAACTCCTAA GGTCCTGGGA    67920
GCCAGTCTCT GTACTTGGCT GCTCCAGGGT CCTACTTCAG TTTCCCAGCT TCTCAGTACT    67980
GTCACTGTCA ATTGTGGGTA ATAATTATTT TTGTCCACCA AAAGACTCTG TATGTGAATG    68040
AGTTTTGAAA TCTGCTGAGT AATACAGTGT CAACCCAGTT AATGATTTGC CGGGCGGCTT    68100
GATCAGGGGC TGTCCAACTA CCGGCATTTT GATTTGGAGC GTCATCTAGT GTCTGAAAGC    68160
ACAAACAACA TCCTACATTG TAAATGCCTT TGGCTACAGA GATTGAAACC AAAGCAAACC    68220
TATGTTTTGA ATTGTTATTC TTCAGCAGTT CTGCTAGCTT TGAAAAATCT AAAAGTTAAA    68280
AAAAAGCTTT ATATTTCATT TTCTGCCTAA ACTCTTTAAA ATTGCTAGTT GACAATTAGA    68340
TATTTTCAAT TTAATGAAAT TTTTTTTTAG TTCACAGATT AATACACAAT GGGGGAGGGT    68400
TCTTATTCTG TTGGACTTTT ACATAACCTC CACTTTAGTG CAGTCTGCTT TATGGGGTCT    68460
TGTTTGAGGT GTGTGTGTGT TTAAGGGAAT GTGGTTTACA ATCAAAATAT TGGGTTGCTC    68520
TTAGGCACAT TGTAAAGTCA CACACCTGTA TTCTTATTGA TACATAATGA TTAATAACAT    68580
TATTATTACA GCCTGATCAC CATCATTATT GATATATCTA AATAATGAAT TTTATAATTT    68640
TGCTTCCTGT CAGGCAAGAG CCAATTTCAG TGCTACCATG TTTGTATAGC AGTATTTATG    68700
TCTGTCATCC TCAGTCATTT TACTTCACTT GTTCTTAGCC AAACGGCCGA GAAGCGATGG    68760
TCATTTTACT TCAAAAATGA AAAGAATTAA TATTTTTACG TTTCCCTTAA AGACCCTATG    68820
TTTAACCTCC ACTCCTGGGT AAAATGGTCT AGTCCCTCCT TTTCATATCA TCTCTGATAT    68880
CTTTTGCACA GCCACTATTA CCTACCGTTT TCTAGATCCC TATTCTTCAA ACACCACCAT    68940
GAAGGTAGAG CCTGTCTGAA TTATTTTCTT GTCCCCTGAA CTCAGTACAT TGTTAGGCTT    69000
CTTGAAGATG TTGATCAGTT GTTTGTGGAG TGAATGAATC AGCTAGCATG ATTTTTCTAG    69060
```

```
ACCACTGAGA CAAGTGTCTA AGACACTTGT TCCTTCCCAT GTTCTTGCCT GCCTGTGCAA    69120

TCCATGCAGT CTCATGGCTT CCCAGTGCCT CAGAATTATC CCCTGTCAAA CAGGCATTAT    69180

AATTTCTGTC CACTGAAAAG GACAAAAAAC TAAGTGTATA GCTAGAAGTT AAAAATTACC    69240

GGCCAGGTAC TGTGGCTCAC TCCTGTTATT CCAACATTTT GGGAGGCTGA GGCGGGCAGA    69300

TCACCTGAGG TCAGGAATTC GATACCAGGC TGGCTAACAT GGCGACCCCG TCTCTATCAA    69360

AAATGTAAAA GTTAGCCAGG TGTGGTGGCT CGCACCTGTG GCCCAGCTA CTCAGGAGGC     69420

TGAGGCAGGA GGATCGTTTG AGCCCTGGAG GTTGAGGCTG CAGAAAAATA GGAATATACT    69480

CTCTTTCAAG AGTTCGTGGT TTTGACTGCC ACCTAGCGTA CATCAGAAAA ACCGCATGAC    69540

ATAGGAAATG CCTGTGACAG AGGGGTAAGG TGAGAGAGGT TGATGAAGAA TGTATTGAAG    69600

GAGTGAAAAC GCTTCCATCC CTCTACTTAC TAAATATATT AGTTAAGTAG TTGGGGCATA    69660

TTTTAATTCA TGCATTTTGT AGATAGAAAA ACAAAAGTTT TATTCTGTTT GATTTAGTTG    69720

ATACTTTAAT ATGTGTGTGT TTAGGATGCA TGATTTATAA TCAGTCTGCA GCACTTCTTG    69780

GAGAAGTCTG AATTCTCATT CTCCATTTCC TTATTGGCAA CGTGAGAATG ATTACAATGG    69840

TGGTTGTCTC ATAGAATGCA GGGAGTCAGA ATGAAAATAG TCCATATAAT GCCTGGTGCA    69900

GAGGAAGGGT TCAGTTAACT GTCTGTATTA ATATTACTGA TAACAGTCAT GACAAACAAA    69960

AGCTTAACAA CAACACCACC AACAACAGTT GCAGAATTGA GCCACCAATT TGCACACAAG    70020

ATTGTAGGTA GGATGTTTTA GAAAAGTTAT TATTTAATAT ATGTATATAT TTTTGTACTT    70080

AAAATATGTC AGAGGTTGTT CTAAGAACTA TTTAAATGTT AACTCCTTAA TCCTCATAAT    70140

GACCCATGAA ACAGGTAGGC TTATTATTGT CTCTTTACAT GTGAGAACAC TGAGACACGA    70200

AAAGGTTTAT TAACTCACCC AAAGTCACAC AGCTGGTAAA ACGCAAAAT TGAATTTGAA     70260

CTCAGACATT CCAGGTTCCA AGACAGTCTA ATTATTCTTT TGACTAATAT ACTAAGCTGC    70320

CTCTGTATTT TTCCTTGATT ACTTTGTAAA AGTATGAGGA AAATATAAGT GCTTCAAGTA    70380

ACCATGAAAA ATATAAACAA TCTATGTATC AACTGAAGCA TAATTACAAA TCCTTTGATA    70440

AGCAAACATA ATAAAAATTT GATATCAATC AAAACTTTCA TGTAATGTAA GCAGGTTGAG    70500

ATGAATTCTA TAGTAAAAAA GTGCAGAGTG CTGGAATACC ATGCTCCTAA TATATTGGCT    70560

AGGCACACCT GCCTGCTATC AAAGGTATGC ACACACCTTG GATACAGAAA GTTGGGACTG    70620

GGTAGTTATG TGAGTGTCAT CAGAATTCTT TCCCACTTGG GAAAGAATTG TCCATCATAA    70680

GCTTGGATGA TGGACAAGGA GTGAGCTCCC AGAACAGTGA TGTGGGGATA CATCCTCACA    70740

TCACAGTGAG AATGAGTGTT CTAGACTGTT TACACACCTA CCACTCCTAA ATGCACACAT    70800

ATAATTGCTT GCACACACAC ACATACACAC TCATCTCTTC TCTGGTGGTC CAGCTCTATC    70860

TCTTATCATT AGGCTTCTTG GGGCTAGTAC CTAGGGCCTG TATCCTTTCA GAGGCAGCTA    70920

AGGGAAGCAC ACATAATTAG AAAGAATGAA CCAGCTTGTT GGATTTGGTC TCTTCGCATC    70980

CAGCCCTCCA AGTTAAGGAG AGTACCATCT TTCTTAGGGT CACCAAAGGA AAAAAAAAA    71040

AAAGAAAGAA ACAGAAGGAT ATCATACAGC AAGGATCTAA TGCAAATATG CCTCAAATGA    71100

GAGGCTACTG TGTGCTGATC CCAATCCCAG GAACTGTATG CACATTATCT AATTTAATCC    71160

TCACTGTATT TCTGGGAGTA TTATTCCCAT TTTACAGAGA AGGAACTTGG CAGGGTAACC    71220

AAGCTCATGA ATGGAGAAAC TGGGATTAAA TATAAAGCTT CCTTGCTCCA GAACTGCTGT    71280

CTTTCTGCTC TTCCACACTA CCAGCTCAGC TGTGCTCTCT ACATGCAGGC AGTTTTACAA    71340

GTTTCAGATT AGCCTGGGAC TTCCAGGGTT TTGAATGGGT TAGGGAATGG GGAACTTTTG    71400

GGTTTACTTT CCATTTTTTC TTCATACATA TGTAATATAT AACATAAATC TATGGTATAT    71460
```

```
ATGATAAATA TATGGCTACA TATGAACTAT ATAATCACAT ATATGCATTA TAAATAAATA    71520

TTAATTTTAT AATATTTTAA AGGTTATCAA ATAAATATTA ATATAAATAA TTAAATAATT    71580

AATACTCAGC TTTGTTTTCC AAAGTGATAA ATGCCTATAT TTAGCAAAAT ATTTTTTGGA    71640

GGCCTGATAG TTTTTAGGAG TGTAAAGAAG TCCTGATATC TAAATGTTTA AGAACCACTA    71700

TTTTAGGCTG TTGTCTTCTG TCTTATTTTC CCAGCTAGAC TGGTAAATAC TTGAAGGCAA    71760

ACGTTTAGCC AGCACATTAA CATTTTATGT TTTTATTCTT TTGTGCTCTC AGTGGCTGTG    71820

TCTTTTCTAT CGATTTCTCA CACTGTATGA TGGTTATATT TGTCTGTATC TGTCCCACCA    71880

GGTATAAGTT CTTGAGAGGA CACACTGCTA GGCTGATCTT AGTTTTTATT ATTTCTCCTG    71940

GTGTCCTGTG CTTAACAAGT GCTCATTAAG TGTGTAAAAA CACAGCACAG TAAAAAACTA    72000

GACATTAAAA AATAATGTCA ACCAATCTAT TGAAATTTGC ATTTCCATGT TTCTTCCAAT    72060

ATAGTCATTG TGTCAGGTTA TGTACTTATT CTGATGAAGA CTATTGCCTA ATATACGTTT    72120

GCATCTTGTG CTTTATAACT GCCTTCATAT AGACACAGAT TGAGAAGGTG TAAAAATGTG    72180

CATATCCTCA CAATTGACAA ATTCTTATCC TTTGAGGGTA GGTTTGACTT TCTGAAATGC    72240

TTTGACATCA TTTGAAAGAA GCTTGAAGAA TAAGATAGCT GTTAATGACC CAGTTTCCTA    72300

TGTCACTTAT ACAATTATAA TGGCAATTTC AAAATGTTAG GTAAATATAT TTTGCAATAT    72360

ATTGTTCCTT TTGTAATACT CTCTATGTAT TTATTTATAT TTTTAAATTT TATATTTATG    72420

TATTTATTTT TCTGGACAGA GTCTTGCTCT GTTGCCCAGG TTAGAGTGAA GTGTTGTGAT    72480

CATAGCTCTC TGCAACTTCA AACTGCTTGG CAAAAGTGAT CCTCCTGCCT CAGCCTCATG    72540

AGTAGAGTAG CGGGAACTAC AGGCGCATGC CACTGCACCC AGCTAATCAC TATTTATTAT    72600

GCTCCTACTG TGTGCTTTAG TATATTTTCT GTTGTTTTCT GCAACCCATT TTGAGGGCGT    72660

GTTAGGGAAT ACAGATGCAG TAACTTTCGT CTCAGCCCTT GAGGTGAGGA AATATTTAGC    72720

CTCAGGTTTA ATCTAATTGT TGGCCATTTG CCTTCAAAGA TTGAAATATG AGCAAAACTG    72780

TGGCTCTGGG TTATATGTTA AAAAAAAGTT TATGGGCTG AAGCCAGGCA ACAGACAAGA     72840

GCCCCTACAA TCTTATTTAG GCTGAAAATA TCCTGGAGTC CCTGTATTGT TGGTCTCAAG    72900

CAGATAGCAA CACTAACACT TACTCTTTGA GGCAGGCACT GCCAGTGGGG TGGCTGTTAT    72960

TATTAGCTTC ATTAATTGGT GAGTCAGGAA AAAACAGCTT TAAATCATTC AAAGTTCTGG    73020

CCTATACAGG ATTTAGTAAT ATTAGGTTAG CTACATCCAA AAGATGACAG AACCCTACTC    73080

TAAGGCTGGG CTTGGTGGTT CACACCTATA ATCTCAAAAC TTTGGGAGGC TGAGGCAGGA    73140

GGATCACTTG GTGCCAAGAG TTTGAGACCA GCCTGAGCAA CATAGTGAGA CCCCTGTCTC    73200

TATCAAAAAC AAAGAACTCT AATTGGCATA GTAGAAGGAA AAAGTGAAAG AAAAACCAGC    73260

TGTCACCCTC ATTCCTTACA CCTGTCCTAA CAACTCCTCT CACTATCCTT TGAATATATC    73320

TTGGCTGTTT GAGTCTCTCT CTAGCCCCAT TACTGCTGTT TGGACTTGAC ATTTTGCTCT    73380

GCATTTTTAA CTTTTCTACC AGGGTTTCCA GACCCTGAAG AGTGTGGCAT GAAACAAAAC    73440

TAGTCAACCT ATAATATTTA TGATGTGTGT GTAAATAAAA GAATACACAA TATATTGCAT    73500

TACAATATTT TAACTGTGTC CTCAATTTGT TTGTGGCTTT CTTGAGGACA TCAGTTTTGG    73560

GTGGGACGAC CACATCCTTA ATCTGAACTT CCCCTTGGAG GTCATTCTTT TTTTTTTGAA    73620

ATAGAGTCTC GCTCTGTCAC CCAGGCTGGA GTGCAGTGGC GCAATCTCAG CTCACTGCAA    73680

CGTCCGCCTC CTGGGTTCAA GTGATTCTCC TGCCTCAGCC TTCCAAGTAG CTGGGATTAC    73740

AGATGCACGC CACCATGCCG AGCTAATTTT TGTATTTTTA GAAGAGACGG AATTTCACCA    73800
```

```
TGTTGGTCAG GCTGGTCTTA AACTCCTGAC CTCATGATCT GCCCACCTCA GCCTCCTAAA    73860
GTGCTGGGAT TACAGGCGTG AGCCACCCCG CCCGGCCAGA GGTCATTCTA ATAGACTTTT    73920
TTTTTGTTGT TGCTCACAGG CTTGTTCAAT CTTATTTCAA AATTTGAGAA ATACAGTTTC    73980
CATGGAACAC CAACCAGATA TCAGGTTGCT ATGGAGTTGA TAGTCAAAAG CTTTGTATCT    74040
TCCAGTTTTT CAGAATGGCT TCTAAAGGTT CTGATTCAGA GCTCTTAGGC GAAATTGAAC    74100
AACCAAGTGT CAAAGTACAA CATTCAGGAA GTTAAAAACA TGACTGACAT ATATGTACTA    74160
TATATAGTGA GCTTGTGTAT GTGTCAATGA ATGATTTAAT TCATTAATGA GGAGGAAGC    74220
AGAATCACAA TTAGGTCAAA GGAAGATACG GGAGAATAAA ATATGTATTT GGTCAGGGAA    74280
AGGATGTATA CTGGAAGAGG AAGGGAAAAT CAGATATAAA GTTGTTTAAT GACTTATTAG    74340
GCAATACAAT AATAACTTTT AGGGTCATTT TTTCTATATT AAGAATTCAT TTCCATCTCT    74400
ATGACAAAAT CCTTATTAAT TTATTAAACT TCTACAAGTG AATGTTTACT TTTAGATAGT    74460
CTGGACCCAA TAAAATGTAA ACATTAAGTC AGAGTTACTT TCACGTAGGA CAGTGTTGTC    74520
CAATAAGGTA CCACTAGCTA CACGTGATCA TTGACCATTT GGACTATAGC TAGACTGATT    74580
TAAAATGTTC TAAAAGTGTA AAATACACAC CAGGTTCTGA AGATTTATCA TTTAAAAAAG    74640
AATGTCAACT GTCTTTTTTT TTAGCTTATT TATTATATGT TGAAGTGATA ATAGTTTAGA    74700
TATATTAAGT TAAATAAAAT ATCTTAAAAT TAATTTTACT TGTTTCTTTT CATTCTTTCA    74760
ATGTGACCAC TAGAAATCTG GAAAGTATTT ATGTGATTCA CATTCTATTT TACTGTCTAG    74820
TATTGCCTTA CATCATCAGG TACCCCATAA GTAGGCTTTT TAGATAATTC TCTAATATAG    74880
CTTGGAAGGA TATGGAGAAA TATTTTTGCG TTGCTTTTAA GTTTTGCATA ACTTTTTCAA    74940
CACACTTTAT AAAGGATCTA GAAAAGGGTT GGTTACATGT TTCTCTGTCT TCTGGCCTCC    75000
ACCATGTTGC CAGGAGGTTG GGGACAAGAT TCTGGGTGGC TGGATGTCCT AATGGCTTGA    75060
GGTCTGGACT TGAGATTTGC ATATAAAGAG ATGTGATTAG ATTGAGTCGA CTAGAAAAAT    75120
CATATTAGAG AACTGAATCA CAGCGATTAA ATTTACATGT CGATTTATAA ACCAGGACAC    75180
CAATTTATAG TGAAAGAAGG TCCAGTTACC TGGTAATCAA GACGTTTCAT AGCTATTTTC    75240
ATGATGGATA TACTTAGCTG AGTTTTAAAT GAGAAGGGGG TTCATTGCAC ATAGAATAAG    75300
ATCTAAGTGA AATGTTTATT TTATTTTTTT TTTTTTGACA TGGAGTCTTG CTCTGTTGCC    75360
CAGGCTGGAG TGCAATGAGG CAATCTCGGC TTCTGGAGTG CAATGAGGCA ATCTCGGCTT    75420
CTGGAGTGCA ACGAGGCAAT CTCGGCTCAC TGCAACCTCC ACCTCCCGGG TTCAAATGAT    75480
TCTCCTGCCT CAGTTTCCTG AGTAGCTGGG ATTAGAGTTG CCTGCCACCA CGCCAGGCTA    75540
ATTTTTGTAT TTTTTTTAGT AGAGATGGGG TTTCACCATG CTGGCCAGGC TGGTCTCGAA    75600
CTCCTGACCT CAGGCGATCT GCCCGCCTCA GCCTCCCAAA GTGCTAGGAT TACAGGCGTG    75660
AGCCACCAAG CCTGGCCTAA GTGACATGTT CTTATATTGT TCCTTTCTTT CTTTTTTTTT    75720
CGACTGAGTC TCACCCTGTT GCACAGGCTG GAGTGCAGTG GCGTCATTTC GGCTCATTGC    75780
AACCTCTGCT TCCCGGGTTC AAGCGATTCC CTTGCCTCAG CCTCCTGAGT GCCACCACCC    75840
CCAGCTAATT TTTGTACTTT TAGTAGAGAT GGTGTTTCAC CATGTCGGCT AGGCTGATCT    75900
CAAACTCCTG GCCTCAGGTG ATCCGCCCCC GAGTCTCCCA AAGTGCTAGG ATTACAGGCG    75960
TGGGCCACGG GGCCCAGCCT TATATTATTT CTTTTACTAC AATATATTAG TATGATGCAG    76020
GTGCTTCAAT TGTTTATACA CTTTCCATAA TTTTGTATAA TTCTTATACC CTGTCACTCT    76080
GAGGAATAGC CGGTCTAAGT GTTTTTCCAC CACTGCTAAT TCATCCATCA CTAATCTCAT    76140
TAGACTGTTA ATTCCCAGAG GACATAAGCA CACAAGCAGA CAATGTTTAC AAATGTTGGA    76200
```

```
CAAATGTTAT TTAATAAAAC AATGGGGTCA CCCTTAGTCT AAAAGATGTT TCACTTTTCA    76260

TTTGTCATTG AACTCTTATT TGTAGGTTCC CTTTTGACTT TCCCACAATC TAAGGCTGTT    76320

CTCTTTAACA CATATTTTCA TGAAAACATA TATTTGAGCA GAAATTGTTG GGGAGTTGTA    76380

ATATTACCTT TGTCCCTAAA TATGAATCTA TAATTATATC AAATATATGG CAGACAATT     76440

TACTTTGCCT TTAATCTCAA GAAAAAAATA GCAATTACTT GGGGTCGGAG AGTAAAATAA    76500

GAAGTAGTGA ACCTTAAAGT AGCAAACTTT AGAACAGAAT AGTTTCAGAG GGGATGAGAA    76560

GAGGTGATTT TTCAGCTCAT CAACAACAGA TCTTATAATA AATTACATGT TCTGGTACTT    76620

TTCTTGTCTT TCTGTGTTAA ATTTTGCTAT TTAAAAAAAT AAATTTCAAA TACATTGTTC    76680

ATCTTAAAAG TCAAGAGTGT GTTTTATTAA AGTCAGTTGC TTTATTTGCA ACTCAAAAGA    76740

TATATTTGAG TTCCCAACTG GAGATTGTCC TATATGGTAA CTTGCGTAAG GTATGGTTAC    76800

TGAAAGTAAC CTACAATTTT CATGGGCTGA AATTCATTTC TATATTGCAG CGTACAAAAA    76860

TAAATAAATA AAAAATGCTT GTTTTCTTTG AAAACATATT ATCTCAGTGC CTCTAACTGC    76920

CAAATCTATT GGCTTTTTTG CAGGCTTAAG GGCTCTCCCT TGTTCCTTTA TGATCTCTAT    76980

CTTGAGGGCC AGACCTCCTG CCTTACACAA CTCAGAGGGG GACCTCAGAG CTCTTTAAAA    77040

AGAGCCCAAT TTCTCGCCTG TAGAGAAGTG AAAAGGATGC CCCACCCCCA TCTATGAAAA    77100

GAGGGATTTG ATAGTTTCAA TGTCTTCAAA TCAAAGATTT AAGTCTGTAG CCCCCCACCA    77160

CCCCGGACCC TAGCAAGGCT CATGAACCCC CTCCCATCCC GCCCTAATTG CTTTGGACTG    77220

GCCGTGGAAT CCTTGTCCCA GTCCACAGTT CCTGTGCGAC TGCACGAAGA ATTCACAGAG    77280

GACCTGTGTT ACTTCCCTTG TGAAGAAACA GAATTATCAT GAAAATTTAG GTGGAAACCA    77340

TTTCGCTTTT TTCTTCAAAA ATAAGGGAAG CATGTGCCCA ACCACCCCTG GAAAAAGAA     77400

CCTTCAGGGG CAAAGGAGCG AACAGGTAAT TTATAAGAAA AACAGAAAGT GGTCTCTGAC    77460

TGCCCCAGAC TTCCTTCGGA GTTGGGGGAA TTGGGGACGC CTGGACGCGT TGTTTTTGTG    77520

TTTGTGGAAA AAATAAATGA AGAGCATGAA GCCCGAGGCT TCTGAGATCC TTTCCTGACC    77580

AAACCCAAGT GATTTGGTGC GGGGAATTTT AATATTTTTC CCCTTTTGTG AGGTGGAACA    77640

AACACAACTT GGGAGCAGCG CAGCGGCTCA GAGCCTGCCA GCCAGGCGGG CGACCAGAGC    77700

ACCAATCAGA GCGCGCCTGC GCTCTATATA TACAGCGGCC CTGCCCAGGC GCTGCTTCAT    77760

CGGCGCTTTG CCACTTGTAC CCGAGTTTTT GATTCTCAAC ATGTCCGAGA CTGCTCCTGC    77820

CGCTCCCGCT GCCGCGCCTC CTGCGGAGAA GGCCCCTGTA AGAAGAAGG CGGCCAAAAA     77880

GGCTGGGGGT ACGCCTCGTA AGGCGTCTGG TCCCCCGGTG TCAGAGCTCA TCACCAAGGC    77940

TGTGGCCGCC TCTAAAGAGC GTAGCGGAGT TTCTCTGGCT GCTCTGAAAA AAGCGTTGGC    78000

TGCCGCCGGC TATGATGTGG AGAAAAACAA CAGCCGTATC AAACTTGGTC TCAAGAGCCT    78060

GGTGAGCAAG GCACTCTGG TGCAAACGAA AGGCACCGGT GCTTCTGGCT CCTTTAAACT     78120

CAACAAGAAG GCAGCCTCCG GGGAAGCCAA GCCCAAGGTT AAAAAGGCGG GCGGAACCAA    78180

ACCTAAGAAG CCAGTTGGGG CAGCCAAGAA GCCCAAGAAG GCGGCTGGCG GCGCAACTCC    78240

GAAGAAGAGC GCTAAGAAAA CACCGAAGAA AGCGAAGAAG CCGGCCGCGG CCACTGTAAC    78300

CAAGAAAGTG GCTAAGAGCC CAAAGAAGGC CAAGGTTGCG AAGCCAAGA AAGCTGCCAA     78360

AAGTGCTGCT AAGGCTGTGA AGCCCAAGGC CGCTAAGCCC AAGGTTGTCA AGCCTAAGAA    78420

GGCGGCGCCC AAGAAGAAAT AGGCGAACGC CTACTTCTAA AACCCAAAAG GCTCTTTTCA    78480

GAGCCACCAC TGATCTCAAT AAAAGAGCTG GATAATTTCT TTACTATCTG CCTTTTCTTG    78540
```

```
TTCTGCCCTG TTACTTAAGG TTAGTCGTAT GGGAGTTACT GAGGTATCAG ACGAATTGGG    78600

TGACGGGGTT GGAGAGTGGC CGTGGTGAGG TTACAGCATT TAAACCTTTA TTGCGGCTTC    78660

TAGGTCCCTG ACCGGAGGCT TTTCTCGCTG GCGGATGGTT TTGGGATGGC AGTCCCGCCC    78720

CAGGCCTGTG AACGGCAGAA AAGACCGCAA AACAAGAGCC AGTTTCTTAG TCTAAAGGGA    78780

TGTCCGGATT GGACTAAAAA ATTTTCAAAA GTCCCGCCCT GCTCCCGGGT TGGTCCGTTC    78840

TTCTAGTACA TGACTTTCAT TCTGTATTTA ATTGGATGGT GGAAGACGTT GCTTATTCTG    78900

TGTTTTTTGC TTTACTGTGA CTTAAAAGTT TTGCCTCTTT TCTCTTTATA TTAATGTCTG    78960

GGATTTCGGA CGCTTTCCAT GTTGTTGGTA GTCAAGTTGA TGTCTCCTGG AGGTAGTGGC    79020

AACATCCAGC CCTGGGAGGA GAGTGCGTGC AGGTACCTTT GTCCTACATT CCTCTGCTGT    79080

TAATTTCTCA TTCCTGTGGC AACGAAGGAA TGCATTTAAA AAACAGCCAC AACAGCGGCA    79140

ATAGCCCTTC CTCCACCCAA GGCAATCGTG GACCTAGGGA GTTTTTTGTG CCACATAACA    79200

TGTAGCCTTC CGCTAAACTG ACAGGTTTGA GCGTATCGAT TTTGAGCGTA TCGAAAGCAC    79260

AACTTTTAGC CAGCCATTTT GTCCTCGCAT GACTACGGTT GCTTATCCTG TTTAGACAGA    79320

CAGCAACATT TAAAAATCGA AGTTCCTTTA AACGTATTTT GTTTGGCAGT CCAAATGTTT    79380

CTATGCAGAA AACAGTATTT GTACTATTAA CTATGAAGAG TGTATGGATA AATGGGAGAC    79440

ATTTCTAATA AAGGCCTTCG TTAATGGTTC CCTCTGTTTG ACATCCATGG TGCTTCTGAA    79500

TACAGAAAGC CTAGCGTCTT ATATTCGCTT CTTTTAAAAT CTGGTGGGCA CATTTTGGTG    79560

AGACCTAAAT TATGGGGACT GGGGCTTCTG GAGATAAGCT GCTCAATTAT TCTACCATCT    79620

CCACAATGAT TAATATAGTG AGTTGATTTG TTAGTGATAG TGACCACGGA TTCATCCCAA    79680

GAAAGAGAAA GGGGAGGGAG GCAAGCAGAG AGACAGGAAG ACAGAGGCAG GGAAGAAGGA    79740

GAAAACATTC TCCCATGGTT TAAGTAATTT TGTGTTGTTA ATTTTACATT ACAACACGGT    79800

TTAACATGGT GAACCCTCTA TTTTGGTGTA AGGTTTAACA TATGGACATA TTTTTCCCAA    79860

GACCATTTAT GAACTTTCAT TTCTGCTTCC CCCTTCTTCC TCCCGTGCCA CCCTCCACGC    79920

TCCTATCAAT TTTGGCTGTT TTGTCATAGG CTAATACGCT ATAATTTCAT GGACAGTTGG    79980

ACTGTCTTAG GTTTCTCAGG TTTCTATTTT GTTCCTTTAG TCATTCCCAC AATTCTTAAG    80040

GTAGAATTGT ATTGTTTTAA ACATTGTGTT GTGTGCTATC CTCAATGCTG AGATGATTAT    80100

GTGACAAATG GCAAGTGTTC AACTAATACC TAAATCTGTA GTATCTTATC AAGCCTAATG    80160

CTACTTCACA ATGCCTACTC CATTCACCTC ACTTTATCTC ATTACTGCA TTCTGTCATC     80220

TCACATCATC ACAAGTAAAA CGGTAAGCTA TTTTGAGAGA GATCACAGTC ATATAATTTA    80280

TATTTATATT TATTTATTTA TTTATGAGAC GGAGTTTCCC TCTGTCACCC AGGCTGGAGT    80340

GCTGTGGCAC GTTCTCGGCT CACTGCAACC TCCGCCTCAC GGGTTCAAGC GATTCTCCTG    80400

CCTCCGCCTC CCGAGTAGCT GAGATTACAG GGGCCTGCCA CCATGCCCGG CTAATTTTTG    80460

TATTTTTAGT AGAGACGGGG TTTCACTAAG TTGGCCAGGC TGGTCTCGAA CTCCTGACCT    80520

CAGGTTATCC GCCCACCTCA TCCTGCCAAA GTGCTTAGAT TACAGGCGTG AACCACCGTT    80580

CACAGACTCA AATCATTTTT ATTACAGTAT ATTGTTATAA TTGTTGTTTT ATTATCAGTT    80640

ATTGCTAATC TCTTACAGTG CCTGATTTAT AAATTAAATT CATCATTGCC ATGTGTATAT    80700

AGAAAAAAAC AGTGTATATA CGGTTCAGTA CTATCTGTGG TTTCAGGCAT CCACTGGGGG    80760

TGCAGTTTAT TAAACATGCA TTTACATTAG TCTCCCCTTT GGGAGACTAA TTAACTGAGA    80820

TGTTGTAACG TGACTTTAAT AGCAGATAGA GCTAATTTTC TCTCATTACT CTTCTTTTTC    80880

AGAATTTTCC TGGTTATTCC ATTTTTTATT TTTCCATATG TATATTAAGA TCTCTTCCAC    80940
```

```
CTCCTCCTGT TTCTCCATCT CAACATCAAA CAATTAAAAA AAAAAAAAAG GCTGGGCGCG    81000

GTGGCTCACG CCTATAATCC CAGCTCTTTG GGAGGCCTAG GCGGGTGGAT CACGAGGTCA    81060

GGAGTTCAAG ACCAGCCTCG CCAAGATGGT GAAATCCCGT CTCTACTAAA AGTATAAAAA    81120

TTAGCCAACC ATGGTGGCAG GCGCCTGTAA TCCCGGCTAC TCGGGAGGCT GAGGCAGAGA    81180

ATTGCTTGAA CCTGGGAGGC GGAGGTTGCA GTGAGGCGAG ACCTTGCACT CCAGCCTGGG    81240

TGACACAGCG AGACTCCGTC ATAAAAAAAA AAAGCCGGAA GCAGTGGCTC ACGCCTGTAA    81300

TTCCAGCACT TTGGGAGGCT GAGTCAGGCA GATTACCTGA GGTCAGGAGT TCAGGACCAG    81360

CCTGGCCATG AAAATACAGC CTGGCCATGA AAACACACAA TAAATTAGCT GGGCGTGGTG    81420

TCACACACCT GTAATCCTAG CTACTCGGGA GGCTGAGACA GGAGAATCAC TTGAACCCAG    81480

GAGGCAGAGG TTGCAGTGAG TTAAGATGAC GCCACTGCAC TCCATCTGGG CGACAGAGCC    81540

AGACTCTCTC TCAAAAAACT AAATAAATAA AAATAAAGTT ATGGTACATT GAACTTCTGT    81600

GTTCCTTTCT CCCTTAGATA CTTTCATGGC TACCCATTTA ATTGATGTTC TTATCATCTC    81660

CAAGAGTTAG TCAGGAGAGG AATCAACCCA AGCAAAAATA GCTGATTTTC TAATTTTCCT    81720

TCAATGCCCT TTGGGGTCTT AATCCATTTG ATTTATGTAC TTTCAATTAA TCCTAACCTC    81780

GAATGTCTTC TGCAAACATG TTTCCACAGA TGAAACTCGT CAAATGAAAC ACATTCCTTT    81840

AATTTATAGA GTTAAAAATT AGAAAAATTT TCAATTCTAT TTGGCCTTTA GATTCAGTCT    81900

TGCATATGTT TTCTCAATTT TGTTCATGCT CTTTAGTTTT GTTTTATTCC ATCACAATTG    81960

TTCACATAGC TTACTGGCTT AGGTCTAATG AACCATTCAT TTGGAAATTA AAATTGGCCA    82020

TTTTAAGATG AAAAGATTC TTGCCTCAAT TTTACTTAGT TTTGAAACT GTCAATGAGG     82080

ACACATGTTT TTCTGTACTC TTAGATTCAC TAAGTAGTGT CTTGCAAATT TAACTGACAA    82140

AGGACAGATT AACATGCGAA AAAAAGAGCA TGCAATTTTA TTAGTATATT ACATGCACAG    82200

AGTTCCCAAA GAAAAAAAAA TTGAAACCTT AAAAACGCGG TTAGACTCAC AGACTTATAC    82260

ACCATTCCAA CAAAGGAAAG GGAGTTTGCA CTTCATGGGA TGACGAATTT GGGAATGTGA    82320

CAAGGAAATA AATACATGGG CAATAAAAAC CATGGAAGAT AAAATGAAAG ATAGAAATAA    82380

TTGTAGTAAG GTTTGTTTTT GCAGAGTCAT CTCAGTGCCA ACCTTCCATA TCTAGTGATA    82440

AGAATTGCTC TCTTTTTCCT GGTATAGCAG TTGGGGACAC TTTTACAAGG GAAATTTCTG    82500

TCACCTTCAC AAAGGGAAAT TTGGGTAAAG AGAAGACAGA GACCTCTTCC TACACCTGTT    82560

GATTTTCAAT TGCCTTCAGC TGAAAATAAC TTTTATGCCA AAGTAGAATA ATTTGGGGGT    82620

GACATCCTGA TATTCTTCAA AACTTATATT TAATTTCACA TTAGTAATTA TATCATTTTT    82680

GATTTTTAAA TTAGTTTTAT AAAATAATTT TGAAAAACGG TAATAATATT CAAATAATTC    82740

CAGAAACACT GCTGATAAGC CAAAAACATC AATGAATATT GCATAAACAA CTGATAATTC    82800

AACCATGAAA ATTTATGACA TTGTTCTTGT GTGATAAAAC TATGAGTAAC ATAAAAACTA    82860

GAGGCTACTT GTAATGCATT ATTCCAAACT TTCTGTTTTT TATTTATTTA TTTATTTATT    82920

TTGAGACATA GTCTCTCTCT GTCACCCAGG TTGGAGTGCA ATGGCGTGAT CTTGGTTCAC    82980

TGCAGCCTCC ACTTCCCCGG TTCAAGCAAT CTCCTGCCT CAGCCTCCTG AGTAACTGGG     83040

ATTACAGGCA CCTGACACCA AACCCGGCTA ATTTTTTTGT ATTTTTAGTA GAGACGGGGT    83100

TTCGCCATGT TTGCCAGGCT AGTCTCGAAC TCCTGACCTC AGTGATCCAC CTACCTCGGC    83160

CTCCCAAAGT GCTAGGATTA CAGGCGTGAG CCACCATGCC CGGCGCATTA TTCCAAACTT    83220

TCATACACAG TGCTATCATG GCTACAAATT GAAGTATCAT ATTATACACT CCTAGGCAAA    83280
```

```
GCTCTGGATA TTTTGGCTAT ATAAGCCTGA GGGAAATGTA GTAAGGACAT TGTGGTTGAA    83340

ATTCATACCA GAGATGAACA GGCCCAGTGC AAGACAGAAT TACATCACTA AAGGATATCA    83400

GAAGAGAATA GGGATTTAGG GTACAGTGGC AACAACAGTT TTGGGAACTA GCATTTTTG     83460

AGCACTTATT TACAATATGC CAAGCACTGT TGCTGATTAC TCTATATTTA TTTTCAAACA    83520

CATTCTTGTC ACAGCACTTT GAAGTAAGTG CCATTGTCAT TCCCACTTCA GGGTGAAGGA    83580

CTAAAGCTTG GTGTCATTAA GGATGTAGCT AGTTAGCTGT GTGTGTGTGT GTGTGTGTGT    83640

GTGCATTTTT TTTTAAATTT AAAGTCAATA AATTTTTATT TGAAGAATTT CACATCAAGG    83700

TAAACTTTGT TCCTCTAAAG AGCTGGAGTC AAAATGTATC TTCAAAAGAT TCATCTTCAA    83760

GTTAGCCCTT CTTAATAGAA CTGATGCTTA ATCCACAGTT GTCAGCCCAC AGTTCTTTTA    83820

TTTTGACTTT TTTTTTTTTT TTTTTTGAG ACGGAGTCTC TCACTGTCAC CCAGGCTGCT     83880

GGGCAGTGGC GTGATCTCGG CTCGCTGCAA CCTCTGCCTC CCGGGTTCAA GTGATTCTCC    83940

TGCCTCAGCC TCCTTAGTAG CTGGGACCAC AGGCGCATGC CATCGTGCTC GGCTAATTTT    84000

TGTATTTTTA TTAGAGACAG GGTTTCACTA TGTTGGCCAG GCTGATCTCA AACTCCTGAC    84060

CTCATGATCC GCCTGCCTTG GCCTCTCAAA GTGCTGGGAT TACAGGTGTG AGCCACTGCA    84120

CCCGGCCTTA TTTTGCCTTC TTTAATCTCC ATTTGAACAT ACACATACTG ATGAAAACTA    84180

CAACATTCTT CACCAAAAAT CTTTGGGATT TAATTTCTTC AACCACTTTA CTTTGGGGTC    84240

ATTTTAAGAT TAGGTGTATC TGCCTGGTTC TCAATTTGAC ACCCTTTCTC TCTAAACATG    84300

AATGAGTTCC AATCATATTT ATTCCTAAGC TATCACACTC AAATATACTA CAGATCTGTG    84360

GAATATGCCA AAAGTTAAGG TGAAAAATTA AATTATTAGG TATTTCATAG TTTTGCTAGT    84420

TTTTGATCTG TGAGTGAATA TAACTATCCT CTATGTCCTG GCACTGTTCC TCAGAAACAT    84480

AGGGTCCACA TATGTAATTT TAAATTTTTT AATAGGCACA TTTTAAAAAG TGAAAAAAGA    84540

AATCTATTTT AATGATTTGA ATCCAGTGTA ACCAAAAATT GTTTCAACAA GGTATCTAAT    84600

ATTAAAATAT TGAGTTTTTA CTTTGTTATT TTACTAGTTC TTTGAAATCT GGTGTGTATT    84660

TTACACTTAA AGCACATCAC AGTTTGGAGT AGCCACATTT CCAATGCTTA ATACTCACAT    84720

ATGGTTAGTG GCAACTATCT TGGACAGGAC AGCTTTTATA CTCTGGGAAG ACACAAGCAA    84780

ATACTTGCTC TGCAGCAGAA TCCAGATGTT TTCCAAGAAA ACACTTTTTC TGACCTGTTC    84840

CTGAAACCCA GGTAGTGTCT CTAATACTTT ATATTTTATT GGTTTGTCCT ATTGTAACCA    84900

CCCAACGGGC TCTCCTTGTC CACTTCCTAG ACAGAGCTGA TTTATCAAGA CAGGGGAATT    84960

GCAATAAGGA GCCAGCGCTA CAGGAGACTA GAGTTTTATT ATTACTCAAA TCAGTCTCCT    85020

TGAGAATTTG GGGACCAAAG TTTTTAAGGA TAATTTGATT GTAGGGGACC AGTGAGTCGG    85080

GAGTGCTGCT TGGTTGGGTC AGAGATGAAA TTATAGGGAG CCTAAGCTGT CCTCTTGTGC    85140

TAAATCAGTT CCTGGGAGTG GTGGGGTGGG GGACTCAAGA CCAGATAATC CAGTTTATCT    85200

ATATGGGTGG TGCCAGCTAA TCCATTGTGT TCAGGGTCTG CAAAATAGCT CAAGCATTGA    85260

TCTTAGGTTT TAAAATAGTG ATTTTATCCC CAGGAGCAAT TTGAGGTTTA GAATCTTGTA    85320

GCTTCCAGCT GCATGACTCC TAAACCATAA TTTATAATCT TGTGGCTAAT TTGTTAGTCC    85380

TGCAAAAGCA GTCTGGTCCC CAGGCAGGAA AGGGGTTTGT TTCTGAAAGG GCTGTTATTG    85440

TTTTTGTTTA AAAGCAAAAG TATAAACTAA GCTCCTCCCA AGTTAGTTA ATCCCAAACT     85500

CAGGAATGAA AAGGACAGCT TGGAGTTTAG ACGTTAGATG GAGTCGGTTA GGTAAGATCT    85560

CTTTCACTGT AATAATTTTC TCAGTTATGA TTTTTGCAAA GGCAGTTTCA CTGTCCACTT    85620

CACCTCACAT CAGGCCTCTG ACTAGAGGAT TCCAACAATA CTTAGGCCAG GACACCACCA    85680
```

```
TGTCTCCTTA TCCACCCTGA GGGAGTCCAA TTTCTGAAAC AAAGGAAACT ATATATGATA    85740

GTATGAAACT ATATATGAGA AGGAAATTAT ATATGATAAT CAATTTTAGG GTTATCTTAT    85800

TGATTAGAAG ATATTAAAGT GTGACACTGC CTGGCAATGA TATCTGCTGG TAGTAAGAAT    85860

TTGGCGAATT TAGTGAAATT CCTGAGGCTG AACCTCCACT TCTGTAAAAT GGAGACAGTG    85920

AGATAATTTG CCTTACAATG CTGAAGTAAG AATTTTACAC AATAATTCAG ACCAACCACT    85980

TCATGTGGTA CTTGGCCCGT GGAAGACTAT CAATGACAGT TAGTTTATAG TTTATACTAT    86040

TAATGAATCC TTTGTTTCAT TGTTATTTCC TTCTACACGT TGGCCTCTCT AAAAGAAGGT    86100

AATATTCAAT ACAAATAAAG TTAAAACAGC TTGCAGAGTT GTCCCAGGGA ACTCACTTAA    86160

CCACTGAAGT GTTCAAATTG CTTAAGGTTG ACTTTATATT CTCCTGACTA ACCTTTCTCC    86220

TTCTGGTATT TCTTCTGAGA ACAGCACCAC CATCCAAAGC ATCATGCAAA CAGTGGTCAT    86280

CCCAGACCAG TAATTCTCAA CTCACAGGGT GCTCCTGCAG AGATGTATTT GAATAGAGTG    86340

GTAGGATGCT GAAGAAGGCC ACGTAAAATT TGGCCAGTGA TCTGGGGCAG ATTTATCCTG    86400

AAGCTAATGA AACACAAGTG TAAGGGCCTG TACTTCCAAG GTGCAGAGAG GGGCCCTACA    86460

AATGTGTTAG TTTGTCTCTC TCTCTCTCTC TGATTTTAAA ATTTGCAGTA TTAAGGTACT    86520

TTAATCACGG ATGGTTCAGG CTGCTATTTT CACTCAATCC TCCTTTTTAT TAAAATCACC    86580

ATTGTCTGAT TATGTTAGAA TCCTGATGAA AATATTTGGA ATTTGAGTAA GAGAAAGTTT    86640

AGTTGAAGAT GTATCTAGTA TGGGGATAAT AAGTTACGTG ATTTGCATAT GTGATCATGT    86700

GTACTTCATT CGTTGCCAGC CAATCTGACG TAAGAATGGC TTCAAGGAGG CCGGGCGCGG    86760

TGGCTCACGC CTGTAATCCT AGCACTTTGG GAGGCCGAGA CGGGCGGATC ACGAGGTCAG    86820

GAGATCGAGA CCATCTTGGC TAACACGGTG AAACCCCGTT TCTACTAAAA ATACAAAAAA    86880

TTAGCCGGGC GTGTTGGCGG GCGCCTGTAG TCCCAGCTAC TTGGGAGGCT GAGGCAGGAG    86940

AATGGCATGA ACCTGGGAGG CGGAGCTTGC AGTGAGCCGA GATTGCGCCA CTGCACTCCA    87000

ACCTGGGAGA CACAGCGAGA CTCCGTCTCA AAAAAAAAAA AAAAAGAATG GCTTCAAGGA    87060

ATGTTCCTAC TGCTCACTGG AATAACTCAC CTAAATTCCT GGCAAGATGC AGGTCTAGAT    87120

AAAATGTTAT GACATCTAAG TATTCAAAAC ACATTCCCAG CACTGAGAGT GAGTGTCTAG    87180

TGGAGAGTAG AAACGTATAG AGCCAGAAGC TAGTCTGGAA AGAATTCTTA CAAAGTTTAC    87240

AACTTACATG TGAAAGGAGC TTAACAGAGG ATTTTCCAAA TTTGAAAACA ATCCTAAAAA    87300

CTTACTTGAC ATTACCAATA ATGTGTTTTG AAACTGAAAT ACTTCTAAGT TATGAAGAAA    87360

ACATATTATC ATCAGCCACC CTGGAGGAAA GATTGAATTC TATTTCCATT ACCTATAGAC    87420

AACATTACAA AATAATTTCG ATCTGAAGAT GGAATCAGAG TATTCAGTCA AAACTACAGG    87480

AAAATATACT TGGTAGTGTC ATATTCAGAA GTTAATAAAA TATGCTATTT TCTGAATTTT    87540

GTGATGGCTG TTGTTTTGTC AGCTTTTATA AAATTGGAAT TTGATTTTAT TTTCCCATTA    87600

TAAATTTATA TTTACAGTCT GCAGTACTTT TGCATTTTTA ATTTTACATT ATAGTTTTTA    87660

ATAGTTAACA AGTTGTAAAA GGTTTGATCC CCAGAAAACC TTGATCTACC CCATCAGTTA    87720

AGTATACTAA TATATTTAGA AAATGGATGA AATCAGCATT TGAATATTTT TAAATATTTA    87780

TTAAAGAGG ACATGGGTAA AAGAGCTTTG CAGTTGCCAC CCTTCATTCT CAAATTCCCT    87840

GGATAAGGAT GACCGCATAA TCTTTGGATG GTCATACGCA AGTCTTGTGT ACTTGTTACA    87900

TAAATCTATT TAGTGGACTT TTGGCAGTGT GTACTGAGGC CAGTTCTTC CACCTGAGCT    87960

CTGACTCCAC CTCCAGCAGC CCAAAACCAA TACTGAATTT TGGGGTCAGC TATTGTTTTT    88020
```

```
GTGGACTTAG GTAACTACAC ACACATTGTC TTTATGATAG CTTTAATAAT ACTGCCATCA   88080
GAACTAAAAT TGTCACGTGG ATTAAAAGGA GTGACGGTGG TGTCCCCAGG AGCCTTTCAA   88140
TATGTAAGTA TTTACACATA TACATGCTAA AAAGACCCCT AGGAATTTTT TAACAAGGGC   88200
AAAACAGTAA CTCAGCTTGT TTTCTCGCAG TAAAACCGGT TGAAAAGGCC TGATAGACTT   88260
GTCTGCAGTT ACAAAACTTG TGTGTAGTTA TCACCTTTAT ATCTCCTGGA AACTAACATA   88320
GACAACCGAA TGGGTTACAA CTGTTTTTAA GTGAAATTGT GAGTGGCTCT GAAAAGAGCC   88380
TTTTCAATGA GGAAGAAACG GGCAGACTTA TGCCCTTTCC CCACGGATGC GACGTGCCAG   88440
CTGGATATCT TTGGGCATGA TGGTGACGCG TTTAGCGTGA ATAGCGCACA GATTGGTGTC   88500
TTCGAAGAGT CCCACCAGGT AGGCCTCACA AGCCTCCTGC AGCGCCATCA CCGCAGAGCT   88560
CTGGAAACGC AGGTCGGTTT TGAAGTCCTG GGCGATTTCT CGCACCAGGC GCTGGAACGG   88620
CAGCTTCCGG ATCAGCAGCT CGGTGGACTT CTGGTAGCGA CGGATTTCGC GCAAGGCCAC   88680
GGTGCCCGGG CGGTAGCGAT GAGGTTTCTT CACGCCACCG GTGGCCGGAG CGCTCTTACG   88740
GGCTGCTTTA GTAGCAAGCT GCTTGCGCGG AGCTTTGCCG CCGGTAGACT TGCGAGCTGT   88800
TTGCTTCGTA CGAGCCATTT GCAATGAGAG CACACACAAA AGTGTAGTGA ACTGAGAGCA   88860
AGTGGCCTTT AAATATAGTG AGAAACATTC TGATTGGTCC TGTAATATTT CAAAAGTCCC   88920
GCGCGATAAA ATCATTGGCT GAAGAGTGAC CAGACTGATT GGTTCATTAC TAGACAATCT   88980
TATTGGATGA GTTGCCCCAC CGCCCATCCT GTCCTTTTCG TTTCAGTTAT CTGCAGCGAC   89040
AAATTGTCTA AAATTCTAGT TCATCCAGTC CCAAAGAACA GAGTGTATAA CAAGGTATCT   89100
AAGGATTTTT AAAATGTAAA TTCCGATTCA GTAAGTTTGA GTGGGACTTG AAATTCTGCA   89160
TTCCTGACAG TCTCGCAAGT TATCAATGCT GGTGAACACT CACTAAACCA CCAGAAACGT   89220
TCAGACTCAT GTCGGGAAAT AACGCTTATA TTCAGAGAAT GAGATTCCAT GCTATTTTGT   89280
TACTGGCGAA CAGCAAGTTT CCTTGCCCTT TGTTTTCTAA GTCCAAGTCA CATTCCCACC   89340
CTGCCTGTTC TCAAAATGTC TTATTTTGGT TGGCCTTAAG TTTCACTTTG TATACTCTAA   89400
AATGTACTTT CTAAAGGAAG GTGTTATTTT CTCGAAACTT AACTTTTTAA CACCATTAGG   89460
CTAGGGGGGC GGTGGCTCAC GCCTGTAATC CCAGCATTTT GGGAGGGCGA GATGGGACGA   89520
TCACTAGAGG CCAGGAGTTC AAGACAACCC TGGCTAAAAT GGTGAAACCC CGTCTCGCAT   89580
AAAAATACAA AAACTAGCTG GGCGCGGTAG CAGACGCCTG TAATCCCAAG TACACAGGAG   89640
GCTGAGGCAT GAGAACCGCG TGAAGCGGCG GGGTGGAGGT TGCAGTAAGC CGATATCGCG   89700
CCGCTGCACT CCAGCCTGGG TGACAGAACT AGACTGTCTC AAAACAAACC AATCCAAACG   89760
AAAAGCAAAA AATACCCTAA CAGAAGCAAG TTATCATCCT TTCTTGTGTA ACTATGGACG   89820
GCTCTGAAAA ATGCCGTTTC AAGTGTAAGC TACGTTTTCT GATTTGAGTG TTTACTTGAC   89880
CTTGGCCTTA TCGTGGCTCT GTTATTTTGG CAACAGGACG GCCTGAATAT TGGACAGGAC   89940
GCCTCCCTGA GCAATAGTGA CGTTGCCCAG CTGCTTGTTG ACCTCCTCGT CGTTTCGGAT   90000
GGCCAGCTGC AGGTGGCGGG GGATGATGCT GCGGGTCTTG TCACGTATGG CGCTGCCCAC   90060
CAGTTCTAAG ATCTCGGCGG CCAGGTATTG TAAGTACACT GGCGCACCGG CTCCGACCGG   90120
CTCAAAATAA TTGCCCTTTC GAAAAGATG ACGGACTCTG CCCTATTGGG AACTGCAAGC   90180
CCGGTAGCGA CGAACAAGTT TTTGCTTTAG CTCCATTTTC CACGTCCGCA ATAGCGACC   90240
TATGAAAGCA GCGGAAAACT GTGAAAGACA AGCAAGCTGG AATGGCGCCT GAACAAATCC   90300
TTTTATACAA ACTGCAAGGC TGCAATAGGA AGCTATCCTA TTGGTCAATT ATGTTTGGTG   90360
CTTTATCCAA TAGAAAAAGA TAACATAAAT TCCATATTTG CATAAACCCC ACCCCTCAGT   90420
```

```
GAAACCGTGT TTCTTTTGTC CAATCAGAAG TGAGGAATCT TAAACCGTCA TTTGAATCTC    90480

AGGACTATAA ATACATGGGC TCTGAACTGT TCTCTGTACT ACTCTGTAGT GGAGAGTGTT    90540

AGTAGCTTTT CTATTCTGTT TAGGAATAGC AATGCCTGAA CCCTCTAAGT CTGCTCCAGC    90600

CCCTAAAAAG GGTTCTAAGA AGGCTATCAC TAAGGCGCAG AAGAAGGATG GTAAGAAGCG    90660

TAAGCGCAGC CGCAAGGAGA GCTATTCTAT CTATGTGTAC AAGGTTCTGA AGCAGGTCCA    90720

CCCCGACACC GGCATCTCAT CCAAGGCCAT GGGGATCATG AATTCCTTCG TCAACGACAT    90780

CTTCGAGCGC ATCGCGGGCG AGGCTTCTCG CCTGGCTCAC TACAATAAGC GCTCGACCAT    90840

CACCTCCAGG GAGATTCAGA CGGCTGTGCG CCTGCTGCTG CCTGGGGAGC TGGCTAAGCA    90900

TGCTGTGTCC GAGGGCACTA AGGCAGTTAC CAAGTACACT AGCTCTAAAT AAGTGCTTAT    90960

GTAAGCACTT CCAAACCCAA AGGCTCTTTT CAGAGCCACC TACTTTGTCA CAAGGAGAGC    91020

TATAACCACA ATTTCTTAAG GTGGTGCTGC TGCTATTCTG TTTCAGTTCT AGAGGATCAA    91080

CTGGAATGTT AGCGAAGACA AGTTTTAGAG CCAAGGTTAA CTTGGACGGG GCCGTGCGCG    91140

GTGCCTCTTG CCTTTAATCC CGGCAATTTG GGAGGCCGAG GCGGGCGGAT CACGAGGTCA    91200

GGAGATGGAG ACCATCCTGC TTAACACGAT GAAACCCCGT CTCTACTAAA AATACAAAAT    91260

AATTAGCTGG GCGTGATGGT GGGCGCCTGT AGTCCCAGCT ACTCGGGAGG CTGAGGCAGG    91320

AGAATGGCGT GAACGCGGGA GGCGGAGCTT GCAGTGAGCC GAGATCGCGC CATGGCACTC    91380

CAGCCTGGGT GACAGAGCGA GACTCCGTCT CAAAAAAAAA AAAAAAAAAA AATTAAAAAA    91440

ATATGAAGTT TTGAAGCAGA AATTATTTTG TCGTATGTTC TTTCATAAAT TTTTTGCCTG    91500

CCTGCCTTCT TCCTTTGTTA CAGAACTCCA ACACTTACCC AAAGGTAGCT GTTGGGTCAG    91560

GGTTTCTGTA CTATAGTCCC TTCTGTGGTG GCCAGAAATA TGTTACAGGA AAGAGGTCCC    91620

CATCCAGACC CCAAGAGAGG GTTCTTGGAT CCCGCGCAAG AAAGAGTTCA GGGTGAGTCC    91680

GCAGTGCAAA GTAAATGCAA GTTTACTAAG AAAGTAAAGT GGTGAAACGA CAACTACTCC    91740

ATAGACGGAG CAGGACATTC CCGAAAGTAA GAGGAGGAAG GCATCCACCC TAGGTACAAT    91800

ACTTGTATAT ATGGGGAGAT GTGCTCTGCT ACAAGTTTGT GATAAAGGAT TAATTTTCTT    91860

AGTTACTATA TTTTGCAAGA ATCAACATTA TTATCTTTAA ACAAAATTAA GAATGCCTTT    91920

GTTCTCCAGA TATAGGGATA TCTGGACACT CCTAAGTCTG AGTCTGTTTA GTAAACATTA    91980

TTTATTTGTT CCCTTAACCG TAAACATCTA GAAGCTAGGA ATGACTGACT TTCTGGGAAT    92040

GCAGCCCAGA AAGTCTCAGC CTCATTTTCC TAGCCCTCAC TCAAAATGGA GTTACTCTGG    92100

TTCAAGTAAC TCTGACACTT TTCTTCTCTT TTTTTCTTCT TTTTTCCTTC CTTTATTTTT    92160

TATTTTTTAT TTTTGAAATA AGAAATCAAG AATACTTGAT GTTTCATCTA AAACAATACC    92220

CATAATTGAT AAGCCAAAAC AAAAACCTAG GTCTTCTAAC TCAAAACTAG GATGTTTTGC    92280

TGTCTCTGCT GATACTCGGC TGATCGTTAA TAGGTAATTA ACAAACAAGC CTTGCTATGT    92340

CCCCCTCAGT TTATTACCAT TAGATCATAT GCCTACTGTC AATCATATTA ATCCACAACT    92400

ATGCATTTCA CAAAACTTGC CATAAAAATT CACAGGTTTC CCGCTTCCCT CGAGTTTTCA    92460

TTTCCGAAGG GTCCCATGTA ATATAAAACT TATATTAAAT ACATTTGTAT GCTTTTCTCT    92520

TGCTAATCTT TTTTTTTGTT TTTTGAGACT GAGCCTTGCT CTGTCACCCA GGCTGGAGTG    92580

CAATGGCGCG ATCTCGGCTC ACTGCAACCT CCGCTTCCCA GGTTCAAGCG ATTCTACTGC    92640

CTCGCCCTCC CGAGTAGCTG GGACCACAGA TACGTGCCAC CATGCCCCGC TAATTTTTGT    92700

ATTTTTAGTA GAGACAGGGT TTCACCGTGT TGGCCAGGAT GTTCTCAATC TCCTTACCTC    92760
```

-continued

```
GTGATCCGCC CGCCTCGTCC TGCCAAAGTG CTCGGATTAC AGACGTGAGC CACTGCACCC   92820

GACCAATCTG TCTTTTTGTA GAGGGGCCTC AAGCATGAAC TTACTGATGG GTGAGAAAAA   92880

CAGAATTTTC TTTTCCCCTA CAATATAAAC ATTAATTGTA ATGTTATCAT TCAGGACATT   92940

TTGGTGACCA ATCTTACAGA AATTTTATCT TGTGCAAGTC TATGCAAACC AATATGTAAA   93000

TCTTCTATAA GTGAGATTGT ATTTCACTTT TCTAGTATCC TTTTAAATTA ATAAAAGAGA   93060

TTCTAATGAT TATTTTCATT ACTGCATTTC ATTGTAGGGA AGTAGATAAT TGCCCTTTAT   93120

TCACTGACCT TCGCTTTTTA AAAATTTAAA CCATGTTACC ATGAAAATGC TTTTCAGTAT   93180

TTCTCTACAC ACAAGATTGC TGTAAGGGCA AAAATAGAGA TAGGAATCAT GCATCCATTG   93240

ATATACATAT TTTGATTTTT AATACATGTT ACCAAGTTGC CTCCTGAAGG TCTGTTTACA   93300

CTCTCACCAA CAGGGTGTTT TTTCCTGACT TCCACAAATG CTCTTGAACA GTGGGTGTGT   93360

TAGTCTGTTC AAATTGCCGA CATGAACAAT TAAATCTCAT TGTTGTTTTT ATTTTTAAGA   93420

CAATTATTGT TTGAGACTGC ACATTTTGAT AATAACATTT CTTCTATTAT GGTTTGATTA   93480

CTCATGATTC TTGCCCATTT TCTTTTGGGA TGTTGCCTTA TGTACATTAT TTTAAATAGA   93540

TAGCTCCATG TATTAAAAGA TTATTAAGTT TGAGGGCTTA TGATATGTCA GTTACATTTC   93600

TAAGATTTTT TTTTTTTTTT TTTTTGAGAC GGAGTTTCAC ACTTGTTGCC CAGGCTGGAG   93660

TGCAATGGTG CGATCTCGGC TCACCGCAAC CTCCGCCTCC AGGGTTCAAG CAATTCTCCT   93720

GCCTCAGCCT CCCCAGTAAT TGGGACTACT GGCAAGCGCC ACCACGCCTG GCTAATTTTG   93780

TATTTTTATT AGAGATGAGG TTTCTCCATG TTGGTCAGAC TGGTCTCGAA CTGCCGACCT   93840

CAGGTGATCC ACCCGCCTCG GCCTCCCAAA GTGCTGGGAT TACAGGTATG AGCCACTGGG   93900

CCCGGCCACA TTTCTAAATT CTTTATAAGT ATAAATTCAT TCAATCTTCA CCAAAACTCA   93960

ATGAAGTGTG AGTACTATTA TTATCATTGT TTTACAGATC AAAACAAGTA ATACAGTCAC   94020

TTACTGAGTT CTATACACCT GGTAATTTTT TTGTTTCGTT GTTCTATCAA TTATTGGGGA   94080

AGGGGTGTTG AAATCTCTAC CTTTAAATCA TGTATGTGTC TATTTCTCCT TTCGGTTCTA   94140

TCAGGTTTTG CTACACATAT TTTGCAGTTC TGTTATTTGG TGCATATACA TTTAGAATTG   94200

CTTGTTTTTC GTATTGGATT GACCCTGTTA TCATTATGTA ATATCCCTGT CTGTTCCTAG   94260

TAATTTTCTT TGCTCTGAAA TATACTTATC TGATATATCA TCCAAAAGAC CACCAGGATG   94320

GCTAAAGAGT AGAAAGGAGA GATTTACTGG CAATACTAAT TTGCAAGCCA GGAAGAGATG   94380

GTCCCAGAAC CTGCCAAAAT TACTCTCTCT TTGGGGAGAA GGAGCAGGTT GGTTATTTTT   94440

ATGCCTCATA GGCTATATAT TACACAATAG AGTCATACAT ATTTAGCACG TTTGGGGGGA   94500

CAGCTATATA TATTATGAGG GGTGCCAAGT GCATTCACAA TGGATAAACA CGTGTAATAT   94560

ACCTCCCATG TTCACTTCGA GGTTAAATTT TGGTTAAAAT GAGGTAGAAT TTAGGTCTTT   94620

ACATCACAAG GTGAACTATA GGAACAAAGT TTACGTGCTG CCTCTAGCAG CTGGCTGAAA   94680

ATGGCTTAAG GTCTACAATT ACGTGTAAGA ATAGAATGTG TGTCAAGGCG GTCCTCTGTC   94740

CAATCAGAGT TGTAGTGGAC TGGACTGTAA ATCAGAGTTA GGAGGGCTTC TGATAGCTCC   94800

TATAGTTAAG GAATTTAGCA AGTGTGAGTT TTTTGGTAGT CTTTGGAATT TAGGAATTTG   94860

CCATGCCAGC CAAGCCATGA ATGCTCTACC AGTAGGTAAC TTTGTTTGCT TAATCTTAGA   94920

GTCTGTCTTA GTTGGTATAG GGGCATCTAT TTTGGTCTTT CAGATCCCAG ATATTATTAA   94980

TACAGATACT CTTGCAGTTT TGGGCTGATG TTTATATGGC TTATCTTTTT TGCAGCCTTT   95040

AATTTCAACC TGCGTTATGT TTATATTTGA AGTGAGATTC TTGCAGACAG TGTACAGTTG   95100

TTGTTTTTTT TTTTTTGAGA TGGAATTTCA CTCTTGTTGT CCAGGCTGGG GTGCAGTGGC   95160
```

```
ACAGTCTCAG CTCACTGCAA CCTCCGCCTC CTGGGTTCAA GGGATTCTCC TGCCTCAGCC    95220

TCTTGAGCAG CTGGGATTGC AGCCATGCGC CACCACACCC GGCTAATTTT TGTATTTTTA    95280

GTAGAGACAG GATTCACCAT GTTGCCCAGG CTGGTCTCGA ACTCCTGACC TCAAGTGATC    95340

CGCCAGCCTC GGCCTACCAA AGTGCTGGGA TTACAGGTGT GAGACCTCGC GCCCAGCCAA    95400

ACTGTTTTTT TATGGGTGTA TTTATACCAC ACACATTTAA TGCAATTATT GATATCTTAG    95460

GGCTTAAGTT CATGAAGGGT AGTGTGGGAA CCATAGTCTC TTGGCCCACT AAATGTTTGC    95520

CAGAAATCAC TGACAAGGCA GATTGATTAA TAGGTGAAAA GGCATTTTAC CTATTGTTTA    95580

ACGTGTCTAT GTGGGAGCAT TCAGAATTAA TTACCTAACT TCCCAATGAG TTATAGATGC    95640

TTATATACCA TTTTTAGATC ACAGAAAGAA TTGGGGCTTA GATTCTGGTA AAACAGGTTA    95700

TGGGAGGCAA AAGAGGTTTG GCTTGCAAAG GTGGCCTTGT TAGGTAGGTG AAGCCTCCCT    95760

CAGAAAGAAC AGATGGTAAA TGTTTCTTTT ATGATTTTTA AGTGTCAGAC TCTCAGTCTC    95820

TCCTGGATCT GGGGAAAGGT ATAGAAAGGT GAGGAGGCAT GGCTGCATTA ATGGAGATTC    95880

TCTACAGATG TAAAATTTTT CCCATTTAAG GCAGCTTTGC AAGCCCATTT CTGCCTGCTG    95940

GCCAAGCAGC AGCCATTTCA AAATATGTCA AAGAAATATA TTTTGGGGTA AAATATTTTG    96000

ATTTCCTTTA GACTGGTGGC CTTATAAGAA AAGGAAGAGA CACCTGAGCT GACACACATA    96060

CCCTTGCTCT CTCAACATGT TATGATGCAG TAAGAAGGCC CTCACCAGAT ACTAATTCCA    96120

TGCCCTTAGC TTCCCAGGTT CTAGAACAGT AGGAAATAAA TTTCTTTTCT TAAAAGTTA    96180

GCCAGTCTGT GGTATTCTGT TATAGTATCA CAAAATGGAC TAAGTAACTA TATTATGATC    96240

ATCTTACATG ACTGATCCCT CCTACATCAT ACACATACAC AGGCCACATT TGGAACATTG    96300

TTAGAGGTTC CTCTGCCCAG TACAAATGTA CTACAAATTA TATATGTATT TTTAAATTTT    96360

TGAGTATCTT CAATAGTATA TTTTCGTTAA CTTTTGTAGT CAAAATGTCA TTATAACATG    96420

TATTCAATAT GCATAATTAT TAGTCAGATG TTTTACATTT TTTCTTCATA CTAAGTGATA    96480

TGGTTTGGAT ATTTGTCCCC TCTAAATCTC ATGTTGAAAT GTAATCTCCA ATGTTGGAAG    96540

TGAAGCCTGG TGAAAGGTTT TTGGATCGTG AGGGTGAACC CCTCATGAAG CGCACTCTTC    96600

AGGGTAATCA ATGGGTTCTC ACTTTGAGTT CACAAGAGAT CTGGTTCTTT AAAAGAGTGT    96660

GACACCTCCC CCATCTCTCT CGCTCAGCTC TCACCATATG ATATGCCTAC TCCCTCTTCA    96720

CCTTCCACCA TGATTGGAAG TTTCCTGAGG ACTTGCCAGT AGCAGATGCC TGCACCACAC    96780

CTCCTGTACA GCCTGCACAA CCGTGAGCCA AAAAAAATTA CTTTTCTTTA TAAATTAGTC    96840

AGTTTCAGGG ATTCCCTTAT AGTAATGCAA GAACGAACTA ACACACTAAG TCTATTTCAT    96900

ATTTACAGAA TAGCTCAATC TGAAGTACCC TTTTTCAACT TCACAGTAGC TACTTGTAGC    96960

TAGTGGGCAC TGATTTGGAG CGTGTTCAAG GGTGAATTGT ATTATGCAAT TAACAGATTT    97020

TTTTTATTGT TTTCGCAAAC CACGAGGCAT AGATTGTCTT ACTTTCTCTG CTCCTGGTGT    97080

TGGAGTTGTT ATTGGGAAAC AACTTATTTT CCTCTTATAT TTATATGGAA TAAATAACCC    97140

CCAATATTTC CCTCCCCAAT ATCTGCCTTT TGTATGTTTT TTGAAGGCAA GTGCCTAGAA    97200

TTTACTGTTT TTGAAGCACT TACTGAAAGG ATTGCCATCA AGTTGTTTTG CTAATAGTAC    97260

ATGCCAGGCG CTTGTTGGTT TGCTTAATTC AAGGTAACTT GGATGAGAAG AAGAGTTTTT    97320

CTCATCCATG GCTCAGTGGA GTATAGATTA CTGATATTGT GACTGGATGT ACTCCTGCTT    97380

TCTAGTCTGA GTTTTTGAAG CTACCCTTAA TCTTGGTTTC AATTTTATCT AGCCCTGTAC    97440

ATATCCAAGG CTCTTTCCAA AATGGTCTAC GATTTGTTTA GGAAGTTAGA ATAGCTGTAC    97500
```

```
TTTCTGAACC ACGGTTCCTG ACATTTTCTG GACTTCAAAC ACATCCAGCA TTTTATCGAA    97560

GTATTTATCC TTCCTACTTG GCTGGCTTCT TCCTTGCCTT CAGGTCTGAA TTCAAATGAC    97620

ATTCTCCTGA TGAAACTTTC CATCCTTATT TCTATTCTTT TTTCTTATCC CCTTTCTTTA    97680

TTTTTCTCCA CAGCACTCAT CACTTATCTC TACATTTTCA TTATGTATTT ACCTTATTGT    97740

GCACCTCCCA CTACAAGACA AGTAGCACCG TAAGGAAACA GGTTGTCTGC TTTTTCACTG    97800

CTATGCTCCC TGCACCTAGA ACACTCTCTG GCACTTAGCA GGTTTTCAGT AAATATATGC    97860

TGAACTAATA ATGCTGGATA TACATCTCCC TCATGAACTC TCTAAATCCT TCTAATTTAC    97920

ATTGATCAAT CTTCTTTTCC ATGTGCTTTT GTATGATTTA TTGCTCAAAA TCTTTATTTT    97980

ATATGCAGAA CGTGCACTGC TATTTAATCT TCATGTACGT AAGTCCTCCC TTCTCTGAGT    98040

ATAATCTCTT CAGGGCACTA TCTGAGATAA CTTTTTAACA TCTCCATCAT GAATCTTGTA    98100

CCTTTTCAAA GAAAATGAGC CAGTGATTAC TGATGTTTAC GGCTATTGTT GAGGGTGAAG    98160

ATCATTATAA TTTTGAAAAG GGAAGTTGAA TATTGTGAAG GGAAAGATAA CACTAGAGTC    98220

AGAAGACTTG GGAGAAGGCA AAAAACAAAC TAAAAATGAG CACTTTTAGT CTCCTGACAG    98280

TTTCTCTGAA TCAAATCCAT AGTTCTGTGA CAGCGTTGGC TTAGAAGCAG ATTTTTTTTT    98340

TTTTTTTTTT TGAAATGGAG TTTCGCTCTT GCCCAGGCTG GAGTGCAGTG GCACGATCTC    98400

GGCTCACTGC AACCTCTGTC TCCAGGGTTC AAGCGATTCT CCTGCTTCAG CCTATGGAGT    98460

AGCTGGGATT ACAGGCTCCC ACAACCACGC CCAGCTAATT TTTTGTATTT TTAGTGAAGA    98520

CTGGGGTTTC ACCATGTTGG CCAGGCTGGT TACGAACTCC TGTTCTCAAG TGATCTGCCC    98580

GCCTTGGCCT CCCAAAGTGT TGGGATTACA GGCATCAGCC ACCGTGCCCA GCCAGGAGCA    98640

GATTTTTTTA CACTCATGTT TCTTTTTCCT TCTGTCATCC TGTTTCAGTA TAAGCAGACC    98700

ACAGATAGAA GTAGTAGATA CCTCAGAAAT TCCTGGAATA ATTAATCCAC GTTCATCTGT    98760

ACTCCATCTG CTCCTATCTC ATGGAATATA AAAGGAAAAA CACCAAGATT TCCCTAGGCA    98820

ATCTGTCTTG ATTTTAGGTT CCTCAACAGG AGAGCCAGAC AATGGCTGTA ATAATATTGT    98880

CCCGGCCAAG GAAAAACTTC CCCTTTGCCC TCCCAAGGTT TATGGAAAAT TACTGGCAAA    98940

ACACAGATTA ACTGGAGAAA AGGCATATAT ATTTATTTCA TCACAATTTT ACAGGAGATT    99000

TTAGAATTAA GACTGAAAGA TACAGGGGAA ATTGCCCATT TTTATGCTTA GGTTCAACAA    99060

GATAAACAGC TGTATAGGGT ACGATCTAAT GCTAACAGAC TGAGTGGGGA AGCCCCGCAA    99120

GGCTTGTCTG TCAAGATTCT TCTTGACCTC TCAGTGCAGC ATTTCTTCCT TCTGGTTATA    99180

GGACAAGACT CTCTTTTAGA ATGGGGGGTC TTATGACCTA CAGGCAAACA AGGTAGGTTA    99240

GAGTAATACT TTTAGGTTTT ATGGCTGGTT CTAGGGAAAA GGAGTTCTGG TTTGTATGGC    99300

CTACCTTGAG GAGGAATTCT GGTTTCTATG GCTAGACTTT GGGGAGAATG GGACTTACAG    99360

ACAGGAAGGC AGAAGGTGGT CAGTGAAACA CTTTTATAAT CATAATCCCA TTTTGAGTAT    99420

TTCTGTGTTA TGGAATGTTT GTTCTCTCAT TTCCTGAAAG ATTCCAGAGA CTCCTCATTC    99480

AGTGTTGTGA AAAAGTTCAG GAAATGCAAC TCAAAAATGT GCCACTTTGT TACGCTGATT    99540

TCTTTGAACT GAGGGCACCT AGGAAACAGT AAATTCAAGG AAGGGCTTTC GCTGAACTCT    99600

AATCAAAAAT TTGAAAATTA AAAAAAAATT CAAAAAGGAA TTTAGTTGTT AAGATTCACT    99660

TCCCTGGGGA ATCTCATCAA CCAGAGAAGA TTAACTGTAT CACAGGAGAG GAGACTGGTG    99720

GTTAACACCA TCTAAACAGA CTTTGTCACA GCTGTCACCT ATTCTTTGAA ACACCCATTT    99780

ATTTTTCTCC AAAATCATAT ACTCTCCCCT AAGTTGCCTA CATCCCCCTT CTTTCTCCCT    99840

TATGAATCAA GAGAGCTTAT AAGCTTCTAC AGTTCACTGG GATTTGGGGT ATTCGCTTTT    99900
```

```
CTTCCCTCCC ACTCCCCCTC CCCTTTTTTT GTCTTTGAGA CACAGTCTTC TGGCTCTGTC    99960
GCCCACGCTG GAGTGTGGTG GCTCTATGTG AACTCACTGC AACCTCCTCC TCTCGGGTTC   100020
AAGCGATCCT CCCACCTCAG CTTCTCGAGT AACTGGAACT ACAGGCGTGC ACTACCAAGC   100080
CCGGCTTTTT TTTTTCTTTT TCTCCCCCGT TTCTTTTTTG GTTATTTTAC TGGAGACAGG   100140
GTTTCTCCAT GTTGTCCACG CTGGTCTCGA ACGCCTGACC CGCCGTCCTC GGCCTCCCAA   100200
AGTGCTGGTA TTACGGGCAT GAGCCACTGC GCCCGATTTG AAGGACCTCT TAAATATCTA   100260
TTTAGAAATT GGTCGGAGTC CACTCCTTTC CAAAAACATG AGTCACAATC CGGGAAAAGC   100320
ACGAGCGGCT GAAAGTCAAA ATAACCAGAA CAAAACCTCC ACTCATGCTT AAAAAAGGTA   100380
TTTTGACAAA ATCCTAATTC GGCCAATTAT TATTAGTATT CAAGTCGAAG CTCGTCAAG   100440
CCAGACTGGG GATTGGGTCA AACATAAACC TTACACCAGA CGGAAGGATT ACATGCAAAT   100500
GAAGGATGCA GATTCTGATT TCCCATTGGG TATTTGACAT TAGCCAATGG GAGAATTCCT   100560
CACAGCCTAC CTCCAGTCAG TATAAATACT TCTCTGCCTT GCGTTCTAAT GTAGTTTCAT   100620
TACATTTTCT TGTGGCGATT TTCCCTTATC AGAAGTAGTT ATGTCTGGTC GCGGCAAACA   100680
AGGCGGTAAA GCTCGCGCCA AGGCTAAGAC TCGGTCTTCT CGTGCAGGTT TGCAGTTTCC   100740
TGTGGGCCGA GTGCACCGCC TGCTCCGCAA AGGCAACTAC TCCGAGCGCG TCGGGCTGG   100800
CGCGCCGGTG TATCTCGCGG CGGTGCTTGA GTACCTGACC GCCGAGATCC TGGAGCTGGC   100860
GGGCAATGCG GCCCGCGACA CAAGAAGAC CCGCATCATC CCGCGCCACC TGCAATTGGC   100920
CATCCGCAAT GACGAGGAGC TTAATAAACT CTTGGGGCGT GTGACCATCG CGCAGGGTGG   100980
CGTTTTGCCT AATATTCAGG CGGTGCTGCT GCCTAAGAAA ACTGAGAGCC ATCATAAGGC   101040
CAAGGGAAAG TGAAGAGTTA ACGCTTCATG CACTGCTGTT TTTCTGTCAG CAGACAAAAT   101100
CAGCCTAACA GCAAAGGCTC TTTTCAGAGC CACCTACGAC TTCCATTAAA TGAGCTGTTG   101160
TGCTTTGGAT TATGCCGCCC ATAAAGATGT TTTTGAGGTG TTTTTAATGG CTTTGAGTGT   101220
GGCACTTTTA GTAATTTGTC CTGCAGAAAT TAGATCCATA GAAACCTCAG GAATTCTAGG   101280
TATGTGGGAG AAGTGCCATG CAGCACAAAA CATGTTTACA GGGGTGATTC GCGTTAAGTT   101340
TCACACACAG CAGTTACTAC ATTTTAGAGG AAGGAAATTA TACCCATGAG TGCATTCCTA   101400
ACTATCTTGA ATGGAAGTGT TAAAACCCGC ATGCCCCACA CAAGTTTGAA TATGTCATAC   101460
CATTTGCTGT AGCAATTAAT GGCATACACA ATTGAGAGCA CACACATTAC CACTGAACAT   101520
TTGAGTATGT ATTTCCCAAA ATGAGCTTTT TTCCAGTTTG GGGATGTTTT GCTTTGTTTT   101580
GGGGTGGAGT CTCCCTCTCG CCCAAGCTGC AGTGCAGCGG CGTGATAACA GCTCACTGTA   101640
ACCTCGAACT CGGGCTCAAG CGATCCTCTT GACAGCCTTC TGAGTAGCTG GGATTACAGG   101700
CGAGAGCCGC CACGCCCGGC TAAGAGCATT TTTCTAATTG CCCACACTTC TTATGCGACA   101760
CCCAGAAAAA TACAATTTTA AATAAAGCGC ATATGCAAAT TTCCCTAATC GTCTCCAATA   101820
TTCTCTGATT TCTTTTTTAT ATTTTAACTA GAAACAATTG GAGGTTTCCG CGTTGCTTTG   101880
TGTGGTTGTA AATTTTAAGA CTTCAGGAAA CTTTTCCAGT ACAAGACTTG TCCACAGTGG   101940
ATATAGCAGC TAAGGGGTTA ACAAAATGAC GTCAGAGTAG CTACGGTAAT GGGCAGGAGC   102000
CTCTCTTAAT CTGCAACCAG GCACAGAGAT GGACCAATCC AAGAAGGGCG CGGGGATTTT   102060
TGAATTTTCT TGGGTCCAAT AGTTGGTGGT CTGACTCTAT AAAAGAAGAG TAGCTCTTTC   102120
CTTTCCTCCA CAGACGTCTC TGCAGGCAAG CTTTTCTGTG GTTTTGCCAT GGCTCGTACT   102180
AAACAGACAG CTCGGAAATC CACCGGCGGT AAAGCGCCAC GCAAGCAGCT GGCTACCAAG   102240
```

```
GCTGCTCGCA AGAGCGCGCC GGCTACCGGC GGCGTGAAAA AGCCTCACCG TTACCGCCCG   102300
GGCACTGTGG CTCTGCGCGA GATCCGCCGC TACCAAAAGT CGACCGAGTT GCTGATTCGG   102360
AAGCTGCCGT TCCAGCGCCT GGTGCGAGAA ATCGCCCAAG ACTTCAAGAC CGATCTTCGC   102420
TTCCAGAGCT CTGCGGTGAT GGCGCTGCAG GAGGCTTGTG AGGCCTACTT GGTAGGGCTC   102480
TTTGAGGACA CAAACCTTTG CGCCATCCAT GCTAAGCGAG TGACTATTAT GCCCAAAGAC   102540
ATCCAGCTCG CTCGCCGCAT TCGCGGAGAA AGAGCGTAAA TGTAAAGTCA CTTTTTCATC   102600
AGTCTTAAAA CCCAAAGGCT CTTTTCAGAG CCACCCACTT ATTCCAACGA AAGTAGCTGT   102660
GATAATTTTT TGTTGTCTTA ACAGAACAAA TTTCTAAGGA CCCCCCCGGA AAGCATTAGA   102720
CTATGGTCTT AAAGTTGATT AACAGAAATA ACGGTTTGGT CAGTCTTGCA GTGTAGGTTA   102780
TTTCTGACCT TATTAAGGTG CTATTTGGAG AGAAGCTGTG TAAGTCCACT ATCATTCAGG   102840
CCTCTAGCTT GCTATGATTA GCATTTGTTT AAACAACTTT GTAAGAGTAA GGGAAAAATC   102900
TGGTAAGTAG TTAACTGGCG CTTACTAGGC ATTTTTGCAA AGCTTTGAAA AGATTAGAAA   102960
ATTGTGTCTT GCGAGTTCCA GTGTCTTCCT CAAAATGCTT AGGAAGATTT TCTCAGCTCA   103020
ATACATAGTC CCCTAGGTTT TCTCATATAT TATATATATA TATATATATA TATATACTGT   103080
TAAATTCATT TGGCTGTTAA CATTAACCTG AAATTTATTC TGGTGCAAAA TGTGAGGCAG   103140
GGATCTAACT GGCTCTCATT TTATCCATAG CTAGCTACCC ACTTTAAATC TGTCAGTCTG   103200
TCGACCAAGC ATAATTTAAT CCCTTATATA TGAATTTTTA TATGTGTGGC TTTGCTTGTA   103260
AATAGTCTAT CTGGTTGCAT TGCTTTGTCT CCTCTAGGAC TATGCACCAT GACATGCCAC   103320
ATTCTTTTTT TCAGTACTTC TTGCCTGTAG TTATTAAAAT CTAGAATTTA CAAGTTTTAA   103380
CCATTTTCTT TCTGTTGATC TTGCTTTTCG GTTTTGGAGG TTGGGATTG AGTACTGAA    103440
GAAAATTTAG AGGGATGGGA ATACTGTACG CAAACAAAAG TAATATTTAC TTTAAAATTT   103500
TTATATTTTG TATTTTTTTA TCATATAGCT TTTACATCAC ATTTTACAGA CTAACTTTAG   103560
AACAACCACA GAATGTCCAA CATTAAAACT ACTAATTCCA AAGACCTTGC CTCACATTCT   103620
TTTTTACAAT AAATATTTTT TACACCTAAC ATTCTTTCTT GGCCTACATC TAGAATGTAA   103680
ACTGATGTAC CATACTAAAA TCGCCTGACC AACTGTCAAC AACAACAAAT CACACACACA   103740
AAAGATTAAA TTTGAATTGC ATCGTTTACT TAAATTCATT TGTGTTCCAG CTTTTAATAA   103800
GGCAGTTTTT GGTTTATAAA GTAATATTTG CATTTTAAAA ATTATGAAAA TGAATATGTC   103860
AGTTTGTTTT ATGATTCGTT TTTCTTGACT CTTATACAAG CGACTCTAAC TGGCATAGAC   103920
ATTTGTTATC CACAGACAGT ATAGATATGT TAGAGATGCC AATGGACTTG GTCTATGCCA   103980
AGGTGACTAC TCACAAGCTC TGGGCCCAGC TGAAGGTCAA GTATTTTTTT TCCAGTTATA   104040
GATGTGCTGG ATCTGATGTA TAGCGCTTGA CTTTTTATAT TTTCTTTATC TGTAGGAAAC   104100
AAATGTGTTG GAGGTACTGG GTCTGACGAA TAGCATAAAA GAATAAAGTT ACATTACTGT   104160
CTGAGGATCA GATGGACAGG GGGTGGTAGC TCAGTCCAGC TATTTTCCAC TCCCTCACTT   104220
ACATTCTTTG CCCCCTCCTC AACAGAACAA GGATTCTGCT GTAACTCTTC ATTGACAGTT   104280
GATATTTAAA AATTAACGAA TGGATGAAAT TCTCATTTGT GAAAGAAAAT TTATTGCA    104340
TTTTGTATTT GTGAGTAGTG CAAACATTTT AATATTATAT TAAGAATCTA TTGTTTTGTA   104400
TTAGAGGAGT AATTAAGGAG AGATTGGAGA CAAAAGGGG GTGTTGTTTG CAGAATATAC    104460
CATCCAAAAA TAGACCACTG TGGGATCAGG ATTCTTTTGA GCTAAAGGCA CTTCAAAAC    104520
AGCATTCAAG AAGGGAATTC TTCTAAACTT TTCTTTCTGA AAACAGGAGA TAAAAGTTCC   104580
AATGTGAAAA ATGCTCTGCT TGTACCAGGT GAAAAGACAT ATTCTTCAGC CCAGAGGCAT   104640
```

-continued

```
AGATGAGATA ATTCTGCACA AACACAGCAG GGAGTCATAG CCGAGAGACT TCTATACACA 104700

AACAAACCTT GTTAAAATAA TCATATATTC CTTTAATCTC CTCATATGGT TTACTTTCCC 104760

ACAATTGCCT CTCTTTAACT TAATGTGAAA GCATTTAGCT TTTGCCATTT CTTTGGGGCT 104820

TCACTTTTTT ATGAGGGTTC TCCTGTCCCA TAAAATTTAC ATTAAATACA TTTGTATGCT 104880

TTCATTCTGC TAATCTGTTT TATGGCAAAT GAATTATCAG GTCCAGCTGG AGACCCTAAC 104940

AGAGTAGAGG TAAAATTTTG CCTCCCTACA AGATAGAGAT TGTGTGCATT AAATGTTGTT 105000

TGTTCCCAGT TGTTCAGTTT GTCAGGCCTC TGAGCCGAAG CTAAGCCATC ATATCCCCTG 105060

TGAACTGCAC GTATGCCTCT AGATGGCCTG AAGTAACTGA AGAAACACAA AAGAAGTGAA 105120

AATGCCCTGT TCCTGCCTTA ACTGATGACA TTACCTTGTG AAATTCCTTC TCCTGGCTCA 105180

TCCTGACTCA AAAGCTCCCC CACTGAGCAC CTTGTGACCC CCACCCCTGC CAGCCAGAGA 105240

ACAACCCCCT TTGACTGTAA TTTTCCACTA TCTACCCAAA TCTTATAAAA CGGACCCACC 105300

CCATCTCCCT TCGCTGACTC TTTTCGGACT CAGCCCGCCT GCACCCAGGT AGAATAAACA 105360

GCCTTGTTGC TCACACAAAC CCTGTTTGAT GGTCTCTTCA CACGGACGCG CCTGAAACAG 105420

TTTAACAGGG TTTTTCCTGC CCAGTCACAA CAAAGTGATG TTATGCTGCA GGCTGAAGTT 105480

TACAGCTAAT GCTGTTGAAG TCTAAAATCA GTTTTGGTTT GTTAGATTTG GGTGAGATGG 105540

CTAAGATTCT CAGAGAAAGA AGTCAAGTTT GGGGTGCATT TTTCAGACTT AAAAATTTAG 105600

CAGTAGCCCT TGCAGTTTTT CCAATAGAAG TGATTTAAGA ATGTTTTCAG GAAATTTAAA 105660

ACAACAGTGA GAAGCGTGTA TGGAGAGTTG AACTACACTC CAGACTTGGC TATAGGAAAG 105720

CACGAATGCT GCTATTGTAT TGCACCTTGG AAAAGAGAAC AAAGGAATAT TTCGGACAA 105780

TTTTAACATG TCACATATGA AAAGCTAAAC GGAATCTGTC AACACCTTGT ACGTTATTAC 105840

AGGCTGTGAT TTTAAAAAAA CAATCCTTAC TAATACATAC ATAGTTGCTG CTAGCAATAT 105900

AGTGTTGGGA GTAAAACAC GAAAATGAGA GTTCAGGACA ATATCCCAAC TCTGAGCAGA 105960

TTTTTTTAAG TAGTAACATC TAAAATTAAA CCATATTATG TAATATTTAT TTCTTTTCCA 106020

CAGTCTCTTC TCATGCCTCG TTCACATTAG CTAATTAAAA GTCCCCTGAG TATCATCATA 106080

ACCCGATTTA CAGATGAAGG CACGGTTGCA ATGAGCTATC ACCCTCTTCT GAATGAGACA 106140

GTACAGTGTG AAGGATAGCA AAACTCCACT CCCATCCTCT TAGGGCTCTG GCTGGACCAG 106200

CAAATTAAAT TAATGTAAAA TGGATTAACA GGAGAAAGGT ATATGCATTT ATTTAACACA 106260

GGTTTTACGT GACACAGGTG CTCTCATAAG GTAATGAAAG CCCAAAAAAA GCAGTTAGCT 106320

ACTTATATAA TGAATTGGAC AATTAGTAAA ATGTAAAAAT GCGCTAAAGC AAAGGGATTT 106380

AGGCTAGAAT ATATAACTGT GTAGAGAAGC GCCCAGCAAG GGCTAGTGCA AGGTTTGTAC 106440

AGAATTCTCT TGGCCTCAGC CTCCTATCCT TGAGAAGAAT GTTGCTTTTT TTAAACTACA 106500

GTGAGAACAT CTTTCATATG AGAATTTCAC CTACTGCTTC TAAGAAACAG GTCAGCTTTC 106560

AAGAAAACAT AAGGCCAGAG TGATCTTTTC ACGCCTGCTC TTTTAAGTAC CTTTGAATAG 106620

TCAATATGTC TTCAAGCACT TGAAAGACTT AAAAAGTTTA CCACTCCGGC ATATTAGTGA 106680

AAGCCCTTAA TATAAGCCCT TATTAAAATT CTCAGTCGAG GGTATAAATT CAGATTCAAA 106740

TAGTAGTGTC GTAAACGGGA GGGAAAAACT AAAGGGATTA AAAAGTGAAA CTATTGTGTT 106800

CTCCCTCGCA GTCCTTAGGT CACTGCCCCT CGAGGGGCGG AGCAAAAAGT GAGGCAGCAA 106860

CGCCTCCTTA TCCTCGCTCC CGCTTTCAGT TCTCAATAAG GTCCGATGTT CGTGTATAAA 106920

TGCTCGTGGC TTGCTTTCTT TTCGCGTACC TGGTTTTTGT TGTCAGCTGG TTAGACATGT 106980
```

```
CTGGTCGCGG CAAAGGCGGT AAAGGTTTGG GTAAGGGAGG TGCCAAGCGT CACCGAAAAG    107040

TGCTGCGGGA TAACATCCAA GGCATCACCA AACCGGCCAT TCGGCGCCTT GCTAGGCGTG    107100

GTGGGGTTAA GCGAATTTCC GGTTTGATTT ATGAGGAGAC TCGTGGCGTT CTCAAGGTGT    107160

TTCTGGAGAA CGTGATCCGG GACGCCGTGA CCTACACGGA GCACGCCAAG CGCAAGACTG    107220

TCACTGCCAT GGATGTGGTT TACGCGCTCA AGCGTCAAGG ACGCACTCTG TACGGCTTCG    107280

GCGGTTAATC TTTTCGTCAG TTTTCTTCCA ATGGCCCTTT TCAGGGCCGC CCACTCCCTC    107340

TCAGAAAGAG CTGTGATTGT ATTCTTTCGG ATGGTAACAT CTCAATGGCT TTACTCGGCT    107400

ATTCTGCCTA GTATGTAGAA CTATTATAAA CCAGTTGGGA GAGACCAGGT TGTTTGGTCT    107460

GAGTGGCTGC TAAAGCAGAA ATCAGCTAAG TAAACGAGGT CTCCGAGATA AGTGAGCTAT    107520

AAACTTCAAT GCTATAGTTT TGACATGTCA AGCAACTTAA CGTGCAGCGC GAGTCCGATA    107580

AATGAGTAGC TCAGCTTTTT AGTTTTAAAA ACGAGTTGTG CGTTATTTGT ACGAGAGCCT    107640

AAGATGCTAG CTGCCTGGAA CTGAGTAGGT GGATTAAAAT GGGTGTCAGG TCTGTTTTCC    107700

CAGGCGTATC TGACTTAACG TCAGCAAAAG CTGTACTTTT AGCTTCCCTG GTAACACCTG    107760

CCGTCCTTAA CCGCCCCCTG CCGGTAGCGC CAGAAGCCTT TACTTCCATT TCTAGTTGAG    107820

CTTGGCGTCC TGCTGAGTGA CGTCACCTCC CCCTTCTCTG GAGTAGGACT GGCGGTTAAA    107880

GCTGCTTTGC TATTTTCAGT CCTCAGGCTG GAGGCTCCCC TAAGCAGGCT GCCTACGCAG    107940

TTCGTAAATT CCCACTTAGT AGACTAAGGG AGTCTGTTTT ATAAATAAGG ACTCAAATTT    108000

CTTCTGACTC CGAGGTCCGT GGCAGCAGCT ATAAGATGGA AGCCCCCTCT GATGTAAGAT    108060

TCTCAGATGA CTTGCATCTT CACTGTACCT GTCAACCCAA TAGTCTTCTA TTCCTGCCTT    108120

AAATTGTAAA TTCCAAAACT GATTTAATTG TGAAAGTTTC AAACTGTACG ACCTAGGAAG    108180

TGTCAAAGTT AGGTGACCAG ATTTTTAGAA GTCAGCCAAA TATTCAGCAT CTTTGATTTA    108240

GTAACAAATA TATTGATGGC TACTTCAGCA AAAAAAATCA ACTTTGTTTT CTGGTTACTT    108300

TGCTAACAAG CTTCTCCTGA CAGGAGGATA TAGTGAATAG GCAGTTGAAT AAGTGAGTTC    108360

GGGTGAGAGG TCTGAGCTGG AGATAAAAAT GTGTGAGTCA TCAGCAGATA AATAAATGCT    108420

GAGACCAGAT GAGATGGCTA AAAACTGAAA CATAATGTAG TGCAGCATTG TTTGTAATAG    108480

TAAATGAGTG GCAACTGTAA AGTTTTCATC AGAAAGGACT AGAGTGATCT ATACATCCAT    108540

AAAATAGAGT ATTTCTCTAC ACAGCCCTAC TAAAGAATGA GAAAGCTGTA CTCCACTACA    108600

TACTCTGGTG TACTCTGGCT CAGTTCTTGG ACTCCTCTTT TCTTGGCTAA CTCAACTGGC    108660

CTCACCACTT ACATGCTCTG TGCTCTGTCA AATAGTTTGT TCAACAGAAC ACCACGGCCT    108720

AGCTGTAAGT GCCACGTTAA CTTCTAGCAA TGCCAAAGCC TGTGATAGTG GCAGCTTCGG    108780

GCTGTTTCTC ATTCCCGGGA TGCCTAACCA CCTCTCCAAA TTCTATCAGT TTGCTTCCAC    108840

CCACTTCAAG CTTCAGAACG AAACATAGAG CTTAAGAAAT ATAGGCCCGG CAAGGTGGCT    108900

CACGCCTGTA ATCCCGGCAC TTTGGAAAGC TGAGCCTGGT GGATCACCTG GGTCAGGGG    108960

TTCGAGACCA GCCTGGCCAA TATTGTGAAA CCCCGTCTCT ACTAAAAAAA AAAAAAAAT    109020

TAGCTGGGCA TGGTTGCGGG CGACTGTAAT CCAAGCTACT CGGGAGGGTG AGACAGGAGA    109080

ATAGCTTGAA CTCGGGAGGC AGAAGTTGCA GTGAGTTGAG ATCGCGCTAT TACACTTAGG    109140

CCTGGGAGAC AAGAGTGAAA CTGTGTCTCT AAATAAGTGT TTGCAATTAT AAACCATCTC    109200

CCTGACCTTA AATCTCTAGA CTCATATACA ACTGCATATT TGATGTATCT AATTGAATAA    109260

TGGGCATCTC GAACTTGTCC AAAATATGTT TATACGTAAA CACCAAGTCT GTTCTTCCTC    109320

TGATATTTGT CATGTCAATC AATAGAACTC CATTCTTCAA GCAGCTTGGG CCAGGAATTG    109380
```

```
TGCAATATTG TTTGTCCTGA GCTTCTTACA ACTTTCACCC AATGCAGTCA GCTCTGTTGA    109440
AAATCAATCA GAATACCTTT CATTGTTTTC TTTGCTGCTT CTCTAGGAGC AAGCTGCCAT    109500
GGCGGTTTGT CTGAATGACC ACAGTGACCC CAAACTGGTC TTTGTTTTCA CTTTTAATCC    109560
CCCTGTCATA CAGTTTTTTC TCTATCCAGC ATCAACAGTG ATCCTTTTTG AAGGTATTAT    109620
GTCCACTGTC TGCTGAAAAG ATTCCACTGG CTTTCCATCA CCTTCATAAT AAAACCAGC     109680
ATCCTTATCA TAGCCTACAA GTAAGATGAC CAACCATTAC AGTTTGCCTG ACTCTCAGGG    109740
GTTTCTCAGG GTGTAAGACT TACAGTGCTG AAACTTAGAA AGTTCCAAGC AAACTAGGAT    109800
GAGCTGCTCA ACCTACTAGA TCTGTACTCT GGCTACCCTC TGACCTCATT CTCTTCGCAG    109860
TTCTTTCTCT TCACTGACCT TGCTGTTTCT GGAATGGACC AAGCATTTCC AGCATCAGCA    109920
CCTTTATATC TATTCTTTCT CCCTAGAAGG GTCTTGTCCT GGATATCTGA ATGGCTCTAG    109980
ATCTCATTTC ATTCAAGCCT CTCCTCAAAT ACCAACCTTA CGAAAGAGAC CTCCCATAAT    110040
CATCCCTTGT AAAATAAGCT TTTCTGCTCA TTTAGCATAT ATATATATAG TTGACTATCC    110100
TCAATAGCAT ATATATATAA CATTTCCCCA CCTAGAATTA TATATGTAAT AATATATTTA    110160
ACAAAAAATA CATATAACTA GATATATTTT ATTTTGTGTT TGTTCTCTCT CCCCCAACTG    110220
GAATATATTT TTTGAAGGTA GGGACTTTGT TTTGTCCCAG AAGTATCCCT AGCACCTTGA    110280
ACAGGGCTGA CGTTTAACAG GTAGTTTATG GAGGTTTGTT GAATGAAAGG ATGTGTGAAT    110340
TTTCTATGTA AGTCTCCAGG CTCTCCACTA AGCCCACCAG AATGCTAACA CAATCAATTC    110400
CCCATCTCAT TCCTTGACCT GCCACTGCCT GAAGCAATCA GCGTGCAGTT TCTCTTTAGA    110460
AAATCTGGGG GATAGTCTAG GGGTTGCAAA TTAAGCAACA TTATCTTTGT TCTGAACAAG    110520
GACTGCATGA GTGTTAGGAC TGAAGAAGGC CCAAGGTGGT GGTGGGTATG CCTAAGATGA    110580
GTATGACATA TCAGCAATGC TATGAACATA GCAATGCTAT GAAAGGCCAG GCAAAACGTA    110640
ACAGGAGCTA GTCGTGGCTT ATTGTTACAA CGACTATACC TCCCATATGG GTAATCGATA    110700
TCCACACACC CCTCTACATT GACTCTGGAA TTCAGGAAAG GGAATTAAAA TTTTCTAACT    110760
TATGTACCCC AATGATTTCA ACAATATCTG GCATATGAGA TCAATAAATA TCTTTAAAAT    110820
ACCAACTAAG AAAGACATAA AATGACCCAC CCTCCATACC AGGCTCATTT TGCTCCTCT    110880
GATTCCTGAA ACTATCCAGA ATGCAGCTAT GAATTCTCTC CATTGTCAGT TTTAAATTAA    110940
GCCAAGCTGG GTACTTGTGT AATTCCTCAA GAAATCCTGG ATGAAAACTG TCAGGTGGAA    111000
AACAGGACCT CAAAATAAAG AGACATCCAT CACTGAAGCT AACATCGTGA GGCTGAAATC    111060
AGTCCTATAA CAATGGTACC AAAAAGAGCA CAATGAGAGG CATTTGTGAA TATTTACTCA    111120
GATGAGAGTA AGATATTTCC CTATCAGCTA ACCTGAAGTT CACATCCCTT TTCCAGCTGA    111180
GTTCTGAAGC TAGATGTACT TAACTGGAAC ACATAACTGC ATCAGGAACA TCCTTTAAAA    111240
CTATGGCTAC CATGGCTTGA CTGGACAAAC CCCAGGCTTC CAGGTTTAGC ACAGGTGGCC    111300
CTTCACAGAC CAACATTGCC TATGCTACCA ACCTCATGTC CTACCACCCT GCTTGCATCA    111360
TTTCTCTCTC TGCATATATA AAAATATATG TGTATGTATA TAATCAGCTT TATTGATATT    111420
TAATGTACCA CAAAATTTGC CCACTTTAGG TACAGTTCAA TGAATTTTAC CGTGTTTTCT    111480
TAGTTGTACA ACCATCATCA CAATTTAATT TCGGAATATT TCTATCACCC AAATTTCCAT    111540
TTCTGCGTAA AGGGGAAAA AAAAAGGTTA ACTGCTGAAG GCCGCGGTAA CACTGAAAAA    111600
GGTGCCTTTT CTCTCTAAAA CAGATTTTAA TCTCCCCTGA ATTTAGTGTC CTGGGTATTC    111660
CAGGAGTCTG AATAGGGTTT CAATTTTCAG GGTCTTTTTA ATAGAGTAAA ACTGTATTGG    111720
```

```
TGGCGATAAA TTTAGTATTG CTCTCAGTAC ATGATTGAGG GATACTTAAA TGTCTCTGTG 111780

ATTTTATTTC ATAATCGCTA AAAGATGGTT TTTTTTTTTC CTAAAACAGG GTTTTTGTTT 111840

TTTCTCAATA AGCTTCTTAG CTTCCCCTCC GGCTCCCTGG CTTGCCTCAG GAAATATTAG 111900

CTCATCAGTT CTGATTGGTT GACAGCTACG AATGGCCCTC ATTGATTGGG CAGCGCTTCT 111960

TTGTCCCTTG GAAACTAATA CAAATTTTTA ACACTACTTT TTTTCCACTC TTTCTTCAGA 112020

GTTGGAATAT CGTTGCTCCC CTACCCATAT GTAGTGAGTG GAGGGCAAAC TTGGAGTTCC 112080

CCTAATCTTT CCTTTTTAGG ATGTCAGCTC AGTATCATTC ATCTTAATTA CACATTGAGC 112140

TTCTTGACTT AATGGATACA GCTCTTCTTT TGTTTAGTTG GGCGGCCCTG AAAAGGGCCT 112200

TTGGTTCAGA AATGCAAGCT GTGGAGAAAT CAGCAACCTT AACCGCCAAA GCCATAAAGG 112260

GTGCGTCCCT GGCGCTTAAG CGCGTAGACC ACGTCCATGG CAGTGACTGT CTTGCGCTTG 112320

GCGTGCTCCG TATAGGTGAC AGCGTCACGG ATCACGTTCT CCAAAAACAC CTTGAGCACC 112380

CCGCGAGTCT CCTCGTAGAT CAGACCGAG ATCCGCTTCA CACCGCCACG CCGGGCCAGA 112440

CGCCGGATGG CCGGCTTGGT GATGCCCTGG ATGTTGTCAC GCAACACCTT GCGGTGGCGC 112500

TTGGCACCCC CCTTACCCAA ACCCTTCCCG CCCTTACCAC GTCCAGACAT GACTTCCCAA 112560

GAAGTGAACC AAGAGCAAGT GAGAGAATAG GAAACCGATC TTTATATATC TACGTTACCC 112620

CTGCCCCCAC CTCCAGCGGA CACTGAGACT GAAAAGCGCG CAGGCGGGAA ATGTGACGCC 112680

TACAGTCCGC TCCTTTAACC CCTCCTCCAA GCCCCAGGAA ATGGCGGGAG CAGCGATTGG 112740

GGGAGGGTGG GGAGATGAGG GTGGGACCAA GCAGGCTTGA CCAATGGCCT TTATTTTCTT 112800

AACAGAGCTA CAGGCTTTGA GGAACTGGGT TAAGAATTAA ATGTAAACCC ATTCTGACTC 112860

CAGAATTATT TTAAGTCGAA CTTTTTTTTT AACCGAATCT CTCTGTCGCC CAGACTGGAG 112920

TACATTAGAG CCATCTCGAT TCACTGAAAC CTCTGCCTCT CAGGTTCAAG TGTTTCTCCT 112980

GCCTCAGCCT TCAGAGTGTA GCTGGGATTA CAAGCGCTCG CCGTCGCGCC CGGCGTGTTT 113040

TTGTATTTTT CGTAGAGACG GGATTCGGCC ATGTTGGCCA GGCTGATCCC GAACTCCTGA 113100

TTTCTGGTAA TCCGCCCGCC TCAGCCTCTC AAAGTGCTTG AATTACAGGC GTGAGTCACC 113160

GCGACCGGCC GAAATCGATT GGTTTTGAAG CCTTCAGTAG CATTAAAACG AAAAGTGCTC 113220

CCAATGCATT CCCTTTTGTC TTAAATTGGT TTCTTACAGC TACTTTACTT GAAAAGGTGG 113280

TGGCTCTGAA AAGAGCCTTT GCTTGGACCG TCAGAGAGAC CACAGTAATC ACGCCCTCTC 113340

TCCGCGGATG CGGCGGGCGA GCTGGATGTC CTTGGGCATG ATAGTGACGC GCTTGGCGTG 113400

GATGGCGCAC AGGTTAGTGT CCTCAAATAG CCCTACCAAG TAGGCCTCGC ACGCCTCCTG 113460

CAGAGCCATC ACAGCGGAGC TCTGGAAACG CAGGTCTGTT TTAAAGTCCT GCGCAATCTC 113520

GCGCACCAGG CGCTGGAAAG GTAGTTTACG AATAAGCAGT TCAGTGGACT TCTGATAACG 113580

GCGGATCTCG CGCAGAGCCA CGGTGCCCGG CCGGTAGCGG TGGGGCTTTT TCACGCCGCC 113640

GGTGGCCGGA GCGCTTTTGC GGGCTGCCTT AGTGGCCAAC TGTTTGCGTG GCGCCTTGCC 113700

ACCAGTAGAC TTCCGAGCAG TTTGCTTAGT GCGAGCCATG ACGGAAAAAC AGCACAGCGG 113760

AACACCCAAC ACTAGCGCAA ATACGCCCAT GAGCTGCTCT ATTTATAGTG TGTAAAGTGC 113820

AGTGATTGGA TGATAGAAGA CGCTAAATAT GACGTTACAC ACTCTGATTG GTCTATCTTT 113880

AAGCCAGCAA CAATCGTGCA GTTTCACCGG CTACATATT CTATTCCAAC TCTACAGATG 113940

ATTATTTAAG TGGTATTTTA TTACTACTAT TATTTTATTT TACTTTTGCT TGTTCCCCA 114000

AGCTGGTCTT AAACTTGGGC TCAAAGGATC TTCCCGCCTC AGCATCCAGA GTAGCTGGGA 114060

TTACAGGGGA GCCCCACTGC GCCGGCTTGG ACTTTAATTT TTTAAACTTG TCCTCTTCTA 114120
```

```
CATCTGGTTT TCATAACCTG AAGGCTGTGT TTATTTTCCA TAAAACAAGG CATTGATTCC    114180

AAAGGTATTA TAATTCCCCA ATTCCGTATA ACCTTCAGCT CTTTAGGAAA AAAAAAAAA     114240

AAAAAAAAAA GAGGGAATAC TGCTCACCTC CTCTCCGGAA ATGTACCCTT TACGGGAATT    114300

TCTGAAACCT TTCACAAGAA TTGGATTCCT TTGTAATGCT TTAATTGACT TAGGAGTGTT    114360

ATTGAAATCT ACAAAGCATC TCAAACATAG TAGGATTACA CTATTACTCA GAAACATTTT    114420

CTATGAGACG TCTTTCTCTT GATTATGCTC TTTGAATCCT AAACTTGCAG CGTTCTGCAG    114480

CTTTTGTTTT CTAAAGCCTA GGTGTACTCT GCCAGTCACA AAATGGCGTT TCTCCAGCAC    114540

TGCCGCCAGG TACCACCAGC TGGGAGTTGT TCCTCTTGCG GAGCAGGAGG TGGACTTGGC    114600

CCAAGAGAAA CTGGATAGTG GTTCGCAAGG AACATAATTT AGCATTGCCA AGAGCTAATG    114660

CAATCATTTT GAAAATCTCA AAACACTGAA AAGTGGATTG TGACCTTTTT AAATTCACAA    114720

GAGACAGGCC ACATTCTATC TTTTGATTGG TTTAGGCTAT TTTCTTGAAC AGCCATTTAG    114780

AAAGCAGATC TATCATCCTT CATTTGCATG GAGCGTTCCC ATTTTATTTG AAACCAGTTT    114840

AACCCAATAG AAAAAAGGGA GGCAGAACCC ATTATTTAAA GTGGAAACTC CTGAATCAGA    114900

TAATTAGGAG TATTTCCTTT TCAAAAGTTG CGTTTTTTCA GATACCTCGC TTATTACACT    114960

AAGAAAGGTT TATATCTTTC ACAAAGGGTT TACTTACAAA AATCTTCCAA TTTTGTATAC    115020

CTGTGTTTCA TAACTGACTA GCCGTCAAAC CAAGATGTAG AGTTTCCAAC CGTTATTTTC    115080

CAAATTTTTA GAAATTACGT GAAATATTTG AATGCATGCC TTCTAATAA ATGGGACGT     115140

AGGAAGCACT GGTGCAGAAG ATGGGTACAA TACTTATCTG GGACCACTCC ATTATTTGGT    115200

TGGCACGTTG TTTGAACAAA AAGGGGAAAA GCTCAGGTTA CTTAGCATGG TTCGGACTTA    115260

TTTGAAAACT ACCACAGCAG GAGCGGAAAT AAGACCGCAT TACCTCACTC TCTGCTGTGC    115320

TGTGCTAGGG GGTTATCCAG AATAGGATTG TAGAAGTGGA TGTCGATTTA ATAGTTTTTT    115380

ATTCTCCCAT TAGCTGAGTC TCTGATTGGC AATGTGAGAT CGTTTTAGCT TATTGATACT    115440

TTGAAATGCA CTTAACAGCC ACAAACAAGT TAAAGGGTTG TTACCATAAA ATCTTATCCC    115500

CAGGGTGTGC TTGCATTTAT CACCCGTGTT TGCTTTCACA CTAAGTGGAC TTAACTCCCC    115560

AGCAGAATGC CTGTCAGGGA ACCGGTTTCG TGGACCCAGC ATTTAACGCC TTTCGCAGGC    115620

TTGTGAGGCC CATAAATATT TGTTGAATAA AGAATGAGT TGACCATGTC ATGGTGCGCT     115680

GATTGCGTGT GCTGACATGG AACACAGGTT GTAAACCTTA ATACCAATTT GGGGCATGTT    115740

GTATGGATGA AAAGGGCATT GGAAATTCCT GAAGTGCATC CCACATTGGA CTGTGGAAAT    115800

AAGTTGCAAG TGCAGAAACG TTTCCACACT TGCAGTTTGA GTATTAATTG CAGCGTTTGT    115860

GAATTCTGGT GTTGTCTACG ATTCATTCTT GTTTGACGTG AAAGGTATTC GCAGACACA     115920

TCGCTCTAAA ACATTGCCAG AAAATGTAAT AGAGTTGATG ACAACTGGCC CTAACACGGC    115980

CTAAAACTCG CACTTTTCTC TCCCTCCGCA ACTATTCAAA ACACTGTATT TTACATTTCT    116040

TGCAAATTAA AAACTAACAT CTCTGGCAAC GGACCTCTAA AAATTTCTAA TAAAACTCCT    116100

CGGATGCTTG TGGCACTGCA TTTGTAAACC GCCCCCTCTC AACCTACTCC CTAAAAAGA     116160

GCTGCTTTTT GAGAGAGAAG CGGTACCCTC TGATGTTACT GGGCGGCAGT CTGCCTACAA    116220

TTTCCTTCAC AATGAGGCAA CCAGAGCGGC TTTTTCTGTG TGTTTGCTTG CGTTGAGGGG    116280

AGCAGGACCA TAGGCCCTAG AGGCCCCCAG CTGCCTTCTG AGACTGGGCG AAACCCTCGG    116340

CAGCGCGCAG GGGGCGCTAG GGCGCGAGGG GCGGGCACTG ACGGGCACCA ATCACGCGCG    116400

AGTCCCACCC TATAAATAGG CTGCGTTGGG GCCTTTTTTT CGCATCCTGC TTCGTCAGGT    116460
```

```
TTATACCACT TTATTTGGTG TGCTGTGTTA GTCACCATGT CTGAAACAGT GCCTCCCGCC 116520

CCCGCCGCTT CTGCTGCTCC TGAGAAACCT TTAGCTGGCA AGAAGGCAAA GAAACCTGCT 116580

AAGGCTGCAG CAGCCTCCAA GAAAAAACCC GCTGGCCCTT CCGTGTCAGA GCTGATCGTG 116640

CAGGCTGCTT CCTCCTCTAA GGAGCGTGGT GGTGTGTCGT TGGCAGCTCT TAAAAAGGCG 116700

CTGGCGGCCG CAGGCTACGA CGTGGAGAAG AACAACAGCC GCATTAAGCT GGGCATTAAG 116760

AGCCTGGTAA GCAAGGGAAC GTTGGTGCAG ACAAAGGGTA CCGGAGCCTC GGGTTCCTTC 116820

AAGCTCAACA AGAAGGCGTC CTCCGTGGAA ACCAAGCCCG GCGCCTCAAA GGTGGCTACA 116880

AAAACTAAGG CAACGGGTGC ATCTAAAAAG CTCAAAAAGG CCACGGGGGC TAGCAAAAAG 116940

AGCGTCAAGA CTCCGAAAAA GGCTAAAAAG CCTGCGGCAA CAAGGAAATC CTCCAAGAAT 117000

CCAAAAAAAC CCAAAACTGT AAAGCCCAAG AAAGTAGCTA AAAGCCCTGC TAAAGCTAAG 117060

GCTGTAAAAC CCAAGGCGGC CAAGGCTAGG GTGACGAAGC CAAAGACTGC CAAACCCAAG 117120

AAAGCGGCAC CCAAGAAAAA GTAAATTCAG TTAGAAGTTT CTTCTAGTAA CCCAACGGCT 117180

CTTTTAAGAG CCACCTACGC ATTTCAGGAA AAGAGCTGTA GTACACAGAT GAAATCCCCC 117240

AAGCAAATGC AACACGCCCT CAATTATATT AGAATCACTT GGAGAGTCGA TAGAACTTTA 117300

ACATAGCCTC ATCTAGTAAG AATTTACTAC TCAATCTATC AAAGATAGCA AGGTGAATTC 117360

AAATGCACCG AGTTAAAATC GAGTTTTAAA GTCACCTGGG TTTCGGTAGC CGGAAGTCCC 117420

GCGTCTCACG ACTCCAAGCT AATTAGTCAT AACCGTATTG AACCAAGGTT GAAGCCCAGT 117480

CCCAGGCTTG AGGCTTTTTA TTATACAAGG TTAAAGTGGG GATATTGCGT TTTGGGGTCA 117540

ATATTGCTAA AGTAGCATTT TCCGAAATTG GGTGGTCCTA AGAAATGCTT CTGGGATAGT 117600

TGGCAAAATA TATGGCTTAA CCACGCCCTC TCCACAGGAG TGGCTAGCGA GCTGTCTGTC 117660

CTTGGGAAGG ACGGTGACCC TGCTGGCGTG GCTGGCGCCC ACGTTGGCGT CCTCTGAAAG 117720

CCCCGCCAGG TAGGCCTAGC TCGCTTGCTT TCTGCAGCGC CATCATGACA AAGCTTTGAA 117780

ACGCAAAATG CTTTCTTTGT GCAGCGCCTT ACCATGGGTG CACTTACGGG CTGTCGACTT 117840

GGTTTAGGCC CTTGTCAGGA CAAAGGAGCT TAGTTTGTTG GAGTTTTAGA GCTGCAACCC 117900

AAAATCCCTT GCTCGGTTTC TCTGTTTTTA GAAACGGAAG CGCCCTGATT GGATATTTGA 117960

AAATTACTGT GCTTAACTGG ATCGTGTTTC ATCAGTCGTG CAGGATTTTC AACCCTGGTG 118020

GAGCCCACAC ATTCAAAACT GAAGATCCTT TTCTCAGAAC TGCCCCTTTA AGCTTTTGCA 118080

ATTTTAATTC TGGGGGTCAG ATTTTAATAA TTGGACTTTT TTGTTTACAT CTGACAAGAG 118140

TATATGATGA GCCAAGTTTA CTCACTTTTA CTTAGTGCAG TTCAATTCTA AAAGTTTATT 118200

TTTGCGTGTG TGCATATGAG TTAATAATCA GTTGTATTTT TCAAACGGTC TTTTTTCAAT 118260

TGTTTTGCTT AGCTCCTTCC ATCGTCTAAA GTCAGGGATA CAGGCACATC ACATCCCTGT 118320

TCCCCCTTCC TCAAACTAAT ATGTAGCTAC CTAGGTTTAT CCTTTAAAAC AAAAATTCTC 118380

ACCTATTTTT GTGAGAAATA TACATGTTTT TCTTTGAACT AAGTATTTTA CATACACCTA 118440

TCTATATACA TGCATACTTG TGGTTTTGTT TTTTAAAAA AAAAAAAAA AAAACACGTT 118500

ATCTTTTGAG ACTGGGTCTC AGTCTGTTGC CCAGACTGGA CTGCAGTGGC ATAATCACAG 118560

CACACTGTAA CCTCCAACTC CTGGGCTCAG GCTATCCTGC AGCCTCAGCA TCCGGAGTAG 118620

CTGGGATTGC ATGCACGCAC CACCAAGCCG GGCTTTTTGT TTTTATTTTT TGTGGAGACA 118680

GTCACACCAT GTTGTCCAAG CTGGTCTAGA AATGGCCTCA AGTGATCATC GACCTCCCAA 118740

AGTGTTGGGA TTACGGTCAC TGTGCCTGGC CTTGTATGCA TAATTGTTTT GTCTTTTGAT 118800

TAGGGTTATT AATTTAAAAA ACAAAGCCTG GACGCAGTGG CTCACATCTG TAATCCCAGC 118860
```

```
ACTTTAGGAA GCCAGATGGG CAGATTACTT GAGCTCAGGA GTTCAAGACC AGCCTGGGCA  118920

ACATGGTGAA ATCCCATCTT GACAAAAAAT ACAAAAAATT AGCAAGGCCC AGTGGCACGC  118980

ACTTATAGTC CCAGCTACTT GGGAGGCTGG GGTGGGAAGA TGACTGGAAC CTGGGAGGTA  119040

GAGGCTGCAG TGAGCAGAGA TCGTGCCACT GCACTCAAGC CTAGGTGACA GAATGAGACC  119100

CAGTCTCAAA ACAAAAATAA TAAAAATTTT TTACAACGAT GTTATATACA CTTCTGCATG  119160

TTGCTTTTCT CTTAACCAAA CTTTTCTAAA ACCCTGTCAT GAAAAAGAA ATCCTTCACA   119220

TGGAATAGCA TAAGTTATTC ATCCATTTCT TATTGATAAG CATTGATGTT TCCAGTTACC  119280

ACTGCTGAAC ATGGTGCAAT TGAATAGAAT TCCAGGGCTG AGATTGCTAG GTTTTAGGTT  119340

GTATTTATT ATTTTATTTA TTTATTTATT TATTTAGACA GAGTCTTACT CTGTCACCCA    119400

TGGTGGAGTA CAGTGCCATG ACCTCAGTTG CAACCTTTGC CTCCTGAGTT CAAGCGATTC  119460

TCATGCCTCT GGTCTCCCGA GTAGCTGGGA TTACAGGCAC CTGCCACCAG GCCTGGCTAA  119520

TTTTTGTATT TTTAGGAGAG ATGGGGTTTC ACCATGTTGG CCAGACTGGT CTCAAACTCC  119580

TGGCCTCAAG TGATCTGGCC ACCTCGGCCT CCCGAAGTGC TGGGATTACA GGTGTGAGCC  119640

ATGGCGCCAG ACCTGGACTT TGTCTTCTGT TTCATCAGTC CTTCTGTTGG TTCAAGCACA  119700

GTATCACACT GAAGACTGAT GATTCTATAT AAATATGGTA AAGACTGTAC ACCCTAACTG  119760

TTCTTATTTT TTAATTTTAA GGCAATTTTA GATTCCAGCT TTCCAAAGAA TTGTGGAATG  119820

CTTAGAGCTA GAGAAGCCTT GGAAGTCATT TAGTTTTTGT TTTGTCAGAG AAAATTCTGT  119880

AGAGACTCTG TCCTGCTCTC ACTGAATACC ATCCCATAGT ACCCCCCAAC AGCTTTAAAG  119940

GGCAATAATA CCTTATGGAC AGTATGCTTT TCCTCAAATA TATTCTAAGC CATGGTCAAT  120000

GCAAAAGAGT GAGAAGGAAA GTAGAATAAG TTATCTAAGA ATCAGTGGGT GCTCTCTTTA  120060

AACTGATTTA TCACTCCCCC TTCCAAACTC TCTTGAAGGT CACTCTGCCT CCCTTTCTAC  120120

ATAAGAACTC CTAACTCCAA GGGAGGAAGG TAAGTTATTC TTATTCCTTG CTTAGAAAAA  120180

GAGAAAATAG GTTTGGTAAG CATCCGCTTT CTGCTACCAT TCTCTGTGTT TCTGTGTTTT  120240

TTATAGGATC ATTCAATTAT TGGTTGGCTC TTGAGAGGGA ATGCAAGGTT CAAGGACACA  120300

AGCCTAGATC TTGCCTGTAT AGAACCTCAT GATGTTATGC TTCTCTAAAA TGAGGCCTGG  120360

AGGAGACATG TTGAAAGTGA CCCATAAATC TGCAGTATCT CATGTCTCTC AATGGGGACA  120420

AGGAGTACCA TGGGAAATAG CATTAGGTCA ATGACAGTAA CAACTCCCAG GTGAGTTGAT  120480

TTATTCTTTT ATTTATAAAG TTGTTAATAT GCTACATAGT CCCTAATTTT GCCACAAATA  120540

GTCATTATTT TAATTTCATA TTTCACTATT GATAAATGAA GGAAAAAATG AGTAGCAGTT  120600

AAGCAGTCCA TAAACCTACA TATAAAGCAA ATTGGAGATT TTAAAATTGA TTCTGGATGC  120660

TTAAAATCCT TCTCATTGAA AAAAAATTTC GTATTAGAAG ATTTCAACAT TCTTTAAACT  120720

GAGAAGCATA ACATATAAAC AGAAAACCAC AGCAAAACAA AAATGCAAAG CTCAATAAAT  120780

GAACACAAAG TGAACACCAT AATAATTGCC ACACAAGTAA AAAACAGAA AATCAGCCAA   120840

CCCTCCCAGA GCCGCCTGAT GCTTGCTTCC AGTCACATTA TCACTCCATC TGCCCTAAAC  120900

ATAACCCCTA TTTTGATTTC CAATGCTGTA ATTTAGTATG CCTGTTTTTG AAACATATAA  120960

AATGGAAATA AAACAAATGT AATCCTATGT ACCTGACATA TTTCACTCCA GAACATTAGG  121020

TTTGAATAGA TTCATCTGTG TTGCTGTGTA TAACTTTAAT TCATTTTTAT TGTTATGTAA  121080

TATTCCATGT TATGAGTGCA ACAATTTAGG TGTCTACTGT TGATGCATAT TTGCTTCCCT  121140

TTTTCAGCTA ATATAAACAA TACCGTGAAT ATTCCTGTGT ATGTGTCTTG GTATATATAG  121200
```

```
GAATACATAT TTTGTTTGTA TACCTAGGAG AGGAATTGTT GGGTCAAATG CTAAACTCTT   121260

TTTGAAAGTG GTGATATTAG GTTTACATGC GATGAAATGA AAATTAAAAC CACAGTTATA   121320

AACAGCATGG ATGAACCTCA CAAACCTAAT GTTGATGGAA TCTAGCTGGG AATTCCTGTT   121380

CTTCCATATA CTTCCCAATA TTTTTTTCCA ATTAAAATTG TTAATCTTTT GAAGATGTTA   121440

TCCATTGTGG CAGATGTGCA GTATTATCTC ATTATGGTTT TATTTTACAT CTTTTGCCCA   121500

TTTTTTCTTA ATTGGATTGT ATATCAGTCG ACTTGGGCTG CCATAACAAA AATACTAGAC   121560

TAGGTAGCTT GAACAAAAGG AGTTTATTAC CTCACAGTTC TAAAGGCCAG GCCAGAAATC   121620

CTAAATTGAG GTGCCAAGAG ATTCAGTTTC TAGTGAGGGC TCTCTTATTG ACCTGAAGAT   121680

AGTTGCTGTC TTAGATTGTT TGGTGCTGAA CAGAATACCA GAGACCAAAT AATTTATAAA   121740

GAATACAGAT TTATTTCTTA CAATTCTGGT GGCTATAAAG CCTATGGTCG AGGGGCCCAC   121800

CTCTGGCAAG GGCCTTCTTA CTGTTATGGC AGATGTGAGA TGTCATCTCA TATTCAAACC   121860

ACAGCAGTCG CCTTTTGTGT CCTCATGTGG CCTCTTCATA TGCCCATAAA ATGACCTCAT   121920

GTCTCTTCCT TTTCTTATAA GGACACCAGA TCTATCAGAC TACTGGCCTA CTCTTATGAC   121980

CTCATTTAAC CTTAAATATC TCCATAAAGT CCCAAAATCC CTATCTCCAA ATATAGGCAC   122040

ATTGGGTGTT AGAGTTTCAA CATCAATTTT GGGGGAACAC AATTTAGGCC AAAAAGATTG   122100

TGTTTTTTCT TGTTGGTTTA AGATAGCTGT CTTTTTGTCC TTTTTGTCCT TTCTTTTTTT   122160

TTGAGGTGGA CTCTTGCTGT GTCACCCGGG TTGGAGTGCA GTGGCGCTGT CTCAGCTCAC   122220

TGCAACCTCC ACCTCCTGGG TTCAAGAAAT TCTCCTCCTC CCAAGTAGCT GGGACTACAG   122280

GTGCATACCA CCGCGCCCTG CTAATTTTTG TATTTTTGAT AGAGACGGGG TTTCACCATG   122340

TTGGCCAGGC TGGTCTCAAA CTCCTGACCT CAGGTGATCC ACCTGCCTCG GCCTCCCAAA   122400

ATGCTGAGAT TACAGGTGTG AGCCACCAAA CCTGGCCTGT CTTTTCTGTT TTAAGTTTTT   122460

AAATTTTGCT CACGAACCCT TTATCCATTT TATGTGTTGC AGGTATTTCC TCTGTAACTT   122520

GTCTTCACTC TGTCAGAGGC TGGAGTGCAG TGGCACAATC ACAGCTCACT GCAGCCTCCA   122580

CCTCCCAGGA TCAAGCGATC CTCCCATCTT ATCCTCCTTA GTAGGTGGGA CTACATGTGC   122640

AGGCCACCAT GCCCAGCTAA TCTTTGTATT TTTTTGTAGA GATGGTGCTG TTGCCCAAGT   122700

TGGTCTCAAA CTCCTGAGCT CAAGCAATCC ATCAACCTTG GCCTCCCAAA GTGTTGGGAC   122760

TAGAGGTGTG AGCCACCACT GCACCCAGCC AATGATATCT CATGATGCAT TAAAGTCATT   122820

AATTTAGTGT ACTCAAATTA AGCACACTGC CCTTTTATGC ACAACCTTTT TTGTATCTTA   122880

TTTAAAAAAT CATTTTCTAT TTCAAGGTCA TGAAGATCTT ATTTTATAAT ACCTTCTTGT   122940

GAAATTAGTT CTCAAGACTA CCCTCACTTC TAACACCAAT TATAAGTTGG GAGGTCTGTG   123000

GTTCCCAATC AACCTTAGGT TAGTAATTTG CTAAAAGGAC TCACAGAACT TGCTGAAGCT   123060

GTTAGCCTCA TGGTTACAAT TTATTATAGG ATATATAGCT TATTATGTCA TTCCAATGCA   123120

ATGTAAAATT ATACAACTAC TTTTAAAAAG ATTTTAGCAT TTGACCCAAC AATTTCACTC   123180

TGAGGTATAC AAACAGCAGA TATGTGTGCA CATATATACC AAGACACATA CACAGCAAAA   123240

TTCATTGTTT GTAATAGTTG AAAAGGGGAA ACAACTCAAG GAATAAAGAT TAAAATCAGC   123300

TGAGAAAAGA AACACACAAG GCAGTATTAT GGATCGAATT GTATGCAGAT CTCCCTTGCC   123360

CCCAGAAGAT ATGTTTAAAG TCCCAACTCC CAGTACCTCA GAATTGTGGC CTTATTTGGA   123420

AATAGGATAG TTGCAGATAT AATTAGTTAA GATGAGGTTA TAGTACAGTA TGATGGGCTG   123480

GTGACTTAGA AGAAGTAGTA TATATATATT TTTTAATAGA ACTAGTATTC TTCTAAGGTG   123540

GTCACGTGAA GACAGACACA CACAGGCAGA GACTGAGGTT ATGCAGCTGC AGGTCAAGGA   123600
```

```
ATGTCAAAGG TTGCCAGCAA GTACGAGAAG CTAGGAAGAG TCAAGGAAGG ATTTTCCTAC    123660

AGGCTTCAGT GGAAGCATAG ATCTAATGAT ACCTTCATGT CAGATTTCTA GCTTCCAGAA    123720

CTACAAGAGA ATATATTTGT TGTTTTAAGC CACCCTAGCT TCTAGCTCTT TGTTACAGCA    123780

GCCCTAGGAA ACTAATATAG GCACAATCCA GGCAAGTTCC AAATATGAGC TTCCAGTTGT    123840

CCTCTCCCAG TAATATGAAC AGTATTACTT TCCCAGCATT AATGTGTGAC AATACACATG    123900

ACGTACAGAG CAGTCCCCAC TTATGCACAA AACATATGTT CCAGGACCTC CAGTGGATGT    123960

CTGAAACCAT GGATAGTACT GAACTCTATA TAGCTGTTTT TTCCTATACA GACACAGCTA    124020

TGATAAGGCT TAATTTATAA ATTAGGCACA GTAAGAGATT AATAACAATA AATTAGAATA    124080

ATTGTTAAGA ATATACTGTA TAAAAGTTAG GTGAATGTTT ATTTCTGAAA TTTACCGTTT    124140

ATTATTTTTG GACTGCAGTA GACCACAGGA ACTAAAACCA TGTAGAAACC GTATACAAGA    124200

GAACTGTATT TCACCCGAGC CTCAGTGTGC AGTTTTAATG GCCTGCCATG GTTGACTGCT    124260

CACATGGCCG ATCTTTTAGT CTACCTCCAC AGGTAGAGCT GATACTGTGT GGCTCAAAGT    124320

TCCTATTATA AATCACATTG TTGACTGTGT GGTGGTCAAA ACCTCCAGGT AAACAAAGAC    124380

ACACTTATCA GTGAGAACAT TTCAAGGGTC TAAAATTCAT CTCCCAGTAG CTGAGGGCAA    124440

AGGCTAGACC TCTTTTTGGG TAAGATAAAT TTTTTACCAT ATACTTTATT TTGCTTTTCA    124500

TGTTTAACTT TATTTTGCTT TTCATGTTAG TTCCCCTGGA ATTGTTTTTT GTGTATAGTG    124560

TGAAGTAGGG GGTCAAGTTT CTTTTTTTTT CCTTTTTGTT CTTTTTCTGT TTAAAAGGCT    124620

ATACAATTGT CCCATGCCAT TTATTTACAA GAGTCCTTTC ACCATTGTTG TATGGTGCCA    124680

CTTTAGATGT AAATCAATGT CCATATTTGT TTGAGCCTGT TCCATTCGTT TGTCTATTTT    124740

TGGACAACAC TGCCCTGATT ATTGTCATTT TATCAGTTTT GATATTTAAT AAAGCAACAG    124800

ATTTGTTTAT TTTGGGCCCT TGGATTTGTG TATTAAATTT GAACCCTGTT TGTCAATTTC    124860

TATAATAAAG CTTATTGGGA ATCTGATTAG GATTACAATG GTTTTGTAGA TCAGTTTGGG    124920

GACAATTAAT ACCTTTAAAA TATTGACCGC TTCAACTGTA AATATACTCC TCCATTATTT    124980

AGTTTTCCTG TTTAATTTAT CTGAGTAATA CATTATAGTT TTCTTCGTAG AAGTCAGATA    125040

CGTAGAAAAT TCAAAGCCCA AGTGCAATAG CTCATGTCTG TAATACCAGC ACTTTGGGAG    125100

GCCGATGTGG GTGGATCACC TGAGGTCAGG AGTTTGAGAC CAGACTGGCC AACATGGTGA    125160

AACCTCATCT CTAGTAAAAA TACAAAAATT AGCTGGGTGT GGTGGCGGGC ACCTGTAATC    125220

CCAGCTAATC AGGAGACTGA GGCAGGAGAA TCGCTTGAAC CCAGGAGGCA GAGGTTGCAG    125280

TGAGCCAAGT TCCTGTCACT GCACCCCACC CTGGGCGACA GAGCGAGACT TCGTCTCAAA    125340

AAAACAAAAA AAAGAACATT CAAATAATCA ATGTAGATAA TTCAAATAAC TAAAAAATGA    125400

ACAGTTATTA AAATATCAGG ATATAAAAGC AAAAAAATCA ATAACCTCCA TATATACAAA    125460

ATGGCCAGTT AGAGAAAAAA AAAAGAATAG GCGAGACTTA AAAAGGCTGG GAATCTCCCT    125520

GAAAATCTTT GAGAGCCTTG GCCCTGCCCT CAGGGATTTC TCTGGCTTCA TGCCCAGATA    125580

CGGGTACAGT TCCTTGTTTA AAAAAATTTT GCTCCATCAA TCAACAAGGG GCTCCTTCCT    125640

CAGAGCACAA GGACCTCCAT AACACCGGAC ACTAGATGTC TAAGGGACAC CTCTTAAGGA    125700

AGTTAGACTT CCAAAGAATG GTGTTTCCTC TGTCCCCAAA CTCTGGAACT CACAGCACAA    125760

CTGCTCCTTG GAGTTCGGTT TCAAATCTAC AAGGCTGTCA TGGAGGTTGC AGACCAAGTC    125820

CGTGGCCTCA GTGTCCGGAT GTACGGTGGC CTTGGCACCT GAATGTGAGA ACATGACCTC    125880

CCTGAAACCA CCACAAGTAT TGTTTCATGT TATGTATGTT TTTTCTTATC TGAAATTCCT    125940
```

```
TTTCTTTAAA AATTCAAATT ACATATTTTG CAAGCCCCTG AACAAGCTTC ATGAGCATTT   126000

ATTGAACCCA CAGCTTTTAA AACCTACTGA ACACTTTGCT CTATGTTGTC ATTCACTATC   126060

CACCAATTAT TTAATTATTG ATCAATATTG TTTCCTTAGT GTTGGGATCA TTTATGCATG   126120

TATTTCTTTT ATATTGCATA TTTTATATTT CTGCATTACA GTTATTACAT ATTACTTTTG   126180

CTACAGTAAT AGTTCAAAAG TGTACATCCA AAATTTAGCT GTGAAGTGGA TGGACTGAGG   126240

CAGAACTGGA GGCAAGAAAA TGTCACAGTA ATTCTAAAAA AGATGATGTA CAATTAGAGC   126300

AAGAGAGTAG CACTGAAATT GAAGAAAAAT AGATGCGTTT GAGAGAAAAT TAGGAGGTAG   126360

AATCAACAGA TTAGATGTAG GGATGAGAAG GGTCAAAGAT GACACTAGGG TTTTTAACTG   126420

GAGCAAGTAG GTAGACAGAA CATTTCTTCC TGAAAGGGCA GGTCAGATCA TGTGTTGTCT   126480

CAAAGGGCAT GAAGAGTAGA AAGCCTGGGA CAGATCCTGA GATGACCAAT ACCCATGGTG   126540

CAGGGAGAGG GAGGGAGATC TGCTAAAAAG ACTGCAAATG TCAGGATAGT AGAAAATCAT   126600

GAGTGTGTGA TGTCCTGGAA GTTGAGACAG TATCACATTT GAGAACATTT AAATTGGTAA   126660

CTCTGACAAA AAGCTGGAGG CCAACTGTGA ATGCCCATGA GAGTGAGAAG CTCCCACACT   126720

TTTGTGGGCA TCAGAAAGCC CACCAGGTTC CTGCAGTGAA GATCTGAGAA GGATCCTCTT   126780

GTGGCTTTGG CAGGGAGAGA AGAATTATTA TGAAATACAC CCCAGAACCT TCTTCAAAAC   126840

AAAGGCCTAC TCTCAAGGGG AAAACATTTT GCCAGAGTCT TATCCCAGCT GGGAGAAGGT   126900

AATTCTTCCC ACTGCAGCCT CATCTAGGCT TTCTGTCTCA CTTAAGGGAA GAAAATTAGT   126960

CAACAGGGAT CAGAGCTTCA TGAAAATAAA TTGGAAATGG TGCAGCCAGG AAAGGAGCAA   127020

AGGTCTGAGG AGGAGGAGAA GGAGGAAGAG GAGTTGTATC ATTATAAATA CTTGAGGAAG   127080

AGGAGGAGAA GGAGGAGGAG GAGGAGTTGT ATCATTATAA ACACTTGAGG AAGAGGAGGA   127140

GGAGAAGGAG GAGGAGGAGT TGTATCATTA TAAACACTTG AGGAAGAGGA GGAGGAGAAG   127200

GAGGAGGAGG AGGAGTTGTA TCATTATAAA CACTTGTGAC GGTCCCAGCC CCAAGATATA   127260

GGCATGCTAA TAAACTGAGG CTTAACACTT TGACTACAGA ATGCTGCTTC TCCCTAACAC   127320

CATCAAGGCT CCAACTGAAT AACAATGAAT TATGAATGAA AGAGCTGTAA GGAGAGACAA   127380

AAGTTAGAAT GAGACAAGTA TTGTTATCTA GAGATGCCAA GAAGGCAAGG AAGATAACTA   127440

AAAAGGCACT CTGGATTTAG AAATAGGAAG TCATTAGTGA CCTTGTAAAT AATGGAGCCA   127500

GAGGAATACC AAGGGCAGAA GCCTCACTAT AGTGTGTTGC ACCTGTCAGA GGTCAGGAGG   127560

TGTAACTGAC TCTCCCACAG TGTGGCTTTG GAAGAGAGAA GTCAGCAGCT GCATGGAGAT   127620

TTGGGAGAGG GAAAGCTTTT TTTTTTTTTT TTTAATTGGA AAAGACTGAG CTATGTGTAA   127680

ATAGAATAAG ACAGGAAGAG TGTAGACACA GGAAAGAGGG CAGACAAAAA CAAGTGCACA   127740

GTTATCTAAG GGAAACAATG GGATCAAGCT GCAAGTATAT AAACTTGTCT TGATAGAAGA   127800

ATCCTTGATC TGGTTTATTC AGTGTTTGGT CCAAACCCAC ATCCCTGTTC TGCCTGTCTC   127860

TGACTTGCTC TGTGCCCCAG AAGCCCAGCT TCTACAGATA GCATTAGCTG GGCAGCCCTG   127920

CCCTCTTGCA ACAGCTGGAT TTGGCCAGTG ATCAGCCCAG CAGGAATGTA GATGGCAAAG   127980

GAGAGAGAGG TTAGTGTACT TATTCCCTGC ATCACCCCCC TGCTTGGTGG GCAGCTCTTC   128040

CTCCACAGTC CCAGCTCTGG CCTAGCTCTG GTTACAGGTT CCCTCCCATT GCCTCTTCAG   128100

ATTTAAAGGT GTGTCTGTCA GGGTATAACT GGGAGCTAGA AATTGCACTG AAATTGAACA   128160

AAGAATTTTA TGGGAATGGT TGTTAACTAG TTATAAGAGG ACTGAAAATG GAAAGTGGA   128220

CAAACGTATC AGAGATAGTA ATGACAGAAA GCAACTACCA CCTCCAGGTT TAGGAGAACA   128280

AGGAAAAGAT TCTTTGAAGA GATCCCCAGA ACTGGGACCT CTGAGGAGTG TATGCTGGAC   128340
```

```
CACTGATGAT GATATGTCTG TAGATAGAGG CATGATGAGG CTGATTTTAG GAGCATGGAA    128400

GATCTCCAAA CTGAAGCCAA CTGCTGTTAC TGGATTCAAC TGCCACTGCC AGGTTGAAGA    128460

ACCCATTCTG TGAGGATGTC AACAAACAAA GTGGGAAATC TTTTCACATC CTTCCAGCCC    128520

TCTAGTCTTC CTCCAGTGCT TTCTATTGGT AGGGTTTGGG GAGGTGGCTA GCAAAGCGGT    128580

ATTGGAAAAG ATAGAAGAGA CTAAATCTTC ATAACCAGCA CAGGGTGACA CTGGATCACT    128640

ACTGTTGCTG ATCTTGGGCT GCCTCATATC CCCTGTTCTT CCCATTAGCC CTGTCACAAC    128700

TTTGTAGATA TCCCTTCATT ATATGCCCTT CATATATTCT TTTGGTTTAA CTTTTTCTGT    128760

TGGAATCCTA ATATGGCACT CCTCCATTTT TCAGGACCAA AAGAGTATAA AAGATTATCT    128820

TTTACCAAAA AAAAGACAAA AAACTGATCT AATTCCTGAT TTGATCATTA CACAATCTAT    128880

ACATGTATCA AAATATCACA TAGTACCCCA TAAATATATA CAACTGTGTC CATTAAAAAT    128940

AAAAATTAAA GAAAAGATGG TAAATATAGC TCTGTCAGGC AGTGGAGGTT TTACCACGAT    129000

GGCTGTTATT TCCCCCATGA AGGGGGGAGT GAGGGAGCAG CTGAAAGTAG GTGCTTATAG    129060

GGGTATAGAG GGGCTCAAAG CTTTGAGAGA GGAGAATGTC TGAAAGAGCT GCCAAATAGC    129120

ATGCAGGTCC CATGGGGCA GAGCCTCTGC TCATTCACCA GTGCCTCTTC AATATCTACA    129180

CTTAAGCCTA ACACAAAGTG TGTGCTTAAT AAGTATTTGC TGAGTATGTA AAGTGGAAAC    129240

AGAACCAATC TGGCAAACTT TGTAGGACTG GTGGGCAATG AAGATCAGTC AGGTAAAATC    129300

TGTGGATATA AATTTATATT GATCAAAAAA TTCAAGGTTA GGTGTTTTTC TTCAGTCATG    129360

CTCAACGATG CTTCAGCCAT GCTCAACTCT TCTGTAGCCA CAGAAAAAAG TTTACCCATA    129420

ATCGAGCTGT GTCTGTGTCT GAATAATGAA AAGACCATGA TGCAAGGGAG TTGGAGACAC    129480

AGAAACAGTG TTTGAAGTAA TGGGTAATGG AAGCATGCTA CCAGGGAAAG GAAAGAAGTG    129540

GCAATAGGAA GGAACAGAGA TCTGTGGTCC TATGTCCCCT GAGCATATTC ACATGTTAAA    129600

GCTAATTCAG TTTTCAATCA TCATTAAAAT TTTGTTCCTA AATATATGGC CATTATTTTC    129660

CACAACCACA CTAAAACTTT ATTACCTCTG GCAAGTGACT ATGCAAGTAA CTAAGAGCAA    129720

AAATATCCAC AACTACCATT TGAGCTATCA ATTTAGGGAA AGTCATCTGG CTATAATCTA    129780

AGTGACCCTC CACTGAATGT CAGTATCTTT GCATATGTGA TTTAAATCTG GCCTTCGCA    129840

ACACCATGAA CTGTTCTTGT CTTGAATATC CAGATTGAAG GAAATAATCT GAGTAGTTAC    129900

GAGTCCTGAA GCTAGAAAGA TGGAAACCCC ATTTGCTCAT CAGAAAGCCT TAGAGCTTGG    129960

GCGCTGGCGG GTCCTGTCTC ACCGGGACAG AGGGGCTCTT TCCTCCCCAT CTGATAGTCT    130020

GATAACTAGA GAAGCCGGCC AACTTATTCT CCAAGAAGGA GCCATCTTAG TTCCTCCTGA    130080

AATGTTCATA TTTAGAAATT ATTGTTTGTC AGTAATTTAA CCCCTTAATG GGCTTGCCTT    130140

GTGGTCCATA CCACTGAGTG CAGAGCTTGC CTGGAAGAAT TGTGAGGGCC ATTCCATCTT    130200

CCAGGCAGTA GAGTTCAGTA CTTCTTTAAA ATTGCTGCTG AACTCTGTAT TTGAAAAGAA    130260

AGAATCATTT GGGTGTGGTA GCTCACACCT GTAATCCTAG CGCTTTGGGA GGCTGAGGTG    130320

GGAGGATCAT TTGATGCCAG GAGGACCACT TGAGACCACC CTGGGTAACA TAGCAAGACC    130380

CTGTCTTTAG AAAAAAAAAA TACAATAAAA TAAATACAAT AAAAATAAAA GCAAAAGAA    130440

AGAGTCCATC TTAGGGACAG ACTGTAACTA CTCACTGGAG CTTACCTTTA CATAGTTCAG    130500

GATCAATTAT AATAAAACAC TTTTGTGCAG ATTCAATAGG ATTATTTTAA TCCCCATCAT    130560

CTCTCTGAGT TTCCAGTCAG TTTCTCTGCA TGTAGACACC CTTCTCCAGC CCACCATTGT    130620

CTCTCCTCCT ATAGCTCCAC CAACAAATCA GAACTTTTTC TAACTGCACC TAGTGCACCT    130680
```

```
AGAGTCTACT CCAGAATGCT CATGGAGAAA GTTTCTGAAA GGTAAAACTC TGAATGATAT   130740

TTGTAGCTAA AGGGAGACTT GCTAGAGACA ATAAGCTAAT AGTTGTAGAC TTCAGTAGAA   130800

GAGGAATGAC ACTGCAATGT CAGGGTGCAG GACTTCAAGA GGGCAGAGTA TGGAAACCCA   130860

ATGGGAAAAA TGCTCACCAG GAACATGAAG AGAAGGAATT ACGTGTAAGG ATTTCTCAAT   130920

GTGTTCCCAA ATTTGCCCAG CAGAGGGAGG CCTCGGGTTG ATGGCAGGCT GACCACACAA   130980

TTAAAGAAGG CTGAACCTGG GGGCTTTTAA CAACCATCGT GGGCTCTACT GTAAGCATTT   131040

AGAAAAAGAA AGTTATCCAT TCAAAAATAT ATATATTTTT AAACTTCAGA ACAAAATTAT   131100

GAAGAGCTAT ATTTACTTTT CTACATTCTA ATTTTTATAA ATCTGAGTAT ATTTTGCATA   131160

TATTGTTATA GTACATATTC AATTTTGTAT TTTGCTGTTT TCACTTAACC ATTTTTACTA   131220

GATTACTCTG TGTTCATAAT AATCACTTTT TTAAAACTTT TATTTTTATT TATTTATTTT   131280

TTTTTTGAGT CAGAGTCACA CTCTGTCGCC CAGGCTGGAG TGCAGTGGCG TGATCTTGGC   131340

TTACTGCAAC TTCCACCTCC TGGATTCAAG CAGTTCTCCT GCCTTAGCCT CCTGAGCAGC   131400

TGGGATTACA GGTGTGCACC ACCAAGCCCG GCTAATTTTT GTATTTTTAG TAAAGACGGG   131460

GTTTCACCAT GTTGGTCAGG CTGGTCTCCA ACTCCTGACC TCATGATCTG CCCACCTTGG   131520

CCTCCCAAAG TGCTGGGATA ATCACTTTTT ATGCTGCATA ATTCTTCAGA TTTGTCAGTA   131580

CGACTGTATT TACACTCATT TGTTTTATTA GAAAGAATTC CAGAATATTT TGGCTGCCCT   131640

AATTAATTTT ACAATTAATA TGATTTTGAA ATTGGGTATT GGCTCCTTCT GAATTGGTTT   131700

ATTAAAATAT ATTCTAATGT AATTTATGAC ATTTTCATCA TATTAGCATA TTTATTCTGT   131760

TAGAATTTCA TAATTTATAA AGCTACAAAC TGTATGTGAT ATAGCTTGTA ACTTTATCTC   131820

ATAACTTTAT GCAGTTACAA GTAGAAATAA AATGTTCCCC TCAAGATTGC TTAAAATTTT   131880

ATTATAAACA AGTGTAAAAA ACAAAATCAC TAAAACACTC CCTCTTTTTT CCCCCAAAAT   131940

GCATGTTTCC ATTTTAACAG AACCCGTATT TAATCAGCAG ATTTCTATGG TGGCTAGATT   132000

TGTAGACTAA ATATTAAAAG TCCCAAAGCA AATGCATTTT TCTCTTAAAT TTTACTGACT   132060

TTTTTTTTTT TTCTTTTTCT GAGACGGAGT CTTGCTCTGT CGCCCAGGCT GGAATGCAGT   132120

GGCACAATCT CGGCTCACTG CAACCTCCGC CTCCCGGATT CACGCCATTC TCCTGCCTCA   132180

ACCTCCCGAG TAGCTGGGAC CACAGGCGCC CGCCACCACG CCCAGCTAAT TTTTTGTATT   132240

TTTAGTAGAG ACAGGGTTTC ACCGTGTTAG CCGGGATGGT CTCGATCTCC TGACCTCATG   132300

ATCTGCCCAC CTCAGCCTCC CAAAGTGCTA GGATCACAGG CATGAGCCAC CGCGCCCCGC   132360

CTACTGACTT TTATCCAAAG AAAATATAAG AGCTCTTCAT CATAACGTAT GTTTCTTGCT   132420

CTTGTTATTA AATATGACAC ATTTAGACTT AAACTGATTT GAAGGTTTAT GACATTGTTT   132480

AAGTTATTAC ATAATTAATT CATAAAGATA ATGACTAGTT TGAACTACTG ACAGCTCACA   132540

CATCATCAGT TGAACAGCAG AAAGCTTACT AAGCTACTTT CTTATGTTTC TGTCTCCCAG   132600

CTACTAAAAG AAACGAAACC CTTCCAGGTG TTAAGGCAAA ACTTTCCTCC CCCTTTCTTC   132660

TATAAATCTG ATTCCATGTT AGTGAAATTT CTACTGATGG CTTTGGTTTC CTCTATAGTA   132720

GAATAGAGAT CCTATGGCAA AAGTCATGTC TGACATGGTA GCAAATAGAA ATGGGGAAAA   132780

GGAAGGTCTG CAAGAGCCAA TGTGGGAAAT GGGGAGAGGA CTGACTACAA AAACCCAGCA   132840

GGAATTCCAG AAGAAAACTC CTCAGGACGG GCACATTGGC TCATGCCTGT AATCCCAGTA   132900

CTTTGGGAGG CCGAGGTGGG CAGATCACTT GAGTCCAGGA GTTTGAGACC AGCCTGGTCA   132960

ACATGGCGAA ACCTCATCTC TACAAAAAAT AAAAAAATTT GTCAGGCGTG GTGGCATGCA   133020

CCTGTAGTCC CAGCTACTCA AGAGACTTAA GTGGGAGAAT CACTCGAGCC TTGGAGGTGG   133080
```

```
AGGTTGGTGA GCCGAGATCA CGCCACTGCA TTCCAGCCTG GGCGACAAAG TGAGACGCCA   133140

TCTCAATCAA TCAGTCTCCT CGAAAAGCAA CATTATGGAG AGACAGGATT CCGTCAAGGC   133200

CTGGGGCACA CAGGAAAATA TTAAGGCAGA AGAGAGTTTC CTCCCCACAC CACACCGTAT   133260

CCCACAGGCA CTGCGGATGT GCATATGCAA GAGGGGTTGA TCCTAAGAAT TTAGAGTCAC   133320

AGAGGAGGAG GCACCAAGCA GACTGTGGAG AAAGTCATGA CCAGAAAGGG ACAGAATGTA   133380

AAGCTTCAGC TGATTATCTG GCCTCAGGGA TTCCAGAGGA ACTGGTCCCA ATGGTCTCCT   133440

GGTGATGTAG GTTCTTAGGT TTCTTTTACA GGGGTTTTCT GGGAGATCGT TGACCCAGTT   133500

AGCATTCAAG CAACTTCCAC CCTGCACTTT TATTCTTTCC CCTTCACCTG CTTAGGTTTT   133560

ATCTGTCCAG GAAATAATAA TAAAATTATT GAGCCCTGGA CATGTACCTG TAAAGCTCCT   133620

TAAAGATGAT GCCTTCTAAC TCCTCATTCA ACAGATACAA AAACATTACA ATAAAATGAC   133680

TCATGCAAGA CACCCAGGTA GTTTATAGCA GCTAATAAAA ACAGAATAAC TATAAAATAT   133740

GGTAAGTTTA TAAAAGTTAC ATTGAGTATA CTTTATAAGA ACTGCTTATT GAGTTTGCCT   133800

AATAACCACA CAGCACAATA ATAATATGTA TATATTTTTA AATATGTGTA AATATGTGTA   133860

ACACAAACTT GTAGAAGGTA TATCTGAGTA CAACCCTATT CTGTTTGGTT ACCTTTTCTA   133920

GTTCATTATG TAAGTGGCAT AGCTACCTAA GGACTTATGC TTATAAATGT TACTCAAAAA   133980

AATACAGAGG ACATATGTGG ATAGATAATG GAAGAGATAA GATAGGTAGG TTGAAGGGTT   134040

GGGCTGCCCC TCCACACCTG TGGTTGTTTC TCGTTAGGTG GAATGAGAGA CTTGGAAAAG   134100

AAAGAGACAC AGAGACAAAG TATAGAGAAA GAAAAAAAGG GGTCCAGGGG ACCGGTGTTC   134160

AGCATACGGA GGATCCCACC GGCCTCTGAG TTCCCTTAGT ATTTATTGAT CATTATTGGG   134220

TGTTTCTCGG AGAGGGGGAT GTGGCAGGGT CAAAGGATAA TAGTGGAGAG AAGGTCAGCA   134280

GGTAAACACG TGAACAAAGG TCTCTGCATC ATAAACAAGG TAAAGAATTA AGTGCTGTGC   134340

TTTAGATATG CATACACATA AACATCTCAA TGACTTGAAG AGCAGTATTG CTGCCAGCAT   134400

GTCCCACCTC CAGCCCTAAG GCAGTTTTCC CCTATCTCAG TAGATGGAAT ATACAATCGG   134460

GTTTTACACT GAGACATTCC ATTGCCCAGG GACGAGCAGG AGACAGATGC CTTCCTCTTG   134520

TCTCAACTGC AAAGAGGCGT TCCTTCCTCT TTTACTAATC CTCCTCAGCA CAGACCCTTT   134580

ACGGGTGTCG GGCTGGGGA CGGTCAGGTC TTTCCCTTCC CACGAGGCCA CATTTCGAC   134640

TATCACATGG GGAGAAACCT TGGACAATAC CTGGCTTTCC TAGGCAGAGG TCCCTGTGGC   134700

CTTCCTCAGT GTTTTGTGTC CCTGAGTACT TGAGATTAGG GAGTGGAGAT GACTCTTAAC   134760

GAGCATGCTG CCTTCAAGCA TTTCTTTAAC AAAGCACATC TTGCACAGCC CTTAATCCAT   134820

TTAACCCTGA GTTGACACAG CATATGTCTC AGGGAGCACA GGGTTGGGC TAGGGTTAGA   134880

TTAACAGCAT CTCAAGGCAG AAGAATTTTT CTTAGTACAG AACAAAATGG AGTCTCCTAT   134940

GTCTACTTCT TTCTACACAG ACACAGTAAC AATGTGATCT CTCTCTCTTT TCCCCACAGG   135000

AGGTGATGGC CGGAAGAACA TGGCAGAGGG CAAAACAAAA CAGCATTGGG AACAAGCTCT   135060

GTTTAAAAGG AGACTTGTGA ACAGCAAAGA GTAGAAAGGG TTCTCTTACA ACTGAAGCCC   135120

ATGGAAGACA AATGTGTACT GCGTGAGTTT TAAGGCAATA GGAGTAGTGG GACCTAGGGC   135180

ACACCAGAGA GCATATTAAC TCTCAAACTT TTAAAAACAT TATATCTGCT GGACACAGTG   135240

GCTCACACCT TAATCCTACA ACTTTGGGAG GCCGAGGCGG GCGGGTGTAG CTTGAGCCCA   135300

GGAGTTCGAG ACCAACCTGG GCAACATGGC AAAATCCCGT CCCTACAAAA CAAACAAACA   135360

AAAAACAAAA TTAGCCAGGC ACGGTGATGC GTACCTGTGG TCCCAGCTAC TCAGAGGCTG   135420
```

```
AGGTGGGAGG ATCGCTTGAG CCCCGGGAGG TTAAGGCTGC AGTGAGCCAT GATAATGCCA    135480

CTGCATCTCA GCCTGGGCAA CAGAGGGAGA ACCTGTCTCA AAACAAAAAC AAAAACACAC    135540

CATACCCAAC CACAATGCAT CTGTCTTAAG TACCAGTACC ACACCCCTCT ACTCACTACT    135600

AAATAGGTGA GTTCCCAATC CCTGGTAGCA GGTTTAAGCA TGTTATATTA AAGGTCTTAG    135660

GCTAGTGACT CATTCACTCA TTAAACAAAT ACTTATTGTG CATCTACTAT AAACTAAGTA    135720

CTGTGCTAGG TACAAAAGCA AATAATCTAA GCTCTATAAA CTTTACTTTC TTCATCAACA    135780

AAATGGAGAT GTTTTAGGCA TCTACTCATC ATTCTGAGCT CCATCTTTTG TGACTGTAGT    135840

TGGCAGAGCT TTTTATCAGT TTCTCTAAAT AGCTCTACCA GTCCCTGGTG GATGCTGGCA    135900

TGCCCAAAGG ATCCATCCTG ATGGCCCTGT CTGCTTACCT TACCTGCCTG CCTTTGCAGC    135960

ACCGCTCTGC TCTTCTGCAG GACTTCCCTT ATCCTTTGGG GTCTTGCTGC TCTTAGGCTG    136020

CTCTGCTTGT TTTGATCTGC TTTGCATCAC ATGTATGTAA AGGTCCTTTC CTTATTTACC    136080

CATGACCAAG GTATTATGAG ATTCTGGAAT TTCCCCAAAC CACATTGATT GCTGGGAGAA    136140

TAGAAGAAGT GGATTACAAG TGGAACTTAG AAGGGGAGTA TTCGAGAAGA CGTCTCTGCA    136200

AATCCATTTA GAGAGACCTT TCTCCAGTGG TGACTCAAAG ATGCAGCTCC TTTCATCCTG    136260

TGGCTTGGCC ATCTTCAGCA CATGGCTCCC AAGGATGTCC TCAGGATGGT CTCTAATCCA    136320

AGGAGCCTGA AGAGAAAAAA AGGCATGGAG TATTGTGAGT GGTAGGTGGT TATGGACCAG    136380

TTATGGAAGA ATACACATCA CTTTTGCCCA CCTTCTACTA ACCAGAACTC ACACAGCCAT    136440

AGACACTGAC AAGTAGGACT TAACAAGAAT CTAATTTTGA GTCTAGGAAT ACGACTGTAG    136500

CAAATATTTA ACAGCTTCAA ACACAGGTGC ATTGCTATCA CTATGCTTGG CCCAGGCCTG    136560

TCTCCCTTTC CTGCCATGTC ACAGGGGCCA GCATTTATGT CTAGATTGGG TTGGTTGGGA    136620

TATTAAGACA ATAATGAACC AATACAACAT CTTGAGCATA AAACCAACTG ATACAATGAT    136680

GTACAAGTCA GATGATTCTG ATGATTATGA ATTATGTCAA TAAAGAAAT GTGATAACTA    136740

AGGTAATTTT TGTTTTGGCA AATTTTTGTT TGTTCATGAC AGGATGAAAT CCTGTCATTT    136800

GTAGCAACAT GGATGGAATT GCAGGATACT ACATTAAGTG AAATAAGCCA GAAACAGAAA    136860

GTTAAACACC ACATGTTCTC ACTTATATGC AGAAGCTAGC TAACTAAGTA AATAAGTTTA    136920

TCTCATTGAA GTAAAAAGTA CAACAGAGAT TACTAGAGGC TGGGAATGGT AGGGGAAAGA    136980

GATGATAAAG AGAGATTCGT TAAAATAAGT TACAGCTAGA TAAGAGCAAT CAGTTCTAGT    137040

GTTCTATTTG TACTACAGAA TGGCAATAGT TAACAGTAAT AAATAATTTC AAAGAGCTAG    137100

AAAAGAGGAC ATTGAATGTT TCCAACACAA AGAAATGAGA AATGCTTGAA ATAATGGATA    137160

TTCTAATTAA TTACCCTGAT CTGATCACTA TACACAGTAT GTATAAAAAT AACACTATGG    137220

GCTGGGCGCA GTGGCTCACA CCTGTAATCC CAGCACTTTG GGAGGCCAAG GTAAGCAGAT    137280

CACTTGAGGT CAGGAGTTAG AGACCAGTCT GGCCAACATA GTGAAACTCC ATCCCTACTA    137340

AAAATACAAA AATCAGCCAG GCGTGGTGGC ATGTGCCTGT AATCCCAGCT ACTCAGGAGG    137400

CTGAGGCAAG AGAATTGCTT GAACCCAGGA GGCGGAGGTT GCAGTGAGCC GAAATCGCGC    137460

CACTGCACTC CAGCCTGGGT AACAGAGCAA GGCTCTGTTT CAAAAATAAA TAATACATA    137520

AATAAATATT TTTTAAAAAA AGAACATCAC TATGCACCCC ATATATACAT ATAATTATTA    137580

TGTCAATTTG AAACATAATT TGAAAAATG AAAAAATGAA ACACAAATAT GAATCAATCC    137640

TCTCCAAGTT GATATACTTA AAAGGAAAAA AGTCCGAGGG CTTAAACTAT TCAATCAAAA    137700

TTTTATTAAA ATGCTATAGT AATCTGGAAA GTATTTCAGA ATGAATTGGT ATAAGGTTAG    137760

ACACAAAGAT CAGTGAAACA AAACAGAGAA CCCAGAAATA GATTCACACA TCTATGGACA    137820
```

```
ACTGGTTTTG ACAAAGGTGT CAAGGCTATT TAATAAGTAA AAAAATCGTC TTTTCAGTAA    137880

ATGTTTCTTG AACAAGTAGA CATCCGGTGT GGGGGAGAGG AGCAGGAGCC TTACCTCAAA    137940

CTTTATGCAA AAATTAACTC AAAATAGACC ATAGACTTAA ATGTAAAAGC TAAAATTATA    138000

AAACTTCTTT AAAAAATAGG AGAAAATCAT CAACACCCTA GGATTAGCAA AGATTTCTTT    138060

AAAACAAAAC AACAGGTTTA TAGTTTATAA AACATAAATA ACAAAATGAT AAATTTCATC    138120

AAAAGTGAAA ATTTGCTTTT CAAAAACAT TATAAAATGA AAAGCAGGAG GCTGAGGCAT    138180

GAGAATCACT GGAACCCGGG AGCTACAGGT TGCAGTGAGC CAAGATGGTG CCACTGCACT    138240

CCAGCCTGGG TGACAAAGTG AGACTCTTCC TAAAAAATAA ATAAATAAAT AAATAAATAG    138300

AAAAGAAAAA GAAAAATCAC AGGCTGAGAG AAAATATTTA TAATACATGT ATCTGACAAA    138360

GGACTCGCAC CTGGAAAATA TAAGGAACCT TATAACTTAG TAAGATGACA AGCCAAAACA    138420

AAGAGTAAAA GTTTTCAACA GACATTTCAC AAAAGAAAAC ATACAAATGG CCAGTATGCA    138480

CATGAAAAGA TTTTAAACAT CATTAGTTAC TAGGGAAATG CAAGTCAAAA CCACAATGAG    138540

ATACTTCACA TTCAACAGAA TAGCTAATGT TAAAAGGACT GACAATCCCC AGGGTGAGCA    138600

AGGGTGTGGA GGAAACTACT CTCATATATT GTGAATGTAA GAGGACAATG TTACAACTAC    138660

TTTGAAAAAA GTTTGGCTGT TTCTAACATA AAATTAAACA CTTATACAGC CCAGCAATAT    138720

TTCTGGGTCA TTTCTCCCAG ATAAATGAAC ACATGTCCAT ACTATGACAT GTACAAATGT    138780

TCATACTGGC TTTGTTTCAC AATGCTATAA ACTGGAAACA ACCCACGTGT CCATCAACAG    138840

GTGAATGGGT AAATAAATTG TAATATATCG GCCAGACGCA GTGGTTCATG CCTGTAATCC    138900

CAGAACTTTG GGAGGCCAAG ATGTACGGAT CACCTGAGAT CAGGAGTTTG AGACCAGCCC    138960

ATCCAACATG GTGAAACCCC ATCTCTACTA AAAATTAGC TGGGCATGGT CACGGGCGCC    139020

TGTAATCCCA GCTACTCGGA AGGCTGAGGC AAGAGAATCA CTTGAACCGA AGAGGCGGAG    139080

GTTGCAGTGA GCCAAGACCA TGCCATTGCA CTTCAGCCTG GCAACAAGA TGGAAACTCC    139140

ATCTCAAAAA AAAAAAAAAT TGCAATATAT CTATATCTTG GAATATTATA AGCAATAAA    139200

AGGGAATAAA CTACTGATAT ATACACAAAA TGGATGAATC TCAAAAATGT GAAGGAAAAT    139260

AAAAAATACA TATGATATAA ATTCCATTCA TATGAAATTT TAGGAATGGG AAAACTAAGC    139320

TGTAATTATG GAAAGTACAT CAGTGGCTGC CTGGGGCCAA GAGGATGGAA GAGGCGGCAC    139380

AGGTGATACT ACAAATGGAA ACTATCTAGG TTGACGGAAG TGTTCTGTAA CTTGATTACA    139440

GTAGTAACTG TTTGGGTATA TAAAACGCAT CAAATTGTAT AATTAATACA GGTGTATTTT    139500

ACTGTGTATA AATTATTCCT CAATAAAGTT GATTTTTCAT TAAATATATT ATTTGCTAAA    139560

ATGAGGAGAG ACAACTATTA TCTTAAAATA GTTAAGCACA ATAAAAATAC TACAATCAAC    139620

TCATTATATA TGGAAATTAA AGGAGAAAAA TAGTGGTATG ATTAATTAAA ATAAAAAGAA    139680

AACCTTCTAA ATTTTATCTT AGCTCATAGT TGTAAAAGCT GCCATCCCTA ACCAAGGCCA    139740

CCCTTGACCC TTTCTCATGT TCCATCTTTC TGTTTGTTTC ATAGTTTATG TCTCACCAAA    139800

ATCTATCAGA TAAACGTATT CATATGAAGA TTTAAATATA TTACATGTTA AGCCTTAGCG    139860

AATACTTCAA TATCTAAAGA AGGTACAAAC AAAACAAAAA TCAACACTTA GTTATAAGAG    139920

ATTACATACT CTCCAGGGAA GACCTGAAGA CTAGCCCCTT TCTGGATCCC ACTAGCCCCT    139980

CATCCCACTC CAAGCCCTCC CCTCCAATCC CATATGCACT GGGCATTCAT ACAAATAAGA    140040

CCATCAGCTC TGGATATCTG TACTGATTGA TGCTCCTGCT AACTACCTGA ATGATTGCGA    140100

TGTAAGGACA GCACTGCCTG AATCCTATTT ATCTCTCGCT ATGCCATAGC GGCCTTCCAT    140160
```

-continued

```
GCTGATGGCG TGTTTGAGGA TCCAGAGGGG TCTTTGGTTG GCAGGATTGT TTTATTTCCC 140220

CAAGAGGAGA GCCTTGATGC AAAAATAGGT GAAGAAATCA GTACAACAAA ACAGAAAGCC 140280

TAGAAACTAC TATGAACACA ATAGAGCAGA AGTAGCCTTA AGAGTTGGTG GAGAAAGGAT 140340

GGTCTATTCA ATTACCTGGG CTGAGAAACT GGCTTTCATA TGGAATAAAA ATAAAATTAT 140400

AGCTATACCC CATATCATAC ACAAAAGTTT CTACATCTAA CAAAGACACA GATGAAAAT 140460

GTTTTAAAAT TTTAGAAGAA AATAGTGCAG AATTTTAGTG CAGAATTTCT TAGACTAGAT 140520

GCAAAAACAA AAATGATTAA AGTGGCCAGG CACGGTGGCT TATGCCTGTA ATCTCAGCAC 140580

TCTGGGAGGC CGAGGTAGGT GGATTAGTGG AGGTCATGAT TTCGAGACCA GCCTGGACAA 140640

CATAGTGAAA CCCCATCTCT ACTAAAATAC AAAAATTGGT AGGGTGTGGT GGCTCACGCT 140700

TTTAATCCCA GCTACTTGGG AGTCTGAGGC AGGAGAATCA CTTGAACCTG GGAGGCAGAG 140760

GTTGCAGTGA GGGGAGATGG CGCCACTGCA CTCCAGCCTG AGCAACACAG CGAGACTCTG 140820

TCTCAAAAAA ATCTAAAAAT AAAAAGATTA TTTTTAAAAG ACTATTTTAA ACAAAAAAAA 140880

TCGTTTAAAT GATATGACAC ACTACATCTA ATATTTGGAA AAGTACTTCT TAATACTTTT 140940

AATAAAAAGA GGCGCTGAGA GCATACAACC TATCCTCAGA AGAGTGTTTG ACCTCTAGGA 141000

GGGACGCAAG CGCGTTCTTC CTTCATTTTA ACTGGTCATT TTCATTTATT TCAGGAACAT 141060

CTGAAGTAAA CACAGTCACA CGTTAACCTT TAAAAATCTA GGAGGTGCGT ACGCATAGTT 141120

CCATTACTTC AATTTTTGTA CTTTTGCATT TTAAAATATC ACAGGGAAGC TCGGTACAGC 141180

TTCAAGGCTA GGAGGGGTGG CTCTCTCTTA AGCCCTGTCC CCGCCAGCCC CAGACCTCTC 141240

GTCCCGCCCC CATTGCCCAG TCCCCACCCT CACTTCCCCA TTTCCCCACT CCCGCGGTCT 141300

CTTAACGCAC CTCGTTTTTC GTCCAGTGGA CTCAGACCTG TAGTCTTCCA CCAGGATCGG 141360

CTCCTTTCCC GGAGCTCTCG CTCTTAGAGG AAATTGAGAG AAGCATCAGC GGAGACCCAT 141420

CTGTGGCTCT CCAGAGGGCG CGGCATTCAG ACCCCAGATC CAGCTGTGAG AACGGACCCC 141480

AGGCTCACAC CAGGCCTGCG GGAGGCGGCC CACCAGAGGC GCTAGAAAAC AAGCCTCGCG 141540

GGGAGGCGCG CAGGGCGACT GCAAGCTGTA GGGGCGCTG GCGCCCTCAC AGGCCAGGGG 141600

CAGGGCCGGC GCTGCGGGCG GGGCTCCTGC GGCGTGAGGG GCGGCCCCAG GCCAGCAGCT 141660

GCGCCCTGGC TGGGAGCCGG GGAGCATTTG CTGCTCTGCT GGACCCTGAG TCTGGCGGCG 141720

GGCGGCCTCC TCTCCGCTCC CCGCCCGCCA TCCCCCAACT CCCGATCTCT CTGCTGCGTC 141780

TGGCCTCAGG CTGAGACCCC AACGAATCAT TCCCCGCATG GGAACATTTT ATGATATAAC 141840

TGAATTCAGT TTTATGTATA ACTGAATTAC GGATATGAGA ATCTCAAATG AGGACGAATG 141900

GTTTTTACGC ACAAAACATG AGACACAAAT CTGTAAGAAA TATAAAGTCG TGACCACGTC 141960

CTTTCAGAAC TTTAACCTGT TTGCTGAAGT ACGTCAGTAA CAATGGCAGG GAAAGGGTAT 142020

CTTAAATTTC ACCACAGCCT CAAAGAGGCC ATTTCGTGGA TCCGCTGAGG CTTGGAGTCG 142080

GCCTTCTGAC CACGAGTCCT GCGGCTATGA AAGAGGAAGC CGCGGTTCAG GGCGTCCTCG 142140

CGAGTCGTGC AGCCCGCCCT GCTCCAGCTG GGGACACCGG TGGTCACGGC GCTTTCCAGC 142200

TGCAGATCCA GGCGGCAGCC CAAGATTTGG TCCAGCCGCC AAGGGGTGGC TCGAGTGACT 142260

GACGGGCCTT GAACGCTCCC AGGACCCACA TCTGGAGAGG GAGGTGGGGG TGGGGTGCTG 142320

AAGTCATTCT TGGGGCCCCT GGGGGCGGGC ATGGACCTGG GTAAGGCCAG AGAAATTGAC 142380

ACCTCGTGAC ATCCCTGGAA GAGAAGTACG TTCAGTGTCA CTCCAGAGCT GAAACCGCCT 142440

TCTGGCTGGT CCCTCCTCAC CTACATACTT TTCTAATTTG TCTGGAGCAG GCCGGGCATC 142500

TGTATTATCT GGTTATTTAA ATATCTGGTT ATTTAAAAGC TCTCCATTAA ATTCACATAC 142560
```

```
ACGAAAATAA AAATTAAAAA AAATTTTAAA AAAAAGAAAC AAAAGCTCTC TAATGACCAA    142620

GTCCTACACG ATAGTGAATA AATTTTTTTG TGTGGTCCCT AAAATTGAGT TCATGCCTTT    142680

TCTGAAGTAA TAGACGCCCA GAGAAGGGAT CGACTTACCC ATCATGCCAC AGAGATTAAT    142740

TGGCCCCAGA ATTCTTTAGC AGACCGTGTA TATGAACGTC CTTTGCAATC ATATAAATTA    142800

ACTGGGAAAA CCTCATTTAG TATGTTACAT GCCTAGCGTT TTGTGCCTGA ACACCTTACA    142860

AGAACCAGGG ACTATTGCCC CAATATTATA TTTCAGGAAA GGAAGGCCCA GACAAATGGT    142920

GTCACTGGTC CACTTTCACC CAGTTGGTAA ATGAAACCAG AAATTATAGC TGTACCACAG    142980

AAAGGTGAAA ACGTTTCTTT TATAATTTCA CATACAATCT TTAATGGACC CAGTGTCCAA    143040

CACATTAAAG CAAGTGCTCA GGAGTGACAT CAAGATGTAA AAAATAGTCC TGTCCTCAGG    143100

GAGTTTAGGT CTTGGAGAAA AGAGACCCAA GGAGACACAA GACAAAGGGG AAAGAGAAGG    143160

AGCGCTGAAG ACTGAGGACC CTGCCTGTGG ACTGAAGTGA GGATGGGGAC ACCCGATGCC    143220

CGGAATATGA CAGTTTGGAG GGGCCTGAAG GACTCTTCTA TTCTCTATCA GAAAAACAGA    143280

ATTACTCTCC TAACCAGAAA AGGTATTTCA ATTTATATTT TCCATCACAG CACTTTTCTG    143340

GTGATAATTT AATGTGTTTT AAAAAATGTA TCACAGTGAT GGCCTGGTGT GAAATAAATA    143400

ATAAAATTTT AAGAATTAAA AAATATAAAA ATCTTTTATA TAGACATTAG GAGTTACAAG    143460

GATAACTGTG AATTATAATT AGTAATTAAA TTGAAATACT GATTATTTTC ATTTTTATTT    143520

AATTATTTAA TAAAACCTAT TTAACATTTA ATATTTATCA GTAATTAAAT CTAATTGTTA    143580

ATATTTATTA TTATAAATTA TTTTAGAATT AAAAATAAGT GTAGAAGCGA GGCATGGTGG    143640

CTCAAGCCTG TAATCCCAAC ACTTTGGGAG GCTAAGGTGG GAGGATTGCT TGAGCCCAGT    143700

AGTTCAAGAC CAGCCTGGGC AACATGGAGA AACCCTGTCT CAATACAAAA AAATGAGCCA    143760

TGTGTGGTGG TGCGTGCCTG TAGTCCCAGC CATTCTGGAG GCTGAGGTGG GAGGATGACT    143820

TGAGCCTAGG CAGTCAAGGC TGCAGTGAGC CCTGATCTTG CCACTGCACT CCAGTCTGGG    143880

CAACAGAGCA AGACCCTGTG TCAATATACA TATGGACAAA CTTAAAATTT AAAATGAAAG    143940

CATACTACTG ATACAGAATT GAGTAGAGAT GCAAAGCTAG TCCTATAACC AGAACAATAA    144000

AGATAAAAAG GAGAGTGGAA GAAGGTATGT CATGAATTTC ATGATAAATG GCAATTGCAA    144060

ATATCCTGTA GCAGAACAAA ACAACAAAAC TGTAGATAAA ACATATCCAA CCCTTTGAAA    144120

GGCCAAGGAG GGAGGATTGT TTGAGCCCAG AAGTTGGAGA CCAGCCTGGG CAACATAGTG    144180

AGACCCTGTA TCTAAAAAGG AAGAAAGAAA AAAAAAAAAA GGATGATAAA GTAGACAATA    144240

TTGAAAGCCA TTTTCTGCAA ATACATAGTG AATTTGATCA GTAATTTTCT TCCAACAGTG    144300

CAAAAATGAA TAGATATTAG TTGCCTGAAA TAAAAATCAA ATATCCAACA AAAAATATTG    144360

ACTATCTAAT AGTATCTAAG CTAGTAAATT TGGCCAGTTA TAAAATGTCT TAAATTTTTA    144420

TTTAAAAAAA GAAAACCATA TTTATAAGAA GAGGTGATAA AGAGAAATTA TTTCAGTTAT    144480

GAAGATTTTG TTAGAAAACT ATGAGAAAAA AACTATTTTT TGTTTTCAAA AAGTGAAAGA    144540

TTAAGTTACC AAACAGTTGC TAAAGAATAC CAGATGGCTG AGCGTGGTGA CTTATGCCTG    144600

TAATCCCAGT ACTTTGGAAG GCCAAGGCAG GAGGATCATT TTAGGCCTGG AGTTCGAGAC    144660

CAGCCTGGGC ACTGTAGCAA GACCCGTCTC TATTAAAAAA AAAAAAAAAA AAAAAAAGA    144720

ATACAAGACC TTGCTAACAA TAGCAAAGAT CAATTAATTC AAAATTTGAA AAACTGTAAT    144780

TTATTTAGCT TTAGAGTACT CTCGTGTATA TGAGATTGCCA AATTAATACT TTGGGTGCAT    144840

TTCTTTTCTC AAAGGACTTG CAAATTTACA AAGAAGTGTT GAAGAAAAGC CACACATTGG    144900
```

```
CAGGTAATGT TTGCAAAAGA CAGATCTGAT GAAGAACAAT ATTTTTAGAA TATACAAAGA    144960

ATACTTAAAA CTCAACAGTA AGAAAATAAC CTGATTTAAA GCAGGCCAAT GACCTGAACA    145020

TCTGTTCACC AAAGAAGATA CACAGATGCA AGTATGCATA TGAAAAGATG CTTGACATCA    145080

TGTCATTAGG GAACTGCAAA TTAAAACAAG TAGATACCAC TGCATACCTA GTAGAATGAC    145140

CAAAATTTAG AACACTGTCA GCACCAAAGG TTGCAAAGAT ATGTAGCAAT AGTAACTTGT    145200

TCATTACTGG TGAGAATGCA AAATGTGCAA TCACTTTGGA AGACAGTTTG GTGGTTTCTT    145260

ACAAAAGTAA CCATACTTTT ACCATAAGAT TCACCAATCA CACTCCTTAG TATTTATCCA    145320

AAGGAATTGA AAACTTATCT CCACACAAAA ACCTGCACAT AGATGTTTAT AGCAGCTTTA    145380

TTCATAATTT ATCCAAAACT TGGAAACAAG ATGTCTTTCA GTAGGTAAGT GGATAACTGT    145440

GGTACTTCTG AATAATGGAA TGTTATTTAG AGTTAAAAAG AAATGCATTC ACTTTGGGAG    145500

GCCGAAGTGG GTGGATTGCT TGAGGCCAGG AGTTTGAGAC CAGCCTGGTC AACATGGGAA    145560

AACCCCAATT AGCCGGGCAT AGTGGCGTGA GCCTGTAATC CCAGCTACTC GGGAGGCTGA    145620

GATATGAGAA TCGTTTGAAC CTGGGAGATG GAGGTTGCAG TGAGCCAGTG CCACTGCACT    145680

TCAGCCTGGG CAACAGAGCA AGACTCCTCT GTCTCAAAAA AAAAAAAAAA AAGAAAGAAA    145740

AGAAAAAAGA AAAGAAAAA GAAAGAAAC GATCAAGCCA TGAAAACACA TGAAGGAAAC    145800

TTAAATGTAT GTTACTAAAA AGCCAACCTG AAAAGACTGC ATACTATATG ACTCCAACTG    145860

ATGCAGGGCA AGCAAGCCAA AAATTAGGGC TTAGCCCGGG AAGAATTCAA GGGTGAAGTG    145920

GTGGTGTTAG CAACTTTTAC TGAAGCAGCA GTGTACAACA GCAGAACAGG TACTGCTCCT    145980

TGCTGAGCAG GGCTAACCCA TAAGTAATGT GCCCAGAGTA GCAGCTCAGG GGCAGTTCTG    146040

CAGTAATATA CCTGCTTTTA GTTAAGTGCA TGTTAAGGGG GATTATGCAG AAATTTCTAG    146100

AAAAAGAGTG GTAACTTCGG AGTAGGTACA GAGGAAAGAA GTCGATAATG TCCTGTTGTT    146160

GCCATGGCAA CGAAAAACTG ACATGGCGCT GGTGGGCGTG TCTTATGGAG AGGTGCTTTA    146220

ACCTCGTCCC TGTTTCGGCT AGTCTTCAAT CTGGTCCGGA GTAAAGTCCC TGCCTCCGGA    146280

GTTCACTCCT GCTTCCTGCT TCACAACTGT ATGACACTCT AGAAAAGACA GTAACTATGG    146340

ACACAGTCAA AAGATTAGTT GATAGAAATT GGGTGACAGG AAGTGTTGAA AAGGCAGAAC    146400

ACAGGATTTT TAGGGCAGTG AAACTTCTGT GATACTATAA TGGTGAATAC ATGACATTAT    146460

ACATTTGTCA AAACCCATAG AAAGCACAAC ACCAAGAATA AACCCTAATG TAAATTACAG    146520

ACTTTCGTTG ATAATGACGT GTCAATGTAA GTTCAATTGT AATAAATGTA CTACTGTGGT    146580

GCTGGATGTC TATGGTGGGG GGACATTTTT GCTTCAATAG TTACAGTTGA AGTAAATGTT    146640

TGTGTTTCCC ACAATGCATA TGTAGAAACT CTCACATTCA ATGTGATGGT CTTTGGAGGT    146700

GGGCTCTTTG GGTGATAGTT AGGTTTAGTT GAGATCCTAG CAGATCGAGT CTTCATGATG    146760

GGCATGATGG GACTGGTCCC TTATAAGAAA AGACCAGAAA GCTAGCTCTC TCTTTGCCAT    146820

GTGAAGACAT AGCAGGAAGG TAGCCATCTG CAAGCTAGGA AAGGGCCTTC ACAAAGAATC    146880

AACTCAGACC TCAGAACAGT GAGAGATAAA TTGTCGTTGT TTAAGTCACT CAGGCTGTGG    146940

TATTTTGTTT CAGCAGCCCA ACCTAAGACT GTTAATTGGA TTAGAAATTT CCTTTTGGGG    147000

ATGGTGTGTG GCGGGCGGGG GGCGGGGAGT ACCTTTGTTA AGCTTTTATA TCAATGAGTT    147060

TGTAGGCTTT TCTTTTTTGG TCATTGACTA GGACAGTTTA AATAGTATGA GTGTGAAGGA    147120

GATTGTTGGT CATCTATTCG ATGTCCCTTC TCTGTTTTTT AATATGAGAA CTCCTGATTT    147180

TCAGCCAACT ACCCTGGAAA AAAAGCTAAT CTTTCTGACT TCTTAAGTGT GGCCATGTAC    147240

TAAATTCTGG CTAATGCAAG GCAAGCCAAA GGTTTTATGA TAGGTTTTAG GACACTAGAG    147300
```

-continued

```
TAAAAGAGAG CTGTTGCACA CATGCTCTTC ACCCTACTTT TGTGTCCTTT TTTCCATCCT  147360

ACAACTTGGG TTGTGAGTAT GATGGCTGGA ACTTTAGTGG CTCTCTTGGA TCCCAGGGGT  147420

AATTGAGGGG TGGCTGGAAG GAATCTGTGA TTTTCTGGAG TTTCCATACA CAAACAAGAC  147480

CTGGATTTTC TGGGCTTCCC AGACTTCCAC ATCTAGACTT GCTTTAAATG GGAGATAAAT  147540

AAACTTGTTT CAGCCACTGT CATTTTGGGC TATTTTATAG AACTTAATCT AATCTTCAAG  147600

GGTACATGAA TTGCTTTTCC TTAAAAAAAA AATCAGCCAT AAAATCATCT TCTTTTTTCT  147660

TTTGTTCCCC ACATTATTTA GTTGGAGCTC TGTAACTTTT TTTTTTTTTT TTTTTGAGAC  147720

AAGGTCTTGC TCTGTCACTT AGGCTGGAAT TCAGTGGCAT GACCATGGCT CACTGCAGCC  147780

TTGCCCTCCT AGGCTCAAGC AATCCTCGTC TCAGCCTCCT GAGTAGCTGA AACTAAGGCA  147840

CATGCCACCA TGCCCAGCTA ATTTCTTTTC TTTTAGAGAT GGGAGCCTTG CCCAGGCTAG  147900

TCTCAAACTC CTAGCCTCAA GTGATCCTCC CATCTCAGCC TCCCAAAGTG ACAGGATTAC  147960

AGGTGTGAGC CACCATGCCT GGCTGCTCTG TAAGTGTCTG AATTTCATTT TGTATTTATC  148020

AGTCTGTTTA GATTTTCTTT CCCTTCTTGG GTCAGTTAGG CCATTGGTTT CTTTTTAAAG  148080

GTTTTCAAAT TTATTTGCAT CTAATTCTTC AAATTACTCT CAAAATTATT CCAGTATATA  148140

TTCTTTTGTT CCTATTTTCT TCTGTATTCT TTATTAAAAT AGCTAATGAT TTATCTAGCA  148200

GGACTTATAT TCTTTCCATA ACTTTCCTGC ACCCCAATTA ATCTCCAATT TTATATTTCT  148260

TCTGGCCTTC CTTATAGTTT CCACAGGTTT ATTTTATTCA TTTTTTAAAA CTTTTATTTA  148320

ATTGTTATT TTATTATCAT TCTTTCTTAT TCAGCAATCT AAGTGCTTAG GGATATAGAA  148380

TTTCCTCTAA GCAGCATATG CTAGGCTTTA ACAATGTTAG GGAGGCCTCC CCTTTCTGGG  148440

GAAGACCACA CTTACATTAA CACAGGACTG TGGGATGCCA AGAGGTAGAG AAGAGCTTAT  148500

GAATATCCAG ATTACATCTT CACTGATCCT GCACAAAGGT GGGGTTCCTC GGTTACCCAC  148560

TGGGTCCTAT TACCCAAGTC TGGGTCAGCA TACCGAGACT ACGGGTATAT AGAACAAGTG  148620

CAACTGGCGA TAATCCTTCT GTTGGGGAGA AAAATCTTTT TTTTCTATTC ATCTTAGGTT  148680

CTCCATCTGT GGCCCTATCA AGTAGACTAA CAAAAGACAG ATTGACAAGA CAGAAACAAA  148740

GCATGTGCAT TGTACAAACA CAGGGGAGTA CTGAGATGAA TACTCAAAAG AGGATTTAGA  148800

ACTTGGGCTT ATATAGCATT TTAAGAAAAG AATACATTTT TTAAGTGACA AGGAAGACGA  148860

AAAGGACTTT GAGTTTCTAG TGCAGTAAAT TGTGGGAAGG CAACTTTTTC TTTCCCTTTT  148920

TTTTTTTTTT TTTTTAAAAA AAAAGACTTC TCTGGTGCTA TGTCCAGGCT GATAAGAGTC  148980

TAAAGTCTCT GGTGACTAAC TTTTGTTCTT CCCCGAGTAA GAAGACACCT TCACAATTTC  149040

ATATCCTGCT TTTAGGCAAA TAGGGAGAGG GCAGAGGTGT TTGTTTGTTT TTAATCTATT  149100

TTTTTTCTCA ATTGTCTTCA ACTCAAAATA CTTCTTATGC CAAAGATGGC ATATTCTGCT  149160

ACCCTTCACT TACTACTTAC AACCCAGCCT CTATCATCAT AATTAGAACT TCTGACCCTG  149220

GGGAACATGG GCAATAGTTT GAACTCTTTT ATATCTCCCT TAGGCAGAGA TGGAGGCCCA  149280

GCCATGCCTC TGACATCTAG ACACAACTGT TGCTTCATTT CTCCTATTCT CAGAGGTGAT  149340

GTTGTAGGAC TTCAACAAAT ATCAGTAAAC ATTAATTTTT TTTTCCTTG  AGGCACAGCA  149400

TGATCTTGGC TTACTGCAGC TGCTGCAGGC TCAAGCAATT CTCCTGCCTT GGCCTCACGA  149460

GTAGCTGGGT TACAGGCCCC TACCACCATG CCCGGCTAAT TTTTGTATTT TTAGTAGAGA  149520

CAGGGTTTCA CCATGTTGGC CAGGCTGGTG TTGAACTCCT GACCTCAAGT GATCCACCTG  149580

CCTCAGCCTC ACATAGTTCT GGGATTACAG GCGTGAGCCA CCATGCCTGG CCATCAATTT  149640
```

```
TTATGTCAAC TCTAAATTAT AACATTTAGC AATTTTGTGA CTTTTTATGG TCATCATTAA 149700
TGTTGTTTAT GTTTTAGTTG TAGTCCTGTC ATTACTCACT CGGGTATGGT AATTTGGTCT 149760
TTTTCAAAAT GAAGTTAAGG TCTATTTGCT CTTCTCTGAA TCATAATAAG AACTGCCAAC 149820
AGCCATTTCA GCAATAACTA TTTACTGAGA TTTTAAAATA TTTCAAGGTA ATTGGTCCTA 149880
GCAGACTGGA AAATACCAAA TTCTTTTCCA GAACTGAATC CCCCATCAAA GTTCAATTTT 149940
ACTCATAATT CCCTTTTCAT TTGAAGCATC TCATTGTAAG CCAGTCTTAA CCCTTCTCTC 150000
ACACTTTGCT TGGCTGTTTC TCAGGTAGAA CTCAGTAAGT CTGGTAGCCT CCAGGACTGC 150060
CGCTTAGATT ATTAAACAAC ATGTCAGTGG TTGGAAGAGT CAATGTTATT TTGATTTTTC 150120
TGTTTTGTTT TGTTTTAAAT GCAGTTGGCG GATAATTGCA GCTTTCTTTC ATTCCCTACA 150180
TGAGTTCAAA TGGCAGCAAA CAAACTAGGA GAACGCAGAC CTTCTGACTT GTGGGTACCC 150240
CTACTCATCA CCTGAAGACC CTTGGAAATC AAAGCCCTGA CCCATTAAAG ACGGATGGAG 150300
ACAGCAACAT ACGATCATCA CTATTATCTT GCTTTGCCCC AGTCCAGGTT AACCATCTGT 150360
GGTATTTTTA GTTGCTAAGT CCATATATTC AACATAAATC AATTATATAT CCACTAAAAT 150420
CTCAGCACTA GTCTAACTAC TAAGGAAATG ACAGCGAAGA AAACAGACCA AACGTCTGCC 150480
CTTATGGGAT TTATATTATT TTCTCTGTGC TGGTTAAACC AAGGAGCTTC TGCTCTTTTC 150540
CTTAGTCACC TGGGGAGGC AGAAACAAAG GAGAATATTG ATAAACCTGG AAATAGGGCC 150600
GGAGAGTATC AGAGAAGGAA GCCTTCGGGA AAGTAAAGAT GTGGCAGCCA GTATTCCCGT 150660
TATAAAAGGA TACAACTCCG GCCTCATAGT CCAGAAAAAT TCCCACAAGC AGGGGCTGCT 150720
CATGCAGATG AAGGGAAGTT GGGGGAGAAG TAAGTGCTAC ATAGCCTTTC TTTTTGCACA 150780
GCCTGAGGGT CCAGAATCCA GACTGAGGCT CTTGCTTCAT GCCAGTGCCC CTCTGCACAT 150840
TTTCCATACA AACTCCTAAA TCCCATCCGG TTCCTTCGCC AACATCCACT TCAAAGTAAC 150900
GTCTTCCTGA GGTGAAGCCT TCACAACCCA AGACACAGGG GAAGGCAGTA AATCTCCTGG 150960
AAGATGTGTC CTGATTCTCC TGGGTGTATC CACGAGTCAC TTGTCTCCGA TCCTCAGAGA 151020
GAATTAGTTC GTGATGAGCT GTATCTGGAT CCAGAGTCAC ACTAACTGCA AAACAAAACA 151080
AAACAAACAA AATAATTTT GTTGCTGTGA AGAACACAGG TTATTTATT TTATTTATT 151140
TTGAGATGGA GTGTTGCTGT CACCCAGGCT GGAGTGCACT GGCACTATCT CAACTCACTG 151200
CAACCTCCAC CTCCTGGATT CAGGCAATTC TCCTGCCTCA GCCTCCGGAG TAACTGCGAC 151260
TACAGGTGCG CACCACCACA AGTGGCTAAT TTTTTTAAAT TTTCTGTAGA GATGGGGTTT 151320
CGCCATGTTG GCCAGGCTGG TCTCAAACTC CTGACCTGAA GTGTTCCACC CACCTCGGCC 151380
TCCCAAAGTG CTGGATTACA CAGGTGTGAG CCACCATGCC CAGCCACAAG TTATTTTCAA 151440
TAAAACCAGC CTGTGTTCAA ACCCAACTAT TGTTTCTTAT AAACTGGGTG AGCTTAGGCA 151500
AATCATTTAA CTTTCTGAGC CTCAGTTTGT TAACTATAAA GTGGAAATTA CCGTATTTGT 151560
TGCAGAGAAT GGTGGGTAGG ATTGAATAAG CTTATGTTTG CTTAATGCTT GGTAAAATTC 151620
CTGGTACATG GTAACCACCT AATAAGTGGT AGTTGTTGGG GTGATCAGGC CCAACACCAG 151680
GCCGTGGGGG CTACAAAGTC CGGCGGGTC AAAGGAATGA GAAAAGACAA GTTAAGAGTG 151740
CATAAAGTGG GTCCAGGGTG CCAGCACTAG ATTGGAGGCT GCAAAGGCCC TAAGCTCTGG 151800
GAGCCCACAC TATTTATTGG TGATCAAACA AGAAGCAGG TGGTGAGGAC GTGAGGGTAA 151860
ACAGGTGAGG GCATGAGGAC ATGGGGGTAG AAAGGTAGTG GTGCATTAAG CGTAGCTGTG 151920
ACAGTTTAGC ATTTTCTTTG ACACATGTAG AATATACTCT GCTGCTTGAG ATAGTAGAGG 151980
ACACGTTTAT GAGTGAAAAG CAAGGAACCA ACAAGTCTGT GCACTTTCCA GAGGCTATGA 152040
```

```
GGGGTTTTAT GCCCTGAGCC CTGGGTTCCA TCCAAGCCAC AAGGGGTTTT ATGCCCTAGG    152100

CTTAGATTTG TGGTGCGGCA GGGCAGCCTT CCACCATTTG GCACAGAGCT TGGTGTTCCA    152160

AAGGCCACGA GGGGTTTTGG ACCCTGGACC CCGGACATCT TCCAAGACTC TTTTACATTA    152220

TGACAGACAA GCCAGTCCTG CTTCAGCTCT TCTAACAACA TGTAGTAATA ATGATATCAT    152280

CAACATCATC TTCGTCTTAA TTATTCAAGG ATGCCAAGGT ACAGAACTAA CCTGTTAATA    152340

TGGTTACCAT CCTGTCCAAA GTTCTTCTCC CATGCAGGAC TTCCAGGAAT CATGAGACAG    152400

TTGAGCAGAA AGATACCTTT TCCCTTCTCT ACTGAATAAC CACCAACATT GAGAATCAGA    152460

GAGGGAAAAT GACTCAGCTA ATGTCTTAGC TTGTTATTGG AAGACCCAGG TCTCATGACA    152520

CATGCCTAGT CCCATGACTT TTAATTGTAA GCTCTTCTCT TTCCCCTCAG ATAATGTTCC    152580

ATAAGCATTA GTATGAGATA ATAATACACT GAGGACCAAT ATACATGAAA AATATCAGAC    152640

TAGAATCAAA CAAGACAGAA AAAGATCTG ATAACCTAAA GTGAGATACT GAACAGTATG    152700

CAGTTTTAAA AATAAAAAAT GGTAATAGGA TGTTCTAACA AGAGAGTTAA GAAACCACTG    152760

TGCTACTGAG TTAAATGTTG ATCAGTTGGT CTGTGACAAT TAAGGAATTC AAGTATTCAG    152820

AAACACTTCC TGTGCTGGAT GCTCTCTGTT TGTTCTTCCA AATAATCCCT CACTTTTCCC    152880

TGTCTTGCTC TGTGCCCAGG AAGGCTGACA TGGACAGATT AACCAGGCTT TCCGCCCTCT    152940

GGCTTGGTTC AGCCAATGGG AAGCACCAGA GGAGACCATA GGGCACAAAG AAGCAGCCTT    153000

GGGAGTATTC AGTACCCCAG TCCCACGCTA TGATTTGGAG GGTCTGCATT CCTCTGCCTC    153060

TGGGCACACT CTAGTATAGT TACAGCTCCC TACACCTGCC ACTTGAGGCC CAGAGGAGGT    153120

GATGGCTCTC TAACTGTTCC TAGTTCTGGG TGCTTCCTGT TCCTTGTGGA TTTCCCAACT    153180

CCTCACCTTT GTAAATACCC TCCTTTTTCA AACTCTATTC AGTTAGCTTT TATCAGCCTG    153240

ACTCACAGAA GTTTGGGGTT TCAATTCATA TTACCTGAAT GACCCAGGAA AACCCATGTT    153300

GAGAAATTAA AATGTTTACG GGGTGGTAAT ACCACTTAAG AGAAAAAATA TCAATTGGAT    153360

TTTTAAAATT CCACCTATCT ATTGGTGTGA CACATCAACA AAAACATATA GAAAGATTGG    153420

AAGCTAAAAG ATAGATAATA TAGTCATATA CTGTTATAGT ATTATATCAA AAGATATTAA    153480

GTCAGAGCAT TATTAAGAAT GGAAGAAGGG CCAGGTGTGG TGGCTCATGC CTGTAATCCC    153540

AGCACTTTGG GAGGCCAAGG CAGGCGGATC ACTTGAAGCC AGGAGTTCAA GACCAGCCTG    153600

CCCAACATGG CAAAACCCTG GCTCTACCAA AAATACAACA ATTAGCTGGG CATTGTGGCA    153660

CATGCCTGTA ATCCCAGCTA CTTGGGAGGC TGAAGCACAA GAATCACTTG AACCGGGGAG    153720

GCAGAGGTTG CAGTGAGCTG AGATTTCGCC ACTACACTAC AGCCTGGGTG ACAGAGAGAG    153780

ATTCTGTCTC AAAAAAAAAA AAAAAGAAAG AATGAAAGGA GTCACCTAAA AAAGATAACA    153840

CAATTTTAAA CATAAATGTA CTACATTATT AGTGAATTCA TGTTTAGAAT TGTGTTAATA    153900

TACAAAGCAA AAATTGTAGA ATTATAGGAG AAATGGACAA ATCTACAATC ATCATGGGAT    153960

GTTTTAACAT TCTTCTTTCC ATAATTGATA GATCAGGCAG ACCAAAAGAA AGAAATAAGG    154020

GAAGATACGG AAGGTCTGAA CAATCTAAGA AGCGCAATCT CATAGTCAAT ACATAAAGCT    154080

CAGCAATTGT TTAATAATAG TAAGCAGAGA ATATGCAGTT TTCTCAGGTA TAGATGGAAC    154140

ATGCACTAAC TGAGTAAATA CTAGGCAGAA AACAGTCTGA ACAAGTTTCA ATAAATCTGT    154200

ATTACACAGA TCATTTTCTC TAGCCTCAAT ATAAGATTAT AAACCAATAA TAAAAGATG    154260

ACTAAAAAGA TTCTAAATAT TAGGAAATGT AAACTACTAA TAAGTCATTA GAAGATGTAT    154320

AGAATGGAAC AATAATAAAA AGTTATTTAT AAAAATATAC AATGAAGCTA AAGCAGAATT    154380
```

```
TTAAGGAAAA TTTGTAGGCT TTAAATGCTT ATCTTAGAAA AATTAAAAAG CTGAACATTA  154440
ATGAGCCAAG CATCTAATTT AAATTTTAAA AAGAACATAG AAAGCCAAAT ATAATTTTTT  154500
AAAAAGAAAA AATAGATATT AAACAATATA ACAGTGAAGT TAAAGAAAAC AAGAATGCAA  154560
TAAAGAGGAA AAACAAACAA AAAAAAAGGT AGCTTCTTTT AAAAGAAATT TAATAAAATA  154620
GACATACCTC CAATGAGATT TATCAAAGTA AGACAGAAGG CACAAATGGA ATGAATACAG  154680
AAACTTTTTA AATATTACAG AACTTTATAA TAAATCTTAT GCTACTAATA AAATTGAAAG  154740
TACTGATAAA ATTATTACTT CCTAGAAAAA ATATTTCTGA GTAAAACTCA CTCAAAAAAC  154800
AAATAAAGCA TGGGCAGACC TAACATTAAA GAAATGAAAT CACTACTTTA AATTTTACCG  154860
ACAGATAATA AAACGTGCAT CTTTATCAAG CAAAAATGGA ACTTGTCAGT TTTATAGGAA  154920
ATTTAGAAGT CAAGGCATGA GTAATGCCAA TCTCATACCA AATCCTACAA AGAATAGAAA  154980
ATTATGGCTC CCGCTTATAG ACATAGATAT AGAACTCCTG CACAAAATAA TATAAATAAC  155040
AAACCAAATT TTATATTTGC AACTATACAT ATTATATGTG TATGTATTAT ATATGTTAAC  155100
ATATACATAT ATAATATGTA TAGCATATGT TCTACATATT ATATATGTAT AGTGTATGTA  155160
TTTTACAATA TATAAATGAA AACCCAATCT TTAATATATT CATCTAGATT GTCATATATG  155220
ACATATATAA TACATTACAT CAAAAATGTG TACAATAATC AGGCCAGGCA CAGTGACTCA  155280
TGCCTGTAAT CCCAGCACGT TGGGAGGCTG AGGCGGGTCA ATCACTTGAG TCCAAGAGTT  155340
TGAGACCAGC CTGGTCAATA TGGCCAAATT CCATCTCTAC AAAAAATATG AAAAATTATC  155400
CAGGCATTGT GGTGCACACC AATAGTCCCA GCTACTCGGG AAGCTGAGGT GAGAGGATCA  155460
CTTGAGCCTG GGAGGTGGAG ATTGCAGTGA GTCGAGATTG CGCCAGTGCA CTCCAGCCTG  155520
GGTGGCAAAG GGAGACCCTG TCTCAAAAAA AAATTAAAAA ATTAGCCAGG TATGGTGGCC  155580
TGTTCCTGTA GTCCCAGCAA CTGGGAGGC TGAGGTGAGA AGATCACTTT AGCTCAGGTG  155640
GTGGAGCCAT GATCGCACCA CTGTACCACT CGGCTTGGGC AACAGAGTGA GAGCCTGTCT  155700
CGAAAAAACA AATATATACA CACAGTAATC AATATATATA TTATATGTAC CAATCAATGC  155760
TTCACTTTTA TATATAATAT AGATTACATC TTATTAGATA TATAGTATTC CTTCTCCATA  155820
GATAGATAGA TACAGATATA GACATAGTAT CCTCTATCCA TATTAGAGAG AGGATACTAT  155880
ATATATCTAT AGCATATAGA GATGCTGTCT CAAAAAAATT TAAACATCAG CCAGATGTGG  155940
TGGCCCATGC CTGTAGTCCC AGCTACTGGG GAGGCTGAAA TGAGAGGATT GCCATTGATC  156000
CTCTCATTGG TTGAGCCATA ATCGCACTAC TGCACCACTC AGCCTGGGAG ACAGAGGGAG  156060
ACCTGAGGTG GAAGGATATA GATATAGATA TATAAATAAA TATGTATAGA GAGAATATAA  156120
TATATGTGTG TATGTGTATA TATATATATT ATGAAGACAC TGGGAGAGAA TACTATATAT  156180
ATATGTGTGT GTGTATATAT ATATTATGAA GACACTGGTG GATGGTTTC ATTACCAATT  156240
GGACCAAGAG TCCAGGTATG GAGCCAACAT GCAATGTTGT TGTTGACTGA GCTGGCAGAG  156300
CACTGGTCAT AGTTACGGGA AAAGAAGGTC TCCAATGAGA CATACTTAAC AAAATATATG  156360
AACTTGCCAT ATACGTGGAG AGTTCTGGTG TGTATATAGC CTTCTCTCAC CAACCTAGCA  156420
ATTGTCTTCA TCATCATTAT AATGCTATCA GAGCAAAGAT GACAGCTAAA TTTTTTTGTC  156480
CCTTTCTTCT TCTTTCTCTT CCTTCCCCTC CCCCACCTCT TTCTCTTCCT CCTCCTCCTT  156540
CATCTCTCTT CTTTTTTTTT TTGAGATGGA GTCTTACTCT GTCGCTCAAG CTGGAGTGCA  156600
GTGGCACAAT CTCAGCTCAC TGCAACCTCT GCCTTCTGGG TTCAAGCAAT TCTGCCTAAG  156660
CCTCCAGAGT AGCTAGGACT GCAAGTGCAC ACCACCACAC CTGGCTAATT TTTGTATTTT  156720
TAGTAGAGAT AGGGTTTCAC AATGCTGGCC AGGCTGGTCT CAAACTCCTG CCCTCAAGTG  156780
```

```
ATCCTCCTGC CTCGGCCTCC CAATGTGCTG GGATTACAGG CGTAAGCCAC TGTACCCGGC    156840

CTCCTCCTTT AATAGACAGG GTCTAGCTCT GTTGCCCAGG CTGGGTACAG TGGCGTGATC    156900

ATAGCTTACT GCAGCCTCGA ACTCCTGGGC TCAGGAGATC CTCCTGCCCT AGTCTCCCCA    156960

GTAGCTGGAA CTACAGGCAT AGCACACGGG GCTAATAAAA TTAATTAGGT GATAAAATTC    157020

ACTGCCCACT GATGACTAAG CTCTTTGGAC ATAAAAGACA CAGACCTTGA AGGAAAATGT    157080

GTCTACTTAA TTTTGAAACC CTATTTATCA AAAAACAGGA TGAAAATGCA AAATGCCATC    157140

CACATGCCAG AAGATATCAG CTATAATAAG TTCCCATAAA TCAATAAGGA AAAGAACCCA    157200

ATAAAAATTA TTAAACCACA GTAAATCATG GGTAAATCAC AGAGGCCTGA AGGGCTAATG    157260

GACATACAAA AAGAATCTCA ATCTCACTAG TGAAATCAGA AAAGCACAAA TTAAGTACAC    157320

AATTAGGTAC CATTTTAAAT CTGTAAGACT GTCAAAATCA TAAATTATAT AAGTAAAGAC    157380

TCAGGGAGTT TTGGAGGAGT GAGAGCTCTT ATATTGCTTG TGGGTAGAA TTGGAACAAT    157440

TTCAAGATCT GTAGTATCTG GTAAAATTAT GATATGCATC CCTCACACCA GCATGTCACT    157500

CCAAGGTATC TCCCTGGAGG GAACATTTAC GGGACACAAG GAAGCATGGA TAAGAATGTT    157560

CACAGTAGTA TTGTCTGCAA CAGCAACAAC AACAAAAAAA CCCAACTACA CACAACTTCA    157620

ATGCCCAGTC CACAAGGCAA TGGATTAAAT AAACTTCAGG CCGGAGATGG TGGTTCATGC    157680

CTGTAATCCC AACACTTTAG AAGGCCGAGG CGAGAGGACT GCTTGAGCCC AGGAGTTCAA    157740

GACCAGCCTG AACAAAATAA AGAGATAGTG TTTCTACAAA AAATTTTTAA AAAATTAGCC    157800

AGACGTGGCA GTGCTTGCCT GTGGTCCCAG CTACTGGGGA AGCTGACGTG GGAGGATTGC    157860

TTAAGCCCAG GAATTTAAGG CTGCAGGGAG CCATGATGGG GCCATTGCAC TCCAGCCTGG    157920

GTGACAGAGT GAGACCCTGT CTAAAAGAGA TAAGTAAATA ACAACTTTGC ATTTTCTGCC    157980

ACATTGCAAA ATGGTGAGAG AGTGGTTTCT AGACTCTAGA CTCTTTCTAT GACTACCTTC    158040

TAGTTATGAG ATCCTACAAC ACTCACCTAA CCTCTCTGTG TCATATTTCC TCCTCTATAA    158100

AGCAAAAATG CCCCATATAG AGAGGACTGT GATATAAAAC AAGAACCAAG AAAAGTAAAG    158160

CTTTTCTAAT CTGTCACAGA CTAAAGAGTG CTCAGTATAT GTGAGTCATT ATTCCTGGTG    158220

CTGGTAGGAG TGTATGTTAC AACTTTGAGT CAAGTAATAT GGTACCATAT ATTAAGATTA    158280

ACAACAACCT CGGCAATCCC AGTTTGGGGT ATGTTCCCAA AAGAAATGAA AGCACCAGGA    158340

TATAAGGATG CATGGACTAG AAAGTTATTG TAGCAACATT GTAATAACTA AGTTCTAAAA    158400

ACAGCCTGAA GCTCCATCAG TAGGGATATG GTTACATATA TTTATTATAT TCTTATGAA    158460

TATTAGACAT AAAAAGTAAC GAGTAACATA GAAGAGACAG TGTATATATG TTACGTTTGT    158520

ACAAACTTAG GGAAAGATAT AGATCACCCT ACCTAGAGAA GTCAGATTGG AGACGGGTGG    158580

GAAAAACCTT GAACTTTCTC CTTATATCCT TTATATTGTT TGACTGATTA AAATGTATTT    158640

GTTGCATCTG CTTGAAGGCA ATGTAAAATA AAATAAACAT ACATTTAAAA ATAAAAATAA    158700

AATTTATTCC TATCACTTTT GTAATAAAGC TGGGCACAGT GACTAACACT TGTAATCCTA    158760

GCACTTTGGG AGGCAGAGAC AGGCAGATCA CCTGAGGTCA GGGGTTTGAG ACCAGCCTGG    158820

CCAACATTGT GAAACCCCAT CTCTACTAAA AATACAAAAA TCAGCCAGGC ATAGTGGTGC    158880

GTACCTGTAA TCCACGCTA CCCGGGAGGC TGAGGCGCTG GAACCCAGGA GGCAGAGGCT    158940

GCAGTGAGCT GAGATTGCGG CACTGCAAGC CAGCCTGGGT AACAGCGAGA CTCCATCTCA    159000

AAAAAAAATT TGAAAAAGA AAAATTTTAA TAAACAGTGT TTAAGAGGGG AGAAATATTT    159060

AGTTAAAAGA TAAGCCCATT TAAGAAATAG TTTCACTTGA CCCGGAAGGC GGAGCTTGCA    159120
```

```
GTGAGCCGAG ATCGCACCAC TGCACTCCAG CCTGGGCGAC AGAGCGAGAC TCTGTCTCAA  159180

AAAAAAAAAA AAAGAAAGAA AGAAAGAAAG AAATAGTTTC ACTTGAACCA TATTATGATT  159240

CCTTCTGTAA AAGATGAGAG TAGGCAAATT GACTCAGTGA AATCCCAGCA AAACTTACAC  159300

AAAGTCTTGT TCTTCCTTCC TGTCATCTGT ATAGGATGAA ATACAGAGTG CTTTTGGGTT  159360

TTGTTGTTGT TTGTTGTTGT GTATTTGAGG GGAACACAGG TCTATAATTC CTTTTCTGAA  159420

ATCCCTGGAA CAAAATGGGC TTTGCCATTC AAATTAGTTT AGAAGTTATA AAGGCAAAAA  159480

AATGCATATA CTCTAAAGTT CAACCCCATC ATGGCCTAAG GCAGAGCCCT GTAATCAAAT  159540

TCATCAATAT ATCTGCAGCA AAACATTTAT TCAAATTAAG TGGGATAAAT AAAGACTTTT  159600

AAATAGTCTC ATCTCAGTGC CGTTCAGGGT TGGCCACTGT GGAAGACAGA CTCAAGGGTG  159660

GCCTTCTATG ATTCCTGCCT CTTGGTGTTC ACACCCTCGT AAAATTCCTT GTCTTTGAGT  159720

GTGAGCAGGG CTTATGAATT GCTTCTGACC AATAGGATAT GGCAAAGATG ATGGGATATA  159780

ATTTCTATGA TTACGTTTCA TTATGTAAGA CTCCATCTTG CTGGCAGATT TTCTCTAAAG  159840

AGTCTGTCTC CTGAGCTCTC TCTGAAGAAA TAACTGGCCA TGTTAGAAGC CCATGTGCAA  159900

AGAGCTGAGG GGTGGCCTGT AGAAGCTGTG GGCAACCTCC AGCCAACAGC CAGAAATAAC  159960

CAGGGCCAAA GTCCTGCAAC CATCAGGAAA GAAATTCTGC CTGCTACCTC AGTGAGCTTG  160020

GAAGTGGATT CTTCCTTAGC CTAGCCTCCA GATAAGAACA CAGCCTGACC AACACCTAA   160080

CTGCAGCCTT ATCAGACCCT AAGCAGCAGG CCCAACTAAG CTGTGCCCAG ATTCCTGAAC  160140

CACAAAAATT GAGATAACAT ATCAGTGTTG TATTAAGGTT CTAAATTATG GTAATTTGTT  160200

TGTACTAATA GATAACTAAT ATAACCACCA AATCATTTCA GGTTAGGCCA GATTTTTGTA  160260

GCCAAATGAA TCATGATAAA ACTTTCCATT TTCAGGGGTT TTTTTGATTT TGTACTTACG  160320

GATACAAATT TGTGAAAGTA TAGTCAGCAC TGATTTAAAA AATCAAGGGA GCAGGAAACT  160380

CAGTAAATGG TTCTAACATT TTGGAATCTG TAAATTGGTT GTAACATTTG TCATCTGTGT  160440

TATCTAAGTC AAGTTCCTAA AATATGTGAA TGATAGGTTA TCATACTCAC CTACTTTTCT  160500

TGCATTGCTC TAAGAGTTGG CTGAGCTATT GATAATAAAC ACTATGATCA GATCTAATAC  160560

CATGATGTGC TATTATGATC ATGTGTCAGT CACAGGGCTA AGCACTTTGT ACATGTTGAT  160620

GCATTTAATT TTGATGATAA CTCAATGAAG TAGGAGCTGT TAATATTTTC ATTTTTCAGA  160680

GGGGGAAACC AAGTCACTTG GAGTAACATG GCTAATAAGT GAAAGAATAA GAATTTGAAA  160740

GGTTTGCACA GATAACCAGA ATGCAATGCT CATCACATTC ACTGAGCAGT GAATCATACT  160800

AACTAGAGAA AGTATGAAAG CTCTACTGAA ATTAACTAAA CAACCTCTCT GGCTGTGAGC  160860

CTGCCAAGGG ACAGGTGGTA AACTTGGTTA CTGCATAAGG CCCCTTCTAT CCACAGTATT  160920

CAGGAATTCT TTAGTGAACA TACCTTGATG ACTCCTTAAC ATTTTCTTCA CATCGAAGTA  160980

AAGCTTGGAA ACATTGCACA TAGTATGAAG TTCCAAGGAG ACAGCCTCTG ATGTTTCCAG  161040

CTTCACAGCC CAACTCCTAG AATAAGCAGA GGCGAGAGAT TTCTTCAGAG GTGCATTCCA  161100

TTCATTTCTA TATACGCACA CCCCTCCCCT CCTGCATTCA AACAGGACTT ACCTGCTCAA  161160

AGTGTCATTC ACATTCTATA AAGAAACAAA AAGAAAGGT GAGCATGGGA ACATCGGTAT   161220

TTCATGGGGC TTGTCATGCA GGGCTATTCT TCTTTGCTTT ACCCGAAGAA GTAAAGAGAG  161280

TTACCCTAGT CTTAGTCTTA GATATTGATG GATACTCAAA CAAAGTAATT CCACCAGTC   161340

TTAGGTATTG ATGGATACCC AGATGGAATA ATTCCTACCA GCTTCTGGGA GATTCAGCAT  161400

GGCAGGATGT TTATCAACAT TTGCATCTAT TCTCATCCTT GCTGAAGTCT GAGGGCCAGG  161460

AGCTTTGTCC ATGCTCCCTC TGTAAGGACT AGCTTTTGGT GATCGGATTT CCTTCACAGT  161520
```

```
GAGCCCAGAT TAGAGAACAC TTATCATAAA GGTCCTTAGT GGTGAATCTG TGCACAGCCC   161580

TGAGACTGGG CCACTGCCAC TAAGATGGTG GTAGCAGGTA TCACACAGTG GTAAAGCAAT   161640

CATGCTATAC ACTCAGCCTT ACAGTATAGT CACCAATCCT GTTAGTTAGA ACCAGAATTA   161700

ATGGCTCCAG ATGTTTATCT TCCTACAGAT AAAGCTGTAG ATTGTACCAT AACAGCTCTG   161760

GAGCAAGGGT TCTACAAGCA AATCAGGGAA AAGGTTATCA CTCATTTTGG CTGCCCCACT   161820

TCATCACCCA TCAGTCACCT AGTGGAGTAT TCAGGAGAG AGTCAACAAC CAGGGTTCTC    161880

TGCACATGGG CCAAGGAGGC AAACAGTGGT AAATGTTATC CCGTGGTTTC ATTTGGCCAA   161940

GCTGTGTTCC CTCAGAAGTT TATTTTTCTA ATTGACATAA AGGTACCCTA TAAATTAGTG   162000

AAGGCCAGCC TGATGGCACT GATGTACATC TAAAAGAAAC ATTACTTTAT CTTCCCATGC   162060

TTCCTTACCA TTCTCCTTTA ATAGCACTAT AACATACCTT TTTTCCCTAC TCCAAGTACA   162120

CAGCCTCACC TGCAGCAATT TCTGGGCTGA GCCCTGACAT TTTTCCTCCA GTTCCAGGAT   162180

GTGGCTCTTG AGTTCATTGC TCTTCAGCCC CAGACCAGCC TCATAGTCCC TCAGTCTACT   162240

CAGAGTCTGT TGTTCTTCTT TCTCCAGCCT CCAGAGATAA GACTTCTCTT CCTCATGTAG   162300

GAAACACTGG AGATTCTTAA AGTCAGACCG GATTTTTTGT CTCTGAATCT GTACCTTCTC   162360

CTGGAGTCAA GAAAGTATGG TCAAAAGGTG GAAGTAAACC AAATGTCCAT CTATGGATGA   162420

ATGGATAAAC AAGAATGAAA GTCTGACACA CGCTACTACA TGACAAGCCT TGAAGACATT   162480

CAAGCAAAAT AAGCCAGAAA CAAAAGGGCA AATATTGTAA GACTTTGCTT ATACAAGGCA   162540

TCTGGAGTAG TTAAGTTCAT AGAGACAGAA AGTAAAATAG TGGTTACAAG GTGTTGGCAA   162600

GACCAGAAAA TGGACAGTTA TTGTTTAATG GGTAGTGAGT TTCAGTTTAG AAGATGAAAG   162660

ATGAAACTGA GTTGCAGTTT GGAGATGGGA ATGGTGATGG TTGCACAACA ATGTAACAAT   162720

GTAAAAGCAC TTAATTCTAC TGAACTATAT ACTTAAAAGT GGTTAAATGC TTAAGTGTTA   162780

TATATATTTT CACACAAACA CACACACACA CACAATCAGC CACTGGGACA TTATTTTCTC   162840

ATGAGTCACT GAAGCTGGAA GAATGTCCCC AGTTTCCTGC TGCAGAGTCA TGTGTGGGAG   162900

GCAGGCACTC AGATGTGGAA GAGGTTGCCT CAGATTCCTT ATAGTCACCC AATTAATTTT   162960

CTTGTTCTTC AGCCAAGACA CAGGAGAAAG CTGGGTTAGG AGTGCTAGAT AATTTAATTG   163020

TGAAACTAGG GCCAAGTTCA AACACTTTAT CAGTTACAAG GATAAAAAGA GGTTTTTACT   163080

TATGATTTAA GAAGTTAGAT TTCTGAGTTG GAGCGATTTT CTTGAAGTAA AAGCTTATAA   163140

TGAACATCAC CCAGACTGGA TTTTAAGACA ACCAGGCTGG TAAGAGGGTC CATAATTCTT   163200

GGCAGGGGA GCTTTGAGTG TGACAGGCAT TTATTATGGT TAACTGAGAA ATACTGTTCT    163260

ACTACCCTAG GGTCATCTTA AGCATTCCTA TGTGTAAGAC TGACAGAAAT CAAGTGAAAC   163320

TCTCATCTGA GGAGATGTAA AGTTGCAATT TCCATTAGTG CTGTCTAAAT TAATGCAGTG   163380

GGAGTGTGTA TTCAGGGCAA TTTGAATCTA TGTTCTTGGA TTGCAGTCTT CAAACTTGGC   163440

CCAAATAAAC TCTCTACTTA TCTTAAAAAA ATAAAAATTA AAAATAAAA ATAAATTCAT    163500

ACAGTGTTTT GATGACTATG ATATAGAAGA AGGGTCTTTG ACTTAGGATG AGGTGGAATT   163560

TTTGTGTAGG AGACAGGTGC AGCTTTAACT CTTGTATAGA CGGGTTTTCA TATATGTTAG   163620

TTACAATCAA GGTCTTCCCC ATTGCCCAAG ATCCTAGAAA TGGGGAAGT AAGAGTGTAC    163680

TCAGGAGCTC AAGAGCAACA TCCACAAACA AAGATCAGGG TAGAGGTTAG AGAGGACTCC   163740

TGAAAGAGAG AAAATTGGTA ATCAGCTTGT GGGATTTTAC TGCAAGCTAG TGAATTATAT   163800

AAATATAAAG ATTGGTGCAA AAGTAATTGT GGTTTTTGCC TTTACTTTAA TGGCAAAGAC   163860
```

```
CGCAATTACT TTTGCACAAA CCTAAATATT TCCATAAAAG AATGTGGCTC TGATAATGTG  163920

GAGGTTAGTC AGCCACGGAA ATAATCTGAA AGTTTGTAGT TGCAAGTGTG TAGGTTGTTG  163980

CATTACTTGT GATGTACTTA TAAATCAAGT ATAGGCCGGG TGCAGTGGCT CACGCCTGTA  164040

ATCCCAGCAC TTTGGGAGGC TGAGGTGGGT GAATCACGAG GTCAGGAGAT CAAGACCATC  164100

CTGGCCAACA TGGTGAAACC CCGTCTCTAC TAAAATACAA AAAATTAGCC AGGCATGGTA  164160

GCACATGCCT GTAATCCCAG CTACTCAAGA GGCTGAGGCA GGGGAATTGC TTGAACCCGG  164220

GAGGTGGACA TTGCAGTGAG CTGAGATCGC ACCACTACAC TCCAGCAAGA CTCCATCTCA  164280

AAAAATAGTA ATAATTTAAA AATAAATAAA TAAATAAAGT ATATTTCTTT CATCAGCTTC  164340

ATGAGCTAGA GTAGTATGAA TTTCAATCTG GAGTGATCCT GTTTTCTAAG TGTTCACAAA  164400

GCTTGGTTTC TGTACCTGTA AAGTTGAGAG CCAGATGCTC CACTGTGGTA AAAGTGCCAG  164460

GGTAATGAGT TGAGGCCTGC AAACCAGGTT TATTTTGACG TATTTAAAGT TTGAGACCCA  164520

CTCGATGCTT TTTCTAGGTA AATAGTCATA CTAATTCTGC TTCTTCTGAC TGAAGTATCA  164580

GGAATCCCAG CCAACTACAG TTTAAAGATG GAAAGATTGG TGCTAAATAC TCATGGATGT  164640

AAACCTGGAA CCAGGGGCAT AAGTACAAAT AATGGTTTCT TCCTTGGGTT TCATTTTTTC  164700

AATCTGGTTT AGTGAGAATA AATCCTCATT GTGCTTTTCC TCAATCATCC CCTATGCCTA  164760

AGCTCTAGAA TGGAAAATAG CTTGAGATCA ATGAAGTCAG ATTCTTACTT TCCATTTAGT  164820

TATTCGCATT GCTGTGGACA GCTTCTGCTC CGTACATCTG TCTTCAAGTT GCTTCAGTTT  164880

TGTCACAGCT TTCTGGAGCT TTTCCTGAAG GAAAAATTTG ATAAGTGAAG CCTATTCAAT  164940

TTGACTCTTC ATTAGGGACC TAGGGGGAAT CCCAATCTTC TAAGATATAT TTGAATAATA  165000

GTGAATATTT ATAGAGTCCT CATTGTTTTT TGCTAGAGAG CATGCTAAAG GCTATATGTG  165060

CAGGAACATA CTGATCCCCT TGGCAACCCT GAATAGTTGG TAGGATTTTA AACTTCATTT  165120

CTGTGCTGTA GAAATGAGA CTAAGAAAGG GGTAAAATAA CTTGCCCAAA GGGCTATGAC  165180

TGCCAGGTGG TGGAGCAACA ATTGCAATCT CATCTGCTGA CCCAGAGCCT GAGCTATGTC  165240

CACCACTAGA GTCCTGCCAG GAAAAAGTTG GATATAGAAC AAGGTAATCA TCATCTAAAA  165300

GATTTTGTAA AACAACATGC TGAACCAAGC AAAACCAATA CCAGTGTTTG GCACACATGA  165360

AATTTTGTGT CTTATGAGTC AGGAAAAATC AGGATGCCAG CTGGTTATTA GAAACAGTTC  165420

ATGGAAGAGG GGAATTCTGG TATCTTTTGA ACAATGGTAT CATGAATCCA ATTTAAAATG  165480

ATTTAGTATT CATGTCAAGC TTTTAGCTTA TTCTTCAAAA CAGTTTCTCA TATTTCTATT  165540

GAAAGTGATT TGAAGCTGAC CCAAATTGCT AATTGTAGTC AATGCTGAAA GAATTGTCTC  165600

CTGTCCTCTG TAAACCCAAC AAGTATACTC ATTCATTCTC GAGTGTTCTC AGGAAAAGGT  165660

TCTATGTAAC TGTTTTAGCA AAAGATGACA TTGTCCTTAC TATATGCCAA GTGCTATTCT  165720

ATGCATTCTA TATTTTAATG TCCTCAAAGC TTATAACCAC CTCCTGTGTA TGTGTTTTAG  165780

GGAGGGAGGA CACTGCTATT ATCCCCATTT ACAGATGGAG AAACCAAGGT GTGAAGACAT  165840

TAAGTAACGT GCCCAAAATT GCCCATCTAG TAAGTGACAA AACTCAATTT CAACATAAGC  165900

TGGTTCCTTT TCTTACTACT TGGTGGAAAA GTAATTCAAA TGGGAATATG ATCATCGCAG  165960

TTATTAGCTG CTCCATGGAG TTTAAGGAAG AGCTGCCATG AGCTGAGTGG TGGTCATGAT  166020

TGACATGTCC TTAGAAGGAC TTAGAGCCTT CATACAAGAC CACCTCTGCC TCATGGAGGA  166080

CAGAATAAGG AGCCTGACAC TGGAGACAAC ATTTTCCTCA AATTTAGGCA GGACAGAGAA  166140

GGAAAAAGGA CATCAGGACT ATGCCCATTC CTCCATGCTG CCAACAGCAA AGTCCCACCT  166200

TCCTTAATAT GCTTTCTGGC AAGAAATCTG GATGGTACAC AAAACCTCTC CCTCTGCTTC  166260
```

```
ACCTTCCACA ACCAAGCATT TCCAAATCTT TGACTCTTCT TCCTGAATCG TGCTTAAAAT    166320

CTGCCCTCTC CTCCCTTTCT TATACGGATA GTTTGAATTT TACTCCTTGA TATTCCTTTT    166380

ATCATAGACA TGCCACAGTA GCTGGGCACA GTGGTTCATG CCTCTAATCC CAGCATTTTG    166440

GGAGGCTGAG ATGGGAGGGA GACCAGGGGT TTGAGGCCAG TATAAGCAAG AAAGGCAGAC    166500

CATGTCTCTA CAAAAAATAA AAAAATTATC CAGGTATGGT GGGGCATCCC TGTAGTCCTA    166560

GCTACTTGGG AGGCTGAGGT GGGAGGATTG CTTGAGCCCC AGAAGGTTGA GGCTGCAGTG    166620

AGCCGAGATT GCACCATTGT ACTCCAACCT GGGATACAGA GCAAGACCCT ACCTCAGGAA    166680

AAAAAAAAAA AAAAAAAAA AAAAGTAGAG GTACCAGAGT GATATTTTCA ATGTCACTGA    166740

CCCTTCATTC CCCAAATGAA AATCCCCCAA TAGGTGTTCA ATTTTTACGT GTCCTTCAGG    166800

AGTTACTTCT AAGATGAACC ACTCTCTACC CTAAATGTCC CTCCCCACCA CCAAAACCAG    166860

GGACCTCCAG GCAGACATTT TTGATGGTTT GTTTTCTTTA CTAGACTGTA GATACCTAAA    166920

AGGTGATGGG TCTTTCTTCC CTGTTTTCAG GCCCTACTGC ATGGCTTTAC ATATTGTGGT    166980

TTTTCAAATG ATATTCATGG TGTGAAACAA GAAAAAATGC GGGTGTTTGG TTTGAGAACA    167040

ACCTGTTCTA AAGCAAAAAG AAATTCATCA TAACACAAAT GGATAGAGAT AAGAGTCCAA    167100

CCATCCCATT GAAGGTCAGG ATGGACAGTC TAGATAATTG AGCAAGAAAT CATCATAAAC    167160

TATTTTTCAG AAGAATGACA TGATGAAAGC TGTATTTCCA AGTCATAATG TTAGGTTTCA    167220

AGTTAAATCA TCTCAGCTCC TGGGGAGCAG GATAAGACTT GGTACTTACC AAAGCTCCCG    167280

GGCCCACACA CTCACCTTGT AGCCCTGGCA TACGTCTTCA ACAAGAGCTG TGGTGTGCCC    167340

TTTGTGCTGT GGTGCCCGCT CACAGCGCCA GCAGATGAGC TGCCCCTCGT CTTCGCAGAA    167400

CAGGTGGAAC TGCTCTCCGT GTTCCTCACA TGACATTTCT TGATCCGTCT CTTTGAGGGC    167460

TTCAATGAGG CTTCCCAGCT GCTTGTTGGG TCGGAGGCTA TCCATATGAA ATGGAGCCCG    167520

ACACTGGGGA CAGCAGAATG TCTCCTGCCT CAGTTGCTTT TGGCTTGGGT TTTTAAAGAA    167580

GTCTGTTATA CACAAGTGGC AGTAGCTGTG TCCACAGTTG ATGCTTACTG GGTTCGTCAT    167640

CAGGCTCAGG CAGATGGAGC AGGTGGCTTC CTCCATCATC TTCTTGGTGC TGGTGGTTGA    167700

GGCCATAGCT TTTATTGAAA AGCTCCAATA TTGGCTCTAG AGATGGAGAT GAAGCAGCCA    167760

GAATTTTCCA CCGTGATGAA AATACACCTC ACCTGCACCT CTATGTGATG AGCTGGCTGC    167820

AACTGACTTC CATAGGTCTT GAAGGTTTTC CTTCCAACCC CTATTATCTC ATTTTGTATT    167880

GAAGAAAAGA GGACCTAAAA GGAAGAAGTT GAGGCTGAGG TTGTTTGGGC CACGTTTGAG    167940

AACTGCAACC CAAGTGCAGA GTTTCAAGTT GCCCTCATTA GCAAGCAGTT ACAAGTGGTT    168000

GTTTAGAGGA AAAAAGCAG TTTTAAAGCA GTTTTAAAGT TGTTTGCCAA GAATTTACAT    168060

TAAAATAGCA TAAGCTTTTG ACTGGCTATA CATTGTTCTT TGTATTACAA ATCTCGGGAA    168120

TATGTAGGTA ATAGATGAGG CAGCCAGTCA GGAACAAAAT GCTTTTAAAC ATGGGGTCTT    168180

AACTGAAGAC CTATACTCCT GCCTCACTTG TCCTGATAAA TTTTGCATAC CTCACATAGC    168240

TCAGACTGCT CTAAATTATT TCATTATTTT TCTTTTCTCA GTCTTCTAAC TTTTTTTTTT    168300

TTTTTTAATG AGACGGAGTC TCACTCTGTC ACCCAGGCTG GAGTGCAGTG ACGCTATCTC    168360

GGCTCACTGC ACCTCCGCCT CCCGGGTTCA AGCGATTCTC CTGCCTCAGC CTCCCGAGTA    168420

GTAGCTGGGT CTACAGGTGT GCACCACTAC GCCCAGCTAA TTTTTGTATT TTTAGTAGAG    168480

ATGGGGTTTC ACCATGTTGG TTGGCTCGAT CTCTTGACCT TGTGATCCAC CCGCCTCAGC    168540

CTCCCAAAGT GCCAGGATTA CAGGCATGAG CCACCGTGCC CAGCCTCTTT TTCTTTTCTT    168600
```

```
ATAAGACAAG TTCTCGCTCT CTTGCCCAGG CTGTAGTGGA GGGCAGTGGC ATGACCACAG   168660

CTCACTGCAG CCTCGACCTC CTGGGTTTAA GCAATCCTCC TGCCTCACCC TGGCAGAGTG   168720

GCTGGGACTA CAGGTATGTG CCACCATGTC CAGCTAAAGT CTTCTCTCCA GAAAGAAGAA   168780

ATGCATTGGA ATTTAGAGGA TACACAAACA TCTAGCTGTA TAGCTAATAC AGTAGCCACT   168840

ATCATGAGTA GGAATTTAAA TTTAACTTAA TAAAAATTAA AATGAAAAAA TTCAGTTTTT   168900

CTGTTCCAGT TGCCACATTT TGATTGCTTA ATAGTTGCAT GTGACTAGTG GCTACATAAC   168960

AGCCTCAATA TACAACATTC TGTTATCACA GAAAGTTACC TTGGACCAAG TGCTGGGAGA   169020

AGCAATGCAG GCTTCCTCAC AAAAGCTGTA AAAGAGAGAA CTCAGGGAGT GTGAAACTCT   169080

TTCCTATTCT AGTTAACTTC AAGAATAATT GTTACCAGGC CAGCACGGTG GCTCACGCCT   169140

GTAATCCTAG CACTTTGGGA AGCCGAGGCG GGCAGATCAC CTGAGGTCAG GAGTTTGAGA   169200

CCAGCCTGAC CAACATGGCA AAACCTCATC TCTACTAAAA ATACAAAAAG TTAGCTAGAT   169260

GTGGTGGTGC ACACCTGTAA TCCCAGCTGC TCAGGAGGCT GAGGAAGGAG AATGACTTGA   169320

GCTCCGGAGG GGGAGGTTGC AGTGAGCCCA GATTACACCA CTGCACTCCA GCCTGGGTGA   169380

AAGAGCGAGA ATCTGTCTTA AAAAAAAAAA AAAGAATAAT TGGTACCAGA ATTACTCTTT   169440

GTAATTAGTA GTAACACTTA TGCAATTGGG TGATCTGTGA CAGATTCCAT TGAAGGAGTA   169500

TGGGGAGCTT CACCCCAATA TATGACTCCC TGGTATAATG AGTATTTTGA ATTAAAGGCC   169560

CTTAGAGATC AGCAGATGCT GGAAGAGACT TTTCCCCTAT CTACATAAAG ACCAGTCACA   169620

CTAGACAAGA AGAACAATTG TTTTTCCTTC CAACCCCTAT TATCTCATTT TGTACTGAAG   169680

AAAAGAGGAC TAAGAATGTA ACCAGACCTA ATCAGACACT TTCACAAAAT AATGTCTGTC   169740

TCTCAGGCTC ATTCATTTTC CAAAGAGAAC CATTTACAAG TTAAACTCTG TTCCTCCATT   169800

CATTCATCCT CCCAAATATT CATTTATTCT CCCTAGTAAT CATTTACTGC CCCTCAAAGA   169860

ATTACCTATA TTCTCCTGAT ATCACCCTTC CCCTCTGAAA TAAATATGTA TACATGTATA   169920

AACGTTATAC ATACATATTT ATACAGTATA CATACATATT TATACATACA TACATATGCA   169980

TACATATTTA TATTTATGTA TTTATACATA AGTATTTATA AATAAGGCTA TATAAGTATC   170040

TACCCCCATT GGCAGAGGGG GTAATCACTC TGTGATTCTA GCCCATGTAC TTGTTAATAA   170100

ATTTGTATGC CTTTTCTCCA ATTAGCCTGC CTTTTGTGAG TCGATTTTTC AGTGAACTTC   170160

AGAAGGCAAA GGGGAAGTGT TCCCTTGGCT CCTACACCAT CATGACAATA AAATTTGACT   170220

CCACCTCGAC CCCCCCCATC CCCCACAAAG AACAACAACC AACACTGGTT AATAAGGTCG   170280

GTTGTTTTTT GTTTGTGTTT TGTTGTTGT TGTTTTTGCT TTCAGGAGCA GAGGTATAAT   170340

AGGCAAAAGA AAGAGAAAGG AGAATAGTGA ATACCTCTTC TGCAGAGAGG GGTGCCTAAG   170400

TGGGACTTCC CTGGCTAATA ACGTCTTGCT AGAGACCCAA CCAGGAGGAT AATGGAAGCA   170460

ATCAAGGCAA CCAGAACAAC CAGAAGAACC GGTTTATCCT TTTTGTGCCC TCTCCCTAAA   170520

CTGAGGGAAT AAGAATTGGA AAGAAGGCTG CAGAGCAGAG GGTTTGCTCC TGAGGAGCAG   170580

TTATTTCTAT GGGATCAGAG CTCCTGCAGA ACTGGGAGT TTACTTTTAC TATCTCTTCT   170640

CCAGGACAGG ACCTATCTCA AGAGACATGT TCAGAGTGAT TGCAACATAA AGAGTTTGCA   170700

GACCCAAGGA GGTAGGGAAG GCAGAAAGAA GATGGGGGAG GCCAGGGATA GGCAACAGAG   170760

GAGTGACCAG GAGCGAAAAA GCCTGCCTCT TCTGAGAACC TAGCTGGGCT CTCCCTGTAC   170820

CCCCGATCCC TCCCCCCCGC CCGCCCCCAC ACCCCTACTC CTGGGAGCTC CTCTAGGACA   170880

GGGGCAGAGT CAGGAGGAAG TTTGAAGAGT GCCTAGAATA AAAAACAGTA ATTTAACTAC   170940

AATTACCGGG TAGGCTGTTT TCCTCTCACA ATTTGATCAG TCTCTTGAAG CCACACAGAA   171000
```

```
TTTCTTCTGA AGACGTGTAT TCCTTGGCAG GCTATTTCCT CCAGTGATAC ACCAGGCCCC   171060

TCTCTGCTGG GGTCACTGCT CTTCTGGGGA GATGGGGCTC CCCTCCTTCC AAGGCTCCAG   171120

GGTTCCTGTC CTGGGCCCCA CTCATCTAAG TTCTGAATCT TCTGAGATTT GGTGTAAAGT   171180

CTGGTGAAAG AAAGAGCAGG AAAGAGGTGA GAGCTGTAAA ACAAAGAAAG TCCTGACCAT   171240

TTTCAGAGTT GGAGGGGCCC TGCTGTCACG AAATATATTC CCCACCCCAC TTGCCATCAG   171300

TACACACTCA CATATCCACT GAGAAAACCT TAGCCTGGAC CTTTTCCGTA ACCTTCACTG   171360

CTCAGACACT TACATATTCG CTGCTAGTCC CCTCTGTTGC TGCCACTTCC TGGGTCAGGA   171420

AGTTAACTCA GACCGGATTA AACTGAGAAG TGAAACTACT GTGGGAGGCG GGGCTCATAA   171480

GATTTAGGAG AAAACTAGTG ACGTTGTTCA TATCATTTGC ACTCCGCCTC TCCGGTAAAG   171540

GAGGGGGAAA CGTAGGAAGA AAATATCCTT CTTTTACAGC AATAAAAAGA AGGAACCAAT   171600

TAATAACCCT GTAAACTATC ATGTGACCCC AACACAGAGT ATCTAAAAAC AGGAAGCCTG   171660

CAGAGGTTCA GTTCACAGAC TCTGATTTGA GATCTTTCTA CTTTTGCCAC CAACTCCCTT   171720

GGGAGTCCTT AAGCCTTCCT AGCTGATGTT ACTTCTTTTG CTATTTATGG GTTGCTTGTG   171780

GTTCTATAAC TGCTCTGAAG GGTGTGGTGG AAAAAGGGGT GGTAACAGCA GTAGGACTCA   171840

TTGGCATCAC AAAATTCATC TGAGTCAGCT TTCTATTCTT CTCTGTCCCG TTCTGTGTCT   171900

TGTTTTTCTC CTTGCTGTCC TTCTGCAGGA CTCAGATCTT CTTCAATAGC GAGGGTCAGC   171960

CAGGATAGAA AATGGGAGTC ACTAGTGGCC CAGCAGTGAG TGCCCCCAGC TTAGAGCTGT   172020

GTGGGATCCC TGGGACCATC ACTCTGCTTT GTGCTTTGTG GAGAAAAGGC TGTGGGGTCC   172080

AGGGTCAAGT CCTTAATGAC TTAGCTCCAG CTTCTCCACT TCAAAATGAA AGGAAAAGTA   172140

CTATCACCAC CCGTTAGAAT TATTATTTCA TGGGGAAAAA AGATGGATTA CTATCTCACA   172200

ATAAGAGCTT GTCACATTTA TAAGTCTCAG GTGTAAGAGG CATTTATGAT AACAACATAA   172260

TAAATGCTGG CTTAAGTAGA TGCAGTGGTC CAAGGGAACC AGTAAGGGGA GCTCAGGACA   172320

CAGGTGGGAG GAGAAATTAA ACTTGAATTC TGGGAGCCAC TGGCCTGTCT GGGCCCCTGG   172380

CCTGCCTGCT GACCCTGATA GCCAATGGAA CATGGAGTTT GGCCCAGCTG CAATCCCTCT   172440

GGTCCAACTA CTCAAAATAA AGGCAAGATT GGGAAACACG TTCCTTTCTT CCTATACCAA   172500

GCAGAAGACT CTTCAGCACT GCACCCTCCT GGGTGCTCAC AGAGCCTTCT GTTGTTTTGC   172560

CACCTACGAT TCATCATGCC CTGGCATGAT GGTTGCAGAC CCCATGCATA GCATGGGACA   172620

TTCTACTCCT GAGGCAACCA GCACACAGAG AGAGGAGAAA GAATGAGCCC CTGAATCCTT   172680

GGTCCCACGA TGAGTCCTTG CAGATATCTA CAACTTTCAT TGTTGTGGAT GTGACTCTGT   172740

ACCCAGGCAT GGCTCATTCC AGATCTGTCC TATTGTCAGA GGTGTTCAAA CCAGAATGAC   172800

TCCATTTTGA ATGGGGCTA GGTAAAATAA GGCTGAGACC TACTGGGCTG CATTCCCAGG   172860

AAGTTAGGCA TTGTAAGTCA CAGGATGAAA TAGGCAGTTG GCACAAGACA CAGGTCATAA   172920

AGATCTTGCT GATAAAACAG GTTGCAGTAA AGAAGCTGAC CAAAACCCAC CAAAATCAAG   172980

ATGGCAACAA GAGTGGCCTC TAGTCATTCT CATTGCTCAT TATACACGAA TTATAATGTG   173040

TTAGCAAGTT AGAAGGCATT CCCACCAGCT CCATAGTGGT TTATAAATAC CATGGCGATG   173100

TCAGGAAGCT ACCCTATATA GTCTAAAAAG GGGAGGAACG CTTGGTTCTG GAATTGCCC   173160

ACATCTTTCC CAGAAAACAT ATGAATAATC CACTCCTTGT TTAGTACATA ATCAAGAAAT   173220

AACTGTAAGT ATCTGTATTA GTCCATTTTC ACACTGCTGA TCCAGACATA CCTGAGACTG   173280

AGTAATTTAT ACCAGGAAAA AATGTTTCAT GCTCTTACAG TCCCACGTGT CTGGGGAGAC   173340
```

-continued

```
CTCACAACCA CAGCAGAAGG CAAGGAGGAG CAAGTCAGGT CTTACATGGA TGGCAGCAGG   173400
CAAAGAGCTT GTGCAGGGAA ATTCCTTTCT ATAAAACCAT CAGGTCTCAT GAAACTTATT   173460
GACTATCATG AGAACAGCAG TATAAATTAC TCAGGGAAAG ACCTGCCCCC ATGATTCAAT   173520
TACCTCCCAC CAGGTCCCTC CCACAATATG TGGGAATTTA AGATGAGAGT TAGGTGGGGA   173580
CACAGCCAAA CCATATCAGT ATCCTTAGTC CAGAAGCTGA TGCTCTGCCT GTAGAGTAGC   173640
CGTTCTTTTA TTCCTTTACT TTCTTGCTTT CACTTTACTG TGTAGACTTG CCCCAAATTC   173700
TTTCTCACAC GAGATCTAAG AACCTTCTCT TAGGGTCTGG GTTGGGACCC CCTTTCTGGT   173760
AACACTATCA AAGGATCAGG AAAAGGAAGC TAGTGAATGC TAAAAAGGAA ACAAACTACC   173820
ATTACCAATA ATAACAGCAA GACAAAAGCA AAACGGATTG TGACAGCTGT CCCATCTCAC   173880
ACCTGTTTCC CATTGCAGGA AGGAGGGGCT GGTTCATGCA CAGAGTGGCC AATATTAGAA   173940
GCAGAGATGG GGTGCAGATG AGACTTCAGG AATATGTTGA CAAAGGCAGG CCTAGGGAGA   174000
AATCAACCTG AACTATCCCC AAGGAGGAAT GCATTATCTC TAATATGTAA AGTTAGGCTT   174060
GATCCTGTGA TTATGGGATA TAGGAGTCCA AAGACTCACA ATGGGAAGTA GGTCACTAGA   174120
GTCTCCTTCA GAAGCTCTGT ACTGTGTGTT CCCACTGTGG GCAAGAGTCA GCACTCAGCT   174180
ATTCCTAGAA TGCCTTTCCT CAACTCCTTC AGATTTTGCC TCTCAACTAA CCCTATCCTG   174240
ACCACTTGTT AGCAAGTGTA CCCCTCTCTC CCTCCCAAAC ATTTTCAAAT CTATTTTGTT   174300
CCCATGGCAC TTATCACTGA ATATTTTACT AATTTATTTT GTTTAGTGTT TGCTTCCCTC   174360
ATGAGAATGC AAAGGGATGG ATTTTTTTCA ATATTGTTCA CTGATGAATC CCAGTAACTA   174420
GAATATTTCT AAGCATAGTG ATGTGCATTA AATCAAAGAG TAACTTTCTG AATTGCACTA   174480
AACACACATC ACAAGAGGTG TGTGCACATA TGTGCATGAT GCACGTAGTG TGGTGTGGGT   174540
GTTGTGTGGG GTATGTGGTA CTGTGTGTGC TGTGTGTGGT ATGTGATACA TAGTTTGTGT   174600
TAGTGTGATG CATGTGATGT GGTATGTGTG TGCGTGTCCA TACATATTAG GGGTGGCGGG   174660
GATGTTAATA TGTCAAATGG TACTAGAAAG TATCAGAACT CATGGTGCTT ACTGGTTTCC   174720
CAGAGAGCTG CTTCTCTCCC ACCTGTAGGA TATACTGATG GTTTGGACAG AGAAGAAATA   174780
AAAAGAAGGC TGTGACCTAC TGGGCTGAGG AAATAAAAAC GAAAGTAAAA GAAGAGCTGG   174840
GAAAAGAGAG TGGAGGGGCC AAGGGAAATT TCCCCTTTGG CTTCTGGGGA AACTTTGCTG   174900
AAAAATCAAC TCACAAATTT ATTAACATGT ACACAGGGAG AACCATAGAA TGATTATCCA   174960
CTTCCCAAGA GGGCTTAAAA GCTTATATAT TATCCTGGCA AAACAGATTA TGGGAGGGA   175020
AGAAGAGAAA CTCTGTTGAT GGGATTACTG TTGCGGATTT TTGCTCCTTC GCTCAGCTAG   175080
GTCCGGGTTT TTGTCTCACA GCCAGGAAGA ATTAGGCATG CAGCCATCAA AGAATGAGTG   175140
GAGTAGAATT TATTAAGTGA AAGGAAAGCT CTCAGCAAAG ACAAGGGTCC TGAAAGCAGA   175200
TTTCTGGTTT GCTCTTCACA GTTGAATACT AGGGCTTAAG ACTCAAATTC CTGACAACTC   175260
CACCCTGTCC TACCAGTGCA TGCAGGCCTT TAGACTGAGC TACTCCATAT TGATTAATTT   175320
CCTGAACTGT GCATGTGTTA AGGAAAGGAA TCATCCACTG CAGGCATGTT TAGGCAAGCC   175380
CCCTGTGCAA GTTCCCTTAT CTGCACAAAA CATCCGGTGT AAGCACTTGT GGGGCAGGTC   175440
AGAGGTTCTC TGGGTACCAT TCCCTTACTG TCTGCCTAAA GCAAGCTGGC CAACTCCTTT   175500
CATTACTAGG GAGAGTAAGT AGATCAGGGA ACAGAGATTA ACTTGAACAT TATCTTGTGA   175560
AAGTCCGTTC GGGCATGGTT ACATTCTTGG TCTTACAGGA AGGGTAAATA AAAATAATTG   175620
CTCTTTTTGG TGGGTCTGGA TCTTAGGTAG ATAAAGAAAC TTTAATTCCA CGATGTGTTT   175680
TGGTAGGGAT AGTTGGTGGC AGGGATGTCA GAGAGACTTT GAGGCTTCTT CAGTTCAATA   175740
```

```
TGACCAAGGG CCATATATTA GGGTATCAAT TTCTGAGCCC CAACAAGAGC TTAGGAGAGA   175800

TGTGATAGCA TCACAGTGTG AAAGCAATTT TTTGTTTGTT TTTAGAGACA GGCTCTTGCA   175860

CTGTCACCCT GGCTGAAGTA CAATGGTACG ATCACAGCTC ACTGTAATCT TGAACTGGGT   175920

TCAAATGATC CTCCCATCTA AGCATTTCAA AGTGTTGGGA TTACAGGCAT GAGCCACGGT   175980

ACCCAGCCTG AAACTGCACC CACTTTCTGA TAAACTTTTC AAATGACTAA AGGGAGAGA   176040

GTAAGCACTA CTCAGAGGTA GGAAGAAAGG ACACAGGATT ATAGGATTAA AACAACAACC   176100

ACCAAAAAAA ACCAGACCGG TGTGGTGGCT CACACCTGTA ATCACAGCAC TTGGGGAGGC   176160

TGAGGTGGGG GGAGTCACTG GAGGCCAGGA GTTCGAGACG AGCCTGGCCA ACATAGCAAG   176220

ATGCTGTCTC TATTAAAAAA AAAAAATACC TGCCTTGAGC TAATCAGAAT CATGGACCCT   176280

GACAAAGGAT GTCCCAAAGT AAGTCTTAGC ATTTTTTTTT TTTTTTTGAG ACAGTCTCGC   176340

TGTGTTGCCC AGGCTGAAGT TCAGTGGCGT GATCTCGGCT CACTGCAACA GCTGCCTCCC   176400

AGGCTCAAGC AATTCTCCCT GCCTTCAGCC TCCCAAGTAG CTGGGATTAC AGATGCCCAC   176460

CACCACGCCT GGCTAATTTT TGTTTTTTTT AATAGAGATG GGGTTTTGCC ATGTTAACCA   176520

GGCAGGTCTT GAACTCCTGA CCTCAAGTGA TCTGCCCACC TTGGCCCCTC CATAGTGCTG   176580

GGATTACAGG CGTGAGTCAC TGCACCCGGC AAAGTCTTAG CATTCTTTAC AAACAGTTTG   176640

TACCCGTATC TCTAAAAGGG AGTAGTGAAT TTCACCCCAA AATGTGGCTT CCTGATATAA   176700

TGAGTATTTT GAATGAAAAA CTCTTAGAGA TCAACAGACA CTAAAGAGAC TTTTCCCTAG   176760

GTACATAAAA ATAGGATGGC CCCACCAGCG AGAACAATTG TTCTTTTCTC CCTCTCTGTT   176820

ATCTCATTGT GCATTATAGG AAAGACCAAG AATGTAACCA CACCTGAACA GACCCTTTTA   176880

TAAGATAATC AGTCTCTAAG CATCATTTAA ATTCCAAGGA GAACTATTTA CAAATTTATC   176940

TGTTCTTTGA TCCAATTAGT CTCTCCTGGT AGTTACATAT TGCCCCTCAA CAGAATTCCT   177000

CTTCTTCTGT TTCCCATAAC CTATTTTGCA AGGATCAAGC CCCTGTTATT TCTTCAACTT   177060

CAAGGTGGCA TATAAGCTTC TAAATTCCAC TGGGATATTG GTACTATGTG CATGAGGAGA   177120

ACCACAGAGT AATTAAATTG TAAAGCCTTT TATCTTATGA ATCTGCCTTT TTTTGTGTTC   177180

ATTTTTCAGC AAAACTTCCA AGGGCAAAGG TATAAAACAA AAATAAAATT CTAAAGCCCC   177240

CCAACCATCT GAATAGACTT TCTCTTCAGT CAGGCTTCTT AAAATGTAAC CTGAAAGACT   177300

GGCTCAGGCC ATTAAGGGAA GTGGGGGTTG AACATGCCTC ATTATTCCTC TCTGGCATTA   177360

ACATCAACAC AGCTTTTAAG TCTGATAAGA AACATTTTAC AACCTATTCT CTCTGAAGCC   177420

TGCTAGCTAA AAACTTCATC CCATAGTACA ACTTTGGTCT TCACAACCTG TTATCACAAC   177480

CTAGTGCTCC TTTCTATTAA TCCCAAATCT TTATACAAAC TCAACCAATT GTCATCACCT   177540

CCACCCCACT CCTCCGCTGC TTCCAGTTGT CCCGCCTCTC TGGACCAAAC CAGTGTACAT   177600

TTCTTAAACG TATTTGATTG ATGTCCCATG CCTCCCTAAA ATGTATAAAG CCAAGGTGCA   177660

TCCCAACCAC CTTGAGCGCT TGTTCTCAGG ACCTCCTGAG GGCTGTGTCA TGGGCCATGG   177720

TCACTCAAAT TTGGCTCAGA ATAAATCTCT TCAAATGTTT TACAGAGTTT GGCTCTTGTC   177780

ATGACACAGA TGACTGCTTC ACTGAAGCCT GCTCTGGAAG TGAGTGGGGG TTTTGCAAGG   177840

ATAATTTTCC CCGGATAGCC CCAGAAGCAG CTAGTAATAA TACACTTAAA GGTAGCTAAA   177900

ATGCATTGAA CACTTGTTTT GTGCCAGACC TATGTCAACA TTTGCTTTGT GCCAGGCTTA   177960

TGCCAGTACT CCTGATTTGT TAATACATTC TAAATAAAAA TTCTGGAGTT TCAAATATAA   178020

TAACTGAAAA ACAGAAAATA AATAAAAATA TATAATAACT GAAATAAAAA TTTACTAAGG   178080
```

```
CTGGGGATGG TGGCTCACTC ACACCTGTAA TCCTGTTACC GGAAAGGGGT CCGTCCAGAT    178140

CCAGACCCCA AGAGAGGGTT CTTGGATCTC ACACAAGAAA GAATTCGGGC GAGTCTGTAA    178200

AGTGAAAGCA AGTTTATTAA GAAAGTAGAG GAATAAAAGA ACGGCTACTC CATAGGCAGA    178260

GCAGCTCTGA GGGCTGCTGG TCGCTCATTT TTATGGTTAT TTCTTGATTA TGTGCTAAAC    178320

AAGGGGTGGA TAATTCATGC CTCCATTTTT TAGACCATAT AAAGTAACTT CCTGACGTTG    178380

CCATGGCATT CGTAAACTGT CGTGGCGCTG GTATGAGCAT AGCAGTGAGG ACGACCGAG     178440

GTCACTCTCA TCGCCATCTT GGATTTGGTG GGGAGCAGTG AGGATGACCA GAGGTCACTC    178500

TCATCGCCAT CTTGGATTTG GTGGGGTTTA GCCAGCTTCT TTACTTTTTT CTTTTTTTTT    178560

TTTGCCCAGG CTGGAGTGCA GTGGCACGAT CTCAGCTCAC TGAAACCTCC AATTTCTGAG    178620

TTCAAGCGAT TCTCGTGCCT CAGCCTCCCA AGTAGCTGGG ATTACAGGCA TGTGCCACCA    178680

CACCCAGCTA ATTTTTTATA TTTTTAATAG AGACCGGGTT TCGCCATGTT GCCTACGCTG    178740

ATCTCCAACT CCTGCGCTCA AGCCATCCAG CCACCTTAGC CTCCCAAAGT GCTGGGCTTA    178800

TAGGTGTGAG CCACCCCACC TGGCCTAGCC GGCTTCTTTA CTGCAACCTG TTTTATCAGC    178860

AAGGTCTTTA TGACCTGTAT TTTGTGCCCA CTGCCTGCCT CATCCTGTGG CTTACAATGC    178920

CTAACTTACA GGGAATGCAG CCCAGCAGGA CTCAGCCTTA TTTCACCCAG CTCCTATTCA    178980

AGATGGAGTC TTTCTTGTTC AAATACCTCT GACAAGCCCA ACACTTTGGG AGGATGACAC    179040

AGGAGGATTG CTTTAGCCTA GGAGCTCAAG ACCAGCCTGG GCAACACAGT GAGACCCCAT    179100

CTCTAAAAAA AAAAATACAA AAAAATTAGC CAGGCATGAT GGTGTGTGCC TGTAGTCCCT    179160

GCTACTCAGG AGGCTGAAGT GGGAAGATGG CTTCAGCCCA GGAATTCAAG GCTGCATTGT    179220

CAGAGGCATT TGAACCAGAA TGACTCTATC TTGAATAGGC GCTGGATAAA ATAAGGCTGA    179280

CACCTGCTAG GCTGCATTTC CAGTATGTTA GGCATTCTTA GTCACAGGAT GAGATAGGAA    179340

GTCAGCACAA GGTACACATC ACAAAGACCT TGCTGATAAA ATAGGTTGTG GTAAAGAAGT    179400

TGGCCAAAAC CCATCAAAAC CAACATGGCC ACCAAAGGGA CCTCTGGTTG TCTTCACTGC    179460

TCATTATATG TTAATTATAA TGTATTAACA TGCTAAAAGA CACTCCTACC AGCATCATGA    179520

CAGCTTACAA ATACTGCGGC AATATCTGGA CTTTACCTTA TATGGTCTAA AAGGTGGAGG    179580

AACCCTCAAT TTTGGGAATT GTCCACCCCT TTTTTGGAAT GCTCATGAAT AATCCACCCC    179640

TTGTTTAGCA CATAATCCAG AAATAACTAT AAGTATGCTT ATTTGAGCAG ACCACGCTGC    179700

TGTTCTGCCT ACAGAGTAGC CATTCTTTTA TTTCCTTACT TTCTTAATAA ACCTGCTTTC    179760

ACTTTACTGT ATGGACTTGC CCTAAATTCT TTCTTGTGTG AGATCCAAGA ACCCTCTCTT    179820

GGGGTCTGGA TCAAGACCCC TTTCTGGTAA CATCTTTCTG GTGACCACGA AGGGACAATA    179880

CTGAGGAGAC TCTGAAGCCA AAGGAAACAG ACTACAGCAC CAACTGGCTG ACTTTGGGTA    179940

AGTGGTGGAG TCCCCGGGTA AAGGATAGGA TTGGGTTAGA GGTGCAACTT AGGGGAGATA    180000

GGGTCTCTCC TAAGACAGAG AGGGTTTCAG TCCGCTCTTA ATAAAGGGCA AGAATGCTTG    180060

ACCGAACTTG GGTTTGAGAC CCAACTTAGG AAGGCTACAG TCCTTAAGAT TTAAGGGGTT    180120

AGAGGCCCCT CTCAGTAAAG TCTCTCTTGG TTAAAAACGG ATTTAGCATT AGGGGATGTT    180180

AACTGCTATT CTGTTTGTAT TAATCTTCCC TGTGCTCTTT GCTGACAGCT ATGGGTGACA    180240

GGATTAGGCA TGTACAGGAT CACGGACAT TGGGAACTTT TCTTCTCTCC AAAAGGGGAA     180300

GCTTGACAGC TGATAGGACT GTTGGAAAAG ATCCCTTTGC TATGACAAGC AGCCGCCTGA    180360

ACTTTTGATT CAGTGTTGCT GCAATGGGTG GGTCTTTCTC TGGCCTCTGT GAACTCCTCA    180420

CCTTCCCCAT CTCACCACAG GCAATGCTTT TCTCCCTTTC TCTCTTTTCT CTTTTCTGTC    180480
```

```
TTTTCTGTTA CTTGAGACAA CCATCTTGCC CAGAGACCAT ATGTTGAAAC TCCTGGTCAG  180540

AAGTTTGATT AAAGATGAAA GGGCCTATCT GGGGGCAAGT TTGAGCCTTC CCAGTTAGAT  180600

ATTGGGTGCT AAGTGGAGTG GCCAATGTCT ATGTTTTGTC ACATGTATAT TGCTCTGGCT  180660

GAAATGGAAA ACGTTAATTT GGTTACTTTA TGTGGCCATT GGGCAGCATC TTACAAAAGT  180720

GAGAGACATT TATTTGCCTG TGGTTCCATG AAACAGAAAA AAGTTGGTTT TCTTTTGTGT  180780

CGTAGCTTGG ACCCAAGGGC TTTGCAGTGA GCAAGGTTGC TAGTGCTGCT CAGTGAAAGA  180840

GAACCCAGAA ACCTGGCATG CCAGCAAAAG GGTAAAGATT TCTTACCAGT CAGGCTTCTG  180900

GCCTCTCTCT CTTAGTGAAA ACTGAATGAA TGGTAAAAAT CACTGTTTAT CACCTCTGTA  180960

AAGTTTTGAT TAATGGGAAC AAGGATTTGT GGGGCTAGTC TTAAGCTGTA ATGAATCTGG  181020

TATACTTTGT GATATCAATT TGTCTTTCTG TATTACTCTG TCATAAAGAG GAATATGGTA  181080

GGATAGAACA TGGGCTCAGG ACTCCATAAG CCTGCTGTTC AAGCCAGCCC AGTAAACTGG  181140

TCCGTTGCAA AGTTTATTAC AGGTCCCTGG AAAAAAAAAA AAATAAAAAC TGGATGAAGT  181200

TTCCTTCTCA TCTTGTTTTA TGTCCTTTGG AGCTTCACCT TGTAACCACG TGGCGGTACT  181260

TTCTCTTGGT CTCTGCCATC CAGGGAACAG GAATTTTGGG GTTTATGTAA TAGTTAACTC  181320

TAAAAATTAT CTCAAGCCAT TGCAAGCTCA AAATTGGCTG CTCTGGACCC CTTCTGGGAA  181380

GGGCAATGGA AACTAACCAG TGTTGTAGCT CAGCAGCTAA GGATTTGTCA TTTTATAATG  181440

GCGGCCAAGG TTCAATCCTG GCTTAGGGAA TGAGTACTTT CTGATTGATA TCTGTGTGAC  181500

CTTTACCATT TGTTGATTCT GTTCTCTTCC CCTCCACACA CTGTCTTGAG TTTTCCTCTC  181560

TCTGAGAACC TGGAGATTA TCTTTGGTAA AGTTCAAAAG CCAGAAATAA TGGCCGTGTG  181620

GGATGGCTAA AGTTGAGTAA TAAGAAACTT AAAAGGACTC CTTTTTTTTT TGCTTTAGAG  181680

TGCTATGGTT TATGGTTAAA AGCTTAATTA AAAGTGGATA TTCAATCTCT AAAAGCCTGG  181740

GACTCCTTGG GAAAAGCAGA GGAGGCACCA CAGACCCCAT TTTGGGAAAA CCTCTGTTTT  181800

CCTCATGAAA CCCCAGGAAC TGGAAGTGGA TAGATCCTTC GCAAAATCTA AGGCTCTGTT  181860

TGGCTTTGCA TTATGTTATC TGATGTTTTT GACTTTGGG GGTATCAGAA ATTACTTTGC  181920

ATTATGAGGG AGATCTGGTG TGTAATAACC AGGTAGGAAA TATACTTCTG GGGATAGCTA  181980

AAGGCAAATA TAGGTGAATA CTTGGCTATT TGCACTTTTG GATCACAAGA AGCATTCTCT  182040

TGACTACCTA GAAGGTATGG AAATGTCTCC ATCCCCACCG AGAGATAAGA TTCCCAGGGG  182100

AGATGGCTGA TCCCCAAAA GAGGGCTGAT TCCCTCTTTT GGGATCCAGG ATCTGGTATA  182160

AAAATGGGAC CCTGGCCAGG CACAGTGGCT CACGCCTGTA ATCTCAACAC TTTGGGAAGC  182220

CTCAGAGTTA TGAATGTCTC ACCATACTGA CACTTTGTGA CTGAGCTCCT CTCTACCCTG  182280

GACACAAGAG ACCCTAATAA TTAGACAGGA ATATCATTGC CCCTATTTAG TCTGAAGAAG  182340

TTATAGAAGA CGGATCTTTA TCCCACTGCA ATCCTTAGGA TTAAGGGTTC CCTGGTAAAA  182400

GGGAGTGGGA AAATATGTCA GAGGCATTTG AATCAGAGTG ACTCCATCTT GAATAGGGGC  182460

TGGGTAAAAT AAGGCTGAGG CCTGCTGGGT TAGGTTAGGC ATTCTAACCA GGAGTTTAGT  182520

CACAGGATGA GATAGAAGGT TGCACAAGGT ACCCGTCACA AAGACCTTGC TGATAAAATA  182580

GGTAACGGTA AAGAAGCCAG CTAAAGCCCA CCAAAACCAA CATGGCCACA AAAGTGACCT  182640

CTTGTCATCC TCACTGCTCA TATACACTAA TTATACTGCA TTAGCATGCT ACAAGACACT  182700

CCCACCAGTG CCACGACAGT TTACAAATAC CATGACAACA TCTGGACGTT ACCTTATATG  182760

GTCTAAAACG GGGAAGAACC CTTAGTTCTG GGAATTGTCC ACCTCTTTCC TGAAAAATTC  182820
```

```
TTGAATAATC CATTAGTTTA GCACATAATC CAGAAATAAC TATACGTCTG CTTATTTGAG    182880

CAGTCCATAC TGCTGCTCTG CCTATGGAGT AGCCATTCTT TTCTTTTATT TTTATTTTTT    182940

AGATAAAGAC TCGCTCTGTC ACTCAGGCTG GAGTCTGGAG TGCAGTGACG TGTTTTGGCT    183000

CACTGCAACC TTCACCTCCC GGGTTCAAGC AATTCTCCTG CCTCAGCCTC CCAACTAGCT    183060

GGGACCACAG GTGGGTGCCA CCATGCCTGG CTAATTTTTG TATTATTAGT AGAGATGGGG    183120

TTTCGCCATG TTGGCCAGGC TGGTCTCGAA CTCCTGGCCT CAAGCGATCC ACTTGCCTTG    183180

GCCTCCCAAA GTGCTAGGAT TACAGGCATT ACCCACTATG CATGACCCAT TCTTTTATTT    183240

CTTAACTTTT TTTTGTTTTT TTGAGACAGA GTCTCACTCT GTCACCCAGG CTAGAGGCTG    183300

GAGTGCAGTG GTGCGATCTT GGTTCACTGC AACCTCTGCC TCCTGGGTTC AAGCGATTCT    183360

TCTGCCTCAG TCTCCTGAGG AGCTGGGACT ACAGACATGT GCCACTACAC CCAGCTAATT    183420

TTGTATTTTT AGTAGAGACA GTGTCTTGCC ATGTTTGTCA GGCTTGTCTC GAACTCCTAA    183480

CCTCAAGTGG TCTGCCTGCC TCAGCCTCCC AAAGTGCTGT GATTACAGGC ATAAATCACT    183540

GCGCTCGGCC CTTCTTTACT TTCTTAATAA ACTTGTTTTC ACTTTACTGT ATGGACTAGC    183600

CCCAAATTCC TTCTTGTGTG AGATCCAATA ACCCTTTTGT GTGTGAAAGA ATGTATTGCT    183660

GCTGTTCAGG CTGGAGCAAG CTGGAGCTCA TGCTGCTGCT CAGACTGGAG CATGCGTGAT    183720

CTGTGATCCC AGTAAGAGGA TCATGGTCAC TCCAGCCTGA ACGACAGCAT GATATCTCAT    183780

CTGTAAGAAA AAAAAATTAC TAGAGGGCTT TAACAGCAAA TTTGAGCAGC AAAAAGAAGT    183840

AATCAGTGAA CTCAAAGATA GGTCAATTGA AATGATCTAC TCTGAAAAAC AGAAAGAAGA    183900

CAGAATGAAG AAAAAGAAAT AGAGCCTTAG AGACAGGGGA TACCATCAAG CATACTAATA    183960

TATGCATAAT GGGACTCCTA GAAGGAGAAA AGTGAGAGGA CAGGGAGAGA GAATGTTTGG    184020

AGAAATAATT TCTCAAAGCT TCCCATGTTT GGCAAAAAAG CATTAACTTG CATACATATT    184080

TTAGGAGCTC AATGAATTCC AAGTAGGATA CACTCAAAGA GATCCATACC TAGACACATC    184140

ATAATCAGAT TATCAAAAGA TGAAGAAGAT GAATCTTGAG AGCAGAAAGA AAGGAACAAT    184200

TCATCACATA CAAATAGTAC TCAAAAGATG TCTGGAGTAG GTATACTAAT ATCGACAAA    184260

ATAAACTTTA AGATAAGCAT TGTTATAATA AATAAAGAAA GGTATTTTGT AATGATAAAA    184320

GTGTCAATTC ATCAAGAAAA CATAACATTA TAAACATACA TGCACCTAAC AACAGAGCCC    184380

TAATATTCAT GAAACAAAAC TGACAGAATT GAAGGGAGAA ATAGAAAATT CGACAATAAT    184440

AGTTGGAGAC ATCAATACCT CACTAGTTAG ACAAGATCAA CAAAAAAATA GAAGACTTAA    184500

CACTTGAAAA CACCTAACCT GACCCTAACA TAAATCTATA GGTCACTACA CCCCAAAACA    184560

GCAGAATAAA CATCCTTCTG AAGCTCACAT GAAACATTTT TCAGGATAGA CTGTATATTA    184620

CTTCATGAAA TAAGTCTCAA TAAATGTAAA AGGACTATAA TAATAGAGTA TATATTCTCT    184680

GACCAAAGTG GAATGAAGAT AGAAATCAAT AACTAGGCTG GGCGTGATGG CTCACGCCTG    184740

TAATCCCAGC ACTTTGGGAG GCCAAGGCGG ACAGATCACG AGGTCAGGAG TTTGAGACCA    184800

GCCTGACCAA CATGGTGAAA CCCTGTCTCT ACTAACAAAA TACAAAAATT AGCCAGGCCT    184860

GGTGGCATCT GCCTGTAGTC CCAGCTACTC GGGACACTGA GGCAGGAGAA TCACTTGAAC    184920

CCAGGAGGCA GAGATTGCAG TGAGCTGAGA TCGCGCCACT GCATTCCAGC CTGGGAGACA    184980

GAGCGAGACT CCGTCTCAAA ATTAAAAAAA AAAAGAAAC TAGAAAAATA AGAACAAATC    185040

AAACCCAAAG CAAGCAAGAG GAAAATGAAA AATTTCAAAG CAGCCAAGAA CAAAAGGCAC    185100

ATTATGTACA GAAGAACAAG TGTATAGATC ACATATTTCT CATAGACACA ATATAAGCAA    185160

AAAGACAGTG GAGCAAAATT TTTTAGATTA ATGAAAGACC TACAATTCTG TACCAAGCAA    185220
```

```
AAAAACTCCC CCCAAATGAG GGTGAAATAA GACAATTTAA TACAGAGAAA AGAGGAAGGA    185280

ATTTATCTAG TCATATGTGA GAGTTTTATG ATACATTTTG TACTGTATAT GTGGATGTTT    185340

TCTATTTCAT TTAAAAAATC AACCGTGCAA TTAAATGGTA GATTGTCTTG CTTCTTTTTG    185400

ATTGACACAG TCATTAACTA AAATATTGTA GTATTTTTTT ATCTCCCTGC CTAAAGGCAA    185460

TAAACATCTA ATCAGCAGAC TAGAACAATA AAAAATATTT TTTAAAAGTC CTTTAGGCAG    185520

AATGATAAAA GTCCCTTAGG CATATTGAAA TTCCTATTTA TACAAAGGAA TAAACAGTAC    185580

TAGAAATTGT AACTATGTGA GTAAACAGAT AATATTTTTT CTCCATAAAA TGTGGTTGAC    185640

TATTTTCACA AAAATAGTTA ACAATGTAAT GTGTGATTTA TAGCATTTAA AAGTAAAACA    185700

GGCCGGGCAC AAAGGTTCGT GCCTGTAATC CCAGCACTTT TGGAGGCCGA GGCGTGCAGA    185760

TCACTTGAGG ACAGGAGTTC AAGACCAGCC TGGCTAACAT GGCAAAACCC CATCTCTACT    185820

AAAAATACAA AAATTAACCA GGCGTGGTGG TGCACGCCTG TAATCCCAGC TACTCTGGAG    185880

GCTGAGGCAC AAGAATCACT TGAATCCAGG AGGTGGAAGT TGCAGTGAGG CAAAATTATA    185940

CCACTGTGCT CCAGCCTAGG CAACAGAGCT AGACTCTGTC ACACACACAC ACACACACAA    186000

AAGAAAAGTG TATGACAACA ACAGTGCAAA AGAAGTGGAA ATGAAAATAA TGTTATTTTA    186060

TATAAGTGGT ATACTTTTAG ATGAACTACG ATAAATTAAT GATGTATACT ATAAACTCTA    186120

AGGCAACCAC TGAAATAATG AAACGAAGAA TTATGGCTAA CAAGCCACAA AAAGAAATAA    186180

AATAGAATGA GAAAAAATAT TTAAGTTGTT CAACAGATGG GAAAAAAAAG AGGAAAAAGA    186240

GAACAAAGAA CAGATGGGAC AAATGGGAAA GTAATAGCAA GATGATAGAC TTAACTCTAC    186300

CCATATAGAT TATCACACTT AAGGTAAATG ATCTAAATAC TCTAATACAA AAGCAGAGGT    186360

TGTCAGATTG AATTAAAAAA ACAGACAACA ACAAAAAAAA GCAAAAAAAG AGCCACAACA    186420

TGCTGCCTAC AAAAAATTCA CTTTAATATA AAGACACAAA TAGTCTAGAA CACCATCACT    186480

TTTAACCTTA TTTACTCAAA CCTCCTGATC CCTATTTATT TATTTATTTA TTTATTTATT    186540

TATTTATTTA TTTATTTATT TTTGAGACAG AGTCTGACTC TGTTGCCCAG GCTGGAGTGC    186600

AGTGGCACCA TCTAGGCTCA CTGCAGCCTC TACCTCTCGG GTTCAAGCGA TTCTCCTGCC    186660

TCAGGCCTCC CAAGTAGCTG GGACTATAGG CACATGCCAC CATGCCCAGC TAATTATTAT    186720

ATTTTTAGTA GAGACGGGGT TTTGCCATGT TGGCCAGGTT GGTCTCAAAC GCCTGACCTC    186780

AGCCTCCCAA AGTGCTGGGA TTACAGGCGT GAGCCACAGC ACCCAGCTCC TCTTCATTTA    186840

TTCTTGCTAC GCTTCCTCCA ATCCATTTTG TGCATTTGAT GATTTTGCCA GTAACTTCTT    186900

TATTTTTCTG GTAAAATTAC TTATGGGTCA CTGAGGACTG GGATGTTCTT TCTTCTAGAG    186960

GGGGTTTGTG TCTGCTTTTG CCAGGAAGCT GGGGTACCAC CAGTCAAGTA TTACTTTAAA    187020

CTCAATTCAT GAATTGAGAC TTTTTTTTTT TTTTTTTTT  TTACGCAGAG TCCTACTCTG    187080

TCACCCAGGC TGGAGTGCAG CGGTGTGAAC ATGGCTCACT GCAGCCTCAA CCTACTGAGC    187140

TCAAGCAATC CTTCTGCCTC ACCATTCTGT ATAGCTAGGA CTACAGGTGT GTGCCACCAT    187200

GCCTGACTAA TTTTTTAAAT ATTTTTTTTA GAGATGGGGC TCACTTTGTT GCCCAGGCCA    187260

GTCTCGAGCT CCTGGGCTCA AGTGATCCTC CCACCTTGGT CTCCCAAAGT GCTGGGGTTA    187320

CAGGCATGAG CCTCTGTGGC TAGCCAAGAC TTTTTATTTT TTAGCCTAAA TGTGTATAAA    187380

AGTTGGCTTG TGGTTACAAC TTATCAGGAT TGATGATCTC TCTCTCTCTC TCTCTCTCTC    187440

TCTGTCTCTC CCCACCTCTC TCACATCCCT TGCTCTGCTG AGAAGCAGAG CAAACATTCT    187500

AGCAGTTTCC AGAGAGTAGG ATGGGATTAC TTCTAGTTTA CTTTTATCAT CCTTTGGGAT    187560
```

```
CGCAGTATTA CTGGGAGAAC ACAAGTATCT CTTATTAGAC ATACCACCTT TGTAGAATCT 187620
GGACTTTCAT TTTAGACTTT ATTTGTTTTC TACTATAAGC AATTTAAGTT ACAGATCTCT 187680
CTACACACTG TTTAAGTTGC ATCCCATGAA TTTTGATGTG CTTTATTGTC ATTATTATAT 187740
AGTACAATGT ATTTTGTAAT TTTTTGTGAT TTGTTTGGAG AGATTGATTA ATTAGAATGA 187800
TGTTTAATTT CCAAATATGT GTGTTTTTTT CTACATTTCT TATTTTTATT GATTTCAAAT 187860
TTATTTCTAC TGTAGTCAGA TTTAATAATT CATTTATTTT TATTATTTTC ATTTTTTTAG 187920
AGACAGGGCC TTTCTGTGTT GCCCAGGTTT GTCCCAAACT CCTAGTCCCA AGCAGTTCTC 187980
CTGCCTCAGC CACCCAAAGT GCTGGGATTA TAGGCACGAG CCACCCGTGC ACAACCAACA 188040
ATTCATTTAA AAAGTGGGCA AGTGAACTGA ACAGACATTT CTCAAAAGAA GGCATACAAT 188100
TGGCCAACAA ATATATGAAA GAATGCTCAA CATCACTGTA TTAGTCTGTT TTCATGCTGC 188160
TAATAAAGAC TTAACCTGAG ACTGGGGAAT TTACAAGAGA AAGAGGTTTA ATGGACTTAC 188220
AGTTCCACAT GGCTGGAGAG ATCTCACAAT CATGGTGGAA GGCAAGGAGG AGCAAGTCAC 188280
ATCTTACATG GATGGCAGCA GGCAAAGAGA GAGCTTGTGC AGGGAAACTC CCGTTTTTAA 188340
AACCATCAGA TCTCGTGAGA CTCATTCACT ATCATAAGAA CAGCATAGGA AAGACCCGGC 188400
CCATAATTCA GTCACCTCCC ACTGGGTTCC TCCCAGGACA CATGGGAATT GTGGGAGTTA 188460
CAATTCAAGA TGAGATTTGG GTAGGGACAC AGCCAAACCA TATAAATAAC TAATCATCAG 188520
GGAAATGCAA ATCAAAACCA CAATAAGGTA TCATCTCACC CCAGTTAGAA TGGCTATTGT 188580
CAAAAAAACA AAAAATAACA AATGCTGGTG AGGATGTACA GAAGAGGGGA CTCTTATGTC 188640
CCACTGGTGG AAATGTCAAT TAGCATAGCC ATTATGCAAA ATAGTATGGA AGTGAGGTAG 188700
GTTACATAGG GTGGTCACAG CCTCCCTTGA AAGGAAACAA GAAACTTGTC AAATTGATGG 188760
AGAGAACAAA TCTCTTGACA TTACACAAAC TGCATCTGGG GCTAGTGGTT AGAATATCCT 188820
CAGTCAAGGA GGTAGAAGAG CAGGAGGGAA AATCCCTAAG TTCGTGCAAG TGCAGAAACC 188880
CACAAGCTGT GTTCTCAGGT TGACATATAC TCATTTTAAT AGTAAGAAAC ACACCCTTGG 188940
GTAGAGAATT AAAATGCTAA TAATACATGT GATGTATGTA CTAGCGTGTA TGGCAATATT 189000
GCATGCACAT TCAAGAGACC ACCCAAAACA TATTTAACAA CAATGCCCAT TCCCACCCCC 189060
TCATGGATAA TCACGTAGGA CTCCCATAAC GGGAGTTTCT TCAGTGTCAA TTGGTGCTGA 189120
AGTAGCCGAC CCTGACTCTG CTATCAGCGT GTACTTTCAC CTTGCAATAA ACTCCTTTGC 189180
CTACTTTTAC TTTGGACTGG CTTTCAAATT CTTTTGTGCA GGGAATTCAA GAATCTGAAC 189240
CAGCCTACTG ACAACAGAGG TTTCTCAGAA ACCTAAAAAT AGATCTACCA GATGAGGCTG 189300
AAAATCTGCT ACTGGCTATT TATCCAAAGG GAAGGAAATC AGTATACAAA GAGACACCTA 189360
CATCCCCATG TTTATTGCGT CACTCTTCAC AAGAGCTGAT ATATAGAGTC AACCCTAAAT 189420
GTTCATTAAC AGACAAATGG ATAGAAAATG TGGCATATAT ACACAATGAA ATACTATTTG 189480
GCCATGAGAA GAATGCAATC TTGTCATTTG TGGCAACGTA GATGAAACTG GAGAACATTA 189540
TGTTAAGTAA GATAAGCTAG GATTGGAAAG ATAAATACTA CATGTTATCA CTCATATGTG 189600
AAAGTAGAGA AAAATTTTTA GCTCATGGAT TTAGAGAACA GAACTGTGGG TACCGGAAGC 189660
TGGGAAGGGT AGCAAGGAGG GGAGGATAGG GAGAGGTTGG TTAATGGTGA CAAAATTACA 189720
GCTAGATTGT AGAAATGAGT TCCGGTGTTC TGCACCATTG TAGGGTGCAT ATGGTTAACT 189780
CTCATTTATT GTATATTTTC AAAAAGCTAG AAAAGAATTT TGAATACTCA CAACAAAATA 189840
AATGATAAAT GTTTAAGGTG ATGGATATAC TAATTACTCT GATTTGATTA TTACACATTG 189900
TGTACACATA TAAAAATATC ACTCTTTATC CCGTATATAT GTACAGTTAT TATATGTCAA 189960
```

```
CTAAAAATAA AAGAAAAAAA GAATATGATC TATCATGATG TATATATCAT GTGTACTTGA    190020

GCAAAATGTG CATGCAGATA TTGTGTATAA TGTTCTATAA ATCAATTAGC TCAAGATAAT    190080

AGATAGGATT GTTCAGATCT TCTGTGTCTT TACTGATATT TTGTCTAGTT ATTGCATCAT    190140

TACCAAAAAA AGGGTGTTAA ACTCTCCAAA TGTGATTGTA GAATTGTCTA TTTTGTCTTT    190200

TCTTTTCCAT TTTTACTTTA TGTATTTTGA AACTCTGTTA TGACATTTTG CTATGTATTT    190260

TAAAACTTCG TTATGTATTT TGAAACTCTG TTGTTAGAAT CATACATTTA TGATTATTAT    190320

GTTTTCTTGA TGAAATGACA CTTTTCTATT GTCATTGTTT TTGTTTTTTC TGAAATGGAG    190380

TCTCACTCTG TTGCCCAGGC TGGAGTACAG TGGCACAATC TTGGTTCACT GCAACCTCCA    190440

CCTCCTGGGT TCAAGCGAGT CTCCTGACTC AGCCTCCAAG TAGCTGGGAT TACAGGCATG    190500

TGCCAGCATG CCAAACTAAT TTTGTATTTT TATTAGAGAC AGAGTTTCAC CACGTTGGCC    190560

AGGCTGGTCT CGAACCTCTG ACCTCAGGTG ATCCGCCCAC CTCGGCATTT TTATTTTATT    190620

TTATTTTTTT GAGACAGAGT CTCACTCTGT CACCCAGGGT AGAATGCGGT GGTGTGATCT    190680

TGGCTCACTG CAACCTCCGC CTCCTGGGTT CAAGCAATTC CCATGCCTCA GCCTCCCGAG    190740

TAGCTGGGAT TACAGGCACA TACCACCATG ACTGGCTAAT TTTTGTATTT TTAGTAGAGA    190800

TGGGGTTTTT CTATGTTGGC CAGGCTGGCA ACTGACTCCT TTAACAATAC AAAATATCAC    190860

TCTGTCTCTG GTAACACTCT CTGTCTTAAA CTCTATTTTA GCTGTTATTA TTATAGCCAT    190920

TTTAGTCTTT TTATGCTTTC TGTTTGCATA GTGTATATAT TTTAATATGT TTATTCTCAA    190980

GTTATCTGTG TTTTTATATT TAAGATGTTT CTCTTCTAGC CAACGTGTTT GGTTCTTGCA    191040

TTTTTAAGTC GATTCTAACA ATCTTTGCCT TTCAATTGAA ATATTTACAC CATTAACATC    191100

TAACATTAAC ATTTATTTTT CTTTCCACAG TACACTGGCT AGCATCTCCC ATATAATATT    191160

GAACATAAAG TGTGATAACT GACATCCTTA TTTCATTCCT ACTCTGAGTG AAAGGGCAG    191220

GGGTGGAGAA AGCATTCAAC AATTTGCCAT AATTATAATG CTTTTTGTTA CACTGTTTTC    191280

TTCTGCATTA AAAAATATCA TTACATTTTG CATGAATTAT TAGGAGAAAA TATTTTCCAA    191340

TTTTCCTGGA AAATGCCATA ACCACGTCTC TCAATTTTGT TTCCATCTTT CTTCCACATT    191400

TTACATAACC TACATAAGAG ACACATTATC AAGTATATTT TACATGGCTT CTCAGTGTCT    191460

TCTCTGTCTG CTAACAGGTT TACCAAGAGA TGGCACTCTT GTATTCTGG TGGCTATGTC    191520

CATATCGTTT TGCCTTTAAG ACAGCGTAAC TACTTCTTTC ACCAGTATTA AAGACATGTA    191580

CATTTGATCT GGTTCTTGTG GATGATTTTA AATGACTCAA GCTAATAATC CTAATTTTAC    191640

CTAAACACTC CATTATTTTA AAATGTATTC CTTTATGCCC ACAATAAACA TTTATTGACA    191700

TTAGGCTGGA CATTAGGCTT CTCTATGGCA GACATTAGGC TGGACCCTAG CCATATATCT    191760

ATTGAGGGAA AAAAAATTAT TTTCTATATA AGTTTCCAGA AAGCCAAGAT GTGTTTTAAA    191820

AACAAAACAA AACATTACAT TCTAAATGCT GTAACAAGAT AAGAAAAAGT GTTGAGGCTG    191880

AGAGAAGAAC AAAGCAGCAA GCAACTCCTG GAAGGACCAC TGCTGCAGAG GTAATAACTG    191940

GTGAACCATG TTTTGGAGAA GGAAAAGGTC ACCAAGAGAA GGAGGGGGTC CAGGGTGTTC    192000

AGAAAGATTG CATGCATAAA GATCAAGGGT AATAAAAAAA ATTCCGTATT ATGTAAATGT    192060

GAAGTTCCAG GACCATGAGC TTGGAGAGCA TGAAGTACAG GAGGAGGGTT GGTTTCAAAT    192120

AAATCTGGGA ATGAAACAGT GAAGCCTCTG GCAGAACTCA CATCTCTTTC CTCCCCTCTT    192180

CCTTGCACAT TCCCTTTATG GAGTAATTGC AGGGATGGGA AAAGTTCAAA ACCACCACTG    192240

AGCCTAGGAA GTGCTAGGGT AAAGTGGAGA ATGAACCTGC GTGATTTGCT CATCCTAAAC    192300
```

```
TAGGTTCTTC TAGGAGAGCC CTTCCCCATA AAATCTGCCC TCCTCGAAGG GGCCCAGACA    192360
GCCTAAGCTC ACCTCCCAAA GACCCCTTAC TTGCTGACTG AATCTGATTC CACCCAGACA    192420
TGGCCTAAAA CCCTTCCATA ACTCTATAGC CAAATTCAAT TTTAGACAGG CCTCATACCA    192480
ACCTTTCTTC CTCTAAGTCT GCCACCCTAG GCAATTCTCA ACATTCTCTA CACACTTTGG    192540
GGCCATAGAC GTGCTACCAA GTCTCCAGAC CTAGACCTGA TGGAGCAGTG CTGTAATGAG    192600
ACGACCACTG GCCTTTGAAC CAGACCCTTC TCTGTGGCTC CTATGCATCT CCAACCTGTT    192660
TTGAGCACTG CTGCCAAGAC ATCTTTGGCA CTTTGTTGTG AAGTTTTAAA ACTGAACTAA    192720
TCTACAAAAC ACCTAACCTT TAAAAATTCA TTGTCATTTC ATATCATGAA AGATAAAGAA    192780
AGGCCAGGAA ACTGTTCCAG GTTAATAGAG ACTAAAGAGA TAGCAACCAA ATGCAATTTG    192840
TGATCCTGGA TTGAGGGGAA AAAGTGTTGT CAGAGACATG ATTGGGACAG CTGGTAAAAT    192900
TTGAATTTGA ATTTAAAGAT AAAGTATTGA GTAATATAGG AAGATGATTA TCTGCAACTT    192960
TCAAATGTTT CAGTAAGTAT ATATATATAT AAAGAGATAT AAAGACATAT AAATAAATGG    193020
ATAGGTAGAG AAAAAGCAAA TGTATAATAT TAACAATCTA GGTAAAAAGT ATATGAGTGT    193080
TCTTTGTACT GTTTTTCTGA TTTTTCTATA TGTTTGAAAT CATTTTAAAA TAAGAAGGTT    193140
TTTGGGTTTT TTTTGTTTGT TTTTTGTTTT TAGAGACAGC ATCTTATTCT GTCACCAGGC    193200
TGTAGCTCAG TGGCCCAATC ATTGCTCACT GCAGCCTCAA CTTCCTGGGC TCCAGTAATT    193260
CCCCCTACCT CAGGCTCATG AGTAGCTGGT ACTTCAGGTG TGCACCACTG CACTCAGCTA    193320
ATTTTTATTT TTTAAATTTT TGTAGAGATG GCATGTTGCT ATGTCACCCA GGCTAGTCTC    193380
AAACTCCTGC CCCCAAGTGA TCCTCCCACT TTGGCCTCCC AAAGTGCTAG AATTATAGGC    193440
ATGAGCCACT GCACCCAGCC CCAAATAAAA AGTATTTTA TTTTAATTAA CTAATTAACT    193500
TTGAGTCAGA GTTTCACCCT TGTCACCCAG GCTGGAGTGC AATGGCATGA TGTTGGCTCA    193560
CTGCAAACTC TGCCTCCTGT GTTTAAGCGA TTCTCTTGCC TCAGACTCCT GAGTAGCTGA    193620
GATTACAGGT GCCTGCCACC ATGCCCAGCT AATTTTTATA TTTTTAGTAG AGACGGGGTT    193680
TCAGCATGTT GGTCAAGCTT GTCTCAAACT CCTGACCTCA GGTGATCCAC CCACCTCCGC    193740
CTCCGAAAGT GTTGATGAGC CACCACACCC GGTCTAAAAA GTATTTTAAA ACCACAGTCC    193800
CACTCTACCT TGTCCTACAC TACCAGGGGC TAGGATCACC CCATGTCTTC TAGGCTATGA    193860
GATAGAGGAA TCCAAGGAAG AAGATAAGCT ACTTGGTTCC TCTATAGGGT CTTGTGTGTG    193920
CTCTCATGTG CTCTCTCTCT CTCTCTCTCT CTCACACACA CACACACACA CACACACACA    193980
CACATGAATA CCAGAGCTAT CACTTTCCCA GTCTAGTACT CATCTCATCC CAAGGGTTTT    194040
GTGTTGTAGT GGTTTGCTCA TTTCTTTGTT TTGTTTGTTT GCTTGGATTA TTCTTTTTCT    194100
CTTTTTGCAG CTGAAGGGAG AATTTCCAGG CCAGCCCTTT GGCCATTAGA GTTACAGTGC    194160
CTCTATTCAG GCTTCATAGA GAGACCTGGG ATTCAGTAGT GGGGGCTTT TATCCAGTTC    194220
AAAATAATGC ATTCTCACCA AGATGTACTT TGAAATAAAA CAATACTAAA ACACAAAATT    194280
TTATTTATGC TGAACATTGA ATCACTTTTT TCTGTATTTT GTGTAGAAAG TTATACACAC    194340
ACAAACACAT TTGCTCCTGC TTTGTTTATT GGCCCAGGGG TATGTTTGGT AATACTTCAT    194400
CAGGCATGAG TAGTACGTCT TGGAAGGTGT GGTCTAAAGC CTAGACTCCT ATCTGCTTCC    194460
TTCAGCATTC TCCAGTGTAT CTGTCATCTG TCTACCTTAG GATAGGGTC TCCAGAACTT    194520
CCATTCACAT TTAGAAGAGG GCAGCGGCTT TCTATGGAAA ATATGAACTC TCATTCATCT    194580
CTATTCCTTC TTCTAGCTAT GGTCCAGCTC AGCTGTTTGG AATAAAGTAT CTATATGAAG    194640
TCTGCGAATG GTTCTCAGAC TGGTTGAACA TTAGAATCAC CTGAGTACCT TCTAAAATTC    194700
```

```
TTATTACCCA GGGCATATCT CAGAATGAGT ACCGCAGGGT AGGGATAGGA TTAGGGATCA    194760

TGATCTCTGG AGTCTGGTTT AGGCACTAGT GCTGTTTAAA ACTACGTTCA TGAGGTGGAG    194820

GTTGCAGTGA GCCGAGATGG CGCCACTGCA CTCCAACCTG GGCGACAGAG TGAGAGTCTG    194880

TCTCAACAAA ACAAAACAAA AAAAACCAAC TACCCTTGTG ATTTGAATGT CCATCCAAAA    194940

TTGAGAACCA TTAGGTAAGG CCAAGCTGTA TAATTAAAGA GCAGTTTTCA TTTGTCTGGT    195000

GTGGTGGCAG CTTTTTGATA AGGGAAGTAT TGTTGCCATC CACATACCTG AGCCTCACTC    195060

CTGAGAACAC TGGTGTGTAT GTTGCTAAAA TTCCCCAGGT GATTCTGAGG TTCCTTCCTG    195120

GATAAAAACC ACTGACCCTG GGAATGTACC CACTGCCAAT CTCCTGCGTA AACCTTGGAT    195180

ACTGGGAAGC CTACAGTTGA AAATATTGGG CTTGAGATCC TGAAACAAAT CTTGTATTTC    195240

ATTAAGACTA ATATTTGGTA CAGTGCAGCA AATCAAGGGA ATTTTGGTGG CTGAGTTCTT    195300

TTAGAACTTT TGCATTGAAA TAGGTTCAAG CAGCAATAAG TTAAAACTAC AACCTCAGCT    195360

AAAGGATTAA AAGACACGTG AGCTGGGTAG GATGAGGTCT AAGGTTGGGT GTGGCGGCTC    195420

ATACCTGTAA TCCCAGCACT TTGGGAGACT GAGGTGGGTG GATCACTTGA GGTCAGGAGT    195480

TCAAAACCAG CCTGGCCAAC ATGGTGAAAA CCCATCTCTA CTAAGAATAC AAAAAAATTA    195540

GCTGGGCGAG GTGCCAGGCA CCTGTAATCC CAGCTACTGG GGAGGCTGAG GGAGGACAAT    195600

CACTTGAACT CAGGAGGCAG AGGTTGTAGT GAGCTGAGAT CGCACCACTG CACTCCAGCC    195660

TGGGTGACAG AGCAAGACTC CATTTAAAAA AAAATAATA ATAATAACAA TAATAATAAT     195720

TCAGACATAT CCAGGCATCA AACAGATACC TGGGGCAGAT GAATAGTCTT GAGATTCAAG    195780

TCACACATGA AATTTAGGTG GAAAATGACA TTGGAGAAAT TTGAGATTAT GATGAATGGA    195840

AATTTTTCAA AGAGGAATTT CAGGCTCTGT TCTTGAGGGG ATAGATGGAC TTCCAACAGC    195900

AATAACACAG GATTAATGAG GACTTGGGAT GTTACATAAA TTAGAGATGT TAGATGGATA    195960

AAGAGATAAA AGTACTCTCT CTAAGAACAT GGGACCAGAG ATAGGCTCAC TTCTAACCAT    196020

CAGATATAAC TAGCAGACTA AACGGTCTAA AAATAAAAAT CATGCCCCAC TCCTGCTTAA    196080

GACATTTTAA TTACTCTCAG TAACTCTTCA GTTTTTCTAC TGTGTTATCT TTAACTACAG    196140

GGTTGGTCTG GGTGTGCAAC ACAAGAAAGC CTGGCATATA CATGGATTCA AGTGTATGCC    196200

ATGTGCAGGT ATTCTTTCAT GTACTATTTC ATGTATTCTT TTTCACATCT GTTTTTTCCT    196260

TCATTGAAGT CAATGGCTGA TATTAGATTC TACTATTCAT GTGTACTAGT TATATATAAT    196320

TGTTACAAAA CAAATTAGCA AAAACTTAGT GGCTTAAAGC AACACACATT TATTATTACC    196380

TAAGGTCTGT GGATAGAAGT TCTGACATGG CTTAACTGGG TTCCCTGCTT CAAGCCTCAT    196440

GTGGCTGCAA TCCAGGTGTT GGCTGAGTCT GAATTCTCAT CAGAGGCTTG ATTGTGGAAA    196500

TTTCCACTTC CAAGCTCCCT CAGGTTTGTT GAAAAATTCA GTTCTTTGCA CCGGTAGAAG    196560

CTTCTTGGTA GAGGCTGATT CAACTTCTAG AGGCTGTCTG CAGTTCCTGT CACCCAGGGT    196620

GGAGTGCAGT GGAGCAATCA TAGCTCACTG CAGCCTTGAC CTCCCAGAAT CAATCTGTTC    196680

TCCCACCTCA GCATCCTGAG TAGCTGGGAC CACAAGTGTG TGCCATCACA CCTGCCTAAA    196740

AAACAAACAA ACGAAAAAAA ACCCCCAGAG AACTTTGTAG AGACAAGCTG GTCTGGAACT    196800

CCTGCGCTCA AGCAATTCTC CTGCCTTAGC CTAAAAGTTC TGGGATTATA GGTATAAGCC    196860

ACCATACCTG GCATATGGCA AGTCTTGAGC AGGACAAATA CAGATGATTT ATGTCTGTCT    196920

TCCATGGTAT TCTAGGTTAT TGTTGAGATG GTCCTCTATT GTCTTGTTCC ATCTATTGAT    196980

TAGATAAAAC GTTGTTCCTT CTGTTATTTT TCAACAGTAG CTTTTATGTG TCTCTCTTTA    197040
```

```
TCTTAAAATT CTAACCAAAG AGCTGCTCTT TTCTTGGTGT ACTTTACCTT TGGTTGATCC  197100
TTCTTAACCT CTTCTTGCCC TCTGGGCCT  AAGATGAGGG CTGTTATCAG ATGTGAGTCT  197160
ATGGGAAAGC AAGCAAGAGG TTCTTCAGCC TCCGTTCAGC CTTAAATGTC TAGGTAGAAA  197220
TCAGTCATGG CCCTTCCAAT GTGGTACAGA CCAGATCACA GAGACAGGGG TCTCAGCCAA  197280
GGTCTTGTGG CCTAAGCCTT ATAGAAATAA TGAGTGTTTA CTTACTTGGA GAACTCCCTT  197340
GGAATATCTT TTTTTGTGAA CCTGAGGCAA CTTTTGGTGA TTTCTTGATG TCTTGGGAAT  197400
CTTGGTCTAG AGCCATTTCA ACCCGATTTC TTTTCATGTC AGTGGCATTT TGTGACCAGA  197460
TAGTAAATAA GTTCTATGAT GTTCACTCAG AGAAATACAA TGACTTATGA TGCGAAGCTT  197520
CTGTGGTTCA GCCCTTACTT CATCTTCATT CCCTCTTATC TGCATCTGTC TCCTGCTTGG  197580
GAACAAAAGT CTGGCTTCAT TCTATGACCC CCACGTTGAG TTTCTTAGTA GCACTTACTT  197640
TTCAATTAGG AGTGTCCTCA CTTCTATCCG TCAGACATAA CTAGCCGACT AAACAGTCTA  197700
AATATAAAAA TCATGTCCTA CTCCTGCTGA AAACATTTTA ATTACTCCCC ATCATTTAAT  197760
TTTTTCTACT GGGTTATCTT TAACTTCAGA GTTGGTCTTG TGTGCAACAC AAGAAAACCT  197820
GGCATATACA TGGATTCAAG TGTATGCCAC GTGCATGTAT TCCTTCATGT ACTATTTCAT  197880
GTATTCTTTT TCACATCTGT TTTTTCCTCT AAAATTTATT TCCTTTTAAA AATGAAAATT  197940
TTGCATTTGA CTAAATTTGT CAAATTTAGT CAAATTTGTT TAAACCATT  TTTAAAATGT  198000
TTCCCGAAGT TTTGAGTGAA GTTAGTACTT CAGAAAAACT GTTTTGTATT TTTCCTGTGA  198060
CCTCAGTGCA CTGCTGTGCA TTTCCATTTC TGCGTCCACA CACATTTGTT TTGAGGAAAT  198120
ATAGGAACGA CAAGATAAAG TTCAAGCTCC TGGACATTGC ATAAAAGACC GTCATGACCT  198180
GGTCCTGTTG ACTTCCCTAG ATTTCCCGCT ATTTCCTAAG TTGAGATTTT TGGTTTGGAT  198240
GCTTTGTGTT TTCCTAAAAT CAAAATAGGT TTTTGCCTTT TATGATTATA CAGTAAATAA  198300
ATGCTATTTG TGTGAAACTT TAAACAATAC AAAAAAAACC TAAGGAAGAA AGTCAGATTC  198360
ATCTAAAAAT CCTTGTGGCC AGAATTAACT ACCTTAGTTA CTATTTTCTC TATCTCTCTC  198420
TCTCAATGTA TATTTGGTGT AGGTATAGGG GTGTGTGTAG TGTGTGTGTA TGTATATATC  198480
TGTTTCTATT CCTGTATGTG GATGTGCACA ACGCATCCTG CTTTGTACAC TACAGTACTA  198540
GCATTTTTCT AATGTAATTC AATATTGTTG AAAACATTTT AAAAAAGCTT GTATATATAC  198600
ACACACATAC ACATACATGC ATGTATGTAC ATATACACAT ACAGACAAAA ATGTATCCTA  198660
TGTATATTCA CACATGTATA CACACTCACA CATACATAGA GTTTTACATC CATAGTTTAT  198720
AAATGTTGCT TTTTTTTGGT CACCTTTTTG CTAAGTCTTA CACTTTTTTT TTTTTTTTT   198780
GAGACGGAGT TTTGTTGTCA TTGCCCAGGC TTAGTGCAGT AGCGCGATCT CACCTCACTG  198840
CAACCTCGAC CTCCCGGGTT CAAGCGGTTC TCCTGCCTTA GCCTCCTGAG TAGCTGGTAC  198900
TACAGGTGTG CGCCACCATG CCTGGCTAAT TTTTGTAGTT TTTTTATAGA GACGAGGTTT  198960
CACCATGTTG GCCAAGCTGG TCTGGAACTC CTGACCTCAA GTGATCTGCC TGCCTCAGAT  199020
TCCCAAAGTT CTGGGATTAC AGATGTGAGC CACTGCACCC GGCCAAGTCT TACACATCTT  199080
TTTTTTACCA CTAAACTGTT TACCCAAACC TGATAACCCA AGTCAACAGC TATTATGGCT  199140
CACACAATCT TATGTAAACA AAGATACAGA TATATAGAAT TTTCTTGATT AATATTCAGA  199200
AAAAAATGGA GTCCCTTTAT ACGTCCTTAG TATCTGCTTT ACTCATTTAA AAATGTATTA  199260
CATTATATGA AAGTATTCAG GTCAAATGTT ATAGATGTGA TTCATTCTTT TTAACTGTGT  199320
TATTTTTCTG CAATGACTAT GTATCACAAA GTACTCAGTC TTCCACTGAT GAAAATTTGG  199380
GCTATTTCCA GTTTGTCTTC CATTTTTCTT TCTTCCTCTT GGATTTTCAC TCAATGTGTT  199440
```

```
TACTAATTTA GGAAGAATCA ATAGTTTTTA TGGTATTACT TCTCCCATTC AAGAATATAG    199500

CATATGGTAT AGTATAGTAG AGTACTTAGT TTAATTTAGC CAGATCCTGT TTTCTGCCCT    199560

TTAATAAAAT TCTATCATTT TCTGCCTTTG AGTCACATTT TCCTTGTTCA TATAATTCTT    199620

AAAAAATGTA TAGTTTTCAT TCTAAGGGAA CATAAAAACT TCTTTCCATT TCTATTCCTG    199680

TCTAGTTAAT TCTACTATTG GGAAAAGTAA CTGTTAAAAA AAATTCTTAT CTTTCCAGTC    199740

AGTTCACCAC ATTTCCTTTA TACCTTTGTA CTTTAATCCC CAGTCATGTT GAACACTTCT    199800

TATTCCTCAC ACCAAGCCTC AACGGGTTTG CTCTTTCTGG AAGGTGCTTC CCCTGTATTA    199860

CTGACTTATT CATACCACAC ATGGAGACTG GCGCAGCCCT GTTCTGCCTG GAAGCCTTC    199920

CCCTGATACC CCCAGTTGGC AGGAGTCTTC ATTTGTTCTT TTCTAGTCAC CTGTGCAAGT    199980

TTGTATTGTT CATGTTTATC ATCCTTCATT CTAGTTGTCT GTCTCTGTGT GTGGTCTCAT    200040

TCAGTGGACT CTGAACTCTT ATGAAGTCAT GTCATGGGTC AGATCTTAAT AAATTAATAT    200100

TGTCGGAAGC TAATGTCATG TCTAGAATAC AGAAAATTTA TCAAAAAAAA ATATAGTATG    200160

TTGGCTGGGC GCAGTGGATC AAGCCCGTAA TCCCAGCACT TGGGAGGCC GAGGCAGGAG    200220

GATCACATGA GGTCAGAAAT TCAAGACCAG CCTGGCCAAA ATGGTGAAAC CTCATCTCTA    200280

CTAAAAATAC AAAAAGTAGC CAGGCGTGGT GGTGCCCACC TGTAATCCCA GCTACTCAGG    200340

AGGCTGAAGC GGGAGGATCA CTTGAACCTG GGAGGCAGAG ATTGCAATGA GCTGAGATCA    200400

TGCCACTGCA CTCCAGCCTG GGCGACAGTG AGACTCCATC TCAAAATAAT AATAATAATA    200460

ATAATAATAA TAATAATAAT AATTGTATGG AATTGAACTG CTCTGATTGG AAATAGCTGT    200520

TTTTTAAAAA ATTATTATTT TTTAAGTTCC TGGGTACAAG TACAGGATGT GCAGGTTTGT    200580

TACATAGGTA AACGTGTGCC ATGGTGATTT GCTGCACCTA TCAACCCATC ACCTAGGTAT    200640

TAAGTACAGC ATGCATTAGC TCTTTTACCT AATGTTCTCC CACACCCCCA CCCCATCCTC    200700

CCCCAACAGG CCCCAGTGAG TGTTGTTCCC CTCCCTGTGT CCACATGTTC TCATTGTTCA    200760

GCTCCCACTC ATAAGTGAGA ACATGAGGTG TTTGGTTTTC TGTTCCTGCC TTAGCTGTTA    200820

ATGTCAGGCC AGAGAGGCTT AAATTTTTAA GGATCTCTGG ACTTTTCTTC TACATTACTC    200880

TTGATGTTTA TAAATGTTAC AACTTCTTTA ATTTCATTTA ATGTATACCT TATTGAGTTG    200940

ATTTAACTGA GTTAACTTTG TTATATGAAA ATCATGATTG GGAGTGAGGG GGTTAAACCA    201000

GCTACAGAGA TCTTGATTGT TGGTGGTGAA GCAATGCAAG AATTCATTCA TTCAGTAAAC    201060

TAATGTTTAT TAAGCGTGTA CTGTCTTAGT CTGTTCAGAC TGCTGTAACA AAATATCATA    201120

AACTGGGTGA CTTATAAACA ACAAAAAATT TATTTCTTAC AGTTCTGGAG GTGGGAAGTC    201180

TAAGATTAAG GCCCTGGCAA ATTTAGTGTC TGGTGAGGAC AGGTAGCCAT CTTTTTGCTG    201240

AGTCCTAACA TGGCAGAAGG GTTGAATAAA CTTCCTTGGG TTTCTTTTAT AAGGACACTA    201300

ATCCTAGTGA TGAGGTTTCT GCCCTCATGG TATAACTACT GCCCAAAGAC CCCTCCTTCT    201360

AATATTATCA CTTTGTGGGT TAGGATTTCA ACATGAGTTT TGAGAGGATA CAGACATTTG    201420

GATCATAGCA CACACCATAG GACAGACACT GTGCCAAGAA TTGTGGATAT AGTGATTCTC    201480

AAAATGAACA AGATCCCCTC AGAGAGCTTG CAAAATCCAG CTATAAAATT ATGCTTTTTA    201540

AACAAATTAT GCAGTTTGAA AAATCTACTC TGAATCTTAC TTGTGGCATT GAATACTTTC    201600

GGCCACTCTT TCCTTATTAT ATTAAATATT TACTCTTGTT TGGGGATCC AGTCTCACCT    201660

ACTTTTTCTA CCAGAACTGG TATCAGCTCA TGCTCTGCCT TATGCAAATT AAGAAAATAT    201720

CATACCTTTT GGGTAAATTA AGCCAAGAAA GTTCTCCTTT CTTCTCTTTC TCTCTTTCTT    201780
```

```
TCTTTCTCTC TTTCTCTTTC TTTCTTTCTC TCTCTCTCTT TCTTTCTTTC TTTCTTTCTT    201840
TCTTTCTTTC TTTCTTTCTT TTTCTTTCTG ACAGGGTCTT GCTCTATTGC CTAGGCTGGA    201900
GTGCAGTGGT GCAATCTCAG CTCACTGCAG CCTTGAACTC CAGGGCTCAA GCAATCCTCC    201960
TGAGTAGCTG GGACTATAGG CATGTGCCAC AACATCAAGC TAATTTTTGC ATTTTTTTGT    202020
GGAGACGGGA TCTCCCTATG TTGCTAAGGC TGGTCTTGGA TTCCTGGGCT TATGCGATTC    202080
TCCTGCCTCA GCCTCCCAAA GTCCTGGGAT TACAGGCATG AGCCACTGCC CCTGGCCATT    202140
ATAACTATTT TCATTGGCTT ATCAGGCACA TGATAACTAT AATAAATCAA TAACCAGAAT    202200
TTTTAAATAA AGAAAGGAAG GAATTGTTTC AACTCTTCCT GCTACCCCTC TATCCCTCAA    202260
AAGGGTAGGC TGAATGTTGT CCTCCAAAGA TATCCATGTC CTAATCCCCA GAACCTGTAA    202320
ATATATTACC TTATATGACA AAAGGGACTT TACATGTTTA ATAAGTTAAG AATTTTGAGA    202380
TGGGCAGATT TTCCTGAATT TTGCAGATGG GCCCTAGTGT AATCACAAGG GTCCTTATAA    202440
GAGACAGGCA GAAGAGTCAG AATAAGAGAA AAATACTTCA AGATGTTACA CTGCTGGCTT    202500
TAAGGTGGAG GAAAGGCCAA GAGCCAAAAA ATGCAGTGGT CACTACAAGC TGAAAAGAAA    202560
AAGAAATGGA TTTTCCCCTA AAGCCTCTGG AGGGGGCACA ACCTTGCCAA TACCTTGATT    202620
TTGGCTCAGT GAAACCCATT TTGGACTTCT GACCTTTAGA ATTGTAAATA AATAAATAAT    202680
TTTGTGTTGT TTCAAGCCAT CACAGTTGTG GTAATTTACT ACAACAGCAA TAAAATAGAA    202740
TTAAATACAG AGATCTGAGG AGTTGAGTAG GATAAGCCTA CTCCAGCAGG TTATTTCGGG    202800
AGTATGGTGA GACTCACTAG GATGGCGGAA CTCAATTAAG GAAGTCTGAA GCTGATAAGC    202860
CAGAGAGGGA AGGCTCTCAT TTCATTTTAT AAGGGTTGCG TCACACTAGG AAGATCCAAT    202920
AGCAACCACA GTCTCAAAAT TAATGATTAC AAATAGGACA CAATTCCAAG AGTCGGGAGC    202980
CAAGCAGAAA ATGGATTAGG GAAGACATGG ATGATATGAA ACAGGAAGGA GGGGTACAAG    203040
GCAGCTTCCT GGGAAGTTGC CAGGGCAGTC ACAGTTCACA TTCATTAGGC TGTGGGCACC    203100
AAATGCATAT GGAAAATCTA GCTGACTTAA CTGAACTCCT GAAGAGGAAT GAACACCTCA    203160
TTTATTGAGG AGCTACTACC AATTAGAATA TGTATTTCAT TTGTTCAATA ACCCCATGAG    203220
TACAGTAACA CAATCCTTGC TTTACTAAAG CGGAAGCCAA TTCAAAGAGG TTCAGTGACT    203280
TGTCCAAGCT CAGGGAAAAC ACTAGGAAGT GAATATGGGT CTGACTCCAT CACTGATTTC    203340
AGGAGCCCTG CCCTTTCCTC CACACCATGC CCCCTTGCTT TCAGAAAAAA AGGCTTGTTG    203400
ACTGAATGGT TGTATGCACA GTTCAAAGCA GAAACACACG ATGACATCTT TTGAGATACT    203460
CTAACAGTGA GAACTTGAAA ATGAAGTTAA AAATTAAGCG GCAAAACCAA GCCGAGGCTT    203520
TCTGAGAAAG TGGGGCCAAA CCTGTTGCCG TCTGACTGCC ACGTGGCTCA CTATTTATCC    203580
CTGTAAAAAT CTGCAAAAGT ATTTGAAAGG GAAGAAGGGA CAGAAAACTC CCTCCTTTTC    203640
CAAGTTAGCC TTATAGTCTA GGGCTTAAAA TACTGGTTTA ATGGTGAAGG TAAGTGCTTT    203700
TCTTCTTTTT GGGTAGAAGG ATTATTACTA ACTTACCAAA GGTCCATTAA GGGGAGGGAA    203760
CAGTTTTAGG AGAAGTCAGA GAAAAGACAT TAACAGCAAC ATAAGGATCT CCATCTGGTA    203820
ATATTGCCTA ATTCCAAAAT GAAGAGACTC TCTGAAAAAG ATAACTGATT CAATGAAGAC    203880
CCTAGGGCAA GCTTGAGAA GCCACTGGTA CCAATGGACA CTGTGGACAA TGGTCATTTC    203940
TCCAAGGACG CTGTGAGTAT TAACTGTGAT GCTGTGATTA GTCAGACTGG GATTGGCTGT    204000
GGAATGAAAT ACTGATCAGA ACTGACAAGA TTTGTGTTTG GGACTGTGGC TAACGAGTCT    204060
TTTCAGACTT CTATATGAAT TTGAAATGGT CTCTCAGGAA AAGGAGAACA TGGCCGGGCC    204120
TGGTGGCTCA CGCCTGTAAT CCCAGCACTT TGGCAGGCTG AGGCGGGCAG ATCACTTGAG    204180
```

```
GTCAGGAGTT TGAGACCAGC CTGGCCAACA TGGTGAAACC CTGTCTCCAC TAAAAATACA    204240

AAAATTAGCA GGGCGTAGCG GCGCGTGCAC CTATGCGCAT GCATAGTGCG CGTGCCAGCT    204300

ATTCAGAAGG CTGAGGCAGG AGAATTGCTT GAACCCAGGA CGTAGAGGTT GCAGTAGTTG    204360

AGATCATACC ACTGCACTCC AGCCTAGGTG ACAGAGTAAG ACTCTGTCTC AAAAAAATAA    204420

TAATAATAAA AGAAAAGGAG AACATGACCA AAGTTATGAA TAAGACTGAA GGCAAGAAAA    204480

TTGTACGCTT GTAGAGATCA CCTAGCTTGT TGCCCTCATT GTACAGCTAA GAAAAGGCAC    204540

CCAGGGACAT TGTGGTCAGC ACCAATTTCT CAGAAAGATA GGCAGATGAT GAGAGGGCCC    204600

TCAGTTTTTC TAACACTGAA GGAATTGCTT CTATGTTTTC TGGTGAACTC CTCCCCACTC    204660

ATCTTGAGGA TTCCAGGCCA GAAGAATCCA CTTTAAAAAA GAAACATTTA AAACCAATTT    204720

AACAACCAAT CAAAGGCACT TTTATAGAAA TACATTTCAT TTGCTGTAGG CCTGTATTTA    204780

TGGATCTGAG AGGGCTAGAC TGCCAATATT GTGACTGTTT ATTATTATTG CTGTTGCTAG    204840

TATCTAGAAT ATTATACAAC ATATAACACT TTGCAATTTA CGAGGCATGT CTCATACTTT    204900

TGTTTTCACT CCAAACTGCC CAGTGAAGTA ACATTATCCC AATTCTTCCT ATGAAACAGT    204960

GAAAGCCCTA AGAGTTTTTG AAACTTTACC TGGTTTACTC AATTTGGGAA TGGCAGAGCA    205020

GAATTCAGTC CTTGAATATC CTCCCACTGC AGGTTCATGC TCTTTGATCT AGGTGTAACA    205080

TTTACTCTGA GTAAACTAGG ACTCTGGGCT AACAGAGATG AAGCAAGACA GGCTGGATAT    205140

TAGGAGAATC TAAGAGCAAT CTAACGACCA TTATAATAAA ATCATGAGTT CTAGACTTAA    205200

AAAAAGGGAA AAACCTGTTT TTTTGCTTAT GCGTATACCA TAATATTTAC ATTATTTATT    205260

TTTTTCTCAA ATTCAACCTA TACTGTGTCA AGTAATTTTT TTTAATATAA CATTTTCCTT    205320

TAACTTAATT TCAATTCATT TTTCTGTGTC TACTTACAAC TTTGGCACTA GAATTCACAA    205380

TTTTTTTTTA GAGGTATATC TCCTTAAAGG GAAGGGTTCT GACACTGTTA CATGTTCTCA    205440

ATTGTTTGCA AATAGGTTAA TAATTATTCC AGTGTCTCTA AGTACATATC AACCATGCCA    205500

GTGTTCAGCC TCCATAATTT TATTAGCTTC TGTGCTTATT TTGGAAAAAC ATTTCCCATT    205560

ACCATGAAAG ACCTCAGTTT AGGATGGTTT GGTATGTTAG CCTGATTTCT GCATTCGTCT    205620

CATGCAAAGG AAAATAGGAA ACGAAGAACT GAAATTACCT ATTGATACAA AATCAAAGTA    205680

GCATTTGAAA CCATAAAACT TAAGTAGGGC TTTTCATCCT TTCTCGTTAG ACAGCAACAG    205740

AGAATGGGAA GAAAAACTAA AGTGATGGGT TTGTGATACA ATTCCAGTAA CATAAAGAGC    205800

AAGGAGAAGT AGTTTGTTG TGTTTATGTT TAATATTCAA AGCTCAACCT AAAAGTATTT    205860

TTCATTATCA AACTTCCTTC TAGAATAAAT GATTAAAACT TGATTTAAAA TATACAAATT    205920

CTCCTTTATA ATACCTCAAA ATGGAGCTAC CCCATTGAGT TTTAAGCTTG TGATTAAAAT    205980

ATTACGAAAA CAAAGGGGAA GTTGTAATAG GTAGAACAAG CAGTAGTCTA GGCATTAGGG    206040

GATCTGGTGC TGGCTCTGTG CATCATGTGG TTTCAGGCAA CTTTTCAAAT TTTCTACGCA    206100

AATTTTCTTA TCAATAAAAT AAACAGTTGG GCCAGAGGAT CTCTGAGTCT CTTTCAGCTT    206160

TCAGTGTTTA TAAGATTGGA GAAGTTGGTG GGAAAGCTTT AAGTGGAGTG TAAGTAATTG    206220

CAGCTGCATG TACAGTTAAA GAGTTGCCTT CAGCCAAGCC ACGGGATCTT GCATAAAAAG    206280

TGAAATCAAA TAGAAAATGG TCCAAACTCT GGGTTTGACC ACAGATGACT TCAGCTAGGA    206340

TCTGAGTGTA GAGCAATGAG CTGAACTCCT GATATCCAGA TGTTAGCAAG ACTTGGAGGC    206400

CTTCTAAGGC AGAGCAACAA CCAGTATCTG TCCTGGTGCT GACCTGATCT TACTAGCAAT    206460

TGGGCCTCCA TTTGGGTCCA TTGTACAAAA CAACAACAAC AACAACAATA AAATCTCCAA    206520
```

-continued

```
ACACCCAAAA TTCAAAATTT AGATGGAGAG ATACTATTCC CAGAATTCTA GAGATATTTG  206580
GAAAGCAGAA AACTATACTT GCCATGCTGA TGAAGTCCAA TTATTGCTCT TTTAAATACA  206640
TTTAGCTACT TCTGAATATA AAATGAGTAT CTACTAATTA TTTACAAAAT CACTTGGTAA  206700
ATATAGAAAG TCACAAAGAA TGAAGTGATC ATCCTGTTTT GTAACCCAGA AATAGTCATT  206760
ACTGGCACTT GTGTGAATCA GTTTCTATTC CTGTATGTGG ATGTGCACAG CGTATCCTGC  206820
TTTGTACACT AGAGTACTAG CATTTTTCTA ATGTAATTCA ATATTGTCGA AAACATTTTA  206880
AAATAGCTTC CATCACAATA ATCTATCAAA TTGACTTGCC AGACTCTCAT TATTAGGTTA  206940
ATTTATCTCT AACATTATGC AGTCATGAGT AATACTACAA AGGATATTTT TGGACACAAT  207000
TTTTCATCTA TGCCTTTCTT TATAATCCTT CATCCTAAGG TCACAGATTA TGAATATCTT  207060
TAAAGTACGG ACAAGTCTTT TAAATTTTGT GTGCAAAAAC AGTGCAAAGC CTTGAATGAT  207120
AAAATAGAGG TTTGATATAT GTGTTTTTTT GTTTGTTTGT TTGAGACGG ATTCCTGCTC  207180
TGTCCCCCAA GCTGTAGTGC AGTGGCACGA TCTTGGCTCA CTGCAACCTT TGCCTCTTGG  207240
GTTCAAGCAA TTATCCTGCC TCAGCCTCCT TAGTAGCAGG GTCTACAGGC ATGTGCCACC  207300
ACACCCGGCT GTTTTTGTAT TTTTAGTAGA GATGGGGTTT CACCATGTTG GCCAGGATGA  207360
TCTCGAACAC CTGACCTCAA GTGATCCACC CACCTCAGTC TCCCAAAGTG CTGGGATTAC  207420
AGGTGTGAGC CACTGCACCC GGCCGATACA TGTGTTTTTA AAGTCACAGA AATTTCAGAT  207480
GTCTTGAAGG ATTTTAAGCA ATTTAAAAAA TAAAGTCATA GAAGCTTCAA TTTAGGAATG  207540
AATGGAAAAT TGATGATATT CTTAGGATAT GGATTTTTCC TAAAAGAAAC AAATGTATGC  207600
ATCCCCAAAG ATAATTTGAT TAGTATACAA ATATTAAATT AAACATGTCC ATATTTAGAG  207660
CCATGAATTC TCTTTGCCTG TCACAATAGC TGGATTTATT CACAATTGTA GTAATTAGTC  207720
CCTGTTCATT ATAATTTTCT AGGTGATATG AAGCTTTGT CAGTCCAAGC AAGTGTCCAC  207780
ATTGTGTGTA GCAAACATGA GAATAAACAT TTTAAACTTT TAAATGTAAT ACATATTAGT  207840
GTTATGTAAT GTCATCCTTC ATGTTCGAAG GCACATGGAA CATTGTTCTG GTGGTACAGA  207900
GGGGAGAGAA ACACCATCAG AATGAAAGGA AAGACCGCTC TGGAACCTTC CTCCTTAGCT  207960
CTTGAGCTTA GTTTAATTGT CCTGTCTTAT GGTCTGCTAC AAGCAATACC ACTCTTCACC  208020
TTCGCATGCT TCTCTGTGGT TTGATAAAGT ACATGCAATT TTTCATTTAA TTCTTCCAGC  208080
TGCACTAAGA AAGGAGCCTT ATCTTTATTG AACAGATGAG GAAATGAATG ATTAGAGAAT  208140
TTAAATGACT AGCTCTAGGT CACACAGCTG GAACTTACAG CCAGATTTCC TTTTAACAAT  208200
CCTGTAACCA AAAGCATACC AGTAGTGCCC CATAAAATGT AAGTTATAGA GCTGTGTTGG  208260
GTCAAAACTT TTACTGATGC TAAGAGGAGG CAACATTAAC AAGGGAAAT TATTTGTGTA  208320
TTATGTTTTG GATTATGTTC TCTCCATAGA TAAAAGACTG TCGTAGTAAA AGAGATTCAG  208380
GGCACAGGGA AACTCCACCA CAAAGCGTGG TACCATTTCC CACAGAAGCT AAATGGACGG  208440
GAAGCCTGCC ACCAGGAAAG GTAAAGCCAC TGCTCTTGTT TGCAGGCTAT GTTAATAAGC  208500
TGAAGCTTAT TCCGACACAT TTACACATCT CTGCATCACA CTGACCCTTC GTAAAGATAC  208560
TCCCAGTGTA ACATTGGAGC CAGCTCCAGC CCCTGATCCT GTTGCTTTTT CCTTAGCCCC  208620
ATGAAATCAT CTGTGAGAAA TTAAGCCAAA TAAGCAATAA ATCCTGGGAT CTAGGGAGTG  208680
GAATAAGTTT TGGGAAAGTC TTTTTTTTTT TTTTTTTGA CTGAGTCTTG CTCTGTCTCA  208740
CAGGCTGGAG TGCAGTGGTG CGATCTCGGC TCACTGCAAC CTCTGCCTCC CGGGTTCAAG  208800
TGATTCTCCT GCCTCAGCCT CCCGAGTAGC TTGGACTACA GGCACACACC ACCATGCCCA  208860
GATGAATTTT TGTATTTTTA GTAGAGATGG AGTTTCGCCG TGTTAGCCAG GATGGTCTCG  208920
```

```
ATCTCCTGAC CTCGTGATCC ACCGGCCTCG GCCTCCCAAA GTGCTGGGAT TACAGGCATG 208980
GGCCACCACG CCTGGCCCGG GAAAGTCATT TTAAACCAAC CTATGTATGA ATCCCTACTA 209040
TAATATTCTC ACCAAGCGGC TGGCTCTTTC TCCTGAGCTT GGAAACCTCC AGTAAAATGG 209100
AAATAATTAT TTCCCAGACC ACCACTCTTA TCTGTGAGCT TTTTTGGCCA TTAAAAATTA 209160
TTTCTTCCAT TATATTTTTA TCTGTGTCTT CACAGGTTTT CTCTTTCTTT CACTTTAGTG 209220
CTTTTCTTCA AATAAGCAGG AAAAATCCAA TCTATCATGC ACATGGGAAC CCTTTCAATA 209280
TTGGTCTGTG GTTGTTCCAT TTTATGGGGA TGCTTTTAAA GAAAAAATTT GTCCTTTCAA 209340
TATATTGAAT ATCTTCCAGC ACCACATCAC CTGCAAGCTT TGTAAAAATA GTTCTACATA 209400
TTAATTTTTT TTTTTTTTTT GAGATTGAGT CTCATTCTGT CACCCAGGCT GGAGTACAGT 209460
GACATGATCT TGGCTCATTG CAACCTCTGC CTCCTGGGTT CAAGTGATTC TCCTGACTCA 209520
GCCTCCCGAG TAGCTGGGAT TACAGGCATG CATCACCATG CCTGGGTAAT TTTTGTATTT 209580
TTAGTAGAGA TGGGGTTTCA CCATGTTGAC CAGGCTGGTC TCAAACTCCT GACCTCAAGT 209640
GATCCACCTG CCTTAGCCTC CCAAAATGCT GGGACTACAG GCGTGAGCCA CTGCACCCCA 209700
CGTAGTTTTT TTTTTTTTTT AAGTTGAACA TATGTGAAGG CAGGACCTAG TGACACATAG 209760
CAATAACATT TCCAAGTAGA CATTACACTA GGGAATTAGT CGAAGTGCTC ATTTAAAGTA 209820
CCATCTCTCA AATGTATTAA AAGAGAATCC TTGGATGTGC AATACCTTAA TTCAAAGGCA 209880
GCTCGTTATG TATAAACTCT CAAGCTTTGT GATAAACAAA TGTGCATAAC AGATGGGACT 209940
ATTCACTTAC AGCCCAGGGA ATTTTATTGA CGCTGAGAAG GTTATGTGAC TGGCTCTGCC 210000
ACTGTCATCC CCATTCACTT CATTTTGGAG CAATATGACA TAAATGCCTT ACATGTGGGT 210060
TTTCTCTATT TATCATGTGT TTCCTATCCC CTTGAAAGAT GGCCATATTT GCTTTACTTG 210120
GTTATAAGAT CCCATATTCG CTGTCTTGAA GCCAACCAAA TAATTTGACA AAGTGGGTTT 210180
GTAGTGCTGG CTATTTTGGT GAAAAAAAGA CAATGAGACT TCATGTGTCA TCCAAAGTTC 210240
TATCAGATCG AGCTGTGAGA GAAAGGAAAA GAAAGGGGTC TCAGTCAGGA TGCTCACTAC 210300
ATACATCTGT GTTGTTGTCT AGGTCCAGAT TTCTGTTCAT TACGCTATGG GCTGGCTCTT 210360
ATCATGCACT TCTCAAACTT CACCATGATA ACGCAGCGTG TGAGTCTGAG CATTGCGATC 210420
ATCGCCATGG TGAACACCAC TCAGCAGCAA GGTCTATCTA ATGCCTCCAC TGAGGGGCCT 210480
GTTGCAGATG CCTTCAATAA CTCCAGCATA TCCATCAAGG AATTTGATAC AAAGGTAAGT 210540
ATGATGGAAA ATAGGGCTCT TGTTGAGAG AAAAAACTTT GAAAGGAAGG CATAGATCTT 210600
GATTCTGTGG AGTATGGAAG TATACATTTC CAATGACAAA TTAAAACTGA CTGGAACTAT 210660
TTTTCTTTGA GACATTGCTT ACTTCAATAA TAAAAATAAG ATTTCATTGA GGTTATTATG 210720
ATTATAAGGT GGGGGAACTG TAGAGTTAAA TGTGAAAAAT TTAAAAATGG AACAGTTTAT 210780
GTGATGTCTT CAATGAAAAA CTAGGTATTA CCTGGGCACA TTCTTATAGG TTACTCAATC 210840
CTATTCAGTT CTCTGCCTGT TTTATTGTTT CTGAGCAATT TTATATCCCT GTAAATTCTA 210900
TATAACCAAT AGAAATGCAA ACGATTCTTG TCCATAGCTT TGCAAATAAA TTTTGCCAAG 210960
AGAAAAATCA GTTAAAACTT TTCTCCACTC ACCTCCCAGT TGAATTAGCC AATTTTGCTG 211020
TTTGTTTGTT TGTTTGTTTT TTGAGATAGA GTCTTCCTCT GTCATTCAGG CTGGAGTGCA 211080
GTGGCATGAT CTCAGCTCAC TGCAGCCTCC GCCTCCCGGG TTCAAGAGAT TTTCCTGTCT 211140
CGGCCTCCCA AGTAGCTGGG AGTAAGGGGG CATGCCACCG CGGCTGGCTA ATTTTTGTAT 211200
TTTTAGTAGA GACAGGGTTT CACTAGGCTG GTCTCGAACT CCTGACCTCA GGTGATCCAC 211260
```

```
CCGCCTCGGC CTCCCAAAGT GTTGGGATTA CAGGTGTGAG CCACTGTGCC AGGCTCTGCT    211320
GTATATTTAA AGTCTATTTC AGCATTGCTT CCTGCTTGTG TTATGCGTGA TTCTTTGAGT    211380
TTTCCTTTGA ACCAGTTATA ACATCTTACT TACTTCCTCC ATTAATCAAT GAGTTAAATA    211440
AAATCTTTGT TGTATGTTTA TTTTACATTT ATATGAAAAC CATGAATTTA CCCAATTAAA    211500
AAAATTATCC TTTAAATTAT CTTGTACTGT ACATTTCCCA TGTCATCCCT ATAATTCATG    211560
ATTAATGATT TTATTACATT GGACCTAGCT TATTTACAAT GAGTACATAA ATTTATTGTC    211620
TCCAGTCTTT CCTCCATTAT CCCGTCTACA TATCCACACT GAGTAGATTC ACTACTCAGG    211680
AATCTTGGAC ACCTTCAAGT TGCCAAACAT GCAGTGTTCA CTGGACATGC TGTGTTCCTT    211740
CAGAATTTGG GCCTGCTTCT CAGCACACTC ACATCTGCTA TCAATGACCC ATGGAAAGTT    211800
TTTGCCCTGA GCAAGCCAGA GTCCCTGTTA GTTTCTTCCA AATGCTACAA GTCACTTTT    211860
GCTATTTTTT CCGATGAGAT AAAATTTTCC TTTTTGACTT TCTACAAATC ATAGTCATTT    211920
TTCAAGGGAT AGTTCAAGTA TTGCTTCCTT TCTGGGACCT TCCCAAATTA TTATTTTCTC    211980
CTCTCAAAGT CTCTGTTTTA TTTATGTTCA TCCTCAAATC TTGATTCTCA CATGAATCAT    212040
ATACCTTGTA TTATTTATAG TTTTTTTGAG TGGGTAAAAT ATTTCATATT TTATATTCTT    212100
TGGCTCTCTA CTTTATAGCA TGATGCCAGA TATTTAGGGG CCTTATTGCA TTTATTTTTT    212160
ATTTTATTTT AAAATCTATT TTATTTTTTA TTTATTTATT TTAAAATCTA TTTATTTTTA    212220
GGTAAATATT CAGGTAATAT AATTTATGTA ATTATTTAGG AATTTTAGGT AGTTATTTTA    212280
AAATAATTCA AATTATTTAT TGAGTTATAT CAGAAGAATG TGATCTTATT CATTTGTAAT    212340
ATGTGTTTTA GGAACTCAGT TCAGCCAGGG CAGACCATGA TTCCCAAACT TGACTTTTCT    212400
TTTTAATTAG GCACTGATTT TGGTTAAGAG TTCAGTAAAG TTTTGTGTGT GTGTTTTAAA    212460
AAATTCTTTG ATATAAGAGT CAAGATGTTA CTCAACTTTT ACTAGAAGCA AAATAGAGGA    212520
AGTGCTTTCA CAGATGAAAT ATCTCTCAAT GTTTTCTTCC ATTTACTTCT TCCTATTATT    212580
CATCTATATA ATCATTTTCT TTACCTCTTT TCTTCATTTC TTCTGTTTTT CTCTCCTTCT    212640
ACTAAGACAA GCAAATTAGG GGTATAATTG GTTATTTGGG AAGGTAGGAA GAATATAGAG    212700
AGAAACAAAA ATCAATATTT TATACTAGGG TCTCACTAAC CTCAAGCAAC TCTGACTGTA    212760
AAGTAGATTT TCATAATAGG ACTTCTTGAC AAAGAGTTTT CCTATTTTTC CCCCAGGCCT    212820
CTGTGTATCA ATGGAGCCCA GAAACTCAGG GTATCATCTT TAGCTCCATC AACTATGGGA    212880
TAATACTGAC TCTGATCCCA AGTGGATATT TAGCAGGGAT ATTTGGAGCA AAAAAAATGC    212940
TTGGTGCTGG TTTGCTGATC TCTTCCCTTC TCACCCTCTT TACACCACTG GCTGCTGACT    213000
TCGGAGTGAT TTTGGTCATC ATGGTTCGGA CAGTCCAGGG CTTGGCCCAG GTATCCAGAT    213060
ACTTTCTCAT TCTTGGTGGG ATCCAGATTT CTGAATTCTA CAAAATATCA AAGGTCTTAA    213120
TGATTTTCAT TTCAGGGAAT GGCATGGACA GGTCAGTTTA CTATTTGGGC AAAGTGGGCT    213180
CCTCCACTTG AACGAAGCAA GCTCACCACC ATTGCAGGAT CAGGTAAGTG TGCACAGATG    213240
GGTCATAGCT TTGTCATCTG TTCCATCCCA CTGTGTCTTA TCTTCTATGA ATCAAATGGT    213300
TTGGGGAAGA GAGAGAAAAA GTACTGCTGA AAAATTCAAC AATATAAGAC ACTTGCATCA    213360
CAAATAGGAA AGATGCATCT GTGCAGTAAA GACATTGAAG CTTAGAAGTA GAAAAAACCA    213420
TTGTGAGCTA GGTTTCAGCT CAGAAAAGCC TTAGTAGTCA GAAAAGCCTT AGTAGTCAGA    213480
AAAGCCTTGT CGGAAAAAGT TTAAACCTTT AAGAATTGCA CACATGGAAA AGATCAAGT    213540
AAGCTATATA TACACCATCT TAGCAATGAT TTTGAAGTGA GAATTAAGGC TACCACAGCT    213600
CCAGGTGGTA AGGAGAGAAA TCAGGCTGGA AGAGTTTGAA GTTTCTGTAT TATTCTAAGC    213660
```

```
TCTTTACTAT TCTATTATGA GCTCATTAAT TCTCACAACA ACCCTCTCAT ATAAGTACCA    213720

TTTTAAATTC TTATTTTACA GAGAAGGGAG TTAAGGAAGG TGGAGATTAA GAAAATTGCC    213780

CAAATACAAA TAGCCAGCAG GTGGTAGGTC TGAGATTTAA GCCCATGCAG ATTTTAGCCC    213840

CAGAGCAGAC ATTCTCAATC ACTATGCTAG ACTGCCTTTC CATGGTATGT GATCCTACTC    213900

AGGCCTCTAC AGCTTTATCA TTGCTGTTCT CCCCAGCCTG TCGTGCTGAG AGTATATACT    213960

CGAAGAGCAG AACTAAAATT CCATCCAGCT TCTCACTCCT AGGTCCACTA CACAGCTGCA    214020

TCCTGCAGAC TTTTACCTCA AGCAACCCTC CTGCGTTCTT GCTTCCTTCC ATCATAGTTG    214080

TAACCATCTC CTCTATTTGC AAATACTATC TGCTGATCTC TCTCTTCTAG ACTGGTTTCT    214140

TTCAACCTTC TTCCCACCAA AACCAAGTTA GCTTGCTAAA ATAAAGATGG CACATTTTTA    214200

CTCACCCGCT TGAGAATTTT CAATGTGTTC CTTCATGCTT ACAGAGTAAA GCCTGACCTC    214260

TTTATTGCAT GAATACAAAA GTTCTTAGCC ATCTGGCCCC AACCTTGTTC CACTCAACTC    214320

CCCTGTGCAA GCATGGCTCC AGTGGCACTG GACATTGGCT GCTCTCCACA TAGATCTGCA    214380

CTGCACTTCC CTCTGGCTCT GCTCCCGTTA GTTTATATGC CTGGAAAGTT CTTTGCCCCT    214440

GTTCCTTGTG CCAAAATTCC ATCTATCCTA TTGCATAGCT TATGTAAAAA CTTCCTAAAC    214500

CTTTTTTTTT TTTTTTTTT TTTTTTTTTG AGACGGTGTC TCACTCTTTC GCCCAGGCCG    214560

GACTGCAGTA GCGCTATCTC GGCTCACTGC AAGCTCCGCC TCCGGGTTC ACGCCATTTT    214620

CCTGCCTCAG CCTCCCGAGT AGCTGGGACT ACAGGCGCCT GCCACCATGA CCGGCTAATT    214680

TTTTGTATTT TTAGTAGAGA CGGGGTTTCA AGCCAGGATG GTCTCAATCT CCTGACCTCG    214740

TGATCCGCCC GCCTCGGCCT CCCAAAGTGC TGGGATTACA GGCGTGAGCC ACCGCGCCCG    214800

GCCAAAACTT CCTAAATCTT ATAATTATTA TCAATTTATC CTCAGATATA CTTCCACGTA    214860

CATTGTAGTT TTATTATATT TATATTTTAC ATCTTTTTTT TCAAATTTCA GTTTGGGACC    214920

CATTAGTGAG TCATAAAATC CATTGAGCGG GTTAAAATCA TTATTTTAAA AAATGAATAG    214980

AATAGAATAG AAATTGTTGG AGTGCATTGG ACATGGTAAA GTTAAATATC GATTCATGAA    215040

ACCATCGTTT GAGGCATATG TGTGTGGTTG TATGTACAAG TGTTTATGCA TATTGGTGTG    215100

TGTGTTATGT TACCCTGTAA AATGCATTTC TTACTATAGG TCTCTGTGAA ATATGTGTCT    215160

TGTTGTTTTT TAATGTAGAC TTCCAAAGCC TACATGGCAT TTCACTAGTG ACAATCAATT    215220

TTATTCACAT TTTTCTCTCC AATTGGACCA GAAGCTCTTT GAGGGCAGGG GCTGTATCTT    215280

ACCGATTTTT GTAAGTCTTT CATTTCCTGC CCCTAGCCTC ATATTAGATC ATGCAAGAAT    215340

GCAACTGTAA TCACAAGAAA ATGCTAATGG GCTGTGATAG CAGAGAGTTA CTGTGACAAA    215400

CTAAGGGATT TAGATTTGGT CACATTGGTG TTGAGGAGCC ATTGAAGAAT CAGAGAGTGT    215460

GTTACTATTA TTTGTTAATT TTAATTATAT CATATTACTT TACTGGGAA AATCTGTGAG    215520

CTATTTTAGA AATAAATACT CTCATTGCCC AATAATTCTA AGTCTGCCAC CTCACTGTTG    215580

GGACATTGTT TAGGGAGGCC ACGAAGTCTC AGCCTTTGAT ATTTTCATAA GTGTTTTTCT    215640

CCCTTTTTCC TTTAGGGTCA GCATTTGGAT CCTTCATCAT CCTCTGTGTG GGGGACTAA    215700

TCTCACAGGC CTTGAGCTGG CCTTTTATCT TCTACATCTT TGGTGAGTCA CTTTCTCTTA    215760

AATCCTAACG CCTCCATTTC CTGAGCATCC ATTTTGGCAC CTACACCACC CACATTCTTC    215820

CTATATGAAA GAAAATGTCC TTTATCAAAT GGAAGATGAT AAAAAATGTC AACGGTTGGT    215880

ATCATTTTTA ATCTAGTCAC ACAACCTGAT TAACACCTTC CTGGTGGTTC TGGGAAGCCA    215940

CACGCACAAG GTAGAGGAGT TGACTATTCA CATGGCACCC ACCGACTTGT GATGCAGTCT    216000
```

```
TGTCCTTCCA TATCAAGCAC CTTCTGCAGA ATCTCTACCA CCACATCTGA AGTGCCTGCT 216060
ATATGCAGTT AAGATGTCAA AGATAGTGAA GTACATTTTC AATGTGTCTT CATATTTCAT 216120
TATAATTATT ATTTCTGTCC AAGATGCCTT TCACCTGTTC TCTACCAAGT TAATCTTGCA 216180
AAGTTCAATT CAAATGTTCC CTTCCCCATG GGCCCTTCCA GGGCTTACCC TATCAGATTC 216240
TGGCATTCTC TCCTTTATGA TATTTCCTCT CTAGGTTATG TTGGTGTGTA ATTATTTATT 216300
TCTCCTTTTC TTTCCACTAG ACTGTGAAAT GCTTGAGGCA AGGAATCCAT TCTATGTTTT 216360
CATCACTTGG GTGTCATCAT GGTGCCTGAT TTTTAGCTTT AAAATAAAAG AATCAGTGAA 216420
TCCAGTAATT AGAGGGGATT TAAAGAAAAC TAGTCCTCAG AATCTTTTAA CATAGAATGT 216480
TCTTCAAATA AGGAATTCCA ATAATAAGAC AATTTTCTAC ACTTGATTTT GTTTTTATAG 216540
CCAAATGGTG TCATTAAATA TAGTCCTGGC CTGAATGGCT TTCTCATTAA TGATGCTAAT 216600
TATTTTGGTT TGTACATGTT AACCAGGTAT TGTACAAAAA TATTTCTTTT GGGAATCCAT 216660
AATGGATGTA TGGCTTGAAT ACAAATAATA CTGTCTCTTG TAAGTGCATT GGAAATTTTT 216720
CCCTGCCACA TGATTTCATG GAAGGTTGTT TCGTGTATGT ATGACTGCAA ACCTGACTAT 216780
TCAGATCTTC CGCAACAAGA CAACTTATGT GTGCATTAAG AAGTTGCTGC CTAAAATACA 216840
TAACACTGTA ATCATTGGAG ACTTTAAAGT AATTAATCAG CTATGCAATG CCACGCTCCT 216900
GTTATCTCCA GAGGGCTCTG ACATTGACAA ATGGTGGCTT TCTATTTGAG ACGTAATATC 216960
TAAAAAGCTT TAACAGGTTT GTAGAAGGAT TGAAAGAAAG AATGGGAACA TTTAGGTCCT 217020
TATGGTAGAA TAAGCATTAA TTGATTAGTG TGTAGAAGGG AGAGGCATGC CACTTCGAG 217080
GAAACTTCCT TCCCCCAGTA AACAAATCTA CCTAAAAACT AATTTTATCC CTTCTTCCCA 217140
GGTAGCACTG GCTGTGTCTG CTGTCTCCTA TGGTTCACAG TGATTATGA TGACCCCATG 217200
CATCACCCGT GCATAAGTGT TAGGGAAAAG GAGCACATCC TGTCCTCACT GGCTCAACAG 217260
GTACAGTGCA CACCTTGTAC CTGTGGCCCA TGCAGAGGTC TCTAGGGCAG GGTGTGGATC 217320
TCCTCTGAGA GGCACCATCT TGGCTGCTCT AATACTCATG CTGATTAGAT CTTTCTTTTC 217380
AGCCCAGTTC TCCTGGACGA GCTGTCCCCA TAAAGGCGAT GGTCACATGC CTACCACTTT 217440
GGGCCATTTT CCTGGGTTTT TTCAGCCATT TCTGGTTGTG CACCATCATC CTAACATACC 217500
TACCAACGTA TATCAGTACT CTGCTCCATG TTAACATCAG AGATGTGAGT TTACTTCCTA 217560
TACTTCTACG AAAATGATAA TGGTAATAAG GAGAAACAGT TCTGTGTTAC CTATTACATT 217620
CTGGCTTTAC ATATAACCAT TAATTTAACC TTCACAATGA CCTTGAGAGA GGCATTGTTA 217680
TAATTCCCTT TTCACAGATG TGGAAACAGG ACACTTAGAG GTGAGATAAC TTGCCCCAGG 217740
TTGCACAATA CTAAGTGATA GAGCTGCTGC AGCATCCATA TTCTTAACCA CTATGCTATA 217800
CTACCACACC AGCTGATTCC AAAGCTTCTT TTAGAAATAA TATTGCTGGG CCAGGCATGG 217860
TGGCTCATGC CTGTAATTCC AGCACTTTGG GAGGCCGAGG CAGGCAGATC ATGAGGTCAG 217920
GAATGCAAGA CCAGCCTGAC CAATATGGTT TACTAAATAT CATCTACTAA AAATACAAAA 217980
ATTAGCCAGG TGTGGTGGCA GGCACCTGTA ATCCCAGCTA TTCAGGAGGC TGAGACAGGA 218040
GAATCGCTTG AACCCAGGAG GTGGAGGTTG CATTGAGCCA AGATCATGCC ACTGCACTCC 218100
AGCCTGGGCG ACAGAGTAAG ACTCCGTTTC AAAAACAAAA AACCCAAGAA ATTAATATTG 218160
CTTTTATCTG GAGCCCAGAG TGATGCAGCT TCTGGCCCTC TTATCTGAGA CAGTGTTCTT 218220
TTAGTGTGAA AAAGGATGCT AATTTTCCCC CAAACAACCC ACAGTATCAT GGGGGTAAGT 218280
TAATGGCTGG TCTGTGTAAC TGACAAATTT TGGTGCTAAC GTATCTCTAT AACTACTCTG 218340
TATAAACTTC CTTCCTTCAG AGTGGAGTTC TGTCCTCCCT GCCTTTTATT GCTGCTGCAA 218400
```

```
GCTGTACAAT TTTAGGAGGT CAGCTGGCAG ATTTCCTTTT GTCCAGGAAT CTTCTCAGAT    218460

TGATCACTGT GCGAAAGCTC TTTTCATCTC TTGGTAAGGA TAAGCGTGTG GGCCCATTTA    218520

ACCAATCCCT TTTCTGCACA TGGTCTCAGA GGGTTCCCTG ACAGCATGTC CTCATTGCCC    218580

AGGGCTCCTC CTTCCATCAA TATGTGCTGT GGCCCTGCCC TTTGTGGCCT CCAGTTACGT    218640

GATAACCATT ATTTTGCTGA TACTTATTCC TGGGACCAGT AACCTATGTG ACTCAGGGTT    218700

TATCATCAAC ACCTTAGATA TCGCCCCCAG GTAAGAGCTC TACCTGTTTT TTCCCCTCCT    218760

CCAGACCCCT CCAGAGGTGT TAGACCTCAG TGGTCGCCGT GAAACTCTTT AATGTTACTG    218820

ACATTGCACT AATGGCAGAA TGACAAATAA CTACAAATAT CTGTCTGTGG CCATTTTTAG    218880

AACAACAAAT GTGGCATTTT TAGAACAACA ATTTCCAATC TTGGCCAGTA ATCATTTTGA    218940

CAAAAACCTT CCCAAGCTTC CCTAACAGAG ATTGAACTGT GTATGCTGGG AAAAGGCCCA    219000

CACACAGGTG ATTTGGAAAA GTTTCCATGG TGTTGTTCAT ATTAGCTACC ATATATATAT    219060

ATATATATAT ATATATATAT ATACAGTCAC AATAAGCCAG CTCCTGTGCC AAGACTTGCC    219120

ATATATCAAC ACATCTAATC CTCACAGTTA TATTAGGTAG GCCCTATTGT TATCCCCATT    219180

TTATAAGGGA GAAGGCTGAG GCACAAGGAG GTTAAATGGT GTGACTATGG TCACATAAAG    219240

GCAGAGCCAG GATTTGGACT GGGGGAGTCT GGCTTTGGAG TCTGTGTCCT GCCCGTTGCA    219300

CAAACTGGCT TCTCCACTGA GCAGCCGGGG TAAAGAAACG TGGTTCCCAG AGAGACTGCA    219360

TTGCTCCCTG GTTATTGACT TGGTAGATTG GTAATTTCAG GTTTGGCAAA TAGACATTGC    219420

CCTGAATGTC TTTAGGTGAA TGAAAAACTG CATTAAGCAA AATGACTTTG CCATTAGAGC    219480

TGAATTGCAT TAAAGTTGAG TTGCTGCAGA AGCTGTAGGT GGCTTTCTAT ATAAAATCAT    219540

TTATAAAATC ATCTTCCCAC AGATATGCAA GTTTCCTCAT GGGAATCTCA AGGGGATTTG    219600

GGCTCATCGC AGGAATCATC TCTTCCACTG CCACTGGATT CCTCATCAGT CAGGTTGGGC    219660

CAGTTTATTG AACATCTTCA AGTGGCAGGT ATTGTTTTAG GTGTTGGAGA TACACACGGT    219720

GCTCTAAAGA TCTGGATGGC AACACAATTA CTCTATTTAC ATGAGCCTCT AAATCAGACT    219780

CTGGTAGGTC AGATTTCCCA GAGGAAGAAA AATATAAGCT TATTTCTCA AGATGAATAG     219840

ATGTTAGATT GATTAAAATG AGCTGTTCCG GTGCAGAAGA CAGCACGTGT GACTTCCTAG    219900

AGGTACATGA GCATGAAACA GTTCTTAGTT ATGACCAGAA TGAAAGACAC ATGTCAAGGA    219960

ATAGCAAGAG ACGAAGACAG AGGGGCAAAA GAAGATCATG AAGAATATGT TCAGACTAAT    220020

CCAATTTTTA AAAAATCACA AAAGGGAAAC AAAGTGTCCT AGGCCAGTTT AAAGATAATT    220080

TAATGTCTGG AAACAGATCG GCTGTGAGAC ATTGCAAGGA GGCTTGCTCG GTGTTTGGAA    220140

ATGCAGGCTC ATGAGGAAGA TGAAAAGACA GACCCAGGCA GGGATGGAAG GACTGACGAG    220200

AACCAACTTA CAAAGAGAAG TTTTGTTTTT ACTACATTTC TATGTGATCA AGTTCCCAGG    220260

TTAATATTTG ACTAAACTGC TAGGAATCCA CTGTGACTAT AATGCTGGAA ATGACTTAGT    220320

AGGGCTTTCT GAGGAGGGTC ACACAGAAGA CCAAAGAGAA CTCATGTTGA ATTGAGATGG    220380

GTTGTAGTGA TAGTTGTCAA CAGCCAATAC AGAAACAAAA AAAAACAAAA CAAACAGCAA    220440

CAACAACAAC AAAAAAAAAC AGAGAAGACA CAAACACAAT GCCACAATGC CATTTTAGGC    220500

ATAATTTTAA ATGAGTAATA TTATATGTTG AAATCCAAAT TTTCAGAAAA ACATTAGTGT    220560

ATTTTATTTT TGTTTAAAGA AATAACCATC TCAACTCAGA ACCCCATGTG CATTTTGGCC    220620

ATTTTGTTTC CAATAGTTTC ATAAACTTTC TTAAGTAACT ACTGCACATT GTTCCTTATA    220680

TTCCTTGTGA TCAACATTGC AATACACAAC TGGGAGGGCT ACTAGAACTG GTGTAGAAGG    220740
```

```
AACTTGTGAG ATTGATCATT TTCTCTGTTT TTTACATCTA GGATTTTGAG TCTGGTTGGA    220800

GGAATGTCTT TTTCCTGTCT GCTGCAGTCA ACATGTTTGG CCTGGTCTTT TACCTCACGT    220860

TTGGACAAGC AGAACTTCAA GACTGGGCCA AAGAGAGGAC CCTTACCCGC CTCTGAGGAC    220920

ATAAAGTTAC AAACTTAAAT GTGGTACTGA GCATGAACTT TTTAAACATT TTTTACTTCT    220980

CTCCATATTC CTGACCATAG ACTCAGCAGT TCTTAACTCT GGCTGTGTGT TAGTCTTCCC    221040

TGGGGAGCCT TTATAAGACA CTGATACTTG GGACCCACTC CAGAGATTCT GAATGAATTG    221100

GTCTGGGGTG GAACCCAGAT ACTACTAATT TTTAGATACT CCTTAGAGGT TTCTAGCATG    221160

CGCCCGGGGT TGACAACAGC TGGACAAACT TGAAAAGTCA ATTCATGTGG CCTTTGAATT    221220

TTCCTCATTG GAAAGTACTA AATAAATAAA AATTCATGTG AAAATGATCA CTGATAAATA    221280

TCTTCATGGT GGGGCAGGTT ATTGGATGCA GAGAAGATCT GCTCGGAATT GTAGCCATAT    221340

GTTACAGATC TCAGCACCGA TCGGAACTGT AAAGCTATAA TCCCCAGAAT TAAAGTTTTT    221400

ATTATTTTTT ATACATTGTA AAACATAGAC GTTTATTTAT GTGATTAAAT TCTATTAAAA    221460

TTTACATGCT AAAATAAAAT AGACCATTTT CAAATTATTT AGATCCAGAT ATTTCCATCA    221520

GATTAAACAG ATATTTATTT ATCCTAGCCC AATTGCAAGA GATTAATGAT GAGAAAATGA    221580

CCAATACAAG ATTAAATAAA TGAGGTTAAC TTAGAAATCA AGGACAGAGA AGATAGAACT    221640

GGAAGGCTTG TATTGTGAGA AGAATGAATG TGAAGGAAGG CAATGTAGAC ACTTCCAGAA    221700

GGGATAGCAA TATAGTTTAG ACCATATAAT GAAAATTGGA GAGAGATGAC AGAGACACTT    221760

TCAAGTGAAA TGACAATTTA TATGGGGGAG AAAAATATTG AAGACATAAC AAGATGAGAA    221820

AAGGCATAGA AATGTATCAC ATACAAGGCA TAGAAGTGTA TCACATACAA GAGAAGTTCC    221880

TTTTGAGCGT AGAAAAAGAT AATTTAACCT TCTTCATATT TTTCTTACTT TCCCAAGATA    221940

CTCAGATAGG CAGCGTCAAC TCTAACAGGA ATTAATTTGG CTCCTAACAC TTAAGACATA    222000

TCCTTTAGTT TGTCTCCTCA CACAGAACTG ATTCTGGTTT TGCCACAACA TGTCTAGAGA    222060

AGAAGTTCCC ACCATATTTT AAATCCTATT AAAAAACTGC TTGGACAAGA ACCTTGGGTT    222120

AATTCAGCAG ATGAAGAGAA TCTCCTAATG CAAATCAATG GGTATTTTTG AGCAAGTTTT    222180

TCAGAAAAAC AGAGTGTCAG GCCCTGAGGG TGGTACTAAG ATGAGAACAT TGATTTTGCC    222240

TTCATGATAT TGACAACACA AAGAGGAAAG GGGGTTTGCA GAAAACTAAA AGAAGAAGTA    222300

GAAGAAAAAA GAAAGACATA GTATAATAGG TAGTCAAATT ATGTACAGAA AAAAGAGAAA    222360

AAAAAAACAA AAAAGGGTGG GGGACAGACA ACCCAACTAA AAAATGGGCC AATGACTTGA    222420

ACAGGGACTT CATAAAAGAG AAAATGTAAG TGGCTCCTTA ACATATAAAA AGATGTTCAA    222480

CTTCATTAGT CATTACAGAA ATGAAAATCA AAACTACAAT GAAATACCAC TATAAAATTA    222540

ACTAATGGAT AAAATGAAAG GAGATGGAAA ACAAAATGTT GCCAGACATG TGGAGCAACT    222600

GGAACTTTCA TACGTTACGA ATGTGAACTT TGGAAAGCTG CTCGGCAATA TCTCCTAAAG    222660

CTAAATGTAC AATTCCAGTG ACTCAAACAT TTTACTTAGA AATGCACATA TACATCCATA    222720

AAACATGTAC AACAATGTTC ATAGGAGCAC TATCTGTAAT AGCCTGAACA GGAAGTTGTC    222780

TGTTAAAAAA AGAATGAGTA AATAAACCAC GGTCTATTTG TATAGCAATG AGAATTAACA    222840

GACCCCAATA TATAATAGAT GAATGGGTCT CATAAGCACA ATATTGATTA AGGAAGACA    222900

AAACGCACAT TCTTTTAAAG GTTTATAAAA TACTTTTTAA AAACAGCTAC AACCAATCTG    222960

TCCTGTTAAA AATCAGTGAG CGATTTCCCT TGTGCAGGGA TGGGGTTGT GGCTGGATGG     223020

ATGGTACTTA AGAAGTGCTC CTGGGGTACT AGAAATATTT TATTTCTTGA CTTGGATGTG    223080

TGTTTACTTT GTGAATATTG TACATTTATG ATTTGTGCAC GTTTATGAAT GTAGAAAATA    223140
```

```
AAACAGAAAG CAAATTCAAA GTATCATCCT TTTGAGAGCT TCTGCTCTGA CTTCGTTTTG  223200

ACCAATGGAG CAGTTGGGAA GGGGTCTTGG TCCTTCGGTC CTTTGCTTTT TTTTTTTTTT  223260

TTTTTTTTTT TAGACAGAGT CTTACTCTGT CGCCCGGGCT GGAGTGCAGT GGCTCGATCT  223320

TAGCTCACTG AAAGCTTTGC CTCCCGGGTT CATGCCATTC TCCTGCCTCA GCCTCCCCAG  223380

TAGCTGGGAC TACAGGCACC TGCCACCATG CCCGGCTAAT TTTTTGTATT TTTTAGTAGA  223440

GACGGGGTTT CACCATGTTA GCCAGGATGG TCTCGATCTC CTGACCTCGT GATCCGCCCA  223500

CCTGAGCCTC CCAAAGTGCT GGGATTACAG GTGTGAGCCA CCGCGCCCGG CCCCTGGTCC  223560

TCTGCTTTCA TGTTCTTCTT GGTCCTGTTC CTCCTCCTCT TTTGTTGGAA CTTCCAGTAT  223620

CAGAGCAGGA AGGAAGGCAA TGGGTCAATC GATGCTGTCA GCTTTTGGAT CAAACTGCAA  223680

GTTCTCAAAC AGCAAAATTA ATGAGCTCAG GCTTTGAAGA AACCATGACC CTGAAAGCAT  223740

CAGTTGCTTC CAATTGCATC AGTTGCCACG GGTGATAAGA ACAATGATGA CTCAGAATGC  223800

CTAGGTTTTC CCAGCAGCTT CTCTGAGGTT TTCCCAGCAG CTTCTCTGAT TGATTCCTGA  223860

CAGATGACTT CGGTGTGTCA GACTTTCAGG GTATCTTTCC TTATGTGATG GTTTGAGGAA  223920

GAGTTACCAT TCACATTCCT AATGGCTTCA GAATAGATGC AATTGTGAAC TGATAGGAAA  223980

CATTTCTAAT TCATCTCCCC TCCCCATCCC TAAAGGATTG TTTCTAACAA TAGTCATGAA  224040

AATTAATTCA CTTTTCTCAA ATAGTTTATT GTCATCTACC TAATGATGAG ATGACTTACT  224100

TTTTCTCCTT GACTGTTAAA TATTATGAAT TATATTAATG TATTTCTTAA TGTTGAGCTT  224160

TCCCTTGAAT ATTCTTTTGA TGTACGACAG AATTTGATTC ACTAATAGTT TATTTAGGAC  224220

TTTGGCTGAT GTACTGATAT ATGAGATTGG CTCTGTATGC ATACATGTGT TTGTGTATC  224280

TTTTTTGTGT CTGGATATGG AGCTTATGCT GATTTCAAAA ACAAGAAAGG AGAACTTTCC  224340

TTTTTCCCCA TTACTCTGAA AAAGATTGAC TAGAATGGAA TTTTTATAAT TGCTGTTGTT  224400

ATTTGAAAGC TTGAAAGCAT TGGTTTGTAA AAATCATGCA GGCTGAAAGC CATTTTGAGG  224460

AGACTTTGAT AACTTTCTCA ATTTCCTTCA GTTACTGGTC TTTTAAGGGG TTTTATATTT  224520

TTCTTTGATC AATTTTGACC ATTTATGTTA TCTTGGAGGA TCATCTATTT TACACACTAT  224580

TTAAAGTATA TTTGCAAAAA TTCAACTGTT TTATCAGGCT ATCTTTTTAA TAATATATTC  224640

ATTTTATCTA TATCTGAGGT TTTAGCTTCT TTGTACTTCT GACCCAATTG CATGTGTGCT  224700

TTCTTTCTCC TTCATTAGAC TACTTAGTCA TTTACTAATT TTAAGAATAG CTTGTCTTTT  224760

ATTTATTTAC TTATTTATTT TTGAGACGGA GTCTCACTCT GTCACCCAGG CTGGAGTGCA  224820

GTGGCGCGAT CTCGGCTCAC TGCAACCTCC GCCTCCCGGG TTCAAGTGAT TCTCCTGCCT  224880

CAGACTCCCG AGTAGCTGGG ATTACAGTCA TGCACCACCA TGTCTGGCTA ATTTCTGTAT  224940

TTTTAATAGA GATGGGGTTT TGCTATGTTG GCCAAGCTGG TCTCAAACTC CTGACCTTAG  225000

ATGATCTACC CACCTTGGCC TCCCAAAGTG CTGGGATTAC AGGCATGAGC CACTGCGCCC  225060

AGCCCTGCTT GTCTTTTTAT TTTATATTTG ATTAGCTTTA TCTTTTATCA GCTTATGTC  225120

CTATTTCCCT TTGCTTTACT TCATATAAAT TTTGTTTTGG ATAGTTTATT TATTTTTCAT  225180

TTAATTATGA AACAGGTTAA AGCTTAGAGG AAAAATTGCTC CTCTAAGTCC AATTTGTGG  225240

GCAGATTACA TTTTGCTGTG TTGTGCTCCC AAATTCATTG TTCTTTTAAT GCTTTATTTC  225300

TCAAGTTAAT AACCTATATA GTAAAAAAGT GGCTGTTGAC TCTCAGCTTT TTTTTTTTTT  225360

TTTTTTTTTT GTAGATACAG GGATCTTGCT GTGTTGCTCA GGCTGGTCTG AAACTGCTGG  225420

CTTCAAGGGA TCCTCCTGCC TTGGTCTCAC AAAATGCTGG GATTGACAGAC ATGAGACACC  225480
```

```
ATGCCTAGCC ATGTCTCTCT CCTTATATAT AATAAGAAAA CAGACACACT GAGGCATCCT  225540

ATCATCTCAC TCTTGGTTTC ACTACTGTTC TCTGGAAGTT TTGCTCTGAC CTTTTGCAGT  225600

TAATGTATTA ATTTTGCATT GAGTAGTTTC CATAGAAGAA TTATAGCATT TGCATTCTGT  225660

TGGGTATTAT ACTTTTCACT GTTATTTGAA CATAATTTGA GGGCTGAAAC CAAGATGAGG  225720

CAAGTGAGGT GCCCAGGAAG CAATATTTAA GGAGGCATCC TTTCTTAGGC TCATGCAAGA  225780

ACAGAATTGG CACATGAGAG TGAGTGCCTC CTTAATTTTG AGTGCTGGAC ACTTCTTGCT  225840

CACTTAGCAT ACCCCTGGAC AATGAAGTGT TTTTTGTTTT GTTTTTTCAT GTCCATCCTT  225900

TATCCTTCTT CATCTCAAAA CATTTCAATG GAGTATTTTT TTGGAGCAGT ACTTGGATGA  225960

GCCTCTGAGT CCCACAGTAG CTGAGAATTT ATTTCATAGT ACTCTTTATG ATCACTGTGG  226020

AGCCTTAAAA CATTGTAATA TTAACTTAGC TGGGAACAGA AATTTTGTTC CACAATTTGT  226080

CTTATTCAGA ACAGTATTGA CTTCCTGCTA GTCTCTTCTG ATGTCCAATA TGAGGAAGTC  226140

TAGTTAGCCA GCTACTTTTT GTAGGAGAGC TATGTTAGG CTAGGTGCTA TAGGATTCTC  226200

TTTATCCTGG AATTCCTTCA CCAAGATGTG CCAAGGTGTT AATCATTTTC TCTTGCTTTT  226260

TGGCTGGTGG TCTTAGAGTT TCCTTCGATT TTGTTTTATT TAGTGATTGT CCTCAATTTG  226320

TTTTCTTTAC TAAGAATCTC TCTTCTATTT ATCTGTATGG TAAAACCTTG TTGCCCATCT  226380

TTCTGGTTTC TGCTGACTTT CATTTTTGGA CCTTTTACTT TGCTTTCTCC ATGGACTTTT  226440

TGGTAGTGGA GGCAGGCAAA CACTTTCCAA AGTCTTTCTC AATTTCCATC AATTTCAACT  226500

TATTTCCTAA AATTGCCTCA GAATGTGCCT ATGTCCACAA TATCCCTCCT TCCACTTTAG  226560

AAAGGAAAGG CATCCACACT TTATTTAGGT GCAATGCCTG AAGTGTAAAC ACTTTCTGGT  226620

TGTCAACAAA GGAGTACTTC CAAATATTGG TTTGGGGATA ACCTGCTAAT GATTAACACA  226680

TTCACCTTGG CTCTTGGTTT GCCTGCTCCC TCTTCTTTTA TCTGCTGTGT GTATTTTTTT  226740

TAATCACTGA GAATATGCAC AGTATTGTAT GTTTTATTAT AAGAGAGGAC TGGCCAGAGT  226800

GGGAATGTTC TGAATTCAGA ATAACTGAAG CAGTACAGGA TAGGAACTCA TTCTTTCAAA  226860

TGAAGCTGGC ATATTTTCCC AGAGCACCAA ATTTCAATAT ATATTAAAA AACTTGATAT  226920

GAATGATACA ATAAAGTGGT TAGAACTTTT ATTAAAATAA ACTTATGTCA TGAAATACTT  226980

ATTCTAATTA TAGTCACTCT TCATCTTATT TCATCTTATA ACATGTTTAA TGTTTTCTTT  227040

TATTTACAAA ACAATTTATT TTTTGATGAA AAGTTTTAGA AATCAAGTTA AAAATATTCA  227100

AAGGAATGCC TAAAGTTTTC AAAATTCTTT TACATGTTGT ACAATCAAAA GAGTCTGAAG  227160

ACCATTTAGC TATCCAAATT GTTTATTTTT AAGCAGTATC CCTTCTAATA TTTACTATTT  227220

ATAATCCTTA AAAATTTGCC TTAGCACAGG AGAATTGCTT GAACCCAGGA GACGGAGGTT  227280

GCAGTGAGCC AACACAGTGC CACTGCCCTC CAGCCTCGGC GACAGAGTGA GACTCTGTCT  227340

CAAAAAAAAA AAAAAAAAA AAAAAAAAG GCCAAAAACA AATAAACAAA CAAAAAAATC  227400

CGCCTTAACA TTATTTGTTC ATTAAAAACT TTCTTTAATA CTACTAGTTT CCCTTTCCTC  227460

TCAGCCCATT GTCATATTTT GATTTTTATC ACTTGCTTTG TAGGACATAT GAGGTTTTTG  227520

TTTTTTTTTT TTTTGGAGA TGCAGTCTCC CTCTGTTGCC CGTGCTGGAG TGCAATGGCG  227580

CAATCTTGGC TCACTGCAAC CTCTGCCTCC TGGGTTCAAG CAATTCTCCT GCCTCAGCCT  227640

TCCAAGTAGC TGGGATTACA GGCACCCACT ACCACGCCTG GCTAATTTTT GTATTTCTGG  227700

TAGAGACGGG GTTTCACCAT GTTGGCCAGG CTGGTCTCGA ACTCCTGACC TCAAGTGATC  227760

CACAATCCTT GGCCTCCCAA AGTGCTATGA TTACAAGCAT GAGCCACCTG CCCAGCCAGA  227820

ATATATGTTC ATTTTGAGTC CTTTAACAAA GTCATAAGAA TTTTAGGAAT TCAGTTACTT  227880
```

```
TCTTGAGAAA ATCTCTGAAA AGATGCCAAT AATTTGTAGC CAATTATATT GATTTCTCTT   227940

TTTCATATTG AGAATTGTTT TTTAAAAAGT TTGTATGTGT GAAGATTTTT GCACTGTAGT   228000

TAAAGAAACC ACCTGTGTGT TGGTTAAGCC ATAAGTACAT GTATTCAAAT AAATTGAGGT   228060

GGGGTTACTC TGAGAATCAA AGGAAAACCT GAAGAAACAG GCAGCCTCAA AAGGTCTTAG   228120

CTGTAGCAAC TTGCTCCATT GTTGAAATAA ATAGGCTTGA ACTTGTATTT TCCCTCTACT   228180

CAACATTTAA GGTCTCAGAA GATAATATAA TTGGTGAAAT TTAAGTAAAG TGCTCACTCT   228240

TTTGCTTTAA CAAACCCTAG AGAGCTGGTA GGCAGAGCCT CAACAGACCG TTTTAGCTTC   228300

CAAAGGGAGT TCAGGACACC ATGATTCACG ACCACAATAC ATCACACATA ATTGAGAAAA   228360

GATAGTTCCA CCAAATAAAG TTGAAATGCT GACAAGAAGG GGTAAGAAAT CTTGGAAATA   228420

AGTTTATATA AAATTTATTT TTTCCTTTTT TATTGTTATG GAATAGGACC AGTTCTACTT   228480

AAGCCACCCA TTTGCCAAAA TAAAGTGAGA ATCGTTTCTT TTGGGGACTC CTCTTTGTAG   228540

CTCCAAGTGC CACTAACAAT TCTTAGGACC TGAGCTATAA GCCAGGTGAT TTCAGTTAAT   228600

ATGATCAATT ATTTCATTTA AATGGCTCTA ATGTGCAGAG GGAACGGAGC CCATCAGCAT   228660

TCCCTGCAGG GAACTGCAGT GGCTTTTATC AACTTGAACA GCTAGCTTTC AACTGTTTTG   228720

AAATCACTTT CAGGGTGGTC ATGTAGTTGC TTTTTTGAAA TCAGAAGATG ATTCTGCCTC   228780

TTTTAATATG TGACTCCTCA GATTCAGAAA GTGCTCGCTA GTCTTAAGAG TGAATTACCC   228840

TCAGTGGTCC AGCGCTTATG AACCCACATC TAACCCTATC CCCTGGGGA ACTATCAGAG    228900

AAATTGGTGC CATGGACATA AGAGGAAGGC ACAGTGAAGC AGAGAGCCCC GCATGATGAA   228960

AATCAGTGGA CAGCATCATT ATTTACAACT TTGTAATCAC CCAGGAGCAT GAAAATCCAG   229020

GCCAATCTGG CACCATGAGC TCTAATTTTT GTTGGAGTTC TTGGAACCGA TTCTGATGAA   229080

TGACTGTTTA GCCATTTTAG AGTGTGGCAT ACGTGGCTGC TGGCATACAG AGGTTGGATG   229140

TAAACGGGCC TTTGCCCTCT CTTATGAACA TAGACAGGAA CTAAACTGTG TCACATAGGT   229200

TCCAAATGGT GGCCTGAATA CTATTTACAA CTAAGGTACA ATGAAATTGA GTAAGTCTTT   229260

TCCTCTTTTG CAGATACCAT CATTATTCAT ATATTTCTTC AAAGTTAACT ATTTGTATTT   229320

GGTAATTTTT AATAGAAATG TAATAATTGC TTCTCAAGTT TAGTCTTTAG TCTTAAGGTT   229380

GATGCTCTCC ATGTCCTTCC AAAAAAAGGT ATGTTGCTTT TATTATATCC TCGCCTTCAG   229440

ATGGGATTAT TCCATTTTGT TCTTTGTTAA TATATACTTT GAGCCACTTT TTTTGTGGCT   229500

CTGGGTGAGA TGCTATAGGT ACAATGACAA GTGATACGTG TGTTGTCCCT GTCACAAAAG   229560

TGGATAGCCT AAGTGGTGAC TTTTACCTCC ACTCCAAATA TATGTATCAC ACACCAGCCG   229620

TATGCCAGGC ACCACTCTAG GTGCTAGGGA TACAGCAGTA AACAGACAAA TGCAACCCCT   229680

GCCCATGTGA AAGAGAATAA GACAATAAAT AAGTAAAGTG CATGTTATAT GGAGGTGGCA   229740

AATGCTAAAA AGAAAAATTA AGCAGGCAAG AGGACTCATT GAAAAGATGA CATTTGGGTA   229800

AAAGCCCATG TATATATGTT CTATTGGTTT TATTTCTCTG GAGAGCCCTG ACTAATACAC   229860

AATGACTTTG AGAAGTTACT GGCTTTTGAT TTATCACACT ATTCGGAGTG CTGAGAGCCT   229920

TCTTAGTGTG TATTCAGTGT TTTAAGAGAG CTTGTGGATG AATAATAAAT AGGACAAAAT   229980

TTATCCAAAC TTAAGCCTTG CTTTAGGTAA AAGGGCTCCT CTTACAAGGT AGAAGGTTAT   230040

TATTTGGCAT TTAAATCCAA CTGAAGACTA ATAAGACTAA TTAATTAAAA GTTTTTAAAT   230100

CACAACTGGG TGCAAAATAA ATGGAACTGC CATGCTCGCC AAGTGTGCAT GAGTGGTGTG   230160

CATGGGAGAC AGCACGAAGC TAATCCCACT CATCTTGCAG GTTGCTCCAT TTTTCTCCTA   230220
```

```
AAATCAGTAA GACAGAAGCT GGTCAGATTA TCAAGAGCCC TAGTTAAACA CAGCAGTAGC  230280

ATTTGGAAGG GGTTGCTCTC ATTAGGCAGT GCCTGACCAC AACAAGAGAT GAACAAGCCC  230340

TGTATCTGAA GCCATCATGC CTAGTTATGG TCCCCCACTG TTCATGATGC CTGAAAGGGA  230400

GGCCCCCTGC ACCCTAGAAA GCTGGGTGGG TTCTACTGTC TGCTTTACTG CTAAAAACCC  230460

TCTTCTTTGG ATCTGGACTT TACCTCTATC TGATTTTTTT TTCTAATATA TGATTTGGCA  230520

CTGAGTCTGT CACTGCTGCT AACTCAGCAG TTCTAGGGTC ATTGCCCCAT TGCCTCACAG  230580

AAAGAATTTC ATAGCTTCCA GCATCCTCTC TCCTTCATTA TACTTTGATT TCAGCATTGC  230640

TATTTTTTCT CTTGGGTGTT GCAGCTCTCT CTCTCCTTCC CATGTCTTGT TGGTTTTCTG  230700

CTAACTCCTG CTTTTTTTCT TTTTTTTTTT TTGAGACGGA GTCTCGTTCT GTCACCCAGG  230760

CTGGAGTGCA GTGGCACAAT CTCGGCTCAC TGCAACCTCC GCCTCCCGGG TTCAAGCTAT  230820

TCTCCTGCCT CAGCCTCCCA AGTAGCTGGG ACTACAGGCG CTCACCACTA TGCCCCACTA  230880

ATTTTTGTAT TTTTAGTATT GCTGTCATCA ATCCACATGT CCAGAAGCAC CTAGAAACTC  230940

TAATTCTTTG TAGGTATCAA ACCCTAGGAC TCTTTCCTCT AATCACAATA TATAATCCCT  231000

GATTCCCAAA CACGGTCTTT TCATATACAT TTTCCACTGT ACATACTTTC TGACCTGGAA  231060

AGCTCTTACA CAAACACGCC CTCCCCTAGG AAGCCTTTAT AAATGTTCCC AGGAAGAATC  231120

AGTCACCCAA CAGTGTCCTT GTCACATCTT AGGTTCTACA CCTTTATTTG TTCTATCTGA  231180

ATGTAATCTC CCAGAGGGTG TTATCATCTT TTTTTTTGAG ATGGAATCTT GCTTTGCTGC  231240

CCAGGCTGGA GTGCAGTGGC ATGATCTCGG CTCACAGCAA CCTCCACCTC CTGGGTTCAA  231300

GTGATTCTCC TGCCTCAGCC TCCTGAGTAG CTGGGATTAC AGACGTGTGT CACCACACCT  231360

GGCTAATTTT TGTATTTTTA GTAGAGACAG GGTTTCACCG TGTTGGCAAG CTTTCCTCG   231420

AACTCCCAAA CTCAGGTGAT CCACCCGCCT CAGCCTCCCA AAGTGCTGGG ATTACAGGTG  231480

TGAGCCACCA TGTCCAGCCC CATCTTTTTC TTTTAGTTTA GTTCTTAACA AATAGTCTGA  231540

CACAAAGTGG ATATAACAAT ATTTTGAATT ATGAATAACT AAATGAATAT TCCAGATTT   231600

CCTGGTGCTC TCAAAGTTTT ATGTTACAAA AGAAAAACAA GTCTAAAATA CCTGCCTCAA  231660

GTTTTTATCT GTACTATGAT TCAAACCAA ATAAAAAACA GGTGGGGTAA AAACTGAAAC   231720

AGGAAATACA TATAACTGAA AAATTTTGGT ATGTTAGTAT GATAATACTA GGTCATTTTT  231780

CCTGTTTCCC CAACTTCATT TTCTATAGCA ATAAAAAGAA ACAAGTAAAT GTATATTAAT  231840

TTAATTTAAA AGAAGTAGTC TACCATCTCT TCTGTTAAAA AGAAAAAAGT ATTTTAAAAA  231900

ATTATCTCTG GAAGGATACA CAGGGAACAT TGCTCTGGTT TCTTCCAAGA GAGAAATGAG  231960

GAACTAGAGA GCATGGCCAA GTGGGGTTTT GCTTTTGTTT TTGTTTGTCT ATCTGTTAGC  232020

TTTTTATTAT TTTCTTTTGT AGGTTTGAAT TTCAAACCAC ATAAATCTGT TACATGCTCA  232080

TAATAATAAG TTTAAAATAA AACTTTTGGC TGGGTGCAAT GACTTACACC TGTAATCCCA  232140

GCGCTTTGGG AAGCAGAGGT GGGAGGATAC TTGAGGCCAG GAATTTGAGA TCAGCCTGGG  232200

CAACATAGTG AGACCCTGCC TCTGTAGAAA TAAACAAAAA TTAGCTGGAT ATGGTGGTGC  232260

ATGCTTGTAC TCCTAGCTAC TTGGGAGGTT GAGGCAGGAG GATCCTTTGA GTCCAGGAGT  232320

TTGAGGCTGC AGTGAGCTAT AATCACCCAC TGCACTATAG CATGGGCAAT AAGGTGAGAA  232380

CTTGTCTCAA AAAAAAAAAA AGGGGGGGGG AAACAAATAA ATAAATATAA ACAAACTTT   232440

TGTTTCAAAA TATGTAATAT TTAGCACTAA AGAATTCTGA ATTGTAGAGC TAAAAGTAC   232500

TTAAAAGTTA ATAATTATTG TCTCCTTTAA AAGAATTGTT ATCAAAGTAT AATTTTTATC  232560

CAGAAAATCA TCCATATCAG CAAGCTAAAC TTTCTCAAAA TGACATATCC ATGTAATTAG  232620
```

```
CTCCCAGGTA ATTAGCAGGC AGCCTCTACT CAGGTTGAGT ATTCCTAATC TAAAAATTGG   232680

AAATTCAAAA TGCTCCAAAA TCGGCAACTT TTTGAATGCT AACATGATTC TCAAAGGAGT   232740

GCTCATGGAA TATTTCAGAT TTTGGATTTT TGGATTTGAG ATACTCAGTA TAATGCAAAC   232800

ATTCCAAATC TGAAAAAATC TGAAATACTT CTGGTTCTAA GCATAAGGGA TACTCAACGT   232860

GTGTTAGCTA ATTAGACCCT TCATGGTCTC TTCTAGACCT CAGCTTCTTC AAGGTAACCT   232920

CTATCCTCAC TTCTAATAGC ATGAACTTTT CTGTTTTAGA ATAATTTGGA TTTTCAGGAA   232980

AGTTGCAAAG ATAGTACAAA GACAGTACAG GAGAGTTCCC ATATATCTTT CACCTAGCTT   233040

TCCCCCATTG TTAGGATTTT ACATTATTAT GATACATTTG TCAAATATAA GCAACTCACA   233100

TTGATACATG AAACTCTATT AACCAAACCC TAGACTTTAT GTGGATTTCA CCACTGTTTC   233160

CACTAATGTT TTCTTTCTGT TCCAAGGTCC AATCTGGAAT ACCACACTGC ATTTTCTTGT   233220

CATATCTCCC TAGTCTTTTT TTGTCTGTGA CAATGTCTCA GTCTTTTCTT GCTTTTCATG   233280

ACCTTAACAG TCCTGAAGAT CATTTGCTTT TTTTTCATAA TTACACCGGA GTTATAGATT   233340

TTTTGAAATA ATACCACAAG GGCAAAGGGC CCTTCTTGTC ACATCATTTT AGGGAGAACA   233400

TGATATCCAC ATGACATCAC TGATATTAAC CTTCATCATG TGGTTTAGGT AATGTTTCAG   233460

GTTTCTCTAC TGCAAAGTGA TTTTTTTCCC TTAATTTAGC CCACCTGAAC TTATCAATTT   233520

TGTTTTCTTC CATGACTAAT ACTTTTGTTA TTATAGCTAA AACTTCATTG GGGCCAAATC   233580

TTAGATCATG TAAATTTTCT TCTATATTTT ATTCTAAAAG CTTGTAATGT TTGATACATT   233640

CTAAAAGATG TAATGTTTGA TACATTACAT CTAGTCCTTT GATTTATTTT TAGTTACTTT   233700

TGTATAAGGT GTGAGAGATG TCTCCAGTTT CACTTTATTA ACACATTGTG GTGTTCCAGT   233760

ACTATTTGTT GCTAAGACTA TCTTTTTTCC ATTGATTACC TTTGCCTTAG TTGGCAATAT   233820

TTTTGTTGGT TTATTTCTAG ACTGTTTATC TCATTCCACT GATTTGTGTC TATCTTTTTG   233880

ACAAAACTGT TGATTACAGT AAGCTTTGAA ATAGTTCATT TTTTGTGTCA ACTTGACTGA   233940

GTCAGGGGAT AACCAGCTAT CTGGTTAAAC ATTATTTCTG GCTGTGTTTG TGAGCGTGTT   234000

TCTGGATGAG ATTAGCCTTT GAATAGGTGA TCCTAGTAAA GTAAACTGTC TTTCCCAGTG   234060

TGGATGGCAT TATGCCACCT GATATTCAGG GTCTGAATAG AAGAAAAGGC AGAGGAAGGG   234120

GGAATTTGGG CCTTTTTTTC TGCCTCACTG CTTGAGCTGG GACATCTCAT CTGGTCTCCT   234180

GCTCTTGAAC TGGGATTTAC ATCATCAGTT CCTCTGGTTC TCAGGCCTTC AGATTCAGAC   234240

TGAATCATAC CACCAGCTTT CCTGGGTCTC CAGCTTGCAG ATTACAGATC ATGGGACTCC   234300

TCATCTTCCA TAAATGCATG AGCCAATTCA GTCTATGTCC TTGAAAACTG CCCCACTGCA   234360

GATTAAGGCT TTTTTCCACT AGGTGAAATA AAGAAGCTTG TTAGACAGAT TTCCCTTCAT   234420

CCAGTGCCCT CTCCTCTTTA AGTTACAACA CATTGGCTAC ACCTAAGTGC AGGGGTGGGG   234480

ATGAGGGTAT AGTCCTCTTG TTTGCTGAGA AGAGAACTGT ATTGGGAAAG CTCTAGAAGT   234540

GTTTGATACA TACATAAACA AGGCATGGTT TTTGCACTTA ATTTCACATT ACATTTTTCC   234600

CAGAAAAAAA GGAATGTATA GGCATCACGT AACTGTACTA GCTGGAGTCA TTCTTCCTGA   234660

TTATCAAAGG TAAACAGTTA TTAATCCTAT ACCAAGATGT CAAGGAGAAG TACTTTTGGA   234720

ACACAAGGAA TTCTCTGGGA GTCCTTACTA CTCTCAAGCC CAGTGAAAAA GTTAATGAAA   234780

AACTATAGTA CCTTCCTATA AGCTGGATGA CTAATTACCA GGCTCATTTA GGAATTTGCC   234840

TTACCAAGTA AAACATAAGG GCAGCTGAGG TGCTGACTGA AGACAAATGG AGCATAGAAT   234900

AAGAGTAGTA AAGAATGCCA AAAATGCTGT CATGTATCCA TTGACAAAAG GAGCTATAAA   234960
```

```
GCCTTTAGGT ATTTTCACAC TTGCTCTGTT ACGTAAATGT ATGTGTGTGT GTGTGTGTGT    235020

GTGTGTGTGT GTG                                                      235033
```

(2) INFORMATION FOR SEQ ID NO: 2:

(i) SEQUENCE CHARACTERISTICS:
        (A) LENGTH: 237326 base pairs
        (B) TYPE: nucleic acid
        (C) STRANDEDNESS: single
        (D) TOPOLOGY: linear (xi) SEQUENCE DESCRIPTION: SEQ ID NO: 2:

```
CACACACACA CACACACACA CACACACACA CACAAATGAG GTATATAAAG GGTCTCCTAA      60

AATGTCATCT GATATTTGTT ATTTCATATT CTCAGATTTT TAATCCATTT AGGTAGGTCT     120

ATTTTAGATA GCCTTGTCTG AAACAGAGCT GGGACCTGAT GAGTGAAAAT GAGCTCACCA     180

GAAGAAAAAT CAAACAGGCA TTTCAGAGAT TGAGGCCAAG AAGTTAAATG TCTTAAATGG     240

GCAGAGCTTA GCTGCTTGAT GTGAAAAGAG ACCAGCGTGG CTGGAACAGC AAAGGAGAAC     300

AGCAGAAGAG GTGAACAGAG GCCAGAGATG GTCACTGAGT GGGCCCTTAA GTCATGGTAA     360

GGAGTATGGA GAATGAATTA TTGCATGTAT TGAATATGTA GGTGACGTGA CTCACAGATA     420

CTTTGGATTT GTAGAGATGA AGGAAATGTA GCAAGTGACA CTCTTAGAAT GTTGATTTGA     480

GTAAATGGTA GTGTCAGTTA TTGAACTGGG GAGAACTGGA AGGGATAACA GGCTTAAGGA     540

GCACGTTTAT TCCTGTGTCT TGGAAGTGTT TAGGGTGAAA GACCTATTAG AGTTCTAAAT     600

GGAGATGTCA AGTGAAAATG TGGCTACACA CATTTGCATT TCAGAAAAAA GGTCAGGCTG     660

GAGATGTAAA ATTGGAAGTT TACTGCATAT AGATAGTCTT TGGAACCGTA GTATTGATGA     720

AGCCATTAAT GAGACAGAAC AAAGACTAGG GACCAGAGCC AAGCTCCAAG TTTCTAAAAT     780

TTAGAGGATA GTATAGTCTG GTCATTTTGA GGTGAATACT TAATAACAGA ACAATTTGCT     840

GAAGTGTAAA TTTAGAGCCC TACACTTTTA GCTCTGACTA TTAACGAATA CAGGAAAGAA     900

TGGATATGGT TATCTGCCTG GTGTCTGTGA AATAATTTAA GCCAGGAAGA GATCCTCACC     960

AGAAACTGAC TATGCTGGCA ACTTGGATCT TAGATTTCCA GCCTGCAGAA TTGTTAGAAA    1020

ATAAATGTCT ATCGTTTAAG CCACCAGTCT GTAGTATTTT GTTATGGCAG TCCAAGCTGA    1080

CTAAGTTTTG GTACCCAGGC GTGGGATGCT GCAACAACAA ATACCTAAAC ATGGGGAAGT    1140

GGCTTTGGAA ATTGGTGATG GGTAAAGGCT GGAAGAGTTT GAGGTTCATA CTAGAAAAAG    1200

CCAATTGTGA AGGGACTATT GAAAGAAATA TGGACATTAA AGGCAATTCT GGCAAAGGCT    1260

CAGAAAGGAA GAGAGCTGGA CAGAAAGCTT CCATTTTCAT AGAAACTTAG ATTTATAACG    1320

ATCATGGATA GAATATTAAA TATGCTGGTT AAAATATGGA CTTTAGGCCA GGCGTGGTGG    1380

CTCACGCCTG TAATCTCAGC ACTTTGGGAG GCTGAGGGCA CAGATCACGA GGTCGGGAGT    1440

TTGAGACCAG CCTGGCCAAT ATGGCGAAAC CCTGTCTCTA CTAAAAATAC AAAAATTAGC    1500

TGGGCATGGT GATGTGCTTC TGTGGTCCCA GCTACTCGGG AGGCTGAGGC TGAAGAATCG    1560

CTTAAACCCG GGGGGTGGAG GTTGCAGTGA CCCAAGATCA CACCACTGCA CTCCAGCCTG    1620

GGATACAGAG CAGGACTCCA CTCCCCCCGC CACACACACA CAAAAAATAT ATATATATGG    1680

ACATTAAAGT CAACTCTTGT GAGGTCTCAG ATGAAAATGA GGGACAGGTT ATTGGAAACT    1740

GTAGAAATCA CTGTTCTTGT TACAATGTGT CAAGAACTTG GCTGAATTAC GCTGTAGTGT    1800

TTACTGGAAA GAACTTATAA GCAGTAAAAC TGGATATTTA CCAGAAGAGA TGTCTAAGCA    1860

AAGTATTGAA GGTGTGATTT AGGTCCTCCT TACTGCTTAA AGTGAAATGT GAGAGGAAAG    1920
```

```
AGCCGAAATA AAGAAGGAAT TTTTAAGCAA AACACAATCA GAACTTGGAG ATTTGGGATA    1980

GATTTCTCAA TCTATATTGT AAAAATTGAG AAAGTTTTTC TTGAAGAGGT ATGGTTGAAC    2040

AATGTTTTCT TTTTCTTTTT TTTTCTTGGT TTTATTTTTA TTTTTATGTT TTTTGAGACA    2100

GGGTCTGGCT ATGTCATCCA GGCTGGAGTG CAGTGGCACA ATCTCAGTTC AGTGCAACCT    2160

TTGCCTTCAG GCTCAAGCAA TCCTCCCACC TCAGCCTCCT AAGTAGCTGG GACTACATGT    2220

ATGCACCACC ACACCCTGGC TAATTTTTTG TTGTTGTTTA TAGAGATGGG GTTTTGACAT    2280

GTTGCCTAGG CTGGTCTCTA ACTCCTGAGC TCAAGTGATC TGCCCTCCTC AGTCTCCCAA    2340

AGTGTTGGGA TTACAGGCGT GAAACACTGA GCCTAGCCTG AACAACCATT TGATAAAGAG    2400

ATAATGGGTG TGACCCAAGG ATTTAATCAG CCATCTCAGC AGAAGCCAGG AAGAGAGATG    2460

GGATTATTCC AGCAGAGACA CTGCCAATTT AAACTAACGT AGGCAGAGAA AACAGAAAGG    2520

AACAAAGGAA GGTTGTCGAC TTTTTGAATT CTATAGAACA GGATCATAGA GCTACCTGGC    2580

TGTCAATGTG TACTATTCTT TAAGAAAAGG AAAGACTGAC CCACCAAAGG CAACTTACAA    2640

GATCACTAGG GCTGACTCTT TTTTGTTTTT TCTTGAGGCA GTCTCACTGT CACCCAGGCT    2700

GTAGGGCAAT GGTGTGATCT CAGCTCACTG CAATCTCCAC CTCCCAGGTT CAAGGGATTC    2760

TCTTGCCTTA GACTCCCAAG TAGCTGGGAT TACAGGCTCT AAATCTGTAC CCTCCCGAGT    2820

AGCGCTCCTG CCACCACTTG CCCAGCTAAT TTTTGTATTT TTAGTAGAGA TGGGGTTTCA    2880

CTATGTTGGC CAGGCTAGTT TGGAACTCCT GACCTCCAGT GATCCATTCT CATTGGCCTC    2940

CCAAAGTGCT GGGATTACAG GCAGGAGCCG CCAGGGCTGC CACTTTGATG TCAGACTCAG    3000

AGAGTACAGA TGGGATAGGG TGGGGGTGGG AACATGTAGT CAAGGCTGAC TCTACCTGTT    3060

TCAAAGATGC CCTGCAGAAC TGTGTGGGAG TCTCTCACAG ATGGCTGCCT GGGTGGGACC    3120

CCACCAAACT GAAAGACCGA GACTTCAGGC AGGGCAGATG GAGTAGGCCA ACTACAGAGC    3180

CAGAGGTGAC ACTGAGACAC CACTGGGCCT GGAAATCAGG GCATCAAGCC AAAGAGGGTT    3240

TTTCTTAAGA CCTAACAGAA TTTGCCTTGC CAGGTTTTGG ACTTGATTAG GACACATTAC    3300

ACCTTCCTTC TTTCCTATTT CTCCATTTTC TAATGGGAAT GTCTATTATG CCTGTTTCAC    3360

CATTGTACCT TAGAAGCATG TAACATTTCT GGTTTCACAC GTTCAAAGCT GGAAAGGAAT    3420

TTTGTCTCTG GATGAATCAC ACATTGAGCC TCACCCGTAA CCTGATTTAG ATGATTTTTT    3480

AGATGACACT TTGAACTTTA GAATTGATGC TAGAATGAGT TAAGACTTTC AGGGGCTGT    3540

TGGGATGGAA TAATTTTTTT TTTTTTTTTG AGACGGAGTC TAGCTCTGTC GCCCAGGCTG    3600

GAGTGCAGTG GCACCATCTT GGCTCACTGC AAGCTCTGCC TCCCGGGTTT ATGCCATTCT    3660

CATGTCTCAG CCTCCAGAGT AGCTGGGACT ACAGGCGCCC GCCACCACGC CTGGCTAATT    3720

TTTTTTTTAT TTTAGTAGAG ATGGGGTTTC ACCGTGTTAG CCAGAACGGT CTCGATCTCT    3780

TGACCTTCTG ATCCGCCTGC CTTGGCTTCC CAAAGTGCTG GGATTACAGG TGTGAGCCAC    3840

CATGCCCGGC TGGGATGGAA TAAATTTATC TTGTATGGGA GAAGGACATA CATTTTGGCA    3900

GGTCAAGGAC AGAATGTTAT GGACTAAACT GTGTCCCCCA AAATTCATTT ATTAAAACCC    3960

TAAACCCCAG TGTGACTGCA TTTGGACATA GAGCCTTTAG GGGTACATA AAACTAAAGA    4020

TCACAGGATA GGGCCCTAAT CCCATTGGGG CTGGTGTCCT TACAGAAGAT GAGACACTTA    4080

GAGCTCTCTC TCCACGCAGG CACCAAGGAA ACACCATACA AACACACAGT GAGATGGCAG    4140

CCATCTGTTA GCCAGGAACA GATTCTCACC ATAAACTATG TTGGCACCTT GATCTTAAAC    4200

TTCCAGGCTC CAAAACTGTG AGAAAATGAA TTTCTGTTCC AAGCCTCTTA GATATGGAAA    4260

AAAAGATTCT GTTGTTTAAG CCATCCAGTC TCTGGTATTT TGTTATGGCA GCCTGAGTAG    4320
```

```
GCTAAGACAA TGAAGGATGT GGTAAAACTT TACGTCCCAA CCACATACCA AGAGGCTGG     4380

AATTTAGCAT GCTTTCTTCT TTCAACTGTA GGCAATGTGC ACAAGTTCTA AATCCTAAGA    4440

CATGTTGGCT CCTTTACTCT GCCCAAACTA CAACTCAAAC AAACAACTGT AATATAATAA    4500

CATCCAATGA AGTTCTGACA TTTCTTCAAC ATGAGTACAG TAATTCAATG CCAGAGAATT    4560

CATTTTATTT TGAAATCTAC ATGCCATATT CCAATTTCTG TTGAAGATGC AATGGTTATA    4620

TTTATTCTTT TTAATATAGA TTTATCAGAC TGGGCGCGGT GGCTCATACC TGTAATCCTA    4680

GCATTTGAGA GGCTGAGGTG GGCATATCAC CTGAGGTCAG GAGTTTGAGA CCAGGCTGGC    4740

CAACATGGTG AAACCCTGTC TCTACTATAA ATATAAAAAT TAGCTGGGTG TGGTGGTGCA    4800

TGCCTGTAGT CCCAGTTACT AGGGAGGCTG AGGTAGAATT GCTTGAACCT GGGAGCAGGA    4860

GGTTGCAATG AGTGGAAATC GCACCAGTAC ACTCCAGCCT GGATGACAGA GCAAAATAAT    4920

AAATACATAA AATAGATTTA TCAGTTTATC AATAATATAG TTTTCTTTTC TAGGTGTAAA    4980

TATAGGTAAT GACTGTCCTT TAGTACATTT TCTCATGATG CTCCTCTTAC TTGGTTTGGT    5040

ACAATATTAA GTATTGAAAT AAAATAGAGA ATCCTGTCGC TACACATGAG CACTTATTCC    5100

ATTTGCTCAT CTCCAATATG CACGGGAAAT TCTCAAATTG CTAATAATCT TGTAACACAC    5160

ATGCATTATA TTCAACAGGA ATATATAAAT TTATAATTAT AATTTAGGAT CAACAGATGA    5220

CAAACCTTTA GAAGGTTTGT ATTTAACCTT AAAATATAAT TTTTTAAAAA TTGGTTATAA    5280

AATTTCTAAT ACTTTCTTTT TTGTGACCTC AAGGGGAAAA TATAATTCTT ATAAAAGTTC    5340

AAATGATTTA CAGAATACAA AAAGTGAATA GAGATGATGA ATGAATTAAA GGAAAGGATA    5400

TTGCTACATA GATTTGGAAA TTTAAAAAGG GAAATTACGA TTGTTGATTT TGTGTTAAAC    5460

TGATCTGCTT TGTTCAAGAT ACCTTATGTA CCAAAAAATG ATTTTATCTC AGCCTCATAT    5520

CTCAGTAAAT TCCTGAGACA AACTTTAGTC CCTGGTGCCC AGGTGCCTTT GGTAATTGGG    5580

AGACCTCTAG GTTTAGCATC CTCATCCACT CGCCCCAATT TAAATAGTCC TCCCCAGGGC    5640

CATTCAGGCA AGGGAGATGA AAACTTGCTC AAGAGTTGGA ATCCAATTGA AGCTACCGAA    5700

ATTCATTGCT CAATAGATAA TTTTCCCTGG AAGTAACTAG GGCTTTTGAA TATAATAGTG    5760

GGCATTTCAA AGTAGAAGGT AAAGTATTTT GGAGATGAGG AGACAGGACA GAGCTACGAG    5820

GAATGTCCTT TGCTCAGGGA CTAGGCTCTT AGCAGTACCT CTTAGGTAAG AACTGGTTAA    5880

CTGGCACCTT CTGTGTTTCT CTGAAGCTCC CTTTGCTTAG GGACTAGGCT CTTAGCAGTA    5940

CCTCTTAGGT AAGAACTGGT TAACTGACAC CTTCTATGTG TCTGAAGCTC CCAGAACAAA    6000

CTGCCAATGA AATTTGGATT TTTGGAATAT AGTTTCTTTT TTGTTGTTAC TTTTTGTTTT    6060

GTTGTTTTTT TTTGAGAGTC TCACTCTCAC TGCAACCTCC CCTCCTATA TTCAAGTGAT    6120

TCTCTTGCCT CAGCCTCCCG AGTAGCTGGG ACTACAGGCG TGCACTAGCA TGCCCAGCTA    6180

ATTTTTGTAT TTTTTAGTAG AGATGGGGTT GGTTTTTTTT TGAGACAGAG TTTCACTTTG    6240

TCGCCCAGGC TGGAGTGCAG TGGCACGATC TTGGCTCACT ACAACCTCCA CCTCCCGGGG    6300

TTCAAGTGAT TCTTCTGCCT CAGTCTCCTG AGTAGCTGGG ACTACAGGCG CCTACAGGTG    6360

AACACCGCCA CACCTGACTA ATTTGTGTAG TTTTATTAGA GATGGGGTTT CGCCATGTTG    6420

GCCAGGCTGG TCTCAAACTC CTGACCTCAG GTGATCTACC CACCTCAGCC TCCCAAGTG    6480

CTGGGATTAC AGATGTGAGA CACCAGATCA GCCTCAGAAG ACATTTTCTA TTGGAAAGAG    6540

AAAACACTAT TAGCAACCTA TTAGTCTAAT ATTTAATACT TAATGTCTTC CTTAGTAATA    6600

AACCAACTCT CTACAACAAA GTGCTTCCTG GCTGCCTAGT CATTGATTCA TTCAGTTCAA    6660
```

-continued

```
CATTTTCTCA ATGCCCAACA GCCAAGTGTC TCCTGTATGC CAAGTTCTAT GCTGATTATC    6720

AGTATTTGAA TAAGAGGGGG TCTACATCTT AAGTACTGCT TAAGATGAAA GCCTCTAGGT    6780

TAACAAACTT AACACAATGT ATCATTCACT ACTAAATAGA CCGAATACAA AATCTTGTTA    6840

TTGGAGCCCA GAGAGAAGAA TTGAAATTCA AGTTTTCTCT CTCTCCTTTT CTCACTCACC    6900

ACAATAAGTC AGTTGCACCA AGTCTTGTAG CTCTTTACTG AGCCATGTTT TCACGTGTCC    6960

CTTTGTTTTA TTTGCCACAC CCTAAATAAA AATTGTACTG CTTTTTTTC CCTGGGTTTA     7020

CAGTATTAAT ACATTGTCAA GATTTACCTC TTCGTGTAGA TTCCCTGGGG AAAATTACCT    7080

TTCCTCCTTC CCTTAAATTC TTCAGAGGTT AGAAAGCCAT TAGTAACATT CTGGTATGTG    7140

GACAAAGTTT ACCCATTATG TATGGATGTT TTACTCTTTC CATTTTTCTG ACAATAATCT    7200

CTTAAGGAGG TGTGGTTATA GAATAGTCAG CTGTTATAAG TACTGTTTTC CTGGCCTTAC    7260

AACTTAAATT CTTTAAGCTG TTTCTTAGTT TGCTCATCTC AAAATTCGGA ATAAGGATAA    7320

AACCTATCTC TTAGATTGTT GGATTAAATG AATTAACATA CTGGAAGCTC ATGAAATGTG    7380

CCTGGCACAC AGTAGTGCCT AATAAACCAT CTCTCTTATT CAGCCTGTTT TCTGATTTCA    7440

GAATCTACAC TTGCTGAGCC AGGTTCTTTT CATTTCAAGG TGAGCAAAAG CATACAAGGA    7500

AGAGATGGAG GTAGGAAGAG ATTAAGCCCT AGGCCAAGGG AGCTGGAATC AAAGGCAATT    7560

TGGTCAGTGA ATAAAAAGGA TTCCAAGGCC CATAAGGCAA TTCTAACCTT AGGATCGAAA    7620

TTCTCGGACA TACAGGAAAT GCTGGGGGGG GGAAAATCCG GTCTTCTCAG CCCAAGAGCC    7680

ATGTGAAACC AGACCTTCAA ATCTGATGAT TCTCAGCCCA GCTGCCCATT AGAATCGTTG    7740

TAATTTAAAA ATACCCTCGG AAAATTCTAA TATGTGGCTA TCAAAGGTGA TCATTTGCTT    7800

TTATGCCACT TTGTTTTCAC CCAAATGGGA CATCCAACCC TTTTCCTTTG AGAGTAGTTG    7860

TAGGGAAAGG AGGGGGTGGA GGGAGGGAAG AGCGGAAAAG GCTGGATCCG CCCCGAGCCG    7920

GTGTCAGTAT CTGGGAAGTG GGAGGCGCGT CAGCAGTAAA CAGCTTCTGC TAGGATTATT    7980

ATCTCCTGCC ACACACTCGG ATTTGAAGGC TCCAAACGAA ACAATGCAAA ACGCTTCAGT    8040

GGAGTTCCAG AAGCGTTAGA CTAAACGACT GGGTCTGTTT GGCCAGTCTG AGCAGCTGGG    8100

CGCAGATGCA TAGGCAAGAC TTAGCCCGCC TAGACTTTTC TGCCCACTTA ATTCCGATCA    8160

AAGCAGAAAC CGGCCGGGCG CGGTGGCTCA CGCCTGTAAT CCCAGCACTT TGGTAGGCAG    8220

AGGCTGGCGG ATCACCTGAG GTCAGGAGTT CGAGACCAGC CCGGCTAACC TGGTGAAACT    8280

CCGTTTCTAC TGGTGGCGGG CGCTTGTAAT CCCATCTACT AGGGAGGCTG AGGCCGGAGA    8340

GTCGTCTGAA CCCGGGAGGC GGAGTTTGTA TGCAGTGAGC CGAGATCGCG CCACTGCATT    8400

CCAGCTTGGG CAACAGGAGC AAAACTCCGT TCAAAAAAG CAAGCAAACA AACAAAAAAA     8460

TGCAGAAACC GAGATCCGGA AGAAAACCTC GGCGAGATTC ACAGAATCCA GGAAAATAGG    8520

TCTCTAGAAA TTTGTCCATG GTCCCAGATC TCCATTTCTT GTGGGTGGGG CAGCTGTTAC    8580

CAGATCCCTA GAAGCAAAGG TTTTTTTGGG GGACCGTGTC TCACTGTTGC CCAGGCTGGA    8640

GGGCAGTGGC ACGATCTCGG CTTACTACAA CCTCCGCCTC CCAGGCTCAA GCGACTCTCC    8700

TGCGTCAGCT TCAAGAGTAG CTGGGAGTAC AAGGTATGTG CCACCACGCC CAACTTATTT    8760

TTTTATTTAT TATTTTTATT TAGTAGAGAG GTGTTTCACC ATGTTGGCCA GGTTAGTGTC    8820

GAAGTCGTGA CCTCAGGTGA TCAGCCCCCT CGGCCTCCCA AAGTGGTAGG ATTAGAGGGG    8880

TGAGCAGAAA GCAAAGGTTT TTGAGTGGCC ACAGGCCCCA CTCTATTTCC TTTTCTGCCT    8940

GTAATGGCAA CCTAGACGCT TGAGCTTCTT AAAATACAAG AGTAAGTTGC ATGTCAGGCA    9000

CCGTTCTACA TTAGGGACAT TAGTCTGTTT TACAGACACC TTTCAACTCC CTGGTTAACT    9060
```

```
TTTAGGTAAT ATACTCTGCA CTTTAGCAGG AATGGAACCT ATAACTCTCA CAGAATTAGG    9120

AAAGTGAGGC TGCCTACAGC CTAAATTGAG AAAAAAATAG ACGGGGGACT AGTCGGAGGA    9180

CCAAACAAGG TTACCAACAC GTTAGAGTTT TGCCTTCAAT TTACATTTTT AAAGTAATCA    9240

CAACGAAGTG TTTAGATCAC GAGGCATCCC TGCATGTAAA CTGTTAGGCA CTAACTATGG    9300

TCGATCTTAC AAAGCATTAA CTAGAATATT TCTTTAGAGT ATGATAGTAC GTAACTGACC    9360

TACTATTACA TACAAACAGA CCAACCTTTA GTAACAGCGC TCCCCAAAAA CCGAAAAGCA    9420

GTAATACGCT TTGCTCAAGG TTGGCATAAA ATTAACTTAC CTTAGTGCCT TTTTTCCTTC    9480

TACCTACAAG CAGTGAGGTT AGCTCTTCCT TTGAAACGGT AGGGGGCTC  TGAAAAGAGC    9540

CTTTGGGTTT GATAGCGTTT CCGGGAGCTC AGATACCTGT CAAATCACTT GCCCTTGGCC    9600

TTGTGGTGAC TCTCGGTCTT CTTAGGCAGA AGCACGGCCT GGATGTTAGG AAGGACGCCG    9660

CCCTGAGCAA TGGTCACCCG GCCTAGCAGT TTGTTGAGCT CCTCGTCGTT GCGGATGGCC    9720

AGCTGCAAGT GGCGCGGGAT GATGCGAGTC TTCTTGTTGT CGCGAGCCGC GTTGCCGGCC    9780

AGCTCCAGGA TCTCGGCGGT CAGATACTCT AACACCGCCG CCAGGTACAC CGGCGCGCCT    9840

GCCCCAACCC GCTCTGCGTA GTTGCCTTTA CGGAGCAGGC GGTGCACTCG GCCCACCGGG    9900

AACTGGAGAC CAGCGCGAGA AGAGCGGGAT TTCGCTTTGG CGCGAGCTTT GCCTCCTTGC    9960

TTACCACGTC CAGACATTGC AATCAGACAA AAATCACCAA AACCAGCAGC CTAAGCTCAC    10020

GAGAAAACAA ACAAAATCAA GAAATATGTA AAACATGGCC GCTTTTATAG GTAGTTCCTG    10080

GGGAGTAAAT CCGACTTTTT GATTGGTCGG TAGCAAATGC TAGTCAGATA GCCAATAGAA    10140

AAGCTGTACT TTCATACCTC ATTTGCATAG CTCTGCCCAC GGATGACAAC TGTGTAGTTT    10200

GTCTTCCAAT TAACTAAGAG GTACTCTCCA TCCCTCATTA GCATAAAAGC CCTATAAGTA    10260

GCAGAAATCC GCTCTTTACT TTCGACACAT TTCTGGTGTT TTAAGATGCC TGAGCCAGCC    10320

AAGTCTGCTC CCGCCCCGAA GAAGGGCTCC AAGAAGGCAG TGACCAAAGC GCAGAAGAAA    10380

GATGGCAAGA AGCGCAAGCG CAGCCGCAAG GAGAGTTACT CTGTGTACGT GTACAAGGTG    10440

CTGAAACAGG TCCATCCCGA CACTGGCATC TCTTCCAAGG CCATGGGCAT CATGAATTCT    10500

TTCGTTAACG ACATATTTGA GCGCATCGCG GGCGAGGCTT CCCGCCTGGC GCATTACAAC    10560

AAGCGCTCGA CCATCACCTC CAGGGAGATC CAGACGGCCG TGCGCCTGCT GCTTCCCGGA    10620

GAGCTGGCCA AGCACGCCGT GTCGGAGGGC ACCAAGGCCG TCACCAAGTA CACCAGCTCC    10680

AAGTAAACAT TCCAAGTAAG CGTCTTAACA CCTAACCCCA AAGGCTCTTT TAAGAGCCAC    10740

CCAGATACCC ACTAAAAGAG CTGTGGCCAG ACGCCAAATT TTATTTGGCG GCGGAGGGGT    10800

ATTAGAATGT AGGAACTGGA GAGGGTGGG  GACAAGTGTT GCAGCTTAGA GAGGGACAAA    10860

GGGTCCTGAA CCCGAAAGAA GCCAGCCATT AAAAATGGGT TTGGGGTCAA TTCGTTGTGC    10920

TTAAATTTAA AATGGGGACA AGCGGCCATT TTGCTAACTC GGCGTTCCCG GAAGAAACCG    10980

CAGGCTCGCT TAGGTTTCAG ACCCAGCTGT CTGTCCCTGT CTACGTCGCC AGGATCAACG    11040

GTTGCCGTAA TGTCATAATT TCGCCACCAG CTTCTAGCCA ATAGGCTGTC CTGTCATTTT    11100

AAATATTAAC CAATCGAGGG AAAGCTGTTT TGAGACTCTG ATTTACATAG CGGACCGGAG    11160

TGGGAACCTG GGCAGTAACT GCCTAAGGAA GGACTCCCCC TCTGTTTTCG TGGCGCACAC    11220

CTTCGTAGTA TACTGAAGGG TGTGTCTCCT GGGTTTCCAA CTGCCCCGGT AATAGTCTTT    11280

TAACCTAATA TGCGTCAGTT TTGATAACAA CACTAAGGCA GTACAGAACT AAAGATGTAA    11340

GCACTGCGCC AGATGTTGCT TCATACATCT TATTCTATTC AACTGGTTTA TTCAAGATTC    11400
```

```
AAATCAAATC AAATTTTGCT TGAATCCCAG TGCTCAGTCA GCCATAAATG GTGTGTTGCC    11460

TGATTGAAAC TTAAAATCTC CGTAGGGGGC TTGTAACATG CAGAAAAGTT TGAAAGTTGC    11520

TTTAGGAGAA GCCAACTCTT AACTGCTGGG TAAATTGACA AGCCTTCGAA CACTGAACTG    11580

AAGGCCAGTA AGGACTAGGC GCTGGGTGGG GGAGAATGAA GAGGAGACGT CATTAAACTT    11640

AGCACATACA CTGTGTCTCC TAGAGGACTC TCCCTTCCTA GACAACTGCA GGCCGCTTTG    11700

TGGCCTGGGA AATTCCACAT TCCCTTAAGT ATTTTACTCA TGGTCTTTTC CAGGTAAAGA    11760

TTTTAAGATG AAGGGTTAGA CGTAGTCTAC CTATCTTTTT ATTCAAGTCT AGAACACGTT    11820

TTTAGCACCT AGAAGTTTGC TTTCTCCATT AAAAACCGGG AATATACAAT AAATAAAATT    11880

AGTGTTAAAG CAGATTTTTA CAAACTTAAA TACCATGTAA TTTAGGTTAC AGTTACTTAA    11940

CATAAGGACT GTGTGATCTT AAATCTGCAA TTTCTTTCAC ACCTGGGAAA TAAACTAAGG    12000

CCTGTCTTTG GTGCCAGACA AGGCCTTATA CTTGAACACT GCTGTGCAAT CACAGGCTGC    12060

CTTGCCTAGA TAACTTATCT GAGAAATTCT GATGAGAAAT GAAATTTCCA GAGTCCCTCA    12120

CAAGTAAATT TTTTTTTCTT TTTTTTTTTT TTTGAGACGA AGTTTCTCTC TTGTTTCCCA    12180

GGCTGGAGTG CAATGGCGCG ATCTTGGCTC ACAGCAACCT CCGCCTCCCG GGTTCAAGCC    12240

ATTCTCCTGC CTCAGCCTCC GGAGTAGCTG GGATTACAGG CATGCGCCAC GACACCCTGG    12300

CTAATTTTGT ATTTTTAGTA GAGACGAGGT TTCTCCATGT CGGTCAGGCT GGTCTCGAAC    12360

TCCGGACATC AGGTGATCTG CCCGCCTTGG CCTCCCAAAG TCCTGGATTA CAGGCTTGAG    12420

CCACCGCGCC GGGCCTAAAT GGTTTTTTTT TTTTCTATGC CTCTAATGGA CCTGGTCACT    12480

TATTCCCATT CAGACTGACC GCTCTCCTAC CTGCCAACTA ACTAATCAGT GTAACCAAAA    12540

TCTGCAAACA AAATTCAGTA TTCTTTCCCC GCCTTTTCCC CTTTCTCTTA CATAGATTAT    12600

GTTTTTGCCT GTGTTAGATG AAATAATTCT ATTGCTTGTT CTCTCTTCTG TACAAGTACC    12660

CAGTAAGCAA ATTATTAACT TCTTGGTCAT TTATTTCTGA ATTTTCCACC AAGACAGTGT    12720

TTATGTGAGT CATACAATAA GAACCAACAG AAATGTGTGT CTTGGAAACA GGTTGTCTAT    12780

CCCTGGACCC TTTGAGTTTT CTGTTCACTT TCCTTTGGCT TTTGCATGCT AAAAGTTTAT    12840

CGTCCGCGTT TGTTTGTTTT GGTTATTCTA ATTGGACTTG GCTGATTGGT TGCATATTGG    12900

TGGCAGTAGT AGAATTTGAA TTCTGGTTTT CTGGTCACAT CATTAAGTGA TTAGTCAGTG    12960

GAGAGGACAG GAAATCTGGT TTATTTATTA ACCTTTTTTT GGGGTGTTTT TGTTTGAAGA    13020

TGTTGATATT CTCTGTGAGG ACACAGGGTT AGAGTTGGTG TTTTTCTTTC TGACTTTACA    13080

TGGGATTTGA TGTTTTGTGC TTGTATGCCT CTTTCCACCT TCCAAAACTT GTCTTTTTTG    13140

AGTCCAAATA GTTGTCGATA TCTGCAAAAC CAGTATTCCT GTGTTAAGAT GATATGAATA    13200

TAAAATGGCT GCCCTGTTAT AACTTTTGAC TTTAAGAAAG TGTTAGGACT AACAGGAGAC    13260

AAAAAGGAAA TCAAGGAAAC CAAATGTCTG GTCTCAATAA CTGCTATGGC AGAGGCTCTA    13320

CAGCTTATTA TTAATTTTAG TAATTTCACA TTATTGCCCC TTCACGTTCT TTAAGTAAGG    13380

TTAGAGGACA GAAGAAACAT AATGTTGTTA CAAATTGGAC TATTGAGTCA GGAAAAAAAA    13440

AGAGTGCTTT CAATATCTGA ATAAAACAAA GATTTAATAT TTTCTAAACC TTAACGAGTT    13500

TATTGTAAGG GATGTGATGC TGGAAACTAG GAAACTAGAA TTTTCTTCTA AACTGAGAAT    13560

CAGAATTATT CATATTCTCA GCAGTGGTGC CACCTGAGGG ACTTCTGATC TTAATTACAT    13620

ACTTTTATTT CTTTAACTGA TCAACATGCT AAATAGATAA CCTATGGCTC TGTTTTTACC    13680

CACTTTAAAT TCTGTTCTAT TAGCACGGTT AGCTTTCCTA ATTGGCAATA AGATTGAGAC    13740

TATCTTTTTT TTTTTTTTGA GACAGAATTT TGCTCTGTGG CCCAGGCTGG GGTGCAGTGG    13800
```

```
CACAATCTCG GCTCACTGCA ACCTCTGCCT CCAGGGTTCT AGCAATTTTC CTGCCTCAGC    13860

CTCCCCAGTA GCTGGGATTA CAGGTGCACC ACCACGCCTG GCTAATTTGT GCATTTTTAG    13920

TAGAGATGGG GTTTCGCCAT GTTGGCCAAA CTGGTCTCGA ACTCAGGTGA TCCACCTCGG    13980

CCTCCCAAAG TGATGAGATT ACAGGCGTGA GCCACCGTGC CCAGAAAAGA CTATCTTATT    14040

TTATGAATTT AAATAATTGT GAAATTATCC ACTTAAGGGA ATTAATAAAT TATAATGTAA    14100

TCTTAAATTT TAGTTGGCTT ACATAAAGAC TTAAAATACA TCAATTTAAA TAAAAACTCA    14160

TTTGTCTAAA AAAAAATCAA AAATTTTCCT TGTGCTTTAA ATGTGCTACC TCTTTAAGTT    14220

CTAATTAAGA GAAAAAAAGT TTAACTGTGA GTTTCATTAG TGGTCTTAGT TAACAGCTTA    14280

AAGTATTTTG TAAAAAAAAT ACTTCACAAT TTTTAAATAA CTTAAAAATA TTAATACCTC    14340

TTTTATTAGG TTTTTTTAAT AAGGAAAATA TATAATACAT CTAATCAAGA TTATTTTTTG    14400

GACAAATTGG CTTAATAATT TCATTTTAAA AATGGCTTCT TTATTCTTAT ACTGTAAAAA    14460

TAATATTAGC AGAATATTAT AGTATACACA AGTTTAGGGT TCATATTCTA AAAAACAAAA    14520

ACAAAAGCTA ATTTAACTTG CATTTACTAA ATTTCTTCCA CTAGTTGTAC TGGTTACATG    14580

AGTTAACATC ACTTTATTTA TTATTCTAAA ATTGTAAATT ATTCATTGAA CCAAATTAAA    14640

TGATAATAGA TAATGTCATT TTTAAAAATG GAATTAAATT TTATGTTACT AATTATAAGG    14700

ATTCAATGTG TGAGCTTAAG TACTGAGTTC ACAGTGTATG ATAACTTTAA GAATTTAGGT    14760

GAATATTATT AAATTGAGTA AATTAATTCT CAATCTTTGG ATACCTGGAC AATTTCTAAA    14820

TTGGAGGGTA CAAAATACAA ATCACAAGAA ACAGTGTAGT TTTATGCAAA TAACATTTTT    14880

ACACAGTTTA GAATAACCAT TGATAAACAG ATAAGAGAAC ATATGATTGC CTTAGAATAG    14940

ATACTGTTGC TTTCGCCACT TTAGATTTGT AAATCATGTA CTGTATACGT GTGGGCGTAG    15000

AGGACCATGC AGGTTTTGGA TGACTGCCTC TGTTTTCGTC ATGCCTATGC GGGAACACAA    15060

TTGCCTGCTT TGTTTAAGGG CTATGGTTAA TCCAAACAGC TCTGACTCTA TCAAGTACTA    15120

TAGCTACAGA GAAACACAAG TAAGCATTCG AGATAATGAC TACCTTGAGC CTTTACTTAT    15180

TTAAAAAGTT GTTACTGTTT GTTAATGTGG TACATTCAAT TTACTATGGA TTGTCACTCT    15240

AAAATAAGAC TTCAATCTTT TTCTTATTTT TATATAGCCA TGATTTATAT TCATATCTTA    15300

ATGTAATAAC CAATCTTCTC TGACAACATT ATAACAATGC TGGAACCTCC ATTTTCAGTA    15360

CTTCAAACAA CAAATACTGC TTTTATACTT CAGAGCAGAT GGATATGTGC TTCCCAGTGT    15420

AAACACATTT GGAATCTCAC TGAGAAATAC ACTATCACTA AAAATACAGT TCTGAGATTC    15480

ATTAAAAGAC CTCCAGAATT CTGGAAGTAG GAAGTTCCT CTTCAAAGTC TACAGAGGAA    15540

GACGAGGTCT GAAATAGACA GCTTCTTCCT TCTTTTACCT GTGGTATTAT TCTGTTTTGT    15600

CCTTTTCTCC ATTATCTGTC TTTCCAGTGA TGAAATTTTG ATCTGGCCCT CCCAAGTATT    15660

AAAAAACAAG CAAATAAACA AATCTCAGTT ATATTTTACT AAGATATTGG CATGCTAACT    15720

TTTTGCAGGT TTGTAACAAG GACCTTTATA ACTTGACTAA AAGTTCCTAA ATAAGAATAT    15780

TTACTAGAAA ATTTATTTCT GCCTGTGGCC CACATTTGAG TCAAAATAAT CAATTAGGAA    15840

AAATGAACTT GTTAACTAA AGTTGGCCAA ACTGATCTTT GAGACCTATT CATCTAAGAC    15900

AAGCCAATTA AATTCTTGGA GACAATTTGT ACTTTAAGGA ATTCTTATAA TATTTGTAAT    15960

TACCCTCATA ACTTTTTTTT TGCCCTACTT CTGTGCTTCT CTAATATGCA GATTATTAAA    16020

TGTTGTTACA AAGCCATTGT CAAAAAAACA AAAACAAAA AACTAAACAA ACTCACATGG    16080

TTAGACTTGC TCCTTTATGA GATATTTTA CCAAAAATGG AGGAGTTGAA AAACTCTGGT    16140
```

```
GCCAGAAATC GTGAAGACAT GGCCTACCTA ACTTGGAAAT GTTGGTTGTC AGTGGAAAAT    16200

ACTACACAGA GATAGCCATA GTGCTGCACA GCCAATCTTA AGTGTTTCTA GAGAATCACT    16260

AATTGTTTCT AGAGAATCAC TAATTGTTTT CTTTTAACAT TCTTGGTTTA TACAAGAAGA    16320

GAGTATCCAT ACTAAACTCT TTTCTACTGA AAATAATGTG CAAACATAAC ATCCTATTCC    16380

TAGACAGTTT GTAGTTTTTT CTCCCATTT CTATTTTATA AATCATCTTT TTAAAATACT     16440

TTGTTGAGTG AAATCAGTCC ATTGCTTGAT ATACCTTGAG CACAAGTAAA TAGTATGCCA    16500

AAAATTAAAT GTCTTTCAGT CACAGTTTGA CAAACTCAAC TACCCTGAGC CTATAGAGTG    16560

GTAATAATTG CCCTACTCAT AAAGATGGGG TGAAGATTAA ATGAAATAGC ACCTATAGAA    16620

CACTAGTTCC AGACGTGGTA TCATGCTAGT AAAATGGCTG CACAGCACTG CTCAATGATG    16680

ACAAAAAGTG AAGCTTCTGG AGACAGACTC CAAGTTTGAC TCCCAGATCA CCACATATAA    16740

GATGTGGGAC TCTGAGGCAG GTCATTTAAT CTCTCTGTGC ATTAGTATCC TTCTCTATAC    16800

CTTTACAGTG ATGGTAATAG CACCTACCTT CTAGAAGTAT GTGAAGATTA AGATCCTTA    16860

ATGCATATAA ACCACTGTGT TTACTGCTGT TTGACAAATT TTATTTATAA CCATCTTTAC    16920

GCTCCTAAAA GGACTTGAAG CAGCTTATGA CTGAAGACTT TGGTAGGAGT TGGCCTTCTA    16980

TAAATTATAA GAATTTCATA AATTATTTGA TATGAAAATG CCAGTTGATC ATAGTATGTT    17040

TACCGGGGTC CAACAGGTTG AGAAAAAATA CACTTTTTTT CCCTGAACAT ATGAAATTAG    17100

CTCTCTAGGC ATATTCCTAA GGACTTAAAG AATGATAACT ATCATTTCTC TTAAATCTTC    17160

CAGATTTGGA AGGATATATA TATTCAGCAC ATTGACAGAC AATCCCAGTA GTCCTAAATT    17220

AAAAGACATT AAAAATTAGT GAAACTTTTC CTACCTTTAG CCTGTGTAAT CCTGGATGAC    17280

CAAGCATAAA ATTAAATTGA GTAGAGTATA CCACTGTAAC ATTTCCTGAA AGGTATTCTA    17340

GGCTCTGAGT AATTTCTTTG GGTCTGAAG ATCAGTTTGA CATATCCTCA AGTATCATGA     17400

GTTCATTATA ATTAAGAAAA AGGGAGTAAA TCTGGAGAAT GAGCCACTTT CTTACTACTC    17460

CTTGACCTCA GTTCTTTTTT TCAGAGACAG GGTCTCACTT TGTTGCCCAG GCTGCCAGGC    17520

TGGAGTGTAG TGGCGCAATC GCATCTCATT GTAACCTCCA CCTTCTGGGC TGAAGCCATC    17580

CTCCTGCCTC AGCATCCTGA GTATCTGGAA CCACAGCAGG TGCACACCAC CATGCCAAGC    17640

TAATTTTTTA AAAGTTTTT TGTAGAGATG GGGTCTTACT ATGTTGCCCA GGCTGGTCTC     17700

AAACTCCTGG GCTTAAGTGA TCCTCCTGCC TCAGCCTCCC AAATTGTTGG GATTACTAGT    17760

GTGAGTCACT GTACCCCGCC CCACTTCAGT TCTGAGGAGG AAAAAATATG TAATAATAAT    17820

GGGACTTTGG TTTGCTGATT TAAAGATTCA TGTAACCTTA TCATCCAATG CGCAATTTGT    17880

AGAATAATTA ATAGAGACAT CTGGTCTCAT GTTTCTACAG TTGCTCATGC CTTGATAGTA    17940

GATCTCCTTG CTGCTGGCTC AGAAGGGTAA AAGAGCAGAA ATGATGGGC TTCTCTCATT     18000

CTATGAGGAA ATAGACCTAT GTAGAGGAGG CTACCTGTGG TAAAACCTTA TCCTCATCAC    18060

TTAAAATTCT AGGCTTATTC TCTGACCATA TCAAGTTTTC AAATGGTAAA AGAATTGGAT    18120

TCAAGAGAAA TATGAATAAA CTTTTGTTTT CACTTTCTC CCTCCTCTCC CCCCATTCTC     18180

CCTTCCTTTA TTTTCTTGTC CTTAGTTTTC TTTTCACTTT TTTGTCTACT ATTATTTGCC    18240

CAAACTCAAC TGTAGGCTAG AACAAAAAAA AATTGAAAAT TAAAATGTGC CCCTTTTGTT    18300

GTTAGACTTG CTTAAACAAT TGGGGTAATG AACCTTGGAC ACTAGATTTT AAAACACACA    18360

CATTTGAGCT TCAGTGCACT GAAATAAATA TATTTTTAAC AATTAAAAAA TAAAATTGCA    18420

TGTTTAAAAA ATCTGCAGAG AACAATACAC GTTGTGAGAT CTTGAATGGA AGGAAAACTG    18480

CTAGCCTCAA GAGTGGATCA AAGATGCTCA GCAGGCAACA GAGTAAGAGC ATGTTGGAGG    18540
```

```
GTTTAGAGAG TGTGCTCAGG GTTCTAGGCT CTAAAAATCA GACAGTCCCC ACGGCCTGGC   18600

CTTCGTCGCT GTATCTTCTT TATGAAAAAC ACTAAGTCTT TTTCCTCACT GGATAAATTT   18660

TTATCCTTCA AGTTTAGATC AAATGGAACT TTAGGACACT GACTAGGTTA CATTCATCTT   18720

TTAAGAGCGT ACAGACATTC AAGGGCTAGA GGATGTGGGT TTACTGCACA GGCTCATTAT   18780

CCAACAGCTG TGCTACCTGG GAAACTTAAC CTCTCTGTGC CTTAATTTCC TCATCTATAA   18840

CGCAGGGAGA ATGACAGTAG GTATCTCATA AGGTTGTTGG AACAACTAAA TGCATTGGTA   18900

TCTATTGTGT AAAGTGCTTA AAACACTGCC TGGCACAGAG CAAACATCCA GTGAACTTTA   18960

GCCATCATCA TTATCATTGT TCTCAGAGTC AAATACAATA TCTCATATCT GATAAATTAC   19020

AGAAGTGAAT CAATCACTCT CTCTCTTTTC TCCAGGGGGA GACAACAGCT TTTAGACATA   19080

TCTTTTCCAA CAGTCGTCAC TGCTGGACAC TGTTTCATCT TGCAAATAAA CCAATGAAAA   19140

TGAGTGATCC TAGAAGAAGA TAAATGGAGG TATTTTGAAC AATCAAAGAA GGACAAATGA   19200

ACACCTGGCT GAGAAAAATT AGCTCTTTTT TCTATGCATA AAACTATTAA AATATTCTTC   19260

ATAGAAATTT ATGACACAGG AAACATAAAG ACAAAATTAA AATAACTCCT AGTATCTCCT   19320

ATTCTTTTTA TATGTATATT ATATATACTC ATATTCATAT ATACATATAT CTCACATCAT   19380

GTATCATATA TAAAATAAAT TTAGGTGTCA TGATATATAT TTAGATAAAT ATACTTAGAA   19440

ACTTTTTTAT GGATGTATAA TTTATGGATA TATTGATAAT TATGTATTTG TTATTGACTA   19500

CTTCAATTGA TTCCCATTTT TATGCATTAT ATTATAGATT ATATAGCTCA CACATCTTTG   19560

TACATAAATC TTTGTTCAAA TATTATTTCC TAAGGATAGA CTTCATGAAG TGGAAATACT   19620

AAATCAAAAG TGAAAAACAT TTTCTAAGGT TCTTAACATA TACATTGCCA AATTGCTATT   19680

CAGGATCATA CCAATTTATA ATCCCAAAAT AATATGAAAA TTCCTGTTTT ATAGCACTCA   19740

TATTTACAAT AAATTTTAAA AATCACTGTT AACCTAATAG TCCTTCAAAA GAAAAAAAA   19800

TTGAAATTAC ATTATTTTAA TGACTCTATT AGTGAGGGTC ATTCTTCCCA TGTTTCTTGT   19860

TAGCCATGAC CCTATAAGAA ATAAACTGCA CTGCAAAATG ATAAACATGA TATCAATCAT   19920

TACATGGGAA GGCACTATAT AAAGAATAAT ACCTTAGGTT AAGGCCACAT AAATATTTAT   19980

CAGGTGCCTT TTCTGCGGAG GACTCTGAAG GGATACTAAA CTGCATTTAG CTGCATGCAA   20040

CTGAAATTAC TTTTACCTAC ATTGTCTCTT ATAAACATTA TAACTACTCT TTGAGAAAGT   20100

GTTTACTATG GACTGAATTG TCTCCCCATC CCCCCAAATT CATATATTGA AGCCATAAAC   20160

CCCAATATGA CTCTATTCCT AGACAGGACT TATAAGAGGT AATTAAGGTT AAATGAGGTC   20220

ATTAGGATGG GTTCCTAACT GGATAGGATT GGTGGCCTTA TAAGAAGAGG AAGATTCTGC   20280

ACTTGGTCTT CCAAATTAAA TAATTTATTT AAAAGAAAAA AAAAAAAGA GGAAGAGAGG   20340

GAGCTCTGCA CATATACTGA GGAAAGGCTA TGTGAGCTCT CACAGTGAGA AGGTAGCACT   20400

CTACAAGCCA GCAAGAGAGC CCTCACCAGA ATCCAGCCAT GCTATACCCT GCTCTGAGAC   20460

TTCCAGCCTC CAGAACTGTG ATAAAATTTT GTTGTTTAAA CCACACAATC TATGGTATTT   20520

TTTTATGGCA GCCCAAGCCA ACAAAGACAG CATCATTGCT GTCACTTACA GACAAGAAAA   20580

CTAAGACTAG GAGAGAGAAA AGTTAAACTT GTCCAAGGTC ACAAAAGCCA GAAACAAGTG   20640

AGGTGAGAAG TTGACCTTGT TCTCCTCAAT CCAAGGCCAG GACTCCTCCA CTCCACATGT   20700

AGATAGCCAC CTCACAGTCA ACAGCCAAAT GTCCACACCC CAGAGTCAGC ATTAGACCAA   20760

GATGTCTTAC CAGGAGACAA ATGCCTCATC TTGAATAAAT ATGTTCTAAC AACTTACCCA   20820

TGTAAAACAT TGAATCTCAT GAGAAACAAA AATGCAAAGT ATGTAGAAAA CTATGTTTAC   20880
```

```
CACTTAACTG ACAGTGATAA AAAGCTTAAT GATATCCTTA TAGTCTTGGA GGGGTTTGTA    20940

TATGTGGTGA AACAGGTGCT CACGCACTGC TGATAGACTG TAAATTGGTC CTAGAGAGAA    21000

AAATAAATAA ACTGGAAGGA GTTATGCTGT ATGTTTACTT TTTTTATGGA AACATATGAT    21060

ATACCTGGAA ATTCGATTGG CCATGCATCT ATTTCTTCAA TGGGTATGCA CAGTTGAGCT    21120

GTTCCCATGC ACCAGGCACT GTAATGGGAC AACTGCACAT GACAGTCAAA AATCTCAGTC    21180

TCATGAAGTC GACATGCTCA TGGAGAGGTG CTACCCACTA AACTAATATT TGTATATCAA    21240

TTATGGATAC ATTGGGCCAC ATTTACAGAA ATTCACTTAC AGTGGGTTAC CAGAAGGGAT    21300

TTTTTTTCTT GATTGGCAAG AAGGCTAGGC TGTTTTGTTG GGGGCTGGCA GGAGCTGTCT    21360

AGGCTGCCCA AGTATGCAGG TCTCTTCTAT CATCCTGTGT TAACCATCTT CCATGTATCT    21420

TTCAACCTCA TGGTCATCTG CAGCATGTCT AGGGGTCATA TCTATGTTCC ATGCAGGAAA    21480

AAAGGGTAAA GGGAAAGGGA AGTAGGCATG TACCATTTTA ATGCACACCT TGGTTTTCAG    21540

AAAATTTAAG AAGAAAGACT TTCTGCTTTT CTCTGACTAT TCTGTATTCT GGATTACAAC    21600

GCAACAGAAA CGTCACCTTA AATTCTAATG TTTTTCTCTC CTTGCTTTCA AAAACTGACT    21660

CATTAACCTC CACGTGGCTT GGAAAAATTA TTTCAGTCAT CCAGTAATGA GCTGTTCATA    21720

GAAATGTTTT GGACATCAAG TCTGTGTTGT TAGCATTATA CATGTTAAGC ATTGAATAAA    21780

AACAACATG ATGTGGGTAC ATTTCTTTAC TTACATATAA GTACTTATAT ACTTATAGCT    21840

GAAAAGAGAG GTTGAAATGT CAGGTGGAAC AGAAATAAGA TTACCTAGAT GTTTCTCCTA    21900

TGGGTGATTT TCAGCTATGC TGATCTTTCT TCTGGGTCAG GTACTCCCAG AACTTCCTAA    21960

TTAAATGGTG GCCCTGATCT TAGTTCCTCT CTCCTCTTAG ACATTTTCCA GGACTACAGA    22020

AGATGTGCAG TTTATAAATG AGTAGCAGAA ACCTACTGAA CAAATTATTC AGGCTCATCT    22080

GAACAGAGAG GACACCTTCT CTGCTATACT CTCTCAGTGA TTTCCCTGCC TTGGGGTCAA    22140

TTATTGTCTT GGACATTGAT TTAAGCACAT AATAATTGTT GTCATTGCTT ATGTTTGGAT    22200

TTCATCTCCC AAAATAGATG GTAAATTCTT TAGTTTAGAG ACCAAGTAAT ACTTACAAAA    22260

AAATTTGTG TGTGTGTGTG TGTTTTTTCT GTGTCTCTCA GCCCTGTAAT AGCATCGTAC    22320

TTACACTTGT TAGATTTTTA GAGACAACTT TTACAAAACA TGGAATTATC TACATACCCT    22380

TTCTACAAAA CAGACAAATT AAATACTCAG TAGTTGAACC AAAAAAAGCA GTTCAAATAA    22440

AATACTTGAA AATGAAGAAA TCATTTGAAC AGAGTTAAAG TTAATCGTAA AATAATGTCT    22500

GTAAAAATTA TTGCCAATCA AATATAAAGT TCAAAAATAG TGCTTGAAAA AGGAAGAATC    22560

ATATGAAAAG GGACTACTCA TTTTAAAAAT GTTAGATATC AGGAAAAGCC AAGAAGTGAG    22620

TATGGTAAGA GTGCTGTCAA GTGAAACCCT GCTAATCTCA CTGAACATGT AAAAATCTGT    22680

AGATGCCTTT ATTTTATTCA CTCACACACA TATGTAGAAA GAGAAATATA TGGTAAACAT    22740

TAAAAAAAC AAATTAGAAT GTAAAATTAA TACTTTAAAA AATGGGCTGT ATACTTTTCT    22800

TATCACCGGA GATAAGAATT TATTATTTTT AAAATAAAGT TATTTCTCT GTGACTGTTT    22860

CCATGACTTT GCTACTTAGA AGTTAGAGAT GCCAAAGTTT ATCTAAGAAA ATGTTTATGG    22920

AAATATTATT TCAATAATGA ATGTTTAGAA GACTGAATTT CCTGACTGGG CACAGTGGCT    22980

CATGCCTGTA ATCCCAGCAC TTTGAGAGGC TGAAGAAGGA GGATCGCTTG AGTCCGGGAG    23040

TTCAAGAGCA TCCTGGGCAA CACAGCGAGA CCCTGCAGCA AAGTAAAAAG AAAAAAGAAT    23100

TGAAAAAGGA AGACTGAATT TCCTTTGGGC AAGTCATGTG ACATTCCTGT GCCTCAGTTT    23160

CTTCATCTAT AAAGTTAATT CCTACATTTT TGGGGAAGGG AGAGAAAAAC TTAGGATAGT    23220

GACTGGCACA GAAGAAGCAC TATATACTAT ATATATGTGG ATATCATTTG TTTTTATGGT    23280
```

```
ACCATTTTAG CTATCTAATG CAAAATATGA ATCTTTTTTT TCTGGGTCTT AAATTATGGA   23340

ATGTAAGAAT TTTCTAAATT CTCTAATTCT GTGTTAGTTT TAAAGCAATG GAGTAACGTA   23400

TCTGTCAACT TGTAAATATA AGGATCAACC TGATCCACAA TTTGACCCCT AGCCACTAAT   23460

ATTTAATAGT ACAACACTCA GAAATTATCA AAGGTCAGAG AAGCCAAACA AATGTAAAAA   23520

CATACAGGTG CTCAGAAAGA TGCACCTGTA ATCTCTCTAA GGAGAAATAT TTTCCAAACT   23580

GAGTGACACG GTGCTTTAGT GAGTTGTGGA ATCAATCTCA TGATTTCCAA CCTAGTGTTC   23640

TTTTAAAAAT GAACTAGTCC ACAGTAGAAT ATACTAAAGT GCTGGTGCTT AAGATAGTAT   23700

TGTTTTCTGG AAAAAAAAAA AAAATTTTTT TTTTTTGAGA CAGGGTCTCG CTCTTGCCCA   23760

GGCTGAAGTG CAGTGGCACA ATCATGCTCA CTGCAGCCTT GACCTCCTGG GCCCAAGTGA   23820

TTCTCCCACC TCAGCCTTTT GAGTAACTGG GACCACAGGT ACGTGCCACC ACACCCGGGT   23880

AATTTTTTAA TTGTAGAGAC AGGGTCTTGC TATGTGCTTA GGCTGGCCTT GTGAACTCCT   23940

GGGCTCTAGT GATCCACTAG CCTCAGCCTC CCAAATTTAT GGGATTATAG GCATGAGCCA   24000

CCCTACCTGG CCTGTTCCCT GAATTTTTTT TTCTTTCAGG TGTTTGTGCA TATGTGTGTG   24060

TGTATGGGTA TAACAGAGAG ACAGAGAGAA AGAAACTTTT CTATCACACT TTGCAATCAG   24120

AAGTTTGAAG TCTTATCTTT TGGCTTTTGT TTCAGAAATA TTTCAAATGT AGACTCTCTC   24180

CTTTACCACA CTGTCCCCTT AGGCAAGGTC TTTGCCATTC TTCTGAGACT ATTGCAACAG   24240

ACTCCCAACT TCTGACTGTG GGCCCTTCTC AAAAATGATT GTTTATGCAA TAAATCTAAA   24300

CCCAAGACAA CTACAACAAT ACAACAAATT CTCTGCTTAA AAACTTCCAA TGTCTGCCGG   24360

GCGCGGCGGC TCACGCATGT ATTCCCAGCA CTTTGGAGGC AGAGGCGGGC AGATCACTTG   24420

AGGTGGGGAG TTCGAGACTA GCCTGGCCAA CATGATGAAA CCCCATCTCT ACTAAAAATA   24480

CAAAAAATTA GCCAGGCATG GTGGTGGGCG CCTATAATCC CAGCTAATTG GGAGGCTGAG   24540

GCAGGAGAAT TGCCTGAACC TGGGAGGTGG AGGTTGCACT GAGCCAAGAT CACACCATTG   24600

CACTCCAGCC TGGGCAACAA GAGCAAAACT CTGTCTCAAA CCAAACCAAA ACAAAACTTC   24660

TAATATCTAC CAAATGTTTC ACACAAGTAT TTGGGGATCT TCACAAATGG CCCTTATGGA   24720

GTTTTCCTTT GCTGAGACCC TATGCTCTGG CCACACTAAA CTCATTCAGC ATCCCAGAAA   24780

GGCCTCAGCC TTTGTGAGCA AGCTCTTATC TCCAGGCCTC TCACAAAGAC CTGTTCCAGT   24840

AGAAGCTCAG GGGAGCACAC TGGACATTAT TCCAACAACC CTTTCCCCAC AGCTATGCAG   24900

CCAAATCTGC CAGCTCAGTT AATTAATTAA GCAATTCAGA GATGAGGGTC TGCCCAGGCT   24960

GGAGTGCAGT AGCTGCGACC TCAAGCTCCT GGGCTCTAAG TGATCCTCTT CAGTCTACCC   25020

AGAAGCTGGG ACTGCAGGCA TGTGCCACCA CACCCAGCTA ATTTTTTTTT TTTTCAGTAG   25080

GGACCAGGCC AACCTAGTCT TGAACTCCTG GCCTCCAGCC TTCCGAAGTG CTGTAATTAC   25140

AGGCATGAAT CACTGCGCCC AGCCAACCCG CCCAGTCTTG TTAGACATGG GGTCTGTAGT   25200

TTCTAGTAGG TTCTTGAGTC TAGGGTTCCT ACCTCATGTT TTATAGTTAA TTTAGGGGAG   25260

GGACTGTGTC TGTTTATCTG GGGATGTAGG GGTGGGCAGG GGGATAGAGG GGACTTCAAT   25320

TAATGAAACC AGAAGCAAAA CTCAGTTGAG GACACCGGTC ATGAGAGTGG CCTGATTATG   25380

GCCAATCTTA CATAATGTGT GAGATCTTGA TATTACCCCA TCCTTGAGAG TCCTCTATAA   25440

AGCTACAGGG ACTTGGGAGC ACCTTTAATT ACAGACAACC CATGTTCCTG TGGATTATGA   25500

TTTATTAGAT TGCACATGCC TAAATAAAGA CATCCTCTGC AGTCTTTTGA CAATTCTATA   25560

AGCATCTTCT GACTCCGCAA TTAGACAGCT AAGAGATCTG TGTTACTTCC CTCACATATA   25620
```

```
TAAATAATTT TAAATAAAAA TCATGGCGTG AATAATTTCT TTCCTCTACC GATTTGAAGC    25680

TATCCATTTG GAAGACCACT CTGAAGAGAT GAAATAAGTC TTCTGCCAAA GATTACTTAT    25740

TAATTTACAA GGAAAAGGGG AAGTTTTGTT CCTCTCCGTG AATTTGATTG AAAATCGAGG    25800

GCTTTCTCGA ATAGTTTTGG CATCCAGGGT CATTTTTCAT TAAAAAGAGA AAAGTCATGT    25860

CAAATATGAA TTTCCGCAGA TTATTCAGCA CTAGACCCTG GGAGATTCTG TAAAGAGGGG    25920

TTTTGTTATA CTCAACTTTT CCGGGTAAAA CAAACACAAA TACTCCTCCT CCAAGGGGCG    25980

GGGGCGGTGC CTAGGTGATG CACCAATCAC AGCGCGCCCT ACCCTATATA AGGCCCCGAG    26040

GCCGCCCGGG TGTTTCATGC TTTTCGCTGG TTATTACATC TTGCGTTTCT CTGTTGTTAT    26100

GTCTGAAACC GTGCCTGCAG CTTCTGCCAG TGCTGGTCTA GCCGCTATGG AGAAACTTCC    26160

AACCAAGAAG CGAGGGAGGA AGCCGGCTGG CTTGATAAGT GCAAGTCGCA AAGTGCCGAA    26220

CCTCTCTGTG TCCAAGTTGA TCACCGAGGC CCTTTCAGTG TCACAGGAAC GAGTAGGTAT    26280

GTCTTTGGTT GCGCTCAAGA AGGCATTGGC CGCTGCTGGC TACGACGTAG AGAAGAATAA    26340

CAGCCGCATC AAACTGTCCC TCAAGAGCTT AGTGAACAAG GGAATCCTGG TGCAAACCAG    26400

GGGTACTGGT GCTTCCGGTT CCTTTAAGCT TAGTAAGAAG GTGATTCCTA AATCTACCAG    26460

AAGCAAGGCT AAAAAGTCAG TTTCTGCCAA GACCAAGAAG CTGGTTTTAT CCAGGGACTC    26520

CAAGTCACCA AAGACTGCTA AAACCAATAA GAGAGCCAAG AAGCCGAGAG CGACAACTCC    26580

TAAAACTGTT AGGAGCGGGA GAAAGGCTAA AGGAGCCAAG GGTAAGCAAA AGCAGAAGAG    26640

CCCAGTGAAG GCAAGGGCTT CGAAGTCAAA ATTGACCCAA CATCATGAAG TTAATGTTAG    26700

AAAGGCCACA TCTAAGAAGT AAAGAGCTTT CCGGGAGGCC AATTTGGAAA GAACCCAAAG    26760

GCTCTTTTAA GAGCCACCCA CATTATTTTA AGATGGCGTA ACACTGGAAA CAAGTTTCTG    26820

TGACAGTTAT CTATAGGTTT AAGTTGTGAT GCAGCTGAGT TGAAAAGGCT TGAGATTGGA    26880

GAATTAATTC AGGCCAGGCT TCAAGACCAT CCTGGGCAAC ATAGCCAGAC TACCATCTAT    26940

ACCAGGGGTC CTCATTCCCC CGGCCACCGA CCGGTAACCG GTCCCTGTCC ATGGCACGTT    27000

ATGAATTGAG CCGCACAGCT GAGGGGTGAG CGAACATTAA CCAACTGAGC TCCACCGCCT    27060

GTCAGGTTAG CTGCAGCATT AGATAGATTC TCATAAGCTC AAACTGTATT GTGAATGGCA    27120

CATGCAAGGG ATCTAGGTTT CAGGCTCCTT GTGACAATCT AATGCCTGAT GATCTGAGGT    27180

TGGAGCAGTT TTAGTCCGGA AATCATTGCT CCCAGCCCCT GCACCCCTG GTCCGTGGTA    27240

TAATTGTCTT ACACAAAACG GTCTCTTGTG TCAAAAAGGT TGGAGACTAC TGGTTTTACA    27300

AAAAAGTAAA TTAGTCAAGC ATGGTTGGCA CGCTCCCTTA GTCCCTGCAC CCAGGCGTTT    27360

AAGGATACAG TGAGCTATGA TGGTGCTACC TCACTCCAGC CTGGGTGACA GCGAGTCAGA    27420

CGTTGTCTCA AAACTTAAAA AAAAAAAAAG TTAAAACAGA AAAGGGCTT CTTGTCAGAG    27480

ACTGCCGTAT ATCTAGAGGT CCAGGAACTA AAAAGTCTGA TGTCCAATCC TGAAAAGCTC    27540

GATGGTGCAC TAGAGGAGGC TTTTACATGT AAGAGCATCT AAGTTCTGGA AATGCCAGTG    27600

TCAGGGAAGG GAAGTGGAGA GCAATTTGGC ATCCAAACAT AACTTGCTGA TACTTTTTTT    27660

TTTTTTAACA CAAGTACTAC ATTCTAGTCT TTCTGTGGTG TCATTGTAAC TATTGTTTCT    27720

TAATATGCTA TCCACTGACT TCAAGGGATC AATAAATAGG AATCAAGGTG TCCCAGAATA    27780

TGGATTAGGG GAGTTTTTTT TTTGTTGTTG TTGTTGTTGT TTTCATCTAT TCATTATCCT    27840

GTAGCTGAAA TTTAGAATTT TCTTCCATTG TGTGTGACTG ATAGAAATAA CAAATTTGTA    27900

GGTTATAGTT GTTGCAAGAA TCTGGAAATC GTGCTTGCTT ATTTCCGAAG TACTATTAGG    27960

TATATCAACA AAAACACACA TATTACGGTC AAGTGGTTTG ATAATTATTT TAATATTATT    28020
```

```
GGTCTAATAC AATTGTAACC CTATGAATTA CTTTAAGTAT CTTATTTATG AAAAGAATCT    28080

GTAAGTTTCA TCAAACTACC AGAGCATACC GAAGACTGAA AAATTTTAAG AATCCAAACC    28140

TTAATGGAAA TGTTGGAGGC TGCCCAATTA GGTTCTGAAT TCCACCTTCC TGAATCACAA    28200

ACTTGTTTTA ACTCTCAGTC TGAGGTAAAC TACGTTTCTC TTTAAACAGA CATAGTTTAA    28260

TTTTCCTTTG ATTTTTGATT TAGTATTCTT ACTGATCATC ATAAATAACC AATGCTAATG    28320

TTAGTCTACT TTGGACCATG GTATTTCGAG AAACTTTGAA CAAAGTCCCC TGCAAAACTA    28380

TGCATTGCAT TATTTCACAT ACATTATGT TTTCCAGACG GTTCAATAGT ACCTCACTTT    28440

TCTGAACTTA TTTGTATAGT TTGGCATCTT TTTAAAAATT GTGTCCTATA ATGAAAGGTT    28500

GTAAACATTA TGTTTTAAAT TTGTATAGAT AAAATCAACC ACAGACCTTT CCTTGCTTGG    28560

ATGTAATTGC CATTGTTTCC CAATGAGTTC GGAATTACTA GGATTGTGCA AAAATATGCC    28620

TCACTTGCCT GACATAGCAG AGAGCCATTT TGCCTAAATG CTGTGCCCAG CAATGGACTG    28680

TCACCAGATT CTCATCACAT ACAGTGAGGA TGAACAACTA GCCTCTCCCA GCAGCTGGCC    28740

GGTCTCTCAA TAATATGGGA CTCCCTCAAG ATGGCTTCCT GCACCTTTGC TCCTCTAGCC    28800

TTGTATGTAT ACAAGGCTAG CATGCCTGGC ATACATAAGG TTAAAAACAA AATCAATAAG    28860

TTATGGTTCT TCCTCCAGTT CTGGGGATTA TTAGACCACT TTTTTGTTTT GTTTTGTTTT    28920

GGATGGAGCC TCGCTCTGTC ACCCAGGCTA GAGTGCAGTG GCACAATCTC GGTTCACTGC    28980

AACCTCTGCC TCCTGGGTTC AAGCAGTTCT CTGGCTCAGC CTCCCACGTA GCTGGGATTA    29040

CAGGTGCCCG CCACCACGCC CAGCTAATTT TTGTATTTTT AGTAGACGGG GTTTCACCAT    29100

CTTGGCCAGG CTGGTCTTGA ACGCCAGACC TCGTGATCCA CCCACCTTGG CCTACCAAAC    29160

TGCTGGGAAT ACAGGCGTGA GCCACCGCGC CCGGACTTAG ACCACTTTGT TTTGGCCAAT    29220

AGGACAACAG CCATAGAACC CTCCGCAAAT GAGAGCTTGT CCCTAAAGAT GCTTTATTTA    29280

CATAGCTGTG TGCCGCATGA GCCAAAAGGT GATAACCTTT GTTCAACACG CGCCTCCAGC    29340

CCTTCGGTTA AGTCCAAAGT ACCATTCTTA GAATGCTCTA AAATACATAA TTTTTTTTTT    29400

TTTTTTTTT TTTTTGAGGA GTCTCTCTCT GTCTCCCAGG CTGGAGGGGA GTGGCGCGAT    29460

CTCGGCTCAC TGCAATCTCT GCTTCCGGGC TAGCTGGGCC TACAGGTGCA GACCACCACG    29520

CCCGGCTAAG TTTTGTATTT TTTTTGGTAG AGGGGGTTTC ACCATTTTGG CCAGGCTGGT    29580

CTCGGATTCT TGATCTCAAG TGATACACTA GCTTTGGCCT CCCAAAGTGC TGGGATTACA    29640

GTCGTGAGCC ACTGCGCCCA GCAAAATGCT TTTTGTGGAG CCAATCACTT TATTAGCGCT    29700

TACCTCTCTA TGCCTACTTT ATGCTTTGAA ATTTTGTCAC AGTGGGGCCG GTCATGGCAA    29760

ACACAATTCA TTCTTATGCA GGCTGTCACG GTTATTTCTG TCATCCAAAC TCATTCTCGC    29820

AACGCATTTC AGCTCTTTAA ACGACTTTGT GAGCGGCCCT GAAAAGGGCC TTTGGGTTTT    29880

TTTGTTTTTG TTTTTTGAAG TTCTCAGGAG ACCGCGTATT CTTAGATTCA GCCGCCGAAG    29940

CCATACAGAG TGCGCCCCTG ACGTTTCAGG GCATATACTA CATCCATGGC TGTGACAGTT    30000

TTGCGCTTGG CGTGCTCCGT ATAGGTGACG GCGTCTCGAA TAACGTTCTC TAAGAAAACC    30060

TTAAGCACAC CTCGAGTCTC CTCATAGATA AGACCGGAAA TGCGCTTGAC GCCACCGCGC    30120

CGAGCCAAAC GGCGGATAGC CGGTTTTGTA ATGCCCTGGA TGTTATCCCG GAGCACCTTA    30180

CGATGGCGCT TAGCACCACC CTTCCCCAAG CCTTTTCCGC CTTTGCCGCG ACCAGACATG    30240

ATTCCTATCG CAGTGGAAGG TATGAACTGA AACAGTTCCT TAAATACAAA CTTGGCGGAC    30300

CTGATTGAAA ACAACATGAG TTGGCGCGGT TTTTTTTTTT TTTCAAATTT GGTCACCGAG    30360
```

```
TGGGTGGAGC AAGAAAAACT GTTTCATTAT GGTTCATTGT TTTGATTGGC CAGTGACAGC    30420

TTGCTCTTTG TGGGAGTGGA AGGGTGTTTG CAAGTTGAAT GCGCTGTATT CCTGTCAGCT    30480

TAATGACGCT AAGCATAGCC CCATTCCACA TTTCTTTTTA TTTCCACTTG CTAACTAATA    30540

AATTACGGAA TAGTTTATTG GGGAACATAC AAATAATGTT TAAAGGAGGT CAGATTTATA    30600

GGTCAAGGGA TTTACCCTCC CAATCATTTT AATATTTTTA TTTAAACCAG CATTTTGAT     30660

GGCCTTCTCT GTGCTGGACA AGGTATAAGT TTGGCTATGA AGTTTCACTC CTAAAGACCC    30720

TATGTTTTGG GAAGGCAAAA AGGTAGCCAA ATAATTGCAA ATTAAAACCT CATAAGTGCA    30780

AACTTCTTCC TCGTCACTTT CCCTATCTCG ATTCAAATAT TTGTTGAATG ACTCATTTTT    30840

CTGCAAAAGT CTGAGAGAGA CAGGGAATAT AAACTTAAGT CTGGATAATA TGTTTTCCCG    30900

GGACGCTCTT CCTGGTCTGC TGTGCCTGTT TGCTGTGCCT GAAATTCCAA ACACTCTTCC    30960

CTTCCCTCCG TTTTTAATCC CCTTTCAACT TGCTACAGCT TTAGAGAAAA GAACATACGT    31020

TTTGTACAGT TGGGGATTAA TTGAAGTGTA GGGCTAATAC TTGATTAAGG TCATTACAAA    31080

ATCTACAGGG TCTTCCTCTG GGAGGTTTTT GTGATAAGAT TATTGGTGTT AAAATAAGGC    31140

TAATCCCCTT GAAAAATAAA TAGAATAGCA GAATTGGGTC TGAATGTGGT TTGAAGAAAG    31200

GGACTTCTCA ATTCAAAATT TTATTCTTAG CTTCCTGTGG GAGCTTTCCA GAATGCCCAT    31260

AAGATCCACT TTTGTTTAAA AAACAAAAAC AACCCCACCC ACCACTCTCT GGTTAATAAA    31320

TGAATTTCTA TTGGGAATAT TTAGAATGGG GCTGTGGCCT GTGAGAGACA TTATATAGTA    31380

ACCTCAGACT TGCTCACATG AAGAGAAGAA ATCCAGGAAT GGAGAAAAAA GACCCAGGAA    31440

AGGCCAGAAT GCTCTACATG TCATATTGTT TGTATCACTT CTGAAATAAT TGATTACATT    31500

CTTCTGCCCC AAATTGAGTT CTTAGGTTCT TCCACTCACT GTCCACATGC CACAACACAG    31560

ACCTTATAAC TAGAGACTTA GCTAGGAAGA AATGTCAAAC ATTACAGAGA AAAAATGCAG    31620

AGTCTGAGAT CATAAGTAAA ACTCTGAAAT CTCAACATGC CTTTTAATTC ATGAAAATAA    31680

AAAATATAGC AGCATATGCA ATATGATAAT TCTCTGAAAA CATACATCAT GTGAACTACC    31740

CTGGAACACA TCTCGCCAAG TGCCATCTTC ATTTTAACCA GAGGTCTAGG ATGCCTTTCC    31800

TTTATTTTGC CTATTATATC ATTTATAAAA CCCCATTTTT ATTTTGATAT TTTATTTACT    31860

TTCTATTTCC TGCTCCTAAT ATCTCCTTTC TAAACTTTTC TCAATGACAG TGACTCAAAA    31920

ACAATGAATG TCAGAACAAA TATTTAAAGG ATCTGTACAT GTAGATATAT ATATTTAAAA    31980

TGGATTCTTC CACTCTGGGA AGAATTCAGG CATACTCAAT CTTATGGTTA GGGAGAGATT    32040

AGGCTCACTC GCCTAATCTG TATGGCTTCT CGTTCGCTTT CCATTTCACC TTCCTCTCAC    32100

CCATCAGATC AAACTCATTC ATTGAACAAG AGACCTAAGC CCTTCAGATT AAAACTCTGC    32160

AAACAAGTTG TGGTTGAGAG GATACATGAA GCATTCAAAC AAATAAATCT ATGATATTAA    32220

TCAGAGGTTA ATCTATGATA TTAATCAGAG GTTAATGCAG TGGCTCACGG CTGTAATCCC    32280

AGCACTTCAG GAGGCTGAGT TGGGAGAATC GCTTGAGCTC AGGAGTTCAA GACCATTTTG    32340

GGCAACATAG CAAGTCTTCA TCTCTACTTA AAAAAAAATA ACCAGAGGTG TTATGAAAAT    32400

ATAAATTGTC CAGAACTACC CTCCACAAAC TAACTCTCTC AGAATATTCG ATATGAGGAA    32460

TGAAATATGG TGTGTGTGTG TGTGTGTGTG TATGTGTGTG TGTGTGTGTG TGTATGCACC    32520

TATATATGGC ACCTATATAT TCAACAAACA ATTCTGATAA TTGGCCAGGG TTGAGAATGA    32580

CTAGCAGCCC AGCATACACT ATCAGTTTTA AGTATATAAT TGCGCTTTAG TAAAATGTAA    32640

AGAAATCCCA GAGTAGAAAT ACTTTTAAGC TATATTACAG GTGAGAAAAT GCATAAGTAT    32700

AGTCTCACCC AACTTAGACT ATGGGGGCTT TATAATGTCA CAACAGTTGT TTCCAGGCAT    32760
```

```
TTGGGGACAT CACCACTGGT CTTGGGCAAG AAACTCCTCT AGCCAATGGC TGATTTATCT    32820

CACTCCCATC TAAGGCTTCA CTGCATTTCT CTTTTTCAGC AACCTAACTT ATTTAAAAAT    32880

ATCCATTTTC TGATTCATTT TTTTCTGAAT TAAACTGTCA GTACCATTGG CACACCTTTG    32940

GTTCCGTAGC ATACCTGTGT CTCTGCTGTG GTTTTTTTTA CCTCCACTCC TTACTTTTCT    33000

AGAAAAAAAT CTCTGCTTTT TCTTTTCAGT TTAAATTATT TCACAAAAAG TTTTCTTGAC    33060

TTGCACTTCC TAGGCTTGCT GTCCTTGTGT GGGCACGCTC CCATAAACAC TATTAATACA    33120

CTTCGATTTG TTAAAAATAA AGATATCTGG ACAGAAAATT TCTTTTCTTT TTTTAAGATT    33180

TTAAAATTTT TAATGTTTAT TTTTTTCCTA GACTGGAGTA CAGTGGCACC ATGATGGCTC    33240

ATGGTAGCCT ACACTTCCCC GGGCTCAAGT GATCCTCCCA CCTCAGCCTC CAAGTAGCT    33300

GGGACTACAG GTGTGCACAA CCACACCTGA CTAATTTTGT TTATTTGTTT GTTTTGTTTT    33360

TTGAGATGGA GTTTCGCTCT TGTTGCCCAG GCTGGAGTGC AATGGCGGGA TCTCGGCTCA    33420

CCGCAACCTC TACCTCCCAG GTTCAAGCAA TTCTCCTGCC TCAGCCTCCC GAGTAGCTGG    33480

GATTACAGGC ATGCATCACC ACGCCCAGCT AATTTTGTAT TTTTAGTAGA GACGGGGTTT    33540

CTCCATGTTG AGGCTGGTCT GGAACTCCTG ACCTCAGGTG ATCTGCCCGC CTCGGCCTCC    33600

CAAAGTGCTG GGATTACAGG CGTGAGCCAC CACGCTCGGC CACTAATTTT GTATATTTTG    33660

TAGAGATGGG CTTTCCCTGT GTTGTCCAGG CTGGTCTTGA ATTCCTGGGC TTAAGTGATC    33720

TGCCCACCTT GTCCTCCCAA AATGCTAGGA TTACTGGCGT GAGCCACCAG GTCTGGCTGG    33780

AAAGATAATT TCTAACATTA TCCTCTCTTA AACATTTGTT TCAAAATTTT TACAAACATG    33840

AGAGTAATTA AATTTGATTT TCAAAATTCC CTTGAATACT TTCTTAATAG CACACAGAAA    33900

GCACAAAGTA TTTTACATTT GTTTTAATGA TGAAATTGTG AACCCAAACT TACACAAAGA    33960

AAAACCGTAA CATTATACCC ATACTTAAAA CAGATGCCCT CATATACATA GTAAAACTCT    34020

TGGGGGCAGT AGTGAAGTTG GTTATTTACT GTTTTATGAA AGTGCCATTC AGCCGGGTGC    34080

AGTGGCTCAT GACTGTAATC CCAGCACTTT GGGAGGTCGA GGCAGGCTGA TCACGAGGTC    34140

AGGAGTTCAA GACCAGCCTG ACCAAAATGA TGAAACCCTG TCTCTACTAA AAATACAAAC    34200

ATTAGCTGGG CGTGGTGGTG TGTGCCTGTA GTCCCAGCTA CTCAGGAGGC TGGGGCAGGA    34260

GAATCGCTTG AACCTGGGAG GCGGAGATTG CAGTGAGCCG AGATCGCACC ACCGCACTCC    34320

AGCCTGGGAG ACAGGGCGAG CTCCGTCTCG AAAAAAAAAA ACAAAAAAGT GCCGTCATAG    34380

TGACTTAGTT TTAAGGAATA AATCAAGGAT ATTTAACTCA ATAGACTACA GTTAGCTAAC    34440

GTGACTTGCA CTGAAAGTTA TACGAATATT GGTACTTATT CCCCTGCCCC TGAAGTATGA    34500

ATTAAAGACT CCAAAATTCT TTTTAGAATC TTCAGAGTAA AAGCTAGAAT TTGATTTTTT    34560

TAAATAATAA AAAAATACTT TGTATCTAAA TCTGGTGTAT AAAATAACTT GGTGGATGAT    34620

GCTTCAAGGC TATCCATCCC CAAATTTCTC CCTGAATGAT AAAGAGAATA AATGAATATG    34680

TCAATTCAAA AGTTAGAAAT TTGGCCGGGC ACGGTGGCTC ACTCCTGATA ATCCTTTCGG    34740

ACGCTGAGGT GGGTGGATCG CATGAGCTCC GGAGTTCAAG ACCAACCTGG CAACATAGC    34800

CAGAACCCGT TTCAATAAAT AATAGAAAAA AATGAGCCAG GCGTGGTGGT CCCAGCTACT    34860

CAGTAGGCTG AGGTGGGAGG ATCACTTGAG CTCAGGAGGT CGAGACTGCA GTGAGCCGTG    34920

ATCGCAGTAC TGCACACCAG CCTTGGTGTC AGACTGAGAC CCTGTCTCAA CAACAACAAA    34980

ACAAGTTAGA AATTTGGCTG GGCGCGGTAG CTCACGCCTG TAATCCCAGC ACTTTGGGAG    35040

GCCAAAAAGG GCGGATCATT TGAGGTCAGG AGTTCGAGAC CAGCCTGGCC AACATGGTGA    35100
```

```
AACTCCATCT CTACTAAAAA TACAAAAAAA CTTAGCCGTG CATGGTGGCA TGCGCCTGTA    35160

GTCTCAGCCA CTTGGGAGGC TGAGGCAGGA AAATTGCTTG AACCCAGGAG GCAGAGGTTG    35220

CAGTGAGCCG AGATCATGCC ACTGCATTCC AGCCTGGGTG ATAGAGTGAG ACTCCATCTC    35280

GAGAAAAAAA AAAAAATTCT GTATGAACTG AACAAAATAT CCTTAAATTT TAAAATACAT    35340

CTGAAAGATA TTTCAAAATA TTTAGGAAAA AAATTATAGG GATCAGGCAA ATTCTGAGAT    35400

TCCTTTTTCC CTGCAGCAAA CATTAGGAGT GCTGCTGTTC CTAAAAACAT GGTAACTGTT    35460

GCCACACCGT ATGTTTCCTT GGCTCAGACA TAAGGTTGTG TAGTTGTTAT TCCAGAATAG    35520

CTAGAATAAA AATCCAGCAC ATCATTTTCT TCAGCAAGTT AACTAACCTC TCTGTGCCTT    35580

GGTTTCATAA CAGCAACATA AGCATAACAG AATAGCAGCA ATAGCTCCTA CCTACCTCAT    35640

AAGATTCTTT GGAAGAATTA AATTAAGATT CAGAACACAG CCTAATATCT AGTAAGTAAT    35700

AATAATTGGC TAAAAAAATT TTCTTAAGAT TATATATATT CATGGGGTAC AAGTACAATT    35760

TTGCTACATT AATATATTGC ATTGTGGTGA ATCAGGGCC TTCAATCCAT CCCGGAAAAA    35820

AAAAGTTTTT GAAAGATTT CTGCCATGGA AAACTTTTAA TGTACAAATT CATCCATCCA    35880

AGAAATAGAA AATATATAAG TATCAACTCC AAATCCACCA TATCTATCTC TTCTGCACCT    35940

TAAACAATTA CTCAGAAATA GAATGCTTGA GATACCAGAA TGCATGCATA TCAAGTAATA    36000

AATGCATGCA GGATGTCAAC GCATCCTAGG CTTTCAAATA AAATTGTCAT ACAAAATACT    36060

TTAATATTGT AGTAACATTC TACATGTTAG AGTGTAGAAG TTAATCGCTG ATGCAAAAAA    36120

GGAAAAGAAC ACATTATACC CAAAGCCTAC AGAGAGAATC ACAATTACAA ATATCAGCCT    36180

GCATGTGAAA ATCTTTAATT TGAAAGTCAG AAATATTTAA ATGATAGTCA TTGTTAAATC    36240

AGATTGTGGT TTGAAAAAAA GTTAGTTTAA AACTGAGTTT ATGAAAAATT TGGGGATTTT    36300

AGAGACAGTG TTTTGTTTTT AAATGTGTGT GAGTTTGTGA AGAATGTTTT ATAAAATACT    36360

GACAGTATTA TAAGATGACA TTATTATAAT ACAACATAAG AATTTTGGCC TGTACCTCTC    36420

AGCAGTCCTC AATCACCTGC TGTACTTGAC TCAATGATTA TCAGAGTGGT TTGTTTTCCT    36480

TCTGTTGTGT TCCCAGTTCA GGCAGCTCAG CAATGGCCTG TGATTCCAGC AATTCAAATA    36540

GCTGGTAAGT AGTTTCTTGT TTGTTTTCTC AAATTTTCAG GGGCTTTTCT CTACAAGTGA    36600

TTTCCAGTGC ACGCCCCTCC ACCCATTCTT TATTCCTTTA CCTTCAGGAA AACCCTCAGC    36660

GCTGCATCTC TGGTCACCGG ACCACCGTGG TACATTTACC TATGCCACC AGGTGTCACC    36720

CTTCTCTTTA CTACCATGGT TTGTGAATGG TTTTGCCAGA GGTGAATAAG AATTTAAAAT    36780

GCAGGTCTTT GATTTTTCAA ATGTAGTTGA CCTTAAGAAT TTATGAATAA AGCCAGAAAA    36840

ATTAAGCTTA AAAACACCG AAAGAAAATG AGGACTAAA ATTTCTATTA AAAAAATTAA    36900

CAGGCCACAG TTGCTGATGT TTAGTAAATG TGTTAGTGAA ATGTGTTACT GTGAAGACTG    36960

GGGTGTTTCT TGAAATCTCA GCCCAGGTGA ATAAAACCA ATATAAAACA AATGCTTACC    37020

TAATAAATTA ATTGTAACAT ATTCCTTATG AGGTAGAAGA GTAAGTGAAG CCTTATAGCA    37080

GTCTGCTTTC AGTATAGTAA GATATTAAGA GAGAAATAAT TTGTCATATG CTTTCAGAAT    37140

GGTTTGCTGG TAAAATAACC AATGTCTTAC AACTTAGACG ACAATGTCCC TAGAGTGAAG    37200

AAACACGATT AATTCGGCTA CCACAGTTGA ATGAAAATAT TCCGTAAGAC AAAATGTAAA    37260

GAAATTAGAA GCAAAATAAA TGTCTCCAAA ATGACAAAGC GATTAAGTAT ATACACAAGA    37320

TGAACAAGAA CTTCAATAAA ATCATGCAGT ATACAATACA ATGTACATTT ATTAAAGTAT    37380

ATGCATTTTT AATGCAACAA TAATACTAAC AGGTAATAGA CAAGTTGTTA ATAGTTTTTC    37440

ACTGGCTAAT TAAATAACAG CTTTAATTGT ATTCATTTTA TAGCTTTTCT ACAATGAGCG    37500
```

```
TAAATCACAT TTACTTTTTT CTACATAACT TTTCTAACCA CAAAAAAAGA AAATGGTTTA    37560

AAAGAAGAGA TGAGATATCT TTGCTAAAAT TTAATGCCTA AAGAAGAAAC TTCTGAGCTG    37620

TATATGGTAT CCTGAAGCAC CTGCCCTTCA AGACAGAATG CTTGTACCAC ATTTATGCAG    37680

CCAAGTGCAT GTAGTAACAT AAAGTAAACA CATGCCATCT GGATATATAT ATTAAGACTC    37740

TTTTGACGGC TGGGCAGGGT GGCTCACACC TGTAATCTCA GCACTTTGGG AGGCCGAGGC    37800

AGGCGGATCA CGAGGTCAGG AGAGTTCGAG ACCAGCCTGG CCAACATGGT GAAACCCTGT    37860

CTCTACTAAA AATACAAAAA TTAGCCGGGC ATGGTGGTGC ACGCCTGTAA TCCCAGCTAC    37920

TTGGGAGGCT GAGACAGGAG AATCGCTTGA ACCTGGGAGG CAGAGGTTAC AGTGAGCCGA    37980

GATCATGCCA TTGCACTCCA GCCTGGGCAA TAGAGTCTCA AAAAAAAAAA AAAGACTCTT    38040

TTGAACATGG TGAACTGATT TCCCAGAATC TAGCAATTCC TGAATGTCCT GGTTAGATTT    38100

TTTTTTTAAT GTGCACCGGA ACCCCAGTGG CTCCATGGAA GGACCTGGGC ATCCTCTAAG    38160

CCACTTGGTG GCTTCCATTA TACCATCTCA AAATGAGAGA GCTTACTCCA CTTCATTGAG    38220

GGAAATACCA CCAGAGTTCT GACTCCAGAG GCACTGGCCT AGGGAGGACA CCGTGTGTGA    38280

AGCCCAGCAG GGCCACTAGC TGTCCCCACC AATTACAGTC CTTGCGTAGG GTCCAAAGAA    38340

ATGAATGCCA AAGAGAGCAA CAGAGGAGCA AGGGAGTCAC ATTCCAGGAC CTTCCTTCAG    38400

GGACTTTTAA AGGAAACATG ACAGCTGAGG ATCAGTTGGT TGTTTTCTGC TGTTCCCCTT    38460

CATGTGATTC AAGCTCATTC AGAAGAAACA CAATGAGACA AGAGAAGAGC CATCTCCTTC    38520

CTTCTCTATT TATTCTAGGC ATCTAAACTA CTGAATGTAG TGGTGTCTGA GATGTATCAA    38580

ACGGTCAGAT TGACTGAGTT TGAAACCTGT TTCTATCACT GACAAACTAT GAGATACTCT    38640

ATACTTCACT TTCTTTTTTT TTTCATTTTT TTATTTTTAT TTTTATTTTT TTGAGATGGA    38700

GTCTCACTCT GTCACCTAGG CTGGAGTGCA GTGGCGCAAA CTCGGCTCAC TGCAAGCTCT    38760

GCCTCCTGGG TTCATGCCAT TCTCCTGCCT CAGCCTTCCG AGTAGCTGGG ACTACAGGCG    38820

TCTGCCACCA CGCCCAGCTA ATTTTTTGTA TTTTTATTAG AGATGGGGTT TCACCATGTT    38880

AGCCAGGATG GTCTCGATCT CCTGACCTCG TGATCCACCC GCTTTGGCCT CCCAAAGTGC    38940

TGGGATTACA GGCGTGAGCC ACCGTGCCCG GCCTACTTCA CTTTCTTCAT TTAAAAAGA    39000

AATGGGGATA ATAGTACCTA TCTCATAGAA TTATTGTAAG AAGTGCATGC AGTAATGCAT    39060

GTAAGTAGGT GCTCAGAAGA GTCGGACACG AAGTAAGTGC TTTTATCATC CTTATCATAA    39120

TTTTCATTAT CAGAACAAGG AGAGACCAGG TAGAAAATTA TTGTGATTCT TCAGGTCTGG    39180

AATACTAGAG TAGCATCCCA AATGAAGGCA CCATTAAACT TTGCAAATCT GTATGACACC    39240

TTCATGCCAA TTAGAAAAAA CACCTCTTCA CAACCCCTTT CAAGATATTT GCCTCCTACC    39300

TGCTAAAAAC ACCCATCATA CTACCCACAG ATAGCCATGA TGCTTTTTCT GGGACAGGTG    39360

CCTCTTCCAT TCGTGCAGTG TACAGCCTTC ATAGCTGTGC AACTCACATC ACAATCAGAT    39420

GGAAGAATCC CCAAGGCTTG GTGACAGATG AGTTACTGGG TAACACAGAG AGAGGATTCA    39480

AAGGAAAAGT TGAACGGGTC CAGAAAATGC ATAGATACAT GTGTAAAAAT CTGGTAAGGT    39540

TATGACTAGC CACGTCCCAG GGTTCAAAGC TTTTCTCAGA TGTTAAAATG AATCATGTAA    39600

GTCCCCCAAA TTTAAGGAGT CCTCTTCCAA AAATAGGAAA TGAAATGACA TAGGTGTATG    39660

TCTCTGAGGT GACGGAGGAA ATGAAGGAAG CCTCTAGATG CAGCTTGAGG TTCATGAGAG    39720

ACAGTTCCAG GGGAGAGGTC ACAGCTAGGG ATCACCGGCA TGCAGGAACT CAGAAACCTA    39780

AATGGGAAA TCTTTTTGAG GAAATGAACA GAGAAGGCTA AAATCAAGGA GTTCGTCAGG    39840
```

```
CAATTTCTAT GTTTAGGTTC AACTCTCTCC TGAAACATGA AGAGCTCATA AATGCACTCC    39900

CTCTTTGAGT CTCTAGTTTT GTCTCCTTCC CACAGTGAGT CTGCAGGCTG CGTGTCACTC    39960

ACGTTCAGCT AAGACGTAGT GCCCCATGGC TCCTCCTGTG GAGACAAGAG ACCCAGGAAA    40020

GAGGCATCAC AAACCTAGGC ACCATCTTGC CTCTTCTCTC TTCCTTATTT TCCTCATTCA    40080

CCCATCTCAA TTTAGACCTG GGCACTATTG GATTTCAAGA ACCATTATCT CTCATCTGGA    40140

AATGCTTATT GGCTTTCTAA CTGGTCTCCT CACCTCTCAT CTAACTTCTT AACAACACAT    40200

TCACCATATA AGGGAGATCG TGGTCCTCCT TTCTTAGGAT CCTTCAATGA CACCCCAGTG    40260

ATCATAACCC AATATCCCAA AAGACCCTTG GACTCTGTAT GAGCTGGCTT CTTTCTGATT    40320

CTCTTTTCCC TACACCACAG ATGTTCAGGG GGTAGAAATG CATAATTGGT GAGTGATAGC    40380

TAAGCAAACT CAGGGTTAAG GTACAGTAAT TATTTCTAAT CTCCCAGTAT GCCTTATACT    40440

CTCCTACTTG GCATGGTTGC TCCGTCTGTG TAGACCTCCC ATCATCTTCA ACCTCACCTA    40500

ATGGAATCCA GCTTCTCCTT CAAGATCCAG AAGGCTATCT TGATCCCCAG CTGAATGTGA    40560

TCATTCTTTC CTTTGACACC CTAAGCATTT GCTTCCTGCC TGCTTTAGGA CCTCATGGGG    40620

TCTTCTTTAA CTACATTTAC TTGCTATCAA TTTCATTCCC TACCAGATTT GGGTTCTGAG    40680

AATAGCCACA GTGACTTCTC AACCTCAAAG CCCCTGTACT ACCTTAAACA GCTCTTGCAA    40740

AATAGTAGGT GCTCTGAAGA TGTTTGTTGA ATTAGAGACT TTCATTCTGG GGAGAACCAT    40800

TATTTTCTGT CTCCCAGGGA GCTGCTGGTG TCCCCAAAGA ATATAAATGA GAAAAATGCT    40860

TCCCATGGAT GCCAGATCCC CTCTGCCCCT CTTCCCACTG TGCCCTGGGG CAGAGGTACT    40920

AAGAGACTTC CCCCTTGTTC CTACTCACTT GAACCCTGCC TCTTCCTTAA TATTATGAAC    40980

AAAATTCCAA TGAACAAGAT GACGACAAAA ACAGCAATTC CACTGATGAC TCCAATGACT    41040

AGGGTGCCAG ACGGTGAGGG CTCTAAAACA GAAAAAGCAA GTTAAAGCCT TTGATTGCCA    41100

CCCTCAGCCC ACCCCCTAAC AAAGAGCAGA TCCTCATCTC ACTGCCATAA TTACCTCCTC    41160

AGGCACTCCT CTCAACCCCC AATAGATTTT CTCAGCTCCT GGCTCTCATC AGTCACATAC    41220

CCCAGATCAC AATGAGGGGC TGATCCAGGC CTGGGTGCTC CACCTGGTAC GTATATCTCT    41280

GCTCTTCCCC AGGGGGTACA GCCAAGGTTA TCCAGCCCTG GTAGGTCCCA TCCCCATTGG    41340

GCAATACGTC TTTAGGTTCG AACTCCTTGG CATCCATTGG CTGCTTATCC TTCAGCCACT    41400

TCATGGTGAT GTTCTGGGGG TAGTAGTTCA AGGCCCGACA CCGTAGAGTG GTCACTGAAG    41460

AGGTCACATG ATGTGTCACC TTCACCAAAG GAGGCACTTG ACAGGAAAGA GGAAGGATGA    41520

GGAGAGGGGA TCTGTTTACC CTTGCCAGGA AGACTGGAAC TTTCACTTCC TTCTATAGGT    41580

TGGAGGAAGG AAATACCCTT TTCAGAAAAA AACAAGCTAC AGGAGAGACA CCATTTTGTG    41640

TCCTAAGATT GGACTCTAAC ACAGTGTCAC TTGGAGAGCA GTCAGATCAG CTTGTTCTCC    41700

TCACATGTAA ATATACATAT CTGTTACCCA TGTTCTTTGT TCTGATAGAT AAAATTGCCC    41760

TTTATGTGCA TTGAAAATGA TTGAATACAG ATGGTCAGTT TCACCTGGGT CAACCTAGGA    41820

GGCATTGTTA TAAGAAGCGG ACTTGTAAGA TAGGTAGCTT CAGTGATTAT TGCTATGTTC    41880

TATGAAAGAA ACTTTTAACC TAAAGGATTC TTCTACTCTG ATAAGTGGCC TCACTTGATA    41940

TTTTGTCCTG GTATTCATAT GATAGCTGAG ATCTCTGAAT TCTCTTTTTT TTTTTTTTT    42000

TTTTTAAGAT GGAGTCTCAC TCTGCTGCCT AGGCTGGAGT GCAGTGGCGC GATCTTGGCT    42060

CAGTGCAACT TCCGCTTCCC AGGTTCAAGC GATGCTCCTG CCTCAGCCTT CCAATTAGCT    42120

GGGACTACAG GTGCGCATGA CTGTGACCAG CTAATTTTTG TATTTTTTTA GAGACGGGTT    42180

TCACCATGTT GGTCAGGCTG GTCTCAAACT CCTGACCTTG TGACCACCCG CCTCGGCCTC    42240
```

```
CCAAAGTGCT GGGATTACAG GGGTGAGCCA CCGTGCCCGG CCTTGACATT TCTGAATTTT   42300

TAACAGGTAT AAATATACAA AAGATTATTG GTTAAATAAA AAGCAAGGGC CATAGACACT   42360

TCCCTTTGAG CCATATGCAT GGAGAAAAGA AATTAAACCC ATGACTTGTG GCTGTCTCAT   42420

ACATCTCAAT TATAAGGTAG AGACTCTAGG ATTGAGAAAG TCCCTTCCCA GAATTTGGAG   42480

AGGCACACAG CCTCAGCCAC CTCTGAAACT CCAACCAGGG ATTCCGTGCC CTGCAACCTC   42540

CTCCACTCTG CCACTAGAGT ATAGGGGCAG AAGTGTGTTT CCACCATACC TTGTTGGTCC   42600

AAAACACCTC TCCCCAGCTC CAGCAACTGC TGCAGCTGTG CAGGGCAGTC CCTCTCCAGG   42660

TAGGCCCTGT TCTGCCTGGC CCGAATCTTG TGCCTTTCCC ACTCCAGCTT GGTGGGCCAG   42720

GCCCTGGGTT CTGCTGCTCT CCAATCCAGT GTGTCAGGGC AGAATTCAAG GTGGTCCTGC   42780

CCATCATACC CGTACTTCCA GTAGCCCTCG GTACTGTTGT CTTCTTGCAT TTCACAGCCC   42840

AGGATGACCT GCAGGGTGTG GGACTCTGGA AAAATCCCCA GCCTTGTTAA CTGCAACCAA   42900

AGGAATAGGT CCCTATTTCC ACCATCCCCA AGGACCAAAT GATCTCAGGA AGCAAATTCC   42960

TTCCCTCTTC CCTGCTCCCA CAAGACCTCA GACTTCCAGC TGTTTCCTTC AAGATGCATG   43020

AAAAGATGAA AAGCTCTGAC AACCTCAGGA AGGTGAGGCC CCCTCTCCAC ATACCCTTGC   43080

TGTGGTTGTG ATTTTCCATA ATAGTCCAGA AGTCAACAGT GAACATGTGA TCCCACCCTT   43140

TCAGACTCTG ACTCAGCTGC AGCCACATCT GGCTTGAAAT TCTACTGGAA ACCCATGGAG   43200

TTCGGGGCTC CACACGGCGA CTCTCATGAT CATAGAACAC GAACAGCTGG TCATCCACGT   43260

AGCCCAAAGC TTCAAACAAG GAAAGACCAA GGTCCTGCTC TGAGGCACCC ATGAAGAGGT   43320

AGTGCAGAGA GTGTGAACCT GGAGACAGAG CAACAGGCCT TAACCATGTG TAGTAGGAGG   43380

GGAGCAGGAT GTTGAGGCTC CACACACCTG CATCAACTCA TACCATCAGC TGTGTCTGGT   43440

CCTCATTTTG TGAAGGGTGA GTTGCAGTCC TGTCTTTCTT CCATATGACA GTCCTGGGTG   43500

CTCTTTCCTT GTGTGCTTTT CTCTGCCACA CGTGGCTGCC ACCCCCTCAC TGCCCCCAGA   43560

TCCTATTCCA ATACTCATGA TTAGACAGAC TCCACTAAAG CTGGTGGATT CTAGAAAATG   43620

TTAAGGTGTG TCTAGCCATG GTAGTTGAAC TCAGGAGTTG GTGCTCAGGG CAAATTAGAC   43680

CCAAATCCTG AGGAATAATT CCTTCAGTTT TTTTTTTTTT TTTTTTTTTT TTTTTTTTT   43740

GAGACAGAGT CTCACTCTAT CACCCAGGCT GGAGTGCAGT GGCACAATCT CAGCTCACTG   43800

CAACCTGCAC CTCCTGGGTT CAAGGGATTC TCCTACCTAA GCCTCCTGAA AACCTGGGAC   43860

TATAGGCGTG CGCCACCACA CCAGGCTAAT TTTTGTATTT TTAGTAGACA TGGGGTTTCA   43920

CCATGTTGGC CAAGCTTGTC TCAAACTCCT GACCTCAAAT GATCTACCTG CCTCAGCCAC   43980

CAAAGTGCTG GGATTACAGA AGTGAGCCAC CGTGCCCAGC CTTGGTCCTG AATTCTTACA   44040

CTGAACTGCC TATGTGGCCT CACCACTTGG AAGCCTGACT GGAATCTCAA ACTTAACATG   44100

TCCAAATGCA GATCCTTGAT TTACCCCAAA CTGCTCTTTC CTCTGCCTTC ACCATCTCAG   44160

AAATGGCATT GCCAATTACC CCACTGCTCA GGCCAATAAA ATTAAAATAA AGAACAAAGT   44220

CAACTTTAAC TCTTCTCTTT TTCAGGGGGT CAGGGGAGAC AGGGTCTTGC TCTGTCACCT   44280

AGGCTGAAGT ACAGTGGCAC AGTCATGGCT CACTGCAGCC TCAACTTCCT GGGCTCAAGC   44340

AATACCCTCC ACCTCAGCCT CCCGAGTAGC TAGGATCACA GGTGCATGCC ACCACACCCA   44400

GCTAATTTTT GTATTTTTTG TAGAGAAGGG GTTTTGCTGT GTTGCCCAGG CTGGTCTTGA   44460

ACTCCTGAGC TCAGGAATCT GCTCTCCTTG GCCTCCTCCT TGGCATGAGC TACTACACCC   44520

AGCCAATTCT TCTCTTTCTC TCACACAACA TAGAATCCTT CAGCAACTTC CTTCAGAATA   44580
```

```
TATTCAGGAG ACAATGGTTT GTCACTCCCT TTTCTGTTCC CACCCAGCCC ACTCCACTAC    44640
CTCTTGCCTG GACTGTGTAA CAGCTTCCTG GCTGGGCTCC CTGCTTTTAC TGTTGCTCCC    44700
TTCATTCTGC TTTCCACATA GCAGCCAGAG CAATCTTTTA AAAGCCTGTG ACAGATCACT    44760
GTTACTCCTT GGCTAGAATT CACACCACAG CCTACAGGCG CCTGCACAAC CTTGTTTGTG    44820
GCTCCTCTTC TGAGCCCATT ACCTACTTCT TGGCCTCTAC TCCCCAGCAC TACTTGTTTA    44880
TTTTTTTCAA CCCGAGCTTC TTAACCAGGA GTTTGTCTAC TAGGTGACAT GTGGCAAAGT    44940
TTAGAGACAT TTTTGGTTGT CAAGACTGGG GGAGTGCTCC TAGCACCTAG TGAGTAGGGA    45000
GGACAGGATA CTGCTAGACA TCCTACATGC AGATGGTAGT CCCCCTTCCC ACCCCCACGC    45060
CGCCCCCCCC CCCACACACA CACACATGAG TAGTGCTGAG AAAACCCGCT TTTTAATCCA    45120
ACTTGCCAGG CCCACTCAGT TTGCCTGGGA AATACTGCTC CCAGTCAATA TCATTCTTAT    45180
TTCCTTCATG TCTCTGCTCA AGTGTCAGCC CCAGAGTGAC TTGCCCTGAC TTCTCTGCTT    45240
CTCACAACAC CCATGATTTC CTGATGTTGT ATATCTTTCT GCTCATTTGC TTATTGTCAT    45300
CTCTCCCACT AGAATGCAAA ATATCAAAGG GTAAAGACTT GTTTCCCTGC TCTCTCCCTT    45360
GGGGCTTGAA CAGTGCAACA CATGGCTGGG ACTCATTTAC ACTTGTAAAC AATGAATATT    45420
TCTGCTCAAC ATGAAATTTT ATTATTCAAC CTCTAATGCA GTGTGATGTT TAAGAATCAT    45480
AGCTATGAAG TGGAGACATG AGCTCTGCCA CCAAAGCCCC GTGTACCATT GAATAAATTT    45540
GCCAGGAAGC AGGCCGTGCC ATGCCTCATT CTTGTCATGT GTAAAATGTG GATACACGTA    45600
GTACCAAAAC TCAAAGTGCT GTGCTGAGGC CGGCGTGTGA CCCACAGAAC ACTGTGCTAC    45660
ACTACAGGGC AAAATCACTG TCAACTAAGA TTAGAAGCAG CTGTAGTACT TGAAATAACA    45720
TCAGAAAACC AGATTATTTA TGTTCTTTGT AACCTGAAAA GAGTTATATA ATCTGAATTC    45780
CAGTTAACTT CTAGTAAAAT AAACGTATTA TTAGCTCCTA CCTCCCTATG CCTAGTGAAA    45840
ATCAAATAAG ATCAGATATG AATGTAACTT AGAAGTGAGT GCATTGCTTA CATGTTCATT    45900
ATCAGTACTT TGTAGAGAGG CCTCTTAATT ACACAGCACA TTGCAAATCA ATAAAGCCTA    45960
GCCGAAAAGA GAATTGTTCA GTTCAAACGT TCAAAACTAA CATATACTTA ATTTTCCAGG    46020
CAAAAGAACA ATTGCCAAGA GTGGGGAAAG GCCCGAGGTA GGCCTCTCTC AGGAGCCTCC    46080
CACCCTAGAG ACCTCCACCC CAGGTCTCAC CAAAAGTGGG TGGAATGGTG AAGAATTCAG    46140
ATCCCCAACG CCACTCTTTC GCGCCCCCAC CGCCCAACGC ATTCGTTCTG AGGTGGAAAC    46200
CCCGTGCGGA TCCTGCTGTG GGTTTGCTCA GCCTTCTCGG CAAGCACTCA GGGAAGAACT    46260
TCCTGTTTGG AGATGACTGG GGAAAAAACT GCACAGCTGA CATTGGAAAT AAACCCGAGT    46320
TCCAGGTTCA AGGAGCCCCA GGCTTAGCTC AGCTCAAGTG AGGAACTACG AGATTTATTT    46380
AAAAGCATTC TAGTTGGGGG AAGGGAGTGG GCGGTTCCAA AAGTCACTCC GCAGAGCCGG    46440
GACAGCCGGG GGAGGGGGCA GGTCCTGGGG CGAGGGACCC CTATCTGCAG TTCAGTGGTA    46500
GGCACTCCCT CACGGGGTCT GGACGCAGAA AGTAGGGAGA GGGGCTTGCG GATTGGGTTG    46560
AGCAGGTCCT CCAAAGTTAG CAAACTCCCA AGCGCAAAGA AAAAGCTAGT TTCGATTTTT    46620
CCACCCCCGC CGCGCCCCTA GTTCGCCCGC AGCCCTCGGA CTCACGCAGC AAGCGCCCCT    46680
GCAGGACCGC GGTCTGCAAA AGCATCAGGA GGAGAAGCGC CGGCCTGGCT CGCGGGCCCA    46740
TTTCCCCAGC TCTGGCCGCA CGTCCCCGTT AAATCTCCGC TTCTTTTGGG GGGCGGGAA    46800
ACGGGGATGG CTCCAGAAGT CACCCTACAG CTATTGCCTA GGCTCAGGAG ATGCCCAGTA    46860
AAACTTCCTG GTGAAAAGCA ACAGGTCTTT CAGAACTTTA GTTCTCTCTC TCCTACAGCA    46920
GAAGGTACCT GCTTGTGAAA CACTAGGTGA TCCAGTGTCC CCCTTGGTTT TTAAATCCTG    46980
```

```
AAGGGGTGTT GTTGATTGGG GAAAGTAGCT TCGCAATGTT CTGATCTGAA CTTTAGATAT   47040

TTAAATATTT ATGATTTTCA AAATTCAATC ATACATTTAA AAATTTTATC TCAACCTTAG   47100

ACCAACTTAT GTCTTATTTG ACTTAGAAAT ATAAAGCTTT TTCATTTTGT TTTTTGATTC   47160

AAATTAATTA AGTCATAACA TTAACCAATT AGATCCTACT GAAACACGTT CCACAGCCTT   47220

CATAATTGAA TTATCTGACA AGTGTTTCAC AAACTTTACA GTATTGGGAT TATCTGGAGA   47280

ATGATTAAAC ATATTGAGGC CTGCTCCTAA CCCCAGACAC ACTGATTTAA TGGGTAATTG   47340

TTAGGTAGTT AGACATTAGC AGTTGGGAGG GGATGACAGA AGAGAGCGGA AAGGCTGTCA   47400

CTAAGACAGC CACTGGCCCA CCTAAATTCA GGCCCAAGAC TACCCTAATG CCACCCTAAG   47460

GGATGGAGTT TATGATAAAG TCTGTGGCCA AAATATCCTG GAGAAAGAGA AAGGAGGGTA   47520

CAGGTGGAAA TTCCCTAAGG TGGCACATGC CCAACAACAC AAAAGCCTGT CTTCAAGTTC   47580

ACCCCAAGTT CATCATGCCA TCATTATAAT AGAATTTACA TACAGTTTTG CCCCCCCATC   47640

CCTGGGAGGC TTTTCTTAAC AAATTATAGG TAAGACCATG CACAGTTTAA TTTTAGATTG   47700

TATAGCTATA AACTTCAATC AAATAACATC ATCCTGTCAC TCAGATACAG CCCAAACCTC   47760

AACTCCTCCC CACAAACCCC ATAAAAGCAC CTTGAGCTCT GTAAAGAAGT GCTGAGTTCA   47820

CTTCGCAGAA ATAAGCCCGC TGTCCCTCAG AGTGTATTAT TGTGCTTCAA TAAACTTTGC   47880

TTTAAGCTTG CATTTTGGTG TTAGTTTGTA GTTCTTTGCT CACTATCACA AGAACTGAGA   47940

TTGCTGCTTC AGAGCTCCGG CTATAATAAT CTCCTCGGTT AAAGGATCCA TCCCAATGCA   48000

TAATTCCCAG TAACAGTATG GGATGCCACC TGGGCAATGG GATTTTAAAA GCTTTCCTTC   48060

TCCCTCAACG AAGTTTGGGA ATTATTGCCT TAGACATTTC AAACAATATT AATAAATTTA   48120

ATACACCTGA TTTGCTCCAA ACCTTTACAT ATCTAGCAAA TTCAACAGGC ATTATTTTTG   48180

TAAGCATGTA TGCAAATTTT GGCAATTCAA GAAAATCAAA CAGGATATCA GGGCCTCGAC   48240

TGTAGGCAAA CAGATACAAT AACATTGGAA ACATGTAGAA TATTGATGAT GGGCACATTG   48300

GGGCTGATAG TACTATTCCT TTTTTTCAAT TTTTGGTAAG ATATAATTAG CATACCATAT   48360

AATTCATCTA TGTAAAATGC AAAAATTGGC CCAGCTCAGT GGCTCACGCT TGTAATCCCA   48420

GCACTTTGGG CGGCCGAGGA AGGCAGATCA CCTGAGATCA GGGGTTCGAG ACCAGCCTGG   48480

CCAACATGGT GAAACCCCGT CTTTACTAAA AATACAAAAA TTAGCCGGGC GTGATAGCAG   48540

GCAACTGTAA TCCCAGCTAC ATTAGAGGCT GAGGCAGGAG AATCGCTTGA ACCCGGGAGG   48600

CGGAGGTTGC AGTGAGCTAA GATCGTGCCA TCGCACTCCA GCATGGGAGA CAAGAGCAAG   48660

ACTTCATCTC AAAAAAAAAA AATTAGCTGG GTGTGGTGGC ATGCACCTGT AATTCCAGCT   48720

ACTCGGGAAG CTGAGACAGG AGAATCGCTT GAACCTGGGA GGCGGAGGTT GTGGTGAGCC   48780

GAGATCATGC CATTGCACTC CAGCCTGGGC AACAAGAGCG AAACTCCGTC TCAAAATAA   48840

AATAAATAAA ATAAAATGCA AAAATTAATG GATTTTAGTA TATTTACAGA GATGTGCAAC   48900

CATTACCAAA ATTTTACATT TCTATCTCCC CAAAAAGAAA CCATGTTCCC CTAATTCAGT   48960

ACCCTTAATT CATCGCCTCC CAGATTCCTC CATTCTCCTC CTCCTCCCCT CCCAGCCCTA   49020

GACAATCTTT AATCTACTTT CTTTCTATTT GGAACATTTA GTATACATAG AGGCATATAA   49080

TATATTGCTT TGCCGTGACT GGCTTCTTTC ATTTAGCATA ATGTTTTTAT GTATGTTTTT   49140

CATGGACCAA TAATATCTAT TATAAGGACA TACCACAACA TATTTTATTT ATTCATTCAT   49200

CAGCCGATGG ACATTGGTTT GTTTCTACTT TATGGCTATT GGGAATAGTG CTGTTATAAA   49260

CATTTATGTA CAAGTTTTTT TGTAGACTTA TGTTTTGATT TCTTTTGGTT ATATATCTAG   49320
```

-continued

```
AAGTGGGTTT GCTGGGTCAT ATGGTAACAC TGTTTAACCT TTTGAGGAAT TGCCACATTC    49380

TTTTCCAAAG TAAGCATTTT ATCCTCCTAT CAGCAGTGTA TGAGAGTTCT GATTTCTCTC    49440

CATCTTTGCC TGGGTTTTTG AATCAGGGCC CCAGATAGAA CAAAAATGTG GTTATTCAGT    49500

TGTTCCACCA TCACTTGTTG AGAAGACTCT TTTTTCATTG AAGTGTTTTG GCACCCTTAT    49560

CAAAAATCAA TCTACCATAA ATGTGAGAGT TTATTTCTGG AGTCTCAATT TTATCCCATT    49620

ATGCTATAAT CTATAATCCT ATCTTTTTTT TTTTTTGACA GAGCCTCACT CTATTGCCCA    49680

GGTTGGAGTG CAGTGGCCCA ATCCCGGCCA CTGGCTCCTC CTCCCAGGTT CAAGCAATTC    49740

TCCTGCCTCA GCCTCCCAAG CAGCTGGGAT TACAGGTACC TGCCACCATG CCTGGTTAAT    49800

TTTTGTATTT TTAGTAGAGA CGGGGTTTCA CCATGTTGGT CAGGCTGGTC TGGAACTCCT    49860

GACCTCAGGT GATCTGCCCA CCTCAGCCTC CCAAAGTGCT GGGATTACAG GCATGAGCCA    49920

CCACACCCAG ACTATAATCC TATCTTTATG TCAGGACTAC ACTGTCTTGA TTACTATAGC    49980

TTTTTAGTAA ATTGAATTCA AGAAGTTTCT CAACTTCAAA TTTGATCTTT TTTTGGAAGA    50040

CTATATTAGC TATTCTCAGT CTGCTGAATT TCCCTAGGAA TTTTAGGATC TATTATCAAT    50100

GTCTATTCTA TTTTTGTATA TGTTTTAATA TTTTCATAAG AAACTTTTTT CATTTAAACT    50160

TTTTTTTTTA AGAAAAATAG TGAAAATCAG AATACTGGGG GTCAGGCGCA TTTAACAGGC    50220

AGAAGAAGAA TAAAAACTTG TCATATAAAC AAAAAGAAA TGACCAATCA CATTGTGGAA     50280

GCCATGGAGT GGTTATAGGT GCCAAAGGCT GCAGAGAAAT GGTGTCAGAT ATACCTGAAA    50340

ATTGTCCATT GTATTTGGCC ATTAAGAGAC TTAGAAGACT TAAGCCATAG ATTGCTCAGT    50400

GAGACCCCGA GGGCAAATGG TCTGAAGGTG AATAGATCAT TTCACCTTTA AGAGAGCAGG    50460

TAGGAAGCTA TAAATCCAAG ATTAAAAAGT TGACTGAACT GTTAAAGAAG AAACTCTAAT    50520

CTTGAGCCAC CCTATCCTTG CTCCACCTTC TGCTGCAAGC AAACAGAAAT GCTGAAATTC    50580

AACACTCACA AAGGCTGGTA AGCTGGAAAT GACAAAAATT ACTCCTGGGA AAGTCAGATT    50640

TAGAATTAGG CCATATTTGT TGGGGTTCAG ATTTTCATGT ACACTTGGGA AAGGGTTTAG    50700

CTTATAGGCA CATGCATGAA GGGAACTGGT ATAGGGCTGT GTTCATAAGG TCAAGAGTTG    50760

AAGGCCAGGC ATGGAGGCTC TTGCCTGTAA TCCCAGCACT TTGGGAGGCC GAGGCAGGAG    50820

GATGGCTTGA GCCCAGGAAT TCAAGACCAG CCTGGGAAAC ATAGGGAGAT GCTGTCTTCA    50880

CAAAACAATT AAAAAATAAA ATTAGTCAGG TGTGGTGGCA CACACTTGTG GTCCCAGCCA    50940

CTCAGGAGGT TGGGAAGATC ACTTAAGCCT GGGACATTGA GGCTGTAGTC AGCCATGATA    51000

GTGCTACTGC ACACCAGTCT AGGTGACAGA ATGAGACCCT GTCTCCAAAA AAAGAGCTGT    51060

ATCCACATCC CAGGAAAGTG GTTGAAGATC TACTTTTCTC TGTAAACCTA ATAAAGAATA    51120

GAGTGACAAA TGTGTGTTGT GGAAAGAAAT GGGGTGAGAG CTACGTAGAT GCAAACAAT     51180

ACATCCCCAC ATACCACTTG TTAATCATCC TTTTCCACCC ACTTATGGGA TGAATTGCAT    51240

CTCCCCAAAA GATACTCTGT CCTAACCCTC AGTACCTGTG AACCTGACCT TATCTGGAAT    51300

ACGGTGAGTT CACTGGTTAA GAAGAGATTA TAGTGGAATA GGGTGAGTCC TCCAACCAAT    51360

GACTGGGGTC CTCACAGACA CAGAGGGATG ATGGCCAGGT AGAGATGGAG GCAGAGATTG    51420

GAGTTATGCT GCCACAAACC AAACACAGGA AGCTGCTAGA AGTGGAAACA GGCAAGAAAG    51480

AATCCTTCCC CAGAGGCTAC AGAGGGATCT TGGCCCTGAT AATACCTTGA CTCAACTGG    51540

CCTACGTAAC TGTGAGAGAA TAAATTTCTT TTGTTCTAAG CCACCCAGTT GATAGTACTT    51600

TGTTACGGCA GCCCTAAGGA ACTTGATATA CATTTCTTTT ACTGTCATAG AAGTTTTGAA    51660

TCTTTTAAGT AGGTCTGTAC CCTTCCTCCC AGTGTCAACG CATGGAATTC CTCTCCTTGT    51720
```

```
GCCTTGAAAA GTGAAAGGTG TTTGAACTGG TAATGAAAGA AATCTCAGCA TGAGGCCAGA    51780

TGCTGTACCT CACACCTGTA ATCTCAGCAC TTCGGGAGGA TGAGGCGGGC AGATCACTTG    51840

AGGTCAGGAG TTCTAGACTA CTCTGGCCAA CATGGTGAAA CCCCATCTCT ACTAAAAACA    51900

AAAAATGTTA TCCTAGCCGG GCATGGTGCC TGTAGTCCCA GCTACTCAGG AGGCTGAGGC    51960

AGGAGAATTG CTTGAACCCG GGAGGTGGAG GTTGCAGTGA ACTGAGATCA CGCCACTGCA    52020

CTCTAGCCTT GGTGAGAGAG CAAGACTTGG TCTTAAAAAA GAGAAAAGAA AAATGAAATT    52080

TCAGCATTAT AGAATAAAAA TGTTTCCCCT TCCCCCCAAA CTTTAAAAAA GCAGAAGTCT    52140

GCATCATAAA ATGGTCTTTG CCAATGTTAT TTTTATTATA ACAAAGGAAT CTTGCAAGGC    52200

TACCAGATCT CAGCAATTGT CACTATGTTC TGTAAAAATC ACTTCCTAAA ATGTCTGAAT    52260

TGACTGCTTG TCTCATTTAT TTGTTTCTCG TGTCATACTG CAATGGATAT CTGTCTTGTT    52320

AGTATAAATA TTTGTGCATT TTGTTGTTGT TAAAACAGCT TTTTTGGCCT GTCTTCTTCC    52380

ACCTATGAGG TAATATAAAA CTCATGTTTA ACACTTATTT TGTAGGAGG  ACAAGCTACA    52440

GACAAAACCC CTCAGACACT GAGTTAAAGA AGGAAGGGCT TTATTCAGCT GGGAGCTTTG    52500

GCAAGACTCA CATCTCCAAA AACCGAGCTC CCTGAGTGAG CAATTCCTGT CCCTTTTAAG    52560

GGCTTGCAAC TCTAAGGGGG TCTGTGTGAG AGGGTCATGA TCGACTGAGC AAGTGGGGGT    52620

ATGTGACTGG CAGCTGCATG CACCAGTAAT CAGAACAGAA CAGGGATTTT CACAGTGTTT    52680

TTCCATACAA TGTCTGGAAT CTATAGATAA CATAACCGGT TAGGTCGGGG GTCAATCTTT    52740

AACCAGACCC AGGGTGCAAC ACCAGGCTGT CTGCCTGTGG ATTTCATTTC TGCCTTTTAG    52800

CTTTTACTTT TTCTTTCTTT GGAGGCAAAA ATTGGGCATA AGACAATATG AGGGGTGGTC    52860

GCCTCACTTA TTCACCCCCT TTGAGAATCT CACTCATTAG TGGGAGTTCT CACTTTTATT    52920

CTCACTACCT ATGTCTTCTT GAAAGACAGA TTGATAATGA TTCATATAGT ACACTTGTGC    52980

TGAAGCATTT TGGTGAGCTA AGGTAGTGAT GAAGCTTTTT ATCATTTGGA GAAGTACAGG    53040

TAGCAAACAA GGAAGCAGTA AGCAGGTTTC TATTAATATT ATAACTCCTA TTATAAGAGT    53100

TTTAAATCTT CTTAGCACTC GGAACCATTT TTCAAACATG GCCCCAGAAA CAAATCCATA    53160

CCACACCTAC ATGGGCACAT GTGCCACTTT TGTCATATTT CTAACTATGT CTTCAACTAC    53220

TTGCCCTTAA TCATCTATGT GTAGACAGCA ATTAGTAAGG TTAAATTTCC TACAGACCCC    53280

TCCTTCAGTT GCTAGCAAGT AGTCGAGAGC CAATCCATTT TGATAGATAG CATTTTGCAT    53340

CTGAGTTTCT TGCCAGGCCA CAGTAGTCAG GGCTCTGCTG GTCTTATTAG TAATTATTTC    53400

TAAGACAGCT TGTAACCGTA TGATTCAGTT GAGCATGTAA ATGGGGTCC  CATATCCCCA    53460

CAAGCCGTCT TGTGCCCAAG TAGCAGGCCC ATAATATTGT ATGATTCTCT CAGGGGGCCA    53520

TTCATTATTT TTCCAATTTT CTATAGCTAT GCTTTTTTTT TTTTTTTTT  TTTTTTTTT    53580

TTGCGGGAAG CATATACAGG GAAGCCCAGG AGTTTGCCTG TCTTTATGGG CAGTAGGAAG    53640

AAAGATGGTT TAATAGTGTC AATAACACAA CTACCTGCCC ACTGGTCAGG TAATTTGGCA    53700

TAAGCTGTAT GCCCACATAT CCAGTATAAT CCAGTGGGGG CTGTCCAGTC CCGGTGGGAC    53760

TCTGGGTGGG TCCACACAGT TTGCAACTTT GGGAATTTAC TAAATAGATT TTTCTTAGTG    53820

TGGTTTGAAC TCCACTAGGT GGCTGTTTTT ATAGTACTAT TATACAGTTT TGCCCAAGG    53880

CAGCTGAGTC TTCCCACAGG AAGGGTGAAG TCCTTCCCCA CTTTTGCTAT ACAGTATTGT    53940

CTAATGATTG AGGCTTTTAG GACCCAGAAG TTATCAGGGT GAGTCTTTTG AGCTGGGAAT    54000

TTATCAGGAA CTGGGTCTGT AGGTACTAAT TCTCGTGCTT CCCATGGCCA TTGATCTCCC    54060
```

```
ATTACAGTTC CTCCACATAC ATACATAACA TGAAGTGACA TTGAGAGACT GGGCTACATG    54120

CTCAGCTAAT TGCAAAAACA AATTTCTTGT TTTTCCTGGA ATTTCTAGTA CTGGCACATT    54180

CAGTTCATCA TAAGAAGGTT TGAAATACTG GCTCAGGGGA GCATTTATAA ACTTCTCCTC    54240

AAACCACCAT ATTTACTCAA GGATCCAGTC CAGCCCCAAC TATTTCTAAG GTTACACGAT    54300

CCCCTTTTTT CCAGTGAGAA TCAAGGGGGT TGGTTATTAC TAGTTCTAAG GGGTTACACT    54360

GACCACTGGT ACAGGAAGGG CCACTTTTCC CTTTCTGAAG GTGGACAGGA TTCTTTTTAT    54420

TTTTTAACCA AGTTGCCTAA ATGACACAAG ACCAGTATCT ACATTTATTT CCACGCAGTC    54480

TTAATTCATG ACAAGCGTAC TTATTTTCTG CCATATAGCC TCTTTCCTAA TGAACAGAAC    54540

CACATCCTAT TTCTAACTTA TTACTATTAA TGACAGCACA GGCATCAAAT TTCAAGGTGA    54600

CTTGTTTGGG CATTCCTTTT TCTTCTGTTT TGGCTAACAC TTTACTCGTA TCGTTTATGA    54660

ACCCCCACCA GTCCTCAGTC CTCAATCTTA TTTCAAAAAC TGTGGTCGTG GGAGGCTCAG    54720

ATGGGTCATA ACACACATCA GGTTGGTCAT TTCTTGGGCT ACCTGCCTTG TATAGAATAG    54780

CATTATACAA ACAAGTTATT TTTAGAGTCT TTGTACACTT ATAATAACCA TAAAATAATA    54840

AGACTGTAGC AACTTTTTGT CCTACCTCAG TGACTTGATG TATACACTGG AACAGCCCT     54900

CAGTCTGAGG AAGGTTAGTT GAAGTCTTTA CTGTGCAAGT CCAAATTTTA AGGAAAATGA    54960

GTCCCTTGAT GAGTTTTCTC ATGTTTCGGC CATGCATGGA CCAGTCAGCT TCCGGGTGTG    55020

ACTGGAGCAG GGCTTGTTGT CTTCTTCAGT CACTTTGCAG GCGTTGGCGA AGCTGCCACG    55080

TACAGCTCAC AGTCTACTGA TGTTCAAGGA TGGTCTTGGA AGTTGGGCCC ACTAGAATTA    55140

ACTGAGTCCA ATACCTCTAC TCAGTCACTT TCAACTGGGC TTTCTGATAC CAGGAGCAAG    55200

GTGGCAGGTT TTAGGGTGTT GCAAATTTCA ATGGTTATGC AGGGATTTTC ACATAGCAAA    55260

CTTTGGTACT TGGTTAATCT AGCATTTGTT AGCCAATGAT GTATTTATTA AAGTCACCAC    55320

AGCATGGAGG GCCTTTAAGT TTAGGTTTTG TCCAAGAGTT AGCTTATCTG CCTCTTGTGC    55380

TAGCAGGGCT GTTGCTGCCA AGGCTCTTAA GCATGGAGGC CAACCCTTAG AAACTCCATC    55440

TAGTTGTTTG GAGGCCCAGC CTCGGCCAGG GCCCCACAGT CTGGGTCAAA ACTCCAACCG    55500

CCATTTTTTC TCTTTCTGAC ACATAGAGTG TAAAGGGTTT TGTCAGGTCA GGTAGCCCCA    55560

GGGCTGGGGC CGACATGAGT TTTTCTTTTA ACTCATGAAA AACTCATTGC TGTTGGTTGT    55620

AATAGATGTA GTTTATCCAA TCTACATTTT TATTAACTGT CACCCACCAA AATATTGACT    55680

CAAATCCTGC AGCTATTTGA TTTTGGGATT TAAATTGATC TGCTATTCCC TGTGGGACTC    55740

CAATTGCATC TAAATAGATG TGAGAGTTGA AAGACACATA AGGGTCTTCT CTTGCTTTAC    55800

GATGTCTTAT TTTTCCTCCC TCTGGTTGAT GAAATGCTAG GGTGAAAGGG ATAGCCAACT    55860

GGACTAAAGT ACAAGTGCCG CTCCAGTTAT TTGGCAGAGT GCCCAGTAAA GGTCCACCAC    55920

AATACCACCA CACATCCGCT TGGGGATGAA CAAAGGCTGA CTGATTGAGA AGCTCCTGAA    55980

AATTCTTAAG CTCACTGCAT CCCTTCAGGT CTCCAAGGAA TGCTAAGTTT CCTCCCTGTC    56040

ATGAGAGACA AGAAGTGAAC TTAGTTTTGG GAGATGGAAG CTGGATGGCC CTCAGGGGTT    56100

GACCTGCAGG GTGCTGGACT TTGGGATATA GCAGAGAGAG CTTGGCACGA CTTATTACTC    56160

CAGGCTGTAG CATCCTGGAA AACAGTTACC ATGCAGCCCA TGCCTGGTCA ACAGGAGGAC    56220

CACCTTAGTG GAAAGGGGAT AATCTGGCCC TCTGGCCTGC CATGTGCACA AGCATAACAA    56280

TTGGTTTTGT TTAATGTGTG GACAGAATAT TTGATCCATT CCAACTGGGC ATTTGCATCT    56340

TGGTATCCTG CTTAATTATC AAAGTTTGTT TTAAGTCTTT AACTTCTATG ACCCTCTAGT    56400

AAAATGAATG TATGATTTTA GGAAATTACA AAAACCGGTT GGGGCAGTCC ATCCTCGCTC    56460
```

```
TTTAGTGGTC CACACAACAT TCGACCAACT ATGGCATAAA AGCTCTACAT CAGGGGGCAA   56520

GACTCCTCGT TGACACTGGG GTCTTTATTG AAATCTCTCT GGATTAAATG GTCTCAGTTT   56580

ACTAAGGCTC AGTCTGAGGA GAGTCAGGAG GGACAGAGGT ACTTTTCTGA AGTACAGAGA   56640

TGTCTTCGAC TTGGCAAGTC CCCACAGGGT ATAACAAGGC AAGCATTAAA TTCAATAGTT   56700

TGAGGCAAAA TTGACTTGGT TATGTTAATA ACTAGATGGT CAGAAATAGA GTGAGGGAAG   56760

AAGAAAGAGT AATAGAATAG ATGAAGGAGT TAAATTTTTC TTAGCTTTAG TTTGGTAGGG   56820

TTTTCCCCTG GGACTATGGC CCATGACTCT GGAGGGGGTG GCACTTTCTT GACTCGGGTG   56880

TGATGAGTCC ATCCCTTTTT CACCGTATGA ACAACAGTCT CGGTGGTTAG CAGCACAAGG   56940

TAGGGTCCTT CCTAGGCTGG CTCAAGTTTT CCTTCTTTCC ACCCTTTGAT GAGAACATGA   57000

TCTTCAGGCT GGTGCTGGTT TACAGAAAAT TCTAGGGGTG GTACATGTGC TAAAAGACTT   57060

TTAGTTTTGA GGGAAAGGAA AGTGGAAGAT AAACCAAGTA TATAACTTTT AAGAAGTTGA   57120

CCTTTTGTTT TAAATGTGGG GACATCAGCA GTGGACTTTA TAGTCCTTGG TGCCTTCTTA   57180

CTGAGAAATT TCCTTTAGCA CCTATTTTTA TTAGTTTTTA GACCAAAGAA AGTCAAATGC   57240

CATTTTATAT TTGACAACGC TTCTTGTATG TTTATACCAG ATAAGCTAGA TTTCACCTTT   57300

ATATTGGTGT GTTATTAATG TTAAACTTAG TTTTAATAAA ACTCTGTAGA CATATTTATT   57360

TGATTTTTAA TGTCTGACCA TAAGGTAAGA TTTTTATAGA CTTTTCTTTA ACCTTTTATA   57420

ATTTTTGTTA AAGAACAGGT TAGTGCTTTA AGAAAACCC GTTGTGTTTT TATTTTAATG    57480

TTCAGTTCAC AGAAAAACTG TATGATACCC CTTAACTTTA GCCAATATGT TTAGACACAG   57540

AATTTTCTTT ACAATTAAGG TTTCAAAACT TGCTTAAACC TTCAAAACAA TTTTTGTAAC   57600

CTTTTAATGT AGGTAAAAAT CCACATTCTT ATGCATCCTC ATAATCCTTT TACCAAAGGT   57660

ATATTTACT TTCCTTACAT ACCTTGCACA TAAACTGTTT ATTCAATAGT TTTACATTTA    57720

GAAGGAGGCC TAATTACTTT TAAATTATAC AACATTTCTT GCATAAATTT ATTTTTCTAA   57780

CACACATTTT TTTCATGACT TTCACAGACA ATTCTTCGAC ATGCCTCAAC TTTCTGACTT   57840

ATTGCAAACA TCCCTTTCTT TAAACAACTA GTTAATTTAT CTCAGGACAA GGATTTTCCA   57900

TACAACATTC TTTTTTATAT AAATTCTGCC TCCTCTTTAT TTCCTTTTTT TTTTTCCGAG   57960

GATGATAACC ATTCTTTTCC AAAGCGAACT TCTTTTATGT CTGTGGACTA GACTGTCTAA   58020

GGCCACAAGA TTAGAAGTTA CTATAATACA TGTTACACTG TTAACTTTTA GCAAACTTTA   58080

CTTTTGTTGA AAACCTTGTA AGTTTGGGAT TTCAATTATC CTTTGCTATT AATAAGACCT   58140

TATTTAGTCC AAATTAACTT AGAATTGGTA TAGATGGCTT TTTTTTTTTT TTTAATTACC   58200

TGGGAGGAAC CATCTATCCT CCTGTCCTGA AGGGAGTTCC TCCTAGGTCT GGTCAGAGCT   58260

TTGTATGGTA ATTAAGATTT AGATCCCCTG TTAGGAAACC TGCCGGGTTA AGAGAATTTT   58320

CAGTGGTTAA TGTTAAATCA TCTTCTTTTT TCTTTTTTCC TTAGGATACT TCTGAACCGG   58380

TGAGGTGTGC TCACAATGAG GTTTCCTGTA AAAGTTATTT TTTTACTTTC TTCTGTTAGC   58440

AAAGCAGTTG CCGCTACAGA TTGAATGCAT TTGGGCCATC CGCGGGTTAC TGGGTTAAGG   58500

ATTTTTGATA GGAAGGCCTT AATGCTTTTG GAATATGCCC TGACAACAAA GTGCCAGTTC   58560

CTTCCCGGTG TTCAGCCACT GCGTTGATCC TCCACGAGGG CCTGCCACGT GCTGCTCTGG   58620

TGAGGCGTTC CACCGGGGCA ATTGCCTACC TGGGAGCGCT CTCCAGATCT GTGTCGCTCA   58680

AACTGGCTGG AGTTCCCCGT AGGGATGCTC CACAGGGCAG GCCTAAGTCG CCTAAGGGGC   58740

TGCCTTGACC GTCCGTTAAT CACCTCTGTC TCCAAAAACC AGCTCCCTGA GTGAGCAATT   58800
```

```
CCTGTCCCTT TTAAGGGCTT ACAACTCTAA GGGGGTCTGC ATGAGAGGGT CGTGATTGAT    58860

TGAGCAAGCA GGGGGTACGT GACTGGGGCT GCATGCATCA GTAATCAGAA CAGAACAGAA    58920

CAGCACAGGG ATTTTCACAA TGCTTTTCCA TACAATGTCT GGAATCTATA GATAACATAA    58980

CCTGTTAGGT CAAAGGTCGA TCTTTAACCA GACCCAGGGT GCGGTGCCGG GCTGTTTGCC    59040

TGTGGATTTC ATTTCTCCCT TTTAATTTTT ACTTTTTCTT TCTTTGGAGG CAGAAATTGG    59100

GCATAAGACA ATATGAGGGG TGGTCTCCTC CCTTAATTTA AACAAAATTT TCAAAGTCCT    59160

ACCCCAAGTA AATTGGCAAA TATTAATAAA GTTATGGCAT AGAAAATAAA AATGATTGTA    59220

AAAGGCGTAA AGATATTTCT GTGGGGAAAA CATTTGTTCA TTAGTTATCA GTTAAAATTC    59280

TGTGAAAAAT AACCACTAGA GACCCTAAAG TACCCAGGGG CTAATAATAA GAAGGGAGGA    59340

ACACCCTCTC AGTCCCCACC GTTACCTCCC CAGAAGGGAA GAGGAAGAGG GTGACTCCAG    59400

GAGAGCTGTG GTCTCCCCTC CCCATATGTC CACATATACC TGACCTCCCC TCCCCAAAAT    59460

ATATACCCAA TATCTCTCCC ATATATACAT ATTTATCTGA CCTCTCCACA TATGTATACC    59520

TAAACTTTCT CTATATATCC ACATATACCT AACCCTCTCA CACACATATA GCTGACCTCC    59580

AGTGGAGGAA AATGGGGAAG AGAGAAGAAG TTATCAAAGG ATAAATCTAG GTCATACTCA    59640

GAAATGTGAA AAACAAAAAC CACACACAGA AAAAAAAAC ACACACAAAA AGAAATTGA     59700

TAAATTTGTT TGTGTCAAAA TTAAGAATTC CGGTTCAATG AAGGATCCCA TGGATAAAGT    59760

TAAGACACTG CTGTAAGGAT GGTAGAGAAT TAAATGTCTG AATCAGACGA AAGGATGAGT    59820

AATTAGAATG CACAAGGCCA AGAAGAACAA AACAGAAACT CCACATAAAA AATGTATGAG    59880

GCCGGGCGCG GTGGCTCATG CCAGTAATCC CAGCGCTTTG GGAGGCCAGG GCGGGCCGAT    59940

CAGGAGTTTG AGACCAGGCT GGCCAACATT GTGAAACCCC ATCTCTACAA AAAATACAAA    60000

AAATTAGCCG GGCGTGGTGG TGGGTGCCTA ATCCCAGC TACTTGGGAG GCTGAGGCAG     60060

GAGAATCACT TAAACTCAGG AGGCAGAGGT TGCAGTGAGC TGAGATCACA CCATTGCACT    60120

CCAGCCTGGG TGACAGTGTG AGACTCTGTC TCAAAAAAAA AAAAAAATTA TATATATATA    60180

TATATATATA TATATATATA TATATATATA TGAAATAAAT GAACAAGAAA TTTAGATACA    60240

GGAAAATCCA AAGCACTTGG TAATGAAAGA AAGGTAAAGT GATGTGTCCT TTTGCATTTA    60300

AAAGAGAGCA TTAACAAATT AGAGAGCTGA ATAATGCTCA GTATTGGTGT GGATATGGAG    60360

ACTCAGGAAT CCTCATACAC TGCTGATGGG AGTGCCCACT CCCTGGGAAT ATTTTCCAAA    60420

TATCATCTCA AACATATCCC ATAAAGGTGA CAGGAAAGTG TGGGCTGACT GATATCCTTC    60480

ACTGAGAGAG GTGGAGGTAA AATGAAGTCA CTGCACAATA TAGAGTTGGA AGCAATGGAT    60540

TAGATGTCCA CATAGTTACG TGGAAGAATC CGTAAGATAC ACACACACAC ACACACACAC    60600

ACCTTTGTGT ATATTGTTCC TGGCAGGTAG GCATGGAGGT TTAGAGGCTT TCTACATCAC    60660

ACCTACTGCA CACAGTAAAT GGCCAGGCTG AGCACTGACT TCCATGAAGG GAGATTGAAG    60720

GTAAGAGATT GAAGATTGTT CCCTGGTCTG GGACCCTGCA ACTGAATATG CAGAAAAAAG    60780

TACACCCCGC CACCCCGCTT CCCATCTTTC CTACCTGATT AGAATAGCTT TTTCAGAAAA    60840

CGTTGGCCAG GGGTTGTGGC TCACACCTGT AATCCCAGCA CTTTGGGAGG CTGAGGCGGG    60900

CAGATCATCT GAGGTCAGAA GTTCCAGACC AGCCTGGCCA ACATGGCGAA ACCCCATCTC    60960

TACTAAAAAT ATAAAAAATT AGCAGGGCAT GGTGGCACAC ACCTGTCATC CCAGCTACTC    61020

GGGAGCCTGA GGCAGGAGAC TCACTTGAAG CACAGTGATG GAGGTTGAAG TTAGCTGAGA    61080

TCTTGCCACT GCACTCCAGC CTGGACAACA GAGTGACACT TTGTCTCAAC AACAACAACA    61140

AAACCCACCA AAACTTTAAA TCTACCTATG GCCAAATGCC TGCTAAAATG AGCACCCAAG    61200
```

```
AAGCAGTGTT CAGGAAAGTC AGATGAATAC CCTAAAATTA GATGCAATGT TGGCTGGTCA    61260

CAGTGGCTCA GGCCCTGTAA TCCCAATCCT TCTTGGGAGG CCGAGGCGAC AGATCGCTTA    61320

AGCTCAGGAG ATCGAGACCA GTCTGGACAA CATGGTGAGA CCGTGTCTCT ACAAAAACGT    61380

ACAAAAATGA GCTGGGAGTG GTGGCGCACA CCTGTAGTCC CAGCTACTCA GGAAGCTGAG    61440

GTGGGAGGAT CTCTTGAACC CAGAAGGCGG AGACTGCAGT GAGCAGAGAT CATGCCACTA    61500

CACCCCAGCC TGGATGATAG AGCCAGACCC CCATCTCCAG AAAAAAAAAT AAAGAGAGAG    61560

AGAGATGCAA TATTTAGGGT TCAACAAGAC TGAACTTCTG ACTCCTTTCC CTACCTCTCC    61620

AGCATGTTAG ATTCTGGGTC CTTCATCCTA ACCCCTGTT CATGCCATAG CCACCCTGTG    61680

GTACCAACTT TGGAAGCCTG GATCTTCATC CCCTCATGAT AATGAGTGTC CCATTCAGGT    61740

CTCCATGCTC AGCTTGGCAA GAGTATCTGT CTTCTCCTCA TGGGACGGTC ACATTCACCC    61800

AGCACTGACA GGTTCCATTC CCACTAGGGT GGCACCCTAT ATGGTCTGAG TCCAGGCCTT    61860

CCTGGTCCCT CAGTAATCTC AGCATGGTAG CACAATCGAA AAGGGCTAGG CACGGCAGCA    61920

CCATTTCCCA CCAAGAGGTC TGATGGCTCA TCACATAGAC TGAAGGAGAT TCTGAAGAGC    61980

AGAGGTGGAA TGAAGAATGA ATCCTGGGCT CTGCTCTTCC TAGGCCTGTC TTCCTCTCTC    62040

CCGAGATGTT AGCTAACTCA TGAGAGCCAG AAACCAACTG CAGGCTGGCC TCAGGCACTT    62100

AGGTAGTGCT TCAGCCTCAG CAGTCCACAT TCTAGGAACC CTCATAATAT GGGTTGAAGT    62160

ATGCATTCCC ACAAAAATAA AGTTGTTGAA GTCCTAACCA CCAGTACTGA ATGGGAAAA    62220

GTTCCCTTGT CCCGCTCGCA TGGCATGTGA TAGGAGTGTG GCTAATTTCT TCAGTGCCTG    62280

GCTGCTCAAA CCTCTAGGGG AACAGTAAGA CGGGCAGGTT GTGGGTCTCC AACCCCATGA    62340

CCCCACCACA GTGTCTAGGG TTGAATGTTT ACAGCTCCTG AAGCCACAGT GGGTGTGTGT    62400

TACAGGGTGC TCTTTTAGTT TTGCCATTTA TAGGCAGCTG GTGTTAACCA ACTCAATTAG    62460

ACCGTCTACC TTGTCCCAAG GACAGAAGAA GGCTTTCTGT ATCCCAGGTT CTTGCCTTGG    62520

TGTACCGGAA TAAATCAGAC CACACCTGGG CTTAGAGAAA GAGTGCAAGG TTTTATTAAG    62580

TGGAGGTAGC TCTCAGCAGT TGGGCAAAGC CAAAAGTGGA TGGAGTGGGA AAGTTTTCCC    62640

TTGGAGTCAG CCACTCAGTG GCCCAGGCTC TCCTGCAACC ACCCCAGTCA AATTCCGCCT    62700

CATTTTGCCA GGCAAACGTT TGTTGTGTGC TCTTCTGCCA GTGTGCTCCC CTGGACGTCC    62760

AGCTATTCGT GTCTTGTGGC AGGCCAGGGG AGGTCTTGGG AAATGCAACA TTTGGGCAGG    62820

AAAACAAAAA TGCCTGTCCT CACCGTGGTC CCTGGGCACA GGCCTGGGGG TGGAGCCCTA    62880

GCCGGGGACC ACGCCCTTCC CTTCCCCACT TCCATATCAT TTAAAGGGAC CATGCCCTTC    62940

CCTTCCCAGC ACTTTCCCCC TCCTGTATCA GGACCTGTGA ATGTGGCCTT ATTTGGAAAT    63000

AGGGTCTTTG CACTTCATCA GTTAAGATAA GAGTGGGCTC TAACCCAACA TAAAGGGTGT    63060

CCTTATAAAA AGGAGAAATG TCATACACAG AGACTGACAC CTATAGAGAG AAAATGTGGT    63120

GAGTAGACAC AGGGAGAATC ACCATTCAAG TCAAGCAATG AGTCTGGGGA TACCAGAAGC    63180

TGGGAGAGAA ACCTGGAACA GATTATCCCT CATTGCCTTC AGAAGGAATC AAACCTGATG    63240

ATACTTTGAT TTCAGACTTC CAGCTTCCAG GACTGTGTGA CGATAAATAT CTGTTGTTAA    63300

GCCAACAAGT TTGAGGTACT TTGTTACTGC AGCCCCAGAA AACTAATACA GTAGGTACTA    63360

TGGACTGAAT TGTGACTCCC CGTCGCAAAA TTCATATGTT GAAACCCTAA CCCCCAGTGT    63420

GATGGTACTT GGAGCTGGGG CGTTTGGGAA GTCATTATAT TTAGACAAAC TCATCAGGAT    63480

GTGTCTCTCA TGATGAAATT CATGCCCTTA TTAAAAGAGA CAACAGGCCA GGTGCAGTGG    63540
```

```
CTCATGCCTG TAATCCCAGC ACTTTGGGAG GCTGAGGTGG ATGGATCACC TGAGGTTGGG    63600

AGTTTGAGAC CAGCCTGGCC AACATGGTAA AACCCCATGT CTACTAAAAA TACAAAAATT    63660

GGCCAGGTGT GGTGGTGCAC GCTTGTACTC CCAGCTACTT GGGAGGCTGA GGCAGGAGAA    63720

TCCCTTGAAC CCAGGAGGTG GAAGTTGCAG TGAGATCACA CCACTGTACT CTAGCCTGGG    63780

TGATAGAGAC TCCATCTCAA AAAAAAAAAA AAAAAAGAC AATAGAGCCA GGTGCTGCAG     63840

CTGATGCCTG TAATTCCAAC ACTATGAGAG GCTGAAGCAG GAGGCTCGCT TTAGCCCAGG    63900

AGTTCAAGAC CAGCTTGGAC AAAATAGTGA GACCCCAAC TTCTAAAAAT TTAAAAAATG     63960

AACTGGGTGT GGTGGTACAC ATCTGAGGCT CCAGCTACTC TGGAGGCTGA GGTGGGAGGA    64020

TTGCTTGAGC CCAGGAGGAG GCTGCAGTGA GCCATTGCTG TCCAGCCTGG GCTACACGAG    64080

AACCTGTCTC GGGAAAAGGA GAAAACAGTG AGACCTCTTT TTCTCTCCTC CTTCTCTCCA    64140

CTGCCTAAGC CCTACAAGCA CAAAAGGAC ACCACATGAG CACATAGTGA GAATGCTGCT     64200

GCCACCAACA AGTCAGGAAG AGAGCGTTCA CCTAGAAACT GAATTGGCCA GCACCTGGAT    64260

CTTGGACTTC TGAGCTTCCA GAACTGTGAG AAAGTTATTT TTTTTTTAGC GACTAAGTCT    64320

ATAGTATTTT ATTACAGCAG CTCAAGGTAA CTAACATAGT AGAAGGGATG AATTATGGAG    64380

ATCACAAGTC CACGCCTCCA GAAAAAGACT TCCCTAAAAA TTAGTCTGAG CAAAATTCGA    64440

ATGATGAATT ATTTTTAAGA ACTTTTAAGG GATCTGACAA GTTTGCAAGA GCTAGAGAAT    64500

GCTTTACAAC GTGATAATAG AATGCTCTGT GATGACAGAA ATCTTTCCAC ACTGTTCAAA    64560

ACTAGCTACT GGCCACTTGT GACTATTGTG CACTTGAAAT GTGACTGGTG TCTGAGGAGC    64620

AGAATGTTTA ATTTTACTTA ATTTTAATTC ATTACAATAG CTACATGTAG CTAGGGCTA    64680

CTGGATTGAA CAGCACAGCT CGAGTCTTTT AGAGGGAGAC AGGACTCACC AAGGTGGATG    64740

CTGGTGGCCA AGCAGCAATG GCAGGTAGTA CACACACAAG AGGCAGATGA TACAACACAT    64800

CCTTCCCAAA CCTGGAGATA AGCTCACCCC ACAATCCCGC CGCTGAAATA GAGTTGATGT    64860

TACCAATGTG CATTTTTATG TCCTTTTCCA TACAGAAAGA TCATTCAACA AGTACTATGG    64920

TACTTAAAAA ACAACATTCA ATTCATTATT ATGACAAAAT TAAATTAATA GCTCTTCCTT    64980

AAACTTTTAA ATTCAATTTA CAATGCTTAC TATTGGCATT TATTAATCTA CCAATTTTTT    65040

CCCATAGAAC CCATAGAACA AATAATCTAC CAAATTTTTA ACATTCATTT TTGGCAAGGC    65100

TTTTGCAATT TGACGAACTT TAAGAAGAAA ACTTATAAAT TGCAATTTTT AAATCTGACA    65160

TACTGGACTT TTAAAGTATC CAATTGACTA ATGAACAAAA CTGCTCCAAA TTTTTCAATT    65220

CTTAAAAATC TTAAGACAAT ACTTAATATG GCAAATCTTA ACTTCTTAAA CTTTGTAAGA    65280

ATGCTAATCA ACTTAGATTG GTATAAAGTT GAGTTAAAAA TCACAGGATA CATCATCTCA    65340

GCTATAAGTT TTCATGAGTT GAGTTTTTAC AATCACTTGA AATGCTTAGA ATAGGAAATA    65400

CGTATAAATT ATTTAACATA AAATATTGTT ACAAAACCTC TGGAGTGTCA GTTTCTCTGG    65460

CCAGACTTTA TGCTGCAGCA CCTTTGCCTG AGTTCTTGTC CTGCATCCAG GAAGAATTAG    65520

GTACAGAGGC AAGAGTCAAG AAGATTAGTT TTCCAATAGT TCAGCTCACC TAGTTAACTC    65580

CTGTTCACAA TCTTCAAAGT TATCAGAAAC CTGCAATTGA GGGTTATAAT CCATTCTTTG    65640

CAGAGTTTCA AAACAAGACA ACATTTGTCT ATGAATGTTA AAATGTCCTA GGGTAGTCAC    65700

AGTCAAAAAC ACAATTGACA AAGAAATTTA GTCACCTCTG TGATTTACAA TAGCCTAACA    65760

CAATAACTCT AATTATAACT GATGACACAA ACTCAGATAT CAGAACTCTA GAAATCCCCT    65820

ATAATTTTGG AACACATATT CACAGTTTTC ACTGAAATAT GACCTGAAGA TCAAATATCA    65880

CCTTATTTCA ACAATCCTAT ATAACTAAAC GTGTCAAATG ATCCTGTTTA CCTCTCCTTT    65940
```

```
GGATACTCCA GGGGCCCTCT GTAGCATCCA AAAGTTAGGG GTTAGCAAAG ACAATTTTGA    66000

AGCTGTAAAG GCTCAAAACA CTTAATGAAC CTCTAGTCAT ATCTGTTCTC TACTCACTAA    66060

ATGCTAGTAG CACCTCTCAG TTGTGGCTAA GCTGGGAGGA TCTCTTGAGC CTAGAAGTTT    66120

GGGGACGCAG TGAGCTATGA TTATGCCACT GCACTCCAGC CTGGGCAACA ATGCAAAATC    66180

CTGTCTCAAA AACAAAAACA AAAACAAAT TGCCTATGCT GTGGTTATCT CACAATTAAT     66240

AAAAAGGAAA AAAAAAGTAT GCAGTCTTTG TAGGTCCTTG GGGTTTGTTG GAACTCAGAA    66300

AACAATACCC CAAAATAAAG ACCGCAGAAG CCAAAGTTTT TCTCTGATCT TCTCCTGCCC    66360

TCCTGTCTCT GAGTCCCATT CTCCCCGGAG TCTAGCCATA GAAATGAGAA TTCCTCTTCC    66420

TCAAGTTAGG TCATAGAAAT CAAAACACCT TTTCCCAGA GCCCAGCCAT AAAACCTAAA     66480

AATATTACTC TAACTTTCCC TCTGTTTTTC TGTGTAAAAA CTGGCCATAA AGAAATTATC    66540

TGAACTACCT TATTTGATCA TAGATCACCA GACCGCATTC CAGAGAGGAT CCAGAAGGAA    66600

GGAATGCTGC ACAGAGAGGC CAAGAAGAAT CTAGACAGAC AGGCCTTGCT GGGTTTCCCT    66660

ACTCTGTTTA TTAGCAATCC TATTTCTACA CGGCGGCCCA TACTTTGTTG AATCTAAAAA    66720

ATAAAAATGG ACAATTTCCC CTGTACATGT TAATACACAT TAATAAATTG GATATAAATT    66780

GGATAATTTA TTAATATACA CATTAATAAA TTGGATGCAG CCGGGTGCAA TGGCTCACGC    66840

CTGTAATCCC AGCACTTTGG GAGCTGAGGC GGGCAGACCA CGAGGTCAAG ACCACCCTAG    66900

CCGAAATGGT GAAACCCCGT CTCTATTAAA AATACAAAAG TTAGCTGGGC GTGGTGGCAC    66960

ATGCCTGTAG TCCCAGCTAC TGGGGAGGCT GAGGCAGGAG AATTGCTTGA ACTCGGGAGG    67020

CGGAGGTTGC AGTGAGCCGA GATTGCGCCA CTGCACTCCA GCCTGGTGAC AGAGTGAGAC    67080

TCCGTCTAAA AATAATAATA ATAATAATAA TAATAATAAT AATAATAATA ATAAATTGGA    67140

TGCATTTTAT CCTATTAATC TTCCTCTTGT CGGTGGTTTT CAGCGACTCT TCAGAGGCCA    67200

AAGAGTAAGT TTTCCCTTAG CCCCTACAGG TTCTTATGTT TAATTTGTTA CTCTCATTTA    67260

AGACATAATT AAAGTGGCTT CTCCATGAAG ATTATTTCTG CATCCATTAT TTGGTAAGAT    67320

TGGCCGTTTT CTCCTTTGAT CTCTACTTCA CACTGACCCA CATAAAACAT CACTGCCTGT    67380

TTTTTTGTTG TTGTTGTTTG GAGACGGAGT CTTGCTCTGT TGCCCAGGCT GGAGTGCAGT    67440

GGTGTGATCT CCGCTCACTG CAAGCTCCGC CTCCCGGATT CACGCCATTC TCCTGCCTCA    67500

GCCTCCTGAG CAGCTGGGAC TACAGGCACC CACCACCAAG CCCGGCTAAT TTTTGTATTT    67560

TTAGTAGATA CGGGGTTTCA CTTTGTTAAC CAGGATGGTC TCGATCTCCT GACCTCGTGA    67620

TCGGCCCGCC TCAGCCTCCC AAAGTGCTGG GATTACAGGA GTGAGCCACT GCGCCCGGCC    67680

CCGTTTTTTT TTTTTGGTT TTTGCATGTC TTCTCCCTTT TACTGTAAAC TATTTCCACT     67740

ACCAGCGTAG TTATCATTTC TACTGCTTAA TAATTGTTTT GGGGAAGTGA ATGCATCAAC    67800

CCACATGAAT TTCTTGTCTA TTTGACAATT TATTCTCTTT AGGAATAGTA TTAACTCCTA    67860

AGGTCCTGGG AGCCAGTCTC TGTACTTGGC TGCTCCAGGG TCCTACTTCA GTTTCCCAGC    67920

TTCTCAGTAC TGTCACTGTC AATTGTGGGT AATAATTATT TTTGTCCACC AAAAGACTCT    67980

GTATGTGAAT GAGTTTTGAA ATCTGCTGAG TAATACAGTG TCAACCCAGT TAATGATTTG    68040

CCGGGCGGCT TGATCAGGGG CTGTCCAACT ACCGGCATTT TGATTGGAG CGTCATCTAG     68100

TGTCTGAAAG CACAAACAAC ATCCTACATT GTAAATGCCT TTGGCTACAG AGATTGAAAC    68160

CAAAGCAAAC CTATGTTTTG AATTGTTATT CTTCAGCAGT TCTGCTAGCC TTGAAAAATC    68220

TAAAAGTTAA AAAAAAGCTT TATATTTCAT TTTCTGCCTA AACTCTTTAA AATTGCTAGT    68280
```

```
TGACAATTAG ATATTTTCAA TTTAATGAAA TTTTTTTTTA GTTCACAGAT TAATACACAA    68340

TGGGGGAGGG TTCTTATTCT GTTGGACTTT TACATAACCT CCACTTTAGT GCAGTCTGCT    68400

TTATGGGGTC TTGTTTGAGG TGTGTGTGTG TTTAAGGGAA TGTGGTTTAC AATCAAAATA    68460

TTGGGTTGCT CTTAGGCACA TTGTAAAGTC ACACACCTGT ATTCTTATTG ATACATAATG    68520

ATTAATAACA TTATTATTAC AGCCTGATCA CCATCATTAT TGATATATCT AAATAATGAA    68580

TTTTATAATT TTGCTTCCTG TCAGGCAAGA GCCAATTTCA GTGCTACCAT GTTTGTATAG    68640

CAGTATTTAT GTCTGTCATC CTCAGTCATT TTACTTCACT TGTTCTTAGC CAAACGGCCG    68700

AGAAGCGATG GTCATTTTAC TTCAAAAATG AAAAGAATTA ATATTTTTAC GTTTCCCTTA    68760

AAGACCCTAT GTTTAACCTC CACTCCCGGG TAAAATGGTC TAGTCCCTCC TTTTCATATC    68820

ATCTCTGATA TCTTTTGCAC AGCCACTATT ACCTACCGTT TTCTAGATCC CTATTCTTCA    68880

AACACCACCA TGAAGGTAGA GCCTGTCTGA ATTATTTTCT TGTCCCGTGA ACTCAGTACA    68940

TTGTTAGGCT TCTTGAAGAT GTTGATCAGT TGTTTGTGGA GTGAATGAAT CAGCTAGCAT    69000

GATTTTTCTA GACCACTGAG ACAAGTGTCT AAGACACTTG TTCCTTCCCA TGTTCTTGCC    69060

TGCCTGTGCA ATCCATGCAG TCTCATGGCT TCCCAGTGCC TCAGAATTAT CCCTGTCAA    69120

ACAGGCATTA TAATTTCTGT CCACTGAAAA GGACAAAAAA CTAAGTGTAT AGCTAGAAGT    69180

TAAAAATTAC CGGCCAGGTA CTGTGGCTCA CTCCTGTTAT TCCAACATTT TGGGAGGCTG    69240

AGGCGGGCAG ATCACCTGAG GTCAGGAATT CGATACCAGG CTGGCTAACA TGGCGACCCC    69300

GTCTCTATCA AAAATGTAAA AGTTAGCCAG GTGTGGTGGC TCGCACCTGT GGCCCCAGCT    69360

ACTCAGGAGG CTGAGGCAGG AGGATCGTTT GAGCCCTGGA GGTTGAGGCT GCAGAAAAAT    69420

AGGAATATAC TCTCTTTCAA GAGTTCGTGG TTTTGACTGC CACCTAGCGT ACATCAGAAA    69480

AACCGCATGA CATAGGAAAT GCCTGTGACA GAGGGGTAAG GTGAGAGAGG TTGATGAAGA    69540

ATGTATTGAA GGAGTGAAAA CGCTTCCATC CCTCTACTTA CTAAATATAT TAGTTAAGTA    69600

GTTGGGGCAT ATTTTAATTC ATGCATTTTG TAGATAGAAA AACAAAAGTT TTATTCTGTT    69660

TGATTTAGTT GATACTTTAA TATGTGTGTG TTTAGGATGC ATGATTTATA ATCAGTCTGC    69720

AGCACTTCTT GGAGAAGTCT GAATTCTCAT TCTCCATTTC CTTATTGGCA ACGTGAGAAT    69780

GATTACAATG GTGGTTGTCT CATAGAATGC AGGGAGTCAG AATGAAAATA GTCCATATAA    69840

TGCCTGGTGC AGAGGAAGGG TTCAGTTAAC TGTCTGTATT AATATTACTG ATAACAGTCA    69900

TGACAAACAA AAGCTTAACA ACAACACCAC CAACAACAGT TGCAGAATTG AGCCACCAAT    69960

TTGCACACAA GATTGTAGGT AGGATGTTTT AGAAAAGTTA TTATTTAATA TATGTATATA    70020

TTTTTGTACT TAAAATATGT CAGAGGTTGT TCTAAGAACT ATTTAAATGT TAACTCCTTA    70080

ATCCTCATAA TGACCCATGA AACAGGTAGG CTTATTATTG TCTCTTTACA TGTGAGAACA    70140

CTGAGACACG AAAAGGTTTA TTAACTCACC CAAAGTCACA CAGCTGGTAA AACGGCAAAA    70200

TTGAATTTGA ACTCAGACAT TCCAGGTTCC AAGACAGTCT AATTATTCTT TTGACTAATA    70260

TACTAAGCTG CCTCTGTATT TTTCCTTGAT TACTTTGTAA AAGTATGAGG AAAATATAAG    70320

TGCTTCAAGT AACCATGAAA AATATAAACA ATCTATGTAT CAACTGAAGC ATAATTACAA    70380

ATCCTTTGAT AAGCAAACAT AATAAAAATT TGATATCAAT CAAAACTTTC ATGTAATGTA    70440

AGCAGGTTGA GATGAATTCT ATAGTAAAAA AGTGCAGAGT GCTGGAATAC CATGCTCCTA    70500

ATATATTGGC TAGGCACACC TGCCTGCTAT CAAAGGTATG CACACACCTT GGATACAGAA    70560

AGTTGGGACT GGGTAGTTAT GTGAGTGTCA TCAGAATTCT TTCCCACTTG GGAAAGAATT    70620

GTCCATCATA AGCTTGGATG ATGGACAAGG AGTGAGCTCC CAGAACAGTG ATGTGGGGAT    70680
```

```
ACATCCTCAC ATCACAGTGA GAATGAGTGT TCTAGACTGT TTACACACCT ACCACTCCTA    70740

AATGCACACA TATAATTGCT TGCACACACA CACATACACA CTCATCTCTT CTCTGGTGGT    70800

CCAGCTCTAT CTCTTATCAT TAGGCTTCTT GGGGCTAGTA CCTAGGGCCT GTATCCTTTC    70860

AGAGGCAGCT AAGGGAAGCA CACATAATTA GAAAGAATGA ACCAGCTTGT TGGATTTGGT    70920

CTCTTCGCAT CCAGCCCTCC AAGTTAAGGA GAGTACCATC TTTCTTAGGG TCACCAAAGG    70980

AAAAAAAAAA AAAAGAAAGA AACAGAAGGA TATCATACAG CAAGGATCTA ATGCAAATAT    71040

GCCTCAAATG AGAGGCTACT GTGTGCTGAT CCCAATCCCA GGAACTGTAT GCACATTATC    71100

TAATTTAATC CTCACTGTAT TTCTGGGAGT ATTATTCCCA TTTTACAGAG AAGGAACTTG    71160

GCAGGGTAAC CAAGCTCATG AATGGAGAAA CTGGGATTAA ATATAAAGCT TCCTTGCTCC    71220

AGAACTGCTG TCTTTCTGCT CTTCCACACT ACCAGCTCAG CTGTGCTCTC TACATGCAGG    71280

CAGTTTTACA AGTTTCAGAT TAGCCTGGGA CTTCCAGGGT TTTGAATGGG TTAGGGAATG    71340

GGGAACTTTT GGGTTTACTT TCCATTTTTT CTTCATACAT ATGTAATATA TAACATAAAT    71400

CTATGGTATA TATGATAAAT ATATGGCTAC ATATGAACTA TATAATCACA TATATGCATT    71460

ATAAATAAAT ATTAATTTTA TAATATTTTA AAGGTTATCA AATAAATATT AATATAAATA    71520

ATTAAATAAT TAATACTCAG CTTTGTTTTC CAAAGTGATA AATGCCTATA TTTAGCAAAA    71580

TATTTTTTGG AGGCCTGATA GTTTTTAGGA GTGTAAAGAA GTCCTGATAT CTAAATGTTT    71640

AAGAACCACT ATTTTAGGCT GTTGTCTTCT GTCTTATTTT CCCAGCTAGA CTGGTAAATA    71700

CTTGAAGGCA AACGTTTAGC CAGCACATTA ACATTTTATG TTTTTATTCT TTTGTGCTCT    71760

CAGTGGCTGT GTCTTTTCTA TCGATTTCTC ACACTGTATG ATGGTTATAT TTGTCTGTAT    71820

CTGTCCCACC AGGTATAAGT TCTTGAGAGG ACACACTGCT AGGCTGATCT TAGTTTTTAT    71880

TATTTCTCCT GGTGTCCTGT GCTTAACAAG TGCTCATTAA GTGTGTAAAA ACACAGCACA    71940

GTAAAAAACT AGACATTAAA AAATAATGTC AACCAATCTA TTGAAATTTG CATTTCCATG    72000

TTTCTTCCAA TATAGTCATT GTGTCAGGTT ATGTACTTAT TCTGATGAAG ACTATTGCCT    72060

AATATACGTT TGCATCTTGT GCTTTATAAC TGCCTTCATA TAGACACAGA TTGAGAAGGT    72120

GTAAAAATGT GCATATCCTC ACAATTGACA AATTCTTATC CTTTGAGGGT AGGTTTGACT    72180

TTCTGAAATG CTTTGACATC ATTTGAAAGA AGCTTGAAGA ATAAGATAGC TGTTAATGAC    72240

CCAGTTTCCT ATGTCACTTA TACAATTATA ATGGCAATTT CAAAATGTTA GGTAAATATA    72300

TTTTGCAATA TATTGTTCCT TTTGTAATAC TCTCTATGTA TTTATTTATA TTTTTAAATT    72360

TTATATTTAT GTATTTATTT TTCTGGACAG AGTCTTGCTC TGTTGCCCAG GTTAGAGTGA    72420

AGTGTTGTGA TCATAGCTCT CTGCAACTTC AAACTGCTGG GCAAAAGTGA TCCTCCTGCC    72480

TCAGCCTCAT GAGTAGAGTA GCGGGAACTA CAGGCGCATG CCACTGCACC CAGCTAATCA    72540

CTATTTATTA TGCTCCTACT GTGTGCTTTA GTATATTTTC TGTTGTTTTC TGCAACCCAT    72600

TTTGAGGGCG TGTTAGGGAA TACAGATGCA GTAACTTTGG TCTCAGCCCT TGAGGTGAGG    72660

AAATATTTAG CCTCAGGTTT AATCTAATTG TTGGCCATTT GCCTTCAAAG ATTGAAATAT    72720

GAGCAAAACT GTGGCTCTGG GTTATATGTT AAAAAAAAGT TTATGGGGCT GAAGCCAGGC    72780

AACAGACAAG AGCCCCTACA ATCTTATTTA GGCTGAAAAT ATCCTGGAGT CCCTGTATTG    72840

TTGGTCTCAA GCAGATAGCA ACACTAACAC TTACTCTTTG AGGCAGGCAC TGCCAGTGGG    72900

GTGGCTGTTA TTATTAGCTT CATTAATTGG TGAGTCAGGA AAAACAGCT TTAAATCATT     72960

CAAAGTTCTG GCCTATACAG GATTTAGTAA TATTAGGTTA GCTACATCCA AAAGATGACA    73020
```

```
GAACCCTACT CTAAGGCTGG GCTTGGTGGT TCACACCTAT AATCTCAAAA CTTTGGGAGG    73080

CTGAGGCAGG AGGATCACTT GGTGCCAAGA GTTTGAGACC AGCCTGAGCA ACATAGTGAG    73140

ACCCCTGTCT CTATCAAAAA CAAAGAACTC TAATTGGCAT AGTAGAAGGA AAAAGTGAAA    73200

GAAAAACCAG CTGTCACCCT CATTCCTTAC ACCTGTCCTA ACAACTCCTC TCACTATCCT    73260

TTGAATATAT CTTGGCTGTT TGAGTCTCTC TCTAGCCCCA TTACTGCTGT TTGGACTTGA    73320

CATTTTGCTC TGCATTTTTA ACTTTTCTAC CAGGGTTTCC AGACCCTGAA GAGTGTGGCA    73380

TGAAACAAAA CTAGTCAACC TATAATATTT ATGATGTGTG TGTAAATAAA GAATACACA     73440

ATATATTGCA TTACAATATT TTAACTGTGT CCTCAATTTG TTTGTGGCTT TCTTGAGGAC    73500

ATCAGTTTTG GGTGGGACGA CCACATCCTT AATCTGAACT TTCCCTTGGA GGTCATTCTT    73560

TTTTTTTTGA AATAGAGTCT CGCTCTGTCA CCCAGGCTGG AGTGCAGTGG CGCAATCTCA    73620

GCTCACTGCA ACGTCCGCCT CCTGGGTTCA AGTGATTCTC CTGCCTCAGC CTTCCAAGTA    73680

GCTGGGATTA CAGATGCACG CCACCATGCC GAGCTAATTT TTGTATTTTT AGAAGAGACG    73740

GAATTTCACC ATGTTGGTCA GGCTGGTCTT AAACTCCTGA CCTCATGATC TGCCCACCTC    73800

AGCCTCCTAA AGTGCTGGGA TTACAGGCGT GAGCCACCCC GCCCGGCCAG AGGTCATTCT    73860

AATAGACTTT TTTTTTGTTG TTGCTCACAG GCTTGTTCAA TCTTATTTCA AAATTTGAGA    73920

AATACAGTTT CCATGGAACA CCAACCAGAT ATCAGGTTGC TATGGAGTTG ATAGTCAAAA    73980

GCTTTGTATC TTCCAGTTTT TCAGAATGGC TTCTAAAGGT TCTGATTCAG AGCTCTTAGG    74040

CGAAATTGAA CAACCAAGTG TCAAAGTACA ACATTCAGGA AGTTAAAAAC ATGACTGACA    74100

TATATGTACT ATATATAGTG AGCTTGTGTA TGTGTCAATG AATGATTTAA TTCATTAATG    74160

AAGGAGGAAG CAGAATCACA ATTAGGTCAA AGGAAGATAC GGGAGAATAA AATATGTATT    74220

TGGTCAGGGA AAGGATGTAT ACTGGAAGAG GAAGGGAAAA TCAGATATAA AGTTGTTTAA    74280

TGACTTATTA GGCAATACAA TAATAACTTT TAGGGTCATT TTTTCTATAT TAAGAATTCA    74340

TTTCCATCTC TATGACAAAA TCCTTATTAA TTTATTAAAC TTCTACAAGT GAATGTTTAC    74400

TTTTAGATAG TCTGGACCCA ATAAAATGTA AACATTAAGT CAGAGTTACT TTCACGTAGG    74460

ACAGTGTTGT CCAATAAGGT ACCACTAGCT ACACGTGATC ATTGACCATT TGGACTATAG    74520

CTAGACTGAT TTAAAATGTT CTAAAAGTGT AAAATACACA CCAGGTTCTG AAGATTTATC    74580

ATTTAAAAAA GAATGTCAAC TGTCTTTTTT TTTAGCTTAT TTATTATATG TTGAAGTGAT    74640

AATAGTTTAG ATATATTAAG TTAAATAAAA TATCTTAAAA TTAATTTTAC TTGTTTCTTT    74700

TCATTCTTTC AATGTGACCA CTAGAAATCT GGAAAGTATT TATGTGATTC ACATTCTATT    74760

TTACTGTCTA GTATTGCCTT ACATCATCAG GTACCCCATA AGTAGGCTTT TTAGATAATT    74820

CTCTAATATA GCTTGGAAGG ATATGGAGAA ATATTTTTGC GTTGCTTTTA AGTTTTGCAT    74880

AACTTTTTCA ACACACTTTA TAAAGGATCT AGAAAAGGGT TGGTTACATG TTTCTCTGTC    74940

TTCTGGCCTC CACCATGTTG CCAGGAGGTT GGGGACAAGA TTCTGGGTGG CTGGATGTCC    75000

TAATGGCTTG AGGTCTGGAC TTGAGATTTG CATATAAAGA GATGTGATTA GATTGAGTCG    75060

ACTAGAAAAA TCATATTAGA GAACTGAATC ACAGCGATTA AATTTACATG TCGATTTATA    75120

AACCAGGACA CCAATTTATA GTGAAAGAAG GTCCAGTTAC CTGGTAATCA AGACGTTTCA    75180

TAGCTATTTT CATGATGGAT ATACTTAGCT GAGTTTTAAA TGAGAAGGGG GTTCATTGCA    75240

CATAGAATAA GATCTAAGTG AAATGTTTAT TTATTTTTTT TTTTTTTGA CATGGAGTCT     75300

TGCTCTGTTG CCCAGGCTGG AGTGCAATGA GGCAATCTCG GCTTCTGGAG TGCAATGAGG    75360

CAATCTCGGC TTCTGGAGTG CAACGAGGCA ATCTCGGCTC ACTGCAACCT CCACCTCCCG    75420
```

```
GGTTCAAATG ATTCTCCTGC CTCAGTTTCC TGAGTAGCTG GGATTAGAGT TGCCTGCCAC    75480

CACGCCAGGC TAATTTTTGT ATTTTTTTTA GTAGAGATGG GGTTTCACCA TGCTGGCCAG    75540

GCTGGTCTCG AACTCCTGAC CTCAGGCGAT CTGCCCGCCT CAGCCTCCCA AAGTGCTAGG    75600

ATTACAGGCG TGAGCCACCA AGCCTGGCCT AAGTGACATG TTCTTATATT GTTCCTTTCT    75660

TTCTTTTTTT TTCGACTGAG TCTCACCCTG TTGCACAGGC TGGAGTGCAG TGGCGTCATT    75720

TCGGCTCATT GCAACCTCTG CTTCCCGGGT TCAAGCGATT CCCTTGCCTC AGCCTCCTGA    75780

GTGCCACCAC CCCCAGCTAA TTTTTGTACT TTTAGTAGAG ATGGTGTTTC ACCATGTCCG    75840

CTAGGCTGAT CTCAAACTCC TGGCCTCAGG TGATCCGCCC CCGAGTCTCC CAAAGTGCTA    75900

GGATTACAGG CGTGGGCCAC GGGGCCCAGC CTTATATTAT TTCTTTTACT ACAATATATT    75960

AGTATGATGC AGGTGCTTCA ATTGTTTATA CACTTTCCAT AATTTTGTAT AATTCTTATA    76020

CCCTGTCACT CTGAGGAATA GCCGGTCTAA GTGTTTTTCC ACCACTGCTA ATTCATCCAT    76080

CACTAATCTC ATTAGACTGT TAATTCCCAG AGGACATAAG CACACAAGCA GACAATGTTT    76140

ACAAATGTTG GACAAATGTT ATTTAATAAA ACAATGGGGT CACCCTTAGT CTAAAAGATG    76200

TTTCACTTTT CATTTGTCAT TGAACTCTTA TTTGTAGGTT CCCTTTTGAC TTTCCCACAA    76260

TCTAAGGCTG TTCTCTTTAA CACATATTTT CATGAAAACA TATATTTGAG CAGAAATTGT    76320

TGGGGAGTTG TAATATTACC TTTGTCCCTA AATATGAATC TATAATTATA TCAAATATAT    76380

GGGCAGACAA TTTACTTTGC CTTTAATCTC AAGAAAAAAA TAGCAATTAC TTGGGGTCGG    76440

AGAGTAAAAT AAGAAGTAGT GAACCTTAAA GTAGCAAACT TTAGAACAGA ATAGTTTCAG    76500

AGGGGATGAG AAGAGGTGAT TTTTCAGCTC ATCAACAACA GATCTTATAA TAAATTACAT    76560

GTTCTGGTAC TTTTCTTGTC TTTCTGTGTT AAATTTTGCT ATTTAAAAAA ATAAATTTCA    76620

AATACATTGT TCATCTTAAA AGTCAAGAGT GTGTTTTATT AAAGTCAGTT GCTTTATTTG    76680

CAACTCAAAA GATATATTTG AGTTCCCAAC TGGAGATTGT CCTATATGGT AACTTGCGTA    76740

AGGTATGGTT ACTGAAAGTA ACCTACAATT TTCATGGGCT GAAATTCATT TCTATATTGC    76800

AGCGTACAAA AATAAATAAA TAAAAAATGC TTGTTTTCTT TGAAAACATA TTATCTCAGT    76860

GCCTCTAACT GCCAAATCTA TTGGCTTTTT TGCAGGCTTA AGGGCTCTCC CTTGTTCCTT    76920

TATGATCTCT ATCTTGAGGG CCAGACCTCC TGCCTTACAC AACTCAGAGG GGACCTCAG    76980

AGCTCTTTAA AAAGAGCCCA ATTTCTCGCC TGTAGAGAAG TGAAAAGGAT GCCCCACCCC    77040

CATCTATGAA AAGAGGGATT TGATAGTTTC AATGTCTTCA AATCAAAGAT TTAAGTCTGT    77100

AGCCCCCCAC CACCCCGGAC CCTAGCAAGG CTCATGAACC CCCTCCCATC CCGCCCTAAT    77160

TGCTTTGGAC TGGCCGTGGA ATCCTTGTCC CAGTCCACAG TTCCTGTGCG ACTGCACGAA    77220

GAATTCACAG AGGACCTGTG TTACTTCCCT TGTGAAGAAA CAGAATTATC ATGAAAATTT    77280

AGGTGGAAAC CATTTCGCTT TTTTCTTCAA AAATAAGGGA AGCATGTGCC CAACCACCCC    77340

TGGGAAAAAG AACCTTCAGG GGCAAAGGAG CGAACAGGTA ATTTATAAGA AAAACAGAAA    77400

GTGGTCTCTG ACTGCCCCAG ACTTCCTTCG GAGTTGGGGG AATTGGGGAC GCCTGGACGC    77460

GTTGTTTTTG CGTTTGTGGA AAAAATAAAT GAAGAGCATG AAGCCCGAGG CTTCTGAGAT    77520

CCTTTCCTGA CCAAACCCAA GTGATTTGGT GCGGGGAATT TTAATATTTT TCCCCTTTTG    77580

TGAGGTGGAA CAAACACAAC TTGGGAGCAG CGCAGCGGCT CAGAGCCTGC CAGCCAGGCG    77640

GGCGACCAGA GCACCAATCA GAGCGCGCCT GCGCTCTATA TATACAGCGG CCCTGCCCAG    77700

ACGCTGCTTC ATCGGCGCTT TGCCACTTGT ACCCGAGTTT TTGATTCTCA ACATGTCCGA    77760
```

```
GACTGCTCCT GCCGCTCCCG CTGCCGCGCC TCCTGCGGAG AAGGCCCCTG TAAAGAAGAA    77820
GGCGGCCAAA AAGGCTGGGG GTACGCCTCG TAAGGCGTCC GGTCCCCCGG TGTCAGAGCT    77880
CATCACCAAG GCTGTGGCCG CCTCTAAAGA GCGTAGCGGA GTTTCTCTGG CTGCTCTGAA    77940
AAAAGCGTTG GCTGCCGCCG GCTATGATGT GGAGAAAAAC AACAGCCGTA TCAAACTTGG    78000
TCTCAAGAGC CTGGTGAGCA AGGGCACTCT GGTGCAAACG AAAGGCACCG GTGCTTCTGG    78060
CTCCTTTAAA CTCAACAAGA AGGCAGCCTC CGGGGAAGCC AAGCCCAAGG TTAAAAAGGC    78120
GGGCGGAACC AAACCTAAGA AGCCAGTTGG GGCAGCCAAG AAGCCCAAGA AGGCGGCTGG    78180
CGGCGCAACT CCGAAGAAGA GCGCTAAGAA AACACCGAAG AAAGCGAAGA AGCCGGCCGC    78240
GGCCACTGTA ACCAAGAAAG TGGCTAAGAG CCCAAAGAAG GCCAAGGTTG CGAAGCCCAA    78300
GAAAGCTGCC AAAAGTGCTG CTAAGGCTGT GAAGCCGAAG GCCGCTAAGC CCAAGGTTGT    78360
CAAGCCTAAG AAGGCGGCGC CCAAGAAGAA ATAGGCGAAC GCCTACTTCT AAAACCCAAA    78420
AGGCTCTTTT CAGAGCCACC ACTGATCTCA ATAAAAGAGC TGGATAATTT CTTTACTATC    78480
TGCCTTTTCT TGTTCTGCCC TGTTACTTAA GGTTAGTCGT ATGGGAGTTA CTGAGGTATC    78540
AGAGACGAAT TGGGTGACGG GGTTGGAGAG TGGCCGTGGT GAGGTTACAG CATTTAAACC    78600
TTTATTGCGG CTTCTAGGTC CCTGACCGGA GGCTTTTCTC GCTGGCGGAT GGTTTTGGGA    78660
TGGCAGTCCC GCCCCAGGCC TGTGAACGGC AGAAAAGACC GCAAAACAAG AGCCAGTTTC    78720
TTAGTCTAAA GGGATGTCCG GATTGGACTA AAAAATTTTC AAAAGTCCCG CCCTGCTCCC    78780
GGGTTGGTCC GTTCTTCTAG TACATGACTT TCATTCTGTA TTTAATTGGA TGGTGGAAGA    78840
CGTTGCTTAT TCTGTGTTTT TTGCTTTACT GTGACTTAAA AGTTTTGCCT CTTTTCTCTT    78900
TATATTAATG TCTGGGATTT CGGACGCTTT CCATGTTGTT GGTAGTCAAG TTGATGTCTC    78960
CTGGAGGTAG TGGCAACATC CAGCCCTGGG AGGAGAGTGC GTGCAGGTAC CTTTGTCCTA    79020
CATTCCTCTG CTGTTAATTT CTCATTCCTG TGGCAACGAA GGAATGCATT TAAAAAACAG    79080
CCACAACAGC GGCAATAGCC CTTCCTCCAC CCAAGGCAAT CGTGGACCTA GGGAGTTTTT    79140
TGTGCCACAT AACATGTAGC CTTCCGCTAA ACTGACAGGT TGAGCGTAT CGATTTTGAG    79200
CGTATCGAAA GCACAACTTT TAGCCAGCCA TTTTGTCCTC GCATGACTAC GGTTGCTTAT    79260
CCTGTTTAGA CAGACAGCAA CATTTAAAAA TCGAAGTTCC TTTAAACGTA TTTTGTTTGG    79320
CAGTCCAAAT GTTTCTATGC AGAAAACAGT ATTTGTACTA TTAACTATGA AGAGTGTATG    79380
GATAAATGGG AGACATTTCT AATAAAGGCC TTCGTTAATG GTTCCCTCTG TTTGACATCC    79440
ATGGTGCTTC TGAATACAGA AAGCCTAGCG TCTTATATTC GCTTCTTTTA AAATCTGGTG    79500
GGCACATTTT GGTGAGACCT AAATTATGGG GACTGGGGCT TCTGGAGATA AGCTGCTCAA    79560
TTATTCTACC ATCTCCACAA TGATTAATAT AGTGAGTTGA TTTGTTAGTG ATAGTGACCA    79620
CGGATTCATC CCAAGAAAGA GAAAGGGGAG GGAGGCAAGC AGAGAGACAG GAAGACAGAG    79680
GCAGGGAAGA AGGAGAAAAC ATTCTCCCAT GGTTTAAGTA ATTTTGTGTT GTTAATTTTA    79740
CATTACAACA CGGTTTAACA TGGTGAACCC TCTATTTTGG TGTAAGGTTT AACATATGGA    79800
CATATTTTTC CCAAGACCAT TTATGAACTT TCATTTCTGC TTCCCCCTTC TTCCTCCCGT    79860
GCCACCCTCC ACGCTCCTAT CAATTTTGGC TGTTTTGTCA TAGGCTAATA CGCTATAATT    79920
TCATGGACAG TTGGACTGTC TTAGGTTTCT CAGGTTTCTA TTTTGTTCCT TTAGTCATTC    79980
CCACAATTCT TAAGGTAGAA TTGTATTGTT TTAAACATTG TGTTGTGTGC TATCCTCAAT    80040
GCTGAGATGA TTATGTGACA AATGGCAAGT GTTCAACTAA TACCTAAATC TGTAGTATCT    80100
TATCAAGCCT AATGCTACTT CACAATGCCT ACTCCATTCA CCGCACTTTA TCTCATTACT    80160
```

```
GGCATTCTGT CATCTCACAT CATCACAAGT AAAACGGTAA GCTATTTTGA GAGAGATCAC    80220

AGTCATATAA TTATATTTAT ATTTATTTAT TTATTTATGA GACGGAGTTT CCCTCTGTCA    80280

CCCAGGCTGG AGTGCTGTGG CACGTTCTCG GCTCACTGCA ACCTCCGCCT CACGGGTTCA    80340

AGCGATTCTC CTGCCTCCGC CTCCCGAGTA GCTGAGATTA CAGGGGCCTG CCACCATGCC    80400

CGGCTAATTT TTGTATTTTT AGTAGAGACG GGGTTTCACT AAGTTGGCCA GGCTGGTCTC    80460

GAACTCCTGA CCTCAGGTTA TCCGCCCACC TCATCCTGCC AAAGTGCTTA GATTACAGGC    80520

GTGAACCACC GTTCACAGAC TCAAATCATT TTTATTACAG TATATTGTTA TAATTGTTGT    80580

TTTATTATCA GTTATTGCTA ATCTCTTACA GTGCCTGATT TATAAATTAA ATTCATCATT    80640

GCCATGTGTA TATAGAAAAA AACAGTGTAT ATACGGTTCA GTACTATCTG TGGTTTCAGG    80700

CATCCACTGG GGGTGCAGTT TATTAAACAT GCATTTACAT TAGTCTCCCC TTTGGGAGAC    80760

TAATTAACTG AGATGTTGTA ACGTGACTTT AATAGCAGAT AGAGCTAATT TTCTCTCATT    80820

ACTCTTCTTT TTCAGAATTT TCCTGGTTAT TCCATTTTTT ATTTTTCCAT ATGTATATTA    80880

AGATCTCTTC CACCTCCTCC TGTTTCTCCA TCTCAACATC AAACAATTAA AAAAAAAAA     80940

AAAGGCTGGG CGCGGTGGCT CACGCCTATA ATCCCAGCTC TTTGGGAGGC CTAGGCGGGT    81000

GGATCACGAG GTCAGGAGTT CAAGACCAGC CTCGCCAAGA TGGTGAAATC CCGTCTCTAC    81060

TAAAAGTATA AAAATTAGCC AACCATGGTG GCAGGCGCCT GTAATCCCGG CTACTCGGGA    81120

GGCTGAGGCA GAGAATTGCT TGAACCCGGG AGGCGGAGGT TGCAGTGAGG CGAGACCTTG    81180

CACTCCAGCC TGGGTGACAC AGCGAGACTC CGTCATAAAA AAAAAGCCG GAAGCAGTGG     81240

CTCACGCCTG TAATTCCAGC ACTTTGGGAG GCTGAGTCAG GCAGATTACC TGAGGTCAGG    81300

AGTTCAGGAC CAGCCTGGCC ATGAAAATAC AGCCTGGCCA TGAAAACACA CAATAAATTA    81360

GCTGGGCGTG GTGTCACACA CCTGTAATCC TAGCTACTCG GGAGGCTGAG ACAGGAGAAT    81420

CACTTGAACC CAGGAGGCAG AGGTTGCAGT GAGTTAAGAT GACGCCACTG CACTCCATCT    81480

GGGCGACAGA GCCAGACTCT CTCTCAAAAA ACTAAATAAA TAAAAATAAA GTTATGGTAC    81540

ATTGAACTTC TGTGTTCCTT TCTCCCTTAG ATACTTTCAT GGCTACCCAT TTAATTGATG    81600

TTCTTATCAT CTCCAAGAGT TAGTCAGGAG AGGAATCAAC CCAAGCAAAA ATAGCTGATT    81660

TTCTAATTTT CCTTCAATGC CCTTTGGGGT CTTAATCCAT TTGATTTATG TACTTTCAAT    81720

TAATCCTAAC CTCGAATGTC TTCTGCAAAC ATGTTTCCAC AGATGAAACT CGTCAAATGA    81780

AACACATTCC TTTAATTTAT AGAGTTAAAA ATTAGAAAAA TTTTCAATTC TATTTGGCCT    81840

TTAGATTCAG TCTTGCATAT GTTTTCTCAA TTTTGTTCAT GCTCTTTAGT TTTGTTTTAT    81900

TCCATCACAA TTGTTCACAT AGCTTACTGG CTTAGGTCTA ATGAACCATT CATTTGGAAA    81960

TTAAAATTGG CCATTTTAAG ATGAAAAAGA TTCTTGCCTC AATTTTACTT AGTTTTTGAA    82020

ACTGTCAATG AGGACACATG TTTTTCTGTA CTCTTAGATT CACTAAGTAG TGTCTTGCAA    82080

ATTTAACTGA CAAAGGACAG ATTAACATGC GAAAAAAAA GCATGCAATT TTATTAGTAT     82140

ATTACATGCA CAGAGTTCCC AAAGAAAAAA AAATTGAAAC CTTAAAAACG CGGTTAGACT    82200

CACAGACTTA TACACCATTC CAACAAAGGA AAGGGAGTTT GCACTTCATG GGATGACGAA    82260

TTTGGGAATG TGACAAGGAA ATAAATACAT GGGCAATAAA AACCATGGAA GATAAAATGA    82320

AAGATAGAAA TAATTGTAGT AAGGTTTGTT TTTGCAGAGT CATCTCAGTG CCAACCTTCC    82380

ATATCTAGTG ATAAGAATTG CTCTCTTTTT CCTGGTATAG CAGTTGGGGA CACTTTTACA    82440

AGGGAAATTT CTGTCACCTT CACAAAGGGA AATTTGGGTA AAGAGAAGAC AGAGACCTCT    82500
```

```
TCCTACACCT GTTGATTTTC AATTGCCTTC AGCTGAAAAT AACTTTTATG CCAAAGTAGA    82560

ATAATTTGGG GGTGACATCC TGATATTCTT CAAAACTTAT ATTTAATTTC ACATTAGTAA    82620

TTATATCATT TTTGATTTTT AAATTAGTTT TATAAAATAA TTTTGAAAAA CGGTAATAAT    82680

ATTCAAATAA TTCCAGAAAC ACTGCTGATA AGCCAAAAAC ATCAATGAAT ATTGCATAAA    82740

CAACTGATAA TTCAACCATG AAAATTTATG ACATTGTTCT TGTGTGATAA AACTATGAGT    82800

AACATAAAAA CTAGAGGCTA CTTGTAATGC ATTATTCCAA ACTTTCTGTT TTTTATTTAT    82860

TTATTTATTT ATTTTGAGAC ATAGTCTCTC TCTGTCACCC AGGTTGGAGT GCAATGGCGT    82920

GATCTTGGTT CACTGCAGCC TCCACTTCCC CGGTTCAAGC AATTCTCCTG CCTCAGCCTC    82980

CTGAGTAACT GGGATTACAG GCACCTGACA CCAAACCCGG CTAATTTTTT TGTATTTTTA    83040

GTAGAGACGG GGTTTCGCCA TGTTTGCCAG GCTAGTCTCG AACTCCTGAC CTCAGTGATC    83100

CACCTACCTC GGCCTCCCAA AGTGCTAGGA TTACAGGCGT GAGCCACCAT GCCCGGCGCA    83160

TTATTCCAAA CTTTCATACA CAGTGCTATC ATGGCTACAA ATTGAAGTAT CATATTATAC    83220

ACTCCTAGGC AAAGCTCTGG ATATTTTGGC TATATAAGCC TGAGGGAAAT GTAGTAAGGA    83280

CATTGTGGTT GAAATTCATA CCAGAGATGA ACAGGCCCAG TGCAAGACAG AATTACATCA    83340

CTAAAGGATA TCAGAAGAGA ATAGGGATTT AGGGTACAGT GGCAACAACA GTTTTGGGAA    83400

CTAGCATTTT TTGAGCACTT ATTTACAATA TGCCAAGCAC TGTTGCTGAT TACTCTATAT    83460

TTATTTTCAA ACACATTCTT GTCACAGCAC TTTGAAGTAA GTGCCATTGT CATTCCCACT    83520

TCAGGGTGAA GGACTAAAGC TTGGTGTCAT TAAGGATGTA GCTAGTTAGC TGTGTGTGTG    83580

TGTGTGTGTG TGTGTGCATT TTTTTTTAAA TTTAAAGTCA ATAAATTTTT ATTTGAAGAA    83640

TTTCACATCA AGGTAAACTT TGTTCCTCTA AAGAGCTGGA GTCAAAATGT ATCTTCAAAA    83700

GATTCATCTT CAAGTTAGCC CTTCTTAATA GAACTGATGC TTAATCCACA GTTGTCAGCC    83760

CACAGTTCTT TTATTTTGAC TTTTTTTTTT TTTTTTTTG AGACGGAGTC TCTCACTGTC    83820

ACCCAGGCTG CTGGGCAGTG GCGTGATCTC GGCTCGCTGC AACCTCTGCC TCCCGGGTTC    83880

AAGTGATTCT CCTGCCTCAG CCTCCTTAGT AGCTGGGACC ACAGGCGCAT GCCATCGTGC    83940

TCGGCTAATT TTTGTATTTT TATTAGAGAC AGGGTTTCAC TATGTTGGCC AGGCTGATCT    84000

CAAACTCCTG ACCTCATGAT CCGCCTGCCT TGGCCTCTCA AAGTGCTGGG ATTACAGGTG    84060

TGAGCCACTG CACCCGGCCT TATTTTGCCT TCTTTAATCT CCATTTGAAC ATGGACATAC    84120

TGATGAAAAC TACAACATTC TTCACCAAAA ATCTTTGGGA TTTAATTTCT TCAACCACTT    84180

TACTTTGGGG TCATTTTAAG ATTAGGTGTA TCTGCCTGGT TCTCAATTTG ACACCCTTTC    84240

TCTCTAAACA TGAATGAGTT CCAATCATAT TTATTCCTAA GCTATCACAC TCAAATATAC    84300

TACAGATCTG TGGAATATGC CAAAAGTTAA GGTGAAAAAT TAAATTATTA GGTATTTCAT    84360

AGTTTTGCTA GTTTTTGATC TGTGAGTGAA TATAACTATC CTCTATGTCC TGGCACTGTT    84420

CCTCAGAAAC ATAGGGTCCA CATATGTAAT TTTAAATTTT TTAATAGGCA CATTTTAAAA    84480

AGTGGAAAAA GAAATCTATT TTAATGATTT GAATCCAGTG TAACCAAAAA TTGTTTCAAC    84540

AAGGTATCTA ATATTAAAAT ATTGAGTTTT TACTTTGTTA TTTTACTAGG TCTTTGAAAT    84600

CTGGTGTGTA TTTTACACTT AAAGCACATC ACAGTTTGGA GTAGCCACAT TTCCAATGCT    84660

TAATACTCAC ATATGGTTAG TGGCAACTAT CTTGGACAGG ACAGCTTTTA TACTCTGGGA    84720

AGACACAAGC AAATACTTGC TCTGCAGCAG AATCCAGATG TTTTCCAAGA AACACTTTT     84780

TCTGACCTGT TCGTGAAACC CAGGTAGTGT CTCTAATACT TTATATTTTA TTGGTTTGTC    84840

CTATTGTAAC CACCCAACGG GCTCTCCTTG TCCACTTCCT AGACAGAGCT GATTTATCAA    84900
```

```
GACAGGGGAA TTGCAATAAG GAGCCAGCGC TACAGGAGAC TAGAGTTTTA TTATTACTCA   84960

AATCAGTCTC CTTGAGAATT TGGGGACCAA AGTTTTTAAG GATAATTTGA TTGTAGGGGA   85020

CCAGTGAGTC GGGAGTGCTG CTTGGTTGGG TCAGAGATGA AATTATAGGG AGCCTAAGCT   85080

GTCCTCTTGT GCTAAATCAG TTCCTGGGAG TGGTGGGGTG GGGGACTCAA GACCAGATAA   85140

TCCAGTTTAT CTATATGGGT GGTGCCAGCT AATCCATTGT GTTCAGGGTC TGCAAAATAG   85200

CTCAAGCATT GATCTTAGGT TTTAAAATAG TGATTTTATC CCCAGGAGCA ATTTGAGGTT   85260

TAGAATCTTG TAGCTTCCAG CTGCATGACT CCTAAACCAT AATTTATAAT CTTGTGGCTA   85320

ATTTGTTAGT CCTGCAAAAG CAGTCTGGTC CCCAGGCAGG AAAGGGGTTT GTTTCTGAAA   85380

GGGCTGTTAT TGTTTTTGTT TAAAAGCAAA AGTATAAACT AAGCTCCTCC CAAAGTTAGT   85440

TAATCCCAAA CTCAGGAATG AAAAGGACAG CTTGGAGGTT AGACGTTAGA TGGAGTCGGT   85500

TAGGTAAGAT CTCTTTCACT GTAATAATTT TCTCAGTTAT GATTTTTGCA AAGGCAGTTT   85560

CACTGTCCAC TTCACCTCAC ATCAGGCCTC TGACTAGAGG ATTCCAACAA TACTTAGGCC   85620

AGGACACCAC CATGTCTCCT TATCCACCCT GAGGGATTCC AATTTCTGAA ACAAAGGAAA   85680

CTATATATGA TAGTATGAAA CTATATATGA GAAGGAAATT ATATATGATA ATCAATTTTA   85740

GGGTTATCTT ATTGATTAGA AGATATTAAA GTGTGACACT GCCTGGCAAT GATATCTGCT   85800

GGTAGTAAGA ATTTGGCGAA TTTAGTGAAA TTCCTGAGGC TGAACCTCCA CTTCTGTAAA   85860

ATGGAGACAG TGAGATAATT TGCCTTACAA TGCTGAAGTA AGAATTTTAC ACAATAATTC   85920

AGACCAACCA CTTCATGTGG TACTTGGCCC GTGGAAGACT ATCAATGACA GTTAGTTTAT   85980

AGTTTATACT ATTAATGAAT CCTTTGTTTC ATTGTTATTT CCTTCTACAC GTTGGCCTCT   86040

CTAAAAGAAG GTAATATTCA ATACAAATAA AGTTAAAACA GCTTGCAGAG TTGTCCCAGG   86100

GAACTCACTT AACCACTGAA GTGTTCAAAT TGCTTAAGGT TGACTTTATA TTCTCCTGAC   86160

TAACCTTTCT CCTTCTGGTA TTTCTTCTGA GAACAGCACC ACCATCCAAA GCATCATGCA   86220

AACAGTGGTC ATCCCAGACC AGTAATTCTC AACTCACAGG GTGCTCCTGC AGAGATGTAT   86280

TTGAATAGAG TGGTAGGATG CTGAAGAAGG CCACGTAAAA TTTGGCCAGT GATCTGGGGC   86340

AGATTTATCC TGAAGCTAAT GAAACACAAG TGTAAGGGCC TGTACTTCCA AGGTGCAGAG   86400

AGGGGCCCTA CAAATGTGTT AGTTTGTCTC TCTCTCTCTC TCTGATTTTA AAATTTGCAG   86460

TATTAAGGTA CTTTAATCAC GGATGGTTCA GGCTGCTATT TTCACTCAAT CCTCCTTTTT   86520

ATTAAAATCA CCATTGTCTG ATTATGTTAG AATCCTGATG AAAATATTTG GAATTTGAGT   86580

AAGAGAAAGT TTAGTTGAAG ATGTATCTAG TATGGGGATA ATAAGTTACG TGATTTGCAT   86640

ATGTGATCAT GTGTACTTCA TTCGTTGCCA GCCAATCTGA CGTAAGAATG GCTTCAAGGA   86700

GGCCGGGCGC GGTGGCTCAC GCCTGTAATC CTAGCACTTT GGGAGGCCGA GACGGGCGGA   86760

TCACGAGGTC AGGAGATCGA GACCATCTTG GCTAACACGG TGAAACCCCG TTTCTACTAA   86820

AAATACAAAA AATTAGCCGG GCGTGTTGGC GGGCGCCTGT AGTCCCAGCT ACTTGGGAGG   86880

CTGAGGCAGG AGAATGGCAT GAACCTGGGA GGCGGAGCTT GCAGTGAGCC GAGATCGCGC   86940

CACTGCACTC CAACCTGGGA GACACAGCGA GACTCCGTCT CAAAAAAAAA AAAAAAGAA   87000

TGGCTTCAAG GAATGTTCCT ACTGCTCACT GGAATAACTC ACCTAAATTC CTGGCAAGAT   87060

GCAGGTCTAG ATAAAATGTT ATGACATCTA AGTATTCAAA ACACATTCCC AGCACTGAGA   87120

GTGAGTGTCT AGTGGAGAGT AGAAACGTAT AGAGCCAGAA GCTAGTCTGG AAAGAATTCT   87180

TACAAAGTTT ACAACTTACA TGTGAAAGGA GCTTAACAGA GGATTTTCCA AATTTGAAAA   87240
```

```
CAATCCTAAA AACTTACTTG ACATTACCAA TAATGTGTTT TGAAACTGAA ATACTTCTAA    87300

GTTATGAAGA AAACATATTA TCATCAGCCA CCCTGGAGGA AAGATTGAAT TCTATTTCCA    87360

TTACCTATAG ACAACATTAC AAAATAATTT CGATCTGAAG ATGGAATCAG AGTATTCAGT    87420

CAAAACTACA GGAAAATATA CTTGGTAGTG TCATATTCAG AAGTTAATAA AATATGCTAT    87480

TTTCTGAATT TTGTGATGGC TGTTGTTTTG TCAGCTTTTA TAAAATTGGA ATTTGATTTT    87540

ATTTTCCCAT TATAAATTTA TATTTACAGT CTGCAGTACT TTTGCATTTT TAATTTTACA    87600

TTATAGCTTT TAATAGTTAA CAAGTTGTAA AAGGTTTGAT CCCCAGAAAA CCTTGATCTA    87660

CCCCCTCAGT TAAGTATACT AATATATTTA GAAAATGGAT GAAATCAGCA TTTGAATATT    87720

TTTAAATATT TATTAAAAGA GGACATGGGT AAAAGAGCTT TGCAGTTGCC ACCCTTCATT    87780

CTCAAATTCC CTGGATAAGG ATGACCGCAT AATCTTTGGA TGGTCATACG CAAGTCTTGT    87840

GTATTTGTTA CATAAATCTA TTTAGTGGAC TTTTGGCAGT GTGTACTGAG GCCAGTTTCT    87900

TCCACCTGAG CTCTGACTCC ACCTCCAGCA GCCCAAAACC AATACTGAAT TTGGGGTCA     87960

GCTATTGTTT TTGTGGACTT AGGTAACTAC ACACACATTG TCTTTATGAT AGCTTTAATA    88020

ATACTGCCAT CAGAACTAAA ATTGTCACGT GGATTAAAAG GAGTGACGGT GGTGTCCCCA    88080

GGAGCCTTTC AATATGTAAG TATTTACACA TATACATGCT AAAAAGACCC CTAGGAATTT    88140

TTTTAACAAG GGCAAAACAG TAACTCAGCT TGTTTTCTCG CAGTAAAACC GGTTGAAAAG    88200

GCCTGATAGA CTTGTCTGCA GTTACAAAAC TTGTGTGTAG TTATCACCTT TATATCTCCT    88260

GGAAACTAAC ATAGACAACC GAATGGGTTA CAACTGTTTT TAAGTGAAAT TGTGAGTGGC    88320

TCTGAAAAGA GCCTTTTCAA TGAGGAAGAA ACGGGCAGAC TTATGCCCTT TCCCCACGGA    88380

TGCGACGTGC CAGCTGGATA TCTTTGGGCA TGATGGTGAC GCGTTTAGCG TGAATAGCGC    88440

ACAGATTGGT GTCTTCGAAG AGTCCCACCA GGTAGGCCTC GCAAGCCTCC TGCAGCGCCA    88500

TCACCGCAGA GCTCTGGAAA CGCAGGTCGG TTTTGAAGTC CTGGGCGATT TCTCGCACCA    88560

GGCGCTGGAA CGGCAGCTTC CGGATCAGCA GCTCGGTGGA CTTCTGGTAG CGACGGATTT    88620

CGCGCAAGGC CACGGTGCCC GGGCGGTAGC GATGAGGTTT CTTCACGCCA CCGGTGGCCG    88680

GAGCGCTCTT ACGGGCTGCT TTAGTAGCAA GCTGCTTGCG CGGAGCTTTG CCGCCGGTAG    88740

ACTTGCGAGC TGTTTGCTTC GTACGAGCCA TTTGCAATGA GAGCACACAC AAAAGTGTAG    88800

TGAACTGAGA GCAAGTGGCC TTTAAATATA GTGAGAAACA TTCTGATTGG TCCTGTAATA    88860

TTTCAAAAGT CCCGCGCGAT AAAATCATTG GCTGAAGAGT GACCAGACTG ATTGGTTCAT    88920

TACTAGACAA TCTTATTGGA TGAGTTGCCC CACCGCCCAT CCTGTCCTTT TCGTTTCAGT    88980

TATCTGCAGC GACAAATTGT CTAAAATTCT AGTTCATCCA GTCCCAAAGA ACAGAGTGTA    89040

TAACAAGGTA TCTAAGGATT TTTAAAATGT AAATTCCGAT TCAGTAAGTT TGAGTGGGAC    89100

TTGAAATTCT GCATTCCTGA CAGTCTCGCA AGTTATCAAT GCTGGTGAAC ACTCACTAAA    89160

CCACCAGAAA CGTTCAGACT CATGTCGGGA AATAACGCTT ATATTCAGAG AATGAGATTC    89220

CATGCTATTT TGTTACTGGC GAACAGCAAG TTTCCTTGCC CTTTGTTTTC TAAGTCCAAG    89280

TCACATTCCC ACCCTGCCTG TTCTCAAAAT GTCTTATTTT GGTTGGCCTT AAGTTTCACT    89340

TTGTATACTC TAAAATGTAC TTTCTAAAGG AAGGTGTTAT TTTCTCGAAA CTTAACTTTT    89400

TAACACCATT AGGCTAGGGG GGCGGTGGCT CACGCCTGTA ATCCCAGCAT TTGGGAGGG    89460

CGAGATGGGA CGATCACTAG AGGCCAGGAG TTCAAGACAA CCCTGGCTAA AATGGTGAAA    89520

CCCCGTCTCG CATAAAAATA CAAAAACTAG CTGGGCGCGG TAGCAGACGC CTGTAATCCC    89580

AAGTACACAG GAGGCTGTGG CATGAGAACC GCGTGAAGCG GCGGGGTGGA GGTTGCAGTA    89640
```

```
AGCCGATATC GCGCCGCTGC ACTCCAGCCT GGGTGACAGA GCTAGACTGT CTCAAAACAA  89700

ACCAATCCAA ACGAAAAGCA AAAAATACCC TAACAGAAGC AAGTTATCAT CCTTTCTTGT  89760

GTAACTATGG ACGGCTCTGA AAAATGCCGT TTCAAGTGTA AGCTACGTTT TCTGATTTGA  89820

GTGTTTACTT GACCTTGGCC TTATCGTGGC TCTGTTATTT TGGCAACAGG ACGGCCTGAA  89880

TATTGGACAG GACGCCTCCC TGAGCAATAG TGACGTTGCC CAGCTGCTTG TTGACCTCCT  89940

CGTCGTTTCG GATGGCCAGC TGCAGGTGGC GGGGGATGAT GCTGCGGGTC TTGTCACGTA  90000

TGGCGCTGCC CACCAGTTCT AAGATCTCGG CGGCCAGGTA CTGTAAGTAC ACTGGCGCAC  90060

CGGCTCCGAC CGGCTCAAAA TAATTGCCCT TTCGAAAAAG ATGACGGACT CTGCCCTATT  90120

GGGAACTGCA AGCCCGGTAG CGACGAACAA GTTTTTGCTT TAGCTCCATT TTCCACGTCC  90180

GCAAATAGCG ACCTATGAAA GCAGCGGAAA ACTGTGAAAG ACAAGCAAGC TGGAATGGCG  90240

CCTGAACAAA TCCTTTTATA CAAACTGCAA GGCTGCAATA GGAAGCTATC CTATTGGTCA  90300

ATTATGTTTG GTGCTTTATC CAATAGAAAA AGATAACATA AATTCCATAT TTGCATAAAC  90360

CCCACCCCTC AGTGAAACCG TGTTTCTTTT GTCCAATCAG AAGTGAGGAA TCTTAAACCG  90420

TCATTTGAAT CTCAGGACTA TAAATACATG GGCTCTGAAC TGTTCTCTGT ACTACTCTGT  90480

AGTGGAGAGT GTTAGTAGCT TTTCTATTCT GTTTAGGAAT AGCAATGCCT GAACCCTCTA  90540

AGTCTGCTCC AGCCCCTAAA AAGGGTTCTA AGAAGGCTAT CACTAAGGCG CAGAAGAAGG  90600

ATGGTAAGAA GCGTAAGCGC AGCCGCAAGG AGAGCTATTC TATCTATGTG TACAAGGTTC  90660

TGAAGCAGGT CCACCCCGAC ACCGGCATCT CATCCAAGGC CATGGGGATC ATGAATTCCT  90720

TCGTCAACGA CATCTTCGAG CGCATCGCGG GCGAGGCTTC TCGCCTGGCT CACTACAATA  90780

AGCGCTCGAC CATCACCTCC AGGGAGATTC AGACGGCTGT GCGCCTGCTG CTGCCTGGGG  90840

AGCTGGCTAA GCATGCTGTG TCCGAGGGCA CTAAGGCAGT TACCAAGTAC ACTAGCTCTA  90900

AATAAGTGCT TATGTAAGCA CTTCCAAACC CAAAGGCTCT TTTCAGAGCC ACCTACTTTG  90960

TCACAAGGAG AGCTATAACC ACAATTTCTT AAGGTGGTGC TGCTGCTATT CTGTTTCAGT  91020

TCTAGAGGAT CAACTGGAAT GTTAGCGAAG ACAAGTTTTA GAGCCAAGGT TAACTTGGAC  91080

GGGGCCGTGC GCGGTGCCTC TTGCCTTTAA TCCCGGCAAT TTGGGAGGCC GAGGCGGGCG  91140

GATCACTTGA GGTCGGGAGT TCGAGACTAG CCCGGCCAAC ATGGCGAAAG CCCGTCTCTA  91200

CTAAAATACA AATGATAGAC GGTCGTGATG GCGCTCTTTC TCATCTGTCT TAGCAAACTT  91260

CTTTGTTCCC CCTGGGTAAG CCTTCGGGTA CTATGTATAA TTCCTTTGAT AAGGTCACTA  91320

CTCCCTCCCT GGTCTAGTAC AGGAAACTTC CCTTTCTGGA TAATGAAGCA GGTAATGGAA  91380

TTCAGGGTAT AGTGTTCCTG TGGGGTCAT TAGCCGTTAA CTTCTTGTGA GATGCGGGGG  91440

AGGGGAGCAG AAAAGTCTAA GCGACAAAAG GGCATGTAGG GATATTTGCT CCTGCAGCTT  91500

GCCTATGCTG TAAATTCTTA CTTCAAGTAT TGAGGAAACA ATAAGCGAAG TCTGATTTCC  91560

CGGGCGCCTT TATACGGAAT ATTTCCCGCT CCACAAAATG AAATCGCAGT AGTTTTGAGT  91620

TATAATTGTT TATCAATGAC AACAGCTATG TAGTTTACAT ATTTCATGCA TCCCAGAAAT  91680

CCAGATTCCC ATTTCCTAAG CCACTTAACG TTCTGATTTC CAGCTCTGCG AGATACAAAA  91740

GGGTTTGGAT TTTGTGCCCT TCCCCATCTG GCGCCACTGC AAAGCTTACT AGGAGGGCCC  91800

CACTTGGAGA GGGAAATCTT TTTCGAGAAG TCCAGGACGC CAAAAACAAT ATAGCTAAAA  91860

AAAAAAAAAA AAAAAAGGCA GGAAGAGCAC TAGTTGAGGA GGAGGACTCA ATGGGCCAAT  91920

TCTGGGGCTG GGGCTGGGGG AAGAAATGCA AGAAGAAAAG ACACTTGTTG ACTGCACAGT  91980
```

```
AAGCAGGAGG GGGTGGGGGA ATCGGAGGGG AGTATTTTCA GCGAATTTAT GGGCATTATA    92040

TGTAGGTGAC ATACAGCAGT GTCTTTGGAT GAAGAAATAA AGTTTCTCAA ACAGTTCTTG    92100

TTTTTGTTTT GAGAAAGGGC CTTTCTCTGT CGGCCAGGCG CCATCATAGC TCACTGCAAC    92160

CTCGACTTCC CCAGCTCAAG CGATCCTCTT ACTTCAGCCC CTTGAGTGGC TGGGACTAGA    92220

GAAATGCACC ACCATACCCA GTTAATTTTT TAATTTTTTG TGGAGGCAAA GGGTCTTACT    92280

TTGTTGCCCA GGCTGGTCAA GCGAACTCCT GGGCTCAAAT GATCCTCCCG CCTTGGCCTC    92340

CCAAAGTCCT GGGATTATAG GAATGAGTCA CCGCGCCCGG CCCAGATTTA ATTTTTAAGA    92400

ATCTTTTAAA AGAGGTTCTG GGCCGGGTGT GGTGCAGCTC ACGCCTGTAA TACCAGCATT    92460

TTGGGAGGCC AAGGTGGGAG GATCACTTGA GCCCAGGAGC TCAAGACCAG TCTGGGCAAC    92520

TTAGTGAGAC CTTTTGTCTC CACCAAAAAT TTAAAAAATT AACCAGGCCT GGTGGCACAT    92580

TTCTGTAGTC CCAAGTACTG GGGAGGCTGA AGTGGGAGGA TCATTTGAGC CTGGAAGGTG    92640

GAGGTTGCAG TAAGCTGTGA CGGCACAACT GCACTCCAGT CTGGGTGAGG ACAGACCCTG    92700

TCTCAAAAAT AAAAAATAAA AAAAAATCTG GATGCCACAC AAAATGTCAG TGAACAACTG    92760

TAAGTGAAGC ACTTCCCATC CTAGTACTGT ATATGCAAAC TGCCGTTGTG AAAGTGACGC    92820

TTGGCTTAAA AATCTACATT CTTTTTTTAA TTATAAAACT ACCACATCCC CAAAAACAT    92880

TACTAAGGAA TTGAGGCTGC AGTTAAGAA GCTGATATTT AGGATCTATC TCCGAGAAG    92940

TGAGACCTGG TAATATAAGC ATTTTCAAAA TGAACTTTTG GGCCAGGTGA GGTGTGTCAT    93000

GCCTGTAATC CCAGCACTTT GGGAGACCTA GTCAGGCAGA TCACTTGAGC TCACAATTCG    93060

AGACCAGCCT GAGCAACATG GCGAAATCCA GTCTCTACAA AAAATTAGCA GGGCGTGGTG    93120

GCATATGCCT ATAGTTCCAG CTACTATAGA GGCTGAGGTG GGAGGATTAC TTGAGCCCGG    93180

GAGGCAGAGG TTGCAGCAAG CCAAGATCGC GCCGCCACAG CCTGAGCGAC AGAATGAGAT    93240

ATGCACCCAC GCCCTAAAAA AAAGCATGAC TCATTAAAAA AAAAAAATTT AGCCGGTCGC    93300

GGTGGCTCAC GCCTGTAATC CCAGCACTTT GGGAGGCCGA GGCGGGCGGA TCACGAGGTC    93360

AGGAGATGGA GACCATCCTG CTTAACACGA TGAAACCCCG TCTCTACTAA AAATACAAAA    93420

TAATTAGCTG GGCGTGATGG TGGGCGCCTG TAGTCCCAGC TACTCGGGAG GCTGAGGCAG    93480

GAGAATGGCG TGAACGCGGG AGGCGGAGCT TGCAGTGAGC CGAGATCGCG CCACGGCACT    93540

CCAGCCTGGG TGACAGAGCG AGACTCCGTC TCAAAAAAAA AAAAAAAAA AAAATTAAAA    93600

AAATATGAAG TTTTGAAGCA GAAATTATTT TGTCGTATGT TCTTTCATAA ATTTTTTGCC    93660

TGCCTGCCTT CTTCCTTTGT TACAGAACTC CAACACTTAC CCAAAGGTAG CTGTTGGGTC    93720

AGGGTTTCTG TACTATAGTC CCTTCTGTGG TGGCCAGAAA TATGTTACAG GAAAGAGGTC    93780

CCCATCCAGA CCCCAAGAGA GGGTTCTTGG ATCCCGCGCA AGAAAGAGTT CAGGGTGAGT    93840

CCGCAGTGCA AAGTAAATGC AAGTTTACTA AGAAAGTAAA GTGGTGAAAC GACAACTACT    93900

CCATAGACAG AGCAGGACAT TCCCGAAAGT AAGAGGAGGA AGGCATCCAC CCTAGGTACA    93960

ATACTTGTAT ATATGGGAG ATGTGCTCTG CTACAAGTTT GTGATAAAGG ATTAATTTTC    94020

TTAGTTACTA TATTTTGCAA GAATCAACAT TATTATCTTT AAACAAAATT AAGAATGCCT    94080

TTGTTCTCCA GATATAGGGA TATCTGGACA CTCCTAAGTC TGAGTCTGTT TAGTAAACAT    94140

TATTTATTTG TTCCCTTAAC CGTAAACATC TAGAAGCTAG GAATGACTGA CTTTCTGGGA    94200

ATGCAGCCCA GAAAGTCTCA GCCTCATTTT CCTAGCCCTC ACTCAAAATG GAGTTACTCT    94260

GGTTCAAGTA ACTCTGACAC TTTTCTTCTC TTTTTTTCTT CTTTTTTCCT TCCTTTATTT    94320

TTTATTTTTT ATTTTTGAAA TAAGAAATCA AGAATACTTG ATGTTTCATC TAAAACAATA    94380
```

```
CCCATAATTG ATAAGCCAAA ACAAAAACCT AGGTCTTCTA ACTCAAAACT AGGATGTTTT    94440

GCTGTCTCTG CTGATACTCG GCTGATCGTT AATAGGTAAT TAACAAACAA GCCTTGCTAT    94500

GTCCCCCTCA GTTTATTACC ATTAGATCAT ATGCCTACTG TCAATCATAT TAATCCACAA    94560

CTATGCATTT CACAAAACTT GCCATAAAAA TTCACAGGTT TCCCGCTTCC CTCGAGTTTT    94620

CATTTCCGAA GGGTCCCATG TAATATAAAA CTTATATTAA ATACATTTGT ATGCTTTTCT    94680

CTTGCTAATC TTTTTTTTTG TTTTTTGAGA CTGAGCCTTG CTCTGTCACC CAGGCTGGAG    94740

TGCAATGGCG CGATCTCGGC TCACTGCAAC CTCCGCTTCC CAGGTTCAAG CGATTCTACT    94800

GCCTCGCCCT CCCGAGTAGC TGGGACCACA GATACGTGCC ACCATGCCCC GCTAATTTTT    94860

GTATTTTTAG TAGAGACAGG GTTTCACCGT GTTGGCCAGG ATGTTCTCAA TCTCCTTACC    94920

TCGTGATCCG CCCGCCTCGT CCTGCCAAAG TGCTCGGATT ACAGACGTGA GCCACTGCAC    94980

CCGACCAATC TGTCTTTTTG TAGAGGGGCC TCAAGCATGA ACTTACTGAT GGGTGAGAAA    95040

AACAGAATTT TCTTTTCCCC TACAATATAA ACATTAATTG TAATGTTATC ATTCAGGACA    95100

TTTTGGTGAC CAATCTTACA GAAATTTTAT CTTGTGCAAG TCTATGCAAA CCAATATGTA    95160

AATCTTCTAT AAGTGAGATT GTATTTCACT TTTCTAGTAT CCTTTTAAAT TAATAAAAGA    95220

GATTCTAATG ATTATTTTCA TTACTGCATT TCATTGTAGG GAAGTAGATA ATTGCCCTTT    95280

ATTCACTGAC CTTCGCTTTT TAAAAATTTA AACCATGTTA CCATGAAAAT GCTTTTCAGT    95340

ATTTCTCTAC ACACAAGATT GCTGTAAGGG CAAAAATAGA GATAGGAATC ATGCATCCAT    95400

TGATATACAT ATTTTGATTT TTAATACATG TTACCAAGTT GCCTCCTGAA GGTCTGTTTA    95460

CACTCTCACC AACAGGGTGT TTTTTCCTGA CTTCCACAAA TGCTCTTGAA CAGTGGGTGT    95520

GTTAGTCTGT TCAAATTGCC GACATGAACA ATTAAATCTC ATTGTTGTTT TTATTTTTAA    95580

GACAATTATT GTTTGAGACT GCACATTTTG ATAATAACAT TTCTTCTATT ATGGTTTGAT    95640

TACTCATGAT TCTTGCCCAT TTTCTTTTGG GATGTTGCCT TATGTACATT ATTTTAAATA    95700

GATAGCTCCA TGTATTAAAA GATTATTAAG TTTGAGGGCT TATGATATGT CAGTTACATT    95760

TCTAAGATTT TTTTTTTTTT TTTTTTGAGA CGGAGTTTCA CACTTGTTGC CCAGGCTGGA    95820

GTGCAATGGT GCGATCTCGG CTCACCGCAA CCTCCGCCTC CAGGGTTCAA GCAATTCTCC    95880

TGCCTCAGCC TCCCCAGTAA TTGGGACTAC TGGCAAGCGC CACCACGCCT GGCTAATTTT    95940

GTATTTTTAT TAGAGATGAG GTTTCTCCAT GTTGGTCAGA CTGGTCTCGA ACTGCCGACC    96000

TCAGGTGATC CACCCGCCTC GGCCTCCCAA AGTGCTGGGA TTACAGGTAT GAGCCACTGG    96060

GCCCGGCCAC ATTTCTAAAT TCTTTATAAG TATAAATTCA TTCAATCTTC ACCAAAACTC    96120

AATGAAGTGT GAGTACTATT ATTATCATTG TTTTACAGAT CAAAACAAGT AATACAGTCA    96180

CTTACTGAGT TCTATACACC TGGTAATTTT TTTGTTTCGT TGTTCTATCA ATTATTGGGG    96240

AAGGGGTGTT GAAATCTCTA CCTTTAAATC ATGTATGTGT CTATTTCTCC TTTCGGTTCT    96300

ATCAGGTTTT GCTACACATA TTTTGCAGTT CTGTTATTTG GTGCATATAC ATTTAGAATT    96360

GCTTGTTTTT CGTATTGGAT TGACCCTGTT ATCATTATGT AATATCCCTG TCTGTTCCTA    96420

GTAATTTTCT TTGCTCTGAA ATATACTTAT CTGATATATC ATCCAAAAGA CCACCAGGAT    96480

GGCTAAAGAG TAGAAAGGAG AGATTACTG GCAATACTAA TTTGCAAGCC AGGAAGAGAT    96540

GGTCCCAGAA CCTGCCAAAA TTACTCTCTC TTTGGGGAGA AGGAGCAGGT TGGTTATTTT    96600

TATGCCTCAT AGGCTATATA TTACACAATA GAGTCATACA TATTTAGCAC GTTTGGGGGG    96660

ACAGCTATAT ATATTATGAG GGGTGCCAAG TGCATTCACA ATGGATAAAC ACGTGTAATA    96720
```

-continued

```
TACCTCCCAT GTTCACTTCG AGGTTAAATT TTGGTTAAAA TGAGGTAGAA TTTAGGTCTT    96780
TACATCACAA GGTGAACTAT AGGAACAAAG TTTACGTGCT GCCTCTAGCA GCTGGCTGAA    96840
AATGGCTTAA GGTCTACAAT TACGTGTAAG AATAGAATGT GTGTCAAGGC GGTCCTCTGT    96900
CCAATCAGAG TTGTAGTGGA CTGGACTGTA AATCAGAGTT AGGAGGGCTT CTGATAGCTC    96960
CTATAGTTAA GGAATTTAGC AAGTGTGAGT TTTTTGGTAG TCTTTGGAAT TTAGGAATTT    97020
GCCATGCCAG CCAAGCCATG AATGCTCTAC CAGTAGGTAA CTTTGTTTGC TTAATCTTAG    97080
AGTCTGTCTT AGTTGGTATA GGGGCATCTA TTTTGGTCTT TCAGATCCCA GATATTATTA    97140
ATACAGATAC TCTTGCAGTT TTGGGCTGAT GTTTATATGG CTTATCTTTT TTGCAGCCTT    97200
TAATTTCAAC CTGCGTTATG TTTATATTTG AAGTGAGATT CTTGCAGACA GTGTACAGTT    97260
GTTGTTTTTT TTTTTTTTGA GATGGAATTT CACTCTTGTT GTCCAGGCTG GGGTGCAGTG    97320
GCACAGTCTC AGCTCACTGC AACCTCCGCC TCCTGGGTTC AAGGGATTCT CCTGCCTCAG    97380
CCTCTTGAGC AGCTGGGATT GCAGCCATGC GCCACCACAC CCGGCTAATT TTTGTATTTT    97440
TAGTAGAGAC AGGATTCACC ATGTTGCCCA GGCTGGTCTC GAACTCCTGA CCTCAAGTGA    97500
TCCGCCAGCC TCGGCCTACC AAAGTGCTGG GATTACAGGT GTGAGACCTC GCGCCCAGCC    97560
AAACTGTTTT TTTATGGGTG TATTTATACC ACACACATTT AATGCAATTA TTGATATCTT    97620
AGGGCTTAAG TTCATGAAGG GTAGTGTGGG AACCATAGTC TCTTGGCCCA CTAAATGTTT    97680
GCCAGAAATC ACTGACAAGG CAGATTGATT AATAGGTGAA AAGGCATTTT ACCTATTGTT    97740
TAACGTGTCT ATGTGGGAGC ATTCAGAATT AATTACCTAA CTTCCCAATG AGTTATAGAT    97800
GCTTATATAC CATTTTTAGA TCACAGAAAG AATTGGGGCT TAGATTCTGG TAAAACAGGT    97860
TATGGGAGGC AAAAGAGGTT TGGCTTGCAA AGGTGGCCTT GTTAGGTAGG TGAAGCCTCC    97920
CTCAGAAAGA ACAGATGGTA AATGTTTCTT TTATGATTTT TAAGTGTCAG ACTCTCAGTC    97980
TCTCCTGGAT CTGGGGAAAG GTATAGAAAG GTGAGGAGGC ATGGCTGCAT TAATGGGAGAT   98040
TCTCTACAGA TGTAAAATTT TTCCCATTTA AGGCAGCTTT GCAAGCCCAT TTCTGCCTGC    98100
TGGCCAAGCA GCAGCCATTT CAAAATATGT CAAAGAAATA TATTTTGGGG TAAAATATTT    98160
TGATTTCCTT TAGACTGGTG GCCTTATAAG AAAAGGAAGA GACACCTGAG CTGACACACA    98220
TACCCTTGCT CTCTCAACAT GTTATGATGC AGTAAGAAGG CCCTCACCAG ATACTAATTC    98280
CATGCCCTTA GCTTCCCAGG TTCTAGAACA GTAGGAAATA AATTTCTTTT CTTTAAAAGT    98340
TAGCCAGTCT GTGGTATTCT GTTATAGTAT CACAAAATGG ACTAAGTAAC TATATTATGA    98400
TCATCTTACA TGACTGATCC CTCCTACATC ATACACATAC ACAGGCCACA TTTGGAACAT    98460
TGTTAGAGGT TCCTCTACCC AGTACAAATG TACTACAAAT TATATATGTA TTTTTAAATT    98520
TTTGAGTATC TTCAATAGTA TATTTTCGTT AACTTTTGTA GTCAAAATGT CATTATAACA    98580
TGTATTCAAT ATGCATAATT ATTAGTCAGA TGTTTTACAT TCTTTCTTCA TACTAAGTGA    98640
TATGGTTTGG ATATTTGTCC CCTCTAAATC TCATGTTGAA ATGTAATCTC CAATGTTGGA    98700
AGTGAAGCCT GGTGAAAGGT TTTTGGATCG TGAGGGTGAA CCCCTCATGA AGCGCACTCT    98760
TCAGGGTAAT CAATGGGTTC TCACTTTGAG TTCACAAGAG ATCTGGTTCT TTAAAAGAGT    98820
GTGACACCTC CCCCATCTCT CTCGCTCAGC TCTCACCATA TGATATGCCT ACTCCCTCTT    98880
CACCTTCCAC CATGATTGGA AGTTTCCTGA GGACTTGCCA GTAGCAGATG CCTGCACCAC    98940
ACCTCCTGTA CAGCCTGCAC AACCGTGAGC CAAAAAAAAT TACTTTTCTT TATAAATTAG    99000
TCAGTTTCAG GGATTCCCTT ATAGTAATGC AAGAACGAAC TAACACACTA AGTCTATTTC    99060
ATATTTACAG AATAGCTCAA TCTGAAGTAC CCTTTTTCAA CTTCACAGTA GCTACTTGTA    99120
```

```
GCTAGTGGGC ACTGATTTGG AGCGTGTTCA AGGGTGAATT GTATTATGCA ATTAACAGAT    99180

TTTTTTTATT GTTTTCGCAA ACCACGAGGC ATAGATTGTC TTACTTTCTC TGCTCCTGGT    99240

GTTGGAGTTG TTATTGGGAA ACAACTTATT TTCCTCTTAT ATTTATATGG AATAAATAAC    99300

CCCCAATATT TCCCTCCCCA ATATCTGCCT TTTGTATGTT TTTTGAAGGC AAGTGCCTAG    99360

AATTTACTGT TTTTGAAGCA CTTACTGAAA GGATTGCCAT CAAGTTGTTT TGCTAATAGT    99420

ACATGCCAGG CGCTTGTTGG TTTGCTTAAT TCAAGGTAAC TTGGATGAGA AGAAGAGTTT    99480

TTCTCATCCA TGGCTCAGTG GAGTATAGAT TACTGATATT GTGACTGGAT GTACTCCTGC    99540

TTTCTAGTCT GAGTTTTTGA AGCTACCCTT AATCTTGGTT TCAATTTTAT CTAGCCCTGT    99600

ACATATCCAA GGCTCTTTCC AAAATGGTCT ACGATTTGTT TAGGAAGTTA GAATAGCTGT    99660

ACTTTCTGAA CCACGGTTCC TGACATTTTC TGGACTTCAA ACACATCCAG CATTTTATCG    99720

AAGTATTTAT CCTTCCTACT TGGCTGGCTT CTTCCTTGCC TTCAGGTCTG AATTCAAATG    99780

ACATTCTCCT GATGAAACTT TCCATCCTTA TTTCTATTCT TTTTTCTTAT CCCCTTTCTT    99840

TATTTTTCTC CACAGCACTC ATCACTTATC TCTACATTTT CATTATGTAT TTACCTTATT    99900

GTGCACCTCC CACTACAAGA CAAGTAGCAC CGTAAGGAAA CAGGTTGTCT GCTTTTTCAC    99960

TGCTATGCTC CCTGCACCTA GAACACTCTC TGGCACTTAG CAGGTTTTCA GTAAATATAT   100020

GCTGAACTAA TAATGCTGGA TATACATCTC CCTCATGAAC TCTCTAAATC CTTCTAATTT   100080

ACATTGATCA ATCTTCTTTT CCATGTGCTT TTGTATGATT TATTGCTCAA ATCTTTATT    100140

TTGTATGCAG AACGTGCACT GCTATTTAAT CTTCATGTAC GTAAGTCCTC CCTTCTCTGA   100200

GTATAATCTC TTCAGGGCAC TATCTGAGAT AACTTTTTAA CATCTCCATC ATGAATCTTG   100260

TACCTTTTCA AAGAAAATGA GCCAGTGATT ACTGATGTTT ACGGCTATTG TTGAGGGTGA   100320

AGATCATTAT AATTTTGAAA AGGGAAGTTG AATATTGTGA AGGGAAAGAT AACACTAGAG   100380

TCAGAAGACT TGGGAGAAGG CAAAAAACAA ACTAAAAATG AGCACTTTTA GTCTCCTGAC   100440

AGTTTCTCTG AATCAAATCC ATAGTTCTGT GACAGCGTTG GCTTAGAAGC AGATTTTTTT   100500

TTTTTTTTTT TTGAAATGGA GTTTCGCTCT TGCCCAGGCT GGAGTGCAGT GGCACGATCT   100560

CGGCTCACTG CAACCTCTGT CTCCAGGGTT CAAGCGATTC TCCTGCTTCA GCCTATGGAG   100620

TAGCTGGGAT TACAGGCTCC CACAACCACG CCCAGCTAAT TTTTTGTATT TTTAGTGAAG   100680

ACTGGGGTTT CACCATGTTG GCCAGGCTGG TTACGAACTC CTGTTCTCAA GTGATCTGCC   100740

CGCCTTGGCC TCCCAAAGTG TTGGGATTAC AGGCATCAGC CACCGTGCCC AGCCAGGAGC   100800

AGATTTTTTT ACACTCATGT TTCTTTTTCC TTCTGTCATC CTGTTTCAGT ATAAGCAGAC   100860

CACAGATAGA AGTAGTAGAT ACCTCAGAAA TTCCTGGAAT AATTAATCCA CGTTCATCTG   100920

TACTCCATCT GCTCCTATCT CATGGAATAT AAAAGGAAAA ACACCAAGAT TCCCTAGGC    100980

AATCTGTCTT GATTTTAGGT TCCTAACAG GAGAGCCAGA CAATGGCTGT AATAATATTG    101040

TCCCGGCCAA GGAAAAACTT CCCCTTTGCC CTCCCAAGGT TTATGAAAAA TTACTGGCAA   101100

AACACAGATT AACTGGAGAA AAGGCATATA TATTTATTTC ATCACAATTT TACAGGAGAT   101160

TTTAGAATTA AGACTGAAAG ATACAGGGGA AATTGCCCAT TTTTATGCTT AGGTTCAACA   101220

AGATAAACAG CTGTATAGGG TACGATCTAA TGCTAACAGA CTGAGTGGGG AAGCCCCGCA   101280

AGGCTTGTCT GTCAAGATTC TTCTTGACCT CTCAGTGCAG CATTTCTTCC TTCTGGTTAT   101340

AGGACAAGAC TCTCTTTTAG AATGGGGGGT CTTATGACCT ACAGGCAAAC AAGGTAGGTT   101400

AGAGTAATAT TTTTAGGTTT TATGGCTGGT TCTAGGGAAA AGGAGTTCTG GTTTGTATGG   101460
```

```
CCTACCTTGA GGAGGAATTC TGGTTTCTAT GGCTAGACTT TGGGGAGAAT GGGACTTACA  101520
GACAGGAAGG CAGAAGGTGG TCAGTGAAAC ACTTTTATAA TCATAATCCC ATTTTGAGTA  101580
TTTCTGTGTT ATGGAATGTT TGTTCTCTCA TTTCCTGAAA GATTCCAGAG ACTCCTCATT  101640
CAGTGTTGTG AAAAAGTTCA GGAAATGCAA CTCAAAAATG TGCCACTTTG TTACGCTGAT  101700
TTCTTTGAAC TGAGGGCACC TAGGAAACAG TAAATTCAAG GAAGGGCTTT CGCTGAACTC  101760
TAATCAAAAA TTTGAAAATT AAAAAAAAAT TCAAAAGGA ATTTAGTTGT TAAGATTCAC  101820
TTCCCTGGGG AATCTCATCA ACCAGAGAAG ATTAACTGTA TCACAGGAGA GGAGACTGGT  101880
GGTTAACACC ATCTAAACAG ACTTTGTCAC AGCTGTCACC TATTCTTTGA AACACCCATT  101940
TATTTTTCTC CAAAATCATA TACTCTCCCC TAAGTTGCCT ACATCCCCCT TCTTTCTCCC  102000
TTATGAATCA AGAGAGCTTA TAAGCTTCTA CAGTTCACTG GGATTTGGGG TATTCGCTTT  102060
TCTTCCCTCC CACTCCCCCT CCCCTTTTTT TGTCTTTGAG ACACAGTCTT CTGGCTCTGT  102120
CGCCCACGCT GGAGTGTGGT GGCTCTATGT GAACTCACTG CAACCTCCTC CTCTCGGGTT  102180
CAAGCGATCC TCCCACCTCA GCTTCTCGAG TAACTGGAAC TACAGGCGTG CACTACCAAG  102240
CCCGGCTTTT TTTTTTTCTT TTTCTCCCCC GTTTCTTTTT TGGTTATTTT ACTGGAGACA  102300
GGGTTTCTCC ATGTTGTCCA CGCTGGTCTC GAACGCCTGA CCCGCCGTCC TCGGCCTCCC  102360
AAAGTGCTGG TATTACGGGC ATGAGCCACT GCGCCCGATT TGAAGGACCT CTTAAATATC  102420
TATTTAGAAA TTGGTCGGAG TCCACTCCTT TCCAAAAACA TGAGTCACAA TCCGGGAAAA  102480
GCACGAGCGG CTGAAAGTCA AAATAACCAG AACAAAACCT CCACTCATGC TTAAAAAAGG  102540
TATTTTGACA AAATCCTAAT TCGGCCAATT ATTATTAGTA TTCAAGTCGA AGGCTCGTCA  102600
AGCCAGACTG GGGATTGGGT CAAACATAAA CCTTACACCA GACGGAAGGA TTACATGCAA  102660
ATGAAGGATG CAGATTCTGA TTTCCCATTG GGTATTTGAC ATTAGCCAAT GGGAGAATTC  102720
CTCACAGCCT ACCTCCAGTC AGTATAAATA CTTCTCTGCC TTGCGTTCTA ATGTAGTTTC  102780
ATTACATTTT CTTGTGGCGA TTTTCCCTTC TTATCAGAAG TAGTTATGTC TGGTCGCGGC  102840
AAACAAGGCG GTAAAGCTCG CGCCAAGGCT AAGACTCGGT CTTCTCGTGC AGGTTTGCAG  102900
TTTCCTGTGG GCCGAGTGCA CCGCCTGCTC CGCAAAGGCA ACTACTCCGA GCGCGTCGGG  102960
GCTGGCGCGC CGGTGTATCT CGCGGCGGTG CTTGAGTACC TGACCGCCGA GATCCTGGAG  103020
CTGGCGGGCA ATGCGGCCCG CGACAACAAG AAGACCCGCA TCATCCCGCG CCACCTGCAA  103080
TTGGCCATCC GCAATGACGA GGAGCTTAAT AAACTTTTGG GGCGTGTGAC CATCGCGCAG  103140
GGTGGCGTTT TGCCTAATAT TCAGGCGGTG CTGCTGCCTA AGAAAACTGA GAGCCATCAT  103200
AAGGCCAAGG GAAAGTGAAG AGTTAACGCT TCATGCACTG CTGTTTTTCT GTCAGCAGAC  103260
AAAATCAGCC TAACAGCAAA GGCTCTTTTC AGAGCCACCT ACGACTTCCA TTAAATGAGC  103320
TGTTGTGCTT TGGATTATGC CGCCCATAAA GATGTTTTTG AGGTGTTTTT AATGGCTTTG  103380
AGTGTGGCAC TTTTAGTAAT TTGTCCTGCA GAAATTAGAT CCATAGAAAC CTCAGGAATT  103440
CTAGGTATGT GGGAGAAGTG CCATGCAGCA CAAAACATGT TTACAGGGGT GATTCGCGTT  103500
AAGTTTCACA CACAGCAGTT ACTACATTTT AGAGGAAGGA AATTATACCC ATGAGTGCAT  103560
TCCTAACTAT CTTGAATGGA AGTGTTAAAA CCCGCATGCC CCACACAAGT TTGAATATGT  103620
CATACCATTT GCTGTAGCAA TTAATGGCAT ACACAATTGA GAGCACACAC ATTACCACTG  103680
AACATTTGAG TATGTATTTC CCAAAATGAG CTTTTTTCCA GTTTGGGGAT GTTTTGCTTT  103740
GTTTTGGGGT GGAGTCTCCC TCTCGCCCAA GCTGGAGTGC AGCGGCGTGA TAACAGCTCA  103800
CTGTAACCTC GAACTCGGGC TCAAGCGATC CTCTTGACAG CCTTCTGAGT AGCTGGGATT  103860
```

```
ACAGGCGAGA GCCGCCACGC CCGGCTAAGA GCATTTTTCT AATTGCCCAC ACTTCTTATG 103920
CGACACCCAG AAAAATACAA TTTTAAATAA AGCGCATATG CAAATTTCCC TAATCGTCTC 103980
CAATATTCTC TGATTTCTTT TTTATATTTT AACTAGAAAC AATTGGAGGT TTCCGCGTTG 104040
CTTTGTGTGG TTGTAAATTT TAAGACTTCA GGAAACTTTT CCAGTACAAG ACTTGTCCAC 104100
AGTGGATATA GCAGCTAAGG GGTTAACAAA ATGACGTCAG AGTAGCTACG GTAATGGGCA 104160
GGAGCCTCTC TTAATCTGCA ACCAGGCACA GAGATGGACC AATCCAAGAA GGGCGCGGGG 104220
ATTTTTGAAT TTTCTTGGGT CCAATAGTTG GTGGTCTGAC TCTATAAAAG AAGAGTAGCT 104280
CTTTCCTTTC CTCCACAGAC GTCTCTGCAG GCAAGCTTTT CTGTGGTTTT GCCATGGCTC 104340
GTACTAAACA GACAGCTCGG AAATCCACCG GCGGTAAAGC GCCACGCAAG CAGCTGGCTA 104400
CCAAGGCTGC TCGCAAGAGC GCGCCGGCTA CCGGCGGCGT GAAAAAGCCT CACCGTTACC 104460
GCCCGGGCAC TGTGGCTCTG CGCGAGATCC GCCGCTACCA AAAGTCGACC GAGTTGCTGA 104520
TTCGGAAGCT GCCGTTCCAG CGCCTGGTGC GAGAAATCGC CCAAGACTTC AAGACCGATC 104580
TTCGCTTCCA GAGCTCTGCG GTGATGGCGC TGCAGGAGGC TTGTGAGGCC TACTTGGTAG 104640
GGCTCTTTGA GGACACAAAC CTTTGCGCCA TCCATGCTAA GCGAGTGACT ATTATGCCCA 104700
AAGACATCCA GCTCGCTCGC CGCATTCGCG GAGAAAGAGC GTAAATGTAA AGTTACTTTT 104760
TCATCAGTCT TAAAACCCAA AGGCTCTTTT CAGAGCCACC CACTTATTCC AACGAAAGTA 104820
GCTGTGATAA TTTTTTGTTG TCTTAACAGA ACAAATTTCT AAGGACCCCC CCGGAAAGCA 104880
TTAGACTATG GTCTTAAAGT TGATTAACAG AAATAACGGT TTGGTCAGTC TTGCAGTGTA 104940
GGTTATTTCT GACCTTATTA AGGTGCTATT TGGAGAGAAG CTGTGTAAGT CCACTATCAT 105000
TCAGGCCTCT AGCTTGCTAT GATTAGCATT TGTTTAAACA ACTTTGTAAG AGTAAGGGAA 105060
AAATCTGGTA AGTAGTTAAC TGGCGCTTAC TAGGCATTTT TGCAAAGCTT TGAAAGATT 105120
AGAAAATTGT GTCTTGCGAG TTCCAGTGTC TTCCTCAAAA TGCTTAGGAA GATTTTCTCA 105180
GCTCAATACA TAGTCCCCTA GGTTTTCTCA TATATTATAT ATATATATAT ATATATATAT 105240
ATATATATAT ATATACTGTT AAATTCATTT GGCTGTTAAC ATTAACCTGA AATTTATTCT 105300
GGTGCAAAAT GTGAGGCAGG GATCTAACTG GCTCTCATTT TATCCATAGC TAGCTACCCA 105360
CTTTAAATCT GTCAGTCTGT CGACCAAGCA TAATTTAATC CCTTATATAT GAATTTTAT 105420
ATGTGTGGCT TTGCTTGTAA ATAGTCTATC TGGTTGCATT GCTTTGTCTC CTCTAGGACT 105480
ATGCACCATG ACATGCCACA TTCTTTTTTT CAGTACTTCT TGCCTGTAGT TATTAAAATC 105540
TAGAATTTAC AAGTTTTAAC CATTTTCTTT CTGTTGATCT TGCTTTTCGG TTTTGGAGGT 105600
TGGGATTGA GTACTGGAAG AAAATTTAGA GGGATGGGAA TACTGTACGC AAACAAAAGT 105660
AATATTTACT TTAAAATTTT TATATTTTGT ATTTTTTTAT CATATAGCTT TTACATCACA 105720
TTTTACAGAC TAACTTTAGA ACAACCACAG AATGTCCAAC ATTAAAACTA CTAATTCAA 105780
AGACCTTGCC TCACATTCTT TTTTACAATA AATATTTTTT ACACCTAACA TTCTTTCTTG 105840
GCCTACATCT AGAATGTAAA CTGATGTACC ATACTAAAAT CGCCTGACCA ACTGTCAACA 105900
ACAACAAATC ACACACACAA AAGATCAAAT TTGAATTGCA TCGTTTACTT AAATTCATTT 105960
GTGTTCCAGC TTTTAATAAG GCAGTTTTTG GTTTATAAAG TAATATTTGC ATTTTAAAAA 106020
TTATGAAAAT GAATATGTCA GTTTGTTTTA TGATTCGTTT TTCTTGACTC TTATACAAGC 106080
GACTCTAACT GGCATAGACA TTTGTTATCC ACAGACAGTA TAGATATGTT AGAGATGCCA 106140
ATGGACTTGG TCTATGCCAA GGTGACTACT CACAAGCTCT GGGCCCAGCT GAAGGTCAAG 106200
```

-continued

```
TATTTTTTTT CCAGTTATAG ATGTGCTGGA TCTGATGTAT AGCGCTTGAC TTTTTATATT    106260
TTCTTTATCT GTAGGAAACA AATGTGTTGG AGGTACTGGG TCTGACGAAT AGCATAAAAG    106320
AATAAAGTTA CATTACTGTC TGAGGATCAG ATGGACAGGG GGTGGTAGCT CAGTCCAGCT    106380
ATTTTCCACT CCCTCACTTA CATTCTTTGC CCCCTCCTCA ACAGAACAAG GATTCTGCTG    106440
TAACTCTTCA TTGACAGTTG ATATTTAAAA ATTAACGAAT GGATGAAATT CTCATTTGTG    106500
AAAGAAAATT TATTGAGCAT TTTGTATTTG TGAGTAGTGC AAACATTTTA ATATTATATT    106560
AAGAATCTAT TGTTTTGTAT TAGAGGAGTA ATTAAGGAGA GATTGGAGAC AAAAAGGGGG    106620
TGTTGTTTGC AGAATATACC ATCCAAAAAT AGACCACTGT GGGATCAGGA TTCTTTTGAG    106680
CTAAAGGCAC TTCAAAAACA GCATTCAAGA AGGGAATTCT TCTAAACTTT TCTTTCTGAA    106740
AACAGGAGAT AAAAGTTCCA ATGTGAAAAA TGCTCTGCTT GTACCAGGTG AAAAGACATA    106800
TTCTTCAGCC CAGAGGCATA GATGAGATAA TTCTGCACAA ACACAGCAGG GAGTCATAGC    106860
CGAGAGACTT CTATACACAA ACAAACCTTG TTAAAATAAT CATATATTCC TTTAATCTCC    106920
TCATATGGTT TACTTTCCCA CAATTGCCTC TCTTTAACTT AATGTGAAAG CATTTAGCTT    106980
TTGCCATTTC TTTGGGGCTT CACTTTTTTA TGAGGGTTCT CCTGTCCCAT AAAATTTACA    107040
TTAAATACAT TTGTATGCTT TCATTCTGCT AATCTGTTTT ATGGCAAATG AATTATCAGG    107100
TCCAGCTGGA GACCCTAACA GAGTAGAGGT AAAATTTTGC CTCCCTACAA GATAGAGATT    107160
GTGTGCATTA AATGTTGTTT GTTCCCAGTT GTTCAGTTTG TCAGGCCTCT GAGCCGAAGC    107220
TAAGCCATCA TATCCCCTGT GAACTGCACG TATGCCTCTA GATGGCCTGA AGTAACTGAA    107280
GAAACACAAA AGAAGTGAAA ATGCCCTGTT CCTGCCTTAA CTGATGACAT TACCTTGTGA    107340
AATTCCTTCT CCTGGCTCAT CCTGACTCAA AAGCTCCCCC ACTGAGCACC TTGTGACCCC    107400
CACCCCTGCC AGCCAGAGAA CAACCCCCTT TGACTGTAAT TTTCCACTAT CTACCCAAAT    107460
CTTATAAAAC GGACCCACCC CATCTCCCTT CGCTGACTCT TTTCGGACTC AGCCCGCCTG    107520
CACCCAGGTA GAATAAACAG CCTTGTTGCT CACACAAACC CTGTTTGATG GTCTCTTCAC    107580
ACGGACGCGC CTGAAACAGT TTAACAGGGT TTTTCCTGCC CAGTCACAAC AAAGTGATGT    107640
TATGCTGCAG GCTGAAGTTT ACAGCTAATG CTGTTGAAGT CTAAAATCAG TTTTGGTTTG    107700
TTAGATTTGG GTGAGATGGC TAAGATTCTC AGAGAAAGAA GTCAAGTTTG GGGTGCATTT    107760
TTCAGACTTA AAAATTTAGC AGTAGCCCTT GCAGTTTTTC CAATAGAAGT GATTTACGAA    107820
TGTTTTCAGG AAATTTAAAA CAACAGTGAG AAGCGTGTAT GGAGAGTTGA ACTACACTCC    107880
AGACTTGGCT ATAGGAAAGC ACGAATGCTG CTATTGTATT GCACCTTGGA AAAGAGAACA    107940
AAGGAATATT TTCGGACAAT TTTAACATGT CACATATGAA AAGCTAAACG GAATCTGTCA    108000
ACACCTTGTA CGTTATTACA GGCTGTGATT TTAAAAAAAC AATCCTTACT AATACATACA    108060
TAGTTGCTGC TAGCAATATA GTGTTGGGAG TAAAAACACG AAAATGAGAG TTCAGGACAA    108120
TATCCCAACT CTGAGCAGAT TTTTTTAAGT AGTAACATCT AAAATTAAAC CATATTATGT    108180
AATATTTATT TCTTTTCCAC AGTCTCTTCT CATGCCTCGT TCACATTAGC TAATTAAAAG    108240
TCCCCTGAGT ATCATCATAA CCCGATTTAC AGATGAAGGC ACGGTTGCAA TGAGCTATCA    108300
CCCTCTTCTG AATGAGACAG TACAGTGTGA AGGATAGCAA AACTCCACTC CCATCCTCTT    108360
AGGGCTCTGG CTGGACCAGC AAATTAAATT AATGTAAAAT GGATTAACAG GAGAAAGGTA    108420
TATGCATTTA TTTAACACAG GTTTTACGTG ACACAGGTGC TCTCATAAGG TAATGAAAGC    108480
CCAAAAAAAG CAGTTAGCTA CTTATATAAT GAATTGGACA ATTAGTAAAA TGTAAAAATG    108540
CGCTAAAGCA AAGGGATTTA GGCTAGAATA TATAACTGTG TAGAGAAGCG CCCAGCAAGG    108600
```

```
GCTAGTGCAA GGTTTGTACA GAATTCTCTT GGCCTCAGCC TCCTATCCTT GAGAAGAATG    108660
TTGCTTTTTT TAAACTACAG TGAGAACATC TTTCATATGA GAATTTCACC TACTGCTTCT    108720
AAGAAACAGG TCAGCTTTCA AGAAAACATA AGGCCAGAGT GATCTTTTCA CGCCTGCTCT    108780
TTTAAGTACC TTTGAATAGT CAATATGTCT TCAAGCACTT GAAAGACTTA AAAGTTTAC     108840
CACTCCGGCA TATTAGTGAA AGCCCTTAAT ATAAGCCCTT ATTAAAATTC TCAGTCGAGG    108900
GTATAAATTC AGATTCAAAT AGTAGTGTCG TAAACGGGAG GGAAAAACTA AAGGGATTAA    108960
AAAGTGAAAC TATTGTGTTC TCCCTCGCAG TCCTTAGGTC ACTGCCCCTC GAGGGCGGA     109020
GCAAAAAGTG AGGCAGCAAC GCCTCCTTAT CCTCGCTCCC GCTTTCAGTT CTCAATAAGG    109080
TCCGATGTTC GTGTATAAAT GCTCGTGGCT TGCTTTCTTT TCGCGTACCT GGTTTTTGTT    109140
GTCAGCTGGT TAGACATGTC TGGTCGCGGC AAAGGCGGTA AAGGTTTGGG TAAGGGAGGT    109200
GCTAAGCGTC ACCGAAAAGT GCTGCGGGAT AACATCCAAG GCATCACCAA ACCGGCCATT    109260
CGGCGCCTTG CTAGGCGTGG TGGGGTTAAG CGAATTTCCG GTTTGATTTA TGAGGAGACT    109320
CGTGGCGTTC TCAAGGTGTT TCTGGAGAAC GTGATCCGGG ACGCCGTGAC CTACACGGAG    109380
CACGCCAAGC GCAAGACTGT CACTGCCATG GATGTGGTTT ACGCGCTCAA GCGTCAAGGA    109440
CGCACTCTGT ACGGCTTCGG CGGTTAATCT TTTCGTCAGT TTTCTTCCAA TGGCCCTTTT    109500
TAGGGCCGCC CACTCCCTCT CAGAAAGAGC TGTGATTGTA TTCTTTCGGA TGGTAACATC    109560
TCAATGGCTT TACTCGGCTA TTCTGCCTAG TATGTAGAAC TATTATAAAC CAGTTGGGAG    109620
AGACCAGGTT GTTTGGTCTG AGTGGCTGCT AAAGCAGAAA TCAGCTAAGT AAACGAGGTC    109680
TCCGAGATAA GTGAGCTATA AACTTCAATG CTATAGTTTT GACATGTCAA GCAACTTAAC    109740
GTGCAGCGCG AGTCCGATAA ATGAGTAGCT CAGCTTTTTA GTTTTAAAAA CGAGTTGTGC    109800
GTTATTTGTA CGAGAGCCTA AGATGCTAGC TGCCTGGAAC TGAGTAGGTG GATTAAAATG    109860
GGTGTCAGGT CTGTTTTCCC AGGCGTATCT GACTTAACGT CAGCAAAAGC TGTACTTTTA    109920
GCTTCCCTGG TAACACCTGC CGTCCTTAAC CGCCCCCTGC CGGTAGCGCC AGAAGCCTTT    109980
ACTTCCATTT CTAGTTGAGC TTGGCGTCCT GCTGAGTGAC GTCACCTCCC CCTTCTGTGG    110040
AGTAGGACTG GCGGTTAAAG CTGCTTTGCT ATTTTCAGTC CTCAGGCTGG AGGCTCCCCT    110100
AAGCAGGCTG CCTACGCAGT TCGTAAATTC CCACTTAGTA GACTAAGGGA GTCTGTTTTA    110160
TAAATAAGGA CTCAAATTTC TTCTGACTCC GAGGTCCGTG GCAGCAGCTA AGATGGAA     110220
GCCCCCTCTG ATGTAAGATT CTCAGATGAC TTGCATCTTC ACTGTACCTG TCAACCCAAT    110280
AGTCTTCTAT TCCTGCCTTA AATTGTAAAT TCCAAAACTG ATTTAATTGT GAAAGTTTCA    110340
AACTGTACGA CCTAGGAAGT GTCAAAGTTA GGTGACCAGA TTTTTAGAAG TCAGCCAAAT    110400
ATTCAGCATC TTTGATTTAG TAACAAATAT ATTGATGGCT ACTTCAGCAA AAAAAATCAA    110460
CTTTGTTTTC TGGTTACTTT GCTAACAAGC TTCTCCTGAC AGGAGGATAT AGTGAATAGG    110520
CAGTTGAATA AGTGAGTTCG GGTGAGAGGT CTGAGCTGGA GATAAAAATG TGTGAGTCAT    110580
CAGCAGATAA ATAAATGCTG AGACCAGATG AGATGGCTAA AAACTGAAAC ATAATGTAGT    110640
GCAGCATTGT TTGTAATAGT AAATGAGTGG CAACTGTAAA GTTTTCATCA GAAAGGACTA    110700
GAGTGATCTA TACATCCATA AAATAGAGTA TTTCTCTACA CAGCCCTACT AAAGAATGAG    110760
AAAGCTGTAC TCCACTACAT ACTCTGGTGT ACTCTGGCTC AGTTCTTGGA CTCCTCTTTT    110820
CTTGGCTAAC TCAACTGGCC TCACCACTTA CATGCTCTGT GCTCTGTCAA ATAGTTTGTT    110880
CAACAGAACA CCACGGCCTA GCTGTAAGTG CCACGTTAAC TTCTAGCAAT GCCAAAGCCT    110940
```

-continued

```
GTGATAGTGG CAGCTTCGGG CTGTTTCTCA TTCCCGGGAT GCCTAACCAC CTCTCCAAAT   111000
TCTATCAGTT TGCTTCCACC CACTTCAAGC TTCAGAACGA AACATAGAGC TTAAGAAATA   111060
TAGGCCCGGC AAGGTGGCTC ACGCCTGTAA TCCCGGCACT TTGGAAAGCT GAGCCTGGTG   111120
GATCACCTGG GGTCAGGGGT TCGAGACCAG CCTGGCCAAT ATTGTGAAAC CCCGTCTCTA   111180
CTAAAAAAAA AAAAAAATTA GCTGGGCATG GTTGCGGGCG ACTGTAATCC AAGCTACTCG   111240
GGAGGGTGAG ACAGGAGAAT AGCTTGAACT CGGGAGGCAG AAGTTGCAGT GAGTTGAGAT   111300
CGCGCTATTA CACTTAGGCC TGGGAGACAA GAGTGAAACT GTGTCTCTAA ATAAGTGTTT   111360
GCAATTATAA ACCATCTCCC TGACCTTAAA TCTCTAGACT CATATACAAC TGCATATTTG   111420
ATGTATCTAA TTGAATAATG GGCATCTCGA ACTTGTCCAA AATATGTTTA TACGTAAACA   111480
CCAAGTCTGT TCTTCCTCTG ATATTTGTCA TGTCAATCAA TAGAACTCCA TTCTTCAAGC   111540
AGCTTGGGCC AGGAATTGTG CAATATTGTT TGTCCTGAGC TTCTTACAAC TTTCACCCAA   111600
TGCAGTCAGC TCTGTTGAAA ATCAATCAGA ATACCTTTCA TTGTTTTCTT TGCTGCTTCT   111660
CTAGGAGCAA GCTGCCATGG CGGTTTGTCT GAATGACCAC AGTGACCCCA AACTGGTCTT   111720
TGTTTTCACT TTTAATCCCC CTGTCATACA GTTTTTCTCT ATCCAGCATC AACAGTGATC   111780
CTTTTTGAAG GTATTATGTC CACTGTCTGC TGAAAAGATT CCACTGGCTT TCCATCACCT   111840
TCATAATAAA AACCAGCATC CTTATCATAG CCTACAAGTA AGATGACCAA CCATTACAGT   111900
TTGCCTGACT CTCAGGGGTT TCTCAGGGTG TAAGACTTAC AGTGCTGAAA CTTAGAAAGT   111960
TCCAAGCAAA CTAGGATGAG CTGCTCAACC TACTAGATCT GTACTCTGGC TACCCTCTGA   112020
CCTCATTCTC TTCGCAGTTC TTTCTCTTCA CTGACCTTGC TGTTTCTGGA ATGGACCAAG   112080
CATTTCCAGC ATCAGCACCT TTATATCTAT TCTTTCTCCC TAGAAGGGTC TTGTCCTGGA   112140
TATCTGAATG GCTCTAGATC TCATTTCATT CAAGCCTCTC CTCAAATACC AACCTTAAGA   112200
AAGAGACCTC CCATAATCAT CCCTTGTAAA ATAAGCTTTT CTGCTCATTT AGCATATATA   112260
TATATAGTTG ACTATCCTCA ATAGCATATA TATATAACAT TTCCCCACCT AGAATTATAT   112320
ATGTAATAAT ATATTTAACA AAAAATACAT ATAACTAGAT ATATTTTATT TTGTGTTTGT   112380
TCTCTCTCCC CCAACTGGAA TATATTTTTT GAAGGTAGGG ACTTTGTTTT GTCCCAGAAG   112440
TATCCCTAGC ACCTTGAACA GGGCTGACGT TTAACAGGTA GTTTATGGAG GTTTGTTGAA   112500
TGAAAGGATG TGTGAATTTT CTATGTAAGT CTCCAGGCTC TCCACTAAGC CCACCAGAAT   112560
GCTAACACAA TCAATTCCCC ATCTCATTCC TTGACCTGCC ACTGCCTGAA GCAATCAGCG   112620
TGCAGTTTCT CTTTAGAAAA TCTGGGGGAT AGTCTAGGGG TTGCAAATTA AGCAACATTA   112680
TCTTTGTTCT GAACAAGGAC TGCATGAGTG TTAGGACTGA AGAAGGCCCA AGGTGGTGGT   112740
GGGTATGCCT AAGATGAGTA TGACATATCA GCAATGCTAT GAACATAGCA ATGCTATGAA   112800
AGGCCAGGCA AAACGTAACA GGAGCTAGTC GTGGCTTATT GTTACAACGA CTATACCTCC   112860
CATATGGGTA ATCGATATCC ACACACCCCT CTACATTGAC TCTGGAATTC AGGAAAGGGA   112920
ATTAAAATTT TCTAACTTAT GTACCCCAAT GATTTCAACA ATATCTGGCA TATGAGATCA   112980
ATAAATATCT TTAAAATACC AACTAAGAAA GACATAAAAT GACCCACCCT CCATACCAGG   113040
CTCATTTTTG CTCCTCTGAT TCCTGAAACT ATCCAGAATG CAGCTATGAA TTCTCTCCAT   113100
TGTCAGTTTT AAATTAAGCC AAGCTGGGTA CTTGTGTAAT TCCTCAAGAA ATCCTGGATG   113160
AAAACTGTCA GGTGGAAAAC AGGACCTCAA AATAAAGAGA CATCCATCAC TGAAGCTAAC   113220
ATCGTGAGGC TGAAATCAGT CCTATAACAA TGGTACCAAA AAGAGCACAA TGAGAGGCAT   113280
TTGTGAATAT TTACTCAGAT GAGAGTAAGA TATTTCCCTA TCAGCTAACC TGAAGTTCAC   113340
```

```
ATCCCTTTTC CAGCTGAGTT CTGAAGCTAG ATGTACTTAA CTGGAACACA TAACTGCATC    113400

AGGAACATCC TTTAAAACTA TGGCTACAAT GGCTTGACTG GACAAACCCC AGGCTTCCAG    113460

GTTTAGCACA GGTGGCCCTT CACAGACCAA CATTGCCTAT GCTACCAACC TCATGTCCTA    113520

CCACCCTGCT TGCATCATTT CTCTCTCTGC ATATATAAAA ATATATGTGT ATGTATATAA    113580

TCAGCTTTAT TGATATTTAA TATACCACAA AATTTGCCCA CTTTAGGTAC AGTTCAATGA    113640

ATTTTACCGT GTTTTCTTAG TTGTACAACC ATCATCACAA TTTAATTTCG GAATATTTCT    113700

ATCACCCAAA TTTCCATTTC TGCGTAAAGG GGGAAAAAAA AAGGTTAACT GCTGAAGGCC    113760

GCGGTAACAC TGAAAAAGGT GCCTTTTCTC TCTAAAACAG ATTTTAATCT CCCCTGAATT    113820

TAGTGTCCTG GGTATTCCAG GAGTCTGAAT AGGGTTTCAA TTTTCAGGGT CTTTTTAATA    113880

GAGTAAAACT GTATTGGTGG CGATAAATTT AGTATTGCTC TCAGTACATG ATTGAGGGAT    113940

ACTTAAATGT CTCTGTGATT TTATTTCATA ATCGCTAAAA GATGGTTTTT TTTTTTCCTA    114000

AAACAGGGTT TTTGTTTTTT CTCAATAAGC TTCTTAGCTT CCCCTCCGGC TCCCTGGCTT    114060

GCCTCAGGAA ATATTAGCTC ATCAGTTCTG ATTGGTTGAC AGCTACGAAT GGCCCTCATT    114120

GATTGGGCAG CGCTTCTTTG TCCCTTGGAA ACTAATACAA ATTTTTAACA CTACTTTTTT    114180

TCCACTCTTT CTTCAGAGTT GGAATATCGT TGCTCCCCTA CCCATATGTA GTGAGTGGAG    114240

GGCAAACTTG GAGTTCCCCT AATCTTTCCT TTTTAGGATG TCAGCTCAGT ATCATTCATC    114300

TTAATTACAC ATTGAGCTTC TTGACTTAAT GGATACAGCT CTTCTTTTGT TTAGTTGGGC    114360

GGCCCTGAAA AGGGCCTTTG GTTCAGAAAT GCAAGCTGTG GAGAAATCAG CAACCTTAAC    114420

CGCCAAAGCC ATAAAGGGTG CGTCCCTGGC GCTTAAGCGC GTAGACCACG TCCATGGCAG    114480

TGACTGTCTT GCGCTTGGCG TGCTCCGTAT AGGTGACAGC GTCACGGATC ACGTTCTCCA    114540

AAAACACCTT GAGCACCCCG CGAGTCTCCT CGTAGATCAG ACCAGAGATC CGCTTCACAC    114600

CGCCACGCCG GGCCAGACGC CGGATGGCCG GCTTGGTGAT GCCCTGGATG TTGTCACGCA    114660

ACACCTTGCG GTGGCGCTTG GCACCCCCCT TACCCAAACC CTTCCCGCCC TTACCACGTC    114720

CAGACATGAC TTCCCAAGAA GTGAACCAAG AGCAAGTGAG AGAATAGGAA ACCGATCTTT    114780

ATATATCTAC GTTACCCCTG CCCCCACCTC CAGCGGACAC AGAGACTGAA AAGCGCGCAG    114840

GCGGGAAATG TGACGCCTAC AGTCCGCTCC TTTAACCCCT CCTCCAAGCC CCAGGAAATG    114900

GCGGGAGCAG CGATTGGGGG AGGGTGGGGA GATGAGGGTG GGACCAAGCA GGCTTGACCA    114960

ATGGCCTTTA TTTTCTTAAC AGAGCTACAG GCTTTGAGGA ACTGGGTTAA GAATTAAATG    115020

TAAACCCATT CTGACTCCAG AATTATTTTA AGTCGAACTT TTTTTTTAAC CGAATCTCTC    115080

TGTCGCCCAG ACTGGAGTAC ATTAGAGCCA TCTCGATTCA CTGAAACCTC TGCCTCTCAG    115140

GTTCAAGTGT TTCTCCTGCC TCAGCCTTCA GAGTGTACCT GGGATTACAA GCGCTCGCCG    115200

TCGCGCCCGG CGTGTTTTTG TATTTTTCGT AGAGACGGGA TTCGGCCATG TTGGCCAGGC    115260

TGATCCCGAA CTCCTGATTT CTGGTAATCC GCCCGCCTCA GCCTCTTAAA GTGCTTGAAT    115320

TACAGGCGTG AGTCACCGCG ACCGGCCGAA ATCGATTGGT TTGAAGCCT TCAGTAGCAT    115380

TAAAACGAAA AGTGCTCCCA ATGCATTCCC TTTTGTCTTA AATTGGTTTC TTACAGCTAC    115440

TTTACTTGAA AAGGTGGTGG CTCTGAAAAG AGCCTTTGCT TGGACCGTCA GAGAGACCAC    115500

AGTAATCACG CCCTCTCTCC GCGGATGCGG CGGGCGAGCT GGATGTCCTT GGGCATGATA    115560

GTGACGCGCT TGGCGTGGAT GGCGCACAGG TTAGTGTCCT CAAATAGCCC TACCAAGTAG    115620

GCCTCGCACG CCTCCTGCAG AGCCATCACA GCGGAGCTCT GGAAACGCAG GTCTGTTTTA    115680
```

```
AAGTCCTGCG CAATCTCGCG CACCAGGCGC TGGAAAGGTA GTTTACGAAT AAGCAGTTCA    115740

GTGGACTTCT GATAACGGCG GATCTCGCGC AGAGCCACGG TGCCCGGCCG GTAGCGGTGG    115800

GGCTTTTTCA CGCCGCCGGT GGCCGGAGCG CTTTTGCGGG CTGCCTTAGT GGCCAACTGT    115860

TTGCGTGGCG CCTTGCCACC AGTAGACTTC CGAGCAGTTT GCTTAGTGCG AGCCATGACG    115920

GAAAAACAGC ACAGCGGAAC ACCCAACACT AGCGCAAATA CGCCCATGAG CTGCTCTATT    115980

TATAGTGTGT AAAGTGCAGT GATTGGATGA TAGAAGACGC TAAATATGAC GTTACACACT    116040

CTGATTGGTC TATCTTTAAG CCAGCAACAA TCGTGCAGTT TCACCGGCTA CTATATTCTA    116100

TTCCAACTCT ACAGATGATT ATTTAAGTGG TATTTTATTA CTACTATTAT TTTATTTTAC    116160

TTTTGCTTTG TTCCCCAAGC TGGTCTTAAA CTTGGGCTCA AAAGATCTTC CCGCCTCAGC    116220

ATCCAGAGTA GCTGGGATTA CAGGGGAGCC CCACTGCGCC GGCTTGGACT TTAATTTTTT    116280

AAACTTGTCC TCTTCTACAT CTGGTTTTCA TAACCTGAAG GCTGTGTTTA TTTTCCATAA    116340

AACAAGGCAT TGATTCCAAA GGTATTATAA TTCCCCAATT CCGTATAACC TTCAGCTCTT    116400

TAGGAAAAAA AAAAAAAAAA AAAAAGAGG GAATACTGCT CACCTCCTCT CCGGAAATGT    116460

ACCCTTTACG GGAATTTCTG AAACCTTTCA CAAGAATTGG ATTCCTTTGT AATGCTTTAA    116520

TTGACTTAGG AGTGTTATTG AAATCTACAA AGCATCTCAA ACATAGTAGG ATTACACTAT    116580

TACTCAGAAA CATTTTCTAT GAGACGTCTT TCTCTTGATT ATGCTCTTTG AATCCTAAAC    116640

TTGCAGCGTT CTGCAGCTTT TGTTTTCTAA AGCCTAGGTG TACTCTGCCA GTCACAAAAT    116700

GGCGTTTCTC CAGCACTGCC GCCAGGTACC ACCAGCTGGG AGTTGTTCCT CTTGCGGAGC    116760

AGGAGGTGGA CTTGGCCCAA GAGAAACTGG ATAGTGGTTC GCAAGGAACA TAATTTAGCA    116820

TTGCCAAGAG CTAATGCAAT CATTTTGAAA ATCTCAAAAC ACTGAAAAGT GGATTGTGAC    116880

CTTTTTAAAT TCACAAGAGA CAGGCCACAT TCTATCTTTT GATTGGTTTA GGCTATTTTC    116940

TTGAACAGCC ATTTAGAAAG CAGATCTATC ATCCTTCATT TGCATGGAGC GTTCCCATTT    117000

TATTTGAAAC CAGTTTAACC CAATAGAAAA AAGGGAGGCA GAACCCATTA TTTAAAGTGG    117060

AAACTCCTGA ATCAGATAAT TAGGAGTATT TCCTTTTCAA AAGTTGCGTT TTTTCAGATA    117120

CCTCGCTTAT TACACTAAGA AAGGTTTATA TCTTTCACAA AGGGTTTACT TACAAAAATC    117180

TTCCAATTTT GTATACCTGT GTTTCATAAC TGACTAGCCG TCAAACCAAG ATGTAGAGTT    117240

TCCAACCGTT ATTTTCCAAA TTTTTAGAAA TTACGTGAAA TATTTGAATG CATGCCTTCT    117300

CAATAAAATG GGACGTAGGA AGCACTGGTG CAGAAGATGG GTACAATACT TATCTGGGAC    117360

CACTCCATTA TTTGGTTGGC ACGTTGTTTG AAGAAAAAGG GGAAAAGCTC AGGTTACTTA    117420

GCATGGTTCG GACTTATTTG AAAACTACCA CAGCAGGAGC GGAAATAAGA CCGCATTACC    117480

TCACTCTCTG CTGTGCTGTG CTAGGGGGTT ATCCAGAATA GGATTGTAGA AGTGGATGTC    117540

GATTTAATAG TTTTTTATTC TCCCATTAGC TGAGTCTCTG ATTGGCAATG TGAGATCGTT    117600

TTAGCTTATT GATACTTTGA AATGCACTTA ACAGCCACAA ACAAGTTAAA GGGTTGTTAC    117660

CATAAAATCT TATCCCCAGG GTGTGCTTGC ATTTATCACC CGTGTTTGCT TTCACACTAA    117720

GTGGACTTAA CTCCCCAGCA GAATGCCTGT CAGGGAACCG GTTTCGTGGA CCCAGCATTT    117780

AACGCCTTTC GCAGGCTTGT GAGGCCCATA AATATTTGTT GAATAAAAGA ATGAGTTGAC    117840

CATGTCATGG TGCGCTGATT GCGTGTGCTG ACATGGAACA CAGGTTGTAA ACCTTAATAC    117900

CAATTTGGGG CATGTTGTAT GGATGAAAAG GGCATTGGAA ATTCCTGAAG TGCATCCCAC    117960

ATTGGACTGT GGAAATAAGT TGCAAGTGCA GAAACGTTTC CACACTTGCA GTTTGAGTAT    118020

TAATTGCAGC GTTTGTGAAT TCTGGTGTTG TCTACGATTC ATTCTTGTTT GACGTGAAAG    118080
```

-continued

```
GTATTCGCGA GACACATCGC TCTAAAACAT TGCCAGAAAA TGTAATAGAG TTGATGACAA    118140
CTGGCCCTAA CACGGCCTAA AACTCGCACT TTTCTCTCCC TCCGCAACTA TTCAAAACAC    118200
TGTATTTTAC ATTTCTTGCA AATTAAAAAC TAACATCTCT GGCAACGGAC CTCTAAAAAT    118260
TTCTAATAAA ACTCCTCGGA TGCTTGTGGC ACTGCATTTG TAAACCGCCC CCTCTCAACC    118320
TACTCCCTAA AAAAGAGCTG CTTTTTGAGA GAGAAGCGGT ACCCTCTGAT GTTACTGGGC    118380
GGCAGTCTGC CTACAATTTC CTTCACAATG AGGCAACCAG AGCGGCTTTT TCTGTGTGTT    118440
TGCTTGCGTT GAGGGGAGCA GGACCATAGG CCCTAGAGGC CCCCAGCTGC CTTCTGGAC     118500
TGGGCGAAAC CCTCGGCAGC GCGCAGGGGG CGCTAGGGCG CGAGGGGCGG GCACTGACGG    118560
GCACCAATCA CGGCGCAGTC CCACCCTATA AATAGGCTGC GTTGGGGCCT TTTTTTCGCA    118620
TCCTGCTTCG TCAGGTTTAT ACCACTTTAT TTGGTGTGCT GTGTTAGTCA CCATGTCTGA    118680
AACAGTGCCT CCCGCCCCCG CCGCTTCTGC TGCTCCTGAG AAACCTTTAG CTGGCAAGAA    118740
GGCAAAGAAA CCTGCTAAGG CTGCAGCAGC CTCCAAGAAA AAACCCGCTG GCCCTTCCGT    118800
GTCAGAGCTG ATCGTGCAGG CTGCTTCCTC CTCTAAGGAG CGTGGTGGTG TGTCGTTGGC    118860
AGCTCTTAAA AAGGCGCTGG CGGCCGCAGG CTACGACGTG GAGAAGAACA ACAGCCGCAT    118920
TAAGCTGGGC ATTAAGAGCC TGGTAAGCAA GGGAACGTTG GTGCAGACAA AGGGTACCGG    118980
AGCCTCGGGT TCCTTCAAGC TCAACAAGAA GGCGTCCTCC GTGGAAACCA AGCCCGGCGC    119040
CTCAAAGGTG GCTACAAAAA CTAAGGCAAC GGGTGCATCT AAAAAGCTCA AAAAGGCCAC    119100
GGGGGCTAGC AAAAAGAGCG TCAAGACTCC GAAAAAGGCT AAAAAGCCTG CGGCAACAAG    119160
GAAATCCTCC AAGAATCCAA AAAAACCCAA AACTGTAAAG CCCAAGAAAG TAGCTAAAAG    119220
CCCTGCTAAA GCTAAGGCTG TAAAACCCAA GGCGGCCAAG GCTAGGGTGA CGAAGCCAAA    119280
GACTGCCAAA CCCAAGAAAG CGGCACCCAA GAAAAAGTAA ATTCAGTTAG AAGTTTCTTC    119340
TAGTAACCCA ACGGCTCTTT TAAGAGCCAC CTACGCATTT CAGGAAAAGA GCTGTAGTAC    119400
ACAGATGAAA TCCCCCAAGC AAATGCAACA CGCCCTCAAT TATATTAGAA TCACTTGGAG    119460
AGTCGATAGA ACTTTAACAT AGCCTCATCT AGTAAGAATT TACTACTCAA TCTATCAAAG    119520
ATAGCAAGGT GAATTCAAAT GCACCGAGTT AAAATCGAGT TTTAAAGTCA CCTGGGTTTC    119580
GGTAGCCGGA AGTCCCGCGT CTCACGACTC CAAGCTAATT AGTCATAACC GTATTGAACC    119640
AAGGTTGAAG CCCAGTCCCA GGCTTGAGGC TTTTTATTAT ACAAGGTTAA AGTGGGGATA    119700
TTGCGTTTTG GGGTCAATAT TGCTAAAGTA GCATTTTCCG AAATTGGGTG GTCCTAAGAA    119760
ATGCTTCTGG GATAGTTGGC AAAATATATG GCTTAACCAC GCCCTCTCCA CAGGAGTGGC    119820
TAGCGAGCTG TCTGTCCTTG GGAAGGACGG TGACCCTGCT GGCGTGGCTG GCGCCCACGT    119880
TGGCGTCCTC TGAAAGCCCC GCCAGGTAGG CCTAGCTCGC TTGCTTTCTG CAGCGCCATC    119940
ATGACAAAGC TTTGAAACGC AAAATGCTTT CTTTGTGCAG CGCCTTACCA TGGGTGCACT    120000
TACGGGCTGT CGACTTGGTT TAGGCCCTTG TCAGGACAAA GGAGCTTAGT TGTTGGAGT     120060
TTTAGAGCTG CAACCCAAAA TCCCTTGCTC GGTTTCTCTG TTTTTAGAAA CGGAAGCGCC    120120
CTGATTGGAT ATTTGAAAAT TACTGTGCTT AACTGGATCG TGTTTCATCA ATCGTGCAGG    120180
ATTTTCAACC CTGGTGGAGC CCACACATTC AAAACTGAAG ATCCTTTTCT CAGAACTGCC    120240
CCTTTAAGCT TTTGCAATTT TAATTCTGGG GGTCAGATTT TAATAATTGG ACTTTTTTGT    120300
TTACATCTGA CAAGAGTATA TGATGAGCCA AGTTTACTCA CTTTTACTTA GTGCAGTTCA    120360
ATTCTAAAAG TTTATTTTTG CGTGTGTGCA TATGAGTTAA TAATCAGTTG TATTTTTCAA    120420
```

```
ACGGTCTTTT TTCAATTGTT TTGCTTAGCT CCTTCCATCG TCTAAAGTCA GGGATACAGG   120480

CACATCACAT CCCTGTTCCC CCTTCCTCAA ACTAATATGT AGCTACCTAG GTTTATCCTT   120540

TAAAACAAAA ATTCTCACCT ATTTTTGTGA GAAATATACA TGTTTTTCTT TGAACTAAGT   120600

ATTTTACATA CACCTATCTA TATACATGCA TACTTGTGGT TTTGTTTTTT TAAAAAAAAA   120660

AAAAAAAAAA CACGTTATCT TTTGAGACTG GGTCTCAGTC TGTTGCCCAG ACTGGACTGC   120720

AGTGGCATAA TCACAGCACA CTGTAACCTC CAACTCCTGG GCTCAGGCTA TCCTGCAGCC   120780

TCAGCATCCG GAGTAGCTGG GATTGCATGC ACGCACCACC AAGCCGGGCT TTTTGTTTTT   120840

ATTTTTTGTG GAGACAGTCA CACCATGTTG TCCAAGCTGG TCTAGAAATG GCCTCAAGTG   120900

ATCATCGACC TCCCAAAGTG TTGGGATTAC GGTCACTGTG CCTGGCCTTG TATGCATAAT   120960

TGTTTTGTCT TTTGATTAGG GTTATTAATT TAAAAAACAA AGCCTGGACG CAGTGGCTCA   121020

CATCTGTAAT CCCAGCACTT TAGGAAGCCG GATGGGCAGA TTACTTGAGC TCAGGAGTTC   121080

AAGACCAGCC TGGGCAACAT GGTGAAATCC CATCTTGACA AAAATACAA AAAATTAGCA   121140

AGGCCCAGTG GCACGCACTT ATAGTCCCAG CTACTTGGGA GGCTGGGGTG GAAGATGAC   121200

TGGAACCTGG GAGGTAGAGG CTGCAGTGAG CAGAGATCGT GCCACTGCAC TCAAGCCTAG   121260

GTGACAGAAT GAGACCCAGT CTCAAAACAA AAATAATAAA AATTTTTTAC AACGATGTTA   121320

TATACACTTC TGCATGTTGC TTTTCTCTTA ACCAAACTTT TCTAAAACCC TGTCATGAAA   121380

AAAGAAATCC TTCACATGGA ATAGCATAAG TTATTCATCC ATTTCTTATT GATAAGCATT   121440

GATGTTTCCA GTTACCACTG CTGAACATGG TGCAATTGAA TAGAATTCCA GGGCTGAGAT   121500

TGCTAGGTTT TAGGTTGTAT TTTATTATTT TATTTATTTA TTTATTTATT TAGACAGAGT   121560

CTTACTCTGT CACCCATGGT GGAGTACAGT GCCATGACCT CAGTTGCAAC CTTTGCCTCC   121620

TGAGTTCAAG CGATTCTCAT GCCTCCGGTC TCCCGAGTAG CTGGGATTAC AGGCACCTGC   121680

CACCAGGCCT GGCTAATTTT TGTATTTTTA GGAGAGATGG GGTTTCACCA TGTTGGCCAG   121740

ACTGGTCTCA AACTCCTGGC CTCAAGTGAT CTGGCCACCT CGGCCTCCCG AAGTGCTGGG   121800

ATTACAGGTG TGAGCCATGG CTCCAGACCT GGACTTTGTC TTCTGTTTCA TCAGTCCTTC   121860

TGTTGGTTCA AGCACAGTAT CACACTGAAG ACTGATGATT CTATATAAAT ATGGTAAAGA   121920

CTGTACACCC TAACTGTTCT TATTTTTTAA TTTTAAGGCA ATTTTAGATT CCAGCTTTCC   121980

AAAGAATTGT GGAATGCTTA GAGCTAGAGA AGCCTTGGAA GTCATTTAGT TTTTGTTTTG   122040

TCAGAGAAAA TTCTGTAGAG ACTCTGTCCT GCTCTCACTG AATACCATCC CATAGTACCC   122100

CCCAACAGCT TTAAAGGGCA ATAATACCTT ATGGACAGTA TGCTTTTCCT CAAATATATT   122160

CTAAGCCATG GTCAATGCAA AAGAGTGAGA AGGAAAGTAG AATAAGTTAT CTAAGAATCA   122220

GTGGGTGCTC TCTTTAAACT GATTTATCAC TCCCCCTTCC AAACTCTCTT GAAGGTCACT   122280

CTGCCTCCCT TTCTACATAA GAACTCCTAA CTCCAAGGGA GGAAGGTAAG TTATTCTTAT   122340

TCCTTGCTTA GAAAAAGAGA AAATAGGTTT GGTAAGCATC CGCTTTCTGC TACCATTCTC   122400

TGTGTTTCTG TGTTTTTTAT AGGATCATTC AATTATTGGT TGGCTCTTGA GAGGGAATGC   122460

AAGGTTCAAG GACACAAGCC TAGATCTTGC CTGTATAGAA CCTCATGATG TTATGCTTCT   122520

CTAAAATGAG GCCTGGAGGA GACATGTTGA AAGTGACCCA TAAATCTGCA GTATCTCATG   122580

TCTCTCAATG GGGACAAGGA GTACCATGGG AAATAGCATT AGGTCAATGA CAGTAACAAC   122640

TCCCAGGTGA GTTGATTTAT TCTTTTATTT ATAAAGTTGT TAATATGCTA CATAGTCCCT   122700

AATTTTGCCA CAAATAGTCA TTATTTTAAT TTCATATTTC ACTATTGATA AATGAAGGAA   122760

AAAATGAGTA GCAGTTAAGC AGTCCATAAA CCTACATATA AAGCAAATTG GAGATTTTAA   122820
```

-continued

```
AATTGATTCT GGATGCTTAA AATCCTTCTC ATTGAAAAAA AATTTCGTAT TAGAAGATTT  122880

CAACATTCTT TAAACTGAGA AGCATAACAT ATAAACAGAA AACCACAGCA AAACAAAAAT  122940

GCAAAGCTCA ATAAATGAAC ACAAAGTGAA CACCATAATA ATTGCCACAC AAGTAAAAAA  123000

ACAGAAAATC AGCCAACCCT CCCAGAGCTG CCTGATGCTT GCTTCCAGTC ACATTATCAC  123060

TCCATCTGCC CTAAACATAA CCCCTATTTT GATTTCCAAT GCTGTAATTT AGTATGCCTG  123120

TTTTTGAAAC ATATAAAATG GAAATAAAAC AAATGTAATC CTATGTACCT GACATATTTC  123180

ACTCCAGAAC ATTAGGTTTG AATAGATTCA TCTGTGTTGC TGTGTATAAC TTTAATTCAT  123240

TTTTATTGTT ATGTAATATT CCATGTTATG AGTGCAACAA TTTAGGTGTC TACTGTTGAT  123300

GCATATTTGC TTCCCTTTTT CAGCTAATAT AAACAATACC GTGAATATTC CTGTGTATGT  123360

GTCTTGGTAT ATATAGGAAT ACATATTTTG TTTGTATACC TAGGAGAGGA ATTGTTGGGT  123420

CAAATGCTAA ACTCTTTTTG AAAGTGGTGA TATTAGGTTT ACATGCGATG AAATGAAAAT  123480

TAAAACCACA GTTATAAACA GCATGGATGA ACCTCACAAA CCTAATGTTG ATGGAATCTA  123540

GCTGGGAATT CCTGTTCTTC CATATACTTC CCAATATTTT TTTCCAATTA AAATTGTTAA  123600

TCTTTTGAAG ATGTTATCCA TTGTGGCAGA TGTGCAGTAT TATCTCATTA TGGTTTTATT  123660

TTACATCTTT TGCCCATTTT TTCTTAATTG GATTGTATAT CAGTCGACTT GGGCTGCCAT  123720

AACAAAAATA CTAGACTAGG TAGCTTGAAC AAAAGGAATT TATTACCTCA CAGTTCTAAA  123780

GGCCAGGCCA GAAATCCTAA ATTGAGGTGC CAAGAGATTC AGTTTCTAGT GAGGGCTCTC  123840

TTATTGACCT GAAGATAGTT GCTGTCTTAG ATTGTTTGGT GCTGAACAGA ATACCAGAGA  123900

CCAAATAATT TATAAAGAAT ACAGATTTAT TTCTTACAAT TCTGGTGGCT ATAAAGCCTA  123960

TGGTCGAGGG GCCCACCTCT GGCAAGGGCC TTCTTACTGT TATGGCAGAT GTGAGATGTC  124020

ATCTCATATT CAAACCACAG CAGTCGCCTT TTGTGTCCTC ATGTGGCCTC TTCATATGCC  124080

CATAAAATGA CCTCATGTCT CTTCCTTTTC TTATAAGGAC ACCAGATCTA TCAGACTACT  124140

GGCCTACTCT TATGACCTCA TTTAACCTTA AATATCTCCA TAAAGTCCCA AAATCCCTAT  124200

CTCCAAATAT AGGCACATTG GGTGTTAGAG TTTCAACATC AATTTTGGGG GAACACAATT  124260

TAGGCCAAAA AGATTGTGTT TTTTCTTGTT GGTTTAAGAT AGCTGTCTTT TGTCCTTTT   124320

TGTCCTTTCT TTTTTTTTGA GGTGGACTCT TGCTGTGTCA CCCGGGTTGG AGTGCAGTGG  124380

CGCTGTCTCA GCTCACTGCA ACCTCCACCT CCTGGGTTCA AGAAATTCTC CTCCTCCCAA  124440

GTAGCTGGGA CTACAGGTGC ATACCACCGC GCCCTGCTAA TTTTTGTATT TTTGATAGAG  124500

ACGGGGTTTC ACCATGTTGG CCAGGCTGGT CTCAAACTCC TGACCTCAGG TGATCCACCT  124560

GCCTCGGCCT CCCAAAATGC TGAGATTACA GGTGTGAGCC ACCAAACCTG GCCTGTCTTT  124620

TCTGTTTTAA GTTTTTAAAT TTTGCTCACG AACCCTTTAT CCATTTTATG TGTTGCAGGT  124680

ATTTCCTCTG TAACTTGTCT TCACTCTGTC AGAGGCTGGA GTGCAGTGGC ACAATCACAG  124740

CTCACTGCAG CCTCCACCTC CCAGGATCAA GCGATCCTCC CATCTTATCC TCCTTAGTAG  124800

GTGGGACTAC ATGTGCAGGC CACCATGCCC AGCTAATCTT TGTATTTTTT TGTAGAGATG  124860

GTGCTGTTGC CCAAGTTGGT CTCAAACTCC TGAGCTCAAG CAATCCATCA ACCTTGGCCT  124920

CCCAAAGTGT TGGGACTAGA GGTGTGAGCC ACCACTGCAC CCAGCCAATG ATATCTCATG  124980

ATGCATTAAA GTCATTAATT TAGTGTACTC AAATTAAGCA CACTGCCCTT TTATGCACAA  125040

CCTTTTTTGT ATCTTATTTA AAAAATCATT TTCTATTTCA AGGTCATGAA GATCTTATTT  125100

TATAATACCT TCTTGTGAAA TTAGTTCTCA AGACTACCCT CACTTCTAAC ACCAATTATA  125160
```

```
AGTTGGGAGG TCTGTGGTTC CCAATCAACC TTAGGTTAGT AATTTGCTAA AAGGACTCAC    125220

AGAACTTGCT GAAGCTGTTA GCCTCATGGT TACAATTTAT TATAGGATAT ATAGCTTATT    125280

ATGTCATTCC AATGCAATGT AAAATTATAC AACTACTTTT AAAAAGATTT TAGCATTTGA    125340

CCCAACAATT TCACTCTGAG GTATACAAAC AGCAGATATG TGTGCACATA TATACCAAGA    125400

CACATACACA GCAAAATTCA TTGTTTGTAA TAGTTGAAAA GGGGAAACAA CTCAAGGAAT    125460

AAAGATTAAA ATCAGCTGAG AAAAGAAACA CACAAGGCAG TATTATGGAT CGAATTGTAT    125520

GCAGATCTCC CTTGCCCCCA GAAGATATGT TTAAAGTCCC AACTCCCAGT ACCTCAGAAT    125580

TGTGGCCTTA TTTGGAAATA GGATAGTTGC AGATATAATT AGTTAAGATG AGGTTATAGT    125640

ACAGTATGAT GGGCTGGTGA CTTAGAAGAA GTAGTATATA TATATTTTTT AATAGAACTA    125700

GTATTCTTCT AAGGTGGTCA CGTGAAGACA GACACACACA GGCAGAGACT GCGGTTATGC    125760

AGCTGCAGGT CAAGGAATGT CAAAGGTTGC CAGCAAGTAC GAGAAGCTAG AAGAGTCAA     125820

GGAAGGATTT TCCTACAGGC TTCAGTGGAA GCATAGATCT AATGATACCT TCATGTCAGA    125880

TTTCTAGCTT CCAGAACTAC AAGAGAATAT ATTTGTTGTT TTAAGCCACC CTAGCTTCTA    125940

GCTCTTTGTT ACAGCAGCCC TAGGAAACTA ATATAGGCAC AATCCAGGCA AGTTCCAAAT    126000

ATGAGCTTCC AGTTGTCCTC TCCCAGTAAT ATGAACAGTA TTACTTTCCC AGCATTAATG    126060

TGTGACAATA CACATGACGT ACAGAGCAGT CCCCACTTAT GCACAAAACA TATGTTCCAG    126120

GACCTCCAGT GGATGTCTGA AACCATGGAT AGTACTGAAC TCTATATAGC TGTTTTTTCC    126180

TATACAGACA CAGCTATGAT AAGGCTTAAT TTATAAATTA GGCACAGTAA GAGATTAATA    126240

ACAATAAATT AGAATAATTG TTAAGAATAT ACTGTATAAA AGTTAGGTGA ATGTTTATTT    126300

CTGAAATTTA CCGTTTATTA TTTTTGGACT GCAGTAGACC ACAGGAACTA AAACCATGTA    126360

GAAACCGTAT ACAAGAGAAC TGTATTTCAC CCGAGCCTCA GTGTGCAGTT TTAATGGCCT    126420

GCCATGGTTG ACTGCTCACA TGGCCGATCT TTTAGTCTAC CTCCACAGGT AGAGCTGATA    126480

CTGTGTGGCT CAAAGTTCCT ATTATAAATC ACATTGTTGA CTGTGTGGTG GTCAAAACCT    126540

CCAGGTAAAC AAAGACACAC TTATCAGTGA GAACATTTCA AGGGTCTAAA ATTCATCTCC    126600

CAGTAGCTGA GGGCAAAGGC TAGACCTCTT TTTGGGTAAG ATAAATTTTT TACCATATAC    126660

TTTATTTTGC TTTTCATGTT TAACTTTATT TTGCTTTTCA TGTTAGTTCC CCTGGAATTG    126720

TTTTTTGTGT ATAGTGTGAA GTAGGGGGTC AAGTTTCTTT TTTTTTCCTT TTTGTTCTTT    126780

TTCTGTTTAA AAGGCTATAC AATTGTCCCA TGCCATTTAT TTACAAGAGT CCTTTCACCA    126840

TTGTTGTATG GTGCCACTTT AGATGTAAAT CAATGTCCAT ATTTGTTTGA GCCTGTTCCA    126900

TTCGTTTGTC TATTTTTGGA CAACACTGCC CTGATTATTG TCATTTTATC AGTTTTGATA    126960

TTTAATAAAG CAACAGATTT GTTTATTTTG GGCCCTTGGA TTTGTGTATT AAATTTGAAC    127020

CCTGTTTGTC AATTTCTATA ATAAAGCTTA TTGGGAATCT GATTAGGATT ACAATGGTTT    127080

TGTAGATCAG TTTGGGGACA ATTAATACCT TTAAAATATT GACCGCTTCA ACTGTAAATA    127140

TACTCCTCCA TTATTTAGTT TTCCTGTTTA ATTTATCTGA GTAATACATT ATAGTTTTCT    127200

TCGTAGAAGT CAGATACGTA GAAAATTCAA AGCCCAAGTG CAATAGCTCA TGTCTGTAAT    127260

ACCAGCACTT TGGGAGGCCG ATGTGGGTGG ATCACCTGAG GTCAGGAGTT TGAGACCAGA    127320

CTGGCCAACA TGGTGAAACC TCATCTCTAG TAAAATACA  AAAATTAGCT GGGTGTGGTG    127380

GCGGGCACCT GTAATCCCAG CTAATCAGGA GACTGAGGCA GGAGAATCGC TTGAACCCAG    127440

GAGGCAGAGG TTGCAGTGAG CCAAGTTCCT GTCACTGCAC CCCACCCTGG GCGACAGAGC    127500

GAGACTTCGT CTCAAAAAAA CAAAAAAAAG AACATTCAAA TAATCAATGT AGATAATTCA    127560
```

```
AATAACTAAA AAATGAACAG TTATTAAAAT ATCAGGATAT AAAAGCAAAA AAATCAATAA    127620

CCTCCATATA TACAAAATGG CCAGTTAGAG AAAAAAAAAA GAATAGGCGA GACTTAAAAA    127680

GGCTGGGAAT CTCCCTGAAA ATCTTTGAGA GCCTTGGCCC TGCCCTCAGG GATTTCTCTG    127740

GCTTCATGCC CAGATATGGG TACAGTTCCT TGTTTAAAAA AATTTTGCTC CATCAATCAA    127800

CAAGGGGCTC CTTCCTCAGA GCACAAGGAC CTCCATAACA CCGGACACTA GATGTCTAAG    127860

GGACACCTCT TAAGGAAGTT AGACTTCCAA AGAATGGTGT TTCCTCTGTC CCCAAACTCT    127920

GGAACTCACA GCACAACTGC TCCTTGGAGT TCGGTTTCAA ATCTACAAGG CTGTCATGGA    127980

GGTTGCAGAC CAAGTCCGTG GCCTCAGTGT CCGGATGTAC GGTGGCCTTG GCACCTGAAT    128040

GTGAGAACAT GACCTCCCTG AAACCACCAC AAGTATTGTT TCATGTTATG TATGTTTTTT    128100

CTTATCTGAA ATTCCTTTTC TTTAAAAATT CAAATTACAT ATTTTTCAAG CCCCTGAACA    128160

AGCTTCATGA GCATTTATTG AACCCACAGC TTTTAAAACC TACTGAACAC TTTGCTCTAT    128220

GTTGTCATTC ACTATCCACC AATTATTTAA TTATTGATCA ATATTGTTTC CTTAGTGTTG    128280

GGATCATTTA TGCATGTATT TCTTTTATAT TGCATATTTT ATATTTCTGC ATTACAGTTA    128340

TTACATATTA CTTTTGCTAC AGTAATAGTT CAGAAGTGTA CATCCAAAAT TTAGCTGTGA    128400

AGTGGATGGA CTGAGGCAGA ACTGGAGGCA AGAAAATGTC ACAGTAATTC TAAAAAAGAT    128460

GATGTACAAT TAGAGCAAGA GAGTAGCACT GAAATTGAAG AAAAATAGAT GCGTTTGAGA    128520

GAAAATTAGG AGGTAGAATC AACAGATTAG ATGTAGGGAT GAGAAGGGTC AAAGATGACA    128580

CTAGGGTTTT TAACTGGAGC AAGTAGGTAG ACAGAACATT TCTTCCTGAA AGGGCAGGTC    128640

AGATCATGTG TTGTCTCAAA GGGCATGAAG AGTAGAAAGC CTGGGACAGA TCCTGAGATG    128700

ACCAATACCC ATGGTGCAGG GAGAGGGAGG GAGATCTGCT AAAAAGACTG CAAATGTCAG    128760

GATAGTAGAA AATCATGAGT GTGTGATGTC CTGGAAGTTG AGACAGTATC ACATTTGAGA    128820

ACATTTAAAT TGGTAACTCT GACAAAACCT GGAGGCCAAC TGTGAATGCC CATGAGAGTG    128880

AGAAGCTCCC ACACTTTTGT GGGCATCAGA AAGCCCACCA GGTTCCTGCA GTGAAGATCT    128940

GAGAAGGATC CTCTTGTGGC TTTGGCAGGG AGAGAAGAAT TATTATGAAA TACACCCCAG    129000

AACCTTCTTC AAAACAAAGG CCTACTCTCA AGGGAAAAC ATTTTGCCAG AGTCTTATCC    129060

CAGCTGGGAG AAGGTAATTC TTCCCACTGC AGCCTCATCT AGGCTTTCTG TCTCACTTAA    129120

GGGAAGAAAA TTAGTCAACA GGGATCAGAG CTTCATGAAA ATAAATTGGA AATGGTGCAG    129180

CCAGGAAAGG AGCAAAGGTC TGAGGAGGAG GAGAAGGAGG AAGAGGAGTT GTATCATTAT    129240

AAATACTTGA GGAAGAGGAG GAGAAGGAGG AGGAGGAGGA GTTGTATCAT TATAAACACT    129300

TGAGGAAGAG GAGGAGGAGA AGGAGGAGGA GGAGTTGTAT CATTATAAAC ACTTGAGGAA    129360

GAGGAGGAGG AGAAGGAGGA GGAGGAGGAG TTGTATCATT ATAAACACTT GTGACGGTCC    129420

CAGCCCCAAG ATATAGGCAT GCTAATAAAC TGAGGCTTAA CACTTTGACT ACAGAATGCT    129480

GCTTCTCCCT AACACCATCA AGGCTCCAAC TGAATAACAA TGAATTATGA ATGAAAGAGC    129540

TGTAAGGAGA GACAAAAGTT AGAATGAGAC AAGTATTGTT ATCTAGAGAT GCCAAGAAGG    129600

CAAGGAAGAT AACTAAAAAG GCACTCTGGA TTTAGAAATA GGAAGTCATT AGTGACCTTG    129660

TAAATAATGG AGCCAGAGGA ATACCAAGGG CAGAAGCCTC ACTATAGTGT GTTGCACCTG    129720

TCAGAGGTCA GGAGGTGTAA CTGACTCTCC CACAGTGTGG CTTTGGAAGA GAAGTCAG    129780

CAGCTGCATG GAGATTTGGG AGAGGGAAAG CTTTTTTTTT TTTTTTTAA TTGGAAAAGA    129840

CTGAGCTATG TGTAAATAGA ATAAGACAGG AAGAGTGTAG ACACAGGAAA GAGGGCAGAC    129900
```

```
AAAAACAAGT GCACAGTTAT CTAAGGGAAA CAATGGGATC AAGCTGCAAG TATATAAACT  129960

TGTCTTGATA GAAGAATCCT TGATCTGGTT TATTCAGTGT TTGGTCCAAA CCCACATCCC  130020

TGTTCTGCCT GTCTCTGACT TGCTCTGTGC CCCAGAAGCC CAGCTTCTAC AGATAGCATT  130080

AGCTGGGCAG CCCTGCCCTC TTGCAACAGC TGGATTTGGC CAGTGATCAG CCCAGCAGGA  130140

ATGTAGATGG CAAAGGAGAG AGAGGTTAGT GTACTTATTC CCTGCATCAC CCCCCTGCTT  130200

GGTGGGCAGC TCTTCCTCCA CAGTCCCAGC TCTGGCCTAG CTCTGGTTAC AGGTTCCCTC  130260

CCATTGCCTC TTCAGATTTA AAGGTGTGTC TGTCAGGGTA TAACTGGGAG CTAGAAATTG  130320

CACTGAAATT GAACAAAGAA TTTTATGGGA ATGGTTGTTA ACTAGTTATA AGAGGACTGA  130380

AAATGGAAAA GTGGAACAAA CGTATCAGAG ATAGTAATGA CAGAAAGCAA CTACCACCTC  130440

CAGGTTTAGG AGAACAAGGA AAAGATTCTT TGAAGAGATC CCCAGAACTG GGACCTCTGA  130500

GGAGTGTATG CTGGACCACT GATGATGATA TGTCTGTAGA TAGAGGCATG ATGAGGCTGA  130560

TTTTAGGAGC ATGGAAGATC TCCAAACTGA AGCCAACTGC TGTTACTGGA TTCAACTGCC  130620

ACTGCCAGGT TGAAGAACCC ATTCTGTGAG GATGTCAACA AACAAAGTGG GAAATCTTTT  130680

CACATCCTTC CAGCCCTCTA GTCTTCCTCC AGTGCTTTCT ATTGGTAGGG TTTGGGGAGG  130740

TGGCTAGCAA AGCGGTATTG GAAAAGATAG AAGAGACTAA ATCTTCATAA CCAGCACAGG  130800

GTGACACTGG ATCACTACTG TTGCTGATCT TGGGCTGCCT CATATCCCCT GTTCTTCCCA  130860

TTAGCCCTGT CACAACTTTG TAGATATCCC TTCATTATAT GCCCTTCATA TATTCTTTTG  130920

GTTTAACTTT TTCTGTTGGA ATCCTAATAT GGCACTCCTC CATTTTTCAG GACCAAAAGA  130980

GTATAAAAGA TTATCTTTTA CCAAAAAAAA GACAAAAAAC TGATCTAATT CCTGATTTGA  131040

TCATTACACA ATCTATACAT GTATCAAAAT ATCACATAGT ACCCCATAAA TATATACAAC  131100

TGTGTCCATT AAAAATAAAA ATTAAAGAAA AGATGGTAAA TATAGCTCTG TCAGGCAGTG  131160

GAGGTTTTAC CACGATGGCT GTTATTTCCC CCATGAAGGG GGGAGTGAGG GAGCAGCTGA  131220

AAGTAGGTGC TTATAGGGGT ATAGAGGGGC TCAAAGCTTT GAGAGAGGAG AATGTCTGAA  131280

AGAGCTGCCA AATAGCATGC AGGTCCCATG GGGGCAGAGC CTCTGCTCAT TCACCAGTGC  131340

CTCTTCAATA TCTACACTTA AGCCTAACAC AAAGTGTGTG CTTAATAAGT ATTTGCTGAG  131400

TATGTAAAGT GGAAACAGAA CCAATCTGGC AAACTTTGTA GGACTGGTGG GCAATGAAGA  131460

TCAGTCAGGT AAAATCTGTG GATATAAATT TATATTGATC AAAAAATTCA AGGTTAGGTG  131520

TTTTTCTTCA GTCATGCTCA ACGATGCTTC AGCCATGCTC AACTCTTCTG TAGCCACAGA  131580

AAAAAGTTTA CCCATAATCG AGCTGTGTCT GTGTCTGAAT AATGAAAAGA CCATGATGCA  131640

AGGGAGTTGG AGACACAGAA ACAGTGTTTG AAGTAATGGG TAATGGAAGC ATGCTACCAG  131700

GGAAAGGAAA GAAGTGGCAA TAGGAAGGAA CAGAGATCTG TGGTCCTATG TCCCCTGAGC  131760

ATATTCACAT GTTAAAGCTA ATTCAGTTTT CAATCATCAT TAAAATTTTG TTCCTAAATA  131820

TATGGCCATT ATTTTCCACA ACCACACTAA AACTTTATTA CCTCTGGCAA GTGACTATGC  131880

AAGTAACTAA GAGCAAAAAT ATCCACAACT ACCATTTGAG CTATCAATTT AGGGAAAGTC  131940

ATCTGGCTAT AATCTAAGTG ACCCTCCACT GAATGTCAGT ATCTTTGCAT ATGTGATTTA  132000

AATCTGGGCC TTCGCAACAC CATGAACTGT TCTTGTCTTG AATATCCAGA TTGAAGGAAA  132060

TAATCTGAGT AGTTACGAGT CCTGAAGCTA GAAAGATGGA AACCCATTT GCTCATCAGA  132120

AAGCCTTAGA GCTTGGGCGC TGGCGGGTCC TGTCTCACCG GGACAGAGGG GCTCTTTCCT  132180

CCCCATCTGA TAGTCTGATA ACTAGAGAAG CCGGCCAACT TATTCTCCAA GAAGGAGCCA  132240

TCTTAGTTCC TCCTGAAATG TTCATATTTA GAAATTATTG TTTGTCAGTA ATTTAACCCC  132300
```

```
TTAATGGGCT TGCCTTGTGG TCCATACCAC TGAGTGCAGA GCTTGCCTGG AAGAATTGTG    132360

AGGGCCATTC CATCTTCCAG GCAGTAGAGT TCAGTACTTC TTTAAAATTG CTGCTGAACT    132420

CTGTATTTGA AAAGAAAGAA TCATTTGGGT GTGGTAGCTC ACACCTGTAA TCCTAGCGCT    132480

TTGGGAGGCT GAGGTGGGAG GATCATTTGA TGCCAGGAGG ACCACTTGAG ACCACCCTGG    132540

GTAACATAGC AAGACCCTGT CTTTAGAAAA AAAAAATACA ATAAAATAAA TACAATAAAA    132600

ATAAAAGCAA AAAGAAAGAG TCCATCTTAG GGACAGACTG TAACTACTCA CTGGAGCTTA    132660

CCTTTACATA GTTCAGGATC AATTATAATA AAACACTTTT GTGCAGATTC AATAGGATTA    132720

TTTTAATCCC CATCATCTCT CTGAGTTTCC AGTCAGTTTC TCTGCATGTA GACACCCTTC    132780

TCCAGCCCAC CATTGTCTCT CCTCCTATAG CTCCACCAAC AAATCAGAAC TTTTTCTAAC    132840

TGCACCTAGT GCACCTAGAG TCTACTCCAG AATGCTCATG GAGAAAGTTT CTGAAAGGTA    132900

AAACTCTGAA TGATATTTGT AGCTAAAGGG AGACTTGCTA GAGACAATAA GCTAATAGTT    132960

GTAGACTTCA GTAGAAGAGG AATGACACTG CAATGTCAGG GTGCAGGACT TCAAGAGGGC    133020

AGAGTATGGA AACCCAATGG GAAAAATGCT CACCAGGAAC ATGAAGAGAA GGAATTACGT    133080

GTAAGGATTT CTCAATGTGT TCCCAAATTT GCCCAGCAGA GGGAGGCCTC GGGTTGATGG    133140

CAGGCTGACC ACACAATTAA AGAAGGCTGA ACCTGGGGGC TTTTAACAAC CATCGTGGGC    133200

TCTACTGTAA GCATTTAGAA AAAGAAAGTT ATCCATTCAA AAATATATAT ATTTTTAAAC    133260

TTCAGAACAA AATTATGAAG AGCTATATTT ACTTTTCTAC ATTCTAATTT TTATAAATCT    133320

GAGTATATTT TGCATATATT GTTATAGTAC ATATTCAATT TTGTATTTTG CTGTTTTCAC    133380

TTAACCATTT TTACTAGATT ACTCTGTGTT CATAATAATC ACTTTTTTAA AACTTTTATT    133440

TTTATTTATT TATTTTTTTT TTGAGTCAGA GTCACACTCT GTCGCCCAGG CTGGAGTGCA    133500

GTGGCGTGAT CTTGGCTTAC TGCAACTTCC ACCTCCTGGA TTCAAGCAGT TCTCCTGCCT    133560

TAGCCTCCTG AGCAGCTGGG ATTACAGGTG TGCACCACCA AGCCCGGCTA ATTTTTGTAT    133620

TTTTAGTAAA GACGGGGTTT CACCATGTTG GTCAGGCTGG TCTCCAACTC CTGACCTCAT    133680

GATCTGCCCA CCTTGGCCTC CCAAAGTGCT GGGATAATCA CTTTTTATGC TGCATAATTC    133740

TTCAGATTTG TCAGTACGAC TGTATTTACA CTCATTTGTT TTATTAGAAA GAATTCCAGA    133800

ATATTTTGGC TGCCCTAATT AATTTTACAA TTAAATATGAT TTTGAAATTG GGTATTGGCT    133860

CCTTCTGAAT TGGTTTATTA AAATATATTC TAATGTAATT TATGACATTT TCATCATATT    133920

AGCATATTTA TTCTGTTAGA ATTTCATAAT TTATAAAGCT ACAAACTGTA TGTGATATAG    133980

CTTGTAACTT TATCTCATAA CTTTATGCAG TTACAAGTAG AAATAAAATG TTCCCCTCAA    134040

GATTGCTTAA AATTTTATTA TAAACAAGTG TAAAAAACAA AATCACTAAA ACACTCCCTC    134100

TTTTTTCCCC CAAAATGCAT GTTTCCATTT TAACAGAACC CGTATTTAAT CAGCAGATTT    134160

CTATGGTGGC TAGATTTGTA GACTAAATAT TAAAAGTCCC AAAGCAAATG CATTTTTCTC    134220

TTAAATTTTA CTGACTTTTT TTTTTTTTCT TTTTCTGAGA CGGAGTCTTG CTCTGTCGCC    134280

CAGGCTGGAA TGCAGTGGCA CAATCTCGGC TCACTGCAAC CTCCGCCTCC CGGATTCACG    134340

CCATTCTCCT GCCTCAACCT CCCGAGTAGC TGGGACCACA GGCGCCCGCC ACCACGCCCA    134400

GCTAATTTTT TGTATTTTTA GTAGAGACAG GGTTTCACCG TGTTAGCCGG GATGGTCTCG    134460

ATCTCCTGAC CTCATGATCT GCCCACCTCA GCCTCCCAAA GTGCTAGGAT CACAGGCATG    134520

AGCCACCGCG CCCCGCCTAC TGACTTTTAT CCAAAGAAAA TATAAGAGCT CTTCATCATA    134580

ACGTATGTTT CTTGCTCTTG TTATTAAATA TGACACATTT AGACTTAAAC TGATTTGAAG    134640
```

```
GTTTATGACA TTGTTTAAGT TATTACATAA TTAATTCATA AAGATAATGA CTAGTTTGAA   134700

CTACTGACAG CTCACACATC ATCAGTTGAA CAGCAGAAAG CTTATTAAGC TACTTTCTTA   134760

TGTTTCTGTC TCCCAGCTAC TAAAAGAAAC GAAACCCTTC CAGGTGTTAA GGCAAAACTT   134820

TCCTCCCCCT TTCTTCTATA AATCTGATTC CATGTTAGTG AAATTTCTAC TGATGGCTTT   134880

GGTTTCCTCT ATAGTAGAAT AGAGATCCTA TGGCAAAAGT CATGTCTGAC ATGGTAGCAA   134940

ATAGAAATGG GGAAAAGGAA GGTCTGCAAG AGCCAATGTG GGAAATGGGG AGAGGACTGA   135000

CTACAAAAAC CCAGCAGGAA TTCCAGAAGA AAACTCCTCA GGACGGGCAC ATTGGCTCAT   135060

GCCTGTAATC CCAGTACTTT GGGAGGCCGA GGTGGGCAGA TCACTTGAGT CCAGGAGTTT   135120

GAGACCAGCC TGGTCAACAT GGCGAAACCT CATCTCTACA AAAATAAAA AAATTTGTCA    135180

GGCGTGGTGG CATGCACCTG TAGTCCCAGC TACTCAAGAG ACTTAAGTGG GAGAATCACT   135240

CGAGCCTTGG AGGTGGAGGT TGGTGAGCCG AGATCACGCC ACTGCATTCC AGCCTGGGCG   135300

ACAAAGTGAG ACGCCATCTC AATCAATCAG TCTCCTCGAA AAGCAACATT ATGGAGAGAC   135360

AGGATTCCGT CAAGGCCTGG GGCACACAGG AAAATATTAA GGCAGAAGAG AGTTTCCTCC   135420

CCACACCACA CCGTATCCCA CAGGCACTGC GGATGTGCAT ATGCAAGAGG GGTTGATCCT   135480

AAGAATTTAG AGTCACAGAG GAGGAGGCAC CAAGCAGACT GTGGAGAAAG TCATGACCAG   135540

AAAGGGACAG AATGTAAAGC TTCAGCTGAT TATCTGGCCT CAGGGATTCC AGAGGAACTG   135600

GTCCCAATGG TCTCCTGGTG ATGTAGGTTC TTAGGTTTCT TTTACAGGGG TTTTCTGGGA   135660

GATCGTTGAC CCAGTTAGCA TTCAAGCAAC TTCCACCCTG CACTTTTATT CTTTCCCCTT   135720

CACCTGCTTA GGTTTTATCT GTCCAGGCAA TAATAATAAA ATTATTGAGC CCTGGACATG   135780

TACCTGTAAA GCTCCTTAAA GATGATGCCT TCTAACTCCT CATTCAACAG ATACAAAAAC   135840

ATTACAATAA AATGACTCAT GCAAGACACC CAGGTAGTTT ATAGCAGCTA ATAAAAACAG   135900

AATAACTATA AATATGGTA AGTTTATAAA AGTTACATTG AGTATACTTT ATAAGAACTG    135960

CTTATTGAGT TTGCCTAATA ACCACACAGC ACAATAATAA TATGTATATA TTTTTAAATA   136020

TGTGTAAATA TGTGTAACAC AAACTTGTAG AAGGTATATC TGAGTACAAC CCTATTCTGT   136080

TTGGTTACCT TTTCTAGTTC ATTATGTAAG TGGCATAGCT ACCTAAGGAC TTATGCTTAT   136140

AAATGTTACT CAAAAAAATA CAGAGGACAT ATGTGGATAG ATAATGGAAG AGATAAGATA   136200

GGTAGGTTGA AGGGTTGGGC TGCCCCTCCA CACCTGTGGG TGTTTCTCGT TAGGTGGAAT   136260

GAGAGACTTG GAAAAGAAAG AGACACAGAG ACAAAGTATA GAGAAAGAAA AAAAGGGGTC   136320

CAGGGGACCG GTGTTCAGCA TACGGAGGAT CCCACCGGCC TCTGAGTTCC CTTAGTATTT   136380

ATTGATCATT ATTGGGTGTT CTCGGAGAG GGGGATGTGG CAGGGTCAAA GGATAATAGT    136440

GGAGAGAAGG TCAGCAGGTA AACACGTGAA CAAAGGTCTC TGCATCATAA ACAAGGTAAA   136500

GAATTAAGTG CTGTGCTTTA GATATGCATA CACATAAACA TCTCAATGAC TTGAAGAGCA   136560

GTATTGCTGC CAGCATGTCC CACCTCCAGC CCTAAGGCAG TTTTCCCCTA TCTCAGTAGA   136620

TGGAATATAC AATCGGGTTT TACACTGAGA CATTCCATTG CCCAGGGACG AGCAGGAGAC   136680

AGATGCCTTC CTCTTGTCTC AACTGCAAAG AGGCGTTCCT TCCTCTTTTA CTAATCCTCC   136740

TCAGCACAGA CCCTTTACGG GTGTCGGGCT GGGGACGGT CAGGTCTTTC CCTTCCCACG    136800

AGGCCACATT TCAGACTATC ACATGGGGAG AAACCTTGGA CAATACCTGG CTTTCCTAGG   136860

CAGAGGTCCC TGTGGCCTTC CTCAGTGTTT TGTGTCCCTG AGTACTTGAG ATTAGGGAGT   136920

GGAGATGACT CTTAACGAGC ATGCTGCCTT CAAGCATTTC TTTAACAAAG CACATCTTGC   136980

ACAGCCCTTA ATCCATTTAA CCCTGAGTTG ACACAGCATA TGTCTCAGGG AGCACAGGGT   137040
```

```
TGGGGCTAGG GTTAGATTAA CAGCATCTCA AGGCAGAAGA ATTTTTCTTA GTACAGAACA   137100

AAATGGAGTC TCCTATGTCT ACTTCTTTCT ACACAGACAC AGTAACAATG TGATCTCTCT   137160

CTCTTTTCCC CACAGGAGGT GATGGCCGGA AGAACATGGC AGAGGGCAAA ACAAAACAGC   137220

ATTGGGAACA AGCTCTGTTT AAAAGGAGAC TTGTGAACAG CAAAGAGTAG AAAGGGTTCT   137280

CTTACAACTG AAGCCCATGG AAGACAAATG TGTACTGCGT GAGTTTTAAG GCAATAGGAG   137340

TAGTGGGACC TAGGGCACAC CAGAGAGCAT ATTAACTCTC AAACTTTTAA AAACATTATA   137400

TCTGCTGGAC ACAGTGGCTC ACACCTTAAT CCTACAACTT TGGGAGGCCG AGGCGGGCGG   137460

GTGTAGCTTG AGCCCAGGAG TTCGAGACCA ACCTGGGCAA CATGGCAAAA TCCCGTCCCT   137520

ACAAAACAAA CAAACAAAAA ACAAAATTAG CCAGGCACGG TGATGCGTAC CTGTGGTCCC   137580

AGCTACTCAG AGGCTGAGGT GGGAGGATCG CTTGAGCCCC GGGAGGTTAA GGCTGCAGTG   137640

AGCCATGATA ATGCCACTGC ATCTCAGCCT GGGCAACAGA GGGAGAACCT GTCTCAAAAC   137700

AAAAACAAAA ACACACCATA CCCAACCACA ATGCATCTGT CTTAAGTACC AGTACCACAC   137760

CCCTCTACTC ACTACTAAAT AGGTGAGTTC CCAATCCCTG GTAGCAGGTT TAAGCATGTT   137820

ATATTAAAGG TCTTAGGCTA GTGACTCATT CACTCATTAA ACAAATACTT ATTGTGCATC   137880

TACTATAAAC TAAGTACTGT GCTAGGTACA AAAGCAAATA ATCTAAGCTC TATAAACTTT   137940

ACTTTCTTCA TCAACAAAAT GGAGATGTTT TAGGCATCTA CTCATCATTC TGAGCTCCAT   138000

CTTTTGTGAC TGTAGTTGGC AGAGCTTTTT ATCAGTTTCT CTAAATAGCT CTACCAGTCC   138060

CTGGTGGATG CTGGCATGCC CAAAGGATCC ATCCTGATGG CCCTGTCTGC TTACCTTACC   138120

TGCCTGCCTT TGCAGCACCG CTCTGCTCTT CTGCAGGACT TCCCTTATCC TTTGGGGTCT   138180

TGCTGCTCTT AGGCTGCTCT GCTTGTTTTG ATCTGCTTTG CATCACATGT ATGTAAAGGT   138240

CCTTTCCTTA TTTACCCATG ACCAAGGTAT TATGAGATTC TGGAATTTCC CCAAACCACA   138300

TTGATTGCTG GGAGAATAGA AGAAGTGGAT TACAAGTGGA ACTTAGAAGG GGAGTATTCG   138360

AGAAGACGTC TCTGCAAATC CATTTAGAGA GACCTTTCTC CAGTGGTGAC TCAAAGATGC   138420

AGCTCCTTTC ATCCTGTGGC TTGGCCATCT TCAGCACATG GCTCCCAAGG ATGTCCTCAG   138480

GATGGTCTCT AATCCAAGGA GCCTGAAGAG AAAAAAAGGC ATGGAGTATT GTGAGTGGTA   138540

GGTGGTTATG GACCAGTTAT GGAAGAATAC ACATCACTTT TGCCCACCTT CTACTAACCA   138600

GAACTCACAC AGCCATAGAC ACTGACAAGT AGGACTTAAC AAGAATCTAA TTTTGAGTCT   138660

AGGAATACGA CTGTAGCAAA TATTTAACAG CTTCAAACAC AGGTGCATTG CTATCACTAT   138720

GCTTGGCCCA GGCCTGTCTC CCTTTCCTGC CATGTCACAG GGGCCAGCAT TTATGTCTAG   138780

ATTGGGTTGG TTGGGATATT AAGACAATAA TGAACCAATA CAACATCTTG AGCATAAAAC   138840

CAACTGATAC AATGATGTAC AAGTCAGATG ATTCTGATGA TTATGAATTA TGTCAATAAA   138900

AGAAATGTGA TAACTAAGGT AATTTTTGTT TTGGCAAATT TTTGTTTGTT CATGACAGGA   138960

TGAAATCCTG TCATTTGTAG CAACATGGAT GGAATTGCAG GATACTACAT TAAGTGAAAT   139020

AAGCCAGAAA CAGAAAGTTA AACACCACAT GTTCTCACTT ATATGCAGAA GCTAGCTAAC   139080

TAAGTAAATA AGTTTATCTC ATTGAAGTAA AAAGTACAAC AGAGATTACT AGAGGCTGGG   139140

AATGGTAGGG GAAAGAGATG ATAAAGAGAG ATTCATTAAA ATAAGTTACA GCTAGATAAG   139200

AGCAATCAGT TCTAGTGTTC TATTTGTACT ACAGAATGGC AATAGTTAAC AGTAATAAAT   139260

AATTTCAAAG AGCTAGAAAA GAGGACATTG AATGTTTCCA ACACAAAGAA ATGAGAAATG   139320

CTTGAAATAA TGGATATTCT AATTAATTAC CCTGATCTGA TCACTATACA CAGTATGTAT   139380
```

```
AAAAATAACA CTATGGGCTG GGCGCAGTGG CTCACACCTG TAATCCCAGC ACTTTGGGAG 139440

GCCAAGGTAA GCAGATCACT TGAGGTCAGG AGTTAGAGAC CAGTCTGGCC AACATAGTGA 139500

AACTCCATCC CTACTAAAAA TACAAAAATC AGCCAGGCGT GGTGGCATGT GCCTGTAATC 139560

CCAGCTACTC AGGAGGCTGA GGCAAGAGAA TTGCTTGAAC CCAGGAGGCG GAGGTTGCAG 139620

TGAGCCGAAA TCGCGCCACT GCACTCCAGC CTGGGTAACA GAGCAAGGCT CTGTTTCAAA 139680

AATAAATAAA TACATAAATA AATATTTTTT AAAAAAAGAA CATCACTATG CACCCCATAT 139740

ATACATATAA TTATTATGTC AATTTGAAAC ATAATTTTGA AAAATGAAAA AATGAAACAC 139800

AAATATGAAT CAATCCTCTC CAAGTTGATA TACTTAAAAG GAAAAAAGTC CGAGGGCTTA 139860

AACTATTCAA TCAAAATTTT ATTAAAATGC TATAGTAATC TGGAAAGTAT TTCAGAATGA 139920

ATTGGTATAA GGTTAGACAC AAAGATCAGT GAAACAAAAT AGAGAACCCA GAAATAGATT 139980

CACACATCTA TGGACAACTG GTTTTGACAA AGGTGTCAAG GCTATTTAAT AAGTAAAAAA 140040

ATCGTCTTTT CAGTAAATGT TTCTTGAACA AGTAGACATC CGGTGTGGGG GAGAGGAGCA 140100

GGAGCCTTAC CTCAAACTTT ATGCAAAAAT TAACTCAAAA TAGACCATAG ACTTAAATGT 140160

AAAAGCTAAA ATTATAAAAC TTCTTTAAAA AATAGGAGAA AATCATCAAC ACCCTAGGAT 140220

TAGCAAAGAT TTCTTTAAAA CAAAACAACA GGTTTATAGT TTATAAAACA TAAATAACAA 140280

AATGATAAAT TTCATCAAAA GTGAAAATTT GCTTTTCAAA AACATTATA AAATGAAAAG 140340

CAGGAGGCTG AGGCATGAGA ATCACTGGAA CCCGGGAGCT ACAGGTTGCA GTGAGCCAAG 140400

ATGGTGCCAC TGCACTCCAG CCTGGGTGAC AAAGTGAGAC TCTTCCTAAA AATAAATAA 140460

ATAAATAAAT AAATAGAAAA GAAAAAGAAA AATCACAGGC TGAGAGAAAA TATTTATAAT 140520

ACATGTATCT GACAAAGGAC TCGCACCTGG AAAATATAAG GAACCTTATA ACTTAGTAAG 140580

ATGACAAGCC AAAACAAAGA GTAAAAGTTT TCAACAGACA TTTCACAAAA GAAAACATAC 140640

AAATGGCCAG TATGCACATG AAAAGATTTT AAACATCATT AGTTACTAGG GAAATGCAAG 140700

TCAAAACCAC AATGAGATAC TTCACATTCA ACAGAATAGC TAATGTTAAA AGGACTGACA 140760

ATCCCCAGGG TGAGCAAGGG TGTGGAGGAA ACTACTCTCA TATATTGTGA ATGTAAGAGG 140820

ACAATGTTAC AACTACTTTG AAAAAAGTTT GGCTGTTTCT AACATAAAAT TAAACACTTA 140880

TACAGCCCAG CAATATTTCT GGGTCATTTC TCCCAGATAA ATGAACACAT GTCCATACTA 140940

TGACATGTAC AAATGTTCAT ACTGGCTTTG TTTCACAATG CTATAAACTG GAAACAACCC 141000

ACGTGTCCAT CAACAGGTGA ATGGGTAAAT AAATTGTAAT ATATCGGCCA GACGCAGTGG 141060

TTCATGCCTG TAATCCCAAA ACTTTGGGAG GCCAAGATGT ACGGATCACC TGAGATCAGG 141120

AGTTTGAGAC CAGCCCATCC AACATGGTGA AACCCCATCT CTACTAAAAA ATTAGCTGGG 141180

CATGGTCACG GGCGCCTGTA ATCCCAGCTA CTCGGAAGGC TGAGGCAAGA GAATCACTTG 141240

AACCGAAGAG GCGGAGGTTG CAGTGAGCCA AGACCATGCC ATTGCACTTC AGCCTGGGCA 141300

ACAAGATGGA AACTCCATCT CAAAAAAAAA AAAAAATTGC AATATATCTA TATCTTGAA 141360

TATTATAAAG CAATAAAAGG GAATAAACTA CTGATATATA CACAAAATGG ATGAATCTCA 141420

AAAATGTGAA GGAAAATAAA AAATACATAT GATATAAATT CCATTCATAT GAAATTTTAG 141480

GAATGGGAAA ACTAAGCTGT AATTATGGAA AGTACATCAG TGGCTGCCTG GGGCCAAGAG 141540

GATGGAAGAG GCGGCACAGG TGATACTACA AATGGAAACT ATCTAGGTTG ACGGAAGTGT 141600

TCTGTAACTT GATTACAGTA GTAACTGTTT GGGTATATAA AACGCATCAA ATTGTATAAT 141660

TAATACAGGT GTATTTTACT GTGTATAAAT TATTCCTCAA TAAAGTTGAT TTTTCATTAA 141720

ATATATTATT TGCTAAAATG AGGAGAGACA ACTATTATCT TAAAATAGTT AAGCACAATA 141780
```

```
AAAATACTAC AATCAACTCA TTATATATGG AAATTAAAGG AGAAAAATAG TGGTATGATT   141840

AATTAAAATA AAAAGAAAAC CTTCTAAATT TTATCTTAGC TCATAGTTGT AAAAGCTGCC   141900

ATCCCTAACC AAGGCCACCC TTGACCCTTT CTCATGTTCC ATCTTTCTGT TTGTTTCATA   141960

GTTTATGTCT CACCAAAATC TATCAGATAA ACGTATTCAT ATGAAGATTT AAATATATTA   142020

CATGTTAAGC CTTAGCGAAT ACTTCAATAT CTAAAGAAGG TACAAACAAA ACAAAAATCA   142080

ACACTTAGTT ATAAGAGATT ACATACTCTC CAGGGAAGAC CTGAAGACTA GCCCCTTTCT   142140

GGATCCCACT AGCCCCTCAT CCCACTCCAA GCCCTCCCCT CCAATCCCAT ATGCACTGGG   142200

CATTCATACA AATAAGACCA TCAGCTCTGG ATATCTGTAC TGATTGATGC TCCTGCTAAC   142260

TACCTGAATG ATTGCGATGT AAGGACAGCA CTGCCTGAAT CCTATTTATC TCTCGCTATG   142320

CCATAGCGGC CTTCCATGCT GATGGCGTGT TTGAGGATCC AGAGGGTCT TTGGTTGGCA    142380

GGATTGTTTT ATTTCCCCAA GAGGAGAGCC TTGATGCAAA ATAGGTGAA GAAATCAGTA    142440

CAACAAAACA GAAAGCCTAG AAACTACTAT GAACACAATA GAGCAGAAGT AGCCTTAAGA   142500

GTTGGTGGAG AAAGGATGGT CTATTCAATT ACCTGAGCTG AGAAACTGGC TTTCATATGG   142560

AATAAAAATA AAATTATAGC TATACCCCAT ATCATACACA AAAGTTTCTA CATCTAACAA   142620

AGACACAGAT AGAAAATGTT TTAAAATTTT AGAAGAAAAT AGTGCAGAAT TTTAGTGCAG   142680

AATTTCTTAG ACTAGATGCA AAAACAAAAA TGATTAAAGT GGCCAGGCAC GGTGGCTTAT   142740

GCCTGTAATC TCAGCACTCT GGGAGGCCGA GGTAGGTGGA TTAGTGGAGG TCATGATTTC   142800

GAGACCAGCC TGGACAACAT AGTGAAACCC CATCTCTACT AAAATACAAA AATTGGTAGG   142860

GTGTGGTGGC TCACGCTTTT AATCCCAGCT ACTTGGGAGT CTGAGGCAGG AGAATCACTT   142920

GAACCTGGGA GGCAGAGGTT GCAGTGAGGG GAGATGGCGC CACTGCACTC CAGCCTGAGC   142980

AACACAGCGA GACTCTGTCT CAAAAAAATC TAAAAATAAA AAGATTATTT TTAAAGACT    143040

ATTTTAAACA AAAAAAATCG TTTAAATGAT ATGATACACT ACATCTAATA TTTGAAAAG    143100

TACTTCTTAA TACTTTTAAT AAAAAGAGGC GCTGAGAGCA TACAACCTAT CCTCAGAAGA   143160

GTGTTTGACC TCTAGGAGGG ACGCAAGCGC GTTCTTCCTT CATTTAACT GGTCATTTTC    143220

ATTTATTTCA GGAACATCTG AAGTAAACAC AGTCACACGT TAACCTTTAA AAATCTAGGA   143280

GGTGCGTACG CATAGTTCCA TTACTTCAAT TTTTGTACTT TTGCATTTTA AAATATCACA   143340

GGGAAGCTCG GTACAGCTTC AAGGCTAGGA GGGGTGGCTC TCTCTTAAGC CCTGTCCCCG   143400

CCAGCCCCAG ACCTCTCGTC CCGCCCCCAT TGCCCAGTCC CCACCCTCAC TTCCCCATTT   143460

CCCCACTCCC GCGGTCTCTT AACGCACCTG TTTTTCGTCC AGTGGACTCA GACCTGTACT   143520

CTTCCACCAG GATCGGCTCC TTTCCCGGAG CTCTCGCTCT TAGAGGAAAT TGAGAGAAGC   143580

ATCAGCGGAG ACCCATCTGT GGCTCTCCAG AGGGCGCGGC ATTCAGACCC CAGATCCAGC   143640

TGTGAGAACG GACCCCAGGC TCACACCAGG CCTGCGGGAG GCGGCCCACC AGAGGCGCTA   143700

GAAAACAAGC CTCGCGGGGA GGCGCGCAGG GCGACTGCAA GCTGTAGGGG GCGCTGGCGC   143760

CCTCACAGGC CAGGGGCAGG GCCGGCGCTG CGGGCGGGGC TCCTGCGGCG TGAGGGGCGG   143820

CCCCAGGCCA GCAGCTGCGC CCTGGCTGGG AGCCGGGGAG CATTTGCTGC TCTGCTGGAC   143880

CCTGAGTCTG GCGGCGGGCG GCCTCCTCTC CGCTCCCCGC CCGCCATCCC CCAACTCCCG   143940

ATCTCTCTGC TGCGTCTGGC CTCAGGCTGA GACCCCAACG AATCATTCCC CGCATGGGAA   144000

CATTTTATGA TATAACTGAA TTCAGTTTTA TGTATAACTG AATTACGGAT ATGAGAATCT   144060

CAAATGAGGA CGAATGGTTT TTACGCACAA AACATGAGAC ACAAATCTGT AAGAAATATA   144120
```

```
AAGTCGTGAC CACGTCCTTT CAGAACTTTA ACCTGTTTGC TGAAGTACGT CAGTAACAAT  144180

GGCAGGGAAA GGGTATCTTA AATTTCACCA CAGCCTCAAA GAGGCCATTT CGTGGATCCG  144240

CTGAGGCTTG GAGTCGGCCT TCTGACCACG AGTCCTGCGG CTATGAAAGA GGAAGCCGCG  144300

GTTCAGGGCG TCCTCGCGAG TCGCGCAGCC CGCCCTGCTC CAGCTGGGGA CACAGGTGGT  144360

CACGGCGCTT TCCAGCTGCA GATCCAGGCG GCAGCCCAAG ATTTGGTCCA GCCGCCAAGG  144420

GGTGGCTCGA GTGACTGACG GGCCTTGAAC GCTCCCAGGA CCCACATCTG GAGAGGGAGG  144480

TGGGGGTGGG GTGCTGAAGT CATTCTTGGG GCCCCTGGGG GCGGGCATGG ACCTGGGTAA  144540

GGCCAGAGAA ATTGACACCT CGTGACATCC CTGGAAGAGA AGTACGTTCA GTGTCACTCC  144600

AGAGCTGAAA GATACCGCCT TCTGGCTGGT CCCTCCTCAC CTACATACTT TTCTAATTTG  144660

TCTGGAGCAG GCCGGGCATC TGTATTATCT GGTTATTTAA ATATCTGGTT ATTTAAAAGC  144720

TCTCCATTAA ATTCACATAC ACGAAAATAA AAATTAAAAA AAATTTTAAA AAAAGAAAC   144780

AAAAGCTCTC TAATGACCAA GTCCTACACG ATAGTGAATA AATTTTTTTG TGTGGTCCCT  144840

AAAATTGAGT TCATGCCTTT TCTGAAGTAA TAGACGCCCA GAGAAGGGAT CGACTTACCC  144900

ATCATGCCAC AGAGATTAAT TGGCCCCAGA ATTCTTTAGC AGACCGTGTA TATGAACGTC  144960

CTTTGCAATC ATATAAATTA ACTGGGAAAA CCTCATTTAG TATGTTACAT GCCTAGCGTT  145020

TTGTGCCTGA ACACCTTACA AGAACCAGGG ACTATTGCCC CAATATTATA TTTCAGGAAA  145080

GGAAGGCCCA GACAAATGGT GTCACTGGTC CACTTTCACC CAGTTGGTAA ATGAAACCAG  145140

AAATTATAGC TGTACCACAG AAAGGTGAAA ACGTTTCTTT TATAATTTCA CATACAATCT  145200

TTAATGGACC CAGTGTCCAA CACATTAAAG CAAGTGCTCA GGAGTGACAT CAAGATGTAA  145260

AAAATAGTCC TGTCCTCAGG GAGTTTAGGT CTTGGAGAAA AGAGACCCAA GGAGACACAA  145320

GACAAAGGGG AAAGAGAAGG AGCGCTGAAG ACTGAGGACC CTGCCTGTGG ACTGAAGTGA  145380

GGATGGGGAC ACCCGATGCC CGGAATATGA CAGTTTGGAG GGGCCTGAAG GACTCTTCTA  145440

TTCTCTATCA GAAAACAGA  ATTACTCTCC TAACCAGAAA AGGTATTTCA ATTTATATTT  145500

TCCATCACAG CACTTTTCTG GTGATAATTT AATGTGTTTT AAAAAATGTA TCACAGTGAT  145560

GGCCTGGTGT GAAATAAATA ATAAAATTTT AAGAATTAAA AAATATAAAA ATCTTTTATA  145620

TAGACATTAG GAGTTACAAG GATAACTGTG AATTATAATT AGTAATTAAA TTGAAATACT  145680

GATTATTTTC ATTTTTATTT AATTATTTAA TAAAACCTAT TTAACATTTA ATATTTATCA  145740

GTAATTAAAT CTAATTGTTA ATATTTATTA TTATAAATTA TTTTAGAATT AAAAATAAGT  145800

GTAGAAGCGA GGCATGGTGG CTCAAGCCTG TAATCCCAAC ACTTTGGGAG GCTAAGGTGG  145860

GAGGATTGCT TGAGCCCAGT AGTTCAAGAC CAGCCTGGGC AACATGGAGA AACCCTGTCT  145920

CAATACAAAA AAATGAGCCA TGTGTGGTGG TGCGTGCCTG TATTCCCAGC CATTCTGGAG  145980

GCTGAGGTGG GAGGATGACT TGAGCCTAGG CAGTCAAGGC TGCAGTGAGC CCTGATCTTG  146040

CCACTGCACT CCAGTCTGGG CAACAGAGCA AGACCCTGTG TCAATATACA TATGGACAAA  146100

CTTAAAATTT AAAATGAAAG CATACTACTG ATACAGAATT GAGTAGAGAT GCAAAGCTAG  146160

TCCTATAACC AGAACAATAA AGATAAAAAG GAGAGTGGAA GAAGGTATGT CATGAATTTC  146220

ATGATAAATG GCAATTGCAA ATATCCTGTA GCAGAACAAA ACAACAAAAT TGTAGATAAA  146280

ACATATCCAA CCCTTTGGAA GGCCAAGGAG GGAGGATTGT TTGAGCCCAG AAGTTGGAGA  146340

CCAGCCTGGG CAACATAGTG AGACCCTGTA TCTAAAAAGG AAGAAAGAAA AAAAAAAAA   146400

AGGATGATAA AGTAGACAAT ATTGAAAGCC ATTTTCTGCA AATACATAGT GAATTTGATC  146460

AGTAATTTTC TTCCAACAGT GCAAAAATGA ATAGATATTA GTTGCCTGAA ATAAAAATCA  146520
```

```
AATATCCAAC AAAAAATATT GACTATCTAA TAGTATCTAA GCTAGTAAAT TTGGCCAGTT    146580

ATAAAATGTC TTAAATTTTT ATTTAAAAAA AGAAAACCAT ATTTATAAGA AGAGGTGATA    146640

AAGAGAAATT ATTTCAGTTA TGAAGATTTT GTTAGAAAAC TATGAGAAAA AAACTATTTT    146700

TTGTTTTCAA AAAGTGAAAG ATTAAGTTAC CAAACAGTTG CTAAAGAATA CCAGATGGCT    146760

GAGCGTGGTG ACTTATGCCT GTAATCCCAG TACTTTGGAA GGCCAAGGCA GGAGGATCAT    146820

TTTAGGCCTG GAGTTCGAGA CCAGCCTGGG CACTGTAGCA AGACCCGTCT CTATTAAAAA    146880

AAAAAAAAAA AAAAAAAAAG AATACCAGAC CTTGCTAACA ATAGCAAAGA TCAATTAATT    146940

CAAAATTTGA AAAACTGTAA TTTATTTAGC TTTAGAGTAC TCTCGTGATA TGAGATTGCC    147000

AAATTAATAC TTTGGGTGCA TTTCTTTTCT CAAAGGACTT GCAAATTTAC AAAGAAGTGT    147060

TGAAGAAAAG CCACACATTG GCAGGTAATG TTTGCAAAAG ACAGATCTGA TGAAGAACAA    147120

TATTTTTAGA ATATACAAAG AATACTTAAA ACTCAACAGT AAGAAAATAA CCTGATTTAA    147180

AGCAGGCCAA TGACCTGAAC ATCTGTTCAC CAAAGAAGAT ACACAGATGC AAGTATGCAT    147240

ATGAAAAGAT GCTTGACATC ATGTCATTAG GGAACTGCAA ATTAAAACAA GTAGATACCA    147300

CTGCATACCT AGTAGAATGA CCAAAATTTA GAACACTGTC AGCACCAAAG GTTGCAAAGA    147360

TATGTAGCAA TAGTAACTTG TTCATTACTG GTGAGAATGC AAAATGTGCA ATCACTTTGG    147420

AAGACAGTTT GGTGGTTTCT TACAAAAGTA ACCATACTTT TACCATAAGA TTCACCAATC    147480

ACACTCCTTA GTATTTATCC AAAGGAATTG AAAACTTATC TCCACACAAA AACCTGCACA    147540

TAGATGTTTA TAGCAGCTTT ATTCATAATT TATCCAAAAC TTGGAAACAA GATGTCTTTC    147600

AGTAGGTAAG TGGATAACTG TGGTACTTCT GAATAATGGA ATGTTATTTA GAGTTAAAAA    147660

GAAATGCATT CACTTTGGGA GGCCGAAGTG GGTGGATTGC TTGAGGCCAG GAGTTTGAGA    147720

CCAGCCTGGT CAACATGGGA AAACCCCAAT TAGCCGGGCA TAGTGGCGTG AGCCTGTAAT    147780

CCCAGCTACT CGGGAGGCTG AGATATGAGA ATCGTTTGAA CCTGGGAGAT GGAGGTTGCA    147840

GTGAGCCAGT GCCACTGCAC TTCAGCCTGG GCAACAGAGC AAGACTCCTC TGTCTCAAAA    147900

AAAAAAAAAA AAAAAAAAAA AAAAAAGAA AGAAAGAAA AAGAAAAAG AAAAAGAAAA    147960

GAAACGATCA AGCCATGAAA ACACATGAAG GAAACTTAAA TGTATGTTAC TAAAAGCCA    148020

ACCTGAAAAG ACTGCATACT ATATGACTCC AACTGATGCA GGGCAAGCAA GCCAAAAATT    148080

AGGGCTTAGC CCGGGAAGAA TTCAAGGGTG AAGTGGTGGT GTTAGCAACT TTTACTGAAG    148140

CAGCAGTGTA CAACAGCAGA ACAGGTACTG CTCCTTGCTG AGCAGGGCTA ACCCATAAGT    148200

AATGTGCCCA GAGTAGCAGC TCAGGGGCAG TTCTGCAGTA ATATACCTGC TTTTAGTTAA    148260

GTGCATGTTA AGGGGATTA TGCAGAAATT TCTAGAAAAA GAGTGGTAAC TTCGGAGTAG    148320

GTACAGAGGA AAGAAGTCGA TAATGTCCTG TTGTTGCCAT GGCAACGAAA AACTGACATG    148380

GCGCTGGTGG GCGTGTCTTA TGGAGAGGTG CTTTAACCTC GTCCCTGTTT CGGCTAGTCT    148440

TCAATCTGGT CCGGAGTAAA GTCCCTGCCT CCGGAGTTCA CTCCTGCTTC CTGCTTCACA    148500

ACTGTATGAC ACTCTAGAAA AGACAGTAAC TATGGACACA GTCAAAAGAT TAGTTGATAG    148560

AAATTGGGTG ACAGGAAGTG TTGAAAAGGC AGAACACAGG ATTTTTAGGG CAGTGAAACT    148620

TCTGTGATAC TATAATGGTG AATACATGAC ATTATACATT TGTCAAAACC CATAGAAAGC    148680

ACAACACCAA GAATAAACCC TAATGTAAAT TACAGACTTT CGTTGATAAT GACGTGTCAA    148740

TGTAAGTTCA ATTGTAATAA ATGTACTACT GTGGTGCTGG ATGTCTATGG TGGGGGACA    148800

TTTTTGCTTC AATAGTTACA GTTGAAGTAA ATGTTTGTGT TTCCCACAAT GCATATGTAG    148860
```

```
AAACTCTCAC ATTCAATGTG ATGGTCTTTG GAGGTGGGCT CTTTGGGTGA TAGTTAGGTT   148920

TAGTTGAGAT CCTAGCAGAT CGAGTCTTCA TGATGGGCAT GATGGGACTG GTCCCTTATA   148980

AGAAAAGACC AGAAAGCTAG CTCTCTCTTT GCCATGTGAA GACATAGCAG GAAGGTAGCC   149040

ATCTGCAAGC TAGGAAAGGG CCTTCACAAA GAATCAACTC AGACCTCAGA ACAGTGAGAG   149100

ATAAATTGTC GTTGTTTAAG TCACTCAGGC TGTGGTATTT TGTTTCAGCA GCCCAACCTA   149160

AGACTGTTAA TTGGATTAGA AATTTCCTTT TGGGGATGGT GTGTGGCGGG GGGTGCGGGG   149220

AGTACCTTTG TTAAGCTTTT ATATCAATGA GTTTGTAGGC TTTTCTTTTT TGGTCATTGA   149280

CTAGGACAGT TTAAATAGTA TGAGTGTGAA GGAGATTGTT GGTCATCTAT TCGATGTCCC   149340

TTCTCTGTTT TTTAATATGA GAACTCCTGA TTTTCAGCCA ACTACCCTGG AAAAAAAGCT   149400

AATCTTTCTG ACTTCTTAAG TGTGGCCATG TACTAAATTC TGGCTAATGC AAGGCAAGCC   149460

AAAGGTTTTA TGATAGGTTT TAGGACACTA GAGTAAAAGA GAGCTGTTGC ACACATGCTC   149520

TTCACCCTAC TTTTGTGTCC TTTTTTCCAT CCTACAACTT GGGTTGTGAG TATGATGGCT   149580

GGAACTTTAG TGGCTCTCTT GGATCCCAGG GGTAATTGAG GGGTGGCTGG AAGGAATCTG   149640

TGATTTTCTG GAGTTTCCAT ACACAAACAA GACCTGGATT TTCTGGGCTT CCCAGACTTC   149700

CACATCTAGA CTTGCTTTAA ATGGGAGAGA AATAAACTTG TTTCAGCCAC TGTCATTTTG   149760

GGCTATTTTA TAGAACTTAA TCTAATCTTC AAGGGTACAT GAATTGCTTT TCCTTAAAAA   149820

AAAAATCAGC CATAAAATCA TCTTCTTTTT TCTTTTGTTC CCCACATTAT TTAGTTGGAG   149880

CTCTGTAACT TTTTTTTTTT TTTTTTTTGA GACAAGGTCT TGCTCTGTCA CTTAGGCTGG   149940

AATTCAGTGG CATGACCATG GCTCACTGCA GCCTTGCCCT CCTAGGCTCA AGCAATCCTC   150000

GTCTCAGCCT CCTGAGTAGC TGAAACTAAG GCACATGCCA CCATGCCCAG CTAATTTCTT   150060

TTCTTTTAGA GATGGGAGCC TTGCCCAGGC TAGTCTCAAA CTCCTAGCCT CAAGTGATCC   150120

TCCCATCTCA GCCTCCCAAA GTGACAGGAT TACAGGTGTG AGCCACCATG CCTGGCTGCT   150180

CTGTAAGTGT CTGAATTTCA TTTTGTATTT ATCAGTCTGT TTAGATTTTC TTTCCCTTCT   150240

TGGGTCAGTT AGGCCATTGG TTTCTTTTTA AAGGTTTTCA AATTTATTTG CATCTAATTC   150300

TTCAAATTAC TCTCAAAATT ATTCCAGTAT ATATTCTTTT GTTCCTATTT TCTTCTGTAT   150360

TCTTTATTAA AATAGCTAAT GATTTATCTA GCAGGACTTA TATTCTTTCC ATAACTTTCC   150420

TGCACCCCAA TTAATCTCCA ATTTTATATT TCTTCTGGCC TTCCTTATAG TTTCCACAGG   150480

TTTATTTTAT TCATTTTTTA AAACTTTTAT TTAATTGTTT ATTTTATTAT CATTCTTTCT   150540

TATTCAGCAA TCTAAGTGCT TAGGGATATA GAATTTCCTC TAAGCAGCAT ATGCTAGGCT   150600

TTAACAATGT TAGGGAGGCC TCCCCTTTCT GGGGAAGACC ACACTTACAT TAACACAGGA   150660

CTGTGGGATG CCAAGAGGTA GAGAAGAGCT TATGAATATC CAGATTACAT CTTCACTGAT   150720

CCTGCACAAA GGTGGGGTTC CTCGGTTACC CACTGGGTCC TATTACCCAA GTCTGGGTCA   150780

GCATACCGAG ACTACGGGTA TATAGAACAA GTGCAACTGG CGATAATCCT TCTGTTGGGG   150840

AGAAAAATCT TTTTTTTCTA TTCATCTTAG GTTCTCCATC TGTGGCCCTA TCAAGTAGAC   150900

TAACAAAAGA CAGATTGACA AGACAGAAAC AAAGCATGTG CATTGTACAA ACACAGGGGA   150960

GTACTGAGAT GAATACTCAA AAGAGGATTT AGAACTTGGG CTTATATAGC ATTTTAAGAA   151020

AAGAATACAT TTTTTAAGTG ACAAGGAAGA CGAAAAGGAC TTTGAGTTTC TAGTGCAGTA   151080

AATTGTGGGA AGGCAACTTT TTCTTTCCCT TTTTTTTTTT TTTTTTTTTA AAAAAAGAC   151140

TTCTCTGGTG CTATGTCCAG GCTGATAAGA GTCTAAAGTC TCTGGTGACT AACTTTTGTT   151200

CTTCCCCGAG TAAGAAGACA CCTTCACAAT TTCATATCCT GCTTTTAGGC AAACAGGGAG   151260
```

```
AGGGCAGAGG TGTTTGTTTG TTTTTAATCT ATTTTTTTTC TCAATTGTCT TCAACTCAAA 151320

ATACTTCTTA TGCCAAAGAT GGCATATTCT GCTACCCTTC ACTTACTACT TACAACCCAG 151380

CCTCTATCAT CATAATTAGA ACTTCTGACC CTGGGGAACA TGGGCAATAG TTTGAACTCT 151440

TTTATATCTC CCTTAGGCAG AGATGGAGGC CCAGCCATGC CTCTGACATC TAGACACAAC 151500

TGTTGCTTCA TTTCTCCTAT TCTCAGAGGT GATGTTGTAG GACTTCAACA AATATCAGTA 151560

AACATTAATT TTTTTTTTCC TTGAGGCACA GCATGATCTT GGCTTACTGC AGCTGCTGCA 151620

GGCTCAAGCA ATTCTCCTGC CTTGGCCTCA CGAGTAGCTG GGTTACAGGC CCCTACCACC 151680

ATGCCCGGCT AATTTTTGTA TTTTTAGTAG AGACAGGGTT TCACCATGTT GGCCAGGCTG 151740

GTGTTGAACT CCTGACCTCA AGTGATCCAC CTGCCTCAGC CTCACATAGT TCTGGGATTA 151800

CAGGCGTGAG CCACCATGCC TGGCCATCAA TTTTTATGTC AACTCTAAAT TATAACATTT 151860

AGCAATTTTG TGACTTTTTA TGGTCATCAT TAATGTTGTT TATGTTTTAG TTGTAGTCCT 151920

GTCATTACTC ACTCGGGTAT GGTAATTTGG TCTTTTTCAA AATGAAGTTA AGGTCTATTT 151980

GCTCTTCTCT GAATCATAAT AAGAACTGCC AACAGCCATT TCAGCAATAA CTATTTACTG 152040

AGATTTTAAA ATATTTCAAG GTAATTGGTC CTAGCAGACT GGAAAATACC AAATTCTTTT 152100

CCAGAACTGA ATCCCCCATC AAAGTTCAAT TTTACTCATA ATTCCCTTTT CATTTGAAGC 152160

ATCTCATTGT AAGCCAGTCT TAACCCTTCT CTCACACTTT GCTTGGCTGT TTCTCAGGTA 152220

GAACTCAGTA AGTCTGGTAG CCTCCAGGAC TGCCGCTTAG ATTATTAAAC AACATGTCAG 152280

TGGTTGGAAG AGTCAATGTT ATTTTGATTT TTCTGTTTTG TTTTGTTTTA AATGCAGTTG 152340

GCGGATAATT GCAGCTTTCT TTCATTCCCT ACATGAGTTC AAATGGCAGC AAACAAACTA 152400

GGAGAACGCA GACCTTCTGA CTTGTGGGTA CCCCTACTCA TCACCTGAAG ACCCTTGGAA 152460

ATCAAAGCCC TGACCCATTA AAGACGGATG GAGACAGCAA CATACGATCA TCACTATTAT 152520

CTTGCTTTGC CCCAGTCCAG GTTAACCATC TGTGGTATTT TTAGTTGCTA AGTCCATATA 152580

TTCAACATAA ATCAATTATA TATCCACTAA AATCTCAGCA CTAGTCTAAC TACTAAGGAA 152640

ATGACAGCGA AGAAAACAGA CCAAACGTCT GCCCTTATGG GATTTATATT ATTTTCTCTG 152700

TGCTGGTTAA ACCAAGGAGC TTCTGCTCTT TTCCTTAGTC ACCTGGGGGA GGCAGAAACA 152760

AAGGAGAATA TTGATAAACC TGGAAATAGG GCCGGAGAGT ATCAGAGAAG GAAGCCTTCG 152820

GGAAAGTAAA GATGTGGCAG CCAGTATTCC CGTTATAAAA GGATACAACT CCGGCCTCAT 152880

AGTCCAGAAA AATTCCCACA AGCAGGGGCT GCTCATGCAG ATGAAGGGAA GTTGGGGGAG 152940

AAGTAAGTGC TACATAGCCT TTCTTTTTGC ACAGCCTGAG GGTCCAGAAT CCAGACTGAG 153000

GCTCTTGCTT CATGCCAGTG CCCCTCTGCA CATTTTCCAT ACAAACTCCT AAATCCCATC 153060

CGGTTCCTTC GCCAACATCC ACTTCAAAGT AACGTCTTCC TGAGGTGAAG CCTTCACAAC 153120

CCAAGACACA GGGAAGGCA GTAAATCTCC TGGAAGATGT GTCCTGATTC TCCTGGGTGT 153180

ATCCACGAGT CACTTGTCTC CGATCCTCAG AGAGAATTAG TTCGTGATGA GCTGTATCTG 153240

GATCAGAGT CACACTAACT GCAAAACAAA ACAAAACAAA CAAAAATAAT TTTGTTGCTG 153300

TGAAGAACAC AGGTTATTTT ATTTTATTTT ATTTGAGAT GGAGTGTTGC TGTCACCCAG 153360

GCTGGAGTGC ACTGGCACTA TCTCAACTCA CTGCAACCTC CACCTCCTGG ATTCAGGCAA 153420

TTCTCCTGCC TCAGCCTCCG GAGTAACTGC GACTACAGGT GCGCACCACC ACAAGTGGCT 153480

AATTTTTTTA AATTTTCTGT AGAGATGGGG TTTCGCCATG TTGGCCAGGC TGGTCTCAAA 153540

CTCCTGACCT GAAGTGTTCC ACCCACCTCG GCCTCCCAAA GTGCTGGATT ACACAGGTGT 153600
```

-continued

```
GAGCCACCAT GCCCAGCCAC AAGTTATTTT CAATAAAACC AGCCTGTGTT CAAACCCAAC 153660

TATTGTTTCT TATAAACTGG GTGAGCTTAG GCAAATCATT TAACTTTCTG AGCCTCAGTT 153720

TGTTAACTAT AAAGTGGAAA TTACCGTATT TGTTGCAGAG AATGGTGGGT AGGATTGAAT 153780

AAGCTTATGT TTGCTTAATG CTTGGTAAAA TTCCTGGTAC ATGGTAACCA CCTAATAAGT 153840

GGTAGTTGTT GGGGTGATCA GGCCCAACAC CAGGCCGTGG GGGCTACAAA GTCCGGCGGG 153900

GTCAAAGGAA TGAGAAAAGA CAAGTTAAGA GTGCATAAAG TGGGTCCAGG GTGCCAGCAC 153960

TAGATTGGAG GCTGCAAAGG CCCTAAGCTC TGGGAGCCCA CACTATTTAT TGGTGATCAA 154020

ACAAAGAAGC AGGTGGTGAG GACGTGAGGG TAAACAGGTG AGGGCATGAG GACATGGGGG 154080

TAGAAAGGTA GTGGTGCATT AAGCGTAGCT GTGACAGTTT AGCATTTTCT TTGACACATG 154140

TAGAATATAC TCTGCTGCTT GAGATAGTAG AGGACACGTT TATGAGTGAA AAGCAAGGAA 154200

CCAACAAGTC TGTGCACTTT CCAGAGGCTA TGAGGGGTTT TATGCCCTGA GCCCTGGGTT 154260

CCATCCAAGC CACAAGGGGT TTTATGCCCT AGGCTTAGAT TTGTGGTGCG GCAGGGCAGC 154320

CTTCCACCAT TTGGCACAGA GCTTGGTGTT CCAAAGGCCA CGAGGGGTTT TGGACCCTGG 154380

ACCCCGGACA TCTTCCAAGA CTCTTTTACA TTATGACAGA CAAGCCAGTC CTGCTTCAGC 154440

TCTTCTAACA ACATGTAGTA ATAATGATAT CATCAACATC ATCTTCGTCT TAATTATTCA 154500

AGGATGCCAA GGTACAGAAC TAACCTGTTA ATATGGTTAC CATCCTGTCC AAAGTTCTTC 154560

TCCCATGCAG GACTTCCAGG AATCATGAGA CAGTTGAGCA GAAAGATACC TTTTCCCTTC 154620

TCTACTGAAT AACCACCAAC ATTGAGAATC AGAGAGGGAA AATGACTCAG CTAATGTCTT 154680

AGCTTGTTAT TGGAAGACCC AGGTCTCATG ACACATGCCT AGTCCCATGA CTTTTAATTG 154740

TAAGCTCTTC TCTTTCCCCT CAGATAATGT TCCATAAGCA TTAGTATGAG ATAATAATAC 154800

ACTGAGGACC AATATACATG AAAAATATCA GACTAGAATC AAACAAGACA GAAAAAAGAT 154860

CTGATAACCT AAAGTGAGAT ACTGAACAGT ATGCAGTTTT AAAAATAAAA AATGGTAATA 154920

GGATGTTCTA ACAAGAGAGT TAAGAAACCA CTGTGCTACT GAGTTAAATG TTGATCAGTT 154980

GGTCTGTGAC AATTAAGGAA TTCAAGTATT CAGAAACACT TCCTGTGCTG GATGCTCTCT 155040

GTTTGTTCTT CCAAATAATC CCTCACTTTT CCCTGTCTTG CTCTGTGCCC AGGAAGGCTG 155100

ACATGGACAG ATTAACCAGG CTTTCCGCCC TCTGGCTTGG TTCAGCCAAT GGGAAGCACC 155160

AGAGGAGACC ATAGGGCACA AGAAGCAGC CTTGGGAGTA TTCAGTACCC CAGTCCCACG 155220

CTATGATTTG GAGGGTCTGC ATTCCTCTGC CTCTGGGCAC ACTCTAGTAT AGTTACAGCT 155280

CCCTACACCT GCCACTTGAG GCCCAGAGGA GGTGATGGCT CTCTAACTGT TCCTAGTTCT 155340

GGGTGCTTCC TGTTCCTTGT GGATTTCCCA ACTCCTCACC TTTGTAAATA CCCTCCTTTT 155400

TCAAACTCTA TTCAGTTAGC TTTTATCAGC CTGACTCACA GAAGTTTGGG GTTTCAATTC 155460

ATATTACCTG AATGACCCAG GAAAACCCAT GTTGAGAAAT TAAAATGTTT ACGGGGTGGT 155520

AATACCACTT AAGAGAAAAA ATATCAATTG GATTTTTAAA ATTCCACCTA TCTATTGGTG 155580

TGACACATCA ACAAAAACAT ATAGAAAGAT TGGAAGCTAA AAGATAGATA ATATAGTCAT 155640

ATACTGTTAT AGTATTATAT CAAAAGATAT TAAGTCAGAG CATTATTAAG AATGAAGAA 155700

GGGCCAGGTG TGGTGGCTCA TGCCTGTAAT CCCAGCACTT TGGGAGGCCA AGGCAGGCGG 155760

ATCACTTGAA GCCAGGAGTT CAAGACCAGC CTGCCCAACA TGGCAAAACC CTGGCTCTAC 155820

CAAAAATACA ACAATTAGCT GGGCATTGTG GCACATGCCT GTAATCCCAG CTACTTGGGA 155880

GGCTGAAGCA CAAGAATCAC TTGAACCGGG GAGGCAGAGG TTGCAGTGAG CTGAGATTTC 155940

GCCACTACAC TACAGCCTGG GTGACAGAGA GAGATTCTGT CTCAAAAAAA AAAAAAAGA 156000
```

```
AAGAATGAAA GGAGTCACCT AAAAAAGATA ACACAATTTT AAACATAAAT GTACTACATT  156060

ATTAGTGAAT TCATGTTTAG AATTGTGTTA ATATACAAAG CAAAAATTGT AGAATTATAG  156120

GAGAAATGGA CAAATCTACA ATCATCATGG GATGTTTTAA CATTCTTCTT TCCATAATTG  156180

ATAGATCAGG CAGACCAAAA GAAAGAAATA AGGGAAGATA CGGAAGGTCT GAACAATCTA  156240

AGAAGCGCAA TCTCATAGTC AATACATAAA GCTCAGCAAT TGTTTAATAA TAGTAAGCAG  156300

AGAATATGCA GTTTTCTCAG GTATAGATGG AACATGCACT AACTGAGTAA ATACTAGGCA  156360

GAAAACAGTC TGAACAAGTT TCAATAAATC TGTATTACAC AGATCATTTT CTCTAGCCTC  156420

AATATAAGAT TATAAACCAA TAATAAAAAG ATGACTAAAA AGATTCTAAA TATTAGGAAA  156480

TGTAAACTAC TAATAAGTCA TTAGAAGATG TATAGAATGG AACAATAATA AAATGTTATT  156540

TATAAAAATA TACAATGAAG CTAAAGCAGA ATTTTAAGGA AAATTTGTAG GCTTTAAATG  156600

CTTATCTTAG AAAAATTAAA AAGCTGAACA TTAATGAGCC AAGCATCTAA TTTAAATTTT  156660

AAAAAGAACA TAGAAAGCCA AATATAATTT TTTAAAAAGA AAAAATAGAT ATTAAACAAT  156720

ATAACAGTGA AGTTAAAGAA AACAAGAATG CAATAAAGAG GAAAACAAA CAAAAAAAAA  156780

AGTAGCTTCT TTTAAAAGAA ATTTAATAAA ATAGACATAC CTCCAATGAG ATTTATCAAA  156840

GTAAGACAGA AGGCACAAAT GGAATGAATA CAGAAACTTT TTAAATATTA CAGAACTTTA  156900

TAATAAATCT TATGCTACTA ATAAAATTGA AAGTACTGAT AAAATTATTA CTTCCTAGAA  156960

AAAATATTTC TGAGTAAAAC TCACTCAAAA AACAAATAAA GCATGGGCAG ACCTAACATT  157020

AAAGAAATGA AATCACTACT TTAAATTTTA CCGACAGATA ATAAAACGTG CATCTTTATC  157080

AAGCAAAAAT GGAACTTGTC AGTTTTATAG GAAATTTAGA AGTCAAGGCA TGAGTAATGC  157140

CAATCTCATA CCAAATCCTA CAAAGAATAG AAAAATTATGG CTCCCGCTTA TAGACATAGA  157200

TATAGAACTC CTGCACAAAA TAATATAAAT AACAAACCAA ATTTTATATT TGCAACTATA  157260

CATATTATAT GTGTATGTAT TATATATGTT AACATATACA TATATAATAT GTATAGCATA  157320

TGTTCTACAT ATTATATATG TATAGTGTAT GTATTTTACA ATATATAAAT GAAAACCCAA  157380

TCTTTAATAT ATTCATCTAG ATTGTCATAT ATGCACATATA TAATACATTA CATCAAAAAT  157440

GTGTACAATA ATCAGGCCAG GCACAGTGAC TCATGCCTGT AATCCCAGCA CGTTGGGAGG  157500

CTGAGGCGGG TCAATCACTT GAGTCCAAGA GTTTGAGACC AGCCTGGTCA ATATGGCCAA  157560

ATTCCATCTC TACAAAAAAT ATGAAAAATT ATCCAGGCAT TGTGGTGCAC ACCAATAGTC  157620

CCAGCTACTC GGGAAGCTGA GGTGAGAGGA TCACTTAAGC CTGGGAGGTG GAGATTGCAG  157680

TGAGTCGAGA TTGCGCCAGT GCACTCCAGC CTGGGTGGCA AAGGGAGACC CTGTCTCAAA  157740

AAAAAATTAA AAAATTAGCC AGGTATGGTG GCCTGTTCCT GTAGTCCCAG CAACTGGGGA  157800

GGCTGAGGTG AGAAGATCAC TTTAGCTCAG GTGGTGGAGC CATGATCGCA CCACTGTACC  157860

ACTCGGCTTG GGCAACAGAG TGAGAGCCTG TCTCGAAAAA ACAAATATAT ACACACAGTA  157920

ATCAATATAT ATATTATATG TACCAATCAA TGCTTCACTT TTATATATAA TATAGATTAC  157980

ATCTTATTAG ATATATAGTA TTCCTTCTCC ATAGATAGAT AGATACAGAT ATAGACATAG  158040

TATCCTCTAT CCATATTAGA GAGAGGATAC TATATATATC TATAGCATAT AGAGATGCTG  158100

TCTCAAAAAA ATTTAAACAT CAGCCAGATG TGGTGGCCCA TGCCTGTAGT CCCAGCTACT  158160

GGGGAGGCTG AAATGAGAGG ATTGCCATTG ATCCTCTCAT TGGTTGAGCC ATAATCGCAC  158220

TACTGCACCA CTCAGCCTGG GAGACAGAGG GAGACCTGAG GTGGAAGGAT ATAGATATAG  158280

ATATATAAAT AAATATGTAT AGAGAGAATA TAATATATGT GTGTATGTGT ATATATATAT  158340
```

```
ATTATGAAGA CACTGGGAGA GAATACTATA TATATATGTG TGTGTGTATA TATATATTAT    158400
GAAGACACTG GTGGGATGGT TTCATTACCA ATTGGACCAA GAGTCCAGGT ATGGAGCCAA    158460
CATGCAATGT TGTTGTTGAC TGAGCTGGCA GAGCACTGGT CATAGTTACG GGAAAAGAAG    158520
GTCTCCAATG AGACATACTT AACAAAATAT ATGAACTTGC CATATACGTG GAGAGTTCTG    158580
GTGTGTATAT AGCCTTCTCT CACCAACCTA GCAATTGTCT TCATCATCAT TATAATGCTA    158640
TCAGAGCAAA GATGACAGCT AAATTTTTTT GTCCCTTTCT TCTTCTTTCT CTTCCTTCCC    158700
CTCCCCCACC TCTTTCTCTT CCTCCTCCTC CTTCATCTCT CTTCTTTTTT TTTTGAGAT    158760
GGAGTCTTAC TCTGTCGCTC AAGCTGGAGT GCAGTGGCAC AATCTCAGCT CACTGCAACC    158820
TCTGCCTTCT GGGTTCAAGC AATTCTGCCT AAGCCTCCAG AGTAGCTAGG ACTGCAAGTG    158880
CACACCACCA CACCTGGCTA ATTTTTGTAT TTTTAGTAGA GATAGGGTTT CACAATGCTG    158940
GCCAGGCTGG TCTCAAACTC CTGCCCTCAA GTGATCCTCC TGCCTCGGCC TCCCAATGTG    159000
CTGGGATTAC AGGCGTAAGC CACTGTACCC GGCCTCCTCC TTTAATAGAC AGGGTCTAGC    159060
TCTGTTGCCC AGGCTGGGTA CAGTGGCGTG ATCATAGCTT ACTGCAGCCT CGAACTCCTG    159120
GGCTCAGGAG ATCCTCCTGC CCTAGTCTCC CCAGTAGCTG GAACTACAGG CATAGCACAC    159180
GGGGCTAATA AAATTAATTA GGTGATAAAA TTCACTGCCC ACTGATGACT AAGCTCTTTG    159240
GACATAAAAG ACACAGACCT TGAAGGAAAA TGTGTCTACT TAATTTTGAA ACCCTATTTA    159300
TCAAAAAACA GGATGAAAAT GCAAAATGCC ATCCACATGC CAGAAGATAT CAGCTATAAT    159360
AAGTTCCCAT AAATCAATAA GGAAAAGAAC CCAATAAAAA TTATTAAACC ACAGTAAATC    159420
ATGGGTAAAT CACAGAGGCC TGAAGGGCTA ATGGACATAC AAAAAGAATC TCAATCTCAC    159480
TAGTGAAATC AGAAAAGCAC AAATTAAGTA CACAATTAGG TACCATTTTA AATCTGTAAG    159540
ACTGTCAAAA TCATAAATTA TATAAGTAAA GACTCAGGGA GTTTTGGAGG AGTGAGAGCT    159600
CTTATATTGC TTGTGGGGTA GAATTGGAAC AATTTCAAGA TCTGTAGTAT CTGGTAAAAT    159660
TATGATATGC ATCCCTCACA CCAGCATGTC ACTCCAAGGT ATCTCCCTGG AGGGAACATT    159720
TACGGGACAC AAGGAAGCAT GGATAAGAAT GTTCACAGTA GTATTGTCTG CAACAGCAAC    159780
AACAACAAAA AAACCCAACT ACACACAACT TCAATGCCCA GTCCACAAGG CAATGGATTA    159840
AATAAACTTC AGGCCGGAGA TGGTGGTTCA TGCCTGTAAT CCCAACACTT TAGAAGGCCG    159900
AGGCGAGAGG ACTGCTTGAG CCCAGGAGTT CAAGACCAGC CTGAACAAAA TAAAGAGATA    159960
GTGTTTCTAC AAAAAATTTT TAAAAAATTA GCCAGACGTG GCAGTGCTTG CCTGTGGTCC    160020
CAGCTACTGG GGAAGCTGAC GTGGGAGGAT TGCTTAAGCC CAGGAATTTA AGGCTGCAGG    160080
GAGCCATGAT GGGGCCATTG CACTCCAGCC TGGGTGACAG AGTGAGACCC TGTCTAAAAG    160140
AGATAAGTAA ATAACAACTT TGCATTTTCT GCCACATTGC AAAATGGTGA GAGAGTGGTT    160200
TCTAGACTCT AGACTCTTTC TATGACTACC TTCTAGTTAT GAGATCCTAC AACACTCACC    160260
TAACCTCTCT GTGTCATATT TCCTCCTCTA TAAAGCAAAA ATGCCCCATA TAGAGAGGAC    160320
TGTGATATAA AACAAGAACC AAGAAAAGTA AAGCTTTTCT AATCTGTCAC AGACTAAAGA    160380
GTGCTCAGTA TATGTGAGTC ATTATTCCTG GTGCTGGTAG GAGTGTATGT TACAACTTTG    160440
AGTCAAGTAA TATGGTACCA TATATTAAGA TTAACAACAA CCTCGGCAAT CCCAGTTTGG    160500
GGTATGTTCC CAAAAGAAAT GAAAGCACCA GGATATAAGG ATGCATGGAC TAGAAAGTTA    160560
TTGTAGCAAC ATTGTAATAA CTAAGTTCTA AAAACAGCCT GAAGCTCCAT CAGTAGGGAT    160620
ATGGTTACAT ATATTTATTA TATTCTTATG GAATATTAGA CATAAAAAGT AACGAGTAAC    160680
ATAGAAGAGA CAGTGTATAT ATGTTACGTT TGTACAAACT TAGGGAAAGA TATAGATCAC    160740
```

```
CCTACCTAGA GAAGTCAGAT TGGAGAGGGG TGGGAAAAAC CTTGAACTTT CTCCTTATAT  160800

CCTTTATATT GTTTGACTGA TTAAAATGTA TTTGTTGCAT CTGCTTGAAG GCAATGTAAA  160860

ATAAAATAAA CATACATTTA AAAATAAAAA TAAAATTTAT TCCTATCACT TTTGTAATAA  160920

AGCTGGGCAC AGTGACTAAC ACTTGTAATC CTAGCACTTT GGGAGGCAGA GACAGGCAGA  160980

TCACCTGAGG TCAGGGGTTT GAGACCAGCC TGGCCAACAT TGTGAAACCC CATCTCTACT  161040

AAAAATACAA AAATCAGCCA GGCATAGTGG TGCGTACCTG TAATCCCACG CTACCCGGGA  161100

GGCTGAGGCG CTGGAACCCA GGAGGCAGAG GCTGCAGTGA GCTGAGATTG CGGCACTGCA  161160

AGCCAGCCTG GGTAACAGCG AGACTCCATC TCAAAAAAAA ATTTGAAAAA AGAAAAATTT  161220

TAATAAACAG TGTTTAAGAG GGGAGAAATA TTTAGTTAAA AGATAAGCCC ATTTAAGAAA  161280

TAGTTTCACT TGACCCGGAA GGCGGAGCTT GCAGTGAGCC GAGATCGCAC CACTGCACTC  161340

CAGCCTGGGC GACAGAGCGA GACTCTGTCT CAAAAAAAAA AAAAAAGAAA GAAAGAAAGA  161400

AAGAAATAGT TTCACTTGAA CCATATTATG ATTCCTTCTG TAAAAGATGA GAGTAGGCAA  161460

ATTGACTCAG TGAAATCCCA GCAAAACTTA CACAAAGTCT TGTTCTTCCT TCCTGTCATC  161520

TGTATAGGAT GAAATACAGA GTGCTTTTGG GTTTTGTTGT TGTTTGTTGT TGTGTATTTG  161580

AGGGGAACAC AGGTCTATAA TTCCTTTTCT GAAATCCCTG GAACAAAATG GGCTTTGCCA  161640

TTCAAATTAG TTTAGAAGTT ATAAAGGCAA AAAAATGCAT ATACTCTAAA GTTCAACCCC  161700

ATCATGGCCT AAGGCAGAGC CCTGTAATCA AATTCATCAA TATATCTGCA GCAAAACATT  161760

TATTCAAATT AAGTGGGATA AATAAAGACT TTTAAATAGT CTCATCTCAG TGCCGTTCAG  161820

GGTTGGCCAC TGTGGAAGAC AGACTCAAGG GTGGCCTTCT ATGATTCCTG CCTCTTGGTG  161880

TTCACACCCT CGTAAAATTC CTTGTCTTTG AGTGTGAGCA GGGCTTATGA ATTGCTTCTG  161940

ACCAATAGGA TATGGCAAAG ATGATGGGAT ATAATTTCTA TGATTACGTT TCATTATGTA  162000

AGACTCCATC TTGCTGGCAG ATTTTCTCTA AAGAGTCTGT CTCCTGAGCT CTCTCTGAAG  162060

AAATAACTGG CCATGTTAGA AGCCCATGTG CAAAGAGCTG AGGGGTGGCC TGTAGAAGCT  162120

GTGGGCAACC TCCAGCCAAC AGCCAGAAAT AACCAGGGCC AAAGTCCTGC AACCATCAGG  162180

AAAGAAATTC TGCCTGCTAT CTCAGTGAGC TTGGAAGTGG ATTCTTCCTT AGCCTAGCCT  162240

CCAGATAAGA ACACAGCCTG ACCAACACCT TAACTGCAGC CTTATCAGAC CCTAAGCAGC  162300

AGGCCCAACT AAGCTGTGCC CAGATTCCTG AACCACAAAA ATTGAGATAA CATATCAGTG  162360

TTGTATTAAG GTTCTAAATT ATGGTAATTT GTTTGTACTA ATAGATAACT AATATAACCA  162420

CCAAATCATT TCAGGTTAGG CCAGATTTTT GTAGCCAAAT GAATCATGAT AAAACTTTCC  162480

ATTTTCAGGG GTTTTTTTGA TTTTGTACTT ACGGATACAA ATTTGTGAAA GTATAGTCAG  162540

CACTGATTTA AAAAATCAAG GGAGCAGGAA ACTCAGTAAA TGGTTCTAAC ATTTTGGAAT  162600

CTGTAAATTG GTTGTAACAT TTGTCATCTG TGTTATCTAA GTCAAGTTCC TAAAATATGT  162660

GAATGATAGG TTATCATACT CACCTACTTT TCTTGCATTG CTCTAAGAGT TGGCTGAGCT  162720

ATTGATAATA AACACTATGA TCAGATCTAA TACCATGATG TGCTATTATG ATCATGTGTC  162780

AGTCACAGGG CTAAGCACTT TGTACATGTT GATGCATTTA ATTTTGATGA TAACTCAATG  162840

AAGTAGGAGC TGTTAATATT TTCATTTTTC AGAGGGGGAA ACCAAGTCAC TTGGAGTAAC  162900

ATGGCTAATA AGTGAAAGAA TAAGAATTTG AAAGGTTTGC ACAGATAACC AGAATGCAAT  162960

GCTCATCACA TTCACTGAGC AGTGAATCAT ACTAACTAGA GAAAGTATGA AAGCTCTACT  163020

GAAATTAACT AAACAACCTC TCTGGCTGTG AGCCTGCCAA GGGACAGGTG GTAAACTTGG  163080
```

-continued

```
TTACTGCATA AGGCCCCTTC TATCCACAGT ATTCAGGAAT TCTTTAGTGA ACATACCTTG    163140
ATGACTCCTT AACATTTTCT TCACATCGAA GTAAAGCTTG GAAACATTGC ACATAGTATG    163200
AAGTTCCAAG GAGACAGCCT CTGATGTTTC CAGCTTCACA GCCCAACTCC TAGAATAAGC    163260
AGAGGCGAGA GATTTCTTCA GAGGTGCATT CCATTCATTT CTATATACGC ACACCCCTCC    163320
CCTCCTGCAT TCAAACAGGA CTTACCTGCT CAAAGTGTCA TTCACATTCT ATAAAGAAAC    163380
AAAAAGAAAA GGTGAGCATG GGAACATCGG TATTTCATGG GGCTTGTCAT GCAGGGCTAT    163440
TCTTCTTTGC TTTACCCGAA GAAGTAAAGA GAGTTACCCT AGTCTTAGTC TTAGATATTG    163500
ATGGATACTC AAACAAAGTA ATTCCCACCA GTCTTAGGTA TTGATGGATA CCCAGATGGA    163560
ATAATTCCTA CCAGCTTCTG GGAGATTCAG CATGGCAGGA TGTTTATCAA CATTTGCATC    163620
TATTCTCATC CTTGCTGAAG TCTGAGGGCC AGGAGCTTTG TCCATGCTCC CTCTGTAAGG    163680
ACTAGCTTTT GGTGATCGGA TTTCCTTCAC AGTGAGCCCA GATTAGAGAA CACTTATCAT    163740
AAAGGTCCTT AGTGGTGAAT CTGTGCACAG CCCTGAGACT GGGCCACTGC CACTAAGATG    163800
GTGGTAGCAG GTATCACACA GTGGTAAAGC AATCATGCTA TACACTCAGC CTTACAGTAT    163860
AGTCACCAAT CCTGTTAGTT AGAACCAGAA TTAATGGCTC CAGATGTTTA TCTTCCTACA    163920
GATAAAGCTG TAGATTGTAC CATAACAGCT CTGGAGCAAG GGTTCTACAA GCAAATCAGG    163980
GAAAAGGTTA TCACTCATTT TGGCTGCCCC ACTTCATCAC CCATCAGTCA CCTAGTGGAG    164040
TATTTCAGGA GAGAGTCAAC AACCAGGGTT CTCTGCACAT GGGCCAAGGA GGCAAACAGT    164100
GGTAAATGTT ATCCCGTGGT TTCATTTGGC CAAGCTGTGT TCCCTCAGAA GTTTATTTTT    164160
CTAATTGACA TAAAGGTACC CTATAAATTA GTGAAGGCCA GCCTGATGGC ACTGATGTAC    164220
ATCTAAAAGA AACATTACTT TATCTTCCCA TGCTTCCTTA CCATTCTCCT TTAATAGCAC    164280
TATAACATAC CTTTTTTCCC TACTCCAAGT ACACAGCCTC ACCTGCAGCA ATTTCTGGGC    164340
TGAGCCCTGA CATTTTTCCT CCAGTTCCAG GATGTGGCTC TTGAGTTCAT TGCTCTTCAG    164400
CCCCAGACCA GCCTCATAGT CCCTCAGTCT ACTCAGAGTC TGTTGTTCTT CTTTCTCCAG    164460
CCTCCAGAGA TAAGACTTCT CTTCCTCATG TAGGAAACAC TGGAGATTCT TAAAGTCAGA    164520
CCGGATTTTT TGTCTCTGAA TCTGTACCTT CTCCTGGAGT CAAGAAAGTA TGGTCAAAAG    164580
GTGGAAGTAA ACCAAATGTC CATCTATGGA TGAATGGATA AACAAGAATG AAAGTCTGAC    164640
ACACGCTACT ACATGACAAG CCTTGAAGAC ATTCAAGCAA AATAAGCCAG AAACAAAAGG    164700
GCAAATATTG TAAGACTTTG CTTATACAAG GCATCTGGAG TAGTTAAGTT CATAGAGACA    164760
GAAAGTAAAA TAGTGGTTAC AAGGTGTTGG CAAGACCAGA AAATGGACAG TTATTGTTTA    164820
ATGGGTAGTG AGTTTCAGTT TAGAAGATGA AAGATGAAAC TGAGTTGCAG TTTGGAGATG    164880
GGAATGGTGA TGGTTGCACA ACAATGTAAC AATGTAAAAG CACTTAATTC TACTGAACTA    164940
TATACTTAAA AGTGGTTAAA TGCTTAAGTG TTATATATAT TTTCACACAA ACACACACAC    165000
ACACACAATC AGCCACTGGG ACATTATTTT CTCATGAGTC ACTGAAGCTG GAAGAATGTC    165060
CCCAGTTTCC TGCTGCAGAG TCATGTGTGG GAGGCAGGCA CTCAGATGTG AAGAGGTTG    165120
CCTCAGATTC CTTATAGTCA CCCAATTAAT TTTCTTGTTC TTCAGCCAAG ACACAGGAGA    165180
AAGCTGGGTT AGGAGTGCTA GATAATTTAA TTGTGAAACT AGGGCCAAGT TCAAACACTT    165240
TATCAGTTAC AAGGATAAAA AGAGGTTTTT ACTTATGATT TAAGAAGTTA GATTTCTGAG    165300
TTGGAGCGAT TTTCTTGAAG TAAAAGCTTA TAATGAACAT CACCCAGACT GGATTTTAAG    165360
ACAACCAGGC TGGTAAGAGG GTCCATAATT CTTGGCAGGG GGAGCTTTGA GTGTGACAGG    165420
CATTTATTAT GGTTAACTGA GAAATACTGT TCTACTACCC TAGGGTCATC TTAAGCATTC    165480
```

```
CTATGTGTAA GACTGACAGA AATCAAGTGA AACTCTCATC TGAGGAGATG TAAAGTTGCA    165540

ATTTCCATTA GTGCTGTCTA AATTAATGCA GTGGGAGTGT GTATTCAGGG CAATTTGAAT    165600

CTATGTTCTT GGATTGCAGT CTTCAAACTT GGCCCAAATA AACTCTCTAC TTATCTTAAA    165660

AAAATAAAAA TTAAAAAATA AAAATAAATT CATACAGTGT TTTGATGACT ATGATATAGA    165720

AGAAGGGTCT TTGACTTAGG ATGAGGTGGA ATTTTTGTGT AGGAGACAGG TGCAGCTTTA    165780

ACTCTTGTAT AGACGGGTTT TCATATATGT TAGTTACAAT CAAGGTCTTC CCCATTGCCC    165840

AAGATCCTAG AAATGGGGGA AGTAAGAGTG TACTCAGGAG CTCAAGAGCA ACATCCACAA    165900

ACAAAGATCA GGGTAGAGGT TAGAGAGGAC TCCTGAAAGA GAGAAAATTG GTAATCAGCT    165960

TGTGGGATTT TACTCCAAGC TAGTGAATTA TATAAATATA AAGATTGGTG CAAAAGTAAT    166020

TGTGGTTTTT GCCTTTACTT TAATGGCAAA GACCGCAATT ACTTTTGCAC AAACCTAAAT    166080

ATTTCCATAA AAGAATGTGG CTCTGATAAT GTGGAGGTTA GTCAGCCACG GAAATAATCT    166140

GAAAGTTTGT AGTTGCAAGT GTGTAGGTTG TTGCATTACT TGTGATGTAC TTATAAATCA    166200

AGTATAGGCC GGGTGCAGTG GCTCACGCCT GTAATCCCAG CACTTTGGGA GGCTGAGGTG    166260

GGTGAATCAC GAGGTCAGGA GATCAAGACC ATCCTGGCCA ACATGGTGAA ACCCCGTCTC    166320

TACTAAAATA CAAAAAATTA GCCAGGCATG GTAGCACATG CCTGTAATCC CAGCTACTCA    166380

AGAGGCTGAG GCAGGGGAAT TGCTTGAACC CGGGAGGTGG ACATTGCAGT GAGCTGAGAT    166440

CGCACCACTA CACTCCAGCA AGACTCCATC TCAAAAAATA GTAATAATTT AAAAATAAAT    166500

AAATAAATAA AGTATATTTC TTTCATCAGC TTCATGAGCT TGAGTAGTAT GAATTTCAAT    166560

CTGGAGTGAT CCTGTTTTCT AAGTGTTCAC AAAGCTTGGT TTCTGTACCT GTAAAGTTGA    166620

GAGCCAGATG CTCCACTGTG GTAAAAGTGC CAGGGTAATG AGTTGAGGCC TGCAAACCAG    166680

GTTTATTTTG AGGTATTTAA AGTTTGAGAC CCACTCGATG CTTTTTCTAG GTAAATAGTC    166740

ATACTAATTC TGCTTCTTCT GACTGAAGTA TCAGGAATCC CAGCCAACTA CAGTTTAAAG    166800

ATGGAAAGAT TGGTGCTAAA TACTCATGGA TGTAAACCTG GAACCAGGGG CATAAGTACA    166860

AATAATGGTT TCTTCCTTGG GTTTCATTTT TTCAATCTGG TTTAGTGAGA ATAAATCCTC    166920

ATTGTGCTTT TCCTCAATCA TCCCCTATGC CTAAGCTCTA GAATGGAAAA TAGCTTGAGA    166980

TCAATGAAGT CAGATTCTTA CTTTCCATTT AGTTATTCGC ATTGCTGTGG ACAGCTTCTG    167040

CTCCGTACAT CTGTCTTCAA GTTGCTTCAG TTTTGTCACA GCTTTCTGGA GCTTTTCCTG    167100

AAGGAAAAAT TTGATAAGTG AAGCCTATTC AATTTGACTC TTCATTAGGG ACCTAGGGGG    167160

AATCCCAATC TTCTAAGATA TATTTGAATA ATAGTGAATA TTTATAGAGT CCTCATTGTT    167220

TTTTGCTAGA GAGCATGCTA AAGGCTATAT GTGCAGGAAC ATACTGATCC CCTTGGCAAC    167280

CCTGAATAGT TGGTAGGATT TTAAACTTCA TTTCTGTGCT GTAGAAAATG AGACTAAGAA    167340

AGGGGTAAAA TAACTTGCCC AAAGGGCTAT GACTGCCAGG TGGTGGAGCA ACAATTGCAA    167400

TCTCATCTGC TGACCCAGAG CCTGAGCTAT GTCCACCACT AGAGTCCTGC CAGGAAAAAG    167460

TTGGATATAG AACAAGGTAA TCATCATCTA AAAGATTTTG TAAAACAACA TGCTGAACCA    167520

AGCAAAACCA ATACCAGTGT TTGGCACACA TGAAATTTTG TGTCTTATGA GTCAGGAAAA    167580

ATCAGGATGC CAGCTGGTTA TTAGAAACAG TTCATGGAAG AGGGGAATTC TGGTATCTTT    167640

TGAACAATGG TATCATGAAT CCAATTTAAA ATGATTTAGT ATTCATGTCA AGCTTTTAGC    167700

TTATTCTTCA AAACAGTTTC TCATATTTCT ATTGAAAGTG ATTTGAAGCT GACCCAAATT    167760

GCTAATTGTA GTCAATGCTG AAAGAATTGT CTCCTGTCCT CTGTAAACCC AACAAGTATA    167820
```

```
CTCATTCATT CTCGAGTGTT CTCAGGAAAA GGTTCTATGT AACTGTTTTA GCAAAAGATG 167880
ACATTGTCCT TACTATATGC CAAGTGCTAT TCTATGCATT CTATATTTTA ATGTCCTCAA 167940
AGCTTATAAC CACCTCCTGT GTATGTGTTT TAGGGAGGGA GGACACTGCT ATTATCCCCA 168000
TTTACAGATG GAGAAACCAA GGTGTGAAGA CATTAAGTAA CGTGCCCAAA ATTGCCCATC 168060
TAGTAAGTGA CAAAACTCAA TTTCAACATA AGCTGGTTCC TTTTCTTACT ACTTGGTGGA 168120
AAAGTAATTC AAATGGGAAT ATGATCATCG CAGTTATTAG CTGCTCCATG GAGTTTAAGG 168180
AAGAGCTGCC ATGAGCTGAG TGGTGGTCAT GATTGACATG TCCTTAGAAG GACTTAGAGC 168240
CTTCATACAA GACCACCTCT GCCTCATGGA GGACAGAATA AGGAGCCTGA CACTGGAGAC 168300
AACATTTTCC TCAAATTTAG GCAGGACAGA GAAGGAAAAA GGACATCAGG ACTATGCCCA 168360
TTCCTCCATG CTGCCAACAG CAAAGTCCCA CCTTCCTTAA TATGCTTTCT GGCAAGAAAT 168420
CTGGATGGTA CACAAAACCT CTCCCTCTGC TTCACCTTCC ACAACCAAGC ATTTCCAAAT 168480
CTTTGACTCT TCTTCCTGAA TCGTGCTTAA AATCTGCCCT CTCCTCCCTT TCTTATACGG 168540
ATAGTTTGAA TTTTACTCCT TGATATTCCT TTTATCATAG ACATGCCACA GTAGCTGGGC 168600
ACAGTGGTTC ATGCCTCTAA TCCCAGCATT TTGGGAGGCT GAGATGGGAG GGAGACCAGG 168660
GGTTTGAGGC CAGTATAAGC AAGAAAGGCA GACCATGTCT CTACAAAAAA TAAAAAAATT 168720
ATCCAGGTAT GGTGGGGCAT CCCTGTAGTC CTAGCTACTT GGGAGGCTGA GGTGGGAGGA 168780
TTGCTTGAGC CCCAGAAGGT TGAGGCTGCA GTGAGCCGAG ATTGCACCAT TGTACTCCAA 168840
CCTGGGATAC AGAGCAAGAC CCTACCTCAG AAAAAAAAAA AAAAAAAAAA AAAGTAGAGG 168900
TACCAGAGTG ATATTTTCAA TGTCACTGAC CCTTCATTCC CCAAATGAAA ATCCCCCAAT 168960
AGGTGTTCAA TTTTTACGTG TCCTTCAGGA GTTACTTCTA AGATGAACCA CTCTCTACCC 169020
TAAATGTCCC TCCCCACCAC CAAAACCAGG GACCTCCAGG CAGACATTTT TGATGGTTTG 169080
TTTTCTTTAC TAGACTGTAG ATACCTAAAA GGTGATGGGT CTTTCTTCCC TGTTTTCAGG 169140
CCCTACTGCA TGGCTTTACA TATTGTGGTT TTTCAAATGA TATTCATGGT GTGAAACAAG 169200
AAAAAATGCG GGTGTTTGGT TTGAGAACAA CCTGTTCTAA AGCAAAAAGA AATTCATCAT 169260
AACACAAATG GATAGAGATA AGAGTCCAAC CATCCCATTG AAGGTCAGGA TGGACAGTCT 169320
AGATAATTGA GCAAGAAATC ATCATAAACT ATTTTTCAGA AGAATGACAT GATGAAAGCT 169380
GTATTTCCAA GTCATAATGT TAGGTTTCAA GTTAAATCAT CTCAGCTCCT GGGGAGCAGG 169440
ATAAGACTTG GTACTTACCA AAGCTCCCGG GCCCACACAC TCACCTTGTA GCCCTGGCAT 169500
ACGTCTTCAA CAAGAGCTGT GGTGTGCCCT TTGTGCTGTG GTGCCCGCTC ACAGCGCCAG 169560
CAGATGAGCT GCCCCTCATC TTCGCAGAAC AGGTGGAACT GCTCTCCGTG TTCCTCACAT 169620
GACATTTCTT GATCCGTCTC TTTGAGGGCT TCAATGAGGC TTCCCAGCTG CTTGTTGGGT 169680
CGGAGGCTAT CCATATGAAA TGGAGCCCGA CACTGGGGAC AGCAGAATGT CTCCTGCCTC 169740
AGTTGCTTTT GGCTTGGGTT TTTAAAGAAG TCTGTTATAC ACAAGTGGCA GTAGCTGTGT 169800
CCACAGTTGA TGCTTACTGG GTTCGTCATC AGGCTCAGGC AGATGGAGCA GGTGGCTTCC 169860
TCCATCATCT TCTTGGTGCT GGTGGTTGAG GCCATAGCTT TTATTGAAAA GCTCCAATAT 169920
TGGCTCTAGA GATGGAGATG AAGCAGCCAG AATTTTCCAC CGTGATGAAA ATACACCTCA 169980
CCTGCACCTC TATGTGATGA GCTGGCTGCA ACTGACTTCC ATAGGTCTTG AAGGTTTTCC 170040
TTCCAACCCC TATTATCTCA TTTTGTATTG AAGAAAGAG GACCTAAAAG GAAGAAGTTG 170100
AGGCTGAGGT TGTTTGGGCC ACGTTTGAGA ACTGCAACCC AAGTGCAGAG TTTCAAGTTG 170160
CCCTCATTAG CAAGCAGTTA CAAGTGGTTG TTTAGAGGAA AAAAAGCAGT TTTAAAGCAG 170220
```

```
TTTTAAAGTT GTTTGCCAAG AATTTACATT AAAATAGCAT AAGCTTTTGA CTGGCTATAC   170280

ATTGTTCTTT GTATTACAAA TCTCGGGAAT ATGTAGGTAA TAGATGAGGC AGCCAGTCAG   170340

GAACAAAATG CTTTTAAACA TGGGGTCTTA ACTGAAGACC TATACTCCTG CCTCACTTGT   170400

CCTGATAAAT TTTGCATACC TCACATAGCT CAGACTGCTC TAAATTATTT CATTATTTTT   170460

CTTTTCTCAG TCTTCTAACT TTTTTTTTTT TTTTTAATGA GACGGAGTCT CACTCTGTCA   170520

CCCAGGCTGG AGTGCAGTGA CGCTATCTCG GCTCACTGCA CCTCCGCCTC CCGGGTTCAA   170580

GCGATTCTCC TGCCTCAGCC TCCCGAGTAG TAGCTGGGTC TACAGGTGTG CACCACTACG   170640

CCCAGCTAAT TTTTGTATTT TTAGTAGAGA TGGGGTTTCA CCATGTTGGT TGGCTAGGAT   170700

GGTCTCGATC TCTCGACCTT GTGATCCACC CGCCTCAGCC TCCCAAAGTG CCAGGATTAC   170760

AGGCATGAGC CACCGTGCCC AGCCTCTTTT TCTTTTCTTA TAAGACAAGT TCTCGCTCTC   170820

TTGCCCAGGC TGTAGTGGAG GGCAGTGGCA TGACCACAGC TCACTGCAGC CTCGACCTCC   170880

TGGGTTTAAG CAATCCTCCT GCCTCACCCT GGCAGAGTGG CTGGGACTAC AGGTATGTGC   170940

CACCATGTCC AGCTAAAGTC TTCTCTCCAG AAAGAAGAAA TGCATTGGAA TTTAGAGGAT   171000

ACACAAACAT CTAGCTGTAT AGCTAATACA GTAGCCACTA TCATGAGTAG GAATTTAAAT   171060

TTAACTTAAT AAAAATTAAA ATGAAAAAAT TCAGTTTTTC TGTTCCAGTT GCCACATTTT   171120

GATTGCTTAA TAGTTGCATG TGACTAGTGG CTACATAACA GCCTCAATAT ACAACATTCT   171180

GTTATCACAG AAAGTTACCT TGGACCAAGT GCTGGGAGAA GCAATGCAGG CTTCCTCACA   171240

AAAGCTGTAA AAGAGAGAAC TCAGGGAGTG TGAAACTCTT TCCTATTCTA GTTAACTTCA   171300

AGAATAATTG TTACCAGGCC AGCACGGTGG CTCACGCCTG TAATCCTAGC ACTTTGGGAA   171360

GCCGAGGCGG GCAGATCACC TGAGGTCAGG AGTTTGAGAC CAGCCTGACC AACATGGCAA   171420

AACCTCATCT CTACTAAAAA TACAAAAAGT TAGCTAGATG TGGTGGTGCA CACCTGTAAT   171480

CCCAGCTGCT CAGGAGGCTG AGGAAGGAGA ATGACTTGAG CTCCGGAGGG GGAGGTTGCA   171540

GTGAGCCCAG ATTACACCAC TGCACTCCAG CCTGGGTGAA AGAGCGAGAA TCTGTCTTAA   171600

AAAAAAAAAA AAAAGAATAA TTGGTACCAG AATTACTCTT TGTAATTAGT AGTAACACTT   171660

ATGCAATTGG GTGATCTGTG ACAGATTCCA TTGAAGGAGT ATGGGGAGCT TCACCCCAAT   171720

ATATGACTCC CTGGTATAAT GAGTATTTTG AATTAAAGGC CCTTAGAGAT CAGCAGATGC   171780

TGGAAGAGAC TTTTCCCCTA TCTACATAAA GACCAGTCAC ACTAGACAAG AAGAACAATT   171840

GTTTTTCCTT CCAACCCCTA TTATCTCATT TTGTACTGAA GAAAAGAGGA CTAAGAATGT   171900

AACCAGACCT AATCAGACAC TTTCACAAAA TAATGTCTGT CTCTCAGGCT CATTCATTTT   171960

CCAAAGAGAA CCATTTACAA GTTAAACTCT GTTCCTCCAT TCATTCATCC TCCCAAATAT   172020

TCATTTATTC TCCCTAGTAA TCATTTACTG CCCCTCAAAG AATTACCTAT ATTCTCCTGA   172080

TATCACCCTT CCCCTCTGAA ATAAATATGT ATACATGTAT AAACGTTATA CATACATATT   172140

TATACAGTAT ACATACATAT TTATACATAC ATACATATGC ATACATATTT ATATTTATGT   172200

ATTTATACAT AAGTATTTAT AAATAAGGCT ATATAAGTAT CTACCCCCAT TGGCAGAGGG   172260

GGTAATCACT CTGTGATTCT AGCCCATGTA CTTGTTAATA AATTTGTATG CCTTTTCTCC   172320

AATTAGCCTG CCTTTTGTGA GTCGATTTTT CAGTGAACTT CAGAAGGCAA AGGGAAGTG    172380

TTCCCTTGGC TCCTACACCA TCATGACAAT AAAATTTGAC TCCACCTCGA CCCCCCCAT    172440

CCCCCACAAA GAACAACAAC CAACACTGGT TAATAAGGTC GGTTGTTTTT TGTTTGTGTT   172500

TTTGTTGTTG TTGTTGTTGT TGTTGTTTTT GCTTTCAGGA GCAGAGGTAT AATAGGCAAA   172560
```

```
AGAAAGAGAA AGGAGAATAG TGAATACCTC TTCTGCAGAG AGGGGTGCCT AAGTGGGACT    172620

TCCCTGGCTA ATAACGTCTT GCTAGAGACC CAACCAGGAG GATAATGGAA GCAATCAAGG    172680

CAACCAGAAC AACCAGAAGA ACCAGTTTAT CCTTTTTGTG CCCTCTCCCT AAACTGAGGG    172740

AATAAGAATT GGAAAGAAGG CTGCAGAGCA GAGGGTTTGC TCCTGAGGAG CAGTTATTTC    172800

TATGGGATCA GAGCTCCTGC AGAACTGGGG AGTTTACTTT TACTATCTCT TCTCCAGGAC    172860

AGGACCTATC TCAAGAGACA TGTTCAGAGT GATTGCAACA TAAAGAGTTT GCAGACCCAA    172920

GGAGGTAGGG AAGGCAGAAA GAAGATGGGG GAGGCCAGGG ATAGGCAACA GAGGAGTGAC    172980

CAGGAGCGAA AAAGCCTGCC TCTTCTGAGA ACCTAGCTGG GCTCTCCCTG TACCCCCGAT    173040

CCCTCCCCCC CGCCCGCCCC CACACCCCTA CTCCTGGGAG CTCCTCTAGG ACAGGGGCAG    173100

AGTCAGGAGG AAGTTTGAAG AGTGCCTAGA ATAAAAAACA GTAATTTAAC TACAATTACC    173160

GGGTAGGCTG TTTTCCTCTC ACAATTTGAT CAGTCTCTTG AAGCCACACA GAATTTCTTC    173220

TGAAGACGTG TATTCCTTGG CAGGCTATTT CCTCCAGTGA TACACCAGGC CCCTCTCTGC    173280

TGGGGTCACT GCTCTTCTGG GGAGATGGGG CTCCCCTCCT TCCAAGGCTC CAGGGTTCCT    173340

GTCCTGGGCC CCACTCATCT AAGTTCTGAA TCTTCTGAGA TTTGGTGTAA AGTCTGGTGA    173400

AAGAAAGAGC AGGAAAGAGG TGAGAGCTGT AAAACAAAGA AAGTCCTGAC CATTTTCAGA    173460

GTTGGAGGGG CCCTGCTGTC ACGAAATATA TTCCCCACCC CACTTGCCAT CAGTACACAC    173520

TCACATATCC ACTGAGAAAA CCTTAGCCTG GACCTTTTCC GTAACCTTCA CTGCTCAGAC    173580

ACTTACATAT TCGCTGCTAG TCCCCTCTGT TGCTGCCACT TCCTGGGTCA GGAAGTTAAC    173640

TCAGACCGGA TTAAACTGAG AAGTGAAACT ACTGTGGGAG GCGGGCTCA TAAGATTTAG    173700

GAGAAAACTA GTGACGTTGT TCATATCATT TGCACTCCGC CTCTCCGGTA AAGGAGGGGG    173760

AAACGTAGGA AGAAAATATC CTTCTTTTAC AGCAATAAAA AGAAGGAACC AATTAATAAC    173820

CCTGTAAACT ATCATGTGAC CCCAACACAG AGTATCTAAA AACAGGAAGC CTGCAGAGGT    173880

TCAGTTCACA GACTCTGATT TGAGATCTTT CTACTTTTGC CACCAACTCC CTTGGGAGTC    173940

CTTAAGCCTT CCTAGCTGAT GTTACTTCTT TTGCTATTTA TGGGTTGCTT GTGGTTCTAT    174000

AACTGCTCTG AAGGGTGTGG TGGAAAAAGG GGTGGTAACA GCAGTAGGAC TCATTGGCAT    174060

CACAAAATTC ATCTGAGTCA GCTTTCTATT CTTCTCTGTC CCGTTCTGTG TCTTGTTTTT    174120

CTCCTTGCTG TCCTTCTGCA GGACTCAGAT CTTCTTCAAT AGCGAGGGTC AGCCAGGATA    174180

GAAAATGGGA GTCACTAGTG GCCCAGCAGT GAGTGCCCCC AGCTTAGAGC TGTGTGGGAT    174240

CCCTGGGACC ATCACTCTGC TTTGTGCTTT GTGGAGAAAA GGCTGTGGGG TCCAGGGTCA    174300

AGTCCTTAAT GACTTAGCTC CAGCTTCTCC ACTTCAAAAT GAAAGGAAAA GTACTATCAC    174360

CACCCGTTAG AATTATTATT TCATGGGGAA AAAAGATGGA TTACTATCTC ACAATAAGAG    174420

CTTGTCACAT TTATAAGTCT CAGGTGTAAG AGGCATTTAT GATAACAACA TAATAAATGC    174480

TGGCTTAAGT AGATGCAGTG GTCCAAGGGA ACCAGTAAGG GGAGCTCAGG ACACAGGTGG    174540

GAGGAGAAAT TAAACTTGAA TTCTGGGAGC CACTGGCCTG TCTGGGCCCC TGGCCTGCCT    174600

GCTGACCCTG ATAGCCAATG GAACATGGAG TTTGGCCCAG CTGCAATCCC TCTGGTCCAA    174660

CTACTCAAAA TAAAGGCAAG ATTGGGAAAC ACGTTCCTTT CTTCCTATAC CAAGCAGAAG    174720

ACTCTTCAGC ACTGCACCCT CCTGGGTGCT CACAGAGCCT CTGTTGTTT TGCCACCTAC    174780

GATTCATCAT GCCCTGGCAT GATGGTTGCA GACCCCATGC ATAGCATGGG ACATTCTACT    174840

CCTGAGGCAA CCAGCACACA GAGAGAGGAG AAAGAATGAG CCCCTGAATC CTTGGTCCCA    174900

CGATGAGTCC TTGCAGATAT CTACAACTTT CATTGTTGTG GATGTGACTC TGTACCCAGG    174960
```

```
CATGGCTCAT TCCAGATCTG TCCTATTGTC AGAGGTGTTC AAACCAGAAT GACTCCATTT   175020

TGAATGGGGG CTAGGTAAAA TAAGGCTGAG ACCTACTGGG CTGCATTCCC AGGAAGTTAG   175080

GCATTGTAAG TCACAGGATG AAATAGGCAG TTGGCACAAG ACACAGGTCA TAAAGATCTT   175140

GCTGATAAAA CAGGTTGCAG TAAAGAAGCT GACCAAAACC CACCAAAATC AAGATGGCAA   175200

CAAGAGTGGC CTCTAGTCAT TCTCATTGCT CATTATACAC GAATTATAAT GTGTTAGCAA   175260

GTTAGAAGGC ATTCCCACCA GCTCCATAGT GGTTTATAAA TACCATGGCG ATGTCAGGAA   175320

GCTACCCTAT ATAGTCTAAA AAGGGGAGGA ACGCTTGGTT CTGGGAATTG CCCACATCTT   175380

TCCCAGAAAA CATATGAATA ATCCACTCCT TGTTTAGTAC ATAATCAAGA AATAACTGTA   175440

AGTATCTGTA TTAGTCCATT TTCACACTGC TGATCCAGAC ATACCTGAGA CTGAGTAATT   175500

TATACCAGGA AAAAATGTTT CATGCTCTTA CAGTCCCACG TGTCTGGGGA GACCTCACAA   175560

CCACAGCAGA AGGCAAGGAG GAGCAAGTCA GGTCTTACAT GGATGGCAGC AGGCAAAGAG   175620

CTTGTGCAGG GAAATTCCTT CCTATAAAAC CATCAGGTCT CATGAAACTT ATTGACTATC   175680

ATGAGAACAG CAGTATAAAT TACTCAGGGA AAGACCTGCC CCCATGATTC AATTACCTCC   175740

CACCAGGTCC CTCCCACAAT ATGTGGGAAT TTAAGATGAG AGTTAGGTGG GGACACAGCC   175800

AAACCATATC AGTATCCTTA GTCCAGAAGC TGATGCTCTG CCTGTAGAGT AGCCATTCTT   175860

TTATTCCTTT ACTTTCTTGC TTTCACTTTA CTGTGTAGAC TTGCCCCAAA TTCTTTCTCA   175920

CACGAGATCT AAGAACCTTC TCTTAGGGTC TGGGTTGGGA CCCCCTTTCT GGTAACACTA   175980

TCAAAGGATC AGGAAAAGGA AGCTAGTGAA TGCTAAAAAG GAAACAAACT ACCATTACCA   176040

ATAATAACAG CAAGACAAAA GCAAAACGGA TTGTGACAGC TGTCCCATCT CACACCTGTT   176100

TCCCATTGCA GGAAGGAGGG GCTGGTTCAT GCACAGAGTG GCCAATATTA GAAGCAGAGA   176160

GGGGGTGCAG ATGAGACTTC AGGAATATGT TGACAAAGGC AGGCCTAGGG AGAAATCAAC   176220

CTGAACTATC CCCAAGGAGG AATGCATTAT CTCTAATATG TAAAGTTAGG CTTGATCCTG   176280

TGATTATGGG ATATAGGAGT CCAAAGACTC ACAATGGGAA GTAGGTCACT AGAGTCTCCT   176340

TCAGAAGCTC TGTACTGTGT GTTCCCACTG TGGGCAAGAG TCAGCACTCA GCTATTCCTA   176400

GAATGCCTTT CCTCAACTCC TTCAGATTTT GCCTCTCAAC TAACCCTATC CTGACCACTT   176460

GTTAGCAAGT GTACCCCTCT CTCCCTCCCA AACATTTTCA AATCTATTTT GTTCCCATGG   176520

CACTTATCAC TGAATATTTT ACTAATTTAT TTTGTTTAGT GTTTGCTTCC CTCATGAGAA   176580

TGCAAAGGGA TGGATTTTTT TCAATATTGT TCACTGATGA ATCCCAGTAA CTAGAATATT   176640

TCTAAGCATA GTGATGTGCA TTAAATCAAA GAGTAACTTT CTGAATTGCA CTAAACACAC   176700

ATCACAAGAG GTGTGTGCAC ATATGTGCAT GATGCACGTA GTGTGGTGTG GTGTTGTGT   176760

GGGGTATGTG GTACTGTGTG TGCTGTGTGT GGTATGTGAT ACATAGTTTG TGTTAGTGTG   176820

ATGCATGTGA TGTGGTATGT GTGTGCGTGT CCATACATAT TAGGGGTGGC GGGGATGTTA   176880

ATATGTCAAA TGGTACTAGA AAGTATCAGA ACTCATGGTG CTTACTGGTT TCCCAGAGAG   176940

CTGCTTCTCT CCCACCTGTA GGATATACTG ATGGTTTGGA CAGAGAAGAA ATAAAAAGAA   177000

GGCTGTGACC TACTGGGCTG AGGAAATAAA AACGAAAGTA AAAGAAGAGC TGGGAAAAGA   177060

GAGTGGAGGG GCCAAGGGAA ATTTCCCCTT TGGCTTCTGG GGAAACTTTG CTGAAAAATC   177120

AACTCACAAA TTTATTAACA TGTACACAGG GAGAACCATA GAATGATTAT CCACTTCCCA   177180

AGAGGGCTTA AAAGCTTATA TATTATCCTG GCAAAACAGA TTATGGGAGG GGAAGAAGAG   177240

AAACTCTGTT GATGGGATTA CTGTTGCGGA TTTTTGCTCC TTCGCTCAGC TAGGTCCGGG   177300
```

```
TTTTTGTCTC ACAGCCAGGA AGAATTAGGC ATGCAGCCAT CAAAGAATGA GTGGAGTAGA    177360

ATTTATTAAG TGAAAGGAAA GCTCTCAGCA AAGACAAGGG TCCTGAAAGC AGATTTCTGG    177420

TTTGCTCTTC ACAGTTGAAT ACTAGGGCTT AAGACTCAAA TTCCTGACAA CTCCACCCTG    177480

TCCTACCAGT GCATGCAGGC CTTTAGACTG AGCTACTCCA TATTGATTAA TTTCCTGAAC    177540

TGCGCATGTG TTAAGGAAAG GAATCATCCA CTGCAGGCAT GTTTAGGCAA GCCCCCTGTG    177600

CAAGTTCCCT TATCTGCACA AAACATCCGG TGTAAGCACT TGTGGGGCAG GTCAGAGGTT    177660

CTCTGGGTAC CATTCCCTTA CTGTCTGCCT AAAGCAAGCT GGCCAACTCC TTTCATTACT    177720

AGGGAGAGTA AGTAGATCAG GGAACAGAGA TTAACTTGAA CATTATCTTG TGAAAGTCCG    177780

TTCGGGCATG GTTACATTCT TGGTCTTACA GGAAGGGTAA ATAAAAATAA TTGCTCTTTT    177840

TGGTGGGTCT GGATCTTAGG TAGATAAAGA AACTTTAATT CCACGATGTG TTTTGGTAGG    177900

GATAGTTGGT GGCAGGGATG TCAGAGAGAC TTTGAGGCTT CTTCAGTTCA ATATGACCAA    177960

GGGCCATATA TTAGGGTATC AATTTCTGAG CCCCAACAAG AGCTTAGGAG AGATGTGATA    178020

GCATCACAGT GTGAAAGCAA TTTTTTGTCT GTTTTTAGAG ACAGGCTCTT GCACTGTCAC    178080

CCTGGCTGAA GTACAATGGT ACGATCACAG CTCACTGTAA TCTTGAACTG GGTTCAAATG    178140

ATCCTCCCAT CTAAGCATTT CAAAGTGTTG GGATTACAGG CATGAGCCAC GGTACCCAGC    178200

CTGAAACTGC ACCCACTTTC TGATAAACTT TTCAAATGAC TAAAGGGGAG AGAGTAAGCA    178260

CTACTCAGAG GTAGGAAGAA AGGACACAGG ATTATAGGAT TAAAACAACA ACCACCAAAA    178320

AAAACCAGAC CGGTGTGGTG GCTCACACCT GTAATCACAG CACTTGGGGA GGCTGAGGTG    178380

GGGGGAGTCA CTGGAGGCCA GGAGTTCGAG ACCAGCCTGG CCAACATAGC AAGACGCTGT    178440

CTCTATTAAA AAAAAAAAAT ACCTGCCTTG AGCTAATCAG AATCATGGAC CCTGACAAAG    178500

GATGTCCCAA AGTAAGTCTT AGCATTTTTT TTTTTTTTT GAGACAGTCT CGCTGTGTTG    178560

CCCAGGCTGA AGTTCAGTGG CGTGATCTCG GCTCACTGCA ACAGCTGCCT CCCAGGCTCA    178620

AGCAATTCTC CCTGCCTTCA GCCTCCCAAG TAGCTGGGAT TACAGATGCC CACCACCACG    178680

CCTGGCTAAT TTTTGTTTTT TTAATAGAG ATGGGGTTTT GCCATGTTAA CCAGGCTGGT    178740

CTTGAACTCC TGACCTCAAG TGATCTGCCC ACCTTGGCCC CTCCATAGTG CTGGGATTAC    178800

AGGCGTGAGT CACTGCACCC GGCAAAGTCT TAGCATTCTT TACAAACAGT TTGTACCCGT    178860

ATCTCTAAAA GGGAGTAGTG AATTTCACCC CAAAATATGG CTTCCTGATA TAATGAGTAT    178920

TTTGAATGAA AAACTCTTAG AGATCAACAG ACACTAAAGA GACTTTTCCC TAGGTACATA    178980

AAAATAGGAT GGCCCCACCA GCGAGAACAA TTGTTCTTTT CTCCCTCCCT GTTATCTCAT    179040

TGTGCATTAT AGGAAAGACC AAGAATGTAA CCACACCTGA ACAGACCCTT TTATAAGATA    179100

ATCAGTCTCT AAGCATCATT TAAATTCCAA GGAGAACTAT TTACAAATTT ATCTGTTCTT    179160

TGATCCAATT AGTCTCTCCT GGTAGTTACA TATTGCCCCT CAACAGAATT CCTCTTCTTC    179220

TGTTTCCCAT AACCTATTTT GCAAGGATCA AGCCCCTGTT ACTTCTTCAA CTTCAAGTTG    179280

GCATATAAGC TTCTAAATTC CACTGGGATA TTGGTACTAT GTGCATGAGG AGAACCACAG    179340

AGTAATTAAA TTGTAAAGCC TTTTATCTTA TGAATCTGCC TTTTTTTGTG TTCATTTTTC    179400

AGCAAAACTT CCAAGGGCAA AGGTATAAAA CAAAATAAA ATTCTAAAGC CCCCCAACCA    179460

TCTGAATAGA CTTTCTCTTC AGTCAGGCTT CTTAAAATGT AACCTGAAAG ACTGGCTCAG    179520

GCCATTAAGG GAAGTGGGGG TTGAACATGC CTCATTATTC CTCTCTGGCA TTAACATCAA    179580

CACAGCTTTT AAGTCTGATA AGAAACATTT TACAACCTAT TCTCTCTGAA GCCTGCTAGC    179640

TAAAAACTTC ATCCCATAGT ACAACTTTGG TCTTCACAAC CTGTTATCAC AACCTAGTGC    179700
```

```
TCCTTTCTAT TAATCCCAAA TCTTTATACA AACTCAACCA ATTGTCATCA CCTCCACCCC  179760

ACTCCTCCGC TGCTTCCAGT TGTCCCGCCT CTCTGGACCA AACCAGTGTA CATTTCTTAA  179820

ACGTATTTGA TTGATGTCCC ATGCCTCCCT AAAATGTATA AAGCCAAGGT GCATCCCAAC  179880

CACCTTGAGC GCTTGTTCTC AGGACCTCCT GAGGGCTGTG TCATGGGCCA TGGTCACTCA  179940

AATTTGGCTC AGAATAAATC TCTTCAAATG TTTTACAGAG TTTGGCTCTT GTCATGACAC  180000

AGATGACTGC TTCACTGAAG CCTGCTCTGG AAGTGAGTGG GGGTTTTGCA AGGATAATTT  180060

TCCCCGGATA GCCCCAGAAG CAGCTAGTAA TAATACACTT AAAGGTAGCT AAAATGCATT  180120

GAACACTTGT TTTGTGCCAG ACCTATGTCA ACATTTGCTT TGTGCCAGGC TTATGCCAGT  180180

ACTCCTGATT TGTTAATACA TTCTAAATAA AAATTCTGGA GTTTCAAATA TAATAACTGA  180240

AAAACAGAAA ATAAATAAAA ATATATAATA ACTGAAATAA AAATTTACTA AGGCTGGGGA  180300

TGGTGGCTCA CTCACACCTG TAATCCTGTT ACCGGAAAGG GGTCCGTCCA GATCCAGACC  180360

CCAAGAGAGG GTTCTTGGAT CTCACACAAG AAAGAATTCG GGCGAGTCTG TAAAGTGAAA  180420

GCAAGTTTAT TAAGAAAGTA GAGGAATAAA AGAACGGCTA CTCCATAGGC AGAGCAGCTC  180480

TGAGGGCTGC TGGTCGCCCA TTTTTATGGT TATTTCTTGA TTATGTGCTA AACAAGGGGT  180540

GGATAATTCA TGCCTCCATT TTTTAGACCA TATAAAGTAA CTTCCTGACG TTGCCATGGC  180600

ATTCGTAAAC TGTCGTGGCG CTGGTATGAG CATAGCAGTG AGGACGACCA GAGGTCACTC  180660

TCATCGCCAT CTTGGATTTG GTGGGAGCA GTGAGGATGA CCAGAGGTCA CTCTCATCGC  180720

CATCTTGGAT TTGGTGGGGT TTAGCCAGCT TCTTTACTTT TTTCCTTTTT TTTTTTTTT  180780

TTTTTTTTTT GCCCAGGCTG GAGTGCAGTG GCACGATCTC AGCTCACTGA AACCTCCAAT  180840

TTCTGAGTTC AAGCGATTCT CGTGCCTCAG CCTCCCAAGT AGCTGGGATT ACAGGCATGT  180900

GCCACCACAC CCAGCTAATT TTTTATATTT TTAATAGAGA CCGGGTTTCG CCATGTTGCC  180960

TACGCTGATC TCCAACTCCT GCGCTCAAGC CATCCAGCCA CCTTAGCCTC CCAAAGTGCT  181020

GGGCTTATAG GTGTGAGCCA CCCCACCTGG CCTAGCCGGC TTCTTTACTG CAACCTGTTT  181080

TATCAGCAAG GTCTTTATGA CCTGTATTTT GTGCCCACTG CCTGCCTCAT CCTGTGGCTT  181140

ACAATGCCTA ACTTACAGGG AATGCAGCCC AGCAGGACTC AGCCTTATTT CACCCAGCTC  181200

CTATTCAAGA TGGAGTCTTT CTTGTTCAAA TACCTCTGAC AAGCCCAACA CTTTGGGAGG  181260

ATGACACAGG AGGATTGCTT TAGCCTAGGA GCTCAAGACC AGCCTGGGCA ACACAGTGAG  181320

ACCCCATCTC TAAAAAAAAA AAATACAAAA AAATTAGCCA GGCATGATGG TGTGTGCCTG  181380

TAGTCCCTGC TACTCAGGAG GCTGAAGTGG GAAGATGGCT TCAGCCCAGG AATTCAAGGC  181440

TGCATTGTCA GAGGCATTTG AACCAGAATG ACTCTATCTT GAATAGGGGC TGGATAAAAT  181500

AAGGCTGAGA CCTGCTAGGC TGCATTTCCA GTATGTTAGG CATTCTTAGT CACAGGATGA  181560

GATAGGAAGT CAGCACAAGG TACACATCAC AAAGACCTTG CTGATAAAAT AGGTTGTGGT  181620

AAAGAAGTTG GCCAAAACCC ATCAAAACCA ACATGGCCAC CAAAGGGACC TCTGGTTGTC  181680

TTCACTGCTC ATTATATGTT AATTATAATG TATTAACATG CTAAAAGACA CTCCTACCAG  181740

CATCATGACA GCTTACAAAT ACTGCGGCAA TATCTGGACT TTACCTTATA TGGTCTAAAA  181800

GGTGGAGGAA CCCTCAATTT TGGGAATTGT CCACCCCTTT TTTGGAATGC TCATGAATAA  181860

TCCACCCCTT GTTTAGCACA TAATCCAGAA ATAACTATAA GTATGCTTAT TTGAGCAGAC  181920

CACGCTGCTG TTCTGCCTAC AGAGTAGCCA TTCTTTTATT TCCTTACTTT CTTAATAAAC  181980

CTGCTTTCAC TTTACTGTAT GGACTTGCCC TAAATTCTTT CTTGTGTGAG ATCCAAGAAC  182040
```

```
CCTCTCTTGG GGTCTGGATC AAGACCCCTT TCTGGTAACA TCTTTCTGGT GACCACGAAG  182100
GGACAATACT GAGGAGACTC TGAAGCCAAA GGAAACAGAC TACAGCACCA ACTGGCTGAC  182160
TTTGGGTAAG TGGTGGAGTC CCCGGGTAAA GGATAGGATT GGGTTAGAGG TGCAACTTAG  182220
GGGAGATAGG GTCTCTCCTA AGACAGAGAG CGTTTCAGTC CGCTCTTAAT AAAGGGCAAG  182280
AATGCTTGAC CGAACTTGGG TTTGAGACCC AACTTAGGAA GGCTACAGTC CTTAAGATTT  182340
AAGGGGTTAG AGGCCCCTCT CAGTAAAGTC TCTCTTGGTT AAAAACGGAT TTAGCATTAG  182400
GGGATGTTAA CTGCTATTCT GTTTGTATTA ATCTTCCCTG TGCTCTTTGC TGACAGCTAT  182460
GGGTGACAGG ATTAGGCATG TACAGGATCA CGGGACATTG GGAACTTTTC TTCTCTCCAA  182520
AAGGGGAAGC TTGACAGCTG ATAGGACTGT TGGAAAAGAT CCCTTTGCTA TGACAAGCAG  182580
CCGCCTGAAC TTTTGATTCA GTGTTGCTGC AATGGGTGGG TCTTTCTCTG GCCTCTGTGA  182640
ACTCCTCACC TTCCCCACCT CACCACAGGC AATGCTTTTC TCCCTTTCTC TCTTTTCTCT  182700
TTTCTGTCTT TTCTGTTACT TGAGACAACC ATCTTGCCCA GAGACCATAT GTTGAAACTC  182760
CTGGTCAGAA GTTTGATTAA AGATGAAAGG GCCTATCTGG GGGCAAGTTT GAGCCTTCCC  182820
AGTTAGATAT TGGGTGCTAA GTGGAGTGGC CAATGTCTAT GTTTTGTCAC ATGTATATTG  182880
CTCTGGCTGA AATGGAAAAC GTTAATTTGG TTACTTTATG TGGCCATTGG GCAGCATCTT  182940
ACAAAAGTGA GAGACATTTA TTTGCCTGTG GTTCCATGAA ACAGAAAAAA GTTGGTTTTC  183000
CTTTGTGTCG TAGCTTGGAC CCAAGGGCTT TGCAGTGAGC AAGGTTGCTA GCGCTGCTCA  183060
GTGAAAGAGA ACCCAGAAAC CTGGCATGCC AGCAAAAGGG TAAAGATTTC TTACCAGTCA  183120
GGCTTCTGGC CTCTCTCTCT TAGTGAAAAC TGAATGAATG GTAAAAATCA CTGTTTATCA  183180
CCTCTGTAAA GTTTTGATTA ATGGGAACAA GGATTTGTGG GGCTAGTCTT AAGCTGTAAT  183240
GAATCTGGTA TACTTTGTGA TATCAATTTG TCTTTCTGTA TTACTCTGTC ATAAAGAGGA  183300
ATATGGTAGG ATAGAACATG GGCTTAGGAC TCCATAAGCC TGCTGTTCAA GCCAGCCAG   183360
TAAACTGGTC CGTTGCAAAG TTTATTACAG GTCCCTGGAA AAAAAAAAA TTAAAAACTG   183420
GATGAAGTTT CCTTCTCATC TTGTTTTATG TCCTTTGGAG CTTCACCTTG TAACCACGTG  183480
GCGGTACTTT CTCTTGGTCT CTGCCATCCA GGGAACAGGA ATTTTGGGGT TTATGTAATA  183540
GTTAACTCTA AAAATTATCT CAAGCCATTG CAAGCTCAAA ATTGGCTGCT CTGGACCCCT  183600
TCTGGGAAGG GCAATGGAAA CTAACCAGTG TTGTAGCTCA GCAGCTAAGG ATTTGTCATT  183660
TTATAATGGC GGCCAAGGTT CAATCCTGGC TTAGGGAATG AGTACTTTCT GATTGATATC  183720
TGTGTGACCT TTACCATTTG TTGATTCTGT TCTCTTCCCC TCCACACACT GTCTTGAGTT  183780
TTCCTCTCTC TGAGAACCTG GGAGATTATC TTTGGTAAAG TTCAAAAGCC AGAAATAATG  183840
GCCGTGTGGG ATGGCTAAAG TTGAGTAATA AGAAACTTAA AAGGACTCCT TTTTTTTTG   183900
CTTTAGAGTG CTATGGTTTA TGGTTAAAAG CTTAATTAAA AGTGGATATT CAATCTCTAA  183960
AAGCCTGGGA CTCCTTGGGA AAAGCAGAGG AGGCACCACA GACCCCATTT TGGGAAAACC  184020
TCTGTTTTCC TCATGAAACC CCAGGAACTG GAAGTGGATA GATCCTTCGC AAAATCTAAG  184080
GCTCTGTTTG GCTTTGCATT ATGTTATCTG ATGTTTTTGA CTTTTGGGGG TATCAGAAAT  184140
TACTTTGCAT TATGAGGGAG ATCTGGTGTG TAATAACCAG GTAGGAAATA TACTTCTGGG  184200
GATAGCTAAA GGCAAATATA GGTGAATACT TGGCTATTTG CACTTTTGGA TCACAAGAAG  184260
CATTCTCTTG ACTACCTAGA AGGTATGGAA ATGTCTCCAT CCCCACCGAG AGATAAGATT  184320
CCCAGGGGAG ATGGCTGATC CCCCAAAAGA GGGCTGATTC CCTCTTTTGG GATCCAGGAT  184380
CTGGTATAAA AATGGGACCC TGGCCAGGCA CAGTGGCTCA CGCCTGTAAT CTCAACACTT  184440
```

```
TGGGAAGCCT CAGAGTTATG AATGTCTCAC CATACTGACA CTTTGTGACT GAGCTCCTCT    184500

CTACCCTGGA CACAAGAGAC CCTAATAATT AGACAGGAAT ATCATTGCCC CTATTTAGTC    184560

TGAAGAAGTT ATAGAAGATG GATCTTTATC CCACTGCAAT CCTTAGGATT AAGGGTTCCC    184620

TGGTAAAAGG GAGTGGGAAA ATATGTCAGA GGCATTTGAA TCAGAGTGAC TCCATCTTGA    184680

ATAGGGGCTG GGTAAAATAA GGCTGAGGCC TGCTGGGTTA GGTTAGGCAT TCTAACCAGG    184740

AGTTTAGTCA CAGGATGAGA TAGAAGGTTG CACAAGGTAC CCGTCACAAA GACCTTGCTG    184800

ATAAAATAGG TAACGGTAAA GAAGCCAGCT AAAGCCCACC AAAACCAACA TGGCCACAAA    184860

AGTGACCTCT TGTCATCCTC ACTGCTCATA TACACTAATT ATACTGCATT AGCATGCTAC    184920

AAGCACACTCC CACCAGTGCC ACGACAGTTT ACAAATACCA TGACAACATC TGGACGTTAC    184980

CTTATATGGT CTAAAACGGG GAAGAACCCT TAGTTCTGGG AATTGTCCAC CTCTTTCCTG    185040

AAAAATTCTT GAATAATCCA TTAGTTTAGC ACATAATCCA GAAATAACTA TACGTCTGCT    185100

TATTTGAGCA GTCCATACTG CTGCTCTGCC TATGGAGTAG CCATTCTTTT CTTTTATTTT    185160

TATTTTTTAG ATAAAGACTC GCTCTGTCAC TCAGGCTGGA GTCTGGAGTG CAGTGACGTG    185220

TTTTGGCTCA CTGCAACCTT CACCTCCCGG GTTCAAGCAA TTCTCCTGCC TCAGCCTCCC    185280

AACTAGCTGG GACCACAGGT GGGTGCCACC ATGCCTGGCT AATTTTTGTA TTATTAGTAG    185340

AGATGGGGTT TCGCCATGTT GGCCAGGCTG GTCTCGAACT CCTGGCCTCA AGCGATCCAC    185400

TTGCCTTGGC CTCCCAAAGT GCTAAGATTA CAGGCATTAC CCACTATGCA TGACCCATTC    185460

TTTTATTTCT TAACTTTTTT TTGTTTTTTT GAGACAGAGT CTCACTCTGT CACCCAGGCT    185520

AGAGGCTGGA GTGCAGTGGT GCGATCTTGG TTCACTGCAA CCTCTGCCTC CTGGGTTCAA    185580

GCGATTCTTC TGCCTCAGTC TCCTGAGGAG CTGGGACTAC AGACATGTGC CACTACACCC    185640

AGCTAATTTT GTATTTTTAG TAGAGACAGT GTCTTGCCAT GTTTGTCAGG CTTGTCTCGA    185700

ACTCCTAACC TCAAGTGGTC TGCCTGCCTC AGCCTCCCAA AGTGCTGTGA TTACAGGCAT    185760

AAATCACTGC GCTCGGCCCT TCTTTACTTT CTTAATAAAC TTGTTTTCAC TTTACTGTAT    185820

GGACTAGCCC CAAATTCCTT CTTGTGTGAG TTCCAATAAC CCTTTTGTGT GTGAAAGAAT    185880

TTATGGCTGC TGTTCAGGCT GGAGCAAGCT GGAGCTCATG CTGCTGCTCA GACTGGAGCA    185940

TGCGTGATCT GTGATCCCAG TAAGAGGATC ATGGTCACTC CAGCCTGAAC GACAGCATGA    186000

TATCTCATCT GTAAGAAAAA AAAAATTACT AGAGGGCTTT AACAGCAAAT TTGAGCAGCA    186060

AAAAGAAGTA ATCAGTGAAC TCAAAGATAG GTCAATTGAA ATGATCTACT CTGAAAAACA    186120

GAAAGAAGAC AGAATGAAGA AAAAGAAATA GAGCCTTAGA GACAGGGGAT ACCATCAAGC    186180

ATACTAATAT ATGCATAATG GGACTCCTAG AAGGAGAAAA GTGAGAGGAC AGGGAGAGAG    186240

AATGTTTGGA GAAATAATTT CTCAAAGCTT CCCATGTTTG GCAAAAAAAC ATTAACTTGC    186300

ATACATATTT TAGGAGCTCA ATGAATTCCA AGTAGGATAC ACTCAAAGAG ATCCATACCT    186360

AGACACATCA TAATCAGATT ATCAAAAGAT GAAGAAGATG AATCTTGAGA GCAGAAAGAA    186420

AGGAACAATT CATCACATAC AAATAGTACT CAAAAGATGT CTGGAGTAGG TATACTAATA    186480

TCAGACAAAA TAAACTTTAA GATAAGCATT GTTATAATAA ATAAAGAAAG GTATTTGTA    186540

ATGATAAAAG TGTCAATTCA TCAAGAAAAC ATAACATTAT AAACATACAT GCACCTAACA    186600

ACAGAGCCCT AATATTCATG AAACAAAACT GACAGAATTG AAGGGAGAAA TAGAAAATTC    186660

GACAATAATA GTTGGAGACA TCAATACCTC ACTAGTTAGA CAAGATCAAC AAAAAAATAG    186720

AAGACTTAAC ACTTGAAAAC ACCTAACCTG ACCCTAACAT AAATCTATAG GTCACTACAC    186780
```

```
CCCAAAACAG CAGAATAAAC ATCCTTCTGA AGCTCACATG AAACATTTTT CAGGATAGAC    186840

TGTATATTAC TTCATGAAAT AAGTCTCAAT AAATGTAAAA GGACTATAAT AATAGAGTAT    186900

ATATTCTCTG ACCAAAGTGG AATGAAGATA GAAATCAATA ACTAGGCTGG GCGTGATGGC    186960

TCACGCCTGT AATCCCAGCA CTTTGGGAGG CCAAGGCGGA CAGATCACGA GGTCAGGAGT    187020

TTGAGACCAG CCTGACCAAC ATGGTGAAAC CCTGTCTCTA CTAACAAAAT ACAAAAATTA    187080

GCCAGGCCTG GTGGCATCTG CCTGTAGTCC CAGCTACTCG GGACACTGAG GCAGGAGAAT    187140

CACTTGAACC CAGGAGGCAG AGATTGCAGT GAGCTGAGAT CGCGCCACTG CATTCCAGCC    187200

TGGGAGACAG AGCGAGACTC CATCTCAAAA TTAAAAAAAA AAAGAAACT AGAAAAATAA    187260

GAACAAATCA AACCCAAAGC AAGCAAGAGG AAAATGAAAA ATTTCAAAGC AGCCAAGAAC    187320

AAAAGGCACA TTATGTACAG AAGAACAAGT GTATAGATCA CATATTTCTC ATAGACACAA    187380

TATAAGCAAA AAGACAGTGG AGCAAAATTT TTTAGATTAA TGAAAGACCT ACAATTCTGT    187440

ACCAAGCAAA AAAACTCCCC CCAAATGAGG GTGAAATAAG ACAATTTAAT ACAGAGAAAA    187500

GAGGAAGGAA TTTATCTAGT CATATGTGAG AGTTTTATGA TACATTTTGT ACTGTATATG    187560

TGGATGTTTT CTATTTCATT TAAAAAATCA ACCGTGCAAT TAAATGGTAG ATTGTCTTGC    187620

TTCTTTTTGA TTGACACAGT CATTAACTAA AATATTGTAG TATTTTTTTA TCTCCCTGCC    187680

TAAAGGCAAT AAACATCTAA TCAGCAGACT AGAACAATAA AAAATATTTT TTAAAAGTCC    187740

TTTAGGCAGA ATGATAAAAG TCCCTTAGGC ATATTGAAAT TCCTATTTAT ACAAAGGAAT    187800

AAACAGTACT AGAAATTGTA ACTATGTGAG TAAACAGATA ATATTTTTTC TCCATAAAAT    187860

GTGGTTGACT ATTTTCACAA AAATAGTTAA CAATGTAATG TGTGATTTAT AGCATTTAAA    187920

AGTAAAACAG GCCGGGCACA AAGGTTCGTG CCTGTAATCC CAGCACTTTT GGAGGCCGAG    187980

GCGTGCAGAT CACTTGAGGA CAGGAGTTCA AGACCAGCCT GGCTAACATG GCAAAACCCC    188040

ATCTCTACTA AAAATACAAA AATTAACCAG GCGTGGTGGT GCACGCCTGT AATCCCAGCT    188100

ACTCTGGAGG CTGAGGCACA AGAATCACTT GAATCCAGGA GGTGGAGGTT GCAGTGAGGC    188160

AAAATTATAC CACTGTGCTC CAGCCTAGGC AACAGAGCTA GACTCTGTCA CACACACACA    188220

CACACACAAA AGAAAAGTGT ATGACAACAA CAGTGCAAAA GAAGCGGAAA TGAAAATAAT    188280

GTTATTTTAT ATAAGTGGTA TACTTTTAGA TGAACTACGA TAAATTAATG ATGTATACTA    188340

TAAACTCTAA GGCAACCACT GAAATAATGA AACGAAGAAT TATGGCTAAC AAGCCACAAA    188400

AAGAAATAAA ATAGAATGAG AAAAAATATT TAAGTTGTTC AACAGATGGG AAAAAAAGA    188460

GGAAAAAGAG AACAAAGAAC AGATGGGACA AATGGGAAAG TAATAGCAAG ATGATAGACT    188520

TAACTCTACC CATATAGATT ATCACACTTA AGGTAAATGA TCTAAATACT CTAATACAAA    188580

AGCAGAGGTT GTCAGATTGA ATTAAAAAAA CAGACAACAA CAAAAAAAAG CAAAAAAAGA    188640

GCCACAACAT GCTGCCTACA AAAAATTCAC TTTAATATAA AGACACAAAT AGTCTAGAAC    188700

ACCATCACTT TTAACCTTAT TTACTCAAAC CTCCTAACTG ATCCCTATTT ATTTATTTAT    188760

TTATTTATTT ATTTATTTAT TTATTTTTGA GACAGAGTCT GACTCTGTTG CCCAGGCTGG    188820

AGTGCAGTGG CACCATCTAG GCTCACTGCA GCCTCTACCT CTCGGGTTCA AGCGATTCTC    188880

CTGCCTCAGG CCTCCCAAGT AGCTGGGACT ATAGCACATG CCACCATGCC CAGCTAATTA    188940

TTATATTTTT AGTAGAGACG GGGTTTTGCC ATGTAGGCCA GGTTGGTCTC AAACGCCTGA    189000

CCTCAGCCTC CCAAAGTGCT GGGATTACAG GCGTGAGCCA CAGCACCCAG CTCCTCTTCA    189060

TTTATTCTTG CTACGCTTCC TCCAATCCAT TTTGTGCATT TGATGATTTT GCCAGTAACT    189120

TCTTTATTTT TCTGGTAAAA TTACTTATGG GTCACTGAGG ACTGGGATGT TCTTTCTTCT    189180
```

```
AGAGGGGGTT TGTGTCTGCT TTTGCCAGGA AGCTGGGGTA CCACCAGTCA AGTATTACTT  189240
TAAAACTCAAT TCATGAATTG AGACTTTTTT TTTTTTTTTT TTTTTTACGC AGAGTCCTAC  189300
TCTGTCACCC AGGCTGGAGT GCAGCGGTGT GAACATGGCT CACTGCAGCC TCAACCTACT  189360
GAGCTCAAGC AATCCTTCTG CCTCACCATT CTGTATAGCT AGGACTACAG GTGTGTGCCA  189420
CCATGCCTGA CTAATTTTTT AAATGTTTTT TTTAGAGATG GGGCTCACTT TGTTGCCCAG  189480
GCCGGTCTCG AGCTCCTGGG CTCAAGTGAT CCTCCCACCT TGGTCTCCCA AAGTGCTGGG  189540
GTTACAGGCA TGAGCCTCTG TGGCTAGCCA AGACTTTTTA TTTTTTAGCC TAAATGTGTA  189600
TAAAAGTTGG CTTGTGGTTA CAACTTATCA GGATTGATGA TCTCTCTCTC TCTCTCTCTC  189660
TCTGTCTCTC CCCACCTCTC TCACATCCCT TGCTCTGCTG AGAAGCAGAG CAAACATTCT  189720
AGCAGTTTCC AGAGAGTAGG ATGGGATTAC TTCTAGTTTA CTTTTATCAT CCTTTGGGAT  189780
CGCAGTATTA CTGGGAGAAC ACAAGTATCT CTTATTAGAC ATACCACCTT TGTAGAATCT  189840
GGACTTTCAT TTTAGACTTT ATTTGTTTTC TACTATAAGC AATTTAAGTT ACAGATCTCT  189900
CTACACACTG TTTAAGTTGC ATCCCATGAA TTTTGATGTG CTTTATTGTC ATTATTATAT  189960
AGTACAATGT ATTTTGTAAT TTTTTGTGAT TTGTTTGGAG AGATTGATTA ATTAGAATGA  190020
TGTTTAATTT CCAAATATGT GTGTTTTTTT CCTACATTTC TTATTTTTAT TGATTTCAAA  190080
TTTATTTCTA CTGTAGTCAG ATTTAATAAT TCATTTATTT TTATTATTTT CATTTTTTTA  190140
GAGACAGGGC CTTTCTGTGT TGCCCAGGTT TGTCCCAAAC TCCTAGTCCC AAGCAGTTCT  190200
CCTGCCTCAG CCACCCAAAG TGCTGGGATT ATAGGCACGA GCCACCCGTG CACAACCAAC  190260
AATTCATTTA AAAAGTGGGC AAGTGAACTG AACAGACATT TCTCAAAAGA AGGCATACAA  190320
TTGGCCAACA AATATATGAA AGAATGCTCA ACATCACTGT ATTAGTCTGT TTTCATGCTG  190380
CTAATAAAGA CTTAACCTGA GACTGGGGAA TTTACAAGAG AAAGAGGTTT AATGGACTTA  190440
CAGTTCCACA TGGCTGGAGA GATCTCACAA TCATGGTGGA AGGCAAGGAG GAGCAAGTCA  190500
CATCTTACAT GGATGGCAGC AGGCAAAGAG AGAGCTTGTG CAGGGAAACT CCCGTTTTTA  190560
AAACCATCAG ATCTCGTGAG ACTCATTCAC TATCATAAGA ACAGCATAGG AAAGACCCGG  190620
CCCATAATTC AGTCACCTCC CACTGGGTTC CTCCCAGGAC ACATGGGAAT TGTGGGAGTT  190680
ACAATTCAAG ATGAGATTTG GGTAGGGACA CAGCCAAACC ATATAAATAA CTAATCATCA  190740
GGGAAATGCA AATCAAAACC ACAATAAGGT ATCATCTCAC CCCAGTTAGA ATGGCTATTG  190800
TCAAAAAAAC AAAAAATAAC AAATGCTGGT GAGGATGTAC AGAAGAGGGG ACTCTTATAT  190860
CCTACTGGTG GAAATGTCAA TTAGCATAGC CATTATGCAA AATAGTATGG AAGTGAGGTA  190920
GGTTACATAG GGTGGTCACA GCCTCCCTTG AAAGGAAACA AGAAACTTGT CAAATTGATG  190980
GAGAGAACAA ATCTCTTGAC ATTACACAAA CTGCATCTGG GGCTAGTGGT TAGAATATCC  191040
TCAGTCAAGG AGGTAGAAGA GCAGGAGGGA AAATCCCTAA GTTCGTGCAA GTGCAGAAAC  191100
CCACAAGCTG TGTTCTCAGG TTGACATATA CTCATTTTAA TAGTAAGAAA CACACCCTTG  191160
GGTAGAGAAT TAAATGCTA ATAATACATG TGATGTATGT ACTAGCGTGT ATGGCAATAT  191220
TGCATGCACA TTCAAGAGAC CACCCAAAAC ATATTTAACA ACAATGCCCA TTCCCACCCC  191280
CTCATGGATA ATCACGTAGG ACTCCCATAA CGGGAGTTTC TTCAGTGTCA ATTGGTGCTG  191340
AAGTAGCCGA CCCTGACTCT GCTATCAGCG TGTACTTTCA CCTTGCAATA AACTCCTTTG  191400
CCTACTTTTA CTTTGGACTG GCTTTCAAAT TCTTTTGTGC AGGGAATTCA AGAATCTGAA  191460
CCAGCCCACT GACAACAGAG GTTTCTCAGA AACCTAAAAA TAGATCTACC AGATGAGGCT  191520
```

-continued

```
GAAAATCTGC TACTGGCTAT TTATCCAAAG GGAAGGAAAT CAGTATACAA AGAGACACCT  191580
ACATCCCCAT GTTTATTGCG TCACTCTTCA CAAGAGCTGA TATATAGAGT CAACCCTAAA  191640
TGTTCATTAA CAGACAAATG GATAGAAAAT GTGGCATATA TACACAATGA AATACTATTT  191700
GGCCATGAGA AGAATGCAAT CTTGTCATTT GTGGCAACGT AGATGAAACT GGAGAACATT  191760
ATGTTAAGTA AGATAAGCTA GGATTGGAAA GATAAATACT ACATGTTATC ACTCATATGT  191820
GAAAGTAGAG AAAAATTTTT AGCTCATGGA TTTAGAGAAC AGAACTGTGG GTACCGGAAG  191880
CTGGGAAGGG TAGCAAGGAG GGGAGGATAG GGAGAGGTTG GTTAATGGTG ACAAAATTAC  191940
AGCTAGATTG TAGAAATGAG TTCCGGTGTT CTGCACCATT GTAGGGTGCA TATGGTTAAC  192000
TCTCATTTAT TGTATATTTT CAAAAAGCTA GAAAAGAATT TTGAATACTC ACAACAAAAT  192060
AAATGATAAA TGTTTAAGGT GATGGATATA CTAATTACTC TGATTTGATT ATTACACATT  192120
GTGTACACAT ATAAAAATAT CACTCTTTAT CCCGTATATA TGTACAGTTA TTATATGTCA  192180
ACTAAAAATA AAGAAAAAA AGAATATGAT CTATCATGAT GTATATATCA TGTGTACTTG  192240
AGCAAAATGT GCATGCAGAT ATTGTGTATA ATGTTCTATA AATCAATTAG CTCAAGATAA  192300
TAGATAGGAT TGTTCAGATC TTCTGTGTCT TTACTGATAT TTTGTCTAGT TATTGCATCA  192360
TTACCAAAAA AAGGGTGTTA AACTCTCCAA ATGTGATTGT AGAATTGTCT ATTTTGTCTT  192420
TTCTTTTCCA TTTTTACTTT ATGTATTTTG AAACTCTGTT ATGACATTTT GCTATGTATT  192480
TTAAAACTTC GTTATGTATT TGAAACTCT GTTGTTAGAA TCATACATTT ATGATTATTA  192540
TGTTTTCTTG ATGAAATGAC CCTTTTCTAT TGTCGTTGTT TTTGTTTTTT CTGAAATGGA  192600
GTCTCACTCT GTTGCCCAGG CTGGAGTACA GTGGCACAAT CTTGGTTCAC TGCAACCTCC  192660
ACCTCCTGGG TTCAAGCGAG TCTCCTGACT CAGCCTCCAA GTAGCTGGGA TTACAGGCAT  192720
GTGCCAGCAT GCCAAACTAA TTTTGTATTT TTATTAGAGA CAGAGTTTCA CCACGTTGGC  192780
CAGGCTGGTC TCGAACCTCT GACCTCAGGT GATCCGCCCA CCTCGGCATT TTTATTTAT  192840
TTTATTTTTT TGAGACAGAG TCTCACTCTG TCACCCAGGG TAGAATGCGG TGGTGTGATC  192900
TTGGCTCACT GCAACCTCCG CCTCCTGGGT TCAAGCAATT CCCATGCCTC AGCCTCCCGA  192960
GTAGCTGGGA TTACAGGCAC ATGCCACCAT GACTGGCTAA TTTTTGTATT TTTAGTAGAG  193020
ATGGGGTTTT TCTATGTTGG CCAGGCTGGC AACTGACTCC TTTAACAATA CAAAATATCA  193080
CTCTGTCTCT GGTAACACTC TCTGTCTTAA ACTCTATTTT AGCTGTTATT ATTATAGCCA  193140
TTTTAGTCTT TTTATGCTTT CTGTTTGCAT AGTGTATATA TTTAATATG TTTATTCTCA  193200
AGTTATCTGT GTTTTTATAT TTAAGATGTT TCTCTTCTAG CCAACGTGTT TGGTTCTTGC  193260
ATTTTTAAGT CGATTCTAAC AATCTTTGCC TTTCAATTGA AATATTTACA CCATTAACAT  193320
CTAACATTAA CATTTATTTT TCTTTCCACA GTACACTGGC TAGCATCTCC CATATAATAT  193380
TGAACATAAA GTGTGATAAC TGACATCCTT ATTTCATTCC TACTCTGAGT GGAAAGGGCA  193440
GGGGTGGAGA AAGCATTCAA CAATTTGCCA TAATTATAAT TCTTTTTGTT ACACTGTTTT  193500
CTTCTGCATT AAAAAATATC ATTACATTTT GCATGAATTA TTAGGAGAAA ATATTTCCA  193560
ATTTTCCTGG AAAATGCCAT AACCACGTCT CTCAATTTTG TTTCCATCTT TCTTCCACAT  193620
TTTACATAAC CTACATAAGA GACACATTAT CAAGTATATT TTACATGGCT TCTCAGTGTC  193680
TTCTCTGTCT GCTAACAGGT TTACCAAGAG ATGGCACTCT TGTATTTCTG GTGGCTATGT  193740
CCATATCGTT TTGCCTTTAA GACAGCGTAA CTACTTCTTT CACCAGTATT AAAGACATGT  193800
ACATTTGATC TGGTTCTTGT GGATGATTTT AAATGACTCA AGCTAATAAT CCTAATTTTA  193860
CCTAAACACT CCATTATTTT AAAATGTATT CCTTTATGCC CACAATAAAC ATTTATTGAC  193920
```

-continued

```
ATTAGGCTGG ACATTAGGCT TCTCTATGGC AGACATTAGG CTGGACCCTA GCCATATATC 193980

TATTGAGGGA AAAAAAATTA TTTTCTATAT AAGTTTCCAG AAAGCCAAGA TGTGTTTTAA 194040

AAACAAAACA AAACATTACA TTCTAAATGC TGTAACAAGA TAAGAAAAAG TGTTGAGGCT 194100

GAGAGAAGAA CAAAGCAGCA AGCAACTCCT GGAAGGACCA CTGCTGCAGA GGTAATAACT 194160

GGTGAACCAT GTTTTGGAGA AGGAAAAGGT CACCAAGAGA AGGAGGGGGT CCAGGGTGTT 194220

CAGAAAGATT GCATGCATAA AGATCAAGGG TAATAAAAAA AATTCCGTAT TATGTAAATG 194280

TGAAGTTCCA GGACCATGAG CTTGGAGAGC ATGAAGTACA GGAGGAGGGT TGGTTTCAAA 194340

TAAATCTGGG AATGAAACAG TGAAGCCTCT GGCAGAACTC ACATCTCTTT CCTCCCCTCT 194400

TCCTTGCACA TTCCCTTTAT GGAGTAATTG CAGGGATGGG AAAAGTTCAA AACCACCACT 194460

GAGCCTAGGA AGTGCTAGGG TAAAGTGGAG AATGAACCTG CGTGATTTGC TCATCCTAAA 194520

CTAGGTTCTT CTAGGAGAGC CCTTCCCCAT AAAATCTGCC CTCCTCGAAG GGCCCCGAC 194580

AGCCTAAGCT CACCTCCCAA AGACCCCTTA CTTGCTGACT GAATCTGATT CCACCCAGAC 194640

ATGGCCTAAA ACCCTTCCAT AACTCTATAG CCAAATTCAA TTTTAGACAG GCCTCATACC 194700

AACCTTTCTT CCTCTAAGTC TGCCACCCTA GGCAATTCTC AACATTCTCT ACACACTTTG 194760

GGGCCATAGA CGTGCTACCA AGTCTCCAGA CCTAGACCTG ATGGAGCAGT GCTGTAATGA 194820

GACGACCACT GGCCTTTGAA CCAGACCCTT CTCTGTGGCT CCTATGCATC TCCAACCTGT 194880

TTTGAGCACT GCTGCCAAGA CATCTTTGGC ACTTTGTTGT GAAGTTTTAA AACTGAACTA 194940

ATCTACAAAA CACCTAACCT TTAAAAATTC ATTGTCATTT CATATCATGA AAGATAAAGA 195000

AAGGCCAGGA AACTGTTCCA GGTTAATAGA GACTAAAGAG ATAGCAACCA AATGCAATTT 195060

GTGATCCTGG ATTGAGGGGA AAAGTGTTG TCAGAGACAT GATTGGGACA GCTGGTAAAA 195120

TTTGAATTTG AATTTAAAGA TAAAGTATTG AGTAATATAG GAAGATGATT ATCTGCAACT 195180

TTCAAATGTT TCAGTAAGTA TATATATATA TAAAGAGATA TAAAGACATA TAAATAAATA 195240

GATGGATAGG TAGAGAAAAA GCAAATGTAT AATATTAACA ATCTAGGTAA AAAGTATATG 195300

AGTGTTCTTT GTACTGTTTT TCTGATTTTT CTATATGTTT GAAATCATTT TAAAATAAGA 195360

AGGTTTTTGG GGTTTTTTTG TTTGTTTTTT GTTTTTAGAG ACAGCATCTT ATTCTGTCAC 195420

CCAGGCTGTA GCTCAGTGGC CCAATCATTG CTCACTGCAG CCTCAACTTC CTGGGCTCCA 195480

GTAATTCCCC CTACCTCAGG CTCATGAGTA GCTGGTACTT CAGGTGTGCA CCACTGCACT 195540

CAGCTAATTT TTATTTTTTA AATTTTTGTA GAGATGGCAT GTTGCTATGT CACCCAGGCT 195600

AGTCTCAAAC TCCTGCCCCC AAGTGATCCT CCCACTTTGG CCTCCCAAAG TGCTAGAATT 195660

ATAGGCATGA GCCACTGCAC CCAGCCCCAA ATAAAAAAGT ATTTTATTTT AATTAACTAA 195720

TTAATTTTGA GTCAGAGTTT CACCCTTGTC ACCCAGGCTG GAGTGCAATG GCATGATGTT 195780

GGCTCACTGC AAACTCTGCC TCCTGTGTTT AAGCGATTCT CTTGCCTCAG ACTCCTGAGT 195840

AGCTGAGATT ACAGGTGCCT GCCACCATGC CCAGCTAATT TTTATATTTT TAGTAGAGAC 195900

GGGGTTTCAG CATGTTGGTC AAGCTTGTCT CAAACTCCTG ACCTCAGGTG ATCCACCCAC 195960

CTCGGCCTCC GAAAGTGTTG ATGAGCCACC ACACCCGGTC TAAAAAGTAT TTTAAAACCA 196020

CAGTCCCACT CTACCTTGTC CTACACTACC AGGGGCTAGG ATCACCCCAT GTCTTCTAGG 196080

CTATGAGATA GAGGAATCCA AGGAAGAAGA TAAGCTACTT GGTTCCTCTA TAGGGTCTTG 196140

TGTGTGCTCT CATGTGCTCT CTCTCTCTCT CTCTCTCTCA CACACACACA CACACACACA 196200

CACACACACA CACACACATG AATACCAGAG CTATCACTTT CCCAGTCTAG TACTCATCTC 196260
```

```
ATCCCAAGGG TTTTGTGTTG TAGTGGTTTG CTCATTTGTT TGTTTTGTTT GTTTGCTTGG   196320
ATTATTCTTT TTCTCTTTTT GCAGCTGAAG GGAGAATTTC CAGGCCAGCC CTTTGGCCAT   196380
TAGAGTTACA GTGCCTCTAT TCAGGCTTCA TAGAGAGACC TGGGATTCAG TAGTGGGGGG   196440
CTTTTATCCA GTTCAAAATA ATGCATTCTC ACCAAGATGT ACTTTGAAAT AAAACAATAC   196500
TAAAACACAA AATTTTATTT ATGCTGAACA TTGAATCACT TTTTTCTGTA TTTTGTGTAG   196560
AAAGTTATAC ACACACAAAC ACATTTGCTC CTGCTTTGTT TATTGGCCCA GGGGTATGTT   196620
TGGTAATACT TCATCAGGCA TGAGTAGTAC GTCTTGGAAG GTGTGGTCTA AAGCCTAGAC   196680
TCCTATCTGC TTCCTTCAGC ATTCTCCAGT GTATCTGTCA TCTGTCTACC TTAGGATGGG   196740
GTCTCCAGAA CTTCCATTCA CATTTAGAAG AGGGCAGCGG CTTTCTATGG AAAATATGAA   196800
CTCTCATTCA TCTCTATTCC TTCTTCTAGC TATGGTCCAG CTCAGCTGTT TGGAATAAAG   196860
TATCTATATG AAGTCTGCGA ATGGTTCTCA GACTGGTTGA ACATTAGAAT CACCTGAGTA   196920
CCTTCTAAAA TTCTTATTAC CCAGGGCATA TCTCAGAATG AGTACCACAG GGTAGGGATA   196980
GGATTAGGGA TCATGATCTC TGGAGTCTGG TTTAGGCACT AGTGCTGTTT AAAACTACGT   197040
TCATGAGGTG GAGGTTGCAG TGAGCCGAGA TGGCGCCACT GCACTCCAAC CTGGGCGACA   197100
GAGTGAGAGT CTGTCTCAAC AACACAAAAC AAAAAAAACC AACTACCCTT GTGATTTGAA   197160
TGTCCATCCA AAATTGAGAA CCATTAGGTA AGGCCAAGCT GTATAATTAA AGAGCAGTTT   197220
TCATTTGTCT GGTGTGGTGG CAGCTTTTTG ATAAGGGAAG TATTGTTGCC ATCCACATAC   197280
CTGAGCCTCA CTCCTGAGAA CACTGGTGTG TATGTTGCTA AAATTCCCCA GGTGATTCTG   197340
AGGTTCCTTC CTGGATAAAA ACCACTGACC CTGGGAATGT ACCCACTGCC AATCTCCTGC   197400
GTAAACCTTG GATACTGGGA AGCCTACAGT TGAAAATATT GGGCTTGAGA TCCTGAAACA   197460
AATCTTGTAT TTCATTAAGA CTAATATTTG GTACAGTGCA GCAAATCAAG GGAATTTTGG   197520
TGGCTGAGTT CTTTTAGAAC TTTTGCATTG AAATAGGTTC AAGCAGCAAT AAGTTAAAAC   197580
TACAACCTCA GCTAAAGGAT TAAAAGACAC GTGAGCTGGG TAGGATGAGG TCTAAGATTG   197640
GGTGTGGCGG CTCATACCTG TAATCCCAGC ACTTTGGGAG ACTGAGGTGG GTGGATCACT   197700
TGAGGTCAGG AGTTCAAAAC CAGCCTGGCC AACATGGTGA AAACCCATCT CTACTAAGAA   197760
TACAAAAAAA TTAGCTGGGC GAGGTGCCAG GCACCTGTAA TCCCAGCTAC TGGGGAGGCT   197820
GAGGGAGGAC AATCACTTGA ACTCAGGAGG CAGAGGTTGT AGTGAGCTGA GATCGCACCA   197880
CTGCACTCCA GCCTGGGTGA CAGAGCAAGA CTCCATTTAA AAAAATAATA ATAATAATAA   197940
CAATAATAAT AATTCAGACA TATCCAGGCA TCAAACAGAT ACCTGGGGCA GATGAATAGT   198000
CTTGAGATTC AAGTCACACA TGAAATTTAG GTGGAAAATG ACATTGGAGA AATTTGAGAT   198060
TATGATGAAT GGAAATTTTT CAAAGAGGAA TTTCAGGCTC TGTTCTTGAG GGGATAGATG   198120
GACTTCCAAC AGCAATAACA CAGGATTAAT GAGGACTTGG GATGTTACAT AAATTAGAGA   198180
TGTTAGATGG ATAAAGAGAT AAAAGTACTC TCTCTAAGAA CATGGGACCA GAGATAGGCT   198240
CACTTCTAAC CATCAGATAT AACTAGCAGA CTAAACGGTC TAAAAATAAA AATCATGCCC   198300
CACTCCTGCT TAAGACATTT TAATTACTCT CAGTAACTCT TCAGTTTTTC TACTGTGTTA   198360
TCTTTAACTA CAGGGTTGGT CTGGGTGTGC AACACAAGAA AGCCTGGCAT ATACATGGAT   198420
TCAAGTGTAT GCCATGTACA GGTATTCTTT CATGTACTAT TTCATGTATT CTTTTTCACA   198480
TCTGTTTTTT CCTTCATTGA AGTCAATGGC TGATATTAGA TTCTACTATT CATGTGTACT   198540
AGTTATATAT AATTGTTACA AAACAAATTA GCAAAAACTT AGTGGCTTAA AGCAACACAC   198600
ATTTATTATT ACCTAAGGTC TGTGGATAGA AGTTCTGACA TGGCTTAACT GGGTTCCCTG   198660
```

```
CTTCAAGCCT CATGTGGCTG CAATCCAGGT GTTGGCTGAG TCTGAATTCT CATCAGAGGC 198720
TTGATTGTGG AAATTTCCAC TTCCAAGCTC CCTCAGGTTT GTTGAAAAAT TCAGTTCTTT 198780
GCACCGGTAG AAGCTTCTTG GTAGAGGCTG ATTCAACTTC TAGAGGCTGT CTGCAGTTCC 198840
TGTCACCCAG GGTGGAGTGC AGTGGAGCAA TCATAGCTCA CTGCAGCCTT GACCTCCCAG 198900
AATCAATCTG TTCTCCCACC TCAGCATCCT GAGTAGCTGG GACCACAAGT GTGTGCCATC 198960
ACACCTGCCT AAAAAACAAA CAAACGAAAA AAAACCCCCA GAGAACTTTG TAGAGACAAG 199020
CTGGTCTGGA ACTCCTGCGC TCAAGCAATT CTCCTGCCTT AGCCTAAAAG TTCTGGGATT 199080
ATAGGTATAA GCCACCATAC CTGGCATATG GCAAGTCTTG AGCAGGACAA ATACAGATGA 199140
TTTATGTCTG TCTTCCATGG TATTCTAGGT TATTGTTGAG ATGGTCCTCT ATTGTCTTGT 199200
TCCATCTATT GATTAGATAA AACGTTGTTC CTTCTGTTAT TTTTCAACAG TAGCTTTTAT 199260
GTGTCTCTCT TTATCTTAAA ATTCTAACCA AAGAGCTGCT CTTTTCTTGG TGTACTTTAC 199320
CTTTGGTTGA TCCTTCTTAA CCTCTTCTTG CCCTCTGGGG CCTAAGATGA GGGCTGTTAT 199380
CAGATGTGAG TCTATGGGAA AGCAAGCAAG AGGTTCTTCA GCCTCCGTTC AGCCTTAAAT 199440
GTCTAGGTAG AAATCAGTCA TGGCCCTTCC AATGTGGTAC AGACCAGATC ACAGAGACAG 199500
GGGTCTCAGC CAAGGTCTTG TGGCCTAAGC CTTATAGAAA TAATGAGTGT TTACTTACTT 199560
GGAGAACTCC CTTGGAATAT CTTTTTTTGT GAACCTGAGG CAACTTTTGG TGATTTCTTG 199620
ATGTCTTGGG AATCTTGGTC TAGAGCCATT TCAACCTGAT TTCTTTTCAT GTCAGTGGCA 199680
TTTTGTGACC AGATAGTAAA TAAGTTCTAT GATGTTCACT CAGAGAAATA CAATGACTTA 199740
TGATGTGAAG CTTCTGTGGT TCAGCCCTTA CTTCATCTTC ATTCCCTCTT ATCTGCATCT 199800
GTCTCCTGCT TGGGAACAAA AGTCTGGCTT CATTCTATGA CCCCCACGTT GAGTTTCTTA 199860
GTAGCACTTA CTTTTCAATT AGGAGTGTCC TCACTTCTAT CCATCAGACA TAACTAGCCG 199920
ACTAAACAGT CTAAATATAA AAATCATGTC CTACTCCTGC TGAAAACATT TTAATTACTC 199980
CCCATCATTT AATTTTTTCT ACTGGGTTAT CTTTAACTTC AGAGTTGGTC TTGTGTGCAA 200040
CACAAGAAAA CCTGGCATAT ACATGGATTC AAGTGTATGC CACGTGCATG TATTCCTTCA 200100
TGTACTATTT CATGTATTCT TTTTCACATC TGTTTTTTCC TCTAAAATTT ATTTCCTTTT 200160
AAAAATGAAA ATTTTGCATT TGACTAAATT TGTCAAATTT AGTCAAATTT GTTTAAAACC 200220
ATTTTTAAAA TGTTTCCCGA AGTTTTGAGT GAAGTTAGTA CTTCAGAAAA ACTGTTTTGT 200280
ATTTTTCATG TGACCTCAGT GCACTGCTGT GCATTTCCAT TTCTGCGTCC ACACACATTT 200340
GTTTTGAGGA AATATAGGAA CGACAAGATA AAGTTCAAGC TCCTGGACAT TGCATAAAAG 200400
ACCGTCATGA CCTGGTCCTG TTGACTTCCC TAGATTTCCC GCTATTTCCT AAGTTGAGAT 200460
TTTTGGTTTG GATGCTTTGT GTTTTCCTAA AATCAAAATA GGTTTTTGCC TTTTATGATT 200520
ATACAGTAAA TAAATGCTAT TTGTGTGAAA CTTTAAACAA TACAAAAAAA ACCTAAGGAA 200580
GAAAGTCAGA TTCATCTAAA AATCCTTGTG GCCAGAATTA ACTACCTTAG TTATTATTTT 200640
CTCTATCTCT CTCTCTCAAT GTATATTTGG TGTAGGTATA GGGGTGTGTG TAGTGTGTGT 200700
GTATGTATAT ATCTGTTTCT ATTCCTGTAT GTGGATGTGC ACAACGCATC CTGCTTTGTA 200760
CACTACAGTA CTAGCATTTT TCTAATGTAA TTCAATATTG TTGAAAACAT TTTAAAAAAG 200820
CTTGTATATA TACACACACA TACACATACA TGCATGTATG TACATATACA CATACAGACA 200880
AAAATGTATC CTATGTATAT TCACACATGT ATACACACTC ACACGTACAT AGAGTTTTAC 200940
ATCCATAGTT TATAAATGTT GCTTTTTTTT GGTCACCTTT TTGCTAAGTC TTACACTTTT 201000
```

```
TTTTTTTTTT TTGAGACGGA GTTTTGTTGT CATTGCCCAG GCTTAGTGCA GTAGCGCGAT    201060
CTCACCTCAC TGCAACCTCG ACCTCCCGGG TTCAAGCGGT TCTCCTGCCT TAGCCTCCTG    201120
AGTAGCTGGT ACTACAGGTG TGCGCCACCA TGCCTGGCTA ATTTTTGTAG TTTTTTTATA    201180
GAGACGAGGT TTCACCATGT TGGCCAAGCT GGTCTGGAAC TCCTGACCTC AAGTGATCTG    201240
CCTGCCTCAG ATTCCCAAAG TGCTGGGATT ACAGATGTGA GCCACTGCAC CCGGCCAAGT    201300
CTTACACATC TTTTTTTTAC CACTAAACTG TTTACCCAAA CCTGATAACC CAAGTCAACA    201360
GCTATTATGG CTCACACAAT CTTATGTAAA CAAAGATACA GATATATAGA ATTTTCTTGA    201420
TTAATATTCA GAAAAAAATG GAGTCCCTTT ATACGTCCTT AGTATCTGCT TTACTCATTT    201480
AAAAATGTAT TACATTATAT GAAAGTATTC AGGTCAAATG TTATAGATGT GATTCATTCT    201540
TTTTAACTGT GTTATTTTTC TGCAATGACT ATGTATCACA AAGTACTCAG TCTTCCACTG    201600
ATGAAAATTT GGGCTATTTC CAGTTTGTCT TCCATTTTTC TTTCTTCCTC TTGGATTTTC    201660
ACTCAATGTG TTTACTAATT TAGGAAGAAT CAATAGTTTT TATGGTATTA CTTCTCCCAT    201720
TCAAGAATAT AGCATATGGT ATAGTATAGT AGAGTACTTA GTTTAATTTA GCCAGATCCT    201780
GTTTTCTGCC CTTTAATAAA ATTCTATCAT TTTCTGCCTT TGAGTCACAT TTTCCTTGTT    201840
CATATAATTC TTAAAAAATG TATAGTTTTC ATTCTAAGGG AACATAAAAA CTTCTTTCCA    201900
TTTCTATTCC TGTCTAGTTA ATTCTACTAT TGGGAAAAGT AACTGTTAAA AAAAATTCTT    201960
ATCTTTCCAG TCAGTTCACC ACATTTCCTT TATACCTTTG TACTTTAATC CCCAGTCATG    202020
TTGAACACTT CTTATTCCTC ACACCAAGCC TCAACGGGTT TGCTCTTTCT GGAAGGTGCT    202080
TCCCCTGTAT TACTGACTTA TTCATACCAC ACATGGAGAC TGGCGCAGCC CTGTTCTGCC    202140
TGGGAAGCCT TCCCCTGATA CCCCTAGTTG GCAGGAGTCT TCATTTGTTC TTTTCTAGTC    202200
ACCTGTGCAA GTTTGTATTG TTCATGTTTA TCATCCTTCA TTCTAGTTGT CTGTCTCTAT    202260
GTGTGGTCTC ATTCAGTGGA CTCTGAACTC TTATGAAGTC ATGTCATGGG TCAGATCTTA    202320
ATAAATTAAT ATTGTCGGAA GCTAATGTCA TGTCTAGAAT ACAGAAAATT TATCAAAAAA    202380
AAATATAGTA TGTTGGCTGG GCGCAGTGGA TCAAGCCCGT AATCCCAGCA CTTTGGGAGG    202440
CCGAGGCAGG AGGATCACAT GAGGTCAGAA ATTCAAGACC AGCCTGGCCA AAATGGTGAA    202500
ACCTCATCTC TACTAAAAAT ACAAAAAGTA GCCAGGCGTG GTGGTGCCCA CCTGTAATCC    202560
CAGCTACTCA GGAGGCTGAA GCGGGAGGAT CACTTGAACC TGGGAGGCAG AGATTGCAAT    202620
GAGCTGAGAT CATGCCACTG CACTCCAGCC TGGGCGACAG TGAGACTCCA ACTCAAAATA    202680
ATAGTAATAA TAATAATAAT AATTGTATGG AATTGAACTG CTCTGATTGG AAATAGCTGT    202740
TTTTTAAAAA ATTATTATTT TTTAAGTTCC TGGGTACATG TACAGGATGT GCAGGTTTGT    202800
TACATAGGTA AACGTGTGCC ATGGTGATTT GCTGCACCTA TCAACCCATC ACCTAGGTAT    202860
TAAGTACAGC ATGCATTAGC TCTTTTACCT AATGTTCTCC CACACCCCCA CCCCATCCTC    202920
CCCCAACAGG CCCCAGTGAG TGTTGTTCCC CTCCCTGTGT CCACGTGTTC TCATTGTTCA    202980
GCTCCCACTC ATAAGTGAGA ACATGAGGTG TTTGGTTTTC TGTTCCTGCC TTAGCTGTTA    203040
ATGTCAGGCC AGAGAGGCTT AAATTTTTAA GGATCTCTGG ACTTTTCTTC TACATTACTC    203100
TTGATGTTTA TAAATGTTAC AACTTCTTTA ATTTCATTAA ATGTATACCT TATTGAGTTG    203160
ATTTAACTGA GTTAACTTTG TTATATGAAA ATCATGATTG GGAGTGAGGG GGTTAAACCA    203220
GCTACAGAGA TCTTGATTGT TGGTGGTGAA GCAATGCAAG AATTCATTCA TTCAGTAAAC    203280
TAATGTTTAT TAAGCGTGTA CTGTCTTAGT CTGTTCAGAC TGCTGTAACA AAATATCATA    203340
AACTGGGTGA CTTATAAACA ACAAAAAATT TATTTCTTAC AGTTCTGGAG GTGGGAAGTC    203400
```

```
TAAGATTAAG GCCCTGGCAA ATTTAGTGTC TGGTGAGGAC AGGTAGCCAT CTTTTTGCTG   203460
AGTCCTAACA TGGCAGAAGG GTTGAATAAA CTTCCTTGGG TTTCTTTTAT AAGGACACTA   203520
ATCCTAGTGA TGAGGTTTCT GCCCTCATGG TATAACTACT GCCCAAAGAC CCCTCCTTCT   203580
AATATTATCA CTTTGTGGGT TAGGATTTCA ACATGAGTTT TGAGAGGATA CAGACATTTG   203640
GATCATAGCA CACACCATAG GACAGACACT GTGCCAAGAA TTGTGGATAT AGTGATTCTC   203700
AAAATGAACA AGATCCCCTC AGAGAGCTTG CAAAATCCAG CTATAAAATT ATGCTTTTTA   203760
AACAAATTAT GCAGTTTGAA AAATCTACTC TGAATCTTAC TTGTGGCATT GAATACTTTC   203820
GGCCACTCTT TCCTTATTAT ATTAAATATT TACTCTTGTT TGGGGATCC AGTCTCACCT    203880
ACTTTTTCTA CCAGAACTGG TATCAGCTCA TGCTCTGCCT TATGCAAATT AAGAAAATAT   203940
CATACCTTTT GGGTAAATTA AGCCAAGAAA GTTCTCCTTT CTTCTCTTTC TCTCTTTCTT   204000
TCTTTCTCTC TTTCTCTTTC TTTCTTTCTC TCTCTTTCTT TCTTTCTTTC TTTCTTTCTT   204060
TCTTTCTTTC TTTCTTTCTT TCTTTCTTTC TTTTTCTTTC TTTCTTTCTT TCTTTCTTTC   204120
TTTTTCTTTC TGACAGGGTC TTGCTCTATT GCCTAGGCTG GAGTGCAGTG GTGCAATCTC   204180
AGCTCACTGC AGCCTTGAAC TCCAGGGCTC AAGCAATCCT CCTGAGTAGC TGGGACTATA   204240
GGCATGTGCC ACAACATCAA GCTAATTTTT GCATTTTTTT GTGGAGACGG GATCTCCCTA   204300
TGTTGCTAAG GCTGGTCTTG GATTCCTGGG CTTATGCGAT TCTCCTGCCT CAGCCTCCCA   204360
AAGTCCTGGG ATTACAGGCA TGAGCCACTG CCCCTGGCCA TTATAACTAT TTTCATTGGC   204420
TTATCAGGCA CATGATAACT ATAATAAATC AATAACCAGA ATTTTTAAAT AAAGAAAGGA   204480
AGGAATTGTT TCAACTCTTC CTGCTACCCC TCTATCCCTC AAAAGGGTAG GCTGAATGTT   204540
GTCCTCCAAA GATATCCATG TCCTAATCCC CAGAACCTGT AAATATATTA CCTTATATGA   204600
CAAAAGGGAC TTTACATGTT TAATAAGTTA AGAATTTTGA GATGGGCAGA TTTTCCTGAA   204660
TTTTGCAGAT GGGCCCTAGT GTAATCACAA GGGTCCTTAT AAGAGACAGG CAGAAGAGTC   204720
AGAATAAGAG AAAAATACTT CAAGATGTTA CACTGCTGGC TTTAAGGTGG AGGAAAGGCC   204780
AAGAGCCAAA AAATGCAGTG GTCACTACAA GCTGAAAAGA AAAAGAAATG GATTTTCCCC   204840
TAAAGCCTCT GGAGGGGGCA CAACCTTGCC AATACCTTGA TTTTGGCTCA GTGAAACCCA   204900
TTTTGGACTT CTGACCTTTA GAACTGTAAA TAAATAAATA ATTTTGTGTT GTTTCAAGCC   204960
ATCACAGTTG TGGTAATTTA CTACAACAGC AATAAAATAG AATTAAATAC AGAGATCTGA   205020
GGAGTTGAGT AGGATAAGCC TACTCCAGCA GGTTATTTCG GGAGTATGGT GAGACTCACT   205080
AGGATGGCGG AACTCAATTA AGGAAGTCTG AAGCTGATAA GCCAGAGAGG GAAGGCTCTC   205140
ACTTCATTTT ATAAGGGTTG CGTCACACTA GGAAGATCCA ATAGCAACCA CAGTCTCAAA   205200
ATTAATGATT ACAAATAGGA CACAATTCCA AGAGTCGGGA GCCAAGCAGA AAATGGATTA   205260
GGGAAGACAT GGATGATATG AAACAGGAAG GAGGGGTACA AGGCAGCTTC CTGGGAAGTT   205320
GCCAGGGCAG TCACAGTTCA CATTCATTAG GCTGTGGGCA CCAAATGCAT ATGGAAAATC   205380
TAGCTGACTT AACTGAACTC CTGAAGAGGA ATGAACACCT CATTTATTGA GGAGCTACTA   205440
CCAATTAGAA TATGTATTTC ATTTGTTCAA TAACCCCATG AGTACAGTAA CACAATCCTT   205500
GCTTTACTAA AGCGGAAGCC AATTCAAAGA GGTTCAGTGA CTTGTCCAAG CTCAGGGAAA   205560
ACACTAGGAA GTGAATATGG GTCTGACTCC ATCACTGATT TCAGGAGCCC TGCCCTTTCC   205620
TCCACACCAT GCCCCCTTGC TTTCAGAAAA AAAGGCTTGT TGACTGAATG GTTGTATGCA   205680
CAGTTCAAAG CAGAAACACA CGATGACATC TTTTGAGATA CTCTAACAGT GAGAACTTGA   205740
```

```
AAATGAAGTT AAAAATTAAG CGGCAAAACC AAGCCGAGGC TTTCTGAGAA AGTGGGGCCA 205800
AACCTGTTGC CGTCTGACTG CCACGTGGCT CACTATTTAT CCCTGTAAAA ATCTGCAAAA 205860
GTATTTGAAA GGGAAGAAGG GACAGAAAAC TCCCTCCTTT TCCAAGTTAG CCTTATAGTC 205920
TAGGGCTTAA AATACTGGTT TAATGGTGAA GGTAAGTGCT TTTCTTCTTT TTGGGTAGAA 205980
GGATTATTAC TAACTTACCA AAGGTCCATT AAGGGGAGGG AACAGTTTTA GGAGAAGTCA 206040
GAGAAAAGAC ATTAACAGCA ACATAAGGAT CTCCATCTGG TAATATTGCC TAATTCCAAA 206100
ATGAAGAGAC TCTCTGAAAA AGATAACTGA TTCAATGAAG ACCCTAGGGC AAGGCTTGAG 206160
AAGCCACTGG TACCAATGGA CACTGTGGAC AATGGTCATT TCTCCAAGGA CGCTGTGAGT 206220
ATTAACTGTG ATGCTGTGAT TAGTCAGACT GGGATTGGCT GTGGAATGAA ATACTGATCA 206280
GAACTGACAA GATTTGTGTT TGGGACTGTG GCTAACGAGT CTTTTCAGAC TTCTATATGA 206340
ATTTGAAATG GTCTCTCAGG AAAAGGAGAA CATGGCCGGG CCTGGTGGCT CACGCCTGTA 206400
ATCCCAGCAC TTTGGCAGGC TGAGGCGGGC AGATCACTTG AGGTCAGGAG TTTGAGACCA 206460
GCCTGGCCAA CATGGTGAAA CCCTGTCTCC ACTAAAAATA CAAAAATTAG CAGGGCGTAG 206520
CGGCGCGTGC ACCTATGCGC ATGCATAGTG CGCGTGCCAG CTATTCAGAA GGCTGAGGCA 206580
GGAGAATTGC TTGAACCCAG GATGTAGAGG TTGCAGTAGT TGAGATCATA CCACTGCACT 206640
CCAGCCTAGG TGACAGAGTA AGACTCTGTC TCAAAAAAAT AATAATAATA AAGAAAAGG 206700
AGAACATGAC CAAAGTTATG AATAAGACTG AAGGCAAGAA AATTGTACGC TTGTAGAGAT 206760
CACCTAGCTT GTTGCCCTCA TTGTACAGCT AAGAAAAGGC ACCCAGGGAC ATTGTGGTCA 206820
GCACCAATTT CTCAGAAAGA TAGGCAGATG ATGAGAGGGC CCTCAGTTTT TCTAACACTG 206880
AAGGAATTGC TTCTATGTTT TCTGGTGAAC TCCTCCCCAC TCATCTTGAG GATTCCAGGC 206940
CAGAAGAATC CACTTTAAAA AAGAAACATT TAAAACCAAT TTAACAACCA ATCAAAGGCA 207000
CTTTTATAGA AATACATTTC ATTTGCTGTT GGCCTGTATT TATGGATCTG AGAGGGCTAG 207060
ACTGCCAATA TTGTGACTGT TTATTATTAT TGCTGTTGCT AGTATCTAGA ATATTATACA 207120
ACATATAACA CTTTGCAATT TACGAGGCAT GTCTCATACT TTTGTTTTCA CTCCAAACTG 207180
CCCAGTGAAG TAACATTATC CCAATTCTTC CTATGAAACA GTGAAAGCCC TAAGAGTTTT 207240
TGAAACTTTA CCTGGTTTAC TCAATTTGGG AATGGCAGAG CAGAATTCAG TCCTTGAATA 207300
TCCTCCCACT GCAGGTTCAT GCTCTTTGAT CTAGGTGTAA CATTTACTCT GAGTAAACTA 207360
GGACTCTGGG CTAACAGAGA TGAAGCAAGA CAGGCTGGAT ATTAGGAGAA TCTAAGCA 207420
ATCTAACGAC CATTATAATA AAATCATGAG TTCTAGACTT AAAAAAAGGG AAAAACCTGT 207480
TTTTTTGCTT ATGCGTATAC CATAATATTT ACATTATTTA TTTTTTTCTC AAATTCAACC 207540
TATACGGTGT CAAGTAATTT TTTTTAATAT AACATTTTCC TTTAACTTAA TTTCAATTCA 207600
TTTTTCTGTG TCTACTTACA ACTTTGGCAC TAGAATTCAC AATTTTTTTT TAGAGGTATA 207660
TCTCCTTAAA GGGAAGGGTT CTGACACTGT TACATGTTCT CAATTGTTTG CAAATAGGTT 207720
AATAATTATT CCAGTGTCTC TAAGTACATA TCAACCATGC CAGTGTTCAG CCTCCATAAT 207780
TTTATTAGCT TCTGTGCTTA TTTTGGAAAA ACATTTCCCA TTACCATGAA AGACCTCAGT 207840
TTAGGATGGT TTGGTATGTT AGCCTGATTT CTGCATTCGT CTCATGCAAA GGAAAATAGG 207900
AAACGAAGAA CTGAAATTAC CTATTGATAC AAAATCAAAG TAGCATTTGA AACCATAAAA 207960
CTTAAGTAGG GCTTTTCATC CTTTCTCGTT AGACAGCAAC AGAGAATGGG AAGAAAAACT 208020
AAAGTGATGG GTTTGTGATA CAATTCCAGT AACATAAAGA GCAAGGAGAA GTAGTTTTGT 208080
TGTGTTTATG TTTAATATTC AAAGCTCAAC CTAAAAGTAT TTTTCATTAT CAAACTTCCT 208140
```

```
TCTAGAATAA ATGATTAAAA CTTGATTTAA AATATACAAA TTCTCCTTTA TAATACCTCA  208200

AAATGGAGCT ACCCCATTGA GTTTTAAGCT TGTGATTAAA ATATTACGAA AACAAAGGGG  208260

AAGTTGTAAT AGGTAGAACA AGCAGTAGTC TAGGCATTAG GGGATCTGGT GCTGGCTCTG  208320

TGCATCATGT GGTTTCAGGC AACTTTTCAA ATTTTCTACG CAAATTTTCT TATCAATAAA  208380

ATAAACAGTT GGGCCAGAGG ATCTCTGAGT CTCTTTCAGC TTTCAGTGTT TATAAGATTG  208440

GAGAAGTTGG TGGGAAAGCT TTAAGTGGAG TGTAAGTAAT TGCAGCTGCA TGTACAGTTA  208500

AAGAGTTGCC TTCAGCCAAG CCACGGGATC TTGCATAAAA AGTGAAATCA AATAGAAAAT  208560

GGTCCAAACT CTGGGTTTGA CCACAGATGA CTTCAGCTAG GATCTGAGTG TAGAGCAATG  208620

AGCTGAACTC CTGATATCCA GATGTTAGCA AGACTTGGAG GCCTTCTAAG GCAGAGCAAC  208680

AACCAGTATC TGTCCTGGTG CTGACCTGAT CTTACTAGCA ATTGGGCCTC CATTTGGGTC  208740

CATTGTACAA AACAACAACA ACAACAACAA TAAAATCTCC AAACACCCAA AATTCAAAT  208800

TTAGATGGAG AGATACTATT CCCAGAATTC TAGAGATATT TGGAAAGCAG AAAACTATAC  208860

TTGCCATGCT GATGAAGTCC AATTATTGCT CTTTTAAATA CATTTAGCTA CTTCTGAATA  208920

TAAAATGAGT ATCTACTAAT TATTTACAAA ATCACTTGGT AAATATAGAA AGTCACAAAG  208980

AATGAAGTGA TCATCCTGTT TTGTAACCCA GAAATAGTCA TTACTGGCAC TTGTGTGAAT  209040

CAGTTTCTAT TCCTGTATGT GGATGTGCAC AGCGTATCCT GCTTTGTACA CTAGAGTACT  209100

AGCATTTTTC TAATGTAATT CAATATTGTC GAAAACATTT TAAAATAGCT TCCATCACAA  209160

TAATCTATCA AATTGACTTG CCAGACTCTC ATTATTAGGT TAATTTATCT CTAACATTAT  209220

GCAGTCATGA GTAATACTAC AAAGGATATT TTTGGACACA ATTTTTCATC TATGCCTTTC  209280

TTTATAATCC TTCATCCTAA GGTCACAGAT TATGAATATC TTTAAAGTAC GGACAAGTCT  209340

TTTAAATTTT GTGTGCAAAA ACAGTGCAAA GCCTTGAATG ATAAAATAGA GGTTTGATAT  209400

ATGTGTTTTT TTGTTTGTTT GTTTTGAGAC GGATTCCTGC TCTGTCCCCC AAGCTGTAGT  209460

GCAGTGGCAC GATCTTGGCT CACTGCAACC TTTGCCTCTT GGGTTCAAGC AATTATCCTG  209520

CCTCAGCCTC CTTAGTAGCA GGGTCTACAG GCATGTGCCA CCACACCCGG CTGTTTTTGT  209580

ATTTTTAGTA GAGATGGGGT TTCACCATGT TGGCCAGGAT GATCTCGAAC ACCTGACCTC  209640

AAGTGATCCA CCCACCTCAG TATCCCAAAG TGCTGGGATT ACAGGTGTGA GCCACTGCAC  209700

CCGGCCGATA CATGTGTTTT TAAAGTCACA GAAATTTCAG ATGTCTTGAA GGATTTTAAG  209760

CAATTTAAAA AATAAAGTCA TAGAAGCTTC AATTTAGGAA TGAATGGAAA ATTGATGATA  209820

TTCTTAGGAT ATGGATTTTT CCTAAAAGAA ACAAATGTAT GCATCCCCAA AGATAATTTG  209880

ATTAGTATAC AAATATTAAA TTAAACATGT CCATATTTGA AGCCATGAAT TCTCTTTGCC  209940

TGTCACAATA GCTGGATTTA TTCACAATTG TAGTAATTAG TCCCTGTTCA TTATAATTTT  210000

CTAGGTGATA TGAAGACTTT GTCAGTCCAA GCAAGTGTCC ACATTGTGTG TAGCAAACAT  210060

GAGAATAAAC ATTTTAAACT TTTAAATGTA ATACATATTA GTGTTATGTA ATGTCATCCT  210120

TCATGTTCGA AGGCACATGG AACATTGTTC TGGTGGTACA GAGGGGAGAG AAACACCATC  210180

AGAATGAAAG GAAAGACCGC TCTGGAACCT TCCTCCTTAG CTCTTGAGCT TAGTTTAATT  210240

GTCCTGTCTT ATGGTCTGCT ACAAGCAATA CCACTCTTCA CCTTCGCATG CTTCTCTGTG  210300

GTTTGATAAA GTACATGCAA TTTTTCATTT AATTCTTCCA GCTGCACTAA GAAAGGAGCC  210360

TTATCTTTAT TGAACAGATG AGGAAATGAA TGATTAGAGA ATTTAAATGA CTAGCTCTAG  210420

GTCACACAGC TGGAACTTAC AGCCAGATTT CCTTTTAACA ATCCTGTAAC CAAAAGCATA  210480
```

```
CCAGTAGTGC CCCATAAAAT GTAAGTTATA GAGCTGTGTT GGGTCAAAAC TTTTACTGAT   210540
GCTAAGAGGA GGCAACATTA ACAAGGGGAA ATTATTTGTG TATTATGTTT TGGATTATGT   210600
TCTCTCCATA GATAAAAGAC TGTCGTAGTA AAAGAGATTC AGGGCACAGG GAAACTCCAC   210660
CACAAAGCGT GGTACCATTT CCCACAGAAG CTAAATGGAC GGGAAGCCTG CCACCAGGAA   210720
AGGTAAAGCC ACTGCTCTTG TTTGCAGGCT ATGTTAATAA GCTGAAGCTT ATTCCGACAC   210780
ATTTACACAT CTCTGCATCA CACTGACCCT TCGTAAAGAT ACTCCCAGTG TAACATTGGA   210840
GCCAGCTCCA GCCCCTGATC CTGTTGCTTT TTCCTTAGCC CCATGAAATC ATCTGCGAGA   210900
AATTAAGCCA AATAAGCAAT AAATCCTGGG ATCTAGGGAG TGGAATAAGT TTTGGGAAAG   210960
TCTTTTTTTT TTTTTTTTTG ACTGAGTCTT GCTCTGTCTC ACAGGCTGGA GTGCAGTGGT   211020
GCGATCTCGG CTCACTGCAA CCTCTGCCTC CCGGGTTCAA GTGATTCTCC TGCCTCAGCC   211080
TCCCGAGTAG CTTGGACTAC AGGCACACAC CACCATGCCC AGCTGAATTT TTGTATTTTT   211140
AGTAGAGATG GAGTTTCGCC GTGTTAGCCA GGATGGTCTC GATCTCCTGA CCTCGTGATC   211200
CACCGGCCTC GGCCTCCCAA AGTGCTGGGA TTACAGGCAT GGGCCACCAC GCCTGGCCCG   211260
GGAAAGTCAT TTTAAACCAA CCTATGTATG AATCCCTACT ATAATATTCT CACCAAGCGG   211320
CTGGCTCTTT CTCCTGAGCT TGGAAACCTC CAGTAAAATG GAAATAATTA TTTCCCAGAC   211380
CACCACTCTT ATCTGTGAGC TTTTTTGGCC ATTAAAAATT ATTTCTTCCA TTATATTTTT   211440
ATCTGTGTCT TCACAGGTTT TCTCTTTCTT TCACTTTAGT GCTTTTCTTC AAATAAGCAG   211500
GAAAAATCCA ATCTATCATG CACATGGGAA CCCTTTCAAT ATTGGTCTGT GGTTGTTCCA   211560
TTTTATGGGG ATGCTTTTAA AGAAAAAATT TGTCCTTTCA ATATATTGAA TATCTTCCAG   211620
CACCACATCA CCTGCAAGCT TTGTAAAAAT AGTTCTACAT ATTAATTTTT TTTTTTTTG   211680
AGATTGAGTC TCATTCTGTC ACCCAGGCTG GAGTACAGTG ACATGATCTT GGCTCATTGC   211740
AACCTCTGCC TCCTGGGTTC AAGTGATTCT CCTGACTCAG CCTCCCGAGT AGCTGGGATT   211800
ACAGGCATGC ATCACCATGC CTGGGTAATT TTTGTATTTT TAGTAGAGAT GGGGTTTCAC   211860
CATGTTGACC AGGCTGGTCT CAAACTCCTG ACCTCAAGTG ATCCACCTGC CTTAGCCTCC   211920
CAAAATGCTG GGACTACAGG CGTGAGCCAC TGCACCCCAC GTAGTTTTTT TTTTTTTTA   211980
AGTTGAACAT ATGTGAAGGC AGGACCTAGT GACACATAGC AATAACATTT CCAAGTAGAC   212040
ATTACACTAG GGAATTAGTC AAAGTGCTCA TTTAAAGTAC CATCTCTCAA ATGTATTAAA   212100
AGAGAATCCT TGGATGTGCA ATACCTTAAT TCAAAGGCAG CTCGTTATGT ATAAACTCTC   212160
AAGCTTTGTG ATAAACAAAT GTGCATAACA GATGGGACTA TTGACTTACA GCCCAGGGAA   212220
TTTTATTGAC GCTGAGAAGG TTATGTGACT GGCTCTGCCA CTGTCATCCC CATTCACTTC   212280
ATTTTGGAGC AATATGACAT AAATGCCTTA CATGTGGGTT TTCTCTATTT ATCATGTGTT   212340
TCCTATCCCC TTGAAAGATG GCCATATTTG CTTTACTTGG TTATAAGATC CCATATTCGC   212400
TGTCTTGAAG CCAACCAAAT AATTTGACAA AGTGGGTTTG TAGTGCTGGC TATTTTGGTG   212460
AAAAAAAGAC AATGAGACTT CATGTGTCAT CCAAAGTTCT ATCAGATCGA GCTGTGAGAG   212520
AAAGGAAAAG AAAGGGGTCT CAGTCAGGAT GCTCACTGCA TACATCTGTG TTGTTGTCTA   212580
GGTCCAGATT TCTGTTCATT ACGCTATGGG CTGGCTCTTA TCATGCACTT CTCAAACTTC   212640
ACCATGATAA CGCAGCGTGT GAGTCTGAGC ATTGCGATCA TCGCCATGGT GAACACCACT   212700
CAGCAGCAAG GTCTATCTAA TGCCTCCACT GAGGGGCCTG TTGCAGATGC CTTCAATAAC   212760
TCCAGCTATT CCATCAAGGA ATTTGATACA AAGGTAAGTA TGATGGAAAA TAGGGCTCTT   212820
TGTTGAGAGA AAAAACTTTG AAAGGAAGGC ATAGATCTTG ATTCTGTGGA GTATGGAAGT   212880
```

```
ATACATTTCC AATGACAAAT TAAAACTGAC TGGAACTATT TTTCTTTGAG ACATTGCTTA  212940

CTTCAATAAT AAAAATAAGA TTTCATTGAG GTTATTATGA TTATAAGGTG GGGGAACTGT  213000

AGAGTTAAAT GTGAAAAATT TAAAAATGGA ACAGTTTATG TGATGTCTTC AATGAAAAAC  213060

TAGGTATTAC CTGGGCACAT TCTTATAGGT TACTCAATCC TATTCAGTTC TCTGCCTGTT  213120

TTATTGTTTC TGAGCAATTT TATATCCCTG TAAATTCTAT ATAACCAATA GAAATGCAAA  213180

CGATTCTTGT CCATAGCTTT GCAAATAAAT TTTGCCAAGA GAAAAATCAG TTAAAACTTT  213240

TCTCCACTCA CCTCCCAGTT GAATTAGCCA ATTTTGCTGT TTGTTTGTTT GTTTGTTTTT  213300

TGAGATAGAG TCTTCCTCTG TCATTCAGGC TGGAGTGCAG TGGCATGATC TCAGCTCACT  213360

GCAGCCTCCG CCTCCCGGGT TCAAGAGATT TTCCTGTCTC AGCCTCCCAA GTAGCTGGGA  213420

GTAAGGGGGC ATGCCACCGC GGCTGGCTAA TTTTTGTATT TTTAGTAGAG ACAGGGTTTC  213480

ACTAGGCTGG TCTCGAACTC CTGACCTCAG GTGATCCACC CGCCTCGGCC TCCCAAAGTG  213540

TTGGGATTAC AGGTGTGAGC CACTGTGCCA GGCTCTGCTG TATATTTAAA GTCTATTTCA  213600

GCATTGCTTC CTGCTTGTGT TATGCGTGAT TCTTTGAGTT TTCCTTTGAA CCAGTTATAA  213660

CATCTTACTT ACTTCCTCCA TTAATCAATG AGTTAAATAA AATCTTTGTT GTATGTTTAT  213720

TTTACATTTA TATGAAAACC ATGAATTTAC CCAATTAAAA AAATTATCCT TTAAATTATC  213780

TTGTACTGTA CATTTCCCAT GTCATCCCTA TAATTCATGA TTAATGATTT TATTACATTG  213840

GACCTAGCTT ATTTACAATG AGTACATAAA TTTATTGTCT CCAGTCTTTC CTCCATTATC  213900

CCGTCTACAT ATCCACACTG AGTAGATTCA CTACTCAGGA ATCTTGGACA CCTTCAAGTT  213960

GCCAAACATG CAGTGTTCAC TGGACATGCT GTGTTCCTTC AGAATTTGGG CCTGCTTCTC  214020

AGCACACTCA CATCTGCTAT CAATGACCCA TGGAAAGTTT TGCCCTGAG CAAGCCAGAG  214080

TCCCTGTTAG TTTCTTCCAA ATGCTACAAG TTCACTTTTG CTATTTTTC CGATGAGATA  214140

AAATTTTCCT TTTTGACTTT CTACAAATCA TAGTCATTTT TCAAGGGATA GTTCAAGTAT  214200

TGCTTCCTTT CTGGGACCTT CCCAAATTAT TATTTTCTCC TCTCAAAGTC TCTGTTTTAT  214260

TTATGTTCAT CCTCAAATCT TGATTCTCAC ATGAATCATA TACCTTGTAT TATTTATAGT  214320

TTTTTTGAGT AGGTAAAATA TTTCATATTT TATATTCTTT GGCTCTCTAC TTTATAGCAT  214380

GATGCCAGAT ATTTAGGGGC CTTACTGCAT TTATTTTTTA TTTTATTTTA AAATCTATTT  214440

TATTTTTTAT TTATTTATTT TAAAATCTAT TTATTTTTAG GTAAATATTC AGGTAATATA  214500

ATTTATGTAA TTATTTAGGA ATTTAGGTA GTTATTTTAA AATAATTCAA ATTATTTATT  214560

GAGTTATATC AGAAGAATGT GATCTTATTC ATTTGTAATA TGTGTTTTAG GAACTCAGTT  214620

CAGCCAGGGC AGACCATAAT TCCCAAACTT GACTTTCTT TTTAATTAGG CACTGATTTT  214680

GGTTAAGAGT TCAGTAAAGT TTTGTGTGTG TGTTTTAAAA AATTCTTTGA TATAAGAGTC  214740

AAGATGTTAC TCAACTTTTA CTAGAAGCAA AATAGAGGAA GTGCTTTCAC AGATGAAATA  214800

TCTCTCAATG TTTTCTTCCA TTTACTTCTT CCTATTATTC ATCTATATAA TCATTTTCTT  214860

TACCTCTTTT CTTCATTTCT TCTGTTTTTC TCTCCTACTA AGACAAGCAA ATTAGGGGTA  214920

TAATTGGTTA TTTGGGAAGG TAGGAAGAAT ACAGAGAGAA ACAAAAATCA ATATTTTATA  214980

CTAGGGTCTC ACTAACCTCA AGCAACTCTG ACTGTAAAGT AGATTTTCAT AATAGGACTT  215040

CTTGACAAAG AGTTTTCCTA TTTTTCCCCC AGGCCTCTGT GTATCAATGG AGCCCAGAAA  215100

CTCAGGGTAT CATCTTTAGC TCCATCAACT ATGGGATAAT ACTGACTCTG ATCCCAAGTG  215160

GATATTTAGC AGGGATATTT GGAGCAAAAA AAATGCTTGG TGCTGGTTTG CTGATCTCTT  215220
```

-continued

```
CCCTTCTCAC CCTCTTTACA CCACTGGCTG CTGACTTCGG AGTGATTTTG GTCATCATGG    215280

TTCGGACAGT CCAGGGCATG GCCCAGGTAT CCAGATACTT TCTCATTCTT GGTGGGATCC    215340

AGATTTCTGA ATTCTACAAA ATATCAAAGG TCTTAATGAT TTTCATTTCA GGGAATGGCA    215400

TGGACAGGTC AGTTTACTAT TTGGGCAAAG TGGGCTCCTC CACTTGAACG AAGCAAGCTC    215460

ACCACCATTG CAGGATCAGG TAAGTGTGCA CAGATGGGTC ATAGCTTTGT CATCTGTTCC    215520

ATCCCACTGT GTCTTATCTT CTATGAATCA AATGGTTTGG GGAAGAGAGA GAAAAAGTAC    215580

TGCTGAAAAA TTCAACAATA TAAGACACTT GCATCACAAA TAGGAAAGAT GCATCTGTGC    215640

AGTAAAGACA TTGAAGCTTA GAAGTAGAAA AAACCATTGT GAGCTAGGTT TCAGCTAGA     215700

AAAGCCTTAG TAGTCAGAAA AGCCTTAGTA GTCAGAAAAG CCTTGTCGGA AAAAGTTTAA    215760

ACCTTTAAGA ATTGCACACA TGGAAAAAGA TCAAGTAAGC TATATATACA CCATCTTAGC    215820

AATGATTTTG AAGTGAGAAT TAAGGCTACC ACAGCTCCAG GTGGTAAGGA GAGAAATCAG    215880

GCTGGAAGAG TTTGAAGTTT CTGTATTATT CTAAGCTCTT TACTATTCTA TTATGAGCTC    215940

ATTAATTCTC ACAACAACCC TCTCATATAA GTACCATTTT AAATTCTTAT TTTACAGAGA    216000

AGGGAGTTAA GGAAGGTGGA GATTAAGAAA ATTGCCCAAA TACAAATAGC CAGCAGGTGG    216060

TAGGTCTGAG ATTTAAGCCC ATGCAGATTT TAGCCCCAGA GCAGACATTC TCAATCACTA    216120

TGCTAGACTG CCTTTCCATG GTATGTGATC CTACTCAGGC CTCTACAGCT TTATCATTGC    216180

TGTTCTCCCC AGCCTGTCGT GCTGAGAGTA TATACTCGAA GAGCAGAACT AAAATTCCAT    216240

CCAGCTTCTC ACTCCTAGGT CCACTACACA GCTGCATCCT GCAGACTTTT ACCTCAAGCA    216300

ACCCTCCTGC GTTCTTGCTT CCTTCCATCA TAGTTGTAAC CATCTCCTCT ATTTGCAAAT    216360

ACTATCTGCT GATCTCTCTC TTCTAGACTG GTTTCTTTCA ACCTTCTTCC CACCAAAACC    216420

AAGTTAGCTT GCTAAAATAA AGATGGCGCA TTTTTACTCA CCCGCTTGAG AATTTTCAAT    216480

GTGTTCCTTC ATGCTTACAG AGTAAAGCCT GACCTCTTTA TTGCATGAAT ACAAAAGTTC    216540

TTAGCCATCT GGCCCCAACC TTGTTCCACT CAACTCCCCT GTGCAAGCAT GGCTCCAGTG    216600

GCACTGGACA TTGGCTGCTC TCCACATAGA TCTGCACTGC ACTTCCCTCT GGCTCTGCTC    216660

CCGTTAGTTT ATATGCCTGG AAAGTTCTTT GCCCCTGTTC CTTGTGCCAA AATTCCATCT    216720

ATCCTATTGC ATAGCTTATG TAAAAACTTC CTAAACCTTT TTTTTTTTTT TTTTTTTTT     216780

TTTTTTTTT TTTTTGAGA CGGTGTCTCA CTCTTCCGCC CAGGCCGGAC TGCAGTAGCG       216840

CTATCTCGGC TCACTGCAAG CTCCGCCTCC CGGGTTCACG CCATTTTCCT GCCTCAGCCT    216900

CCCGAGTAGC TGGGACTACA GGCGCCTGCC ACCATGACCG GCTAATTTTT TGTATTTTTA    216960

GTAGAGACGG GGTTTCAAGC CAGGATGGTC TCAATCTCCT GACCTCGTGA TCCGCCCGCC    217020

TCGGCCTCCC AAAGTGCTGG GATTACAGGC GTGAGCCACC GTGCCCGGCC AAAACTTCCT    217080

AAATCTTATA ATTATTATCA ATTTATCCTC AGATATACTT CCACGTACAT TGTAGTTTTA    217140

TTATATTTAT ATTTTACATC TTTTTTTTCA AATTGCAGTT TGGGACCCAT TAGTGAGTCA    217200

TAAAATCCAT TGAGCGGGTT AAAATCATTA TTTTAAAAAA TGAGTAGAAT AGAATAGAAA    217260

TTGTTGGAGT GCATTGGACA TGGTAAAGTT AAATATCGAT TCATGAAACC ATCGTTTGAG    217320

GCATATGTGT GTGGTTGTAT GTACAAGTGT TTATGCATAT TGGTGTGTGT GTTATGTTAC    217380

CCTGTAAAAT GCATTTCTTA CTATAGGTCT CTGTGAAATA TGTGTCTTGT TGTTTTTTAA    217440

TGTAGACTTC CAAAGCCTAC ATGGCATTTC ACTAGTGACA ATCAATTTTA TTCACATTTT    217500

TCTCTCCAAT TGGACCAGAA GCTCTTTGAG GGCAGGGGCT GTATCTTACC GATTTTTGTA    217560

AGTCTTTCAT TTCCTGCCCC TAGCCTCATA TTAGATCATG CAAGAATGCA ACTGTAATCA    217620
```

```
CAAGAAAATG CTAATGGGCT GTGATAGCAG AGAGTTACTG TGACAAACTA AGGGATTTAG   217680

ATTTGGTCAC ATTGGTGTTG AGGAGCCATT GAAGAATCAG AGAGTGTGTT ACTATTATTT   217740

GTTAATTTTA ATTATATCAT ATTACTTTAC TGGGGAAAAT CTGTGAGCTA TTTTAGAAAT   217800

AAATACTCTC ATTGCCCAAT AATTCTAAGT CTGCCACCTC ACTGTTGGGA CATTGTTTAG   217860

GGAGGCCACG AAGTCTCAGC CTTTGATATT TTCATAAGTG TTTTTCTCCC TTTTTCCTTT   217920

AGGGTCAGCA TTTGGATCCT TCATCATCCT CTGTGTGGGG GGACTAATCT CACAGGCCTT   217980

GAGCTGGCCT TTTATCTTCT ACATCTTTGG TGAGTCACTT TCTCTTAAAT CCTAATGCCT   218040

CCATTTCCTG AGCATCCATT TTGGCACCTA CACCACCCAC ATTCTTCCTA TATGAAAGAA   218100

AATGTCCTTT ATCAAATGGA AGATGATAAA AAATGTCAAC GGTTGGTATC ATTTTTAATC   218160

TAGTCACACA ACCTGATTAA CACCTTCCTG GTGGTTCTGG GAAGCCACAC GCAAAAGGTA   218220

GAGGAGTTGA CTATTCACAT GGCACCCACC GACTTGTGAT GCAGTCTTGT CCTTCCATAT   218280

CAAGCACCTT CTGCAGAATC TCTACCACCA CATCTGAAGT GCCTGCTATA TGCAGTTAAG   218340

ATGTCAAAGA TAGTGAAGTA CATTTTCAAT GTGTCTTCAT ATTTCATTAT AATTATTATT   218400

TCTGTCCAAG ATGCCTTTCA CCTGTTCTCT ACCAAGTTAA TCTTGCAAAG TTCAATTCAA   218460

ATGTTCCCTT CCCCATGGGC CCTTCCAGGG CTTACCCTGT CAGATTCTGG CATTCTCTCC   218520

TTTATGATAT TTCCTCTCTA GGTTATGTTG GTGTGTAATT ATTTATTTCT CCTTTTCTTT   218580

CCACTAGACT GTGAAATGCT TGAGGCAAGG AATCCATTCT ATGTTTTCAT CACTTGGGTG   218640

TCATCATGGT GCCTGATTTT TAGCTTTAAA ATAAAAGAAT CAGTGAATCC AGTAATTAGA   218700

GGGGATTTAA AGAAAACTAG TCCTCAGAAT CTTTTAACAT AGAATGTTCT TCAAATAAGG   218760

AATTCCAATA ATAAGACAAT TTTCTACACT TGATTTTGTT TTTATAGCCA AATGGTGTCA   218820

TTAAATATAG TCCTGGCCTG AATGGCTTTC TCATTAATGA TGCTAATTAT TTTGGTTTGT   218880

ACATGTTAAC CAGGTATTGT ACAAAAATAT TTCTTTTGGG AATCCATAAT GGATGTATGG   218940

CTTGAATACA ATAATACTG TCTCTTGTAA GTGCATTGGA AATTTTTCCC TGCCACATGA   219000

TTTCATGGAA GGTTGTTTCG TGTATGTATG ACTGCAAACC TGACTATTCA GATCTTCCGC   219060

AACAAGACAA CTTATGTGTG CATTAAGAAG TTGCTGCCTA AAATACATAA CACTGTAATC   219120

ATTGGAGACT TTAAAGTAAT TAATCAGCTA TGCAATGCCA CGCTCCTGTT ATCTCCAGAG   219180

GGCTCTGACA TTGACAAATG GTGGCTTTCT ATTTGAGACG TAATATCTAA AAAGCTTTAA   219240

CAGGTTTGTA GAAGGATTGA AAGAAAGAAT GGGAACATTT AGGTCCTTAT GGTAGAATAA   219300

GCATTAATTG ATTAGTGTGT AGAAGGGAGA GGCATGCCAC TTCAGAGGAA ACTTCCTTCC   219360

CCCAGTAAAC AAATCTACCT AAAAACTAAT TTTATCCCTT CTTCCCAGGT AGCACTGGCT   219420

GTGTCTGCTG TCTCCTATGG TTCACAGTGA TTTATGATGA CCCCATGCAT CACCCGTGCA   219480

TAAGTGTTAG GGAAAAGGAG CACATCCTGT CCTCACTGGC TCAACAGGTA CAGTGCACAC   219540

CTTGTACCTG TGGCCCATGC AGAGGTCTCT AGGGCAGGGT GTGGATCTCC TCTGAGAGGC   219600

ACCATCTTGG CTGCTCTAAT ACTCATGCTG ATTAGATCTT TCTTTTCAGC CCAGTTCTCC   219660

TGGACGAGCT GTCCCCATAA AGGCGATGGT CACATGCCTA CCACTTTGGG CCATTTTCCT   219720

GGGTTTTTTC AGCCATTTCT GGTTATGCAC CATCATCCTA ACATACCTAC CAACGTATAT   219780

CAGTACTCTG CTCCATGTTA ACATCAGAGA TGTGAGTTTA CTTCCTATAC TTCTACGAAA   219840

ATGATAATGG TAATAAGGAG AAACAGTTCT GTGTTACCTA TTACATTCTG GCTTTACATA   219900

TAACCATTAA TTTAACCTTC ACAATGACCT TGAGAGAGGC ATTGTTATAA TTCCCTTTTC   219960
```

```
ACAGATGTGG AAACAGGACA CTTAGAGGTG AGATAACTTG CCCCAGGTTG CACAATACTA 220020

AGTGATAGAG CTGCTGCAGC ATCCATATTC TTAACCACTA TGCTATACTA CCACACCAGC 220080

TGATTCCAAA GCTTCTTTTA GAAATAATAT TGCTGGGCCA GGCATGGTGG CTCATGCCTG 220140

TAATTCCAGC ACTTTGGGAG GCCGAGGCAG GCAGATCATG AGGTCAGGAA TGCAAGACCA 220200

GCCTGACCAA TATGGTTTAC TAAATATCAT CTACTAAAAA TACAAAAATT AGCCAGGTGT 220260

GGTGGCAGGC ACCTGTAATC CCAGCTATTC AGGAGGCTGA GACAGGAGAA TCGCTTGAAC 220320

CCAGGAGGTG GAGGTTGCAT TGAGCCAAGA TCATGCCACT GCACTCCAGC CTGGGCGACA 220380

GAGTAAGACT CCGTTTCAAA AACAAAAAAC CCAAGAAATT AATATTGCTT TTATCTGGAG 220440

CCCAGAGTGA TGCAGCTTCT GGCCCTCTTA TCTGAGACAG TGTTCTTTTA GTGTGAAAAA 220500

GGATGCTAAT TTTCCCCCAA ACAACCCACA GTATCATGGG GGTAAGTTAA TGGCTGGTCT 220560

GTGTAACTGA CAAATTTTGG TGCTAACGTA TCTCTATAAC TACTCTGTAT AAACTTCCTT 220620

CCTTCAGAGT GGAGTTCTGT CCTCCCTGCC TTTTATTGCT GCTGCAAGCT GTACAATTTT 220680

AGGAGGTCAG CTGGCAGATT TCCTTTTGTC CAGGAATCTT CTCAGATTGA TCACTGTGCG 220740

AAAGCTCTTT TCATCTCTTG GTAAGGATAA GCGTGTGGGC CCATTTAACC AATCCCTTTT 220800

CTGCACATGG TCTCAGAGGG TTCCCTGACA GCATGTCCTC ATTGCCCAGG GCTCCTCCTT 220860

CCATCAATAT GTGCTGTGGC CCTGCCCTTT GTGGCCTCCA GTTACGTGAT AACCATTATT 220920

TTGCTGATAC TTATTCCTGG GACCAGTAAC CTATGTGACT CAGGGTTTAT CATCAACACC 220980

TTAGATATCG CCCCCAGGTA AGAGCTCTAC CTGTTTTTTC CCCTCCTCCA GACCCCTCCA 221040

GAGGTGTTAG ACCTCAGTGG TCGCCGTGAA ACTCTTTAAT GTTACTGACA TTGCACTAAT 221100

GGCAGAATGA CAAATAACTA CAAATATCTG TCTGTGGCCA TTTTTAGAAC AACAAATGTG 221160

GCATTTTTAG AACAACAATT TCCAATCTTG GCCAGTAATC ATTTTGACAA AAACCTTCCC 221220

AAGCTTCCCT AACAGAGATT GAACTGTGTA TGCTGGGAAA AGGCCCACAC ACAGGTGATT 221280

TGGAAAAGTT TCCATGGTGT TGTTCATATT AGCTACCACA TATATATATA TATATATATA 221340

TATATATATA TATATATATA TATATATATA TACAGTCACA ATAAGCCAGC TCCTGTGCCA 221400

AGACTTGCCA TATATCAACA CATCTAATCC TCACAGTTAT ATTAGGTAGG CCCTATTGTT 221460

ATCCCCATTT TATAAGGGAG AAGGCTGAGG CACAAGGAGG TTAAATGGTG TGACTATGGT 221520

CACATAAAGG CAGAGCCAGG ATTTGGACTG GGGGAGTCTG GCTTTGGAGT CTGTGTCCTG 221580

CCCGTTGCAC AAACTGGCTT CTACACTGAG CAGCCAGGGT AAAGAAACGT GGTTCCCAGA 221640

GAGACTGCAT TGCTCCCTGG TTATTGACTT GGTAGATTGG TAATTTCAGG TTTGGCAAAT 221700

AGACATTGCC CTGAATGTCT TTAGGTGAAT GAAAAACTGC ATTAAGCAAA ATGACTTTGC 221760

CATTAGAGCT GAATTGCATT AAAGTTGAGT TGCTGCAGAA GCTGTAGGTG GCTTTCTATA 221820

TAAAATCATT TATAAAATCA TCTTCCCATA GATATGCAAG TTTCCTCATG GAATCTCAA 221880

GGGGATTTGG GCTCATCGCA GGAATCATCT CTTCCACTGC CACTGGATTC CTCATCAGTC 221940

AGGTTGGGTC AGTTTATTGA ACATCTTCAA GTGGCAGGTA TTGTTTTAGG TGTTGGAGAT 222000

ACACACGGTG CTCTAAAGAT CTGGATGGCA ACACAATTAC TCTATTTACA TGAGCCTCTA 222060

AATCAGACTC TGGTAGGTCA GATTTCCCAG AGGAAGAAAA ATATAAGCTT ATTTTCTCAA 222120

GATGAATAGA TGTTAGATTG ATTAAAATGA GCTGTTCCGG TGCAGAAGAC AGCACGTATG 222180

ACTTCCTAGA GGTACATGAG CATGAAACAG TTCTTAGTTA TGACCAGAAT GAAAGACACA 222240

TGTCAAGGAA TAGCAAGAGA CGAAGACAGA GGGGCAAAAG AAGATCATGA AGAATATGTT 222300

CAGACTAATC CAATTTTTAA AAAATCACAA AAGGGAAACA AAGTGTCCTA GGCCAGTTTA 222360
```

```
AAGATAATTT AATGTCTGGA AACAGATCGG CTGTGAGACA TTGCAAGGAG GCTTGCTCGG   222420

TGTTTGGAAA TGCAGGCTCA TGAGGAAGAT GAAAAGACAG ACCCAGGCAG GGATGGAAGG   222480

ACTGACTAGA ACCAACTTAC AAAGAGAAGT TTTGTTTTTA CTACATTTCT ATGTGATCAA   222540

GTTCCCAGGT TAATATTTGA CTAAACTGCT AGGAATCCAC TGTGACTATA ATGCTGGAAA   222600

TGACTTAGTA GGGCTTTCTG AGGAGGGTCA CACAGAAGAC CAAAGAGAAC TCATGTTGAA   222660

TTGAGATGGG TTATAGTGAT AGTTGTCAAC AGCCAATACA GAAACAAAAA AAAACAAAAC   222720

AAACAGCAAC AACAACAACA ACAAAAAAAA AAAACAGAGA AGACACAAAC ACAATGCCAC   222780

AATGCCATTT TAGGCATAAT TTTAAATGAG TAATATTATA TGTTGAAATC CAAATTTTCA   222840

GAAAAACATT AGTGTATTTT ATTTTTGTTT AAAGAAATAA CCATCTCAAC TCAGAACCCC   222900

ATGTGCATTT TGGCCATTTT GTTCCAATA GTTTCATAAA CTTTCTTAAG TAACTACTGC   222960

ACATTGTTCC TTATATTCCT TGTGATCAAC ATTGCAATAC ACAACTGGGA GGGCTACTAG   223020

AACTGGTGTA GAAGGAACTT GTGAGATTGA TCATTTTCTC TGTTTTTTAC ATCTAGGATT   223080

TTGAGTCTGG TTGGAGGAAT GTCTTTTTCC TGTCTGCTGC AGTCAACATG TTTGGCCTGG   223140

TCTTTTACCT CACGTTTGGA CAAGCAGAAC TTCAAGACTG GCCAAAGAG AGGACCCTTA   223200

CCCGCCTCTG AGGACATAAA GTTACAAACT TAAATGTGGT ACTGAGCATG AACTTTTTAA   223260

ACATTTTTTA CTTCTCTCCA TATTCCTGAC CATAGACTCA GCAGTTCTTA ACTCTGGCTG   223320

TGTGTTAGTC TTCCCTGGGG AGCCTTTATA AGACACTGAT ACTTGGGACC CACTCCAGAG   223380

ATTCTGAATG AATTGGTCTG GGGTGGAACC CAGATACTAC TAATTTTTAG ATACTCCTTA   223440

GAGGTTTCTA GCATGCGCCC GGGGTTGACA ACAGCTGGAC AAACTTGAAA AGTCAATTCA   223500

TGTGGCCTTT GAATTTTCCT CATTGGAAAG TACTAAATAA ATAAAAATTC ATGTGAAAAT   223560

GATCACTGAT AAATATCTTC ATGGTGGGGC AGGTTATTGG ATGCAGAGAA GATCTGCTCG   223620

GAATTGTAGC CATATGTTAC AGATCTCAGC ACCGATCAGA ACTGTAAAGC TATAATCCCC   223680

AGAATTAAAG TTTTTATTAT TTTTTATACA TTGTAAAACA TAGACGTTTA TTTATGTGAT   223740

TAAATTCTAT TAAAATTTAC ATGCTAAAAT AAAATAGACC ATTTTCAAAT TATTTAGATC   223800

CAGATATTTC CATCAGATTA AACAGATATT TATTTATCCT AGCCCAATTG CAAGAGATTA   223860

ATGATGAGAA AATGACCAAT ACAAGATTAA ATAAATGAGG TTAACTTAGA AATCAAGGAC   223920

AGAGAAGATA GAACTGGAAA GCTTGTATTG TGAGAAGAAT GAATGTGAAG GAAGGCAATG   223980

TAGACACTTC CAGAAGGGAT AGCAATATAG TTTAGACCAT ATAATGAAAA TTGGAGAGAG   224040

ATGACAGAGA CACTTTCAAG TGAAATGACA ATTTATATGG GGGAGAAAAA TATTGAAGAC   224100

ATAACAAGAT GAGAAAAGGC ATAGAAATGT ATCACATACA AGGCATAGAA GTGTATCACA   224160

TACAAGAGAA GTTCCTTTTG AGCGTAGAAA AAGATAATTT AACCTTCTTC ATATTTTTCT   224220

TACTTTCCCA AGATACTCAG ATAGGCAGCG TCAACTCTAA CAGGAATTAA TTTGGCTCCT   224280

AACACTTAAG ACATATCCTT TAGTTTGTCT CCTCACACAG AACTGATTCT GGTTTTGCCA   224340

CAACATGTCT AGAGAAGAAG TTCCCACCAT ATTTTAAATC CTATTAAAAA ACTGCTTGGA   224400

CAAGAACCTT GGGCTAATTC AGCAGATGAA GAGAATCTCC TAATGCAAAT CAATGGGTAT   224460

TTTTGAGCAA GTTTTTCAGA AAAACAGAGT GTCAGGCCCT GAGGGTGGTA CTAAGATGAG   224520

AACATTGATT TTGCCTTCAT GATATTGACA ACACAAAGAG GAAAGGGGGT TTGCAGAAAA   224580

CTAAAAGAAG AAGTAGAAGA AAAAAGAAAG ACATAGTATA ATAGGTAGTC AAATTATGTA   224640

CAGAAAAAAG AGGAAAAAAA ACCAAAAAAG GGTGGGGGAC AGACAACCCA ACTAAAAAAT   224700
```

-continued

```
GGGCCAATGA CTTGAACAGG GACTTCATAA AAGAGAAAAT GTAAGTGGCT CCTTAACATA 224760

TAAAAAGATG TTCAACTTCA TTAGTCATTA CAGAAATGAA AATCAAAACT ACAATGAAAT 224820

ACCACTATAA AATTAACTAA TGGATAAAAT GAAAGGAGAT GGAAAACAAA ATGTTGCCAG 224880

ACATGTGGAG CAACTGGAAC TTTCATACGT TACGAATGTG AACTTTGGAA AGCTGCTCGG 224940

CAATATCTCC TAAAGCTAAA TGTACAATTC CAGTGACTCA GACATTTTAC TTAGAAATGC 225000

ACATATACAT CCATAAAACA TGTACAACAA TGTTCATAGG AGCACTATCT GTAATAGCCT 225060

GAACAGGAAG TTGTCTGTTA AAAAAAGAAT GAGTAAATAA ACCACGGTCT ATTTGTATAG 225120

CAATGAGAAT TAACAGACCC CAATATATAA TAGATGAATG GGTCTCATAA GCACAATATT 225180

GATTAAAGGA AGACAAAACG CACATTCTTT TAAAGGTTTA TAAAATACTT TTTAAAAACA 225240

GCTACAACCA ATCCGTCCTG TTAAAAATCA GTGAGCGATT TCCCTTGTGC AGGGATGGGG 225300

GTTGTGGCTG GATGGATGGT ACTTAAGAAG TGCTCCTGGG GTACTAGAAA TATTTTATTT 225360

CTTGACTTGG ATGTGTGTTT ACTTTGTGAA TATTGTACAT TTATGATTTG TGCACGTTTA 225420

TGAATGTAGA AAATAAAACA GAAAGCAAAT TCAAAGTATC ATCCTTTTGA GAGCTTCTGC 225480

TCTGACTTCG TTTTGACCAA TGGAGCAGTT GGGAAGGGGT CTTGGTCCTT CGGTCCTTTG 225540

CTTTTTTTTT TTTTTTTTTT TTTTAGACAG AGTCTCACTC TGTCGCCCGG GCTGGAGTGC 225600

AGTGGCTCGA TCTTAGCTCA CTGAAAGCTT TGCCTCCCGG GTTCATGCCA TTCTCCTGCC 225660

TCAGCCTCCC CAGTAGCTGG GACTACAGGC ACCTGCCACC ATGCCCGGCT AATTTTTTGT 225720

ATTTTTTAGT AGAGACGGGG TTTCACCATG TTAGCCAGGA TGGTCTCGAT CTCCTGACCT 225780

CGTGATCCGC CCACCTGAGC CTCCCAAAGT GCTGGGATTA CAGGTGTGAG CCACCGCGCC 225840

CGGCCCCTGG TCCTCTGCTT TCATGTTCTT CTTGGTCCTG TTCCTCCTCC TCTTTTGTTG 225900

GAACTTCCAG TATCAGAGCA GGAAGGAAGG CAATGGGTCA ATCGATGCTG TCAGCTTTTG 225960

GATCAAACTG CAAGTTCTCA AACAGCAAAA TTAATGAGCT CAGGCTTTGA AGAAACCATG 226020

ACCCTGAAAG CATCAGTTGC TTCCAATTGC ATCAGTTGCC ACGGGTGATA AGAACAATGA 226080

TGACTCAGAA TGCCTAGGTT TTCCCAGCAG CTTCTCTGAG GTTTTCCCAG CAGCTTCTCT 226140

GATTGATTCC TGACAGATGA CTTCGGTGTG TCAGACTTTC AGGGTATCTT TCCTTATGTG 226200

ATGGTTTGAG GAAGAGTTAC CATTCACATT CCTAATGGCT TCAGAATAGA TGCAATTGTG 226260

AACTGATAGG AAACATTTCT AATTCATCTC CCCTCCCCAT CCCTAAAGGA TTGTTTCTAA 226320

CAATAGTCAT GAAAATTAAT TCACTTTTCT CAAATAGTTT ATTGTCATCT ACCTAATGAT 226380

GAGATGACTT ACTTTTTCTC CTTGACTGTT AAATATTATG AATTATATTA ATGTATTTCT 226440

TAATGTTGAG CTTTCCCTTG AATATTCTTT TGATGTACGA CAGAATTTGA TTCACTAATA 226500

GTTTATTTAG GACTTTGGCT GATGTACTGA TATATGAGAT TGGCTCTGTA TGCATACATG 226560

TGTTTTGTGT ATCTTTTTTG TGTCTGGATA TGGAGCTTAT GCTGATTTCA AAACAAGAA 226620

AGGAGAACTT TCCTTTTTCC CCATTACTCT GAAAAGATT GACTAGAATG GAATTTTTAT 226680

AATTGCTGTT GTTATTTGAA AGCTTGAAAG CATTGGTTTG TAAAAATCAT GCAGGCTGAA 226740

AGCCATTTTG AGGAGACTTT GATAACTTTC TCAATTTCCT TCAGTTACTG GTCTTTTAAG 226800

GGGTTTTATA TTTTTCTTTG ATCAATTTTG ACCATTTATG TTATCTTGGA GGATCATCTA 226860

TTTTACACAC TATTTAAAGT ATATTTGCAA AAATTCAACT GTTTTATCAG GCTATCTTTT 226920

TAATAATATA TTCATTTTAT CTATATCTGA GGTTTTAGCT TCTTTGTACT TCTGACCCAA 226980

TTGCATGTGT GCTTTCTTTC TCCTTCATTA GACTACTTAG TCATTTACTA ATTTTAAGAA 227040

TAGCTTGTCT TTTATTTATT TACTTATTTA TTTTTGAGAC GGAGTCTCAC TCTGTCACCC 227100
```

```
AGGCTGGAGT GCAGTGGCGC GATCTCGGCT CACTGCAACC TCCGCCTCCC GGGTTCAAGT  227160
GATTCTCCTG CCTCAGACTC CCGAGTAGCT GGGATTACAG TCATGCACCA CCATGTCTGG  227220
CTAATTTCTG TATTTTTAAT AGAGATGGGG TTTTGCCATG TTGGCCAAGC TGGTCTCAAA  227280
CTCCTGACCT TAGATGATCT ACCCACCTTG GCCTCCCAAA GTGCTGGGAT TACAGGCATG  227340
AGCCACTGCG CCCAGCCCTG CTTGTCTTTT TATTTTATAT TTGATTAGCT TTATCTTTTA  227400
TCAAGCTTAT GTCCTATTTC CCTTTGCTTT ACTTCATATA AATTTTGTTT TGGATAGTTT  227460
ATTTATTTTT CATTTAATTA TGAAACAGGT TAAAGCTTAG AGGAAAATTG CTCCTCTAAG  227520
TCCACTTTTG TGGGCAGATT ACATTTTGCT GTGTTGTGCT CCCAAATTCA TTGTTCTTTT  227580
AATGCTTTAT TTCTCAAGTT AATAACCTAT ATAGTAAAAA AGTGGCTGTT GACTCTCAGC  227640
TTTTTTTTTT TTTTTTTTTT TTTTTTGTA GATACAGGGA TCTTGCTGTG TTGCTCAGGC  227700
TGGTCTGAAA CTCCTGGCTT CAAGGGATCC TCCTGCCTTG GTCTCACAAA ATGCTGGGAT  227760
GACAGACATG AGACACCATG CCCAGCCATG TCTCTCTCCT TATATATAAT AAGAAAACAG  227820
ACACACTGAG GCATCCTATC ATCTCACTCT TGGTTTCACT ACTGTTCTCT GGAAGTTTTG  227880
CTCTGACCTT TTGCAGTTAA TGTATTAATT TTGCATTGAG TAGTTTCCAT AGAAGAATTA  227940
TAGCATTTGC ATTCTGTTGG GTATTATACT TTTCACTGTT ATTTGAACAT AATTTGAGGG  228000
CTGAAACCAA GATGAGGCAA GTGAGGTGCC CAGGAAGCAA TATTTAAGGA GGCATCCTTT  228060
CTTAGGCTCA TGCAAGAACA GAATTGGCAC ATGAGAGTGA GTGCCTCCTT AATTTTGAGT  228120
GCTGGACACT TCTTGCTCAC TTAGCATACC CCTGGACAAT GAAGTGTTTT TTGTTTTGTT  228180
TTTTCATGTC CATCCTTTAT CCTTCTTCAT CTCAAAACAT TTCAATGGAG TATTTTTTG   228240
GAGCAGTACT TGGATGAGCC TCTGAGTCCC ACAGTAGCTG AGAATTTATT TCATAGTACT  228300
CTTTATGATC ACTGTGGAGC CTTAAAACAT TGTAATATTA ACTTAGCTGG GAACAGAAAT  228360
TTTGTTCCAC AATTTGTCTT ATTCAGAACA GTATTGACTT CCTGCTAGTC TCTTCTGATG  228420
TCCAATATGA GGAAGTCTAG TTAGCCAGCT ACTTTTTGTA GGAGAGCTAT GTTTAGGCTA  228480
GGTGCTATAG GATTCTCTTT ATCCTGGAAT TCCTTCACCA AGATGTGCCA AGGTGTTAAT  228540
CATTTTCTCT TGCTTTTTGG CTGGTGGTCT TAGAGTTTCC TTCGATTTTG TTTTATTTAG  228600
TGATTGTCCT CAATTTGTTT TCTTTACTAA GAATCTCTCT TCTATTTATC TGTATGGTAA  228660
AACCTTGTTG CCCATCTTTC TGGTTTCTGC TGACTTTCAT TTTTGGACCT TTTACTTTGC  228720
TTTCTCCATG GACTTTTTGG TAGTGGAGGC AGGCAAACAC TTTCCAAAGT CTTTCTCAAT  228780
TTCCATCAAT TTCAACTTAT TTCCTAAAAT TGCCTCAGAA TGTGCCTATG TCCACAATAT  228840
CCCTCCTTCC ACTTTAGAAA GGAAAGGCAT CCACACTTTA TTTAGGTGCA ATGCCTGAAG  228900
TGTAAACACT TTCTGGTTGT CAACAAAGGA GTACTTCCAA ATATTGGTTT GGGGATAACC  228960
TGCTAATGAT TAACACATTC ACCTTGGCTC TTGGTTTGCC TGCTCCCTCT TCTTTTATCT  229020
GCTGTGTGTA TTTTTTTTAA TCACTGAGAA TATGCACAGT ATTGTATGTT TTATTATAAG  229080
AGAGGACTGG CCAGAGTGGG AATGTTCTGA ATTCAGAATA ACTGAAGCAG TACAGGATAG  229140
GAACTCATTC TTTCAAATGA AGCTGGCATA TTTTCCCAGA GCACCAAATT TCAATATATA  229200
TTTAAAAAAC TTGATATGAA TGATACAATA AAGTGGTTAG AACTTTTATT AAAATAAACT  229260
TATGTCATGA AATACTTATT CTAATTATAG TCACTCTTCA TCTTATTTCA TCTTATAACA  229320
TGTTTAATGT TTTCTTTTAT TTACAAAACA ATTTATTTTT TGATGAAAAG TTTTAGAAAT  229380
CAAGTTAAAA ATATTCAAAG GAATGCCTAA AGTTTTCAAA ATTCTTTTAC ATGTTGTACA  229440
```

```
ATCAAAAGAG TCTGAAGACC ATTTAGCTAT CCAAATTGTT TATTTTTAAG CAGTATCCCT    229500

TCTAATATTT ACTATTTATA ATCCTTAAAA ATTTGCCTTA GCACAGGAGA ATTGCTTGAA    229560

CCCAGGAGAC GGAGGTTGCA GTGAGCCAAC ACAGTGCCAC TGCCCTCCAG CCTCGGCGAC    229620

AGAGTGAGAC TCTGTCTCAA AAAAAAAAAA AAAAAAAAA  AAAAAAGGCC AAAAACAAAT    229680

AAACAAACAA AAAAATCCGC CTTAACATTA TTTGTTCATT AAAAACTTTC TTTAATACTA    229740

CTAGTTTCCC TTTCCTCTCA GCCCATTGTC ATATTTTGAT TTTTATCACT TGCTTTGTAG    229800

GACATATGAG GTTTTTGTTT TTTTTTTTTT TTGGAGATGC AGTCTCCCTC TGTTGCCCGT    229860

GCTGGAGTGC AATGGCGCAA TCTTGGCTCA CTGCAACCTC TGCCTCCTGG GTTCAAGCAA    229920

TTCTCCTGCC TCAGCCTTCC AAGTAGCTGG GATTACAGGC ACCCACTACC ACGCCTGGCT    229980

AATTTTTGTA TTTCTGGTAG AGACGGGGTT TCACCATGTT GGCCAGGCTG GTCTCGAACT    230040

CCTGACCTCA AGTGATCCAC AATCCTTGGC CTCCCAAAGT GCTATGATTA CAAGCATGAG    230100

CCACCTGCCC AGCCAGAATA TATGTTCATT TTGAGTCCTT AACAAAGTC  ATAAGAATTT    230160

TAGGAATTCA GTTACTTTCT TGAGAAAATC TCTGAAAAGA TGCCAATAAT TTGTAGCCAA    230220

TTATATTGAT TTCTCTTTTT CATATTGAGA ATTGTTTTTT AAAAGTTTG  TATGTGTGAA    230280

GATTTTTGCA CTGTAGTTAA AGAAACCACC TGTGTGTTGG TTAAGCCATA AGTACATGTA    230340

TTCAAATAAA TTGAGGTGGG GTTACTCTGA GAATCAAAGG AAAACCTGAA GAAACAGGCA    230400

GCCTCAAAAG GTCTTAGCTG TAGCAACTTG CTCCATTGTT GAAATAAATA GGCTTGAACT    230460

TGTATTTTCC CTCTACTCAA CATTTAAGGT CTCAGAAGAT AATATAATTG GTGAAATTTA    230520

AGTAAAGTGC TCACTCTTTT GCTTTAACAA ACCCTAGAGA GCTGGTAGGC AGAGCCTCAA    230580

CAGACCGTTT TAGCTTCCAA AGGGAGTTCA GGACACCATG ATTCACGACC ACAATACATC    230640

ACACATAATT GAGAAAAGAT AGTTCCACCA AATAAAGTTG AAATGCTGAC AAGAAGGGGT    230700

AAGAAATCTT GGAATAGGT  TTATATAAAA TTTATTTTTT CCTTTTTTAT TGTTATGAA   230760

TAGGACCAGT TCTACTTAAG CCACCCATTT GCCAAAATAA AGTGAGAATC GTTTCTTTTG    230820

GGGACTCCTC TTTGTAGCTC CAAGTGCCAC TAACAATTCT TAGGACCTGA GCTATAAGCC    230880

AGGTGATTTC AGTTAATATG ATCAATTATT TCATTTAAAT GGCTCTAATG TGCAGAGGGA    230940

ACGGAGCCCA TCAGCATTCC CTGCAGGGAA CTGCAGTGGC TTTTATCAAC TTGAACAGCT    231000

AGCTTTCAAC TGTTTTGAAA TCACTTTCAG GGTGGTCATG TAGTTGCTTT TTTGAAATCA    231060

GAAGATGATT CTGCCTCTTT TAATATGTGA CTCCTCAGAT TCAGAAAGTG CTCGCTAGTC    231120

TTAAGAGTGA ATTACCCTCA GTGGTCCAGC GCTTATGAAC CCACATCTAA CCCTATCCCC    231180

TGGGGGAACT ATCAGAGAAA TTGGTGCCAT GGACATAAGA GGAAGGCACA GTGAAGCAGA    231240

GAGCCCCGCA TGATGAAAAT CAGTGGACAG CATCATTATT TACAACTTTG TAATCACCCA    231300

GGAGCATGAA AATCCAGGCC AATCTGGCAC CATGAGCTCT AATTTTTGTT GGAGTTCTTG    231360

GAACCGATTC TGATGAATGA CTGTTTAGCC ATTTTAGAGT GTGGCATACG TGGCTGCTGG    231420

CATACAGAGG TTGGATGTAA ACGGGCCTTT GCCCTCTCTT ATGAACATAG ACAGGAACTA    231480

AACTGTGTCA CATAGGTTCC AAATGGTGGC CTGAATACTA TTTACAACTA AGGTACAATG    231540

AAATTGAGTA AGTCTTTTCC TCTTTTGCAG ATACCATCAT TATTCATATA TTTCTTCAAA    231600

GTTAACTATT TGTATTTGGT AATTTTTAAT AGAAATGTAA TAATTGCTTC TCAAGTTTAG    231660

TCTTTAGTCT TAAGGTTGAT GCTCTCCATG TCCTTCCAAA AAAAGGTATG TTGCTTTTAT    231720

TATATCCTCG CCTTCAGATG GGATTATTCC ATTTTGTTCT TTGTTAATAT ATACTTTGAG    231780

CCACTTTTTT TGTGGCTCTG GGTGAGATGC TATAGGTACA ATGACAAGTG ATACGTGTGT    231840
```

```
TGTCCCTGTC ACAAAAGTGG ATAGCCTAAG TGGTGACTTT TACCTCCACT CCAAATATAT   231900

GTATCACACA CCAGCCGTAT GCCAGGCACC ACTCTAGGTG CTAGGGATAC AGCAGTAAAC   231960

AGACAAATGC AACCCCTGCC CATGTGAAAG AGAATAAGAC AATAAATAAG TAAAGTGCAT   232020

GTTATATGGA GGTGGCAAAT GCTAAAAAGA AAAATTAAGC AGGCAAGAGG ACTCATTGAA   232080

AAGATGACAT TTGGGTAAAA GCCCATGTAT ATATGTTCTA TTGGTTTTAT TTCTCTGGAG   232140

AGCCCTGACT AATACACAAT GACTTTGAGA AGTTACTGGC TTTTGATTTA TCACACTATT   232200

CGGAGTGCTG AGAGCCTTCT TAGTGTGTAT TCAGTGTTTT AAGAGAGCTT GTGGATGAAT   232260

AATAAATAGG ACAAAATTTA TCCAAACTTA AGCCTTGCTT TAGGTAAAAG GGCTCCTCTT   232320

ACAAGGTAGA AGGTTATTAT TTGACATTTA AATCCAACTG AAGACTAATA AGACTAATTA   232380

ATTAAAAGTT TTTAAATCAC AACTGCGTGC AAAATAAATG GAACTGCCAT GCTCGCCAAG   232440

TGTGCATGAG TGGTGTGCAT GGGAGACAGC ACGAAGCTAA TCCCACTCAT CTTGCAGGTT   232500

GCTCCATTTT TCTCCTAAAA TCAGTAAGAC AGAAGCTGGT CAGATTATCA AGAGCCCTAG   232560

TTAAACACAG CAGTAGCATT TGGAAGGGGT TGCTCTCATT AGGCAGTGCC TGACCACAAC   232620

AAGAGATGAA CAAGCCCTGT ATCTGAAGCC ATCATGCCTA GTTATGGTCC CCGACTGTTC   232680

ATGATGCCTG GAAGGGAGGC CCCCTGCACC CTAGAAAGCT GGGTGGGTTC TACTGTCTGC   232740

TTTACTGCTA AAAACCCTCT TCTTTGGATC TGGACTTTAC CTCTATCTGA TTTTTTTTTC   232800

TAATATATGA TTTGGCACTG AGTCTGTCAC TGCTGCTAAC TCAGCAGTTC TAGGGTCATT   232860

GCCCCATTGC CTCACAGAAA GAATTTCATA GCTTCCAGCA TCCTCTCTCC TTCATTATAC   232920

TTTGATTTCA GCATTGCTAT TTTTTCTCTT GGGTGTTGCA GCTCTCTCTC TCCTTCCCAT   232980

GTCTTGTTGG TTTTCTGCTA ACTCCTGCTT TTTTTCTTTT TTTTTTTTG AGACGGAGTC   233040

TCGTTCTGTC ACCCAGGCTG GAGTGCAGTG GCACAATCTC GGCTCACTGC AACCTCCGCC   233100

TCCCGGGTTC AAGCTATTCT CCTGCCTCAG CCTCCCAAGT AGCTGGGACT ACAGGCGCTC   233160

ACCACTATGC CCCACTAATT TTTGTATTTT TAGTATTGCT GTCATCAATC CACATGTCCA   233220

GAAGCACCTA GAAACTCTAA TTCTTTGTAG GTATCAAACC CTAGGACTCT TCCTCTAAT   233280

CACAATATAT AATCCCTGAT TCCCAAACAC GGTCTTTTCA TATACATTTT CCACTGTACA   233340

TACTTTCTGA CCTGGAAAGC TCTTACACAA ACACGCCCTC CCCTAGGAAG CCTTTATAAA   233400

TGTTCCCAGG AAGAATCAGT CACCCAACAG TGTCCTTGTC ACATCTTAGG TTCTACACCT   233460

TTATTTGTTC TATCTGAATG TAATCTCCCA GAGGGTGTTA TCATCTTTTT TTTTGAGATG   233520

GAGTCTTGCT TTGCTGCCCA GGCTGGAGTG CAGTGGCATG ATCTCGGCTC ACAGCAACCT   233580

CCACCTCCTG GGTTCAAGTG ATTCTCCTGC CTCAGCCTCC TGAGTAGCTG GGATTACAGA   233640

CGTGTGTCAC CACACCTGGC TAATTTTTGT ATTTTTAGTA GAGACAGGGT TTCACCGTGT   233700

TGGCAAGGCT TTCCTCGAAC TCCCAAACTC AGGTGATCCA CCCACCTCAG CCTCCCAAAG   233760

TGCTGGGATT ACAGGTGTGA GCCACCATGT CCAGCCCCAT CTTTTTCTTT TAGTTTAGTT   233820

CTTAACAAAT AGTCTGACAC AAAGTGGATA TAACAATATT TTGAATTATG AATAACTAAA   233880

TGAATATTTC CAGATTTCCT GGTGCTCTCA AAGTTTTATG TTACAAAAGA AAAACAAGTC   233940

TAAAATACCT GCCTCAAGTT TTTATCTGTA CTATGATTTC AAACCAAATA AAAAACAGGT   234000

GGGGTAAAAA CTGAAACAGG AAATACATAT AACTGAAAAA TTTTGGTATG TTAGTATGAT   234060

AATACTAGGT CATTTTTCCT GTTTCCCCAA CTTCATTTTC TATAGCAATA AAAGAAAACA   234120

AGTAAATGTA TGTTAATTTA ATTTAAAAGA AGTAGTCTAC CATCTCTTCT GTTAAAAAGA   234180
```

```
AAAAAGTATT TTAAAAAATT ATCTCTGGAA GGATACACAG GGAACATTGC TCTGGTTTCT   234240
TCCAAGAGAG AAATGAGGAA CTAGAGAGCA TGGCCAAGTG GGGTTTTGCT TTTGTTTTTG   234300
TTTGTCTATC TGTTAGCTTT TTATTATTTT CTTTTGTAGG TTTGAATTTC AAACCACATA   234360
AATCTGTTAC ATGCTCATAA TAATAAGTTT AAAATAAAAC TTTTGGCTGG GTGCAATGAC   234420
TTACACCTGT AATCCCAGCG CTTTGGGAAG CAGAGGTGGG AGGATACTTG AGGCCAGGAA   234480
TTTGAGATCA GCCTGGGCAA CATAGTGAGA CCCTGCCTCT GTAGAAATAA ACAAAAATTA   234540
GCTGGATATG GTGGTGCATG CTTGTACTCC TAGCTACTTG GGAGGTTGAG GCAGGAGGAT   234600
CCTTTGAGTC CAGGAGTTTG AGGCTGCAGT GAGCTATAAT CACCCACTGC ACTATAGCAT   234660
GGGCAATAAG GTGAGAACTT GTCTCAAAAA AAAAAGGGGG GGGGGAAACA AATAAATAAA   234720
TATAAACAAA ACTTTTGTTT CAAAATATGT AATATTTAGC ACTAAAGAAT CTGAATTGT    234780
AGAGCTAAAA AGTACTTAAA AGTTAATAAC TATTGTCTCC TTTAAAAGAA TTGTTATCAA   234840
AGTATAATTT TTATCCAGAA AATCATCCAT ATCAGCAAGC TAAACTTTCT CAAAATGACA   234900
TATCCATGTA ATTAGCTCCC AGGTAATTAG CAGGCAGCCT CTACTCAGGT TGAGTATTCC   234960
TAATCTAAAA ATTGGAAATT CAAAATGCTC CAAAATCTGC AACTTTTTGA ATGCTAACAT   235020
GATTCTCAAA GGAGTGCTCA TGGAGTATTT CAGATTTTGG ATTTTTGGAT TTGAGATACT   235080
CAGTATAATG CAAACATTCC AAATCTGAAA AAATCTGAAA TACTTCTGGT TCTAAGCATA   235140
AGGGATACTC AACGTGTGTT AGCTAATTAG ACCCTTCATG GTCTCTTCTA GACCTCAGCT   235200
TCTTCAAGGT AACCTCTATC CTCACTTCTA ATAGCATGAA CTTTTCTGTT TTAGAATAAT   235260
TTGGATTTTC AGGAAAGTTG CAAAGATAGT ACAAAGACAG TACAGGAGAG TTCCCATATA   235320
TCTTTCACCT AGCTTTCCCC CATTGTTAGG ATTTTACATT ATTATGATAC ATTTGTCAAA   235380
TATAAGCAAC TCACATTGAT ACATGAAACT CTATTAACCA AACCCTAGAC TTTATGTGGA   235440
TTTCACCACT GTTTCCACTA ATGTTTTCTT TCTGTTCCAA GGTCCAATCT GGAATACCAC   235500
ACTGCATTTT CTTGTCATAT CTCCCTAGTC TTTTTTTGTC TGTGACAATG TCTCAGTCTT   235560
TTCTTGCTTT TCATGACCTT AACAGTCCTG AAGATCATTT GCTTTTTTTT CATAATTACA   235620
CCGGAGTTAT AGATTTTTTG AAATAATACC ACAAGGGCAA AGGGCCCTTC TTGTCACATC   235680
ATTTTAGGGA GAACATGATA TCCACATGAC ATCACTGATA TTAACCTTCA TCATGTGGTT   235740
TAGGTAATGT TTCAGGTTTC TCTACTGCAA AGTGATTTTT TTCCCTTAAT TTAGCCCACC   235800
TGAACTTATC AATTTTGTTT TCTTCCATGA CTAAATACTTT TGTTATTATA GCTAAAACTT   235860
CATTGGGGCC AAATCTTAGA TCATGTAAAT TTTCTTCTAT ATTTTATTCT AAAAGCTTGT   235920
AATGTTTGAT ACATTCTAAA AGATGTAATG TTTGATACAT TACATCTAGT CCTTTGATTT   235980
ATTTTTAGTT ACTTTTGTAT AAGGTGTGAG AGATGTCTCC AGTTTCACTT TATTAACACA   236040
TTGTGGTGTT CCAGTACTAT TTGTTGCTAA GACTATCTTT TTTCCATTGA TTACCTTTGC   236100
CTTAGTTGGC AATATTTTTG TTGGTTTATT TCTAGACTGT TTATCTCATT CCACTGATTT   236160
GTGTCTATCT TTTTGACAAA ACTGTTGATT ACAGTAAGCT TTGAAATAGT TCATTTTTTG   236220
TGTCAACTTG ACTGAGTCAG GGGATAACCA GCTATCTGGT TAAACATTAT TTCTGGCTGT   236280
GTTTGTGAGC GTGTTTCTGG ATGAGATTAG CCTTTGAATA GGTGATCCTA GTAAAGTAAA   236340
CTGTCTTTCC CAGTGTGGAT GGCATTATGC CACCTGATAT TCAGGGTCTG AATAGAAGAA   236400
AAGGCAGAGG AAGGGGGAAT TTGGGCCTTT TTTTCTGCCT CACTGCTTGA GCTGGGACAT   236460
CTCATCTGGT CTCCTGCTCT TGAACTGGGA TTTACATCAT CAGTTCCTCT GGTTCTCAGG   236520
CCTTCAGATT CAGACTGAAT CATACCACCA GCTTTCCTGG GTCTCCAGCT TGCAGATTAC   236580
```

```
AGATCATGGG ACTCCTCATC TTCCATAAAT GCATGAGCCA ATTCAGTCTA TGTCCTTGAA    236640

AACTGCCCCA CTGCAGATTA AGGCTTTTTT CCACTAGGTG AAATAAAGAA GCTTGTTAGA    236700

CAGATTTCCC TTCATCCAGT GCCCTCTCCT CTTTAAGTTA CAACACATTG GCTACACCTA    236760

AGTGCAGGGG TGGGGATGAG GGTATAGTCC TCTTGTTTGC TGAGAAGAGA ACTGTATTGG    236820

GAAAGCTCTA GAAGTGTTTG ATACATACAT AAACAAGGCA TGGTTTTTGC ACTTAATTTC    236880

ACATTACATT TTTCCCAGAA AAAAGGAAT GTATAGGCAT CACGTAACTG TACTAGCTGG     236940

AGTCATTCTT CCTGATTATC AAAGGTAAAC AGTTATTAAT CCTATACCAA GATGTCAAGG    237000

AGAAGTACTT TTGGAACACA AGGAATTCTC TGGGAGTCCT TACTACTCTC AAGCCCAGTG    237060

AAAAAGTTAA TGAAAAACTA TAGTACCTTC CTATAAGCTG GATGACTAAT TACCAGGCTC    237120

ATTTAGGAAT TTGCCTTACC AAGTAAAACA TAAGGGCAGC TGAGGTGCTG ACTGAAGACA    237180

AATGGAGCAT AGAATAAGAG TAGTAAAGAA TGCCAAAAAT GCTGTCATGT ATCCATTGAC    237240

AAAAGGAGCT ATAAAGCCTT TAGGTATTTT CACACTTGCT CTGTTACGTA AATGTATGTG    237300

TGTGTGTGTG TGTGTGTGTG TGTGTG                                        237326

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 3:

CGTTAGAACG CGGCTACAAT                                                    20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 4:

GCCGATTCAT TAATGCAGGT                                                    20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 5:

CTGTAAAACG ACGGCCAGTC                                                    20

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 6:

GCAGGAAACA GCTATGACC                                                     19
```

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

GCATCAGCGA TTAACTTCTA C                                21

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 8:

TTGCATTGTG GTGAAATCAG GG                              22

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 9:

CTGAGTAATT GTTTAAGGTG C                                21

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 10:

CTGAGTAATT GTTTAAGGTG T                                21

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 11:

AGAAGAGATA GATATGGTGG                                  20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

GAATGTGACC GTCCCATGAG                                  20

(2) INFORMATION FOR SEQ ID NO: 13:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (xi) SEQUENCE DESCRIPTION: SEQ ID NO: 13:

CAACTGAATA TGCAGAAAAA AGTACACC                                      28

(2) INFORMATION FOR SEQ ID NO: 14:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO: 14:

AGTAGCTGGG ACTCACGGTG T                                             21

(2) INFORMATION FOR SEQ ID NO: 15:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO: 15:

AGTAGCTGGG ACTCACGGTG C                                             21

(2) INFORMATION FOR SEQ ID NO: 16:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO: 16:

GCGCCACCAC TCCCAGCTCA T                                             21

(2) INFORMATION FOR SEQ ID NO: 17:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO: 17:

TCACACACCG ATTGG                                                    15

(2) INFORMATION FOR SEQ ID NO: 18:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (xi) SEQUENCE DESCRIPTION: SEQ ID NO: 18:

CCAAACTGAT CTTTGA                                                   16

(2) INFORMATION FOR SEQ ID NO: 19:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 19:

TATATATATA TATA                                                          14

(2) INFORMATION FOR SEQ ID NO: 20:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 20:

AAAAAAAAAA AAAA                                                          14

(2) INFORMATION FOR SEQ ID NO: 21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 21:

AGGATGGTCT                                                               10

(2) INFORMATION FOR SEQ ID NO: 22:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 22:

TTGTTGTTGT TG                                                            12

(2) INFORMATION FOR SEQ ID NO: 23:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 23:

CTTTTTTTTT TTTT                                                          14

(2) INFORMATION FOR SEQ ID NO: 24:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 24:

AATAATAATA AT                                                            12

(2) INFORMATION FOR SEQ ID NO: 25:

-continued

```
    (i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO: 25:

TTTTTTTTTT T                                                        11

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 26:

ATATATATAT ATATATATAT                                               20
```

POLYMORPHISMS IN THE REGION OF THE HUMAN HEMOCHROMATOSIS GENE

This application is a divisional of U.S. application Ser. No. 08/852,495, filed May 7, 1997, which is a continuation-in-part of U.S. patent application Ser. No. 08/724,394, filed Oct. 1, 1996, (now U.S. Pat. No. 5,872,237, issued Feb. 16, 1999), which is a continuation-in-part of U.S. patent application Ser. No. 08/630,912, filed Apr. 4, 1996, and U.S. patent application Ser. No. 08/652,265, filed May 23, 1996, (now U.S. Pat. No. 6,025,130, issued Feb. 15, 2000), each of which is incorporated herein by reference in its entirety for all purposes.

BACKGROUND OF THE INVENTION

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses. The gene which is defective in this disease was disclosed in copending U.S. Ser. No. 08/652,265.

HH is typically inherited as a recessive trait; in the current state of knowledge, homozygotes carrying two defective copies of the gene are most frequently affected by the disease. In addition, heterozygotes for the HH gene are more susceptible to sporadic porphyria cutanea tarda and potentially other disorders (Roberts et al., *Lancet* 349:321–323 (1997). It is estimated that approximately 10–15% of individuals of Northern European descent carry one copy of the HH gene mutation and that there are about one million homozygotes in the United States. HH, thus, represents one of the most common genetic disease mutations in individuals of Northern European descent. Although ultimately HH produces debilitating symptoms, the majority of homozygotes and heterozygotes have not been diagnosed.

The need for such diagnostics is documented, for example, in Barton, J. C. et al. *Nature Medicine* 2:394–395 (1996); Finch, C. A. *West J Med* 153:323–325 (1990); McCusick, V. *Mendelian Inheritance in Man* pp. 1882–1887, 11th ed., (Johns Hopkins University Press, Baltimore (1994)); *Report of a Joint World Health Organization/Hemochromatosis Foundation/French Hemochromatosis Association Meeting on the Prevention and Control of Hemochromatosis* (1993); Edwards, C. Q. et al. *New Engl J Med* 328:1616–1620 (1993); Bacon, B. R. *New Engl J Med* 326:126–127 (1992); Balan, V. et al. *Gastroenterology* 107:453–459 (1994); Phatak, P. D. et al. *Arch Int Med* 154:769–776 (1994).

A single mutation in the HH gene, designated 24d1 in copending U.S. Ser. No. 08/630,912, gave rise to the majority of disease-causing chromosomes present in the population today. This is referred to herein as the "common" or "ancestral" or "common ancestral" mutation. These terms are used interchangeably. It appears that about 80% to 90% of all HH patients carry at least one copy of the common ancestral mutation which is closely linked to specific alleles of certain genetic markers close to this ancestral HH gene defect. These markers are, as a first approximation, in the allelic form in which they were present at the time the ancestral HH mutation occurred. See, for example, Simon, M. et al. *Am J Hum Genet* 41:89–105 (1987); Jazwinska, E. C. et al. *Am J Hum Genet* 53:242–257 (1993); Jazwinska, E. C. et al. *Am J Hum Genet* 56:428–433 (1995); Worwood, M. et al. *Brit J Hematol* 86:863–866 (1994); Summers, K. M. et al. *Am J Hum Genet* 45:41–48 (1989).

Several polymorphic markers in the HH region have been described and shown to have alleles that are associated with HH disease. These markers include the published microsatellite markers D6S258, D6S306 (Gyapay, G. et al. *Nature Genetics* 7:246–339 (1994)), D6S265 (Worwood, M. et al. *Brit J Hematol* 86:833–846 (1994)), D6S105 (Jazwinska, E. C. et al. *Am J Hum Genet* 53:242–257 (1993); Jazwinska, E. C. et al. *Am J Hum Genet* 56:428–433 (1995)), D6S1001 (Stone, C. et al. *Hum Molec Genet* 3:2043–2046 (1994)), D6S1260 (Raha-Chowdhury et al. *Hum Molec Genet* 4:1869–1874 (1995)) as well as additional microsatellite and single-nucleotide-polymorphism markers disclosed in co-pending PCT application WO 96/06583, the disclosure of which is hereby incorporated by reference in its entirety. Additionally, copending U.S. Ser. No. 08/630,912 disclosed additional markers 24d2 and 24d7.

The symptoms of HH are often similar to those of other conditions, and the severe effects of the disease often do not appear immediately. Accordingly, it would be desirable to provide a method to identify persons who may be destined to become symptomatic in order to intervene in time to prevent excessive tissue damage associated with iron overload. One reason for the lack of early diagnosis is the inadequacy of presently available diagnostic methods to ascertain which individuals are at risk, especially while such individuals are presymptomatic.

Although blood iron parameters can be used as a screening tool, a confirmed diagnosis often employs liver biopsy which is undesirably invasive, costly, and carries a risk of mortality. Thus, there is a clear need for the development of an inexpensive and noninvasive diagnostic test for detection of homozygotes and heterozygotes in order to facilitate diagnosis in symptomatic individuals, provide presymptomatic detection to guide intervention in order to prevent organ damage, and for identification of heterozygote carriers.

SUMMARY OF THE INVENTION

One aspect of the invention is an oligonucleotide comprising at least 8 to about 100 consecutive bases from the sequence of FIG. 1 or FIG. 2, or the complement of the sequence, wherein the at least 8 to about 100 consecutive bases includes at least one polymorphic site of Table 1.

Another aspect of the invention is an oligonucleotide pair selected from the sequence of FIG. 1 or FIG. 2 or its complement for amplification of a polymorphic site of Table 1.

Another aspect of the invention is an isolated nucleic acid molecule comprising about 100 consecutive bases to about 235 KB substantially identical to the sequence of FIG. 1 or FIG. 2, wherein the DNA molecule comprises at least one polymorphic site of Table 1.

Another aspect of the invention is a method to determine the presence or absence of the common hereditary hemochromatosis (HH) gene mutation in an individual comprising:
  providing DNA or RNA from the individual; and
  assessing the DNA or RNA for the presence or absence of a haplotype of Table 1,
  wherein, as a result, the absence of a haplotype of Table 1 indicates the likely absence of the HH gene mutation in the genome of the individual and the presence of the haplotype indicates the likely presence of the HH gene mutation in the genome of the individual.

Another aspect of the invention is a method to determine the presence or absence of the common hereditary hemochromatosis (HH) gene mutation in an individual comprising:

providing DNA or RNA from the individual; and assessing the DNA or RNA for the presence or absence of a genotype defined by a polymorphic allele of Table 1, wherein, as a result, the absence of a genotype defined by a polymorphic allele of Table 1 indicates the likely absence of the HH gene mutation in the genome of the individual and the presence of the genotype indicates the likely presence of the HH gene mutation in the genome of the individual.

Another aspect of the invention is a culture of lymphoblastoid cells having the designation HC14.

BRIEF DESCRIPTION OF THE DRAWINGS

FIG. 1 depicts the nucleotide sequence of approximately 235 KB in the HH subregion from an unaffected individual.

FIG. 2 depicts the nucleotide sequence of approximately 235 KB in the HH subregion from an affected individual.

DETAILED DESCRIPTION

A. Definitions

Abbreviations for the twenty naturally occurring amino acids follow conventional usage. In the polypeptide notation used herein, the left-hand direction is the amino terminal direction and the right-hand direction is the carboxyl-terminal direction, in accordance with standard usage and convention. Similarly, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA. The complement of any nucleic acid sequence of the invention is understood to be included in the definition of that sequence.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981), or by the triester method according to Matteucci, et al., *J. Am. Chem. Soc.* 103:3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning: a Laboratory Manual* (2nd ed.), Vols. 1–3, Cold Spring Harbor Laboratory, (1989) or *Current Protocols in Molecular Biology,* F. Ausubel et al., ed. Greene Publishing and Wiley-Interscience, New York (1987).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It being further understood that the sequence includes the degenerate codons of the native sequence or sequences which may be introduced to provide codon preference in a specific host cell.

The phrase "isolated" or "substantially pure" refers to nucleic acid preparations that lack at least one protein or nucleic acid normally associated with the nucleic acid in a host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "gene" as used herein is intended to refer to a nucleic acid sequence which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The term "plasmid" refers to an autonomous circular DNA molecule capable of replication in a cell, and includes both the expression and nonexpression types. Where a recombinant microorganism or cell culture is described as hosting an "expression plasmid", this includes both extra-chromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein. The terms "protein" and "polypeptide" are used interchangeably herein.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. U.S.A.* 85:2444 (1988), or by computerized implementations of these algorithms (for example, GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity, more preferably at least 95 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the protein in the presence of a heterogeneous population of proteins and other biologies. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, a Laboratory Manual,* Cold Spring Harbor Publications, New York, for a description of immunoassay formats and conditions that can be used to determine specific immunoreactivity.

As used herein, "EST" or "Expressed Sequence Tag" refers to a partial DNA or cDNA sequence of about 150 to 500, more preferably about 300, sequential nucleotides of a longer sequence obtained from a genomic or cDNA library prepared from a selected cell, cell type, tissue or tissue type, or organisms which longer sequence corresponds to an mRNA or a gene found in that library. An EST is generally DNA. One or more libraries made from a single tissue type typically provide at least 3000 different (i.e. unique) EST's and potentially the full complement of all possible EST's representing all possible cDNAs, e.g., 50,000–100,000 in an animal such as a human. (See, for example, Adams et al. *Science* 252:1651–1656 (1991)).

"Stringent" as used herein refers to hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

B. Polymorphic Markers

The invention provides 397 new polymorphic sites in the region of the HH gene. These polymorphisms are listed in Table 1. As described below, these polymorphisms were identified by comparison of the DNA sequence of an affected individual homozygous for the common ancestral HH mutation with that of an unaffected individual disclosed in copending U.S. Ser. No. 08/724,394.

These polymorphisms provide surrogate markers for use in diagnostic assays to detect the likely presence of the mutations 24d1 and/or 24d2, in preferably 24d1, in homozygotes or heterozygotes. Thus, for example, DNA or RNA from an individual is assessed for the presence or absence of a genotype defined by a polymorphic allele of Table 1, wherein, as a result, the absence of a genotype defined by a polymorphic allele of Table 1 indicates the likely absence of the HH gene mutation in the genome of the individual and the presence of the genotype indicates the likely presence of the HH gene mutation in the genome of the individual.

These markers may be used singly, in combination with each other, or with other polymorphic markers (such as those disclosed in co-pending PCT application WO 96/06583) in diagnostic assays for the likely presence of the HH gene mutation in an individual. For example, any of the markers defined by the polymorphic sites of Table 1 can be used in diagnostic assays in combination with 24d1 or 24d2, or at least one of polymorphisms HHP-1, HHP-19, or HHP-29, or microsatellite repeat alleles 19D9:205; 18B4:235; 1A2:239; 1E4:271; 24E2:245; 2B8:206; 3321-1:98; 4073-1:182; 4440-1:180; 4440-2:139; 731-1:177; 5091-1:148; 3216-1:221; 4072-2:170; 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, D6S258:199, D6S265:122, D6S105:124; D6S306:238; D6S464:206; and D6S1001:180.

Table 2 lists the frequency of about 100 of the alleles defined by the polymorphic sites of the invention in the general population. As is evident from the Table, certain of these alleles are present rarely in the general population. These polymorphisms are thus preferred as surrogate markers in diagnostic assays for the presence of a mutant HH allele ("gene mutation") such as 24d1 or 24d2. Preferably, the frequency of the polymorphic allele used in the diagnostic assay in the general population is less than about 50%, more preferably less than about 25%, and most preferably less than about 5%. Thus, of the genotypes defined by the alleles listed in Table II, polymorphisms occurring at base 35983 and base 61465 of FIG. 1 are preferred.

It will be understood by those of skill in the art that because they were identified in an ancestral HH homozygote, the haplotypes defined by the polymorphic sites of Table 1 are predictive of the likely presence of the HH gene mutation 24d1. Thus, for example, the likelihood of any affected individual having at least two or more of any of the polymorphic alleles defined by Table 1 is greater than that for any unaffected individual. Similarly, the likelihood of any affected individual having at least three or more of any of the polymorphic alleles defined by Table 1 is greater than that for any unaffected individual.

Thus, for example, in a diagnostic assay for the likely presence of the HH gene mutation in the genome of the individual, DNA or RNA from the individual is assessed for the presence or absence of a haplotype of Table 1, wherein, as a result, the absence of a haplotype of Table 1 indicates the likely absence of the HH gene mutation in the genome of the individual and the presence of the haplotype indicates the likely presence of the HH gene mutation in the genome of the individual.

The markers defined by the polymorphic sites of Table 1 are additionally useful as markers for genetic analysis of the inheritance of certain HH alleles and other genes which occur within the chromosomal region corresponding to the sequence of FIG. 1 which include, for example, those disclosed in copending U.S. Ser. No. 08/724,394.

As the entire nucleotide sequence of the region is provided in FIG. 1, it will be evident to those of ordinary skill in the art which sequences to use as primers or probes for detecting each polymorphism of interest. Thus, in some embodiments of the invention, the nucleotide sequences of the invention include at least one oligonucleotide pair selected from the sequence of FIG. 1 or FIG. 2 or its complement for amplification of a polymorphic site of Table 1. Furthermore, in some embodiments of the invention a preferred hybridization probe is an oligonucleotide comprising at least 8 to about 100 consecutive bases from the sequence of FIG. 1 or FIG. 2, or the complement of the sequence, wherein the at least 8 to about 100 consecutive bases includes at least one polymorphic site of Table 1. In some embodiments the polymorphic site is at base 35983 or base 61465 of FIG. 1.

It will also be appreciated that the nucleic acid sequences of the invention include isolated nucleic acid molecules comprising about 100 consecutive bases to about 235 KB substantially identical to the sequence of FIG. 1 or FIG. 2, wherein the DNA molecule comprises at least one polymorphic site of Table 1. Such isolated DNA sequences are useful as primers, probes, or as the component of a kit in diagnostic assays for detecting the likely presence of the HH gene mutation in an individual.

C. Nucleic Acid Based Screening

Individuals carrying polymorphic alleles of the invention may be detected at either the DNA, the RNA, or the protein level using a variety of techniques that are well known in the art. The genomic DNA used for the diagnosis may be obtained from body cells, such as those present in peripheral blood, urine, saliva, bucca, surgical specimen, and autopsy specimens. The DNA may be used directly or may be amplified enzymatically in vitro through use of PCR (Saiki et al. *Science* 239:487–491 (1988)) or other in vitro amplification methods such as the ligase chain reaction (LCR) (Wu and Wallace *Genomics* 4:560–569 (1989)), strand displacement amplification (SDA) (Walker et al. *Proc. Natl. Acad. Sci. U.S.A.* 89:392–396 (1992)), self-sustained sequence replication (3SR) (Fahy et al. *PCR Methods Appl.* 1:25–33 (1992)), prior to mutation analysis. The methodology for preparing nucleic acids in a form that is suitable for mutation detection is well known in the art.

The detection of polymorphisms in specific DNA sequences, such as in the region of the HH gene, can be accomplished by a variety of methods including, but not limited to, restriction-fragment-length-polymorphism detection based on allele-specific restriction-endonuclease cleavage (Kan and Dozy *Lancet* ii:910–912 (1978)), hybridization with allele-specific oligonucleotide probes (Wallace et al. *Nucl Acids Res* 6:3543–3557 (1978)), including immobilized oligonucleotides (Saiki et al. *Proc. Natl. Acad. Sci. U.S.A.* 86:6230–6234 (1989)) or oligonucleotide arrays (Maskos and Southern *Nucl Acids Res* 21:2269–2270 (1993)), allele-specific PCR (Newton et al. *Nucl Acids Res* 17:2503–2516 (1989)), mismatch-repair detection (MRD)

(Faham and Cox *Genome Res* 5:474–482 (1995)), binding of MutS protein (Wagner et al. *Nucl Acids Res* 23:3944–3948 (1995), denaturing-gradient gel electrophoresis (DGGE) (Fisher and Lerman et al. *Proc. Natl. Acad. Sci. U.S.A.* 80:1579–1583 (1983)), single-strand-conformation-polymorphism detection (Orita et al. *Genomics* 5:874–879 (1983)), RNAase cleavage at mismatched base-pairs (Myers et al. *Science* 230:1242 (1985)), chemical (Cotton et al. *Proc. Natl. Acad. Sci. U.S.A.* 85:4397–4401 (1988)) or enzymatic (Youil et al. *Proc. Natl. Acad. Sci. U.S.A.* 92:87–91 (1995)) cleavage of heteroduplex DNA, methods based on allele specific primer extension (Syvänen et al. *Genomics* 8:684–692 (1990)), genetic bit analysis (GBA) (Nikiforov et al. *Nucl Acids Res* 22:4167–4175 (1994)), the oligonucleotide-ligation assay (OLA) (Landegren et al. *Science* 241:1077 (1988)), the allele-specific ligation chain reaction (LCR) (Barrany *Proc. Natl. Acad. Sci. U.S.A.* 88:189–193 (1991)), gap-LCR (Abravaya et al. *Nucl Acids Res* 23:675–682 (1995)), radioactive and/or fluorescent DNA sequencing using standard procedures well known in the art, and peptide nucleic acid (PNA) assays (Orum et al., *Nucl. Acids Res.* 21:5332–5356 (1993); Thiede et al., *Nucl. Acids Res.* 24:983–984 (1996)).

In addition to the genotypes defined by the polymorphisms of the invention, as described in co-pending PCT application WO 96/35802 published Nov. 14, 1996, genotypes characterized by the presence of the alleles 19D9:205; 18B4:235; 1A2:239; 1E4:271; 24E2:245; 2B8:206; 3321-1:98 (denoted 3321-1:197 therein); 4073-1:182; 4440-1:180; 4440-2:139; 731-1:177; 5091-1:148; 3216-1:221; 4072-2:170 (denoted 4072-2:148 therein); 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, alleles D6S258:199, D6S265:122, D6S105:124, D6S306:238, D6S464:206; and D6S1001:180, and/or alleles associates with the HHP-1, the HHP-19 or HHP-29 single base-pair polymorphisms can also be used to assist in the identification of an individual whose genome contains 24d1 and/or 24d2. For example, the assessing step can be performed by a process which comprises subjecting the DNA or RNA to amplification using oligonucleotide primers flanking a polymorphism of Table 1, and oligonucleotides flanking 24d1 and/or 24d2, oligonucleotide primers flanking at least one of the base-pair polymorphisms HHP-1, HHP-19, and HHP-29, oligonucleotide primers flanking at least one of the microsatellite repeat alleles, or oligonucleotide primers for any combination of polymorphisms or microsatellite repeat alleles thereof.

Oligonucleotides useful in diagnostic assays are typically at least 8 consecutive nucleotides in length, and may range upwards of 18 nucleotides in length to greater than 100 or more consecutive nucleotides. Such oligonucleotides can be derived from either the genomic DNA of FIG. 1 or 2, or cDNA sequences derived therefrom, or may be synthesized.

Additionally, the proteins encoded by such cDNAs are useful in the generation of antibodies for analysis of gene expression and in diagnostic assays, and in the purification of related proteins.

D. General Methods

The nucleic acid compositions of this invention, whether RNA, cDNA, genomic DNA, or a hybrid of the various combinations, may be isolated from natural sources, including cloned DNA, or may be synthesized in vitro. The nucleic acids claimed may be present in transformed or transfected whole cells, in a transformed or transfected cell lysate, or in a partially purified or substantially pure form.

Techniques for nucleic acid manipulation of the nucleic acid sequences of the invention such as subcloning nucleic acid sequences encoding polypeptides into expression vectors, labeling probes, DNA hybridization, and the like are described generally in Sambrook et al., *Molecular Cloning—a Laboratory Manual* (2nd Ed.), Vol. 1–3, Cold Spring Harbor Laboratory, Cold Spring Harbor, N.Y., (1989), which is incorporated herein by reference. This manual is hereinafter referred to as "Sambrook et al."

There are various methods of isolating the nucleic acid sequences of the invention. For example, DNA is isolated from a genomic or cDNA library using labeled oligonucleotide probes having sequences complementary to the sequences disclosed herein. Such probes can be used directly in hybridization assays. Alternatively probes can be designed for use in amplification techniques such as PCR.

To prepare a cDNA library, mRNA is isolated from tissue such as heart or pancreas, preferably a tissue wherein expression of the gene or gene family is likely to occur. cDNA is prepared from the mRNA and ligated into a recombinant vector. The vector is transfected into a recombinant host for propagation, screening and cloning. Methods for making and screening cDNA libraries are well known. See Gubler, U. and Hoffman, B. J. *Gene* 25:263–269 (1983) and Sambrook et al.

For a genomic library, for example, the DNA is extracted from tissue and either mechanically sheared or enzymatically digested to yield fragments of about 12–20 KB. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton and Davis, *Science* 196:180–182 (1977). Colony hybridization is carried out as generally described in M. Grunstein et al. *Proc. Natl. Acad. Sci. USA.* 72:3961–3965 (1975).

DNA of interest is identified in either cDNA or genomic libraries by its ability to hybridize with nucleic acid probes, for example on Southern blots, and these DNA regions are isolated by standard methods familiar to those of skill in the art. See Sambrook, et al.

In PCR techniques, oligonucleotide primers complementary to the two 3' borders of the DNA region to be amplified are synthesized. The polymerase chain reaction is then carried out using the two primers. See *PCR Protocols: a Guide to Methods and Applications* (Innis, M, Gelfand, D., Sninsky, J. and White, T., eds.), Academic Press, San Diego (1990). Primers can be selected to amplify the entire regions encoding a full-length sequence of interest or to amplify smaller DNA segments as desired.

PCR can be used in a variety of protocols to isolate cDNA's encoding a sequence of interest. In these protocols, appropriate primers and probes for amplifying DNA encoding a sequence of interest are generated from analysis of the DNA sequences listed herein. Once such regions are PCR-amplified, they can be sequenced and oligonucleotide probes can be prepared from sequence obtained.

Oligonucleotides for use as primers or probes are chemically synthesized according to the solid phase phosphoramidite triester method first described by Beaucage, S. L. and Carruthers, M. H., *Tetrahedron Lett.*, 22(20):1859–1862 (1981) using an automated synthesizer, as described in Needham-VanDevanter, D. R., et al., *Nucleic Acids Res.* 12:6159–6168 (1984). Purification of oligonucleotides is by either native acrylamide gel electrophoresis or by anion-exchange HPLC as described in Pearson, J. D. and Regnier, F. E., *J. Chrom.*, 255:137–149 (1983). The sequence of the synthetic oligonucleotide can be verified using the chemical degradation method of Maxam, A. M. and Gilbert, W., in Grossman, L. and Moldave, D., eds. Academic Press, New York, *Methods in Enzymology* 65:499–560 (1980).

E. Expression

Once DNA encoding a sequence of interest is isolated and cloned, one can express the encoded proteins in a variety of recombinantly engineered cells. It is expected that those of skill in the art are knowledgeable in the numerous expression systems available for expression of DNA encoding a sequence of interest. No attempt to describe in detail the various methods known for the expression of proteins in prokaryotes or eukaryotes is made here.

In brief summary, the expression of natural or synthetic nucleic acids encoding a sequence of interest will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence of interest. To obtain high level expression of a cloned gene, it is desirable to construct expression plasmids which contain, at the minimum, a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Sambrook et al. Examples of expression of ATP-sensitive potassium channel proteins in both prokaryotic and eukaryotic systems are described below.

1. Expression in Prokaryotes

A variety of procaryotic expression systems may be used to express the proteins of the invention. Examples include *E. coli, Bacillus, Streptomyces,* and the like.

It is preferred to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., *J. Bacteriol.* 158:1018–1024 (1984) and the leftward promoter of phage lambda (Pλ) as described by Herskowitz, I. and Hagen, D., *Ann. Rev. Genet.* 14:399–445 (1980). The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli.*

To enhance proper folding of the expressed recombinant protein, during purification from *E. coli*, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503.

Detection of the expressed antigen is achieved by methods known in the art as radioimmunoassay, or Western blotting techniques or immunoprecipitation. Purification from *E. coli* can be achieved following procedures such as those described in U.S. Pat. No. 4,511,503.

2. Expression in Eukaryotes

A variety of eukaryotic expression systems such as yeast, insect cell lines, bird, fish, and mammalian cells, are known to those of skill in the art. As explained briefly below, a sequence of interest may be expressed in these eukaryotic systems.

Synthesis of heterologous proteins in yeast is well known. *Methods in Yeast Genetics,* Sherman, F., et al., Cold Spring Harbor Laboratory, (1982) is a well recognized work describing the various methods available to produce the protein in yeast.

Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8:17–24 (1979); Broach, et al., *Gene* 8:121–133 (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, *Nature* (London) 275:104–109 (1978); and Hinnen, a., et al., *Proc. Natl. Acad. Sci. U.S.A.* 75:1929–1933 (1978). The second procedure does not involve removal of the cell wall. Instead the cells are treated with lithium chloride or acetate and PEG and put on selective plates (Ito, H., et al., *J. Bact.* 153:163–168 (1983)).

The proteins of the invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding the proteins of the invention can also be ligated to various expression vectors for use in transforming cell cultures of, for instance, mammalian, insect, bird or fish origin. Illustrative of cell cultures useful for the production of the polypeptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk promoter or pgk (phosphoglycerate kinase) promoter), an enhancer (Queen et al. *Immunol. Rev.* 89:49 (1986)), and necessary processing information sites, such as ribosome binding sites, RNA splice sites, polyadenylation sites (e.g., an SV40 large T Ag poly a addition site), and transcriptional terminator sequences. Other animal cells useful for production of ATP-sensitive potassium channel proteins are available, for instance, from the American Type Culture Collection Catalogue of Cell Lines and Hybridomas (7th edition, (1992)).

Appropriate vectors for expressing the proteins of the invention in insect cells are usually derived from the SF9 baculovirus. Suitable insect cell lines include mosquito larvae, silkworm, armyworm, moth and Drosophila cell lines such as a Schneider cell line (See Schneider *J. Embryol. Exp. Morphol.* 27:353–365 (1987).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., *J. Virol.* 45: 773–781 (1983)).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. *Biochemical Methods in Cell Culture and Virology,* Kuchler, R. J., Dowden, Hutchinson and Ross, Inc., (1977). The expressed polypeptides are isolated from cells grown as suspensions or as monolayers. The latter are recovered by well known mechanical, chemical or enzymatic means.

D. Purification

The proteins produced by recombinant DNA technology may be purified by standard techniques well known to those of skill in the art. Recombinantly produced proteins can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired polypeptide.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice,* Springer-Verlag: New York (1982), incorporated herein by reference. For example, antibodies may be raised to the proteins of the invention as described herein. Cell membranes are isolated from a cell line expressing the recombinant protein, the protein is extracted from the membranes and immunoprecipitated. The proteins may then be further purified by standard protein chemistry techniques as described above.

F. Antibodies

As mentioned above, antibodies can also be used for the screening of polypeptide products encoded by the polymorphic nucleic acids of the invention. In addition, antibodies are useful in a variety of other contexts in accordance with the present invention. Such antibodies can be utilized for the diagnosis of HH and, in certain applications, targeting of affected tissues.

Thus, in accordance with another aspect of the present invention a kit is provided that is suitable for use in screening and assaying for the presence of polypeptide products encoded by the polymorphic nucleic acids of the invention by an immunoassay through use of an antibody which specifically binds to polypeptide products encoded by the polymorphic nucleic acids of the invention in combination with a reagent for detecting the binding of the antibody to the gene product.

Once hybridoma cell lines are prepared, monoclonal antibodies can be made through conventional techniques of priming mice with pristane and interperitoneally injecting such mice with the hybrid cells to enable harvesting of the monoclonal antibodies from ascites fluid.

In connection with synthetic and semi-synthetic antibodies, such terms are intended to cover antibody fragments, isotype switched antibodies, humanized antibodies (mouse-human, human-mouse, and the like), hybrids, antibodies having plural specificities, fully synthetic antibody-like molecules, and the like.

This invention also embraces diagnostic kits for detecting DNA or RNA comprising a polymorphism of Table 1 in tissue or blood samples which comprise nucleic acid probes as described herein and instructional material. The kit may also contain additional components such as labeled compounds, as described herein, for identification of duplexed nucleic acids.

The following examples are provided to illustrate the invention but not to limit its scope. Other variants of the invention will be readily apparent to one of ordinary skill in the art and are encompassed by the appended claims.

EXPERIMENTAL EXAMPLES

I. Sequencing of 235 KB from a Homozygous Ancestral (Affected) Individual

In these studies the entire genomic sequence was determined from an HH affected individual for a region corresponding to a 235,033 bp region surrounding the HH gene between the flanking markers D6S2238 and D6S2241. The sequence was derived from a human lymphoblastoid cell line, HC14, that is homozygous for the ancestral HH mutation and region. The sequence from the ancestral chromosome (FIG. 2) was compared to the sequence of the region in an unaffected individual disclosed in copending U.S. Ser. No. 08/724,394 (a portion of which is provided in FIG. 1) to identify polymorphic sites. A subset of the polymorphic alleles so defined were further studied to determine their frequency in a collection of random individuals.

A. Cosmid Library Screening

The strategy and methodology for sequencing the genomic DNA for the affected individual was essentially as described in copending U.S. Ser. No. 08/724,394, hereby incorporated by reference in its entirety. Basically, a cosmid library was constructed using high molecular weight DNA from HC14 cells. The library was constructed in the supercos vector (Stratagene, La Jolla, Calif.). Colonies were replicated onto Biotrans nylon filters (ICN) using standard techniques. Probes from genomic subclones used in the generation of the sequence of the unaffected sequence disclosed in Ser. No. 08/724,394 were isolated by gel electrophoresis and electroporation. Subclones were chosen at a spacing of approximately 20 KB throughout the 235 KB region. The DNA was labeled by incorporation of 32P dCTP by the random primer labeling approach. Positively hybridizing clones were isolated to purity by a secondary screening step. Cosmid insert ends were sequenced to determine whether full coverage had been obtained, and which clones formed a minimal path of cosmids through the 235 KB region.

B. Sample Sequencing

A minimal set of cosmid clones chosen to cover the 235 KB region were prepped with the Qiagen Maxi-Prep system. Ten micrograms of DNA from each cosmid preparation were sonicated in a Heat Systems Sonicator XL and end-repaired with Klenow (USB) and T4 polymerase (USB). The sheared fragments were size selected between three to four kilobases on a 0.7% agarose gel and then ligated to BstXI linkers (Invitrogen). The ligations were gel purified on a 0.7% agarose gel and cloned into a pSP72 derivative plasmid vector. The resulting plasmids were transformed into electrocompetent DH5a cells and plated on LB-carbenicillin plates. A sufficient number of colonies was picked to achieve 15-fold clone coverage. The appropriate number of colonies was calculated by the following equation to generate a single-fold sequence coverage: Number of colonies=size of bacterial clone (in KB)/average sequence read length (0.4 KB). These colonies were prepped in the 96-well Qiagen REAL, and the 5' to 3' DNA Prep Kit, and AGCT end-sequenced with oligo MAP1 using standard ABI Dye Terminator protocols. MAP1 was CGTTAGAACGCGGCTACAAT.

C. Genomic Sequencing

The MAP1 sequences from the cosmid clones HC182, HC187, HC189, HC195, HC199, HC200, HC201, HC206, HC207, and HC212 were assembled into contigs with the Staden package (available from Roger Staden, MRC). A minimal set of 3 KB clones was selected for sequencing with oligo labeled MAP2 that sits on the opposite end of the plasmid vector. The sequence of MAP2 was GCCGATTCATTAATGCAGGT. The MAP2 sequences were entered into the Staden database in conjunction with the MAP1 sequences to generate a tiling path of 3 KB clones across the region. The plasmid 3 KB libraries were concurrently transformed in 96 well format into pox38UR (available from C. Martin, Lawrence Berkeley Laboratories). The transformants were subsequently mated with JGM (Strathman et al. *P.N.A.S.* 88:1247–1250 (1991) in 96 well format. All matings of the 3 KB clones within the tiling path were streaked on LB-carbenicillin-kanamycin plates and a random selection of 12 colonies per 3 KB clone was prepped in the AGCT system. The oligos-21: CTGTAAAACGACGGCCAGTC, and REV: GCAGGAAACAGCTATGACC were used to sequence off both ends of the transposon. Each 3 KB clone was assembled in conjunction with the end sequence information from all cosmid clones in the region.

In some regions, the coverage of the genomic sequence by cosmids was incomplete. Any gaps in the sequence were filled by using standard PCR techniques to amplify genomic DNA in those regions and standard ABI dye terminator chemistry to sequence the amplification products.

D. Identification of Polymorphic Sites

The assembled sequence of the cosmid clones in connection with the PCR amplified genomic DNA (FIG. 2) was compared to the genomic sequence of the unaffected individual (FIG. 1) using the FASTA algorithm. Numeric values were assigned to the sequenced regions of 1 to 235,303, wherein base 1 refers to the first C in the CA repeat of D6S2238 and base 235,303 is the last T in the GT repeat of D6S2241 of the unaffected sequence (FIG. 1). Table 1 lists the differences between the two compared sequences. Note that previously disclosed (Feder et al., *Nature Genetics* 13:399–408 (1996)) polymorphic sites D6S2238 (base 1), D6S2241 (base 235,032), 24d1 (base 41316), and D6S2239 (base 84841) are not included in the list of new polymorphisms, although they are provided for reference in a footnote to the Table and were observed in the ancestral sequence. In the Table, a single base change such as C-T refers to a C in the unaffected sequence at the indicated base position that occurred as a T in the corresponding position in the affected sequence. Similarly, an insertion of one or more bases, such as TTT in the affected sequence, is represented as "TTT INS" between the indicated bases of the unaffected sequence. A deletion of one or more bases occurring in the affected sequence, such as AAA DEL, is represented as the deletion of the indicated bases in the unaffected sequence.

II. Characterization of Rare Polymorphisms

In this study about 100 of the polymorphisms of Table 1 were arbitrarily chosen for further characterization. Allele frequencies in the general population were estimated by OLA analysis using a population of random DNAs (the "CEPH" collection, J. Dausset et al., *Genomics* 6(3): 575–577 (1990)). These results are provided in Table 2.

One single base pair difference, occurring at base 35983 and designated C182.1G7T/C (an A to G change on the opposite strand) was present in the ancestral chromosome and rare in the random DNAs. This change occurred in a noncoding region of the hemochromatosis gene near exon 7 approximately 5.3 KB from the 24d1 (Cys282Tyr) mutation. OLA was used to genotype 90 hemochromatosis patients for the C182.1G7T/C base pair change. The frequency for C occurring at this position in the patients was 79.4% as compared to 5% in the random DNAs. Eighty-five of the 90 patients assayed contained identical 24d1 and C182.1G7T/C genotypes. Four of the remaining 5 patients were homozygous at 24d1 and heterozygous at C182.1G7T/C; one was heterozygous at 24d1 and homozygous at C182.1G7T/C. The primers used for this analysis were as follows.

PCR primers for detection:

182.1G7.F 5'-GCATCAGCGATTAACTTCTAC-3'
182.1G7.R 5'-TTGCATTGTGGTGAAATCAGGG-3'

For the detection assay, the biotinylated primers used were as follows.

182.1G7.C 5' (b)CTGAGTAATTGTTTAAGGTGC-3'
182.1G7.T 5' (b)CTGAGTAATTGTTTAAGGTGT-3'

The phosphorylated digoxigenin-labeled primer used was:

182.1G7.D 5' (p)AGAAGAGATAGATATGGTGG-3'

A further rare single base pair change was detected at 61,465 bp. The inheritance pattern of this polymorphism, C195.1H5C/T (a G to A change on the opposite strand), is identical to that of 24d1. The frequency of T occurring at that position (C195.1H5T) observed in a set of 76 patients was 78.5% as compared to 5% in random individuals.

PCR primers for detection:

1951H5.3F 5'-GAATGTGACCGTCCCATGAG-3'
1951H5.3R
 5'-CAACTGAATATGCAGAAAAAAGTACACC-3'

For the detection assay, the biotinylated primers used were:

1951H5.3.4 5' (b) AGTAGCTGGGACTCACGGTGT-3'
1957H5.3.5 5' (b) AGTAGCTGGGACTCACGGTGC-3'

The phosphorylated digoxigenin-labeled primer used was:

1951H5.3.6 5' (p)GCGCCACCACTCCCAGCTCAT-3'

These rare alleles are thus preferred surrogate markers for 24d1 and are especially useful in screening assays for the likely presence of 24d1 and/or 24d2.

All publications, patents, and patent applications cited herein are hereby incorporated by reference in their entirety.

TABLE 1

Polymorphic Sites in the HH Region*

| BASE LOCATION | DIFFERENCE |
|---|---|
| 35–36 | AC DEL |
| 841 | T-C |
| 2662–2663 | TT DEL |
| 3767 | T-C |
| 3829 | C-G |
| 4925–4928 | TAAA DEL |
| 5691 | C-T |
| 5839 | T-C |
| 6011 | G-A |
| 6047 | C-G |
| 6231 | G-A |
| 6643 | A DEL |
| 6698 | T-C |
| 7186 | T-C |
| 7273 | G-A |
| 7545–7558 | TCACACACCGATTGG DEL |
| 7672 | G DEL |
| 7933 | T-C |
| 8746 | T-G |
| 9115 | G-A |
| 9823 | G-A |
| 10027 | G-A |
| 10214 | C-T |
| 10828 | A-G |
| 10918 | C-G |
| 10955 | A-G |
| 11524 | C-A |
| 11674 | A-G |
| 11955 | T-C |
| 12173–12175 | TTT DEL |
| 13304 | G-A |
| 13455 | G-A |
| 14416–14417 | A INS |
| 14998 | C-T |
| 15564 | T-C |
| 15887 | A-G |
| 15904–15919 | CCAAACTGATCTTTGA DEL |
| 16019 | T DEL |
| 16211 | A-T |
| 17461 | A-G |
| 19755 | G-A |
| 19949 | C-T |
| 20085 | C-T |
| 20366–20367 | A INS |
| 20463 | C-A |
| 20841 | A-T |
| 21059 | A-T |
| 21117 | A-G |
| 21837 | A-C |
| 22293 | A-C |
| 22786 | C-A |
| 23009 | G-A |
| 24143 | T-A |
| 26175 | G-C |
| 26667 | C-A |
| 26994 | T-C |
| 27838 | G-T |
| 27861 | T DEL |
| 28132 | G-A |
| 29100 | G-A |
| 29454–29457 | TTTT DEL |
| 29787 | T-G |
| 29825 | A-C |
| 30009 | T-C |
| 30177 | A-G |
| 30400 | A-G |
| 31059 | T-A |
| 31280 | C-T |
| 31749 | C-T |
| 32040 | C-G |
| 32556–32559 | TGTG DEL |
| 33017 | T-G |
| 33026 | T DEL |
| 34434 | C-T |
| 35179 | A-C |
| 35695 | G-A |
| 35702 | G-A |
| 35983 | A-G |
| 37411 | A-G |
| 38526 | C-T |
| 40431 | C-A |
| 42054–42055 | TT DEL |
| 43783–43784 | TTTT INS |
| 45120 | C DEL |
| 45567 | A-C |
| 46601 | A-T |
| 47255 | C-G |
| 47758 | C-A |
| 47994 | G-C |
| 48440 | G-A |
| 48650 | T-G |
| 48680 | A-G |
| 50240 | C-T |
| 50553 | G-A |
| 50586 | G-T |
| 51322 | G-C |
| 51747 | A-G |
| 52474 | C-G |
| 52733 | C-A |
| 52875 | G-A |
| 53631–53637 | TTTTTTT DEL |
| 53707 | G-A |
| 54819 | A-G |
| 55913 | T-C |
| 56225 | A-C |
| 56510 | T-C |
| 56566 | G-A |
| 56618 | A-T |
| 57815 | A-G |
| 58011 | T DEL |
| 58247–58248 | T INS |
| 58926 | C-G |
| 59406 | C-G |
| 59422 | G-C |
| 60221–60222 | A INS |
| 60656–60657 | CA DEL |
| 61162 | G-A |
| 61465 | G-A |
| 61607 | A DEL |
| 61653 | T-C |
| 61794–61795 | T INS |
| 62061 | G-C |
| 62362 | T-G |
| 62732 | C-G |
| 63364 | G-A |
| 63430–63431 | GT INS |
| 63754 | C-T |
| 63785 | A-C |
| 63870–63871 | A INS |
| 64788 | A-G |
| 64962 | G-A |
| 65891 | C-T |
| 66675 | G-C |
| 67186–67187 | ATT INS |
| 67746–67747 | TT INS |
| 68259 | T-C |
| 68836 | T-C |
| 68976 | C-G |
| 72508 | T-G |
| 72688 | C-G |
| 75323–75324 | T INS |
| 75887 | G-C |
| 77519 | T-C |
| 77749 | G-A |
| 77908 | T-C |
| 78385 | C-G |
| 78592–78593 | AG INS |
| 80189 | T-G |
| 80279 | T DEL |
| 80989–80990 | A INS |

TABLE 1-continued

Polymorphic Sites in the HH Region*

| BASE LOCATION | DIFFERENCE |
|---|---|
| 81193 | T-C |
| 81273 | A DEL |
| 82166 | G-A |
| 83847 | T DEL |
| 84161–84162 | CA-GG |
| 84533 | A-G |
| 84638 | T-G |
| 85526 | T-G |
| 85705 | G-T |
| 86984 | T-C |
| 87655 | T-C |
| 87713 | A-C |
| 87892 | C-T |
| 88192 | T DEL |
| 88528 | A-G |
| 89645 | A-T |
| 89728 | A-G |
| 90088 | T-C |
| 91193–91194 | 2209bp INS |
| 91373 | T-C |
| 91433–91434 | A INS |
| 91747 | G-A |
| 93625 | T DEL |
| 95116–95117 | T INS |
| 96315 | G-A |
| 97981 | A-G |
| 98351 | T DEL |
| 99249 | C-T |
| 100094–100095 | T INS |
| 100647–100648 | TTC INS |
| 100951 | C-T |
| 101610 | C-G |
| 102589 | C-T |
| 103076–103077 | TATATATATATATA INS |
| 103747 | T-C |
| 105638 | A-C |
| 107024 | C-T |
| 107322 | C-T |
| 107858 | C-G |
| 109019 | A DEL |
| 109579 | T DEL |
| 110021 | C-A |
| 111251 | C-A |
| 111425 | G-A |
| 112644 | T-A |
| 113001 | G-C |
| 113130 | C-T |
| 114026 | G-A |
| 114250 | A DEL |
| 115217 | C-G |
| 117995 | G-A |
| 118874 | A-G |
| 119470 | T-C |
| 119646 | G-T |
| 120853 | C-T |
| 121582 | G-A |
| 123576 | A-C |
| 125581 | C-T |
| 125970 | G-T |
| 126197 | A-G |
| 126672 | A DEL |
| 126672 | G-C |
| 128220–128221 | A INS |
| 132569 | C-T |
| 133572 | A-C |
| 134064 | T-G |
| 136999 | G-A |
| 137784 | C-T |
| 138903 | G-A |
| 139159–139160 | A INS |
| 140359 | G-A |
| 140898 | C-T |
| 141313 | C DEL |
| 141343 | T-C |
| 142148 | T-C |
| 142178 | C-A |
| 142433–142434 | ATAGA INS |
| 143783 | C-T |
| 144090 | C-T |
| 144220–144221 | A INS |
| 144725 | A-C |
| 145732–145733 | AAAAAAAAAAAAAA INS |
| 147016–147017 | CG DEL |
| 147021 | G-T |
| 147536 | T-G |
| 148936 | T-A |
| 149061 | T-C |
| 154341 | A-T |
| 154588 | G-A |
| 155464 | G-A |
| 158574 | C-G |
| 160007 | C-T |
| 164348 | A-T |
| 164499 | C-G |
| 166677–166678 | AAAG INS |
| 167389 | G-A |
| 168506–168507 | AGGATGGTCT INS |
| 168515 | T-C |
| 169413–169414 | AA INS |
| 170300–170301 | TTGTTGTTGTTG INS |
| 170491 | G-A |
| 173428 | T-C |
| 173642 | G-A |
| 173948 | T-G |
| 175330 | T-C |
| 175836 | T-C |
| 1176200 | G-C |
| 176222 | T-C |
| 176524 | A-T |
| 176684 | G-A |
| 176815 | T-C |
| 177049 | T-C |
| 177065 | G-T |
| 178285 | T-C |
| 178551–178552 | CTTTTTTTTTTTTT INS |
| 179114–179115 | A INS |
| 179260 | C-G |
| 179281 | C-G |
| 180023 | G-C |
| 180430 | T-C |
| 180773 | T-C |
| 180824 | T-C |
| 181097 | C-T |
| 181183 | A-T |
| 182351 | C-T |
| 183197 | G-A |
| 183623 | A-T |
| 183653 | G-T |
| 183657 | T-G |
| 183795–183796 | A INS |
| 184060 | G-A |
| 184993 | G-A |
| 185918 | A-G |
| 186036 | T-C |
| 186506–186507 | TAAC INS |
| 186561–186568 | TATTTATT DEL |
| 186690 | G DEL |
| 186751 | T-A |
| 187221 | A-G |
| 187260 | A-G |
| 187444–187447 | CTCT DEL |
| 187831–187832 | C INS |
| 188638 | G-A |
| 188642 | C-T |
| 189246 | T-C |
| 190340 | A-C |
| 190354 | A-G |
| 190762 | A-G |
| 191260 | G-T |
| 193018–193019 | AGAT INS |

TABLE 1-continued

Polymorphic Sites in the HH Region*

| BASE LOCATION | DIFFERENCE |
|---|---|
| 193147 | T-G |
| 193196–193197 | C INS |
| 193499 | C-T |
| 193738 | C-G |
| 193984–193985 | ACACACAC INS |
| 194064 | C-G |
| 194504 | A DEL |
| 194734 | G-A |
| 194890 | A-C |
| 195404 | G-A |
| 195693 | A-T |
| 196205 | G-A |
| 197424 | C-T |
| 197513 | C-T |
| 197670 | G-A |
| 198055 | C-A |
| 198401 | C-T |
| 198692 | A-G |
| 198780 | T DEL |
| 199030 | T-G |
| 199933 | C-T |
| 200027 | G-A |
| 200439 | T-A |
| 200452 | A-G |
| 200472–200483 | AATAATAATAAT DEL |
| 200559 | A-T |
| 200745 | A-G |
| 200919 | T-A |
| 201816 | C-T |
| 201861–201862 | 42bp INS |
| 202662 | T-C |
| 202880 | T-C |
| 204341 | C-T |
| 204768 | A-T |
| 205284 | T-G |
| 207400 | C-A |
| 208634 | T-C |
| 208718 | T DEL |
| 208862 | A-C |
| 209419–209420 | TT DEL |
| 209802 | G-A |
| 209944 | C-G |
| 210299 | A-G |
| 211142 | G-A |
| 212072 | G-A |
| 212146 | T-C |
| 212379 | G-A |
| 212637–212639 | TCT DEL |
| 212696 | T-C |
| 213042 | T-A |
| 214192 | A-G |
| 214529–214530 | TTTTTTTTTTT INS |
| 214549 | T-C |
| 214795 | C-T |
| 214908 | T-G |
| 214977 | A-G |
| 215769 | C-T |
| 215947 | C-A |
| 216232 | A-G |
| 217478 | G-A |
| 219052 | T-C |
| 219082–219083 | ATATATATATATATATAT INS |
| 219314 | C-A |
| 219327 | G-A |
| 219560 | C-T |
| 219660 | C-T |
| 219889 | G-A |
| 220198 | G-T |
| 220384 | G-A |
| 220451–220452 | CAAAAA INS |
| 221383 | G-A |
| 221645 | G-A |
| 222119 | T-C |
| 222358 | A-G |
| 222367 | A-C |
| 222686 | A-G |
| 222959 | T-C |
| 223270–223271 | TT DEL |
| 223283 | T-C |
| 224964 | T-C |
| 225232 | A-C |
| 225366–225367 | TTTT INS |
| 225416 | G-C |
| 225486 | T-C |
| 226088 | A-G |
| 228421 | A-G |
| 230047 | G-A |
| 230109 | G-C |
| 230376 | C-G |
| 230394 | A-G |
| 231226 | A-G |
| 231447 | G-A |
| 231835 | A-G |
| 232400–232402 | AAA DEL |
| 232402–232403 | G INS |
| 232515 | T-C |
| 232703 | G-T |
| 232750 | A-G |

*D6S2238 occurs at base 1. 24d1 occurs at base 41316. D6S2239 occurs at base 84841. D6S2241 occurs at base 235032

TABLE 2

Polymorphic Allele Frequencies

| Location | Frequency of ancestral variant in random chromosomes | Frequency of unaffected variant in random chromosomes |
|---|---|---|
| 232703 | 53% | 47% |
| 231835 | 53% | 47% |
| 230394 | 85% | 15% |
| 230376 | 25% | 75% |
| 230109 | 53% | 47% |
| 225486 | 45% | 55% |
| 225416 | 75% | 25% |
| 220198 | 43% | 57% |
| 219660 | 58% | 42% |
| 219560 | 53% | 47% |
| 214977 | 65% | 35% |
| 214908 | 50% | 50% |
| 214795 | 24% | 76% |
| 214549 | 53% | 47% |
| 214192 | 65% | 35% |
| 210299 | 53% | 47% |
| 208862 | 80% | 20% |
| 208634 | 48% | 52% |
| 207400 | 25% | 75% |
| 205284 | 50% | 50% |
| 204341 | 53% | 47% |
| 202880 | 58% | 42% |
| 202662 | 98% | 2% |
| 200027 | 25% | 75% |
| 199030 | 58% | 42% |
| 198692 | 55% | 45% |
| 198401 | 55% | 45% |
| 198055 | 55% | 45% |
| 195693 | 60% | 40% |
| 195404 | 25% | 75% |
| 194890 | 55% | 45% |
| 175330 | 53% | 47% |
| 173948 | 83% | 17% |
| 173642 | 55% | 45% |
| 173428 | 80% | 20% |
| 168515 | 80% | 20% |
| 160007 | 18% | 82% |
| 149061 | 58% | 42% |

TABLE 2-continued

Polymorphic Allele Frequencies

| Location | Frequency of ancestral variant in random chromosomes | Frequency of unaffected variant in random chromosomes |
|---|---|---|
| 148936 | 82% | 18% |
| 147536 | 100% | 0% |
| 147021 | 46% | 54% |
| 141343 | 55% | 45% |
| 140359 | 55% | 45% |
| 138903 | 55% | 45% |
| 132569 | 81% | 19% |
| 125581 | 18% | 82% |
| 121582 | 80% | 20% |
| 120853 | 18% | 82% |
| 118874 | 85% | 15% |
| 115217 | 50% | 50% |
| 113130 | 40% | 60% |
| 113001 | 48% | 52% |
| 107858 | 48% | 52% |
| 103747 | 50% | 50% |
| 96315 | 25% | 75% |
| 91194 | 80% | 20% |
| 90088 | 75% | 25% |
| 89728 | 50% | 50% |
| 89645 | 50% | 50% |
| 88528 | 63% | 37% |
| 87892 | 75% | 25% |
| 87713 | 60% | 40% |
| 87655 | 50% | 50% |
| 86984 | 79% | 21% |
| 85705 | 50% | 50% |
| 85526 | 50% | 50% |
| 84638 | 50% | 50% |
| 84533 | 50% | 50% |
| 82166 | 78% | 22% |
| 81193 | 58% | 42% |
| 80189 | 50% | 50% |
| 78385 | 80% | 20% |
| 77908 | 88% | 12% |
| 68976 | 50% | 50% |
| 68259 | 51% | 49% |

TABLE 2-continued

Polymorphic Allele Frequencies

| Location | Frequency of ancestral variant in random chromosomes | Frequency of unaffected variant in random chromosomes |
|---|---|---|
| 66675 | 80% | 20% |
| 62732 | 50% | 50% |
| 62362 | 40% | 60% |
| 61653 | 48% | 52% |
| 61465 | 5% | 95% |
| 61162 | 60% | 40% |
| 53707 | 100% | 0% |
| 52875 | 50% | 50% |
| 52733 | 74% | 26% |
| 52474 | 47% | 53% |
| 50586 | 50% | 50% |
| 50553 | 50% | 50% |
| 50240 | 50% | 50% |
| 48680 | 53% | 47% |
| 48650 | 63% | 37% |
| 48440 | 50% | 50% |
| 47255 | 50% | 50% |
| 46601 | 53% | 47% |
| 45567 | 49% | 51% |
| 41316 | 5% | 95% |
| 40431 | 20% | 80% |
| 38526 | 23% | 77% |
| 37411 | 70% | 30% |
| 35983 | 5% | 95% |

What is claimed is:

1. A method for determining an individual's predisposition for hereditary hemochromatosis (HH) comprising:
   (a) providing a sample comprising the individual's nucleic acid;
   (b) detecting the nucleotide present at position 35983 of a HH gene comprising SEQ ID NO: 1, or its complement in a strand complementary to SEQ ID NO: 1, in said sample, wherein the presence of a C at position 35983 of the HH gene comprising SEQ ID NO: 1, or a G at its complementary position in the strand complementary to SEQ ID NO: 1, indicates an increased predisposition for HH.

2. A method for determining the likely presence or absence of a 24d1 hereditary hemochromatosis (HH) mutation in a nucleic acid comprising:
   (a) providing a sample comprising said nucleic acid; and
   (b) detecting the nucleotide present at position 35983 of a HH gene comprising SEQ ID NO: 1, or its complement in a strand complementary to SEQ ID NO: 1, in the nucleic acid, wherein the presence of a C at position 35983 of the HH gene comprising SEQ ID NO: 1, or a G at its complementary position in the strand complementary to SEQ ID NO: 1, indicates the likely presence of said 24d1 HH mutation and the absence of a C at position 35983 of a HH gene comprising SEQ ID NO: 1, or a G at its complementary position in the strand complementary to SEQ ID NO: 1, indicates the likely absence of said 24d1 HH mutation in said nucleic acid.

3. The method of claim 1 or 2, wherein said nucleic acid comprises genomic DNA.

4. The method of claim 1 or 2, wherein said nucleic acid comprises cDNA.

5. The method of claim 1 or 2, wherein said nucleic acid comprises RNA.

6. The method of claim 1 or 2, wherein said nucleic acid is amplified.

7. The method of claim 6, wherein said nucleic acid is amplified by PCR, LCR SDA or 3SR.

8. The method of claim 1 or 2, wherein said nucleotide at position 35983 of a HH gene comprising SEQ ID NO:1, or its complement in the strand complementary to SEQ ID NO:1, is detected by restriction-fragment-length-polymorphism detection.

9. The method of claim 1 or 2, wherein said nucleotide at position 35983 of a HH gene comprising SEQ ID NO:1, or its complement in the strand complementary to SEQ ID NO:1, is detected by hybridization with allele-specific oligonucleotides.

10. The method of claim 1 or 2, wherein said nucleotide at position 35983 of a HH gene comprising SEQ ID NO:1, or its complement in the strand complementary to SEQ ID NO:1, is detected by allele-specific PCR.

11. The method of claim 1 or 2, wherein said nucleotide at position 35983 of a HH gene comprising SEQ ID NO:1, or its complement in the strand complementary to SEQ ID NO:1, is detected by mismatch-repair detection.

12. The method of claim 1 or 2, wherein said nucleotide at position 35983 of a HH gene comprising SEQ ID NO:1, or its complement in the strand complementary to SEQ ID NO:1, is detected by denaturing-gradient gel electrophoresis.

13. The method of claim 1 or 2, wherein said nucleotide at position 35983 of a HH gene comprising SEQ ID NO:1, or its complement in the strand complementary to SEQ ID NO:1, is detected by sequencing.

14. The method of claim 1 or 2, wherein said nucleotide at position 35983 of a HH gene comprising SEQ ID NO:1, or its complement in the strand complementary to SEQ ID NO:1, is detected by single-strand-conformation-polymorphism detection.

15. The method of claim 1 or 2, wherein said nucleotide at position 35983 of a HH gene comprising SEQ ID NO:1, or its complement in the strand complementary to SEQ ID NO:1, is detected by RNase cleavage at mismatched base pairs.

16. The method of claim 1 or 2, wherein said nucleotide at position 35983 of a HH gene comprising SEQ ID NO:1, or its complement in the strand complementary to SEQ ID NO:1, is detected by chemical or enzymatic cleavage of heteroduplex DNA.

17. The method of claim 1 or 2, wherein said nucleotide at position 35983 of a HH gene comprising SEQ ID NO:1, or its complement in the strand complementary to SEQ ID NO:1, is detected by binding of MutS protein.

18. The method of claim 1 or 2, wherein said nucleotide at position 35983 of a HH gene comprising SEQ ID NO:1, or its complement in the strand complementary to SEQ ID NO:1, is detected by genetic bit analysis.

19. The method of claim 1 or 2, wherein said nucleotide at position 35983 of a HH gene comprising SEQ ID NO:1, or its complement in the strand complementary to SEQ ID NO:1, is detected by oligonucleotide-ligation assay.

20. The method of claim 1 or 2, wherein said nucleotide at position 35983 of a HH gene comprising SEQ ID NO:1, or its complement in the strand complementary to SEQ ID NO:1, is detected by allele-specific ligation chain reaction.

21. The method of claim 1 or 2, wherein said nucleotide at position 35983 of a HH gene comprising SEQ ID NO:1, or its complement in the strand complementary to SEQ ID NO:1, is detected with radioactive or fluorescent sequencing of the nucleic acid.

22. The method of claim 1 or 2, wherein said nucleotide at position 35983 of a HH gene comprising SEQ ID NO:1, or its complement in the strand complementary to SEQ ID NO:1, is detected with peptide nucleic acid assays.

23. The method of claim 1, wherein the method further comprises detecting a nucleotide present at a polymorphic site at position 230376, 214795, 207400, 200027, 195404, 160007, 125581, 120853, 96315, 61465, 40431, or 38526, of a HH gene comprising SEQ ID NO: 1, or a nucleotide in the complementary position to position 230376, 214795, 207400, 200027, 195404, 160007, 125581, 120853, 96315, 61465, 40431, or 38526, of a HH gene comprising SEQ ID NO: 1 in a strand complementary to SEQ ID NO: 1, in said sample.

24. The method of claim 2, wherein the method further comprises detecting a nucleotide present at a polymorphic site at position 230376, 214795, 207400, 200027, 195404, 160007, 125581, 120853, 96315, 61465, 40431, or 38526, of a HH gene comprising SEQ ID NO: 1, or a nucleotide in the complementary position to position 230376, 214795, 207400, 200027, 195404, 160007, 125581, 120853, 96315, 61455, 40431, or 38526, of a HH gene comprising SEQ ID NO: 1 in a strand complementary to SEQ ID NO: 1, in the nucleic acid.

25. A method for determining an individual's predisposition for hereditary hemochromatosis (HH) comprising:
    (a) providing a sample comprising the individual's nucleic acid;
    (b) detecting the nucleotide present at position 61465 of a HH gene comprising SEQ ID NO: 1, or its complement in a strand complementary to SEQ ID NO: 1, in said sample, wherein the presence of a T at position 61465 of the HH gene comprising SEQ ID NO: 1 or an A at its complementary position in the strand complementary to SEQ ID NO: 1, indicates an increased predisposition for HH.

26. A method for determining the likely presence or absence of a 24d1 hereditary hemochromatosis (HH) mutation in a nucleic acid comprising:
    (a) providing a sample comprising said nucleic acid; and
    (b) detecting the nucleotide present at position 61465 of a HH gene comprising SEQ ID NO: 1, or its complement in a strand complementary to SEQ ID NO: 1, in the nucleic acid, wherein the presence of a T at position 61465 of the HH gene comprising SEQ ID NO: 1, or an A at its complementary position in the strand complementary to SEQ ID NO: 1, indicates the likely presence of said 24d1 HH mutation and the absence of a T at position 61465 of a HH gene comprising SEQ ID NO: 1, or an A at its complementary position in the strand complementary to SEQ ID NO: 1, indicates the likely absence of said 24d1 HH mutation in said nucleic acid.

27. The method of claim 25 or 26, wherein said nucleic acid comprises genomic DNA.

28. The method of claim 25 or 26, wherein said nucleic acid comprises cDNA.

29. The method of claim 25 or 26, wherein said nucleic acid comprises RNA.

30. The method of claim 25 or 26, wherein said nucleic acid is amplified.

31. The method of claim 30, wherein said nucleic acid is amplified by PCR, LCR SDA or 3SR.

32. The method of claim 25 or 26, wherein said nucleotide at position 61465 of a HH gene comprising SEQ ID NO:1, or its complement in the strand complementary to SEQ ID NO:1, is detected by restriction-fragment-length-polymorphism detection.

33. The method of claim 25 or 26, wherein said nucleotide at position 61465 of a HH gene comprising SEQ ID NO:1, or its complement in the strand complementary to SEQ ID NO:1, is detected by hybridization with allele-specific oligonucleotides.

34. The method of claim 25 or 26, wherein said nucleotide at position 61465 of a HH gene comprising SEQ ID NO:1, or its complement in the strand complementary to SEQ ID NO:1, is detected by allele-specific PCR.

35. The method of claim 25 or 26, wherein said nucleotide of a position 61465 of a HH gene comprising SEQ ID NO:1, or its complement in the strand complementary to SEQ ID NO:1, is detected by mismatch-repair detection.

36. The method of claim 25 or 26, wherein said nucleotide at position 61465 of a HH gene comprising SEQ ID NO:1, or its complement in the strand complementary to SEQ ID NO:1, is detected by denaturing-gradient gel electrophoresis.

37. The method of claim 25 or 26, wherein said nucleotide at position 61465 of a HH gene comprising SEQ ID NO:1, or its complement in the strand complementary to SEQ ID NO:1, is detected by sequencing.

38. The method of claim 25 or 26, wherein said nucleotide at position 61465 of a HH gene comprising SEQ ID NO:1, or its complement in the strand complementary to SEQ ID NO:1, is detected by single-strand-conformation-polymorphism detection.

39. The method of claim 25 or 26, wherein said nucleotide at position 61465 of a HH gene comprising SEQ ID NO:1, or its complement in the strand complementary to SEQ ID NO:1, is detected by RNase cleavage at mismatched base pairs.

40. The method of claim 25 or 26, wherein said nucleotide at position 61465 of a HH gene comprising SEQ ID NO:1, or its complement in the strand complementary to SEQ ID NO:1, is detected by chemical or enzymatic cleavage of heteroduplex DNA.

41. The method of claim 25 or 26, wherein said nucleotide at position 61465 of a HH gene comprising SEQ ID NO:1, or its complement in the strand complementary to SEQ ID NO:1, is detected by binding of MutS protein.

42. The method of claim 25 or 26, wherein said nucleotide at position 61465 of a HH gene comprising SEQ ID NO:1, or its complement in the strand complementary to SEQ ID NO:1, is detected by genetic bit analysis.

43. The method of claim 25 or 26, wherein said nucleotide at position 61465 of a HH gene comprising SEQ ID NO:1, or its complement in the complementary to SEQ ID NO:1, is detected by oligonucleotide-ligation assay.

44. The method claim 25 or 26, wherein said nucleotide at position 61465 of a HH gene comprising SEQ ID NO:1, or its complement in the strand complementary to SEQ ID NO:1, is detected by allele-specific ligation chain reaction.

45. The method of claim 25 or 26, wherein said nucleotide at position 61465 of a HH gene comprising SEQ ID NO:1, or its complement in the strand complementary to SEQ ID NO:1, is detected with radioactive or fluorescent sequencing of the nucleic acid.

46. The method of claim 25 or 26, wherein said nucleotide at position 61465 of a HH gene comprising SEQ ID NO:1, or its complement in the strand complementary to SEQ ID NO:1, is detected with peptide nucleic acid assays.

47. The method of claim 25, the method further comprises detecting a nucleotide present at a polymorphic site at position 230376, 214795, 207400, 200027, 195404, 160007, 125581, 120853, 96315, 40431, or 38526, of a HH gene comprising SEQ ID NO: 1, or a nucleotide in the complementary position to position 230376, 214795, 207400, 200027, 195404, 160007, 125581, 120853, 96315, 40431, or 38526, of a HH gene comprising SEQ ID NO: 1 in strand complementary to SEQ ID NO: 1, in said sample.

48. The method of claim 26, wherein the method further comprises detecting a nucleotide present at a polymorphic site at position 230376, 214795, 207400, 200027, 195404, 160007, 125581, 120853, 96315, 40431, or 38526, of a HH gene comprising SEQ ID NO: 1, or a nucleotide in the complementary position to position 230376, 214795, 207400, 200027, 195404, 160007, 125581, 120853, 96315, 40431, or 38526, of a HH gene comprising SEQ ID NO: 1 in a strand complementary to SEQ ID NO: 1, in the nucleic acid.

* * * * *